US010519152B2

United States Patent
Yang et al.

(10) Patent No.: US 10,519,152 B2
(45) Date of Patent: Dec. 31, 2019

(54) COMPOUNDS AND THEIR USE IN TREATING CANCER

(71) Applicant: AstraZeneca AB, Södertälje (SE)

(72) Inventors: Bin Yang, Wilmington, DE (US); Jason Grant Kettle, Cambridge (GB); Thomas George Christopher Hayhow, Cambridge (GB); Timothy Gordon Rasmusson, Wilmington, DE (US); Johannes Wilhelmus Maria Nissink, Cambridge (GB); Charlene Fallan, Cambridge (GB); Gillian McGregor Lamont, Cambridge (GB)

(73) Assignee: AstraZeneca AB, Södertälje (SE)

(*) Notice: Subject to any disclaimer, the term of this patent is extended or adjusted under 35 U.S.C. 154(b) by 0 days.

(21) Appl. No.: 16/223,224

(22) Filed: Dec. 18, 2018

(65) Prior Publication Data

US 2019/0194190 A1    Jun. 27, 2019

Related U.S. Application Data

(60) Provisional application No. 62/608,847, filed on Dec. 21, 2017.

(51) Int. Cl.
*A61K 31/437* (2006.01)
*C07D 471/04* (2006.01)
*C07D 519/00* (2006.01)
*C07K 5/062* (2006.01)

(52) U.S. Cl.
CPC ......... *C07D 471/04* (2013.01); *C07D 519/00* (2013.01); *C07K 5/06034* (2013.01)

(58) Field of Classification Search
None
See application file for complete search history.

(56) References Cited

U.S. PATENT DOCUMENTS

2010/0158858 A1* 6/2010 Cao ..................... A61K 31/437
424/85.2

FOREIGN PATENT DOCUMENTS

| CN | 106317052 A | 1/2017 |
|---|---|---|
| EP | 2985285 A1 | 2/2016 |
| WO | 2014108452 A1 | 7/2014 |
| WO | 2015000867 A1 | 1/2015 |
| WO | 2015000868 A1 | 1/2015 |
| WO | 2017030814 A1 | 2/2017 |

OTHER PUBLICATIONS

Sakamota, Protacs for Treatment of Cancer, Pediatric Res., 2010, 67(5):505-508.
Burks, et al., Discovery of an Acrylic Acid Based Tetrahydroisoquinoline as an Orally Bioavailable Selective Estrogen Receptor Degrader for ERα+ Breast Cancer, J. Med. Chem., 2017, 60:2790-2818.
Int'l Search Report and Written Opinion for PCT/IB2018/060425 dated May 14, 2019.

* cited by examiner

Primary Examiner — Samantha L Shterengarts

(57) ABSTRACT

The specification generally relates to compounds of Formula (I):

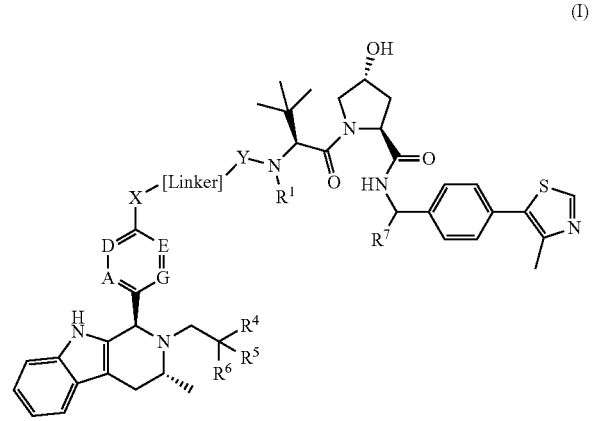

and pharmaceutically acceptable salts and prodrugs thereof, where $R^1$, $R^4$, $R^5$, $R^6$, $R^7$, Linker, X, Y, A, G, D and E have any of the meanings defined herein. This specification also relates to the use of such compounds and pharmaceutically acceptable salts and prodrugs thereof in methods of treatment of the human or animal body, for example in prevention or treatment of cancer. This specification also relates to processes and intermediate compounds involved in the preparation of such compounds and to pharmaceutical compositions containing them.

12 Claims, No Drawings

COMPOUNDS AND THEIR USE IN TREATING CANCER

CROSS-REFERENCE TO RELATED APPLICATIONS

This application claims benefit under 35 U.S.C. § 119(e) of U.S. provisional application 62/608,847 filed Dec. 21, 2017, which is incorporated by reference herein in its entirety.

FIELD

The compounds of the specification have been found to possess potent anti-tumour activity, being useful in inhibiting the uncontrolled cellular proliferation which arises from malignant disease. The compounds of the specification provide an anti-tumour effect by, as a minimum, acting as Proteolysis Targeting Chimeras (PROTACs) to selectively degrade estrogen receptor alpha. For example, the compounds of the specification may exhibit anti-tumour activity via the ability to degrade the estrogen receptor in a number of different breast cancer cell-lines, for example against the MCF-7, CAMA-1, and/or BT474 breast cancer cell-lines. Such compounds may be expected to be more suitable as therapeutic agents, particularly for the treatment of cancer. This specification also relates to processes and intermediate compounds involved in the preparation of said compounds and to pharmaceutical compositions containing them.

BACKGROUND

Estrogen receptor alpha (ERα, ESR1, NR3A) and estrogen receptor beta (ERβ, ESR2, NR3b) are steroid hormone receptors which are members of the large nuclear receptor family. Structured similarly to all nuclear receptors, ERα is composed of six functional domains (named A-F) (Dahlman-Wright, et al., *Pharmacol. Rev.*, 2006, 58:773-781) and is classified as a ligand-dependent transcription factor because after its association with the specific ligand, (the female sex steroid hormone 17b estradiol), the complex binds to genomic sequences, named Estrogen Receptor Elements (ERE) and interacts with co-regulators to modulate the transcription of target genes. The ERα gene is located on 6q25.1 and encodes a 595AA protein and multiple isoforms can be produced due to alternative splicing and translational start sites. In addition to the DNA binding domain (Domain C) and the ligand binding domain (Domain E) the receptor contains a N-terminal (A/B) domain, a hinge (D) domain that links the C and E domains and a C-terminal extension (F domain). While the C and E domains of ERα and ERβ are quite conserved (96% and 55% amino acid identity respectively) conservation of the A/B, D and F domains is poor (below 30% amino acid identity). Both receptors are involved in the regulation and development of the female reproductive tract and in addition play roles in the central nervous system, cardiovascular system and in bone metabolism. The genomic action of ERs occurs in the nucleus of the cell when the receptor binds EREs directly (direct activation or classical pathway) or indirectly (indirect activation or non-classical pathway). In the absence of ligand, ERs are associated with heat shock proteins, Hsp90 and Hsp70, and the associated chaperone machinery stabilizes the ligand binding domain (LBD) making it accessible to ligand. Liganded ER dissociates from the heat shock proteins leading to a conformational change in the receptor that allows dimerisation, DNA binding, interaction with co-activators or co-repressors and modulation of target gene expression. In the non-classical pathway, AP-1 and Sp-1 are alternative regulatory DNA sequences used by both isoforms of the receptor to modulate gene expression. In this example, ER does not interact directly with DNA but through associations with other DNA bound transcription factors e.g. c-Jun or c-Fos (Kushner et al., *Pure Applied Chemistry* 2003, 75:1757-1769). The precise mechanism whereby ER affects gene transcription is poorly understood but appears to be mediated by numerous nuclear factors that are recruited by the DNA bound receptor. The recruitment of co-regulators is primarily mediated by two protein surfaces, AF2 and AF1 which are located in E-domain and the A/B domain respectively. AF1 is regulated by growth factors and its activity depends on the cellular and promoter environment whereas AF2 is entirely dependent on ligand binding for activity. Although the two domains can act independently, maximal ER transcriptional activity is achieved through synergistic interactions via the two domains (Tzukerman, et al., *Mol. Endocrinology*, 1994, 8:21-30). Although ERs are considered transcription factors they can also act through non-genomic mechanisms as evidenced by rapid ER effects in tissues following estradiol administration in a timescale that is considered too fast for a genomic action. It is still unclear if receptors responsible for the rapid actions of estrogen are the same nuclear ERs or distinct G-protein coupled steroid receptors (Warner, et al., *Steroids* 2006 71:91-95) but an increasing number of estradiol induced pathways have been identified e.g. MAPK/ERK pathway and activation of endothelial nitric oxide synthase and PI3K/Akt pathway. In addition to ligand dependent pathways, ERα has been shown to have ligand independent activity through AF-1 which has been associated with stimulation of MAPK through growth factor signalling e.g. insulin like growth factor 1 (IGF-1) and epidermal growth factor (EGF). Activity of AF-1 is dependent on phosphorylation of Ser118 and an example of cross-talk between ER and growth factor signalling is the phosphorylation of Ser118 by MAPK in response to growth factors such as IGF-1 and EGF (Kato, et al., *Science*, 1995, 270:1491-1494).

A large number of structurally distinct compounds have been shown to bind to ER. Some compounds such as endogenous ligand estradiol, act as receptor agonists whereas others competitively inhibit estradiol binding and act as receptor antagonists. These compounds can be divided into 2 classes depending on their functional effects. Selective estrogen receptor modulators (SERMs) such as tamoxifen have the ability to act as both receptor agonists and antagonists depending on the cellular and promoter context as well as the ER isoform targeted. For example tamoxifen acts as an antagonist in breast but acts as a partial agonist in bone, the cardiovascular system and uterus. All SERMs appear to act as AF2 antagonists and derive their partial agonist characteristics through AF1. A second group, fulvestrant being an example, are classified as full antagonists and are capable of blocking estrogen activity via the complete inhibition of AF1 and AF2 domains through induction of a unique conformation change in the ligand binding domain (LBD) on compound binding which results in complete abrogation of the interaction between helix 12 and the remainder of the LBD, blocking co-factor recruitment (Wakeling, et al., *Cancer Res.*, 1991, 51:3867-3873; Pike, et al., *Structure*, 2001, 9:145-153).

Intracellular levels of ERα are down-regulated in the presence of estradiol through the ubiquitin/proteosome (Ub/26S) pathway. Polyubiquitinylation of liganded ERα is catalysed by at least three enzymes; the ubiquitin-activating enzyme E1 activated ubiquitin is conjugated by E2 conjugating enzyme with lysine residues through an isopeptide bond by E3 ubiquitin ligase and polyubiquitinated ERα is then directed to the proteosome for degradation. Although ER-dependent transcription regulation and proteosome-mediated degradation of ER are linked (Lonard, et al., *Mol. Cell*, 2000 5:939-948), transcription in itself is not required for ERα degradation and assembly of the transcription initiation complex is sufficient to target ERα for nuclear proteosomal degradation. This estradiol induced degradation process is believed necessary for its ability to rapidly activate transcription in response to requirements for cell proliferation, differentiation and metabolism (Stenoien, et al., *Mol. Cell Biol.*, 2001, 21:4404-4412). Fulvestrant is also classified as a selective estrogen receptor degrader (SERD), a subset of antagonists that can also induce rapid down-regulation of ERα via the 26S proteosomal pathway. In contrast a SERM such as tamoxifen can increase ERα levels although the effect on transcription is similar to that seen for a SERD.

PROTACs are heterobifunctional molecules containing two small molecule binding moieties, joined together by a linker. One of the small molecule ligands is designed to bind with high affinity to a target protein in the cell whilst the other ligand is able to bind with high affinity to an E3 ligase. In the cell, the PROTAC seeks out and selectively binds to the target protein of interest. The PROTAC then recruits a specific E3 ligase to the target protein to form a ternary complex with both the target protein and the E3 ligase held in close proximity. The E3 ligase then recruits an E2 conjugating enzyme to the ternary complex. E2 is then able to ubiquitinate the target protein, labelling an available lysine residue on the protein and then dissociates from the ternary complex. E3 can then recruit additional E2 molecules resulting in poly-ubiquitination of the target protein, labelling the target protein for potential degradation by the cell's proteasome machinery. A PROTAC is then able to dissociate from the target protein and initiate another catalytic cycle. The poly-ubiquitinated target protein is then recognized and degraded by the proteasome. Here the designated PROTACs targeting ER for degradation contain an ER ligand moiety at one end of the linker and an E3 ligase (such as the von Hippel-Lindau tumour suppressor, VHL) ligand at the other end. In the cells, the ER PROTAC selectively recruits VHL E3 ligase to ER and leads to the degradation of ER by the Ub/26S system.

Approximately 70% of breast cancers express ER and/or progesterone receptors implying the hormone dependence of these tumour cells for growth. Other cancers such as ovarian and endometrial are also thought to be dependent on ERα signalling for growth. Therapies for such patients can inhibit ER signalling either by antagonising ligand binding to ER e.g. tamoxifen which is used to treat early and advanced ER positive breast cancer in both pre and post menopausal setting; antagonising and down-regulating ERα e.g. fulvestrant which is used to treat breast cancer in women which have progressed despite therapy with tamoxifen or aromatase inhibitors; or blocking estrogen synthesis e.g. aromatase inhibitors which are used to treat early and advanced ER positive breast cancer. Although these therapies have had an enormously positive impact on breast cancer treatment, a considerable number of patients whose tumours express ER display de novo resistance to existing ER therapies or develop resistance to these therapies over time. Several distinct mechanisms have been described to explain resistance to first-time tamoxifen therapy which mainly involve the switch from tamoxifen acting as an antagonist to an agonist, either through the lower affinity of certain co-factors binding to the tamoxifen-ERα complex being off-set by over-expression of these co-factors, or through the formation of secondary sites that facilitate the interaction of the tamoxifen-ERα complex with co-factors that normally do not bind to the complex. Resistance could therefore arise as a result of the outgrowth of cells expressing specific co-factors that drive the tamoxifen-ERα activity. There is also the possibility that other growth factor signalling pathways directly activate the ER receptor or co-activators to drive cell proliferation independently of ligand signalling.

More recently, mutations in ESR1 have been identified as a possible resistance mechanism in metastatic ER-positive patient derived tumour samples and patient-derived xenograft models (PDX) at frequencies varying from 17-25%. These mutations are predominantly, but not exclusively, in the ligand-binding domain leading to mutated functional proteins; examples of the amino acid changes include Ser463Pro, Val543Glu, Leu536Arg, Tyr537Ser, Tyr537Asn and Asp538Gly, with changes at amino acid 537 and 538 constituting the majority of the changes currently described. These mutations have been undetected previously in the genomes from primary breast samples characterised in the Cancer Genome Atlas database. Of 390 primary breast cancer samples positive for ER expression not a single mutation was detected in ESR1 (Cancer Genome Atlas Network, 2012 Nature 490: 61-70). The ligand binding domain mutations are thought to have developed as a resistance response to aromatase inhibitor endocrine therapies as these mutant receptors show basal transcriptional activity in the absence of estradiol. The crystal structure of ER, mutated at amino acids 537 and 538, showed that both mutants favoured the agonist conformation of ER by shifting the position of helix 12 to allow co-activator recruitment and thereby mimicking agonist activated wild type ER. Published data has shown that endocrine therapies such as tamoxifen and fulvestrant can still bind to ER mutant and inhibit transcriptional activation to some extent and that fulvestrant is capable of degrading Try537Ser but that higher doses may be needed for full receptor inhibition (Toy et al., *Nat. Genetics* 2013, 45: 1439-1445; Robinson et al., *Nat. Genetics* 2013, 45: 144601451; Li, S. et al. *Cell Rep.* 2013, 4, 1116-1130). It is therefore feasible that certain compounds of the Formula (I) or pharmaceutically acceptable salts or prodrugs thereof (as described hereinafter) will be capable of antagonising mutant ER although it is not known at this stage whether ESR1 mutations are associated with an altered clinical outcome.

Regardless of which resistance mechanism or combination of mechanisms takes place, many are still reliant on ER-dependent activities and antagonism or degradation of the receptor offers a way of inhibiting ERα. There is therefore an ongoing need for therapies which selectively degrade estrogen receptor alpha.

SUMMARY

The compounds of the specification have been found to provide an anti-tumour effect by inducing ER degradation, or as a minimum, acting as ER antagonists. The compounds described herein may provide greater ER degradation compared to fulvestrant and may also provide greater ER degradation compared to oral SERDs. The compounds of the specification may be expected to be suitable as therapeutic agents, particularly for the treatment of cancer.

This specification relates to certain compounds and pharmaceutically acceptable salts or prodrugs thereof that selectively degrade the estrogen receptor and possess anti-cancer activity. This specification also relates to use of said compounds and pharmaceutically acceptable salts or prodrugs thereof in methods of treatment of the human or animal body, for example in prevention or treatment of cancer. This specification also relates to processes and intermediate compounds involved in the preparation of said compounds and to pharmaceutical compositions containing them.

According to one aspect of the specification there is provided a compound of Formula (I):

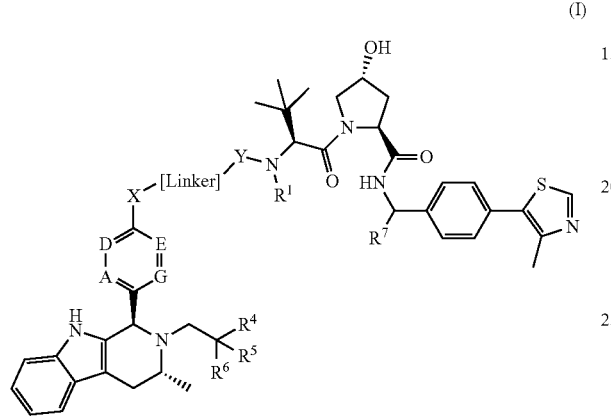

(I)

or a pharmaceutically acceptable salt or prodrug thereof, wherein:
$R^1$ is H or methyl;
A and G are independently $CR^2$ or N;
$R^2$ is independently selected from H, F, Cl, CN, methyl or methoxy;
D and E are independently $CR^3$ or N;
$R^3$ is independently selected from H, F, Cl, or methyl;
$R^4$ is H, methyl or F;
$R^5$ is H, methyl or F;
or $R^4$ and $R^5$ taken together with the carbon atom to which they are attached form a cyclopropyl ring or an oxetanyl ring;
$R^6$ is H, methyl, F, $CH_2F$, $CHF_2$, $CF_3$, CN, $CH_2CN$, $CH_2OMe$, $CH_2OH$, C(O)OH, C(O)OMe or $SO_2Me$;
$R^7$ is H, methyl, —$CH_2NHMe$, —$CH_2NMe_2$ or $CH_2NH_2$;
X represents —O—, —CH=CH—C(O)NH—, —NHC(O)—, —C(O)NH— or -pyrrolidinyl-NMeC(O)—;
Y represents a bond or —C(O)—;
Linker is an optionally substituted linking moiety comprising a branched or unbranched, cyclized or uncyclized, saturated or unsaturated chain of 4 to 20 carbon atoms in length, wherein 1 to 6 of the carbon atoms are optionally replaced with a heteroatom independently selected from O, N and S.

This specification also describes, in part, a pharmaceutical composition which comprises a compound of Formula (I), or a pharmaceutically acceptable salt or prodrug thereof, and at least one pharmaceutically acceptable excipient.

This specification also describes, in part, a compound of Formula (I), or a pharmaceutically acceptable salt or prodrug thereof, for use in therapy.

This specification also describes, in part, a compound of Formula (I), or a pharmaceutically acceptable salt thereof, for use in the treatment of cancer.

This specification also describes, in part, a method for treating cancer in a warm-blooded animal in need of such treatment, which comprises administering to the warm-blooded animal a therapeutically effective amount of a compound of Formula (I), or a pharmaceutically acceptable salt or prodrug thereof.

DESCRIPTION OF ILLUSTRATIVE EMBODIMENTS

Many embodiments of the invention are detailed throughout the specification and will be apparent to a reader skilled in the art. The invention is not to be interpreted as being limited to any particular embodiment(s) thereof.

In a first embodiment there is provided a compound of Formula (I):

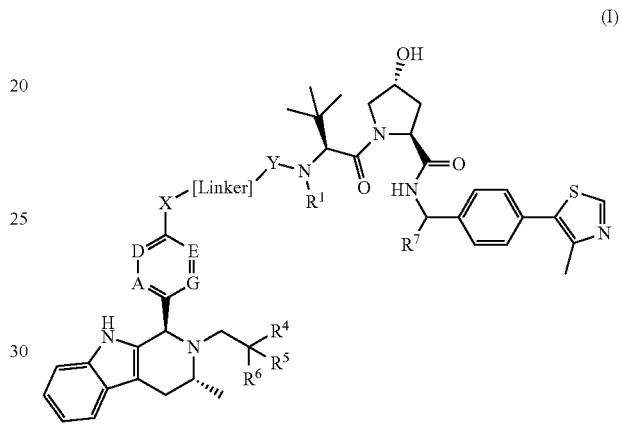

(I)

or a pharmaceutically acceptable salt or prodrug thereof, wherein:
$R^1$ is H or methyl;
A and G are independently $CR^2$ or N;
$R^2$ is independently selected from H, F, Cl, CN, methyl or methoxy;
D and E are independently $CR^3$ or N;
$R^3$ is independently selected from H, F, Cl, or methyl;
$R^4$ is H, methyl or F;
$R^5$ is H, methyl or F;
or $R^4$ and $R^5$ taken together with the carbon atom to which they are attached form a cyclopropyl ring or an oxetanyl ring;
$R^6$ is H, methyl, F, $CH_2F$, $CHF_2$, $CF_3$, CN, $CH_2CN$, $CH_2OMe$, $CH_2OH$, C(O)OH, C(O)OMe or $SO_2Me$;
$R^7$ is H, methyl, —$CH_2NHMe$, —$CH_2NMe_2$ or $CH_2NH_2$;
X represents —O—, —CH=CH—C(O)NH—, —NHC(O)—, —C(O)NH— or -pyrrolidinyl-NMeC(O)—;
Y represents a bond or —C(O)—;
Linker is an optionally substituted linking moiety comprising a branched or unbranched, cyclized or uncyclized, saturated or unsaturated chain of 4 to 20 carbon atoms in length, wherein 1 to 6 of the carbon atoms are optionally replaced with a heteroatom independently selected from O, N and S.

The Linker is 4 to 20 carbon atoms in length, wherein 1 to 6 of the carbon atoms are optionally replaced with a heteroatom independently selected from O, N and S. For example, 1 to 6 of the carbon atoms are optionally replaced with a heteroatom independently selected from O and N. When the Linker comprises a cyclized chain, i.e. the Linker contains a ring, the length of the Linker chain is calculated based on the shortest route around the ring. For example, if the Linker contains the group

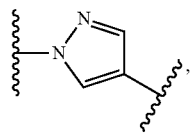 [SMILES: *c1cnn(*)c1]

this group contributes 3 atoms to the chain length as this is the shortest route around the ring.

In the context of the present specification, unless otherwise indicated, the term "alkyl" includes both linear and branched chain alkyl groups. The prefix $C_{p-q}$ in $C_{p-q}$ alkyl and other terms (where p and q are integers) indicates the range of carbon atoms that are present in the group, for example $C_{1-3}$ alkyl includes $C_1$ alkyl (methyl), $C_2$ alkyl (ethyl) and $C_3$ alkyl (propyl as n-propyl and isopropyl).

The term "$C_{3-14}$ alkoxy" is an alkyl chain of 3 to 14 carbon atoms which may be branched or unbranched and contains 1 to 6 intervening oxygen atoms in the alkyl chain, wherein the Linker, or the compound of Formula (I), does not contain an acetal or peroxide group, for example, there are at least two methylene groups between each oxygen atom.

The term "$C_{3-14}$ alkenyloxy" is an alkyl chain of 3 to 14 carbon atoms which may be branched or unbranched and contains 1 to 6 intervening oxygen atoms in the alkyl chain and one or more double bonds in the alkyl chain. For example, the alkenyloxy contains one double bond. The Linker, or the compound of Formula (I), does not contain an acetal or peroxide group, for example, there are at least two methylene groups between each oxygen atom.

The term "$C_{3-14}$ alkynyloxy" is an alkyl chain of 3 to 14 carbon atoms which may be branched or unbranched and contains 1 to 6 intervening oxygen atoms in the alkyl chain and one or more triple bonds in the alkyl chain. For example, the alkynyloxy contains two triple bonds. The Linker, or the compound of Formula (I), does not contain an acetal or peroxide group, for example, there are at least two methylene groups between each oxygen atom.

As used herein the term "branched" means that the total number of carbon atoms in the branch is no more than 4. An example of a branched $C_{3-14}$ alkoxy is —$C_2H_4$OCH(Me)CH(Me)O$C_2H_4$OCH$_2$— which has one carbon atom in each branch.

Aryl is a 6 membered aromatic ring containing no heteroatoms. Aryl includes phenyl. Aryl groups may be optionally substituted with one or more (for example, one, two or three) substituents selected from the group comprising F, Cl, $C_{1-2}$ alkyl, $C_{1-2}$ alkoxy, CN and CF$_3$.

Heterocycloalkyl is a 4 to 10 membered monocyclic or spirocyclic bicyclic saturated non-aromatic ring comprising one or more heteroatoms independently selected from N and O. For example, the heterocycloalkyl comprises one or more nitrogen heteroatoms. Heterocycloalkyl groups include azetidinyl, piperidinyl, piperazinyl, 3,9-diazaspiro[5.5]undecane-3-yl and 2,7-diazaspiro[3.5]nonan-2-yl. The heterocycloalkyl may be connected to the remainder of the Linker via a carbon atom and/or a heteroatom atom.

Heteroaryl is a 3 to 6 membered aromatic ring comprising one or more heteroatoms independently selected from N, O and S, for example, one or more heteroatoms independently selected from N and O. For example, heteroaryl comprises one or more nitrogen heteroatoms. Heteroaryl includes pyrazolyl and pyridinyl. Heteroaryl groups may be optionally substituted with one or more (for example, one, two or three) substituents selected from the group comprising F, Cl, $C_{1-2}$ alkyl, $C_{1-2}$ alkoxy, CN and CF$_3$. The heteroaryl may be connected to the remainder of the Linker via a carbon atom and/or a heteroatom.

For the further avoidance of doubt, the use of "∼∼" or "⊤" in formulae of this specification denotes the point of attachment between different groups.

Where the term "optionally" is used, it is intended that the subsequent feature may or may not occur. As such, use of the term "optionally" includes instances where the feature is present, and also instances where the feature is not present. For example, a group "optionally substituted by F" includes groups with and without an F substituent.

The term "substituted" means that one or more hydrogens (for example one or two hydrogens, or alternatively one hydrogen) on the designated group is replaced by the indicated substituent(s) (for example one or two substituents, or alternatively one substituent), provided that any atom(s) bearing a substituent maintains a permitted valency. Substituent combinations encompass only stable compounds and stable synthetic intermediates. "Stable" means that the relevant compound or intermediate is sufficiently robust to be isolated and have utility either as a synthetic intermediate or as an agent having potential therapeutic utility. If a group is not described as "substituted", or "optionally substituted", it is to be regarded as unsubstituted (i.e. that none of the hydrogens on the designated group have been replaced).

The term "pharmaceutically acceptable" is used to specify that an object (for example a salt, prodrug, dosage form or excipient) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich: Wiley-VCH/VHCA, 2002.

A suitable pharmaceutically acceptable salt of a compound of the Formula (I) is, for example, a salt formed within the human or animal body after administration of a compound of the Formula (I), to said human or animal body.

A further embodiment provides any of the embodiments defined herein (for example the embodiment of claim 1) with the proviso that one or more specific Examples (for instance one, two or three specific Examples) selected from the group consisting of Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 70, 71, 72, 73, 74, 77, 78, 79, 80, 82, 83, 84, 85, 86, 89, 90, 91, 92, 93, 94, 95, 96, 97, 98, 99, 100, 101, 102, 104, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 151, 152, 153, 154, 155, 156, 157, 158, 159, 161, 162, 164, 165, 166, 167 and 168 is individually disclaimed.

A further embodiment provides any of the embodiments defined herein (for example the embodiment of claim 1) with the proviso that one or more specific Examples (for instance one, two or three specific Examples) selected from the group consisting of Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67 and 68 is individually disclaimed.

Some values of variable groups in Formula (I) are as follows.

$R^1$ is H or methyl. In one embodiment, $R^1$ is H. In another embodiment, $R^1$ is methyl.

A and G are independently $CR^2$ or N. In one embodiment, A and G are both independently $CR^2$. In another embodiment, A is $CR^2$ and G is N.

$R^2$ is independently selected from H, F, Cl, CN, methyl or methyl. In one embodiment $R^2$ is H. In another embodiment, $R^2$ is F.

In one embodiment, A and G are both CH or both CF or A is CH or CF and G is N.

D and E are independently $CR^3$ or N. In one embodiment, D and E are both independently $CR^3$. In one embodiment, D and E are both N.

$R^3$ is independently selected from H, F, Cl or methyl. In one embodiment, $R^3$ is H.

In one embodiment, D and E are both CH or are both N.

In one embodiment, the moiety:

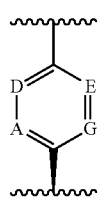

is selected from the group consisting of

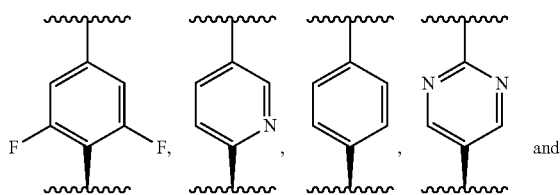

In one embodiment, the moiety:

is selected from the group consisting of

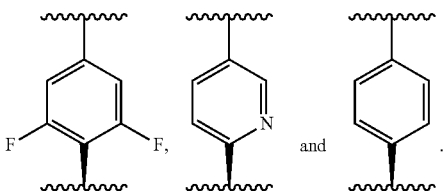

$R^4$ is H, methyl or F. In one embodiment $R^4$ is H. In another embodiment, $R^4$ is methyl. In another, embodiment $R^4$ is F.

$R^5$ is H, methyl or F. In one embodiment, $R^5$ is H. In another embodiment, $R^5$ is methyl. In another embodiment, $R^5$ is F.

In one embodiment, $R^4$ and $R^5$ taken together with the carbon atom to which they are attached form a cyclopropyl ring or an oxetane ring.

$R^6$ is H, methyl, F, $CH_2F$, $CHF_2$, $CF_3$, CN, $CH_2CN$, $CH_2OMe$, $CH_2OH$, $C(O)OH$, $C(O)OMe$ or $SO_2Me$. In one embodiment, $R^6$ is selected from H, methyl, F, $C(O)OH$ and $C(O)OMe$. In one embodiment, $R^6$ is H. In another embodiment, $R^6$ is methyl. In another embodiment, $R^6$ is F. In another embodiment, $R^6$ is $CH_2F$. In another embodiment, $R^6$ is $CHF_2$. In another embodiment, $R^6$ is $CF_3$. In another embodiment, $R^6$ is CN. In another embodiment, $R^6$ is $CH_2CN$. In another embodiment, $R^6$ is $CH_2OMe$. In another embodiment, $R^6$ is $CH_2OH$. In another embodiment, $R^6$ is $C(O)OH$. In another embodiment, $R^6$ is $C(O)OMe$. In another embodiment, $R^6$ is $SO_2Me$.

In one embodiment, $R^4$ is H, methyl or F, $R^5$ is H, methyl or F, or $R^4$ and $R^5$ taken together with the carbon to which they are attached form a cyclopropyl ring, and $R^6$ is H, methyl, F, $C(O)OH$ or $C(O)OMe$.

In one embodiment, $R^4$ is H or methyl, $R^5$ is methyl or F and $R^6$ is methyl, F, $C(O)OH$ or $C(O)OMe$.

In one embodiment, the group $—CH_2—C(R^4)(R^5)(R^6)$ is selected from the group consisting of:

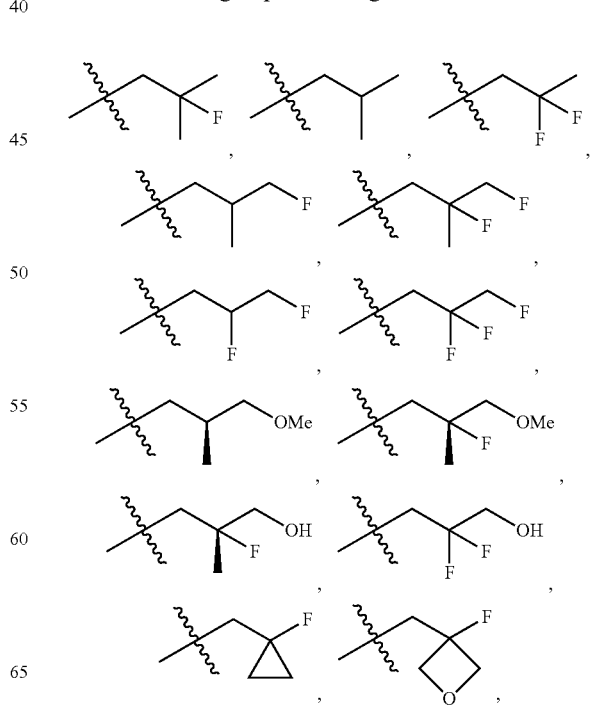

-continued

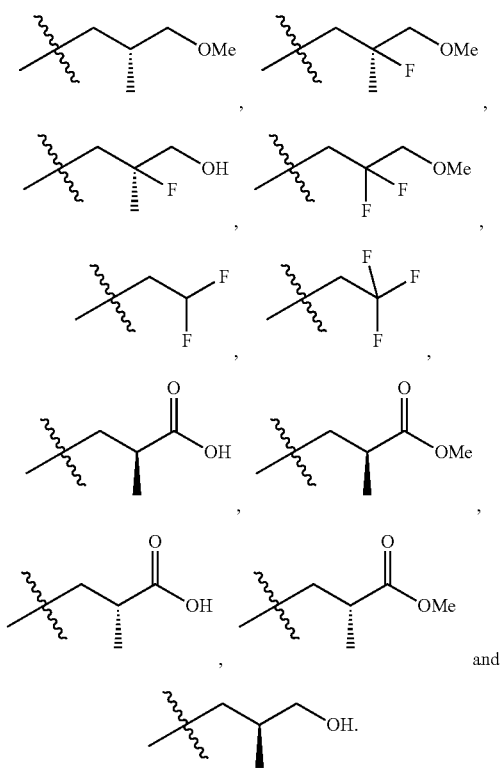

In one embodiment, the group —CH$_2$—C(R$^4$)(R$^5$)(R$^6$) is selected from the group consisting of:

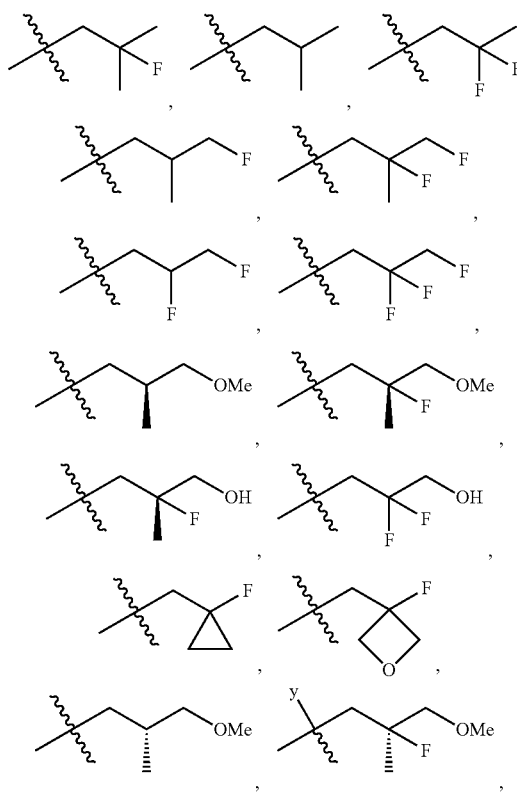

-continued

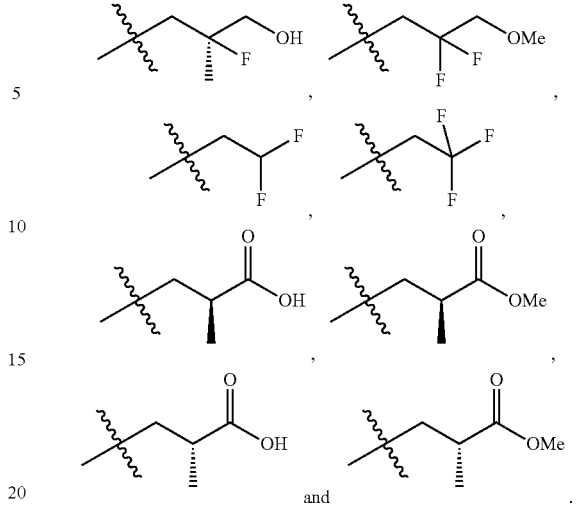

In one embodiment, the group —CH$_2$—C(R$^4$)(R$^5$)(R$^6$) is selected from the group consisting of:

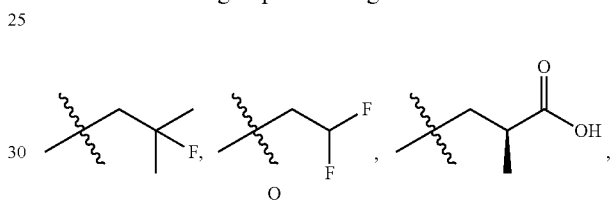

In one embodiment, the group —CH$_2$—C(R$^4$)(R$^5$)(R$^6$) is selected from the group consisting of:

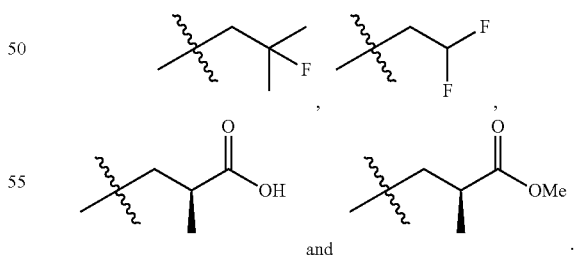

R$^7$ represents H, methyl, —CH$_2$NHMe, —CH$_2$NMe$_2$ or CH$_2$NH$_2$. In one embodiment, R$^7$ represents H, methyl, CH$_2$NH$_2$ or CH$_2$NMe$_2$. In one embodiment, R$^7$ represents H or methyl. In one embodiment, R$^7$ is H. In another embodiment, R$^7$ is methyl. In another embodiment, R$^7$ is CH$_2$NH$_2$. In one embodiment, R$^7$ is CH$_2$Me$_2$.

X represents —O—, —CH═CH—C(O)NH—, —NHC(O)—, —C(O)NH— or -pyrrolidinyl-NMeC(O)—. In one embodiment, X is —O—, —CH=CH—C(O)NH—, —NHC(O)— or —C(O)NH—. In one embodiment, X is —O—, —CH=CH—C(O)NH— or —NHC(O)—. In another embodiment, X is —O—. In another embodiment, X is —CH=CH—C(O)NH—. In another embodiment, X is —NHC(O)—. In another embodiment, X is —C(O)NH—. In another embodiment, X is -pyrrolidinyl-NMeC(O)—. In another embodiment, X is

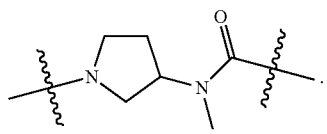 [SMILES: *C(=O)N(C)C1CCN(*)C1]

Y represents a bond or —C(O)—. In one embodiment, Y is a bond. In another embodiment, Y is —C(O)—.

The Linker is an optionally substituted linking moiety comprising a branched or unbranched, cyclized or uncyclized, saturated or unsaturated chain of 4 to 20 carbon atoms in length, wherein 1 to 6 of the carbon atoms are optionally replaced with a heteroatom independently selected from O, N and S.

In one embodiment, the Linker is an unbranched, uncyclized, saturated chain. In another embodiment, the Linker is a branched, uncyclized, saturated chain. In another embodiment, the Linker is an unbranched, uncyclized, unsaturated chain. In another embodiment, the Linker is an unbranched, cyclized, saturated chain.

In one embodiment, 1 to 6 of the carbon atoms of the Linker are replaced with a heteroatom independently selected from O and N. In another embodiment, 1 to 6 of the carbon atoms are replaced with O. When a carbon atom in a saturated chain or ring is replaced with a N atom, the N atom will be attached to a hydrogen atom or may be optionally substituted.

In one embodiment, the Linker is selected from the group comprising:

a) a $C_{4-14}$ alkyl chain;
b) a $C_{3-14}$ alkoxy chain;
c) a $C_{3-14}$ alkenyloxy chain;
d) a $C_{3-14}$ alkynyloxy chain;
e) $L^1$-Ar-$L^2$ or $L^1$-Het-$L^2$; wherein $L^1$ is a bond, $C_{1-6}$ alkyl, $C_{1-2}$ alkyl-C(O)— or $C_{1-4}$ alkoxy; Ar is a 6 membered optionally substituted aryl; Het is a 4 to 6 membered heterocycloalkyl or a 9 to 10 membered spirocyclic bicyclic heterocycloalkyl or a 3 to 6 membered optionally substituted heteroaryl; $L^2$ is a bond, $C_{1-4}$ alkyl, $C_{1-6}$ alkoxy or -Ph-, wherein a carbon atom in the $C_{1-4}$ alkyl is optionally replaced with an optionally substituted N;

optionally wherein a carbon atom in the chain of any one of groups a) to d) is replaced with an optionally substituted N; and optionally wherein a carbon atom in the chain of any one of groups a) to d) is substituted with one or more F groups, a cyclopropyl group or oxo, or two adjacent carbon atoms in the chain of any one of groups a) to d) are substituted so that taken together they form a cyclopropyl group.

In group e), aryl or heteroaryl is optionally substituted with one or more (for example, one, two or three) substituents selected from the group comprising F, Cl, $C_{1-2}$ alkyl, $C_{1-2}$ alkoxy, CN and $CF_3$.

In one embodiment, the Linker is a $C_{4-14}$ alkyl chain. In another embodiment, the Linker is a $C_{4-10}$ alkyl chain. In one embodiment, the Linker is $C_4$ alkyl. In another embodiment, the Linker is $C_6$ alkyl. In another embodiment, the Linker is $C_8$ alkyl. In one embodiment, the Linker is $C_9$ alkyl. In another embodiment, the Linker is $C_{10}$ alkyl.

In one embodiment, the Linker is an unbranched alkyl chain. In another embodiment, the Linker is an unbranched $C_4$-$C_{10}$ alkyl chain.

In one embodiment, the Linker is a $C_{3-14}$ alkoxy chain. In one embodiment, the Linker is a $C_{3-12}$ alkoxy chain.

Examples of the $C_{3-14}$ alkoxy chain include —$C_2H_4O$— $C_{3-5}$ alkyl-$OCH_2$—, —$(C_2H_4O)_{2-4}CH_2$—, —$C_{3-8}$ alkyl-$OCH_2$—, —$CH_2(OC_2H_4)_{2-5}OCH_2$—, —$C_2H_4C(F)_2C_2H_4OCH_2$, —$C_4H_8OC_3H_6OCH_2$—, —$C_4H_8OC_2H_4OCH_2$, —$C_6H_{12}OC(F)_2$—, —$C_3H_6OC_3H_6OCH_2$—, —$C_2H_4C(F)_2C_2H_4OC_2H_4OCH_2$—, —$C_6H_{12}OC(Me)_2$-, —$C_5H_{10}OC_2H_4OCH_2$—, —$C_3H_6OC_3H_6OCH_2$—, —$C_6H_{12}OC(cyclopropyl)$-, —$C_3H_6OC_4H_8OCH_2$—, —$C_5H_{10}OC_3H_6OCH_2$—, —$C_3H_6OC_3H_6OC(F)_2$—, —$C_3H_6OC_5H_{10}OCH_2$—, —$C_7H_{14}OC_2H_4$—, —$C_5H_{10}OC_4H_8$—, —$C_6H_{12}OC_3H_6$—, —$C_2H_4OC_7H_{14}$—, —$C_3H_6OC_5H_{12}$—, —$C_2H_4OCH(Me)CH(Me)OC_2H_4OCH_2$—, —$C_4H_8OC_5H_{10}$—, —$C_3H_6OC_4H_8OCH_2$—, —$C_4H_8OC_2H_4OC_2H_4OCH_2$—, —$C_3H_6OC_2H_4OC_2H_4OCH_2$—, —$C_4H_8OC_2H_4$—, —$C_4H_8OC_2H_4OC(F)_2$—, —$C_3H_6OCH_2C(F)_2CH_2OCH_2$—, —$C_5H_{10}OCH_2C(F)_2CH_2OCH_2$—, —$C_2H_4OCH_2$-cyclopropyl-$CH_2OCH_2$— and —$C_3H_6OC_3H_6OC(cyclopropyl)$-.

In one embodiment, the Linker is a $C_{3-14}$ alkenyloxy chain. In one embodiment, the Linker is a $C_{6-10}$ alkenyloxy. In one embodiment, the alkenyloxy chain contains one or two double bonds. In one embodiment, the alkenyloxy contains one double bond. In one embodiment, the alkenyloxy is —$C_2H_4CH=CHC_2H_4OCH_2$—. In one embodiment, the Linker is a $C_{3-14}$ alkynyloxy chain. In one embodiment, the Linker is a $C_{6-10}$ alkynyloxy chain. In one embodiment, the alkynyloxy chain contains one or two triple bonds. In one embodiment, the alkynyloxy chain contains two triple bonds. In one embodiment, the alkynyloxy chain is —$CH_2C\equiv C$—$C\equiv C$—$CH_2OCH_2$—.

In one embodiment, a carbon atom in the chain of any one of groups a) to d) above is replaced with an optionally substituted N. For example, one or two carbon atoms in the chain of any one of groups a) to d) is replaced with an optionally substituted N. When a carbon atom in is replaced with a N atom, the N atom may be attached to a hydrogen atom or may be optionally substituted. The N may be optionally substituted with methyl or —C(O)OCH$_2$Ph. In one embodiment, a carbon atom in the chain of a $C_{3-14}$ alkoxy chain is replaced with an optionally substituted N. In one embodiment, a carbon atom in the chain of a $C_3$-$C_{14}$ alkoxy chain is replaced with an unsubstituted N, i.e. N(H). In one embodiment, a carbon atom in the chain of a $C_{8-10}$ alkoxy chain is replaced with an optionally substituted N. In one embodiment, the N is substituted with methyl or —C(O) OCH$_2$Ph. In one embodiment, the N is substituted with methyl. In another embodiment, the N is substituted with C(O)OCH$_2$Ph. In one embodiment, a carbon atom in the chain of a $C_{4-14}$ alkyl is replaced with an optionally substituted N. In one embodiment, a carbon atom in the chain of a $C_{4-14}$ alkyl chain is replaced with an unsubstituted N, i.e. N(H). In one embodiment, the N is substituted with methyl.

Examples of a $C_{3-14}$ alkoxy chain where a carbon atom in the chain is replaced with an optionally substituted N include —$C_2H_4N(H)C_5H_{10}OCH_2$—, —$C_2H_4N(Me)C_5H_{10}OCH_2$—, —$C_2H_4N(C(O)OCH_2Ph)C_5H_{10}OCH_2$—, —$C_2H_4N(Me)C(O)C_4H_8OCH_2$— and —$C_2H_4N(H)C(O)C_4H_8OCH_2$—.

Examples of a $C_{4-14}$ alkyl chain where a carbon atom in the chain is replaced with an optionally substituted N include —$C_8H_{16}N(H)CH_2$—, —$C_4H_8N(H)C_5H_{10}$—, —$C_2H_4C(F)_2C_2H_4N(H)CH_2$—, —$C_6H_{12}N(H)C_3H_6$—, —$C_2H_4N(Me)C_2H_4N(Me)C_4H_8$—, —$C_5H_{10}N(H)CH_2$— and —$C_5H_{10}N(Me)CH_2$.

In one embodiment, the Linker represents $L^1$-Ar-$L^2$ or $L^1$-Het-$L^2$; wherein $L^1$ is a bond, $C_{1-6}$ alkyl, $C_{1-2}$ alkyl(O) or $C_{1-4}$ alkoxy; Ar is a 6 membered optionally substituted aryl; Het is a 4 to 6 membered heterocycloalkyl or a 9 to 10 membered spirocyclic bicyclic heterocycloalkyl or a 3 to 6 membered optionally substituted heteroaryl; $L^2$ is a bond, $C_{1-3}$ alkyl, $C_{1-6}$ alkoxy or Ph.

The aryl and heteroaryl groups are optionally substituted with one or more (for example, one, two or three) substituents selected from the group comprising F, Cl, $C_{1-2}$ alkyl, $C_{1-2}$ alkoxy, CN and $CF_3$.

In one embodiment, $L^1$ is a bond, $C_{1-5}$ alkyl, —$CH_2C(O)$— or $C_{2-4}$ alkoxy. In one embodiment, $L^1$ is a bond, $C_{1-5}$ alkyl, —$C_2H_4OC_2H_4O$—, —$C_2H_4OC_2H_4$—, —$C_2H_4O$— or —$CH_2C(O)$—. In one embodiment, $L^1$ is a bond. In one embodiment, $L^1$ is $C_{1-6}$ alkyl, for example $C_{1-5}$ alkyl. In one embodiment, $L^1$ is $C_{1-2}$ alkyl(O), for example, —$CH_2C(O)$—. In one embodiment, $L^1$ is $C_{1-4}$ alkoxy, for example $C_{2-4}$ alkoxy.

In one embodiment, Het is a nitrogen containing ring.

In one embodiment, Het is selected from the group consisting of:

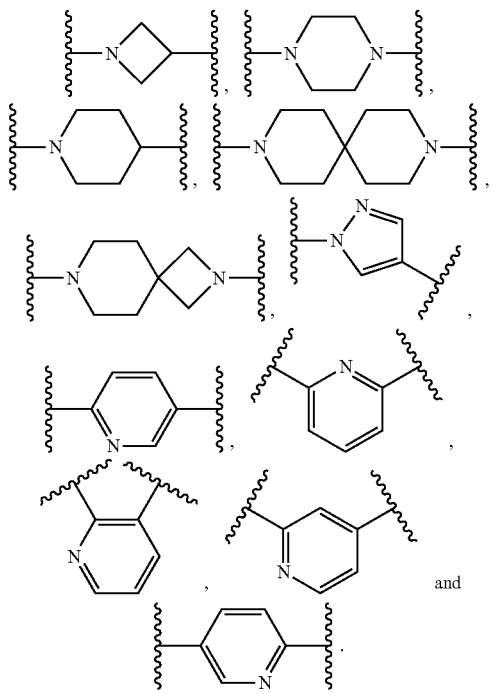

In one embodiment, Het is selected from the group consisting of:

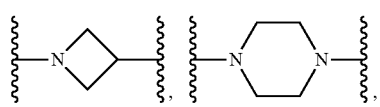

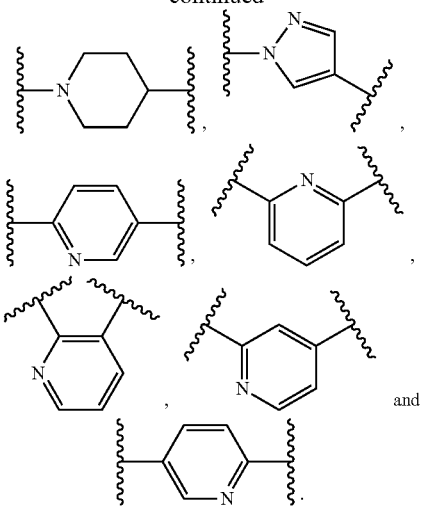

In one embodiment, Ar is selected from

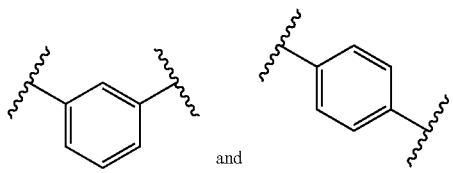

In one embodiment, $L^2$ represents a bond, $C_{1-4}$ alkyl, —$OCH_2$—, —$OC_2H_4OCH_2$—, —$OC_3H_6$—, —$CH_2OCH_2$—, —$C_2H_4OCH_2$—, —$C_3H_6OCH_2$—, —$C_5H_{10}OCH_2$— or -Ph-, wherein a carbon atom in the $C_{1-4}$ alkyl is optionally replaced with an unsubstituted N, i.e. N(H).

In one embodiment, $L^2$ represents a bond. In another embodiment, $L^2$ represents $C_{1-4}$ alkyl. In another embodiment, $L^2$ represents —$CH_2N(H)CH_2$—. In another embodiment, $L^2$ represents —$N(H)C_3H_6$—. In another embodiment, $L^2$ represents —$OCH_2$—. In another embodiment, $L^2$ represents —$OC_2H_4OCH_2$—. In another embodiment, $L^2$ represents —$OC_3H_6$—. In another embodiment, $L^2$ represents —$CH_2OCH_2$—. In another embodiment, $L^2$ represents —$C_2H_4OCH_2$—. In another embodiment, $L^2$ represents —$C_3H_6OCH_2$—. In another embodiment, $L^2$ represents —$C_5H_{10}OCH_2$—. In another embodiment, $L^2$ represents -Ph-.

In one embodiment, the Linker is selected from the group comprising:

a) —$C_{4-10}$alkyl-, wherein one or two —$CH_2$— units are optionally independently replaced with —NH—, —NMe- or —$CF_2$—, or wherein two adjacent —$CH_2$— units are optionally replaced with —N(H)C(O)— or —N(Me)C(O)—;

b) —$C_{2-5}$alkyl-O—$C_{2-5}$alkyl-O—$CH_2$, —$C_{2-7}$alkyl-O—$C_{1-7}$alkyl, —$(C_2H_4O)_{2-4}CH_2$— or —$C_{1-3}$alkyl$(OC_2H_4)OCH_2$—, wherein one or two —$CH_2$— units are optionally independently replaced with a unit selected from —$CF_2$—, —CHMe-, —$CMe_2$-, —C(cyclopropyl)-, —NH—, —NMe-, —N(C(O)OCH$_2$Ph), or wherein two adjacent —$CH_2$— units are optionally replaced with —N(H)C(O)—, —N(Me)C(O)— or a cyclopropyl;

c) —C₂H₄CH=CHC₂H₄OCH₂—;

d) —CH₂C≡C—C≡C—CH₂OCH₂—;

e) L¹-Ar-L² or L¹-Het-L²;

wherein L¹ represents a bond, $C_{1-5}$alkyl, —(C₂H₄O)$_{1-2}$—, —C₂H₄OC₂H₄— or —CH₂C(O)—; Ar represents phenyl; Het represents a group selected from:

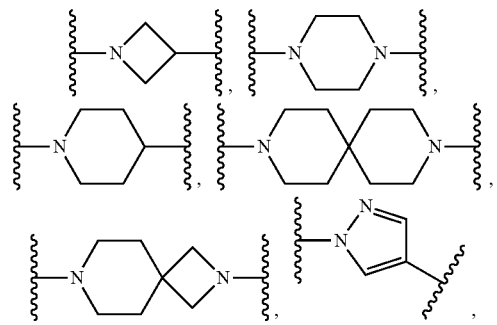

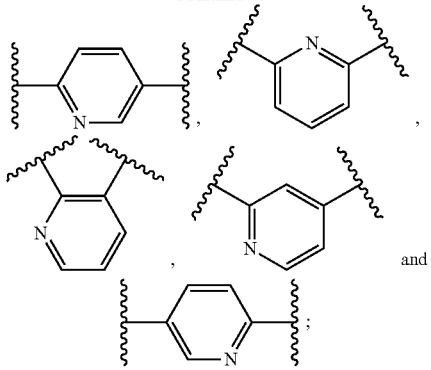

and L² represents a bond, —$C_{1-4}$ alkyl-, —$C_{1-5}$alkyl-O—CH₂—, —O—$C_{1-3}$alkyl-, —OC₂H₄OCH₂— or phenyl, wherein one —CH₂— unit in the —$C_{1-4}$ alkyl- is optionally replaced with NH.

In one embodiment, the group —X-[Linker]-Y— is selected from the group consisting of:

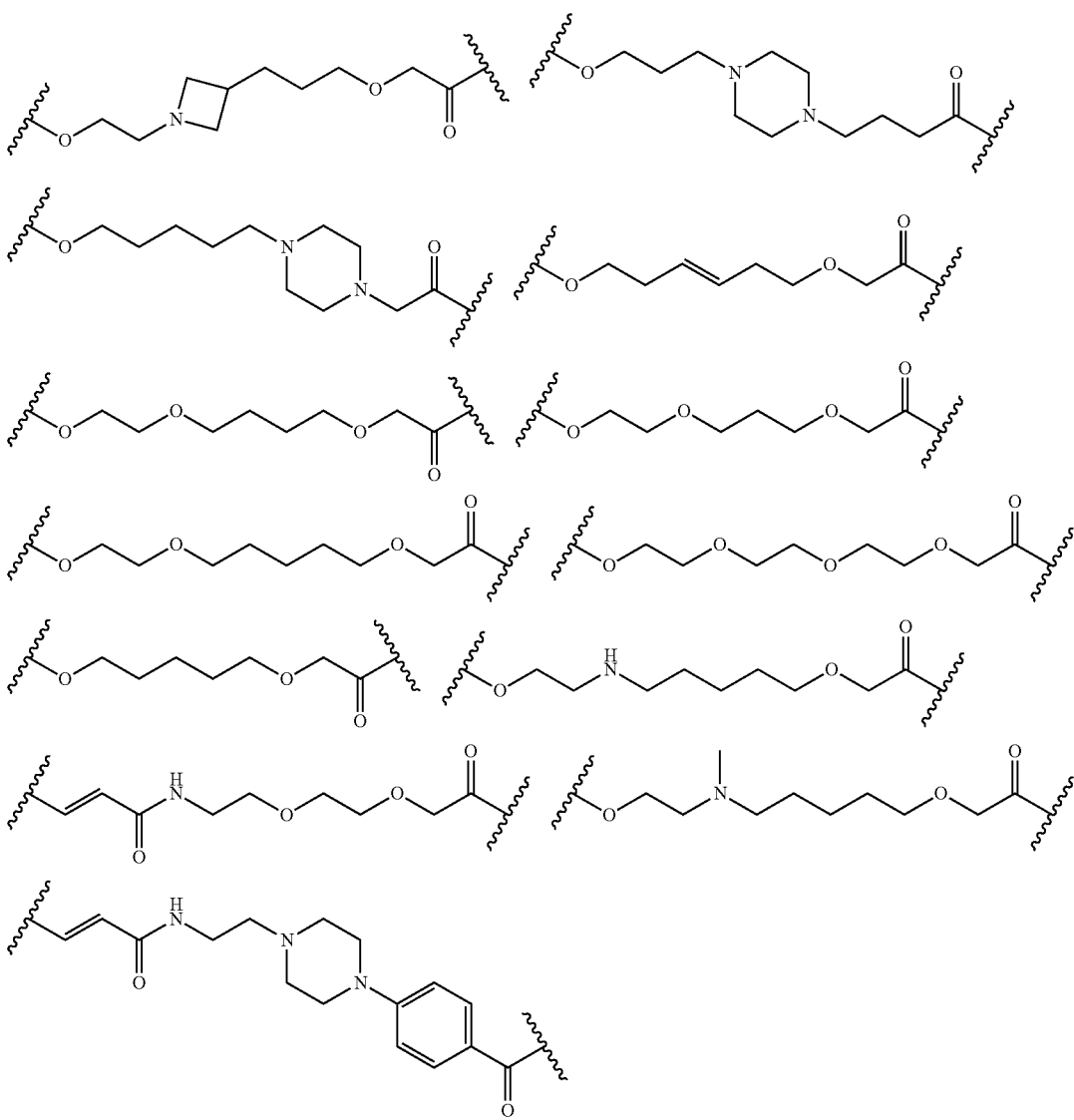

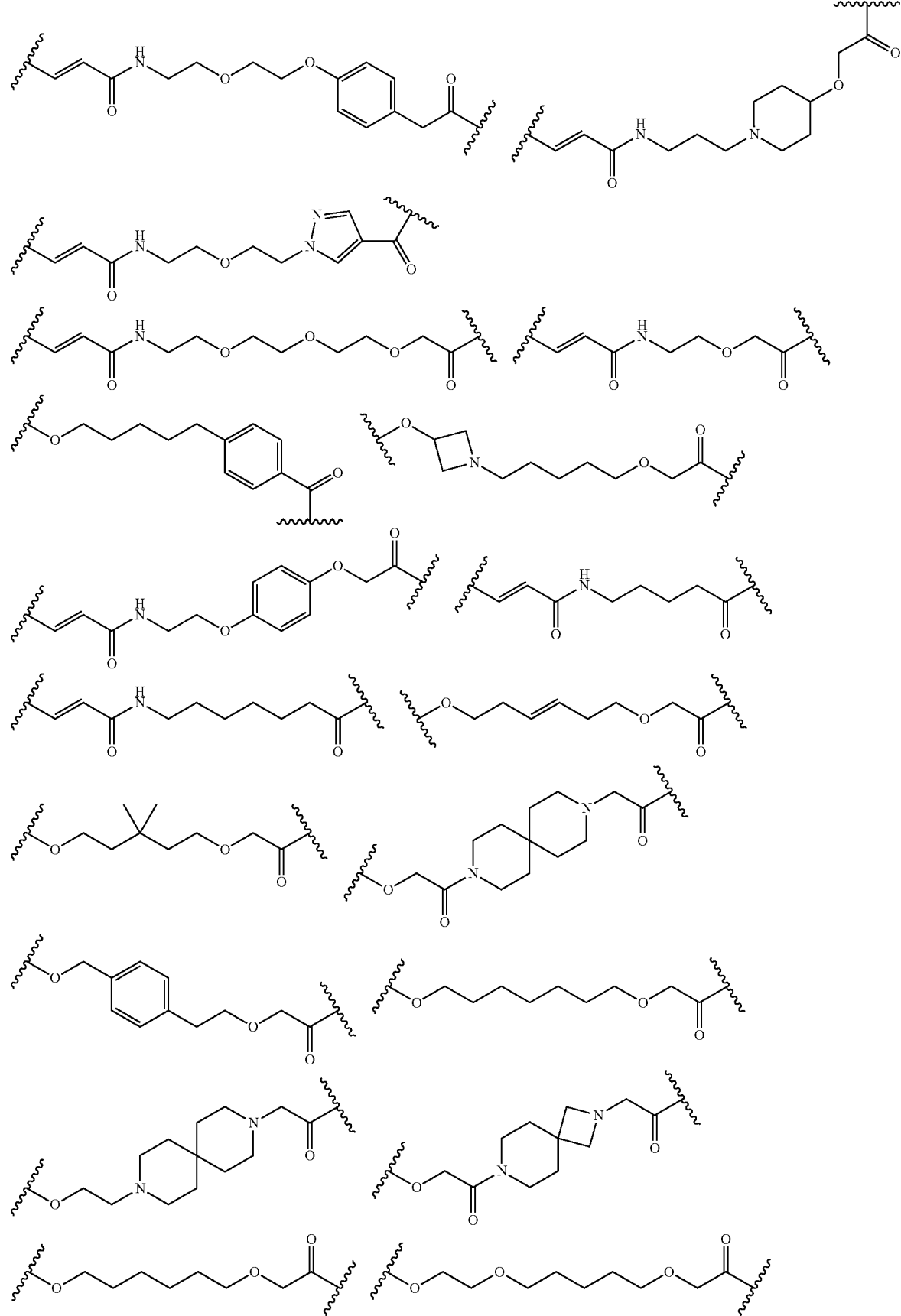

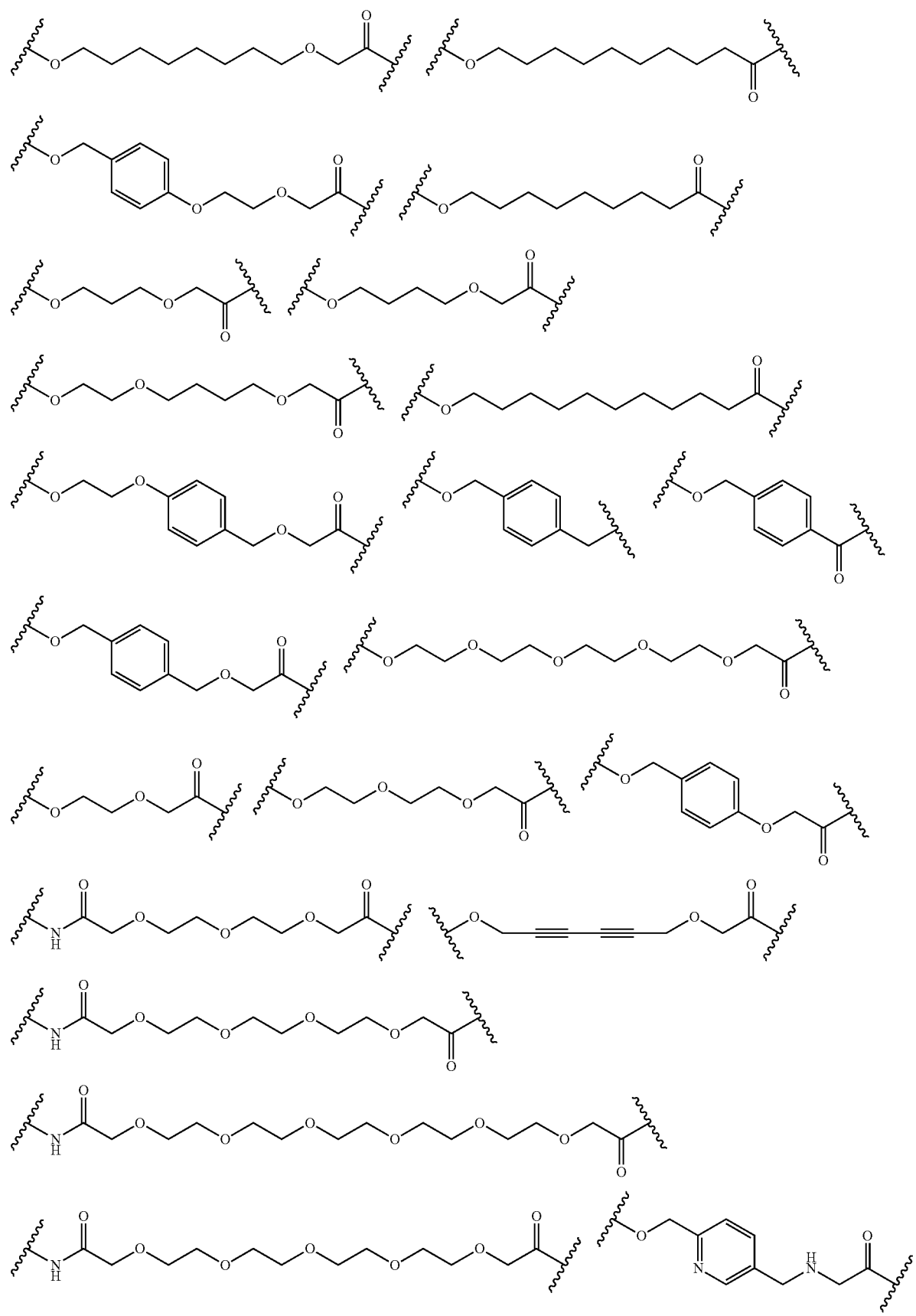

-continued
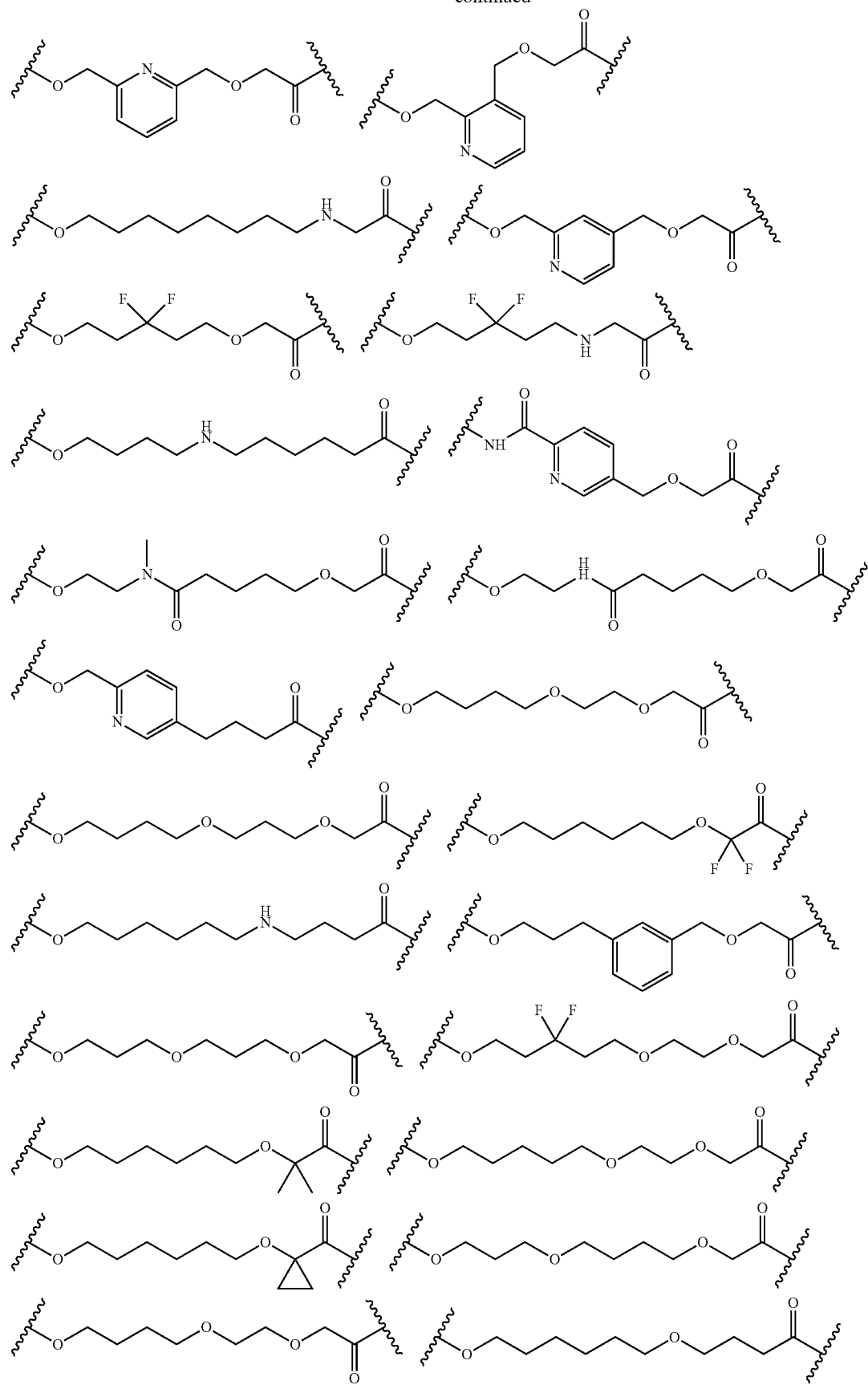

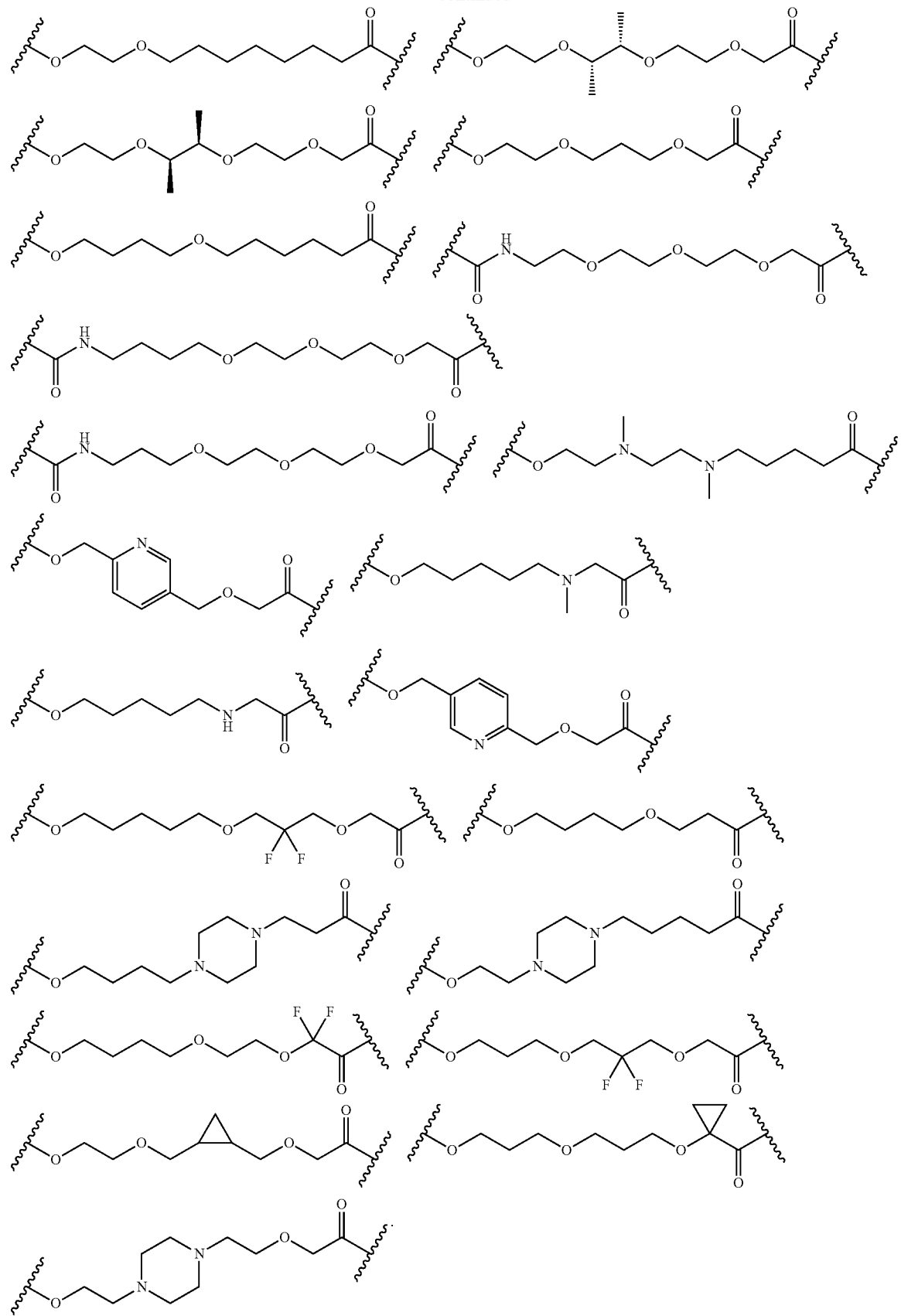

In one embodiment, the Linker is selected from the group comprising:

a) a $C_{4-14}$ alkyl chain;
b) a $C_{3-14}$ alkoxy chain;
c) a $C_{3-14}$ alkenyloxy chain;
d) a $C_{3-14}$ alkynyloxy chain;
e) $L^1$-Ar-$L^2$ or $L^1$-Het-$L^2$; wherein $L^1$ is a bond, $C_{1-6}$ alkyl, $C_{1-2}$ alkyl-C(O)— or $C_{1-4}$ alkoxy; Ar is a 6 membered optionally substituted aryl; Het is a 4 to 6 membered heterocycloalkyl or a 9 to 10 membered spirocyclic bicyclic heterocycloalkyl or a 3 to 6 membered optionally substituted heteroaryl; $L^2$ is a bond $C_{1-3}$ alkyl, $C_{1-6}$ alkoxy or -Ph-;

optionally wherein a carbon atom in the chain of any one of groups a) to d) is replaced with an optionally substituted N.

In group e), the aryl and heteroaryl groups are optionally substituted with one or more (for example, one, two or three) substituents selected from the group comprising F, Cl, $C_{1-2}$ alkyl, $C_{1-2}$ alkoxy, CN and $CF_3$.

In one embodiment, the Linker is a $C_{4-14}$ alkyl chain. In another embodiment, the Linker is a $C_{4-10}$ alkyl chain. In one embodiment, the Linker is $C_4$ alkyl. In another embodiment, the Linker is $C_6$ alkyl. In another embodiment, the Linker is $C_8$ alkyl. In one embodiment, the Linker is $C_9$ alkyl. In another embodiment, the Linker is $C_{10}$ alkyl.

In one embodiment, the Linker is an unbranched alkyl chain. In another embodiment, the Linker is an unbranched $C_4$-$C_{10}$ alkyl chain.

In one embodiment, the Linker is a $C_{3-14}$ alkoxy chain. In one embodiment, the Linker is a $C_{3-12}$ alkoxy chain. Examples of the $C_{3-14}$ alkoxy chain include —$C_2H_4O$—$C_{3-5}$ alkyl-$OCH_2$—, —$(C_2H_4O)_{1-4}CH_2$—, —$C_{3-8}$ alkyl-$OCH_2$— and —$CH_2(OC_2H_4)_{2-5}OCH_2$—.

In one embodiment, the Linker is a $C_{3-14}$ alkenyloxy chain. In one embodiment, the Linker is a $C_{6-10}$ alkenyloxy. In one embodiment, the alkenyloxy chain contains one or two double bonds. In one embodiment, the alkenyloxy contains one double bond. In one embodiment, the alkenyloxy is —$C_2H_4CH=CHC_2H_4OCH_2$—.

In one embodiment, the Linker is a $C_{3-14}$ alkynyloxy chain. In one embodiment, the Linker is a $C_{6-10}$ alkynyloxy chain. In one embodiment, the alkynyloxy chain contains one or two triple bonds. In one embodiment, the alkynyloxy chain contains two triple bonds. In one embodiment, the alkynyloxy chain is —$CH_2C\equiv C$—$C\equiv C$—$CH_2OCH_2$—.

In one embodiment, a carbon atom in the chain of any one of groups a) to d) above is replaced with an optionally substituted N. When a carbon atom in is replaced with a N atom, the N atom may be attached to a hydrogen atom or may be optionally substituted. The N may be optionally substituted with methyl or —$C(O)OCH_2Ph$. In one embodiment, a carbon atom in the chain of a $C_{3-14}$ alkoxy chain is replaced with an optionally substituted N. In one embodiment, a carbon atom in the chain of a $C_3$-$C_{14}$ alkoxy chain is replaced with an unsubstituted N, i.e. N(H). In one embodiment, a carbon atom in the chain of a $C_{8-10}$ alkoxy chain is replaced with an optionally substituted N. In one embodiment, the N is substituted with methyl or —$C(O)OCH_2Ph$. In one embodiment, the N is substituted with methyl. In another embodiment, the N is substituted with $C(O)OCH_2Ph$.

Examples of a $C_{3-14}$ alkoxy chain where a carbon atom in the chain is replaced with an optionally substituted N include —$C_2H_4N(H)C_5H_{10}OCH_2$—, —$C_2H_4N(Me)$ $C_5H_{10}OCH_2$— and —$C_2H_4N(C(O)OCH_2Ph)$ $C_5H_{10}OCH_2$—.

In one embodiment, the Linker represents $L^1$-Ar-$L^2$ or $L^1$-Het-$L^2$; wherein $L^1$ is a bond, $C_{1-6}$ alkyl, $C_{1-2}$ alkyl(O) or $C_{1-4}$ alkoxy; Ar is a 6 membered optionally substituted aryl; Het is a 4 to 6 membered heterocycloalkyl or a 9 to 10 membered spirocyclic bicyclic heterocycloalkyl or a 3 to 6 membered optionally substituted heteroaryl; $L^2$ is a bond, $C_{1-3}$ alkyl, $C_{1-6}$ alkoxy or Ph.

The Ar and heteroaryl groups are optionally substituted with one or more (for example, one, two or three) substituents selected from the group comprising F, Cl, $C_{1-2}$ alkyl, $C_{1-2}$ alkoxy, CN and $CF_3$.

In one embodiment, $L^1$ is a bond, $C_{1-5}$ alkyl, —$CH_2C$ (O)— or $C_{2-4}$ alkoxy. In one embodiment, $L^1$ is a bond, $C_{1-5}$ alkyl, —$C_2H_4OC_2H_4O$—, —$C_2H_4OC_2H_4$—, —$C_2H_4O$— or —$CH_2C(O)$—. In one embodiment, $L^1$ is a bond. In one embodiment, $L^1$ is $C_{1-6}$ alkyl, for example $C_{1-5}$ alkyl. In one embodiment, $L^1$ is $C_{1-2}$ alkyl(O), for example, —$CH_2C$ (O)—. In one embodiment, $L^1$ is $C_{1-4}$ alkoxy, for example $C_{2-4}$ alkoxy.

In one embodiment, Het is a nitrogen containing ring.

In one embodiment, Het is selected from the group consisting of:

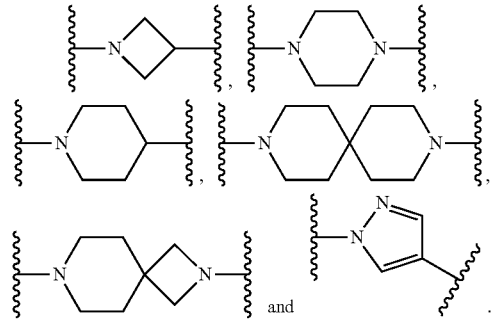

In one embodiment, $L^2$ represents a bond, $C_{1-3}$ alkyl, —$OCH_2$—, —$OC_2H_4OCH_2$—, —$CH_2OCH_2$—, —$C_2H_4OCH_2$—, —$C_3H_6OCH_2$—, —$C_5H_{10}OCH_2$— or -Ph-.

In one embodiment, $L^2$ represents a bond. In another embodiment, $L^2$ represents $C_{1-3}$ alkyl. In another embodiment, $L^2$ represents —$OCH_2$—. In another embodiment, $L^2$ represents —$OC_2H_4OCH_2$—. In another embodiment, $L^2$ represents —$CH_2OCH_2$—. In another embodiment, $L^2$ represents —$C_2H_4OCH_2$—. In another embodiment, $L^2$ represents —$C_3H_6OCH_2$—. In another embodiment, $L^2$ represents —$C_5H_{10}OCH_2$—. In another embodiment, $L^2$ represents -Ph-.

In one embodiment, the group —X-[Linker]-Y— is selected from the group consisting of:

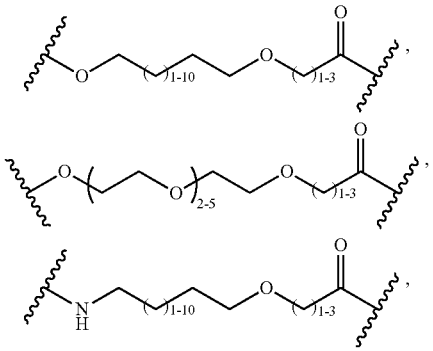

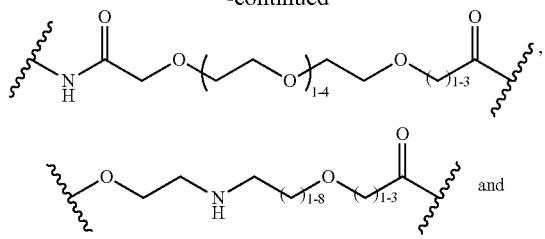
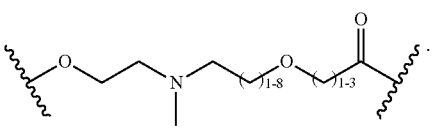
In one embodiment, the group —X-[Linker]-Y— is selected from the group consisting of:
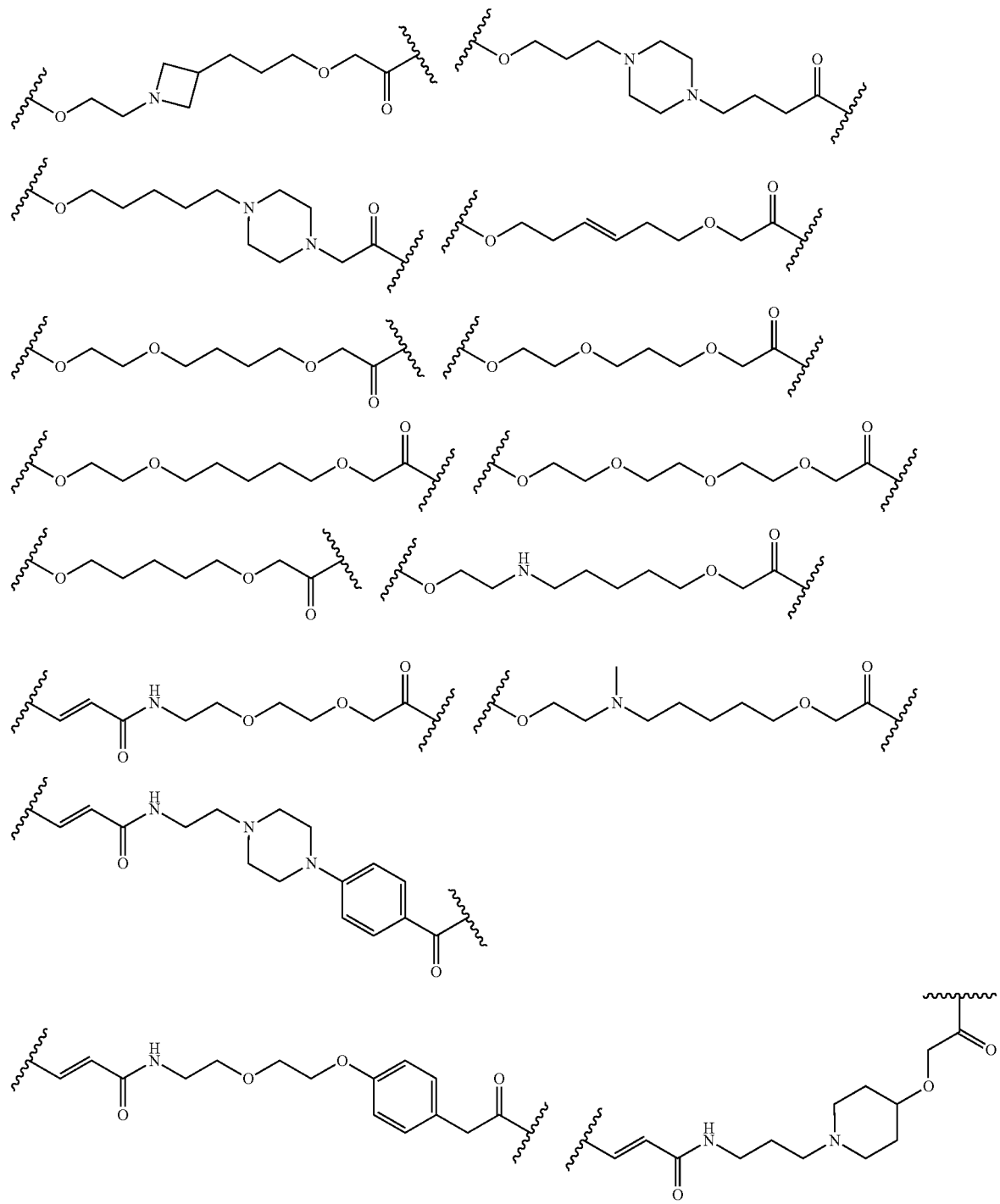

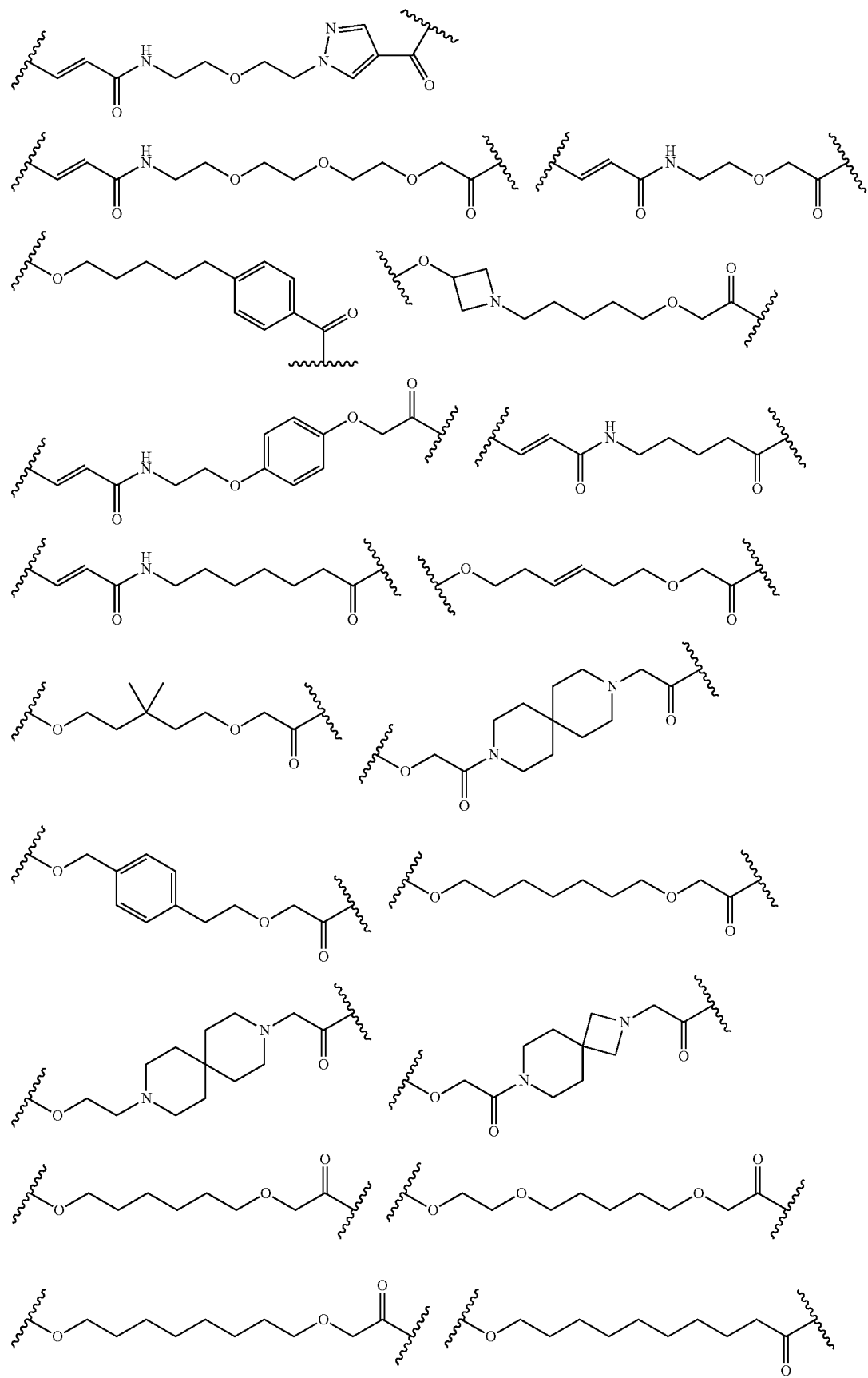

-continued

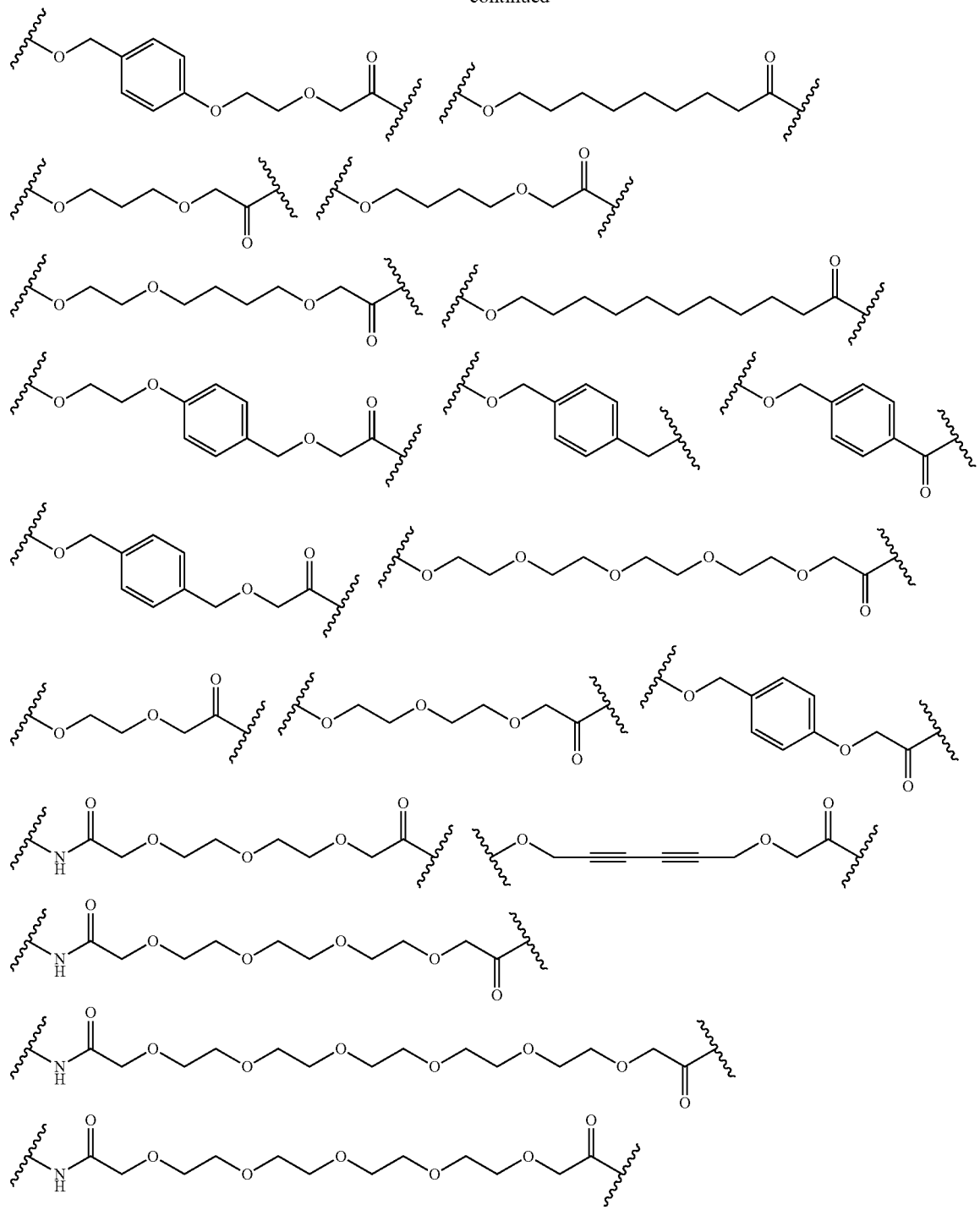

In one embodiment, there is provided a compound of Formula (I), or a pharmaceutically acceptable salt or prodrug thereof, wherein:

$R^1$ represents H or methyl;

A and G either both independently represent $CR^2$ or A represents $CR^2$ and G represents N;

$R^2$ independently represents H or F;

D and E either both independently represent $CR^3$ or both represent N;

$R^4$ represents H or methyl or F;

$R^5$ represents H, methyl or F;

or $R^4$ and $R^5$ taken together with the carbon to which they are attached form a cyclopropyl ring;

$R^6$ represents H, methyl, F, C(O)OH or C(O)OMe;

$R^7$ represents H, methyl, $CH_2NH_2$ or $CH_2NMe_2$;

X represents —O—, —CH=CH—C(O)NH—, —NHC(O)— or —C(O)NH—;

Y represents a bond or —C(O)—;

The Linker is an optionally substituted linking moiety comprising a branched or unbranched, cyclized or uncyclized, saturated or unsaturated chain of 4 to 20 carbon atoms in length, wherein 1 to 6 of the carbon atoms are optionally replaced with a heteroatom independently selected from O and N, wherein the branch contains no more than 4 carbon atoms.

In one embodiment, there is provided a compound of Formula (I), or a pharmaceutically acceptable salt or prodrug thereof, wherein:

$R^1$ represents H or methyl;

A and G either both independently represent $CR^2$ or A represents $CR^2$ and G represents N;

$R^2$ independently represents H or F;

D and E either both independently represent $CR^3$ or both represent N;

$R^3$ represents H;

$R^4$ represents H, methyl or F;

$R^5$ represents H, methyl or F;

or $R^4$ and $R^5$ taken together with the carbon to which they are attached form a cyclopropyl ring;

$R^6$ represents H, methyl, F, C(O)OH or C(O)OMe;

$R^7$ represents H, methyl, $CH_2NH_2$ or $CH_2NMe_2$;

X represents —O—, —CH=CH—C(O)NH—, —NHC(O)— or —C(O)NH—;

Y represents a bond or —C(O)—;

The Linker represents:
a) —$C_{4-10}$alkyl-, wherein one or two —$CH_2$— units are optionally independently replaced with —NH—, —NMe- or —$CF_2$—, or wherein two adjacent —$CH_2$— units are optionally replaced with —N(H)C(O)— or —N(Me)C(O)—;
b) —$C_{2-5}$alkyl-O—$C_{2-5}$alkyl-O—$CH_2$, —$C_{2-7}$alkyl-O—$C_{1-7}$alkyl, —($C_2H_4O)_{2-4}CH_2$— or —$C_{1-3}$alkyl($OC_2H_4$)$OCH_2$—, wherein one or two —$CH_2$— units are optionally independently replaced with a unit selected from —$CF_2$—, —CHMe-, —$CMe_2$-, —C(cyclopropyl)-, —NH—, —NMe-, —N(C(O)$OCH_2$Ph), or wherein two adjacent —$CH_2$— units are optionally replaced with —N(H)C(O)—, —N(Me)C(O)— or a cyclopropyl;
c) —$C_2H_4$CH=CH$C_2H_4OCH_2$—;
d) —$CH_2C≡C$—C≡C—$CH_2OCH_2$—; or
e) $L^1$-Ar-$L^2$ or $L^1$-Het-$L^2$; wherein $L^1$ represents a bond, $C_{1-5}$alkyl, —($C_2H_4O)_{1-2}$—, —$C_2H_4OC_2H_4$— or —$CH_2C(O)$—; Ar represents phenyl; Het represents a group selected from:

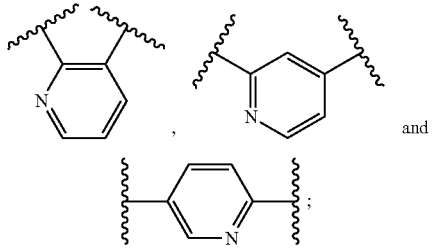

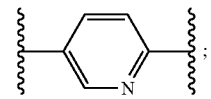

and $L^2$ represents a bond, —$C_{1-4}$ alkyl-, —$C_{1-5}$alkyl-O—$CH_2$—, —O—$C_{1-3}$alkyl-, —$OC_2H_4OCH_2$— or phenyl, wherein one —$CH_2$— unit in the —$C_{1-4}$ alkyl- is optionally replaced with NH.

In one embodiment, there is provided a compound of Formula (I), or a pharmaceutically acceptable salt or prodrug thereof, wherein:

$R^1$ represents H or methyl;

the moiety:

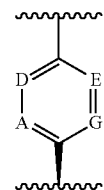

is selected from the group consisting of

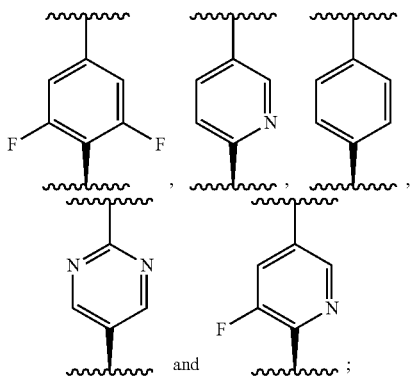

the group —$CH_2$—$C(R^4)(R^5)(R^6)$ is selected from the group consisting of:

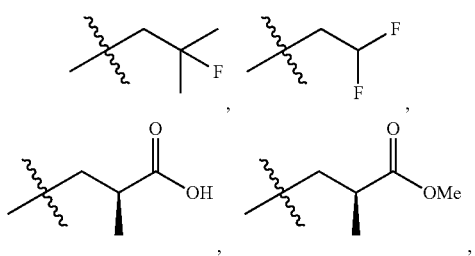

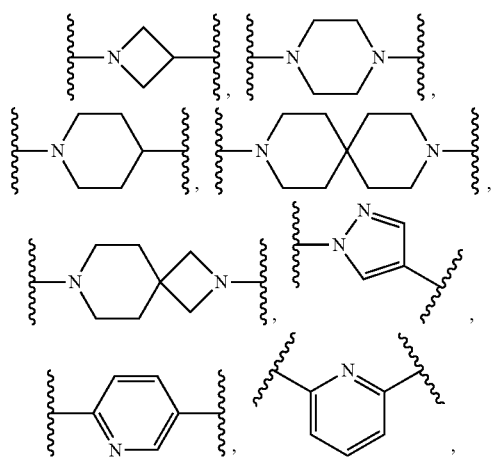

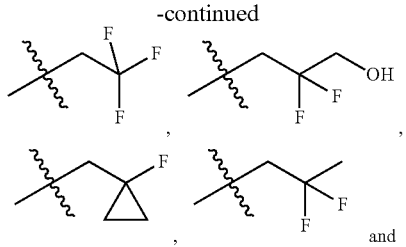
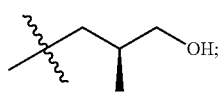
$R^7$ represents H, methyl, $CH_2NH_2$ or $CH_2NMe_2$; and
the group —X-[Linker]-Y— is selected from the group consisting of:
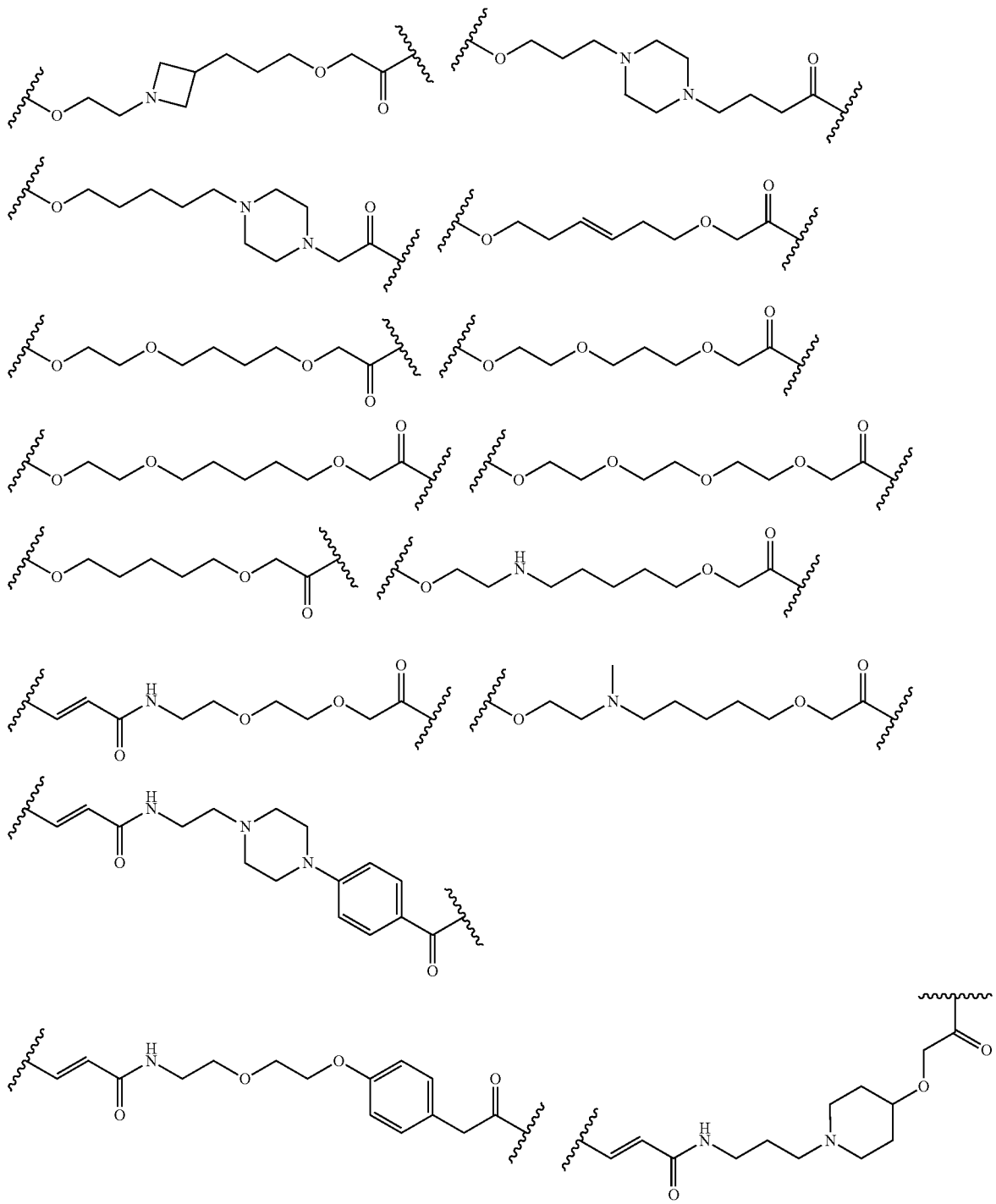

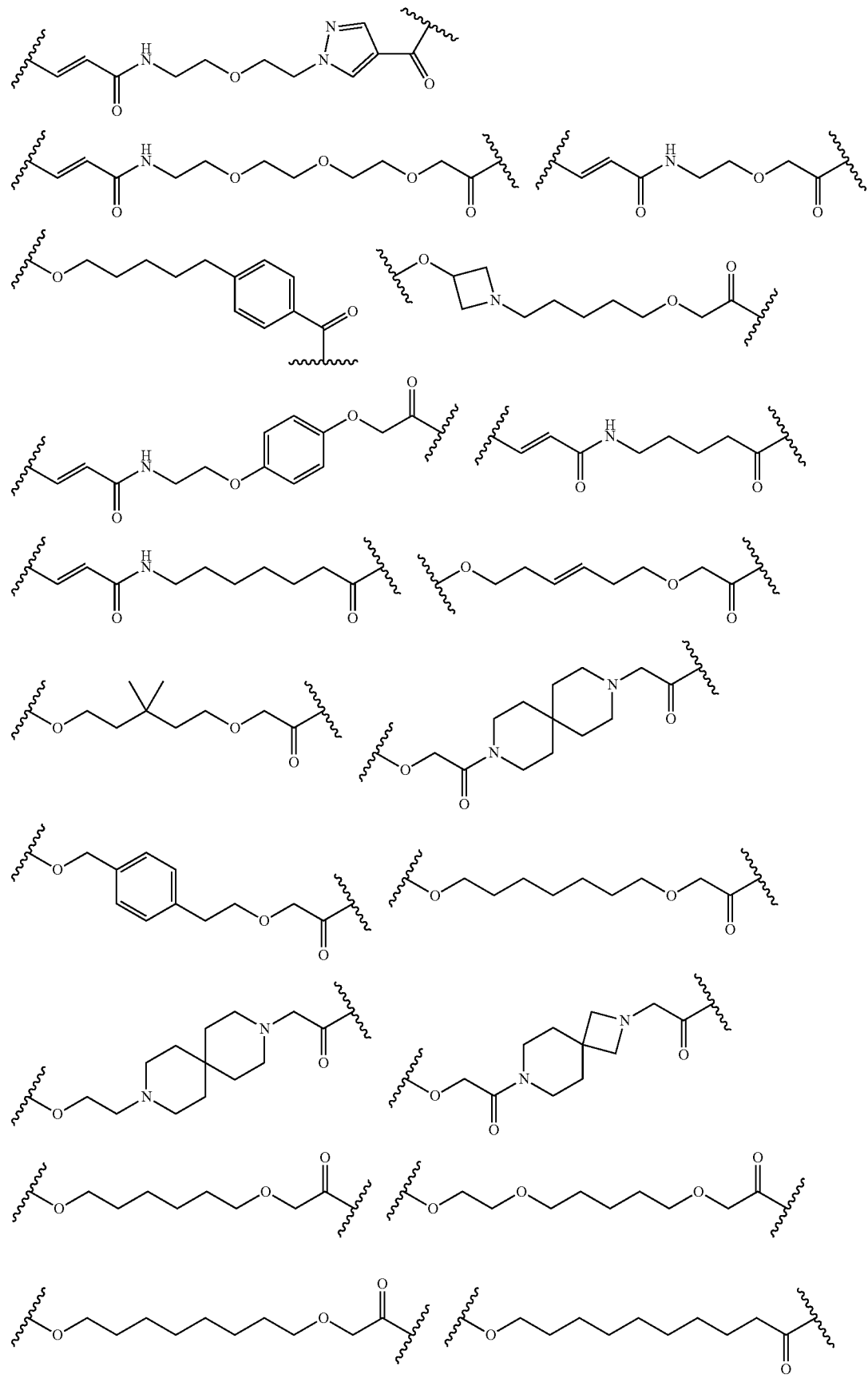

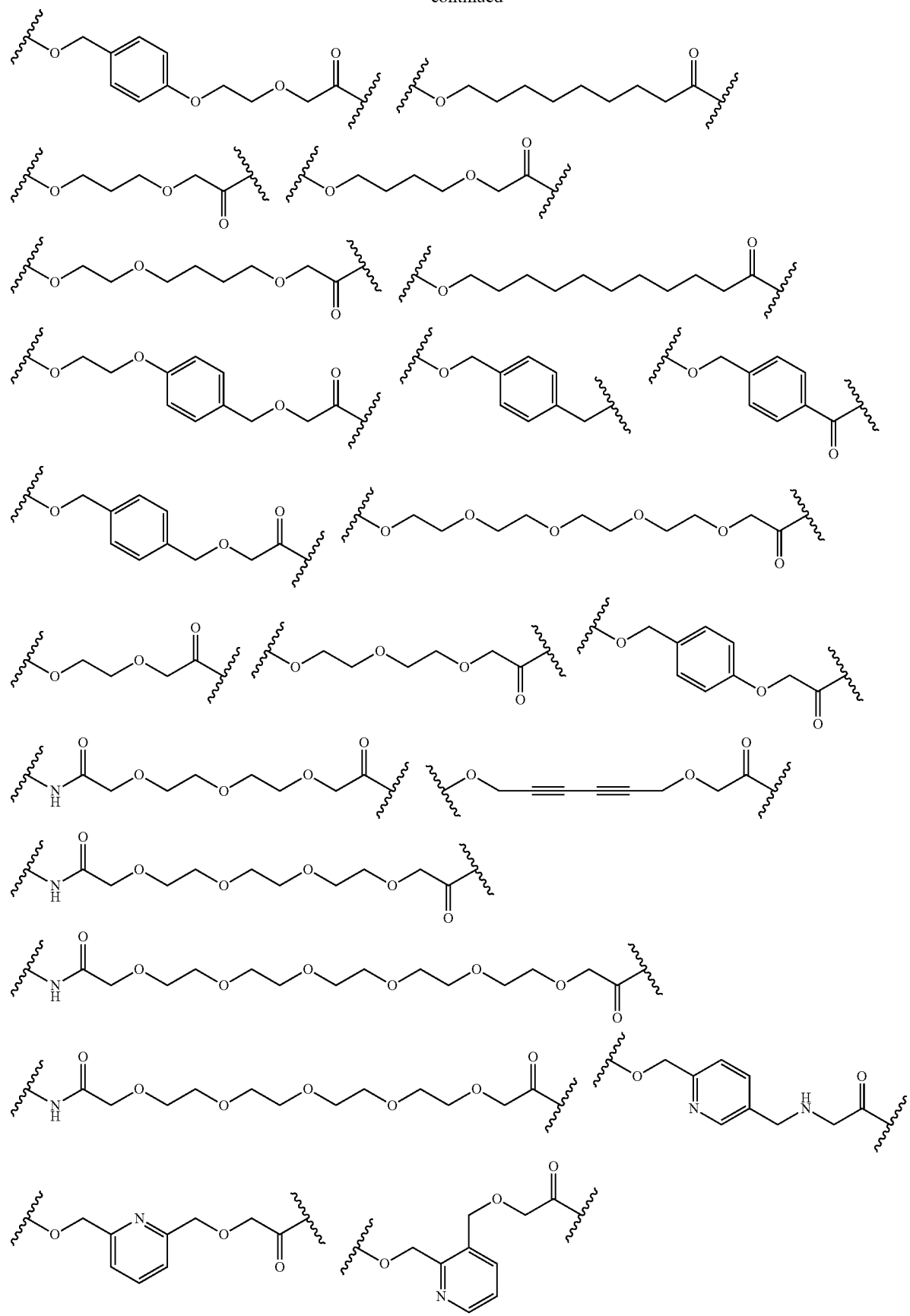

-continued
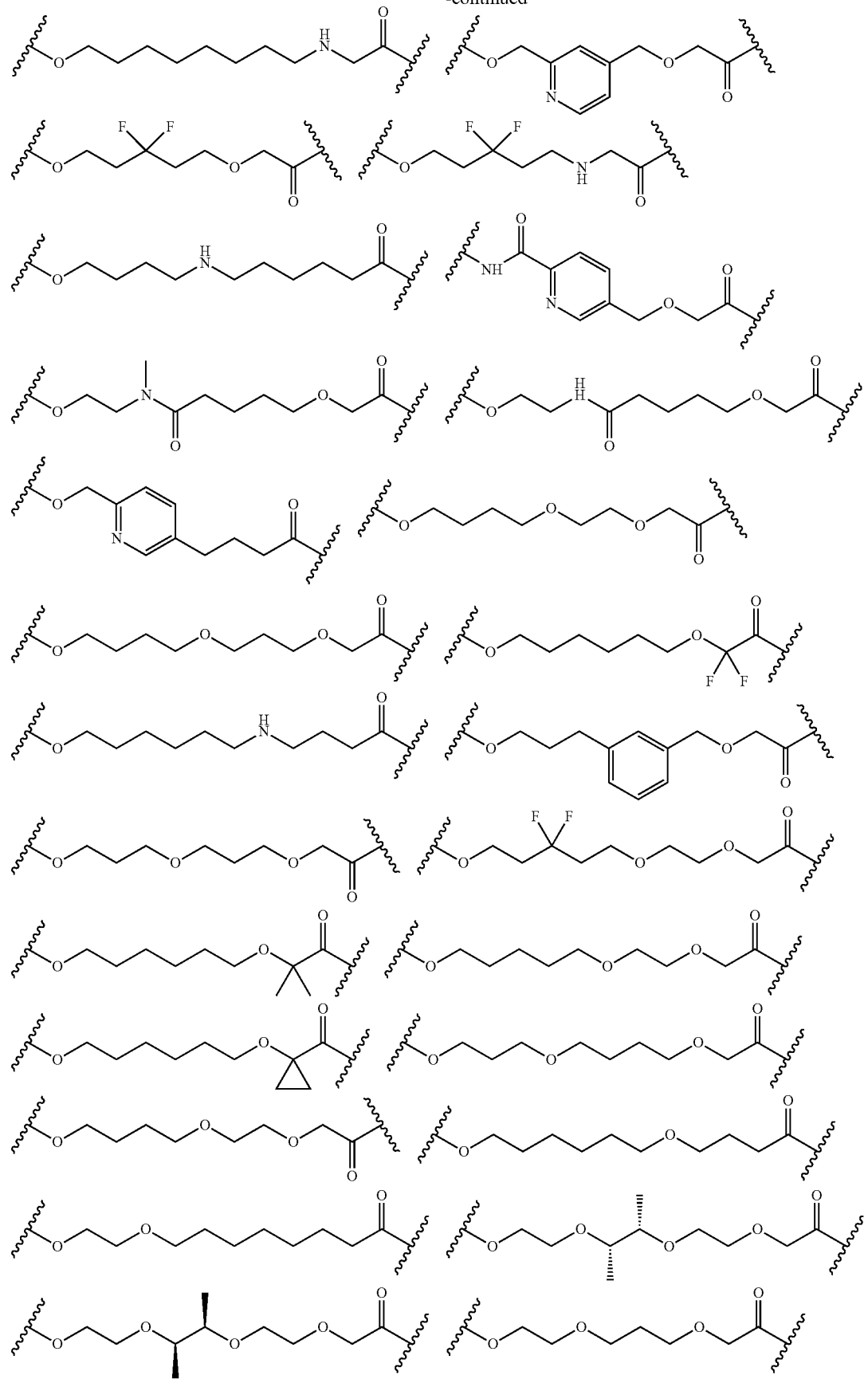

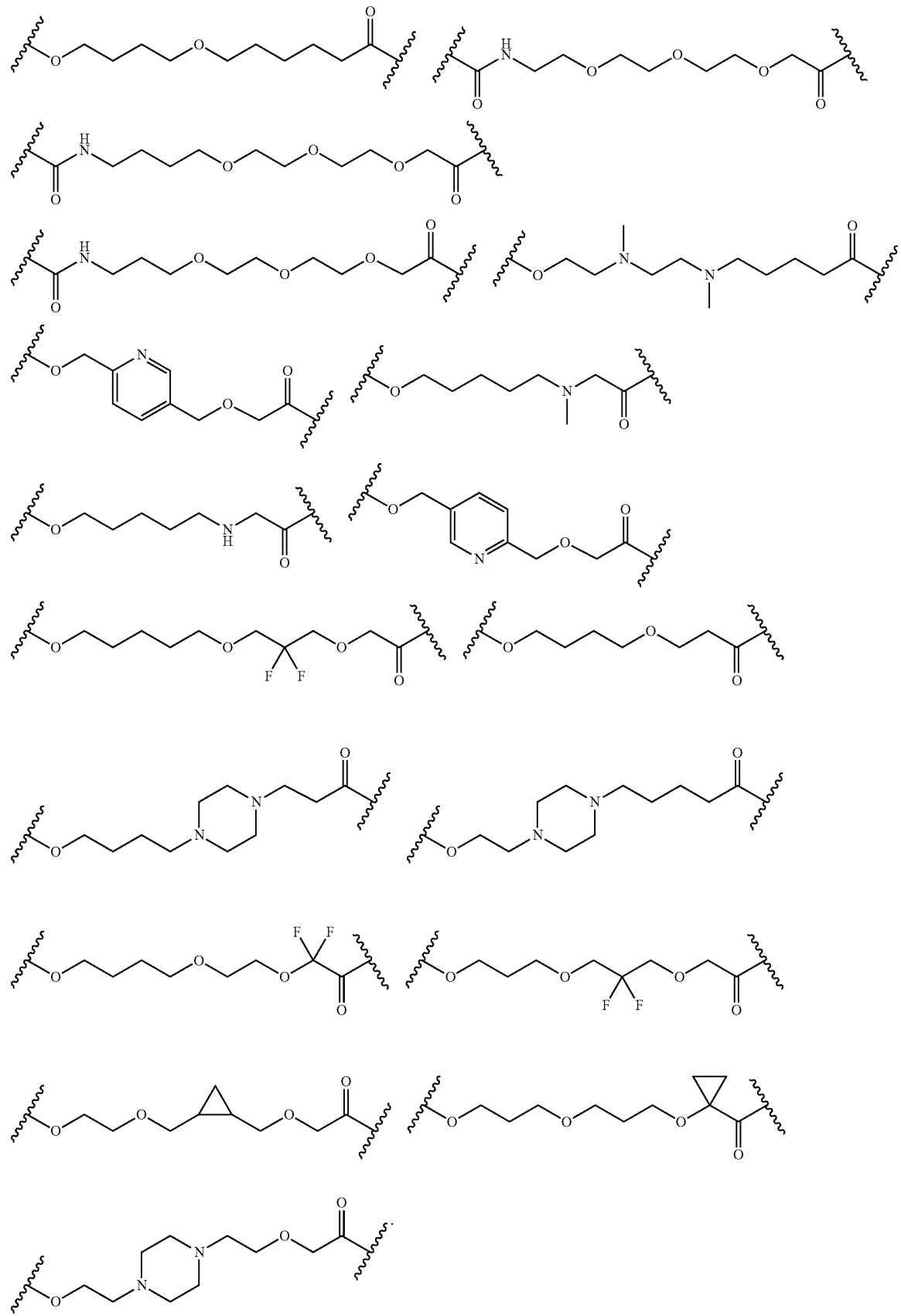

In one embodiment, there is provided a compound of Formula (I), or a pharmaceutically acceptable salt or prodrug thereof, wherein:

$R^1$ represents H;

the moiety:

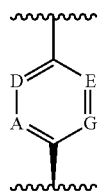

is selected from the group consisting of

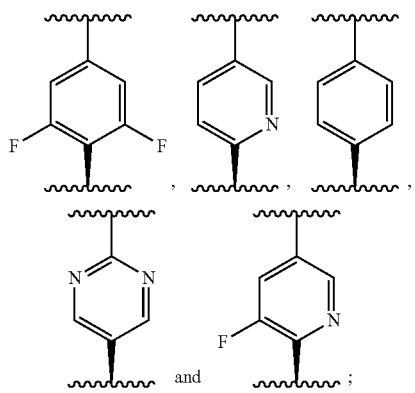

the group —CH$_2$—C(R$^4$)(R$^5$)(R$^6$) is selected from the group consisting of:

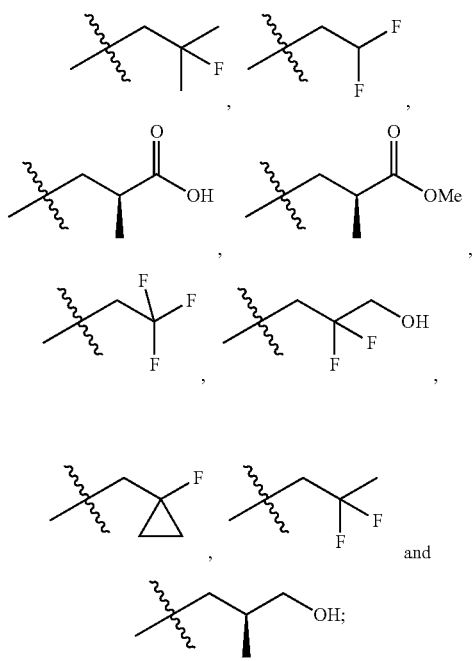

$R^7$ represents H or Me; and the group —X-[Linker]-Y— represents

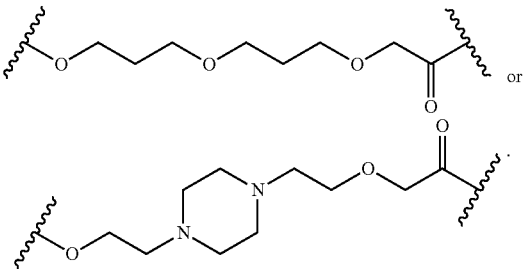

In one embodiment, there is provided a compound of Formula (I), or a pharmaceutically acceptable salt or prodrug thereof, wherein:

$R^1$ represents H or Me;

the moiety:

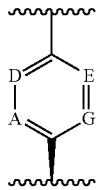

is selected from the group consisting of

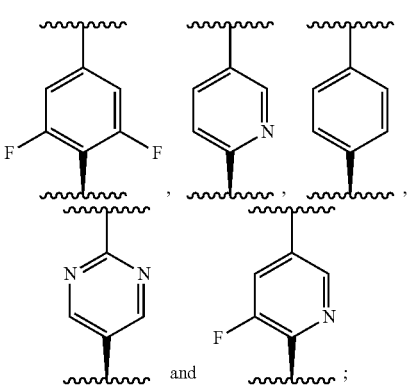

the group —CH$_2$—C(R$^4$)(R$^5$)(R$^6$) is selected from the group consisting of:

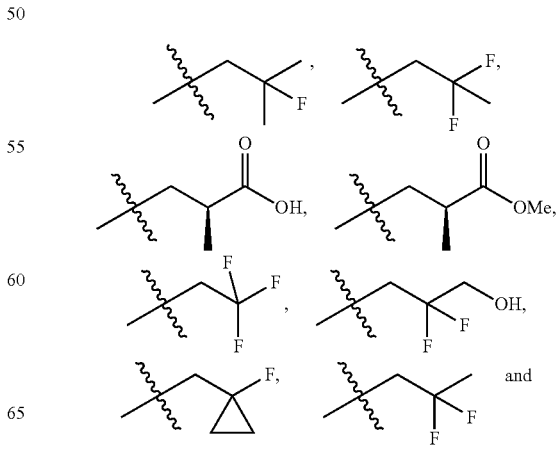

-continued

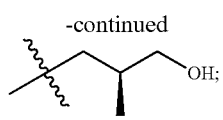

$R^7$ represents H; and
the group —X-[Linker]-Y— represents

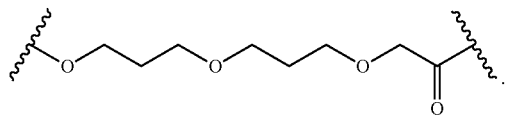 [SMILES: *OCCCOCCCOCC(*)=O]

It is further to be understood that a suitable pharmaceutically acceptable prodrug of a compound of Formula (I) also forms an aspect of the present specification. Accordingly, the compounds of the specification may be administered in the form of a prodrug, which is a compound that is broken down in the human or animal body to release a compound of the specification. A prodrug may be used to alter the physical properties and/or the pharmacokinetic properties of a compound of the specification. A prodrug can be formed when the compound of the specification contains a suitable group or substituent to which a property-modifying group can be attached. Examples of prodrugs include in vivo cleavable ester derivatives that may be formed at a hydroxy group in a compound of Formula (I).

Accordingly, the present specification includes those compounds of Formula (I) as defined hereinbefore when made available by organic synthesis and when made available within the human or animal body by way of cleavage of a prodrug thereof. Accordingly, the present specification includes those compounds of Formula (I) that are produced by organic synthetic means and also such compounds that are produced in the human or animal body by way of metabolism of a precursor compound, that is a compound of Formula (I) may be a synthetically-produced compound or a metabolically-produced compound.

A suitable pharmaceutically-acceptable prodrug of a compound of the Formula (I) is one that is based on reasonable medical judgement as being suitable for administration to the human or animal body without undesirable pharmacological activities and without undue toxicity.

Various forms of prodrug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable prodrug of a compound of Formula (I) that possesses a hydroxy group is, for example, an in vivo cleavable ester thereof. An in vivo cleavable ester of a compound of Formula (I) containing a hydroxy group is, for example, a pharmaceutically-acceptable ester which is cleaved in the human or animal body to produce the parent alcohol. Suitable pharmaceutically-acceptable esters for hydroxy include carboxylate esters and phosphate esters. Examples of carboxylate esters include —OC(O)Me, —OC(O)Et and other carboxylate ester groups derived from single alpha-amino acids, dipeptides or tripeptides.

In one embodiment, cleavable esters of a compound of Formula (I) include:

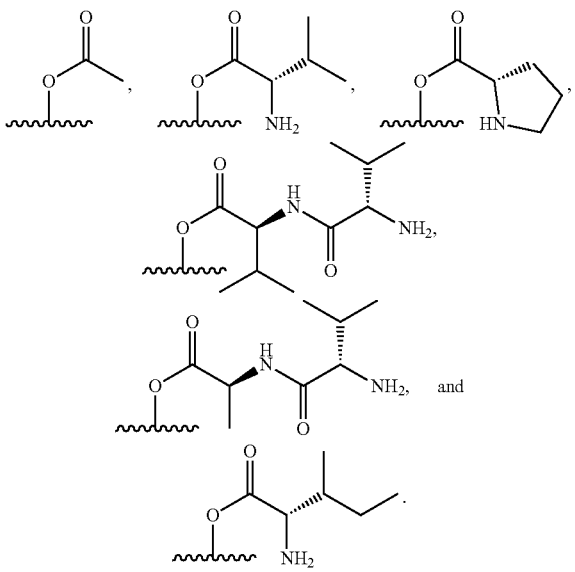

For example, cleavable esters of a compound of Formula (I) includes:

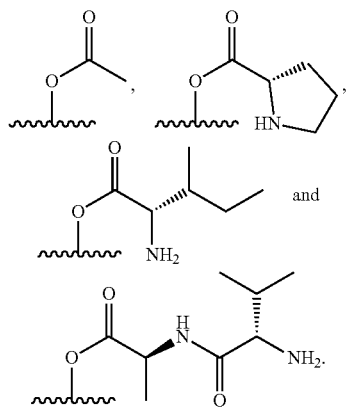

In one embodiment, cleavable esters of a compound of Formula (I) include:

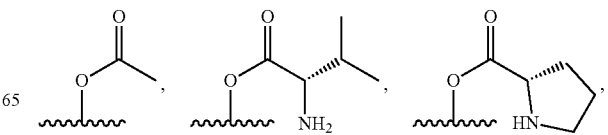

-continued

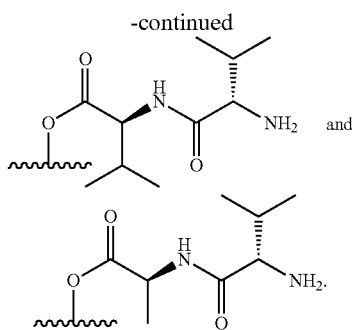 and

For example, cleavable esters of a compound of Formula (I) include:

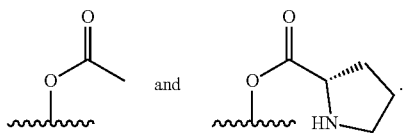 and

In the above structures, the " ⊥ " line indicates the attachment position of the cleavable ester group to the pyrrolidinyl ring at the position of the hydroxy group.

In another embodiment, prodrugs of the invention include a compound of Formula (I), or a pharmaceutically acceptable salt thereof, wherein the compound is selected the group consisting of:

(3R,5S)-1-((S)-2-(11-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)undecanamido)-3,3-dimethylbutanoyl)-5-((4-(4-methylthiazol-5-yl)benzyl)carbamoyl)pyrrolidin-3-yl L-prolinate;

(3R,5S)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-5-((4-(4-methylthiazol-5-yl)benzyl)carbamoyl)pyrrolidin-3-yl acetate;

(3R,5S)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)acetamido)-3,3-dimethylbutanoyl)-5-((4-(4-methylthiazol-5-yl)benzyl)carbamoyl)pyrrolidin-3-yl acetate;

(3R,5S)-1-((S)-2-(2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetamido)-3,3-dimethylbutanoyl)-5-((4-(4-methylthiazol-5-yl)benzyl)carbamoyl)pyrrolidin-3-yl L-valyl-L-alaninate; and (3R,5S)-1-((S)-2-(2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetamido)-3,3-dimethylbutanoyl)-5-((4-(4-methylthiazol-5-yl)benzyl)carbamoyl)pyrrolidin-3-yl L-isoleucinate.

In one embodiment there is provided a compound of Formula (I), or a pharmaceutically acceptable salt thereof, wherein the compound is selected from the group consisting of:

(2S,4R)-1-((S)-2-(4-(4-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propyl)piperazin-1-yl)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)piperazin-1-yl)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-4-hydroxy-N—((S)-1-(4-(4-methylthiazol-5-yl)phenyl)ethyl)pyrrolidine-2-carboxamide;

(2S,4R)-1-((S)-2-(2-((4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)benzyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-(4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((7-((6-((1S,3R)-2-(2,2-Difluoroethyl)-3-methyl-2,3,4,9-tetrahydro-1H-pyrido[3,4-b]indol-1-yl)pyridin-3-yl)oxy)heptyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((7-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy) acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((6-((6-((1S,3R)-2-(2,2-Difluoroethyl)-3-methyl-2,3,4,9-tetrahydro-1H-pyrido[3,4-b]indol-1-yl)pyridin-3-yl)oxy)hexyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(2-((6-((1S,3R)-2-(2,2-Difluoroethyl)-3-methyl-2,3,4,9-tetrahydro-1H-pyrido[3,4-b]indol-1-yl)pyridin-3-yl)oxy)ethoxy)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(10-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)decanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((8-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)octyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((8-((6-((1S,3R)-2-(2,2-Difluoroethyl)-3-methyl-2,3,4,9-tetrahydro-1H-pyrido[3,4-b]indol-1-yl)pyridin-3-yl)oxy)octyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy)acetamido)-3,3- dimethylbutanoyl)-4-hydroxy-N-(4-(4-methylthiazol-5-yl)benzyl)pyrrolidine-2-carboxamide;

(2S,4R)-1-((S)-2-(9-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)nonanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-((6-((1S,3R)-2-(2,2-Difluoroethyl)-3-methyl-2,3,4,9-tetrahydro-1H-pyrido[3,4-b]indol-1-yl)pyridin-3-yl)oxy)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy) acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(((E)-6-((6-((1S,3R)-2-(2,2-Difluoroethyl)-3-methyl-2,3,4,9-tetrahydro-1H-pyrido[3,4-b]indol-1-yl)pyridin-3-yl)oxy)hex-3-en-1-yl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(((E)-6-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)hex-3-en-1-yl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-3,3-dimethylpentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(2-((6-((1S,3R)-2-(2,2-Difluoroethyl)-3-methyl-2,3,4,9-tetrahydro-1H-pyrido[3,4-b]indol-1-yl)pyridin-3-yl)oxy)ethoxy)butoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(2-((6-((1S,3R)-2-(2,2-Difluoroethyl)-3-methyl-2,3,4,9-tetrahydro-1H-pyrido[3,4-b]indol-1-yl)pyridin-3-yl)oxy)ethoxy)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(4-(5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)benzamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy) acetamido)-3,3-dimethylbutanoyl)-4-hydroxy-N—((S)-1-(4-(4-methylthiazol-5-yl)phenyl)ethyl)pyrrolidine-2-carboxamide;

(Methyl (S)-3-((1R,3R)-1-(2,6-difluoro-4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)-3-methyl-1,3,4,9-tetrahydro-2H-pyrido[3,4-b]indol-2-yl)-2-methylpropanoate;

(S)-3-((1R,3R)-1-(2,6-Difluoro-4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)-3-methyl-1,3,4,9-tetrahydro-2H-pyrido[3,4-b]indol-2-yl)-2-methylpropanoic acid;

(2S,4R)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3-methyl-4-oxo-6,9,12-trioxa-3-azatetradecanoyl)-4-hydroxy-N-(4-(4-methylthiazol-5-yl)benzyl)pyrrolidine-2-carboxamide;

(2S,4R)-1-((S)-2-(11-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)undecanamido)-3,3-dimethylbutanoyl)-4-hydroxy-N-(4-(4-methylthiazol-5-yl)benzyl)pyrrolidine-2-carboxamide;

(3R,5S)-1-((S)-2-(11-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)undecanamido)-3,3-dimethylbutanoyl)-5-((4-(4-methylthiazol-5-yl)benzyl)carbamoyl)pyrrolidin-3-yl L-prolinate;

(3R,5S)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-5-((4-(4-methylthiazol-5-yl)benzyl)carbamoyl)pyrrolidin-3-yl acetate;

(2S,4R)-1-((S)-2-((4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzyl)amino)-3,3-dimethylbutanoyl)-4-hydroxy-N-(4-(4-methylthiazol-5-yl)benzyl)pyrrolidine-2-carboxamide;

(2S,4R)-1-((S)-2-(4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-Butyl)-17-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12,15-tetraoxa-3-azaheptadecanoyl)-4-hydroxy-N-(4-(4-methylthiazol-5-yl)benzyl)pyrrolidine-2-carboxamide;

(2S,4R)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide;

(2S,4R)-1-((S)-2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)acetamido)-3,3- dimethylbutanoyl)-4-hydroxy-N-(4-(4-methylthiazol-5-yl)benzyl)pyrrolidine-2-carboxamide;

(2S,4R)-1-((S)-2-(2-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(7-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-2,7-diazaspiro[3.5]nonan-2-yl)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-3,9-diazaspiro[5.5]undecan-3-yl)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetyl)-3,9-diazaspiro[5.5]undecan-3-yl)acetamido)-3,3-dimethylbutanoyl)-4-hydroxy-N-(4-(4-methylthiazol-5-yl)benzyl)pyrrolidine-2-carboxamide;

Benzyl (2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(5-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)pentyl)carbamate;

(2S,4R)-1-((S)-2-(2-((5-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)azetidin-1-yl)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(1-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)azetidin-3-yl)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexa-2,4-diyn-1-yl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)acetamido)-3,3-dimethylbutanoyl)-4-hydroxy-N-(4-(4-methylthiazol-5-yl)benzyl)pyrrolidine-2-carboxamide;

(3R,5S)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)acetamido)-3,3-dimethylbutanoyl)-5-((4-(4-methylthiazol-5-yl)benzyl)carbamoyl)pyrrolidin-3-yl acetate;

(2S,4R)-1-((S)-2-(2-(4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenethoxy)acetamido)-3,3-dimethylbutanoyl)-4-hydroxy-N-(4-(4-methylthiazol-5-yl)benzyl)pyrrolidine-2-carboxamide;

$N^1$-(4-((1R,3R)-2-(2-fluoro-2-methylpropyl)-3-methyl-2,3,4,9-tetrahydro-1H-pyrido[3,4-b]indol-1-yl)phenyl)-$N^{18}$—((S)-1-((2S,4R)-4-hydroxy-2-(4-(4-methylthiazol-5-yl)benzylcarbamoyl)pyrrolidin-1-yl)-3,3-dimethyl-1-oxobutan-2-yl)-2,5,8,11,14,17-hexaoxaoctadecane-1,18-dicarboxamide;

$N^1$-(4-((1R,3R)-2-(2-fluoro-2-methylpropyl)-3-methyl-2,3,4,9-tetrahydro-1H-pyrido[3,4-b]indol-1-yl)phenyl)-$N^{14}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12-tetraoxatetradecanediamide;

$N^1$-(4-((1R,3R)-2-(2-fluoro-2-methylpropyl)-3-methyl-2,3,4,9-tetrahydro-1H-pyrido[3,4-b]indol-1-yl)phenyl)-$N^{17}$—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaheptadecanediamide;

(2S,4R)-1-((S)-2-(tert-butyl)-14-((4-((1R,3R)-2-(2-fluoro-2-methylpropyl)-3-methyl-2,3,4,9-tetrahydro-1H-pyrido[3,4-b]indol-1-yl)phenyl)amino)-4,14-dioxo-6,9,12-trioxa-3-azatetradecanoyl)-4-hydroxy-N-(4-(4-methylthiazol-5-yl)benzyl)pyrrolidine-2-carboxamide;

(2S,4R)-1-((S,E)-2-(tert-butyl)-15-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-4,13-dioxo-6,9-dioxa-3,12-diazapentadec-14-enoyl)-4-hydroxy-N-(4-(4-methylthiazol-5-yl)benzyl)pyrrolidine-2-carboxamide;

(2S,4R)-1-((S)-2-(7-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)heptanamido)-3,3-dimethylbutanoyl)-4-hydroxy-N-(4-(4-methylthiazol-5-yl)benzyl)pyrrolidine-2-carboxamide;

(2S,4R)-1-((S)-2-(5-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)pentanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)phenoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S,E)-2-(tert-butyl)-18-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-4,16-dioxo-6,9,12-trioxa-3,15-diazaoctadec-17-enoyl)-4-hydroxy-N-(4-(4-methylthiazol-5-yl)benzyl)pyrrolidine-2-carboxamide;

1-(2-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)ethyl)-N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-1H-pyrazole-4-carboxamide;

(2S,4R)-1-((S)-2-(2-((1-(3-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)propyl)piperidin-4-yl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(2-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)ethoxy)phenyl)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(4-(4-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethyl)piperazin-1-yl)benzamido)-3,3-dimethylbutanoyl)-4-hydroxy-N-(4-(4-methylthiazol-5-yl)benzyl)pyrrolidine-2-carboxamide; and N1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-N14-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12-tetraoxatetradecanediamide.

In one embodiment there is provided a compound of Formula (I), or a pharmaceutically acceptable salt thereof, wherein the compound is selected from the group consisting of:

(2S,4R)-1-[(2S)-2-[[2-[6-[3,5-difluoro-4-[(1R,3R)-2-(2-fluoro-2-methyl-propyl)-3-methyl-1,3,4,9-tetrahydro-pyrido[3,4-b]indol-1-yl]phenoxy]hexoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[2-[2-[2-[2-[4-[(1R,3R)-2-(2-fluoro-2-methyl-propyl)-3-methyl-1,3,4,9-tetrahydropyrido[3,4-b]indol-1-yl]anilino]-2-oxo-ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide;

[(3R,5S)-1-[(2S)-2-[[2-[6-[3,5-difluoro-4-[(1R,3R)-2-(2-fluoro-2-methyl-propyl)-3-methyl-1,3,4,9-tetrahydro-pyrido[3,4-b]indol-1-yl]phenoxy]hexoxy]acetyl]amino]-3,3-dimethyl-butanoyl]-5-[[4-(4-methylthiazol-5-yl)phenyl]methylcarbamoyl]pyrrolidin-3-yl] acetate;

(2S,4R)-1-[(2S)-2-[[2-[2-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[[4-[[3,5-difluoro-4-[(1R,3R)-2-(2-fluoro-2-methyl-propyl)-3-methyl-1,3,4,9-tetrahydro-pyrido[3,4-b]indol-1-yl]phenoxy]methyl]phenyl]methoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[[3,5-difluoro-4-[(1R,3R)-2-(2-fluoro-2-methyl-propyl)-3-methyl-1,3,4,9-tetrahydro-pyrido[3,4-b]indol-1-yl]phenoxy]methyl]phenyl]methylamino]-3,3-dimethyl-butanoyl]-4-hydroxy-N-[[4-(4-methylthiazol-5-yl)phenyl]methyl]pyrrolidine-2-carboxamide;

[(3R,5S)-1-[(2S)-2-[[2-[2-[2-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethoxy]ethoxy]ethoxy]acetyl]amino]-3,3-dimethyl-butanoyl]-5-[[4-(4-methylthiazol-5-yl)phenyl]methylcarbamoyl]pyrrolidin-3-yl] acetate;

(2S,4R)-1-[(2S)-2-[[2-[5-[3,5-difluoro-4-[(1R,3R)-2-(2-fluoro-2-methyl-propyl)-3-methyl-1,3,4,9-tetrahydro-pyrido[3,4-b]indol-1-yl]phenoxy]pentoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[4-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethoxy]butoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[7-[3,5-difluoro-4-[(1R,3R)-2-(2-fluoro-2-methyl-propyl)-3-methyl-1,3,4,9-tetrahydro-pyrido[3,4-b]indol-1-yl]phenoxy]heptoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[10-[3,5-difluoro-4-[(1R,3R)-2-(2-fluoro-2-methyl-propyl)-3-methyl-1,3,4,9-tetrahydro-pyrido[3,4-b]indol-1-yl]phenoxy]decanoylamino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[8-[[6-[(1S,3R)-2-(2,2-difluoro-ethyl)-3-methyl-1,3,4,9-tetrahydropyrido[3,4-b]indol-1-yl]-3-pyridyl]oxy]octoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[5-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethoxy]pentoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[6-[[6-[(1S,3R)-2-(2,2-difluoro-ethyl)-3-methyl-1,3,4,9-tetrahydropyrido[3,4-b]indol-1-yl]-3-pyridyl]oxy]hexoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[7-[[6-[(1S,3R)-2-(2,2-difluoro-ethyl)-3-methyl-1,3,4,9-tetrahydropyrido[3,4-b]indol-1-yl]-3-pyridyl]oxy]heptoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[5-[3,5-difluoro-4-[(1R,3R)-2-(2-fluoro-2-methyl-propyl)-3-methyl-1,3,4,9-tetrahydro-pyrido[3,4-b]indol-1-yl]phenoxy]-3,3-dimethyl-pentoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[(E)-6-[3,5-difluoro-4-[(1R,3R)-2-(2-fluoro-2-methyl-propyl)-3-methyl-1,3,4,9-tetrahydro-pyrido[3,4-b]indol-1-yl]phenoxy]hex-3-enoxy]acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[2-[2-[[(E)-3-[3,5-difluoro-4-[(1R,3R)-2-(2-fluoro-2-methyl-propyl)-3-methyl-1,3,4,9-tetrahydropyrido[3,4-b]indol-1-yl]phenyl]prop-2-enoyl] amino]ethoxy]ethoxy]acetyl]amino]-3,3-dimethyl-butanoyl]-4-hydroxy-N-[[4-(4-methylthiazol-5-yl) phenyl]methyl]pyrrolidine-2-carboxamide;

(2S,4R)-1-[(2S)-2-[7-[[(E)-3-[3,5-difluoro-4-[(1R,3R)-2-(2-fluoro-2-methyl-propyl)-3-methyl-1,3,4,9-tetrahydro-pyrido[3,4-b]indol-1-yl]phenyl]prop-2-enoyl]amino]heptanoylamino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[4-[2-[[(E)-3-[3,5-difluoro-4-[(1R,3R)-2-(2-fluoro-2-methyl-propyl)-3-methyl-1,3,4,9-tetrahydropyrido[3,4-b]indol-1-yl]phenyl]prop-2-enoyl]amino]ethoxy]phenoxy]acetyl]amino]-3,3-dimethyl-butanoyl]-4-hydroxy-N-[[4-(4-methylthiazol-5-yl) phenyl]methyl]pyrrolidine-2-carboxamide;

(2S,4R)-1-[(2S)-2-[[2-[2-[[(E)-3-[3,5-difluoro-4-[(1R,3R)-2-(2-fluoro-2-methyl-propyl)-3-methyl-1,3,4,9-tetrahydropyrido[3,4-b]indol-1-yl]phenyl]prop-2-enoyl]amino]ethoxy]acetyl]amino]-3,3-dimethyl-butanoyl]-4-hydroxy-N-[[4-(4-methylthiazol-5-yl)phenyl]methyl] pyrrolidine-2-carboxamide;

(2S,4R)-1-[(2S)-2-[[2-[2-[2-[2-[[(E)-3-[3,5-difluoro-4-[(1R,3R)-2-(2-fluoro-2-methyl-propyl)-3-methyl-1,3,4,9-tetrahydropyrido[3,4-b]indol-1-yl]phenyl]prop-2-enoyl] amino]ethoxy]ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide;

methyl (2S)-3-[(1R,3R)-1-[2,6-difluoro-4-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy] ethoxy]phenyl]-3-methyl-1,3,4,9-tetrahydropyrido[3,4-b] indol-2-yl]-2-methyl-propanoate;

(2S)-3-[(1R,3R)-1-[2,6-difluoro-4-[2-[2-[2-[2-[[(1S)-1-[(2S,4R)-4-hydroxy-2-[[4-(4-methylthiazol-5-yl)phenyl] methylcarbamoyl]pyrrolidine-1-carbonyl]-2,2-dimethyl-propyl]amino]-2-oxo-ethoxy]ethoxy]ethoxy]ethoxy] phenyl]-3-methyl-1,3,4,9-tetrahydropyrido[3,4-b]indol-2-yl]-2-methyl-propanoic acid;

(2S,4R)-1-[(2S)-2-[[2-[5-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethyl-methyl-amino] pentoxy]acetyl]amino]-3,3-dimethyl-butanoyl]-4-hydroxy-N-[[4-(4-methylthiazol-5-yl)phenyl]methyl] pyrrolidine-2-carboxamide;

(2S,4R)-1-[(2S)-2-[[2-[5-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethylamino]pentoxy] acetyl]amino]-3,3-dimethyl-butanoyl]-4-hydroxy-N-[[4-(4-methylthiazol-5-yl)phenyl]methyl]pyrrolidine-2-carboxamide;

(2S,4R)-1-[(2S)-2-[[2-[2-[2-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethoxy]ethoxy]ethoxy] acetyl]amino]-3,3-dimethyl-butanoyl]-4-hydroxy-N-[(1 S)-1-[4-(4-methylthiazol-5-yl)phenyl]ethyl]pyrrolidine-2-carboxamide;

(2S,4R)-1-[(2S)-2-[[2-[3-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethoxy]propoxy]acetyl] amino]-3,3-dimethyl-butanoyl]-4-hydroxy-N-[[4-(4-methylthiazol-5-yl)phenyl]methyl]pyrrolidine-2-carboxamide; (2S,4R)-1-[(2S)-2-[[2-[2-[2-[2-[3,5-difluoro-4-[(1R,3R)-2-(2-fluoro-2-methyl-propyl)-3-methyl-1,3,4,9-tetrahydropyrido[3,4-b]indol-1-yl] anilino]-2-oxo-ethoxy]ethoxy]ethoxy]ethoxy]acetyl] amino]-3,3-dimethyl-butanoyl]-4-hydroxy-N-[[4-(4-methylthiazol-5-yl)phenyl]methyl]pyrrolidine-2-carboxamide;

(2S,4R)-1-((S)-2-(2-((5-(4-((1R,3R)-2-(2,2-difluoro-3-hydroxypropyl)-3-methyl-2,3,4,9-tetrahydro-1H-pyrido[3, 4-b]indol-1-yl)-3,5-difluorophenoxy)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-14-(4-((1R,3R)-2-(2,2-difluoro-3-hydroxypropyl)-3-methyl-2,3,4,9-tetrahydro-1H-pyrido[3,4-b]indol-1-yl)-3,5-difluorophenoxy)-4-oxo-6, 9,12-trioxa-3-azatetradecanoyl)-4-hydroxy-N-(4-(4-methylthiazol-5-yl)benzyl)pyrrolidine-2-carboxamide;

(2S,4R)-1-((S)-2-(2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(3-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenyl) propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propyl)benzyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-14-(3,5-difluoro-4-((1R,3R)-2-((1-fluorocyclopropyl)methyl)-3-methyl-2,3,4,9-tetrahydro-1H-pyrido[3,4-b]indol-1-yl)phenoxy)-4-oxo-6,9, 12-trioxa-3-azatetradecanoyl)-4-hydroxy-N-(4-(4-methylthiazol-5-yl)benzyl)pyrrolidine-2-carboxamide;

(2S,4R)-1-((S)-2-(2-((7-(4-((1R,3R)-2-(2,2-difluoro-3-hydroxypropyl)-3-methyl-2,3,4,9-tetrahydro-1H-pyrido[3, 4-b]indol-1-yl)-3,5-difluorophenoxy)heptyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-difluoro-4-((1R,3R)-2-((1-fluorocyclopropyl)methyl)-3-methyl-2,3,4,9-tetrahydro-1H-pyrido[3,4-b]indol-1-yl)phenoxy)pentyl)oxy) acetamido)-3,3-dimethylbutanoyl)-4-hydroxy-N-(4-(4-methylthiazol-5-yl)benzyl)pyrrolidine-2-carboxamide;

(2S,4R)-1-((2S,10R,11R)-2-(tert-butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-10,11-dimethyl-4-oxo-6,9,12-trioxa-3-azatetradecanoyl)-4-hydroxy-N-(4-(4-methylthiazol-5-yl)benzyl)pyrrolidine-2-carboxamide;

(2S,4R)-1-((2S,10S,11 S)-2-(tert-butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-10,11-dimethyl-4-oxo-6,9,12-trioxa-3-azatetradecanoyl)-4-hydroxy-N-(4-(4-methylthiazol-5-yl)benzyl)pyrrolidine-2-carboxamide;

(2S,4R)-1-((S)-17-(tert-butyl)-1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1,15-dioxo-7, 10,13-trioxa-2,16-diazaoctadecan-18-oyl)-4-hydroxy-N-(4-(4-methylthiazol-5-yl)benzyl)pyrrolidine-2-carboxamide;

(2S,4R)-1-((S)-16-(tert-butyl)-1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1,14-dioxo-6, 9,12-trioxa-2,15-diazaheptadecan-17-oyl)-4-hydroxy-N-(4-(4-methylthiazol-5-yl)benzyl)pyrrolidine-2-carboxamide;

(2S,4R)-1-((S)-2-(2-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)methoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)amino)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)(methyl)amino)acetamido)-3,3-dimethylbutanoyl)-4-hydroxy-N-(4-(4-methylthiazol-5-yl)benzyl)pyrrolidine-2-carboxamide;

(2S,4R)-1-((S)-15-(tert-butyl)-1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1,13-dioxo-5,8,11-trioxa-2,14-diazahexadecan-16-oyl)-4-hydroxy-N-(4-(4-methylthiazol-5-yl)benzyl)pyrrolidine-2-carboxamide;

(2S,4R)-1-((S)-2-(3-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)butoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(2-(3,5-difluoro-4-((1R,3R)-3-methyl-2-(2,2,2-trifluoroethyl)-2,3,4,9-tetrahydro-1H-pyrido[3,4-b]indol-1-yl)phenoxy)ethoxy)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-14-(3,5-difluoro-4-((1R,3R)-3-methyl-2-(2,2,2-trifluoroethyl)-2,3,4,9-tetrahydro-1H-pyrido[3,4-b]indol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide;

(2S,4R)-1-((S)-2-(2-((5-(3,5-difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(3-(4-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butyl)piperazin-1-yl)propanamido)-3,3-dimethylbutanoyl)-4-hydroxy-N-(4-(4-methylthiazol-5-yl)benzyl)pyrrolidine-2-carboxamide;

(3R,5S)-1-((S)-2-(2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetamido)-3,3-dimethylbutanoyl)-5-((4-(4-methylthiazol-5-yl)benzyl)carbamoyl)pyrrolidin-3-yl L-isoleucinate;

(3R,5S)-1-((S)-2-(2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetamido)-3,3-dimethylbutanoyl)-5-((4-(4-methylthiazol-5-yl)benzyl)carbamoyl)pyrrolidin-3-yl L-valyl-L-alaninate;

(2S,4R)-1-((S)-2-(tert-butyl)-14-(3,5-difluoro-4-((1R,3R)-2-((S)-3-hydroxy-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide;

(2S,4R)-1-((S)-2-(5-(4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)pentanamido)-3,3-dimethylbutanoyl)-4-hydroxy-N-(4-(4-methylthiazol-5-yl)benzyl)pyrrolidine-2-carboxamide;

(2S,4R)-1-[(2S)-2-[[2-[2-[2-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethoxy]ethoxy]ethoxy]acetyl]amino]-3,3-dimethyl-butanoyl]-N-[(1R*)-2-(dimethylamino)-1-[4-(4-methylthiazol-5-yl)phenyl]ethyl]-4-hydroxy-pyrrolidine-2-carboxamide;

(2S,4R)—N-[(1R*)-2-amino-1-[4-(4-methylthiazol-5-yl)phenyl]ethyl]-1-[(2S)-2-[[2-[2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-4-hydroxy-pyrrolidine-2-carboxamide;

(2S,4R)-1-[(2S)-2-[[2-[2-[2-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethoxy]ethoxy]ethoxy]acetyl]amino]-3,3-dimethyl-butanoyl]-N-[(1R*)-2-(dimethylamino)-1-[4-(4-methylthiazol-5-yl)phenyl]ethyl]-4-hydroxy-pyrrolidine-2-carboxamide;

(2S,4R)-1-((S)-2-(5-((2-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)ethyl)(methyl)amino)pentanamido)-3,3-dimethylbutanoyl)-4-hydroxy-N-(4-(4-methylthiazol-5-yl)benzyl)pyrrolidine-2-carboxamide;

(2S,4R)-1-((S)-2-(6-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)hexanamido)-3,3-dimethylbutanoyl)-4-hydroxy-N-(4-(4-methylthiazol-5-yl)benzyl)pyrrolidine-2-carboxamide;

(2S,4R)-1-((S)-2-(7-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)heptanamido)-3,3-dimethylbutanoyl)-4-hydroxy-N-(4-(4-methylthiazol-5-yl)benzyl)pyrrolidine-2-carboxamide;

(2S,4R)-1-((S)-2-(8-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)octanamido)-3,3-dimethylbutanoyl)-4-hydroxy-N-(4-(4-methylthiazol-5-yl)benzyl)pyrrolidine-2-carboxamide;

(2S,4R)-1-((S)-2-(4-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(5-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)pentanamido)-3,3-dimethylbutanoyl)-4-hydroxy-N-(4-(4-methylthiazol-5-yl)benzyl)pyrrolidine-2-carboxamide;

(2S,4R)-1-((S)-2-(3-((7-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)propanamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(3-((7-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)-2,2-difluoroacetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)-2-methylpropanamido)-3,3-dimethylbutanoyl)-4-hydroxy-N-(4-(4-methylthiazol-5-yl)benzyl)pyrrolidine-2-carboxamide;

(2S,4R)-1-((S)-2-(1-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)cyclopropane-1-carboxamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)-2,2-difluoroacetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)-2,2-difluoroacetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)-2,2-difluoroacetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)-2,2-difluoroacetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-[(2S)-2-[[2-[[(1R*,2S*)-2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxymethyl]cyclopropyl]methoxy]acetyl]amino]-3,3-dimethylbutanoyl]-4-hydroxy-N-[[4-(4-methylthiazol-5-yl)phenyl]methyl]pyrrolidine-2-carboxamide, isomer 1;

(2S,4R)-1-[(2S)-2-[[2-[[(1R*,2S*)-2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxymethyl]cyclopropyl]methoxy]acetyl]amino]-3,3-dimethylbutanoyl]-4-hydroxy-N-[[4-(4-methylthiazol-5-yl)phenyl]methyl]pyrrolidine-2-carboxamide, isomer 2;

(2S,4R)-1-((S)-2-(2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)-2,2-difluoropropoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)-2,2-difluoropropoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)oxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)amino)acetamido)-3,3-dimethylbutanoyl)-4-hydroxy-N-(4-(4-methylthiazol-5-yl)benzyl)pyrrolidine-2-carboxamide;

(2S,4R)-1-((S)-2-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)methoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((2-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((2-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-4-yl)methoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(1-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)cyclopropane-1-carboxamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)pentyl)oxy)

acetamido)-3,3-dimethylbutanoyl)-4-hydroxy-N-(4-(4-methylthiazol-5-yl)benzyl)pyrrolidine-2-carboxamide;

(2S,4R)-1-[(2S)-2-[[2-[3-[5-[3,5-difluoro-4-[(1R,3R)-2-(2-fluoro-2-methyl-propyl)-3-methyl-1,3,4,9-tetrahydro-pyrido[3,4-b]indol-1-yl]phenoxy]pentoxy]propoxy]acetyl]amino]-3,3-dimethyl-butanoyl]-4-hydroxy-N-[(1S)-1-[4-(4-methylthiazol-5-yl)phenyl]ethyl]pyrrolidine-2-carboxamide;

(2S,4R)-1-((S)-2-(2-(3-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-(3,5-difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-(3,5-difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(4-(6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)-5-oxopentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)-5-oxopentyl)oxy)acetamido)-3,3-dimethylbutanoyl)-4-hydroxy-N-(4-(4-methylthiazol-5-yl)benzyl)pyrrolidine-2-carboxamide;

N-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-5-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)methyl)picolinamide;

(2S,4R)-1-((S)-2-(6-((4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butyl)amino)hexanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methyl)amino)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((8-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)octyl)amino)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(4-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)amino)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)acetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(2-(4-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)butoxy)acetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(2-(3-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)propoxy)acetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(2-((5-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)pentyl)oxy)acetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(2-(6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-(6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)ethoxy)acetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(4-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)oxy)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(4-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)oxy)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-((6-((1S,3R)-2-(2,2-difluoropropyl)-3-methyl-2,3,4,9-tetrahydro-1H-pyrido[3,4-b]indol-1-yl)-5-fluoropyridin-3-yl)oxy)pentyl)oxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-((5-fluoro-6-((1S,3R)-3-methyl-2-(2,2,2-trifluoroethyl)-2,3,4,9-tetrahydro-1H-pyrido[3,4-b]indol-1-yl)pyridin-3-yl)oxy)pentyl)oxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-(4-((1R,3R)-2-(2,2-difluoropropyl)-3-methyl-2,3,4,9-tetrahydro-1H-pyrido[3,4-b]indol-1-yl)-3,5-difluorophenoxy)pentyl)oxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-(4-((1R,3R)-2-(2,2-difluoroethyl)-3-methyl-2,3,4,9-tetrahydro-1H-pyrido[3,4-b]indol-1-yl)-3,5-difluorophenoxy)pentyl)oxy)ethoxy)acetamido)-3,3-dimethylbutanoyl)-4-hydroxy-N-(4-(4-methylthiazol-5-yl)benzyl)pyrrolidine-2-carboxamide; and (2S,4R)-1-((S)-2-(2-(2-(4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)ethoxy)acetamido)-3,3-dimethylbutanoyl)-4-hydroxy-N-(4-(4-methylthiazol-5-yl)benzyl)pyrrolidine-2-carboxamide.

The compounds of Formula (I) have five or more chiral centres and it will be recognised that the compounds of Formula (I) may be prepared, isolated and/or supplied with or without the presence, in addition, of one or more of the other possible enantiomeric and/or diastereomeric isomers of the compounds of Formula (I) in any relative proportions. The preparation of enantioenriched/enantiopure and/or diastereoenriched/diastereopure compounds may be carried out by standard techniques of organic chemistry that are well known in the art, for example by synthesis from enantioenriched or enantiopure starting materials, use of an appropriate enantioenriched or enantiopure catalyst during synthesis, and/or by resolution of a racemic or partially enriched mixture of stereoisomers, for example via chiral chromatography.

For use in a pharmaceutical context it may be preferable to provide a compound of Formula (I) or a pharmaceutically acceptable salt or prodrug thereof without large amounts of the other stereoisomeric forms being present.

Accordingly, in one embodiment there is provided a composition comprising a compound of Formula (I) or a pharmaceutically acceptable salt or prodrug thereof, optionally together with one or more of the other stereoisomeric forms of the compound of Formula (I) or pharmaceutically acceptable salt or prodrug thereof, wherein the compound of Formula (I) or pharmaceutically acceptable salt or prodrug thereof is present within the composition with a diastereomeric excess (% de) of ≥90%.

In a further embodiment the % de in the above-mentioned composition is ≥95%.

In a further embodiment the % de in the above-mentioned composition is ≥98%.

In a further embodiment the % de in the above-mentioned composition is ≥99%.

In a further embodiment there is provided a composition comprising a compound of Formula (I) or a pharmaceutically acceptable salt or prodrug thereof, optionally together with one or more of the other stereoisomeric forms of the compound of Formula (I) or pharmaceutically acceptable salt or prodrug thereof, wherein the compound of Formula (I) or pharmaceutically acceptable salt or prodrug thereof is present within the composition with an enantiomeric excess (% ee) of ≥90%.

In a further embodiment the % ee in the above-mentioned composition is ≥95%.

In a further embodiment the % ee in the above-mentioned composition is ≥98%.

In a further embodiment the % ee in the above-mentioned composition is ≥99%.

In a further embodiment there is provided a composition comprising a compound of Formula (I) or a pharmaceutically acceptable salt or prodrug thereof, optionally together with one or more of the other stereoisomeric forms of the compound of Formula (I), or pharmaceutically acceptable salt or prodrug thereof, wherein the compound of Formula (I), or pharmaceutically acceptable salt or prodrug thereof is present within the composition with an enantiomeric excess (% ee) of ≥90% and a diastereomeric excess (% de) of ≥90%.

In further embodiments of the above-mentioned composition the % ee and % de may take any combination of values as listed below:

The % ee is ≤5% and the % de is ≥80%.
The % ee is ≤5% and the % de is ≥90%.
The % ee is ≤5% and the % de is ≥95%.
The % ee is ≤5% and the % de is ≥98%.
The % ee is ≥95% and the % de is ≥95%.
The % ee is ≥98% and the % de is ≥98%.
The % ee is ≥99% and the % de is ≥99%.

In a further embodiment there is provided a pharmaceutical composition which comprises a compound of the Formula (I), or a pharmaceutically acceptable salt or prodrug thereof, in association with a pharmaceutically acceptable excipient.

In one embodiment there is provided a pharmaceutical composition which comprises a compound of the Formula (I), or a pharmaceutically acceptable salt or prodrug thereof, in association with a pharmaceutically acceptable excipient, optionally further comprising one or more of the other stereoisomeric forms of the compound of Formula (I), or pharmaceutically acceptable salt or prodrug thereof, wherein the compound of Formula (I), or pharmaceutically acceptable salt or prodrug thereof is present within the composition with an enantiomeric excess (% ee) of ≥90%.

In a further embodiment the % ee in the above-mentioned composition is ≥95%.

In a further embodiment the % ee in the above-mentioned composition is ≥98%.

In a further embodiment the % ee in the above-mentioned composition is ≥99%.

In one embodiment there is provided a pharmaceutical composition which comprises a compound of the Formula (I), or a pharmaceutically acceptable salt or prodrug thereof, in association with a pharmaceutically acceptable excipient, optionally further comprising one or more of the other stereoisomeric forms of the compound of Formula (I), or pharmaceutically acceptable salt or prodrugs thereof, wherein the compound of Formula (I), or pharmaceutically acceptable salt thereof is present within the composition with a diastereomeric excess (% de) of ≥90%.

In a further embodiment the % de in the above-mentioned composition is ≥95%.

In a further embodiment the % de in the above-mentioned composition is ≥98%.

In a further embodiment the % de in the above-mentioned composition is ≥99%.

In one embodiment there is provided a pharmaceutical composition which comprises a compound of the Formula (I), or a pharmaceutically acceptable salt or prodrug thereof, in association with a pharmaceutically acceptable excipient, optionally further comprising one or more of the other stereoisomeric forms of the compound of Formula (I), or pharmaceutically acceptable salt or prodrug thereof, wherein the compound of Formula (I), or pharmaceutically acceptable salt thereof is present within the composition with an enantiomeric excess (% ee) of ≥90% and a diastereomeric excess (% de) of ≥90%.

In further embodiments of the above-mentioned pharmaceutical composition the % ee and % de may take any combination of values as listed below:

The % ee is ≥95% and the % de is ≥95%.
The % ee is ≥98% and the % de is ≥98%.
The % ee is ≥99% and the % de is ≥99%.

The compounds of Formula (I), and pharmaceutically acceptable salts thereof may be prepared, used or supplied in amorphous form, crystalline form, or semicrystalline form and any given compound of Formula (I), or pharmaceutically acceptable salt or prodrug thereof may be capable of being formed into more than one crystalline/polymorphic form, including hydrated (e.g. hemi-hydrate, a mono-hydrate, a di-hydrate, a tri-hydrate or other stoichiometry of hydrate) and/or solvated forms. It is to be understood that the present specification encompasses any and all such solid forms of the compound of Formula (I), and pharmaceutically acceptable salts and prodrugs thereof.

In further embodiments there is provided a compound of Formula (I) which is obtainable by the methods described in the 'Examples' section hereinafter.

The present specification is intended to include all isotopes of atoms occurring in the present compounds. Isotopes will be understood to include those atoms having the same atomic number but different mass numbers.

For the avoidance of doubt it is to be understood that where in this specification a group is qualified by 'hereinbefore defined' or 'defined herein' the said group encompasses the first occurring and broadest definition as well as each and all of the alternative definitions for that group.

Another aspect of the present specification provides a process for preparing a compound of the Formula (I), or a pharmaceutically acceptable salt or prodrug thereof. A suitable process is illustrated by the following representative process variants in which, unless otherwise stated, A, D, E, G, X, Y, Linker and $R^1$ to $R^7$ have any of the meanings defined hereinbefore. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

Compounds of Formula (I) where $R^1$ and $R^7$ are both H may be made by, for example:

a) Amide coupling reaction of a compound of Formula (II) with a compound of Formula (III) under conditions known in the art as suitable amide coupling reactions (such as in the presence of a suitable amide coupling reagent (such as HATU) and a suitable base (such as trimethylamine) and in a suitable solvent (for example DMF) and a suitable temperature (such as room temperature). In certain aspect, the linker group is with a protecting group (such as Boc or Cbz) on a nitrogen that may be removed under conditions known in the art.

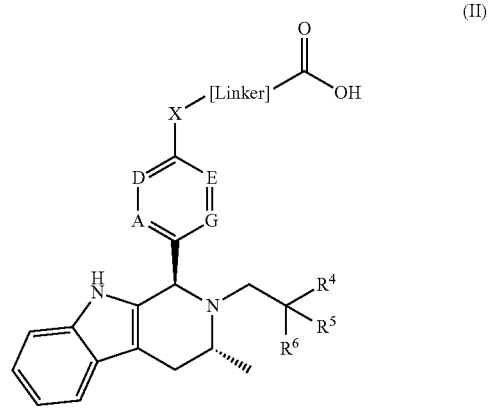

(II)

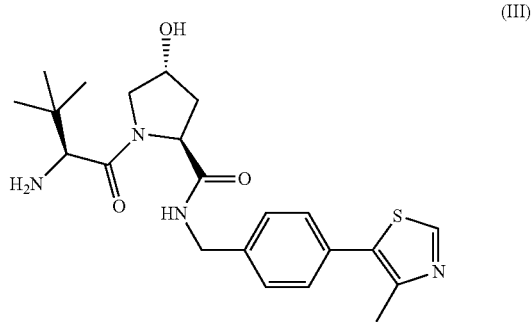

(III)

b) Amide coupling reaction of a compound of Formula (IV) with an acid compound of Formula (V) under conditions known in the art as suitable amide coupling reactions (such as in the presence of a suitable amide coupling reagent (for example HATU) and a suitable base (such as trimethylamine) and in a suitable solvent (for example DMF) and a suitable temperature (such as room temperature)). In certain aspect, the linker group is with a protecting group (such as Boc or Cbz) on the nitrogen that may be removed under conditions known in the art.

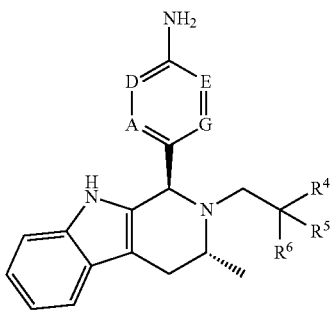

(IV)

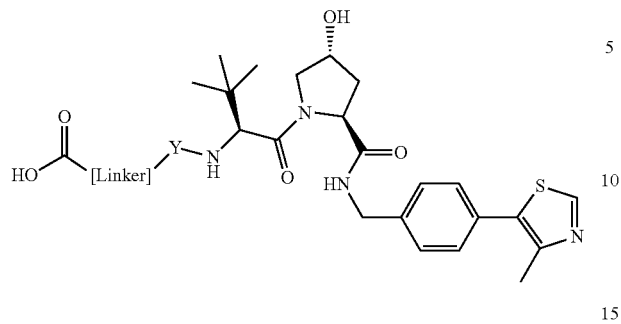

(V)

c) Amide coupling reaction of an acid compound of Formula (VI) with an amine compound of Formula (VII) where R is H or an alkyl group (such as methyl) under conditions known in the art as suitable amide coupling reactions, such as in the presence of a suitable amide coupling reagent (such as HATU) and a suitable base (such as trimethylamine) and in a suitable solvent (for example DMF) and a suitable temperature (such as room temperature). In certain aspect, the linker group is with a protecting group (such as Boc or Cbz) on a nitrogen that may be removed under conditions known in the art.

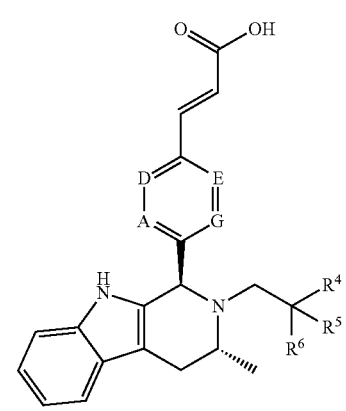

(VI)

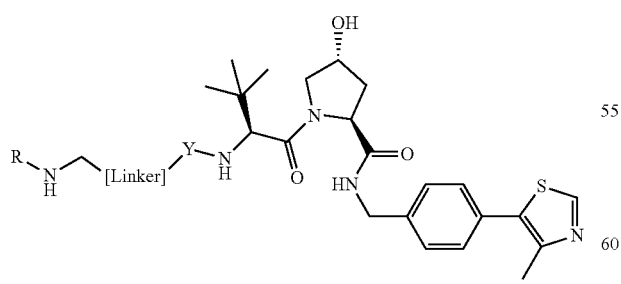

(VII)

d) Alkylation of a suitable amine of Formulas (VII) or (IX), with a compound of Formula (VIII) where LG is a leaving group known in the art, for example halides (such as bromide), in a suitable solvent (for example acetonitrile) in the presence of a suitable base (for example potassium carbonate) and at a suitable temperature (such as 80-90° C.).

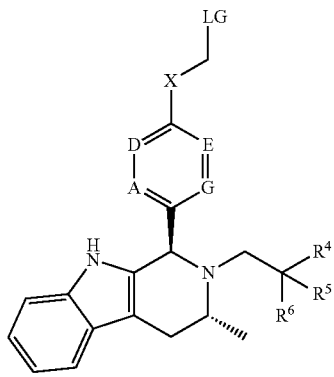

(VIII)

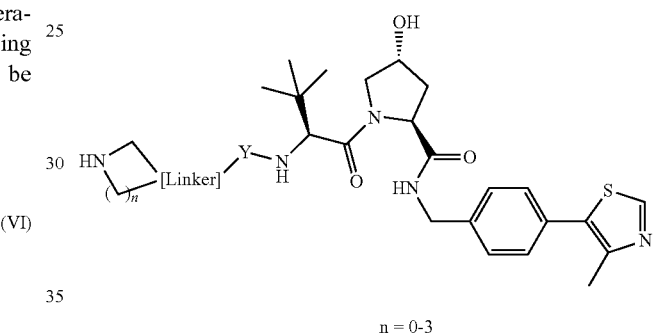

(IX)

n = 0-3 e) Terminal alkyne heterodimerization of compounds of Formula (X) and Formula (XI) under suitable Glaser coupling conditions, for example, using a suitable catalyst (such as diacetoxycopper), a suitable base (such as pyridine), in a suitable solvent (such as acetonitrile), and in the presence of air for oxygen exposure. The dialkyne linker can be further reduced to form an alkanyl group under suitable hydrogenation conditions, such as using 10% palladium on carbon as the catalyst and under hydrogen atmosphere.

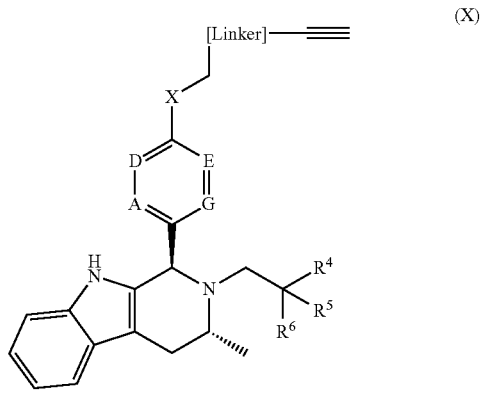

(X)

(XI)

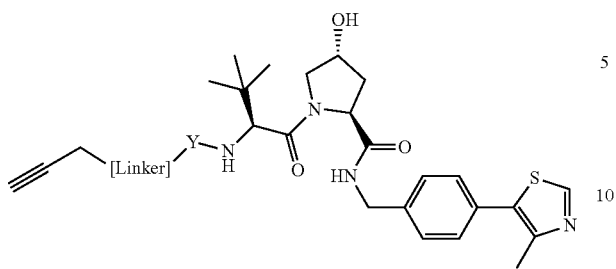

(XII)

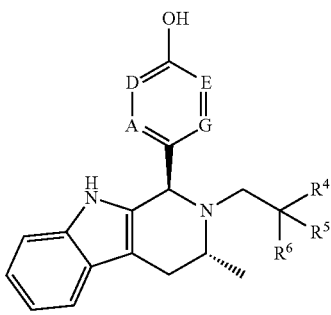

(XIII)

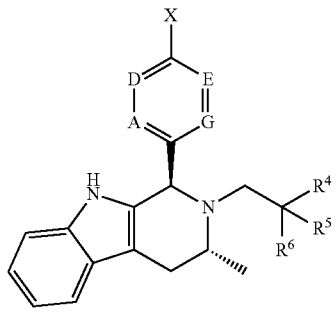

(XIV)

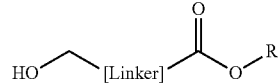

(XV)

(XVI)

(XVII)

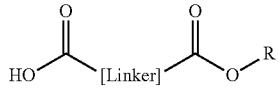

(XVIII)

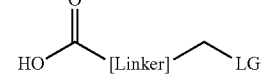

(XIX)

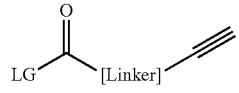

Compounds of Formula (II) may be made by, for example:

a) Reaction of a compound of Formula (XII) with a compound of Formula (XIV) where R is an alkyl group (such as methyl, ethyl, or t-butyl) under conditions known in the art as suitable for Mitsunobu reactions, such as in the presence of diisopropyl (E)-diazene-1,2-dicarboxylate and triphenylphosphine, and in a suitable solvent (for example dichloromethane) and a suitable temperature (such as room temperature); followed by hydrolysis of the methyl or ethyl ester under a suitable condition, such as in the presence of a suitable base (for example sodium hydroxide) in a suitable solvent system (for example a cosolvent of water, THF, and MeOH); or followed by conversion of the tert-butyl ester to the acid compounds of Formula (II) under a suitable anhydrous acid treatment conditions, such as anhydrous hydrochloric acid in a suitable solvent, for example THF.

b) Amide coupling reaction of a compound of Formula (IV) with a compound of Formula (XVII) under conditions known in the art as suitable amide coupling reactions, such as in the presence of a suitable amide coupling reagent (for example HATU) and a suitable base (for example trimethylamine) and in a suitable solvent (for example DMF) and a suitable temperature (such as room temperature), followed by hydrolysis of the methyl or ethyl ester under a suitable condition, such as in the presence of a suitable base (for example sodium hydroxide) in a suitable solvent system (for example a cosolvent of water, THF, and MeOH); followed by conversion of the tert-butyl ester to the acid compounds of Formula (II) under a suitable anhydrous acid treatment, such as anhydrous hydrochloric acid in a suitable solvent, for example THF. In certain aspect, the linker group is with a protecting group (such as Boc or Cbz) on the nitrogen that may be removed under conditions known in the art.

c) Etherification of a suitable compound of Formula (XIII), where X is for example a halogen (such as Br) or a trifluoromethanesulfonyl (triflate) group, with an alcohol of Formula (XIV) using a suitable metal catalyst (for example RockPhos 3rd Generation Precatalyst or BrettPhos 3rd Generation Precatalyst) in a suitable solvent (for example toluene, THF or DME) in the presence of a suitable base (for example cesium carbonate or potassium carbonate) and a suitable temperature (such as 90-120° C.), followed by hydrolysis of the methyl or ethyl ester where R is methyl or ethyl in Formula (XIV) under a suitable condition, such as in the presence of a suitable base (for example sodium hydroxide) in a suitable solvent system (for example a cosolvent of water, THF, and MeOH); or followed by conversion of the tert-butyl ester where R is a tert-butyl in Formula (XIV) to the acid compounds of Formula (II) under a suitable anhydrous acid treatment condition, such as anhydrous hydrochloric acid in a suitable solvent (for example THF).

Compounds of Formula (VIII) can be made by, for example:

a) Reaction of a compound of Formula (XII) with a compound of Formula (XV) where LG is a leaving group (such as bromide) under conditions known in the art as suitable for Mitsunobu reactions, such as in the presence of diisopropyl (E)-diazene-1,2-dicarboxylate and triphenylphosphine, and in a suitable solvent (for example dichloromethane) and a suitable temperature (such as room temperature).

b) Amide coupling reaction of a compound of Formula (IV) with a compound of Formula (XVIII) under conditions known in the art as suitable amide coupling reactions, such as in the presence of a suitable amide coupling reagent (such as HATU) and a suitable base (such as trimethylamine) and in a suitable solvent (for example DMF) and a suitable temperature (such as room temperature).

Compounds of Formula (X) may be made by, for example:

c) Alkylation of a suitable compound of Formulas (XII) or Formula (IV), with a compound of Formula (XVI) where LG is a leaving group known in the art, for example halide (such as Br), in a suitable solvent (for example acetonitrile) in the presence of a suitable base (for example potassium carbonate) and a suitable temperature (such as 80-90° C.).

d) Amide coupling reaction of a compound of Formula (IV) with a compound of Formula (XIX) under conditions known in the art as suitable amide coupling reactions, such as in the presence of a suitable amide coupling reagent (such as HATU) and a suitable base (such as trimethylamine) and in a suitable solvent (for example DMF) and a suitable temperature (such as room temperature).

Compounds of Formula (V) may be made by, for example:

a) Amide coupling reaction of a compound of Formula (III) with a compound of Formula (XVII) where R is an alkyl group (such as methyl, ethyl, or tert-butyl) under conditions known in the art as suitable amide coupling reactions, such as in the presence of a suitable amide coupling reagent (such as HATU) and a suitable base (such as trimethylamine) and in a suitable solvent (for example DMF) and a suitable temperature (such as room temperature); followed by hydrolysis of the methyl or ethyl ester where R is methyl or ethyl in Formula (XVII) under a suitable condition, such as in the presence of a suitable base (for example sodium hydroxide) in a suitable solvent system (for example a cosolvent of water, THF, and MeOH); or followed by conversion of the tert-butyl ester where R is a tert-butyl in Formula (XVII) to the acid compounds of Formula (V) under a suitable anhydrous acid treatment, such as anhydrous hydrochloric acid in a suitable solvent (for example THF).

b) Alkylation of an amine compound Formula (III) with a compound of Formula (XVIII) where LG is a leaving group known in the art, for example halide (such as Br), in a suitable solvent (for example acetonitrile) in the presence of a suitable base (for example potassium carbonate) and a suitable temperature (such as 80-90° C.).

Compounds of Formula (VII) may be made by, for example:

a) Amide coupling reaction of an amine compound of Formula (III) with an acid of Formula (XX) where R is an alkyl group and PG is a nitrogen protecting group known in the art (such as Boc or Cbz groups) under conditions known in the art as suitable amide coupling reactions, such as in the presence of a suitable amide coupling reagent (such as HATU) and a suitable base (such as trimethylamine) and in a suitable solvent (for example DMF) and a suitable temperature (such as room temperature); followed by protecting group removal under suitable conditions, such as anhydrous hydrochloric acid treatment in THF for Boc deprotection.

b) Alkylation of an amine compound Formula (III) with a compound of Formula (XXI) where R is an alkyl group (such as methyl) and PG is a nitrogen protecting group known in the art (such as Boc or Cbz groups) in a suitable solvent (for example acetonitrile) in the presence of a suitable base (for example potassium carbonate) and a suitable temperature (such as 80-90° C.); followed by protecting group removal under suitable conditions, such as anhydrous hydrochloric acid treatment in THF for Boc deprotection.

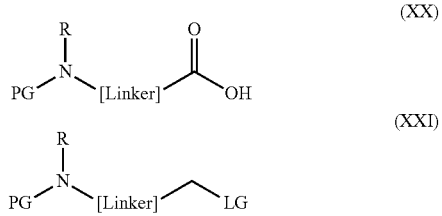

Compounds of Formula (IX) may be made by, for example:

a) Amide coupling reaction of an amine compound of Formula (III) with an acid of Formula (XXII) where PG is a nitrogen protecting group known in the art (for example Boc or Cbz) under conditions known in the art as suitable amide coupling reactions, such as in the presence of a suitable amide coupling reagent (such as HATU) and a suitable base (such as trimethylamine) and in a suitable solvent (for example DMF) and a suitable temperature (such as room temperature); followed by protecting group removal under suitable conditions known in the art, such as anhydrous hydrochloric acid treatment in THF for Boc deprotection.

b) Alkylation of an amine compound Formula (III) with a compound of Formula (XXIII) where PG is a nitrogen protecting group known in the art (for example Boc or Cbz) in a suitable solvent (for example acetonitrile) in the presence of a suitable base (for example potassium carbonate) and a suitable temperature (such as 80-90° C.); followed by protecting group removal under suitable conditions known in the art, such as anhydrous hydrochloric acid treatment in THF for Boc deprotection.

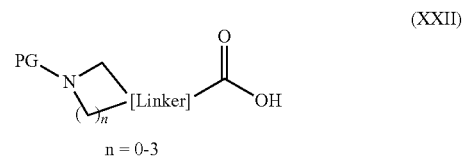

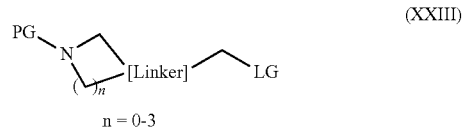

Compounds of Formula (XI) may be made by, for example:

a) Amide coupling reaction of an amine compound of Formula (III) with an acid of Formula (XIX) under conditions known in the art as suitable amide coupling reactions, such as in the presence of a suitable amide coupling reagent (such as HATU) and a suitable base (such as trimethylamine) and in a suitable solvent (for example DMF) and a suitable temperature (such as room temperature).

b) Alkylation of an amine compound Formula (III) with a compound of Formula (XVI) where LG is a leaving group known in the art, for example halide (such as Br) in a suitable solvent (for example acetonitrile) in the presence of a suitable base (for example potassium carbonate) and a suitable temperature (such as 80-90° C.).

Compounds of Formulas (IV), (XII), and (XIII) may be made by, for example:

Reaction of a compound of Formula (XXIV) with a compound of Formula (XXV) where X is hydroxyl, amino, or halides (for example bromide) under conditions known in the art as suitable for Pictet-Spengler reactions (such as in the presence of acid (such as acetic acid) and in a suitable solvent (for example toluene) and a suitable temperature (such as 80-100° C.) with or without a protecting group (PG) on the nitrogen that may be removed under conditions known to the art.

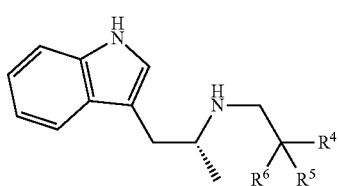
(XXIV)

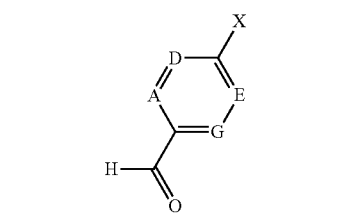
(XXV)

Compounds of Formula (VI) may be prepared according to the procedures described in WO2014191726 A1, herein incorporated by reference, for those having ordinary skill in the art.

Compounds of Formulas (XXIV) may be made by, for example:

a) Reaction of a compound of Formula (XXVI) with an aldehyde of Formula (XXVII), in a suitable solvent (for example THF) in the presence of a suitable reducing agent (such as sodium triacetoxyborohydride) and at a suitable temperature (such as 20-30° C.);

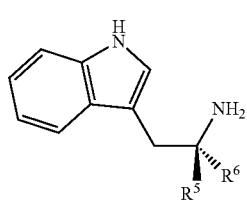
(XXVI)

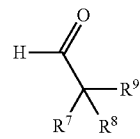
(XXVII)

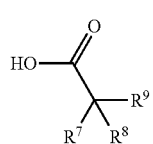
(XXVIII)

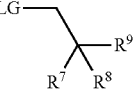
(XXIX)

b) (i) Reaction of a compound of Formula (XXVI) with an acid of Formula (XXVIII) under standard amide bond forming conditions (for example in the presence of an amide coupling reagent (such as HATU) and a suitable base (such as triethylamine) in a suitable solvent (such as DMF)), followed by (ii) reduction of the resultant amide bond using a suitable reducing agent (such as borane) in a suitable solvent (such as THF) at a suitable temperature (such as 60-70° C.);

c) Alkylation of a compound of Formula (XXVI) with a compound of Formula (XXIX), wherein LG is a suitable leaving group (for example a halogen atom (such as bromide or chloride) or trifluoromethanesulfone), in the presence of a suitable base (such as diisopropylethylamine) in a suitable solvent (for example DCM or dioxane) and at a suitable temperature (such as 20-85° C.)).

Compounds of Formula (III) may be prepared in reference to the procedures described in WO2016149668 A1, herein incorporated by reference, for those having ordinary skill in the art.

It is to be understood that other permutations of the process steps in the process variants described above are also possible.

When a pharmaceutically acceptable salt of a compound of Formula (I) is required it may be obtained by, for example, reaction of said compound with a suitable acid or suitable base. When a pharmaceutically acceptable prodrug of a compound of Formula (I) is required, it may be obtained using a conventional procedure.

It will also be appreciated that, in some of the reactions mentioned hereinbefore, it may be necessary or desirable to protect any sensitive functionalities in the compounds. The instances where protection is necessary or desirable, and suitable methods for protection, are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy, it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an alkoxycarbonyl group such as a t-butoxycarbonyl group may be removed, for example, by treatment with a suitable acid as hydrochloric, sulphuric, formic, phosphoric or trifluoroacetic acid, and an arylmethoxycarbonyl group such as a benzyloxycarbonyl group may be removed, for example, by hydrogenation over a catalyst such as palladium-on-carbon, or by treatment with a Lewis acid, such as boron tris(trifluoroacetate). A suitable alternative protecting group for a primary amino group is, for example, a phthaloyl group, which may be removed by treatment with an alkylamine, for example dimethylaminopropylamine, or hydrazine.

A suitable protecting group for a hydroxy group is, for example, an acyl group, for example an alkanoyl group such as acetyl, an aroyl group, for example benzoyl, an arylmethyl group, for example benzyl, or a trialkyl or diarylalkyl silane, such as TBDMS or TBDPS. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain of the intermediates defined herein are novel and these are provided as further features of the specification.

Biological Assays

The following assays were used to measure the effects of the compounds of the present specification.

ERα Binding Assay

The ability of compounds to bind to isolated Estrogen Receptor Alpha Ligand binding domain (ER alpha-LBD (GST)) was assessed in competition assays using a LanthaScreen™ Time-Resolved Fluorescence Resonance Energy Transfer (TR-FRET) detection end-point. For the LanthaScreen TR-FRET endpoint, a suitable fluorophore (Fluormone ES2, ThermoFisher, Product code P2645) and recombinant human Estrogen Receptor alpha ligand binding domain, residues 307-554 (expressed and purified in-house) were used to measure compound binding. The assay principle is that ER alpha-LBD (GST) is added to a fluorescent ligand to form a receptor/fluorophore complex. A terbium-labelled anti-GST antibody (Product code PV3551) is used to indirectly label the receptor by binding to its GST tag, and competitive binding is detected by a test compound's ability to displace the fluorescent ligand, resulting in a loss of TR-FRET signal between the Tb-anti-GST antibody and the tracer. The assay was performed as follows with all reagent additions carried out using the Beckman Coulter BioRAPTR FRD microfluidic workstation:

1. Acoustic dispense 120 nL of the test compound into a black low volume 384 well assay plates.
2. Prepare 1×ER alpha-LBD/Tb-antiGST Ab in ES2 screening buffer and incubate for 15 minutes.
3. Dispense 6 µL of the 1×AR-LBD/Tb-anti-GST Ab reagent into each well of the assay plate followed by 6 µL of Fluorophore reagent into each well of the assay plate
4. Cover the assay plate to protect the reagents from light and evaporation, and incubate at room temperature for 4 hours.
5. Excite at 337 nm and measure the fluorescent emission signal of each well at 490 nm and 520 nm using the BMG PheraSTAR.

Compounds were dosed directly from a compound source microplate containing serially diluted compound (4 wells containing 10 mM, 0.1 mM, 1 mM and 10 nM final compound respectively) to an assay microplate using the Labcyte Echo 550. The Echo 550 is a liquid handler that uses acoustic technology to perform direct microplate-to-microplate transfers of DMSO compound solutions and the system can be programmed to transfer multiple small nL volumes of compound from the different source plate wells to give the desired serial dilution of compound in the assay which is then back-filled to normalise the DMSO concentration across the dilution range.

In total 120 nL of compound plus DMSO were added to each well and compounds were tested in a 12-point concentration response format over a final compound concentration range of 10, 2.917, 1.042, 0.2083, 0.1, 0.0292, 0.0104, 0.002083, 0.001, 0.0002917, 0.0001042, and 0.00001 µM respectively. TR-FRET dose response data obtained with each compound was exported into a suitable software package (such as Origin or Genedata) to perform curve fitting analysis. Competitive ER alpha binding was expressed as an $IC_{50}$ value. This was determined by calculation of the concentration of compound that was required to give a 50% reduction in tracer compound binding to ER alpha-LBD.

MCF-7 ER Degradation Assay

The ability of compounds to down-regulate Estrogen Receptor (ER) numbers was assessed in a cell based immuno-fluorescence assay using the MCF-7 human ductal carcinoma breast cell line. MCF-7 cells were revived directly from a cryovial (approx $5 \times 10^6$ cells) in Assay Medium (phenol red free Dulbecco's Modified Eagle's medium (DMEM); Sigma D5921) containing 2 mM L-Glutamine and 5% (v/v) Charcoal/Dextran treated foetal calf serum. Cells were syringed once using a sterile 18 G×1.5 inch (1.2×40 mm) broad gauge needle and cell density was measured using a Coulter Counter (Beckman). Cells were further diluted in Assay Medium to a density of $3.75 \times 10^4$ cells per mL and 40 µL per well added to transparent bottomed, black, tissue culture-treated 384 well plates (Costar, No. 3712) using a Thermo Scientific Matrix WellMate or Thermo Multidrop. Following cell seeding, plates were incubated overnight at 37° C., 5% $CO_2$ (Liconic carousel incubator). Test data was generated using the LabCyte Echo™ model 555 compound reformatter which is part of an automated workcell (Integrated Echo 2 workcell). Compound stock solutions (10 mM) of the test compounds were used to generate a 384 well compound dosing plate (Labcyte P-05525-CV1). 40 µL of each of the 10 mM compound stock solutions was dispensed into the first quadrant well and then 1:100 step-wise serial dilutions in DMSO were performed using a Hydra II (MATRIX UK) liquid handling unit to give 40 µL of diluted compound into quadrant wells 2 (0.1 mM), 3 (1 µM) and 4 (0.01 µM), respectively. 40 µL of DMSO added to wells in row P on the source plate allowed for DMSO normalisation across the dose range. To dose the control wells 40 µL of DMSO was added to row O1 and 40 µL of 100 µM fulvestrant in DMSO was added to row O3 on the compound source plate.

The Echo uses acoustic technology to perform direct microplate-to-microplate transfers of DMSO compound solutions to assay plates. The system can be programmed to transfer volumes as low as 2.5 nL in multiple increments between microplates and in so doing generates a serial dilution of compound in the assay plate which is then back-filled to normalise the DMSO concentration across the dilution range. Compounds were dispensed onto the cell plates with a compound source plate prepared as above producing a 12 point duplicate 3 µM to 3 µM dose range with 3-fold dilutions and one final 10-fold dilution using the Integrated Echo 2 workcell. The maximum signal control wells were dosed with DMSO to give a final concentration of 0.3%, and the minimum signal control wells were dosed with fulvestrant to give a final concentration of 100 nM accordingly. Plates were further incubated for 18-22 hours at 37° C., 5% $CO_2$ and then fixed by the addition of 20 µL of 11.1% (v/v) formaldehyde solution (in phosphate buffered saline (PBS)) giving a final formaldehyde concentration of 3.7% (v/v). Cells were fixed at room temperature for 20 mins before being washed two times with 250 µL PBS/Proclin (PBS with a Biocide preservative) using a BioTek plate-washer, 40 µL of PBS/Proclin was then added to all wells and the plates stored at 4° C. The fixing method described above was carried out on the Integrated Echo 2 workcell. Immunostaining was performed using an automated AutoElisa workcell. The PBS/Proclin was aspirated from all wells and the cells permeabilised with 40 µL PBS containing 0.5% Tween™ 20 (v/v) for 1 hour at room temperature. The plates were washed three times in 250 µL of PBS/0.05% (v/v) Tween 20 with Proclin (PBST with a Biocide preservative) and then 20 µL of ERα (SP1) Rabbit monoclonal antibody (Thermofisher) 1:1000 in PBS/Tween™/3% (w/v) Bovine Serum Albumin was added. The plates were incubated overnight at 4° C. (Liconic carousel incubator) and then washed three times in 250 µL of PBS/0.05% (v/v) Tween™ 20 with Proclin (PBST). The plates were then incubated with 20 µL/well of a goat anti-rabbit IgG AlexaFluor 594 antibody with Hoechst at 1:5000 in PBS/Tween™/3% (w/v) Bovine Serum Albumin for 1 hour at room temperature. The plates were then washed three times in 250 µL of PBS/0.05% (v/v) Tween™ 20 with Proclin (PBST with a Biocide preservative). 20 µL of PBS was added to each well and the plates covered with a black plate seal and stored at 4° C. before being read.

Plates were read using a Cellomics Cellinsight reading the 594 nm to measure the ERα receptor level in each well. The MEAN_CircSpotTotalInten algorithm was calculated used to represent ERα expression. The data was exported into Genedata to perform curve fitting analysis. Down-regulation of the ERα receptor was expressed as an $IC_{50}$ value and was determined by calculation of the concentration of compound that was required to give a 50% reduction of ERα expression.

The data shown in Table A were generated (the data below may be a result from a single experiment or an average of two or more experiments). Certain compounds of the invention showed greater than or equal to 90% of ERα degradation at 0.3 µM in the MCF-7 ER degradation cellular assay, where ER degradation by fulvestrant at 0.3 µM is defined as 100%. Compounds with 90-99% ERα degradation are marked with "●" in the fourth column of Table A and compounds with greater than or equal to 100% ERα degradation are marked with "●●".

TABLE A

| Ex. | ER binding IC50 (nM) | MCF-7 ER degradation IC50 (nM) | ER degradation ≥ 90% at 0.3 µM |
|---|---|---|---|
| 1 | 0.9 | 0.7 | |
| 2 | 0.6 | 2.9 | |
| 3 | 0.8 | 0.3 | ●● |
| 4 | 0.8 | 2.1 | ● |
| 5 | 0.8 | 2.6 | ● |
| 6 | 4.2 | 3.6 | ●● |
| 7 | 1.2 | 1.6 | ●● |
| 8 | 6.8 | 9.4 | ●● |
| 9 | 0.8 | 0.7 | ●● |
| 10 | 39 | 12 | ●● |
| 11 | 1.5 | 3.2 | ●● |
| 12 | 1.6 | 6.6 | ●● |
| 13 | 5.0 | 3.7 | ● |
| 14 | 0.9 | 1.4 | ● |
| 15 | 1.5 | 3.9 | ● |
| 16 | 0.8 | 0.8 | ●● |
| 17 | 5.5 | 41 | ● |
| 18 | 0.6 | 1.0 | ● |
| 19 | NT | 3.2 | ●● |
| 20 | 1.0 | 1.7 | ● |
| 21 | 13 | 300 | |
| 22 | 0.7 | 3.0 | ● |
| 23 | 1.1 | 1.0 | ●● |
| 24 | 18 | 300 | |
| 25 | 0.5 | 0.4 | ●● |
| 26 | 25 | 7.5 | ● |
| 27 | 1.1 | 22 | |
| 28 | 0.8 | 0.8 | ● |
| 29 | 5.9 | 2.4 | ●● |
| 30 | 4.1 | 174 | |
| 31 | 0.6 | 0.3 | |
| 32 | 2.3 | 13 | ● |
| 33 | 8.9 | 29 | ●● |
| 34 | 0.9 | 1.0 | ● |
| 35 | 1.0 | 9.1 | |
| 36 | 1.0 | 1.0 | |
| 37 | 6.4 | 3.0 | ●● |
| 38 | 0.7 | 0.3 | ●● |
| 39 | 0.7 | 0.8 | ● |
| 40 | 1.3 | 0.6 | ● |
| 41 | 0.7 | 1.7 | |
| 42 | 1.3 | 1.9 | |
| 43 | 2.3 | 4.8 | |
| 44 | 1.3 | 1.8 | |
| 45 | 1.2 | 12 | ●● |
| 46 | 0.8 | 2.0 | |
| 47 | 0.7 | 0.6 | ● |
| 48 | 1.0 | 1.8 | ● |
| 49 | 1.0 | 0.9 | ● |
| 50 | 1.2 | 6.6 | |
| 51 | 2.0 | 6.8 | ● |
| 52 | 1.1 | 2.1 | |
| 53 | 1.0 | 3.5 | ● |
| 54 | 16 | 1.7 | ●● |
| 55 | 12 | 1.2 | ● |
| 56 | 20 | 1.5 | ●● |
| 57 | 8.8 | 0.9 | ● |
| 58 | 0.9 | 0.4 | ● |
| 59 | NT | 0.8 | ●● |
| 60 | 0.7 | 0.5 | ● |
| 61 | 1.0 | 0.7 | ●● |
| 62 | 0.5 | 0.6 | ● |
| 63 | 1.0 | 0.6 | ●● |
| 64 | 0.4 | 0.5 | ● |
| 65 | 1.1 | 4.5 | |
| 66 | 1.2 | 2.2 | ● |
| 67 | 1.1 | 4.5 | ● |
| 68 | 1.0 | 6.2 | ●● |
| 70 | 0.8 | 0.9 | |
| 71 | 1.3 | 0.5 | ● |
| 72 | 0.6 | 0.4 | ●● |
| 73 | 1.0 | 4.9 | ●● |
| 74 | 0.8 | 14.3 | ●● |
| 77 | 2.6 | 1.0 | ●● |
| 78 | 0.5 | 0.6 | ●● |
| 79 | 0.9 | 2.0 | ● |
| 80 | 0.7 | 0.7 | ●● |
| 82 | 0.9 | 0.2 | ●● |

TABLE A-continued

| Ex. | ER binding IC50 (nM) | MCF-7 ER degradation IC50 (nM) | ER degradation ≥ 90% at 0.3 μM |
|---|---|---|---|
| 83 | 1.1 | 0.6 | •• |
| 84 | 1.3 | 0.7 | •• |
| 85 | 0.9 | 0.6 | •• |
| 86 | 0.7 | 0.6 | •• |
| 89 | 0.7 | 0.7 | • |
| 90 | 1.2 | 102 | |
| 91 | 1.3 | 0.3 | •• |
| 92 | 0.6 | 0.4 | |
| 93 | 0.7 | 0.9 | • |
| 94 | 0.9 | 0.6 | • |
| 95 | 1.2 | 0.4 | •• |
| 96 | 0.6 | 1.3 | • |
| 97 | 0.5 | 0.8 | •• |
| 98 | 0.6 | 0.4 | |
| 99 | 1.2 | 1.6 | • |
| 100 | 0.8 | 0.4 | •• |
| 101 | 3.3 | 1.8 | • |
| 102 | 0.6 | 0.9 | |
| 104 | 4.6 | 54 | |
| 106 | 0.8 | 0.9 | • |
| 107 | 4.0 | 1.0 | •• |
| 108 | 0.6 | 1.1 | |
| 109 | 0.6 | 1.0 | •• |
| 110 | 0.7 | 1.7 | •• |
| 111 | 0.6 | 0.8 | • |
| 112 | 0.5 | 2.2 | •• |
| 113 | 0.6 | 0.9 | •• |
| 114 | 0.9 | 3.6 | •• |
| 115 | 0.7 | 3.4 | •• |
| 116 | 1.0 | 5.3 | • |
| 117 | 0.8 | 22 | |
| 118 | 0.7 | 4.7 | • |
| 119 | 0.8 | 1.4 | • |
| 120 | 0.9 | 1.6 | •• |
| 121 | 0.7 | 2.6 | • |
| 122 | 1.5 | 2.0 | • |
| 123 | NT | 0.5 | • |
| 124 | NT | 0.8 | • |
| 125 | 1.0 | 0.7 | •• |
| 126 | NT | 1.8 | • |
| 127 | 0.5 | 0.8 | •• |
| 128 | 0.6 | 0.6 | •• |
| 129 | 1.0 | 0.8 | •• |
| 130 | 0.9 | 0.5 | • |
| 131 | 1.6 | 0.8 | • |
| 132 | 0.5 | 0.6 | • |
| 133 | 0.7 | 0.8 | |
| 134 | 0.6 | 0.5 | • |
| 135 | NT | 2.0 | • |
| 136 | 1.2 | 1.1 | •• |
| 137 | 0.8 | 0.8 | •• |
| 138 | 0.6 | 1.1 | •• |
| 139 | 0.5 | 1.1 | •• |
| 140 | 0.5 | 0.6 | •• |
| 141 | 1.2 | 0.9 | • |
| 142 | 1.1 | 0.2 | •• |
| 143 | 1.1 | 0.2 | •• |
| 144 | 1.3 | 0.5 | •• |
| 145 | 1.1 | 2.7 | |
| 146 | 0.8 | 0.6 | • |
| 147 | 1.0 | 5.8 | • |
| 151 | 3.6 | 54 | |
| 152 | 0.5 | 0.8 | •• |
| 153 | 0.3 | 0.4 | •• |
| 154 | 0.4 | 0.7 | • |
| 155 | 0.3 | 0.7 | |
| 156 | 0.6 | 1.5 | •• |
| 157 | 0.8 | 0.4 | •• |
| 158 | 0.8 | 0.8 | • |
| 159 | 0.7 | 0.5 | •• |
| 161 | 0.7 | 1.2 | • |
| 162 | 1.1 | 1.8 | • |
| 164 | 6.6 | 4.2 | •• |
| 165 | 11.4 | 4.4 | •• |
| 166 | 0.8 | 0.8 | •• |
| 167 | 0.9 | 0.6 | •• |
| 168 | NT | 0.5 | • |

NT = not tested

According to a further aspect of the specification there is provided a pharmaceutical composition, which comprises a compound of the Formula (I) or a pharmaceutically acceptable salt or prodrug thereof, as defined hereinbefore in association with a pharmaceutically acceptable excipient.

The compositions may be in a form suitable for oral use (for example as tablets, lozenges, hard or soft capsules, aqueous or oily suspensions, emulsions, dispersible powders or granules, syrups or elixirs) or for parenteral administration (for example as a sterile aqueous or oily solution for intravenous, subcutaneous or intramuscular dosing). The compositions may be obtained by conventional procedures using conventional pharmaceutical excipients, well known in the art. Thus, compositions intended for oral use may contain, for example, one or more colouring, sweetening, flavouring and/or preservative agents.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration.

The size of the dose for therapeutic or prophylactic purposes of compounds of the present specification will naturally vary according to the nature and severity of the disease state, the age and sex of the animal or patient and the route of administration, according to well known principles of medicine.

As stated above, it is known that signalling through ERα causes tumorigenesis by one or more of the effects of mediating proliferation of cancer and other cells, mediating angiogenic events and mediating the motility, migration and invasiveness of cancer cells. We have found that the compounds of the present specification possess potent anti-proliferative activity in ER positive breast cancer cell lines which is believed to be a result of antagonism and degradation of ERα protein.

Accordingly, the compounds of the present specification may be of value as anti-tumour agents, in particular as selective inhibitors of the proliferation, survival, motility, dissemination and invasiveness of mammalian cancer cells leading to inhibition of tumour growth and survival and to inhibition of metastatic tumour growth. Particularly, the compounds of the present specification may be of value as anti-proliferative and anti-invasive agents in the containment and/or treatment of solid tumour disease. Particularly, the compounds of the present specification may be useful in the prevention or treatment of those tumours which are sensitive to inhibition of ERα and that are involved in the signal transduction steps which lead to the proliferation and survival of tumour cells and the migratory ability and invasiveness of metastasising tumour cells. Further, the compounds of the present specification may be useful in the prevention or treatment of those tumours which are mediated alone or in part by antagonism and degradation of ERα, i.e. the compounds may be used to produce an ERα inhibitory effect in a warm-blooded animal in need of such treatment.

According to a further aspect of the specification there is provided a compound of the Formula (I) or a pharmaceutically acceptable salt or prodrug thereof, as defined hereinbefore for use as a medicament in a warm-blooded animal such as man.

According to a further aspect of the specification, there is provided a compound of the Formula (I), or a pharmaceutically acceptable salt or prodrug thereof, as defined hereinbefore for use in the production of an anti-proliferative effect in a warm-blooded animal such as man.

According to a further aspect of the specification there is provided the use of a compound of the Formula (I), or a pharmaceutically acceptable salt or prodrug thereof, as defined hereinbefore, in the manufacture of a medicament for use in the production of an anti-proliferative effect in a warm-blooded animal such as man.

According to a further aspect of the specification there is provided a method for producing an anti-proliferative effect in a warm-blooded animal, such as man, in need of such treatment which comprises administering to said animal an effective amount of a compound of the Formula (I), or a pharmaceutically acceptable salt or prodrug thereof, as defined hereinbefore.

According to a further aspect of the specification there is provided a compound of the Formula (I), or a pharmaceutically acceptable salt or prodrug thereof, as defined hereinbefore for use in a warm-blooded animal such as man as an anti-invasive agent in the containment and/or treatment of solid tumour disease.

According to a further aspect of the specification there is provided the use of a compound of the Formula (I), or a pharmaceutically acceptable salt or prodrug thereof, as defined hereinbefore, in the manufacture of a medicament for use in a warm-blooded animal such as man as an anti-invasive agent in the containment and/or treatment of solid tumour disease.

According to a further aspect of the specification there is provided a method for producing an anti-invasive effect by the containment and/or treatment of solid tumour disease in a warm-blooded animal, such as man, in need of such treatment which comprises administering to said animal an effective amount of a compound of the Formula (I), or a pharmaceutically acceptable salt or prodrug thereof, as defined hereinbefore.

According to a further aspect of the specification, there is provided a compound of the Formula (I), or a pharmaceutically acceptable salt or prodrug thereof, as defined hereinbefore, for use in the prevention or treatment of cancer in a warm-blooded animal such as man.

According to a further aspect of the specification there is provided the use of a compound of the Formula (I), or a pharmaceutically acceptable salt or prodrug thereof, as defined hereinbefore in the manufacture of a medicament for use in the prevention or treatment of cancer in a warm-blooded animal such as man.

According to a further aspect of the specification there is provided a method for the prevention or treatment of cancer in a warm-blooded animal, such as man, in need of such treatment which comprises administering to said animal an effective amount of a compound of the Formula (I), or a pharmaceutically acceptable salt or prodrug thereof, as defined hereinbefore.

According to a further aspect of the specification, there is provided a compound of the Formula (I), or a pharmaceutically acceptable salt or prodrug thereof, as defined hereinbefore for use in the prevention or treatment of solid tumour disease in a warm-blooded animal such as man.

According to a further aspect of the specification there is provided the use of a compound of the Formula (I), or a pharmaceutically acceptable salt or prodrug thereof, as defined hereinbefore, in the manufacture of a medicament for use in the prevention or treatment of solid tumour disease in a warm-blooded animal such as man.

According to a further aspect of the specification there is provided a method for the prevention or treatment of solid tumour disease in a warm-blooded animal, such as man, in need of such treatment which comprises administering to said animal an effective amount of a compound of the Formula (I), or a pharmaceutically acceptable salt or prodrug thereof, as defined hereinbefore.

According to a further aspect of the specification there is provided a compound of the Formula (I), or a pharmaceutically acceptable salt or prodrug thereof, as defined hereinbefore, for use in the prevention or treatment of those tumours which are sensitive to inhibition of ERα that are involved in the signal transduction steps which lead to the proliferation, survival, invasiveness and migratory ability of tumour cells.

According to a further aspect of the specification there is provided the use of a compound of the Formula (I), or a pharmaceutically acceptable salt or prodrug thereof, as defined hereinbefore, in the manufacture of a medicament for use in the prevention or treatment of those tumours which are sensitive to inhibition of ERα that are involved in the signal transduction steps which lead to the proliferation, survival, invasiveness and migratory ability of tumour cells.

According to a further aspect of the specification there is provided a method for the prevention or treatment of those tumours which are sensitive to inhibition of ERα that are involved in the signal transduction steps which lead to the proliferation, survival, invasiveness and migratory ability of tumour cells which comprises administering to said animal an effective amount of a compound of the Formula (I), or a pharmaceutically acceptable salt or prodrug thereof, as defined hereinbefore.

According to a further aspect of the specification there is provided a compound of the Formula (I), or a pharmaceutically acceptable salt or prodrug thereof, as defined hereinbefore for use in providing an inhibitory effect on ERα.

According to a further aspect of the specification there is provided the use of a compound of the Formula (I), or a pharmaceutically acceptable salt or prodrug thereof, as defined hereinbefore in the manufacture of a medicament for use in providing an inhibitory effect on ERα.

According to a further aspect of the specification there is also provided a method for providing an inhibitory effect on ERα which comprises administering an effective amount of a compound of the Formula (I), or a pharmaceutically acceptable salt or prodrug thereof, as defined hereinbefore.

According to a further aspect of the specification there is provided a compound of the Formula (I), or a pharmaceutically acceptable salt or prodrug thereof, as defined hereinbefore, for use in providing a selective inhibitory effect on ERα.

According to a further aspect of the specification there is provided the use of a compound of the Formula (I), or a pharmaceutically acceptable salt or prodrug thereof, as defined hereinbefore, in the manufacture of a medicament for use in providing a selective inhibitory effect on ERα.

According to a further aspect of the specification there is also provided a method for providing a selective inhibitory effect on ERα which comprises administering an effective amount of a compound of the Formula (I), or a pharmaceutically acceptable salt or prodrug thereof, as defined hereinbefore.

Described herein are compounds that can bind to ERα ligand binding domain and selectively induce ERα degradation. In biochemical and cell based assays the compounds of the present specification are shown to be potent estrogen receptor binders and reduce cellular levels of ERα and may therefore be useful in the treatment of estrogen sensitive diseases or conditions (including diseases that have developed resistance to endocrine therapies), i.e. for use in the treatment of cancer of the breast and gynaecological cancers (including endometrial, ovarian and cervical) and cancers expressing ERα mutated proteins which may be de novo mutations or have arisen as a result of treatment with a prior endocrine therapy such as an aromatase inhibitor.

According to a further aspect of the specification there is provided a compound of the Formula (I), or a pharmaceutically acceptable salt or prodrug thereof, as defined hereinbefore, for use in the treatment of breast or gynaecological cancers.

According to a further aspect of the specification there is provided the use of a compound of the Formula (I), or a pharmaceutically acceptable salt or prodrug thereof, as defined hereinbefore, in the manufacture of a medicament for use in the treatment of breast or gynaecological cancers.

According to a further aspect of the specification there is provided a method for treating breast or gynaecological cancers, which comprises administering an effective amount of a compound of the Formula (I), or a pharmaceutically acceptable salt or prodrug thereof, as defined hereinbefore.

According to a further aspect of the specification there is provided a compound of the Formula (I), or a pharmaceutically acceptable salt or prodrug thereof, as defined hereinbefore, for use in the treatment of cancer of the breast, endometrium, ovary or cervix.

According to a further aspect of the specification there is provided the use of a compound of the Formula (I), or a pharmaceutically acceptable salt or prodrug thereof, as defined hereinbefore, in the manufacture of a medicament for use in the treatment of cancer of the breast, endometrium, ovary or cervix.

According to a further aspect of the specification there is provided a method for treating cancer of the breast, endometrium, ovary or cervix, which comprises administering an effective amount of a compound of the Formula (I), or a pharmaceutically acceptable salt or prodrug thereof, as defined hereinbefore.

According to a further aspect of the specification there is provided a compound of the Formula (I), or a pharmaceutically acceptable salt or prodrug thereof, as defined hereinbefore, for use in the treatment of breast cancer.

According to a further aspect of the specification there is provided the use of a compound of the Formula (I), or a pharmaceutically acceptable salt or prodrug thereof, as defined hereinbefore, in the manufacture of a medicament for use in the treatment of breast cancer.

According to a further aspect of the specification there is provided a method for treating breast cancer, which comprises administering an effective amount of a compound of the Formula (I), or a pharmaceutically acceptable salt or prodrug thereof, as defined hereinbefore.

According to a further aspect of the specification there is provided a compound of the Formula (I), or a pharmaceutically acceptable salt or prodrug thereof, as defined hereinbefore, for use in the treatment of breast cancer, wherein the cancer has developed resistance to one or more other endocrine therapies.

According to a further aspect of the specification there is provided the use of a compound of the Formula (I), or a pharmaceutically acceptable salt or prodrug thereof, as defined hereinbefore, in the manufacture of a medicament for use in the treatment of breast cancer, wherein the cancer has developed resistance to one or more other endocrine therapies.

According to a further aspect of the specification there is provided a method for treating breast cancer, wherein the cancer has developed resistance to one or more other endocrine therapies, which comprises administering an effective amount of a compound of the Formula (I), or a pharmaceutically acceptable salt or prodrug thereof, as defined hereinbefore.

According to a further aspect of the specification there is provided a compound of the Formula (I), or a pharmaceutically acceptable salt or prodrug thereof, as defined hereinbefore, for use in the treatment of ER+ve breast cancer.

According to a further aspect of the specification there is provided the use of a compound of the Formula (I), or a pharmaceutically acceptable salt or prodrug thereof, as defined herein before in the manufacture of a medicament for use in the treatment of ER+ve breast cancer.

According to a further aspect of the specification there is provided a method for treating ER+ve breast cancer, which comprises administering an effective amount of a compound of the Formula (I), or a pharmaceutically acceptable salt or prodrug thereof, as defined hereinbefore.

The anti-cancer treatment defined herein may be applied as a sole therapy or may involve, in addition to the compounds of the specification, conventional surgery or radiotherapy or chemotherapy. Such chemotherapy may include one or more of the following categories of anti-tumour agents:—

The anti-cancer treatment defined herein may be applied as a sole therapy or may involve, in addition to the compounds of the specification, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) antihormonal agents such as antioestrogens (for example tamoxifen, fulvestrant, toremifene, raloxifene, droloxifene and iodoxyfene), progestogens (for example megestrol acetate), aromatase inhibitors (for example as anastrozole, letrozole, vorazole and exemestane);

(iii) inhibitors of growth factor function and their downstream signalling pathways: included are Ab modulators of any growth factor or growth factor receptor targets, reviewed by Stern et al. *Critical Reviews in Oncology/Haematology*, 2005, 54, pp 11-29); also included are small molecule inhibitors of such targets, for example kinase inhibitors—examples include the anti-erbB2 antibody trastuzumab [Herceptin™], the anti-EGFR antibody panitumumab, the anti-EGFR antibody cetuximab [Erbitux, C225] and tyrosine kinase inhibitors including inhibitors of the erbB receptor family, such as epidermal growth factor family receptor (EGFR/erbB1) tyrosine kinase inhibitors such as gefitinib or erlotinib, erbB2 tyrosine kinase inhibitors such as lapatinib, and mixed erb1/2 inhibitors such as afatanib; similar strategies are available for other classes of growth factors and their receptors, for example inhibitors of the hepatocyte growth factor family or their receptors including c-met and ron; inhibitors of the insulin and insulin growth factor family or their receptors (IGFR, IR) inhibitors of the platelet-derived growth factor family or their receptors (PDGFR), and inhibitors of signalling mediated by other receptor tyrosine kinases such as c-kit, AnLK, and CSF-1R; also included are modulators which target signalling proteins in the PI3-kinase signalling pathway, for example, inhibitors of PI3-kinase isoforms such as PI3K-α/β/γ and ser/thr kinases such as AKT, mTOR (such as AZD2014, everolimus), PDK, SGK, PI4K or PIP5K; also included are inhibitors of serine/threonine kinases not listed above, for example raf inhibitors such as vemurafenib, MEK inhibitors such as selumetinib (AZD6244), Abl inhibitors such as imatinib or nilotinib, Btk inhibitors such as ibrutinib, Syk inhibitors such as fostamatinib, aurora kinase inhibitors (for example AZD1152, AZD2811), inhibitors of other ser/thr kinases such as JAKs, STATs and IRAK4, and cyclin dependent kinase inhibitors for example inhibitors of CDK1, CDK2, CDK7, CDK9 and CDK4/6 such as palbociclib;

iv) modulators of DNA damage signalling pathways, for example PARP inhibitors (e.g. Olaparib), ATR inhibitors or ATM inhibitors;

v) modulators of apoptotic and cell death pathways such as Bcl family modulators (e.g. ABT-263/Navitoclax, ABT-199);

(vi) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as sorafenib, axitinib, pazopanib, sunitinib and vandetanib (and compounds that work by other mechanisms (for example linomide, inhibitors of integrin αvβ3 function and angiostatin)];

(vii) vascular damaging agents, such as Combretastatin A4;

(viii) anti-invasion agents, for example c-Src kinase family inhibitors like (dasatinib, *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. Specific examples include monoclonal antibodies targeting PD-1 (e.g. BMS-936558), CTLA4 (e.g. ipilimumab and tremelimumab), PD-L1 (durvalumab, atezolizumab, and Avelumab);

(x) Antisense or RNAi based therapies, for example those which are directed to the targets listed.

(xi) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

In one aspect the above combinations, pharmaceutical compositions, uses and methods of treating cancer, are methods for the treatment of breast or gynaecological cancers, such as cancer of the breast, endometrium, ovary or cervix, particularly breast cancer, such as ER+ve breast cancer.

According to a further aspect of the present specification there is provided a kit comprising a compound of Formula (I), or a pharmaceutically acceptable salt or prodrug thereof in combination with an anti-tumour agent selected from one listed above.

Combination therapy as described above may be added on top of standard of care therapy typically carried out according to its usual prescribing schedule.

Although the compounds of the Formula (I) are primarily of value as therapeutic agents for use in warm-blooded animals (including man), they are also useful whenever it is required to inhibit ER-α. Thus, they are useful as pharmacological standards for use in the development of new biological tests and in the search for new pharmacological agents.

EXAMPLES

The invention will now be further explained by reference to the following illustrative examples.

Unless stated otherwise, starting materials were commercially available. All solvents and commercial reagents were of laboratory grade and were used as received.

General Experimental

The invention will now be illustrated in the following Examples in which, generally:

(i) operations were carried out at room temperature (RT), i.e. in the range 17 to 25° C. and under an atmosphere of an inert gas such as $N_2$ or Ar unless otherwise stated;

(ii) in general, the course of reactions was followed by thin layer chromatography (TμC) and/or analytical high-performance liquid chromatography (HPLC or UPLC) which was usually coupled to a mass spectrometer (LCMS). The reaction times that are given are not necessarily the minimum attainable;

(iii) when necessary, organic solutions were dried over anhydrous $MgSO_4$ or $Na_2SO_4$, work-up procedures were carried out using traditional phase separating techniques or by using SCX as described in (xiii), evaporations were carried out either by rotary evaporation in vacuo or in a Genevac HT-4/EZ-2 or Biotage V10;

(iv) yields, where present, are not necessarily the maximum attainable, and when necessary, reactions were repeated if a larger amount of the reaction product was required;

(v) in general, the structures of the end-products of the Formula (I) were confirmed by nuclear magnetic resonance (NMR) and/or mass spectral techniques; electrospray mass spectral data were obtained using a Waters Acquity UPLC coupled to a Waters single quadrupole mass spectrometer acquiring both positive and negative ion data, and generally, only ions relating to the parent structure are reported, the error inherent to the instrument is ±0.3 Da and masses were recorded as observed; proton NMR chemical shift values were measured on the delta scale using either a Bruker AV500 spectrometer operating at a field strength of 500 MHz, a Bruker AV400 operating at 400 MHz or a Bruker AV300 operating at 300 MHz. Unless otherwise stated, NMR spectra were obtained at 500 MHz in d6-dimethylsulfoxide. The following abbreviations have been used: s, singlet; d, doublet; t, triplet; q, quartet; m, multiplet; br, broad; qn, quintet; electrospray high resolution mass spectrometry data were obtained using a Waters Acquity UPLC coupled to a Bruker micrOTOF-Q II quadrupole time-of-flight mass spectrometer acquiring positive ion data or equivalent;

(vi) Unless stated otherwise compounds containing an asymmetric carbon and/or sulfur atom were not resolved;

(vii) Intermediates were not necessarily fully purified but their structures and purity were assessed by TLC, analytical HPLC/UPLC, and/or NMR analysis and/or mass spectrometry;

(viii) unless otherwise stated, flash column chromatography was performed on Merck Kieselgel silica (Art. 9385) or on reversed phase silica (Fluka silica gel 90 C18) or on Silicycle cartridges (40-63 μm silica, 4 to 330 g weight) or on Grace resolv cartridges (4-120 g) or on RediSep Rf 1.5 Flash columns or on RediSep Rf high performance Gold Flash columns (150-415 g weight) or on RediSep Rf Gold C18 Reversed-phase columns (20-40 μm silica) either manually or automated using a Teledyne Isco CombiFlash Companion, Teledyne Isco Combiflash Rf or Teledyne Isco Rf Lumen system or similar system;

(ix) Preparative reverse phase HPLC (RP HPLC) was performed on C18 reversed-phase silica typically using a Waters XSelect CSH C18 OBD column (5 μm silica, 30 mm diameter, 100 mm length) using decreasingly polar mixtures as eluent, for example utilising water as solvent A and acetonitrile as solvent B [with additional modifier stream to provide a mobile phase containing 0.1-5% formic acid or 0.1-5% aqueous ammonium hydroxide (d=0.91)]; a typical procedure would be as follows: a solvent gradient over 10-20 minutes, at 40-50 mL per minute, from a 95:5 mixture of solvents A and B respectively to a 5:95 mixture of solvents A and B (or alternative ratio as appropriate).

(x) The following analytical UPLC methods were used; in general, reverse-phase C18 silica was used with a flow rate of 1 mL/minute and detection was by Electrospray Mass Spectrometry and by UV absorbance recording a wavelength range of 220-320 nm. Analytical UPLC was performed on CSH C18 reverse-phase silica, using a Waters XSelect CSH C18 column with dimensions 2.1×50 mm and particle size 1.7 micron). Gradient analysis was employed using decreasingly polar mixtures as eluent, for example decreasingly polar mixtures of water (containing 0.1% formic acid or 0.1% ammonia) as solvent A and acetonitrile as solvent B. A typical 2 minute analytical UPLC method would employ a solvent gradient over 1.3 minutes, at approximately 1 mL per minute, from a 97:3 mixture of solvents A and B respectively to a 3:97 mixture of solvents A and B.

(xi) Where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;

(xii) Where reactions refer to the use of a microwave, one of the following microwave reactors were used: Biotage Initiator, Personal Chemistry Emrys Optimizer, Personal Chemistry Smithcreator or CEM Explorer; (xiii) Compounds were purified by strong cation exchange (SCX) chromatography using Isolute SPE flash SCX-2 or SCX-3 columns (International Sorbent Technology Limited, Mid Glamorgan, UK);

(xiv) the following preparative chiral HPLC methods were carried out using a Gilson GX-281 HPLC and a DAICEL CHIRALPAK IC (2×25 cm, 5 um) or DAICEL CHIRALPAK IF (2×25 cm, 5 um); in general a flow rate of between 10-350 mL/minute and detection was by UV absorbance at a typical wavelength of 254 nm. A sample concentration of about 1-100 mg/mL was used in a suitable solvent mixture with an injection volume of between 0.5-10 mL and run time of between 10-150 minutes and a typical oven temperature of 25-35° C.;

(xv) the following analytical chiral HPLC methods were carried out using Shimadzu UFLC and a Daicel CHIRALPAK IC-3 (50×4.6 mm 3 um) or Daicel CHIRALPAK IF-3 (50×4.6 mm 3 um); in general a flow rate of 1 mL/minute and detection was by UV absorbance at a typical wavelength of 254 nm. A sample concentration of about 1 mg/mL was used in a suitable solvent such as EtOH with an injection volume of about 10 μL and run time of between 10-60 minutes and a typical oven temperature of 25-35° C.;

(xvi) the following preparative chiral supercritical fluid chromatography (SFC) methods were used; in general a flow rate of about 70 mL/minute and detection was by UV absorbance at a typical wavelength of 254 nm. A sample concentration of about 100 mg/mL was used in a suitable solvent such as MeOH with an injection volume of about 0.5 mL and run time of between 10-150 minutes and a typical oven temperature of 25-35° C.;

(xvii) in general Examples and intermediate compounds were named using ACD Name, "Structure to Name" part of ChemDraw Ultra (CambridgeSoft) or Biovia Draw 2016;

(xviii) In addition to the ones mentioned above, the following abbreviations have been used:

| | | | |
|---|---|---|---|
| AcOH | acetic acid | aq. | Aqueous |
| DCM | dichloromethane | DIPEA | N,N-diisopropylethylamine |
| DIAD | diisopropyl azodicarboxylate | | |
| DMF | N,N-dimethylformamide | DMSO | Dimethyl sulfoxide |
| eq. | equivalents | ESI-HRMS | electrospray ionisation - high resolution mass spectrometry |
| $Et_2O$ | diethyl ether | EtOAc | ethyl acetate |
| EtOH | ethanol | HATU | 2-(3H-[1,2,3]Triazolo[4,5-b]pyridin-3-yl)-1,1,3,3-tetramethyl-isouronium hexafluoro-phosphate(V) |
| MeCN | acetonitrile | MeOD | $d_4$-methanol |
| MeOH | methanol | m/z | mass spectrometry peak(s) |
| RockPhos Pd G3 | [(2-Di-tert-butylphosphino-3-methoxy-6-methyl-2',4',6'-triiso-propyl-1,1'-biphenyl)-2-(2-amino-bi-phenyl)]palladium(II) methanesulfonate | RT | room temperature |
| TBAF | tetra n-butylammonium fluoride | THF | tetrahydrofuran |
| Sat. | saturated | $scCO_2$ | Supercritical carbon dioxide |
| SCX | Strong cation exchange | SFC | Supercritical fluid chromatography |

Intermediate 1a: 3,5-Difluoro-4-((1R,3R)-2-(2-fluoro-2-methylpropyl)-3-methyl-2,3,4,9-tetrahydro-1H-pyrido[3,4-b]indol-1-yl)phenol

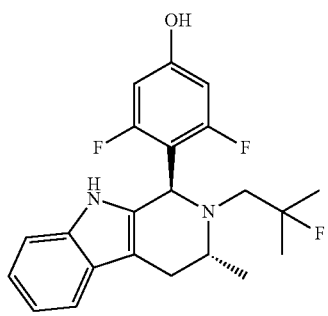 [SMILES: C[C@@H]1Cc2c([nH]c3ccccc23)[C@@H](c2c(F)cc(O)cc2F)N1CC(C)(C)F]

A solution of (R)—N-(1-(1H-indol-3-yl)propan-2-yl)-2-fluoro-2-methylpropan-1-amine (preparation described in WO2016/97072A1) (4.95 g, 19.93 mmol) in toluene (10 mL) was added to a stirred solution of 2,6-difluoro-4-hydroxybenzaldehyde (3.18 g, 20.13 mmol) in toluene (120 mL) and AcOH (9 mL) at 20° C. under air. The resulting solution was stirred at 80° C. for 18 hours. The reaction was cooled to RT and stirred for 18 hours. The reaction was warmed again to 80° C. for 8 hours. The reaction mixture was cooled to RT. The crude product was purified by ion exchange chromatography, using an SCX column. The desired product was eluted from the column using 1M NH$_3$/MeOH and pure fractions were evaporated to dryness to crude product. The crude product was purified by flash silica chromatography, elution gradient 0 to 30% EtOAc in DCM. Pure fractions were evaporated to dryness to afford the title compound (4.60 g, 59%) as an orange solid; $^1$H NMR (400 MHz, CDCl$_3$, 30° C.) 1.10 (3H, d), 1.18 (3H, d), 1.21-1.26 (3H, m), 2.39 (1H, dd), 2.60 (1H, m), 2.86 (1H, dd), 3.08 (1H, m), 3.61-3.72 (1H, m), 5.18 (1H, s), 6.32-6.38 (2H, m), 7.06-7.14 (2H, m), 7.21-7.24 (1H, m), 7.41 (1H, s), 7.47-7.54 (1H, m); m/z: ES+ [M+H]$^+$ 389.2.

Intermediate 1b: tert-Butyl 4-(4-methoxy-4-oxobutyl)piperazine-1-carboxylate

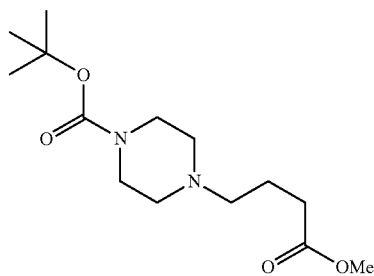 [SMILES: COC(=O)CCCN1CCN(C(=O)OC(C)(C)C)CC1]

Methyl 4-bromobutanoate (2.48 mL, 19.73 mmol) was added at RT to a solution of tert-butyl piperazine-1-carboxylate (3.50 g, 18.79 mmol) and DIPEA (3.94 mL, 22.55 mmol) in anhydrous THF (50 mL) and the reaction stirred at RT for 18 hours. EtOAc and 10% aq. NaHCO$_3$ were added to the mixture and the phases separated. The aqueous phase was extracted with EtOAc, then the organic extracts were combined, washed with H$_2$O and sat. aq. NaCl, dried (Na$_2$SO$_4$), filtered and the filtrate concentrated in vacuo. The crude product was purified by flash silica chromatography, elution gradient 0 to 60% EtOAc in heptane. Pure fractions were evaporated to dryness to afford the title compound (0.586 g, 10.9%) as a colourless oil; $^1$H NMR (400 MHz, CDCl$_3$, 30° C.) 1.46 (9H, s), 1.77-1.85 (2H, m), 2.32-2.4 (8H, m), 3.37-3.44 (4H, m), 3.67 (3H, s); m/z: ES+ [M+H]$^+$ 287.3.

Intermediate 1c: Methyl 4-(piperazin-1-yl)butanoate, Hydrochloride

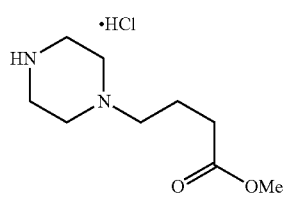 [SMILES: Cl ; COC(=O)CCCN1CCNCC1]

A solution of 4M HCl in dioxane (2.56 mL, 10.23 mmol) was added at RT to a solution of tert-butyl 4-(4-methoxy-4-oxobutyl)piperazine-1-carboxylate (586 mg, 2.05 mmol) in dioxane (10 mL) and the reaction stirred at RT for 2 hours. Et$_2$O (100 mL) was added. The resulting solid was filtered under vacuum and washed with Et$_2$O to afford the crude title compound (520 mg, 114%) as a white solid that was used in the next step without further purification; $^1$H NMR (400 MHz, DMSO-d6, 30° C.) 1.95 (2H, m), 2.45 (2H, t), 3.12 (2H, s), 3.28 (2H, s), 3.46 (4H, s), 3.62 (5H, s), 9.72 (2H, s); m/z: ES+ [M+H]$^+$ 187.2.

Intermediate 1d: Methyl 4-(4-(3-hydroxypropyl)piperazin-1-yl)butanoate

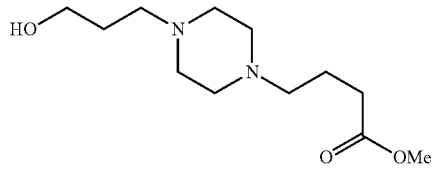 [SMILES: COC(=O)CCCN1CCN(CCCO)CC1]

3-Bromopropan-1-ol (0.22 mL, 2.46 mmol) was added to methyl 4-(piperazin-1-yl)butanoate, HCl (457 mg, 2.05 mmol) and potassium carbonate (850 mg, 6.15 mmol) in MeCN (5 mL) at 20° C. The resulting suspension was stirred at 85° C. for 4 hours. The reaction mixture was cooled to RT, diluted with EtOAc (20 mL) and filtered. The filtrate was concentrated under reduced pressure. The crude product was purified by flash silica chromatography, elution gradient 0 to 10% MeOH in DCM. Pure fractions were evaporated to dryness to afford the title compound (318 mg, 64%) as a colourless oil; $^1$H NMR (400 MHz, CDCl3, 30° C.) 1.68-1.74 (2H, m), 1.81 (2H, q), 2.34 (4H, m), 2.38-2.57 (8H, m), 2.58-2.62 (2H, m), 3.67 (3H, s), 3.76-3.8 (2H, m), 3.81-4.2 (1H, m); m/z: ES+ [M+H]$^+$ 245.3.

Intermediate 1e: Methyl 4-(4-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propyl)piperazin-1-yl)butanoate

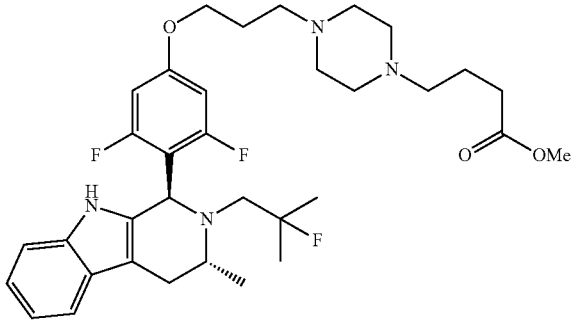 [SMILES: COC(=O)CCCN1CCN(CCCOc2cc(F)c([C@@H]3c4[nH]c5ccccc5c4C[C@@H](C)N3CC(C)(C)F)c(F)c2)CC1]

Diisopropyl (E)-diazene-1,2-dicarboxylate (0.152 mL, 0.77 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (0.150 g, 0.39 mmol), methyl 4-(4-(3-hydroxypropyl)piperazin-1-yl)butanoate (0.189 g, 0.77 mmol) and triphenylphosphine (0.203 g, 0.77 mmol) in DCM (7 mL) at 5° C. The resulting mixture was stirred at 5° C. for 30 minutes and then at 21° C. for 1 hour. The reaction mixture was diluted with DCM (20 mL) and water (20 mL) and passed through a phase separating cartridge. The solvents were removed under reduced pressure. The crude product was purified by flash silica chromatography, elution gradient 0 to 10% MeOH in DCM. Pure fractions were evaporated to dryness to afford the title compound (0.20 g, 84%) as a pale yellow oil; (JACS) $^1$H NMR (400 MHz, CDCl$_3$, 30° C.) 1.10 (3H, d), 1.17 (3H, d), 1.23 (3H, d), 1.80 (2H, q), 1.94 (2H, p), 2.35 (6H, m), 2.47 (9H, q), 2.60 (1H, dd), 2.86 (1H, dd), 3.09 (1H, dd), 3.67 (4H, s), 3.96 (2H, t), 5.18 (1H, s), 6.36-6.45 (2H, m), 7.04-7.13 (2H, m), 7.18-7.24 (1H, m), 7.43 (1H, d), 7.46-7.54 (1H, m); m/z: ES+ [M+H]$^+$ 615.4.

Intermediate 1f: 4-(4-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propyl)piperazin-1-yl)butanoic Acid

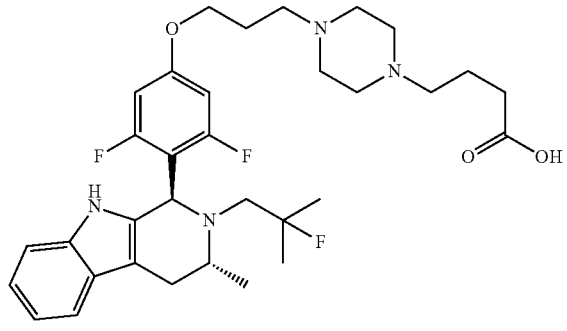 [SMILES: C[C@@H]1Cc2c([nH]c3ccccc23)[C@@H](c2c(F)cc(OCCCN3CCN(CCCC(=O)O)CC3)cc2F)N1CC(C)(C)F]

Lithium hydroxide monohydrate (27 mg, 0.65 mmol) was added to a stirred solution of methyl 4-(4-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propyl)piperazin-1-yl)butanoate (200 mg, 0.33 mmol), in THF (3 mL) and water (1 mL) at RT. The resulting mixture was stirred for 30 minutes at RT. 2 M aq. HCl (0.325 mL) was added and the crude product was purified by ion exchange chromatography, using an SCX column. The desired product was eluted from the column using 1M NH$_3$/MeOH and pure fractions were evaporated to dryness to afford the title compound as a yellow solid; m/z: ES+ [M+H]$^+$ 601.4.

Example 1: (2S,4R)-1-((S)-2-(4-(4-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propyl)piperazin-1-yl)butanamido)-3,3-dimethylbutanoyl)-4-hydroxy-N-(4-(4-methylthiazol-5-yl)benzyl)pyrrolidine-2-carboxamide

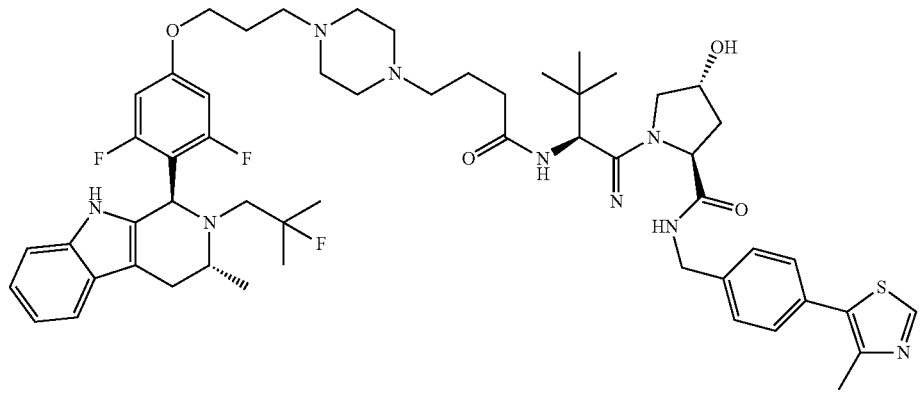 [SMILES: Cc1ncsc1-c1ccc(CNC(=O)[C@@H]2C[C@@H](O)CN2C(=N)[C@@H](NC(=O)CCCN2CCN(CCCOc3cc(F)c([C@@H]4c5[nH]c6ccccc6c5C[C@@H](C)N4CC(C)(C)F)c(F)c3)CC2)C(C)(C)C)cc1]

HATU (188 mg, 0.50 mmol) was added portionwise to 4-(4-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propyl)piperazin-1-yl)butanoic acid (198 mg, 0.33 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (preparation described in WO02014/108452A1) (135 mg, 0.31 mmol) and triethylamine (0.184 mL, 1.32 mmol) in DMF (5 mL) at 20° C. under nitrogen. The resulting mixture was stirred at 20° C. for 30 mins. The reaction mixture was diluted with EtOAc (25 mL), and washed sequentially with saturated NaHCO$_3$ (25 mL), water (25 mL), and saturated brine (25 mL). The organic layer was dried with MgSO$_4$, filtered and evaporated to afford crude product. The crude product was purified by preparative HPLC (Waters XBridge Prep C18 OBD column, 5μ silica, 30 mm diameter, 100 mm length), using decreasingly polar mixtures of water (containing 1% by volume of NH$_4$OH (28-30% in H$_2$O)) and MeCN as eluents. Fractions containing the desired compound were evaporated to dryness to afford the title compound (25 mg, 7.58%) as a white solid; $^1$H NMR (400 MHz, CDCl$_3$, 30° C.) 0.93 (9H, s), 1.10 (3H, d), 1.17 (3H, d), 1.23 (3H, d), 1.74-1.82 (2H, m), 1.89-1.98 (2H, m), 2.12 (1H, dd), 2.21-2.31 (3H, m), 2.33-2.42 (3H, m), 2.50 (12H, s), 2.54-2.64 (2H, m), 2.86 (2H, dd), 3.05-3.14 (1H, m), 3.56 (1H, dd), 3.68 (1H, s), 3.95 (2H, t), 4.16 (1H, d), 4.33 (1H, dd), 4.44-4.55 (2H, m), 4.58 (1H, dd), 4.73 (1H, t), 5.19 (1H, s), 6.39 (3H, d), 7.05-7.13 (2H, m), 7.21 (1H, dd), 7.28 (1H, d), 7.32-7.39 (4H, m), 7.48-7.53 (1H, m), 7.59 (1H, s), 8.65 (1H, s); m/z: ES+ [M+H]$^+$ 1013.5; ESI-HRMS calculated for C$_{55}$H$_{72}$F$_3$N$_8$O$_5$S [M+H]$^+$=1013.5293, measured 1013.5260.

Intermediate 2a: tert-Butyl 4-(2-ethoxy-2-oxoethyl)piperazine-1-carboxylate

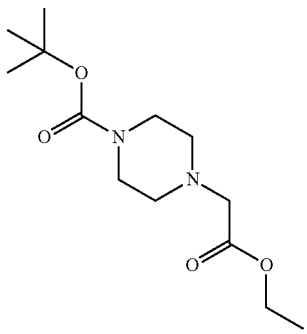 [SMILES: CCOC(=O)CN1CCN(C(=O)OC(C)(C)C)CC1]

Ethyl 2-bromoacetate (3.13 mL, 28.19 mmol) was added at RT to a solution of tert-butyl piperazine-1-carboxylate (5.00 g, 26.8 mmol) and DIPEA (5.63 mL, 32.21 mmol) in anhydrous THF (100 mL), and the reaction stirred at RT for 18 hours. EtOAc and 10% NaHCO$_3$ were added to the mixture and the phases separated. The aqueous phase was extracted with EtOAc, then the organic extracts were combined, washed with H$_2$O and sat. aq. NaCl, dried (Na$_2$SO$_4$), filtered and the filtrate concentrated in vacuo. The crude product was purified by flash silica chromatography, elution gradient 0 to 60% EtOAc in heptane. Pure fractions were evaporated to dryness to afford the title compound (6.84 g, 94%) as a white solid; $^1$H NMR (400 MHz, CDCl$_3$, 30° C.) 1.28 (3H, t), 1.46 (9H, s), 2.46-2.59 (4H, m), 3.22 (2H, s), 3.39-3.55 (4H, m), 4.19 (2H, q); m/z: ES+ [M+H]$^+$ 273.3.

Intermediate 2b: Ethyl 2-(piperazin-1-yl)acetate, Hydrochloride

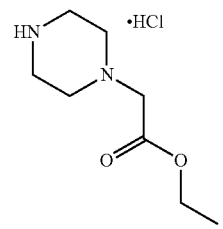

A solution of 4 M HCl in dioxane (31.2 mL, 124.84 mmol) was added at RT to a solution of tert-butyl 4-(2-ethoxy-2-oxoethyl)piperazine-1-carboxylate (6.80 g, 24.97 mmol) in dioxane (25 mL) and the reaction stirred at RT for 2 hours. Et$_2$O (100 mL) was added. The resulting solid was filtered under vacuum and washed with Et$_2$O to afford the title compound (4.03 g, 77%) as a white solid; $^1$H NMR (400 MHz, DMSO-d6, 30° C.) 1.24 (3H, t), 3.27 (8H, d), 3.91 (2H, s), 4.18 (2H, q), 9.50 (2H, s); m/z: ES+ [M+H]$^+$ 173.4.

Intermediate 2c: Ethyl 2-(4-(5-hydroxypentyl)piperazin-1-yl)acetate

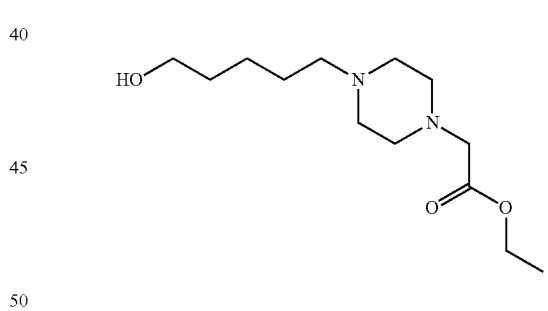

5-Bromopentan-1-ol (0.696 mL, 5.75 mmol) was added to ethyl 2-(piperazin-1-yl)acetate, HCl (1.0 g, 4.79 mmol) and potassium carbonate (1.987 g, 14.38 mmol) in MeCN (20 mL) at 20° C. The resulting suspension was stirred at 85° C. for 4 hours. The reaction mixture was cooled to RT, diluted with EtOAc and filtered. The filtrate was concentrated under reduced pressure. The crude product was purified by flash silica chromatography, elution gradient 0 to 10% MeOH in DCM. Pure fractions were evaporated to dryness to afford the title compound (0.65 g, 53%) as a colourless oil; $^1$H NMR (400 MHz, CDCl$_3$, 30° C.) 1.27 (3H, t), 1.37-1.44 (2H, m), 1.48-1.56 (2H, m), 1.57-1.64 (2H, m), 2.06 (1H, s), 2.33-2.4 (2H, m), 2.53 (4H, s), 2.62 (4H, s), 3.20 (2H, s), 3.63 (2H, t), 4.18 (2H, q); m/z: ES+ [M+H]$^+$ 259.3.

Intermediate 2d: Ethyl 2-(4-(5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)piperazin-1-yl)acetate

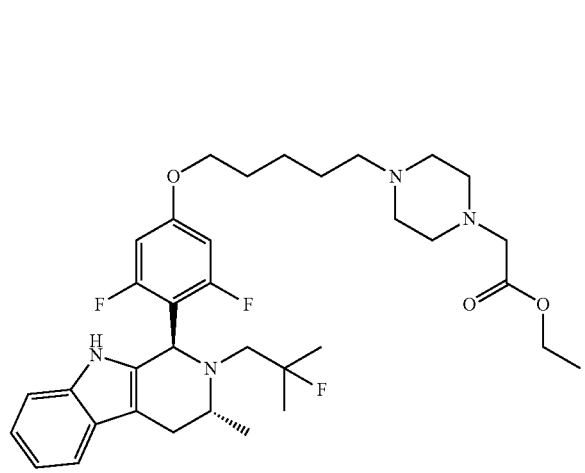 [SMILES: CCOC(=O)CN1CCN(CCCCCOc2cc(F)c([C@@H]3c4[nH]c5ccccc5c4C[C@@H](C)N3CC(C)(C)F)c(F)c2)CC1]

RockPhos Pd G3 (25.8 mg, 0.03 mmol) was added in one portion to a degassed mixture of ethyl 2-(4-(5-hydroxypentyl)piperazin-1-yl)acetate (230 mg, 0.89 mmol), (1R,3R)-1-(4-bromo-2,6-difluorophenyl)-2-(2-fluoro-2-methylpropyl)-3-methyl-2,3,4,9-tetrahydro-1H-pyrido[3,4-b]indole, HCl (300 mg, 0.62 mmol) and cesium carbonate (701 mg, 2.15 mmol) in toluene (4.4 mL) at 20° C. under nitrogen. The resulting mixture was stirred at 90° C. for 4 hours. The reaction was allowed to cool to RT and diluted with DCM (20 mL) and water (5 mL) and the mixture was passed through a phase separating filtercup and evaporated to afford crude product as a orange gum. The crude product was purified by flash silica chromatography, elution gradient 0 to 70% EtOAc in heptane. Pure fractions were evaporated to dryness to afford the title compound (134 mg, 35%) as a orange gum; $^1$H NMR (400 MHz, CDCl$_3$, 30° C.) 1.10 (3H, d), 1.18 (3H, d), 1.23 (3H, d), 1.25 (3H, d), 1.41-1.54 (5H, m), 1.78 (2H, m), 2.33-2.46 (3H, m), 2.46-2.67 (8H, m), 2.86 (1H, dd), 3.09 (1H, dd), 3.20 (2H, s), 3.68 (1H, s), 3.90 (2H, t), 4.18 (2H, q), 5.18 (1H, s), 6.38 (2H, d), 7.05-7.14 (2H, m), 7.19-7.24 (1H, m), 7.41 (1H, s), 7.51 (1H, dd); m/z: ES+ [M+H]$^+$ 629.4.

Intermediate 2e: 2-(4-(5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)piperazin-1-yl)acetic Acid

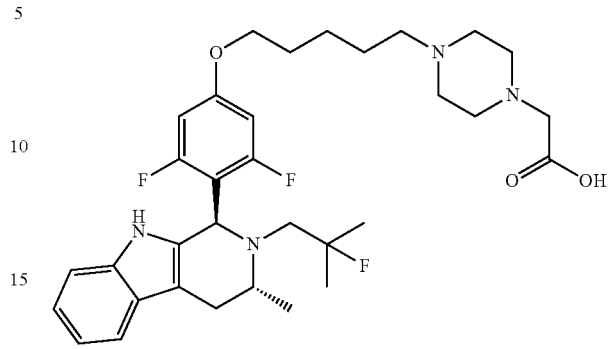

A solution of 2M aq. sodium hydroxide (0.103 mL, 0.21 mmol) was added to a stirred solution of ethyl 2-(4-(5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)piperazin-1-yl)acetate (130 mg, 0.21 mmol), in ethanol (1 mL) at RT. The resulting mixture was stirred for 30 minutes at RT. The reaction mixture was quenched with 2 M aq. HCl (0.103 mL) and evaporated to afford the title compound (assumed quantitative) that was used in the next step without further purification; m/z: ES+ [M+H]$^+$ 601.6.

Example 2: (2S,4R)-1-((S)-2-(2-(4-(5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)piperazin-1-yl)acetamido)-3,3-dimethylbutanoyl)-4-hydroxy-N-(4-(4-methylthiazol-5-yl)benzyl)pyrrolidine-2-carboxamide

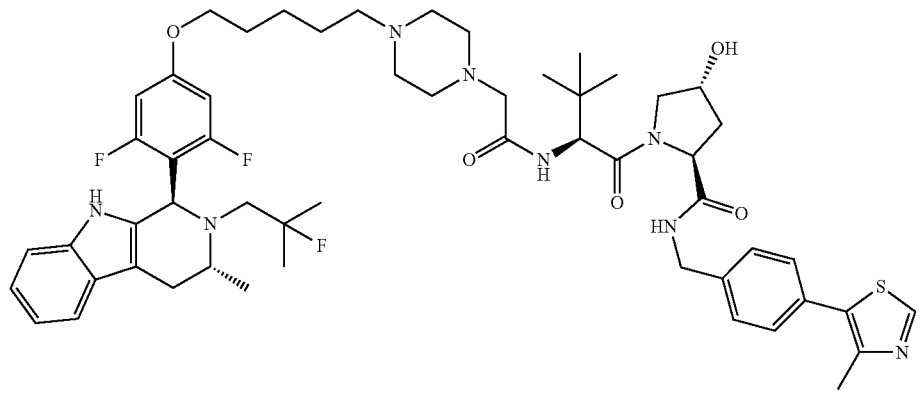 [SMILES: Cc1ncsc1-c1ccc(CNC(=O)[C@@H]2C[C@@H](O)CN2C(=O)[C@@H](NC(=O)CN2CCN(CCCCCOc3cc(F)c([C@@H]4c5[nH]c6ccccc6c5C[C@@H](C)N4CC(C)(C)F)c(F)c3)CC2)C(C)(C)C)cc1]

HATU (120 mg, 0.32 mmol) was added portionwise to 2-(4-(5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)piperazin-1-yl)acetic acid (126 mg, 0.21 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (86 mg, 0.20 mmol) and triethylamine (0.117 mL, 0.84 mmol) in DMF (5 mL) at 20° C. under nitrogen. The resulting mixture was stirred at 20° C. for 30 minutes. The reaction mixture was diluted with EtOAc (25 mL), and washed sequentially with saturated aq. NaHCO$_3$ (25 mL), water (25 mL), and saturated brine (25 mL). The organic layer was dried with MgSO$_4$, filtered and evaporated to afford crude product. The crude product was purified by preparative HPLC (Waters CSH C18 OBD column, 30×100 mm id, 5 micron particle size), using decreasingly polar mixtures of water (containing 1% by volume of NH$_4$OH (28-30% in H$_2$O)) and MeCN as eluents. Fractions containing the desired compound were evaporated to dryness to afford the title compound (80 mg, 38%) as a white solid; $^1$H NMR (400 MHz, CDCl$_3$, 30° C.) 0.94 (9H, s), 1.10 (3H, d), 1.18 (3H, d), 1.23 (3H, d), 1.42-1.49 (2H, m), 1.5-1.55 (2H, m), 1.78 (2H, p), 2.12 (1H, dd), 2.35 (3H, dd), 2.42 (1H, d), 2.48 (2H, s), 2.52 (4H, s), 2.55-2.59 (4H, m), 2.59-2.64 (2H, m), 2.86 (1H, dd), 2.99 (3H, s), 3.09 (1H, dd), 3.57 (1H, dd), 3.63-3.72 (1H, m), 3.90 (2H, t), 4.20 (1H, d), 4.3-4.41 (2H, m), 4.48-4.61 (2H, m), 4.75 (1H, t), 5.19 (1H, s), 6.37 (2H, d), 7.05-7.14 (2H, m), 7.22 (1H, dd), 7.29-7.39 (5H, m), 7.47-7.53 (2H, m), 7.83 (1H, d), 8.66 (1H, s); m/z: ES+ [M+H]$^+$ 1013.5; ESI-HRMS calculated for C$_{55}$H$_{72}$F$_3$N$_8$O$_5$S [M+H]$^+$=1013.5293, measured 1013.5284.

Example 3: (2S,4R)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-4-hydroxy-N—((S)-1-(4-(4-methylthiazol-5-yl)phenyl)ethyl)pyrrolidine-2-carboxamide

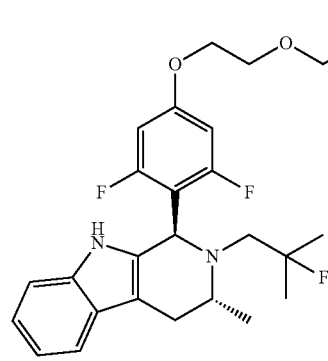
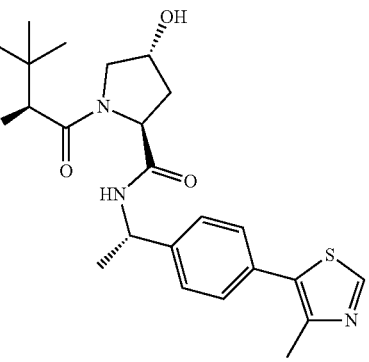

HATU (98 mg, 0.26 mmol) was added portionwise to 2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetic acid (99 mg, 0.17 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (72.3 mg, 0.16 mmol) and triethylamine (0.095 mL, 0.68 mmol) in DMF (5 mL) at 20° C. under nitrogen. The resulting mixture was stirred at 20° C. for 30 minutes. The reaction mixture was diluted with EtOAc (25 mL), and washed sequentially with sat. aq. NaHCO$_3$ (25 mL), water (25 mL), and sat. aq. brine (25 mL). The organic layer was dried with MgSO$_4$, filtered and evaporated to afford crude product. The crude product was purified by preparative HPLC (Waters XBridge Prep C$_{18}$ OBD column, 5µ silica, 30 mm diameter, 100 mm length), using decreasingly polar mixtures of water (containing 1% by volume of NH$_4$OH (28-30% in H$_2$O)) and MeCN as eluents. Fractions containing the desired compound were evaporated to dryness to afford the title compound (50.0 mg, 29%) as a white solid; $^1$H NMR (400 MHz, CDCl$_3$, 30° C.) 1.06 (9H, s), 1.09 (3H, d), 1.17 (3H, d), 1.22 (3H, d), 1.46 (3H, d), 1.96-2.05 (1H, m), 2.39 (1H, dd), 2.50 (3H, s), 2.53-2.64 (2H, m), 2.65 (1H, d), 2.84 (1H, dd), 3.08 (1H, dd), 3.58 (1H, dd), 3.64-3.74 (9H, m), 3.81 (2H, t), 3.88-4.02 (2H, m), 4.02-4.06 (2H, m), 4.06-4.11 (1H, m), 4.49 (1H, s), 4.55 (1H, d), 4.73 (1H, t), 5.08 (1H, p), 5.19 (1H, s), 6.35-6.41 (2H, m), 7.05-7.12 (2H, m), 7.21-7.24 (1H, m), 7.3-7.38 (3H, m), 7.38-7.46 (3H, m), 7.49-7.53 (1H, m), 8.16 (1H, s), 8.65 (1H, s); m/z: ES+ [M+H]$^+$ 1005.6; ESI-HRMS calculated for C$_{53}$H$_{68}$F$_3$N$_6$O$_8$S [M+H]$^+$=1005.4766, measured 1005.4744.

Intermediate 4a: 4-(2-((tert-Butyldimethylsilyl)oxy)ethoxy)benzaldehyde

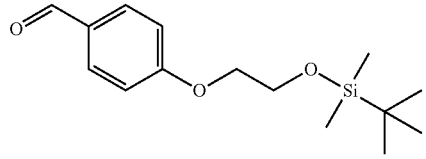 [SMILES: CC(C)(C)[Si](C)(C)OCCOc1ccc(C=O)cc1]

tert-Butylchlorodimethylsilane (1.227 g, 8.14 mmol) was added in one portion to 4-(2-hydroxyethoxy)benzaldehyde (1.23 g, 7.40 mmol) and 1H-imidazole (0.554 g, 8.14 mmol) in DCM (12 mL) at 20° C. under nitrogen. The resulting white suspension was stirred for 2 hours. The reaction mixture was diluted with DCM (100 mL), and washed with saturated brine (100 mL). The organic layer was dried with MgSO$_4$, filtered and evaporated to afford crude product. The crude product was absorbed onto silica and purified by flash column chromatography, elution gradient 0 to 20% EtOAc in heptane to afford the title compound (1.750 g, 84%) as a colourless oil; $^1$H NMR (400 MHz, CDCl$_3$) 0.10 (6H, s), 0.91 (9H, s), 4.00 (2H, dd), 4.13 (2H, t), 6.98-7.06 (2H, m), 7.78-7.87 (2H, m), 9.89 (1H, s); m/z: ES+ [M+H]$^+$ 281.2.

Intermediate 4b: (4-(2-((tert-Butyldimethylsilyl)oxy)ethoxy)phenyl)methanol

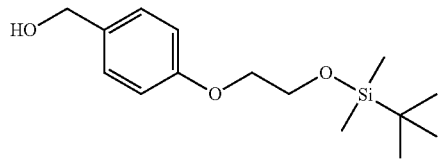 [SMILES: CC(C)(C)[Si](C)(C)OCCOc1ccc(CO)cc1]

4-(2-((tert-Butyldimethylsilyl)oxy)ethoxy)benzaldehyde (1.75 g, 6.24 mmol) was added to MeOH (83 mL), to this was slowly added portionwise sodium borohydride (0.142 g, 3.74 mmol) and the reaction was stirred for 1 hour. The reaction mixture evaporated to almost dryness, to this was added water (10 mL) and the mixture was stirred for 30 minutes. The mixture was extracted with EtOAc (2×50 mL). The combined extracts were washed with saturated brine solution (20 mL), dried (MgSO₄) and filtered to afford the crude title compound (1.89 g, 107%) as a colourless oil that was used in the next step without further purification; ¹H NMR (400 MHz, CDCl₃) 0.10 (6H, s), 0.91 (9H, s), 3.94-3.99 (2H, m), 4.02-4.06 (2H, m), 4.62 (2H, s), 6.87-6.93 (2H, m), 7.28 (2H, d), OH proton not observed.

Intermediate 4c: Ethyl 2-((4-(2-((tert-butyldimethylsilyl)oxy)ethoxy)benzyl)oxy)acetate

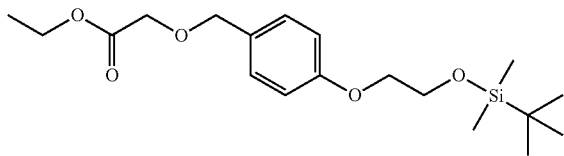 [SMILES: CCOC(=O)COCc1ccc(OCCO[Si](C)(C)C(C)(C)C)cc1]

Ethyl 2-diazoacetate (0.652 mL, 6.20 mmol) in DCM (2.89 mL) was added slowly to (4-(2-((tert-butyldimethylsilyl)oxy)ethoxy)phenyl)methanol (500 mg, 1.77 mmol) and diacetoxyrhodium (39.1 mg, 0.09 mmol) in DCM (7.5 mL) at 20° C. over a period of 3 hours under nitrogen. The resulting solution was stirred for 3 hours. The mixture was diluted with water (10 mL) and the DCM layer was passed through phase separating filter and evaporated to dryness. The crude product was purified by flash column chromatography, elution gradient 0 to 10% EtOAc in heptane to afford the title compound (475 mg, 73%) as a colourless liquid; ¹H NMR (400 MHz, CDCl₃) 0.10 (6H, s), 0.91 (9H, s), 1.29 (3H, t), 3.94-3.99 (2H, m), 4.01-4.07 (4H, m), 4.19-4.25 (2H, m), 4.56 (2H, s), 6.89 (2H, d), 7.28 (2H, d).

Intermediate 4d: Ethyl 2-((4-(2-hydroxyethoxy)benzyl)oxy)acetate

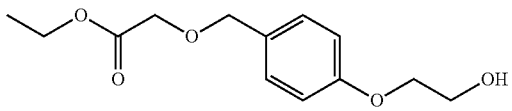 [SMILES: CCOC(=O)COCc1ccc(OCCO)cc1]

A solution of 1M TBAF in THF (1.3 mL, 1.29 mmol) was added in one portion to ethyl 2-((4-(2-((tert-butyldimethylsilyl)oxy)ethoxy)benzyl)oxy)acetate (475 mg, 1.29 mmol) in THF (5.2 mL) at 20° C. The resulting solution was stirred at 20° C. for 1 hour. The reaction mixture was diluted with EtOAc (100 mL), and washed sequentially with saturated NH₄Cl (25 mL), water (2×50 mL), and saturated brine (20 mL). The organic layer was dried with MgSO₄, filtered and evaporated to afford crude product. The crude product was purified by flash column chromatography, elution gradient 0 to 100% EtOAc in heptane to afford the title compound (230 mg, 70%) as a colourless oil; ¹H NMR (400 MHz, CDCl₃) 1.29 (3H, t), 1.98 (1H, t), 3.92-3.99 (2H, m), 4.06 (2H, s), 4.07-4.11 (2H, m), 4.23 (2H, q), 4.57 (2H, s), 6.87-6.93 (2H, m), 7.27-7.33 (2H, m).

Intermediate 4e: Ethyl 2-((4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)benzyl)oxy)acetate

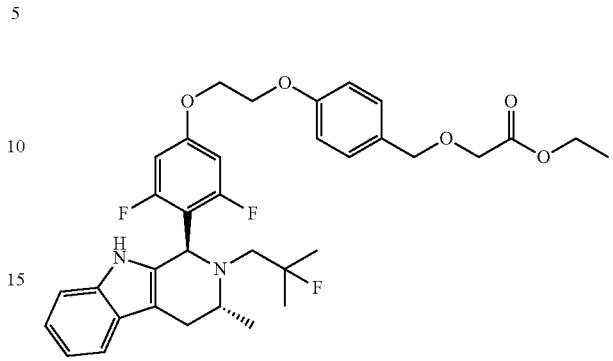

RockPhos Pd G3 (18.98 mg, 0.02 mmol) was added in one portion to a degassed mixture of ethyl 2-((4-(2-hydroxyethoxy)benzyl)oxy)acetate (230 mg, 0.90 mmol), (1R,3R)-1-(4-bromo-2,6-difluorophenyl)-2-(2-fluoro-2-methylpropyl)-3-methyl-2,3,4,9-tetrahydro-1H-pyrido[3,4-b]indole, HCl (221 mg, 0.45 mmol) and cesium carbonate (516 mg, 1.58 mmol) in toluene (4.393 mL) at 20° C. under nitrogen. The resulting mixture was stirred at 90° C. for 4 hours. The reaction was allowed to cool to RT and diluted with DCM (20 mL) and water (5 mL) and the mixture was passed through a phase separating filtercup and evaporated to afford crude product as a orange gum. The crude product was purified by flash column chromatography, elution gradient 0 to 70% EtOAc in heptane to afford the title compound (157 mg, 56%) as an orange gum; ¹H NMR (400 MHz, DMSO-d6, 30° C.) 1.05 (3H, d), 1.12 (9H, s), 2.3-2.42 (1H, m), 2.58 (1H, d), 2.78-2.97 (2H, m), 3.53 (1H, d), 4.08-4.19 (4H, m), 4.26-4.4 (4H, m), 4.47 (2H, s), 5.14 (1H, s), 6.73 (2H, d), 6.9-7.05 (4H, m), 7.15-7.23 (1H, m), 7.28 (2H, d), 7.40 (1H, d), 10.50 (1H, s); m/z: ES+ [M+H]⁺ 625.3.

Intermediate 4f: 2-((4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)benzyl)oxy)acetic Acid

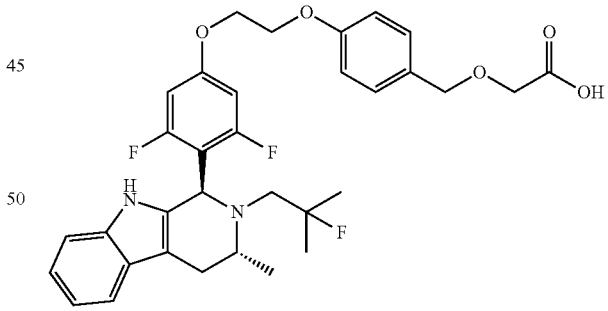

Lithium hydroxide hydrate (21.09 mg, 0.50 mmol) was added in one portion to ethyl 2-((4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)benzyl)oxy)acetate (157 mg, 0.25 mmol) in THF (0.94 mL) and water (0.3 mL) at 20° C. The resulting solution was stirred for 2 hours. The organic solvent was removed under reduced pressure. The resulting mixture was acidified with 2M aq. HCl and extracted into EtOAc (50 mL). The organic layer was washed with brine (15 mL) and evaporated to afford the title compound (147 mg, 98%) as a colourless gum that was used in the next step without further purification; m/z: ES+ [M+H]⁺ 597.3.

Example 4: (2S,4R)-1-((S)-2-(2-((4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)benzyl)oxy)acetamido)-3,3-dimethylbutanoyl)-4-hydroxy-N-(4-(4-methylthiazol-5-yl)benzyl)pyrrolidine-2-carboxamide

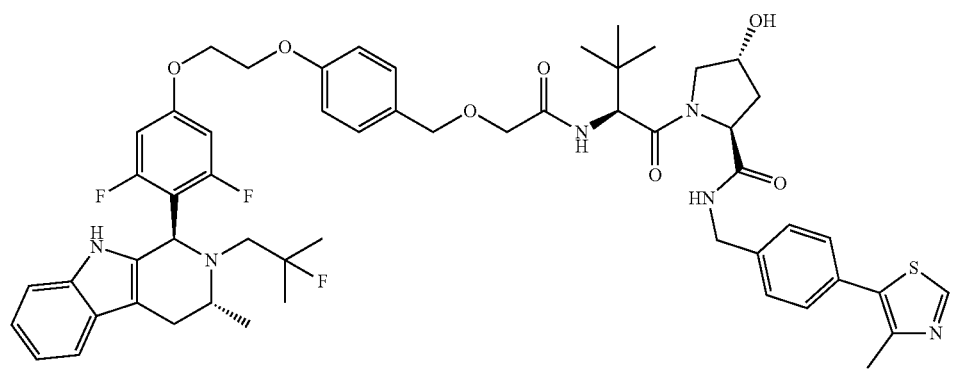 [SMILES: Cc1ncsc1-c1ccc(CNC(=O)[C@@H]2C[C@@H](O)CN2C(=O)[C@@H](NC(=O)COCc2ccc(OCCOc3cc(F)c([C@@H]4c5[nH]c6ccccc6c5C[C@@H](C)N4CC(C)(C)F)c(F)c3)cc2)C(C)(C)C)cc1]

HATU (141 mg, 0.37 mmol) was added portionwise to 2-((4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)benzyl)oxy)acetic acid (147 mg, 0.25 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (115 mg, 0.25 mmol) and triethylamine (0.14 mL, 0.99 mmol) in DMF (4.8 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (175 mg, 70%) as a white solid; $^1$H NMR (400 MHz, DMSO-d6) 0.94 (9H, s), 1.05 (3H, d), 1.17 (6H, t), 1.91 (1H, m), 2.03-2.12 (1H, m), 2.29-2.42 (1H, m), 2.45 (3H, d), 2.53-2.6 (1H, m), 2.78-2.96 (2H, m), 3.53 (1H, q), 3.59-3.72 (2H, m), 3.92-4.03 (2H, m), 4.22-4.49 (8H, m), 4.50 (2H, s), 4.57 (1H, d), 5.14 (2H, s), 6.73 (2H, d), 6.91-7.02 (4H, m), 7.19 (1H, d), 7.31 (2H, d), 7.37-7.47 (6H, m), 8.58 (1H, t), 8.97 (1H, s), 10.50 (1H, s); m/z: ES+ [M+H]$^+$ 1009.4; ESI-HRMS calculated for C55H64F3N6O7S [M+H]$^+$=1009.4504, measured 1009.4482.

Intermediate 5a: (1R,3R)-1-(4-((4-(2-((tert-Butyldimethylsilyl)oxy)ethoxy)benzyl)oxy)-2,6-difluorophenyl)-2-(2-fluoro-2-methylpropyl)-3-methyl-2,3,4,9-tetrahydro-1H-pyrido[3,4-b]indole

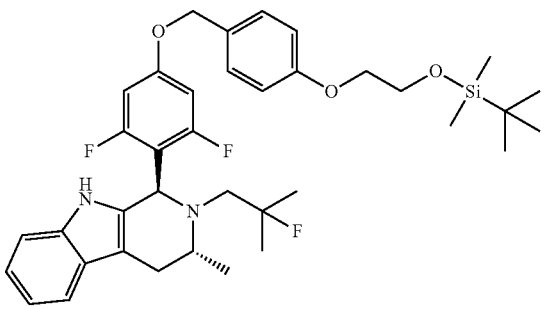 [SMILES: C[C@@H]1Cc2c([nH]c3ccccc23)[C@@H](c2c(F)cc(OCc3ccc(OCCO[Si](C)(C)C(C)(C)C)cc3)cc2F)N1CC(C)(C)F]

RockPhos Pd G3 (43.0 mg, 0.05 mmol) was added in one portion to a degassed mixture of (4-(2-((tert-butyldimethylsilyl)oxy)ethoxy)phenyl)methanol (579 mg, 2.05 mmol), (1R,3R)-1-(4-bromo-2,6-difluorophenyl)-2-(2-fluoro-2-methylpropyl)-3-methyl-2,3,4,9-tetrahydro-1H-pyrido[3,4-b]indole, HCl (500 mg, 1.03 mmol) and cesium carbonate (1.17 g, 3.59 mmol) in toluene (10 mL) at 20° C. under nitrogen. The resulting mixture was stirred at 90° C. for 4 hours. The reaction was allowed to cool to RT and diluted with DCM (20 mL) and water (5 mL) and the mixture was passed through a phase separating filtercup and evaporated to afford crude product as a orange gum. The crude product was purified by flash column chromatography, elution gradient 0 to 30% EtOAc in heptane to afford the title compound (726 mg) as a orange gum that was used in the next step without further purification; ¹H NMR (400 MHz, DMSO-d6) 0.07 (6H, s), 0.86 (9H, d), 1.04 (3H, d), 1.08-1.22 (6H, m), 2.28-2.4 (1H, m), 2.54-2.61 (1H, m), 2.77-2.94 (3H, m), 3.51 (1H, d), 3.88-3.94 (2H, m), 4-4.06 (2H, m), 5.03 (2H, s), 5.12 (1H, s), 6.72 (2H, d), 6.89-7.03 (4H, m), 7.18 (1H, d), 7.32-7.39 (2H, m), 10.49 (1H, s); m/z: ES− [M+H]⁻ 651.7.

Intermediate 5b: 2-(4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)ethan-1-ol

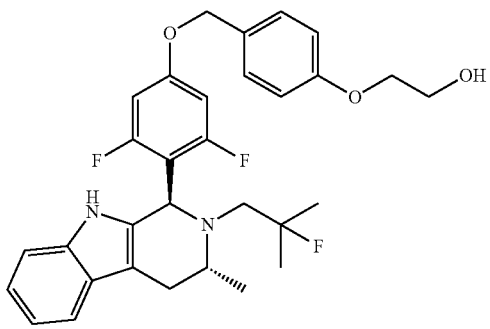 [SMILES: C[C@@H]1Cc2c([nH]c3ccccc23)[C@@H](c2c(F)cc(OCc3ccc(OCCO)cc3)cc2F)N1CC(C)(C)F]

A solution of 1 M TBAF in THF (1.11 mL, 1.11 mmol) was added in one portion to (1R,3R)-1-(4-((4-(2-((tert-butyldimethylsilyl)oxy)ethoxy)benzyl)oxy)-2,6-difluorophenyl)-2-(2-fluoro-2-methylpropyl)-3-methyl-2,3,4,9-tetrahydro-1H-pyrido[3,4-b]indole (726 mg, 1.11 mmol) in THF (4.4 mL) at 20° C. The resulting solution was stirred at 20° C. for 1 hour. The reaction mixture was diluted with EtOAc (100 mL), and washed sequentially with saturated NH₄Cl (25 mL), water (2×50 mL), and saturated brine (20 mL). The organic layer was dried with MgSO₄, filtered and evaporated to afford crude product. The crude product was purified by flash column chromatography, elution gradient 0 to 70% EtOAc in heptane to afford the title compound (406 mg, 68%) as a colourless gum; ¹H NMR (400 MHz, DMSO-d6) 1.05 (3H, d), 1.1-1.27 (6H, m), 2.28-2.42 (1H, m), 2.56 (1H, dd), 2.78-2.96 (2H, m), 3.52 (1H, q), 3.72 (2H, q), 3.97-4.02 (2H, m), 4.84 (1H, t), 5.03 (2H, s), 5.13 (1H, s), 6.73 (2H, d), 6.9-7.03 (4H, m), 7.16-7.23 (1H, m), 7.32-7.43 (3H, m), 10.51 (1H, s); m/z: ES− [M−H]⁻ 537.4.

Intermediate 5c: Ethyl 2-(2-(4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)ethoxy)acetate

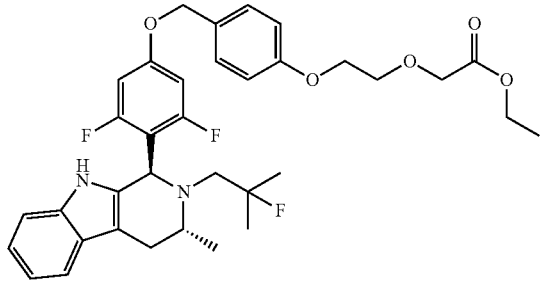 [SMILES: CCOC(=O)COCCOc1ccc(COc2cc(F)c([C@@H]3c4[nH]c5ccccc5c4C[C@@H](C)N3CC(C)(C)F)c(F)c2)cc1]

Ethyl 2-diazoacetate (0.119 mL, 1.13 mmol) in DCM (1.2 mL) was added slowly to 2-(4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)ethan-1-ol (406 mg, 0.75 mmol) and diacetoxyrhodium (16.66 mg, 0.04 mmol) in DCM (3.2 mL) at 20° C. over a period of 1 hour under nitrogen. The resulting solution was stirred at 20° C. for 30 minutes. The mixture was diluted with water (10 mL) and the DCM layer was separated and passed through phase separating filter and evaporated to dryness. The crude product was purified by flash column chromatography, elution gradient 0 to 30% EtOAc in heptane to afford the title compound (206 mg, 44%) as a colourless gum; ¹H NMR (400 MHz, DMSO-d6) 1.05 (3H, d), 1.11 (9H, s), 2.27-2.42 (1H, m), 2.54-2.58 (1H, m), 2.77-2.95 (2H, m), 3.46-3.57 (1H, m), 3.81-3.85 (2H, m), 4.08-4.16 (4H, m), 4.19 (2H, s), 5.04 (2H, s), 5.13 (1H, s), 6.73 (2H, d), 6.9-7.03 (4H, m), 7.19 (1H, d), 7.33-7.44 (3H, m), 10.51 (1H, s); m/z: ES+ [M+H]⁺ 625.4.

Intermediate 5d: 2-(2-(4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)ethoxy)acetic Acid

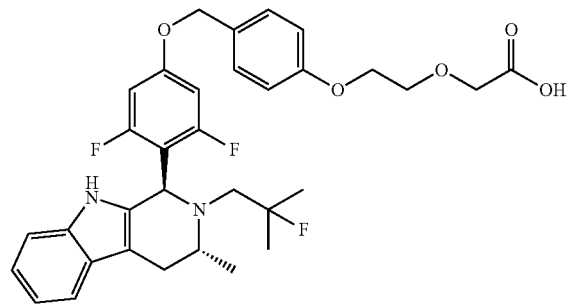 [SMILES: C[C@@H]1Cc2c([nH]c3ccccc23)[C@@H](c2c(F)cc(OCc3ccc(OCCOCC(=O)O)cc3)cc2F)N1CC(C)(C)F]

Lithium hydroxide hydrate (26.9 mg, 0.64 mmol) was added in one portion to ethyl 2-(2-(4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)ethoxy)acetate (200 mg, 0.32 mmol) in THF (1.2 mL) and water (0.4 mL) at 20° C. The resulting solution was stirred at 20° C. for 2 hours. The mixture was diluted with water (10 mL). The resulting mixture was acidified with 2M aq. HCl and extracted into EtOAc (50 mL). The organic layer was washed with brine (15 mL) and evaporated to afford the title compound (221 mg) as a colourless gum that was used in the next step without further purification; m/z: ES+ [M+H]⁺ 597.4.

Example 5: (2S,4R)-1-((S)-2-(2-(2-(4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)ethoxy)acetamido)-3,3-dimethylbutanoyl)-4-hydroxy-N-(4-(4-methylthiazol-5-yl)benzyl)pyrrolidine-2-carboxamide

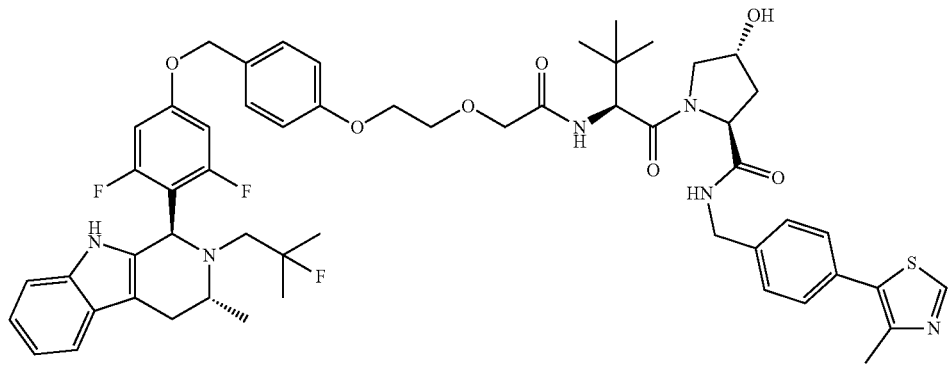 [SMILES: Cc1ncsc1-c1ccc(CNC(=O)[C@@H]2C[C@@H](O)CN2C(=O)[C@@H](NC(=O)COCCOc2ccc(COc3cc(F)c([C@@H]4c5[nH]c6ccccc6c5C[C@@H](C)N4CC(C)(C)F)c(F)c3)cc2)C(C)(C)C)cc1]

HATU (183 mg, 0.48 mmol) was added portionwise to 2-(2-(4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)ethoxy)acetic acid (191 mg, 0.32 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (150 mg, 0.32 mmol) and triethylamine (0.18 mL, 1.28 mmol) in DMF (6.2 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (176 mg, 55%) as a yellow solid; $^1$H NMR (400 MHz, DMSO-d6) 0.95 (9H, d), 1.05 (3H, d), 1.16 (6H, dd), 1.92 (1H, m), 2.02-2.12 (1H, m), 2.27-2.41 (1H, m), 2.42 (3H, s), 2.53-2.6 (1H, m), 2.78-2.96 (2H, m), 3.45-3.57 (1H, m), 3.59-3.74 (2H, m), 3.85 (2H, t), 4.05 (2H, s), 4.12-4.2 (2H, m), 4.26 (1H, dd), 4.33-4.52 (3H, m), 4.60 (1H, d), 4.99 (2H, s), 5.13 (2H, s), 6.70 (2H, d), 6.91-7.05 (4H, m), 7.18 (1H, d), 7.32 (2H, d), 7.34-7.44 (5H, m), 7.48 (1H, d), 8.58 (1H, t), 8.95 (1H, s), 10.51 (1H, s); m/z: ES+ [M+H]$^+$ 1009.7; ESI-HRMS calculated for C$_{55}$H$_{64}$F$_3$N$_6$O$_7$S [M+H]$^+$=1009.4504, measured 1009.4475.

Intermediate 6a: Ethyl 2-((7-hydroxyheptyl)oxy)acetate

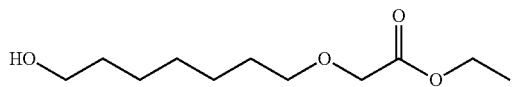

Ethyl 2-diazoacetate (0.655 mL, 5.29 mmol) was added slowly to heptane-1,7-diol (7 g, 52.95 mmol) and diacetoxyrhodium (0.023 g, 0.05 mmol) at 20° C. over a period of 3 hours under nitrogen. The resulting solution was stirred at 20° C. for 18 hours. The reaction mixture was diluted with Et$_2$O (75 mL), and washed sequentially with water (4×75 mL) and saturated brine (50 mL). The organic layer was dried with MgSO$_4$, filtered and evaporated to afford the title compound (0.970 g, 84%) as a colourless liquid; $^1$H NMR (400 MHz, CDCl$_3$) 1.24 (1H, t), 1.29 (3H, t), 1.32-1.44 (6H, m), 1.53-1.67 (4H, m), 3.52 (2H, m), 3.6-3.68 (2H, m), 4.05 (2H, s), 4.22 (2H, q).

Intermediate 6b: (R)—N-(2,2-Difluoroethyl)-1-(1H-indol-3-yl)propan-2-amine

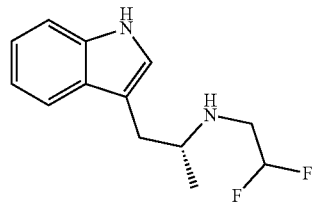 [SMILES: C[C@H](Cc1c[nH]c2ccccc12)NCC(F)F]

Trifluoromethanesulfonic anhydride (9.4 mL, 55.87 mmol) was added to a cooled solution of 2,2-difluoroethane-1-ol (3.37 mL, 53.21 mmol) in DCM (110 mL). 2,6-Dimethylpyridine (6.82 mL, 58.54 mmol) in DCM (11 mL) was then added dropwise and the reaction was stirred at 0° C. for 1 hour. 2N HCl (200 mL) was added and the layers were separated. The organic phase was dried over Na$_2$SO$_4$ to afford a 0.4 M solution of 2,2-difluoroethyl trifluoromethanesulfonate in DCM (133 mL, 53 mmol) which was added in portions (over 20 minutes) to a stirred suspension of (R)-1-(1H-indol-3-yl)propan-2-amine (7.70 g, 44.17 mmol) and DIPEA (10.68 mL, 61.83 mmol) in 1,4-dioxane (68.8 mL). The reaction was stirred at RT for 2 hours. The mixture was washed with sat. NH$_4$Cl solution, dried over MgSO$_4$, filtered and evaporated. The crude product was purified by flash column chromatography, elution gradient 20 to 60% EtOAc in heptane to afford the title compound (9.45 g, 90%) as a pale yellow oil; $^1$H NMR (400 MHz, DMSO-d6) 0.97 (3H, d), 1.76 (1H, s), 2.59 (1H, dd), 2.84 (1H, dd), 2.88-3.02 (3H, m), 5.96 (1H, m), 6.97 (1H, m), 7.06 (1H, m), 7.14 (1H, d), 7.33 (1H, m), 7.52 (1H, d), 10.79 (1H, s); m/z: ES+ [M+H]$^+$ 239.2.

Intermediate 6c: 6-((1S,3R)-2-(2,2-Difluoroethyl)-3-methyl-2,3,4,9-tetrahydro-1H-pyrido[3,4-b]indol-1-yl)pyridin-3-ol

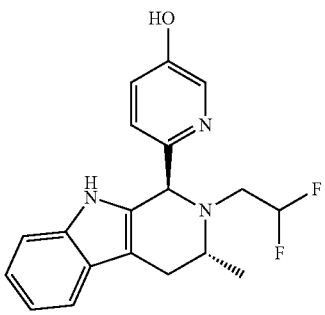 [SMILES: C[C@@H]1Cc2c([nH]c3ccccc23)[C@@H](c2ccc(O)cn2)N1CC(F)F]

(R)—N-(2,2-Difluoroethyl)-1-(1H-indol-3-yl)propan-2-amine (4 g, 16.79 mmol) and 5-hydroxypicolinaldehyde (2.118 g, 17.21 mmol) were heated to 80° C. in toluene (80 mL) and AcOH (8.88 mL) for 2 hours under nitrogen. The mixture was evaporated, then the residue was dissolved in EtOAc (100 mL) and washed with sat. aq. NaHCO$_3$ solution (50 mL), dried (MgSO$_4$) and evaporated to afford crude product as a dark orange oil. The crude product was absorbed onto silica and purified by flash column chromatography, elution gradient 0 to 50% EtOAc in heptane to afford the title compound (4.30 g, 75%) as a cream solid; $^1$H NMR (400 MHz, DMSO-d6) 1.12 (3H, d), 2.57 (1H, q), 2.62-2.76 (2H, m), 3.13 (1H, m), 3.28 (1H, d), 4.94 (1H, s), 5.99 (1H, m), 6.95 (1H, m), 7-7.09 (1H, m), 7.15 (1H, dd), 7.24 (2H, dd), 7.41 (1H, d), 8.06 (1H, dd), 9.81 (1H, s), 10.53 (1H, s); m/z: ES+ [M+H]$^+$ 344.2.

Intermediate 6d: Ethyl 2-((7-((6-((1S,3R)-2-(2,2-difluoroethyl)-3-methyl-2,3,4,9-tetrahydro-1H-pyrido[3,4-b]indol-1-yl)pyridin-3-yl)oxy)heptyl)oxy)acetate

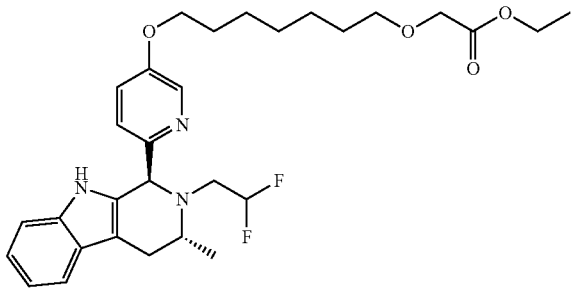 [SMILES: CCOC(=O)COCCCCCCCOc1ccc([C@@H]2c3[nH]c4ccccc4c3C[C@@H](C)N2CC(F)F)nc1]

Diisopropyl azodicarboxylate (0.17 mL, 0.87 mmol) was added dropwise to a stirred solution of 6-((1S,3R)-2-(2,2-difluoroethyl)-3-methyl-2,3,4,9-tetrahydro-1H-pyrido[3,4-b]indol-1-yl)pyridin-3-ol (150 mg, 0.44 mmol), ethyl 2-((7-hydroxyheptyl)oxy)acetate (191 mg, 0.87 mmol) and triphenylphosphine (229 mg, 0.87 mmol) in DCM (3.5 mL) at 20° C. The resulting mixture was stirred for 2 hours. The reaction was incomplete and further ethyl 2-((7-hydroxyheptyl)oxy)acetate (191 mg, 0.87 mmol), triphenylphosphine (229 mg, 0.87 mmol) and diisopropyl azodicarboxylate (0.17 mL, 0.87 mmol) was added and the suspension was stirred at 20° C. for a further 30 minutes. DCM (50 mL) and water (25 mL) were added and the layers were separated. The DCM layer was passed through a phase separating cartridge and concentrated to give the crude product as an orange oil. The crude product was purified by flash column chromatography, elution gradient 0 to 25% EtOAc in heptane to afford the title compound (135 mg, 57%) as a pale yellow gum; $^1$H NMR (400 MHz, DMSO-d6) 1.13 (3H, d), 1.17-1.21 (3H, m), 1.25-1.46 (6H, m), 1.51 (2H, d), 1.71 (2H, m), 2.54-2.59 (1H, m), 2.64-2.75 (1H, m), 3.08-3.22 (1H, m), 3.41-3.47 (2H, m), 4-4.06 (4H, m), 4.08-4.15 (2H, m), 4.78 (2H, m), 4.98 (1H, s), 5.85-6.19 (1H, m), 6.92-6.98 (1H, m), 6.99-7.06 (1H, m), 7.26 (1H, d), 7.29-7.44 (3H, m), 8.20 (1H, d), 10.55 (1H, s); m/z: ES+ [M+H]$^+$ 544.4.

Intermediate 6e: 2-((7-((6-((1S,3R)-2-(2,2-Difluoroethyl)-3-methyl-2,3,4,9-tetrahydro-1H-pyrido[3,4-b]indol-1-yl)pyridin-3-yl)oxy)heptyl)oxy)acetic Acid

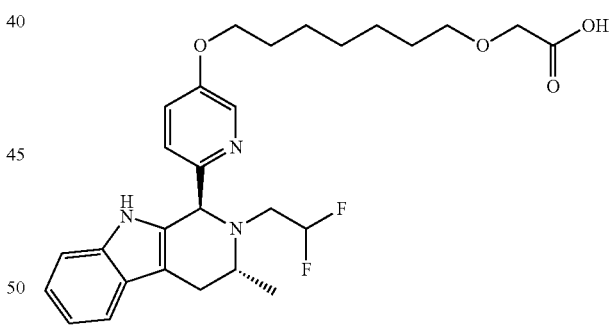

Lithium hydroxide hydrate (19.91 mg, 0.47 mmol) was added in one portion to ethyl 2-((7-((6-((1S,3R)-2-(2,2-difluoroethyl)-3-methyl-2,3,4,9-tetrahydro-1H-pyrido[3,4-b]indol-1-yl)pyridin-3-yl)oxy)heptyl)oxy)acetate (129 mg, 0.24 mmol) in THF (0.90 mL) and water (0.30 mL) at 20° C. The resulting solution was stirred at 20° C. for 30 minutes. The reaction mixture was diluted with water (10 mL), acidified with 2M aq. HCl and extracted into EtOAc (50 mL). The organic layer was washed with brine (15 mL) and evaporated to afford the title compound (131 mg) as a colourless gum that was used in the next step without further purification; m/z: ES+ [M+H]$^+$ 516.4.

Example 6: (2S,4R)-1-((S)-2-(2-((7-((6-((1S,3R)-2-(2,2-Difluoroethyl)-3-methyl-2,3,4,9-tetrahydro-1H-pyrido[3,4-b]indol-1-yl)pyridin-3-yl)oxy)heptyl)oxy)acetamido)-3,3-dimethylbutanoyl)-4-hydroxy-N-(4-(4-methylthiazol-5-yl)benzyl)pyrrolidine-2-carboxamide

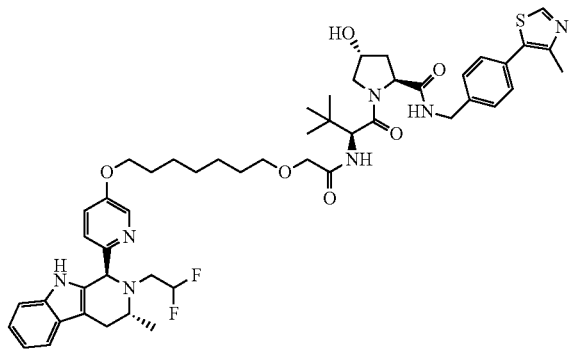 [SMILES: Cc1ncsc1-c1ccc(CNC(=O)[C@@H]2C[C@@H](O)CN2C(=O)[C@@H](NC(=O)COCCCCCCCOc2ccc([C@@H]3c4[nH]c5ccccc5c4C[C@@H](C)N3CC(F)F)nc2)C(C)(C)C)cc1]

HATU (133 mg, 0.35 mmol) was added portionwise to (2S,4R)-1-((S)-2-amino-3,3-dimethylbutanoyl)-4-hydroxy-N-(4-(4-methylthiazol-5-yl)benzyl)pyrrolidine-2-carboxamide, HCl (109 mg, 0.23 mmol), 2-((7-((6-((1S,3R)-2-(2,2-difluoroethyl)-3-methyl-2,3,4,9-tetrahydro-1H-pyrido[3,4-b]indol-1-yl)pyridin-3-yl)oxy)heptyl)oxy)acetic acid (120 mg, 0.23 mmol) and triethylamine (0.13 mL, 0.93 mmol) in DMF (4.5 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO₄, filtered and evaporated to afford crude material. The crude product was purified by preparative HPLC to afford the title compound (76 mg, 35%) as a white solid; ¹H NMR (400 MHz, DMSO-d6) 0.93 (9H, s), 1.13 (3H, d), 1.28-1.48 (6H, m), 1.55 (2H, q), 1.68 (2H, q), 1.91 (1H, m), 2.02-2.14 (1H, m), 2.44 (3H, s), 2.54-2.61 (1H, m), 2.61-2.77 (2H, m), 3.14 (1H, m), 3.26 (1H, s), 3.48 (2H, m), 3.57-3.71 (2H, m), 3.91 (2H, s), 3.98 (2H, t), 4.25 (1H, dd), 4.32-4.5 (3H, m), 4.56 (1H, d), 4.98 (1H, s), 5.14 (1H, s), 5.86-6.2 (1H, m), 6.95 (1H, m), 6.98-7.07 (1H, m), 7.2-7.48 (9H, m), 8.14-8.21 (1H, m), 8.57 (1H, t), 8.96 (1H, s), 10.55 (1H, s); m/z: ES+ [M+H]⁺ 928.6; ESI-HRMS calculated for $C_{50}H_{64}F_2N_7O_6S$ [M+H]⁺=928.4601, measured 928.4583.

Intermediate 7a: Ethyl 2-((7-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)acetate

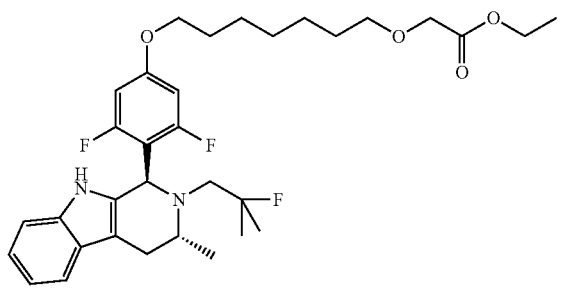 [SMILES: CCOC(=O)COCCCCCCCOc1cc(F)c([C@@H]2c3[nH]c4ccccc4c3C[C@@H](C)N2CC(C)(C)F)c(F)c1]

Diisopropyl azodicarboxylate (0.496 mL, 2.52 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (489 mg, 1.26 mmol), ethyl 2-((7-hydroxyheptyl)oxy)acetate (550 mg, 2.52 mmol) and triphenylphosphine (661 mg, 2.52 mmol) in DCM (21 mL) at 20° C. The resulting mixture was stirred for 1 hour. DCM (20 mL) and water (20 mL) were added and the layers were separated by passing through a phase separating cartridge and concentrated to give the crude product. The crude product was purified by flash column chromatography, elution gradient 0 to 30% EtOAc in heptane to afford the title compound (455 mg, 61%) as a pale yellow gum; ¹H NMR (400 MHz, DMSO-d6) 1.05 (3H, d), 1.1-1.23 (9H, m), 1.36 (6H, dd), 1.51 (2H, d), 1.68 (2H, q), 2.29-2.41 (1H, m), 2.54-2.59 (1H, m), 2.78-2.94 (2H, m), 3.44 (2H, t), 3.52 (1H, d), 3.98 (2H, t), 4.05 (2H, s), 4.12 (2H, m), 5.13 (1H, s), 6.64 (2H, d), 6.9-7.05 (2H, m), 7.16-7.22 (1H, m), 7.39 (1H, d), 10.49 (1H, s); m/z: ES+ [M+H]⁺ 589.4.

Intermediate 7b: 2-((7-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)acetic Acid

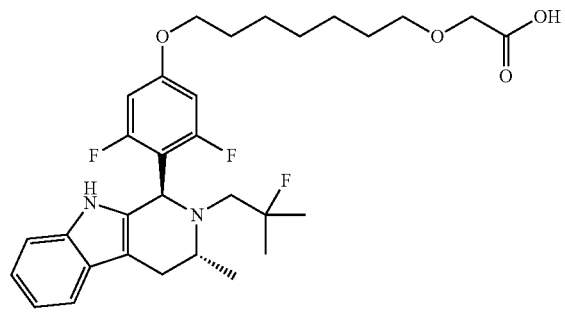 [SMILES: C[C@@H]1Cc2c([nH]c3ccccc23)[C@@H](c2c(F)cc(OCCCCCCCOCC(=O)O)cc2F)N1CC(C)(C)F]

Lithium hydroxide hydrate (64.9 mg, 1.55 mmol) was added in one portion to ethyl 2-((7-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)acetate (455 mg, 0.77 mmol) in THF (2.9 mL) and water (0.97 mL) at 20° C. The resulting solution was stirred for 2 hours. The mixture was diluted with water (10 mL). The resulting mixture was acidified with 2M aq. HCl and extracted into EtOAc (50 mL). The organic layer was washed with brine (15 mL) and evaporated to afford the title compound (480 mg) as a colourless gum that was used in the next step without further purification; ¹H NMR (400 MHz, DMSO-d6) 1.05 (3H, d), 1.1-1.24 (6H, m), 1.36 (6H, dd), 1.46-1.56 (2H, m), 1.68 (2H, q), 2.29-2.41 (1H, m), 2.56 (1H, dd), 2.78-2.94 (2H, m), 3.4-3.47 (2H, m), 3.49-3.57 (1H, m), 3.97 (4H, d), 5.13 (1H, s), 6.64 (2H, d), 6.97 (2H, m), 7.15-7.24 (1H, m), 7.40 (1H, d), 10.49 (1H, s), 12.49 (1H, s); m/z: ES+ [M+H]⁺ 561.3.

Example 7: (2S,4R)-1-((S)-2-(2-((7-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)acetamido)-3,3-dimethylbutanoyl)-4-hydroxy-N-(4-(4-methylthiazol-5-yl)benzyl)pyrrolidine-2-carboxamide

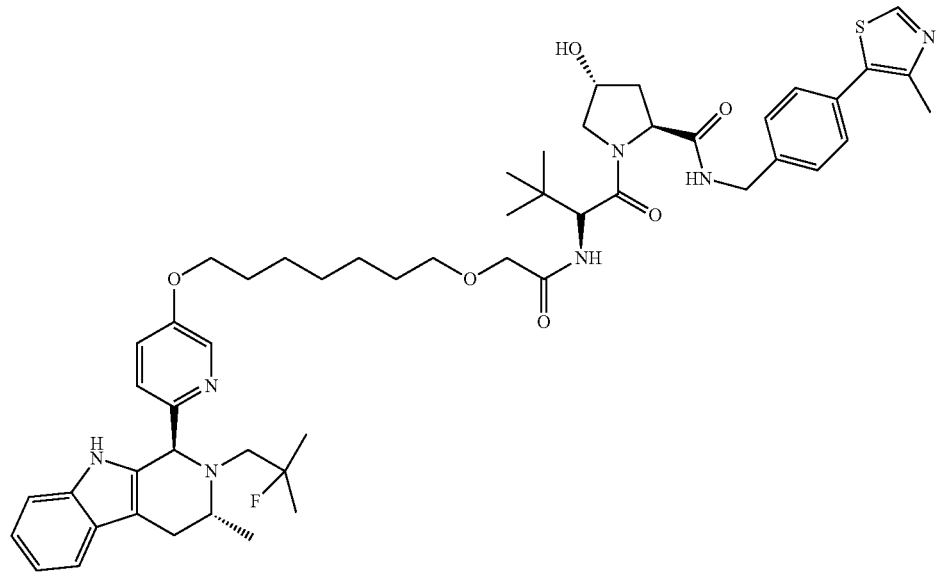

HATU (440 mg, 1.16 mmol) was added portionwise to 2-((7-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)acetic acid (433 mg, 0.77 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (361 mg, 0.77 mmol) and triethylamine (0.431 mL, 3.09 mmol) in DMF (15 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (393 mg, 52%) as a cream solid; $^1$H NMR (400 MHz, DMSO-d6) 0.94 (9H, s), 1.04 (3H, d), 1.16 (6H, t), 1.36 (6H, s), 1.51-1.63 (2H, m), 1.63-1.74 (2H, m), 1.91 (1H, m), 2.02-2.12 (1H, m), 2.29-2.41 (1H, m), 2.44 (3H, s), 2.54-2.59 (1H, m), 2.78-2.94 (2H, m), 3.42-3.57 (3H, m), 3.57-3.7 (2H, m), 3.85-4.01 (4H, m), 4.26 (1H, dd), 4.33-4.5 (3H, m), 4.56 (1H, d), 5.12 (2H, s), 6.61 (2H, d), 6.96 (2H, m), 7.18 (1H, d), 7.34 (1H, d), 7.36-7.47 (5H, m), 8.57 (1H, t), 8.97 (1H, s), 10.49 (1H, s); m/z: ES+ [M+H]$^+$ 973.8; ESI-HRMS calculated for $C_{53}H_{68}F_3N_6O_6S$ [M+H]$^+$=973.4868, measured 973.4842.

Intermediate 8a: Ethyl 2-((6-hydroxyhexyl)oxy)acetate

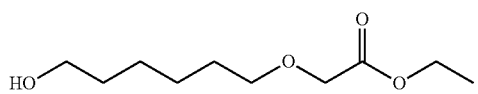

Ethyl 2-diazoacetate (1.131 mL, 9.14 mmol) was added slowly to hexane-1,6-diol (10.8 g, 91.39 mmol) and diacetoxyrhodium (0.040 g, 0.09 mmol) in DCM (20 mL) at 20° C. over a period of 1 hour under nitrogen. The resulting solution was stirred at 20° C. for 18 hours.

The reaction mixture was diluted with Et$_2$O (75 mL), and washed sequentially with water (4×75 mL) and saturated brine (50 mL). The organic layer was dried with MgSO$_4$, filtered and evaporated to afford the title compound (1.310 g, 70%) as a colourless liquid; $^1$H NMR (400 MHz, CDCl$_3$) (4H, t), 1.40 (4H, m), 1.62 (4H, m), 3.53 (2H, m), 3.65 (2H, q), 4.05 (2H, d), 4.22 (2H, q).

Intermediate 8b: Ethyl 2-((6-((6-((1S,3R)-2-(2,2-difluoroethyl)-3-methyl-2,3,4,9-tetrahydro-1H-pyrido[3,4-b]indol-1-yl)pyridin-3-yl)oxy)hexyl)oxy)acetate

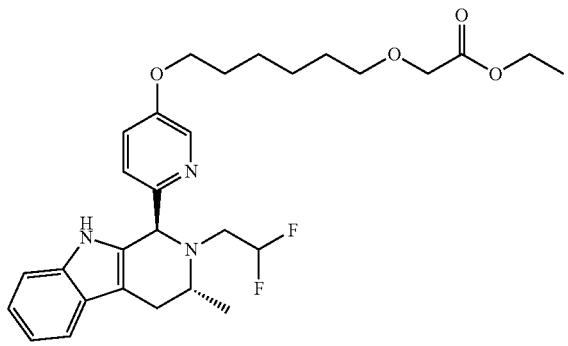

Diisopropyl azodicarboxylate (0.17 mL, 0.87 mmol) was added dropwise to a stirred solution of 6-((1S,3R)-2-(2,2-difluoroethyl)-3-methyl-2,3,4,9-tetrahydro-1H-pyrido[3,4-b]indol-1-yl)pyridin-3-ol (150 mg, 0.44 mmol), ethyl 2-((6-hydroxyhexyl)oxy)acetate (178 mg, 0.87 mmol) and triphenylphosphine (229 mg, 0.87 mmol) in DCM (3.5 mL) at 20° C. The resulting mixture was stirred for 1 hour. DCM (50 mL) and water (25 mL) were added and the layers were separated. The DCM layer was passed through a phase separating cartridge and concentrated to give the crude product as an orange oil. The crude product was purified by flash column chromatography, elution gradient 0 to 25% EtOAc in heptane to afford the title compound (113 mg, 49%) as a pale yellow gum that was used in the next step without further purification; m/z: ES+ [M+H]+ 530.4.

Intermediate 8c: 2-((6-(((6-(((1S,3R)-2-(2,2-Difluoroethyl)-3-methyl-2,3,4,9-tetrahydro-1H-pyrido[3,4-b]indol-1-yl)pyridin-3-yl)oxy)hexyl)oxy)acetic Acid

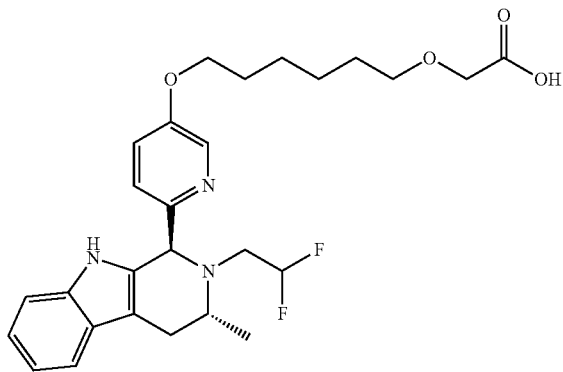

Lithium hydroxide hydrate (17.91 mg, 0.43 mmol) was added in one portion to ethyl 2-((6-(((6-(((1S,3R)-2-(2,2-difluoroethyl)-3-methyl-2,3,4,9-tetrahydro-1H-pyrido[3,4-b]indol-1-yl)pyridin-3-yl)oxy)hexyl)oxy)acetate (113 mg, 0.21 mmol) in THF (0.80 mL) and water (0.27 mL) at 20° C. The resulting solution was stirred for 30 minutes. The reaction mixture was diluted with water (10 mL), acidified with 2M HCl and extracted into EtOAc (50 mL). The organic layer was washed with brine (15 mL) and evaporated to afford the title compound (123 mg) as a colourless gum that was used in the next step without further purification; m/z: ES+ [M+H]+ 502.4.

Example 8: (2S,4R)-1-((S)-2-(2-((6-(((6-(((1S,3R)-2-(2,2-Difluoroethyl)-3-methyl-2,3,4,9-tetrahydro-1H-pyrido[3,4-b]indol-1-yl)pyridin-3-yl)oxy)hexyl)oxy)acetamido)-3,3-dimethylbutanoyl)-4-hydroxy-N-(4-(4-methylthiazol-5-yl)benzyl)pyrrolidine-2-carboxamide HATU (122 mg, 0.32 mmol) was added portionwise to (2S,4R)-1-((S)-2-amino-3,3-dimethylbutanoyl)-4-hydroxy-N-(4-(4-methylthiazol-5-yl)benzyl)pyrrolidine-2-carboxamide, HCl (100 mg, 0.21 mmol), 2-((6-(((6-(((1S,3R)-2-(2,2-difluoroethyl)-3-methyl-2,3,4,9-tetrahydro-1H-pyrido[3,4-b]indol-1-yl)pyridin-3-yl)oxy)hexyl)oxy)acetic acid (107 mg, 0.21 mmol) and triethylamine (0.12 mL, 0.85 mmol) in DMF (4.1 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO4, filtered and evaporated to afford crude material. The crude product was purified by preparative HPLC to afford the title compound (62.0 mg, 32%) as a white solid; $^1$H NMR (400 MHz, DMSO-d6) 0.94 (9H, s), 1.13 (3H, d), 1.42 (4H, d), 1.57 (2H, q), 1.66-1.78 (2H, m), 1.90 (1H, m), 2.01-2.11 (1H, m), 2.44 (3H, s), 2.54-2.63 (1H, m), 2.64-2.76 (1H, m), 3.07-3.22 (1H, m), 3.26 (1H, s), 3.44-3.53 (2H, m), 3.57-3.71 (2H, m), 3.92 (2H, s), 4.00 (2H, hours), 4.24 (1H, dd), 4.32-4.48 (3H, m), 4.56 (1H, d), 4.98 (1H, s), 5.14 (1H, s), 6.02 (2H, m), 6.9-7 (1H, m), 7.02 (1H, m), 7.26 (1H, d), 7.28-7.47 (8H, m), 8.18 (1H, dd), 8.58 (1H, t), 8.96 (1H, s), 10.55 (1H, s); m/z: ES+ [M+H]+ 914.5; ESI-HRMS calculated for $C_{49}H_{62}F_2N_7O_6S$ [M+H]+=914.4445, measured 914.4469.

Intermediate 9a: 2-((5-(2-(Benzyloxy)ethoxy)pentyl)oxy)tetrahydro-2H-pyran

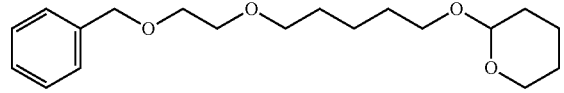

Tetrabutylammonium hydrogen sulfate (0.214 g, 0.63 mmol) was added in one portion to 2-(benzyloxy)ethan-1-ol (0.598 mL, 4.20 mmol) and 2-((5-bromopentyl)oxy)tetrahydro-2H-pyran (1.16 g, 4.62 mmol) in 50% aq. NaOH solution (2.5 mL) at 20° C. The resulting mixture was stirred at 70° C. for 4 hours. The cooled reaction mixture was diluted with water (10 mL) and extracted with Et2O (20 mL) and EtOAc (20 mL). The combined extracts were washed with water (10 mL), saturated brine solution (10 mL), dried

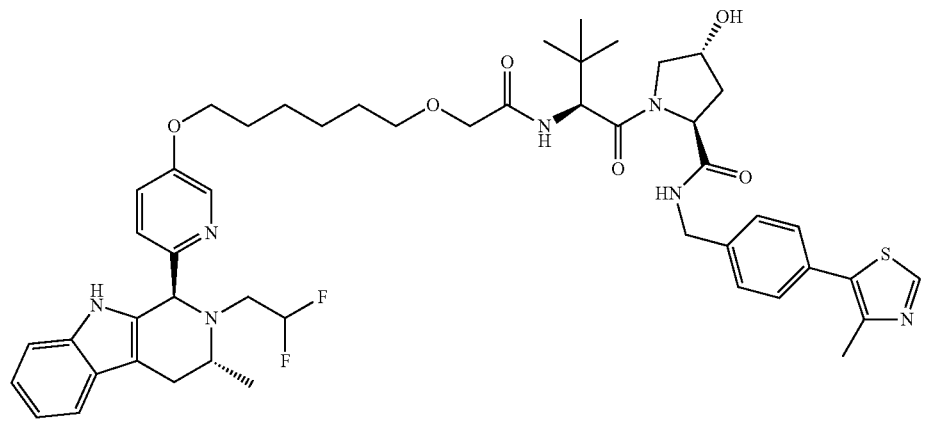 [SMILES: Cc1ncsc1-c1ccc(CNC(=O)[C@@H]2C[C@@H](O)CN2C(=O)[C@@H](NC(=O)COCCCCCCOc2ccc([C@@H]3c4[nH]c5ccccc5c4C[C@@H](C)N3CC(F)F)nc2)C(C)(C)C)cc1]

(MgSO$_4$), filtered and evaporated to afford crude product as a colourless oil. The crude product was purified by flash column chromatography, elution gradient 0 to 10% EtOAc in heptane to afford the title compound (0.900 g, 67%) as a colourless oil; $^1$H NMR (400 MHz, CDCl$_3$) 1.38-1.47 (2H, m), 1.48-1.75 (9H, m), 1.82 (1H, m), 3.39 (1H, m), 3.48 (3H, q), 3.57-3.65 (4H, m), 3.74 (1H, m), 3.86 (1H, m), 4.57 (3H, s), 7.27-7.3 (1H, m), 7.3-7.37 (4H, m).

Intermediate 9b:
5-(2-(Benzyloxy)ethoxy)pentan-1-ol

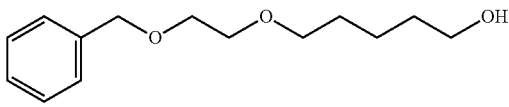 [SMILES: OCCCCCOCCOCc1ccccc1]

2-((5-(2-(Benzyloxy)ethoxy)pentyl)oxy)tetrahydro-2H-pyran (900 mg, 2.79 mmol) was dissolved in MeOH (7.5 mL) and 1M aq. HCl (3.75 mL) was added. The resulting mixture was stirred at 20° C. for 3 hours. The reaction mixture was diluted with water (20 mL), and extracted with EtOAc (3×30 mL). The combined organics were washed with saturated brine (20 mL). The organic layer was dried with MgSO$_4$, filtered and evaporated to afford the crude title compound (700 mg) as a colourless liquid that was used without further purification; $^1$H NMR (400 MHz, CDCl$_3$) 1.41-1.49 (2H, m), 1.61 (5H, m), 3.48 (2H, m), 3.56-3.68 (6H, m), 4.58 (2H, s), 7.26-7.3 (1H, m), 7.3-7.37 (4H, m).

Intermediate 9c: Ethyl 2-((5-(2-(benzyloxy)ethoxy)pentyl)oxy)acetate

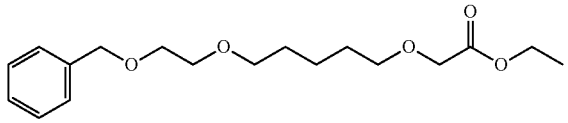 [SMILES: CCOC(=O)COCCCCCOCCOCc1ccccc1]

Ethyl 2-diazoacetate (1.134 mL, 9.25 mmol) in DCM (7.50 mL) was added slowly to 5-(2-(benzyloxy)ethoxy)pentan-1-ol (700 mg, 2.64 mmol) and diacetoxyrhodium (58.4 mg, 0.13 mmol) in DCM (19.500 mL) at 20° C. over a period of 1 hour under nitrogen. The resulting solution was stirred for 18 hours. The mixture was diluted with DCM (50 mL) and washed with water (20 mL). The organic layer was collected and dried using phase separating cartridge then evaporated to dryness. The crude product was purified by flash column chromatography, elution gradient 0 to 10% EtOAc in heptane to afford the title compound (540 mg, 63%) a colourless liquid; $^1$H NMR (400 MHz, CDCl$_3$) 1.29 (3H, t), 1.39-1.48 (2H, m), 1.58-1.69 (4H, m), 3.47 (2H, t), 3.52 (2H, t), 3.57-3.64 (4H, m), 4.05 (2H, s), 4.18-4.27 (2H, m), 4.57 (2H, s), 7.26-7.3 (1H, m), 7.31-7.36 (4H, m).

Intermediate 9d: Ethyl 2-((5-(2-hydroxyethoxy)pentyl)oxy)acetate

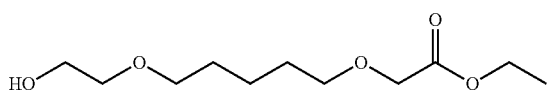 [SMILES: CCOC(=O)COCCCCCOCCO]

Ethyl 2-((5-(2-(benzyloxy)ethoxy)pentyl)oxy)acetate (540 mg, 1.66 mmol) and 10% palladium on carbon (17.71 mg, 0.17 mmol) in ethanol (10 mL) were stirred under an atmosphere of hydrogen (0.5 bar) at RT for 18 hours. The reaction mixture was filtered and evaporated to afford the title compound (413 mg) as a colourless oil that was used in the next step without further purification; $^1$H NMR (400 MHz, CDCl$_3$) 1.28 (3H, t), 1.42-1.51 (2H, m), 1.63 (4H, m), 1.99 (1H, s), 3.49 (2H, t), 3.51-3.56 (4H, m), 3.72 (2H, d), 4.05 (2H, d), 4.18-4.27 (2H, m).

Intermediate 9e: Ethyl 2-((5-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)pentyl)oxy)acetate

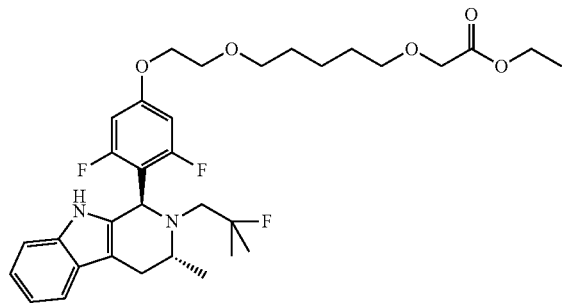 [SMILES: CCOC(=O)COCCCCCOCCOc1cc(F)c([C@@H]2c3[nH]c4ccccc4c3C[C@@H](C)N2CC(C)(C)F)c(F)c1]

Diisopropyl azodicarboxylate (81 μL, 0.41 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (80 mg, 0.21 mmol), ethyl 2-((5-(2-hydroxyethoxy)pentyl)oxy)acetate (97 mg, 0.41 mmol) and triphenylphosphine (108 mg, 0.41 mmol) in DCM (1.7 mL) at 20° C. The resulting mixture was stirred for 16 hours. DCM (15 mL) and water (25 mL) were added and the layers were separated. The aqueous layer was extracted with DCM (2×25 mL). The combined organics were washed with brine (25 mL), dried (MgSO$_4$) and concentrated to give the crude product. The crude product was purified by flash column chromatography, elution gradient 0 to 20% EtOAc in heptane to afford the title compound (121 mg, 97%) as a yellow gum; m/z: ES+ [M+H]$^+$ 605.4.

Intermediate 9f: 2-((5-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)pentyl)oxy)acetic Acid

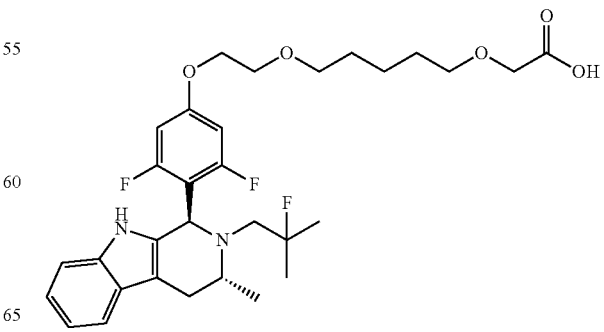

Lithium hydroxide hydrate (16.65 mg, 0.40 mmol) was added in one portion to ethyl 2-((5-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)pentyl)oxy)acetate (120 mg, 0.20 mmol) in THF (0.74 mL) and water (0.25 mL) at 20° C. The resulting solution was stirred for 2 hours. The reaction mixture was diluted with water (10 mL), acidified with 2M aq. HCl and extracted into EtOAc (50 mL). The organic layer was washed with brine (15 mL) and evaporated to afford the title compound (156 mg) as a colourless gum that was used in the next step without further purification; m/z: ES+ [M+H]$^+$ 577.4.

Example 9: (2S,4R)-1-((S)-2-(2-((5-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)pentyl)oxy)acetamido)-3,3-dimethylbutanoyl)-4-hydroxy-N-(4-(4-methylthiazol-5-yl)benzyl)pyrrolidine-2-carboxamide Intermediate 10a: Ethyl 2-((5-(2-((6-((1S,3R)-2-(2,2-difluoroethyl)-3-methyl-2,3,4,9-tetrahydro-1H-pyrido[3,4-b]indol-1-yl)pyridin-3-yl)oxy)ethoxy)pentyl)oxy)acetate

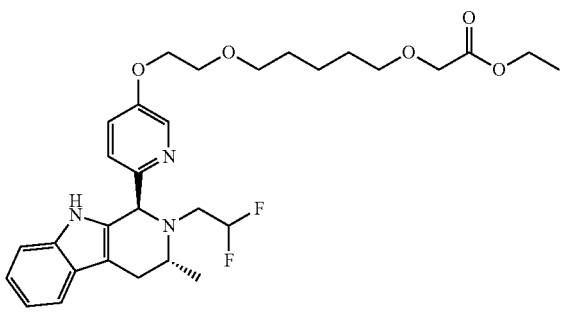

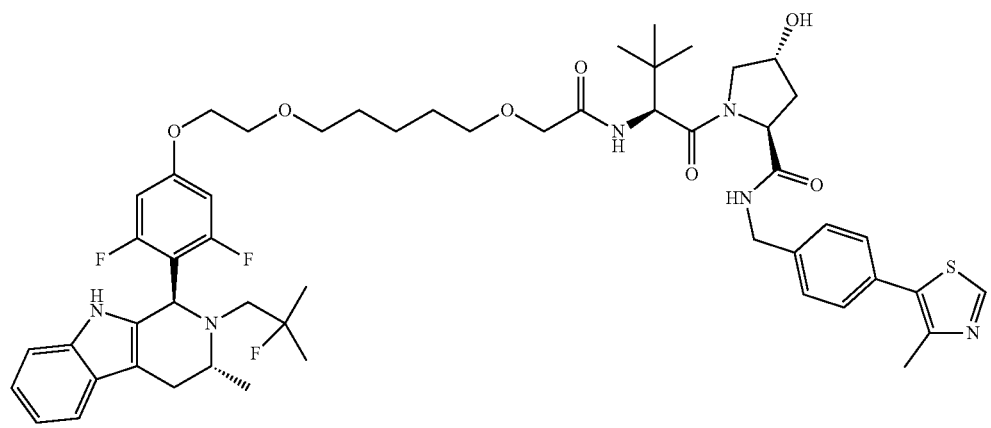 [SMILES: Cc1ncsc1-c1ccc(CNC(=O)[C@@H]2C[C@@H](O)CN2C(=O)[C@@H](NC(=O)COCCCCCOCCOc2cc(F)c([C@@H]3c4[nH]c5ccccc5c4C[C@@H](C)N3CC(C)(C)F)c(F)c2)C(C)(C)C)cc1]

HATU (113 mg, 0.30 mmol) was added portionwise to 2-((5-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)pentyl)oxy)acetic acid (114 mg, 0.20 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (92 mg, 0.20 mmol) and triethylamine (0.11 mL, 0.79 mmol) in DMF (3.8 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (82 mg, 42%) as a white solid; $^1$H NMR (400 MHz, DMSO-d6) 0.93 (9H, d), 1.04 (3H, d), 1.16 (6H, t), 1.38 (2H, m), 1.55 (4H, m), 1.91 (1H, m), 2.03-2.12 (1H, m), 2.28-2.41 (1H, m), 2.45 (3H, d), 2.57 (1H, d), 2.78-2.95 (2H, m), 3.38-3.56 (5H, m), 3.57-3.73 (4H, m), 3.91 (2H, s), 4.05-4.13 (2H, m), 4.26 (1H, dd), 4.32-4.5 (3H, m), 4.56 (1H, d), 5.13 (2H, s), 6.66 (2H, d), 6.97 (2H, m), 7.18 (1H, d), 7.34 (1H, d), 7.36-7.47 (5H, m), 8.57 (1H, t), 8.97 (1H, s), 10.50 (1H, s); m/z: ES+ [M+H]$^+$ 989.6; ESI-HRMS calculated for C$_{53}$H$_{68}$F$_3$N$_6$O$_7$S [M+H]$^+$=989.4817, measured 989.4787.

Diisopropyl azodicarboxylate (0.345 mL, 1.75 mmol) was added dropwise to a stirred mixture of 6-((1S,3R)-2-(2,2-difluoroethyl)-3-methyl-2,3,4,9-tetrahydro-1H-pyrido[3,4-b]indol-1-yl)pyridin-3-ol (300 mg, 0.87 mmol), ethyl 2-((5-(2-hydroxyethoxy)pentyl)oxy)acetate (410 mg, 1.75 mmol) and triphenylphosphine (459 mg, 1.75 mmol) in DCM (14.500 mL) at 0° C. The resulting mixture was stirred at RT for 18 hours. DCM (50 mL) and water (25 mL) were added and the layers were separated. The DCM layer was passed through a phase separating cartridge and concentrated to give the crude product. The crude product was purified by flash column chromatography, elution gradient 0 to 50% EtOAc in heptane to afford the title compound (726 mg, contains solvents) as a pale yellow gum that was used in the next step without further purification; m/z: ES+ [M+H]$^+$ 560.4.

Intermediate 10b: 2-((5-(2-((6-((1S,3R)-2-(2,2-Difluoroethyl)-3-methyl-2,3,4,9-tetrahydro-1H-pyrido[3,4-b]indol-1-yl)pyridin-3-yl)oxy)ethoxy)pentyl)oxy)acetic Acid

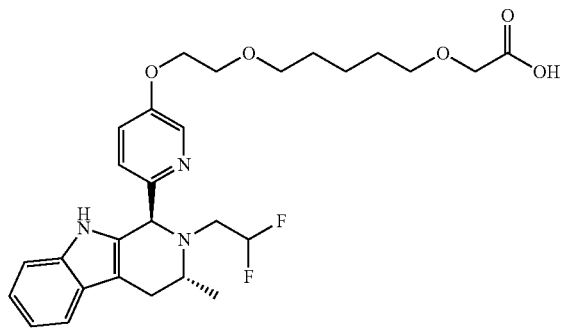 [SMILES: C[C@@H]1Cc2c([nH]c3ccccc23)[C@@H](c2ccc(OCCOCCCCCOCC(=O)O)cn2)N1CC(F)F]

Lithium hydroxide hydrate (73.5 mg, 1.75 mmol) was added in one portion to ethyl 2-((5-(2-((6-((1S,3R)-2-(2,2-difluoroethyl)-3-methyl-2,3,4,9-tetrahydro-1H-pyrido[3,4-b]indol-1-yl)pyridin-3-yl)oxy)ethoxy)pentyl)oxy)acetate (490 mg, 0.88 mmol) in THF (3.3 mL) and water (1.1 mL) at 20° C. The resulting solution was stirred for 30 minutes. The reaction mixture was diluted with water (10 mL) then was acidified with 2M HCl and extracted into EtOAc (50 mL). The organic layer was washed with brine (15 mL) and evaporated to afford the title compound (479 mg) as a yellow gum that was used in the next step without further purification; m/z: ES+ [M+H]+ 532.4.

Example 10: (2S,4R)-1-((S)-2-(2-((5-(2-((6-((1S,3R)-2-(2,2-Difluoroethyl)-3-methyl-2,3,4,9-tetrahydro-1H-pyrido[3,4-b]indol-1-yl)pyridin-3-yl)oxy)ethoxy)pentyl)oxy)acetamido)-3,3-dimethylbutanoyl)-4-hydroxy-N-(4-(4-methylthiazol-5-yl)benzyl)pyrrolidine-2-carboxamide

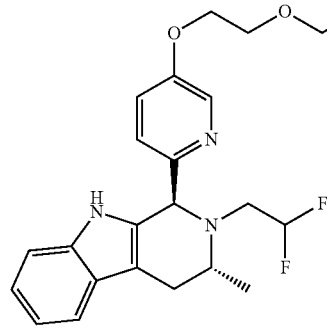

HATU (499 mg, 1.31 mmol) was added portionwise to (2S,4R)-1-((S)-2-amino-3,3-dimethylbutanoyl)-4-hydroxy-N-(4-(4-methylthiazol-5-yl)benzyl)pyrrolidine-2-carboxamide, HCl (409 mg, 0.87 mmol), 2-((5-(2-((6-((1S,3R)-2-(2,2-difluoroethyl)-3-methyl-2,3,4,9-tetrahydro-1H-pyrido[3,4-b]indol-1-yl)pyridin-3-yl)oxy)ethoxy)pentyl)oxy) acetic acid (465 mg, 0.87 mmol) and triethylamine (0.488 mL, 3.50 mmol) in DMF (17 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO4, filtered and evaporated to afford crude material. The crude product was purified by preparative HPLC to afford the title compound (344 mg, 42%) as a white solid; $^1$H NMR (400 MHz, CDCl3) 0.94 (9H, s), 1.23 (3H, d), 1.39-1.5 (2H, m), 1.61 (4H, q), 2.11 (1H, m), 2.51 (3H, s), 2.52-2.69 (2H, m), 2.83 (2H, m), 3.11 (1H, m), 3.31 (1H, s), 3.34-3.5 (3H, m), 3.53 (2H, t), 3.62 (1H, dd), 3.76 (3H, dd), 3.87 (1H, d), 4.03-4.21 (3H, m), 4.34 (1H, dd), 4.47-4.6 (3H, m), 4.74 (1H, t), 4.96 (1H, s), 5.53-5.91 (1H, m), 7.03-7.22 (4H, m), 7.27-7.39 (6H, m), 7.42 (1H, d), 7.49 (1H, d), 8.20 (1H, d), 8.65 (1H, s), 8.72 (1H, s); m/z: ES+ [M+H]+ 944.6; ESI-HRMS calculated for C50H64F2N7O7S [M+H]+=944.4551, measured 944.4519.

Intermediate 11a: Methyl 10-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)decanoate

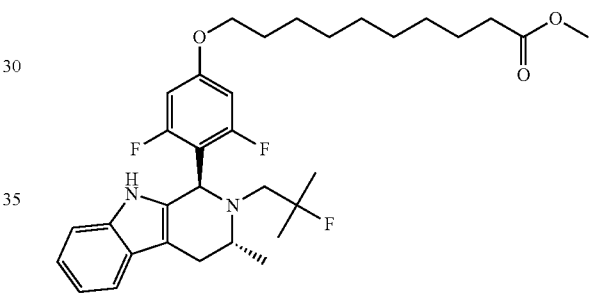

Methyl 10-bromodecanoate (82 mg, 0.31 mmol) was added in one portion to 3,5-difluoro-4-((1R,3R)-2-(2-fluoro-2-methylpropyl)-3-methyl-2,3,4,9-tetrahydro-1H-pyrido[3,4-b]indol-1-yl)phenol (120 mg, 0.31 mmol) and potassium carbonate (64.0 mg, 0.46 mmol) in MeCN (2 mL) at 20° C. The resulting suspension was stirred at 70° C. for 18 hours. The mixture was cooled to RT and was diluted with DCM (10 mL) and water (2 mL). The DCM layer was collected

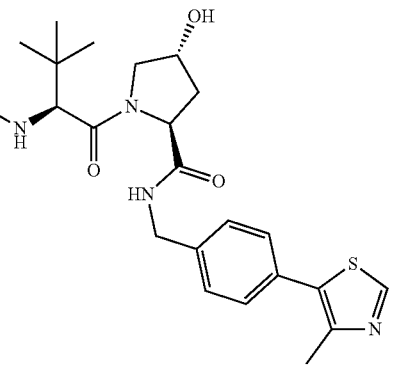

and evaporated to afford crude material as a yellow gum. The crude product was purified by flash column chromatography, elution gradient 0 to 30% EtOAc in heptane to afford the title compound (134 mg, 76%) as a colourless gum; ¹H NMR (400 MHz, DMSO-d6) 1.05 (3H, d), 1.09-1.23 (6H, m), 1.23-1.33 (8H, m), 1.35-1.44 (2H, m), 1.46-1.59 (2H, m), 1.69 (2H, p), 2.29 (2H, t), 2.34-2.42 (1H, m), 2.55-2.6 (1H, m), 2.78-2.96 (2H, m), 3.48-3.55 (1H, m), 3.58 (3H, s), 3.97 (2H, t), 5.13 (1H, s), 6.64 (2H, d), 6.97 (2H, m), 7.18 (1H, d), 7.39 (1H, d), 10.49 (1H, s); m/z: ES+ [M+H]⁺ 573.4.

Intermediate 11b: 10-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)decanoic Acid

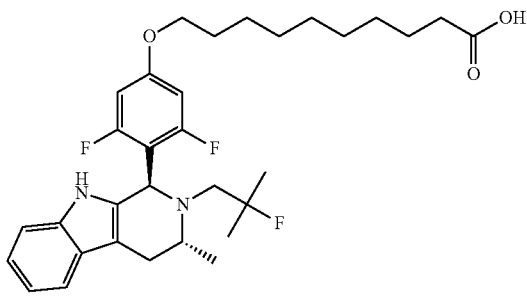 [SMILES: C[C@@H]1Cc2c([nH]c3ccccc23)[C@@H](c2c(F)cc(OCCCCCCCCCC(=O)O)cc2F)N1CC(C)(C)F]

Lithium hydroxide hydrate (19.64 mg, 0.47 mmol) was added in one portion to methyl 10-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)decanoate (134 mg, 0.23 mmol) in THF (0.9 mL) and water (0.29 mL) at 20° C. The resulting solution was stirred at 40° C. for 2 hours. The organic solvent was removed under reduced pressure. The resulting mixture was acidified with 2M aq. HCl and extracted into EtOAc (50 mL). The organic layer was washed with brine (15 mL) and evaporated to afford the title compound (131 mg, 100%) as a colourless gum; m/z: ES+ [M+H]⁺ 559.4.

Example 11: (2S,4R)-1-((S)-2-(10-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)decanamido)-3,3-dimethylbutanoyl)-4-hydroxy-N-(4-(4-methylthiazol-5-yl)benzyl)pyrrolidine-2-carboxamide

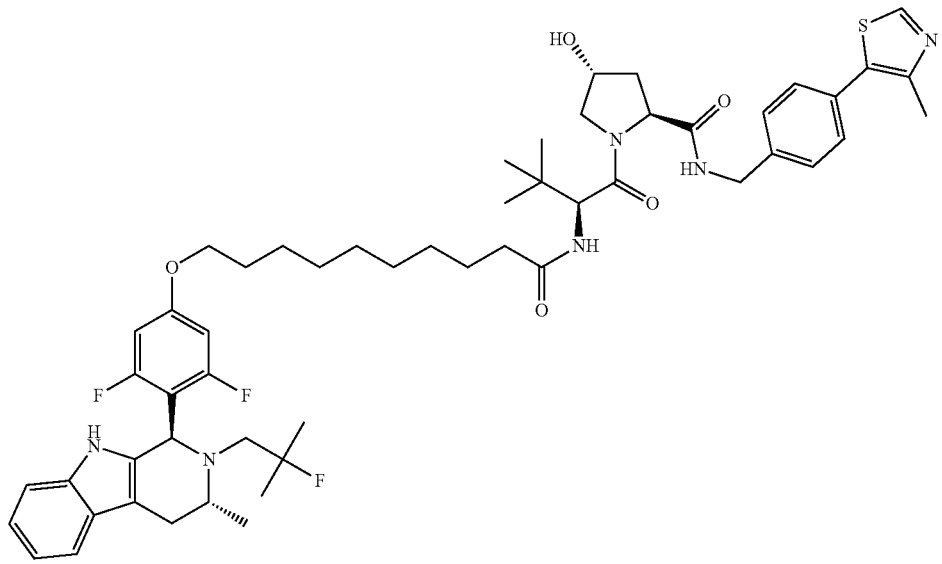 [SMILES: Cc1ncsc1-c1ccc(CNC(=O)[C@@H]2C[C@@H](O)CN2C(=O)[C@@H](NC(=O)CCCCCCCCCOc2cc(F)c([C@@H]3c4[nH]c5ccccc5c4C[C@@H](C)N3CC(C)(C)F)c(F)c2)C(C)(C)C)cc1]

HATU (134 mg, 0.35 mmol) was added portionwise to 10-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)decanoic acid (131 mg, 0.23 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (110 mg, 0.23 mmol) and triethylamine (0.13 mL, 0.94 mmol) in DMF (4.6 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO₄, filtered and evaporated to afford crude material. The crude product was purified by preparative HPLC to afford the title compound (142 mg, 62%) as a white solid; ¹H NMR (400 MHz, DMSO-d6) 0.94 (9H, s), 1.04 (3H, d), 1.08-1.58 (18H, m), 1.62-1.75 (2H, m), 1.91 (1H, m), 1.99-2.18 (2H, m), 2.2-2.42 (2H, m), 2.45 (3H, s), 2.57 (1H, d), 2.75-2.94 (2H, m), 3.52 (1H, q), 3.6-3.72 (2H, m), 3.97 (2H, t), 4.23 (1H, dd), 4.36 (1H, s), 4.38-4.49 (2H, m), 4.55 (1H, d), 5.11 (2H, d), 6.64 (2H, d), 6.97 (2H, m), 7.13-7.24 (1H, m), 7.31-7.52 (5H, m), 7.80 (1H, d), 8.53 (1H, t), 8.98 (1H, s), 10.49 (1H, s); m/z: ES+ [M+H]⁺ 971.6; ESI-HRMS calculated for C₅₄H₇₀F₃N₆O₅S [M+H]⁺=971.5075, measured 971.5066.

Intermediate 12a: Ethyl 2-((8-hydroxyoctyl)oxy)acetate

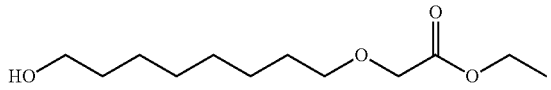

Ethyl 2-diazoacetate (0.846 mL, 6.84 mmol) was added slowly to a suspension of octane-1,8-diol (10 g, 68.39 mmol) and diacetoxyrhodium (0.030 g, 0.07 mmol) in DCM (5 mL) at 20° C. over a period of 3 hours under nitrogen. The resulting suspension was stirred at 20° C. for 18 hours. The reaction mixture was filtered and the filtrate was then diluted with EtOAc (75 mL), and washed sequentially with water (4×75 mL) and saturated brine (50 mL). The organic layer was dried with MgSO$_4$, filtered and evaporated to afford crude product. The crude material was suspended in 1:1 heptane: diethyl ether (10 mL) and filtered. The filtrate was evaporated to afford the title compound (1.100 g, 69%) as a yellow liquid; $^1$H NMR (400 MHz, CDCl$_3$) 1.22-1.41 (12H, m), 1.60 (4H, m), 3.52 (2H, m), 3.64 (2H, t), 4.05 (2H, s), 4.22 (2H, q).

Intermediate 12b: Ethyl 2-((8-(3,5-difluoro-4-((1R, 3R)-2-(2-fluoro-2-methylpropyl)-3-methyl-2,3,4,9-tetrahydro-1H-pyrido[3,4-b]indol-1-yl)phenoxy)octyl)oxy)acetate

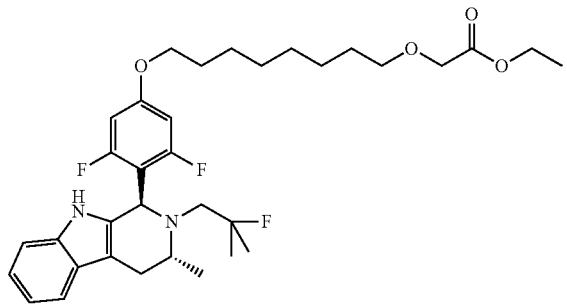

Diisopropyl azodicarboxylate (0.10 mL, 0.51 mmol) was added dropwise to a stirred solution of 3,5-difluoro-4-((1R, 3R)-2-(2-fluoro-2-methylpropyl)-3-methyl-2,3,4,9-tetrahydro-1H-pyrido[3,4-b]indol-1-yl)phenol (100 mg, 0.26 mmol), ethyl 2-((8-hydroxyoctyl)oxy)acetate (120 mg, 0.51 mmol) and triphenylphosphine (135 mg, 0.51 mmol) in DCM (2.1 mL) at 20° C. The resulting mixture was stirred for 16 hours. DCM (15 mL) and water (25 mL) were added and the layers were separated. The aqueous layer was extracted with DCM (2×25 mL). The combined organics were washed with brine (25 mL), dried (Na$_2$SO$_4$) and concentrated to give the crude product. The crude product was purified by flash column chromatography, elution gradient 0 to 20% EtOAc in heptane to afford the title compound (81 mg, 52%) as a pale yellow gum; m/z: ES+ [M+H]$^+$ 603.4.

Intermediate 12c: 2-((8-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)octyl)oxy)acetic Acid

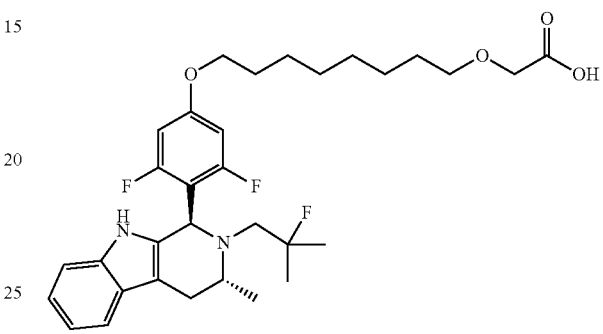

Lithium hydroxide hydrate (11.14 mg, 0.27 mmol) was added in one portion to ethyl 2-((8-(3,5-difluoro-4-((1R, 3R)-2-(2-fluoro-2-methylpropyl)-3-methyl-2,3,4,9-tetrahydro-1H-pyrido[3,4-b]indol-1-yl)phenoxy)octyl)oxy)acetate (80 mg, 0.13 mmol) in THF (0.5 mL) and water (0.17 mL) at 20° C. The resulting solution was stirred for 2 hours. The mixture was diluted with water (10 mL). The resulting mixture was acidified with 2M HCl and extracted into EtOAc (50 mL). The organic layer was washed with brine (15 mL) and evaporated to afford the title compound (70.0 mg, 92%) as a colourless gum; m/z: ES+ [M+H]$^+$ 575.4.

Example 12: (2S,4R)-1-((S)-2-(2-((8-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)octyl)oxy)acetamido)-3,3-dimethylbutanoyl)-4-hydroxy-N-(4-(4-methylthiazol-5-yl)benzyl)pyrrolidine-2-carboxamide

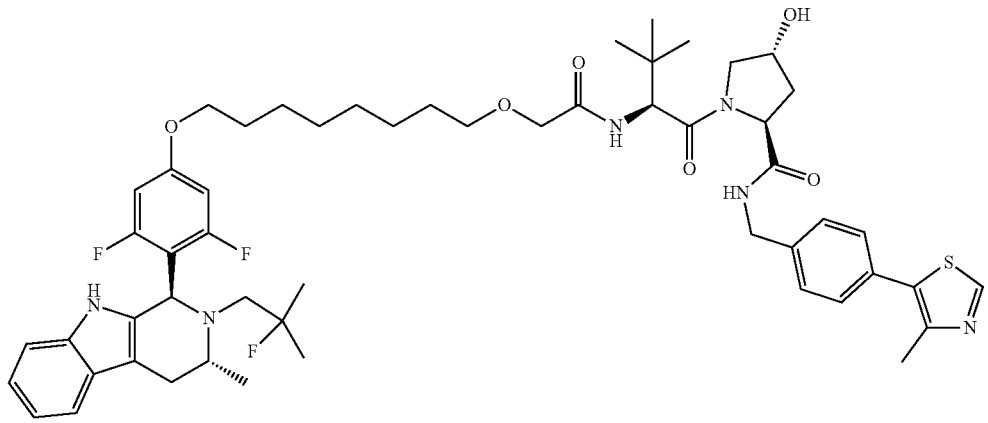 [SMILES: Cc1ncsc1-c1ccc(CNC(=O)[C@@H]2C[C@@H](O)CN2C(=O)[C@@H](NC(=O)COCCCCCCCCOc2cc(F)c([C@@H]3c4[nH]c5ccccc5c4C[C@@H](C)N3CC(C)(C)F)c(F)c2)C(C)(C)C)cc1]

HATU (70 mg, 0.18 mmol) was added portionwise to 2-((8-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)octyl)oxy)acetic acid (70 mg, 0.12 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (56.9 mg, 0.12 mmol) and triethylamine (0.068 mL, 0.49 mmol) in DMF (2.4 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (38.0 mg, 32%) as a yellow solid; $^1$H NMR (400 MHz, DMSO-d6) 0.93 (9H, d), 1.04 (3H, d), 1.16 (6H, t), 1.32 (8H, s), 1.55 (2H, q), 1.6-1.72 (2H, m), 1.91 (1H, m), 2.03-2.11 (1H, m), 2.29-2.41 (1H, m), 2.44 (3H, s), 2.56 (1H, dd), 2.77-2.95 (2H, m), 3.44-3.56 (3H, m), 3.58-3.72 (2H, m), 3.85-3.99 (4H, m), 4.25 (1H, dd), 4.32-4.5 (3H, m), 4.56 (1H, d), 5.12 (2H, s), 6.62 (2H, d), 6.97 (2H, m), 7.18 (1H, d), 7.33 (1H, d), 7.36-7.47 (5H, m), 8.58 (1H, t), 8.97 (1H, s), 10.49 (1H, s); m/z: ES+ [M+H]$^+$ 987.6; ESI-HRMS calculated for C$_{54}$H$_{70}$F$_3$N$_6$O$_6$S [M+H]$^+$=987.5024, measured 987.5027.

Intermediate 13a: Ethyl 2-((8-((6-((1S,3R)-2-(2,2-difluoroethyl)-3-methyl-2,3,4,9-tetrahydro-1H-pyrido[3,4-b]indol-1-yl)pyridin-3-yl)oxy)octyl)oxy)acetate

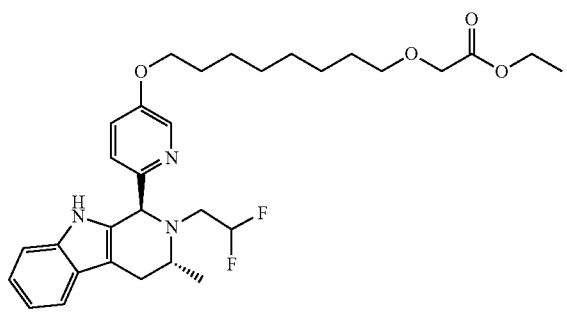 [SMILES: CCOC(=O)COCCCCCCCCOc1ccc([C@@H]2c3[nH]c4ccccc4c3C[C@@H](C)N2CC(F)F)nc1]

Diisopropyl azodicarboxylate (0.19 mL, 0.95 mmol) was added dropwise to a stirred solution of 6-((1S,3R)-2-(2,2-difluoroethyl)-3-methyl-2,3,4,9-tetrahydro-1H-pyrido[3,4-b]indol-1-yl)pyridin-3-ol (163 mg, 0.47 mmol), ethyl 2-((8-hydroxyoctyl)oxy)acetate (221 mg, 0.95 mmol) and triphenylphosphine (249 mg, 0.95 mmol) in DCM (3.8 mL) at 20° C. The resulting mixture was stirred for 16 hours. DCM (50 mL) and water (25 mL) were added and the layers were separated. The DCM layer was passed through a phase separating cartridge and concentrated to give the crude product. The crude product was purified by flash column chromatography, elution gradient 0 to 50% EtOAc in heptane to afford the title compound (256 mg, 97%) as a yellow gum; m/z: ES+ [M+H]$^+$ 558.3.

Intermediate 13b: 2-((8-((6-((1S,3R)-2-(2,2-Difluoroethyl)-3-methyl-2,3,4,9-tetrahydro-1H-pyrido[3,4-b]indol-1-yl)pyridin-3-yl)oxy)octyl)oxy)acetic Acid

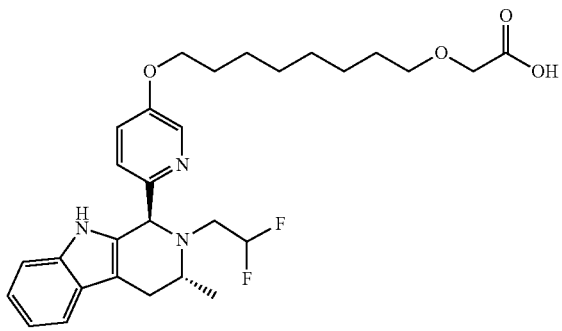 [SMILES: C[C@@H]1Cc2c([nH]c3ccccc23)[C@@H](c2ccc(OCCCCCCCCOCC(=O)O)cn2)N1CC(F)F]

Lithium hydroxide hydrate (39.9 mg, 0.95 mmol) was added in one portion to ethyl 2-((8-((6-((1S,3R)-2-(2,2-difluoroethyl)-3-methyl-2,3,4,9-tetrahydro-1H-pyrido[3,4-b]indol-1-yl)pyridin-3-yl)oxy)octyl)oxy)acetate (265 mg, 0.48 mmol) in THF (1.8 mL) and water (0.6 mL) at 20° C. The resulting solution was stirred for 2 hours. The reaction mixture was diluted with water (10 mL), acidified with 2M HCl and extracted into EtOAc (50 mL). The organic layer was washed with brine (15 mL) and evaporated to afford the title compound (290 mg) as a colourless gum that was used in the next step without purification; m/z: ES+ [M+H]$^+$ 530.

Example 13: (2S,4R)-1-((S)-2-(2-((8-((6-((1S,3R)-2-(2,2-Difluoroethyl)-3-methyl-2,3,4,9-tetrahydro-1H-pyrido[3,4-b]indol-1-yl)pyridin-3-yl)oxy)octyl)oxy)acetamido)-3,3-dimethylbutanoyl)-4-hydroxy-N-(4-(4-methylthiazol-5-yl)benzyl)pyrrolidine-2-carboxamide

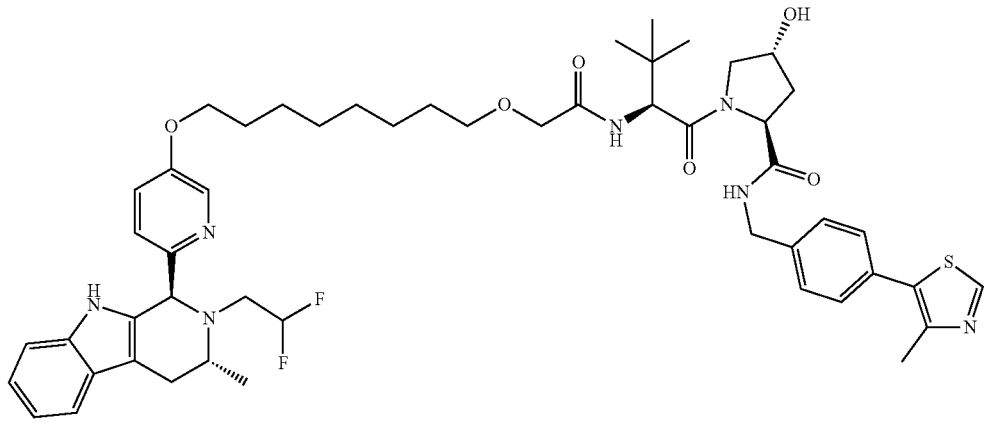 [SMILES: Cc1ncsc1-c1ccc(CNC(=O)[C@@H]2C[C@@H](O)CN2C(=O)[C@@H](NC(=O)COCCCCCCCCOc2ccc([C@@H]3c4[nH]c5ccccc5c4C[C@@H](C)N3CC(F)F)nc2)C(C)(C)C)cc1]

HATU (269 mg, 0.71 mmol) was added portionwise to 2-((8-((6-((1S,3R)-2-(2,2-difluoroethyl)-3-methyl-2,3,4,9-tetrahydro-1H-pyrido[3,4-b]indol-1-yl)pyridin-3-yl)oxy)octyl)oxy)acetic acid (250 mg, 0.47 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (220 mg, 0.47 mmol) and triethylamine (0.26 mL, 1.89 mmol) in DMF (9.1 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (65 mg, 15%) as a white solid; $^1$H NMR (400 MHz, DMSO-d6) 0.93 (9H, d), 1.13 (3H, d), 1.34 (8H, d), 1.54 (2H, q), 1.67 (2H, m), 1.91 (1H, m), 2.03-2.11 (1H, m), 2.44 (3H, s), 2.54-2.63 (1H, m), 2.65-2.75 (2H, m), 3.14 (1H, m), 3.26 (1H, s), 3.47 (2H, m), 3.57-3.71 (2H, m), 3.91 (2H, s), 3.98 (2H, t), 4.25 (1H, dd), 4.33-4.49 (3H, m), 4.55 (1H, d), 4.98 (1H, s), 5.14 (1H, s), 5.85-6.21 (1H, m), 6.95 (1H, m), 7.02 (1H, m), 7.26 (1H, d), 7.29-7.47 (8H, m), 8.16-8.22 (1H, m), 8.58 (1H, t), 8.97 (1H, s), 10.55 (1H, s); m/z: ES+ [M+H]$^+$ 942.6; ESI-HRMS calculated for C51H66F2N7O6S [M+H]$^+$=942.4758, measured 942.4732.

Intermediate 14a: Ethyl 2-(4-hydroxybutoxy)acetate

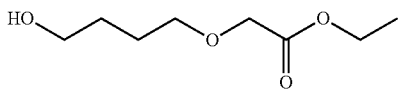

Ethyl diazoacetate (1.037 mL, 10 mmol) in DCM (10 mL) was added slowly to a solution of butane-1,4-diol (1.772 mL, 20 mmol) and BF$_3$.OEt$_2$ (0.127 mL, 1 mmol) in DCM (40 mL) at 0° C. The reaction was stirred at RT for 2 hours. The mixture was washed with water (50 mL) and brine (50 mL). The organics were dried with MgSO$_4$, filtered and concentrated to give the title compound (1.40 g, 79%) as a yellow oil; $^1$H NMR (400 MHz, CDCl$_3$) 1.29 (3H, m), 1.65-1.79 (4H, m), 1.91 (1H, t), 3.57-3.61 (2H, m), 3.68 (2H, q), 4.07 (2H, s), 4.21 (2H, m)

Intermediate 14b: Ethyl 2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)acetate

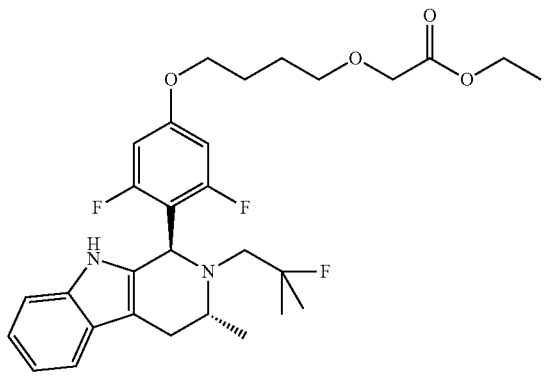 [SMILES: CCOC(=O)COCCCCOc1cc(F)c([C@@H]2c3[nH]c4ccccc4c3C[C@@H](C)N2CC(C)(C)F)c(F)c1]

Diisopropyl azodicarboxylate (0.10 mL, 0.51 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (100 mg, 0.26 mmol), ethyl 2-(4-hydroxybutoxy)acetate (91 mg, 0.51 mmol) and triphenylphosphine (135 mg, 0.51 mmol) in DCM (2.1 mL) at 20° C. The resulting mixture was stirred for 2 hours. DCM (50 mL) and water (25 mL) were added and the layers were separated. The organic layer was washed with brine (25 mL), dried using a phase separating filter and concentrated to give the crude product. The crude product was purified by flash column chromatography, elution gradient 0 to 50% EtOAc in heptane to afford the title compound (123 mg, 87%) as a pale yellow gum; $^1$H NMR (400 MHz, DMSO-d6) 1.05 (3H, d), 1.08-1.25 (9H, m), 1.64 (2H, m), 1.72-1.84 (2H, m), 2.28-2.42 (1H, m), 2.55-2.61 (1H, m), 2.78-2.96 (2H, m), 3.45-3.54 (3H, m), 3.99-4.04 (2H, m), 4.08 (2H, s), 4.09 (2H, d), 5.13 (1H, s), 6.65 (2H, d), 6.97 (2H, m), 7.19 (1H, d), 7.40 (1H, d), 10.50 (1H, s); m/z: ES+ [M+H]$^+$ 547.3.

Intermediate 14c: 2-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy) acetic Acid

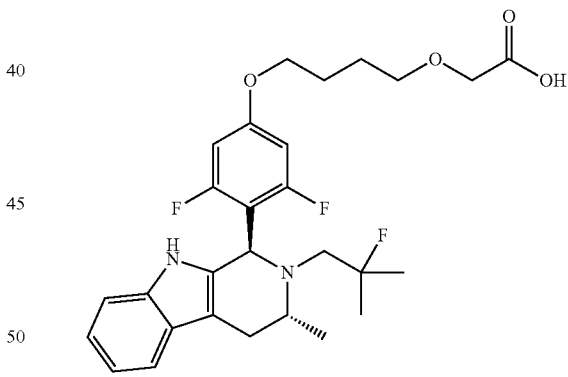

Lithium hydroxide hydrate (18.88 mg, 0.45 mmol) was added in one portion to ethyl 2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)acetate (123 mg, 0.23 mmol) in THF (0.84 mL) and water (0.28 mL) at 20° C. The resulting solution was stirred at 40° C. for 2 hours. The mixture was diluted with water (10 mL). The resulting mixture was acidified with 2M HCl and extracted into EtOAc (50 mL). The organic layer was washed with brine (15 mL) and evaporated to afford the title compound (139 mg) as a colourless gum that was used in the next step without further purification; m/z: ES+ [M+H]$^+$ 519.3.

Example 14: (2S,4R)-1-((S)-2-(2-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy)acetamido)-3,3-dimethylbutanoyl)-4-hydroxy-N-(4-(4-methylthiazol-5-yl)benzyl)pyrrolidine-2-carboxamide

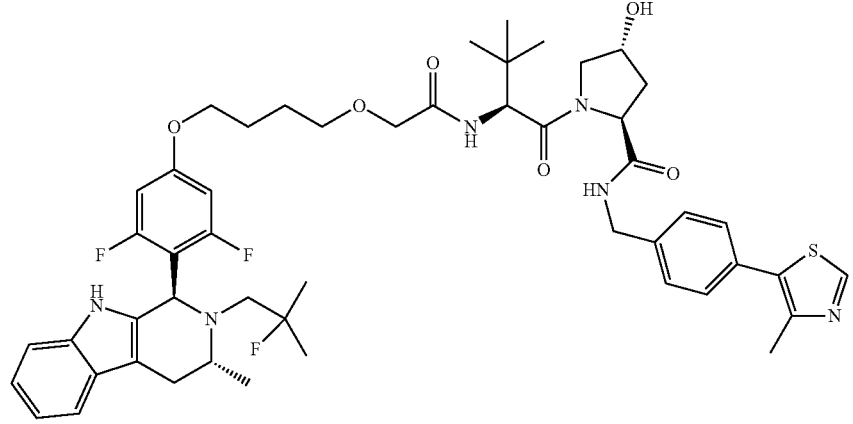 [SMILES: Cc1ncsc1-c1ccc(CNC(=O)[C@@H]2C[C@@H](O)CN2C(=O)[C@@H](NC(=O)COCCCCOc2cc(F)c([C@@H]3c4[nH]c5ccccc5c4C[C@@H](C)N3CC(C)(C)F)c(F)c2)C(C)(C)C)cc1]

HATU (129 mg, 0.34 mmol) was added portionwise to 2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)acetic acid (117 mg, 0.23 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (105 mg, 0.23 mmol) and triethylamine (0.13 mL, 0.90 mmol) in DMF (4.4 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (76 mg, 36%) as a yellow foam; $^1$H NMR (400 MHz, DMSO-d6) 0.93 (9H, d), 1.05 (3H, d), 1.16 (6H, t), 1.69 (2H, q), 1.77 (2H, q), 1.91 (1H, m), 2.08 (1H, s), 2.35 (1H, dd), 2.44 (3H, s), 2.53-2.59 (1H, m), 2.77-2.95 (2H, m), 3.54 (3H, t), 3.58-3.72 (2H, m), 3.95 (2H, d), 4.01 (2H, t), 4.27 (1H, dd), 4.32-4.5 (3H, m), 4.57 (1H, d), 5.13 (2H, d), 6.63 (2H, d), 6.97 (2H, m), 7.18 (1H, d), 7.40 (6H, s), 8.56 (1H, t), 8.96 (1H, s), 10.50 (1H, s); m/z: ES+ [M+H]$^+$ 931.5; ESI-HRMS calculated for C$_{50}$H$_{62}$F$_3$N$_6$O$_6$S [M+H]$^+$=931.4398, measured 931.4362.

Intermediate 15a: Ethyl 9-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)nonanoate

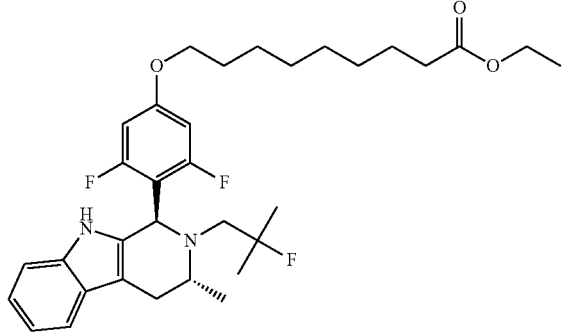 [SMILES: CCOC(=O)CCCCCCCCOc1cc(F)c([C@@H]2c3[nH]c4ccccc4c3C[C@@H](C)N2CC(C)(C)F)c(F)c1]

Ethyl 9-bromononanoate (102 mg, 0.39 mmol) was added in one portion to 3,5-difluoro-4-((1R,3R)-2-(2-fluoro-2-methylpropyl)-3-methyl-2,3,4,9-tetrahydro-1H-pyrido[3,4-b]indol-1-yl)phenol (150 mg, 0.39 mmol) and potassium carbonate (80 mg, 0.58 mmol) in MeCN (2 mL) at 20° C. The resulting suspension was stirred at 70° C. for 18 hours. The mixture was cooled to RT and was diluted with DCM (10 mL) and water (2 mL). The DCM layer was collected and evaporated to afford crude material as a yellow gum. The crude product was purified by flash column chromatography, elution gradient 0 to 30% EtOAc in heptane to afford the title compound (172 mg, 78%) as a colourless gum; $^1$H NMR (400 MHz, DMSO-d6) 1.05 (3H, d), 1.09-1.24 (9H, m), 1.27 (6H, m), 1.36 (2H, m), 1.47-1.59 (2H, m), 1.69 (2H, p), 2.27 (2H, t), 2.32-2.41 (1H, m), 2.58 (1H, d), 2.77-2.96 (2H, m), 3.52 (1H, q), 3.97 (2H, t), 4.04 (2H, m), 5.13 (1H, s), 6.64 (2H, d), 6.97 (2H, m), 7.16-7.21 (1H, m), 7.39 (1H, d), 10.49 (1H, s); m/z: ES+ [M+H]$^+$ 573.4.

Intermediate 15b: 9-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)nonanoic Acid

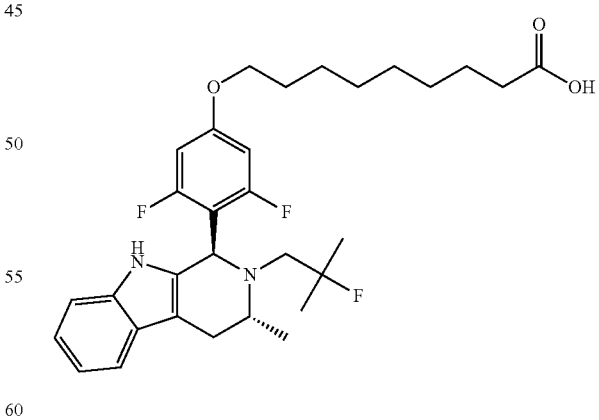

Lithium hydroxide hydrate (25.2 mg, 0.60 mmol) was added in one portion to ethyl 9-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)nonanoate (172 mg, 0.30 mmol) in THF (1.1 mL) and water (0.4 mL) at 20° C. The resulting solution was stirred at 40° C. for 2 hours. The organic solvent was removed under reduced pressure. The resulting mixture was acidified with 2M aq. HCl and extracted into EtOAc (50 mL). The organic layer was washed with brine (15 mL) and evaporated to afford the title compound (175 mg) as a colourless gum that was used in the next step without further purification; $^1$H NMR (400 MHz, DMSO-d6) 1.05 (3H, d), 1.09-1.24 (6H, m), 1.28 (6H, s), 1.37 (2H, m), 1.45-1.57 (2H, m), 1.69 (2H, p), 2.19 (2H, t), 2.29-2.42 (1H, m), 2.56 (1H, dd), 2.77-2.95 (2H, m), 3.52 (1H, q), 3.97 (2H, t), 5.13 (1H, s), 6.64 (2H, d), 6.97 (2H, m), 7.16-7.22 (1H, m), 7.39 (1H, d), 10.49 (1H, s), 11.94 (1H, s); m/z: ES+ [M+H]$^+$ 545.3.

Example 15: (2S,4R)-1-((S)-2-(9-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)nonanamido)-3,3-dimethylbutanoyl)-4-hydroxy-N-(4-(4-methylthiazol-5-yl)benzyl)pyrrolidine-2-carboxamide

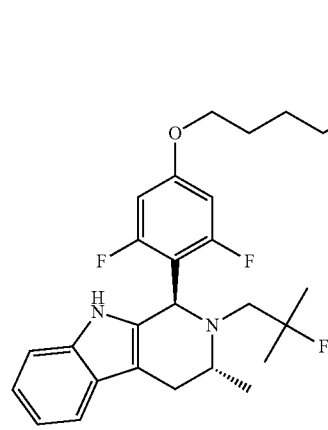
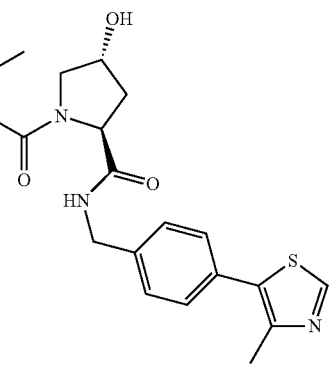

HATU (183 mg, 0.48 mmol) was added in one portion to 9-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)nonanoic acid (175 mg, 0.32 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (150 mg, 0.32 mmol) and triethylamine (0.18 mL, 1.29 mmol) in DMF (6.2 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (160 mg, 52%) as a cream foam; $^1$H NMR (400 MHz, DMSO-d6) 0.94 (9H, s), 1.04 (3H, d), 1.16 (6H, t), 1.27 (5H, s), 1.38 (2H, s), 1.50 (2H, m), 1.63-1.74 (2H, m), 1.91 (1H, s), 1.99-2.16 (2H, m), 2.22-2.41 (3H, m), 2.45 (3H, s), 2.57 (1H, d), 2.77-2.95 (2H, m), 3.52 (1H, q), 3.59-3.72 (2H, m), 3.97 (2H, t), 4.22 (1H, dd), 4.35 (1H, s), 4.39-4.49 (2H, m), 4.55 (1H, d), 5.11 (2H, d), 6.64 (2H, d), 6.97 (2H, m), 7.15-7.22 (1H, m), 7.35-7.48 (5H, m), 7.80 (1H, d), 8.53 (1H, t), 8.98 (1H, s), 10.49 (1H, s); m/z: ES+ [M+H]$^+$ 957.7; ESI-HRMS calculated for $C_{53}H_{68}F_3N_6O_5S$ [M+H]$^+$=957.4919, measured 957.4916.

Intermediate 16a: 2-(4-((tert-Butyldimethylsilyl)oxy)butoxy)ethan-1-ol

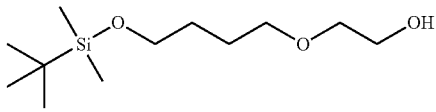 [SMILES: CC(C)(C)[Si](C)(C)OCCCCOCCO]

60% Sodium hydride in mineral oil (1.145 g, 47.73 mmol) was added in one portion to ethane-1,2-diol (2.66 mL, 28.64 mmol) in DMF (50 mL) and THF (100 mL) at 0° C. under nitrogen. The resulting mixture was stirred at 0° C. for 30 minutes then tert-butyl(4-iodobutoxy)dimethylsilane (5.00 g, 15.91 mmol) was added in one portion and the reaction was then stirred at 20° C. for 2 days. The reaction mixture was quenched with saturated NH$_4$Cl solution (50 mL) and diluted with Et$_2$O (200 mL) and water (100 mL), and washed sequentially with water (2×100 mL) and saturated brine (50 mL). The organic layer was dried with MgSO$_4$, filtered and evaporated to afford crude product. The crude product was purified by flash column chromatography, elution gradient 0 to 50% EtOAc in heptane to afford the title compound (2.050 g, 52%) as a colourless liquid; $^1$H NMR (400 MHz, CDCl$_3$) 0.05 (6H, s), 0.90 (9H, s), 1.54-1.7 (4H, m), 1.96 (1H, t), 3.47-3.57 (4H, m), 3.63 (2H, t), 3.72 (2H, m).

Intermediate 16b: (1R,3R)-1-(4-(2-(4-((tert-Butyldimethylsilyl)oxy)butoxy)ethoxy)-2,6-difluorophenyl)-2-(2-fluoro-2-methylpropyl)-3-methyl-2,3,4,9-tetrahydro-1H-pyrido[3,4-b]indole

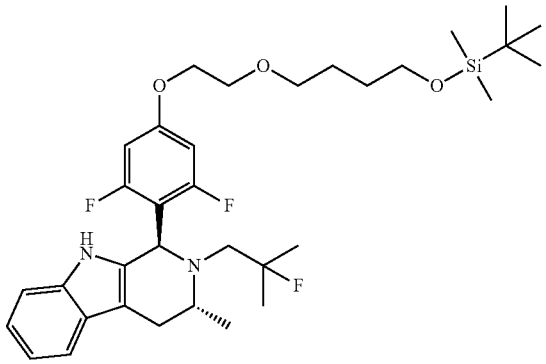 [SMILES: C[C@@H]1Cc2c([nH]c3ccccc23)[C@@H](c2c(F)cc(OCCOCCCCO[Si](C)(C)C(C)(C)C)cc2F)N1CC(C)(C)F]

RockPhos Pd G3 (43.0 mg, 0.05 mmol) was added in one portion to a degassed mixture of 2-(4-((tert-butyldimethylsilyl)oxy)butoxy)ethan-1-ol (764 mg, 3.08 mmol), (1R,3R)-1-(4-bromo-2,6-difluorophenyl)-2-(2-fluoro-2-methylpropyl)-3-methyl-2,3,4,9-tetrahydro-1H-pyrido[3,4-b]indole, HCl (500 mg, 1.03 mmol) and cesium carbonate (1.17 g, 3.59 mmol) in toluene (7.5 mL) at 20° C. under nitrogen. The resulting mixture was stirred at 90° C. for 4 hours. The reaction was allowed to cool to RT and diluted with DCM (20 mL) and water (5 mL) and the mixture was passed through a phase separating filtercup and evaporated to afford crude product as a orange gum. The crude product was purified by flash column chromatography, elution gradient 0 to 100% EtOAc in heptane to afford the title compound (501 mg, 79%) as a orange gum; m/z: ES+ [M+H]+ 619.4.

Intermediate 16c: 4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butan-1-ol

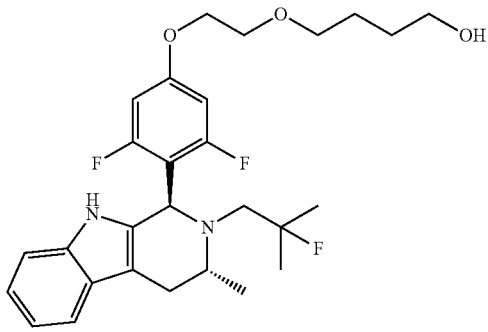 [SMILES: C[C@@H]1Cc2c([nH]c3ccccc23)[C@@H](c2c(F)cc(OCCOCCCCO)cc2F)N1CC(C)(C)F]

A solution of 1M TBAF in THF (0.81 mL, 0.81 mmol) was added in one portion to (1R,3R)-1-(4-(2-(4-((tert-butyldimethylsilyl)oxy)butoxy)ethoxy)-2,6-difluorophenyl)-2-(2-fluoro-2-methylpropyl)-3-methyl-2,3,4,9-tetrahydro-1H-pyrido[3,4-b]indole (501 mg, 0.81 mmol) in THF (3.2 mL) at 20° C. The resulting solution was stirred for 1 hour. The reaction mixture was diluted with EtOAc (100 mL), and washed sequentially with saturated NH4Cl (25 mL), water (2×50 mL), and saturated brine (20 mL). The organic layer was dried with MgSO4, filtered and evaporated to afford crude product. The crude product was purified by flash column chromatography, elution gradient 0 to 100% EtOAc in heptane to afford the title compound (286 mg, 70%) as a white foam; 1H NMR (400 MHz, DMSO-d6) 1.05 (3H, d), 1.09-1.27 (6H, m), 1.39-1.49 (2H, m), 1.49-1.59 (2H, m), 2.28-2.42 (1H, m), 2.58 (1H, dd), 2.78-2.96 (2H, m), 3.36-3.47 (4H, m), 3.52 (1H, d), 3.68 (2H, dd), 4.07-4.16 (2H, m), 4.35 (1H, t), 5.13 (1H, s), 6.67 (2H, d), 6.97 (2H, m), 7.14-7.24 (1H, m), 7.40 (1H, d), 10.50 (1H, s); m/z: ES+ [M+H]+ 505.4.

Intermediate 16d: Ethyl 2-(4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butoxy)acetate

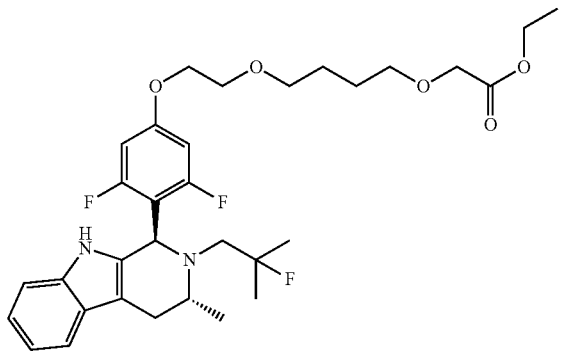 [SMILES: CCOC(=O)COCCCCOCCOc1cc(F)c([C@@H]2c3[nH]c4ccccc4c3C[C@@H](C)N2CC(C)(C)F)c(F)c1]

Ethyl 2-diazoacetate (0.17 mL, 1.64 mmol) in DCM (0.76 mL) was added slowly to 4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butan-1-ol (236 mg, 0.47 mmol) and diacetoxyrhodium (10.34 mg, 0.02 mmol) in DCM (2.0 mL) at 20° C. over a period of 1 hour under nitrogen. The resulting solution was stirred for 3 hours. The mixture was diluted with water (10 mL) and the DCM layer was passed through phase separating filter and evaporated to dryness and the crude product was purified by flash column chromatography, elution gradient 0 to 100% EtOAc in heptane to afford the title compound (30.0 mg, 10.86%) as a colourless liquid; m/z: ES+ [M+H]+ 591.3.

Intermediate 16e: 2-(4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butoxy)acetic Acid

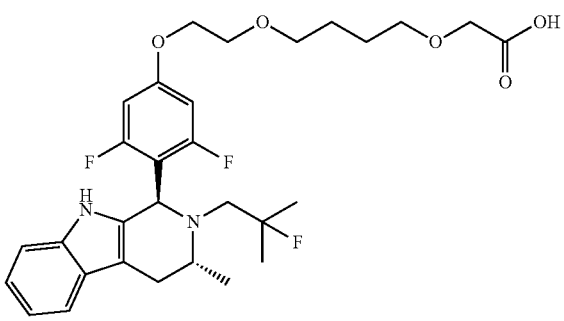 [SMILES: C[C@@H]1Cc2c([nH]c3ccccc23)[C@@H](c2c(F)cc(OCCOCCCCOCC(=O)O)cc2F)N1CC(C)(C)F]

Lithium hydroxide hydrate (7.96 mg, 0.19 mmol) was added in one portion to ethyl 2-(4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butoxy)acetate (56 mg, 0.09 mmol) in THF (0.36 mL) and water (0.12 mL) at 20° C. The resulting solution was stirred for 2 hours. The organic solvent was removed under reduced pressure. The resulting mixture was acidified with 2M aq. HCl and extracted into EtOAc (50 mL). The organic layer was washed with brine (15 mL) and evaporated to afford the title compound (43.0 mg, 81%) as a colourless gum; m/z: ES+ [M+H]+ 563.3.

Example 16: (2S,4R)-1-((S)-2-(2-(4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butoxy)acetamido)-3,3-dimethylbutanoyl)-4-hydroxy-N-(4-(4-methylthiazol-5-yl)benzyl)pyrrolidine-2-carboxamide

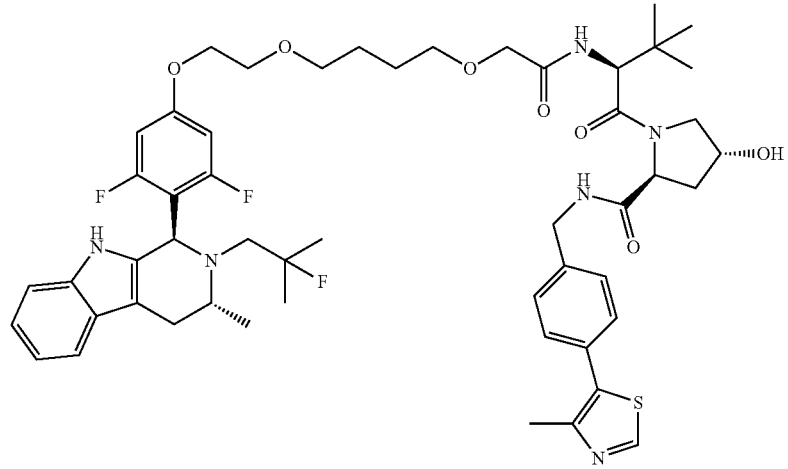 [SMILES: Cc1ncsc1-c1ccc(CNC(=O)[C@@H]2C[C@@H](O)CN2C(=O)[C@@H](NC(=O)COCCCCOCCOc2cc(F)c([C@@H]3c4[nH]c5ccccc5c4C[C@@H](C)N3CC(C)(C)F)c(F)c2)C(C)(C)C)cc1]

HATU (43.6 mg, 0.11 mmol) was added in one portion to 2-(4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butoxy)acetic acid (43 mg, 0.08 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (35.7 mg, 0.08 mmol) and triethylamine (0.043 mL, 0.31 mmol) in DMF (1.5 mL) at 20° C. under nitrogen. The resulting mixture was stirred at 20° C. for 30 minutes. The reaction mixture was diluted with EtOAc (50 mL), and washed sequentially with water (20 mL) and saturated brine (20 mL). The organic layer was dried with MgSO$_4$, filtered and evaporated to afford crude material. The crude product was purified by preparative HPLC to afford the title compound (34.0 mg, 46%) as a yellow solid; $^1$H NMR (400 MHz, DMSO-d6) 0.93 (9H, d), 1.04 (3H, d), 1.16 (6H, t), 1.59 (4H, d), 1.91 (1H, m), 2.02-2.12 (1H, m), 2.28-2.41 (1H, m), 2.45 (3H, d), 2.52-2.61 (1H, m), 2.76-2.95 (2H, m), 3.47 (5H, dd), 3.58-3.72 (4H, m), 3.85-3.98 (2H, m), 4.05-4.14 (2H, m), 4.21-4.51 (4H, m), 4.56 (1H, d), 5.13 (2H, s), 6.65 (2H, d), 6.96 (2H, m), 7.18 (1H, d), 7.28-7.51 (6H, m), 8.57 (1H, t), 8.97 (1H, s), 10.50 (1H, s); m/z: ES+ [M+H]$^+$ 975.7; ESI-HRMS calculated for C$_{52}$H$_{66}$F$_3$N$_6$O$_7$S [M+H]$^+$=975.4660, measured 975.4630.

Intermediate 17a: Ethyl 2-((5-hydroxypentyl)oxy)acetate

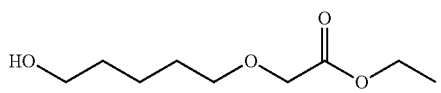

Ethyl 2-diazoacetate (2.97 mL, 24.00 mmol) was added slowly to pentane-1,5-diol (25.3 mL, 240.04 mmol) and diacetoxyrhodium (0.106 g, 0.24 mmol) at 20° C. over a period of 3 hours under nitrogen. The resulting solution was stirred at 20° C. for 1 day. The reaction mixture was diluted with EtOAc (150 mL), and washed sequentially with water (6×100 mL) and saturated brine (50 mL). The organic layer was dried with MgSO$_4$, filtered and evaporated to afford the title compound (1.950 g, 43%) as a pale yellow liquid; $^1$H NMR (400 MHz, CDCl$_3$) 1.23-1.35 (4H, m), 1.44-1.52 (2H, m), 1.65 (4H, m), 3.54 (2H, t), 3.66 (2H, q), 4.06 (2H, s), 4.22 (2H, q).

Intermediate 17b: Ethyl 2-((5-((6-((1S,3R)-2-(2,2-difluoroethyl)-3-methyl-2,3,4,9-tetrahydro-1H-pyrido[3,4-b]indol-1-yl)pyridin-3-yl)oxy)pentyl)oxy)acetate

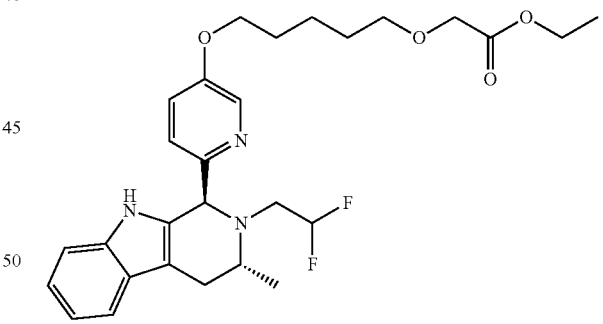

Diisopropyl azodicarboxylate (87 µL, 0.44 mmol) was added dropwise to a stirred solution of 6-((1S,3R)-2-(2,2-difluoroethyl)-3-methyl-2,3,4,9-tetrahydro-1H-pyrido[3,4-b]indol-1-yl)pyridin-3-ol (76 mg, 0.22 mmol), ethyl 2-((5-hydroxypentyl)oxy)acetate (84 mg, 0.44 mmol) and triphenylphosphine (116 mg, 0.44 mmol) in DCM (1.8 mL) at 20° C. The resulting mixture was stirred for 2 hours. DCM (25 mL) and water (10 mL) were added and the layers were separated. The DCM layer was passed through a phase separating cartridge and concentrated to give the crude product. The crude product was purified by flash column chromatography, elution gradient 0 to 25% EtOAc in heptane to afford the title compound (141 mg) as a pale yellow gum that was used in the next step without further purification; m/z: ES+ [M+H]$^+$ 516.4.

Intermediate 17c: 2-((5-((6-((1S,3R)-2-(2,2-Difluoroethyl)-3-methyl-2,3,4,9-tetrahydro-1H-pyrido[3,4-b]indol-1-yl)pyridin-3-yl)oxy)pentyl)oxy)acetic Acid

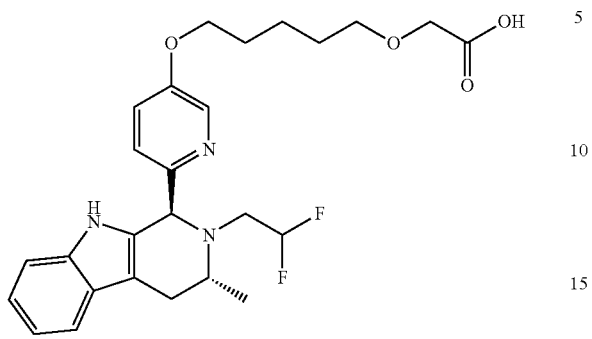

Lithium hydroxide hydrate (22.95 mg, 0.55 mmol) was added in one portion to ethyl 2-((5-((6-((1S,3R)-2-(2,2-difluoroethyl)-3-methyl-2,3,4,9-tetrahydro-1H-pyrido[3,4-b]indol-1-yl)pyridin-3-yl)oxy)pentyl)oxy)acetate (141 mg, 0.27 mmol) in THF (1.0 mL) and water (0.34 mL) at 20° C. The resulting solution was stirred for 2 hours. The mixture was diluted with water (10 mL). The resulting mixture was acidified with 2M aq. HCl and extracted into EtOAc (50 mL). The organic layer was washed with brine (15 mL) and evaporated to afford the title compound (139 mg) as a colourless gum that was used in the next step without further purification; m/z: ES+ [M+H]$^+$ 488.

Example 17: (2S,4R)-1-((S)-2-(2-((5-((6-((1S,3R)-2-(2,2-Difluoroethyl)-3-methyl-2,3,4,9-tetrahydro-1H-pyrido[3,4-b]indol-1-yl)pyridin-3-yl)oxy)pentyl)oxy)acetamido)-3,3-dimethylbutanoyl)-4-hydroxy-N-(4-(4-methylthiazol-5-yl)benzyl)pyrrolidine-2-carboxamide

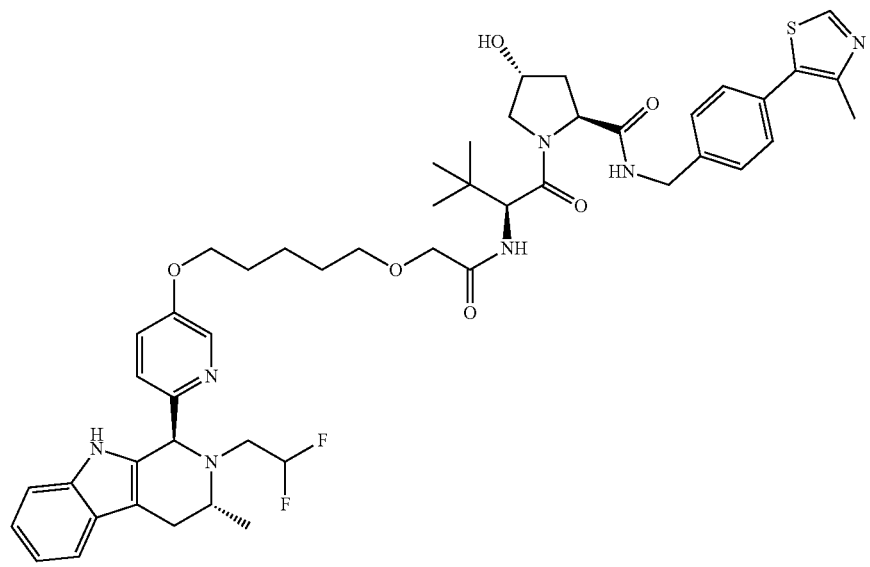 [SMILES: Cc1ncsc1-c1ccc(CNC(=O)[C@@H]2C[C@@H](O)CN2C(=O)[C@@H](NC(=O)COCCCCCOc2ccc([C@@H]3c4[nH]c5ccccc5c4C[C@@H](C)N3CC(F)F)nc2)C(C)(C)C)cc1]

HATU (156 mg, 0.41 mmol) was added portionwise to 2-((5-((6-((1S,3R)-2-(2,2-difluoroethyl)-3-methyl-2,3,4,9-tetrahydro-1H-pyrido[3,4-b]indol-1-yl)pyridin-3-yl)oxy)pentyl)oxy)acetic acid (133 mg, 0.27 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (127 mg, 0.27 mmol) and triethylamine (0.15 mL, 1.1 mmol) in DMF (5.3 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (49.0 mg, 19.96%) as a cream solid. m/z: ES+ [M+H]$^+$ 900.7; ESI-HRMS calculated for C$_{48}$H$_{60}$F$_2$N$_7$O$_6$S [M+H]$^+$=900.4288, measured 900.4272.

Intermediate 18a: Ethyl 2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)acetate

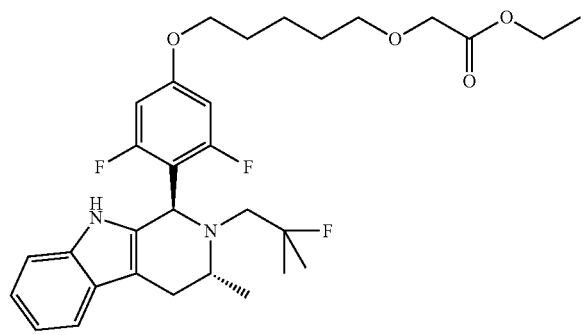 [SMILES: CCOC(=O)COCCCCCOc1cc(F)c([C@@H]2c3[nH]c4ccccc4c3C[C@@H](C)N2CC(C)(C)F)c(F)c1]

Diisopropyl azodicarboxylate (1.52 mL, 7.72 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (1.5 g, 3.86 mmol), ethyl 2-((5-hydroxypentyl)oxy)acetate (1.469 g, 7.72 mmol) and triphenylphosphine (2.026 g, 7.72 mmol) in DCM (60 mL) at 20° C. The resulting mixture was stirred for 1 hour. DCM (60 mL) and water (60 mL) were added and the layers were separated by passing through a phase separating cartridge and concentrated to give the crude product. The crude product was purified by flash column chromatography, elution gradient 0 to 30% EtOAc in heptane to afford the title compound (1.660 g, 77%) as a pale yellow gum; m/z: ES+ [M+H]$^+$561.4.

Intermediate 18b: 2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)acetic Acid

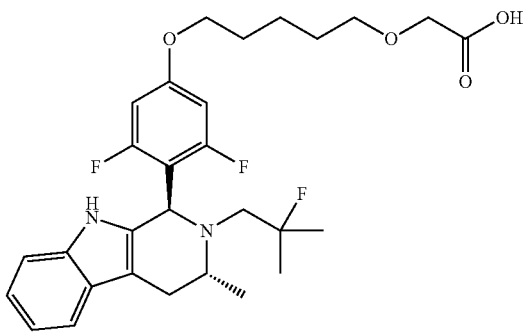 [SMILES: C[C@@H]1Cc2c([nH]c3ccccc23)[C@@H](c2c(F)cc(OCCCCCOCC(=O)O)cc2F)N1CC(C)(C)F]

Lithium hydroxide hydrate (0.248 g, 5.92 mmol) was added in one portion to ethyl 2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)acetate (1.66 g, 2.96 mmol) in THF (11 mL) and water (3.7 mL) at 20° C. The resulting solution was stirred for 2 hours. The mixture was diluted with water (10 mL). The resulting mixture was acidified with 2M aq. HCl and extracted into EtOAc (50 mL). The organic layer was washed with brine (15 mL) and evaporated to afford the title compound (1.630 g) as a colourless gum that was used in the next step without further purification; $^1$H NMR (400 MHz, DMSO-d6) 1.05 (3H, d), 1.09-1.24 (6H, m), 1.45 (2H, m), 1.57 (2H, m), 1.68-1.8 (2H, m), 2.3-2.42 (1H, m), 2.55 (1H, dd), 2.77-2.95 (2H, m), 3.46 (3H, t), 3.52 (1H, q), 3.98 (3H, d), 5.13 (1H, s), 6.65 (2H, d), 6.97 (2H, m), 7.15-7.23 (1H, m), 7.40 (1H, d), 10.50 (1H, s), 12.50 (1H, s); m/z: ES+ [M+H]$^+$ 533.3.

Example 18: (2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)acetamido)-3,3-dimethylbutanoyl)-4-hydroxy-N-(4-(4-methylthiazol-5-yl)benzyl)pyrrolidine-2-carboxamide

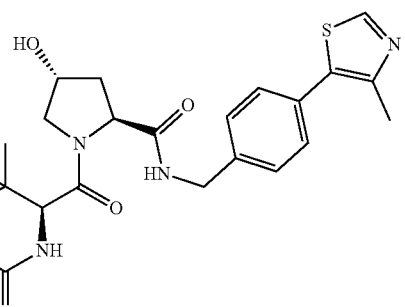

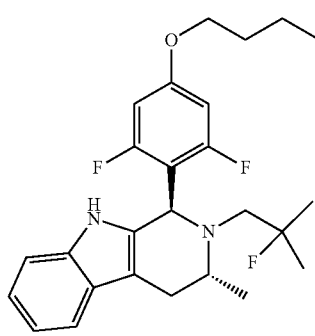

HATU (1.692 g, 4.45 mmol) was added portionwise to 2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)acetic acid (1.58 g, 2.97 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (1.385 g, 2.97 mmol) and triethylamine (1.654 mL, 11.87 mmol) in DMF (57.7 mL) at 20° C. under nitrogen. The resulting mixture was stirred at 20° C. for 30 minutes. The reaction mixture was diluted with EtOAc (150 mL), and washed sequentially with water (2×75 mL) and saturated brine (50 mL). The organic layer was dried with MgSO$_4$, filtered and evaporated to afford crude material. The crude product was purified by flash column chromatography, elution gradient 0 to 10% MeOH in DCM. Pure fractions were evaporated to dryness to afford impure product (2.2 g, 87% by LCMS). The crude product was then purified by preparative SFC to afford the title compound (1.450 g, 52%) as a white solid; $^1$H NMR (400 MHz, CDCl$_3$) 0.94 (9H, s), 1.10 (3H, d), 1.20 (6H, dd), 1.54 (2H, m), 1.65 (2H, s), 1.78 (2H, m), 2.06 (1H, dd), 2.45 (1H, s), 2.47 (3H, s), 2.49-2.65 (2H, m), 2.79-2.91 (2H, m), 3.08 (1H, dd), 3.52 (2H, tq), 3.64 (2H, m), 3.8-3.99 (4H, m), 4.06 (1H, d), 4.29 (1H, dd), 4.47-4.62 (3H, m), 4.69 (1H, t), 5.19 (1H, s), 6.34 (2H, d), 7.04-7.13 (2H, m), 7.16 (1H, d), 7.2-7.25 (1H, m), 7.27-7.39 (5H, m), 7.47-7.56 (1H, m), 8.16 (1H, s), 8.63 (1H, s); m/z: ES+ [M+H]$^+$ 945.6; ESI-HRMS calculated for C$_{51}$H$_{64}$F$_3$N$_6$O$_6$S [M+H]$^+$=945.4555, measured 945.4518.

Intermediate 19a: (4-(((tert-Butyldimethylsilyl)oxy)methyl)phenyl)methanol

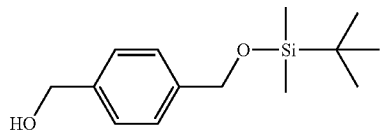 [SMILES: CC(C)(C)[Si](C)(C)OCc1ccc(CO)cc1]

tert-Butylchlorodimethylsilane (1.353 g, 8.97 mmol) was added in one portion to 1,4-phenylenedimethanol (3.1 g, 22.44 mmol) and imidazole (0.611 g, 8.97 mmol) in THF (150 mL) at 20° C. under nitrogen. The resulting mixture was allowed to warm to RT and was stirred for 18 hours. The reaction mixture was diluted with EtOAc (100 mL), and washed with saturated brine (100 mL). The organic layer was dried with MgSO$_4$, filtered and evaporated to afford crude product. The crude product was absorbed onto silica and purified by flash column chromatography, elution gradient 0 to 100% EtOAc in heptane to afford the title compound (1.840 g, 81%) as a colourless oil; $^1$H NMR (400 MHz, CDCl$_3$) 0.10 (6H, s), 0.94 (9H, s), 1.56 (1H, t), 4.68 (2H, d), 4.74 (2H, s), 7.33 (4H, m).

Intermediate 19b: tert-butyl 2-((4-(((tert-butyldimethylsilyl)oxy)methyl)benzyl)oxy)acetate

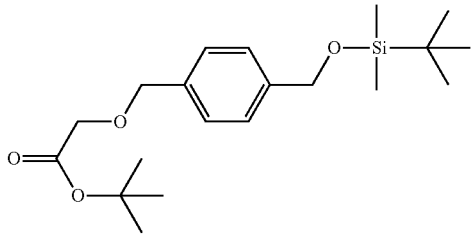 [SMILES: CC(C)(C)OC(=O)COCc1ccc(CO[Si](C)(C)C(C)(C)C)cc1]

tert-Butyl 2-bromoacetate (2.340 mL, 15.85 mmol) was added in one portion to (4-(((tert-butyldimethylsilyl)oxy)methyl)phenyl)methanol (1 g, 3.96 mmol) and tetrabutylammonium chloride (1.101 g, 3.96 mmol) in DCM (14 mL) and sodium hydroxide solution (35% solution) (14 mL) at 20° C. The resulting mixture was stirred for 3 hours. The reaction mixture was diluted with DCM (50 mL) and water (20 mL). The layers were separated and the organic layer was washed with saturated brine (20 mL) and was dried with a phase separating cartridge, filtered and evaporated to afford crude product. The crude product was purified by flash column chromatography, elution gradient 0 to 10% EtOAc in heptane to afford the title compound (0.970 g, 67%) as a colourless oil; $^1$H NMR (400 MHz, CDCl$_3$) 0.09 (6H, s), 0.94 (9H, s), 1.48 (9H, s), 3.97 (2H, s), 4.61 (2H, s), 4.74 (2H, s), 7.35 (4H, m).

Intermediate 19c: tert-Butyl 2-((4-(hydroxymethyl)benzyl)oxy)acetate

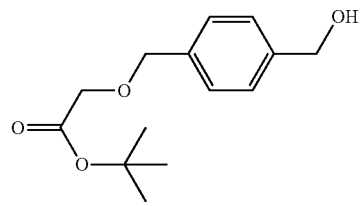 [SMILES: CC(C)(C)OC(=O)COCc1ccc(CO)cc1]

A solution of 1 M TBAF in THF (2.65 mL, 2.65 mmol) was added in one portion to tert-butyl 2-((4-(((tert-butyldimethylsilyl)oxy)methyl)benzyl)oxy)acetate (0.97 g, 2.65 mmol) in THF (10.5 mL) at 20° C. The resulting solution was stirred for 1 hour. The reaction mixture was diluted with EtOAc (100 mL), and washed sequentially with saturated NH$_4$Cl (25 mL), water (2×50 mL), and saturated brine (20 mL). The organic layer was dried with MgSO$_4$, filtered and evaporated to afford crude product. The crude product was purified by flash column chromatography, elution gradient 0 to 50% EtOAc in heptane to afford the title compound (0.630 g, 94%) as a colourless liquid; $^1$H NMR (400 MHz, CDCl$_3$) 1.49 (9H, s), 1.61 (1H, t), 3.98 (2H, s), 4.62 (2H, s), 4.70 (2H, d), 7.32-7.42 (4H, m).

Intermediate 19d: tert-Butyl 2-((4-(bromomethyl)benzyl)oxy)acetate

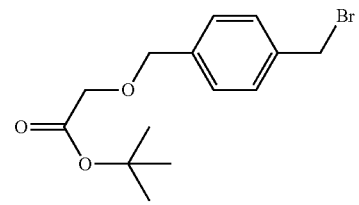 [SMILES: CC(C)(C)OC(=O)COCc1ccc(CBr)cc1]

Perbromomethane (591 mg, 1.78 mmol) in THF (3 mL) was added dropwise to a solution of tert-butyl 2-((4-(hydroxymethyl)benzyl)oxy)acetate (300 mg, 1.19 mmol) and triphenylphosphane (468 mg, 1.78 mmol) in THF (7 mL) at 0° C. over a period of 15 minutes. The resulting solution was stirred at 20° C. for 2 hours. The reaction mixture was filtered and the filtrate was collected and evaporated to dryness to afford crude product as a yellow liquid. The crude product was purified by flash column chromatography, elution gradient 0 to 10% EtOAc in heptane to afford the title compound (156 mg, 42%) as a colourless liquid; $^1$H NMR (400 MHz, CDCl$_3$) 1.49 (9H, s), 3.99 (2H, s), 4.49 (2H, s), 4.61 (2H, s), 7.33-7.41 (4H, m).

Intermediate 19e: tert-Butyl 2-((4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzyl)oxy)acetate

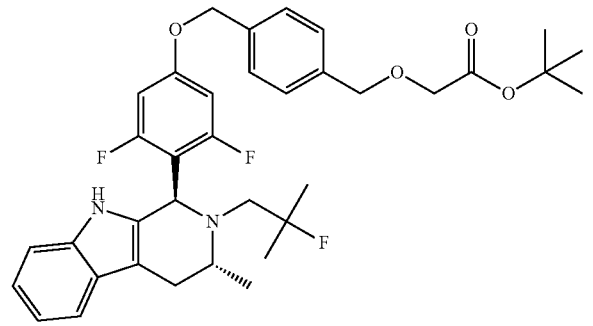 [SMILES: C[C@@H]1Cc2c([nH]c3ccccc23)[C@@H](c2c(F)cc(OCc3ccc(COCC(=O)OC(C)(C)C)cc3)cc2F)N1CC(C)(C)F]

tert-Butyl 2-((4-(bromomethyl)benzyl)oxy)acetate (150 mg, 0.48 mmol) was added in one portion to 3,5-difluoro-4-((1R,3R)-2-(2-fluoro-2-methylpropyl)-3-methyl-2,3,4,9-tetrahydro-1H-pyrido[3,4-b]indol-1-yl)phenol (154 mg, 0.40 mmol) and potassium carbonate (82 mg, 0.59 mmol) in MeCN (2 mL) at 20° C. The resulting suspension was stirred at 20° C. for 3 days. The mixture was diluted with DCM (10 mL) and water (2 mL). The DCM layer was collected and evaporated to afford crude material as a yellow gum. The crude product was purified by flash column chromatography, elution gradient 0 to 30% EtOAc in heptane to afford the title compound (177 mg, 72%) as a yellow gum; $^1$H NMR (400 MHz, DMSO-d6) 1.05 (3H, d), 1.08-1.27 (6H, m), 1.44 (9H, s), 2.29-2.41 (1H, m), 2.53-2.62 (1H, m), 2.77-2.97 (2H, m), 3.52 (1H, d), 4.03 (2H, s), 4.54 (2H, s), 5.13 (3H, s), 6.74 (2H, d), 6.97 (2H, m), 7.18 (1H, d), 7.32-7.49 (5H, m), 10.51 (1H, s); m/z: ES+ [M+H]$^+$ 623.3.

Intermediate 19f: 2-((4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzyl)oxy)acetic Acid

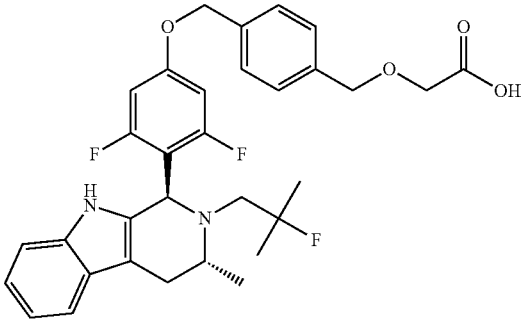 [SMILES: C[C@@H]1Cc2c([nH]c3ccccc23)[C@@H](c2c(F)cc(OCc3ccc(COCC(=O)O)cc3)cc2F)N1CC(C)(C)F]

Trifluoroacetic acid (0.25 mL) was added in one portion to tert-butyl 2-((4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzyl)oxy)acetate (177 mg, 0.28 mmol) in DCM (0.5 mL) at 20° C. The solution was stirred for 1 hour. MeOH (1 mL) was added and the solution was purified by ion exchange chromatography, using an SCX column. The desired product was eluted from the column using 1M NH$_3$/MeOH and pure fractions were evaporated to dryness to afford mixture of product plus Methy ester. The mixture of desired product and Methyl ester was treated with 0.5 mL of 1M NaOH solution and stirred for 10 mins. The mixture was neutralised with HCl and extracted with EtOAc (2×20 mL) to afford the title compound (18.0 mg, 11%) as a yellow gum; m/z: ES+ [M+H]$^+$ 567.2.

Example 19: (2S,4R)-1-((S)-2-(2-((4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzyl)oxy)acetamido)-3,3-dimethylbutanoyl)-4-hydroxy-N-(4-(4-methylthiazol-5-yl)benzyl)pyrrolidine-2-carboxamide

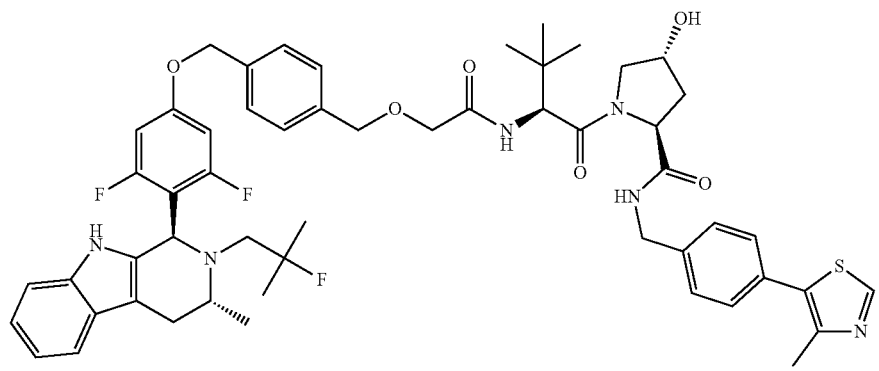 [SMILES: Cc1ncsc1-c1ccc(CNC(=O)[C@@H]2C[C@@H](O)CN2C(=O)[C@@H](NC(=O)COCc2ccc(COc3cc(F)c([C@@H]4c5[nH]c6ccccc6c5C[C@@H](C)N4CC(C)(C)F)c(F)c3)cc2)C(C)(C)C)cc1]

HATU (18.12 mg, 0.05 mmol) was added portionwise to 2-((4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzyl)oxy)acetic acid (18 mg, 0.03 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (14.84 mg, 0.03 mmol) and triethylamine (18 μL, 0.13 mmol) in DMF (0.6 mL) at 20° C. under nitrogen. The resulting mixture was stirred at 20° C. for 30 minutes. The reaction was incomplete and further (2S,4R)-1-((S)-2-amino-3,3-dimethylbutanoyl)-4-hydroxy-N-(4-(4-methylthiazol-5-yl)benzyl)pyrrolidine-2-carboxamide, HCl (14.84 mg, 0.03 mmol), triethylamine (18 μL, 0.13 mmol) and HATU (18.12 mg, 0.05 mmol) were added and the mixture was stirred at 20° C. for a further 2 days. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (3.0 mg, 9.6%) as a white solid; $^1$H NMR (400 MHz, CDCl$_3$) 0.94 (9H, s), 1.10 (3H, d), 1.20 (6H, dd), 2.11 (1H, dd), 2.40 (1H, dd), 2.48 (3H, s), 2.55-2.64 (2H, m), 2.69 (1H, s), 2.86 (1H, dd), 3.09 (1H, dd), 3.61 (1H, dd), 3.67 (1H, d), 3.91-4.04 (2H, m), 4.10 (1H, d), 4.33 (1H, dd), 4.49 (1H, d), 4.52-4.64 (4H, m), 4.74 (1H, t), 4.97 (2H, s), 5.20 (1H, s), 6.44 (2H, d), 7.05-7.13 (2H, m), 7.22 (2H, dd), 7.29 (1H, d), 7.32-7.41 (8H, m), 7.51 (1H, dd), 7.81 (1H, s), 8.63 (1H, s); m/z: ES+ [M+H]$^+$ 979.5.

Intermediate 20a: Ethyl 2-(3-(hydroxymethyl)phenoxy)acetate

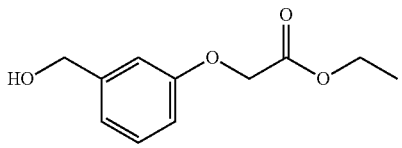

Ethyl 2-bromoacetate (4.47 mL, 40.28 mmol) was added in one portion to 3-(hydroxymethyl)phenol (5 g, 40 mmol) and potassium carbonate (11.1 g, 80.6 mmol) in acetone (200 mL) at 20° C. under nitrogen. The resulting mixture was stirred at 60° C. for 18 hours. The reaction mixture was evaporated and the resulting white solid was suspended in EtOAc (100 mL), and washed sequentially with water (100 mL) and saturated brine (50 mL). The organic layer was dried with MgSO$_4$, filtered and evaporated to afford crude product. The crude product was purified by flash column chromatography, elution gradient 0 to 50% EtOAc in heptane to afford the title compound (6.17 g, 73%) as a colourless oil; $^1$H NMR (400 MHz, CDCl$_3$) 1.30 (3H, t), 1.69 (1H, t), 4.27 (2H, q), 4.63 (2H, s), 4.67 (2H, d), 6.83 (1H, dd), 6.93-7.01 (2H, m), 7.25-7.3 (1H, m).

Intermediate 20b: Ethyl 2-(3-(bromomethyl)phenoxy)acetate

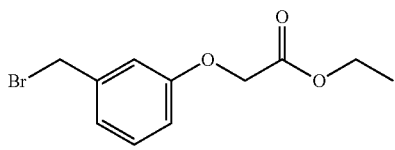

Perbromomethane (2.051 g, 6.18 mmol) in DCM (5.00 mL) was added dropwise to a solution of ethyl 2-(3-(hydroxymethyl)phenoxy)acetate (1.00 g, 4.76 mmol) and triphenylphosphane (1.62 g, 6.18 mmol) in DCM (15 mL) at 0° C. over a period of 5 minutes. The resulting solution was stirred at 0° C. for 30 minutes. The reaction mixture was quenched with saturated NaHCO$_3$ (50 mL), extracted with DCM (1×50 mL), the organic layer was passed through a phase separating cartridge and evaporated to afford colourless liquid. The crude product was purified by flash column chromatography, elution gradient 0 to 20% EtOAc in heptane to afford the title compound (1.090 g, 84%) as a colourless liquid; $^1$H NMR (400 MHz, CDCl$_3$) 1.30 (3H, t), 4.28 (2H, q), 4.45 (2H, s), 4.62 (2H, s), 6.84 (1H, m), 6.91-6.97 (1H, m), 6.99-7.05 (1H, m), 7.23-7.28 (1H, m).

Intermediate 20c: Ethyl 2-(3-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)acetate

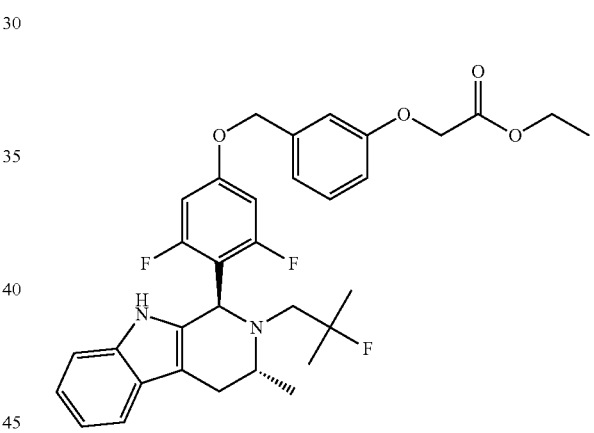

Ethyl 2-(3-(bromomethyl)phenoxy)acetate (77 mg, 0.28 mmol) was added in one portion to 3,5-difluoro-4-((1R,3R)-2-(2-fluoro-2-methylpropyl)-3-methyl-2,3,4,9-tetrahydro-1H-pyrido[3,4-b]indol-1-yl)phenol (100 mg, 0.26 mmol) and potassium carbonate (53.4 mg, 0.39 mmol) in MeCN (2 mL) at 20° C. The resulting suspension was stirred at 20° C. for 18 hours. The mixture was diluted with DCM (10 mL) and water (2 mL). The DCM layer was collected and evaporated to afford crude material as a yellow gum. The crude product was purified by flash column chromatography, elution gradient 0 to 30% EtOAc in heptane to afford the title compound (118 mg, 79%) as a yellow gum; $^1$H NMR (400 MHz, DMSO-d6) 1.05 (3H, d), 1.09-1.27 (9H, m), 2.28-2.41 (1H, m), 2.58 (1H, dd), 2.87 (2H, m), 3.51 (1H, d), 4.17 (2H, q), 4.78 (2H, s), 5.10 (2H, s), 5.13 (1H, s), 6.74 (2H, d), 6.87-7.09 (5H, m), 7.16-7.22 (1H, m), 7.27-7.36 (1H, m), 7.40 (1H, d), 10.51 (1H, s); m/z: ES+ [M+H]$^+$ 581.3.

Intermediate 20d: 2-(3-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)acetic Acid

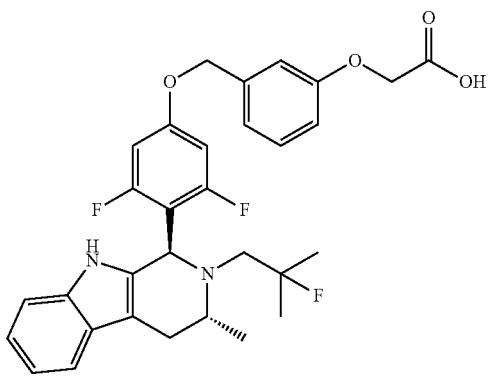 [SMILES: C[C@@H]1Cc2c([nH]c3ccccc23)[C@@H](c2c(F)cc(OCc3cccc(OCC(=O)O)c3)cc2F)N1CC(C)(C)F]

Lithium hydroxide hydrate (17.06 mg, 0.41 mmol) was added in one portion to ethyl 2-(3-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)acetate (118 mg, 0.20 mmol) in THF (0.76 mL) and water (0.25 mL) at 20° C. The resulting solution was stirred for 2 hours. The organic solvent was removed under reduced pressure. The resulting mixture was acidified with 2M aq. HCl and extracted into EtOAc (2×10 mL). The organic extracts were washed with brine (5 mL) and evaporated to afford the title compound (112 mg, 100%) as a colourless gum; m/z: ES+ [M+H]$^+$ 553.3.

Example 20: (2S,4R)-1-((S)-2-(2-(3-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)acetamido)-3,3-dimethylbutanoyl)-4-hydroxy-N-(4-(4-methylthiazol-5-yl)benzyl)pyrrolidine-2-carboxamide

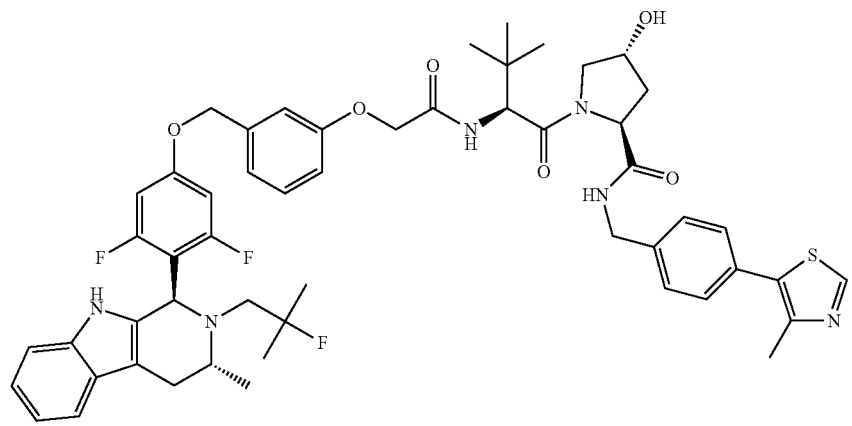 [SMILES: Cc1ncsc1-c1ccc(CNC(=O)[C@@H]2C[C@@H](O)CN2C(=O)[C@@H](NC(=O)COc2cccc(COc3cc(F)c([C@@H]4c5[nH]c6ccccc6c5C[C@@H](C)N4CC(C)(C)F)c(F)c3)c2)C(C)(C)C)cc1]

HATU (116 mg, 0.30 mmol) was added portionwise to 2-(3-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)acetic acid (112 mg, 0.20 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (95 mg, 0.20 mmol) and triethylamine (0.11 mL, 0.81 mmol) in DMF (3.9 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude product. The crude material was purified by preparative HPLC to afford the title compound (116 mg, 59%) as a white solid; $^1$H NMR (400 MHz, DMSO-d6) 0.93 (9H, s), 1.05 (3H, d), 1.16 (6H, dd), 1.91 (1H, m), 2.03-2.13 (1H, m), 2.29-2.4 (1H, m), 2.45 (3H, s), 2.54-2.61 (1H, m), 2.77-2.93 (2H, m), 3.45-3.57 (1H, m), 3.59-3.72 (2H, m), 4.07 (1H, d), 4.26 (1H, dd), 4.35-4.48 (2H, m), 4.57-4.71 (3H, m), 5.09 (2H, s), 5.13 (2H, s), 6.74 (2H, d), 6.9-7.08 (5H, m), 7.18 (1H, d), 7.32 (1H, t), 7.37-7.44 (5H, m), 7.84 (1H, d), 8.57 (1H, t), 8.98 (1H, s), 10.52 (1H, s); m/z: ES+ [M+H]$^+$965.6; ESI-HRMS calculated for C53H60F3N6O6S [M+H]$^+$=965.4242, measured 965.4223.

Intermediate 21a: (E)-Hex-3-ene-1,6-diol

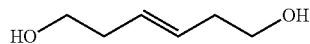

Aluminum(III) lithium hydride 1M in THF (30.2 mL, 30.20 mmol) was added dropwise to a solution of dimethyl (E)-hex-3-enedioate (4 g, 23 mmol) in THF anhydrous (15 mL) at 0° C. over a period of 15 minutes under nitrogen. The suspension was stirred at 20° C. for 18 hours.

The reaction mixture was cooled to 0° C. and quenched with careful dropwise addition of water (1 mL) and the mixture was stirred for 5 minutes 2M aq. NaOH solution (2 mL) was then added and the suspension stirred for 5 minutes. Water (3 mL) was added and the mixture was stirred for 5 minutes. The solids were removed by filtration and the filtrate was evaporated to dryness to afford the title compound (2.21 g, 82%) as a colourless liquid; $^1$H NMR (400 MHz, CDCl$_3$) 1.98 (2H, s), 2.24-2.33 (4H, m), 3.64 (4H, t), 5.52 (2H, m).

Intermediate 21b: (E)-6-((tert-Butyldimethylsilyl)oxy)hex-3-en-1-ol

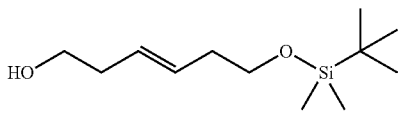

Imidazole (2.33 g, 34.3 mmol) was added to (E)-hex-3-ene-1,6-diol (2.21 g, 19.0 mmol) in DCM (63 mL). tert-butyldimethylsilyl chloride (2.87 g, 19.03 mmol) was added and the resulting suspension was stirred at RT for 18 hours. The reaction mixture was diluted with DCM (50 mL), washed with water (20 mL) and brine (20 mL). The organic phase was filtered through a phase separating cartridge and evaporated to dryness. The crude product was purified by flash column chromatography, elution gradient 0 to 20% EtOAc in heptane to afford the title compound (1.530 g, 35%) as a colourless oil; $^1$H NMR (400 MHz, CDCl$_3$) 0.05 (6H, s), 0.89 (9H, s), 1.43 (1H, t), 2.26 (4H, m), 3.58-3.68 (4H, m), 5.45 (1H, m), 5.51-5.61 (1H, m).

Intermediate 21c: Ethyl (E)-2-((6-((tert-butyldimethylsilyl)oxy)hex-3-en-1-yl)oxy)acetate

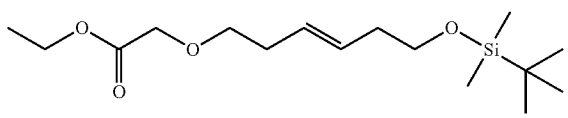 [SMILES: CCOC(=O)COCC/C=C/CCO[Si](C)(C)C(C)(C)C]

Ethyl 2-diazoacetate (2.85 mL, 23.24 mmol) in DCM (18.83 mL) was added slowly to (E)-6-((tert-butyldimethylsilyl)oxy)hex-3-en-1-ol (1.53 g, 6.64 mmol) and diacetoxyrhodium (0.147 g, 0.33 mmol) in DCM (50 mL) at 20° C. over a period of 1 hour under nitrogen. The resulting solution was stirred at 20° C. for 18 hours. The mixture was diluted with DCM (50 mL) and washed with water (20 mL). The organic layer was collected and dried using phase separating cartridge then evaporated to dryness. The crude product was purified by flash column chromatography, elution gradient 0 to 10% EtOAc in heptane to afford the title compound (1.550 g, 74%) a colourless liquid; $^1$H NMR (400 MHz, CDCl$_3$) 0.04 (6H, s), 0.89 (9H, s), 1.27-1.34 (3H, m), 2.22 (2H, q), 2.31-2.38 (2H, m), 3.55 (2H, t), 3.61 (2H, t), 4.07 (2H, s), 4.19-4.3 (2H, m), 5.42-5.58 (2H, m).

Intermediate 21d: Ethyl (E)-2-((6-hydroxyhex-3-en-1-yl)oxy)acetate

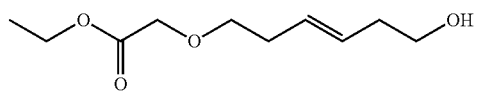

A solution of 1 M TBAF in THF (4.90 mL, 4.90 mmol) was added in one portion to ethyl (E)-2-((6-((tert-butyldimethylsilyl)oxy)hex-3-en-1-yl)oxy)acetate (1.55 g, 4.90 mmol) in THF (20 mL) at 20° C. The resulting solution was stirred at 20° C. for 1 hour. The reaction mixture was diluted with EtOAc (100 mL), and washed sequentially with saturated NH$_4$Cl (25 mL), water (2×50 mL), and saturated brine (20 mL). The organic layer was dried with MgSO$_4$, filtered and evaporated to afford crude product. The crude product was purified by flash column chromatography, elution gradient 0 to 50% EtOAc in heptane to afford the title compound (0.57 g, 58%) as a colourless oil; $^1$H NMR (400 MHz, CDCl$_3$) 1.28 (3H, t), 1.56 (1H, s), 2.28 (2H, q), 2.36 (2H, q), 3.56 (2H, t), 3.64 (2H, q), 4.06 (2H, s), 4.22 (2H, q), 5.55 (2H, m).

Intermediate 21e: Ethyl 2-(((E)-6-((6-((1S,3R)-2-(2,2-difluoroethyl)-3-methyl-2,3,4,9-tetrahydro-1H-pyrido[3,4-b]indol-1-yl)pyridin-3-yl)oxy)hex-3-en-1-yl)oxy)acetate

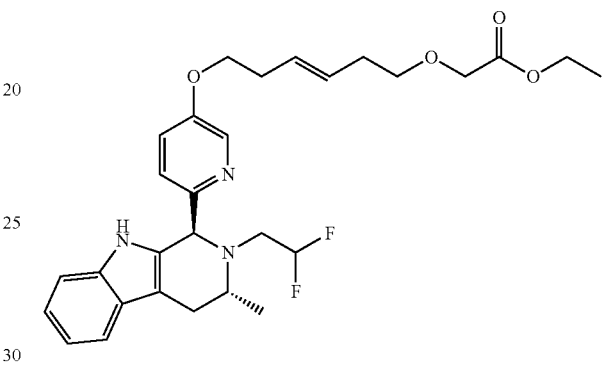

Diisopropyl azodicarboxylate (0.243 mL, 1.24 mmol) was added dropwise to a stirred solution of 6-((1S,3R)-2-(2,2-difluoroethyl)-3-methyl-2,3,4,9-tetrahydro-1H-pyrido[3,4-b]indol-1-yl)pyridin-3-ol (212 mg, 0.62 mmol), ethyl (E)-2-((6-hydroxyhex-3-en-1-yl)oxy)acetate (250 mg, 1.24 mmol) and triphenylphosphine (324 mg, 1.24 mmol) in THF (10 mL) at 0° C. The resulting mixture was stirred at RT for 18 hours. DCM (50 mL) and water (25 mL) were added and the layers were separated. The DCM layer was passed through a phase separating cartridge and concentrated to give the crude product as an orange oil. The crude product was purified by flash column chromatography, elution gradient 0 to 30% EtOAc in heptane to afford the title compound (302 mg, 93%) as a pale yellow gum; m/z: ES+ [M+H]$^+$ 528.4.

Intermediate 21f: 2-(((E)-6-((6-((1S,3R)-2-(2,2-Difluoroethyl)-3-methyl-2,3,4,9-tetrahydro-1H-pyrido[3,4-b]indol-1-yl)pyridin-3-yl)oxy)hex-3-en-1-yl)oxy)acetic Acid

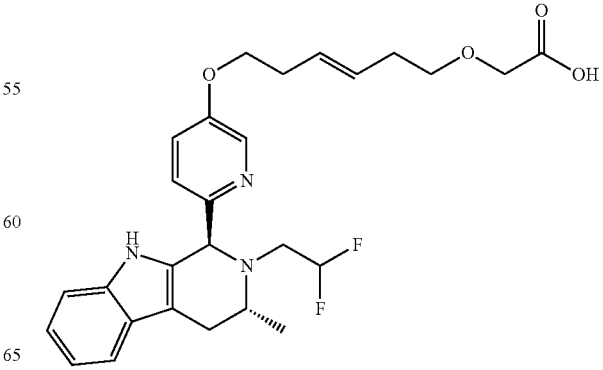

Lithium hydroxide hydrate (47.7 mg, 1.14 mmol) was added in one portion to ethyl 2-(((E)-6-((6-((1S,3R)-2-(2,2-difluoroethyl)-3-methyl-2,3,4,9-tetrahydro-1H-pyrido[3,4-b]indol-1-yl)pyridin-3-yl)oxy)hex-3-en-1-yl)oxy)acetate (300 mg, 0.57 mmol) in THF (2.1 mL) and water (0.7 mL) at 20° C. The resulting solution was stirred for 30 minutes. The reaction mixture was diluted with water (10 mL) then was acidified with 2M aq. HCl and extracted into EtOAc (50 mL). The organic layer was washed with brine (15 mL) and evaporated to afford the title compound (280 mg, 99%) as a cream solid; m/z: ES+ [M+H]+ 500.4.

Example 21: (2S,4R)-1-((S)-2-(2-(((E)-6-((6-((1S,3R)-2-(2,2-Difluoroethyl)-3-methyl-2,3,4,9-tetrahydro-1H-pyrido[3,4-b]indol-1-yl)pyridin-3-yl)oxy)hex-3-en-1-yl)oxy)acetamido)-3,3-dimethylbutanoyl)-4-hydroxy-N-(4-(4-methylthiazol-5-yl)benzyl)pyrrolidine-2-carboxamide Intermediate 22a: Ethyl 2-(((E)-6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hex-3-en-1-yl)oxy)acetate

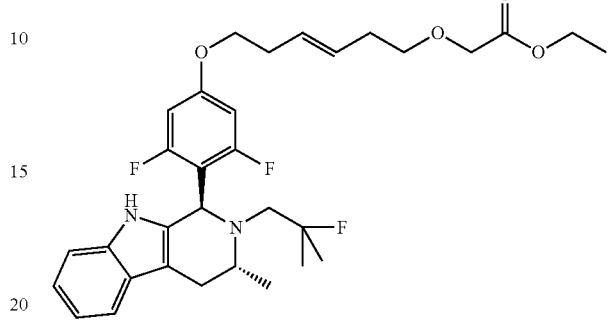

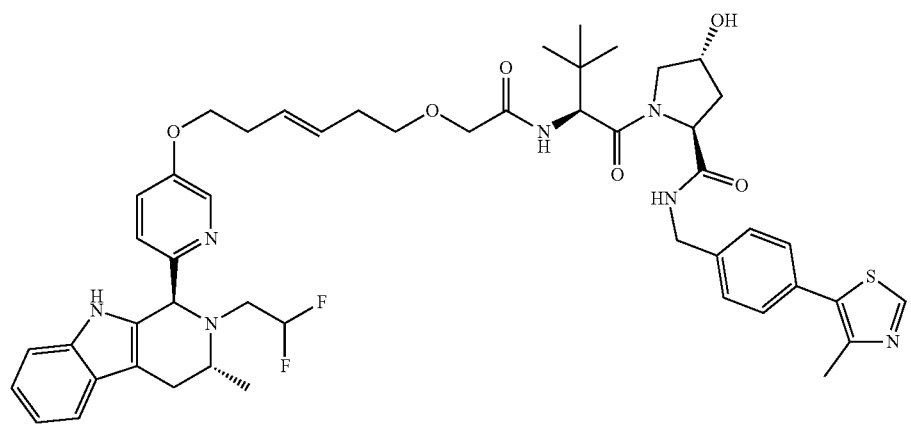 [SMILES: Cc1ncsc1-c1ccc(CNC(=O)[C@@H]2C[C@@H](O)CN2C(=O)[C@@H](NC(=O)COCC/C=C/CCOc2ccc([C@@H]3c4[nH]c5ccccc5c4C[C@@H](C)N3CC(F)F)nc2)C(C)(C)C)cc1]

HATU (320 mg, 0.84 mmol) was added in one portion to (2S,4R)-1-((S)-2-amino-3,3-dimethylbutanoyl)-4-hydroxy-N-(4-(4-methylthiazol-5-yl)benzyl)pyrrolidine-2-carboxamide, HCl (262 mg, 0.56 mmol), 2-(((E)-6-((6-((1S,3R)-2-(2,2-difluoroethyl)-3-methyl-2,3,4,9-tetrahydro-1H-pyrido[3,4-b]indol-1-yl)pyridin-3-yl)oxy)hex-3-en-1-yl)oxy)acetic acid (280 mg, 0.56 mmol) and triethylamine (0.312 mL, 2.24 mmol) in DMF (10.9 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO4, filtered and evaporated to afford crude material. The crude product was purified by preparative HPLC to afford the title compound (190 mg, 37%) as a white solid; $^1$H NMR (400 MHz, CDCl3) 0.95 (9H, s), 1.21 (3H, d), 2.09 (1H, dd), 2.31 (2H, q), 2.42-2.55 (6H, m), 2.63 (1H, dd), 2.78 (1H, dd), 2.91 (1H, dd), 3.08 (1H, dd), 3.36-3.49 (2H, m), 3.55 (2H, m), 3.64 (1H, dd), 3.73-3.92 (2H, m), 3.93-4.13 (3H, m), 4.29 (1H, dd), 4.47-4.6 (3H, m), 4.72 (1H, t), 4.95 (1H, s), 5.51-5.87 (3H, m), 7.03-7.2 (4H, m), 7.27 (1H, d), 7.3-7.39 (5H, m), 7.44-7.53 (2H, m), 8.16 (1H, d), 8.64 (1H, s), 8.78 (1H, s); m/z: ES+ [M+H]+ 912.6; ESI-HRMS calculated for $C_{49}H_{60}F_2N_7O_6S$ [M+H]+=912.4288, measured 912.4286.

Diisopropyl azodicarboxylate (0.12 mL, 0.62 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (120 mg, 0.31 mmol), ethyl (E)-2-((6-hydroxyhex-3-en-1-yl)oxy)acetate (125 mg, 0.62 mmol) and triphenylphosphine (162 mg, 0.62 mmol) in DCM (2.5 mL) at 20° C. The resulting mixture was stirred for 1 hour. DCM (15 mL) and water (25 mL) were added and the layers were separated by passing through a phase separating cartridge and concentrated to give the crude product. The crude product was purified by flash column chromatography, elution gradient 0 to 50% EtOAc in heptane to afford the title compound (133 mg, 75%) as a pale yellow gum; $^1$H NMR (400 MHz, DMSO-d6) 1.05 (3H, d), 1.1-1.24 (9H, m), 2.24 (2H, q), 2.41 (3H, d), 2.57 (1H, s), 2.77-2.93 (2H, m), 3.49 (3H, q), 4.00 (2H, t), 4.07 (2H, s), 4.11 (2H, q), 5.13 (1H, s), 5.5-5.61 (2H, m), 6.65 (2H, d), 6.97 (2H, m), 7.18 (1H, d), 7.40 (1H, d), 10.50 (1H, s); m/z: ES+ [M+H]+ 573.4.

Intermediate 22b: 2-(((E)-6-(3,5-Difluoro-4-((1R, 3R)-2-(2-fluoro-2-methylpropyl)-3-methyl-2,3,4,9-tetrahydro-1H-pyrido[3,4-b]indol-1-yl)phenoxy)hex-3-en-1-yl)oxy)acetic Acid

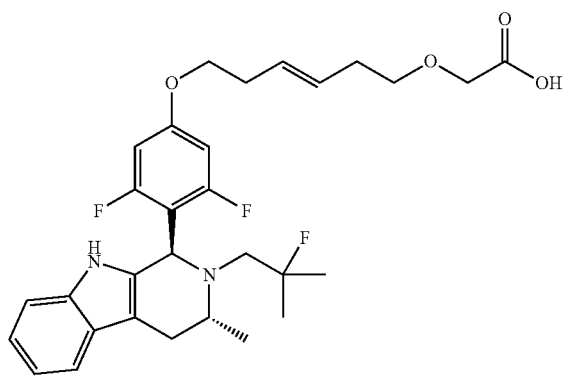 [SMILES: C[C@@H]1Cc2c([nH]c3ccccc23)[C@@H](c2c(F)cc(OCC/C=C/CCOCC(=O)O)cc2F)N1CC(C)(C)F]

Lithium hydroxide hydrate (19.05 mg, 0.45 mmol) was added in one portion to ethyl 2-(((E)-6-(3,5-difluoro-4-((1R, 3R)-2-(2-fluoro-2-methylpropyl)-3-methyl-2,3,4,9-tetrahydro-1H-pyrido[3,4-b]indol-1-yl)phenoxy)hex-3-en-1-yl)oxy)acetate (130 mg, 0.23 mmol) in THF (0.85 mL) and water (0.28 mL) at 20° C. The resulting solution was stirred for 2 hours. The mixture was diluted with water (10 mL). The resulting mixture was acidified with 2M aq. HCl and extracted into EtOAc (50 mL). The organic layer was washed with brine (15 mL) and evaporated to afford the title compound (137 mg) as a colourless gum that was used in the next step without further purification; m/z: ES− [M−H]⁻ 543.5.

Example 22: (2S,4R)-1-((S)-2-(2-(((E)-6-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)hex-3-en-1-yl)oxy)acetamido)-3,3-dimethylbutanoyl)-4-hydroxy-N-(4-(4-methylthiazol-5-yl)benzyl)pyrrolidine-2-carboxamide HATU (130 mg, 0.34 mmol) was added portionwise to 2-(((E)-6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hex-3-en-1-yl)oxy)acetic acid (124 mg, 0.23 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (106 mg, 0.23 mmol) and triethylamine (0.13 mL, 0.91 mmol) in DMF (4.4 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO₄, filtered and evaporated to afford crude material. The crude product was purified by preparative HPLC to afford the title compound (146 mg, 67%) as a cream solid; ¹H NMR (400 MHz, DMSO-d6) 0.94 (9H, s), 1.04 (3H, d), 1.16 (6H, t), 1.91 (1H, m), 2.02-2.12 (1H, m), 2.25-2.37 (3H, m), 2.38-2.45 (5H, m), 2.53-2.59 (1H, m), 2.76-2.96 (2H, m), 3.51 (3H, m), 3.58-3.72 (2H, m), 3.86-4.06 (4H, m), 4.26 (1H, dd), 4.32-4.52 (3H, m), 4.56 (1H, d), 5.12 (2H, s), 5.58 (2H, q), 6.61 (2H, d), 6.97 (2H, m), 7.18 (1H, d), 7.31-7.48 (6H, m), 8.56 (1H, t), 8.96 (1H, s), 10.50 (1H, s); m/z: ES+ [M+H]⁺ 957.6; ESI-HRMS calculated for $C_{52}H_{64}F_3N_6O_6S$ [M+H]⁺=957.4555, measured 957.4537.

Intermediate 23a: 3,3-Dimethylpentane-1,5-diol

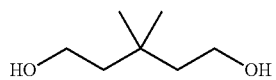

3,3-Dimethylpentanedioic acid (5 g, 31.22 mmol) in THF (50 mL) was added dropwise to a suspension of aluminum (III) lithium hydride (2.370 g, 62.43 mmol) in THF (167 mL) at 0° C. over a period of 30 minutes under nitrogen. The suspension was stirred at 20° C. for 18 hours. The reaction mixture was cooled to 0° C. and quenched with careful dropwise addition of water (1.6 mL) and the mixture was stirred for 10 minutes 2M aq. NaOH solution (1.6 mL) was then added and the suspension stirred for 10 minutes. Water (5 mL) was added and the mixture was stirred for 10 minutes. The solids were removed by filtration and the filtrate was evaporated to dryness to afford the title compound (3.64 g, 88%) as a colourless liquid; ¹H NMR (400 MHz, CDCl₃) 0.95 (6H, s), 1.57 (4H, t), 3.73 (4H, t).

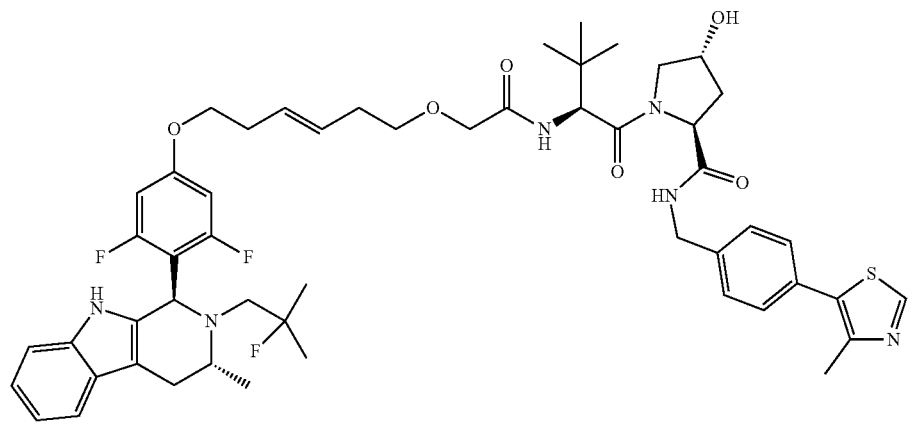 [SMILES: Cc1ncsc1-c1ccc(CNC(=O)[C@@H]2C[C@@H](O)CN2C(=O)[C@@H](NC(=O)COCC/C=C/CCOc2cc(F)c([C@@H]3c4[nH]c5ccccc5c4C[C@@H](C)N3CC(C)(C)F)c(F)c2)C(C)(C)C)cc1]

Intermediate 23b: 5-((tert-Butyldimethylsilyl)oxy)-3,3-dimethylpentan-1-ol

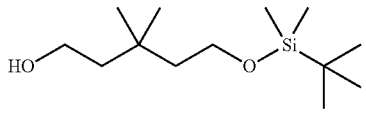 [SMILES: CC(C)(CCO)CCO[Si](C)(C)C(C)(C)C]

Imidazole (3.37 g, 49.56 mmol) was added to 3,3-dimethylpentane-1,5-diol (3.64 g, 27.53 mmol) in DCM (92 mL). tert-Butyldimethylsilyl chloride (4.15 g, 27.53 mmol) was added and the resulting suspension was stirred at RT for 18 hours. The reaction mixture was diluted with DCM (50 mL), washed with water (20 mL) and brine (20 mL). The organic phase was filtered through a phase separating cartridge and evaporated to dryness. The crude product was purified by flash column chromatography, elution gradient 0 to 20% EtOAc in heptane to afford the title compound (2.66 g, 39%) as a colourless oil; $^1$H NMR (400 MHz, CDCl$_3$) 0.06 (6H, s), 0.90 (9H, s), 0.94 (6H, s), 1.52-1.59 (4H, m), 1.70 (1H, t), 3.70 (4H, m).

Intermediate 23c: Ethyl 2-((5-((tert-butyldimethylsilyl)oxy)-3,3-dimethylpentyl)oxy)acetate

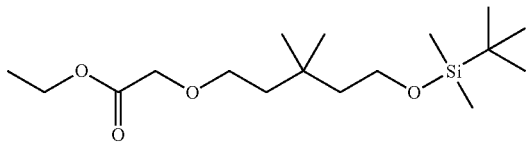 [SMILES: CCOC(=O)COCCC(C)(C)CCO[Si](C)(C)C(C)(C)C]

Ethyl 2-diazoacetate (4.63 mL, 37.77 mmol) in DCM (30.8 mL) was added slowly to 5-((tert-butyldimethylsilyl)oxy)-3,3-dimethylpentan-1-ol (2.66 g, 10.79 mmol) and diacetoxyrhodium (0.239 g, 0.54 mmol) in DCM (80 mL) at 20° C. over a period of 1 hour under nitrogen. The resulting solution was stirred at 20° C. for 18 hours. The mixture was diluted with DCM (50 mL) and washed with water (20 mL). The organic layer was collected and dried using phase separating cartridge then evaporated to dryness. The crude product was purified by flash column chromatography, elution gradient 0 to 10% EtOAc in heptane to afford the title compound (3.13 g, 87%) as a colourless liquid; $^1$H NMR (400 MHz, CDCl$_3$) 0.05 (6H, s), 0.89 (9H, s), 0.93 (6H, s), 1.27-1.3 (3H, m), 1.45-1.53 (2H, m), 1.57-1.63 (2H, m), 3.54-3.62 (2H, m), 3.64-3.72 (2H, m), 4.04 (2H, s), 4.19-4.25 (2H, m).

Intermediate 23d: Ethyl 2-((5-hydroxy-3,3-dimethylpentyl)oxy)acetate

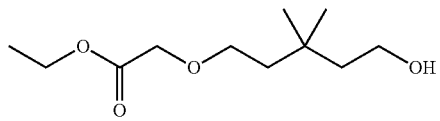

A solution of 1M TBAF in THF (9.41 mL, 9.41 mmol) was added in one portion to ethyl 2-((5-((tert-butyldimethylsilyl)oxy)-3,3-dimethylpentyl)oxy)acetate (3.13 g, 9.41 mmol) in THF (37.6 mL) at 20° C. The resulting solution was stirred for 1 hour. The reaction mixture was diluted with EtOAc (100 mL), and washed sequentially with saturated aq. NH$_4$Cl (25 mL), water (2×50 mL), and saturated brine (20 mL). The organic layer was dried with MgSO$_4$, filtered and evaporated to afford crude product. The crude product was purified by flash column chromatography, elution gradient 0 to 50% EtOAc in heptane to afford the title compound (1.090 g, 53%) as a colourless oil; $^1$H NMR (400 MHz, CDCl$_3$) 0.95 (6H, s), 1.29 (3H, t), 1.57-1.67 (5H, m), 3.60 (2H, t), 3.72 (2H, d), 4.05 (2H, s), 4.22 (2H, q).

Intermediate 23e: Ethyl 2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-dimethylpentyl)oxy)acetate

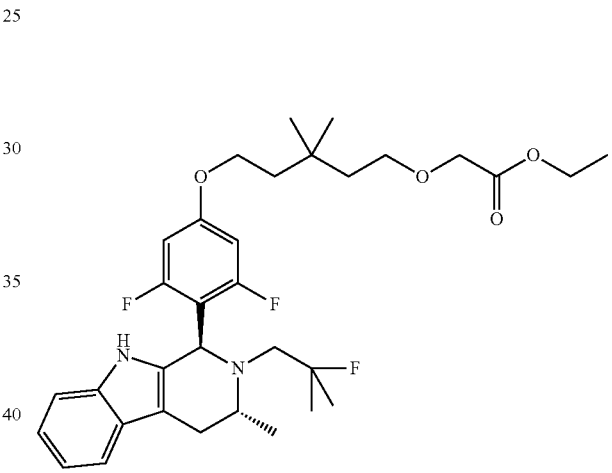

Diisopropyl azodicarboxylate (0.15 mL, 0.77 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (150 mg, 0.39 mmol), ethyl 2-((5-hydroxy-3,3-dimethylpentyl)oxy)acetate (169 mg, 0.77 mmol) and triphenylphosphine (203 mg, 0.77 mmol) in DCM (3.1 mL) at 20° C. The resulting mixture was stirred for 1 hour. DCM (15 mL) and water (25 mL) were added and the layers were separated by passing through a phase separating cartridge and concentrated to give the crude product. The crude product was purified by flash column chromatography, elution gradient 0 to 50% EtOAc in heptane to afford the title compound (204 mg, 90%) as a pale yellow gum; $^1$H NMR (400 MHz, DMSO-d6) 0.95 (6H, s), 1.05 (3H, d), 1.16-1.23 (9H, m), 1.54 (2H, t), 1.68 (2H, t), 2.29-2.41 (1H, m), 2.55-2.6 (1H, m), 2.78-2.94 (2H, m), 3.53 (3H, t), 4.03 (2H, t), 4.06 (2H, s), 4.11 (2H, q), 5.13 (1H, s), 6.66 (2H, d), 6.97 (2H, m), 7.15-7.22 (1H, m), 7.40 (1H, d), 10.50 (1H, s); m/z: ES+ [M+H]$^+$ 589.4.

Intermediate 23f: 2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-3,3-dimethylpentyl)oxy)acetic Acid

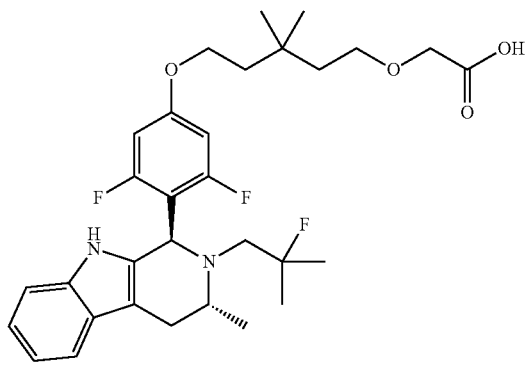 [SMILES: C[C@@H]1Cc2c([nH]c3ccccc23)[C@@H](c2c(F)cc(OCCC(C)(C)CCOCC(=O)O)cc2F)N1CC(C)(C)F]

Lithium hydroxide hydrate (28.5 mg, 0.68 mmol) was added in one portion to ethyl 2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-dimethylpentyl)oxy)acetate (200 mg, 0.34 mmol) in THF (1.3 mL) and water (0.43 mL) at 20° C. The resulting solution was stirred for 2 hours. The mixture was diluted with water (10 mL). The resulting mixture was acidified with 2M aq. HCl and extracted into EtOAc (50 mL). The organic layer was washed with brine (15 mL) and evaporated to afford the crude title compound (220 mg, 116%) as a colourless gum; m/z: ES+ [M+H]$^+$ 561.4.

Example 23: (2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-3,3-dimethylpentyl)oxy)acetamido)-3,3-dimethylbutanoyl)-4-hydroxy-N-(4-(4-methylthiazol-5-yl)benzyl)pyrrolidine-2-carboxamide

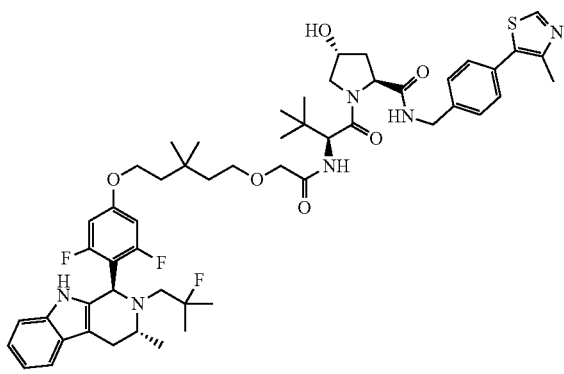 [SMILES: Cc1ncsc1-c1ccc(CNC(=O)[C@@H]2C[C@@H](O)CN2C(=O)[C@@H](NC(=O)COCCC(C)(C)CCOc2cc(F)c([C@@H]3c4[nH]c5ccccc5c4C[C@@H](C)N3CC(C)(C)F)c(F)c2)C(C)(C)C)cc1]

HATU (193 mg, 0.51 mmol) was added portionwise to 2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-dimethylpentyl)oxy)acetic acid (190 mg, 0.34 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (158 mg, 0.34 mmol) and triethylamine (0.19 mL, 1.36 mmol) in DMF (6.6 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (162 mg, 49%) as a cream solid; $^1$H NMR (400 MHz, DMSO-d6) 0.93 (9H, d), 0.97 (6H, s), 1.04 (3H, d), 1.16 (6H, t), 1.58 (2H, t), 1.68 (2H, t), 1.91 (1H, m), 2.02-2.11 (1H, m), 2.29-2.4 (1H, m), 2.44 (3H, s), 2.55-2.59 (1H, m), 2.76-2.95 (2H, m), 3.43-3.71 (5H, m), 3.93 (2H, s), 4.03 (2H, t), 4.26 (1H, dd), 4.32-4.5 (3H, m), 4.56 (1H, d), 5.13 (2H, d), 6.65 (2H, d), 6.96 (2H, m), 7.18 (1H, d), 7.33 (1H, d), 7.40 (5H, s), 8.56 (1H, t), 8.97 (1H, s), 10.49 (1H, s); m/z: ES+ [M+H]$^+$973.7; ESI-HRMS calculated for C$_{53}$H$_{68}$F$_3$N$_6$O$_6$S [M+H]$^+$=973.4868, measured 973.4856.

Intermediate 24a: 2-(4-(2-(Benzyloxy)ethoxy)butoxy)tetrahydro-2H-pyran

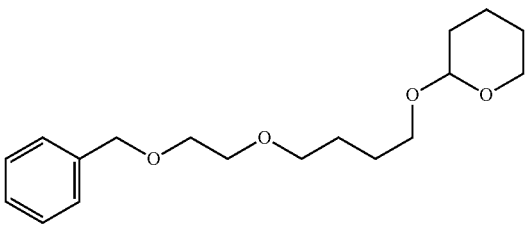 [SMILES: c1ccc(COCCOCCCCOC2CCCCO2)cc1]

Tetrabutylammonium hydrogen sulfate (0.895 g, 2.64 mmol) was added in one portion to 2-(benzyloxy)ethan-1-ol (2.5 mL, 17.6 mmol) and 2-(4-bromobutoxy)tetrahydro-2H-pyran (5.0 g, 21.1 mmol) in 50% aq. NaOH solution (11.6 mL) at 20° C. The resulting mixture was stirred at 70° C. for 4 hours. The cooled reaction mixture was diluted with water (20 mL) and extracted with EtOAc (3×25 mL). The combined organic extracts were washed with water (20 mL), saturated brine solution (20 mL), dried (MgSO$_4$), filtered and evaporated to afford crude product. The crude product was purified by flash column chromatography, elution gradient 0 to 10% EtOAc in heptane to afford the title compound (4.54 g, 84%) as a colourless oil; $^1$H NMR (400 MHz, CDCl$_3$) 1.47-1.62 (4H, m), 1.62-1.75 (5H, m), 1.82 (1H, m), 3.41 (1H, m), 3.45-3.54 (3H, m), 3.62 (4H, s), 3.75 (1H, m), 3.86 (1H, m), 4.57 (3H, s), 7.24-7.38 (5H, m).

Intermediate 24b: 4-(2-(Benzyloxy)ethoxy)butan-1-ol

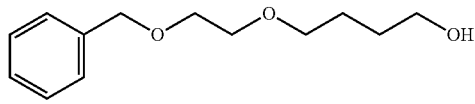 [SMILES: OCCCCOCCOCc1ccccc1]

2-(4-(2-(Benzyloxy)ethoxy)butoxy)tetrahydro-2H-pyran (4.54 g, 14.72 mmol) was dissolved in MeOH (39 mL) and 1M aq. HCl (19.5 mL) was added. The resulting mixture was stirred at 20° C. for 3 hours. The reaction mixture was diluted with water (100 mL), and extracted with EtOAc (2×100 mL). The combined organics were washed with saturated brine (75 mL). The organic layer was dried with MgSO₄, filtered and evaporated to afford the title compound (3.3 g, 100%) as a colourless liquid that was used in the next step without further purification; ¹H NMR (400 MHz, CDCl₃) 1.62-1.76 (4H, m), 2.26 (1H, s), 3.53 (2H, t), 3.59-3.69 (6H, m), 4.57 (2H, s), 7.28 (1H, m), 7.3-7.39 (4H, m).

Intermediate 24c: Ethyl 2-(4-(2-(benzyloxy)ethoxy)butoxy)acetate

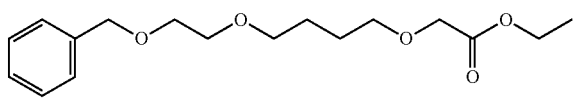 [SMILES: CCOC(=O)COCCCCOCCOCc1ccccc1]

Ethyl 2-diazoacetate (4.92 mL, 40.1 mmol) in DCM (16.5 mL) was added slowly to 4-(2-(benzyloxy)ethoxy)butan-1-ol (3.6 g, 16.1 mmol) and diacetoxyrhodium (0.355 g, 0.80 mmol) in DCM (43 mL) at 20° C. over a period of 1 hour under nitrogen. The resulting solution was stirred for 18 hours. The mixture was diluted with DCM (50 mL) and washed with water (20 mL). The organic layer was collected and dried using phase separating cartridge then evaporated to dryness. The crude product was purified by flash column chromatography, elution gradient 0 to 10% EtOAc in heptane to afford the title compound (3.43 g, 69%) a colourless liquid; ¹H NMR (400 MHz, CDCl₃) 1.29 (3H, t), 1.66-1.73 (4H, m), 3.48-3.53 (2H, m), 3.53-3.58 (2H, m), 3.61 (4H, m), 4.05 (2H, s), 4.18-4.27 (2H, m), 4.57 (2H, s), 7.27-7.31 (1H, m), 7.31-7.37 (4H, m).

Intermediate 24d: Ethyl 2-(4-(2-hydroxyethoxy)butoxy)acetate

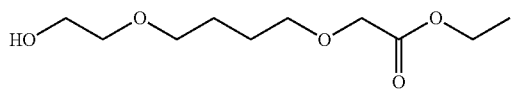

Ethyl 2-(4-(2-(benzyloxy)ethoxy)butoxy)acetate (3.43 g, 11.05 mmol) and 10% palladium on carbon (0.118 g, 1.11 mmol) in ethanol (22 mL) were stirred under an atmosphere of hydrogen (1.5 bar) at RT for 4 hours. The reaction mixture was filtered and evaporated to afford crude product. The crude product was purified by flash column chromatography, elution gradient 0 to 100% EtOAc in heptane to afford the title compound (1.85 g, 76%) as a colourless oil; ¹H NMR (400 MHz, CDCl₃) 1.29 (3H, t), 1.70 (4H, tq), 2.04 (1H, t), 3.48-3.62 (6H, m), 3.67-3.79 (2H, m), 4.06 (2H, s), 4.22 (2H, q).

Intermediate 24e: Ethyl 2-(4-(2-((6-((1S,3R)-2-(2,2-difluoroethyl)-3-methyl-2,3,4,9-tetrahydro-1H-pyrido[3,4-b]indol-1-yl)pyridin-3-yl)oxy)ethoxy)butoxy)acetate

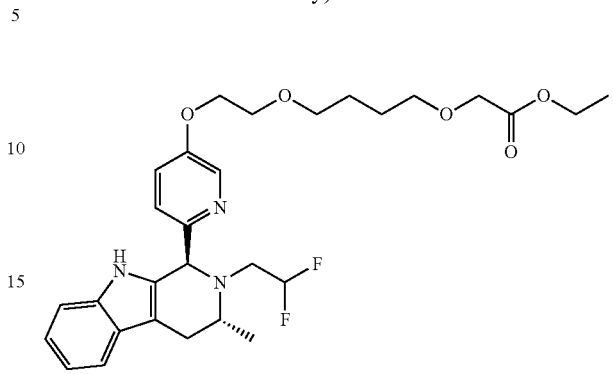

Diisopropyl azodicarboxylate (0.29 mL, 1.46 mmol) was added dropwise to a stirred solution of 6-((1S,3R)-2-(2,2-difluoroethyl)-3-methyl-2,3,4,9-tetrahydro-1H-pyrido[3,4-b]indol-1-yl)pyridin-3-ol (250 mg, 0.73 mmol), ethyl 2-(4-(2-hydroxyethoxy)butoxy)acetate (321 mg, 1.46 mmol) and triphenylphosphine (382 mg, 1.46 mmol) in THF (5.9 mL) at 0° C. The resulting mixture was stirred at RT for 18 hours. DCM (50 mL) and water (25 mL) were added and the layers were separated. The DCM layer was passed through a phase separating cartridge and concentrated to give the crude product. The crude product was purified by flash column chromatography, elution gradient 0 to 30% EtOAc in heptane to afford the title compound (342 mg, 86%) as a pale yellow gum; m/z: ES+ [M+H]⁺ 546.4.

Intermediate 24f: 2-(4-(2-((6-((1S,3R)-2-(2,2-Difluoroethyl)-3-methyl-2,3,4,9-tetrahydro-1H-pyrido[3,4-b]indol-1-yl)pyridin-3-yl)oxy)ethoxy)butoxy)acetic Acid

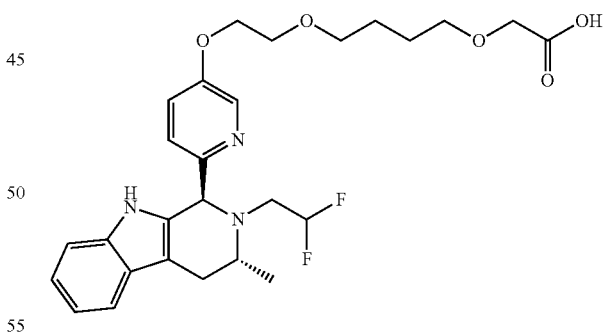

Lithium hydroxide hydrate (52.6 mg, 1.25 mmol) was added in one portion to ethyl 2-(4-(2-((6-((1S,3R)-2-(2,2-difluoroethyl)-3-methyl-2,3,4,9-tetrahydro-1H-pyrido[3,4-b]indol-1-yl)pyridin-3-yl)oxy)ethoxy)butoxy)acetate (342 mg, 0.63 mmol) in THF (2.4 mL) and water (0.8 mL) at 20° C. The resulting solution was stirred for 30 minutes. The reaction mixture was diluted with water (10 mL) then was acidified with 2M HCl and extracted into EtOAc (50 mL). The organic layer was washed with brine (15 mL) and evaporated to afford the title compound (324 mg, 100%) as a yellow gum; m/z: ES+ [M+H]⁺ 518.4.

Example 24: (2S,4R)-1-((S)-2-(2-(4-(2-((6-((1S,3R)-2-(2,2-Difluoroethyl)-3-methyl-2,3,4,9-tetrahydro-1H-pyrido[3,4-b]indol-1-yl)pyridin-3-yl)oxy)ethoxy)butoxy)acetamido)-3,3-dimethylbutanoyl)-4-hydroxy-N-(4-(4-methylthiazol-5-yl)benzyl)pyrrolidine-2-carboxamide

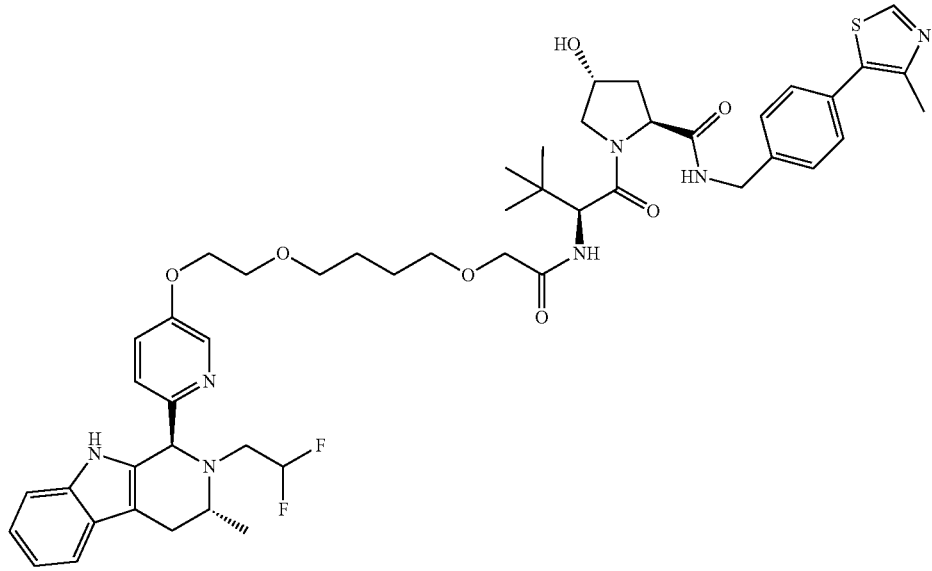 [SMILES: Cc1ncsc1-c1ccc(CNC(=O)[C@@H]2C[C@@H](O)CN2C(=O)[C@@H](NC(=O)COCCCCOCCOc2ccc([C@@H]3c4[nH]c5ccccc5c4C[C@@H](C)N3CC(F)F)nc2)C(C)(C)C)cc1]

HATU (357 mg, 0.94 mmol) was added in one portion to (2S,4R)-1-((S)-2-amino-3,3-dimethylbutanoyl)-4-hydroxy-N-(4-(4-methylthiazol-5-yl)benzyl)pyrrolidine-2-carboxamide, HCl (292 mg, 0.63 mmol), 2-(4-(2-((6-((1S,3R)-2-(2,2-difluoroethyl)-3-methyl-2,3,4,9-tetrahydro-1H-pyrido[3,4-b]indol-1-yl)pyridin-3-yl)oxy)ethoxy)butoxy)acetic acid (324 mg, 0.63 mmol) and triethylamine (0.349 mL, 2.50 mmol) in DMF (14 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (212 mg, 36%) as a white solid; $^1$H NMR (400 MHz, CDCl$_3$) 0.95 (9H, s), 1.22 (3H, d), 1.69 (5H, m), 2.13 (1H, dd), 2.51 (3H, s), 2.52-2.7 (2H, m), 2.79 (1H, m), 2.92 (1H, dd), 3.10 (1H, m), 3.40 (1H, m), 3.50 (2H, t), 3.56 (2H, t), 3.63 (1H, dd), 3.70 (1H, d), 3.77 (2H, t), 3.87 (1H, d), 4.13 (3H, m), 4.34 (1H, dd), 4.48-4.6 (3H, m), 4.74 (1H, t), 4.96 (1H, s), 5.5-5.87 (1H, m), 7.02-7.22 (4H, m), 7.28 (1H, d), 7.3-7.44 (6H, m), 7.49 (1H, d), 8.19 (1H, d), 8.66 (1H, s), 8.81 (1H, s); m/z: ES+ [M+H]$^+$ 930.6; ESI-HRMS calculated for C$_{49}$H$_{62}$F$_2$N$_7$O$_7$S [M+H]$^+$=930.4394, measured 930.4391.

Intermediate 25a: 2-(3-(2-(Benzyloxy)ethoxy)propoxy)tetrahydro-2H-pyran

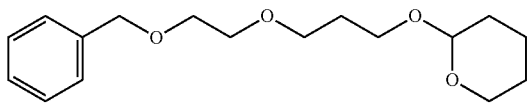 [SMILES: c1ccc(COCCOCCCOC2CCCCO2)cc1]

Tetrabutylammonium hydrogen sulfate (0.951 g, 2.80 mmol) was added in one portion to 2-(benzyloxy)ethan-1-ol (2.66 mL, 18.7 mmol) and 2-(3-bromopropoxy)tetrahydro-2H-pyran (5.0 g, 22.4 mmol) in 50% aq. NaOH solution (12.3 mL) at 20° C. The resulting mixture was stirred at 70° C. for 4 hours. The cooled reaction mixture was diluted with water (20 mL) and extracted with EtOAc (3×25 mL). The combined organic extracts were washed with water (20 mL), saturated brine solution (20 mL), dried (MgSO$_4$), filtered and evaporated to afford crude product. The crude product was purified by flash column chromatography, elution gradient 0 to 10% EtOAc in heptane to afford the title compound (4.31 g, 78%) as a colourless oil; $^1$H NMR (400 MHz, CDCl$_3$) 1.47-1.6 (4H, m), 1.65-1.74 (1H, m), 1.80 (1H, m), 1.89 (2H, p), 3.45-3.53 (2H, m), 3.54-3.65 (6H, m), 3.83 (2H, m), 4.57 (3H, s), 7.23-7.37 (5H, m).

Intermediate 25b: 3-(2-(Benzyloxy)ethoxy)propan-1-ol

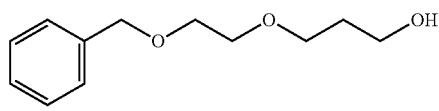 [SMILES: OCCCOCCOCc1ccccc1]

2-(3-(2-(Benzyloxy)ethoxy)propoxy)tetrahydro-2H-pyran (4.3 g, 14.6 mmol) was dissolved in MeOH (39.0 mL) and 1M aq. HCl (19.5 mL) was added. The resulting mixture was stirred at 20° C. for 3 hours. The reaction mixture was diluted with water (100 mL), and extracted with EtOAc (3×100 mL). The combined organics were washed with saturated brine (20 mL). The organic layer was dried with MgSO$_4$, filtered and evaporated to afford the title compound (2.95 g, 96%) as a colourless liquid; $^1$H NMR (400 MHz, CDCl$_3$) 1.85 (2H, p), 2.38 (1H, s), 3.59-3.66 (4H, m), 3.68 (2H, t), 3.78 (2H, s), 4.57 (2H, s), 7.27-7.3 (1H, m), 7.34 (4H, d).

Intermediate 25c: Ethyl 2-(3-(2-(benzyloxy)ethoxy)propoxy)acetate

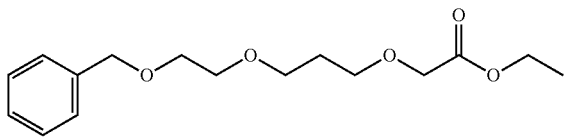 [SMILES: CCOC(=O)COCCCOCCOCc1ccccc1]

Ethyl 2-diazoacetate (4.30 mL, 35.07 mmol) in DCM (14.39 mL) was added slowly to 3-(2-(benzyloxy)ethoxy)propan-1-ol (2.95 g, 14.0 mmol) and diacetoxyrhodium (0.310 g, 0.70 mmol) in DCM (37 mL) at 20° C. over a period of 1 hour under nitrogen. The resulting solution was stirred at 20° C. for 18 hours. The mixture was diluted with DCM (50 mL) and washed with water (20 mL). The organic layer was collected and dried using phase separating cartridge then evaporated to dryness. The crude product was purified by flash column chromatography, elution gradient 0 to 10% EtOAc in heptane to afford the title compound (3.47 g, 83%) as a colourless liquid; $^1$H NMR (400 MHz, CDCl$_3$) 1.29 (3H, m), 1.92 (2H, p), 3.56-3.67 (8H, m), 4.05 (2H, s), 4.18-4.26 (2H, m), 4.57 (2H, s), 7.27-7.3 (1H, m), 7.31-7.37 (4H, m).

Intermediate 25d: Ethyl 2-(3-(2-hydroxyethoxy)propoxy)acetate

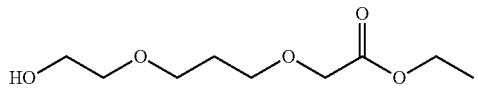

Ethyl 2-(3-(2-(benzyloxy)ethoxy)propoxy)acetate (3.47 g, 11.71 mmol) and 10% palladium on carbon (0.125 g, 1.17 mmol) in EtOH (23 mL) were stirred under an atmosphere of hydrogen (1.5 bar) at RT for 4 hours. The reaction mixture was filtered and evaporated to afford crude product. The crude product was purified by flash column chromatography, elution gradient 0 to 100% EtOAc in heptane to afford the title compound (1.750 g, 73%) as a colourless oil; $^1$H NMR (400 MHz, CDCl$_3$) 1.28 (3H, t), 1.91 (2H, p), 2.25 (1H, t), 3.53-3.59 (2H, m), 3.63 (4H, m), 3.73 (2H, m), 4.07 (2H, s), 4.22 (2H, q).

Intermediate 25e: Ethyl 2-(3-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)propoxy)acetate

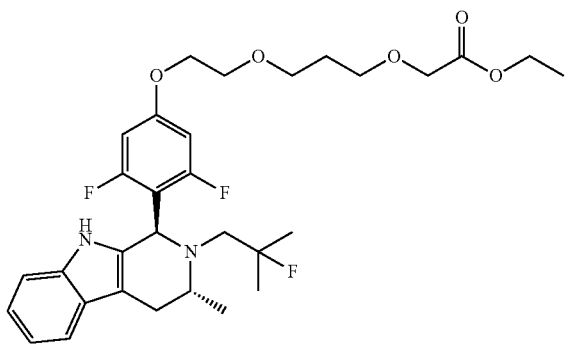 [SMILES: CCOC(=O)COCCCOCCOc1cc(F)c([C@@H]2c3[nH]c4ccccc4c3C[C@@H](C)N2CC(C)(C)F)c(F)c1]

Diisopropyl azodicarboxylate (0.152 mL, 0.77 mmol) was added dropwise to a stirred mixture of 3,5-difluoro-4-((1R,3R)-2-(2-fluoro-2-methylpropyl)-3-methyl-2,3,4,9-tetrahydro-1H-pyrido[3,4-b]indol-1-yl)phenol (150 mg, 0.39 mmol), ethyl 2-(3-(2-hydroxyethoxy)propoxy)acetate (159 mg, 0.77 mmol) and triphenylphosphine (203 mg, 0.77 mmol) in DCM (6.3 mL) at 0° C. The resulting mixture was stirred at RT for 18 hours. DCM (50 mL) and water (25 mL) were added and the layers were separated. The DCM layer was passed through a phase separating cartridge and concentrated to give the crude product. The crude product was purified by flash column chromatography, elution gradient 0 to 25% EtOAc in heptane to afford the title compound (327 mg, contains solvents) as a pale yellow gum that was used in the next step without further purification; m/z: ES+ [M+H]$^+$ 577.4.

Intermediate 25f: 2-(3-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)propoxy)acetic Acid

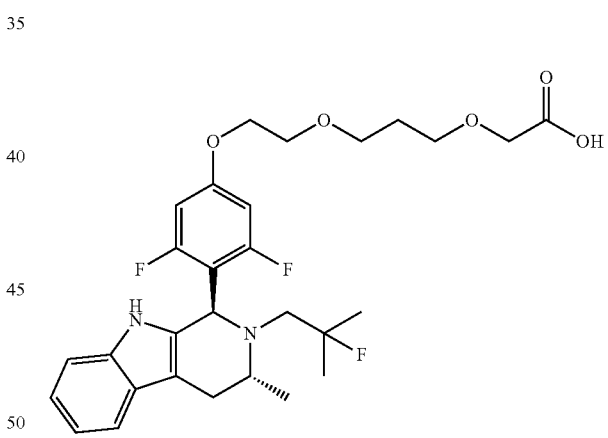

Lithium hydroxide hydrate (32.5 mg, 0.77 mmol) was added in one portion to ethyl 2-(3-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)propoxy)acetate (223 mg, 0.39 mmol) in THF (1.5 mL) and water (0.5 mL) at 20° C. The resulting solution was stirred for 30 minutes. The reaction mixture was diluted with water (10 mL) then was acidified with 2M aq. HCl and extracted into EtOAc (50 mL). The organic layer was washed with brine (15 mL) and evaporated to afford the title compound (212 mg, 100%) as a yellow gum; m/z: ES+ [M+H]$^+$ 549.3.

Example 25: (2S,4R)-1-((S)-2-(2-(3-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)propoxy)acetamido)-3,3-dimethylbutanoyl)-4-hydroxy-N-(4-(4-methylthiazol-5-yl)benzyl)pyrrolidine-2-carboxamide Diisopropyl azodicarboxylate (0.287 mL, 1.46 mmol) was added dropwise to a stirred mixture of 6-((1S,3R)-2-(2,2-difluoroethyl)-3-methyl-2,3,4,9-tetrahydro-1H-pyrido[3,4-b]indol-1-yl)pyridin-3-ol (250 mg, 0.73 mmol), ethyl 2-(3-(2-hydroxyethoxy)propoxy)acetate (300 mg, 1.46 mmol) and triphenylphosphine (382 mg, 1.46 mmol) in DCM (12 mL) at 0° C. The resulting mixture was stirred at RT for 18 hours. DCM (50 mL) and water (25 mL) were added and the

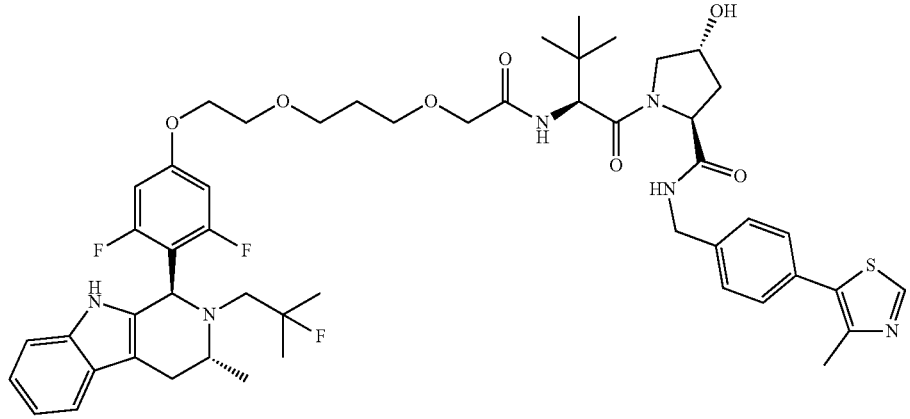 [SMILES: Cc1ncsc1-c1ccc(CNC(=O)[C@@H]2C[C@@H](O)CN2C(=O)[C@@H](NC(=O)COCCCOCCOc2cc(F)c([C@@H]3c4[nH]c5ccccc5c4C[C@@H](C)N3CC(C)(C)F)c(F)c2)C(C)(C)C)cc1]

HATU (220 mg, 0.58 mmol) was added in one portion to (2S,4R)-1-((S)-2-amino-3,3-dimethylbutanoyl)-4-hydroxy-N-(4-(4-methylthiazol-5-yl)benzyl)pyrrolidine-2-carboxamide, HCl (180 mg, 0.39 mmol), 2-(3-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)propoxy)acetic acid (212 mg, 0.39 mmol) and triethylamine (0.215 mL, 1.55 mmol) in DMF (14.200 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (151 mg, 41%) as a white solid; $^1$H NMR (400 MHz, CDCl$_3$) 0.94 (9H, s), 1.09 (3H, d), 1.21 (6H, dd), 1.87 (2H, p), 2.04-2.13 (1H, m), 2.40 (1H, dd), 2.48 (3H, s), 2.51-2.65 (2H, m), 2.78-2.9 (2H, m), 3.07 (1H, dd), 3.55 (2H, t), 3.58-3.69 (5H, m), 3.76 (2H, m), 3.87 (1H, d), 3.96-4.11 (3H, m), 4.33 (1H, dd), 4.55 (3H, t), 4.72 (1H, t), 5.19 (1H, s), 6.34-6.42 (2H, m), 7.01-7.12 (2H, m), 7.17 (1H, d), 7.2-7.25 (2H, m), 7.3-7.41 (4H, m), 7.50 (1H, m), 8.49 (1H, s), 8.64 (1H, s); m/z: ES+ [M+H]$^+$ 961.6; ESI-HRMS calculated for $C_{51}H_{64}F_3N_6O_7S$ [M+H]$^+$=961.4504, measured 961.4467.

Intermediate 26a: Ethyl 2-(3-(2-((6-((1S,3R)-2-(2,2-difluoroethyl)-3-methyl-2,3,4,9-tetrahydro-1H-pyrido[3,4-b]indol-1-yl)pyridin-3-yl)oxy)ethoxy)propoxy)acetate

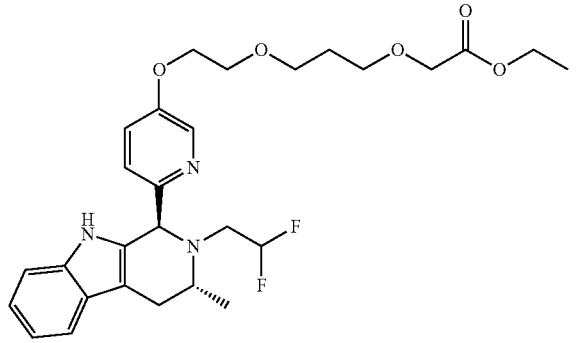 [SMILES: CCOC(=O)COCCCOCCOc1ccc([C@@H]2c3[nH]c4ccccc4c3C[C@@H](C)N2CC(F)F)nc1]

layers were separated. The DCM layer was passed through a phase separating cartridge and concentrated to give the crude product as an orange oil. The crude product was purified by flash column chromatography, elution gradient 0 to 50% EtOAc in heptane to afford (444 mg) as a pale yellow gum that was used in the next step without further purification; m/z: ES+ [M+H]$^+$ 532.4.

Intermediate 26b: 2-(3-(2-((6-((1S,3R)-2-(2,2-Difluoroethyl)-3-methyl-2,3,4,9-tetrahydro-1H-pyrido[3,4-b]indol-1-yl)pyridin-3-yl)oxy)ethoxy)propoxy)acetic Acid

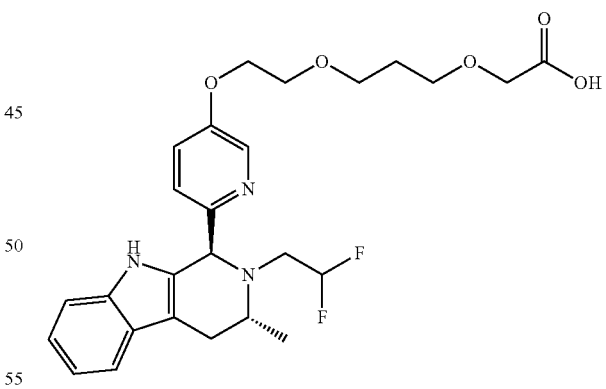

Lithium hydroxide hydrate (61 mg, 1.46 mmol) was added in one portion to ethyl 2-(3-(2-((6-((1S,3R)-2-(2,2-difluoroethyl)-3-methyl-2,3,4,9-tetrahydro-1H-pyrido[3,4-b]indol-1-yl)pyridin-3-yl)oxy)ethoxy)propoxy)acetate (387 mg, 0.73 mmol) in THF (2.7 mL) and water (0.9 mL) at 20° C. The resulting solution was stirred for 30 minutes. The reaction mixture was diluted with water (10 mL) then was acidified with 2M aq. HCl and extracted into EtOAc (50 mL). The organic layer was washed with brine (15 mL) and evaporated to afford the title compound (367 mg, 100%) as a yellow gum; m/z: ES+ [M+H]$^+$ 504.3.

Example 26: (2S,4R)-1-((S)-2-(2-(3-(2-((6-((1S,3R)-2-(2,2-Difluoroethyl)-3-methyl-2,3,4,9-tetrahydro-1H-pyrido[3,4-b]indol-1-yl)pyridin-3-yl)oxy)ethoxy)propoxy)acetamido)-3,3-dimethylbutanoyl)-4-hydroxy-N-(4-(4-methylthiazol-5-yl)benzyl)pyrrolidine-2-carboxamide

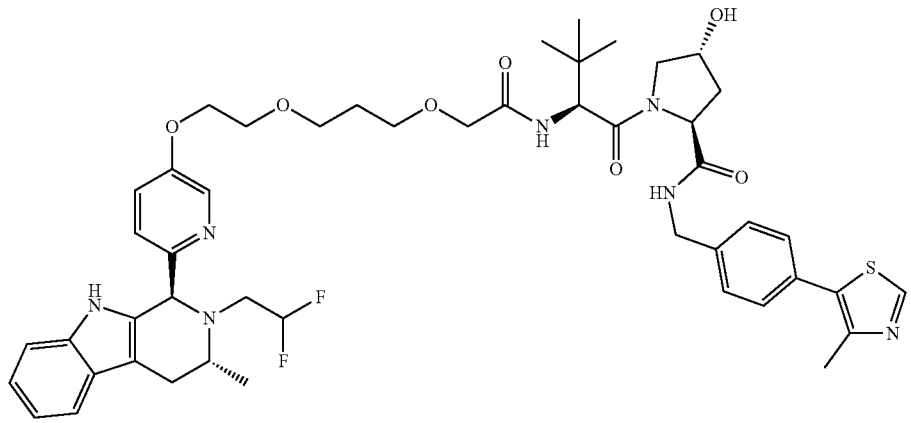 [SMILES: Cc1ncsc1-c1ccc(CNC(=O)[C@@H]2C[C@@H](O)CN2C(=O)[C@@H](NC(=O)COCCCOCCOc2ccc([C@@H]3c4[nH]c5ccccc5c4C[C@@H](C)N3CC(F)F)nc2)C(C)(C)C)cc1]

HATU (416 mg, 1.09 mmol) was added in one portion to (2S,4R)-1-((S)-2-amino-3,3-dimethylbutanoyl)-4-hydroxy-N-(4-(4-methylthiazol-5-yl)benzyl)pyrrolidine-2-carboxamide, HCl (340 mg, 0.73 mmol), 2-(3-(2-((6-((1S,3R)-2-(2,2-difluoroethyl)-3-methyl-2,3,4,9-tetrahydro-1H-pyrido[3,4-b]indol-1-yl)pyridin-3-yl)oxy)ethoxy)propoxy)acetic acid (367 mg, 0.73 mmol) and triethylamine (0.406 mL, 2.92 mmol) in DMF (14 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (192 mg, 29%) as a white solid; $^1$H NMR (400 MHz, CDCl$_3$) 0.97 (9H, s), 1.19 (3H, d), 1.84 (2H, p), 2.23 (1H, dd), 2.52 (4H, s), 2.61-2.84 (2H, m), 2.97-3.15 (2H, m), 3.28 (1H, d), 3.4-3.57 (3H, m), 3.59-3.76 (4H, m), 3.80 (1H, d), 3.88-3.97 (1H, m), 4.02 (1H, m), 4.18-4.26 (2H, m), 4.42 (1H, dd), 4.56 (3H, m), 4.64 (1H, d), 4.79 (1H, t), 4.94 (1H, s), 5.60 (1H, s), 7.03-7.15 (3H, m), 7.15-7.23 (2H, m), 7.28 (2H, d), 7.34-7.42 (4H, m), 7.50 (1H, d), 8.02 (1H, d), 8.67 (1H, s), 9.31 (1H, s); m/z: ES+ [M+H]$^+$ 916.5; ESI-HRMS calculated for C$_{48}$H$_{60}$F$_2$N$_7$O$_7$S [M+H]$^+$=916.4238, measured 916.4260.

Intermediate 27a: Methyl 4-(5-hydroxypent-1-yn-1-yl)benzoate

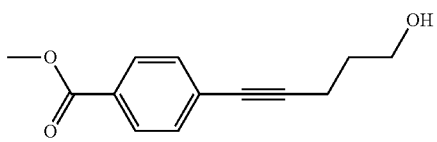 [SMILES: COC(=O)c1ccc(C#CCCCO)cc1]

Bis(triphenylphosphine)palladium(II) dichloride (0.670 g, 0.95 mmol) was added in one portion to methyl 4-iodobenzoate (5.0 g, 19.1 mmol) and copper(I) iodide (0.182 g, 0.95 mmol) in degassed THF (87 mL) at 20° C. under nitrogen. The resulting mixture was stirred for 5 minutes then pent-4-yn-1-ol (3.55 mL, 38.2 mmol) and triethylamine (5.31 mL, 38.2 mmol) was added. The reaction was stirred at 20° C. for 18 hours. The reaction mixture was diluted with EtOAc (200 mL), and washed sequentially with water (100 mL) and saturated brine (50 mL). The organic layer was dried with MgSO$_4$, filtered and evaporated to afford crude product. The crude product was purified by flash column chromatography, elution gradient 0 to 50% EtOAc in heptane to afford the title compound (3.65 g, 88%) as a cream solid; $^1$H NMR (400 MHz, CDCl$_3$) 1.45 (1H, t), 1.83-1.96 (2H, m), 2.57 (2H, t), 3.82 (2H, q), 3.91 (3H, s), 7.39-7.5 (2H, m), 7.9-8.02 (2H, m); m/z: ES+ [M+H]$^+$ 219.1.

Intermediate 27b: Methyl 4-(5-hydroxypentyl)benzoate

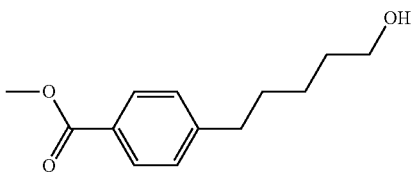 [SMILES: COC(=O)c1ccc(CCCCCO)cc1]

Methyl 4-(5-hydroxypent-1-yn-1-yl)benzoate (3.65 g, 16.7 mmol) and 10% palladium on carbon (0.178 g, 1.67 mmol) in EtOAc (50 mL) was stirred under an atmosphere of hydrogen (1.5 bar) at RT for 18 hours. The catalyst was removed by filtration and replaced with fresh catalyst and the reaction charged once more with hydrogen once more. The reaction was stirred for 1 hour. The catalyst was removed by filtration and solvent was evaporated to afford the title compound (3.85 g) as a colourless oil that was used in the next step without further purification; $^1$H NMR (400 MHz, CDCl$_3$) 1.36-1.46 (2H, m), 1.63 (4H, m), 2.63-2.73 (2H, m), 3.64 (2H, t), 3.90 (3H, s), 7.24 (2H, d), 7.92-7.97 (2H, m), exchangeable proton not observed.

Intermediate 27c: Methyl 4-(5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)benzoate

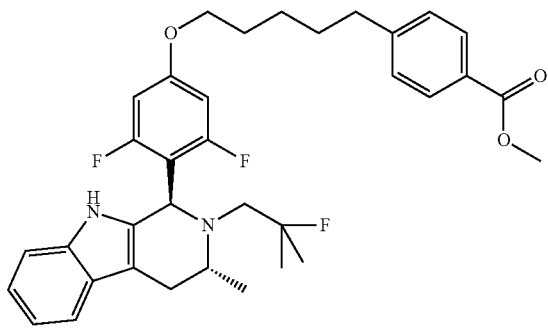 [SMILES: COC(=O)c1ccc(CCCCCOc2cc(F)c([C@@H]3c4[nH]c5ccccc5c4C[C@@H](C)N3CC(C)(C)F)c(F)c2)cc1]

Diisopropyl azodicarboxylate (0.12 mL, 0.62 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (120 mg, 0.31 mmol), methyl 4-(5-hydroxypentyl)benzoate (137 mg, 0.62 mmol) and triphenylphosphine (162 mg, 0.62 mmol) in DCM (2.5 mL) at 20° C. The resulting mixture was stirred for 1 hour. DCM (15 mL) and water (25 mL) were added and the layers were separated by passing through a phase separating cartridge and concentrated to give the crude product. The crude product was purified by flash column chromatography, elution gradient 0 to 30% EtOAc in heptane to afford the title compound (121 mg, 66%) as a pale yellow gum; $^1$H NMR (400 MHz, DMSO-d6) 1.05 (3H, d), 1.16 (6H, m), 1.41 (2H, p), 1.69 (4H, m), 2.26-2.45 (1H, m), 2.52-2.59 (1H, m), 2.68 (2H, t), 2.77-2.93 (2H, m), 3.52 (1H, q), 3.84 (3H, s), 3.97 (2H, t), 5.12 (1H, s), 6.63 (2H, d), 6.97 (2H, m), 7.13-7.22 (1H, m), 7.38 (3H, dd), 7.84-7.93 (2H, m), 10.49 (1H, s); m/z: ES+ [M+H]$^+$ 593.4.

Intermediate 27d: 4-(5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)benzoic Acid

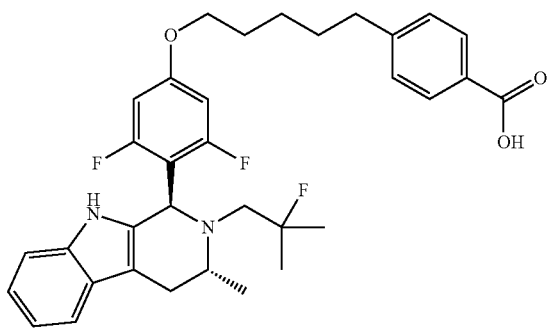 [SMILES: C[C@@H]1Cc2c([nH]c3ccccc23)[C@@H](c2c(F)cc(OCCCCCc3ccc(C(=O)O)cc3)cc2F)N1CC(C)(C)F]

Lithium hydroxide hydrate (17.13 mg, 0.41 mmol) was added in one portion to methyl 4-(5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)benzoate (121 mg, 0.20 mmol) in THF (0.77 mL) and water (0.26 mL) at 20° C. The resulting solution was stirred at 50° C. for 24 hours. The mixture was diluted with water (10 mL). The resulting mixture was acidified with 2M aq. HCl and extracted into EtOAc (50 mL). The organic layer was washed with brine (15 mL) and evaporated to afford the title compound (123 mg) as a colourless gum that was used in the next step without purification; $^1$H NMR (400 MHz, DMSO-d6) 1.05 (3H, d), 1.1-1.24 (6H, m), 1.42 (2H, p), 1.6-1.8 (4H, m), 2.29-2.42 (1H, m), 2.56 (1H, dd), 2.64-2.73 (2H, m), 2.78-2.95 (2H, m), 3.52 (1H, d), 3.98 (2H, t), 5.12 (1H, s), 6.63 (2H, d), 6.88-7.06 (2H, m), 7.14-7.23 (1H, m), 7.33 (2H, d), 7.39 (1H, d), 7.79-7.92 (2H, m), 10.49 (1H, s), 12.74 (1H, s); m/z: ES+ [M+H]$^+$ 579.4.

Example 27: (2S,4R)-1-((S)-2-(4-(5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)benzamido)-3,3-dimethylbutanoyl)-4-hydroxy-N-(4-(4-methylthiazol-5-yl)benzyl)pyrrolidine-2-carboxamide

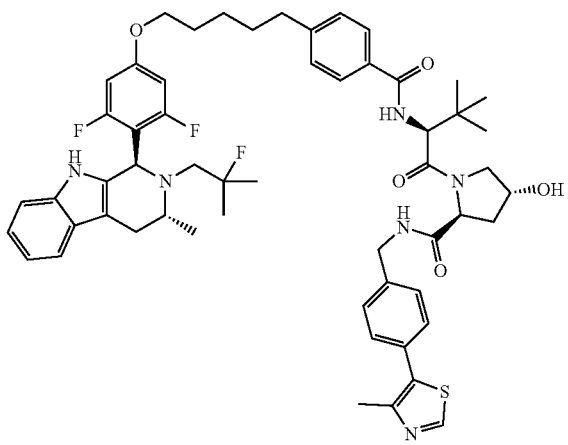 [SMILES: Cc1ncsc1-c1ccc(CNC(=O)[C@@H]2C[C@@H](O)CN2C(=O)[C@@H](NC(=O)c2ccc(CCCCCOc3cc(F)c([C@@H]4c5[nH]c6ccccc6c5C[C@@H](C)N4CC(C)(C)F)c(F)c3)cc2)C(C)(C)C)cc1]

HATU (108 mg, 0.29 mmol) was added portionwise to 4-(5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)benzoic acid (110 mg, 0.19 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (89 mg, 0.19 mmol) and triethylamine (0.11 mL, 0.76 mmol) in DMF (3.7 mL) at 20° C. under nitrogen. The resulting mixture was stirred at 20° C. for 30 minutes. The reaction mixture was diluted with EtOAc (50 mL), and washed sequentially with water (50 mL) and saturated brine (25 mL). The organic layer was dried with MgSO$_4$, filtered and evaporated to afford crude material. The crude product was purified by preparative HPLC to afford the title compound (126 mg, 67%) as a cream solid; $^1$H NMR (400 MHz, DMSO-d6) 1.04 (12H, d), 1.16 (6H, t), 1.41 (2H, p), 1.69 (4H, m), 1.93 (1H, m), 2.06 (1H, m), 2.29-2.42 (1H, m), 2.46 (3H, s), 2.54-2.6 (1H, m), 2.63-2.71 (2H, m), 2.77-2.96 (2H, m), 3.45-3.59 (1H, m), 3.73 (2H, d), 3.97 (2H, t), 4.26 (1H, dd), 4.34-4.52 (3H, m), 4.77 (1H, d), 5.12 (2H, s), 6.64 (2H, d), 6.96 (2H, m), 7.18 (1H, d), 7.29 (2H, d), 7.35-7.47 (5H, m), 7.73-7.88 (3H, m), 8.55 (1H, t), 8.98 (1H, s), 10.49 (1H, s); m/z: ES+ [M+H]$^+$ 991.8; ESI-HRMS calculated for $C_{56}H_{66}F_3N_6O_5S$ [M+H]$^+$=991.4762, measured 991.4747.

Example 28: (2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)acetamido)-3,3-dimethylbutanoyl)-4-hydroxy-N—((S)-1-(4-(4-methylthiazol-5-yl)phenyl)ethyl)pyrrolidine-2-carboxamide

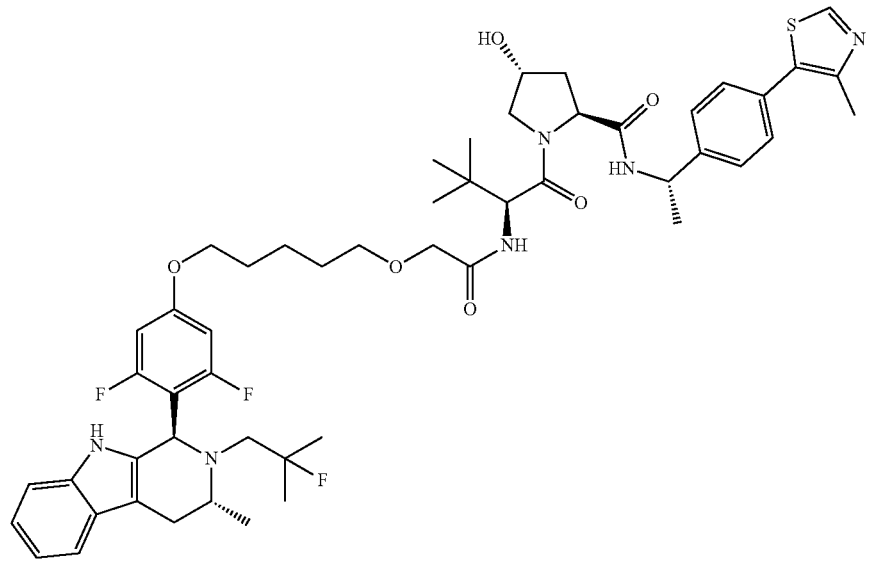 [SMILES: Cc1ncsc1-c1ccc([C@H](C)NC(=O)[C@@H]2C[C@@H](O)CN2C(=O)[C@@H](NC(=O)COCCCCCOc2cc(F)c([C@@H]3c4[nH]c5ccccc5c4C[C@@H](C)N3CC(C)(C)F)c(F)c2)C(C)(C)C)cc1]

HATU (134 mg, 0.35 mmol) was added portionwise to 2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)acetic acid (125 mg, 0.23 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (99 mg, 0.22 mmol) and triethylamine (0.131 mL, 0.94 mmol) in DMF (5 mL) at 20° C. under nitrogen. The resulting mixture was stirred at 20° C. for 30 minutes. The reaction mixture was diluted with EtOAc (25 mL), and washed sequentially with sat. aq. NaHCO$_3$ (25 mL), water (25 mL), and sat. aq. brine (25 mL). The organic layer was dried with MgSO$_4$, filtered and evaporated to afford crude product. The crude product was purified by preparative HPLC (Waters CSH C$_{18}$ OBD column, 30×100 mm id, 5 micron particle size), using decreasingly polar mixtures of water (containing 1% by volume of NH$_4$OH (28-30% in H$_2$O)) and MeCN as eluents. Fractions containing the desired compound were concentrated under reduced pressure to afford the title compound (65.0 mg, 29%) as a white solid; $^1$H NMR (400 MHz, DMSO-d6, 100° C.) 0.98 (9H, s), 1.08 (3H, d), 1.17 (3H, d), 1.22 (3H, d), 1.40 (1H, s), 1.42 (2H, d), 1.49-1.55 (2H, m), 1.62-1.69 (2H, m), 1.73-1.8 (2H, m), 1.94 (1H, d), 2.05 (1H, s), 2.39 (1H, d), 2.47 (3H, s), 2.55 (1H, s), 2.60 (1H, d), 2.8-2.87 (1H, m), 2.89-2.93 (1H, m), 3.52 (2H, m), 3.56-3.62 (2H, m), 3.67 (1H, s), 3.92 (1H, d), 4.01 (1H, t), 4.03-4.07 (2H, m), 4.34 (1H, s), 4.48-4.61 (2H, m), 4.80 (1H, d), 4.9-5.01 (1H, m), 5.18 (1H, s), 6.59 (2H, d), 6.92-7.02 (2H, m), 7.21 (1H, dd), 7.41 (5H, q), 7.97 (1H, d), 8.91 (1H, s), 10.21 (1H, s); m/z: ES+ [M+H]$^+$ 959.6; ESI-HRMS calculated for C52H66F3N6O6S [M+H]$^+$=959.4711, measured 959.4715.

Intermediate 29a: Methyl (S)-3-((1R,3R)-1-(4-bromo-2,6-difluorophenyl)-3-methyl-1,3,4,9-tetrahydro-2H-pyrido[3,4-b]indol-2-yl)-2-methylpropanoate

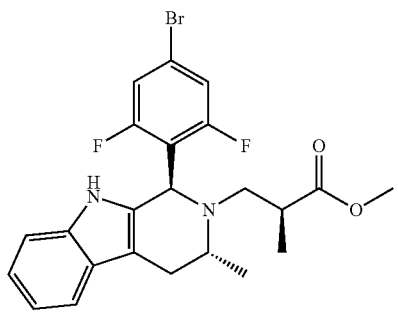 [SMILES: COC(=O)[C@@H](C)CN1[C@H](c2c(F)cc(Br)cc2F)c2[nH]c3ccccc3c2C[C@H]1C]

A solution of methyl (S)-3-(((R)-1-(1H-indol-3-yl)propan-2-yl)amino)-2-methylpropanoate (1.85 g, 6.74 mmol) (preparation described in *J. Med. Chem* 2015, 58, 8128-8140) in toluene (12 mL) was added to a stirred solution of 4-bromo-2,6-difluorobenzaldehyde (1.64 g, 7.42 mmol) in toluene (16 mL) and AcOH (1.8 mL) at 20° C. under air. The resulting solution was stirred at 80° C. for 18 hours. The resulting mixture was evaporated to dryness. The crude product was purified by ion exchange chromatography, using an SCX column. The desired product was eluted from the column using 1M NH$_3$/MeOH and pure fractions were evaporated to dryness to afford crude (1R,3R)-1-(4-bromo-2,6-difluorophenyl)-2-(2-fluoro-2-methylpropyl)-3-methyl-2,3,4,9-tetrahydro-1H-pyrido[3,4-b]indole as a brown gum. The crude product was purified by flash silica chromatography, elution gradient 0 to 50% EtOAc in heptane. Pure fractions were evaporated to dryness to afford methyl (S)-3-((1R,3R)-1-(4-bromo-2,6-difluorophenyl)-3-methyl-1,3,4,9-tetrahydro-2H-pyrido[3,4-b]indol-2-yl)-2-methylpropanoate (1.25 g, 39%); ¹H NMR (400 MHz, CDCl₃, 30° C.) 0.97 (3H, d), 1.10 (3H, d), 2.35 (1H, dd), 2.53 (1H, q), 2.63 (1H, dd), 2.92-3.09 (2H, m), 3.44 (1H, q), 3.64 (3H, s), 5.16 (1H, s), 7.03-7.09 (2H, m), 7.09-7.15 (2H, m), 7.2-7.25 (1H, m), 7.41 (1H, s), 7.48-7.53 (1H, m); m/z: ES– [M–H]⁻ 477.3.

Intermediate 29b: Methyl (S)-3-((1R,3R)-1-(2,6-difluoro-4-hydroxyphenyl)-3-methyl-1,3,4,9-tetrahydro-2H-pyrido[3,4-b]indol-2-yl)-2-methylpropanoate

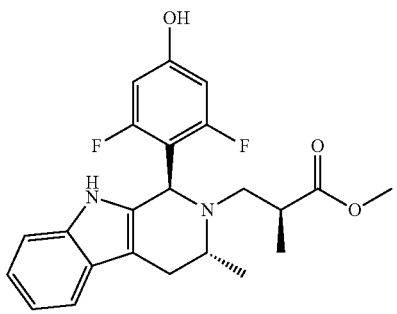 [SMILES: COC(=O)[C@@H](C)CN1[C@H](c2c(F)cc(O)cc2F)c2[nH]c3ccccc3c2C[C@H]1C]

Methyl (S)-3-((1R,3R)-1-(4-bromo-2,6-difluorophenyl)-3-methyl-1,3,4,9-tetrahydro-2H-pyrido[3,4-b]indol-2-yl)-2-methylpropanoate (100 mg, 0.21 mmol), (E)-benzaldehyde oxime (25.4 mg, 0.21 mmol), cesium carbonate (218 mg, 0.67 mmol) and Rockphos Pd G3 (5.27 mg, 6.28 µmol) were suspended in DMF (0.5 mL), sealed into a microwave tube and vacuum degassed, backfilling with N₂. The reaction was heated to 80° C. for 4 hours in the microwave reactor and cooled to RT. The reaction mixture was diluted with EtOAc (20 mL), and washed sequentially with water (2×5 mL) and sat. aq. brine (5 mL). The organic layer was dried with MgSO₄, filtered and evaporated to afford crude product. The crude product was purified by flash silica chromatography, elution gradient 20 to 50% EtOAc in heptane. Pure fractions were evaporated to dryness to afford the title compound (76 mg, 88%) as a pale yellow solid; ¹H NMR (400 MHz, CDCl₃, 30° C.) 0.98 (3H, d), 1.11 (3H, d), 2.40 (1H, dd), 2.52-2.66 (2H, m), 2.93-3.06 (2H, m), 3.4-3.51 (1H, m), 3.60 (OH, d), 3.66 (3H, s), 5.12 (1H, s), 6.33 (2H, d), 7.05-7.14 (2H, m), 7.22 (1H, d), 7.42-7.53 (2H, m); m/z: ES– [M–H]⁻ 413.3.

Intermediate 29c: Methyl (S)-3-((1R,3R)-1-(2,6-difluoro-4-((3-oxo-1-phenyl-2,5,8,11-tetraoxatridecan-13-yl)oxy)phenyl)-3-methyl-1,3,4,9-tetrahydro-2H-pyrido[3,4-b]indol-2-yl)-2-methylpropanoate

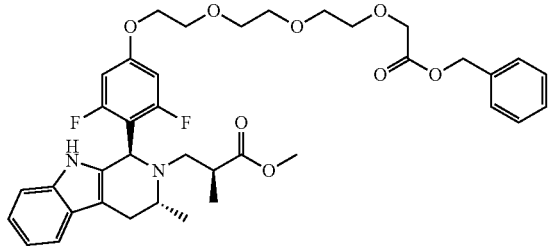 [SMILES: COC(=O)[C@@H](C)CN1[C@H](c2c(F)cc(OCCOCCOCCOCC(=O)OCc3ccccc3)cc2F)c2[nH]c3ccccc3c2C[C@H]1C]

Diisopropyl (E)-diazene-1,2-dicarboxylate (0.219 mL, 1.11 mmol) was added dropwise to a stirred solution of methyl (S)-3-((1R,3R)-1-(2,6-difluoro-4-hydroxyphenyl)-3-methyl-1,3,4,9-tetrahydro-2H-pyrido[3,4-b]indol-2-yl)-2-methylpropanoate (0.23 g, 0.55 mmol), benzyl 2-(2-(2-(2-hydroxyethoxy)ethoxy)ethoxy)acetate (0.331 g, 1.11 mmol) and triphenylphosphine (0.291 g, 1.11 mmol) in DCM (7 mL) at 5° C. The resulting mixture was stirred at 5° C. for 30 minutes and then at 21° C. for 18 hours. The solvent was removed under reduced pressure. The crude product was purified by flash silica chromatography, elution gradient 0 to 50% EtOAc in heptane. Pure fractions were evaporated to dryness to afford the title compound (0.221 g, 57%) as a pale yellow oil; m/z: ES+ [M+H]⁺ 695.5.

Intermediate 29d: 2-(2-(2-(2-(3,5-Difluoro-4-((1R,3R)-2-((S)-3-methoxy-2-methyl-3-oxopropyl)-3-methyl-2,3,4,9-tetrahydro-1H-pyrido[3,4-b]indol-1-yl)phenoxy)ethoxy)ethoxy)ethoxy)acetic Acid

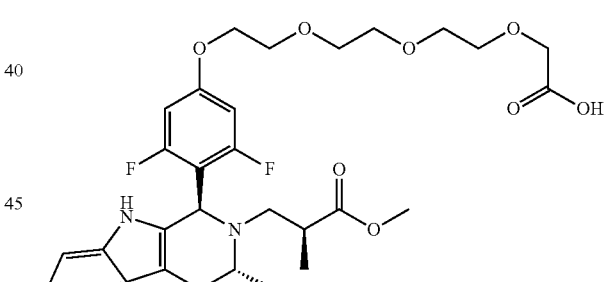

Methyl (S)-3-((1R,3R)-1-(2,6-difluoro-4-((3-oxo-1-phenyl-2,5,8,11-tetraoxatridecan-13-yl)oxy)phenyl)-3-methyl-1,3,4,9-tetrahydro-2H-pyrido[3,4-b]indol-2-yl)-2-methylpropanoate (221 mg, 0.32 mmol) was dissolved in EtOAc (5 mL) at RT. The flask was evacuated and back filled with nitrogen (×3). Palladium on carbon (10%) (33.9 mg, 0.03 mmol) was added under a blanket of nitrogen. The flask was evacuated and back filled with nitrogen (×3). The reaction was stirred under an atmosphere of hydrogen for 4 hours. The reaction mixture was filtered through celite and washed with EtOAc. The filtrate was concentrated under reduced pressure to afford the title compound (186 mg, 97%) as a white solid; m/z: ES+ [M+H]⁺ 605.3.

Example 29: (Methyl (S)-3-((1R,3R)-1-(2,6-difluoro-4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)-3-methyl-1,3,4,9-tetrahydro-2H-pyrido[3,4-b]indol-2-yl)-2-methylpropanoate

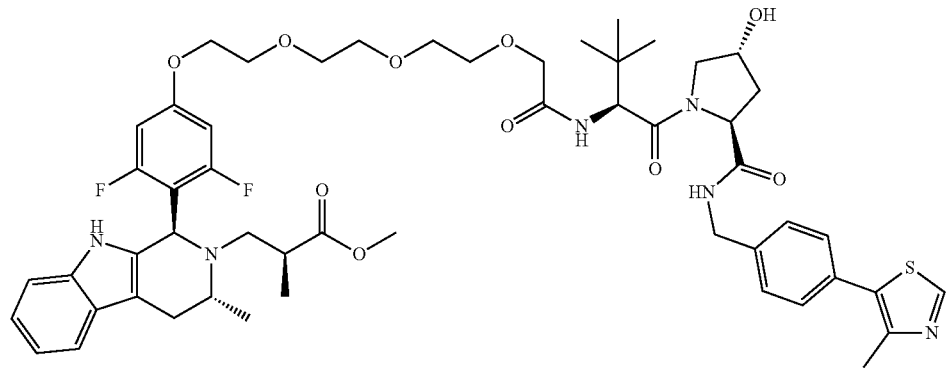 [SMILES: COC(=O)[C@@H](C)CN1[C@H](c2c(F)cc(OCCOCCOCCOCC(=O)N[C@H](C(=O)N3C[C@H](O)C[C@H]3C(=O)NCc3ccc(-c4scnc4C)cc3)C(C)(C)C)cc2F)c2[nH]c3ccccc3c2C[C@H]1C]

HATU (175 mg, 0.46 mmol) was added portionwise to 2-(2-(2-(2-(3,5-difluoro-4-((1R,3R)-2-((S)-3-methoxy-2-methyl-3-oxopropyl)-3-methyl-2,3,4,9-tetrahydro-1H-pyrido[3,4-b]indol-1-yl)phenoxy)ethoxy)ethoxy)ethoxy)acetic acid (186 mg, 0.31 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (126 mg, 0.29 mmol) and triethylamine (0.172 mL, 1.23 mmol) in DMF (5 mL) at 20° C. under nitrogen. The resulting mixture was stirred at 20° C. for 18 hours. The reaction mixture was diluted with EtOAc (25 mL), and washed sequentially with sat. aq. NaHCO$_3$ (25 mL), water (25 mL), and saturated brine (25 mL). The organic layer was dried with Na$_2$SO$_4$, filtered and evaporated to afford crude product. The crude product was purified by flash silica chromatography, elution gradient 0 to 5% MeOH in DCM. Pure fractions were evaporated to dryness to afford the title compound (156 mg, 50%) as a white solid; $^1$H NMR (400 MHz, DMSO-d6, 30° C.) 0.88 (3H, d), 0.94 (10H, d), 1.03 (3H, d), 1.25 (1H, s), 1.87-1.96 (1H, m), 2.03-2.1 (1H, m), 2.27 (1H, dd), 2.56 (1H, d), 2.83 (1H, d), 2.92 (1H, dd), 3.34-3.4 (1H, m), 3.56 (3H, s), 3.60 (10H, dd), 3.65-3.75 (3H, m), 3.97 (2H, s), 4.08-4.12 (2H, m), 4.26 (1H, dd), 4.39 (2H, dd), 4.45 (1H, t), 4.57 (1H, d), 5.04 (1H, s), 5.13 (1H, d), 6.67 (2H, d), 6.89-7.02 (2H, m), 7.18 (1H, d), 7.40 (7H, d), 8.56 (1H, t), 8.97 (1H, s), 10.49 (1H, s); m/z: ES+ [M+H]$^+$ 1017.5, ESI-HRMS calculated for C$_{53}$H$_{67}$F$_2$N$_6$O$_{10}$S [M+H]$^+$=1017.4602, measured 1017.4599.

Example 30: (S)-3-((1R,3R)-1-(2,6-Difluoro-4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)-3-methyl-1,3,4,9-tetrahydro-2H-pyrido[3,4-b]indol-2-yl)-2-methylpropanoic Acid

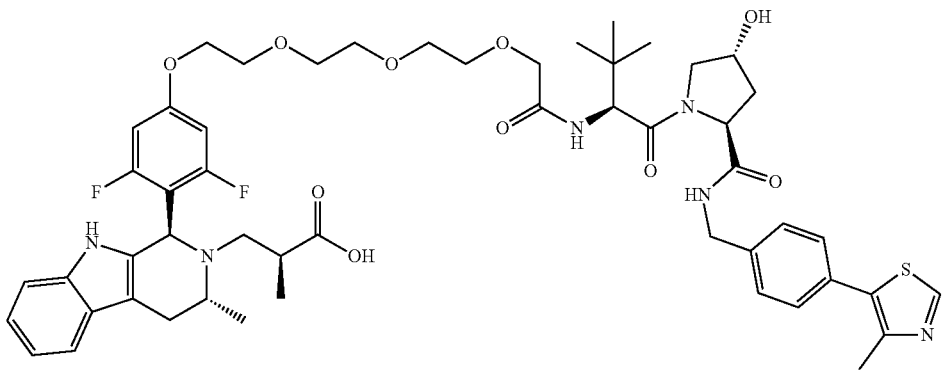 [SMILES: Cc1ncsc1-c1ccc(CNC(=O)[C@@H]2C[C@@H](O)CN2C(=O)[C@@H](NC(=O)COCCOCCOCCOc2cc(F)c([C@@H]3c4[nH]c5ccccc5c4C[C@@H](C)N3C[C@H](C)C(=O)O)c(F)c2)C(C)(C)C)cc1]

Lithium hydroxide hydrate (6.3 mg, 0.15 mmol) was added to methyl (S)-3-((1R,3R)-1-(2,6-difluoro-4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)-3-methyl-1,3,4,9-tetrahydro-2H-pyrido[3,4-b]indol-2-yl)-2-methylpropanoate (76 mg, 0.07 mmol), in THF (6 mL) and water (2 mL) at 20° C. The resulting mixture was stirred at 20° C. for 18 hours. The reaction mixture was diluted with EtOAc (25 mL), and washed sequentially with sat. aq. NaHCO$_3$ (25 mL), water (25 mL), and sat. brine (25 mL). The organic layer was dried with MgSO$_4$, filtered and evaporated to afford the title compound (35 mg, 47%) as a solid; $^1$H NMR (400 MHz, CDCl$_3$, 30° C.) 0.95 (10H, s), 1.12 (3H, d), 1.33 (3H, d), 2.09 (2H, s), 2.14 (1H, d), 2.48 (3H, s), 2.52 (2H, m), 2.71 (1H, dd), 2.78-2.92 (2H, m), 3.03 (1H, d), 3.66 (12H, m), 3.81 (2H, t), 4-4.07 (2H, m), 4.11 (1H, m), 4.33 (1H, dd), 4.52 (1H, d), 4.53-4.59 (2H, m), 4.72 (1H, t), 5.48 (1H, s), 6.47 (2H, d), 7.15 (2H, m), 7.28 (1H, s), 7.31 (1H, d), 7.33-7.38 (4H, m), 7.5-7.54 (1H, m), 8.65 (1H, s), 8.88 (1H, s); m/z: ES+ [M+H]+ 1003.6; ESI-HRMS calculated for $C_{52}H_{65}F_2N_6O_{10}S$ [M+H]+=1003.4445, measured 1003.4428.

Intermediate 31a: (2S,4R)-1-((S)-3,3-Dimethyl-2-(methylamino)butanoyl)-4-hydroxy-N-(4-(4-methylthiazol-5-yl)benzyl)pyrrolidine-2-carboxamide

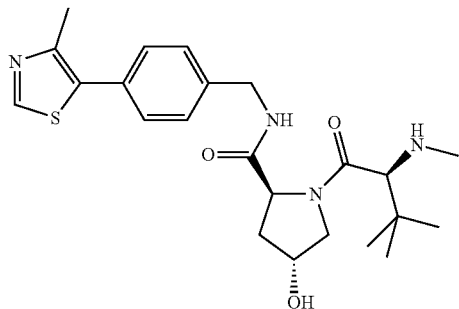 [SMILES: CN[C@H](C(=O)N1C[C@H](O)C[C@H]1C(=O)NCc1ccc(-c2scnc2C)cc1)C(C)(C)C]

To a solution of (2S,4R)-1-((S)-2-amino-3,3-dimethylbutanoyl)-4-hydroxy-N-(4-(4-methylthiazol-5-yl)benzyl)pyrrolidine-2-carboxamide, HCl (500 mg, 1.16 mmol) in ethanol (10 mL) was added formaldehyde (0.865 mL, 11.61 mmol) followed by sodium tetrahydroborate (220 mg, 5.81 mmol). The reaction was stirred at RT overnight. 1 N aq. HCl was added and the solution was concentrated to remove the organics then partitioned between EtOAc (25 mL) and water (25 mL). The aqueous phase was made basic with sat. aq. NaHCO₃ and extracted with EtOAc (25 mL) The combined organic layers were washed with brine, dried over MgSO₄, filtered, concentrated. The sample was dissolved in MeOH and purified using the SFC conditions: Column: Princeton Diol, 30×250 mm, 5 micron; Mobile phase: A=MeOH+0.1% NH₃, B=scCO₂; Gradient 15-30% A over 7.5 minutes; Flow rate: 100 mL/min; BPR: 120 bar; Column temperature: 40° C. The fractions were evaporated to give the title compound (122 mg, 24%) as a colourless oil; ¹H NMR (400 MHz, CDCl₃, 30° C.) 0.87 (9H, s), 1.55 (2H, s), 2.00 (1H, m), 2.27 (3H, s), 2.51 (3H, d), 2.99 (1H, s), 3.49 (1H, d), 3.63 (2H, d), 4.33 (1H, dd), 4.53 (1H, dd), 4.64 (1H, s), 4.85 (1H, dd), 7.29-7.39 (4H, m), 7.62 (1H, s), 8.66 (1H, s); m/z: ES+ [M+H]+ 445.9.

Example 31: (2S,4R)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3-methyl-4-oxo-6,9,12-trioxa-3-azatetradecanoyl)-4-hydroxy-N-(4-(4-methylthiazol-5-yl)benzyl)pyrrolidine-2-carboxamide

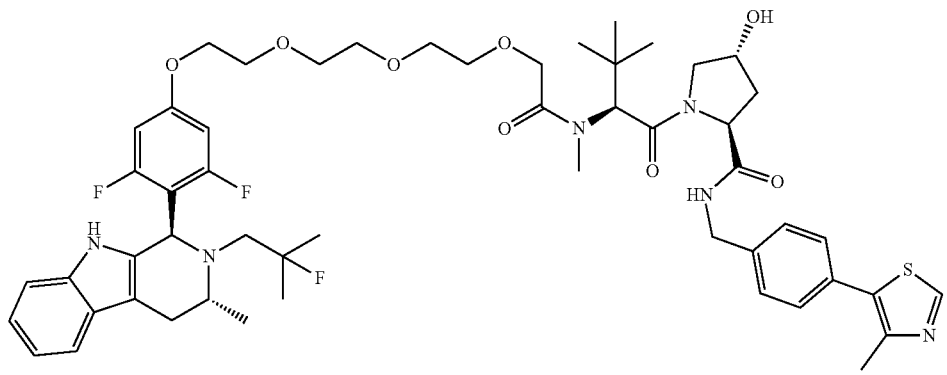 [SMILES: Cc1ncsc1-c1ccc(CNC(=O)[C@@H]2C[C@@H](O)CN2C(=O)[C@@H](N(C)C(=O)COCCOCCOCCOc2cc(F)c([C@@H]3c4[nH]c5ccccc5c4C[C@@H](C)N3CC(C)(C)F)c(F)c2)C(C)(C)C)cc1]

HATU (157 mg, 0.41 mmol) was added portionwise to 2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetic acid (159 mg, 0.27 mmol), (2S,4R)-1-((S)-3,3-dimethyl-2-(methylamino)butanoyl)-4-hydroxy-N-(4-(4-methylthiazol-5-yl)benzyl)pyrrolidine-2-carboxamide (122 mg, 0.27 mmol) and triethylamine (0.153 mL, 1.10 mmol) in DMF (5 mL) at 20° C. under nitrogen. The resulting mixture was stirred at 20° C. for 18 hours. The reaction mixture was diluted with EtOAc (25 mL), and washed sequentially with saturated NaHCO$_3$ (25 mL), water (25 mL), and saturated brine (25 mL). The organic layer was dried with MgSO$_4$, filtered and evaporated to afford crude product. The crude product was purified by preparative HPLC (Waters CSH C$_{18}$ OBD column, 30×100 mm id, 5 micron particle size), using decreasingly polar mixtures of water (containing 1% by volume of NH$_4$OH (28-30% in H$_2$O)) and MeCN as eluents. Fractions containing the desired compound were evaporated to dryness to afford the title compound (14.00 mg, 5.08%); $^1$H NMR (400 MHz, DMSO-d6, 30° C.) 0.98 (9H, s), 1.04 (3H, d), 1.17 (7H, t), 1.25 (1H, s), 1.86-1.94 (1H, m), 2.03 (1H, s), 2.45 (3H, s), 2.56 (1H, d), 2.78-2.94 (2H, m), 2.98 (3H, s), 3.51-3.64 (11H, m), 3.71-3.76 (2H, m), 4.09-4.14 (2H, m), 4.18-4.34 (5H, m), 4.37 (1H, t), 5.06 (1H, s), 5.13 (1H, s), 6.68 (2H, d), 6.91-7.04 (2H, m), 7.18 (1H, d), 7.40 (5H, s), 8.44 (1H, t), 8.98 (1H, s), 10.50 (1H, s); m/z: ES+ [M+H]$^+$ 1005.8; ESI-HRMS calculated for C$_{53}$H$_{68}$F$_3$N$_6$O$_8$S [M+H]$^+$=1005.4766, measured 1005.4745.

Intermediate 32a: Methyl 11-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)undecanoate

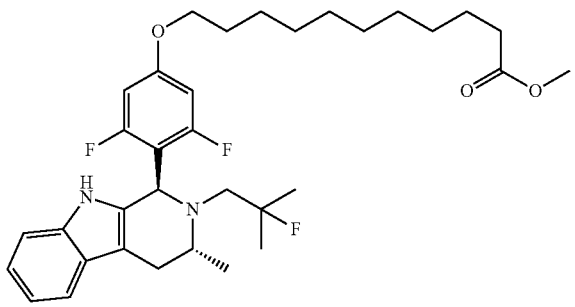 [SMILES: COC(=O)CCCCCCCCCCOc1cc(F)c([C@@H]2c3[nH]c4ccccc4c3C[C@@H](C)N2CC(C)(C)F)c(F)c1]

Methyl 11-bromoundecanoate (158 mg, 0.57 mmol) was added in one portion to 3,5-difluoro-4-((1R,3R)-2-(2-fluoro-2-methylpropyl)-3-methyl-2,3,4,9-tetrahydro-1H-pyrido[3,4-b]indol-1-yl)phenol (200 mg, 0.51 mmol) and potassium carbonate (107 mg, 0.77 mmol) in MeCN (2 mL) at 20° C. under air. The resulting suspension was stirred at 70° C. for 18 hours. The mixture was cooled to RT and was diluted with DCM (10 mL) and water (2 mL). The DCM layer was collected and evaporated to afford crude material as a yellow gum. The crude product was purified by flash silica chromatography, elution gradient 0 to 30% EtOAc in heptane. Pure fractions were evaporated to dryness to afford the title compound (255 mg, 84%) as a colourless gum; $^1$H NMR (400 MHz, DMSO-d6, 30° C.) 1.05 (3H, d), 1.17 (6H, t), 1.26 (12H, s), 1.46-1.56 (2H, m), 1.63-1.74 (2H, m), 2.29 (2H, t), 2.38 (1H, d), 2.54-2.59 (1H, m), 2.76-2.94 (2H, m), 3.48-3.55 (1H, m), 3.58 (3H, s), 3.97 (2H, t), 5.13 (1H, s), 6.64 (2H, d), 6.97 (2H, m), 7.16-7.21 (1H, m), 7.39 (1H, d), 10.49 (1H, s); m/z: ES+ [M+H]$^+$ 587.4.

Intermediate 32b: 11-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)undecanoic Acid

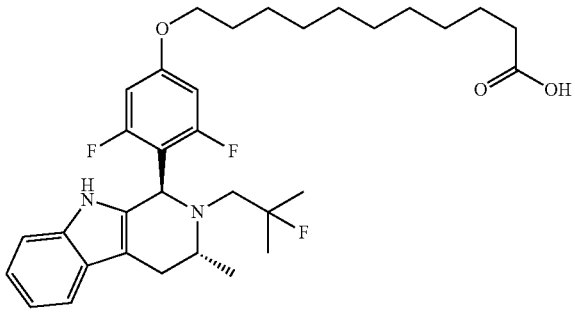 [SMILES: C[C@@H]1Cc2c([nH]c3ccccc23)[C@@H](c2c(F)cc(OCCCCCCCCCCC(=O)O)cc2F)N1CC(C)(C)F]

Lithium hydroxide hydrate (37 mg, 0.87 mmol) was added in one portion to methyl 11-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)undecanoate (255 mg, 0.43 mmol) in THF (1.6 mL) and water (0.5 mL) at 20° C. The resulting solution was stirred at 25° C. for 2 hours. The organic solvent was removed under reduced pressure. The resulting mixture was acidified with 2M aq. HCl and extracted into EtOAc (2×10 mL). The organic extracts were washed with brine (5 mL) and evaporated to afford the title compound (250 mg, 100%) as a colourless gum that was used in the next step without further purification; m/z: ES+ [M+H]$^+$ 573.4.

Example 32: (2S,4R)-1-((S)-2-(11-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)undecanamido)-3,3-dimethylbutanoyl)-4-hydroxy-N-(4-(4-methylthiazol-5-yl)benzyl)pyrrolidine-2-carboxamide

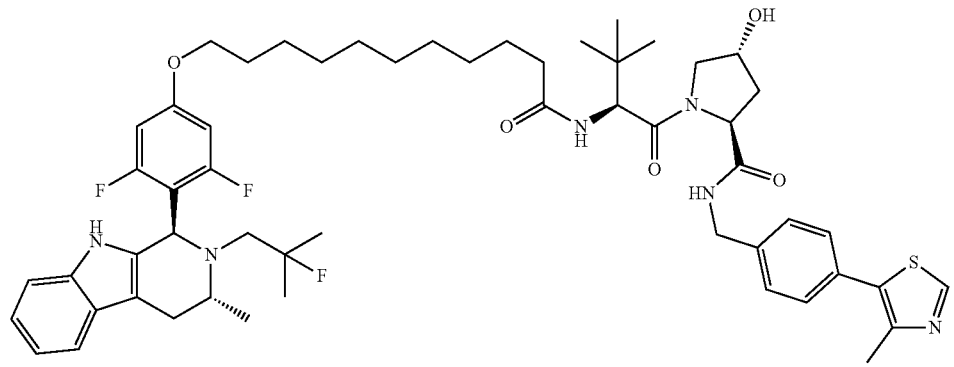 [SMILES: Cc1ncsc1-c1ccc(CNC(=O)[C@@H]2C[C@@H](O)CN2C(=O)[C@@H](NC(=O)CCCCCCCCCCOc2cc(F)c([C@@H]3c4[nH]c5ccccc5c4C[C@@H](C)N3CC(C)(C)F)c(F)c2)C(C)(C)C)cc1]

HATU (245 mg, 0.65 mmol) was added portionwise to 11-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)undecanoic acid (246 mg, 0.43 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (201 mg, 0.43 mmol) and triethylamine (0.240 mL, 1.72 mmol) in DMF (3 mL) at 20° C. under nitrogen. The resulting mixture was stirred at 20° C. for 30 minutes. Further HATU (245 mg, 0.65 mmol) and triethylamine (0.240 mL, 1.72 mmol) was added and the reaction stirred at RT overnight. The reaction mixture was diluted with EtOAc (25 mL), and washed sequentially with saturated aq. NaHCO$_3$ (25 mL), water (25 mL), and saturated brine (25 mL). The organic layer was dried with MgSO$_4$, filtered and evaporated to afford crude product. The crude product was purified by flash silica chromatography, elution gradient 0 to 10% MeOH in DCM. Pure fractions were evaporated to dryness to afford the title compound (324 mg, 76%) as a pale yellow oil which solidified on standing; $^1$H NMR (400 MHz, DMSO-d6, 30° C.) 0.94 (9H, s), 1.04 (3H, d), 1.09-1.22 (7H, m), 1.32 (11H, d), 1.44-1.56 (2H, m), 1.63-1.73 (2H, m), 1.94 (1H, s), 2-2.08 (1H, m), 2.08-2.15 (1H, m), 2.22-2.28 (1H, m), 2.38 (1H, d), 2.45 (3H, s), 2.54-2.59 (1H, m), 2.68 (OH, p), 2.74 (OH, d), 2.78-2.93 (2H, m), 3.52 (1H, d), 3.6-3.74 (2H, m), 3.97 (2H, t), 4.22 (1H, dd), 4.35 (1H, s), 4.39-4.47 (2H, m), 4.55 (1H, d), 5.06-5.15 (2H, m), 6.64 (2H, d), 6.97 (2H, m), 7.18 (1H, d), 7.33-7.5 (5H, m), 7.80 (1H, d), 8.52 (1H, t), 8.98 (1H, s), 10.49 (1H, s); m/z: ES+ [M+H]$^+$985.6; ESI-HRMS calculated for $C_{55}H_{72}F3N_6O5S$ [M+H]$^+$=985.5232, measured 985.5222.

Intermediate 33a: 1-(tert-Butyl) 2-((3R,5S)-1-((S)-2-(11-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)undecanamido)-3,3-dimethylbutanoyl)-5-((4-(4-methylthiazol-5-yl)benzyl)carbamoyl)pyrrolidin-3-yl) (S)-pyrrolidine-1,2-dicarboxylate

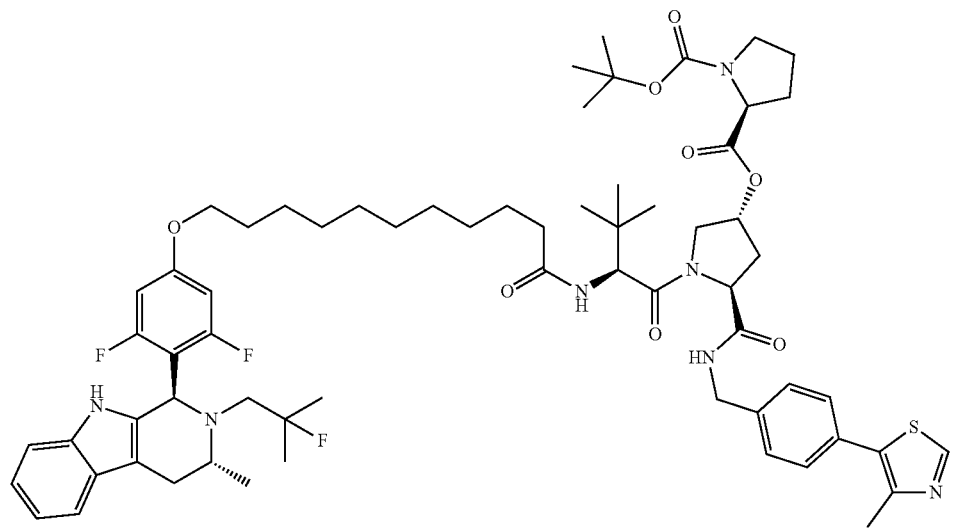 [SMILES: Cc1ncsc1-c1ccc(CNC(=O)[C@@H]2C[C@@H](OC(=O)[C@@H]3CCCN3C(=O)OC(C)(C)C)CN2C(=O)[C@@H](NC(=O)CCCCCCCCCCOc2cc(F)c([C@@H]3c4[nH]c5ccccc5c4C[C@@H](C)N3CC(C)(C)F)c(F)c2)C(C)(C)C)cc1]

To a solution of (2S,4R)-1-((S)-2-(11-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)undecanamido)-3,3-dimethylbutanoyl)-4-hydroxy-N-(4-(4-methylthiazol-5-yl)benzyl)pyrrolidine-2-carboxamide (169 mg, 0.17 mmol) and (tert-butoxycarbonyl)-L-proline (73.8 mg, 0.34 mmol) in DCM (4 mL) and DMF (3 mL) was added 3-(((ethylimino)methylene)amino)-N,N-dimethylpropan-1-amine hydrochloride (65.8 mg, 0.34 mmol) and N,N-dimethylpyridin-4-amine (4.19 mg, 0.03 mmol). The clear colorless solution was stirred at RT for 2 hours. The mixture was diluted with DCM and washed with water, 1M aq. HCl and sat. aq. NaHCO$_3$. The crude product was purified by flash silica chromatography, elution gradient 0 to 10% MeOH in DCM. Fractions containing product were evaporated to dryness to afford the title compound (281 mg, contains solvents) as a yellow oil that was used in the next step without further purification; m/z: ES+ [M+H]$^+$ 1182.7.

Example 33: (3R,5S)-1-((S)-2-(11-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)undecanamido)-3,3-dimethylbutanoyl)-5-((4-(4-methylthiazol-5-yl)benzyl)carbamoyl)pyrrolidin-3-yl L-prolinate

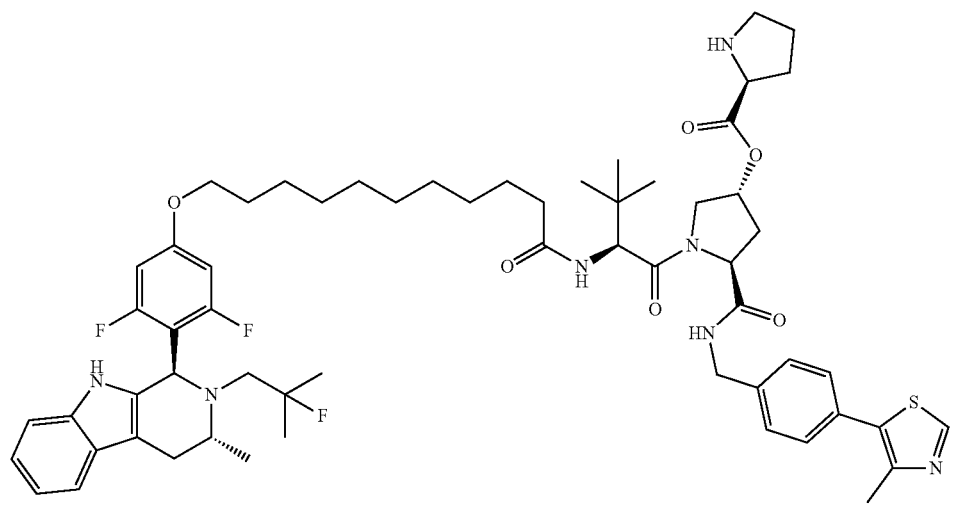 [SMILES: Cc1ncsc1-c1ccc(CNC(=O)[C@@H]2C[C@@H](OC(=O)[C@@H]3CCCN3)CN2C(=O)[C@@H](NC(=O)CCCCCCCCCCOc2cc(F)c([C@@H]3c4[nH]c5ccccc5c4C[C@@H](C)N3CC(C)(C)F)c(F)c2)C(C)(C)C)cc1]

To a solution of 1-(tert-butyl) 2-((3R,5S)-1-((S)-2-(11-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)undecanamido)-3,3-dimethylbutanoyl)-5-((4-(4-methylthiazol-5-yl)benzyl)carbamoyl)pyrrolidin-3-yl) (S)-pyrrolidine-1,2-dicarboxylate (200 mg, 0.17 mmol) in DCM (4 mL) was added 2,2,2-trifluoroacetic acid (0.65 mL, 8.5 mmol) and the solution was stirred at RT for 1 hour. The solvent was removed under reduced pressure. The crude product was purified by preparative HPLC (Waters XSelect CSH $C_{18}$ column, 30×100 mm id, 5 micron particle size), using decreasingly polar mixtures of water (containing 0.1% formic acid) and MeCN as eluents. Fractions containing the desired compound were evaporated to dryness to afford the title compound (16 mg, 9%) as a light yellow solid; $^1$H NMR (400 MHz, CDCl$_3$, 30° C.) 0.93 (9H, s), 1.10 (3H, d), 1.20 (7H, dd), 1.41 (2H, d), 1.5-1.59 (2H, m), 1.74 (2H, p), 2.00 (3H, s), 2.03 (2H, m), 2.08-2.17 (1H, m), 2.21 (2H, m), 2.31 (2H, dd), 2.35-2.46 (1H, m), 2.51 (3H, s), 2.58 (OH, d), 2.62 (1H, s), 2.73 (1H, m), 2.86 (1H, dd), 3.09 (1H, dd), 3.33 (2H, m), 3.66 (2H, m), 3.88 (2H, t), 4.24 (1H, d), 4.32 (2H, dd), 4.38 (1H, d), 4.60 (7H, dd), 4.79 (1H, t), 5.19 (1H, s), 5.33 (1H, s), 6.17 (1H, d), 6.37 (2H, d), 7.04-7.13 (2H, m), 7.21 (1H, dd), 7.31-7.39 (4H, m), 7.45-7.54 (2H, m), 7.70 (1H, s), 8.27 (1H, s), 8.67 (1H, s); m/z: ES+ [M+H]$^+$1082.7.

Intermediate 34a: (3R,5S)-1-((S)-2-((tert-butoxycarbonyl)amino)-3,3-dimethylbutanoyl)-5-((4-(4-methylthiazol-5-yl)benzyl)carbamoyl)pyrrolidin-3-yl Acetate

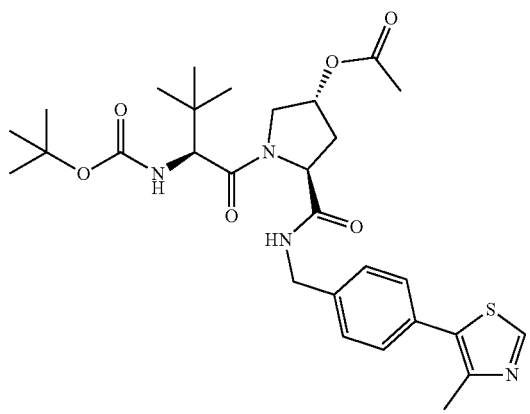 [SMILES: CC(=O)O[C@@H]1C[C@@H](C(=O)NCc2ccc(-c3scnc3C)cc2)N(C(=O)[C@@H](NC(=O)OC(C)(C)C)C(C)(C)C)C1]

N,N-Dimethylpyridin-4-amine (3.03 mg, 0.02 mmol), triethylamine (0.083 mL, 0.59 mmol) and acetic anhydride (0.056 mL, 0.59 mmol) were added to tert-butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate (preparation described in WO2014/108452 A1) (263 mg, 0.50 mmol) in DCM (5 mL) at 0° C. under nitrogen. The resulting mixture was stirred at RT for 30 minutes. The mixture was quenched with 1M aq. HCl and the organics separated. The aqueous layer was extracted with EtOAc (50 mL). The combined organics were dried over MgSO$_4$, filtered and concentrated under reduced pressure. The crude product was purified by flash silica chromatography, elution gradient 0 to 100% EtOAc in heptane. Pure fractions were evaporated to dryness to the title compound (290 mg, 102%) as a colourless oil that was used in the next step without further purification; $^1$H NMR (400 MHz, DMSO-d6, 30° C.) 0.95 (9H, s), 1.38 (9H, s), 2.00 (3H, d), 2.11 (1H, s), 2.26 (1H, dd), 2.45 (3H, s), 3.76 (1H, s), 3.97-4.03 (2H, m), 4.26 (1H, dd), 4.43 (1H, dd), 4.52 (1H, t), 5.25 (1H, s), 6.66 (1H, d), 7.40 (4H, s), 8.59 (1H, t), 8.98 (1H, s); m/z: ES+ [M+H]$^+$573.3.

Intermediate 34b: (3R,5S)-1-((S)-2-amino-3,3-dimethylbutanoyl)-5-((4-(4-methylthiazol-5-yl)benzyl)carbamoyl)pyrrolidin-3-yl acetate

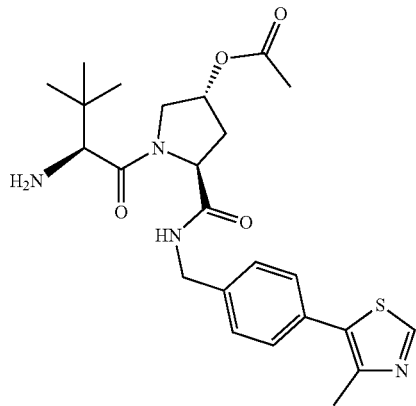 [SMILES: CC(=O)O[C@@H]1C[C@@H](C(=O)NCc2ccc(-c3scnc3C)cc2)N(C(=O)[C@@H](N)C(C)(C)C)C1]

A solution of 4 M HCl in dioxane (1.17 mL, 4.68 mmol) was added in one portion to (3R,5S)-1-((S)-2-((tert-butoxycarbonyl)amino)-3,3-dimethylbutanoyl)-5-((4-(4-methylthiazol-5-yl)benzyl)carbamoyl)pyrrolidin-3-yl acetate (0.268 g, 0.47 mmol) at 20° C. under air. The reaction mixture was stirred at RT for 3 hours then loaded onto an SCX column and washed with DCM, then with 1M NH$_3$ in MeOH. The solvent was evaporated to afford the title compound (0.200 g, 90%) as a pale yellow foamy solid; $^1$H NMR (400 MHz, CDCl$_3$, 30° C.) 0.94 (9H, s), 1.12 (2H, s), 2.05 (3H, s), 2.17-2.27 (1H, m), 2.51 (3H, s), 2.66 (1H, s), 3.43 (1H, s), 3.77-3.88 (2H, m), 4.38 (1H, dd), 4.49 (1H, dd), 4.75 (1H, t), 5.34 (1H, s), 7.35 (4H, t), 7.52 (1H, s), 8.67 (1H, s); m/z: ES+ [M+H]$^+$ 473.4.

Example 34: (3R,5S)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-5-((4-(4-methylthiazol-5-yl)benzyl)carbamoyl)pyrrolidin-3-yl Acetate

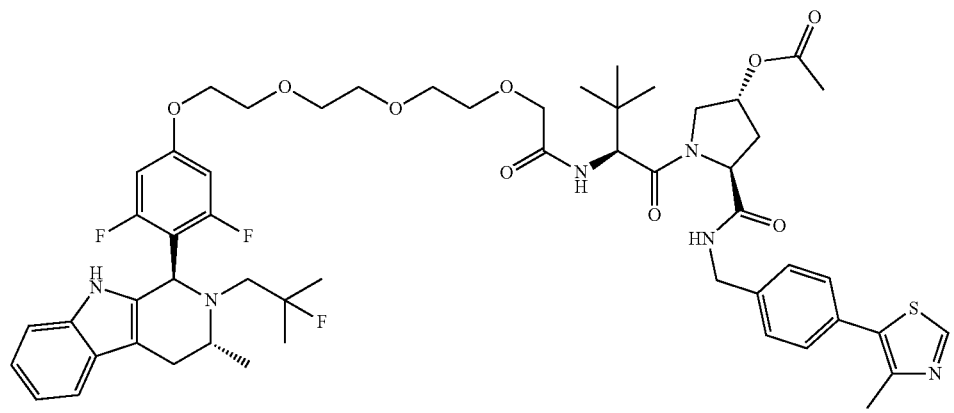 [SMILES: CC(=O)O[C@@H]1C[C@@H](C(=O)NCc2ccc(-c3scnc3C)cc2)N(C(=O)[C@@H](NC(=O)COCCOCCOCCOc2cc(F)c([C@@H]3c4[nH]c5ccccc5c4C[C@@H](C)N3CC(C)(C)F)c(F)c2)C(C)(C)C)C1]

HATU (53.2 mg, 0.14 mmol) was added portionwise to 2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetic acid (54 mg, 0.09 mmol), (3R,5S)-1-((S)-2-amino-3,3-dimethylbutanoyl)-5-((4-(4-methylthiazol-5-yl)benzyl)carbamoyl)pyrrolidin-3-yl acetate (44.1 mg, 0.09 mmol) and triethylamine (0.052 mL, 0.37 mmol) in DMF (3 mL) at 20° C. under nitrogen. The resulting mixture was stirred at 20° C. for 30 minutes. The crude product was initially purified by preparative HPLC (Waters CSH C18 OBD column, 30×100 mm id, 5 micron particle size), using decreasingly polar mixtures of water (containing 1% by volume of $NH_4OH$ (28-30% in $H_2O$)) and MeCN as eluents. Clean fractions containing the desired compound were evaporated to dryness to afford 36 mg of product. The mixture was repurified in acid by preparative HPLC (Waters XSelect CSH Cis column, 30×100 mm id, 5 micron particle size), using decreasingly polar mixtures of water containing 0.1% formic acid) and MeCN as eluents. Fractions containing the desired compound were evaporated to dryness to afford the title compound (20 mg, 21%); $^1$H NMR (400 MHz, DMSO-d6, 30° C.) 0.95 (9H, d), 1.04 (3H, d), 1.16 (7H, t), 2.00 (3H, s), 2.08-2.17 (2H, m), 2.22-2.3 (2H, m), 2.35 (1H, s), 2.45 (4H, s), 2.57 (2H, d), 2.79-2.93 (3H, m), 3.68-3.73 (2H, m), 3.84 (1H, dd), 3.92 (1H, s), 3.96 (3H, s), 4.07-4.11 (2H, m), 4.28 (2H, dd), 4.38 (1H, d), 4.42-4.51 (3H, m), 5.13 (1H, s), 5.27 (1H, s), 6.66 (2H, d), 6.96 (3H, m), 7.18 (1H, d), 7.40 (4H, s), 7.42 (1H, d), 8.58 (1H, t), 8.98 (1H, d), 10.50 (1H, s); m/z: ES+ [M+H]$^+$ 1033.6; ESI-HRMS calculated for $C_{54}H_{68}F_3N_6O_9S$ [M+H]$^+$=1033.4715, measured 1033.4725.

Intermediate 35a: 4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzaldehyde

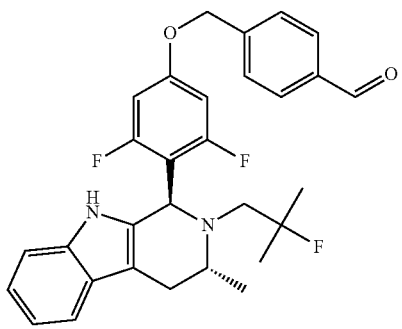 [SMILES: C[C@@H]1Cc2c([nH]c3ccccc23)[C@@H](c2c(F)cc(OCc3ccc(C=O)cc3)cc2F)N1CC(C)(C)F]

4-(Bromomethyl)benzaldehyde (113 mg, 0.57 mmol) was added in one portion to 3,5-difluoro-4-((1R,3R)-2-(2-fluoro-2-methylpropyl)-3-methyl-2,3,4,9-tetrahydro-1H-pyrido[3,4-b]indol-1-yl)phenol (200 mg, 0.51 mmol) and potassium carbonate (107 mg, 0.77 mmol) in MeCN (2 mL) at 20° C. under air. The resulting suspension was stirred at 20° C. for 18 hours. The reaction was diluted with DCM (20 mL) and water (5 mL) and the passed through a phase separating cartridge. The solvent was removed in vacuo. The crude product was purified by flash silica chromatography, elution gradient 0 to 50% EtOAc in heptane. Pure fractions were evaporated to dryness to afford the title compound (204 mg, 78%) as a orange solid; $^1$H NMR (400 MHz, DMSO-d6, 30° C.) 1.05 (3H, d), 1.08-1.12 (3H, m), 1.16 (3H, d), 2.28-2.39 (1H, m), 2.53-2.59 (1H, m), 2.82-2.95 (2H, m), 3.44-3.58 (1H, m), 5.14 (1H, s), 5.27 (2H, s), 6.78 (2H, d), 6.92-7.02 (2H, m), 7.15-7.22 (1H, m), 7.40 (1H, d), 7.66 (2H, d), 7.9-8 (2H, m), 10.03 (1H, s), 10.52 (1H, s); m/z: ES+ [M+H]$^+$ 507.3.

Example 35: (2S,4R)-1-((S)-2-((4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzyl)amino)-3,3-dimethylbutanoyl)-4-hydroxy-N-(4-(4-methylthiazol-5-yl)benzyl)pyrrolidine-2-carboxamide

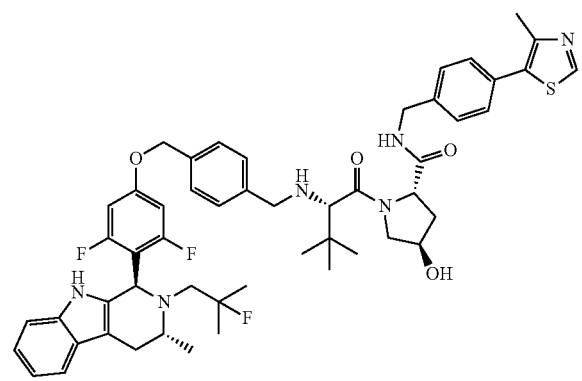

(2S,4R)-1-((S)-2-Amino-3,3-dimethylbutanoyl)-4-hydroxy-N-(4-(4-methylthiazol-5-yl)benzyl)pyrrolidine-2-carboxamide, HCl (0.097 g, 0.21 mmol) was dissolved in MeOH (5 mL) and passed through an SCX cartridge (eluted with 1M $NH_3$ in MeOH). The solvents were removed in vacuo and the residue was dissolved in 1,2-dichloroethane (5 mL). 4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzaldehyde (0.100 g, 0.20 mmol) was added and the mixture stirred at RT for 30 mins before sodium triacetoxyborohydride (0.063 g, 0.30 mmol) was added and the reaction stirred for 18 hours. The reaction mixture was quenched with saturated aq. $NH_4Cl$ (10 mL), the organics separated and the aqueous extracted with DCM (2×25 mL), the organic layer was dried over $MgSO_4$, filtered and evaporated to afford crude product. The crude product was purified by preparative HPLC (Waters CSH Cis OBD column, 30×100 mm id, 5 micron particle size), using decreasingly polar mixtures of water (containing 1% by volume of $NH_4OH$ (28-30% in $H_2O$)) and MeCN as eluents. Fractions containing the desired compound were evaporated to dryness to afford the title compound (0.089 g, 49%); $^1$H NMR (400 MHz, DMSO-d6, 30° C.) 0.92 (9H, s), 1.05 (3H, d), 1.1-1.23 (6H, m), 1.88-1.96 (1H, m), 2.02-2.12 (1H, m), 2.18-2.28 (1H, m), 2.29-2.37 (1H, m), 2.39 (1H, s), 2.45 (3H, s), 2.58 (1H, d), 2.79-2.93 (2H, m), 3.00 (1H, d), 3.46 (4H, dd), 3.71 (1H, dd), 4.23-4.46 (3H, m), 4.59 (1H, t), 5.03-5.16 (4H, m), 6.75 (2H, d), 6.97 (2H, m), 7.19 (1H, d), 7.37-7.43 (8H, m), 8.56 (1H, t), 8.97 (1H, d), 10.51 (1H, s); m/z: ES+ [M+H]$^+$ 921.5; ESI-HRMS calculated for $C_{52}H_{60}F_3N_6O_4S$ [M+H]$^+$=921.4343, measured 921.4347.

Intermediate 36a: Methyl 4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzoate

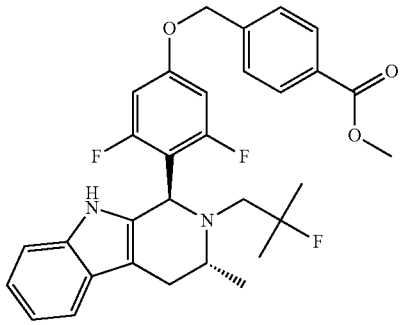 [SMILES: COC(=O)c1ccc(COc2cc(F)c([C@@H]3c4[nH]c5ccccc5c4C[C@@H](C)N3CC(C)(C)F)c(F)c2)cc1]

Methyl 4-(bromomethyl)benzoate (128 mg, 0.56 mmol) was added in one portion to 3,5-difluoro-4-((1R,3R)-2-(2-fluoro-2-methylpropyl)-3-methyl-2,3,4,9-tetrahydro-1H-pyrido[3,4-b]indol-1-yl)phenol (197 mg, 0.51 mmol) and potassium carbonate (105 mg, 0.76 mmol) in MeCN (2 mL) at 20° C. under air. The resulting suspension was stirred at 20° C. for 18 hours. The mixture was diluted with DCM (10 mL) and water (5 mL) and passed through a phase separator cartridge. The solvent was evaporated and the crude material was purified by flash silica chromatography, elution gradient 0 to 50% EtOAc in heptane. Pure fractions were evaporated to dryness to afford the title compound (207 mg, 76%) as a white foam; $^1$H NMR (400 MHz, DMSO-d6, 30° C.) 1.05 (3H, d), 1.08-1.24 (6H, m), 2.28-2.39 (1H, m), 2.53-2.59 (1H, m), 2.77-2.93 (2H, m), 3.46-3.55 (1H, m), 3.87 (3H, s), 5.14 (1H, s), 5.24 (2H, s), 6.77 (2H, d), 6.88-7.06 (2H, m), 7.14-7.26 (1H, m), 7.40 (1H, d), 7.59 (2H, d), 7.94-8.06 (2H, m), 10.52 (1H, s); m/z: ES+ [M+H]$^+$ 537.3.

Intermediate 36b: 4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzoic Acid

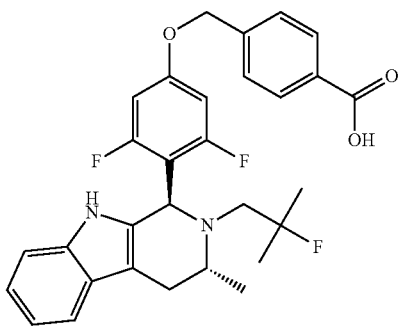 [SMILES: C[C@@H]1Cc2c([nH]c3ccccc23)[C@@H](c2c(F)cc(OCc3ccc(C(=O)O)cc3)cc2F)N1CC(C)(C)F]

Lithium hydroxide monohydrate (39.1 mg, 0.93 mmol) was added in one portion to methyl 4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzoate (200 mg, 0.37 mmol) in THF (3 mL) at 20° C. under air. The resulting suspension was stirred at 20° C. for 72 hours. The organic solvent was removed under reduced pressure. The resulting mixture was acidified with 2M HCl and extracted into EtOAc (2×10 mL). The organic extracts were washed with brine (5 mL) and evaporated to afford the title compound (205 mg) as a pale yellow solid that was used in the next step without further purification; $^1$H NMR (400 MHz, DMSO-d6, 30° C.) 1.05 (3H, d), 1.08-1.18 (5H, m), 1.21 (1H, s), 2.28-2.4 (1H, m), 2.56 (1H, dd), 2.78-2.93 (2H, m), 3.45-3.59 (1H, m), 5.14 (1H, s), 5.23 (2H, s), 6.77 (2H, d), 6.92-7.02 (2H, m), 7.19 (1H, d), 7.40 (1H, d), 7.56 (2H, d), 7.94-8.02 (2H, m), 10.51 (1H, s), 12.94 (1H, s); m/z: ES+ [M+H]$^+$ 523.3.

Example 36: (2S,4R)-1-((S)-2-(4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzamido)-3,3-dimethylbutanoyl)-4-hydroxy-N-(4-(4-methylthiazol-5-yl)benzyl)pyrrolidine-2-carboxamide

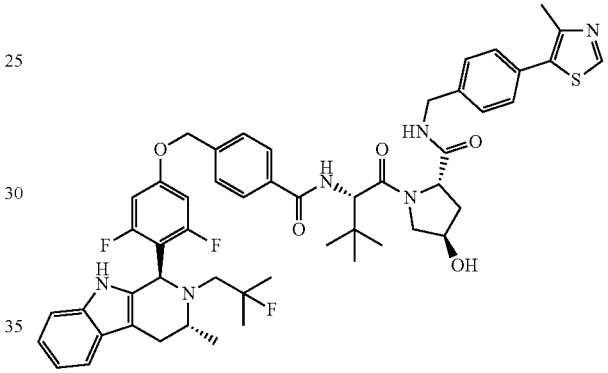

HATU (211 mg, 0.56 mmol) was added portionwise to 4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzoic acid (193 mg, 0.37 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (173 mg, 0.37 mmol) and triethylamine (0.206 mL, 1.48 mmol) in DMF (5 mL) at 20° C. under nitrogen. The resulting mixture was stirred at 20° C. for 30 minutes. The reaction mixture was diluted with EtOAc (50 mL) and washed with water (25 mL) and brine (25 mL). the organics were dried over anhydrous MgSO$_4$, filtered and concentrated. The crude product was purified by preparative HPLC (Waters CSH Cis OBD column, 30×100 mm id, 5 micron particle size), using decreasingly polar mixtures of water (containing 1% by volume of NH$_4$OH (28-30% in H$_2$O))) and MeCN as eluents. Fractions containing the desired compound were evaporated to dryness to afford the title compound (171 mg, 49%); $^1$H NMR (400 MHz, DMSO-d6, 30° C.) 1.05 (12H, d), 1.16 (6H, dd), 1.93 (1H, m), 2.02-2.1 (1H, m), 2.29-2.39 (1H, m), 2.46 (3H, s), 2.56 (1H, dd), 2.78-2.94 (2H, m), 3.45-3.56 (1H, m), 3.74 (2H, d), 4.25 (1H, dd), 4.36-4.51 (3H, m), 4.78 (1H, d), 5.13 (2H, s), 5.21 (2H, s), 6.76 (2H, d), 6.97 (2H, m), 7.15-7.21 (1H, m), 7.37-7.45 (5H, m), 7.52 (2H, d), 7.90 (2H, d), 7.99 (1H, d), 8.56 (1H, t), 8.99 (1H, s), 10.51 (1H, s); m/z: ES+ [M+H]$^+$ 935.6; ESI-HRMS calculated for C$_{52}$H$_{58}$F$_3$N$_6$O$_5$S [M+H]$^+$=935.4136, measured 935.4126.

Intermediate 37a: 2-(2-(2-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)ethan-1-ol

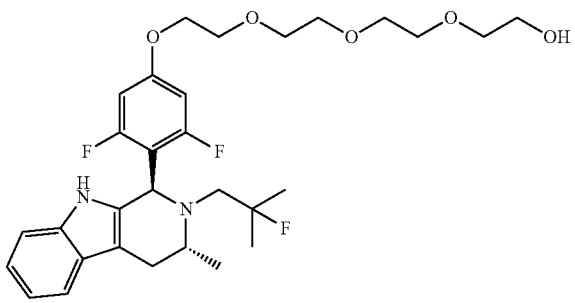 [SMILES: C[C@@H]1Cc2c([nH]c3ccccc23)[C@@H](c2c(F)cc(OCCOCCOCCOCCO)cc2F)N1CC(C)(C)F]

RockPhos Pd G3 (86 mg, 0.10 mmol) was added in one portion to a degassed mixture of 2,2'-((oxybis(ethane-2,1-diyl))bis(oxy))bis(ethan-1-ol) (1.77 mL, 10.25 mmol), (1R,3R)-1-(4-bromo-2,6-difluorophenyl)-2-(2-fluoro-2-methylpropyl)-3-methyl-2,3,4,9-tetrahydro-1H-pyrido[3,4-b]indole, HCl (500 mg, 1.03 mmol) 4 Å molecular sieves (100 mg), and cesium carbonate (1169 mg, 3.59 mmol) in toluene (7.5 mL) at 20° C. under nitrogen. The resulting mixture was stirred at 90° C. for 4 hours. The reaction was allowed to cool to RT and diluted with DCM (10 mL), filtered and evaporated to afford crude product as a orange gum. The residue was dissolved in DCM, washed with water. The crude product was purified by flash silica chromatography, elution gradient 0 to 100% EtOAc in heptane. Pure fractions were evaporated to dryness to afford the title compound (261 mg, 45%) as an orange gum; $^1$H NMR (400 MHz, CDCl$_3$, 30° C.) 1.10 (3H, d), 1.20 (6H, dd), 2.31-2.47 (2H, m), 2.53-2.67 (1H, m), 2.86 (1H, dd), 3.04-3.14 (1H, m), 3.55-3.62 (2H, m), 3.63-3.73 (11H, m), 3.83 (2H, dd), 4.05-4.12 (2H, m), 5.18 (1H, s), 6.39-6.5 (2H, m), 7.03-7.14 (2H, m), 7.18-7.24 (1H, m), 7.51 (1H, dd), 7.59 (1H, s); m/z: ES+ [M+H]$^+$ 565.3.

Intermediate 37b: tert-Butyl 14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,6,9,12-tetraoxatetradecanoate

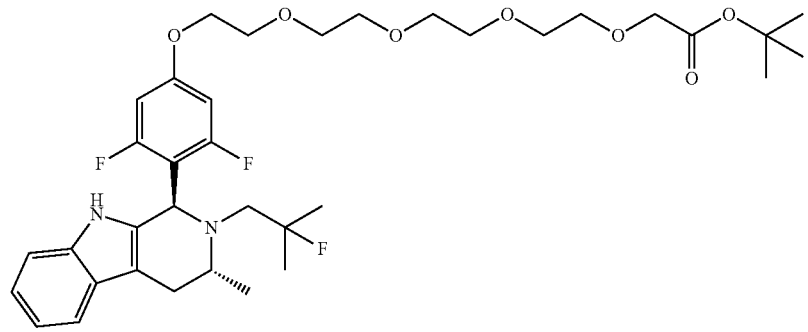 [SMILES: C[C@@H]1Cc2c([nH]c3ccccc23)[C@@H](c2c(F)cc(OCCOCCOCCOCCOCC(=O)OC(C)(C)C)cc2F)N1CC(C)(C)F]

60% Sodium hydride in mineral oil (8.50 mg, 0.21 mmol) was added in one portion to 2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)ethan-1-ol (100 mg, 0.18 mmol), in THF (5 mL) at 20° C. under nitrogen. tert-butyl 2-bromoacetate (0.031 mL, 0.21 mmol) was added after 10 mins and the reaction was stirred at RT for 2 hours. Further 60% sodium hydride in mineral oil (8.50 mg, 0.21 mmol) was added and the reaction stirred for 1 hour. The reaction was quenched with water (slowly) and extracted with EtOAc (2×20 mL). The combined organics were washed with brine (20 mL), dried over anhydrous MgSO$_4$, filtered and evaporated under reduced pressure. The crude product was purified by flash silica chromatography, elution gradient 0 to 100% EtOAc in heptane. Pure fractions were evaporated to dryness to afford the title compound (49.0 mg, 41%) as a colourless oil; $^1$H NMR (400 MHz, CDCl$_3$, 30° C.) 1.09 (3H, d), 1.17 (3H, d), 1.23 (3H, d), 1.46 (9H, s), 2.38 (1H, dd), 2.60 (1H, m), 2.86 (1H, dd), 3.05-3.14 (1H, m), 3.63-3.72 (13H, m), 3.83 (2H, dd), 3.99 (2H, s), 4.05-4.1 (2H, m), 5.18 (1H, s), 6.38-6.48 (2H, m), 7.03-7.14 (2H, m), 7.19-7.25 (1H, m), 7.47-7.57 (2H, m); m/z: ES+ [M+H]$^+$ 679.4.

Intermediate 37c: 14-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-3,6,9,12-tetraoxatetradecanoic Acid

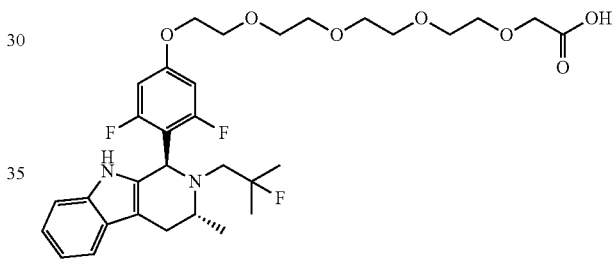

tert-Butyl 14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,6,9,12-tetraoxatetradecanoate (49 mg, 0.07 mmol) was dissolved in formic acid (0.5 mL) at 20° C. under air. The resulting mixture was stirred at 20° C. for 5 hours. The solvent was removed under reduced pressure. The residue was re-dissolved in formic acid (0.5 mL) and stirred for a further 2 hours. The solvent was removed under reduced pressure to afford the title compound as a yellow oil that was used in the next step without further purification (assumed quantitative); m/z: ES+ [M+H]$^+$ 623.3.

Example 37: (2S,4R)-1-((S)-2-(tert-Butyl)-17-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12,15-tetraoxa-3-azaheptadecanoyl)-4-hydroxy-N-(4-(4-methylthiazol-5-yl)benzyl)pyrrolidine-2-carboxamide

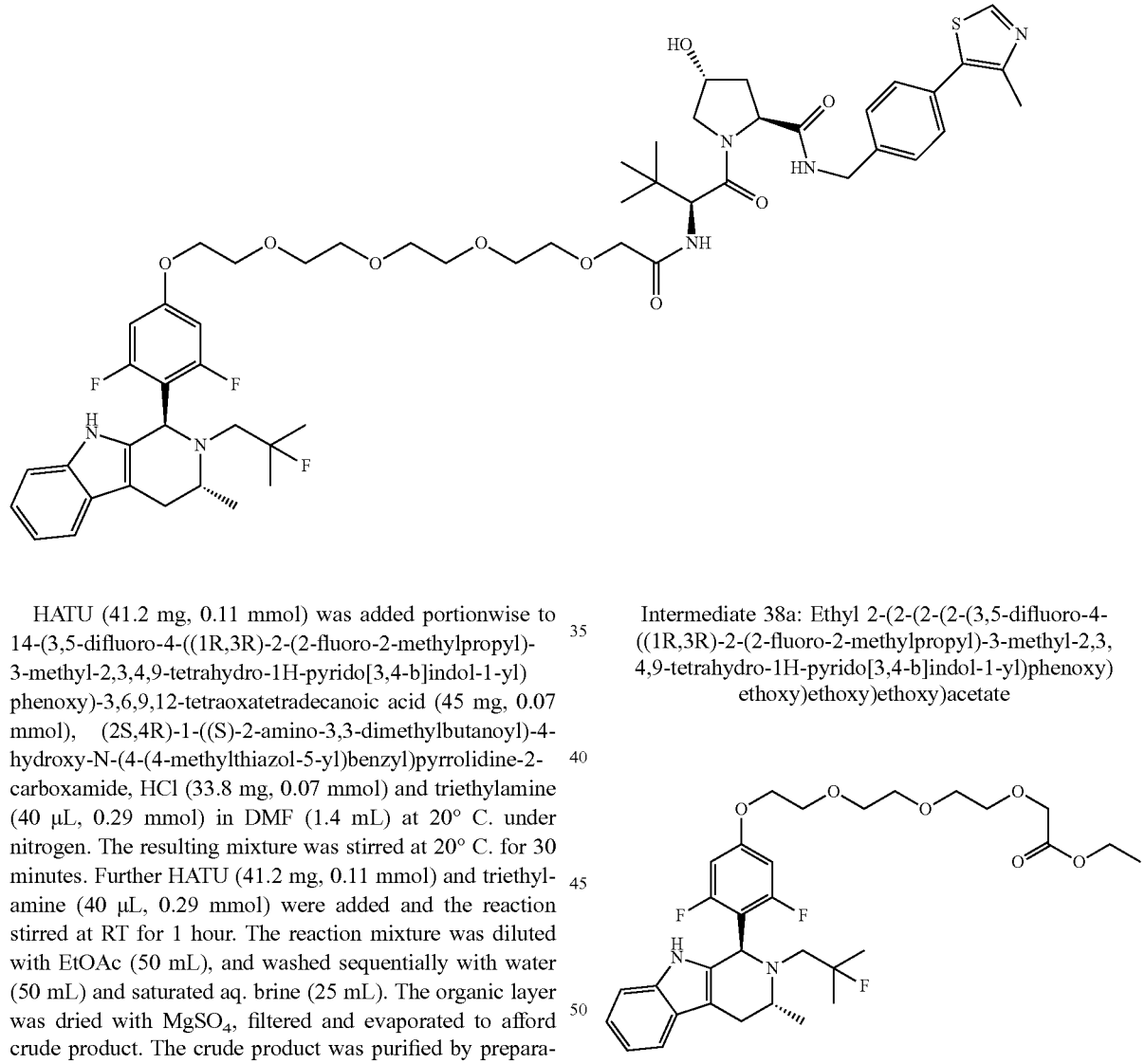

HATU (41.2 mg, 0.11 mmol) was added portionwise to 14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,6,9,12-tetraoxatetradecanoic acid (45 mg, 0.07 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (33.8 mg, 0.07 mmol) and triethylamine (40 µL, 0.29 mmol) in DMF (1.4 mL) at 20° C. under nitrogen. The resulting mixture was stirred at 20° C. for 30 minutes. Further HATU (41.2 mg, 0.11 mmol) and triethylamine (40 µL, 0.29 mmol) were added and the reaction stirred at RT for 1 hour. The reaction mixture was diluted with EtOAc (50 mL), and washed sequentially with water (50 mL) and saturated aq. brine (25 mL). The organic layer was dried with $MgSO_4$, filtered and evaporated to afford crude product. The crude product was purified by preparative HPLC (Waters XSelect CSH $C_{18}$ column, 30×100 mm id, 5 micron particle size), using decreasingly polar mixtures of water (containing 0.1% formic acid) and MeCN as eluents. Fractions containing the desired compound were evaporated to dryness to afford the title compound (9 mg, 12%); $^1$H NMR (400 MHz, MeOD, 30° C.) 1.02 (9H, d), 1.21 (9H, d), 1.41-1.55 (1H, m), 2.08 (1H, m), 2.16-2.26 (1H, m), 2.46 (4H, s), 2.63 (1H, d), 2.91 (1H, s), 3.04 (1H, s), 3.59-3.72 (14H, m), 3.76-3.88 (4H, m), 4.01 (2H, d), 4.12 (2H, d), 4.34 (1H, dd), 4.44-4.61 (3H, m), 4.69 (1H, d), 5.20 (1H, s), 6.55 (2H, s), 6.98 (2H, s), 7.19 (1H, d), 7.36-7.48 (5H, m), 7.62 (1H, d), 8.58 (1H, t), 8.84 (1H, d); m/z: ES+ [M+H]$^+$ 1035.5; ESI-HRMS calculated for $C_{54}H_{70}F_3N_6O_9S$ [M+H]$^+$=1035.4872, measured 1035.4830.

Intermediate 38a: Ethyl 2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetate

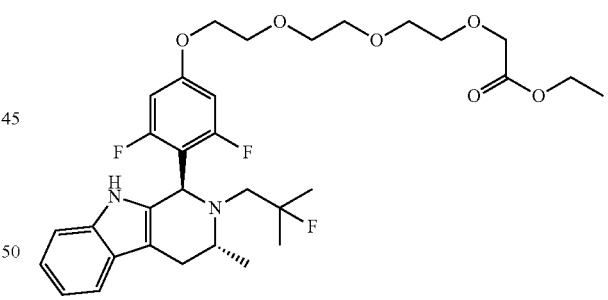

Diisopropyl azodicarboxylate (1.673 mL, 8.50 mmol) was added dropwise to 3,5-difluoro-4-((1R,3R)-2-(2-fluoro-2-methylpropyl)-3-methyl-2,3,4,9-tetrahydro-1H-pyrido[3,4-b]indol-1-yl)phenol (1.65 g, 4.25 mmol), triphenylphosphine (2.228 g, 8.50 mmol) and ethyl 2-(2-(2-(2-hydroxyethoxy)ethoxy)ethoxy)acetate (1.505 g, 6.37 mmol) in DCM (50 mL) cooled to 0° C. over a period of 2 minutes under nitrogen. The resulting solution was stirred at 0° C. for 45 minutes and warmed to 20° C. for 1 hour. The reaction was incomplete and further triphenylphosphine (0.557 g, 2.13 mmol) and diisopropyl azodicarboxylate (0.418 mL, 2.13 mmol) were added and the solution was stirred at 20° C. for a further 30 minutes. The crude reaction mixture was purified by ion exchange chromatography, using an SCX column. The desired product was eluted from the column using 1M NH$_3$/MeOH and pure fractions were evaporated to dryness to afford crude product. The crude product was purified by flash silica chromatography, elution gradient 10 to 50% EtOAc in heptane. Pure fractions were evaporated to dryness to afford the title compound (1.09 g, 42%) as a colourless gum; $^1$H NMR (400 MHz, DMSO-d6, 30° C.) 1.05 (3H, d), 1.15-1.3 (9H, m), 2.35 (1H, dd), 2.53-2.61 (1H, m), 2.78-2.95 (2H, m), 3.48-3.62 (9H, m), 3.71-3.77 (2H, m), 4.08-4.16 (6H, m), 5.13 (1H, s), 6.68 (2H, d), 6.89-7.07 (2H, m), 7.15-7.24 (1H, m), 7.40 (1H, d), 10.50 (1H, s). m/z: ES+ [M+H]$^+$ 607.5.

Intermediate 38b: 2-(2-(2-(2-(3,5-Difluoro-4-((1R, 3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetic Acid

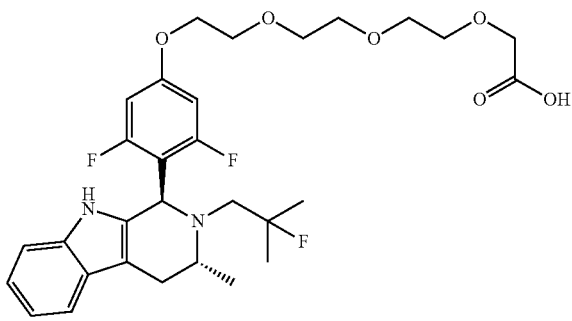 [SMILES: C[C@@H]1Cc2c([nH]c3ccccc23)[C@@H](c2c(F)cc(OCCOCCOCCOCC(=O)O)cc2F)N1CC(C)(C)F]

Lithium hydroxide hydrate (0.151 g, 3.59 mmol) was added in one portion to ethyl 2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetate (1.09 g, 1.80 mmol) in THF (15 mL) and water (5 mL) at 20° C. The resulting solution was stirred at RT for 30 mins. The organic solvent was removed under reduced pressure. The resulting mixture was acidified with 2M aq. HCl and extracted into EtOAc (2×10 mL). The organic extracts were washed with saturated brine (5 mL) and evaporated to afford the title compound (0.884 g, 85%) that was used without further purification; JACS $^1$H NMR (400 MHz, DMSO-d6)$^1$H NMR (400 MHz, DMSO-d6, 30° C.) 1.05 (3H, d), 1.11 (3H, s), 1.23 (2H, d), 2.38 (1H, d), 2.58 (1H, d), 2.78-2.95 (2H, m), 3.52-3.56 (5H, m), 3.58 (5H, dd), 3.71-3.76 (2H, m), 4.02 (2H, s), 4.12 (2H, s), 5.13 (1H, s), 6.68 (2H, d), 6.97 (2H, m), 7.19 (1H, d), 7.40 (1H, d), 10.50 (1H, s), 12.49 (1H, s); m/z: ES+ [M+H]$^+$ 579.3.

Example 38: (2S,4R)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide

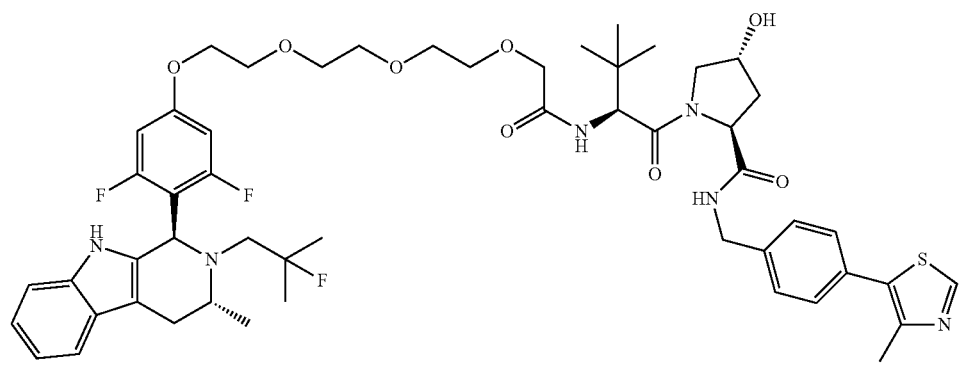 [SMILES: Cc1ncsc1-c1ccc(CNC(=O)[C@@H]2C[C@@H](O)CN2C(=O)[C@@H](NC(=O)COCCOCCOCCOc2cc(F)c([C@@H]3c4[nH]c5ccccc5c4C[C@@H](C)N3CC(C)(C)F)c(F)c2)C(C)(C)C)cc1]

HATU (1.95 g, 5.14 mmol) was added portionwise to 2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetic acid (1.98 g, 3.42 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (1.48 g, 3.25 mmol) and triethylamine (1.91 mL, 13.71 mmol) in DMF (10 mL) at 20° C. under nitrogen. The resulting mixture was stirred at 20° C. for 30 minutes. The reaction mixture was diluted with EtOAc (25 mL), and washed sequentially with saturated NaHCO$_3$ (25 mL), water (25 mL), and saturated brine (25 mL). The organic layer was dried with Na$_2$SO$_4$, filtered and evaporated to afford crude product. The crude product was purified by flash silica chromatography, elution gradient 0 to 10% MeOH in DCM. Pure fractions were evaporated to dryness to afford a yellow oil. The samples were dissolved in MeOH and purified using the SFC conditions: Column: Princeton Diol, 30×250 mm, 5 micron; Mobile phase: A=MeOH+0.1% NH$_3$, B=scCO$_2$; Gradient: 20-30% A over 8 minutes; Flow rate: 100 mL/min; BPR: 120 bar; Column temperature: 40° C. The title compound (1.1 g, 32%) was obtained as a pale yellow solid; $^1$H NMR (400 MHz, CDCl$_3$, 30° C.) 0.94 (9H, s), 1.10 (3H, d), 1.17 (3H, d), 1.22 (3H, d), 2.01-2.1 (1H, m), 2.39 (1H, dd), 2.48 (3H, s), 2.52-2.64 (2H, m), 2.77 (1H, d), 2.84 (1H, dd), 3.08 (1H, dd), 3.59 (1H, dd), 3.63-3.71 (9H, m), 3.79 (2H, t), 4.00 (2H, s), 4.01-4.11 (3H, m), 4.31 (1H, dd), 4.49 (2H, d), 4.56 (1H, dd), 4.71 (1H, t), 5.19 (1H, s), 6.31-6.44 (2H, m), 7.05-7.12 (2H, m), 7.2-7.24 (1H, m), 7.35 (6H, q), 7.51 (1H, dd), 8.27 (1H, s), 8.63 (1H, s); m/z: ES+ [M+H]$^+$ 991.7; ESI-HRMS calculated for C$_{52}$H$_{66}$F$_3$N$_6$O$_8$S [M+H]$^+$=991.4609, measured 991.4584.

Intermediate 39a: 2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethan-1-ol

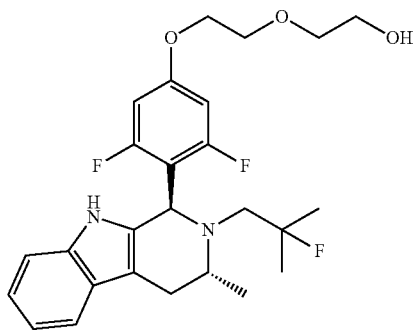 [SMILES: C[C@@H]1Cc2c([nH]c3ccccc23)[C@@H](c2c(F)cc(OCCOCCO)cc2F)N1CC(C)(C)F]

Diethylene glycol (0.47 mL, 4.92 mmol) was added to (1R,3R)-1-(4-bromo-2,6-difluorophenyl)-2-(2-fluoro-2-methylpropyl)-3-methyl-2,3,4,9-tetrahydro-1H-pyrido[3,4-b]indole, HCl (400 mg, 0.82 mmol), cesium carbonate (935 mg, 2.87 mmol) and RockPhos Pd G3 (34.4 mg, 0.04 mmol) in toluene (6.0 mL) at 20° C. under nitrogen. The resulting solution was vacuum degassed and stirred at 90° C. for 4.5 hours. After cooling down to 20° C. the crude product was purified by flash silica chromatography, elution gradient 5 to 80% EtOAc in heptane. Pure fractions were evaporated to dryness to afford the title compound (191 mg, 49%) as a colourless dry film; $^1$H NMR (400 MHz, CDCl3, 30° C.) 1.09 (3H, d), 1.14-1.25 (6H, m), 2.05 (1H, s), 2.39 (1H, dd), 2.60 (1H, m), 2.86 (1H, dd), 3.08 (1H, m), 3.6-3.7 (3H, m), 3.71-3.76 (2H, m), 3.8-3.84 (2H, m), 4.07 (2H, dd), 5.18 (1H, s), 6.39-6.45 (2H, m), 7.05-7.13 (2H, m), 7.17-7.23 (1H, m), 7.47-7.53 (1H, m), 7.55 (1H, s); m/z: ES− [M−H]$^-$ 475.3.

Intermediate 39b: tert-butyl 2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)acetate

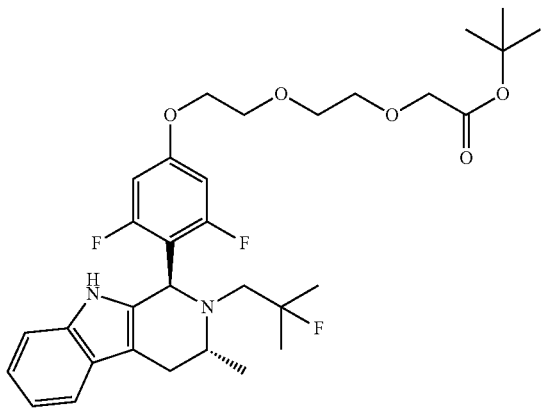 [SMILES: C[C@@H]1Cc2c([nH]c3ccccc23)[C@@H](c2c(F)cc(OCCOCCOCC(=O)OC(C)(C)C)cc2F)N1CC(C)(C)F]

2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethan-1-ol (240 mg, 0.50 mmol) and 60% sodium hydride in mineral oil (14.50 mg, 0.36 mmol) in THF (7 mL) was stirred at 20° C. for 5 minutes under nitrogen. tert-butyl 2-bromoacetate (0.089 mL, 0.60 mmol) was added and the resulting suspension was stirred at 20° C. for 2.5 hours under nitrogen. The reaction was incomplete and further 60% sodium hydride in mineral oil (7 mg, 0.17 mmol) was added and the mixture was stirred at 20° C. for a further 1 hour. The reaction was incomplete and further 60% sodium hydride in mineral oil (7 mg, 0.17 mmol) was added and the suspension was stirred at 20° C. for a further 17 hours. The reaction was incomplete and further tert-butyl 2-bromoacetate (20 μL, 0.13 mmol) was added and the suspension was stirred at 20° C. for a further 2 hours. The reaction was incomplete and further tert-butyl 2-bromoacetate (20 μL, 0.13 mmol) was added and the suspension was stirred at 20° C. for a further 2 hours. The reaction was incomplete and further tert-butyl 2-bromoacetate (20 μL, 0.13 mmol) was added and the suspension was stirred at 20° C. for a further 2 hours. The reaction was incomplete and further tert-butyl 2-bromoacetate (20 μL, 0.13 mmol) was added and the suspension was stirred at 20° C. for a further 2 hours. The reaction was incomplete and further 60% sodium hydride in mineral oil (7 mg, 0.17 mmol) and 1 mL of THF was added and the suspension was stirred at 20° C. for a further hours. The reaction mixture was slowly quenched with water (15 mL), extracted with EtOAc (3×15 mL), the organic layer was dried over MgSO$_4$, filtered and evaporated. The crude product was purified by flash silica chromatography, elution gradient 5 to 70% EtOAc in heptane. Pure fractions were evaporated to dryness to afford the title compound (161 mg, 54%) as a colourless dry film; $^1$H NMR (400 MHz, CDCl3, 30° C.) 1.10 (3H, dd), 1.15-1.26 (6H, m), 1.48 (9H, s), 2.38 (1H, dd), 2.57-2.64 (1H, m), 2.87 (1H, dd), 3.06-3.14 (1H, m), 3.69 (1H, dd), 3.74 (4H, s), 3.83-3.87 (2H, m), 4.02 (2H, d), 4.06-4.11 (2H, m), 5.19 (1H, s), 6.41-6.46 (2H, m), 7.10 (2H, m), 7.2-7.24 (1H, m), 7.47 (1H, s), 7.5-7.53 (1H, m); m/z: ES+ [M+H]+ 591.4.

Intermediate 39c: 2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)acetic Acid

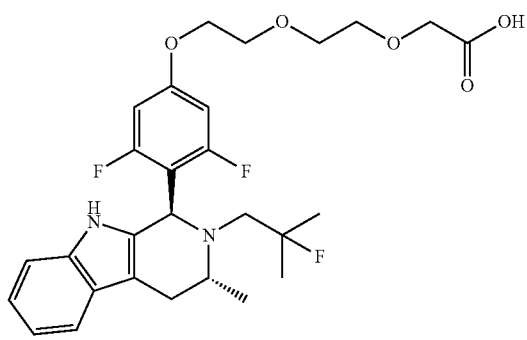 [SMILES: C[C@@H]1Cc2c([nH]c3ccccc23)[C@@H](c2c(F)cc(OCCOCCOCC(=O)O)cc2F)N1CC(C)(C)F]

Formic acid (0.50 mL, 13 mmol) was added in one portion to tert-butyl 2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)acetate (155 mg, 0.26 mmol) at 20° C. under air. The resulting solution was stirred at 20° C. for 1 hour. The reaction was incomplete so the temperature was increased to 40° C. and the reaction mixture was stirred for further 2.5 hours. The reaction mixture was evaporated to dryness to afford the title compound (141 mg) as a pale yellow dry film that was used in the next step without further purification; m/z: ES+ [M+H]+ 535.4.

Example 39: (2S,4R)-1-((S)-2-(2-(2-(2-(3,5-difluoro-4-((R,3R)-2-(2-fluoro-2-methylpropyl)-3-methyl-2,3,4,9-tetrahydro-1H-pyrido[3,4-b]indol-1-yl)phenoxy)ethoxy)ethoxy)acetamido)-3,3-dimethylbutanoyl)-4-hydroxy-N-(4-(4-methylthiazol-5-yl)benzyl)pyrrolidine-2-carboxamide

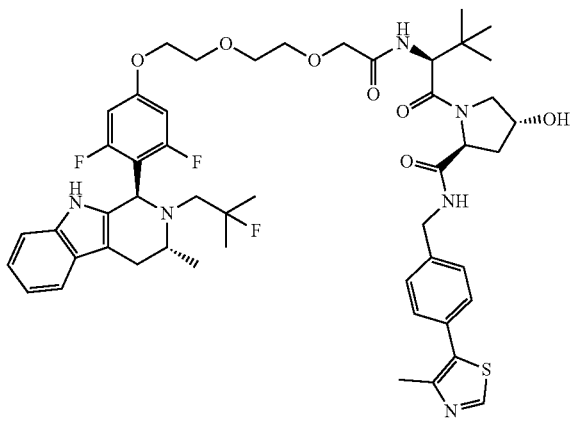 [SMILES: Cc1ncsc1-c1ccc(CNC(=O)[C@@H]2C[C@@H](O)CN2C(=O)[C@@H](NC(=O)COCCOCCOc2cc(F)c([C@@H]3c4[nH]c5ccccc5c4C[C@@H](C)N3CC(C)(C)F)c(F)c2)C(C)(C)C)cc1]

2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)acetic acid (131 mg, 0.25 mmol), HATU (112 mg, 0.29 mmol), and DIPEA (0.128 mL, 0.74 mmol) were dissolved in N,N-dimethylformamide (4 mL) at 20° C. and stirred for 15 minutes under nitrogen. (2S,4R)-1-((S)-2-amino-3,3-dimethylbutanoyl)-4-hydroxy-N-(4-(4-methylthiazol-5-yl)benzyl)pyrrolidine-2-carboxamide, HCl (119 mg, 0.25 mmol) was added and the resulting solution was stirred at 20° C. for 3 hours under nitrogen. The reaction was incomplete and further HATU (112 mg, 0.29 mmol), and DIPEA (0.128 mL, 0.74 mmol) were added and the solution was stirred at 20° C. for further 19 hours. The reaction mixture was diluted with EtOAc (10 mL), and washed sequentially with water (10 mL), saturated brine (10 mL), and water (10 mL). The organic layer was dried with MgSO4, filtered and evaporated to afford crude product. The crude product was purified by preparative HPLC (Waters CSH C18 OBD column, 30×100 mm id, 5 micron particle size), using decreasingly polar mixtures of water (containing 1% by volume of NH4OH (28-30% in H2O)) and MeCN as eluents. Fractions containing the desired compound were evaporated to dryness to afford 45.9 mg of the title compound (46 mg, 20%) as a white solid; 1H NMR (400 MHz, MeOD, 30° C.) 1.01 (9H, d), 1.07-1.21 (9H, m), 2.08 (1H, m), 2.18-2.25 (1H, m), 2.32-2.42 (1H, m), 2.44 (3H, s), 2.58 (1H, dd), 2.88 (1H, dd), 3.02 (1H, dd), 3.58-3.75 (5H, m), 3.76-3.91 (4H, m), 4.01-4.06 (2H, m), 4.12 (2H, t), 4.32 (1H, d), 4.47-4.59 (3H, m), 4.69 (1H, s), 5.18 (1H, s), 6.45-6.53 (2H, m), 6.91-7.02 (2H, m), 7.13-7.21 (1H, m), 7.36-7.47 (5H, m), 8.80 (1H, s), exchangeable protons not observed; m/z: ES+ [M+H]+ 947.6; ESI-HRMS calculated for C50H62F3N6O7S [M+H]+=947.4347, measured 947.4343.

Intermediate 40a: 2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethan-1-ol

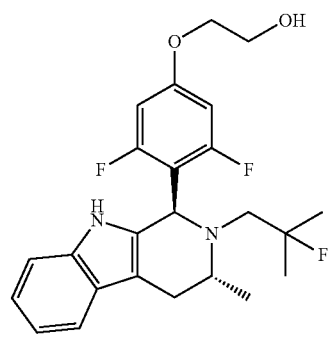 [SMILES: C[C@@H]1Cc2c([nH]c3ccccc23)[C@@H](c2c(F)cc(OCCO)cc2F)N1CC(C)(C)F]

Ethane-1,2-diol (0.17 mL, 4.0 mmol) was added to (1R, 3R)-1-(4-bromo-2,6-difluorophenyl)-2-(2-fluoro-2-methylpropyl)-3-methyl-2,3,4,9-tetrahydro-1H-pyrido[3,4-b]indole (300 mg, 0.66 mmol), cesium carbonate (758 mg, 2.33 mmol) and RockPhos Pd G3 (27.9 mg, 0.03 mmol) in toluene (5.1 mL) at 20° C. under nitrogen. The resulting solution was vacuum degassed and stirred at 90° C. for 4.5 hours. The crude product was purified by flash silica chromatography, elution gradient 5 to 70% EtOAc in heptane. Pure fractions were evaporated to dryness to afford the title compound (87 mg, 30%) as a pale yellow dry film; 1H NMR (400 MHz, CDCl3, 30° C.) 1.10 (3H, d), 1.21 (6H, dd), 1.89 (1H, t), 2.39 (1H, dd), 2.60 (1H, dd), 2.86 (1H, dd), 3.09 (1H, dd), 3.62-3.73 (1H, m), 3.91-4 (2H, m), 4.04 (2H, q), 5.20 (1H, s), 6.4-6.47 (2H, m), 7.05-7.15 (2H, m), 7.22 (1H, dd), 7.39 (1H, s), 7.51 (1H, dd); m/z: ES− [M−H]⁻ 431.2.

Intermediate 40b: 2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy) acetic Acid

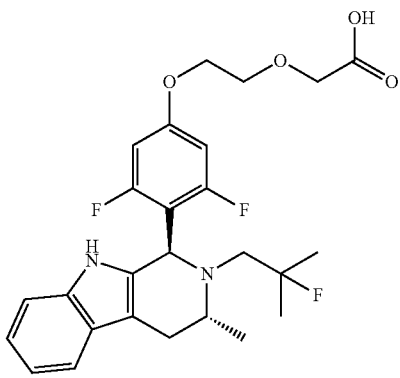 [SMILES: C[C@@H]1Cc2c([nH]c3ccccc23)[C@@H](c2c(F)cc(OCCOCC(=O)O)cc2F)N1CC(C)(C)F]

2-(3,5-Difluoro-4-((1R,3R)-2-(2-fluoro-2-methylpropyl)-3-methyl-2,3,4,9-tetrahydro-1H-pyrido[3,4-b]indol-1-yl) phenoxy)ethan-1-ol (80 mg, 0.18 mmol) was added to 60% sodium hydride in mineral oil (5.33 mg, 0.13 mmol) in THF (2.5 mL) and was stirred at 20° C. for 5 minutes under nitrogen. tert-butyl bromoacetate (33 µL, 0.22 mmol) was added and the resulting suspension was stirred at 20° C. for 2 hours. The reaction was incomplete and further 60% sodium hydride in mineral oil (3.5 mg, 0.09 mmol) was added and the suspension was stirred at 20° C. for a further 2 hours. The reaction was incomplete and further tert-butyl bromoacetate (6.6 µL, 0.036 mmol) was added and the suspension was stirred at 20° C. for a further 2 hours. The reaction was incomplete and further 60% sodium hydride in mineral oil (2.1 mg, 0.05 mmol) and 0.5 mL THF was added and the suspension was stirred at 20° C. for a further 2.5 hours. The reaction was incomplete and further 60% sodium hydride in mineral oil (2.1 mg, 0.05 mmol) and tert butyl bromoacetate (5.5 µL, 0.04 mmol) were added and the suspension was stirred at 20° C. for a further 12.5 hours. The reaction was incomplete and 0.25 mL DMF was added and the temperature was increased to 50° C. and the reaction mixture was stirred for a further 2 hours. The reaction mixture was slowly quenched with water (15 mL), extracted with EtOAc (3×15 mL), the organic layer was dried over MgSO₄, filtered and evaporated to a dry film (130 mg) that was used in the next step without further purification; m/z: ES+ [M+H]⁺ 491.4

Example 40: (2S,4R)-1-((S)-2-(2-(2-(3,5-Difluoro-4-((1R,3R)-2-(2-fluoro-2-methylpropyl)-3-methyl-2,3,49-tetrahydro-1H-pyrido[3,4-b]indol-1-yl)phenoxy)ethoxy)acetamido)-3,3-dimethylbutanoyl)-4-hydroxy-N-(4-(4-methylthiazol-5-yl)benzyl) pyrrolidine-2-carboxamide

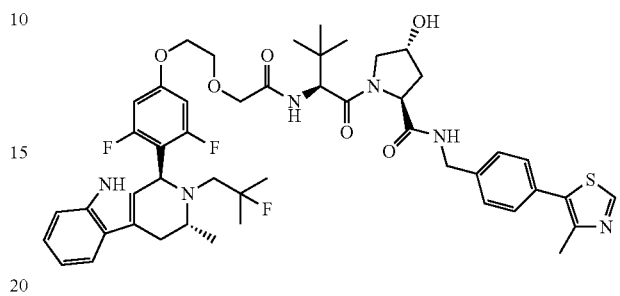

Crude 2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)acetic acid (0.060 g, 0.12 mmol), N-ethyl-N-isopropylpropan-2-amine (0.085 mL, 0.49 mmol), and HATU (0.070 g, 0.18 mmol) were dissolved in N,N-dimethylformamide (4 mL) and stirred at 20° C. over a period of 15 minutes under nitrogen. (2S,4R)-1-((S)-2-amino-3,3-dimethylbutanoyl)-4-hydroxy-N-(4-(4-methylthiazol-5-yl)benzyl)pyrrolidine-2-carboxamide, HCl (0.057 g, 0.12 mmol) was added to the reaction mixture at 20° C. under nitrogen. The resulting solution was stirred at 20° C. for 3.5 hours The reaction mixture was diluted with EtOAc (10 mL), and washed sequentially with water (10 mL), saturated brine (10 mL), and water (10 mL). The organic layer was dried with MgSO₄, filtered and evaporated to afford crude product. The sample was purified using the following SFC conditions: Column: Princeton Diol, 30×250 mm, 5 micron Mobile phase: A=MeOH+0.1% NH₃/ B=scCO₂ Gradient: 20-30% A over 10 minutes Flow rate: 100 mL/min BPR: 120 bar Temperature: 40° C. Fractions containing the desired compound were evaporated to dryness to afford the title compound (0.036 g, 32%) as a pale yellow solid; ¹H NMR (400 MHz, MeOD, 30° C.) 1.02 (9H, s), 1.07-1.22 (9H, m), 2.10 (1H, m), 2.18-2.25 (1H, m), 2.34-2.41 (1H, m), 2.44 (3H, s), 2.58 (1H, dd), 2.83-2.92 (2H, m), 3.02 (1H, d), 3.67 (2H, s), 3.79-3.88 (2H, m), 3.88-3.92 (2H, m), 4.09 (2H, s), 4.15-4.2 (2H, m), 4.37 (1H, s), 4.44 (1H, s), 4.49 (2H, d), 4.55-4.6 (1H, m), 4.69-4.73 (1H, m), 5.19 (1H, s), 6.64 (2H, d), 6.92-7 (2H, m), 7.16 (1H, dd), 7.36-7.45 (5H, m), 7.63 (1H, d), 8.79 (1H, s); m/z: ES+ [M+H]⁺ 903.6; ESI-HRMS calculated for C₄₈H₅₈F₃N₆O₆S [M+H]⁺=903.4085, measured 903.4068.

Intermediate 41a: Ethyl 2-(3-hydroxypropoxy)acetate

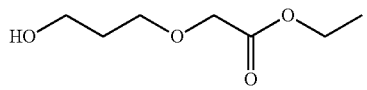

Rhodium diacetate (10 mg, 0.02 mmol) was added to propane-1,3-diol (5.00 mL, 94.62 mmol) at 20° C. under nitrogen. The resulting solution was stirred at 20° C. for 5 minutes and cooled to 0° C. Ethyl 2-diazoacetate (0.540 mL, 4.36 mmol) was added drop wise at 0° C. and the reaction mixture was stirred at 20° C. for 22 h. The reaction mixture was diluted with EtOAc (10 mL), and washed with water (3×5 mL). The organic layer was dried with MgSO$_4$, filtered and evaporated to afford crude product. The crude product was purified by flash silica chromatography, elution gradient 0 to 80% EtOAc in heptane. Pure fractions were evaporated to dryness to afford the title compound (0.364 g, 51%) as a colourless oil; $^1$H NMR (400 MHz, CDCl3, 30° C.) 1.26 (3H, t), 1.81 (2H, p), 2.83 (1H, s), 3.66 (2H, t), 3.76 (2H, t), 4.04 (2H, s), 4.19 (2H, q).

Intermediate 41b: Ethyl 2-(3-(3,5-difluoro-4-((1R, 3R)-2-(2-fluoro-2-methylpropyl)-3-methyl-2,3,4,9-tetrahydro-1H-pyrido[3,4-b]indol-1-yl)phenoxy) propoxy)acetate

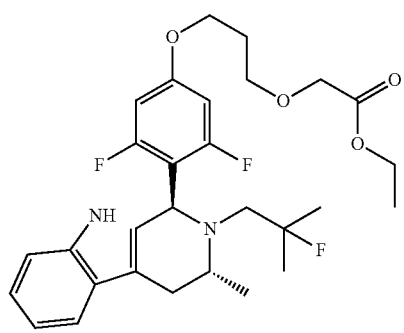 [SMILES: CCOC(=O)COCCCOc1cc(F)c([C@@H]2C=C(c3ccccc3N)C[C@@H](C)N2CC(C)(C)F)c(F)c1]

Diisopropyl azodicarboxylate (0.16 mL, 0.82 mmol) was added dropwise to a stirred solution of 3,5-difluoro-4-((1R, 3R)-2-(2-fluoro-2-methylpropyl)-3-methyl-2,3,4,9-tetrahydro-1H-pyrido[3,4-b]indol-1-yl)phenol (160 mg, 0.41 mmol), ethyl 2-(3-hydroxypropoxy)acetate (134 mg, 0.82 mmol) and triphenylphosphine (216 mg, 0.82 mmol) in DCM (3.3 mL) at 5° C. under nitrogen. The resulting solution was stirred at 5° C. for 20 min and then at 21° C. for 1 hour. DCM (7 mL) and water (10 mL) were added and the organic layer was separated. The aqueous layer was extracted with DCM (2×10 mL). The combined organic layers were washed with brine, dried over MgSO$_4$ and concentrated to give the crude product. The crude product was purified by flash silica chromatography, elution gradient 0 to 80% EtOAc in heptane. Pure fractions were evaporated to dryness to afford the title compound (181 mg, 83%) as a colourless dry film; $^1$H NMR (400 MHz, CDCl3, 30° C.) 1.10 (3H, d), 1.15-1.3 (9H, m), 2.04-2.12 (2H, m), 2.39 (1H, dd), 2.60 (1H, dd), 2.87 (1H, dd), 3.09 (1H, dd), 3.70 (3H, t), 4.07 (4H, d), 4.21 (2H, q), 5.19 (1H, s), 6.38-6.44 (2H, m), 7.06-7.13 (2H, m), 7.22 (1H, dd), 7.42 (1H, s), 7.51 (1H, dd); m/z: ES+ [M+H]$^+$533.4.

Intermediate 41c: 2-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy) propoxy)acetic Acid

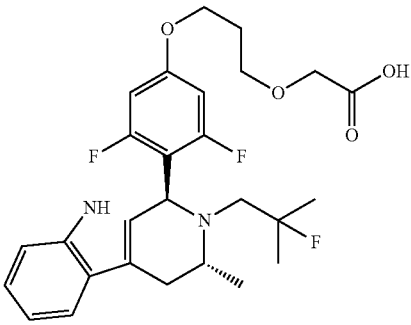 [SMILES: C[C@@H]1CC(c2ccccc2N)=C[C@@H](c2c(F)cc(OCCCOCC(=O)O)cc2F)N1CC(C)(C)F]

Lithium hydroxide hydrate (26.9 mg, 0.64 mmol) was added to ethyl 2-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)acetate (171 mg, 0.32 mmol) in THF (1.2 mL) at 20° C. The resulting solution was stirred at 40° C. for 2 hours. The organic solvent was removed under reduced pressure. The resulting mixture was acidified with 2M HCl (0.64 mmol; 320 µL) and extracted into EtOAc (50 mL). The organic layer was washed with brine (2×15 mL) and evaporated to dryness to afford the title compound (149 mg, 92%) as a yellow dry film which was used in the next step without further purification; m/z: ES− [M−H]$^-$ 503.4.

Example 41: (2S,4R)-1-((S)-2-(2-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy) propoxy)acetamido)-3,3-dimethylbutanoyl)-4-hydroxy-N-(4-(4-methylthiazol-5-yl)benzyl) pyrrolidine-2-carboxamide

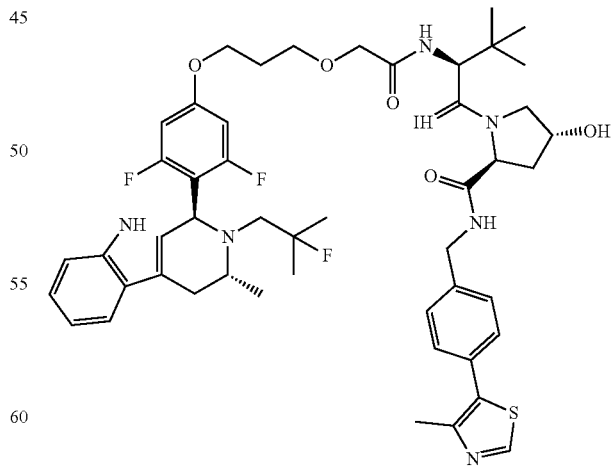

HATU (158 mg, 0.42 mmol) was added to DIPEA (0.145 mL, 0.83 mmol), and 2-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)acetic acid (140 mg, 0.28 mmol) in DMF (0.75 mL) at 20° C. under air. The resulting solution was stirred at 20° C. for 15 minutes. (2S,4R)-1-((S)-2-amino-3,3-dimethylbutanoyl)-4-hydroxy-N-(4-(4-methylthiazol-5-yl)benzyl)pyrrolidine-2-carboxamide, HCl (131 mg, 0.31 mmol) was added and the resulting solution was stirred for 1 hour. The reaction mixture was diluted with EtOAc (10 mL), and washed sequentially with water (15 mL), saturated brine (10 mL), and water (15 mL). The organic layer was dried with MgSO$_4$, filtered and evaporated to afford crude product. The crude product was purified by preparative HPLC (Waters CSH C18 OBD column, 30×100 mm id, 5 micron particle size), using decreasingly polar mixtures of water (containing 1% by volume of NH$_4$OH (28-30% in H$_2$O)) and MeCN as eluents. Fractions containing the desired compound were evaporated to dryness to afford the title compound (173 mg, 68%) as a white solid; $^1$H NMR (400 MHz, CDCl3, 30° C.) 0.93 (9H, s), 1.10 (3H, d), 1.21 (6H, dd), 2.03-2.12 (3H, m), 2.41 (1H, dd), 2.48 (3H, s), 2.5-2.56 (1H, m), 2.60 (1H, dd), 2.78-2.89 (2H, m), 3.06 (1H, dd), 3.59-3.73 (4H, m), 3.79-4.09 (5H, m), 4.29 (1H, dd), 4.53 (3H, dd), 4.68 (1H, t), 5.20 (1H, s), 6.39-6.45 (2H, m), 7.05-7.12 (2H, m), 7.13-7.23 (3H, m), 7.32 (4H, q), 7.50 (1H, m), 7.99 (1H, s), 8.65 (1H, s); m/z: ES+ [M+H]$^+$ 917.5; ESI-HRMS calculated for C$_{49}$H$_{60}$F$_3$N$_6$O$_6$S [M+H]$^+$=917.4242, measured 917.4257.

Intermediate 42a: (1R,3R)-1-(4-(2-Bromoethoxy)-2,6-difluorophenyl)-2-(2-fluoro-2-methylpropyl)-3-methyl-2,3,4,9-tetrahydro-1H-pyrido[3,4-b]indole

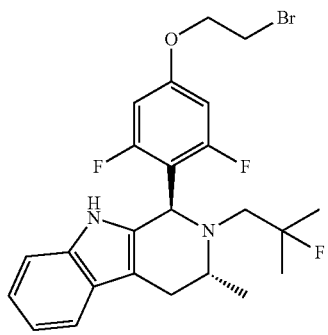 [SMILES: C[C@@H]1Cc2c([nH]c3ccccc23)[C@@H](c2c(F)cc(OCCBr)cc2F)N1CC(C)(C)F]

Diisopropyl azodicarboxylate (0.601 mL, 3.09 mmol) was added slowly to 2-bromoethan-1-ol (0.274 mL, 3.86 mmol), triphenylphosphine (810 mg, 3.09 mmol) and 3,5-difluoro-4-((1R,3R)-2-(2-fluoro-2-methylpropyl)-3-methyl-2,3,4,9-tetrahydro-1H-pyrido[3,4-b]indol-1-yl)phenol (600 mg, 1.54 mmol) in dichloromethane (12 mL) cooled to 0° C. over a period of 5 minutes under nitrogen. The resulting solution was stirred at 20° C. for 2 hours. The reaction mixture was diluted with EtOAc (25 mL), and washed sequentially with saturated aq. NaHCO$_3$ (10 mL), saturated aq. NaHCO$_3$ (5 mL), and saturated brine (2 mL). The organic layer was dried with MgSO$_4$, filtered and evaporated to afford crude product. The crude product was purified by flash silica chromatography, elution gradient 0 to 25% EtOAc in heptane. Product containing fractions were evaporated to dryness to afford impure (1R,3R)-1-(4-(2-bromoethoxy)-2,6-difluorophenyl)-2-(2-fluoro-2-methylpropyl)-3-methyl-2,3,4,9-tetrahydro-1H-pyrido[3,4-b]indole as a brown gum. The crude product was purified by flash silica chromatography, elution gradient 0 to 20% EtOAc in heptane. Pure fractions were evaporated to dryness to afford the title compound (340 mg, 44%) as a pale yellow gum; $^1$H NMR (400 MHz, DMSO-d6, 30° C.) 1.05 (3H, d), 1.1-1.24 (6H, m), 2.29-2.44 (1H, m), 2.56 (1H, dd), 2.75-2.97 (2H, m), 3.52 (1H, q), 3.76-3.82 (2H, m), 4.35 (2H, dd), 5.14 (1H, s), 6.71 (2H, d), 6.91-7.04 (2H, m), 7.15-7.23 (1H, m), 7.40 (1H, d), 10.51 (1H, s); m/z: ES+ [M+H]$^+$ 495.3.

Intermediate 42b: tert-Butyl 2-(2-methoxy-2-oxoethyl)-2,7-diazaspiro[3.5]nonane-7-carboxylate

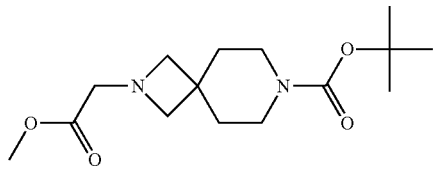 [SMILES: COC(=O)CN1CC2(CCN(C(=O)OC(C)(C)C)CC2)C1]

Methyl 2-bromoacetate (0.341 mL, 3.6 mmol) was added to potassium carbonate (3317 mg, 24 mmol) and tert-butyl 2,7-diazaspiro[3.5]nonane-7-carboxylate hydrochloride (788 mg, 3 mmol) in acetonitrile (12 mL) at 20° C. under nitrogen. The resulting suspension was stirred at 85° C. for 1 hour. The reaction mixture was diluted with EtOAc (75 mL), and washed sequentially with water (20 mL), saturated NaHCO$_3$ (10 mL), and saturated brine (10 mL). The organic layer was dried with MgSO$_4$, filtered and evaporated to afford crude product. The crude product was purified by flash silica chromatography, elution gradient 0 to 7% 1M NH$_3$/MeOH in dichloromethane. Pure fractions were evaporated to dryness to afford the title compound (464 mg, 52%) as a colourless oil. $^1$H NMR (400 MHz, CDCl3, 30° C.) 1.45 (9H, s), 1.67-1.76 (4H, m), 3.18 (4H, s), 3.27-3.38 (6H, m), 3.70 (3H, s). $^{13}$C NMR (101 MHz, CDCl3, 30° C.) 28.44, 34.90, 35.82, 40.98, 51.60, 59.41, 64.33, 79.42, 154.85, 170.77.

Intermediate 42c: Methyl 2-(2,7-diazaspiro[3.5]nonan-2-yl)acetate

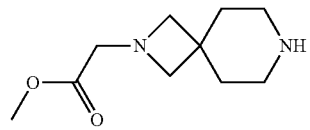

A solution of 6N HCl in isopropanol (5 mL, 30 mmol) was added to tert-butyl 2-(2-methoxy-2-oxoethyl)-2,7-diazaspiro[3.5]nonane-7-carboxylate (459 mg, 1.54 mmol) at 20° C. under air. The resulting suspension was stirred at 20° C. for 4 hours. The reaction mixture was evaporated to dryness. The crude product was purified by ion exchange chromatography, using an SCX column. The desired product was eluted from the column using 1M NH$_3$/MeOH and pure fractions were evaporated to dryness to afford the title compound (297 mg, 97%) as a colourless oil; $^1$H NMR (400 MHz, CDCl3, 30° C.) 1.67-1.76 (4H, m), 2.66-2.82 (4H, m), 3.15 (4H, s), 3.30 (2H, s), 3.70 (3H, s), amine NH not observed.

Intermediate 42d: Methyl 2-(7-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-2,7-diazaspiro[3.5]nonan-2-yl)acetate

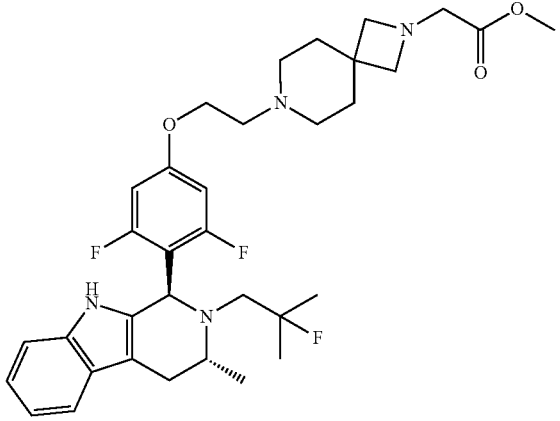 [SMILES: COC(=O)CN1CC2(CCN(CCOc3cc(F)c([C@@H]4c5[nH]c6ccccc6c5C[C@@H](C)N4CC(C)(C)F)c(F)c3)CC2)C1]

Potassium carbonate (279 mg, 2.02 mmol) was added to methyl 2-(2,7-diazaspiro[3.5]nonan-2-yl)acetate (75 mg, 0.38 mmol) and (1R,3R)-1-(4-(2-bromoethoxy)-2,6-difluorophenyl)-2-(2-fluoro-2-methylpropyl)-3-methyl-2,3,4,9-tetrahydro-1H-pyrido[3,4-b]indole (125 mg, 0.25 mmol) in acetonitrile (1 mL) at 20° C. under air. The resulting suspension was stirred at 80° C. for 16 hours. The reaction mixture was diluted with EtOAc (20 mL), and washed sequentially with water (5 mL), saturated NaHCO$_3$ (2×5 mL), and saturated brine (2×5 mL). The organic layer was dried with MgSO$_4$, filtered and evaporated to afford crude product. The crude product was purified by flash silica chromatography, elution gradient 0 to 10% 1M NH$_3$/MeOH in dichloromethane. Pure fractions were evaporated to dryness to afford the title compound (84 mg, 54%) as a white foam; $^1$H NMR (400 MHz, CDCl3, 30° C.) 1.10 (3H, d), 1.20 (6H, dd), 1.79 (4H, t), 2.32-2.5 (5H, m), 2.60 (1H, dd), 2.72 (2H, t), 2.86 (1H, dd), 3.08 (1H, dd), 3.14 (4H, s), 3.30 (2H, s), 3.70 (4H, s), 4.02 (2H, t), 5.19 (1H, s), 6.34-6.47 (2H, m), 7.04-7.14 (2H, m), 7.18-7.24 (1H, m), 7.41 (1H, s), 7.51 (1H, dd); m/z: ES+ [M+H]$^+$ 613.4.

Intermediate 42e: 2-(7-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-2,7-diazaspiro[3.5]nonan-2-yl)acetic Acid

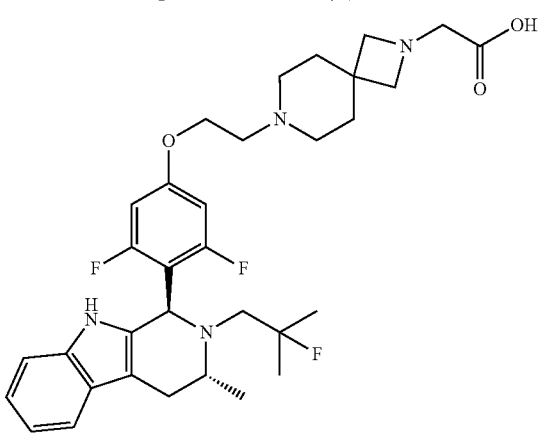

A solution of 2M aq. sodium hydroxide (0.122 mL, 0.24 mmol) was added to methyl 2-(7-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-2,7-diazaspiro[3.5]nonan-2-yl)acetate (75 mg, 0.12 mmol) in methanol (3 mL) at 20° C. under air. The resulting solution was stirred at 20° C. for 1 hour. The reaction was incomplete so the temperature was increased to 65° C. and the reaction mixture was stirred for a further 3 hours. The crude product was purified by ion exchange chromatography, using an SCX column. The desired product was eluted from the column using 1M NH$_3$/MeOH and pure fractions were evaporated to dryness to afford the title compound (62.0 mg, 85%) as a white solid; $^1$H NMR (400 MHz, CDCl3, 30° C.) 1.09 (3H, d), 1.20 (6H, dd), 1.85 (3H, s), 2.39 (4H, q), 2.54-2.64 (2H, m), 2.70 (2H, t), 2.85 (2H, dd), 3.07 (2H, dd), 3.53-3.85 (7H, m), 3.98 (2H, t), 5.19 (1H, s), 6.38 (2H, d), 7.03-7.14 (2H, m), 7.17-7.24 (1H, m), 7.37-7.59 (2H, m); m/z: ES+ [M+H]$^+$ 599.5.

Example 42: (2S,4R)-1-((S)-2-(2-(7-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-2,7-diazaspiro[3.5]nonan-2-yl)acetamido)-3,3-dimethylbutanoyl)-4-hydroxy-N-(4-(4-methylthiazol-5-yl)benzyl)pyrrolidine-2-carboxamide

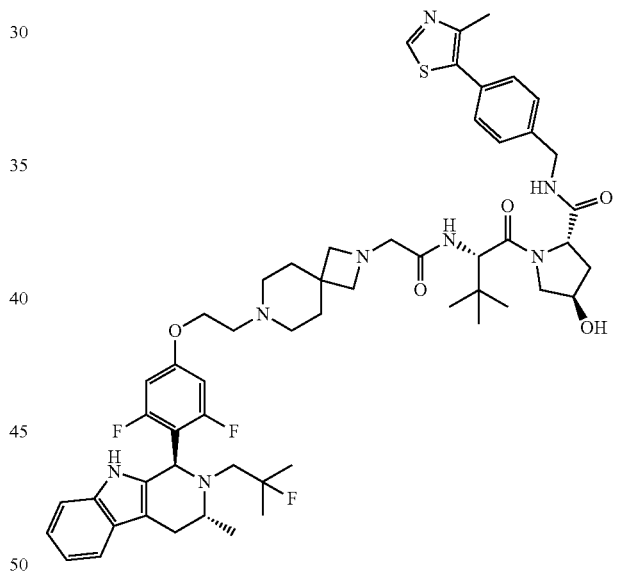

HATU (61.9 mg, 0.16 mmol) was added to 2-(7-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-2,7-diazaspiro[3.5]nonan-2-yl)acetic acid (65 mg, 0.11 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (49.1 mg, 0.11 mmol) and trietylamine (28 mg, 0.28 mmol) in N,N-dimethylformamide (2 mL) at 20° C. under air. The resulting solution was stirred at 20° C. for 1 hour. The reaction mixture was diluted with EtOAc (25 mL), and washed sequentially with 2 M aq. potassium carbonate (3×5 mL) and saturated brine (5 mL). The organic layer was dried with MgSO$_4$, filtered and evaporated to afford crude product. The crude product was purified by preparative HPLC (Waters XSelect CSH C18 column, 5μ silica, 30 mm diameter, 100 mm length), using decreasingly polar mixtures of water (containing 1% by volume of NH₄OH (28-30% in H₂O)) and MeCN as eluents. Fractions containing the desired compound were evaporated to dryness to afford the title compound (49.0 mg, 45%) as a white solid; ¹H NMR (400 MHz, DMSO-d6, 30° C.) 0.94 (9H, s), 1.05 (3H, d), 1.17 (6H, t), 1.67 (4H, t), 1.91 (1H, m), 2.01-2.07 (1H, m), 2.28-2.42 (5H, m), 2.45 (3H, s), 2.54-2.64 (3H, m), 2.78-2.93 (2H, m), 2.99-3.15 (6H, m), 3.47-3.74 (3H, m), 4.05 (2H, t), 4.27 (1H, dd), 4.33-4.54 (4H, m), 5.13 (2H, s), 6.66 (2H, d), 6.97 (2H, m), 7.15-7.23 (1H, m), 7.36-7.46 (5H, m), 7.59 (1H, d), 8.57 (1H, t), 8.97 (1H, s), 10.50 (1H, s); m/z: ES+ [M+H]⁺ 1011.7; ESI-HRMS calculated for $C_{55}H_{70}F_3N_8O_5S$ [M+H]⁺=1011.5136, measured 1011.5137.

Intermediate 43a: tert-Butyl 9-(2-methoxy-2-oxoethyl)-3,9-diazaspiro[5.5]undecane-3-carboxylate

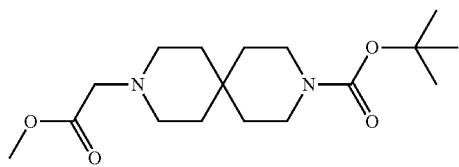 [SMILES: COC(=O)CN1CCC2(CC1)CCN(C(=O)OC(C)(C)C)CC2]

Methyl 2-bromoacetate (0.406 mL, 4.29 mmol) was added to potassium carbonate (3.95 g, 28.61 mmol) and tert-butyl 3,9-diazaspiro[5.5]undecane-3-carboxylate hydrochloride (1.04 g, 3.58 mmol) in acetonitrile (12 mL) at 20° C. under nitrogen. The resulting suspension was stirred at 85° C. for 3 hours. The reaction mixture was diluted with EtOAc (75 mL), and washed sequentially with water (10 mL), saturated NaHCO₃ (10 mL), and saturated brine (5 mL). The organic layer was dried with MgSO₄, filtered and evaporated to afford crude product. The crude product was purified by flash silica chromatography, elution gradient 0 to 5% 1M NH₃/MeOH in dichloromethane. Pure fractions were evaporated to dryness to afford the title compound (1.163 g, 100%) as a colourless oil; ¹H NMR (400 MHz, DMSO-d6, 30° C.) 1.30-1.37 (4H, m), 1.39 (9H, s), 1.40-1.47 (4H, m), 2.4-2.49 (4H, m), 3.21 (2H, s), 3.24-3.30 (4H, m), 3.61 (3H, s).

Intermediate 43b: Methyl 2-(3,9-diazaspiro[5.5]undecan-3-yl)acetate

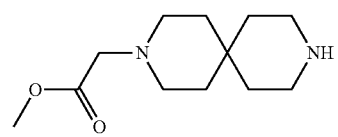

A solution of 6 N HCl in isopropanol (5 mL, 30 mmol) was added to tert-butyl 9-(2-methoxy-2-oxoethyl)-3,9-diazaspiro[5.5]undecane-3-carboxylate (1.16 g, 3.55 mmol) at 20° C. under air. The resulting suspension was stirred at 20° C. for 4 hours. The reaction mixture was evaporated to dryness. The crude product was purified by ion exchange chromatography, using an SCX column. The desired product was eluted from the column using 1M NH₃/MeOH and pure fractions were evaporated to dryness to afford the title compound (0.762 g, 95%) as a colourless oil; ¹H NMR (400 MHz, DMSO-d6, 30° C.) 1.28-1.33 (4H, m), 1.38-1.44 (4H, m), 2.39-2.48 (4H, m), 2.58-2.66 (4H, m), 3.18 (1H, s), 3.19 (2H, s), 3.60 (3H, s).

Intermediate 43c: Methyl 2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-3,9-diazaspiro[5.5]undecan-3-yl)acetate

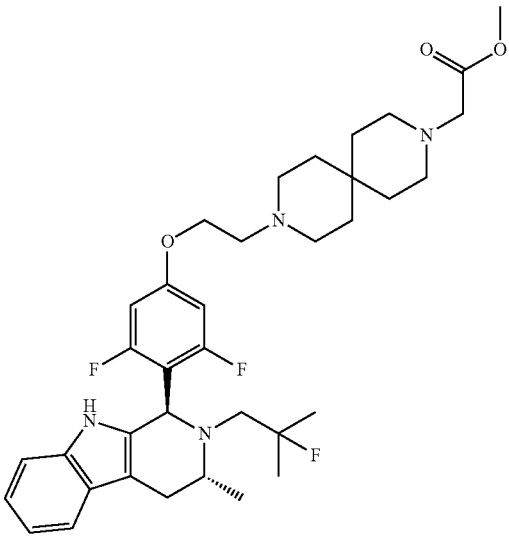 [SMILES: COC(=O)CN1CCC2(CCN(CCOc3cc(F)c([C@@H]4c5[nH]c6ccccc6c5C[C@@H](C)N4CC(C)(C)F)c(F)c3)CC2)CC1]

Methyl 2-(3,9-diazaspiro[5.5]undecan-3-yl)acetate (54.8 mg, 0.24 mmol) was added to potassium carbonate (223 mg, 1.61 mmol) and (1R,3R)-1-(4-(2-bromoethoxy)-2,6-difluorophenyl)-2-(2-fluoro-2-methylpropyl)-3-methyl-2,3,4,9-tetrahydro-1H-pyrido[3,4-b]indole (100 mg, 0.20 mmol) in acetonitrile (4 mL) at 20° C. under air. The resulting suspension was stirred at 80° C. for 18 hours. The reaction mixture was diluted with EtOAc (20 mL), and washed sequentially with water (2×5 mL) and saturated brine (5 mL). The organic layer was dried with MgSO₄, filtered and evaporated to afford crude product. The crude product was purified by flash silica chromatography, elution gradient 0 to 10% 1M NH₃/MeOH in dichloromethane. Pure fractions were evaporated to dryness to afford the title compound (93 mg, 72%) as a white solid; ¹H NMR (400 MHz, DMSO-d6, 30° C.) 1.05 (3H, d), 1.17 (6H, t), 1.34-1.47 (8H, m), 2.29-2.48 (9H, m), 2.57 (1H, d), 2.65 (2H, t), 2.76-2.96 (2H, m), 3.20 (2H, s), 3.52 (1H, d), 3.60 (3H, s), 4.07 (2H, t), 5.13 (1H, s), 6.66 (2H, d), 6.85-7.04 (2H, m), 7.18 (1H, d), 7.40 (1H, d), 10.50 (1H, s); m/z: ES+ [M+H]⁺ 641.6.

Intermediate 43d: 2-(9-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-3,9-diazaspiro[5.5]undecan-3-yl)acetic Acid

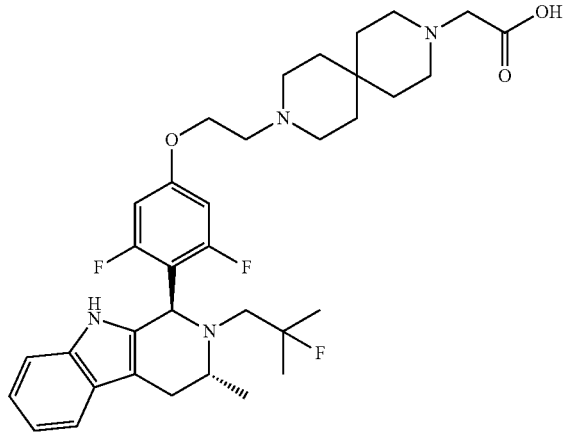 [SMILES: C[C@@H]1Cc2c([nH]c3ccccc23)[C@@H](c2c(F)cc(OCCN3CCC4(CC3)CCN(CC(=O)O)CC4)cc2F)N1CC(C)(C)F]

A solution of 2M aq. sodium hydroxide (0.145 mL, 0.29 mmol) was added to methyl 2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-3,9-diazaspiro[5.5]undecan-3-yl)acetate (93 mg, 0.15 mmol) in methanol (3 mL) at 20° C. under air. The resulting solution was stirred at 60° C. for 2 hours. The crude product was purified by ion exchange chromatography, using an SCX column. The desired product was eluted from the column using 1M $NH_3$/MeOH and pure fractions were evaporated to dryness to afford the title compound (95 mg) as a white solid that was used in the next step without further purification; $^1$H NMR (400 MHz, DMSO-d6, 30° C.) 1.03 (3H, d), 1.15 (6H, t), 1.3-1.6 (8H, m), 2.24-2.44 (6H, m), 2.53 (1H, dd), 2.65 (2H, t), 2.75-2.92 (5H, m), 3.16 (2H, s), 3.49 (1H, m), 4.06 (2H, t), 5.11 (1H, s), 6.64 (2H, d), 6.87-7.02 (2H, m), 7.16 (1H, d), 7.37 (1H, d), 10.49 (1H, s) missing proton thought to be under DMSO-d6; m/z: ES+ [M+H]$^+$ 627.4.

Example 43: (2S,4R)-1-((S)-2-(2-(9-(2-(3,5-difluoro-4-((R,3R)-2-(2-fluoro-2-methylpropyl)-3-methyl-2,3,4,9-tetrahydro-1H-pyrido[3,4-b]indol-1-yl)phenoxy)ethyl)-3,9-diazaspiro[5.5]undecan-3-yl)acetamido)-3,3-dimethylbutanoyl)-4-hydroxy-N-(4-(4-methylthiazol-5-yl)benzyl)pyrrolidine-2-carboxamide

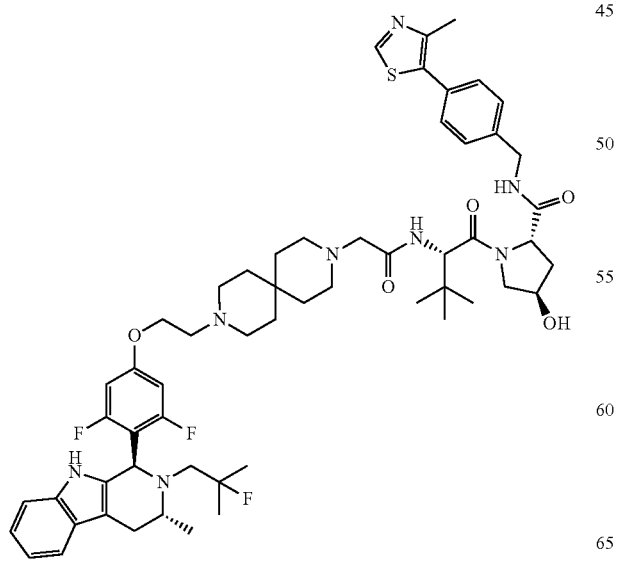

HATU (82 mg, 0.22 mmol) was added to 2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-3,9-diazaspiro[5.5]undecan-3-yl)acetic acid (90 mg, 0.14 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (64.9 mg, 0.15 mmol) and triethylamine (0.050 mL, 0.36 mmol) in N,N-dimethylformamide (1.5 mL) at 20° C. under air. The resulting solution was stirred at 20° C. for 1 hour. The crude reaction mixture was purified by preparative HPLC (Waters XSelect CSH C18 column, 5μ silica, 30 mm diameter, 100 mm length), using decreasingly polar mixtures of water (containing 1% by volume of $NH_4OH$ (28-30% in $H_2O$)) and MeCN as eluents. Fractions containing the desired compound were evaporated to dryness to afford impure (2S,4R)-1-((S)-2-(2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-3,9-diazaspiro[5.5]undecan-3-yl)acetamido)-3,3-dimethylbutanoyl)-4-hydroxy-N-(4-(4-methylthiazol-5-yl)benzyl)pyrrolidine-2-carboxamide (92 mg) as a tan solid. The crude product was purified by preparative HPLC (Waters XSelect CSH C18 column, 30×100 mm id, 5 micron particle size), using decreasingly polar mixtures of water (containing 0.1% formic acid) and MeCN as eluents. Fractions containing the desired compound were evaporated to dryness to afford 56.4 mg of product. The product was dissolved EtOAc (5 mL), and washed sequentially with saturated aq. $NaHCO_3$ (2×1 mL) and saturated brine (1 mL). The organic layer was dried with $MgSO_4$, filtered and evaporated to afford the title compound (45 mg, 30.2%) as a pale yellow solid; $^1$H NMR (400 MHz, DMSO-d6, 30° C.) 0.94 (9H, s), 1.05 (3H, d), 1.1-1.24 (6H, m), 1.42 (8H, d), 1.85-1.95 (1H, m), 2.02-2.12 (1H, m), 2.42 (13H, d), 2.65 (2H, t), 2.76-2.93 (3H, m), 3.01 (1H, d), 3.46-3.72 (3H, m), 4.07 (2H, d), 4.26 (1H, dd), 4.33-4.48 (3H, m), 4.50 (1H, d), 5.12 (2H, d), 6.67 (2H, d), 6.9-7.05 (2H, m), 7.18 (1H, d), 7.34-7.47 (5H, m), 7.79 (1H, d), 8.57 (1H, t), 8.98 (1H, s), 10.50 (1H, s); m/z: ES+ [M+H]$^+$ 1039.8; ESI-HRMS calculated for $C_{57}H_{74}F_3N_8O_5S$ [M+H]$^+$=1039.5450, measured 1039.5413.

Intermediate 44a: 2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetic Acid

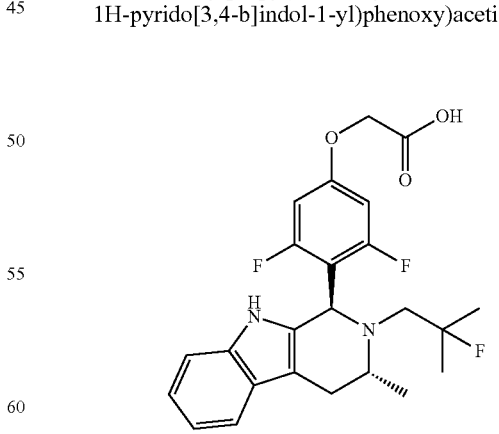

Potassium carbonate (78 mg, 0.57 mmol) was added to 3,5-difluoro-4-((1R,3R)-2-(2-fluoro-2-methylpropyl)-3-methyl-2,3,4,9-tetrahydro-1H-pyrido[3,4-b]indol-1-yl)phenol (100 mg, 0.26 mmol) in acetone (2.5 mL) at 20° C. under air. The resulting suspension was stirred at 40° C. for 15 minutes. A solution of bromoacetic acid (37 mg, 0.27 mmol) in acetone (0.25 mL) was added. The resulting suspension was stirred at 60° C. for 1 day. The reaction was incomplete and further bromoacetic acid (37 mg, 0.27 mmol) and potassium carbonate (78 mg, 0.57 mmol) were added and the suspension was stirred at 60° C. for a further 1 day. The reaction mixture was diluted with water (5 mL) and purified by ion exchange chromatography, using an SCX column. The desired product was eluted from the column using 1M $NH_3$/MeOH and pure fractions were evaporated to dryness to afford 2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetic acid (105 mg, 91%) as a yellow solid that was used in the next step without further purification; m/z: ES+ $[M+H]^+$ 447.3.

Intermediate 44b: Methyl 2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetyl)-3,9-diazaspiro[5.5]undecan-3-yl)acetate

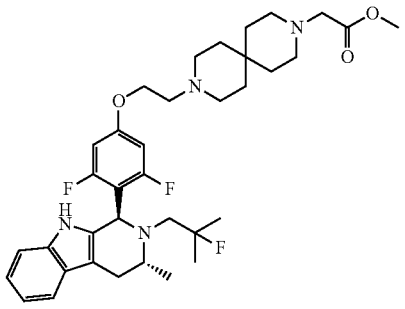 [SMILES: COC(=O)CN1CCC2(CCN(CCOc3cc(F)c([C@@H]4c5[nH]c6ccccc6c5C[C@@H](C)N4CC(C)(C)F)c(F)c3)CC2)CC1]

HATU (116 mg, 0.31 mmol) was added to 2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetic acid (105 mg, 0.24 mmol), methyl 2-(3,9-diazaspiro[5.5]undecan-3-yl)acetate (63.9 mg, 0.28 mmol) and triethylamine (0.049 mL, 0.35 mmol) in dichloromethane (3.5 mL) at 20° C. under air. The resulting solution was stirred at 20° C. for 3 hours. The reaction mixture was diluted with EtOAc (25 mL), and washed sequentially with water (5 mL), saturated aq. $NaHCO_3$ (2×5 mL), and saturated brine (2 mL). The organic layer was dried with $MgSO_4$, filtered and evaporated to afford crude product. The crude product was purified by flash silica chromatography, elution gradient 0 to 5% 1M $NH_3$/MeOH in dichloromethane. Pure fractions were evaporated to dryness to afford the title compound (111 mg, 72%) as a yellow solid that was used in the next step without further purification; m/z: ES+ $[M+H]^+$ 655.5.

Intermediate 44c: 2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetyl)-3,9-diazaspiro[5.5]undecan-3-yl)acetic Acid

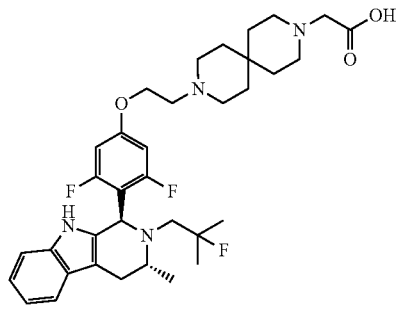 [SMILES: C[C@@H]1Cc2c([nH]c3ccccc23)[C@@H](c2c(F)cc(OCCN3CCC4(CC3)CCN(CC(=O)O)CC4)cc2F)N1CC(C)(C)F]

A solution of 2M aq. Sodium hydroxide (0.170 mL, 0.34 mmol) was added to methyl 2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetyl)-3,9-diazaspiro[5.5]undecan-3-yl)acetate (111 mg, 0.17 mmol) in methanol (3 mL) at 20° C. under air. The resulting solution was stirred at 60° C. for 2 hours. The crude product was purified by ion exchange chromatography, using an SCX column. The desired product was eluted from the column using 1M $NH_3$/MeOH and pure fractions were evaporated to dryness to afford the title compound (103 mg, 95%) as a solid that was used in the next step without further purification; m/z: ES+ $[M+H]^+$ 641.6.

Example 44: (2S,4R)-1-((S)-2-(2-(9-(2-(3,5-difluoro-4-((R,3R)-2-(2-fluoro-2-methylpropyl)-3-methyl-2,3,4,9-tetrahydro-1H-pyrido[3,4-b]indol-1-yl)phenoxy)acetyl)-3,9-diazaspiro[5.5]undecan-3-yl)acetamido)-3,3-dimethylbutanoyl)-4-hydroxy-N-(4-(4-methylthiazol-5-yl)benzyl)pyrrolidine-2-carboxamide

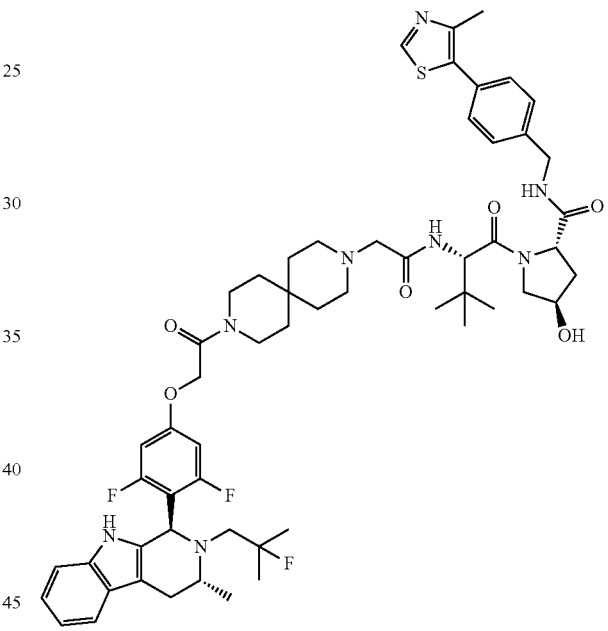

HATU (92 mg, 0.24 mmol) was added to 2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetyl)-3,9-diazaspiro[5.5]undecan-3-yl)acetic acid (103 mg, 0.16 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (72.7 mg, 0.17 mmol) and triethylamine (0.056 mL, 0.40 mmol) in N,N-dimethylformamide (1.5 mL) at 20° C. under air. The resulting solution was stirred at 20° C. for 1 hour. The crude product was purified by preparative HPLC (Waters XSelect CSH C18 column, 5µ silica, 30 mm diameter, 100 mm length), using decreasingly polar mixtures of water (containing 1% by volume of $NH_4OH$ (28-30% in $H_2O$)) and MeCN as eluents. Fractions containing the desired compound were evaporated to dryness to afford impure (2S,4R)-1-((S)-2-(2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetyl)-3,9-diazaspiro[5.5]undecan-3-yl)acetamido)-3,3-dimethylbutanoyl)-4-hydroxy-N-(4-(4-methylthiazol-5-yl)

benzyl)pyrrolidine-2-carboxamide. The crude product was purified by preparative HPLC (Waters XSelect CSH C18 column, 30×100 mm id, 5 micron particle size), using decreasingly polar mixtures of water (containing 0.1% formic acid) and MeCN as eluents. Fractions containing the desired compound were evaporated to dryness to afford the title compound (21.00 mg, 12.40%) as a brown solid; $^1$H NMR (400 MHz, DMSO-d6, 30° C.) 0.94 (10H, d), 1.05 (3H, d), 1.11-1.28 (7H, m), 1.31-1.59 (9H, m), 1.91 (1H, m), 2.01-2.11 (1H, m), 2.46 (6H, d), 2.76-3.08 (4H, m), 3.32-3.56 (5H, m), 3.60 (1H, d), 3.67 (1H, dd), 4.28 (1H, dd), 4.32-4.48 (3H, m), 4.51 (1H, d), 4.85 (2H, s), 5.1-5.18 (2H, m), 6.65 (2H, d), 6.92-7.05 (2H, m), 7.19 (1H, d), 7.35-7.45 (5H, m), 7.77 (1H, d), 8.57 (1H, t), 8.98 (1H, d), 10.55 (1H, s); m/z: ES+ [M+H]$^+$ 1053.8; ESI-HRMS calculated for $C_{57}H_{72}F_3N_8O_6S$ [M+H]$^+$=1053.5242, measured 1053.5215.

Intermediate 45a: Ethyl 2-((5-((tert-butoxycarbonyl)amino)pentyl)oxy)acetate

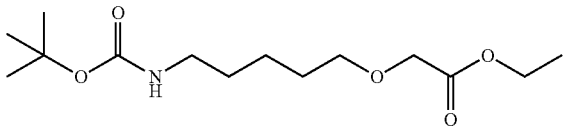 [SMILES: CCOC(=O)COCCCCCNC(=O)OC(C)(C)C]

A solution of ethyl diazoacetate (2.74 mL, 21.6 mmol) in dichloromethane (10 mL) was added dropwise to a stirred suspension of 5-(Boc-amino)-1-pentanol (4.0 mL, 19.7 mmol) and rhodium(II) acetate dimer (0.087 g, 0.20 mmol) in dichloromethane (10 mL) cooled to 0° C., over a period of 20 minutes under air. The resulting suspension was stirred at 20° C. for 1 hour. The reaction was incomplete, the mixture was cooled to 0 C and further ethyl diazoacetate (2.74 mL, 21.6 mmol) dissolved in dichloromethane was added dropwise over 20 min and the solution was stirred at 20° C. for a further 1 hour. The reaction mixture was evaporated to dryness and purified by flash silica chromatography, elution gradient 0 to 35% EtOAc in heptane. Pure fractions were evaporated to dryness to afford the title compound (4.61 g, 81%) as a colourless oil; $^1$H NMR (400 MHz, DMSO-d6, 30° C.) 1.20 (3H, t), 1.24-1.32 (2H, m), 1.32-1.42 (11H, m), 1.50 (2H, m), 2.90 (2H, q), 3.43 (2H, t), 4.05 (2H, s), 4.12 (2H, q), 6.73 (1H, s).

Intermediate 45b: Ethyl 2-((5-aminopentyl)oxy)acetate

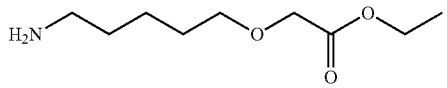

Trifluoroacetic acid (1 mL, 13 mmol) was added to ethyl 2-((5-((tert-butoxycarbonyl)amino)pentyl)oxy)acetate (1.01 g, 3.49 mmol) in dichloromethane (5 mL) at 20° C. under air. The resulting solution was stirred at 20° C. for 30 minutes. The reaction was incomplete and further trifluoroacetic acid (2 mL, 26 mmol) were added and the solution was stirred at 20° C. for a further 1 hour. The resulting mixture was evaporated to dryness and the residue dissolved in 1M NH$_3$/MeOH (10 mL). The resulting mixture was evaporated to dryness. The crude product was purified by flash silica chromatography, elution gradient 2 to 20% 1M NH$_3$/MeOH in dichloromethane. Pure fractions were evaporated to dryness to afford the title compound (0.672 g) as a colourless oil that was used in the next step without further purification; $^1$H NMR (400 MHz, DMSO-d6, 30° C.) 1.21 (3H, t), 1.3-1.41 (2H, m), 1.45-1.61 (4H, m), 2.69-2.77 (2H, m), 3.45 (2H, t), 4.07 (2H, s), 4.12 (2H, q), 6.32 (2H, br.s).

Intermediate 45c: Ethyl 2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetate

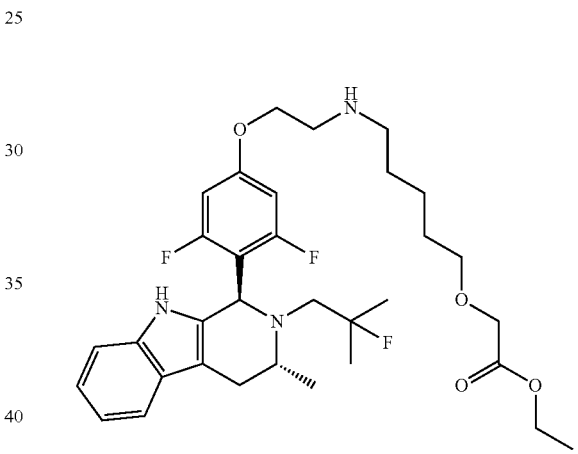

Ethyl 2-((5-aminopentyl)oxy)acetate (218 mg, 1.04 mmol) was added to (1R,3R)-1-(4-(2-bromoethoxy)-2,6-difluorophenyl)-2-(2-fluoro-2-methylpropyl)-3-methyl-2,3,4,9-tetrahydro-1H-pyrido[3,4-b]indole (343 mg, 0.69 mmol) and potassium carbonate (766 mg, 5.54 mmol) in acetonitrile (8 mL) at 20° C. under air. The resulting suspension was stirred at 80° C. for 24 hours. The reaction mixture was filtered through a sintered glass funnel rinsing with MeCN (10 mL). The filtrate was evaporated to dryness. The crude product was dry loaded on to silica and purified by flash silica chromatography, elution gradient 0 to 8% 1M NH$_3$/MeOH in dichloromethane. Pure fractions were evaporated to dryness to afford the title compound (224 mg, 54%) as a pale yellow gum; $^1$H NMR (400 MHz, DMSO-d6, 30° C.) 1.05 (3H, d), 1.1-1.24 (9H, m), 1.27-1.37 (2H, m), 1.41 (2H, q), 1.51 (2H, p), 1.71 (1H, s), 2.29-2.41 (1H, m), 2.55 (2H, d), 2.76-2.95 (4H, m), 3.44 (2H, t), 3.52 (1H, q), 4.02 (2H, t), 4.05 (2H, s), 4.11 (2H, q), 5.13 (1H, s), 6.66 (2H, d), 6.97 (2H, m), 7.16-7.22 (1H, m), 7.40 (1H, d), 10.50 (1H, s). m/z: ES+ [M+H]$^+$ 604.6.

Intermediate 45d: Ethyl 2-((5-(((benzyloxy)carbonyl)(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetate

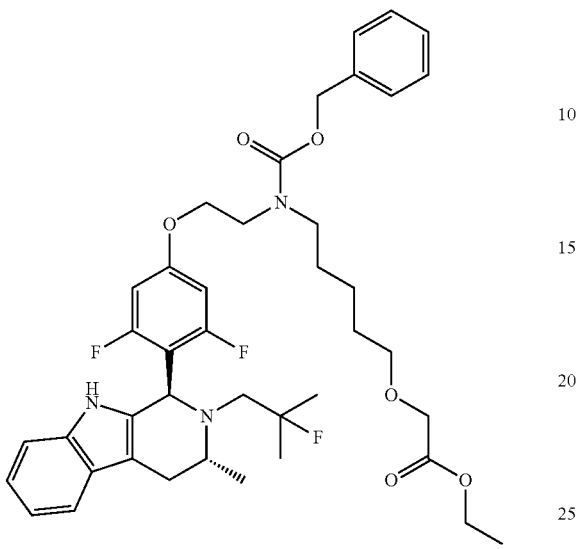

Benzyl chloroformate (0.018 mL, 0.13 mmol) was added to ethyl 2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetate (73 mg, 0.12 mmol) and potassium carbonate (33.4 mg, 0.24 mmol) in acetonitrile (2 mL) at 20° C. under air. The resulting suspension was stirred at 20° C. for 3 hours. The reaction mixture was diluted with EtOAc (10 mL), and washed sequentially with water (2×2 mL) and saturated brine (2 mL). The organic layer was dried with MgSO₄, filtered and evaporated to afford the title compound (61.0 mg, 68%) as a yellow gum that was used in the next step without further purification; m/z: ES+ [M+H]⁺ 738.7.

Intermediate 45e: 2-((5-(((Benzyloxy)carbonyl)(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetic Acid, Hydrochloride

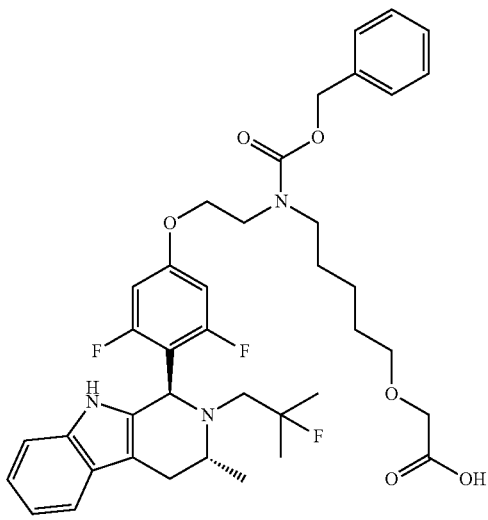 [SMILES: C[C@@H]1Cc2c([nH]c3ccccc23)[C@@H](c2c(F)cc(OCCN(CCCCCOCC(=O)O)C(=O)OCc3ccccc3)cc2F)N1CC(C)(C)F]

A solution of 2 M aq. sodium hydroxide (0.083 mL, 0.17 mmol) was added to ethyl 2-((5-(((benzyloxy)carbonyl)(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetate (61 mg, 0.08 mmol) in methanol (2 mL) at 20° C. under air. The resulting solution was stirred at 60° C. for 20 minutes. The resulting mixture was evaporated to dryness. 4 M hydrogen chloride in dioxane (0.083 mL, 0.33 mmol) was added and the mixture evaporated to dryness to afford the title compound (65 mg) as a yellow solid that was used in the next step without further purification; m/z: ES+ [M+H]⁺ 710.6.

Example 45: Benzyl (2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(5-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)pentyl)carbamate

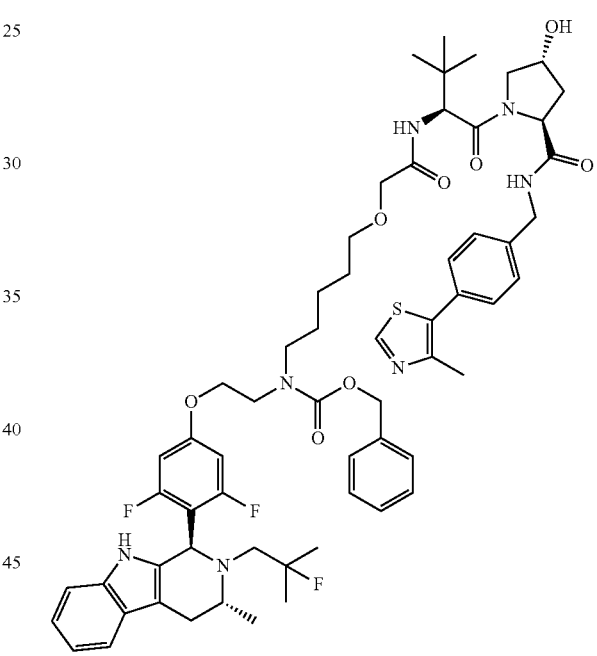

HATU (47.4 mg, 0.12 mmol) was added to 2-((5-(((benzyloxy)carbonyl)(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetic acid, 2HCl (65 mg, 0.08 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (37.5 mg, 0.09 mmol) and triethylamine (0.052 mL, 0.37 mmol) in N,N-dimethylformamide (1.5 mL) at 20° C. under air. The resulting solution was stirred at 20° C. for 1 hour. The crude product was purified by preparative HPLC (Waters XSelect CSH C18 column, 5μ silica, 30 mm diameter, 100 mm length), using decreasingly polar mixtures of water (containing 1% by volume of NH₄OH (28-30% in H₂O)) and MeCN as eluents. Fractions containing the desired compound were evaporated to dryness to afford the title compound (37.0 mg, 40%) as a grey solid; $^1$H NMR (400 MHz, DMSO-d6, 30° C.) 0.93 (9H, d), 1.04 (3H, d), 1.16 (6H, t), 1.29 (3H, s), 1.52 (4H, d), 1.91 (1H, m), 2.08 (1H, s), 2.26-2.47 (5H, m), 2.53-2.59 (1H, m), 2.73-2.97 (2H, m), 3.26 (1H, s), 3.38-3.72 (7H, m), 3.89 (2H, s), 4.09 (2H, s), 4.27 (1H, dd), 4.32-4.49 (3H, m), 4.56 (1H, d), 5.07 (2H, s), 5.13 (2H, d), 6.48-6.71 (2H, m), 6.97 (2H, m), 7.18 (1H, d), 7.26-7.5 (10H, m), 8.56 (1H, t), 8.96 (1H, s), 10.49 (1H, s); m/z: ES+ [M+H]$^+$ 1122.8; ESI-HRMS calculated for $C_{61}H_{75}F_3N_7O_8S$ [M+H]$^+$=1122.5344, measured 1122.5320.

Intermediate 46a: tert-Butyl 3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)azetidine-1-carboxylate

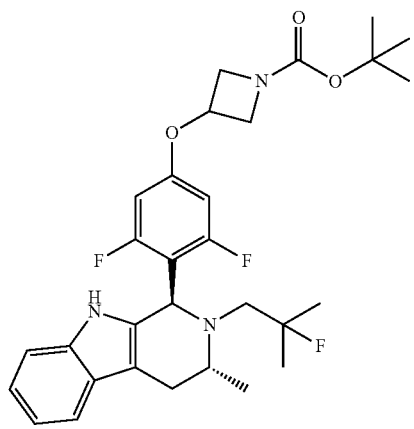 [SMILES: C[C@@H]1Cc2c([nH]c3ccccc23)[C@@H](c2c(F)cc(OC3CN(C(=O)OC(C)(C)C)C3)cc2F)N1CC(C)(C)F]

(1R,3R)-1-(4-Bromo-2,6-difluorophenyl)-2-(2-fluoro-2-methylpropyl)-3-methyl-2,3,4,9-tetrahydro-1H-pyrido[3,4-b]indole, HCl (200 mg, 0.41 mmol), cesium carbonate (468 mg, 1.44 mmol), RockPhos Pd G3 (17.21 mg, 0.02 mmol) and tert-butyl 3-hydroxyazetidine-1-carboxylate (142 mg, 0.82 mmol) were suspended in toluene (3 mL), sealed into a microwave tube and vacuum degassed, backfilling with nitrogen. The reaction was heated to 90° C. for 4 hours in the microwave reactor and cooled to RT. The reaction mixture was diluted with EtOAc (15 mL), and washed sequentially with water (3×2 mL) and saturated brine (2×2 mL). The organic layer was dried with MgSO$_4$, filtered and evaporated to afford crude product. The crude product was purified by flash silica chromatography, elution gradient 0 to 30% EtOAc in heptane. Pure fractions were evaporated to dryness to afford the title compound (137 mg, 62%) as a pale yellow solid; $^1$H NMR (400 MHz, DMSO-d6, 30° C.) 1.05 (3H, d), 1.15-1.21 (6H, m), 1.39 (9H, s), 2.27-2.4 (1H, m), 2.54-2.6 (1H, m), 2.87 (2H, m), 3.45-3.58 (1H, m), 3.78 (2H, dd), 4.31 (2H, t), 5.02 (1H, m), 5.14 (1H, s), 6.59 (2H, d), 6.9-7.03 (2H, m), 7.13-7.25 (1H, m), 7.37-7.43 (1H, m), 10.50 (1H, d); m/z: ES+ [M+H]$^+$ 544.5.

Intermediate 46b: (1R,3R)-1-(4-(azetidin-3-yloxy)-2,6-difluorophenyl)-2-(2-fluoro-2-methylpropyl)-3-methyl-2,3,4,9-tetrahydro-1H-pyrido[3,4-b]indole

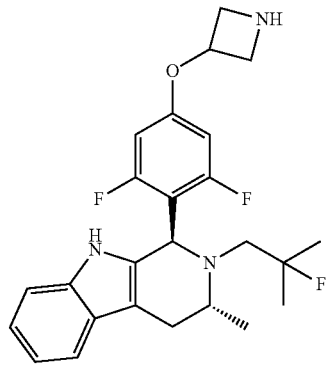 [SMILES: C[C@@H]1Cc2c([nH]c3ccccc23)[C@@H](c2c(F)cc(OC3CNC3)cc2F)N1CC(C)(C)F]

A solution of 6 N HCl in IPA (3 mL, 18.00 mmol) was added to tert-butyl 3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)azetidine-1-carboxylate (134 mg, 0.25 mmol) at 20° C. under air. The resulting suspension was stirred at 20° C. for 2 hours. The reaction mixture was diluted with EtOAc (50 mL) and sat. aq. NaHCO$_3$ (25 mL), the layers were separated, and the aqueous layer was extracted with (EtOAc) (3×25 mL). The organic layer was dried with MgSO$_4$, filtered and evaporated to afford crude product. The crude product was purified by flash silica chromatography, elution gradient 0 to 10% 1M NH$_3$/MeOH in dichloromethane. Pure fractions were evaporated to dryness to afford the title compound (60.0 mg, 55%) as a pale yellow solid; $^1$H NMR (400 MHz, DMSO-d6, 30° C.) 1.10 (3H, d), 1.15-1.3 (6H, m), 2.32-2.46 (1H, m), 2.59-2.65 (1H, m), 2.82-2.98 (2H, m), 3.46-3.6 (3H, m), 3.81 (2H, d), 5.05 (1H, p), 5.18 (1H, s), 6.58 (2H, d), 6.93-7.1 (2H, m), 7.2-7.28 (1H, m), 7.45 (1H, d), 10.57 (1H, s), basic NH not observed; m/z: ES– [M–H]$^-$ 442.3.

Intermediate 46c: Ethyl 2-((5-oxopentyl)oxy)acetate

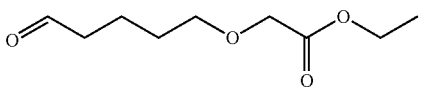

Dess-Martin periodinane (564 mg, 1.33 mmol) was added to ethyl 2-((5-hydroxypentyl)oxy)acetate (230 mg, 1.21 mmol) in dichloromethane (4 mL) at 20° C. under air. The resulting suspension was stirred at 20° C. for 1 hour. The reaction mixture was filtered through sintered glass funnel and the filtrate evaporated to dryness. The crude product was purified by flash silica chromatography, elution gradient 5 to 35% EtOAc in heptane. Pure fractions were evaporated to dryness to afford the title compound (182 mg, 80%) as a colourless oil; $^1$H NMR (400 MHz, DMSO-d6, 30° C.) 1.21 (3H, t), 1.52-1.6 (4H, m), 2.46 (2H, m), 3.45 (2H, t), 4.06 (2H, s), 4.12 (2H, q), 9.68 (1H, t).

225

Intermediate 46d: Ethyl 2-((5-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)azetidin-1-yl)pentyl)oxy)acetate

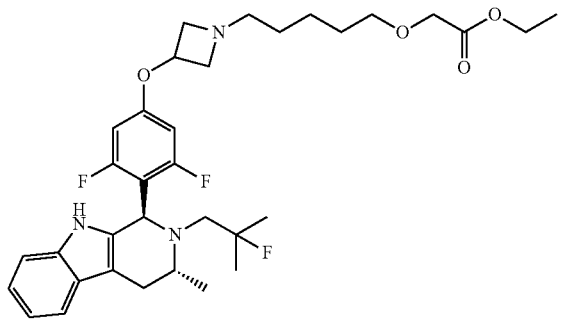 [SMILES: CCOC(=O)COCCCCCN1CC(Oc2cc(F)c([C@@H]3c4[nH]c5ccccc5c4C[C@@H](C)N3CC(C)(C)F)c(F)c2)C1]

Sodium triacetoxyborohydride (57.3 mg, 0.27 mmol) was added to acetic acid (0.015 mL, 0.27 mmol), (1R,3R)-1-(4-(azetidin-3-yloxy)-2,6-difluorophenyl)-2-(2-fluoro-2-methylpropyl)-3-methyl-2,3,4,9-tetrahydro-1H-pyrido[3,4-b]indole (60 mg, 0.14 mmol) and ethyl 2-((5-oxopentyl)oxy)acetate (60 mg, 0.27 mmol) in dichloromethane (2 mL) at 20° C. under air. The resulting suspension was stirred at 20° C. for 16 hours. The reaction mixture was diluted with EtOAc (15 mL), and washed sequentially with saturated Na₂CO₃ (3×2 mL) and saturated brine (5 mL). The organic layer was dried with MgSO₄, filtered and evaporated to afford crude product. The crude product was purified by flash silica chromatography, elution gradient 0 to 10% 1M NH₃/MeOH in dichloromethane. Pure fractions were evaporated to dryness to afford the title compound (64.0 mg, 77%) as a pale yellow oil that was used in the next step without further purification; m/z: ES+ [M+H]⁺ 616.4.

226

Intermediate 46e: 2-((5-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)azetidin-1-yl)pentyl)oxy)acetic Acid

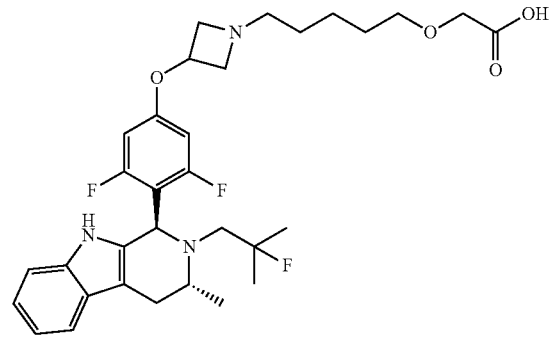 [SMILES: C[C@@H]1Cc2c([nH]c3ccccc23)[C@@H](c2c(F)cc(OC3CN(CCCCCOCC(=O)O)C3)cc2F)N1CC(C)(C)F]

A solution of 2 M aq. sodium hydroxide (0.097 mL, 0.19 mmol) was added to ethyl 2-((5-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)azetidin-1-yl)pentyl)oxy)acetate (60 mg, 0.10 mmol) in methanol (1 mL) at 20° C. under air. The resulting solution was stirred at 20° C. for 3 hours. 2 M aq. HCl (0.097 mL, 0.19 mmol) was added and the reaction mixture evaporated to dryness to afford the title compound (57.3 mg, 100%) as a yellow solid that was used in the next step without further purification; m/z: ES+ [M+H]⁺ 588.5.

Example 46: (2S,4R)-1-((S)-2-(2-((5-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)azetidin-1-yl)pentyl)oxy)acetamido)-3,3-dimethylbutanoyl)-4-hydroxy-N-(4-(4-methylthiazol-5-yl)benzyl)pyrrolidine-2-carboxamide

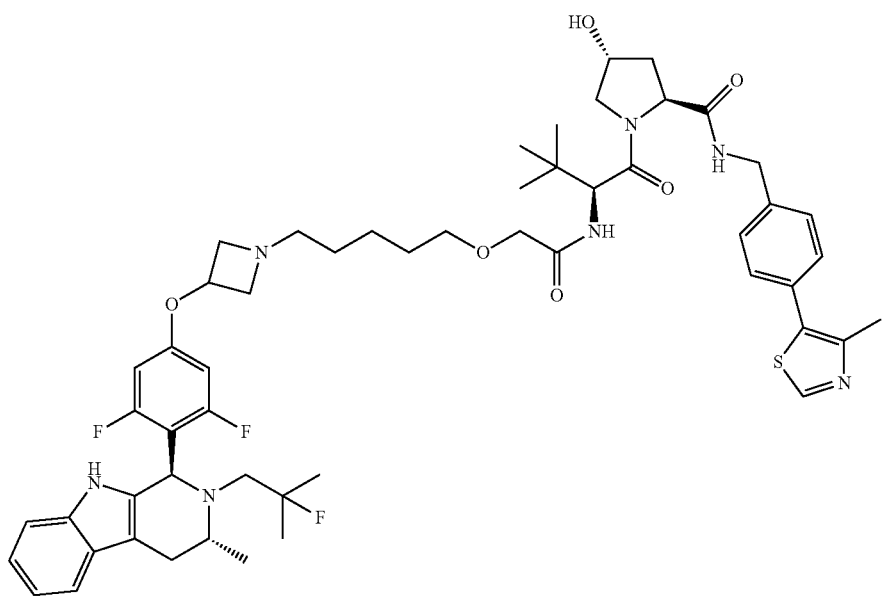 [SMILES: Cc1ncsc1-c1ccc(CNC(=O)[C@@H]2C[C@@H](O)CN2C(=O)[C@@H](NC(=O)COCCCCCN2CC(Oc3cc(F)c([C@@H]4c5[nH]c6ccccc6c5C[C@@H](C)N4CC(C)(C)F)c(F)c3)C2)C(C)(C)C)cc1]

HATU (55.3 mg, 0.15 mmol) was added to 2-((5-(3-(3, 5-difluoro-4-((1R,3R)-2-(2-fluoro-2-methylpropyl)-3-methyl-2,3,4,9-tetrahydro-1H-pyrido[3,4-b]indol-1-yl)phenoxy)azetidin-1-yl)pentyl)oxy)acetic acid (57 mg, 0.10 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (43.8 mg, 0.10 mmol) and triethylamine (0.034 mL, 0.24 mmol) in N,N-dimethylformamide (1.5 mL) at 20° C. under air. The resulting suspension was stirred at 20° C. for 16 hours. The reaction was incomplete and further (2S,4R)-1-((S)-2-amino-3,3-dimethylbutanoyl)-4-hydroxy-N-(4-(4-methylthiazol-5-yl)benzyl)pyrrolidine-2-carboxamide, HCl (43.8 mg, 0.10 mmol), triethylamine (0.034 mL, 0.24 mmol) and HATU (55.3 mg, 0.15 mmol) were added and the suspension was stirred at 20° C. for a further 1 hour. The crude reaction mixture was purified by preparative HPLC (Waters XSelect CSH C18 column, 5µ silica, 30 mm diameter, 100 mm length), using decreasingly polar mixtures of water (containing 1% by volume of $NH_4OH$ (28-30% in $H_2O$)) and MeCN as eluents. Fractions containing the desired compound were evaporated to dryness to afford the title compound (14.00 mg, 14.43%) as a grey solid.

$^1$H NMR (400 MHz, DMSO-d6, 30° C.) 0.94 (9H, d), 1.01-1.07 (3H, m), 1.08-1.41 (12H, m), 1.48-1.6 (2H, m), 1.82-2.12 (3H, m), 2.37-2.46 (5H, m), 2.83-2.92 (3H, m), 3.42-3.54 (3H, m), 3.56-3.72 (4H, m), 3.91 (2H, s), 4.26 (1H, dd), 4.33-4.49 (3H, m), 4.56 (1H, d), 4.74-4.86 (1H, m), 5.14 (2H, d), 6.54 (2H, d), 6.97 (2H, m), 7.18 (1H, d), 7.33 (1H, d), 7.37-7.49 (5H, m), 8.57 (1H, t), 8.97 (1H, s), 10.51 (1H, s); m/z: ES+ [M+H]$^+$ 1000.7; ESI-HRMS calculated for $C_{54}H_{69}F_3N_7O_6S$ [M+H]$^+$=1000.4977, measured 1000.4970.

Intermediate 47a: tert-Butyl 3-(3-(benzyloxy)propylidene)azetidine-1-carboxylate

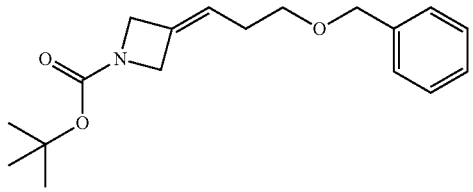 [SMILES: CC(C)(C)OC(=O)N1CC(=CCCOCc2ccccc2)C1]

A solution of 1.6 M n-Butyllithium in hexanes (2.63 mL, 4.21 mmol) was added dropwise to (3-(benzyloxy)propyl)triphenylphosphonium bromide (2069 mg, 4.21 mmol) in THF (10 mL) cooled to 0° C. over a period of 10 minutes under nitrogen. The resulting suspension was stirred at 20° C. for 20 minutes. N-Boc-3-oxoazetidine (361 mg, 2.11 mmol) dissolved in THF (5 mL) was added dropwise to the reaction mixture over 1 minute. The resulting suspension was stirred at 20° C. for 3 hours. The reaction mixture was diluted with aq. saturated $NH_4Cl$ (10 mL) and dichloromethane (100 mL), the layers were separated, and the aqueous layer was extracted with (dichloromethane×15 mL). The combined organic layers were dried with $MgSO_4$, filtered and evaporated to afford crude product. The crude product was purified by flash silica chromatography, elution gradient 0 to 20% EtOAc in heptane. Pure fractions were evaporated to dryness to afford the title compound (469 mg, 73%) as a colourless liquid; $^1$H NMR (400 MHz, DMSO-d6, 30° C.) 1.39 (9H, s), 2.16 (2H, q), 3.45 (2H, t), 4.38 (4H, d), 4.46 (2H, s), 5.37 (1H, m), 7.24-7.4 (5H, m); m/z: ES+ [M+H]$^+$ 304.3.

Intermediate 47b: tert-Butyl 3-(3-hydroxypropyl)azetidine-1-carboxylate

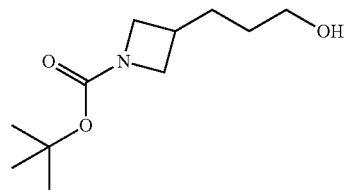

10% Palladium on carbon (164 mg, 0.15 mmol) was added to tert-butyl 3-(3-(benzyloxy)propylidene)azetidine-1-carboxylate (467 mg, 1.54 mmol) in ethanol (8 mL) at 20° C. under hydrogen. The resulting suspension was stirred at 20° C. for 16 hours. The reaction mixture was filtered through celite and the filtrate evaporated to afford crude product. The crude product was purified by flash silica chromatography, elution gradient 50 to 100% EtOAc in heptane. Pure fractions were evaporated to dryness to afford the title compound (305 mg, 92%) as a colourless oil; $^1$H NMR (400 MHz, DMSO-d6, 30° C.) 1.28-1.41 (11H, m), 1.47-1.6 (2H, m), 2.4-2.49 (1H, m), 3.33-3.49 (4H, m), 3.89 (2H, t), 4.36 (1H, t); m/z: ES+ [M+H]$^+$ 216.2.

Intermediate 47c: tert-Butyl 3-(3-(2-ethoxy-2-oxoethoxy)propyl)azetidine-1-carboxylate

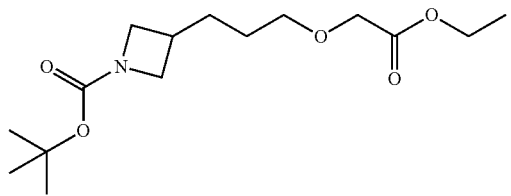 [SMILES: CCOC(=O)COCCCC1CN(C(=O)OC(C)(C)C)C1]

A solution of ethyl diazoacetate (163 mg, 1.19 mmol) in dichloromethane (1 mL) was added dropwise to a stirred suspension of tert-butyl 3-(3-hydroxypropyl)azetidine-1-carboxylate (128 mg, 0.59 mmol) and Rhodium(II) acetate dimer (13.14 mg, 0.03 mmol) in dichloromethane (1 mL) at 20° C., over a period of 2 minutes under air. The resulting suspension was stirred at 20° C. for 30 minutes. The reaction was incomplete and further ethyl diazoacetate (231 mg, 1.69 mmol) was added and the suspension was stirred at 20° C. for a further 20 minutes. The reaction mixture was diluted with EtOAc (15 mL), and washed sequentially with water (2×2 mL) and saturated brine (2 mL). The organic layer was dried with $MgSO_4$, filtered and evaporated to afford crude product. The crude product was purified by flash silica chromatography, elution gradient 0 to 35% EtOAc in heptane. Pure fractions were evaporated to dryness to afford the title compound (121 mg, 68%) as a colourless oil; $^1$H NMR (400 MHz, DMSO-d6, 30° C.) 1.21 (4H, t), 1.37 (9H, s), 1.4-1.51 (2H, m), 1.51-1.64 (2H, m), 3.43 (4H, t), 3.89 (2H, t), 4.06 (2H, s), 4.12 (2H, q).

Intermediate 47d: tert-Butyl 3-(3-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)propyl)azetidine-1-carboxylate mL). The organic layer was dried with MgSO$_4$, filtered and evaporated to afford the title compound (201 mg, 74%) as a white foam; $^1$H NMR (400 MHz, DMSO-d6, 30° C.) 0.94 (9H, d), 1.36 (9H, d), 1.44-1.67 (4H, m), 1.91 (1H, m), 2.02-2.11 (1H, m), 2.46 (3H, s), 2.70 (1H, s), 3.39-3.51 (4H, m), 3.58-3.71 (2H, m), 3.84-3.95 (4H, m), 4.27 (1H, dd), 4.32-4.49 (3H, m), 4.56 (1H, d), 5.13 (1H, d), 7.31-7.47 (5H, m), 8.57 (1H, t), 8.99 (1H, d); m/z: ES+ [M+H]$^+$ 686.5.

Intermediate 47e: (2S,4R)-1-((S)-2-(2-(3-(azetidin-3-yl)propoxy)acetamido)-3,3-dimethylbutanoyl)-4-hydroxy-N-(4-(4-methylthiazol-5-yl)benzyl)pyrrolidine-2-carboxamide

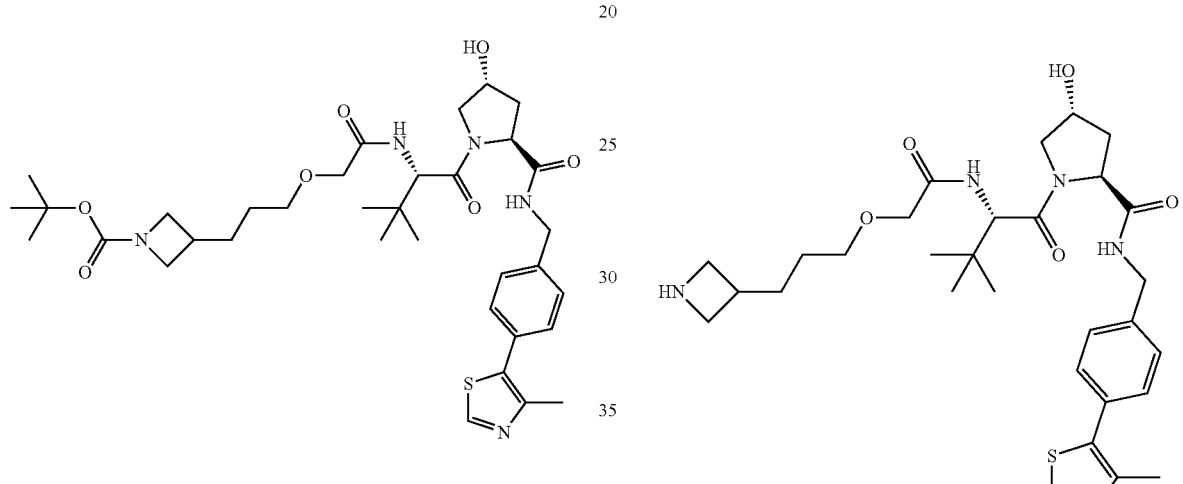

A solution of 2 M aq. sodium hydroxide (0.398 mL, 0.80 mmol) was added to tert-butyl 3-(3-(2-ethoxy-2-oxoethoxy)propyl)azetidine-1-carboxylate (120 mg, 0.40 mmol) in ethanol (1 mL) at 20° C. under air. The resulting solution was stirred at 20° C. for 15 minutes. The resulting mixture was evaporated to dryness and resuspended in DMF (1 mL). (2S,4R)-1-((S)-2-amino-3,3-dimethylbutanoyl)-4-hydroxy-N-(4-(4-methylthiazol-5-yl)benzyl)pyrrolidine-2-carboxamide, HCl (223 mg, 0.48 mmol) and triethylamine (0.166 mL, 1.19 mmol) were added and the suspension stirred for 5 minutes. HATU (303 mg, 0.80 mmol) was added and the resulting suspension stirred at 20° C. under air for 16 hours. The reaction was incomplete and further HATU (303 mg, 0.80 mmol), triethylamine (0.166 mL, 1.19 mmol) and DMF (1 mL) were added and the suspension was stirred at 20° C. for a further 2 hours. The reaction mixture was diluted with EtOAc (50 mL), and washed sequentially with water (10 mL), water (2×5 mL), and saturated brine (2 mL). The organic layer was dried with MgSO$_4$, filtered and evaporated to afford crude product. The crude product was purified by flash silica chromatography, elution gradient 0 to 8% MeOH in dichloromethane. Product containing fractions were evaporated to dryness. The residue was suspended in EtOAc (50 mL), and washed sequentially with saturated NaHCO$_3$ (10 mL), saturated NaHCO$_3$ (5 mL), and saturated brine (5 mL). The organic layer was dried with MgSO$_4$, filtered and evaporated to afford the title compound (201 mg, 74%) as a white foam;

A solution of 6N hydrogen chloride in isopropanol (2 mL, 12.00 mmol) was added to tert-butyl 3-(3-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)propyl)azetidine-1-carboxylate (201 mg, 0.29 mmol) at 40° C. under air. The resulting solution was stirred at 40° C. for 30 minutes. The reaction mixture was evaporated to dryness. The crude product was purified by flash silica chromatography, elution gradient 5 to 20% 1M NH$_3$/MeOH in dichloromethane. Fractions were evaporated to dryness. The crude product was purified by ion exchange chromatography, using an SCX column. The desired product was eluted from the column using 1M NH$_3$/MeOH and pure fractions were evaporated to dryness to afford the title compound (81 mg, 47%) as a white solid; $^1$H NMR (400 MHz, CDCl$_3$, 30° C.) 0.97 (9H, s), 1.47-1.76 (5H, m), 2.14 (1H, dd), 2.51 (5H, s), 2.70 (1H, m), 3.29 (2H, m), 3.47 (2H, m), 3.59-3.72 (3H, m), 3.85 (1H, d), 3.96 (1H, d), 4.04 (1H, d), 4.34 (1H, dd), 4.56 (3H, dd), 4.72 (1H, t), 7.19 (1H, d), 7.36 (4H, s), 7.66 (1H, s), 8.67 (1H, s); m/z: ES+ [M+H]$^+$ 586.5.

Example 47: (2S,4R)-1-((S)-2-(2-(3-(1-(2-(3,5-dif-luoro-4-((1R,3R)-2-(2-fluoro-2-methylpropyl)-3-methyl-2,3,4,9-tetrahydro-1H-pyrido[3,4-b]indol-1-yl)phenoxy)ethyl)azetidin-3-yl)propoxy)acetamido)-3,3-dimethylbutanoyl)-4-hydroxy-N-(4-(4-methylthiazol-5-yl)benzyl)pyrrolidine-2-carboxamide

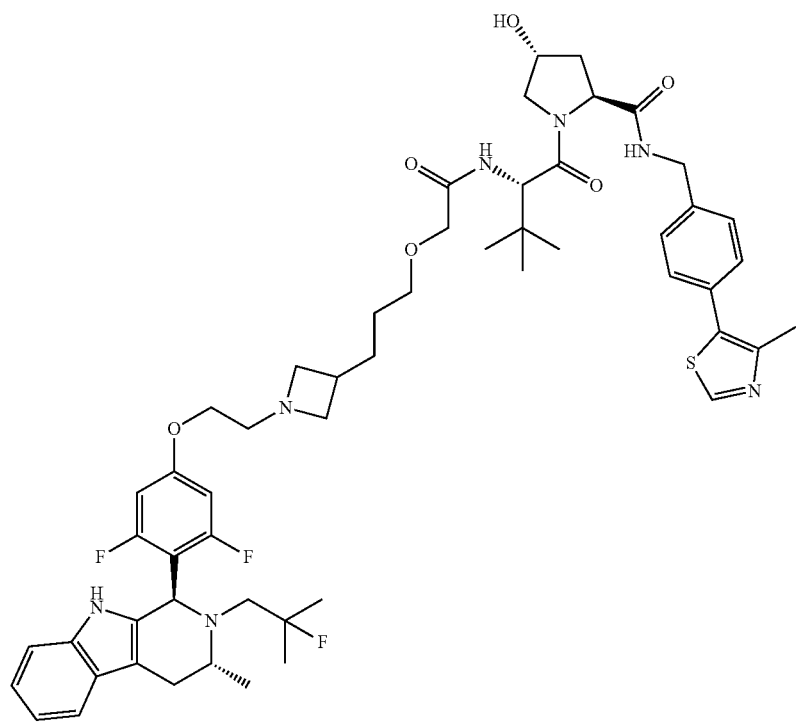 [SMILES: Cc1ncsc1-c1ccc(CNC(=O)[C@@H]2C[C@@H](O)CN2C(=O)[C@@H](NC(=O)COCCCC2CN(CCOc3cc(F)c([C@@H]4c5[nH]c6ccccc6c5C[C@@H](C)N4CC(C)(C)F)c(F)c3)C2)C(C)(C)C)cc1]

Potassium carbonate (153 mg, 1.11 mmol) was added to (1R,3R)-1-(4-(2-bromoethoxy)-2,6-difluorophenyl)-2-(2-fluoro-2-methylpropyl)-3-methyl-2,3,4,9-tetrahydro-1H-pyrido[3,4-b]indole (90 mg, 0.18 mmol) and (2S,4R)-1-((S)-2-(2-(3-(azetidin-3-yl)propoxy)acetamido)-3,3-dimethylbutanoyl)-4-hydroxy-N-(4-(4-methylthiazol-5-yl)benzyl)pyrrolidine-2-carboxamide (81 mg, 0.14 mmol) in acetonitrile (3 mL) at 20° C. under nitrogen. The resulting suspension was stirred at 80° C. for 17 hours. The reaction mixture was diluted with EtOAc (15 mL), and washed sequentially with water (3 mL), saturated NaHCO$_3$ (2 mL), and saturated brine (2 mL). The organic layer was dried with MgSO$_4$, filtered and evaporated to afford crude product. The crude product was purified by flash silica chromatography, elution gradient 0 to 20% 1M NH$_3$/MeOH in dichloromethane. Product containing fractions were evaporated to dryness to afford crude product (64 mg). The crude product was purified by preparative HPLC (Waters XSelect CSH C18 column, 5μ silica, 30 mm diameter, 100 mm length), using decreasingly polar mixtures of water (containing 1% by volume of NH$_4$OH (28-30% in H$_2$O)) and MeCN as eluents. Fractions containing the desired compound were evaporated to dryness to afford the title compound (22 mg, 16%) as a brown solid; $^1$H NMR (400 MHz, DMSO-d6, 30° C.) 0.94 (9H, d), 1.04 (3H, d), 1.16 (6H, t), 1.42-1.62 (4H, m), 1.91 (1H, m), 2.07 (1H, q), 2.27-2.41 (2H, m), 2.44 (3H, s), 2.53-2.59 (1H, m), 2.65 (2H, t), 2.74 (2H, t), 2.78-2.94 (2H, m), 3.35 (2H, t), 3.45 (2H, m), 3.48-3.56 (1H, m), 3.61 (1H, d), 3.67 (1H, dd), 3.84-3.94 (4H, m), 4.26 (1H, dd), 4.32-4.5 (3H, m), 4.56 (1H, d), 5.08-5.19 (2H, m), 6.61 (2H, d), 6.91-7.03 (2H, m), 7.16-7.21 (1H, m), 7.34 (1H, d), 7.37-7.49 (5H, m), 8.58 (1H, t), 8.97 (1H, s), 10.50 (1H, s); m/z: ES+ [M+H]$^+$ 1000.7; ESI-HRMS calculated for C$_{54}$H$_{69}$F$_3$N$_7$O$_6$S [M+H]$^+$=1000.4977, measured 1000.4967.

Intermediate 48a: Ethyl 2-((5-((tert-butoxycarbonyl) (2-(3,5-difluoro-4-((1R,3R)-2-(2-fluoro-2-methyl-propyl)-3-methyl-2,3,4,9-tetrahydro-1H-pyrido[3,4-b]indol-1-yl)phenoxy)ethyl)amino)pentyl)oxy) acetate

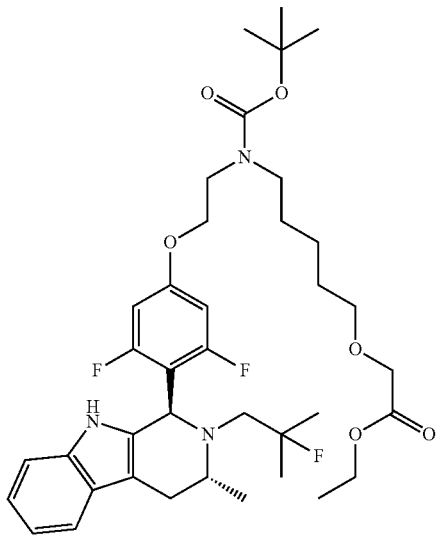 [SMILES: CCOC(=O)COCCCCCN(CCOc1cc(F)c([C@@H]2c3[nH]c4ccccc4c3C[C@@H](C)N2CC(C)(C)F)c(F)c1)C(=O)OC(C)(C)C]

A solution of ethyl 2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetate (110 mg, 0.18 mmol) in ethanol (1.4 mL) was added to di-tert-butyl dicarbonate (72 mg, 0.33 mmol) at 20° C. under air. The resulting solution was stirred at 20° C. for 1 hour. The reaction mixture was diluted with EtOAc (25 mL), and washed sequentially with saturated NaHCO₃ (2 mL), saturated NaHCO₃ (2 mL), and saturated brine (2 mL). The organic layer was dried with MgSO₄, filtered and evaporated to afford the title compound (153 mg) as a brown gum that was used in the next step without further purification; ¹H NMR (400 MHz, DMSO-d6, 30° C.) 1.05 (3H, d), 1.15-1.24 (10H, m), 1.39 (9H, s), 1.51 (3H, d), 2.28-2.41 (1H, m), 2.54-2.6 (1H, m), 2.75-2.94 (2H, m), 3.19 (2H, t), 3.4-3.56 (5H, m), 3.99-4.15 (8H, m), 5.13 (1H, s), 6.66 (2H, d), 6.91-7.04 (2H, m), 7.16-7.21 (1H, m), 7.40 (1H, d), 10.49 (1H, s); m/z: ES+ [M+H]⁺ 704.7.

Intermediate 48b: 2-((5-(((tert-butoxycarbonyl)(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetic Acid

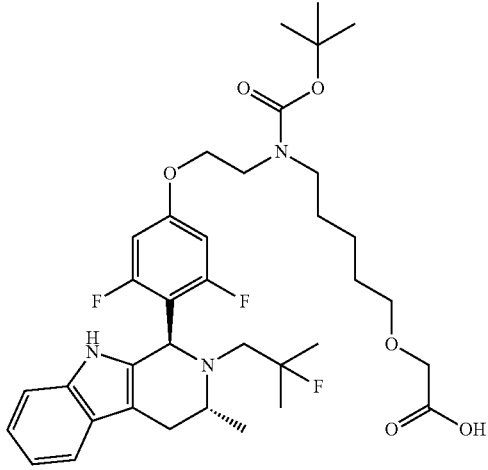 [SMILES: C[C@@H]1Cc2c([nH]c3ccccc23)[C@@H](c2c(F)cc(OCCN(CCCCCOCC(=O)O)C(=O)OC(C)(C)C)cc2F)N1CC(C)(C)F]

A solution of 2 M aq. sodium hydroxide (0.213 mL, 0.43 mmol) was added to ethyl 2-((5-(((tert-butoxycarbonyl)(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetate (150 mg, 0.21 mmol) in ethanol (1 mL) at 20° C. under air. The resulting solution was stirred at 20° C. for 1 hour. The reaction mixture was quenched with 2M HCl (0.213 mL) and evaporated to afford the title compound (142 mg, 99%) as a yellow foam that was used in the next step without further purification; m/z: ES+ [M+H]⁺ 676.7.

Intermediate 48c: tert-Butyl (2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(5-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)pentyl)carbamate

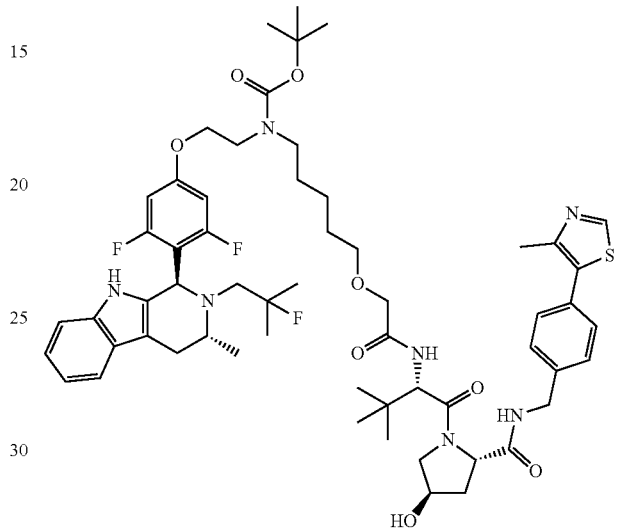

(2S,4R)-1-((S)-2-Amino-3,3-dimethylbutanoyl)-4-hydroxy-N-(4-(4-methylthiazol-5-yl)benzyl)pyrrolidine-2-carboxamide, HCl (108 mg, 0.23 mmol) was added to 2-((5-(((tert-butoxycarbonyl)(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetic acid (142 mg, 0.21 mmol), HATU (120 mg, 0.32 mmol) and triethylamine (0.073 mL, 0.53 mmol) in DMF (1 mL) at 20° C. under air. The resulting suspension was stirred at 20° C. for 30 minutes. The reaction mixture was diluted with EtOAc (25 mL), and washed sequentially with water (3×2 mL), saturated NaHCO₃ (3×1 mL), and saturated brine (2 mL). The organic layer was dried with MgSO₄, filtered and evaporated to afford crude product. The crude product was purified by flash silica chromatography, elution gradient 50 to 100% EtOAc in heptane, followed by 0 to 10% MeOH in dichloromethane. Pure fractions were evaporated to dryness to afford the title compound (165 mg, 72%) as an orange gum; ¹H NMR (400 MHz, DMSO-d6, 30° C.) 0.93 (9H, d), 1.04 (3H, d), 1.08-1.24 (6H, m), 1.30 (3H, d), 1.37 (9H, s), 1.45-1.66 (5H, m), 1.92 (1H, m), 2.02-2.11 (1H, m), 2.44 (3H, s), 2.81-2.89 (1H, m), 3.19 (2H, t), 3.42-3.55 (5H, m), 3.58-3.7 (2H, m), 3.91 (2H, s), 4.04-4.14 (2H, m), 4.27 (1H, dd), 4.3-4.5 (3H, m), 4.56 (1H, d), 5.13 (2H, d), 6.65 (2H, d), 6.9-7.06 (2H, m), 7.18 (1H, d), 7.33 (1H, d), 7.40 (5H, s), 7.96 (1H, s), 8.56 (1H, t), 8.97 (1H, s), 10.49 (1H, s); m/z: ES+ [M+H]⁺ 1088.9.

Example 48: (2S,4R)-1-((S)-2-(2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetamido)-3,3-dimethylbutanoyl)-4-hydroxy-N-(4-(4-methylthiazol-5-yl)benzyl)pyrrolidine-2-carboxamide

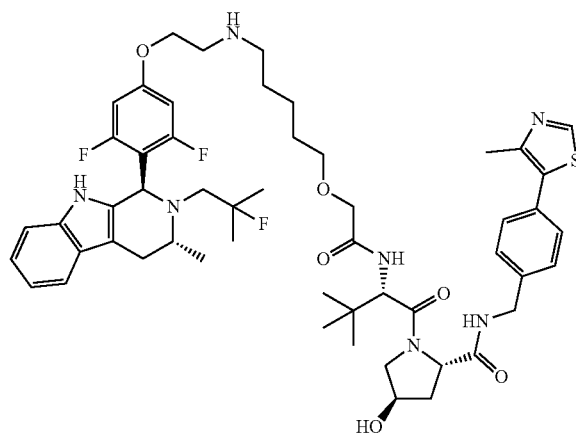 [SMILES: Cc1ncsc1-c1ccc(CNC(=O)[C@@H]2C[C@@H](O)CN2C(=O)[C@@H](NC(=O)COCCCCCNCCOc2cc(F)c([C@@H]3c4[nH]c5ccccc5c4C[C@@H](C)N3CC(C)(C)F)c(F)c2)C(C)(C)C)cc1]

A solution of 6 M hydrogen chloride in isopropanol (2 mL, 12 mmol) was added to tert-butyl (2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(5-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)pentyl)carbamate (165 mg, 0.15 mmol) at 20° C. under air. The resulting solution was stirred at 45° C. for 15 minutes. The solution was sonicated at 20° C. for 15 minutes. The reaction mixture was diluted with EtOAc (25 mL), and washed sequentially with 2 M aq. potassium carbonate (5 mL), water (2 mL), and saturated brine (2 mL). The organic layer was dried with MgSO$_4$, filtered and evaporated to afford crude product. The crude product was purified by preparative HPLC (Waters XSelect CSH C18 column, 5µ silica, 30 mm diameter, 100 mm length), using decreasingly polar mixtures of water (containing 1% by volume of NH$_4$OH (28-30% in H$_2$O)) and MeCN as eluents. Fractions containing the desired compound were evaporated to dryness to afford the title compound (64 mg, 43%) as a tan solid; $^1$H NMR (400 MHz, DMSO-d6, 30° C.) 0.94 (9H, d), 1.04 (3H, d), 1.16 (6H, t), 1.39 (4H, m), 1.56 (2H, p), 1.66 (1H, s), 1.91 (1H, m), 2.01-2.14 (1H, m), 2.28-2.41 (1H, m), 2.45 (3H, s), 2.52-2.6 (3H, m), 2.86 (4H, m), 3.43-3.56 (3H, m), 3.61 (1H, d), 3.67 (1H, dd), 3.91 (2H, s), 3.99 (2H, t), 4.27 (1H, dd), 4.33-4.49 (3H, m), 4.56 (1H, d), 5.06-5.21 (2H, m), 6.64 (2H, d), 6.89-7.04 (2H, m), 7.16-7.22 (1H, m), 7.34 (1H, d), 7.37-7.47 (5H, m), 8.58 (1H, t), 8.97 (1H, s), 10.50 (1H, s); m/z: ES+ [M+H]$^+$ 988.7; ESI-HRMS calculated for C$_{53}$H$_{69}$F$_3$N$_7$O$_6$S [M+H]$^+$=988.4977, measured 988.4963.

Intermediate 49a: Ethyl 2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)pentyl)oxy)acetate

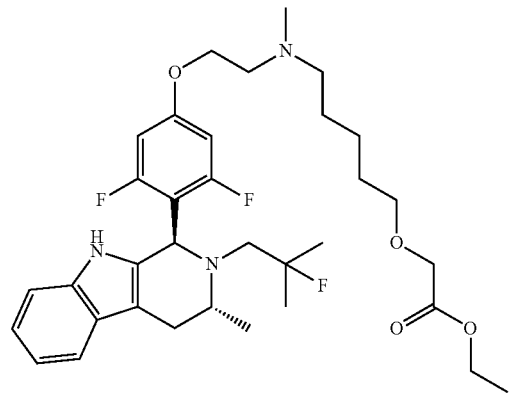 [SMILES: CCOC(=O)COCCCCCN(C)CCOc1cc(F)c([C@@H]2c3[nH]c4ccccc4c3C[C@@H](C)N2CC(C)(C)F)c(F)c1]

Sodium triacetoxyborohydride (116 mg, 0.55 mmol) was added to 37% w/v aq. formaldehyde (0.444 mL, 5.47 mmol), ethyl 2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetate (110 mg, 0.18 mmol) and acetic acid (0.063 mL, 1.09 mmol) in ethanol (1.4 mL) at 20° C. under air. The resulting solution was stirred at 20° C. for 1 hour. The reaction mixture was diluted with EtOAc (25 mL), and washed sequentially with saturated NaHCO$_3$ (5 mL), saturated NaHCO$_3$ (2 mL), and saturated brine (2 mL). The organic layer was dried with MgSO$_4$, filtered and evaporated to afford crude product. The crude product was purified by flash silica chromatography, elution gradient 0 to 5% 1M NH$_3$/MeOH in dichloromethane. Pure fractions were evaporated to dryness to afford the title compound (60 mg, 53%) as a tan gum; $^1$H NMR (400 MHz, DMSO-d6, 30° C.) 1.05 (3H, d), 1.09-1.24 (9H, m), 1.29 (3H, m), 1.42 (2H, p), 1.52 (2H, m), 2.21 (3H, s), 2.35 (2H, d), 2.53-2.6 (1H, m), 2.63-2.72 (2H, m), 2.77-2.94 (2H, m), 3.43 (2H, t), 3.52 (1H, d), 4-4.15 (6H, m), 5.13 (1H, s), 6.66 (2H, d), 6.97 (2H, m), 7.19 (1H, d), 7.40 (1H, d), 10.50 (1H, s); m/z: ES+ [M+H]$^+$ 618.6.

Intermediate 49b: 2-((5-((2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)pentyl)oxy)acetic Acid

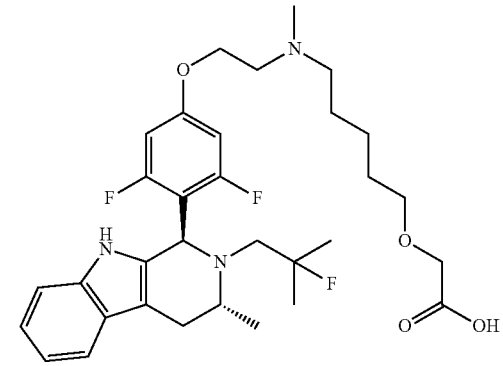 [SMILES: C[C@@H]1Cc2c([nH]c3ccccc23)[C@@H](c2c(F)cc(OCCN(C)CCCCCOCC(=O)O)cc2F)N1CC(C)(C)F]

A solution of 2 M aq. sodium hydroxide (0.089 mL, 0.18 mmol) was added to ethyl 2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)pentyl)oxy)acetate (55 mg, 0.09 mmol) in ethanol (1 mL) at 20° C. under air. The resulting solution was stirred at 20° C. for 1 hour. The reaction mixture was quenched with 2M HCl (0.089 mL) and evaporated to afford the title compound (53 mg) as a white foam that was used in the next step without further purification; m/z: ES+ [M+H]+ 590.6

Example 49: (2S,4R)-1-((S)-2-(2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)pentyl)oxy)acetamido)-3,3-dimethylbutanoyl)-4-hydroxy-N-(4-(4-methylthiazol-5-yl)benzyl)pyrrolidine-2-carboxamide

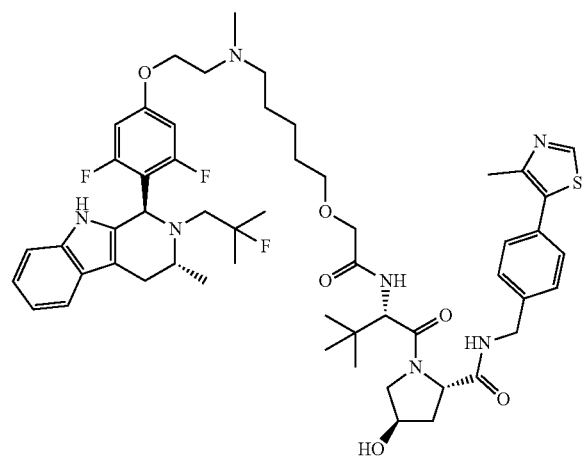 [SMILES: Cc1ncsc1-c1ccc(CNC(=O)[C@@H]2C[C@@H](O)CN2C(=O)[C@@H](NC(=O)COCCCCCN(C)CCOc2cc(F)c([C@@H]3c4[nH]c5ccccc5c4C[C@@H](C)N3CC(C)(C)F)c(F)c2)C(C)(C)C)cc1]

(2S,4R)-1-((S)-2-Amino-3,3-dimethylbutanoyl)-4-hydroxy-N-(4-(4-methylthiazol-5-yl)benzyl)pyrrolidine-2-carboxamide, HCl (108 mg, 0.23 mmol) was added to 2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)pentyl)oxy)acetic acid (53.1 mg, 0.09 mmol), HATU (51.3 mg, 0.14 mmol) and triethylamine (0.031 mL, 0.23 mmol) in DMF (1 mL) at 20° C. under air. The resulting suspension was stirred at 20° C. for 30 minutes. The crude reaction mixture was purified by preparative HPLC (Waters XSelect CSH C18 column, 5µ silica, 30 mm diameter, 100 mm length), using decreasingly polar mixtures of water (containing 1% by volume of NH4OH (28-30% in H2O)) and MeCN as eluents. Fractions containing the desired compound were evaporated to dryness to afford the title compound (48 mg, 53%) as a white solid; 1H NMR (400 MHz, DMSO-d6, 30° C.) 0.93 (9H, d), 1.04 (3H, d), 1.16 (6H, t), 1.33 (2H, m), 1.42 (2H, q), 1.56 (2H, p), 1.91 (1H, m), 2.03-2.11 (1H, m), 2.18 (3H, s), 2.3-2.39 (3H, m), 2.44 (3H, s), 2.53-2.61 (1H, m), 2.62-2.73 (2H, m), 2.77-2.97 (2H, m), 3.36-3.55 (3H, m), 3.57-3.71 (2H, m), 3.91 (2H, s), 4.03 (2H, t), 4.26 (1H, dd), 4.33-4.49 (3H, m), 4.56 (1H, d), 5.13 (2H, d), 6.64 (2H, d), 6.97 (2H, m), 7.15-7.24 (1H, m), 7.33 (1H, d), 7.36-7.49 (5H, m), 8.57 (1H, t), 8.97 (1H, s), 10.50 (1H, s); m/z: ES+ [M+H]+ 1002.8; ESI-HRMS calculated for C54H71F3N7O6S [M+H]+=1002.5133, measured 1002.5095.

Intermediate 50a: (1R,3R)-1-(2,6-difluoro-4-(prop-2-yn-1-yloxy)phenyl)-2-(2-fluoro-2-methylpropyl)-3-methyl-2,3,4,9-tetrahydro-1H-pyrido[3,4-b]indole

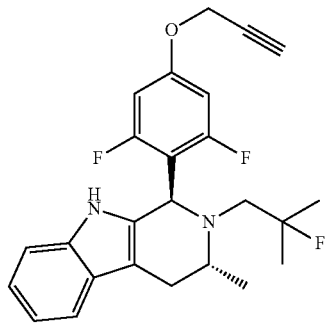 [SMILES: C#CCOc1cc(F)c([C@@H]2c3[nH]c4ccccc4c3C[C@@H](C)N2CC(C)(C)F)c(F)c1]

3-Bromoprop-1-yne (0.53 mL, 4.80 mmol) was added dropwise to a stirred mixture of 3,5-difluoro-4-((1R,3R)-2-(2-fluoro-2-methylpropyl)-3-methyl-2,3,4,9-tetrahydro-1H-pyrido[3,4-b]indol-1-yl)phenol (0.93 g, 2.39 mmol), potassium carbonate (0.827 g, 5.99 mmol) in acetonitrile (10 mL) at 25° C. The resulting mixture was stirred at RT for 72 hours. Concentration under reduced pressure removed the solvent. To the residue was added EtOAc (10 mL) and water (10 mL). After partition, the organic layer was dried (Na2SO4) and concentrated. The crude product was added to a silica gel column (40 g) and was eluted with EtOAc/hexane (0-80%). Collected fractions were concentrated to give the title compound (0.85 g, 83%). m/z: ES+ [M+H]+ 427.3.

Intermediate 50b: Ethyl 2-(prop-2-yn-1-yloxy)acetate

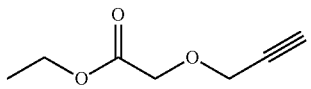

Ethyl 2-hydroxyacetate (9.3 mL, 96.1 mmol) was added to a 200-mL round-bottomed flask in THF (100 mL). To the solution was added 60% sodium hydride 60% in mineral oil (4.61 g, 115 mmol) slowly over 5 mins. The suspension was stirred at RT for 1 hour before 3-bromoprop-1-yne (10.7 mL, 96.1 mmol) was added. The reaction mixture was stirred at RT over the weekend. The mixture was concentrated under reduced pressure. To the residue was added diethyl ether (30 mL) and water (50 mL). After partition, the organic phase was washed with water (2×50 mL). The organic layer was dried (Na2SO4) and concentrated to give the crude product. The crude product was added to a silica gel column (80 g) and was eluted with EtOAc/hexane (0-25%). Collected fractions were concentrated to give the title compound (7.0 g, 51%). 1H NMR (DMSO-d6) 1.21 (3H, t), 3.49 (1H, s), 4.08-4.18 (4H, m), 4.23 (2H, d).

Intermediate 50c: ethyl 2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexa-2,4-diyn-1-yl)oxy)acetate

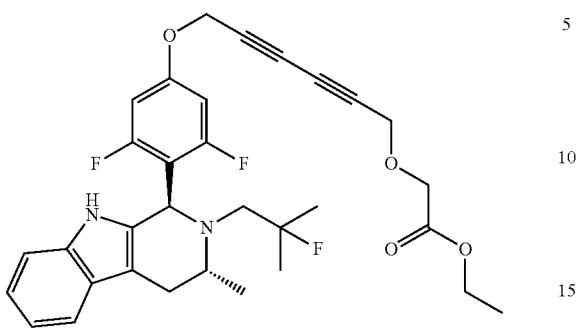

A solution of (1R,3R)-1-(2,6-difluoro-4-(prop-2-yn-1-yloxy)phenyl)-2-(2-fluoro-2-methylpropyl)-3-methyl-2,3,4,9-tetrahydro-1H-pyrido[3,4-b]indole (0.16 g, 0.38 mmol) (Intermediate 50b) and ethyl 2-(prop-2-yn-1-yloxy)acetate and pyridine (0.152 mL, 1.88 mmol) in acetonitrile (15 mL) was added diacetoxycopper (0.204 g, 1.13 mmol). The reaction mixture was stirred at 80° C. for 1 hour. After cooling to room temperature, the reaction was quenched with water (10 mL) and extracted twice with EtOAc (2×5 mL). The organic layer were washed twice with brine (2×10 mL), dried over $Na_2SO_4$, and concentrated under reduced pressure. The residue was purified by flash chromatography (silica gel column, EtOAc/DCM, EtOAc from 0% to 80%) to afford the title compound (0.150 g, 71%) as a clear gum. m/z: ES+ $[M+H]^+$ 567.2.

Example 50: (2S,4R)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexa-2,4-diyn-1-yl)oxy)acetamido)-3,3-dimethylbutanoyl)-4-hydroxy-N-(4-(4-methylthiazol-5-yl)benzyl)pyrrolidine-2-carboxamide

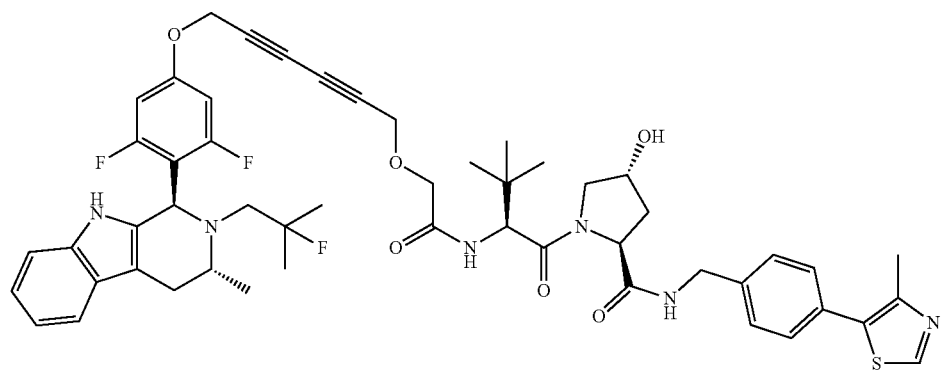 [SMILES: Cc1ncsc1-c1ccc(CNC(=O)[C@@H]2C[C@@H](O)CN2C(=O)[C@@H](NC(=O)COCC#CC#CCOc2cc(F)c([C@@H]3c4[nH]c5ccccc5c4C[C@@H](C)N3CC(C)(C)F)c(F)c2)C(C)(C)C)cc1]

Ethyl 2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexa-2,4-diyn-1-yl)oxy)acetate (0.072 g, 0.13 mmol) and lithium hydroxide (0.012 g, 0.52 mmol) (Intermediate 50a) were added to a 50-mL round-bottomed flask in a co-solvent of THF (5 mL), MeOH (1 mL), and water (1 mL). The mixture was stirred at RT for 2 hours. Concentration under reduced pressure gave the crude acid as a solid residue. To the crude acid was added DMF (1 mL) HATU (0.059 g, 0.16 mmol), (2S,4R)-1-((S)-2-amino-3,3-dimethylbutanoyl)-4-hydroxy-N-(4-(4-methylthiazol-5-yl)benzyl)pyrrolidine-2-carboxamide (0.056 g, 0.13 mmol), and triethylamine (0.054 mL, 0.39 mmol) at RT under nitrogen. The resulting solution was stirred at RT for 0.5 hour. To the solution was added water (10 mL) and EtOAc (5 mL). After partition, the organic layer was washed with water (2×5 mL). The organic layer was dried ($Na_2SO_4$) and concentrated under reduced pressure. The crude product was added to a silica gel column and was eluted with MeOH/DCM (0-20%). Collected fractions were concentrated to give the title compound (0.050 g, 40%). $^1$H NMR (DMSO-d6) 0.90-0.96 (9H, m), 1.04 (3H, d), 1.08-1.23 (6H, m), 1.86-1.97 (1H, m), 2.01-2.11 (1H, m), 2.30-2.40 (1H, m), 2.53-2.60 (1H, m), 2.69 (3H, s), 2.76-2.95 (2H, m), 3.44-3.55 (1H, m), 3.57-3.72 (2H, m), 4.02 (2H, s), 4.24-4.31 (1H, m), 4.43 (5H, s), 4.51-4.58 (1H, m), 5.04 (2H, s), 5.13 (2H, d), 6.71-6.78 (2H, m), 6.91-7.03 (2H, m), 7.16-7.22 (1H, m), 7.40 (5H, s), 7.51-7.57 (1H, m), 8.51-8.62 (1H, m), 8.98 (1H, s), 10.55 (1H, s); m/z ES+ $[M+H]^+$ 951.4; ESI-HRMS calculated for $C_{52}H_{58}F_3N_6O_6S$ $[M+H]^+$=951.4085, measured 951.4052.

Intermediate 51a: Ethyl 2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)acetate

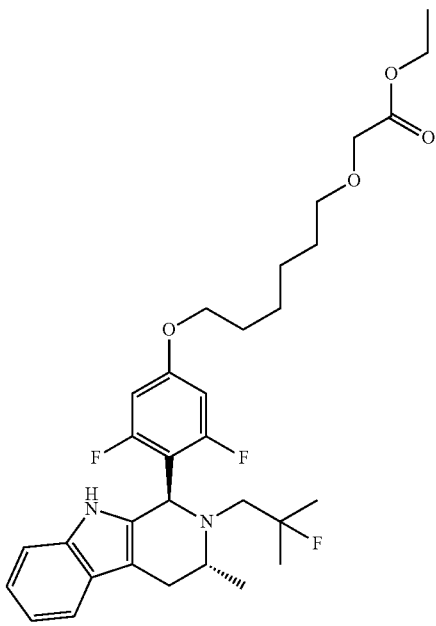 [SMILES: CCOC(=O)COCCCCCCOc1cc(F)c([C@@H]2c3[nH]c4ccccc4c3C[C@@H](C)N2CC(C)(C)F)c(F)c1]

Ethyl 2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexa-2,4-diyn-1-yl)oxy)acetate (0.05 g, 0.09 mmol) was added to a 50-mL round-bottomed flask in MeOH (10 mL). To the solution was bubbled in a stream of nitrogen for 5 min before 10% Pd/C (9.39 mg, 0.09 mmol) was added. The reaction was stirred under hydrogen (1 atmosphere) for 2 hours. The mixture was filtered through a pad of celite and concentrated under reduced pressure to give the title compound without further purification (0.048 g, 89%). m/z: ES+ [M+H]$^+$ 575.3.

Example 51: (2S,4R)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)acetamido)-3,3-dimethylbutanoyl)-4-hydroxy-N-(4-(4-methylthiazol-5-yl)benzyl)pyrrolidine-2-carboxamide Ethyl 2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)acetate (0.045 g, 0.08 mmol) and lithium hydroxide (3.75 mg, 0.16 mmol) (Intermediate 52a) was added to a solution of THF (5 mL), water (1 mL), and MeOH (1 mL). Lithium hydroxide (4 mg, 0.15 mmol) was added. The mixture was stirred at RT for 4 hours. The reaction mixture was concentrated under reduced pressure to give a solid residue as the crude 2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)acetic acid. To the crude acid was added DMF (1 mL). To the crude solution was added (2S,4R)-1-((S)-2-amino-3,3-dimethylbutanoyl)-4-hydroxy-N-(4-(4-methylthiazol-5-yl)benzyl)pyrrolidine-2-carboxamide (0.038 g, 0.09 mmol) and O-(7-Azabenzotriazol-1-yl)-N,N,N',N'-tetramethyluronium hexafluorophosphate (HATU, 0.040 g, 0.11 mmol). Triethylamine (0.037 mL, 0.26 mmol) was added. The resulting solution was stirred at RT for 0.5 hours. The resulting residue was purified by preparative HPLC (Gemini NX C18 column, 2.0 mm×30 mm 3 μm), using an elution gradient of 20-60% acetonitrile in water containing 0.1% trifluoroacetic acid. Fractions containing the product were concentrated under reduced pressure to afford the title compound as a white solid (9.60 mg, 11.4%). $^1$H NMR (MeOD) 0.86-0.94 (12H, m), 1.15-1.21 (3H, m), 1.41 (14H, br d), 1.53-1.60 (3H, m), 1.64-1.73 (2H, m), 1.93-2.03 (1H, m), 2.07-2.17 (1H, m), 2.31-2.35 (2H, m), 2.89-2.97 (1H, m), 3.42-3.50 (2H, m), 3.66-3.73 (1H, m), 3.74-3.79 (1H, m), 3.83-3.93 (4H, m), 3.94-4.12 (1H, m), 4.19-4.28 (1H, m), 4.34-4.51 (3H, m), 6.54-6.60 (1H, m), 6.93-7.08 (2H, m), 7.15-7.22 (1H, m), 7.33 (6H, br), 7.40-7.47 (2H, m), 8.50-8.65 (1H, m); m/z: ES+ [M+H]$^+$ 959.3; ESI-HRMS calculated for $C_{52}H_{66}F_3N_6O_6S$ [M+H]$^+$=959.4711, measured 959.4693.

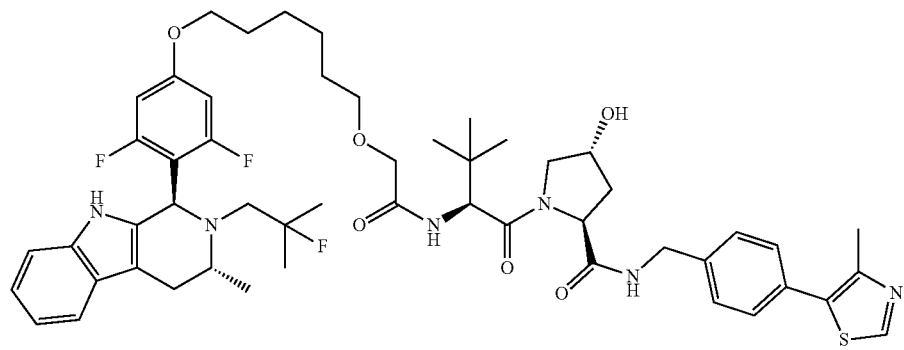 [SMILES: Cc1ncsc1-c1ccc(CNC(=O)[C@@H]2C[C@@H](O)CN2C(=O)[C@@H](NC(=O)COCCCCCCOc2cc(F)c([C@@H]3c4[nH]c5ccccc5c4C[C@@H](C)N3CC(C)(C)F)c(F)c2)C(C)(C)C)cc1]

Example 52: (3R,5S)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)acetamido)-3,3-dimethylbutanoyl)-5-((4-(4-methylthiazol-5-yl)benzyl)carbamoyl)pyrrolidin-3-yl acetate

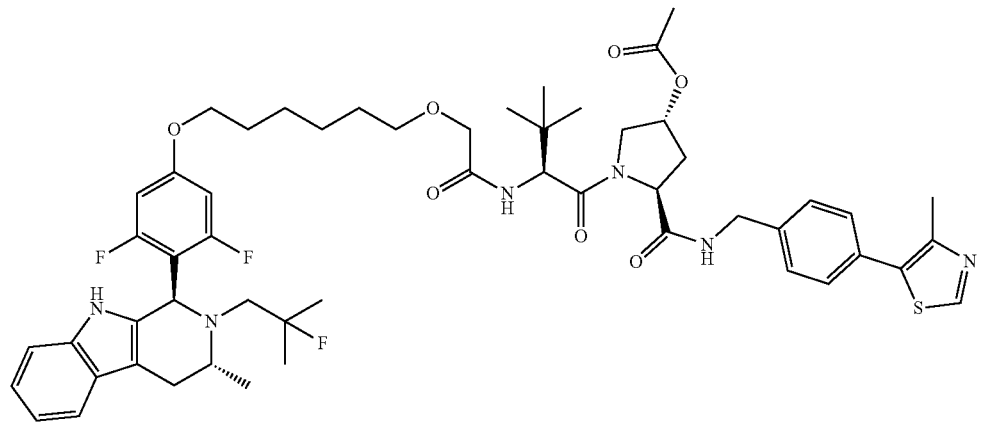 [SMILES: CC(=O)O[C@@H]1C[C@@H](C(=O)NCc2ccc(-c3scnc3C)cc2)N(C(=O)[C@@H](NC(=O)COCCCCCCOc2cc(F)c([C@@H]3c4[nH]c5ccccc5c4C[C@@H](C)N3CC(C)(C)F)c(F)c2)C(C)(C)C)C1]

In 100-mL round-bottomed flask (2S,4R)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)acetamido)-3,3-dimethylbutanoyl)-4-hydroxy-N-(4-(4-methylthiazol-5-yl)benzyl)pyrrolidine-2-carboxamide (0.040 g, 0.04 mmol) (Example 51) was dissolved in dichloromethane (5 mL) and the solution was cooled to 0° C. in an ice-water bath. At 0° C. triethylamine (0.012 mL, 0.08 mmol), 4-dimethylaminopyridine (0.255 mg, 2.09 µmol) and acetic anhydride (5 L, 0.05 mmol) were added. The solution was kept at 0° C. for 2 hours. Sat. aq. NH$_4$Cl (10 mL) was added and the mixture was diluted with dichloromethane (10 mL). The organic solution was washed with brine, sat. aq. NaHCO$_3$ and water and dried with magnesium sulfate. The solution was concentrated under reduced pressure. The residual crude product was chromatographed on silica gel column using 0-7% MeOH/DCM as eluent to give the title compound (0.030 g, 71.9%) as a white solid. $^1$H NMR (DMSO-d6) 0.96 (9H, s), 1.02-1.07 (3H, m), 1.11-1.16 (3H, m), 1.16-1.22 (3H, m), 1.36-1.46 (4H, m), 1.53-1.60 (2H, m), 1.69 (2H, br d), 2.01 (3H, s), 2.09-2.17 (1H, m), 2.23-2.36 (2H, m), 2.45 (3H, s), 2.53-2.58 (2H, m), 2.80-2.93 (2H, m), 3.45-3.55 (3H, m), 3.81-3.87 (1H, m), 3.92 (2H, d), 3.94-3.98 (2H, m), 4.25-4.32 (1H, m), 4.37-4.51 (3H, m), 5.09-5.15 (1H, m), 5.25-5.31 (1H, m), 6.63 (2H, br d), 6.89-7.02 (2H, m), 7.18 (1H, d), 7.34-7.48 (6H, m), 8.62 (1H, s), 8.96-9.00 (1H, m), 10.52 (1H, s); m/z: ES+ [M+H]$^+$ 1001.5; ESI-HRMS calculated for C$_{54}$H$_{68}$F$_3$N$_6$O$_7$S [M+H]$^+$=1001.4817, measured 1001.4807.

Intermediate 53a:
2-(4-(Bromomethyl)phenyl)ethan-1-ol

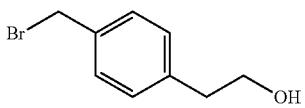

A solution of 2 M borane-dimethylsulfide complex in THF (8.73 mL, 17.5 mmol) was added dropwise to 2-(4-(bromomethyl)phenyl)acetic acid (2.00 g, 8.73 mmol) in THF (40 mL) at 20° C. over a period of 10 minutes under nitrogen. The resulting solution was stirred at 20° C. for 30 minutes. The reaction mixture was quenched with MeOH (20 mL) and the reaction was stirred for 18 hours. The solvent was evaporated and the crude material was purified by flash silica chromatography, elution gradient 0 to 50% EtOAc in heptane to afford the title compound (0.437 g, 23%) as a white solid; $^1$H NMR (400 MHz, CDCl$_3$) 1.35 (1H, t), 2.87 (2H, t), 3.87 (2H, q), 4.49 (2H, s), 7.21 (2H, d), 7.34 (2H, d); m/z: ES+ [M+H]$^+$ 214

Intermediate 53b: Ethyl 2-(4-(bromomethyl)phenethoxy)acetate

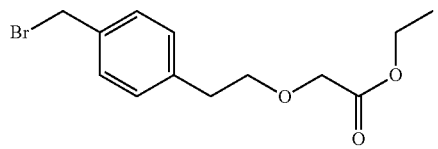 [SMILES: CCOC(=O)COCCc1ccc(CBr)cc1]

Ethyl 2-diazoacetate (0.62 mL, 5.08 mmol) in DCM (2 mL) was added slowly to 2-(4-(bromomethyl)phenyl)ethan-1-ol (437 mg, 2.03 mmol) and diacetoxyrhodium (45 mg, 0.10 mmol) in DCM (5.4 mL) at 20° C. over a period of 1 hour under nitrogen. The resulting solution was stirred for 18 hours. The mixture was diluted with DCM (50 mL) and washed with water (50 mL). The organic layer was collected and dried using phase separating cartridge then evaporated to dryness. The crude product was purified by flash silica chromatography, elution gradient 0 to 40% EtOAc in heptane to afford the title compound (480 mg, 78%) as a colourless liquid; $^1$H NMR (400 MHz, CDCl$_3$) 1.28 (3H, t), 2.94 (2H, t), 3.75 (2H, t), 4.07 (2H, s), 4.21 (2H, q), 4.48 (2H, s), 7.22 (2H, d), 7.32 (2H, d).

Intermediate 53c: Ethyl 2-(4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenethoxy)acetate

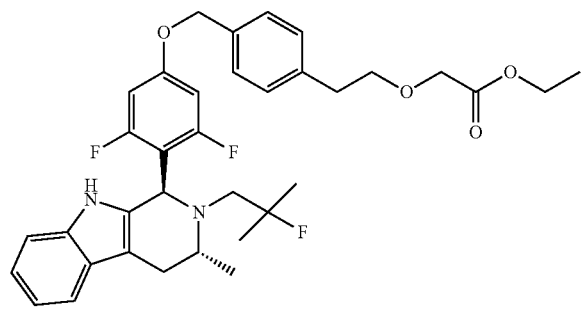 [SMILES: CCOC(=O)COCCc1ccc(COc2cc(F)c([C@@H]3c4[nH]c5ccccc5c4C[C@@H](C)N3CC(C)(C)F)c(F)c2)cc1]

Ethyl 2-(4-(bromomethyl)phenethoxy)acetate (174 mg, 0.58 mmol) was added in one portion to 3,5-difluoro-4-((1R,3R)-2-(2-fluoro-2-methylpropyl)-3-methyl-2,3,4,9-tetrahydro-1H-pyrido[3,4-b]indol-1-yl)phenol (0.344 mL, 0.58 mmol) and potassium carbonate (120 mg, 0.87 mmol) in acetonitrile (2 mL) at 20'C under air. The resulting suspension was stirred at 70° C. for 18 hours. The mixture was cooled to RT and was diluted with DCM (10 mL) and water (2 mL). The DCM layer was collected and evaporated to afford crude material as a yellow gum. The crude product was purified by flash silica chromatography, elution gradient 0 to 100% EtOAc in hexane. Pure fractions were evaporated to dryness to afford the title compound (112 mg, 32%) as a colourless gum. m/z: ES+ [M+H]$^+$ 609.3.

Example 53: (2S,4R)-1-((S)-2-(2-(4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenethoxy)acetamido)-3,3-dimethylbutanoyl)-4-hydroxy-N-(4-(4-methylthiazol-5-yl)benzyl)pyrrolidine-2-carboxamide

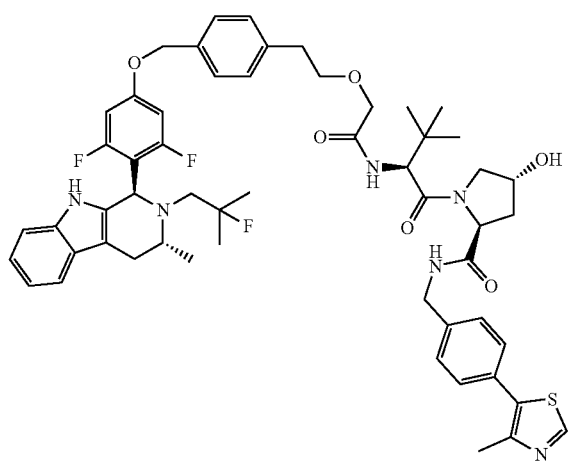 [SMILES: Cc1ncsc1-c1ccc(CNC(=O)[C@@H]2C[C@@H](O)CN2C(=O)[C@@H](NC(=O)COCCc2ccc(COc3cc(F)c([C@@H]4c5[nH]c6ccccc6c5C[C@@H](C)N4CC(C)(C)F)c(F)c3)cc2)C(C)(C)C)cc1]

Lithium hydroxide hydrate (38.6 mg, 0.92 mmol) was added in one portion to ethyl 2-(4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenethoxy)acetate (112 mg, 0.18 mmol) in THF (15.00 mL) and water (5 mL) at RT. The resulting solution was stirred at RT for 30 mins. The organic solvent was removed under reduced pressure. The resulting mixture was acidified with 2M HCl and extracted into EtOAc (2×10 mL). The organic extracts were washed with brine (5 mL) and evaporated to afford the crude 2-(4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenethoxy)acetic acid as a colourless gum. The crude 2-(4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenethoxy)acetic acid (112 mg, 0.19 mmol) was added to the solution of HATU (220 mg, 0.58 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (90 mg, 0.19 mmol), and triethylamine (0.108 mL, 0.77 mmol) in DMF (3 mL) at 20° C. under nitrogen. The resulting mixture was stirred at 20° C. overnight. The reaction mixture was diluted with EtOAc (25 mL), and washed sequentially with saturated NaHCO$_3$ (25 mL), water (25 mL), and saturated brine (25 mL). The organic layer was dried with MgSO$_4$, filtered, and evaporated to afford crude product. The crude product was purified by flash silica chromatography, elution gradient 0 to 10% MeOH in DCM. Pure fractions were evaporated to dryness to afford the title product (27.0 mg, 14.1%) as a pale yellow solid. $^1$H NMR (300 MHz, DMSO-d6) 0.92 (9H, s), 1.01-1.07 (3H, m), 1.08-1.23 (6H, m), 1.86-1.96 (1H, m), 2.02-2.14 (1H, m), 2.42 (3H, s), 2.54 (1H, br s), 2.81-2.95 (4H, m), 3.45-3.53 (1H, m), 3.57-3.74 (4H, m), 3.92-3.97 (2H, m), 4.18-4.30 (1H, m), 4.32-4.58 (4H, m), 5.02-5.08 (2H, m), 5.10-5.15 (2H, m), 6.71 (2H, d), 6.90-7.03 (2H, m), 7.15-7.20 (1H, m), 7.32 (6H, br), 7.40 (4H, d), 8.53-8.63 (1H, m), 8.96 (1H, s), 10.51 (1H, s); m/z ES+ [M+H]$^+$ 993.6; ESI-HRMS calculated for C$_{55}$H$_{64}$F$_3$N$_6$O$_6$S [M+H]$^+$=993.4555, measured 993.4521.

Intermediate 54a: (1R,3R)-2-(2-fluoro-2-methylpropyl)-3-methyl-1-(4-nitrophenyl)-2,3,4,9-tetrahydro-1H-pyrido[3,4-b]indole

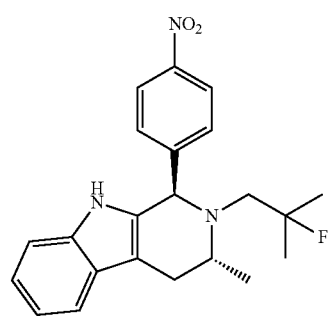 [SMILES: C[C@@H]1Cc2c([nH]c3ccccc23)[C@@H](c2ccc([N+](=O)[O-])cc2)N1CC(C)(C)F]

4-Nitrobenzaldehyde (1.022 g, 6.76 mmol) was added to a solution of (R)—N-(1-(1H-indol-3-yl)propan-2-yl)-2-fluoro-2-methylpropan-1-amine (5.0 g, 6.44 mmol) in a cosolvent of toluene (29 mL) and acetic acid (3.2 ml) and the reaction was heated to 80° C. for 3 hours. After cooling to RT, the volatiles were evaporated, and the crude product was added to a silica gel column (80 g) and was eluted with EtOAc/hexane (0-25%). Collected fractions were concentrated under reduced pressure to give the title compound (2.0 g, 81%) as a bright yellow solid. $^1$H NMR (400 MHz, DMSO, 30° C.) 1.07 (3H, d), 1.1-1.29 (6H, m), 2.29-2.44 (1H, m), 2.58-2.7 (1H, m), 2.85-2.99 (2H, m), 3.51 (1H, q), 5.31 (1H, s), 6.91-7.11 (2H, m), 7.20 (1H, d), 7.44 (1H, d), 8.00 (2H, d), 10.61 (1H, s); m/z: ES+ [M+H]$^+$ 382.1

Intermediate 54b: 4-((1R,3R)-2-(2-fluoro-2-methyl-propyl)-3-methyl-2,3,4,9-tetrahydro-1H-pyrido[3,4-b]indol-1-yl)aniline

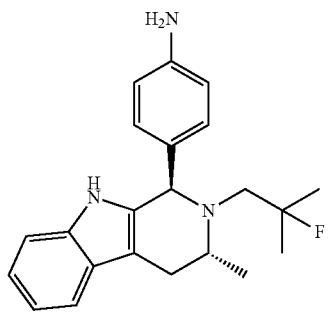 [SMILES: C[C@@H]1Cc2c([nH]c3ccccc23)[C@@H](c2ccc(N)cc2)N1CC(C)(C)F]

Platinum(IV) oxide (0.015 g, 0.07 mmol) was added to a solution of (1R,3R)-2-(2-fluoro-2-methylpropyl)-3-methyl-1-(4-nitrophenyl)-2,3,4,9-tetrahydro-1H-pyrido[3,4-b]indole (0.26 g, 0.68 mmol) in MeOH (12 mL), and stirred under hydrogen atmosphere for 2 hours. The mixture was filtered through a pad of celite and washed with MeOH (10 mL). The filtrate was concentrated to give the crude product. The crude product was added to a silica gel column and was eluted with EtOAc/hexane (20-70%). Collected fractions were concentrated to give the product as a white solid as the title compound (0.180 g, 75%). $^1$H NMR (DMSO-d6) 1.00-1.09 (2H, m), 1.23-1.33 (3H, m), 1.42 (3H, d), 2.40-2.47 (2H, m), 2.53-2.63 (1H, m), 2.67-2.76 (2H, m), 3.14-3.24 (1H, m), 4.85-4.97 (3H, m), 6.48 (2H, d), 6.85-7.05 (4H, m), 7.21-7.26 (1H, m), 7.40 (1H, d), 10.66 (1H, br s); m/z: ES+ [M+H]$^+$352.2

General Procedure A

A solution of HATU (1.5 eq.) in DMF (0.5 M) was added to a stirred mixture of a PEG di-acid (1.5 eq.), (2S,4R)-1-((S)-2-amino-3,3-dimethylbutanoyl)-4-hydroxy-N-(4-(4-methylthiazol-5-yl)benzyl)pyrrolidine-2-carboxamide (1 eq) and DIPEA (1 eq.) in DMF (0.3 M). The resulting solution was stirred at 20° C. for 2 hours. The reaction mixture was diluted with EtOAc (25 mL), and washed sequentially with water (×3) and saturated brine (×1). The organic layer was dried over Na$_2$SO$_4$, filtered and evaporated to afford crude product. The crude product was purified by C18-flash chromatography, elution gradient 0 to 50% MeCN in water. Product fractions were evaporated to dryness. The crude product was purified by preparative HPLC (XBridge Prep C18 OBD column, silica, 19 mm diameter, 150 mm length), using decreasingly polar mixtures of water (containing 0.01M NH$_4$HCO$_3$) and MeOH as eluents. Fractions containing the desired compound were evaporated to dryness and further purified by preparative HPLC (Waters XBridge Prep C18 OBD column, 5µ silica, 19 mm diameter, 150 mm length), using decreasingly polar mixtures of water (containing 0.01% Formic acid) and MeCN as eluents. Fractions containing the desired compound were evaporated to dryness to afford desired intermediate.

General Procedure B

A reaction vessel was charged with intermediate isolated from general procedure A (0.02 mmol), HATU (0.03 mmol, 1.5 eq.), and triethylamine (0.06 mmol, 3 eq.) in DMF (0.4 mL). 4-((1R,3R)-2-(2-fluoro-2-methylpropyl)-3-methyl-2,3,4,9-tetrahydro-1H-pyrido[3,4-b]indol-1-yl)aniline (0.02 mmol) in DMF (0.4 mL) was added and the reaction was stirred at 20° C. for 4-16 hours. The crude product was purified directly by preparative HPLC (Atlantis T3 OBD column, 5 m silica, 19 mm diameter, 100 mm length), using decreasingly polar mixtures of MeCN and water (containing 0.1% trifluoroacetic acid) as eluents. Fractions containing the desired compound were evaporated to dryness to afford the example products.

Intermediate 54c: (S)-22-((2S,4R)-4-hydroxy-2-(4-(4-methylthiazol-5-yl)benzylcarbamoyl)pyrrolidine-1-carbonyl)-23,23-dimethyl-20-oxo-3,6,9,12,15,18-hexaoxa-21-azatetracosan-1-oic Acid

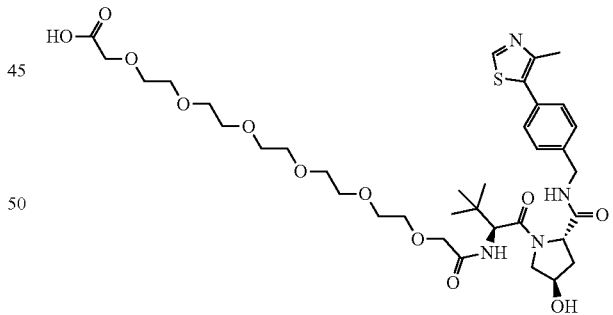

Prepared according to general procedure A using 2-[2-[2-[2-[2-[2-(carboxymethoxy)ethoxy]ethoxy]ethoxy]ethoxy]acetic acid and replacing DIPEA with triethylamine (4 eq.). Isolated as a white foam (0.228 g, 7.90%). $^1$H NMR (300 MHz, DMSO-d6, 25° C.) δ 0.94 (9H, s), 1.90 (1H, m), 2.00-2.13 (1H, m), 2.45 (3H, s), 3.49 (4H, s), 3.50 (4H, s), 3.51 (2H, d), 3.53 (4H, d), 3.57 (6H, m), 3.61 (3H, dd), 3.68 (1H, dd), 3.97 (2H, s), 4.01 (2H, s), 4.25 (1H, dd), 4.38 (2H, d), 4.45 (1H, t), 4.57 (1H, d), 7.41 (3H, s), 7.42-7.47 (1H, m), 8.62 (1H, t), 8.99 (1H, s); m/z: ES+ [M+H]$^+$ 767.3.

Example 54: $N^1$-(4-((1R,3R)-2-(2-fluoro-2-methyl-propyl)-3-methyl-2,3,4,9-tetrahydro-1H-pyrido[3,4-b]indol-1-yl)phenyl)-$N^{18}$—((S)-1-((2S,4R)-4-hydroxy-2-(4-(4-methylthiazol-5-yl)benzylcarbamoyl)pyrrolidin-1-yl)-3,3-dimethyl-1-oxobutan-2-yl)-2,5,8,11,14,17-hexaoxaoctadecane-1,18-dicarboxamide, Trifluoroacetic Acid

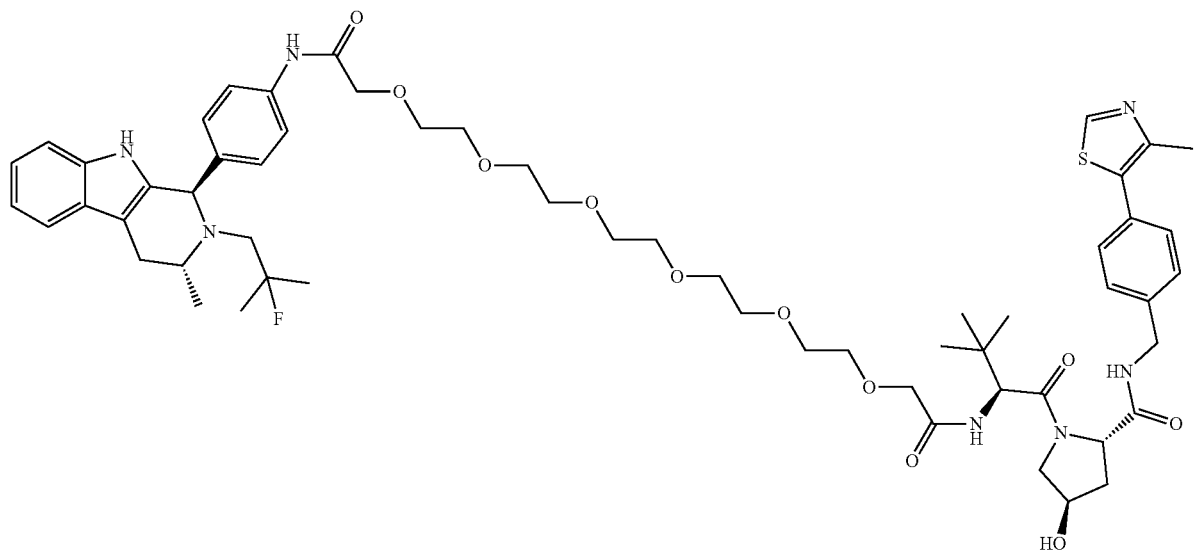 [SMILES: Cc1ncsc1-c1ccc(CNC(=O)[C@@H]2C[C@@H](O)CN2C(=O)[C@@H](NC(=O)COCCOCCOCCOCCOCCOCC(=O)Nc2ccc([C@@H]3c4[nH]c5ccccc5c4C[C@@H](C)N3CC(C)(C)F)cc2)C(C)(C)C)cc1]

Prepared according to general procedure B using (S)-22-((2S,4R)-4-hydroxy-2-(4-(4-methylthiazol-5-yl)benzylcarbamoyl)pyrrolidine-1-carbonyl)-23,23-dimethyl-20-oxo-3,6,9,12,15,18-hexaoxa-21-azatetracosan-1-oic acid and 4-((1R,3R)-2-(2-fluoro-2-methylpropyl)-3-methyl-2,3,4,9-tetrahydro-1H-pyrido[3,4-b]indol-1-yl)aniline. White powder (21.4 mg, 89%). $^1$H NMR (300 MHz, MeOD, 30° C.) 1.02 (9H, s), 1.55 (6H, d), 1.64 (3H, br s), 2.05-2.14 (1H, m), 2.17-2.27 (1H, m), 2.43-2.50 (3H, m), 3.01 (1H, dd), 3.34-3.46 (2H, m), 3.52-3.59 (8H, m), 3.60-3.68 (8H, m), 3.70-3.76 (4H, m), 3.78-3.87 (2H, m), 3.99 (2H, d), 4.12 (2H, s), 4.20-4.28 (1H, m), 4.29-4.37 (1H, m), 4.48 (1H, s), 4.51-4.60 (1H, m), 4.63-4.71 (1H, m), 6.01 (1H, br s), 7.07-7.13 (1H, m), 7.18 (1H, m), 7.28-7.48 (7H, m), 7.58 (1H, d), 7.77 (2H, d), 8.93 (1H, s); m/z: ES+ [M+H]$^+$ 1100.5; ESI-HRMS calculated for $C_{58}H_{79}FN_7O_{11}S$ [M+H]$^+$=1100.5537, measured 1100.5513.

Intermediate 55a: (S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecanoic Acid

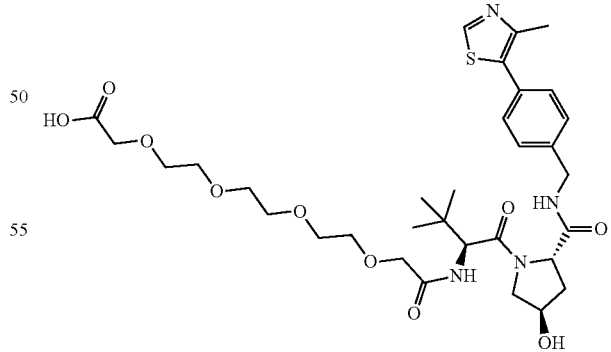

Prepared according to general procedure A using 2-[2-[2-[2-(carboxymethoxy)ethoxy]ethoxy]ethoxy]acetic acid. White foam (0.318 g, 9.36%). $^1$H NMR (400 MHz, Methanol-d4, 25° C.) δ 1.07 (9H, s), 2.11 (1H, m), 2.25 (1H, dd), 2.50 (3H, s), 3.64-3.74 (12H, m), 3.82 (1H, dd), 3.90 (1H, d), 4.07 (2H, d), 4.12 (2H, s), 4.38 (1H, d), 4.53 (2H, d), 4.56-4.61 (1H, m), 4.73 (1H, d), 7.47 (4H, q), 8.90 (1H, s); m/z: ES+ [M+H]$^+$ 679.3.

Example 55: N¹-(4-((1R,3R)-2-(2-fluoro-2-methylpropyl)-3-methyl-2,3,4,9-tetrahydro-1H-pyrido[3,4-b]indol-1-yl)phenyl)-N¹⁴—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12-tetraoxatetradecanediamide, Trifluoroacetic Acid

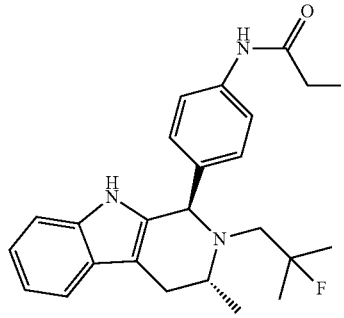
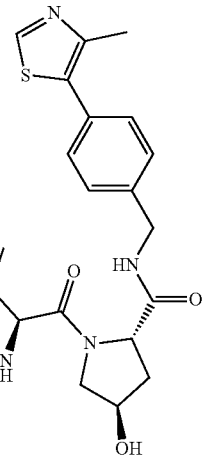

Prepared according to general procedure B using (S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecanoic acid and 4-((1R,3R)-2-(2-fluoro-2-methylpropyl)-3-methyl-2,3,4,9-tetrahydro-1H-pyrido[3,4-b]indol-1-yl)aniline. White powder (21.50 mg, 96%) ¹H NMR (300 MHz, MeOD, 30° C.) 1.00 (9H, s), 1.50-1.68 (9H, m), 1.98-2.13 (1H, m), 2.16-2.27 (1H, m), 2.46 (3H, s), 3.01 (1H, dd), 3.33-3.47 (2H, m), 3.58-3.75 (13H, m), 3.75-3.87 (3H, m), 3.92 (2H, d), 4.09-4.13 (2H, m), 4.20-4.28 (1H, m), 4.29-4.37 (1H, m), 4.48 (1H, s), 4.52-4.58 (1H, m), 4.61-4.71 (1H, m), 6.01 (1H, br s), 7.06-7.23 (2H, m), 7.28-7.47 (7H, m), 7.52-7.62 (2H, m), 7.75 (2H, d), 8.93 (1H, s); m/z: ES+ [M+H]⁺ 1012.5; ESI-HRMS calculated for $C_{54}H_{71}FN_7O_9S$ [M+H]⁺=1012.5013, measured 1012.4985.

Intermediate 56a: (S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoic Acid

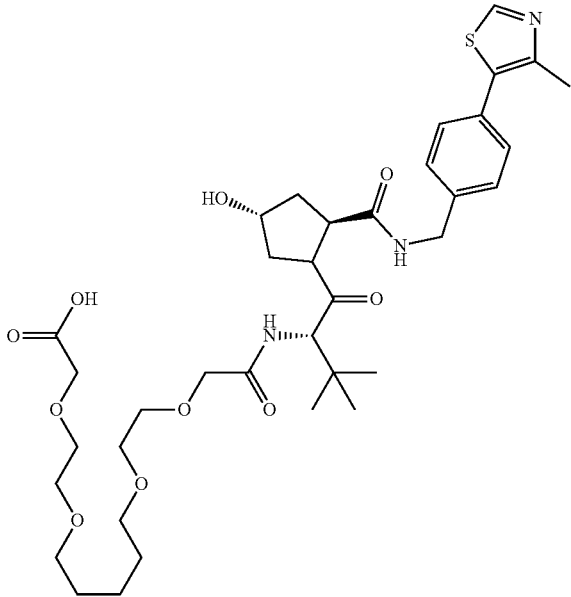 [SMILES: Cc1ncsc1-c1ccc(CNC(=O)[C@@H]2C[C@@H](O)CC2C(=O)[C@@H](NC(=O)COCCOCCCCCOCCOCC(=O)O)C(C)(C)C)cc1]

Prepared according to general procedure A using 2-[2-[2-[2-[2-(carboxymethoxy)ethoxy]ethoxy]ethoxy]ethoxy]acetic acid. White foam (0.204 g, 6.58%). ¹H NMR (400 MHz, Methanol-d4, 25° C.) δ 0.94 (9H, s), 1.91 (1H, m), 2.00-2.13 (1H, m), 2.45 (3H, s), 3.49 (4H, s), 3.52 (4H, dd), 3.54-3.60 (7H, m), 3.60-3.64 (3H, m), 3.68 (1H, dd), 3.97 (2H, s), 4.00 (2H, s), 4.25 (1H, dd), 4.32-4.40 (2H, m), 4.40-4.48 (1H, m), 4.57 (1H, d), 7.41 (3H, s), 7.43 (1H, d), 8.61 (1H, t), 8.99 (1H, s). m/z: ES+ [M+H]⁺723.3

Example 56: N¹-(4-((1R,3R)-2-(2-fluoro-2-methylpropyl)-3-methyl-2,3,4,9-tetrahydro-1H-pyrido[3,4-b]indol-1-yl)phenyl)-N¹⁷—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaheptadecanediamide, Trifluoroacetic Acid

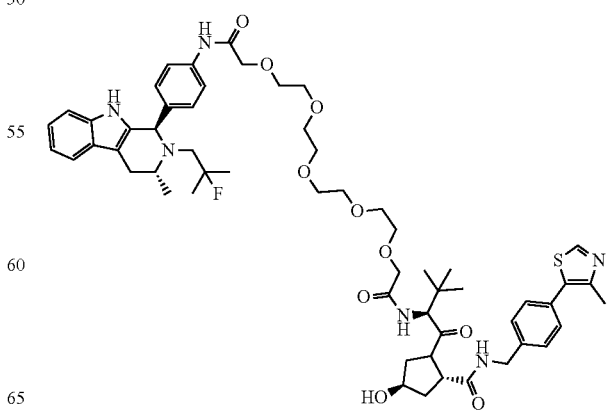

253

Prepared according to general procedure B using (S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoic acid and 4-((1R,3R)-2-(2-fluoro-2-methylpropyl)-3-methyl-2,3,4,9-tetrahydro-1H-pyrido[3,4-b]indol-1-yl)aniline. Yellow powder (30.0 mg, 90%). $^1$H NMR (300 MHz, MeOD, 30° C.) 1.01 (9H, s), 1.55 (4H, br d), 1.64 (3H, br s), 2.02-2.14 (1H, m), 2.16-2.27 (1H, m), 2.46 (3H, s), 3.01 (1H, dd), 3.37 (2H, br d), 3.55-3.66 (12H, m), 3.69-3.75 (4H, m), 3.78-3.87 (2H, m), 3.96 (2H, d), 4.12 (2H, s), 4.29-4.38 (1H, m), 4.48 (1H, s), 4.53-4.59 (1H, m), 4.65-4.71 (1H, m), 6.01 (1H, br s), 7.06-7.14 (1H, m), 7.18 (1H, m), 7.24-7.32 (1H, m), 7.33-7.47 (6H, m), 7.58 (2H, d), 7.77 (2H, d), 8.97 (1H, s); m/z: ES+ [M+H]$^+$ 1056.5; ESI-HRMS calculated for $C_{56}H_{75}FN_7O_{10}S$ [M+H]$^+$=1056.5275, measured 1056.5261.

Intermediate 57a: (S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoic Acid

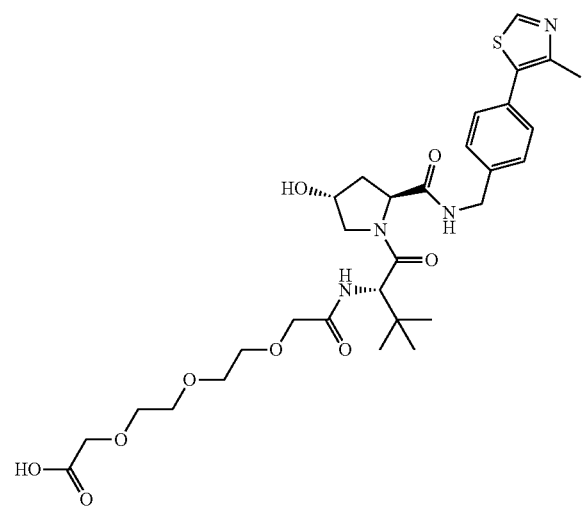 [SMILES: Cc1ncsc1-c1ccc(CNC(=O)[C@@H]2C[C@@H](O)CN2C(=O)[C@@H](NC(=O)COCCOCCOCC(=O)O)C(C)(C)C)cc1]

Prepared according to general procedure A using 2-[2-[2-(carboxymethoxy)ethoxy]ethoxy]acetic acid. White solid (0.210 g, 9.50%). $^1$H NMR (400 MHz, Methanol-d4, 25° C.) δ 1.14 (9H, s), 2.05-2.15 (1H, m), 2.20-2.29 (1H, m), 2.50 (3H, s), 3.78-3.68 (8H, m), 3.83 (1H, dd), 3.90 (1H, d), 4.08 (2H, d), 4.12 (2H, s), 4.39 (1H, d), 4.49-4.63 (3H, m), 4.72 (1H, s), 7.47 (4H, q), 8.90 (1H, s); m/z: ES+ [M+H]$^+$ 635.3

254

Example 57: (2S,4R)-1-((S)-2-(tert-butyl)-14-((4-((1R,3R)-2-(2-fluoro-2-methylpropyl)-3-methyl-2,3,4,9-tetrahydro-1H-pyrido[3,4-b]indol-1-yl)phenyl)amino)-4,14-dioxo-6,9,12-trioxa-3-azatetradecanoyl)-4-hydroxy-N-(4-(4-methylthiazol-5-yl)benzyl)pyrrolidine-2-carboxamide, Trifluoroacetic Acid

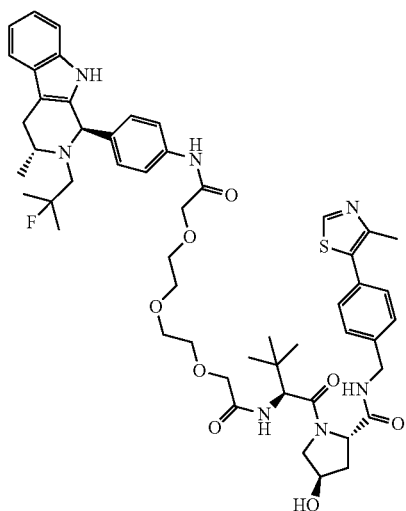 [SMILES: Cc1ncsc1-c1ccc(CNC(=O)[C@@H]2C[C@@H](O)CN2C(=O)[C@@H](NC(=O)COCCOCCOCC(=O)Nc2ccc([C@@H]3c4[nH]c5ccccc5c4C[C@@H](C)N3CC(C)(C)F)cc2)C(C)(C)C)cc1]

Prepared according to general procedure B using (S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoic acid and 4-((1R,3R)-2-(2-fluoro-2-methylpropyl)-3-methyl-2,3,4,9-tetrahydro-1H-pyrido[3,4-b]indol-1-yl)aniline. Yellow powder (16.1 mg, 52%). $^1$H NMR (300 MHz, MeOD, 30° C.) δ 0.99 (9H, s), 1.50-1.69 (8H, m), 2.00-2.14 (1H, m), 2.16-2.27 (1H, m), 2.46 (3H, s) 3.01 (1H, dd), 3.34-3.46 (2H, m), 3.63-3.86 (12H, m), 3.92-4.00 (1H, m), 4.02-4.16 (2H, m), 4.19-4.38 (2H, m), 4.46-4.67 (4H, m), 5.99 (1H, br s), 7.06-7.14 (1H, m), 7.14-7.22 (1H, m), 7.26-7.48 (7H, m), 7.52-7.61 (2H, m), 7.69 (2H, d), 8.89 (1H, s); m/z: ES+ [M+H]$^+$ 968.4.

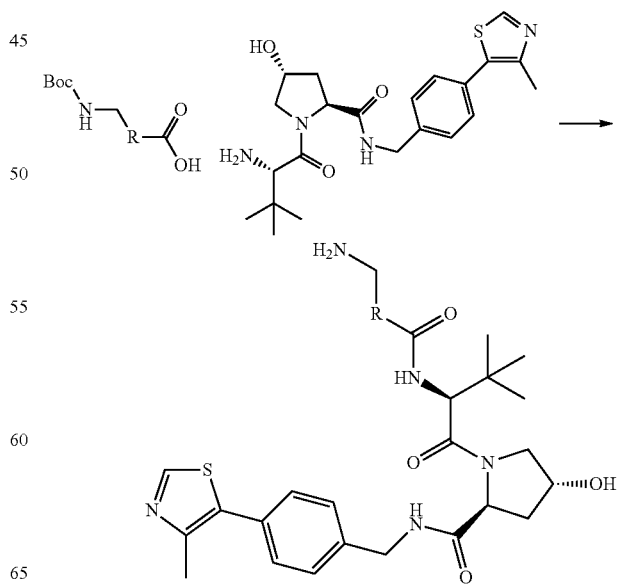

General Procedure C:

Triethylamine (6 equiv.) was added to a mixture of a Boc-protected amino carboxylic acid (1 equiv.), and HATU (2 equiv) in DMF (0.11 M). The mixture was stirred at 25° C. for 1 hour. The reaction mixture was diluted with EtOAc, and washed with saturated brine 3 times. The organic layer was dried over Na$_2$SO$_4$, filtered and evaporated to afford crude product. The crude product was purified by flash silica chromatography, elution gradient 0 to 5% MeOH in DCM. Pure fractions were evaporated to dryness to afford Boc-protected amino intermediate.

A solution of 4 M HCl in dioxane (30 eq.) was added to protected intermediate (1 equiv.), then the mixture was stirred at 25° C. for 2 hours. The solvent was removed under reduced pressure. The crude product was purified by preparative HPLC (Xselect CSH OBD column 30*150 mm, 5 μm silica) using decreasingly polar mixtures of MeCN and water (containing 0.05% trifluoroacetic acid) as eluents. Fractions containing the desired compound were evaporated to dryness to afford desired product.

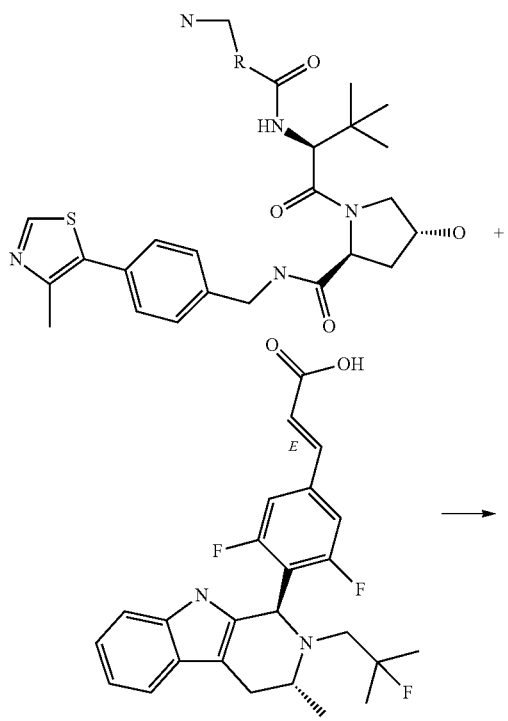

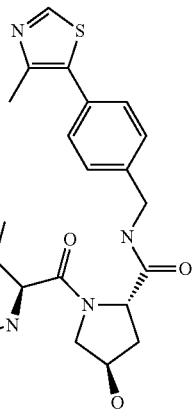

General Procedure D:

(E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid (preparation described in WO2014/191726 A1) (6 mg, 0.01 mmol), HATU (7.73 mg, 0.02 mmol), and triethylamine (5.7 μL, 0.04 mmol) were dissolved in DMF (0.4 mL). This was added to a solution of the requisite amine (0.01 mmol) in DMF (0.4 mL). The reaction was stirred at 20° C. for 16 hours, then the crude product was purified directly by preparative HPLC (Atlantis T3 OBD column, 5 μm silica, 19 mm diameter, 100 mm length), using decreasingly polar mixtures of MeCN and water (containing 0.1% trifluoroacetic acid) as eluents. Fractions containing the desired compound were evaporated to dryness to afford the example products.

Intermediate 58a: (2S,4R)-1-((S)-2-(2-(2-(2-aminoethoxy)ethoxy)acetamido)-3,3-dimethylbutanoyl)-4-hydroxy-N-(4-(4-methylthiazol-5-yl)benzyl)pyrrolidine-2-carboxamide

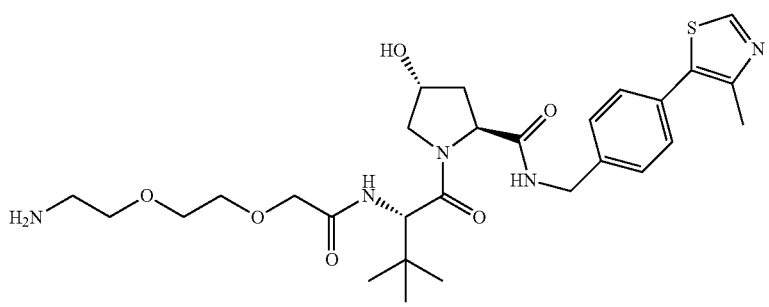 [SMILES: Cc1ncsc1-c1ccc(CNC(=O)[C@@H]2C[C@@H](O)CN2C(=O)[C@@H](NC(=O)COCCOCCN)C(C)(C)C)cc1]

Prepared according to general procedure C using 2,2-dimethyl-4-oxo-3,8,11-trioxa-5-azatridecane-13-oic acid. Yellow solid (1.0 g, 50.0%). ¹H NMR (400 MHz, DMSO-d6, 25° C.) δ 0.94 (9H, s), 1.90 (1H, m), 2.09 (1H, dd), 2.45 (3H, s), 2.96 (2H, q), 3.54-3.70 (8H, m), 3.92-4.07 (2H, m), 4.25-4.59 (8H, m), 7.40 (4H, s), 7.50 (1H, d), 8.18 (3H, br s), 8.76 (1H, t), 9.04 (1H, 2); m/z: ES+ [M+H]⁺ 576.4

Example 58: (2S,4R)-1-((S,E)-2-(tert-butyl)-15-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-4,13-dioxo-6,9-dioxa-3,124-diazapentadec-4-enoyl)-4-hydroxy-N-(4-(4-methylthiazol-5-yl)benzyl)pyrrolidine-2-carboxamide, Trifluoroacetic Acid

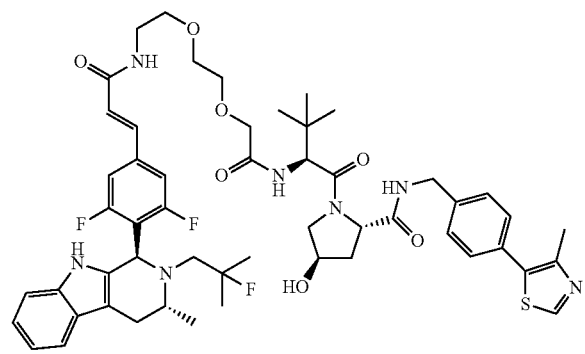 [SMILES: Cc1ncsc1-c1ccc(CNC(=O)[C@@H]2C[C@@H](O)CN2C(=O)[C@@H](NC(=O)COCCOCCNC(=O)/C=C/c2cc(F)c([C@@H]3c4[nH]c5ccccc5c4C[C@@H](C)N3CC(C)(C)F)c(F)c2)C(C)(C)C)cc1]

Prepared according to general procedure D using (2S,4R)-1-((S)-2-(2-(2-(2-aminoethoxy)ethoxy)acetamido)-3,3-dimethylbutanoyl)-4-hydroxy-N-(4-(4-methylthiazol-5-yl)benzyl)pyrrolidine-2-carboxamide. Colourless gum (3.6 mg, 23.9%). ¹H NMR (300 MHz, MeOD, 30° C.) δ 1.00 (9H, s), 1.21-1.51 (9H, m), 1.99-2.11 (1H, m), 2.18-2.27 (1H, m), 2.44 (3H, s), 3.43-3.74 (9H, m), 3.75-3.88 (2H, m), 3.93-4.12 (2H, m), 4.32-4.40 (1H, m), 4.46 (1H, br s), 4.57 (1H, t), 4.72 (1H, d), 6.73 (1H, d), 7.00-7.13 (2H, m), 7.20-7.31 (3H, m), 7.35-7.51 (6H, m), 7.69 (1H, br d), 8.57 (1H, t), 8.84 (1H, s); m/z: ES+ [M+H]⁺ 1000.5.

Intermediate 59a: (2S,4R)-1-((S)-2-(7-aminoheptanamido)-3,3-dimethylbutanoyl)-4-hydroxy-N-(4-(4-methylthiazol-5-yl)benzyl)pyrrolidine-2-carboxamide

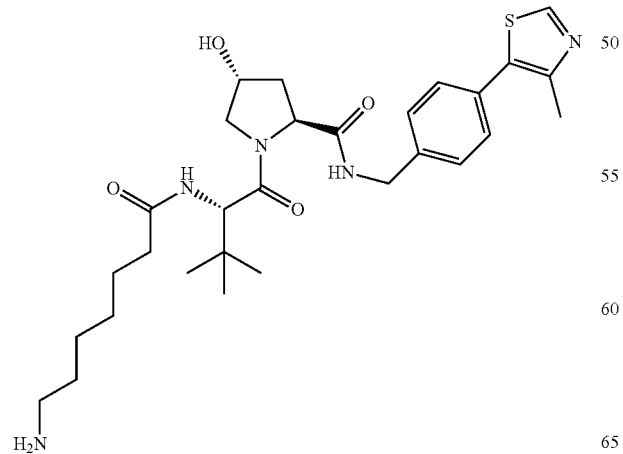

Prepared according to general procedure C using 7-(tert-butoxycarbonylamino)heptanoic acid. Colourless solid (1.000 g, 49%)¹H NMR (300 MHz, DMSO-d6, 25° C.) δ 0.94 (9H, s), 1.20-1.35 (4H, m), 1.42-1.58 (4H, m), 1.86-1.97 (1H, m), 1.98-2.19 (2H, m) 2.28 (1H, m), 2.45 (3H, s), 2.52 (1H, s), 2.76 (2H, d), 3.66 (2H, d), 4.04-4.72 (5H, m), 7.36-4.47 (4H, m), 7.64 (3H, br s), 7.86 (1H, d), 8.57 (1H, t), 9.0 (1H, s); m/z: ES+ [M+H]⁺ 558.2

Example 59: (2S,4R)-1-((S)-2-(7-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)heptanamido)-3,3-dimethylbutanoyl)-4-hydroxy-N-(4-(4-methylthiazol-5-yl)benzyl)pyrrolidine-2-carboxamide, Trifluoroacetic Acid

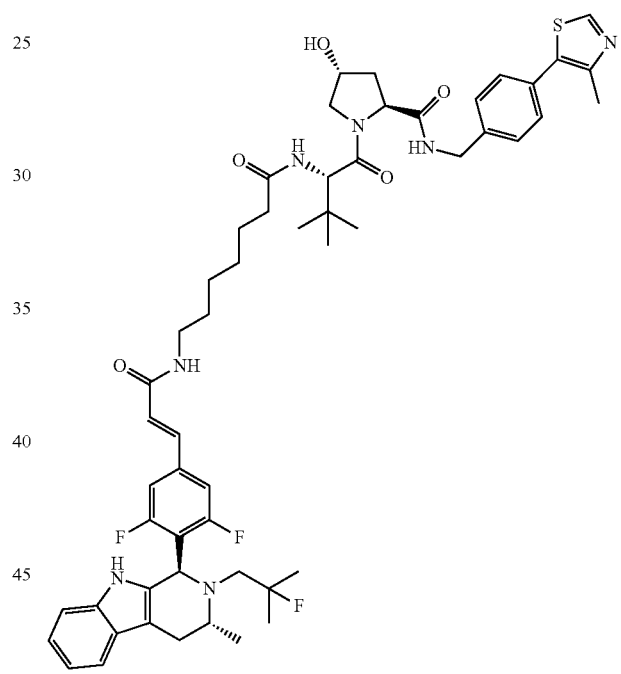

Prepared according to general procedure D using (2S,4R)-1-((S)-2-(7-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)heptanamido)-3,3-dimethylbutanoyl)-4-hydroxy-N-(4-(4-methylthiazol-5-yl)benzyl)pyrrolidine-2-carboxamide. Colourless gum (5.0 mg, 30%). ¹H NMR (300 MHz, MeOD, 30° C.) δ 1.02 (9H, s), 1.31-1.44 (4H, m), 1.51-1.65 (12H, m), 2.00-2.12 (1H, m), 2.16-2.22 (1H, m), 2.27 (2H, m), 2.47 (3H, s), 3.07 (1H, dd), 3.35-3.50 (1H, m), 3.74-3.83 (1H, m), 3.84-3.94 (1H, m), 4.12-4.25 (1H, m), 4.29-4.40 (1H, m), 4.46-4.64 (4H, m), 6.28 (1H, br s), 6.71 (1H, d), 7.05-7.20 (2H, m), 7.26-7.38 (3H, m), 7.38-7.49 (5H, m), 7.55 (1H, d), 8.96 (1H, s); m/z: ES+ [M+H]⁺ 982.6; ESI-HRMS calculated for $C_{54}H_{67}F_3N_7O_5S$ [M+H]⁺=982.4871, measured 982.4840.

Intermediate 60a: (2S,4R)-1-((S)-2-(5-aminopentanamido)-3,3-dimethylbutanoyl)-4-hydroxy-N-(4-(4-methylthiazol-5-yl)benzyl)pyrrolidine-2-carboxamide

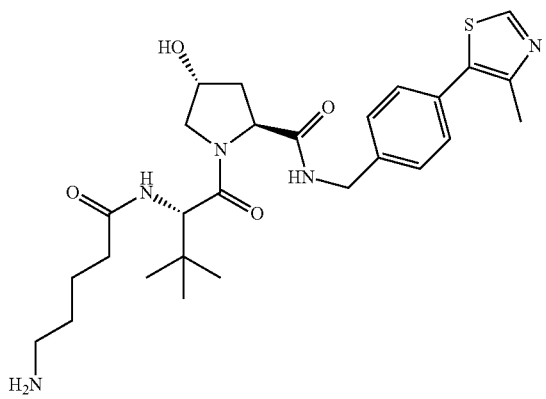

Prepared according to general procedure C using 5-(tert-butoxycarbonylamino)pentanoic acid. Colourless solid (0.500 g, 23.18%). $^1$H NMR (300 MHz, DMSO-d6, 25° C.) δ 0.95 (s, 9H), 1.52 (dd, 4H), 1.91 (m, 1H), 1.99-2.11 (m, 1H), 2.17 (m, 1H), 2.24-2.37 (m, 1H), 2.45 (s, 3H), 2.52 (1H, s), 2.79 (2H, q), 3.39-3.85 (2H, m), 4.22 (1H, dd), 4.24-4.55 (3H, m), 4.56 (tH, d), 7.38-7.46 (4H, m), 7.75 (3H, br s), 7.92 (1H, d), 8.58 (1H, t), 9.00 (1H, s); m/z: ES+ [M+H]$^+$ 530.2.

Example 60: (2S,4R)-1-((S)-2-(5-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)pentanamido)-3,3-dimethylbutanoyl)-4-hydroxy-N-(4-(4-methylthiazol-5-yl)benzyl)pyrrolidine-2-carboxamide, Trifluoroacetic Acid

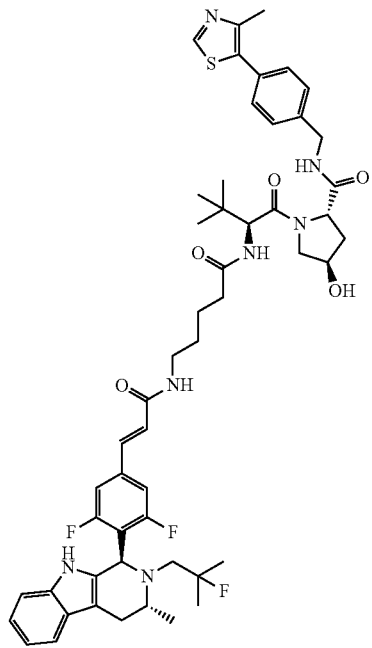 [SMILES: Cc1ncsc1-c1ccc(CNC(=O)[C@@H]2C[C@@H](O)CN2C(=O)[C@@H](NC(=O)CCCCNC(=O)/C=C/c2cc(F)c([C@@H]3c4[nH]c5ccccc5c4C[C@@H](C)N3CC(C)(C)F)c(F)c2)C(C)(C)C)cc1]

Prepared according to general procedure D using (2S,4R)-1-((S)-2-(5-aminopentanamido)-3,3-dimethylbutanoyl)-4-hydroxy-N-(4-(4-methylthiazol-5-yl)benzyl)pyrrolidine-2-carboxamide. Colourless gum (11.5 mg, 75%). $^1$H NMR (300 MHz, MeOD, 30° C.) δ 1.02 (9H, s), 1.50-1.67 (12H, m), 2.02-2.14 (1H, m), 2.15-2.25 (1H, m), 2.27-2.37 (2H, m), 2.47 (3H, s), 3.08 (1H, dd), 3.33-3.51 (1H, m), 3.73-3.93 (3H, m), 4.13-4.26 (1H, m), 4.31-4.42 (1H, m), 4.45-4.63 (3H, m), 6.30 (1H, br s), 6.71 (1H, d), 7.05-7.12 (1H, m), 7.17 (1H, m), 7.27-7.49 (8H, m), 7.55 (1H, d), 9.03 (1H, s); m/z: ES+ [M+H]$^+$ 954.5; ESI-HRMS calculated for $C_{52}H_{63}F_3N_7O_5S$ [M+H]$^+$=954.4558, measured 954.4529.

Intermediate 61a: 2-(4-(2-((tert-butoxycarbonyl)amino)ethoxy)phenoxy)acetic Acid

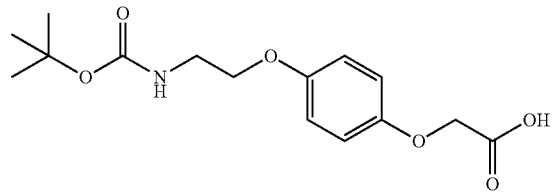 [SMILES: CC(C)(C)OC(=O)NCCOc1ccc(OCC(=O)O)cc1]

$Cs_2CO_3$ (16.10 g, 49.40 mmol) was added to a mixture of methyl 2-(4-hydroxyphenoxy)acetate (3 g, 16.47 mmol) and tert-butyl (2-bromoethyl)carbamate (5.54 g, 24.70 mmol) in DMF (150 mL), then the mixture was stir at 80° C. for 1 hour. 2 M aq. HCl (20 mL) was added, and the reaction extracted with EtOAc (3×50 mL). The combined the organic layer was washed with brine (2×50 mL), dried over $Na_2SO_4$, filtered and evaporated to dryness. The residue was dissolved in MeOH (50 mL). A solution of LiOH (3.87 g, 161.67 mmol) in $H_2O$ (25 mL) was added, then the mixture was stirred at 25° C. for 2 hours. The MeOH was removed under reduced pressure. EtOAc (20 mL) was added, and the organic layer was extracted with $H_2O$ (3×20 mL). The combined aqueous layers and were adjusted to pH 2 with 2M aq. HCl. The aqueous layer was extracted with DCM (3×20 mL). The organic layer was dried $Na_2SO_4$, filtered, and concentrated under reduced pressure to afford the title compound (3.80 g, 75%) as a orange liquid that was used in the next step without further purification. $^1$H NMR (400 MHz, DMSO-d6, 25° C.) δ 1.39 (9H, s), 3.26 (2H, q), 3.88 (2H, t), 4.59 (2H, s), 6.78-6.90 (4H, m), 6.98 (1H, t), 12.73 (1H, br s).

Intermediate 61b: (2S,4R)-1-((S)-2-(2-(4-(2-aminoethoxy)phenoxy)acetamido)-3,3-dimethylbutanoyl)-4-hydroxy-N-(4-(4-methylthiazol-5-yl)benzyl)pyrrolidine-2-carboxamide, Hydrochloride

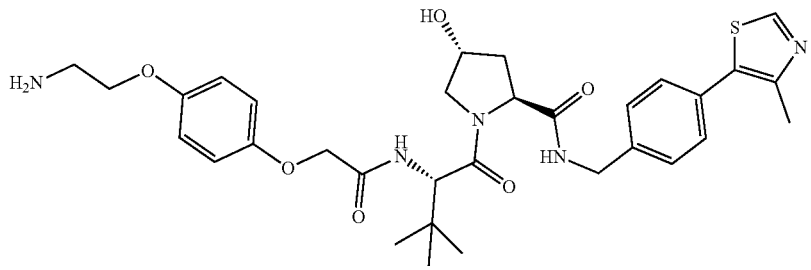 [SMILES: Cc1ncsc1-c1ccc(CNC(=O)[C@@H]2C[C@@H](O)CN2C(=O)[C@@H](NC(=O)COc2ccc(OCCN)cc2)C(C)(C)C)cc1]

Prepared according to general procedure C using 2-(4-(2-((tert-butoxycarbonyl)amino)ethoxy)phenoxy)acetic acid. White powder (1.65 g, 38.9%). ¹H NMR (400 MHz, DMSO-d6, 25° C.) δ 0.92 (9H, s), 1.91 (1H, m), 2.06 (1H, t), 2.45 (3H, s), 3.03 (2H, d), 3.66 (2H, dd) 4.0 (2H, d), 4.25 (1H, dd), 4.32-4.59 (6H, m), 6.90 (4H, s), 7.40 (4H, s) 7.73 (1H, d) 8.33 (1H, s) 8.61 (1H, t), 8.99 (1H, s); m/z: ES+ [M+H]⁺ 624.3

Example 61: (2S,4R)-1-((S)-2-(2-(4-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)phenoxy)acetamido)-3,3-dimethylbutanoyl)-4-hydroxy-N-(4-(4-methylthiazol-5-yl)benzyl)pyrrolidine-2-carboxamide, Trifluoroacetic Acid

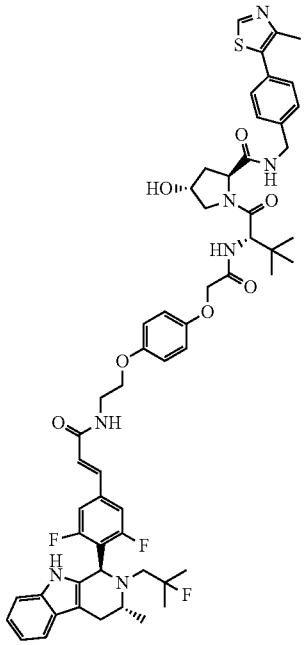 [SMILES: Cc1ncsc1-c1ccc(CNC(=O)[C@@H]2C[C@@H](O)CN2C(=O)[C@@H](NC(=O)COc2ccc(OCCNC(=O)/C=C/c3cc(F)c([C@@H]4c5[nH]c6ccccc6c5C[C@@H](C)N4CC(C)(C)F)c(F)c3)cc2)C(C)(C)C)cc1]

Prepared according to general procedure D using (2S,4R)-1-((S)-2-(2-(4-(2-aminoethoxy)phenoxy)acetamido)-3,3-dimethylbutanoyl)-4-hydroxy-N-(4-(4-methylthiazol-5-yl) benzyl)pyrrolidine-2-carboxamide, hydrochloride. Colourless gum (11.1 mg, 67%). H NMR (300 MHz, MeOD, 30° C.) δ 0.98 (9H, s), 1.53-1.63 (9H, m), 2.02-2.14 (1H, m), 2.17-2.28 (1H, m), 2.48 (3H, s), 3.02-3.14 (1H, m), 3.35-3.50 (1H, m), 3.66 (2H, t), 3.77-3.90 (2H, m), 4.05 (2H, t), 4.15-4.25 (1H, m), 4.30-4.40 (1H, m), 4.45-4.61 (5H, m), 4.71 (1H, s), 6.27-6.33 (1H, m), 6.76 (1H, d), 6.86-6.96 (4H, m), 7.05-7.12 (1H, m), 7.17 (1H, m), 7.27-7.38 (3H, m), 7.40-7.48 (4H, m), 7.52 (2H, dd), 9.02 (1H, s); m/z: ES+ [M+H]⁺ 1048.6; ESI-HRMS calculated for C₅₇H₆₅F₃N₇O₇S [M+H]⁺=1048.4613, measured 1048.4581.

Intermediate: 62a: (2S,4R)-1-((S)-2-(2-(2-aminoethoxy)acetamido)-3,3-dimethylbutanoyl)-4-hydroxy-N-(4-(4-methylthiazol-5-yl)benzyl)pyrrolidine-2-carboxamide

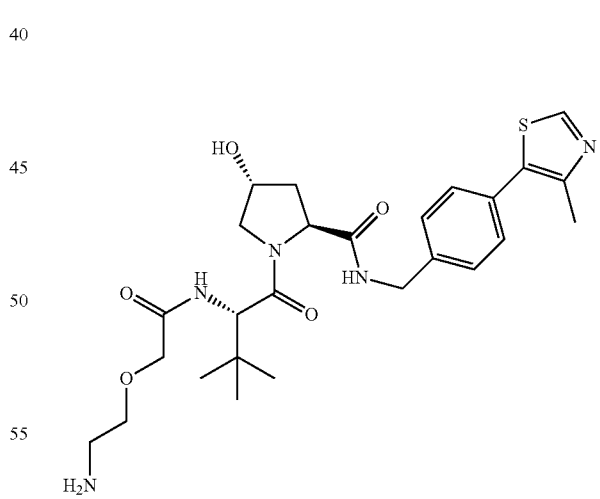

Prepared according to general procedure C using 2-(2-((tert-butoxycarbonyl)amino)ethoxy)acetic acid. Yellow solid (8.0 g, 30.7%). ¹H NMR (400 MHz, DMSO-d6, 25° C.) δ 0.97 (9H, s) 1.81-2.0 (1H, m), 2.08 (1H, t), 2.46 (3H, s), 2.94 (2H, t), 3.23-3.78 (4H, m), 4.04 (2H, s), 4.16-4.53 (5H, m), 4.61 (2H, d), 7.42 (4H, s), 7.80 (1H, d), 8.40 (1H, s), 8.64 (1H, t), 9.0 (1H, s); m/z: ES+ [M+H]⁺ 532.4

Example 62: (2S,4R)-1-((S)-2-(2-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)acetamido)-3,3-dimethylbutanoyl)-4-hydroxy-N-(4-(4-methylthiazol-5-yl)benzyl)pyrrolidine-2-carboxamide, Trifluoroacetic Acid

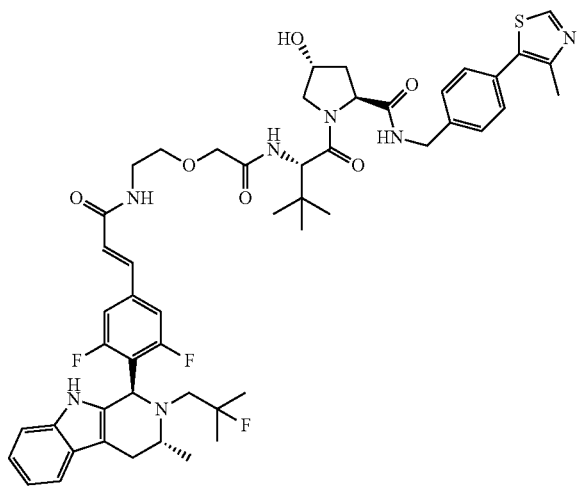 [SMILES: Cc1ncsc1-c1ccc(CNC(=O)[C@@H]2C[C@@H](O)CN2C(=O)[C@@H](NC(=O)COCCNC(=O)/C=C/c2cc(F)c([C@@H]3c4[nH]c5ccccc5c4C[C@@H](C)N3CC(C)(C)F)c(F)c2)C(C)(C)C)cc1]

Prepared according to general procedure C using (2S,4R)-1-((S)-2-(2-(2-aminoethoxy)acetamido)-3,3-dimethylbutanoyl)-4-hydroxy-N-(4-(4-methylthiazol-5-yl)benzyl)pyrrolidine-2-carboxamide. Colourless gum (11.8 mg, 73%). m/z: ES+ [M+H]+ 956.5; ESI-HRMS calculated for $C_{51}H_{61}F_3N_7O_6S$ [M+H]+=956.4351, measured 956.4317.

Example 63: (2S,4R)-1-((S,E)-2-(tert-butyl)-18-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-4,16-dioxo-6,9,12-trioxa-3,15-diazaoctadec-17-enoyl)-4-hydroxy-N-(4-(4-methylthiazol-5-yl)benzyl)pyrrolidine-2-carboxamide, Trifluoroacetic Acid

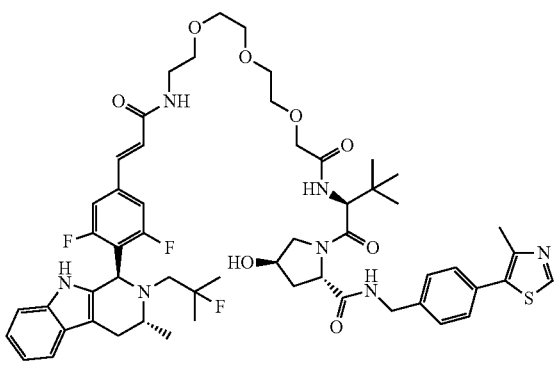 [SMILES: Cc1ncsc1-c1ccc(CNC(=O)[C@@H]2C[C@@H](O)CN2C(=O)[C@@H](NC(=O)COCCOCCOCCNC(=O)/C=C/c2cc(F)c([C@@H]3c4[nH]c5ccccc5c4C[C@@H](C)N3CC(C)(C)F)c(F)c2)C(C)(C)C)cc1]

Prepared according to general procedure D using (2S,4R)-1-[(2S)-2-[[2-[2-[2-(2-aminoethoxy)ethoxy]ethoxy]acetyl]amino]-3,3-dimethyl-butanoyl]-4-hydroxy-N-[[4-(4-methylthiazol-5-yl)phenyl]methyl]pyrrolidine-2-carboxamide (preparation described in WO2016/146985 A1). Colourless gum (9.1 mg, 52%). $^1$H NMR (300 MHz, MeOD, 30° C.) δ 1.01 (9H, s), 1.50-1.64 (10H, m), 2.01-2.12 (1H, m), 2.21 (1H, br dd), 2.46 (3H, s), 3.07 (1H, br dd), 3.33-3.50 (3H, m), 3.54-3.71 (8H, m), 3.73-3.87 (2H, m), 3.94-4.07 (2H, m), 4.19 (1H, m), 4.31-4.39 (1H, m), 4.41-4.50 (1H, m), 4.51-4.61 (1H, m), 4.68 (1H, s), 6.28 (1H, br s), 6.73 (1H, d), 7.04-7.12 (1H, m), 7.16 (1H, m), 7.26-7.49 (8H, m), 7.55 (1H, d), 8.94 (1H, s); m/z: ES+ [M+H]+ 1044.6; ESI-HRMS calculated for $C_{55}H_{69}F_3N_7O_8S$ [M+H]+=1044.4875, measured 1044.4840.

Intermediate 64a: 1-(2-(2-((tert-butoxycarbonyl)amino)ethoxy)ethyl)-1H-pyrazole-4-carboxylic Acid

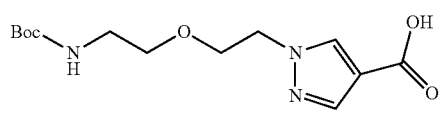 [SMILES: CC(C)(C)OC(=O)NCCOCCn1cc(C(=O)O)cn1]

Potassium carbonate (4.14 g, 29.97 mmol) was added to the mixture of ethyl 1H-pyrazole-4-carboxylate (1.4 g, 9.99 mmol), 2-(2-((tert-butoxycarbonyl)amino)ethoxy)ethyl methanesulfonate (3.40 g, 12.0 mmol) in DMF (50 mL), the mixture was stirred at 80° C. for 1 hour. The reaction mixture was diluted with EtOAc (150 mL), and washed with 3 times with brine. The organic was dried over $Na_2SO_4$, filtered, and the solvent was removed under reduced pressure to afford ethyl 1-(2-(2-((tert-butoxycarbonyl)amino)ethoxy)ethyl)-1H-pyrazole-4-carboxylate (3.27 g, 100%) as a yellow oil. The crude product was used in the next step directly without further purification. KOH (2.0 M) (94 mL, 187.55 mmol) was added to the mixture of ethyl 1-(2-(2-((tert-butoxycarbonyl)amino)ethoxy)ethyl)-1H-pyrazole-4-carboxylate (3.07 g, 9.38 mmol) in MeOH (10 mL), then the mixture was stir at 25° C. for 2 hours. MeOH was removed under reduced pressure. 50 mL EtOAc was added and the organic layer was extracted with $H_2O$ (3×50 mL). The aqueous layers were combined and adjusted to pH 2 with 2M aq. HCl. The aqueous layer was extracted with DCM (3×100 mL). The organic layer was dried over $Na_2SO_4$, filtered, and the solvent was removed under reduced pressure to afford the title compound (2.81 g, 100%) as a yellow oil. $^1$H NMR (300 MHz, DMSO-d6, 30° C.) δ 1.42 (s, 9H), 3.17 (t, 2H), 3.45 (t, 2H), 3.81 (dd, 2H), 4.33 (dd, 2H), 7.87 (d, 1H), 8.15 (d, 1H); ES+ [M+H]+ 300.1.

Intermediate 64b: 1-(2-(2-aminoethoxy)ethyl)-N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-1H-pyrazole-4-carboxamide

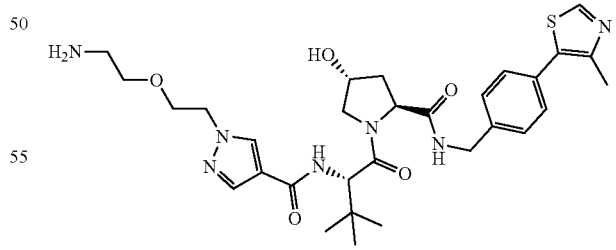

Prepared according to general procedure C using 1-(2-(2-((tert-butoxycarbonyl)amino)ethoxy)ethyl)-1H-pyrazole-4-carboxylic acid. White solid. $^1$H NMR (300 MHz, DMSO-d6, 25° C.) δ 1.00 (s, 9H), 1.92 (m, 1H), 2.04 (q, 1H), 2.46 (s, 3H), 2.87 (br s, 2H), 3.54 (s, 3H), 3.71 (d, 5H), 4.20-4.51 (m, 7H), 4.76 (d, 1H), 7.30-7.50 (m, 4H), 7.78 (d, 1H), 8.01 (s, 1H), 8.43 (s, 2H), 8.62 (t, J=6.1 Hz, 1H), 8.99 (s, 1H); m/z: ES+ [M+H]+612.2.

Example 64: 1-(2-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)ethyl)-N—((S)-1-((2S,4R)-4-hydroxy-2-((4-(4-methylthiazol-5-yl)benzyl)carbamoyl)pyrrolidin-5-yl)-3,3-dimethyl-1-oxobutan-2-yl)-1H-pyrazole-4-carboxamide, Trifluoroacetic Acid

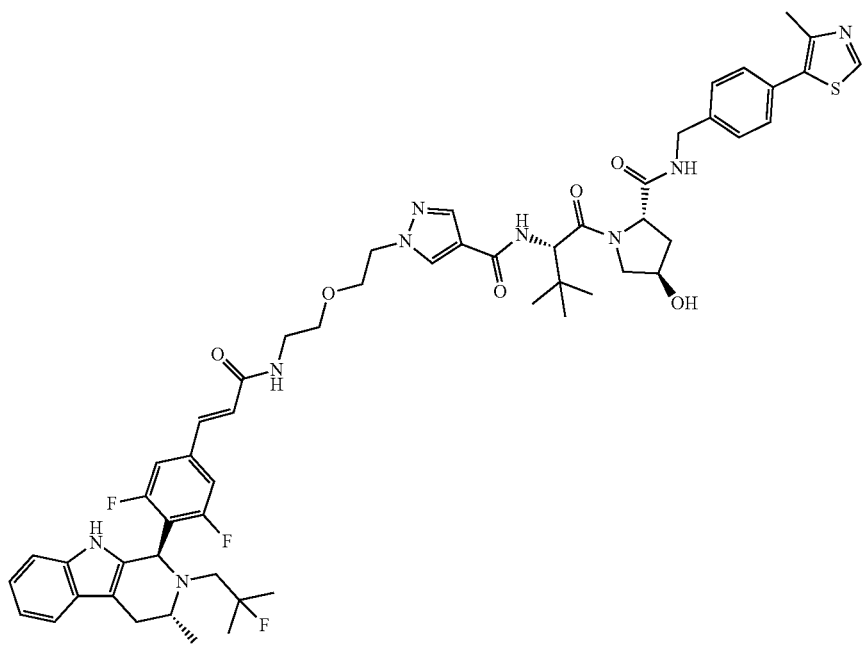 [SMILES: Cc1ncsc1-c1ccc(CNC(=O)[C@@H]2C[C@@H](O)CN2C(=O)[C@@H](NC(=O)c2cnn(CCOCCNC(=O)/C=C/c3cc(F)c([C@@H]4c5[nH]c6ccccc6c5C[C@@H](C)N4CC(C)(C)F)c(F)c3)c2)C(C)(C)C)cc1]

Prepared according to general procedure D using 1-(2-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)ethyl)-N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-1H-pyrazole-4-carboxamide. Colourless gum (14.3 mg, 83%). m/z: ES+ [M+H]$^+$ 1036.6; ESI-HRMS calculated for $C_{55}H_{65}F_3N_9O_6S$ [M+H]$^+$=1036.4725, measured 1036.4702.

Intermediate 65a: tert-butyl (3-(4-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)piperidin-1-yl)propyl)carbamate

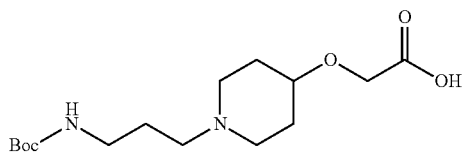 [SMILES: CC(C)(C)OC(=O)NCCCN1CCC(OCC(=O)O)CC1]

Potassium carbonate (13.83 g, 100.05 mmol) was added to the solution of piperidin-4-ol (5.06 g, 50.03 mmol) and tert-butyl (3-bromopropyl)carbamate (14.29 g, 60.03 mmol) in DMF (200 mL) then stirred at 25° C. for 3 hours. The reaction was diluted with water (500 mL), extracted with EtOAc (3×200 mL), and concentrated in vacuo. The crude product was washed with Pet. ether (2×100 mL) to a yellow oil that was used in the next step without further purification. A solution of ethyl 2-diazoacetate (6.85 g, 59.99 mmol) in DCM (30 mL) was added dropwise over 6 hours to the mixture of tert-butyl (3-(4-hydroxypiperidin-1-yl)propyl)carbamate (7.75 g, 30.00 mmol) and rhodium acetate dimer (0.398 g, 0.90 mmol) in DCM (120 mL), then stirred at 25° C. for 16 hours. The solvent was evaporated in vacuo. The crude product was purified by flash silica chromatography, elution gradient 0 to 5% MeOH in DCM. Pure fractions were evaporated to dryness to afford a brown oil. Lithium hydroxide (0.945 g, 39.48 mmol) was added to the solution of ethyl 2-((1-(3-((tert-butoxycarbonyl)amino)propyl)piperidin-4-yl)oxy)acetate (3.4 g, 9.87 mmol) in MeOH (40 mL) and water (10 mL) and then stirred at RT for 3 hours. The solvent was evaporated in vacuo to afford the title compound (4.20 g, 46%) as a white solid. $^1$H NMR (300 MHz, DMSO-d6, 25° C.) δ 1.38 (9H, s), 1.46-1.66 (2H, m), 1.74-2.03 (4H, m), 2.22 (2H, t), 2.70 (2H, br d), 2.92 (2H, br s), 3.18 (2H, s), 3.63 (2H, s), 6.80 (1H, s).

Intermediate 65b: (2S,4R)-1-((S)-2-(2-((1-(3-aminopropyl)piperidin-4-yl)oxy)acetamido)-3,3-dimethylbutanoyl)-4-hydroxy-N-(4-(4-methylthiazol-5-yl)benzyl)pyrrolidine-2-carboxamide

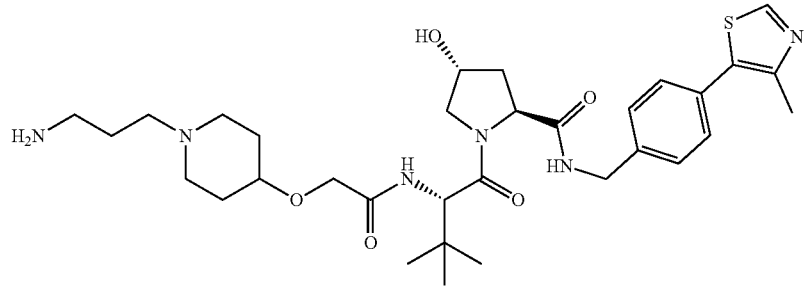 [SMILES: Cc1ncsc1-c1ccc(CNC(=O)[C@@H]2C[C@@H](O)CN2C(=O)[C@@H](NC(=O)COC2CCN(CCCN)CC2)C(C)(C)C)cc1]

Prepared according to general procedure C using tert-butyl (3-(4-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)piperidin-1-yl)propyl)carbamate. Yellow gum (1.200 g, 43.8%). $^1$H NMR (400 MHz, DMSO-d6, 25° C.) δ 0.95 (9H, s) 1.64 (1H, d), 1.77-2.13 (6H, m), 2.19 (1H, d), 2.45 (3H, s), 2.79-3.20 (6H, m), 3.33 (1H, d), 3.48 (1H, d), 3.54-3.72 (2H, m), 3.96-4.10 (2H, m), 4.21-4.47 (4H, m), 4.57 (1H, dd), 7.40-7.49 (5H, m), 7.59 (1H, d), 7.91 (3H, br s), 8.58 (1H, t), 9.00 (1H, s), 9.77 (1H, br d); m/z: ES+ [M+H]$^+$ 629.3.

Example 65: (2S,4R)-1-((S)-2-(2-((1-(3-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)propyl)piperidin-4-yl)oxy)acetamido)-3,3-dimethylbutanoyl)-4-hydroxy-N-(4-(4-methylthiazol-5-yl)benzyl)pyrrolidine-2-carboxamide, Trifluoroacetic Acid Prepared according to general procedure C using (2S,4R)-1-((S)-2-(2-((1-(3-aminopropyl)piperidin-4-yl)oxy)acetamido)-3,3-dimethylbutanoyl)-4-hydroxy-N-(4-(4-methylthiazol-5-yl)benzyl)pyrrolidine-2-carboxamide. Colourless gum (7.3 mg, 38%). $^1$H NMR (300 MHz, MeOD, 30° C.) δ1.04 (9H, s), 1.48-1.61 (10H, m), 1.94-2.05 (3H, m), 2.05-2.13 (1H, m), 2.14-2.37 (3H, m), 2.45 (3H, s), 2.95-3.10 (2H, m), 3.12-3.27 (3H, m), 3.33-3.46 (4H, m), 3.58-3.74 (2H, m), 3.75-3.91 (2H, m), 3.99-4.19 (3H, m), 4.32-4.41 (1H, m), 4.46-4.60 (3H, m), 4.67-4.75 (1H, m), 6.21 (1H, br s), 6.72 (1H, dd), 7.05-7.12 (1H, m), 7.15 (1H, m), 7.27-7.37 (3H, m), 7.38-7.47 (4H, m), 7.47-7.64 (3H, m), 8.86-8.93 (1H, m); m/z: ES+ [M+H]$^+$ 1053.7; ESI-HRMS calculated for $C_{57}H_{72}F_3N_8O_6S$ [M+H]$^+$=1053.5242, measured 1053.5203.

Intermediate 66a: 2-(4-(2-(2-((tert-butoxycarbonyl)amino)ethoxy)ethoxy)phenyl)acetic Acid

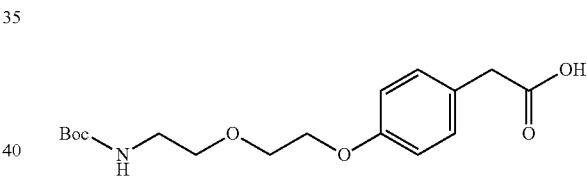

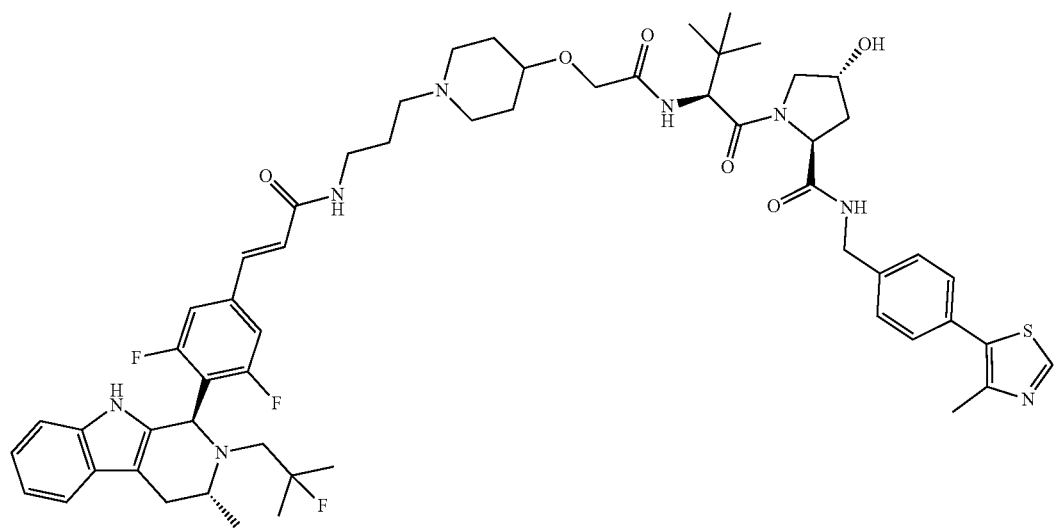 [SMILES: Cc1ncsc1-c1ccc(CNC(=O)[C@@H]2C[C@@H](O)CN2C(=O)[C@@H](NC(=O)COC2CCN(CCCNC(=O)/C=C/c3cc(F)c([C@@H]4c5[nH]c6ccccc6c5C[C@@H](C)N4CC(C)(C)F)c(F)c3)CC2)C(C)(C)C)cc1]

Potassium carbonate (3.33 g, 24.07 mmol) was added to the mixture of methyl 2-(4-hydroxyphenyl)acetate (2.0 g, 12.04 mmol), 2-(2-((tert-butoxycarbonyl)amino)ethoxy)ethyl methanesulfonate (4.09 g, 14.44 mmol) in DMF (60 mL), then the mixture was stirred at 80° C. for 5 hours. The reaction mixture was diluted with EtOAc (100 mL), and washed with saturated brine 3 times. The organic layer was dried over $Na_2SO_4$, filtered and evaporated to afford crude product. The crude product was purified by flash silica chromatography, elution gradient 0 to 25% EtOAc in petroleum ether. Pure fractions were evaporated to dryness to afford a yellow oil (2.000 g, 47%). Lithium hydroxide (1.525 g, 63.66 mmol) was added to the yellow oil (1.5 g) in MeOH (30 mL) and $H_2O$ (15 mL), the mixture was stirred at 25° C. for 4 hours. MeOH was removed under reduced pressure and EtOAc was added (20 mL), the organic layer was extracted with MeOH (3×20 mL). The combined aqueous layers was adjusted to pH 2 with 2M aq. HCl. The aqueous layer was extracted with DCM (3×20 mL). The organic was dried over $Na_2SO_4$, filtered and concentrated to dryness to afford the title compound (1.400 g, 97%) as a white solid. m/z: ES+ [M+H]$^+$ 362.2.

Intermediate 66b: (2S,4R)-1-((S)-2-(2-(4-(2-(2-aminoethoxy)ethoxy)phenyl)acetamido)-3,3-dimethylbutanoyl)-4-hydroxy-N-(4-(4-methylthiazol-5-yl)benzyl)pyrrolidine-2-carboxamide

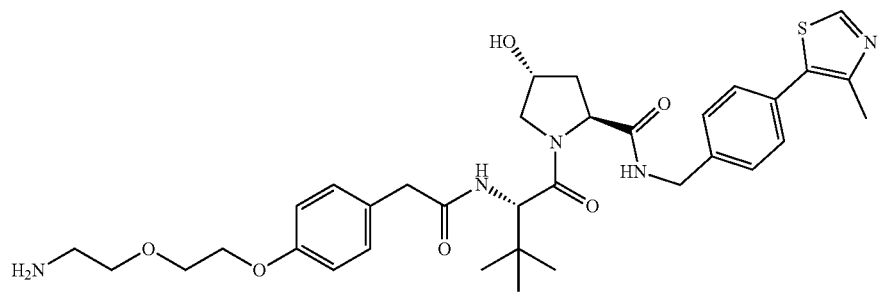 [SMILES: Cc1ncsc1-c1ccc(CNC(=O)[C@@H]2C[C@@H](O)CN2C(=O)[C@@H](NC(=O)Cc2ccc(OCCOCCN)cc2)C(C)(C)C)cc1]

DIPEA (2.470 mL, 14.14 mmol) was added to the mixture of 2-(4-(2-(2-((tert-butoxycarbonyl)amino)ethoxy)ethoxy)phenyl)acetic acid (1.6 g, 4.71 mmol), (2S,4R)-1-((S)-2-amino-3,3-dimethylbutanoyl)-4-hydroxy-N-(4-(4-methylthiazol-5-yl)benzyl)pyrrolidine-2-carboxamide (2.030 g, 4.71 mmol), HOBT (0.866 g, 5.66 mmol), N-(3-dimethylaminopropyl)-N'-ethylcarbodiimide hydrochloride (1.085 g, 5.66 mmol) in DCM (100 mL), then the mixture was stirred at 25° C. for 2 h. The reaction mixture was washed with 0.1M aq. HCl, sat. aq. $NaHCO_3$, and brine. The organic layer was dried $Na_2SO_4$, filtered and concentrated to dryness. The crude product was purified by flash silica chromatography, elution gradient 0 to 3% MeOH in DCM. Pure fractions were evaporated to dryness to afford a yellow solid. 4 M HCl in dioxane (24 mL, 96 mmol) was added to the yellow intermediate, the mixture was stirred at 25° C. for 2 hours. The solvent was removed under reduced pressure. The crude product was purified by preparative HPLC (Xselect CSH OBD column 30*150 mm, 5 μm silica) using decreasingly polar mixtures of MeCN and water (containing 0.05% trifluoroacetic acid) as eluents. Fractions containing the desired compound were evaporated to dryness to afford the title compound as a yellow solid (1.0 g, 47.5%) $^1$H NMR (400 MHz, DMSO-d6, 25° C.) δ 0.91 (9H, s) 1.90-2.09 (2H, m) 2.46 (3H, s), 2.91 (2H, t), 3.37 (1H, d), 3.52-3.70 (5H, m), 3.70-3.84 (2H, m), 4.02-4.12 (2H, m), 4.23 (1H, dd), 4.35 (1H, s), 4.39-4.48 (2H, m), 4.52 (1H, d), 6.80-6.97 (2H, m), 7.12-7.26 (2H, m), 7.31-7.54 (4H, m), 8.00 (1H, d), 8.39 (1H, s), 8.60 (1H, t), 8.99 (1H, s); m/z: ES+ [M+H]$^+$ 652.4

Example 66: (2S,4R)-1-((S)-2-(2-(4-(2-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)ethoxy)phenyl)acetamido)-3,3-dimethylbutanoyl)-4-hydroxy-N-(4-(4-methylthiazol-5-yl)benzyl)pyrrolidine-2-carboxamide, Trifluoroacetic Acid

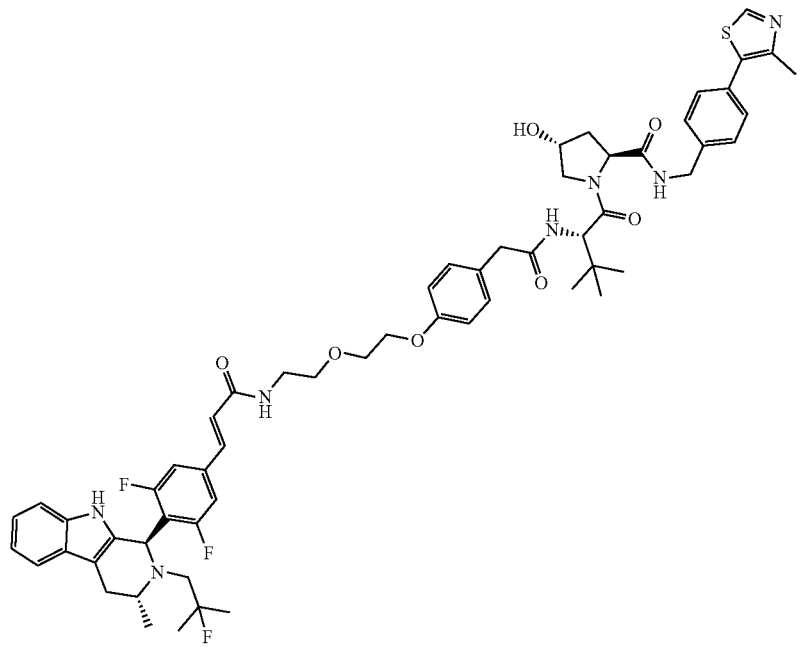 [SMILES: Cc1ncsc1-c1ccc(CNC(=O)[C@@H]2C[C@@H](O)CN2C(=O)[C@@H](NC(=O)Cc2ccc(OCCOCCNC(=O)/C=C/c3cc(F)c([C@@H]4c5[nH]c6ccccc6c5C[C@@H](C)N4CC(C)(C)F)c(F)c3)cc2)C(C)(C)C)cc1]

Prepared according to general procedure D using (2S,4R)-1-((S)-2-(2-(4-(2-(2-aminoethoxy)ethoxy)phenyl)acetamido)-3,3-dimethylbutanoyl)-4-hydroxy-N-(4-(4-methylthiazol-5-yl)benzyl)pyrrolidine-2-carboxamide. Colourless gum (10.1 mg, 56%). H NMR (300 MHz, MeOD, 30° C.) δ 0.96 (9H, s), 1.52-1.64 (10H, m), 2.01-2.11 (1H, m), 2.14-2.26 (1H, m), 2.47 (3H, s), 3.07 (1H, dd), 3.34-3.55 (6H, m), 3.62-3.68 (2H, m), 3.70-3.88 (5H, m), 4.10 (2H, dd), 4.15-4.25 (1H, m), 4.30-4.38 (1H, m), 4.43-4.56 (3H, m), 4.57-4.62 (1H, m), 6.29 (1H, br s), 6.71 (1H, d), 6.84-6.91 (1H, m), 7.05-7.13 (1H, m), 7.15-7.21 (3H, m), 7.27-7.35 (3H, m), 7.38-7.47 (5H, m), 7.47-7.65 (2H, m), 8.97 (1H, s); m/z: ES+ [M+H]$^+$1076.7; ESI-HRMS calculated for $C_{59}H_{69}F_3N_7O_7S$ [M+H]$^+$=1076.4926, measured 1076.4887.

Intermediate 67a: 4-(4-(2-((tert-butoxycarbonyl)amino)ethyl)piperazin-1-yl)benzoic Acid

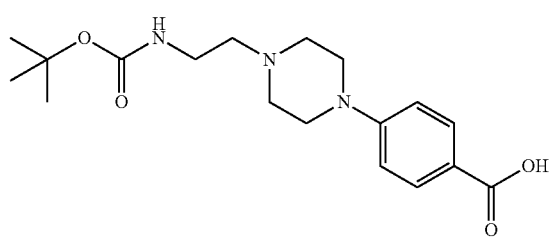 [SMILES: CC(C)(C)OC(=O)NCCN1CCN(c2ccc(C(=O)O)cc2)CC1]

Potassium carbonate (10.85 g, 78.49 mmol) was added to the mixture of ethyl 4-fluorobenzoate (4.4 g, 26.16 mmol), tert-butyl (2-(piperazin-1-yl)ethyl)carbamate (6.60 g, 28.78 mmol) in DMSO (300 mL), the mixture was stirred at 120° C. for 20 hours. The reaction mixture was diluted with EtOAc (300 mL) and washed with brine 3 times. The organic layer was dried over Na$_2$SO$_4$, filtered and concentrated. The crude product was purified by flash silica chromatography, elution gradient 0 to 3% MeOH in DCM. Pure fractions were evaporated to dryness to afford a yellow oil.

A solution of LiOH (0.502 g, 20.98 mmol) in H$_2$O (5 mL) was added to a mixture of ethyl 4-(4-(2-((tert-butoxycarbonyl)amino)ethyl)piperazin-1-yl)benzoate (3.6 g, 9.54 mmol) in MeOH (20 mL), the mixture was stirred at 25° C. for 1 hour. The solvent was removed under reduced pressure and the crude product washed with DCM (50 mL), then dried to afford the title compound (3.3 g, 99%) as a white solid. m/z: ES+ [M+H]$^+$ 350.3.

Intermediate 67b: (2S,4R)-1-((S)-2-(4-(4-(2-amino-ethyl)piperazin-1-yl)benzamido)-3,3-dimethylbu-tanoyl)-4-hydroxy-N-(4-(4-methylthiazol-5-yl)benzyl)pyrrolidine-2-carboxamide

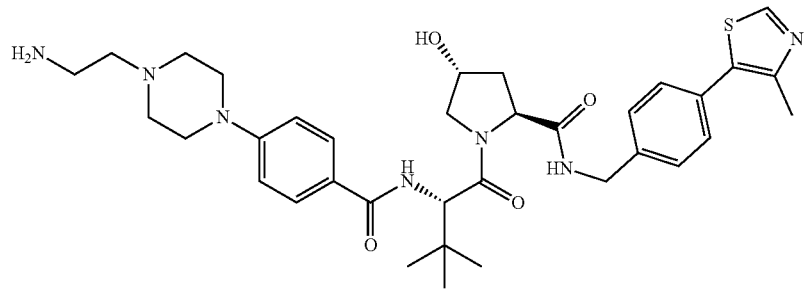 [SMILES: Cc1ncsc1-c1ccc(CNC(=O)[C@@H]2C[C@@H](O)CN2C(=O)[C@@H](NC(=O)c2ccc(N3CCN(CCN)CC3)cc2)C(C)(C)C)cc1]

Prepared according to general procedure C using 4-(4-(2-((tert-butoxycarbonyl)amino)ethyl)piperazin-1-yl)benzoic acid. Yellow solid (0.3 g, 11.29%). $^1$H NMR (400 MHz, DMSO-d6, 25° C.) δ 1.01 (9H, s), 1.92 (1H, m), 2.05 (1H, m), 2.43-2.55 (8H, m), 2.93 (3H, t), 3.28 (4h, t) 4.25 (2H, dd), 4.34-4.49 (4H, m), 4.75 (1H, d), 6.96 (2H, d), 7.41 (4H, s), 7.58 (1H, d), 7.78 (2H, d), 8.31 (2H, s), 8.58 (1H, t), 8.99 (1H, s); m/z: ES+ [M+H]$^+$662.3

Example 67: (2S,4R)-1-((S)-2-(4-(4-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethyl)piperazin-1-yl)benzamido)-3,3-dimethylbutanoyl)-4-hydroxy-N-(4-(4-methylthiazol-5-yl)benzyl)pyrrolidine-2-carboxamide, Trifluoroacetic Acid

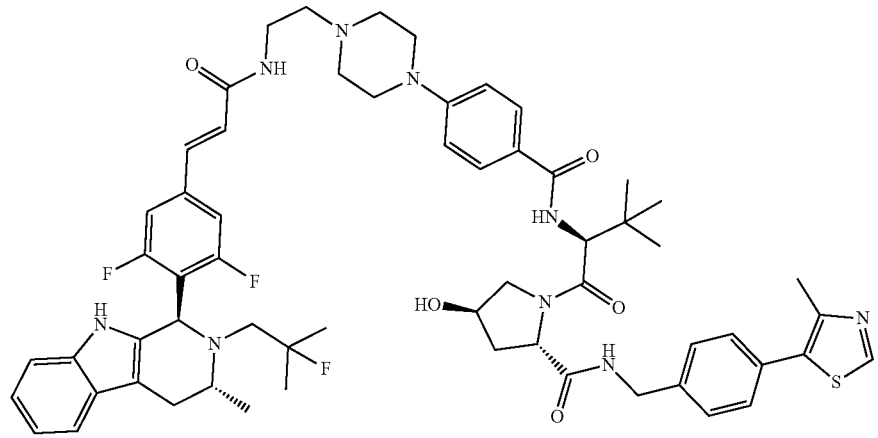 [SMILES: Cc1ncsc1-c1ccc(CNC(=O)[C@@H]2C[C@@H](O)CN2C(=O)[C@@H](NC(=O)c2ccc(N3CCN(CCNC(=O)/C=C/c4cc(F)c([C@@H]5c6[nH]c7ccccc7c6C[C@@H](C)N5CC(C)(C)F)c(F)c4)CC3)cc2)C(C)(C)C)cc1]

Prepared according to general procedure D using (2S,4R)-1-((S)-2-(4-(4-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethyl)piperazin-1-yl)benzamido)-3,3-dimethylbutanoyl)-4-hydroxy-N-(4-(4-methylthiazol-5-yl)benzyl)pyrrolidine-2-carboxamide. Colourless gum (6.9 mg, 35%). $^1$H NMR (300 MHz, MeOD, 30° C.) δ 1.09 (9H, s), 1.49-1.62 (10H, m), 2.05-2.16 (1H, m), 2.19-2.28 (1H, m), 2.48 (3H, s), 2.97-3.10 (1H, m), 3.41 (2H, br t), 3.63-3.80 (3H, m), 3.85 (1H, dd), 3.93-4.01 (1H, m), 4.11-4.21 (1H, m), 4.34 (1H, d), 4.50-4.63 (3H, m), 4.87-4.93 (1H, m), 6.22 (1H, br s), 6.75 (1H, d), 7.03-7.12 (3H, m), 7.15 (1H, m), 7.24-7.31 (1H, m), 7.35 (2H, d), 7.40-7.47 (4H, m), 7.48-7.64 (3H, m), 7.77-7.83 (2H, m), 8.93 (1H, s); m/z: ES+ [M+H]$^+$ 1086.7; ESI-HRMS calculated for $C_{60}H_{71}F_3N_9O_5S$ [M+H]$^+$=1086.5245, measured 1086.5217.

Intermediate 68a: 1-(tert-Butyl) 14-ethyl 3,6,9,12-tetraoxatetradecanedioate

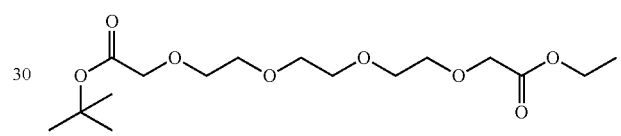

tert-Butyl 2-diazoacetate (15% solution in toluene) (6.53 mL, 6.03 mmol) was added dropwise to ethyl 2-(2-(2-(2-hydroxyethoxy)ethoxy)ethoxy)acetate (0.95 g, 4.02 mmol) and diacetoxyrhodium (0.053 g, 0.12 mmol) in DCM (10 mL) at 20° C. over 1 hour under nitrogen. The resulting solution was stirred at 20° C. for 18 hours. The mixture was diluted with DCM (50 mL) and washed with water (2×50 mL). The organic layer was collected and dried using phase separating cartridge then evaporated to dryness. The crude product was purified by flash silica chromatography, elution gradient 0 to 50% EtOAc in heptane to afford the title compound (0.690 g, 49%) as a colourless liquid; $^1$H NMR (400 MHz, CDCl$_3$) 1.28 (3H, t), 1.47 (9H, s), 3.65-3.76 (12H, m), 4.02 (2H, s), 4.14 (2H, s), 4.21 (2H, q).

Intermediate 68b: 14-Oxo-3,6,9,12,15-pentaoxaheptadecanoic Acid

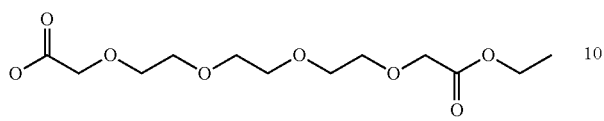

HCl (4N in dioxane) (5 mL, 19.69 mmol) was added to 1-(tert-butyl) 14-ethyl 3,6,9,12-tetraoxatetradecanedioate (690 mg, 1.97 mmol). The resulting solution was stirred at 20° C. for 4 hours. The solvent was removed by evaporation to afford the crude title compound (690 mg) as a colourless oil which was used in the next step without purification; $^1$H NMR (400 MHz, CDCl$_3$) 1.28 (3H, t), 3.61-3.82 (12H, m), 4.11-4.18 (4H, m), 4.22 (2H, q)

Intermediate 68c: (1R,3R)-1-(2,6-Difluoro-4-nitrophenyl)-2-(2-fluoro-2-methylpropyl)-3-methyl-2,3,4,9-tetrahydro-1H-pyrido[3,4-b]indole

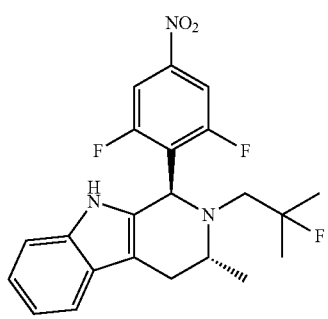 [SMILES: C[C@@H]1Cc2c([nH]c3ccccc23)[C@@H](c2c(F)cc([N+](=O)[O-])cc2F)N1CC(C)(C)F]

(R)—N-(1-(1H-indol-3-yl)propan-2-yl)-2-fluoro-2-methylpropan-1-amine (33% solution in toluene) (3.8 g, 5.09 mmol) was added to a stirred solution of 2,6-difluoro-4-nitrobenzaldehyde (1.0 g, 5.34 mmol) in toluene (24.05 mL) and AcOH (2.67 mL) at 20° C. The resulting solution was stirred at 80° C. for 4 hours. The reaction was cooled to RT. The crude product was purified by ion exchange chromatography, using an SCX column. The desired product was eluted from the column using 1M NH$_3$/MeOH and evaporated to dryness. The crude product was purified by flash silica chromatography, elution gradient 0 to 30% EtOAc in heptane to afford the title compound (1.76 g, 83%) as an orange solid; $^1$H NMR (400 MHz, DMSO) 1.07 (3H, d), 1.1-1.29 (6H, m), 2.29-2.44 (1H, m), 2.58-2.7 (1H, m), 2.85-2.99 (2H, m), 3.51 (1H, q), 5.31 (1H, s), 6.91-7.11 (2H, m), 7.20 (1H, d), 7.44 (1H, d), 8.00 (2H, d), 10.61 (1H, s); m/z: ES+ [M+H]$^+$ 418.3.

Intermediate 68d: 3,5-Difluoro-4-((1R,3R)-2-(2-fluoro-2-methylpropyl)-3-methyl-2,3,4,9-tetrahydro-1H-pyrido[3,4-b]indol-1-yl)aniline

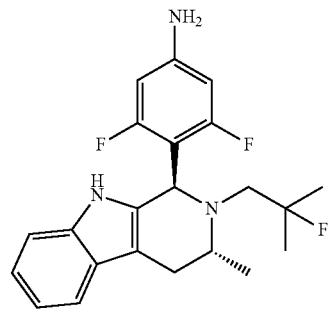

Water (1.4 mL) was added to a stirred mixture of (1R,3R)-1-(2,6-difluoro-4-nitrophenyl)-2-(2-fluoro-2-methylpropyl)-3-methyl-2,3,4,9-tetrahydro-1H-pyrido[3,4-b]indole (200 mg, 0.48 mmol), iron (161 mg, 2.87 mmol) and ammonia hydrochloride (18 mg, 0.34 mmol) in EtOH (8.2 mL) and the resulting slurry was heated to 70° C. for 2 hours. The cooled reaction mixture was filtered and the EtOH was removed by evaporation. The residue was diluted with EtOAc (50 mL) and water (20 mL). The organic layer was separated, washed with saturated brine solution, dried (MgSO$_4$) and evaporated to afford the title compound (192 mg, 103%) as a yellow gum which was used directly in the next step without purification; m/z: ES+ [M+H]$^+$ 388.3

Intermediate 68e: Ethyl 14-((3,5-difluoro-4-((1R,3R)-2-(2-fluoro-2-methylpropyl)-3-methyl-2,3,4,9-tetrahydro-1H-pyrido[3,4-b]indol-1-yl)phenyl)amino)-14-oxo-3,6,9,12-tetraoxatetradecanoate

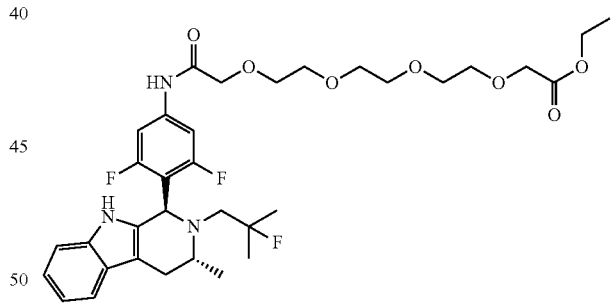

HATU (283 mg, 0.74 mmol) was added in one portion to 3,5-difluoro-4-((1R,3R)-2-(2-fluoro-2-methylpropyl)-3-methyl-2,3,4,9-tetrahydro-1H-pyrido[3,4-b]indol-1-yl)aniline (192 mg, 0.50 mmol), 14-oxo-3,6,9,12,15-pentaoxaheptadecanoic acid (146 mg, 0.50 mmol) and triethylamine (0.3 mL, 1.98 mmol) in DMF (10 mL) at 20° C. under nitrogen. The resulting mixture was stirred at 20° C. for 18 hours. The reaction mixture was diluted with EtOAc (50 mL), and washed sequentially with water (50 mL) and saturated brine (25 mL). The organic layer was dried with MgSO$_4$, filtered and evaporated to afford the crude product. The crude product was purified by flash silica chromatography, elution gradient 0 to 50% EtOAc in heptane to afford the title compound (241 mg, 73.3%) as a yellow gum; m/z: ES+ [M+H]$^+$ 664.4

Intermediate 68f: 14-((3,5-Difluoro-4-((1R,3R)-2-(2-fluoro-2-methylpropyl)-3-methyl-2,3,4,9-tetrahydro-1H-pyrido[3,4-b]indol-1-yl)phenyl)amino)-14-oxo-3,6,9,12-tetraoxatetradecanoic Acid

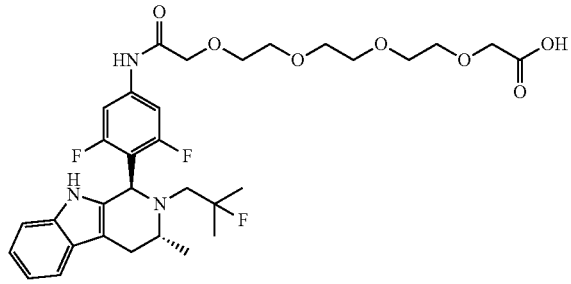 [SMILES: C[C@@H]1Cc2c([nH]c3ccccc23)[C@@H](c2c(F)cc(NC(=O)COCCOCCOCCOCC(=O)O)cc2F)N1CC(C)(C)F]

Lithium hydroxide hydrate (30.5 mg, 0.73 mmol) was added in one portion to ethyl 14-((3,5-difluoro-4-((1R,3R)-2-(2-fluoro-2-methylpropyl)-3-methyl-2,3,4,9-tetrahydro-1H-pyrido[3,4-b]indol-1-yl)phenyl)amino)-14-oxo-3,6,9,12-tetraoxatetradecanoate (241 mg, 0.36 mmol) in THF (1.4 mL) and water (0.5 mL) at 20° C. The mixture was stirred at 20° C. for 30 minutes. The reaction mixture was diluted with water (10 mL) then was acidified with 2M aq. HCl and extracted into EtOAc (50 mL). The organic layer was washed with brine (15 mL) and evaporated to afford the title compound (172 mg, 74.5%) as a yellow gum which was used in the next step without purification; m/z: ES+ [M+H]+ 636.3

Example 68: N1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-N14-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12-tetraoxatetradecanediamide HATU (158 mg, 0.42 mmol) was added in one portion to 14-((3,5-difluoro-4-((1R,3R)-2-(2-fluoro-2-methylpropyl)-3-methyl-2,3,4,9-tetrahydro-1H-pyrido[3,4-b]indol-1-yl)phenyl)amino)-14-oxo-3,6,9,12-tetraoxatetradecanoic acid (176 mg, 0.28 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (129 mg, 0.28 mmol) and triethylamine (154 µL, 1.11 mmol) in DMF (5.4 mL) at 20° C. under nitrogen. The resulting mixture was stirred for 30 minutes. The reaction mixture was diluted with EtOAc (50 mL), and washed sequentially with water (50 mL) and saturated brine (25 mL). The organic layer was dried with MgSO$_4$, filtered, and evaporated to afford the crude product. The crude product was purified by preparative HPLC (Waters CSH C18 OBD column, 30×100 mm id, 5 micron particle size), using decreasingly polar mixtures of water (containing 1% by volume NH$_4$OH) and MeCN as eluents. Fractions containing the desired compound were evaporated to dryness to afford the title compound (137 mg, 47.2%) as a white solid; $^1$H NMR (400 MHz, CDCl$_3$) 0.94 (9H, s), 1.09 (3H, d), 1.20 (6H, dd), 2.11 (1H, dd), 2.34-2.54 (5H, m), 2.61 (1H, dd), 2.85 (1H, dd), 3.09 (1H, dd), 3.47-3.88 (17H, m), 3.96-4.09 (3H, m), 4.30 (1H, dd), 4.43 (1H, dd), 4.52 (2H, d), 4.64 (1H, t), 5.24 (1H, s), 7.03-7.15 (4H, m), 7.15-7.25 (3H, m), 7.30 (2H, d), 7.36 (2H, d), 7.50 (1H, dd), 8.66 (1H, s), 8.71 (1H, s), 9.05 (1H, s); m/z: ES+ [M+H]+ 1048.4

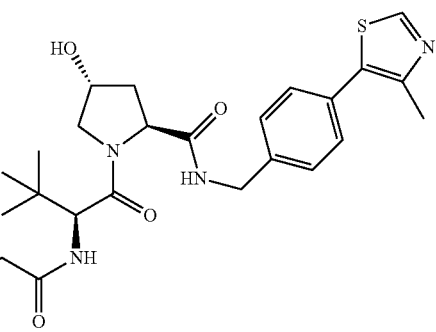

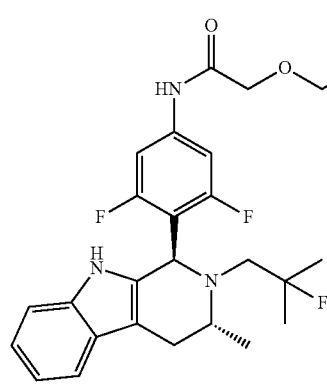

Intermediate 70a: (R)—N-(1-(1H-indol-3-yl)propan-2-yl)-3-((tert-butyldiphenylsilyl)oxy)-2,2-difluoropropan-1-amine

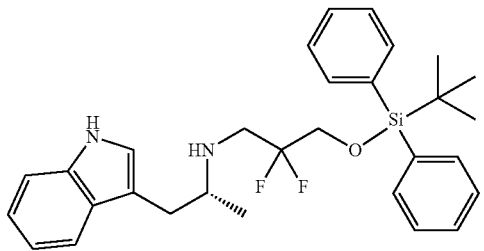 [SMILES: C[C@H](Cc1c[nH]c2ccccc12)NCC(F)(F)CO[Si](c1ccccc1)(c1ccccc1)C(C)(C)C]

Trifluoromethanesulfonic anhydride (14.44 mL, 85.84 mmol) followed by 2,6-dimethylpyridine (10.91 mL, 93.64 mmol) was added to a solution of 3-((tert-butyldiphenylsilyl)oxy)-2,2-difluoropropan-1-ol (preparation described in WO2016/97072 A1) (27.35 g, 78.04 mmol) in DCM (300 mL) cooled in an ice bath. The reaction mixture was warmed to room temperature and stirred for 1 hour. The reaction mixture was washed with 1N HCl (2×100 mL), brine (100 mL), dried over MgSO$_4$, filtered and carefully evaporated to afford impure 3-((tert-butyldiphenylsilyl)oxy)-2,2-difluoropropyl trifluoromethanesulfonate (37.7 g) as an oil, which was used without characterisation or further purification. 3-((tert-Butyldiphenylsilyl)oxy)-2,2-difluoropropyl trifluoromethanesulfonate (37.7 g, 78.04 mmol) was dissolved in 1,4-dioxane (300 mL) and (R)-1-(1H-indol-3-yl)propan-2-amine (14.24 g, 81.75 mmol) was added followed by DIPEA (24.01 mL, 138.98 mmol). The reaction was stirred at 90° C. for 18 hours, then evaporated to dryness and dissolved in EtOAc (250 mL). The organic layer was washed sequentially with water (2×100 mL) and saturated brine (100 mL). The combined aqueous phases were back-extracted with EtOAc (2×100 mL), the combined organics dried over MgSO$_4$, filtered and evaporated to dryness to afford crude product. The crude product was purified by flash silica chromatography, elution gradient 0 to 40% EtOAc in heptane to afford the title compound (28.0 g, 70%) as a straw coloured syrup; $^1$H NMR (500 MHz, CDCl$_3$, 27° C.) 1.04 (9H, s), 1.11 (3H, d), 2.79 (1H, ddd), 2.84-2.91 (1H, m), 3.04-3.25 (3H, m), 3.76-3.89 (2H, m), 6.97 (1H, d), 7.10 (1H, ddd), 7.18 (1H, ddd), 7.32 (1H, dt), 7.35-7.4 (4H, m), 7.41-7.46 (2H, m), 7.59 (1H, dd), 7.65 (4H, dq), 7.87 (1H, s); m/z: ES+ [M+H]$^+$ 507.4.

Intermediate 70b: (1R,3R)-1-(4-Bromo-2,6-difluorophenyl)-2-(3-((tert-butyldiphenylsilyl)oxy)-2,2-difluoropropyl)-3-methyl-2,3,4,9-tetrahydro-1H-pyrido[3,4-b]indole

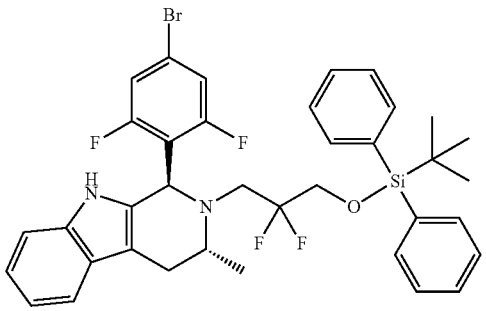 [SMILES: C[C@@H]1Cc2c([nH]c3ccccc23)[C@@H](c2c(F)cc(Br)cc2F)N1CC(F)(F)CO[Si](c1ccccc1)(c1ccccc1)C(C)(C)C]

4-Bromo-2,6-difluorobenzaldehyde (13.13 g, 59.40 mmol) was added to a solution of (R)—N-(1-(1H-indol-3-yl)propan-2-yl)-3-((tert-butyldiphenylsilyl)oxy)-2,2-difluoropropan-1-amine (28 g, 55.26 mmol) in toluene (200 mL) and acetic acid (22 mL). The reaction mixture was heated at 80° C. for 16 hours. The cooled reaction mixture was concentrated, the residue dissolved in DCM (350 mL), washed with 1M aq NaOH (100 mL), saturated NaHCO$_3$ solution (100 mL), brine (100 mL), the combined aqueous phases extracted with DCM (3×75 mL), the combined organics dried over MgSO$_4$, filtered and the filtrate evaporated to a gum. The crude product was purified by flash silica chromatography, elution gradient 0 to 15% EtOAc in heptane to afford the title compound (32.3 g, 82%) as a cream foam; $^1$H NMR (500 MHz, CDCl$_3$, 27° C.) 1.05 (9H, s), 1.15 (3H, d), 2.60 (1H, ddd), 2.71-2.82 (1H, m), 2.98 (1H, ddd), 3.28 (1H, ddd), 3.55-3.68 (2H, m), 3.89-4.01 (1H, m), 5.28 (1H, d), 6.92-6.97 (2H, m), 7.12 (2H, pd), 7.21-7.23 (1H, m), 7.35-7.45 (7H, m), 7.5-7.53 (1H, m), 7.6-7.66 (4H, m); m/z: ES– [M–H]$^-$ 707.1

Intermediate 70c: Ethyl 2-((5-(4-((1R,3R)-2-(3-((tert-butyldiphenylsilyl)oxy)-2,2-difluoropropyl)-3-methyl-2,3,4,9-tetrahydro-1H-pyrido[3,4-b]indol-1-yl)-3,5-difluorophenoxy)pentyl)oxy)acetate

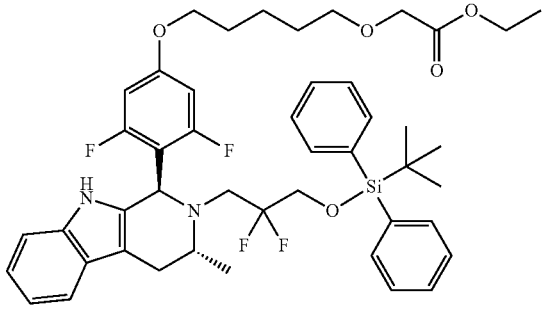 [SMILES: CCOC(=O)COCCCCCOc1cc(F)c([C@@H]2c3[nH]c4ccccc4c3C[C@@H](C)N2CC(F)(F)CO[Si](c2ccccc2)(c2ccccc2)C(C)(C)C)c(F)c1]

RockPhos Pd G3 (23.6 mg, 0.03 mmol) was added in one portion to a degassed mixture of ethyl 2-((5-hydroxypentyl)oxy)acetate (214 mg, 1.13 mmol), (1R,3R)-1-(4-bromo-2,6-difluorophenyl)-2-(3-((tert-butyldiphenylsilyl)oxy)-2,2-difluoropropyl)-3-methyl-2,3,4,9-tetrahydro-1H-pyrido[3,4-b]indole (400 mg, 0.56 mmol) and cesium carbonate (459 mg, 1.41 mmol) in toluene (4 mL) at 20° C. under nitrogen. The resulting mixture was stirred at 90° C. for 6 hours. The reaction was allowed to cool to RT and was filtered, the filtercup was washed with DCM (10 mL) then the mixture evaporated to afford crude product as a orange gum. The crude product was purified by flash silica chromatography, elution gradient 0 to 30% EtOAc in heptane. Pure fractions were evaporated to dryness to afford the title compound (100 mg, 22%) as a yellow gum; m/z: ES+ [M+H]$^+$819.3.

281

Intermediate 70d: 2-((5-(4-((1R,3R)-2-(3-((tert-Butyldiphenylsilyl)oxy)-2,2-difluoropropyl)-3-methyl-2,3,4,9-tetrahydro-1H-pyrido[3,4-b]indol-1-yl)-3,5-difluorophenoxy)pentyl)oxy)acetic Acid

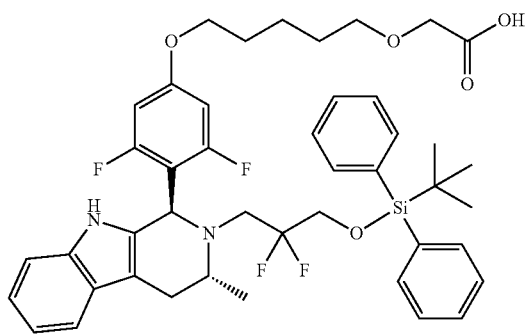 [SMILES: C[C@@H]1Cc2c([nH]c3ccccc23)[C@@H](c2c(F)cc(OCCCCCOCC(=O)O)cc2F)N1CC(F)(F)CO[Si](c1ccccc1)(c1ccccc1)C(C)(C)C]

Lithium hydroxide hydrate (10 mg, 0.24 mmol) was added in one portion to ethyl 2-((5-(4-((1R,3R)-2-(3-((tert-butyldiphenylsilyl)oxy)-2,2-difluoropropyl)-3-methyl-2,3,4,9-tetrahydro-1H-pyrido[3,4-b]indol-1-yl)-3,5-difluorophenoxy)pentyl)oxy)acetate (100 mg, 0.12 mmol) in THF (0.5 mL) and water (0.2 mL) at 20° C. The resulting solution was stirred at 20° C. for 30 minutes. The reaction mixture was diluted with water (10 mL) then was acidified with 2M HCl and extracted into EtOAc (50 mL). The organic layer was washed with brine (15 mL) and evaporated to afford the title compound (100 mg) as a yellow gum which was used in the next step without further purification; m/z: ES+ [M+H]+ 791.5.

Intermediate 70e: (2S,4R)-1-((S)-2-(2-((5-(4-((1R,3R)-2-(3-((tert-Butyldiphenylsilyl)oxy)-2,2-difluoropropyl)-3-methyl-2,3,4,9-tetrahydro-1H-pyrido[3,4-b]indol-1-yl)-3,5-difluorophenoxy)pentyl)oxy)acetamido)-3,3-dimethylbutanoyl)-4-hydroxy-N-(4-(4-methylthiazol-5-yl)benzyl)pyrrolidine-2-carboxamide

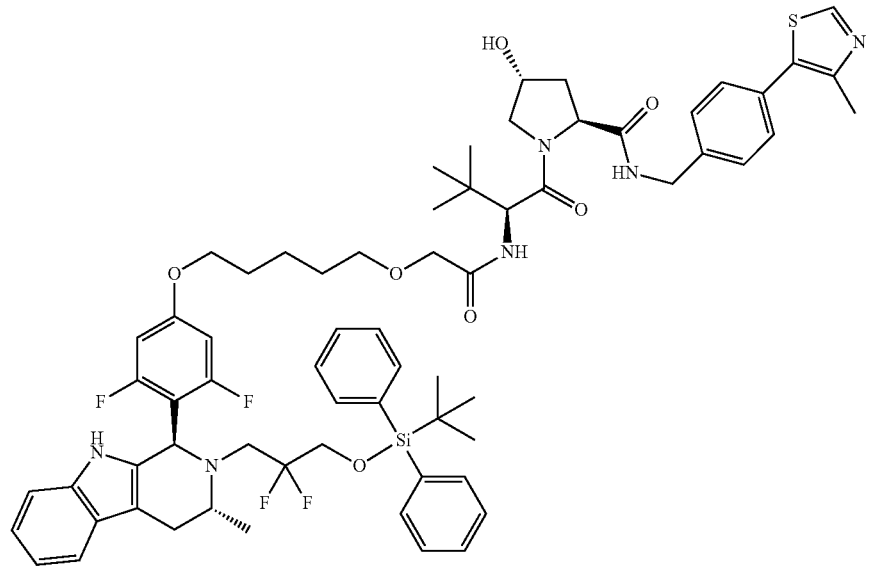 [SMILES: Cc1ncsc1-c1ccc(CNC(=O)[C@@H]2C[C@@H](O)CN2C(=O)[C@@H](NC(=O)COCCCCCOc2cc(F)c([C@@H]3c4[nH]c5ccccc5c4C[C@@H](C)N3CC(F)(F)CO[Si](c3ccccc3)(c3ccccc3)C(C)(C)C)c(F)c2)C(C)(C)C)cc1]

The title compound was prepared in a similar manner to Example 68 using the appropriate carboxylic acid and amine to afford the desired product (148 mg, 100%) which was used directly in the next step without purification; m/z: ES+ [M+H]+ 1203.6.

Example 70: (2S,4R)-1-((S)-2-(2-((5-(4-((1R,3R)-2-(2,2-Difluoro-3-hydroxypropyl)-3-methyl-2,3,4,9-tetrahydro-1H-pyrido[3,4-b]indol-1-yl)-3,5-difluorophenoxy)pentyl)oxy)acetamido)-3,3-dimethylbutanoyl)-4-hydroxy-N-(4-(4-methylthiazol-5-yl)benzyl)pyrrolidine-2-carboxamide

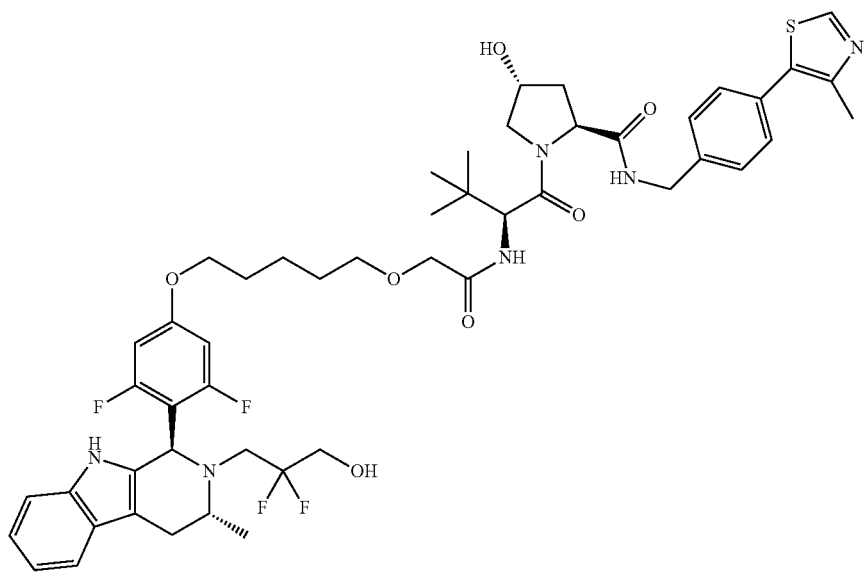 [SMILES: Cc1ncsc1-c1ccc(CNC(=O)[C@@H]2C[C@@H](O)CN2C(=O)[C@@H](NC(=O)COCCCCCOc2cc(F)c([C@@H]3c4[nH]c5ccccc5c4C[C@@H](C)N3CC(F)(F)CO)c(F)c2)C(C)(C)C)cc1]

A solution of TBAF 1M in THF (0.18 mL, 0.18 mmol) was added in one portion to (2S,4R)-1-((S)-2-(2-((5-(4-((1R,3R)-2-(3-((tert-butyldiphenylsilyl)oxy)-2,2-difluoropropyl)-3-methyl-2,3,4,9-tetrahydro-1H-pyrido[3,4-b]indol-1-yl)-3,5-difluorophenoxy)pentyl)oxy)acetamido)-3,3-dimethylbutanoyl)-4-hydroxy-N-(4-(4-methylthiazol-5-yl)benzyl)pyrrolidine-2-carboxamide (148 mg, 0.12 mmol) in THF (2 mL) at 20° C. The resulting solution was stirred for 18 hours. The reaction mixture was diluted with EtOAc (50 mL), and washed sequentially with saturated NH4Cl (20 mL), water (20 mL), and saturated brine (20 mL). The organic layer was dried with MgSO4, filtered and evaporated to afford crude product. The crude product was purified by preparative HPLC (Waters CSH C18 OBD column, 30×100 mm id, 5 micron particle size), using decreasingly polar mixtures of water (containing 1% by volume of NH4OH (28-30% in H2O)) and MeCN as eluents. Fractions containing the desired compound were evaporated to dryness to afford 60 mg impure product. The sample was dissolved in MeOH (1 ml) and re-purified using SFC, Column, Phenomenex C2, 30×250 mm, 5 micron, Mobile phase: 37% MeOH+0.1% NH3/63% scCO2, Flow rate: 100 mL/min, BPR: 120 bar, Column temperature: 40° C., to afford the title compound (23 mg, 19%) as a white solid; $^1$H NMR (400 MHz, CDCl3, 30° C.) 0.94 (9H, s), 1.18 (3H, d), 1.67 (2H, q), 1.81 (2H, p), 2.08 (1H, dd), 2.46 (3H, s), 2.56 (1H, ddd), 2.63-2.73 (2H, m), 2.8-2.96 (1H, m), 3.11 (1H, dd), 3.18-3.29 (1H, m), 3.46-3.78 (8H, m), 3.8-3.99 (4H, m), 4.08 (1H, d), 4.28 (1H, dd), 4.47-4.64 (3H, m), 4.69 (1H, t), 5.19 (1H, s), 6.40 (2H, d), 7.05-7.21 (3H, m), 7.21-7.25 (2H, m), 7.3-7.4 (4H, m), 7.47-7.56 (1H, m), 8.28 (1H, s), 8.62 (1H, s); m/z: ES+ [M+H]+ 965.7

Intermediate 71a: 2-(2-(2-(2-(4-((1R,3R)-2-(3-((tert-Butyldiphenylsilyl)oxy)-2,2-difluoropropyl)-3-methyl-2,3,4,9-tetrahydro-1H-pyrido[3,4-b]indol-1-yl)-3,5-difluorophenoxy)ethoxy)ethoxy)ethoxy)acetic Acid

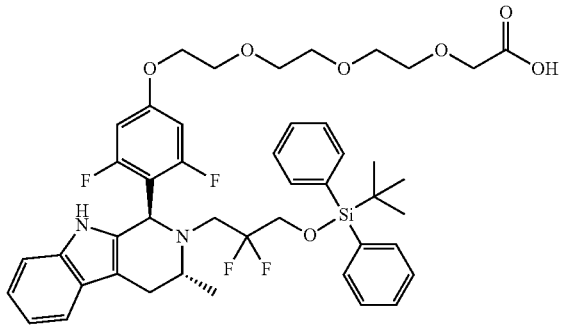 [SMILES: C[C@@H]1Cc2c([nH]c3ccccc23)[C@@H](c2c(F)cc(OCCOCCOCCOCC(=O)O)cc2F)N1CC(F)(F)CO[Si](c1ccccc1)(c1ccccc1)C(C)(C)C]

RockPhos Pd G3 (23.7 mg, 0.03 mmol) was added in one portion to a degassed mixture of ethyl 2-(2-(2-(2-hydroxyethoxy)ethoxy)ethoxy)acetate (preparation described in *Tetrahedron Letters* 1988, 29, 3803-3806) (266 mg, 1.13 mmol), (1R,3R)-1-(4-bromo-2,6-difluorophenyl)-2-(3-((tert-butyldiphenylsilyl)oxy)-2,2-difluoropropyl)-3-methyl-2,3,4,9-tetrahydro-1H-pyrido[3,4-b]indole (400 mg, 0.56 mmol) and cesium carbonate (459 mg, 1.41 mmol) in toluene (4 mL) at 20° C. under nitrogen. The resulting mixture was stirred at 90° C. for 6 hours. The reaction was allowed to cool to RT and was filtered, the filtercup was washed with DCM (10 mL), the mixture evaporated to afford crude product as a orange gum. The gum was dissolved in THF (4 mL) and treated with 2M sodium hydroxide (0.56 mL, 1.13 mmol). The reaction was stirred for 2 hours. The reaction mixture was diluted with water (20 mL) and washed with EtOAc (2×30 mL). The aqueous phase was acidified and then extracted with EtOAc (2×30 mL). All the EtOAc layers were mixture of desired product and impurities so were combined, washed with saturated brine solution (50 mL), dried MgSO$_4$, filtered, evaporated to afford crude material (441 mg) as a yellow gum. The crude product was purified by preparative HPLC (Waters CSH C18 OBD column, 30×100 mm id, 5 micron particle size), using decreasingly polar mixtures of water (containing 1% by volume of NH$_4$OH (28-30% in H$_2$O)) and MeCN as eluents. Fractions containing the desired compound were evaporated to dryness to afford the title compound (80 mg, 22%) as a yellow gum; m/z: ES+ [M+H]$^+$ 837.5.

Intermediate 71b: (2S,4R)-1-((S)-2-(tert-Butyl)-14-(4-((1R,3R)-2-(3-((tert-butyldiphenylsilyl)oxy)-2,2-difluoropropyl)-3-methyl-2,3,4,9-tetrahydro-1H-pyrido[3,4-b]indol-1-yl)-3,5-difluorophenoxy)-4-oxo-6,9,12-trioxa-3-azatetradecanoyl)-4-hydroxy-N-(4-(4-methylthiazol-5-yl)benzyl)pyrrolidine-2-carboxamide

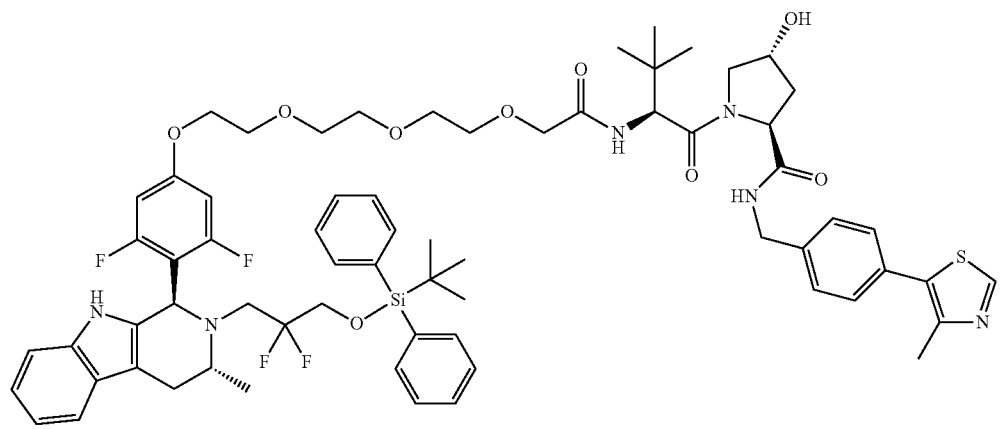 [SMILES: Cc1ncsc1-c1ccc(CNC(=O)[C@@H]2C[C@@H](O)CN2C(=O)[C@@H](NC(=O)COCCOCCOCCOc2cc(F)c([C@@H]3c4[nH]c5ccccc5c4C[C@@H](C)N3CC(F)(F)CO[Si](c3ccccc3)(c3ccccc3)C(C)(C)C)c(F)c2)C(C)(C)C)cc1]

HATU (50 mg, 0.13 mmol) was added in one portion to (2S,4R)-1-((S)-2-amino-3,3-dimethylbutanoyl)-4-hydroxy-N-(4-(4-methylthiazol-5-yl)benzyl)pyrrolidine-2-carboxamide, HCl (41 mg, 0.09 mmol), 2-(2-(2-(2-(4-((1R,3R)-2-(3-((tert-butyldiphenylsilyl)oxy)-2,2-difluoropropyl)-3-methyl-2,3,4,9-tetrahydro-1H-pyrido[3,4-b]indol-1-yl)-3,5-difluorophenoxy)ethoxy)ethoxy)ethoxy)acetic acid (73 mg, 0.09 mmol) and triethylamine (0.05 mL, 0.35 mmol) in DMF (1.7 mL) at 20° C. under nitrogen. The resulting mixture was stirred for 30 minutes. The reaction mixture was diluted with EtOAc (50 mL), and washed sequentially with water (50 mL) and saturated brine (25 mL). The organic layer was dried with MgSO$_4$, filtered and evaporated to afford the title compound (109 mg, 100%) which was used directly in the next step without further purification; m/z: ES+ [M+H]$^+$ 1249.6.

Example 71: (2S,4R)-1-((S)-2-(tert-Butyl)-14-(4-((1R,3R)-2-(2,2-difluoro-3-hydroxypropyl)-3-methyl-2,3,4,9-tetrahydro-1H-pyrido[3,4-b]indol-1-yl)-3,5-difluorophenoxy)-4-oxo-6,9,12-trioxa-3-azatetradecanoyl)-4-hydroxy-N-(4-(4-methylthiazol-5-yl)benzyl)pyrrolidine-2-carboxamide

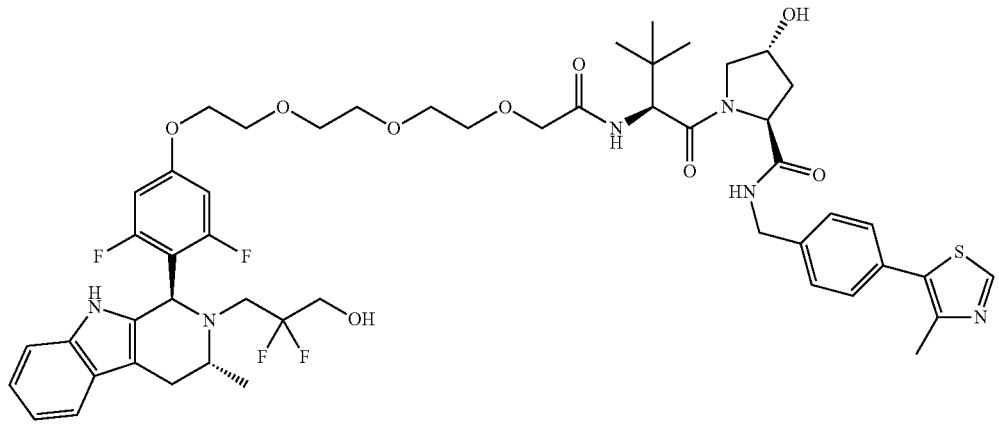 [SMILES: Cc1ncsc1-c1ccc(CNC(=O)[C@@H]2C[C@@H](O)CN2C(=O)[C@@H](NC(=O)COCCOCCOCCOc2cc(F)c([C@@H]3c4[nH]c5ccccc5c4C[C@@H](C)N3CC(F)(F)CO)c(F)c2)C(C)(C)C)cc1]

A solution of TBAF 1M in THF (0.120 mL, 0.12 mmol) was added in one portion to (2S,4R)-1-((S)-2-(tert-butyl)-14-(4-((1R,3R)-2-(3-((tert-butyldiphenylsilyl)oxy)-2,2-difluoropropyl)-3-methyl-2,3,4,9-tetrahydro-1H-pyrido[3,4-b]indol-1-yl)-3,5-difluorophenoxy)-4-oxo-6,9,12-trioxa-3-azatetradecanoyl)-4-hydroxy-N-(4-(4-methylthiazol-5-yl)benzyl)pyrrolidine-2-carboxamide (100 mg, 0.08 mmol) in THF (2 mL) at 20° C. The resulting solution was stirred for 18 hours. The reaction mixture was diluted with EtOAc (50 mL), and washed sequentially with saturated NH₄Cl (20 mL), water (20 mL), and saturated brine (20 mL). The organic layer was dried with MgSO₄, filtered and evaporated to afford crude product. The crude product was purified by preparative HPLC (Waters CSH C18 OBD column, 30×100 mm id, 5 micron particle size), using decreasingly polar mixtures of water (containing 1% by volume of NH₄OH (28-30% in H₂O)) and MeCN as eluents. Fractions containing the desired compound were evaporated to dryness to afford impure product (50 mg). The sample was dissolved in MeOH (1 ml) and re-purified using SFC, Column, Phenomenex C2, 30×250 mm, 5 micron, Mobile phase: 37% MeOH+0.1% NH₃/63% scCO2, Flow rate: 100 mL/min, BPR: 120 bar, Column temperature: 40 deg C. to afford the title compound (21 mg, 26%) as a white solid; ¹H NMR (400 MHz, CDCl₃, 30° C.) 0.94 (9H, s), 1.17 (3H, d), 2.03-2.12 (1H, m), 2.48 (3H, s), 2.5-2.58 (1H, m), 2.67 (1H, dd), 2.81-2.95 (2H, m), 3.11 (1H, dd), 3.16-3.28 (1H, m), 3.55-3.76 (13H, m), 3.80 (2H, t), 3.85-4.02 (2H, m), 4.02-4.11 (3H, m), 4.31 (1H, dd), 4.47-4.61 (3H, m), 4.70 (1H, t), 5.19 (1H, s), 6.45 (2H, d), 7.05-7.16 (2H, m), 7.26 (3H, s), 7.31-7.39 (4H, m), 7.46-7.55 (1H, m), 8.38 (1H, s), 8.63 (1H, s); m/z: ES+ [M+H]⁺ 1011.7.

Intermediate 72a: 2-(3-(3-(Benzyloxy)propoxy)propoxy)tetrahydro-2H-pyran

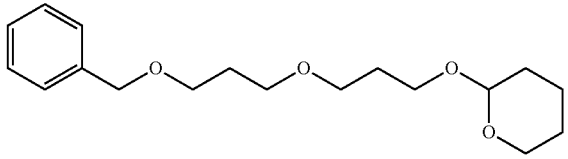 [SMILES: c1ccc(COCCCOCCCOC2CCCCO2)cc1]

Tetrabutylammonium hydrogen sulfate (0.951 g, 2.80 mmol) was added in one portion to 3-(benzyloxy)propan-1-ol (2.96 mL, 18.68 mmol) and 2-(3-bromopropoxy)tetrahydro-2H-pyran (5 g, 22.41 mmol) in 50% sodium hydroxide solution (11.98 mL) at 20° C. The resulting mixture was stirred at 70° C. for 18 hours. The cooled reaction mixture was diluted with water (20 mL) and extracted with EtOAc (3×25 mL). The combined organic extracts were washed with water (20 mL), saturated brine solution (20 mL), dried over MgSO₄, filtered and evaporated to afford crude product as a yellow oil. The crude product was purified by flash silica chromatography, elution gradient 0 to 10% EtOAc in heptane to afford the title compound (3.42 g, 59%) as a colourless oil; ¹H NMR (400 MHz, CDCl₃) 1.49-1.61 (4H, m), 1.65-1.73 (1H, m), 1.78-1.92 (5H, m), 3.43-3.6 (8H, m), 3.75-3.9 (2H, m), 4.50 (2H, s), 4.54-4.59 (1H, m), 7.23-7.28 (1H, m), 7.32 (4H, d).

Intermediate 72b: 3-(3-(Benzyloxy)propoxy)propan-1-ol

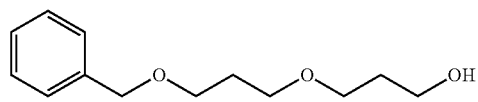 [SMILES: OCCCOCCCOCc1ccccc1]

2-(3-(3-(Benzyloxy)propoxy)propoxy)tetrahydro-2H-pyran (3.42 g, 11.1 mmol) was dissolved in MeOH (30 mL) and 1M aq. HCl (15 mL) was added. The resulting mixture was stirred at 20° C. for 1 hour. The reaction mixture was diluted with water (100 mL), and extracted with EtOAc (3×100 mL). The combined organics were washed with saturated brine (50 mL). The organic layer was dried with MgSO₄, filtered and evaporated to afford the title compound (2.58 g) which was used directly in the next step without further purification; ¹H NMR (400 MHz, CDCl₃, 30° C.) 1.78-1.92 (4H, m), 2.36 (1H, s), 3.55 (4H, td), 3.61 (2H, t), 3.76 (2H, t), 4.50 (2H, s), 7.27-7.31 (1H, m), 7.31-7.38 (4H, m); m/z: ES+ [M+H]⁺ 225.2.

Intermediate 72c: Ethyl 2-(3-(3-(benzyloxy)propoxy)propoxy)acetate

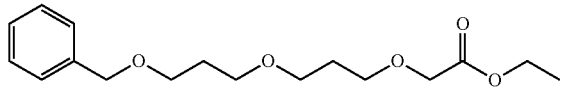 [SMILES: CCOC(=O)COCCCOCCCOCc1ccccc1]

Ethyl 2-diazoacetate (3.42 mL, 27.9 mmol) in DCM (10 mL) was added slowly to 3-(3-(benzyloxy)propoxy)propan-1-ol (2.5 g, 11.2 mmol) and diacetoxyrhodium (0.246 g, 0.56 mmol) in DCM (30 mL) at 20° C. over a period of 1 hour under nitrogen. The resulting solution was stirred for 18 hours. The mixture was diluted with DCM (50 mL) and washed with water (3×50 mL). The organic layer was collected and filtered through a phase separating cartridge then evaporated to dryness. The crude product was purified by flash silica chromatography, elution gradient 0 to 10% EtOAc in heptane to afford the title compound (2.27 g, 66%) as a colourless liquid; $^1$H NMR (400 MHz, CDCl$_3$, 30° C.) 1.29 (3H, dt), 1.88 (4H, p), 3.48-3.63 (8H, m), 4.05 (2H, s), 4.18-4.27 (2H, m), 4.50 (2H, s), 7.26-7.29 (1H, m), 7.33 (4H, d); m/z: ES+ [M+H]$^+$ 311.2.

Intermediate 72d: Ethyl 2-(3-(3-hydroxypropoxy)propoxy)acetate

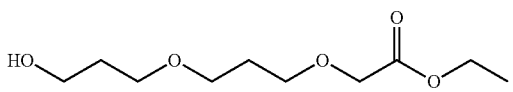

Ethyl 2-(3-(3-(benzyloxy)propoxy)propoxy)acetate (2.2 g, 7.09 mmol) and 10% palladium on carbon (0.075 g, 0.71 mmol) in ethanol (14 mL) were stirred under an atmosphere of hydrogen at RT for 4 hours. The reaction mixture was filtered, washing with EtOH then the solvent was evaporated to afford crude product. The crude product was purified by flash silica chromatography, elution gradient 0 to 100% EtOAc in heptane to afford the title compound (1.11 g, 71%) as a colourless oil; $^1$H NMR (400 MHz, CDCl$_3$, 30° C.) 1.29 (3H, t), 1.83 (2H, p), 1.89 (2H, p), 2.42 (1H, t), 3.57 (2H, t), 3.62 (4H, td), 3.77 (2H, q), 4.06 (2H, s), 4.22 (2H, q).

Intermediate 72e: Ethyl 2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)acetate

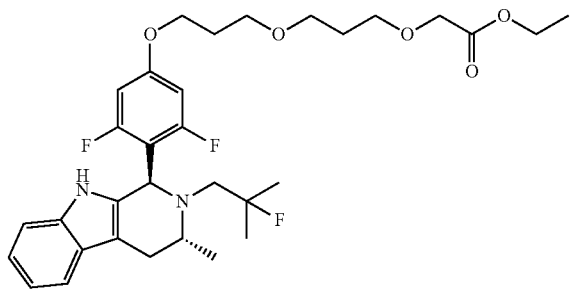 [SMILES: CCOC(=O)COCCCOCCCOc1cc(F)c([C@@H]2c3[nH]c4ccccc4c3C[C@@H](C)N2CC(C)(C)F)c(F)c1]

Diisopropyl azodicarboxylate (0.101 mL, 0.51 mmol) was added dropwise over 15 minutes to a stirred mixture of 3,5-difluoro-4-((1R,3R)-2-(2-fluoro-2-methylpropyl)-3-methyl-2,3,4,9-tetrahydro-1H-pyrido[3,4-b]indol-1-yl)phenol (100 mg, 0.26 mmol), ethyl 2-(3-(3-hydroxypropoxy)propoxy)acetate (113 mg, 0.51 mmol) and triphenylphosphine (135 mg, 0.51 mmol) in DCM (6 mL) at 0° C. The resulting mixture was stirred at room temperature for 1 hour. DCM (50 mL) and water (25 mL) were added and the layers were separated. The DCM layer was passed through a phase separating cartridge and concentrated to give the crude product as an orange oil. The crude product was purified by flash silica chromatography, elution gradient 0 to 25% EtOAc in heptane to afford the title compound (141 mg, 93%) as a pale yellow gum; $^1$H NMR (400 MHz, CDCl$_3$, 30° C.) 1.10 (3H, d), 1.15-1.25 (6H, m), 1.25-1.29 (3H, t), 1.87 (2H, p), 1.97-2.07 (2H, m), 2.39 (1H, dd), 2.60 (1H, dd), 2.86 (1H, dd), 3.09 (1H, dd), 3.51-3.61 (6H, m), 3.64-3.73 (1H, m), 3.99-4.04 (3H, m), 4.98 (2H, hept), 5.19 (1H, s), 6.28 (1H, s), 6.37-6.45 (2H, m), 7.05-7.14 (2H, m), 7.18-7.24 (1H, m), 7.51 (1H, dd), 7.56 (1H, s); m/z: ES+ [M+H]$^+$ 591.4.

Intermediate 72f: 2-(3-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)acetic Acid

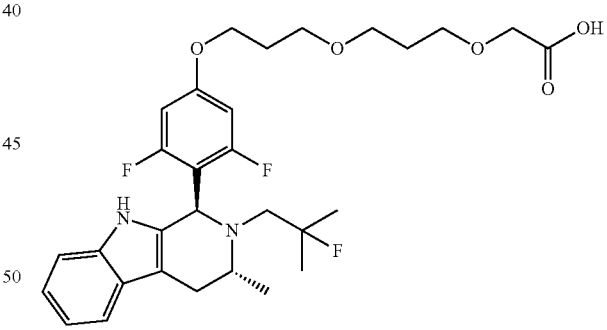

Lithium hydroxide hydrate (20 mg, 0.48 mmol) was added in one portion to ethyl 2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)acetate (141 mg, 0.24 mmol) in THF (1 mL) and water (0.3 mL) at 20° C. The resulting solution was stirred for 30 minutes. The reaction mixture was diluted with water (10 mL) then was acidified with 2M HCl and extracted into EtOAc (50 mL). The organic layer was washed with brine (15 mL) and evaporated to afford the title compound (134 mg, 100%) as a yellow gum which was used in the next step without purification; m/z: ES+ [M+H]$^+$ 563.3.

Example 72: (2S,4R)-1-((S)-2-(2-(3-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)acetamido)-3,3-dimethylbutanoyl)-4-hydroxy-N-(4-(4-methylthiazol-5-yl)benzyl)pyrrolidine-2-carboxamide

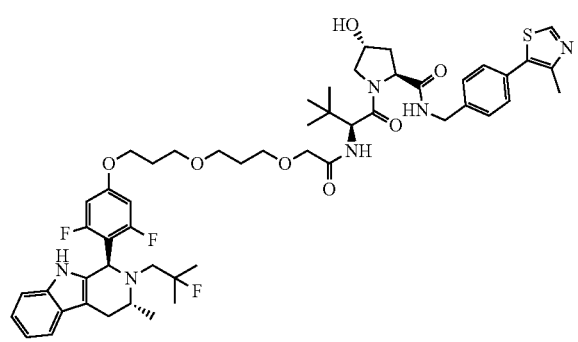 [SMILES: Cc1ncsc1-c1ccc(CNC(=O)[C@@H]2C[C@@H](O)CN2C(=O)[C@@H](NC(=O)COCCCOCCCOc2cc(F)c([C@@H]3c4[nH]c5ccccc5c4C[C@@H](C)N3CC(C)(C)F)c(F)c2)C(C)(C)C)cc1]

HATU (136 mg, 0.36 mmol) was added in one portion to (2S,4R)-1-((S)-2-amino-3,3-dimethylbutanoyl)-4-hydroxy-N-(4-(4-methylthiazol-5-yl)benzyl)pyrrolidine-2-carboxamide, HCl (111 mg, 0.24 mmol), 2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)acetic acid (134 mg, 0.24 mmol) and triethylamine (0.13 mL, 0.95 mmol) in DMF (5 mL) at 20° C. under nitrogen. The resulting mixture was stirred for 30 minutes. The reaction mixture was diluted with EtOAc (50 mL), and washed sequentially with water (50 mL) and saturated brine (25 mL). The organic layer was dried with MgSO$_4$, filtered and evaporated to afford crude product. The crude product was purified by preparative HPLC (Waters CSH C18 OBD column, 30×100 mm id, 5 micron particle size), using decreasingly polar mixtures of water (containing 1% by volume of NH$_4$OH (28-30% in H$_2$O)) and MeCN as eluents to afford the title compound (106 mg, 45.6%) as a white foamy solid; $^1$H NMR (400 MHz, CDCl$_3$, 30° C.) 0.94 (9H, s), 1.09 (3H, d), 1.21 (6H, dd), 1.8-1.9 (2H, m), 1.99 (3H, d), 2.05-2.15 (1H, m), 2.42 (1H, dd), 2.50 (3H, s), 2.53-2.65 (2H, m), 2.83 (1H, dd), 3.05 (1H, dd), 3.45-3.6 (7H, m), 3.6-3.7 (2H, m), 3.80 (1H, d), 3.91-4.08 (3H, m), 4.34 (1H, dd), 4.5-4.62 (3H, m), 4.74 (1H, t), 5.20 (1H, s), 6.36 (2H, d), 7.02-7.12 (2H, m), 7.15 (1H, d), 7.2-7.25 (2H, m), 7.3-7.42 (4H, m), 7.46-7.55 (1H, m), 8.65 (2H, s); m/z: ES+ [M+H]$^+$975.6.

Intermediate 73a: Methyl 3-(3-hydroxyprop-1-yn-1-yl)benzoate

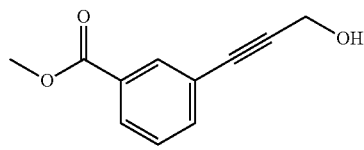

Bis(triphenylphosphine)palladium(II) dichloride (0.67 g, 0.95 mmol) was added in one portion to methyl 3-iodobenzoate (5 g, 19.08 mmol) and copper(I) iodide (0.18 g, 0.95 mmol) in degassed THF (90 mL) at 20° C. under nitrogen. The resulting mixture was stirred for 5 minutes then prop-2-yn-1-ol (2.22 mL, 38.16 mmol) and triethylamine (5.31 mL, 38.16 mmol) was added. The reaction was stirred at 20° C. for 18 hours. The reaction mixture was diluted with EtOAc (200 mL), and washed sequentially with water (2×100 mL) and saturated brine (50 mL). The organic layer was dried with MgSO$_4$, filtered and evaporated to afford crude product. The crude product was purified by flash silica chromatography, elution gradient 0 to 50% EtOAc in heptane to afford the title compound (3.10 g, 85%) as a yellow solid; $^1$H NMR (400 MHz, CDCl$_3$, 30° C.) 1.69 (1H, t), 3.92 (3H, s), 4.51 (2H, d), 7.40 (1H, t), 7.61 (1H, dt), 7.99 (1H, dt), 8.11 (1H, d).

Intermediate 73b: Methyl 3-(3-hydroxypropyl)benzoate

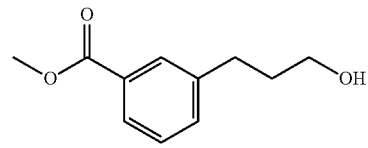

Methyl 3-(3-hydroxyprop-1-yn-1-yl)benzoate (3.1 g, 16.30 mmol) and 10% palladium on carbon (0.173 g, 1.63 mmol) in ethyl acetate (30 mL) were stirred under 1.5 bar of hydrogen at RT for 18 hours. Catalyst was filtered off and replaced with fresh catalyst and the reaction charged with hydrogen as before and stirred for a further 24 hours. The reaction mixture was filtered, washing with EtOAc then the solvent was evaporated to afford the title compound (3.08 g, 97%) as a pale yellow oil, which was used in the next step without further purification; $^1$H NMR (400 MHz, CDCl$_3$, 30° C.) 1.86-1.98 (2H, m), 2.74-2.8 (2H, m), 3.68 (2H, t), 3.91 (3H, s), 7.37 (2H, dt), 7.83-7.94 (2H, m).

Intermediate 73c: Methyl 3-(3-((tert-butyldimethylsilyl)oxy)propyl)benzoate

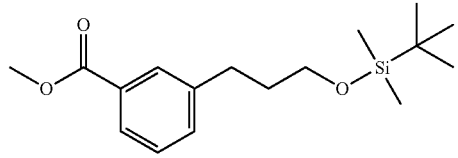 [SMILES: COC(=O)c1cccc(CCCO[Si](C)(C)C(C)(C)C)c1]

tert-Butylchlorodimethylsilane (1.69 g, 11.2 mmol) was added in one portion to methyl 3-(3-hydroxypropyl)benzoate (1.98 g, 10.2 mmol) and 1H-imidazole (0.76 g, 11.2 mmol) in DCM (16 mL) at 20° C. under nitrogen. The resulting white suspension was stirred for 2 hours. The reaction mixture was diluted with DCM (100 mL), and washed with water (50 mL) and saturated brine (100 mL). The organic layer was dried with MgSO$_4$, filtered and evaporated to afford crude product. The crude product was purified by flash silica chromatography, elution gradient 0 to 5% EtOAc in heptane to afford the title compound (1.28 g, 41%) as a colourless oil; $^1$H NMR (400 MHz, CDCl$_3$, 30° C.) 0.05 (6H, s), 0.91 (9H, s), 1.8-1.89 (2H, m), 2.69-2.78

(2H, m), 3.63 (2H, t), 3.91 (3H, s), 7.3-7.43 (2H, m), 7.82-7.92 (2H, m); m/z: ES+ [M+H]+ 309.3

Intermediate 73d: (3-(3-((tert-Butyldimethylsilyl)oxy)propyl)phenyl)methanol

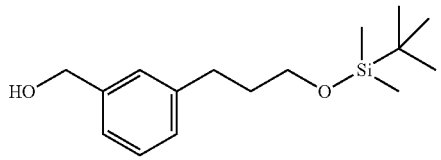 [SMILES: CC(C)(C)[Si](C)(C)OCCCc1cccc(CO)c1]

A solution of lithium aluminum hydride 1M in THF (5.39 mL, 5.39 mmol) was added dropwise to a solution of methyl 3-(3-((tert-butyldimethylsilyl)oxy)propyl)benzoate (1.28 g, 4.15 mmol) in THF (15 mL) at 0° C. over a period of 15 minutes under nitrogen. The resulting mixture was stirred at 20° C. for 2 hours. The reaction mixture was cooled to 0° C. and quenched with careful dropwise addition of water (0.18 mL), 2M NaOH solution (0.36 mL) and water (0.54 mL). The mixture was stirred for 5 minutes. The solids were removed by filtration and the filtrate was evaporated to dryness. The crude product was purified by flash silica chromatography, elution gradient 0 to 25% EtOAc in heptane to afford the title compound (0.788 g, 68%) as a colourless liquid; $^1$H NMR (400 MHz, CDCl$_3$, 30° C.) 0.05 (6H, s), 0.91 (9H, s), 1.58 (1H, t), 1.79-1.9 (2H, m), 2.65-2.72 (2H, m), 3.63 (2H, t), 4.67 (2H, d), 7.13 (1H, d), 7.15-7.23 (2H, m), 7.28 (1H, d); m/z: ES+ [M+H]+ 281.3.

Intermediate 73e: (1R,3R)-1-(4-((3-(3-((tert-Butyldimethylsilyl)oxy)propyl)benzyl)oxy)-2,6-difluorophenyl)-2-(2-fluoro-2-methylpropyl)-3-methyl-2,3,4,9-tetrahydro-1H-pyrido[3,4-b]indole

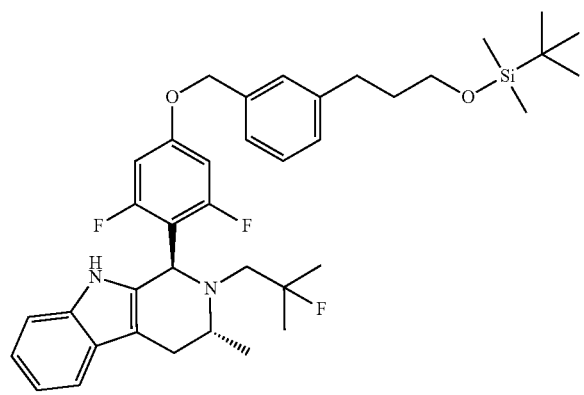 [SMILES: C[C@@H]1Cc2c([nH]c3ccccc23)[C@@H](c2c(F)cc(OCc3cccc(CCCO[Si](C)(C)C(C)(C)C)c3)cc2F)N1CC(C)(C)F]

The title compound was prepared in a similar manner to Intermediate 72e using the appropriate phenol and alcohol to afford the desired product (333 mg, 79%) as a pale yellow gum; $^1$H NMR (400 MHz, CDCl$_3$, 30° C.) 0.05 (6H, s), 0.91 (9H, s), 1.10 (3H, d), 1.20 (6H, dd), 1.79-1.89 (2H, m), 2.39 (1H, dd), 2.60 (1H, dd), 2.66-2.74 (2H, m), 2.86 (1H, dd), 3.05-3.14 (1H, m), 3.6-3.73 (3H, m), 4.98 (2H, s), 5.19 (1H, s), 6.48 (2H, d), 7.05-7.14 (2H, m), 7.15-7.25 (4H, m), 7.30 (1H, t), 7.41 (1H, s), 7.48-7.55 (1H, m); m/z: ES+ [M+H]+ 651.4.

Intermediate 73f: 3-(3-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenyl)propan-1-ol

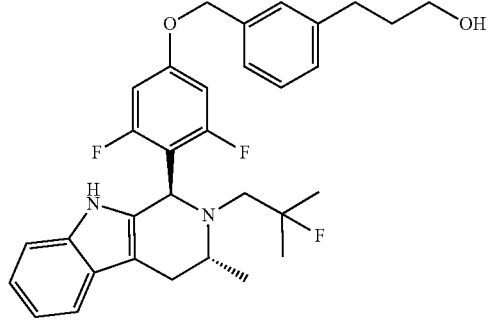 [SMILES: C[C@@H]1Cc2c([nH]c3ccccc23)[C@@H](c2c(F)cc(OCc3cccc(CCCO)c3)cc2F)N1CC(C)(C)F]

TBAF 1M in THF (0.77 mL, 0.77 mmol) was added in one portion to (1R,3R)-1-(4-((3-(3-((tert-butyldimethylsilyl)oxy)propyl)benzyl)oxy)-2,6-difluorophenyl)-2-(2-fluoro-2-methylpropyl)-3-methyl-2,3,4,9-tetrahydro-1H-pyrido[3,4-b]indole (333 mg, 0.51 mmol) in THF (4 mL) at 20° C. The resulting solution was stirred for 2 hours. The reaction mixture was diluted with EtOAc (50 mL), and washed sequentially with saturated NH$_4$Cl (20 mL), water (20 mL), and saturated brine (20 mL). The organic layer was dried with MgSO$_4$, filtered and evaporated to afford crude product. The crude product was purified by flash silica chromatography, elution gradient 0 to 50% EtOAc in heptane to afford the title compound (207 mg, 75%) as a yellow gum; $^1$H NMR (400 MHz, CDCl$_3$, 30° C.) 1.10 (3H, d), 1.14-1.23 (6H, m), 1.86-1.95 (2H, m), 2.39 (1H, dd), 2.53-2.65 (1H, m), 2.7-2.77 (2H, m), 2.8-2.91 (1H, m), 3.09 (1H, d), 3.64 (3H, q), 5.01 (2H, s), 5.19 (1H, s), 6.47 (2H, d), 7.04-7.15 (2H, m), 7.14-7.25 (4H, m), 7.31 (1H, t), 7.47-7.57 (2H, m); m/z: ES+ [M+H]+ 537.4.

Intermediate 73g: Ethyl 2-(3-(3-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenyl)propoxy)acetate

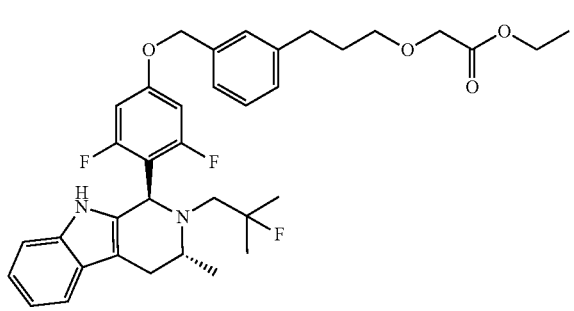 [SMILES: CCOC(=O)COCCCc1cccc(COc2cc(F)c([C@@H]3c4[nH]c5ccccc5c4C[C@@H](C)N3CC(C)(C)F)c(F)c2)c1]

The title compound was prepared in a similar manner to Intermediate 72c using the appropriate alcohol to afford the desired product (109 mg, 45%) as a colourless gum; $^1$H NMR (400 MHz, CDCl$_3$, 30° C.) 1.10 (3H, d), 1.20 (6H, dd), 1.29 (3H, t), 1.89-2.01 (2H, m), 2.39 (1H, dd), 2.60 (1H, dd), 2.71-2.78 (2H, m), 2.86 (1H, dd), 3.09 (1H, d), 3.54 (2H, t), 3.69 (1H, s), 4.06 (2H, d), 4.22 (2H, q), 4.99 (2H, s), 5.19 (1H, s), 6.48 (2H, d), 7.05-7.15 (2H, m), 7.16-7.25 (4H, m), 7.31 (1H, t), 7.47 (1H, s), 7.49-7.55 (1H, m); m/z: ES+ [M+H]+ 623.5.

Intermediate 73h: 2-(3-(3-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenyl)propoxy)acetic Acid

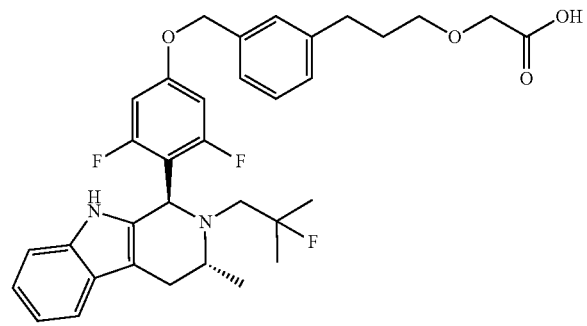 [SMILES: C[C@@H]1Cc2c([nH]c3ccccc23)[C@@H](c2c(F)cc(OCc3cccc(CCCOCC(=O)O)c3)cc2F)N1CC(C)(C)F]

The title compound was prepared in a similar manner to Intermediate 72f using the appropriate ester to afford the desired product (104 mg, 100%) as a yellow gum which was used in the next step without further purification; m/z: ES+ [M+H]+ 595.4.

Example 73: (2S,4R)-1-((S)-2-(2-(3-(3-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenyl)propoxy)acetamido)-3,3-dimethylbutanoyl)-4-hydroxy-N-(4-(4-methylthiazol-5-yl)benzyl)pyrrolidine-2-carboxamide

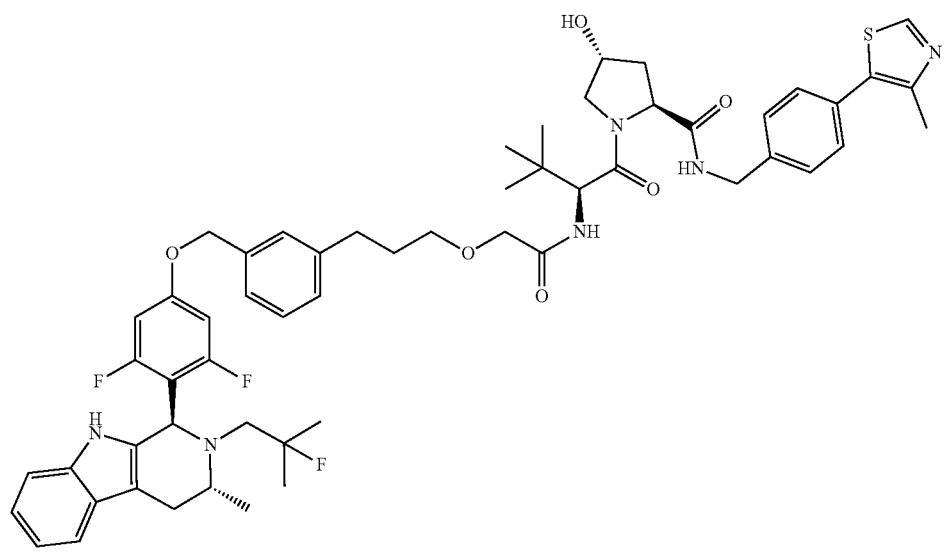 [SMILES: Cc1ncsc1-c1ccc(CNC(=O)[C@@H]2C[C@@H](O)CN2C(=O)[C@@H](NC(=O)COCCCc2cccc(COc3cc(F)c([C@@H]4c5[nH]c6ccccc6c5C[C@@H](C)N4CC(C)(C)F)c(F)c3)c2)C(C)(C)C)cc1]

The title compound was prepared in a similar manner to Example 68 using the appropriate carboxylic acid and amine to afford the desired product (80 mg, 47%) as a white foamy solid; 1H NMR (400 MHz, CDCl3, 30° C.) 0.94 (9H, s), 1.10 (3H, d), 1.20 (6H, dd), 1.85-2 (2H, m), 2.01-2.12 (1H, m), 2.40 (1H, dd), 2.48 (3H, s), 2.52-2.68 (3H, m), 2.73 (2H, t), 2.84 (1H, dd), 3.07 (1H, dd), 3.42-3.53 (3H, m), 3.55-3.72 (2H, m), 3.76-3.97 (2H, m), 4.09 (1H, d), 4.31 (1H, dd), 4.45-4.62 (3H, m), 4.71 (1H, t), 4.92-5.02 (2H, m), 5.21 (1H, s), 6.36-6.53 (2H, m), 7.03-7.13 (2H, m), 7.12-7.24 (5H, m), 7.27-7.39 (6H, m), 7.46-7.57 (1H, m), 8.08 (1H, s), 8.64 (1H, s). m/z: ES+ [M+H]+ 1007.4.

Intermediate 74a: Ethyl 2-((3-(3-((tert-butyldimethylsilyl)oxy)propyl)benzyl)oxy)acetate

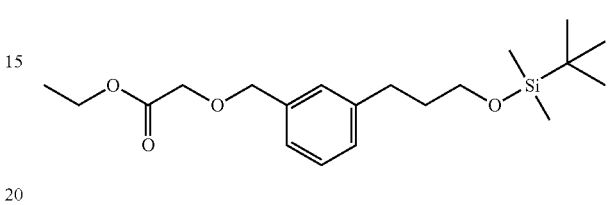

The title compound was prepared in a similar manner to Intermediate 72c using the appropriate alcohol to afford the desired product (349 mg, 68%) as a colourless gum; 1H NMR (400 MHz, CDCl3, 30° C.) 0.05 (6H, s), 0.91 (9H, s), 1.29 (3H, t), 1.78-1.89 (2H, m), 2.63-2.72 (2H, m), 3.63 (2H, t), 4.08 (2H, s), 4.23 (2H, q), 4.61 (2H, s), 7.13 (1H, d), 7.18 (2H, d), 7.26 (1H, s); m/z: ES+ [M+H]+ 367.3.

Intermediate 74b: Ethyl 2-((3-(3-hydroxypropyl)benzyl)oxy)acetate

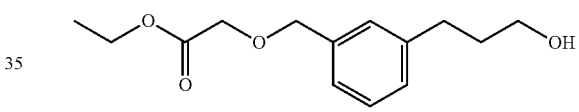

A solution of 1M TBAF in THF (1.43 mL, 1.43 mmol) was added in one portion to ethyl 2-((3-(3-((tert-butyldimethylsilyl)oxy)propyl)benzyl)oxy)acetate (349 mg, 0.95 mmol) in THF (8 mL) at 20° C. The resulting solution was stirred for 2 hours. The reaction mixture was diluted with EtOAc (50 mL), and washed sequentially with saturated NH₄Cl (20 mL), water (20 mL), and saturated brine (20 mL). The organic layer was dried with MgSO₄, filtered and evaporated to afford crude product. The crude product was purified by flash silica chromatography, elution gradient 0 to 50% EtOAc in heptane to afford the title compound (144 mg, 60%) as a yellow gum; ¹H NMR (400 MHz, CDCl₃, 30° C.) 1.23-1.33 (4H, m), 1.86-1.95 (2H, m), 2.68-2.75 (2H, m), 3.67 (2H, q), 4.09 (2H, s), 4.23 (2H, q), 4.61 (2H, s), 7.15 (1H, d), 7.17-7.23 (2H, m), 7.28 (1H, d).

Intermediate 74c: Ethyl 2-((3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propyl)benzyl)oxy)acetate

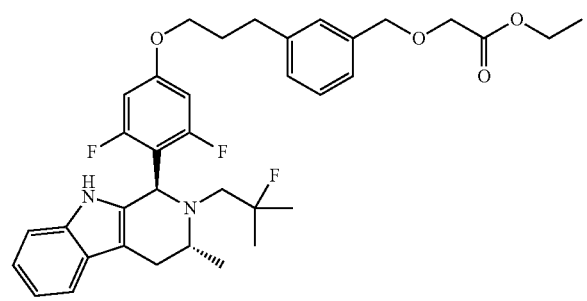 [SMILES: CCOC(=O)COCc1cccc(CCCOc2cc(F)c([C@@H]3c4[nH]c5ccccc5c4C[C@@H](C)N3CC(C)(C)F)c(F)c2)c1]

The title compound was prepared in a similar manner to Intermediate 72e using the appropriate phenol and alcohol to afford the desired product (130 mg, 73%) as a yellow gum; ¹H NMR (400 MHz, CDCl₃, 30° C.) 1.10 (3H, d), 1.14-1.32 (9H, m), 2.08 (2H, dq), 2.39 (1H, dd), 2.60 (1H, dd), 2.75-2.94 (3H, m), 3.09 (1H, dd), 3.68 (1H, d), 3.90 (2H, t), 4.08 (2H, s), 4.22 (2H, q), 4.60 (2H, s), 5.19 (1H, s), 6.38 (2H, d), 7.04-7.17 (3H, m), 7.17-7.24 (3H, m), 7.29 (1H, d), 7.46-7.55 (2H, m); m/z: ES+ [M+H]⁺ 623.3.

Intermediate 74d: 2-((3-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propyl)benzyl)oxy)acetic Acid

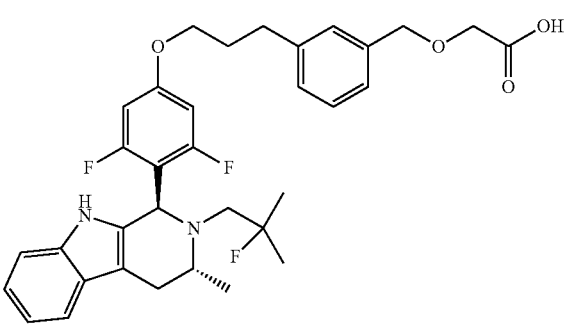 [SMILES: C[C@@H]1Cc2c([nH]c3ccccc23)[C@@H](c2c(F)cc(OCCCc3cccc(COCC(=O)O)c3)cc2F)N1CC(C)(C)F]

The title compound was prepared in a similar manner to Intermediate 72f using the appropriate ester to afford the desired product (124 mg, 100%) as a yellow gum which was used in the next step without further purification; m/z: ES+ [M+H]⁺ 595.3.

Example 74: (2S,4R)-1-((S)-2-(2-((3-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propyl)benzyl)oxy)acetamido)-3,3-dimethylbutanoyl)-4-hydroxy-N-(4-(4-methylthiazol-5-yl)benzyl)pyrrolidine-2-carboxamide

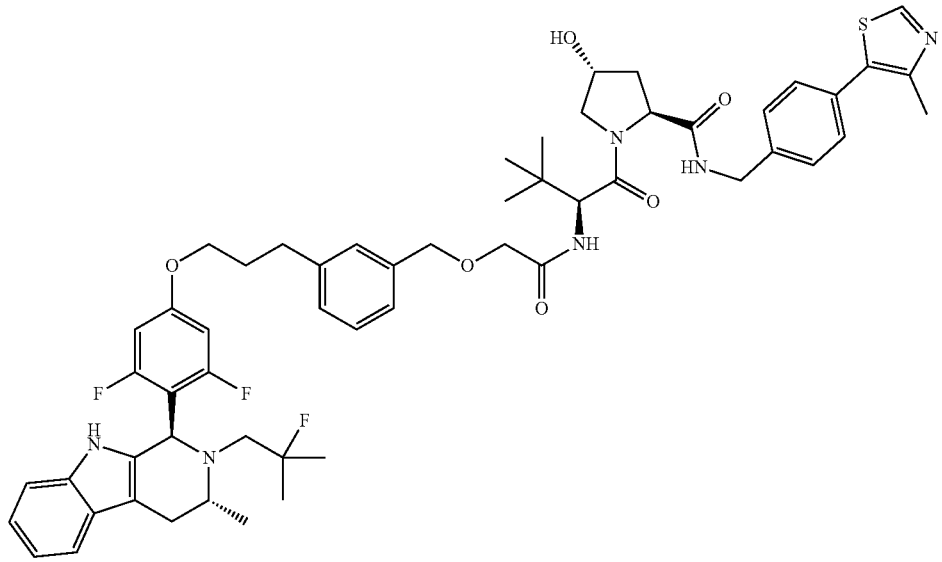 [SMILES: Cc1ncsc1-c1ccc(CNC(=O)[C@@H]2C[C@@H](O)CN2C(=O)[C@@H](NC(=O)COCc2cccc(CCCOc3cc(F)c([C@@H]4c5[nH]c6ccccc6c5C[C@@H](C)N4CC(C)(C)F)c(F)c3)c2)C(C)(C)C)cc1]

The title compound was prepared in a similar manner to Example 68 using the appropriate carboxylic acid and amine to afford the desired product (124 mg, 59%) as a pale yellow solid; ¹H NMR (400 MHz, CDCl₃, 27° C.) 0.94 (9H, s), 1.10 (3H, d), 1.21 (6H, dd), 2.07 (3H, p), 2.41 (1H, dd), 2.49 (3H, s), 2.59 (3H, dq), 2.74-2.92 (3H, m), 3.07 (1H, dd), 3.62 (2H, ddd), 3.8-3.97 (4H, m), 4.06 (1H, d), 4.31 (1H, dd), 4.47-4.62 (5H, m), 4.73 (1H, t), 5.20 (1H, s), 6.31 (2H, d), 7.03-7.19 (5H, m), 7.2-7.25 (2H, m), 7.27-7.31 (2H, m), 7.32-7.39 (4H, m), 7.47-7.55 (1H, m), 8.26 (1H, s), 8.64 (1H, s); m/z: ES+ [M+H]+ 1007.4

Intermediate 77a: (R)—N-(1-(1H-Indol-3-yl)propan-2-yl)-1-fluorocyclopropane-1-carboxamide

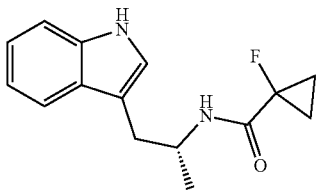 [SMILES: C[C@H](Cc1c[nH]c2ccccc12)NC(=O)C1(F)CC1]

To a suspension of 1-fluorocyclopropane-1-carboxylic acid (1 g, 9.61 mmol) and (R)-1-(1H-indol-3-yl)propan-2-amine (1.40 g, 8.01 mmol) in DCM (60 mL) was added DIPEA (4.20 mL, 24.0 mmol) and HATU (4.57 g, 12.0 mmol). The white suspension was stirred at RT for 90 minutes. The reaction mixture was diluted with DCM (50 mL) and washed with water (100 mL). The organic phase was evaporated. The crude product was purified by flash silica chromatography, elution gradient 0 to 70% EtOAc in heptane to afford the title compound (1.90 g, 91%) as a white solid; $^1$H NMR (400 MHz, CDCl$_3$, 30° C.) 1.16-1.29 (5H, m), 1.32-1.42 (2H, m), 2.92 (1H, dd), 3.06 (1H, dd), 4.35-4.49 (1H, m), 6.36 (1H, s), 7.05 (1H, d), 7.13 (1H, td), 7.16-7.23 (1H, m), 7.36 (1H, d), 7.67 (1H, d), 8.06 (1H, s); m/z: ES+ [M+H]+ 261.2.

Intermediate 77b: (R)—N-((1-Fluorocyclopropyl)methyl)-1-(1H-indol-3-yl)propan-2-amine

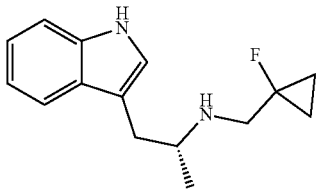 [SMILES: C[C@H](Cc1c[nH]c2ccccc12)NCC1(F)CC1]

A solution of 1M borane-THF complex THF (25.5 mL, 25.5 mmol) was added to a stirred solution of (R)—N-(1-(1H-indol-3-yl)propan-2-yl)-1-fluorocyclopropane-1-carboxamide (1.9 g, 7.30 mmol) in THF (30 mL, 30 mmol), under nitrogen. The reaction mixture was heated to 60° C. for 8 hours. Reaction was incomplete so further 1M borane-THF complex THF (10 mL, 10 mmol) was added and reaction was heated at 60° C. for 24 hours. The reaction was allowed to cool to RT and MeOH (10 mL) was added dropwise. The reaction was heated at 60° C. for 2 hours then solvent was evaporated to afford crude product as a yellow oil. The crude product was purified by flash silica chromatography, elution gradient 0 to 30% MeOH in EtOAc to afford the title compound (1.13 g, 63%) as an oil which crystallised on standing; $^1$H NMR (400 MHz, CDCl$_3$, 30° C.) 0.5-0.59 (2H, m), 0.99 (2H, dq), 1.13 (3H, d), 2.76-3.05 (4H, m), 3.15 (1H, h), 7.06 (1H, d), 7.08-7.15 (1H, m), 7.16-7.23 (1H, m), 7.36 (1H, d), 7.62 (1H, d), 8.01 (1H, s); m/z: ES+ [M+H]+ 247.2.

Intermediate 77c: 3,5-Difluoro-4-((1R,3R)-2-((1-fluorocyclopropyl)methyl)-3-methyl-2,3,4,9-tetrahydro-1H-pyrido[3,4-b]indol-1-yl)phenol

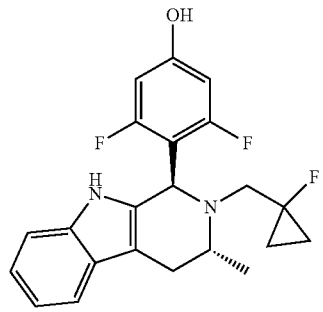 [SMILES: C[C@@H]1Cc2c([nH]c3ccccc23)[C@@H](c2c(F)cc(O)cc2F)N1CC1(F)CC1]

A solution of (R)—N-((1-fluorocyclopropyl)methyl)-1-(1H-indol-3-yl)propan-2-amine (1.13 g, 4.59 mmol) in toluene (15 mL) was added to a stirred solution of 2,6-difluoro-4-hydroxybenzaldehyde (0.733 g, 4.63 mmol) in toluene (30 mL) and AcOH (2 mL) at 20° C. The resulting solution was stirred at 85° C. for 18 hours. The reaction was cooled to RT. The crude product was purified by ion exchange chromatography, using an SCX column. The crude product was eluted from the column using 1M NH$_3$/MeOH and evaporated to dryness. The crude product was purified by flash silica chromatography, elution gradient 0 to 50% EtOAc in heptane to afford the title compound (0.700 g, 40%) as an orange solid; $^1$H NMR (400 MHz, DMSO, 30° C.) 0.42-0.61 (2H, m), 0.88-0.96 (2H, m), 1.06 (3H, d), 2.55-2.71 (2H, m), 2.88 (1H, dd), 3.06 (1H, dd), 3.57 (1H, q), 5.13 (1H, s), 6.39 (2H, d), 6.89-7.06 (2H, m), 7.19 (1H, d), 7.39 (1H, d), 10.35 (1H, d), 10.49 (1H, s); m/z: ES+ [M+H]+ 387.3.

Intermediate 77d: Ethyl 2-(2-(2-(2-(3,5-difluoro-4-((1R,3R)-2-((1-fluorocyclopropyl)methyl)-3-methyl-2,3,4,9-tetrahydro-1H-pyrido[3,4-b]indol-1-yl)phenoxy)ethoxy)ethoxy)ethoxy)acetate

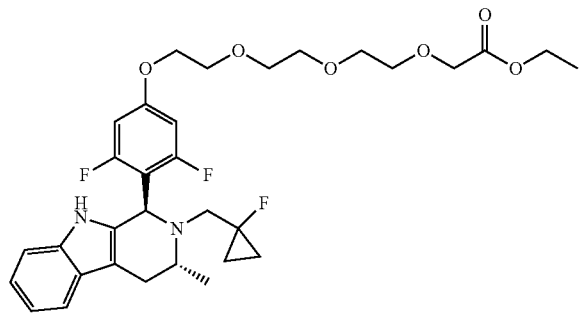 [SMILES: CCOC(=O)COCCOCCOCCOc1cc(F)c([C@@H]2c3[nH]c4ccccc4c3C[C@@H](C)N2CC2(F)CC2)c(F)c1]

DIAD (0.153 mL, 0.78 mmol) was added dropwise to a stirred solution of 3,5-difluoro-4-((1R,3R)-2-((1-fluorocyclopropyl)methyl)-3-methyl-2,3,4,9-tetrahydro-1H-pyrido[3,4-b]indol-1-yl)phenol (150 mg, 0.39 mmol), ethyl 2-(2-(2-(2-hydroxyethoxy)ethoxy)ethoxy)acetate (183 mg, 0.78 mmol) and triphenylphosphine (204 mg, 0.78 mmol) in DCM (5 mL) at 20° C. The resulting mixture was stirred for 30 minutes. DCM (15 mL) and water (25 mL) were added and the layers were separated and concentrated to give the crude product. The crude product was purified by flash silica chromatography, elution gradient 0 to 50% EtOAc in heptane to afford the title compound (160 mg, 68%); m/z: ES+ [M+H]$^+$ 605.4.

Intermediate 77e: 2-(2-(2-(2-(3,5-Difluoro-4-((1R, 3R)-2-((1-fluorocyclopropyl)methyl)-3-methyl-2,3, 4,9-tetrahydro-1H-pyrido[3,4-b]indol-1-yl)phenoxy) ethoxy)ethoxy)ethoxy)acetic Acid

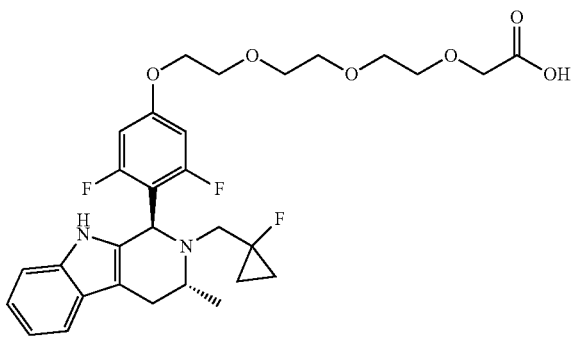 [SMILES: C[C@@H]1Cc2c([nH]c3ccccc23)[C@@H](c2c(F)cc(OCCOCCOCCOCC(=O)O)cc2F)N1CC1(F)CC1]

Lithium hydroxide hydrate (22 mg, 0.53 mmol) was added in one portion to ethyl 2-(2-(2-(2-(3,5-difluoro-4-((1R,3R)-2-((1-fluorocyclopropyl)methyl)-3-methyl-2,3,4, 9-tetrahydro-1H-pyrido[3,4-b]indol-1-yl)phenoxy)ethoxy) ethoxy)acetate (160 mg, 0.26 mmol) in THF (1 mL) and water (0.3 mL) at 20° C. The resulting solution was stirred for 30 minutes. The reaction mixture was diluted with water (10 mL) then was acidified with 2M HCl and extracted into EtOAc (50 mL). The organic layer was washed with brine (15 mL) and evaporated to afford the title compound (153 mg, 100%) as a yellow gum which was used in the next step without further purification; m/z: ES+ [M+H]$^+$ 577.3.

Example 77: (2S,4R)-1-((S)-2-(tert-Butyl)-14-(3,5-difluoro-4-((1R,3R)-2-((1-fluorocyclopropyl) methyl)-3-methyl-2,3,4,9-tetrahydro-1H-pyrido[3,4-b]indol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide HATU (151 mg, 0.40 mmol) was added in one portion to 2-(2-(2-(2-(3,5-difluoro-4-((1R,3R)-2-((1-fluorocyclopropyl)methyl)-3-methyl-2,3,4,9-tetrahydro-1H-pyrido[3,4-b] indol-1-yl)phenoxy)ethoxy)ethoxy)ethoxy)acetic acid (153 mg, 0.27 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (124 mg, 0.27 mmol) and triethylamine (0.15 mL, 1.1 mmol) in DMF (5 mL) at 20° C. under nitrogen. The resulting mixture was stirred for 30 minutes. The reaction mixture was diluted with EtOAc (50 mL), and washed sequentially with water (50 mL) and saturated brine (25 mL). The organic layer was dried with MgSO$_4$, filtered and evaporated to afford crude product. The crude product was purified by preparative HPLC (Waters CSH C18 OBD column, 30×100 mm id, 5 micron particle size), using decreasingly polar mixtures of water (containing 1% by volume of NH$_4$OH (28-30% in H$_2$O)) and MeCN as eluents to afford the title compound (129 mg, 49%) as a white solid; $^1$H NMR (400 MHz, CDCl$_3$, 30° C.) 0.38-0.59 (2H, m), 0.89-1.00 (11H, m), 1.13 (3H, d), 2.01-2.11 (1H, m), 2.48 (3H, s), 2.51-2.76 (4H, m), 3.03-3.2 (2H, m), 3.58 (1H, dd), 3.63-3.76 (9H, m), 3.79 (2H, t), 3.88-4.11 (5H, m), 4.31 (1H, dd), 4.46-4.61 (3H, m), 4.71 (1H, t), 5.24 (1H, s), 6.39 (2H, d), 7.02-7.13 (2H, m), 7.23 (1H, dd), 7.26-7.39 (6H, m), 7.46-7.55 (1H, m), 8.24 (1H, s), 8.64 (1H, s); m/z: ES+ [M+H]$^+$ 989.6.

Intermediate 78a: Ethyl 2-((7-(4-((1R,3R)-2-(3-((tert-butyldiphenylsilyl)oxy)-2,2-difluoropropyl)-3-methyl-2,3,4,9-tetrahydro-1H-pyrido[3,4-b]indol-1-yl)-3,5-difluorophenoxy)heptyl)oxy)acetate

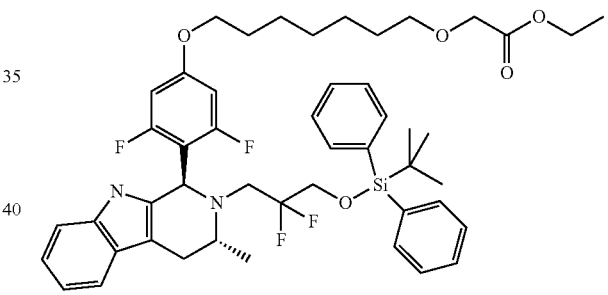

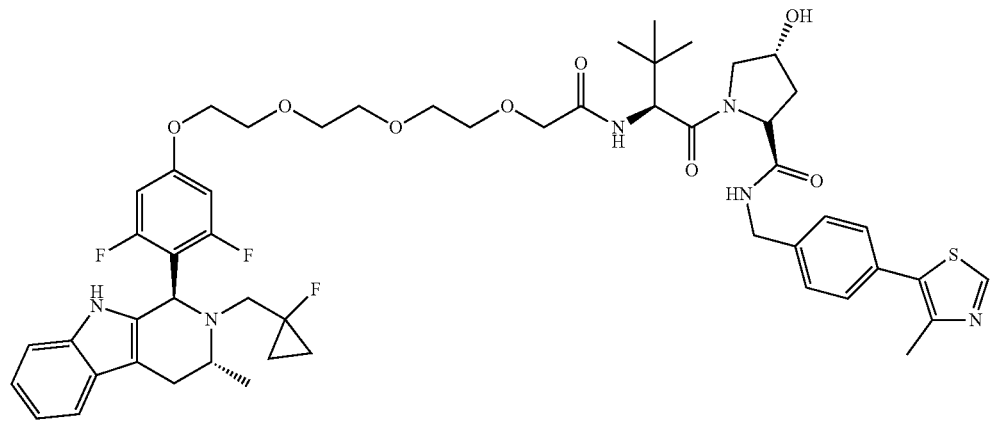

RockPhos Pd G3 (23.66 mg, 0.03 mmol) was added in one portion to a degassed mixture of ethyl 2-((7-hydroxyheptyl)oxy)acetate (246 mg, 1.13 mmol), (1R,3R)-1-(4-bromo-2,6-difluorophenyl)-2-(3-((tert-butyldiphenylsilyl)oxy)-2,2-difluoropropyl)-3-methyl-2,3,4,9-tetrahydro-1H-pyrido[3,4-b]indole (400 mg, 0.56 mmol) and cesium carbonate (460 mg, 1.4 mmol) in toluene (4 mL) at 20° C. under nitrogen. The resulting mixture was stirred at 90° C. for 18 hours. The reaction was allowed to cool to RT and was filtered, the filtercup was washed with DCM (10 mL) then the mixture evaporated to afford crude product as a orange gum. The crude product was purified by flash silica chromatography, elution gradient 0 to 15% EtOAc in heptane to afford the title compound (131 mg, 27%) as a yellow gum; m/z: ES+ [M+H]+ 847.5.

Intermediate 78b: 2-((7-(4-((1R,3R)-2-(3-((tert-Butyldiphenylsilyl)oxy)-2,2-difluoropropyl)-3-methyl-2,3,4,9-tetrahydro-1H-pyrido[3,4-b]indol-1-yl)-3,5-difluorophenoxy)heptyl)oxy)acetic Acid

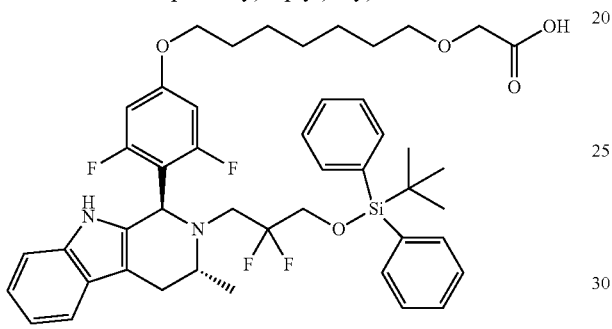

The title compound was prepared in a similar manner to Intermediate 72f using the appropriate ester to afford the desired product (129 mg) as a yellow gum which was used in the next step without further purification; m/z: ES+ [M+H]+ 819.5.

Intermediate 78c: (2S,4R)-1-((S)-2-(2-((7-(4-((1R,3R)-2-(3-((tert-Butyldiphenylsilyl)oxy)-2,2-difluoropropyl)-3-methyl-2,3,4,9-tetrahydro-1H-pyrido[3,4-b]indol-1-yl)-3,5-difluorophenoxy)heptyl)oxy)acetamido)-3,3-dimethylbutanoyl)-4-hydroxy-N-(4-(4-methylthiazol-5-yl)benzyl)pyrrolidine-2-carboxamide

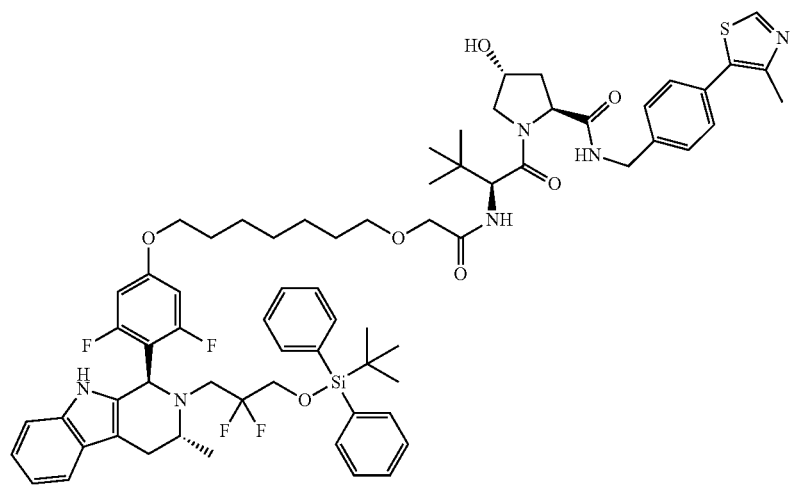 [SMILES: Cc1ncsc1-c1ccc(CNC(=O)[C@@H]2C[C@@H](O)CN2C(=O)[C@@H](NC(=O)COCCCCCCCOc2cc(F)c([C@@H]3c4[nH]c5ccccc5c4C[C@@H](C)N3CC(F)(F)CO[Si](c3ccccc3)(c3ccccc3)C(C)(C)C)c(F)c2)C(C)(C)C)cc1]

The title compound was prepared in a similar manner to Example 68 using the appropriate carboxylic acid and amine to afford the desired product (191 mg, 100%) which was used directly in the next step without purification; m/z: ES+ [M+H]+ 1232.7.

Example 78: (2S,4R)-1-((S)-2-(2-((7-(4-((1R,3R)-2-(2,2-Difluoro-3-hydroxypropyl)-3-methyl-2,3,4,9-tetrahydro-1H-pyrido[3,4-b]indol-1-yl)-3,5-difluorophenoxy)heptyl)oxy)acetamido)-3,3-dimethylbutanoyl)-4-hydroxy-N-(4-(4-methylthiazol-5-yl)benzyl)pyrrolidine-2-carboxamide

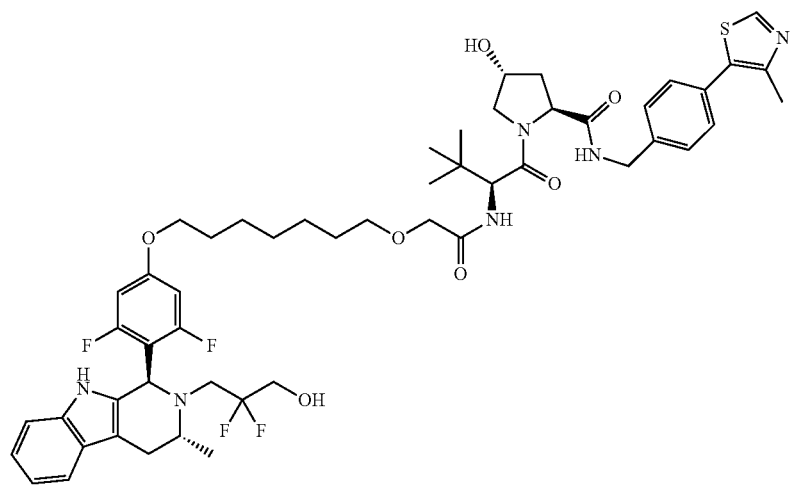 [SMILES: Cc1ncsc1-c1ccc(CNC(=O)[C@@H]2C[C@@H](O)CN2C(=O)[C@@H](NC(=O)COCCCCCCCOc2cc(F)c([C@@H]3c4[nH]c5ccccc5c4C[C@@H](C)N3CC(F)(F)CO)c(F)c2)C(C)(C)C)cc1]

A solution of 1M TBAF in THF (0.233 mL, 0.23 mmol) was added in one portion to (2S,4R)-1-((S)-2-(2-((7-(4-((1R,3R)-2-(3-((tert-butyldiphenylsilyl)oxy)-2,2-difluoropropyl)-3-methyl-2,3,4,9-tetrahydro-1H-pyrido[3,4-b]indol-1-yl)-3,5-difluorophenoxy)heptyl)oxy)acetamido)-3,3-dimethylbutanoyl)-4-hydroxy-N-(4-(4-methylthiazol-5-yl)benzyl)pyrrolidine-2-carboxamide (191 mg, 0.16 mmol) in THF (2 mL) at 20° C. The resulting solution was stirred for 18 hours. The reaction mixture was diluted with EtOAc (50 mL), and washed sequentially with saturated NH4Cl (20 mL), water (20 mL), and saturated brine (20 mL). The organic layer was dried with MgSO4, filtered and evaporated to afford crude product. The crude product was purified by preparative HPLC (Waters CSH C18 OBD column, 30×100 mm id, 5 micron particle size), using decreasingly polar mixtures of water (containing 1% by volume of NH4OH (28-30% in H2O)) and MeCN as eluents. Fractions containing the desired compound were evaporated to dryness to afford impure product. The sample was dissolved in MeOH (1 mL) and re-purified using SFC, Column, Phenomenex C1, 30×250 mm, 5 micron, Mobile phase: 40% MeOH+ 0.1% NH3/60% scCO2, Flow rate: 100 mL/min, BPR: 120 bar, Column temperature: 40 deg C. to afford the title compound (23.00 mg, 14.93%) as a white solid; 1H NMR (400 MHz, CDCl3, 30° C.) 0.94 (9H, s), 1.18 (3H, d), 1.36-1.5 (6H, m), 1.6-1.66 (2H, m), 1.72-1.81 (2H, m), 2.09 (1H, dd), 2.47 (3H, s), 2.53-2.79 (3H, m), 2.81-2.96 (1H, m), 3.12 (1H, dd), 3.18-3.3 (1H, m), 3.49-3.52 (2H, m), 3.58-3.79 (5H, m), 3.82-3.96 (4H, m), 4.11 (1H, d), 4.31 (1H, dd), 4.46-4.63 (3H, m), 4.73 (1H, t), 5.19 (1H, s), 6.40 (2H, d), 7.06-7.24 (4H, m), 7.27-7.39 (5H, m), 7.48-7.54 (1H, m), 8.17 (1H, s), 8.61 (1H, s); m/z: ES+ [M+H]+ 993.7.

Intermediate 79a: Ethyl 2-((5-(3,5-difluoro-4-((1R,3R)-2-((1-fluorocyclopropyl)methyl)-3-methyl-2,3,4,9-tetrahydro-1H-pyrido[3,4-b]indol-1-yl)phenoxy)pentyl)oxy)acetate

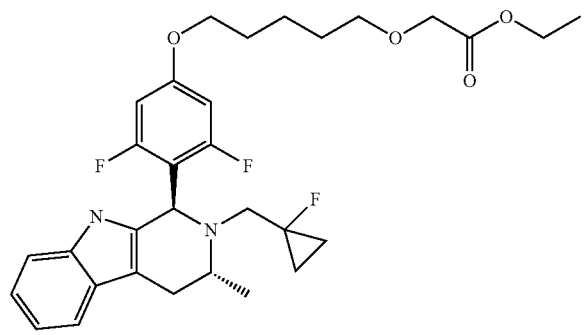 [SMILES: CCOC(=O)COCCCCCOc1cc(F)c([C@@H]2c3[nH]c4ccccc4c3C[C@@H](C)N2CC2(F)CC2)c(F)c1]

The title compound was prepared in a similar manner to Intermediate 72e using the appropriate phenol and alcohol to afford the desired product (152 mg, 70%); 1H NMR (400 MHz, DMSO, 30° C.) 0.53 (2H, t), 0.83-0.97 (2H, m), 1.07 (3H, d), 1.20 (3H, t), 1.45 (2H, dt), 1.57 (2H, dt), 1.72 (2H, p), 2.54-2.72 (2H, m), 2.88 (1H, dd), 3.06 (1H, dd), 3.47 (2H, t), 3.58 (1H, q), 3.99 (2H, t), 4.07 (2H, s), 4.12 (2H, q), 5.17 (1H, s), 6.65 (2H, d), 6.9-7.05 (2H, m), 7.19 (1H, d), 7.40 (1H, d), 10.51 (1H, s); m/z: ES+ [M+H]+ 559.4

Intermediate 79b: 2-((5-(3,5-Difluoro-4-((1R,3R)-2-((1-fluorocyclopropyl)methyl)-3-methyl-2,3,4,9-tetrahydro-1H-pyrido[3,4-b]indol-1-yl)phenoxy)pentyl)oxy)acetic Acid

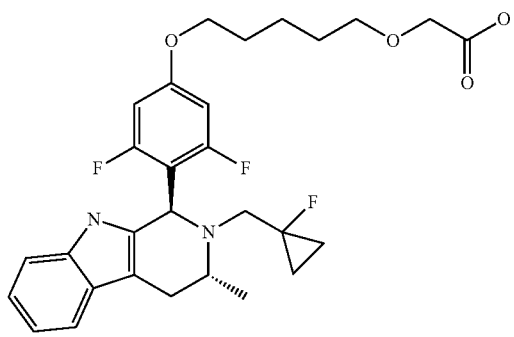 [SMILES: C[C@@H]1Cc2c([nH]c3ccccc23)[C@@H](c2c(F)cc(OCCCCCOCC(=O)O)cc2F)N1CC1(F)CC1]

The title compound was prepared in a similar manner to Intermediate 72f using the appropriate ester to afford the desired product (144 mg, 100%) as a yellow gum which was used in the next step without further purification; m/z: ES+ [M+H]+ 531.3.

Example 79: (2S,4R)-1-((S)-2-(2-((5-(3,5-difluoro-4-((1R,3R)-2-((1-fluorocyclopropyl)methyl)-3-methyl-2,3,4,9-tetrahydro-1H-pyrido[3,4-b]indol-1-yl)phenoxy)pentyl)oxy)acetamido)-3,3-dimethylbutanoyl)-4-hydroxy-N-(4-(4-methylthiazol-5-yl)benzyl)pyrrolidine-2-carboxamide The title compound was prepared in a similar manner to Example 68 using the appropriate carboxylic acid and amine to afford the desired product (121 mg, 47%) as a pale yellow solid; 1H NMR (400 MHz, CDCl3, 30° C.) 0.45-0.58 (2H, m), 0.94 (11H, s), 1.16 (3H, d), 1.51-1.59 (2H, m), 1.64-1.71 (2H, m), 1.79 (2H, dt), 2.07 (1H, dd), 2.46 (3H, s), 2.54 (1H, ddd), 2.61-2.82 (2H, m), 3.04-3.22 (2H, m), 3.53 (2H, tt), 3.61 (1H, dd), 3.75 (1H, s), 3.81-3.98 (4H, m), 4.07 (1H, d), 4.29 (1H, dd), 4.47-4.62 (3H, m), 4.69 (1H, t), 5.29 (1H, s), 6.36 (2H, d), 7.05-7.13 (2H, m), 7.15-7.3 (3H, m), 7.31-7.38 (4H, m), 7.47-7.55 (1H, m), 8.20 (1H, s), 8.63 (1H, s); m/z: ES+ [M+H]+ 943.5.

Intermediate 80a: (2R,3R)-3-(2-(Benzyloxy)ethoxy)butan-2-ol

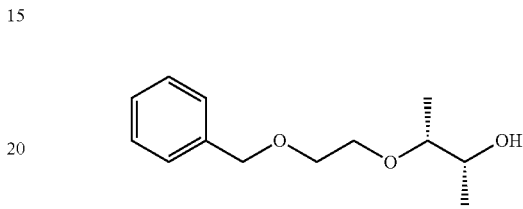

Tetrabutylammonium hydrogen sulfate (0.565 g, 1.66 mmol) was added in one portion to ((2-bromoethoxy)methyl)benzene (3.86 mL, 24.4 mmol) and (2R,3R)-butane-2,3-diol (1.01 mL, 11.1 mmol) in 50% sodium hydroxide solution (6 mL) at 20° C. The resulting mixture was stirred at 70° C. for 18 hours. The cooled reaction mixture was separated and the organics were washed with water (20 mL), saturated brine solution (20 mL), dried with MgSO4, filtered and evaporated to afford crude product as a yellow oil. The crude product was purified by flash silica chromatography, elution gradient 0 to 20% EtOAc in heptane to afford the title compound (0.970 g, 39%) as a yellow oil; 1H NMR (400 MHz, CDCl3, 30° C.) 1.12 (6H, t), 3.15-3.25 (2H, m), 3.52-3.67 (4H, m), 3.8-3.87 (1H, m), 4.57 (2H, s), 7.26-7.39 (5H, m); m/z: ES+ [M+H]+ 225.2.

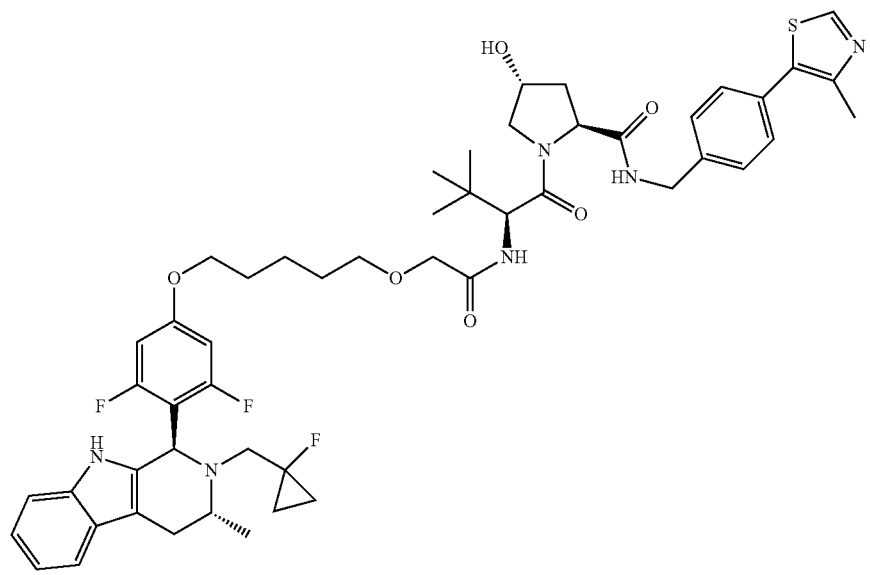 [SMILES: Cc1ncsc1-c1ccc(CNC(=O)[C@@H]2C[C@@H](O)CN2C(=O)[C@@H](NC(=O)COCCCCCOc2cc(F)c([C@@H]3c4[nH]c5ccccc5c4C[C@@H](C)N3CC3(F)CC3)c(F)c2)C(C)(C)C)cc1]

Intermediate 80b: 2-(2-(((2R,3R)-3-(2-(Benzyloxy)ethoxy)butan-2-yl)oxy)ethoxy)tetrahydro-2H-pyran

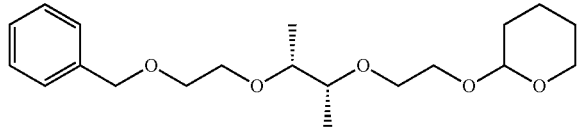 [SMILES: C[C@@H](OCCOCc1ccccc1)[C@@H](C)OCCOC1CCCCO1]

Tetrabutylammonium hydrogen sulfate (220 mg, 0.65 mmol) was added in one portion to 2-(2-bromoethoxy)tetrahydro-2H-pyran (0.78 mL, 5.2 mmol) and (2R,3R)-3-(2-(benzyloxy)ethoxy)butan-2-ol (970 mg, 4.32 mmol) in 50% sodium hydroxide solution (3.5 mL) at 20° C. The resulting mixture was stirred at 70° C. for 18 hours. The cooled reaction mixture was diluted with EtOAc (50 mL) and water (10 mL). The organics were separated washed with water (20 mL), saturated brine solution (20 mL), dried (MgSO$_4$), filtered and evaporated to afford crude product as a yellow oil. The crude product was purified by flash silica chromatography, elution gradient 0 to 30% EtOAc in heptane to afford 2-(2-(((2R,3R)-3-(2-(benzyloxy)ethoxy)butan-2-yl)oxy)ethoxy)tetrahydro-2H-pyran (407 mg, 27%) as a colourless oil; $^1$H NMR (400 MHz, CDCl$_3$, 30° C.) 1.07-1.16 (6H, m), 1.46-1.63 (4H, m), 1.66-1.75 (1H, m), 1.77-1.88 (1H, m), 3.46-3.76 (10H, m), 3.84 (2H, ddt), 4.57 (2H, d), 4.61-4.65 (1H, m), 7.26-7.36 (5H, m).

Intermediate 80c: 2-(2-(((2R,3R)-3-(2-(Benzyloxy)ethoxy)butan-2-yl)oxy)ethan-1-ol

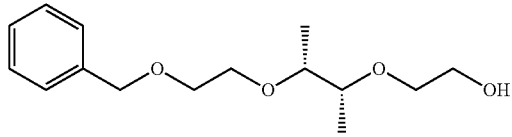 [SMILES: C[C@@H](OCCO)[C@@H](C)OCCOCc1ccccc1]

2-(2-(((2R,3R)-3-(2-(Benzyloxy)ethoxy)butan-2-yl)oxy)ethoxy)tetrahydro-2H-pyran (400 mg, 1.13 mmol) was dissolved in MeOH (3 mL) and 1M aq. HCl (1.5 mL) was added. The resulting mixture was stirred at 20° C. for 1 hour. The reaction mixture was diluted with water (10 mL) and saturated brine solution (10 mL), and extracted with EtOAc (3×50 mL). The combined organics were dried with MgSO$_4$, filtered and evaporated to afford the title compound (324 mg) which was used directly in the next step without purification; $^1$H NMR (400 MHz, CDCl$_3$, 30° C.) 1.10 (6H, d), 3.41-3.47 (2H, m), 3.51-3.57 (1H, m), 3.59-3.64 (3H, m), 3.65-3.7 (3H, m), 3.7-3.78 (2H, m), 4.57 (2H, d), 7.26-7.38 (5H, m); m/z: ES+ [M+H]$^+$ 269.3.

Intermediate 80d: Ethyl (6R,7R)-6,7-dimethyl-1-phenyl-2,5,8,11-tetraoxatridecan-13-oate

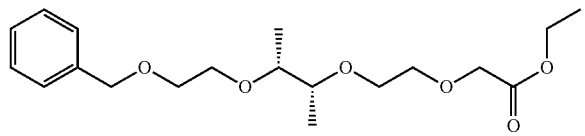 [SMILES: CCOC(=O)COCCO[C@H](C)[C@@H](C)OCCOCc1ccccc1]

Ethyl 2-diazoacetate (0.34 mL, 2.8 mmol) in DCM (1 mL) was added slowly to 2-(((2R,3R)-3-(2-(benzyloxy)ethoxy)butan-2-yl)oxy)ethan-1-ol (300 mg, 1.12 mmol) and diacetoxyrhodium (25 mg, 0.06 mmol) in DCM (3 mL) at 20° C. over a period of 1 hour under nitrogen. The resulting solution was stirred for 4 hours. The mixture was diluted with DCM (50 mL) and washed with water (50 mL). The organic layer was collected and dried using phase separating cartridge then evaporated to dryness. The crude product was purified by flash silica chromatography, elution gradient 0 to 40% EtOAc in heptane to afford the title compound (230 mg, 58%) a colourless liquid; $^1$H NMR (400 MHz, CDCl$_3$, 30° C.) 1.07-1.13 (6H, m), 1.28 (3H, t), 3.49 (2H, dt), 3.59-3.75 (8H, m), 4.13 (2H, s), 4.21 (2H, q), 4.56 (2H, s), 7.26-7.37 (5H, m).

Intermediate 80e: Ethyl 2-(2-(((2R,3R)-3-(2-hydroxyethoxy)butan-2-yl)oxy)ethoxy)acetate

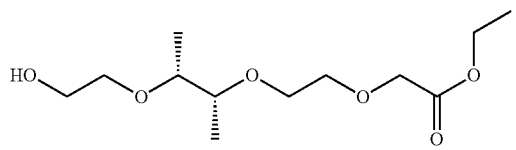 [SMILES: CCOC(=O)COCCO[C@H](C)[C@@H](C)OCCO]

Ethyl (6R,7R)-6,7-dimethyl-1-phenyl-2,5,8,11-tetraoxatridecan-13-oate (230 mg, 0.65 mmol) and 10% palladium on carbon (6.91 mg, 0.06 mmol) in ethanol (1.3 mL) stirred under an atmosphere of hydrogen (1.5 bar) at RT for 4 hours. The reaction mixture was filtered, washing with more EtOH then the solvent was evaporated to afford the title compound (164 mg, 96%) as a colourless oil which was used in the next step without purification; $^1$H NMR (400 MHz, CDCl$_3$, 30° C.) 1.11 (6H, dd), 1.28 (3H, t), 2.74-2.89 (1H, m), 3.4-3.47 (2H, m), 3.5-3.6 (1H, m), 3.65-3.8 (7H, m), 4.14 (2H, d), 4.21 (2H, q); m/z: ES+ [M+H]$^+$ 265.2.

Intermediate 80f: Ethyl 2-(2-(((2R,3R)-3-(2-(3,5-difluoro-4-((R,3R)-2-(2-fluoro-2-methylpropyl)-3-methyl-2,3,4,9-tetrahydro-1H-pyrido[3,4-b]indol-1-yl)phenoxy)ethoxy)butan-2-yl)oxy)ethoxy)acetate

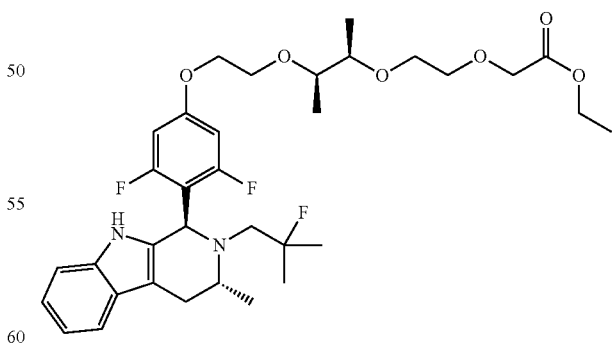

DIAD (0.122 mL, 0.62 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (121 mg, 0.31 mmol), ethyl 2-(2-(((2R,3R)-3-(2-hydroxyethoxy)butan-2-yl)oxy)ethoxy)acetate (164 mg, 0.62 mmol) and triphenylphosphine (163 mg, 0.62 mmol) in DCM (5 mL) at 20° C. The resulting mixture was stirred for 18 hours. DCM (15 mL) and water (25 mL) were added and the layers were separated and concentrated to give the crude product. The crude product was purified by flash silica chromatography, elution gradient 0 to 50% EtOAc in heptane to afford the title compound (172 mg, 87%) as a cream solid; $^1$H NMR (400 MHz, CDCl$_3$, 30° C.) 1.08-1.25 (18H, m), 2.38 (1H, dd), 2.60 (1H, dd), 2.87 (1H, dd), 3.10 (1H, d), 3.38-3.52 (2H, m), 3.61-3.76 (5H, m), 3.79-3.91 (2H, m), 4.04-4.09 (2H, m), 4.13 (2H, d), 4.19 (2H, q), 5.18 (1H, s), 6.43 (2H, d), 7.04-7.14 (2H, m), 7.22 (1H, dd), 7.48-7.55 (1H, m), 7.61 (1H, s); m/z: ES+ [M+H]$^+$ 635.3.

Intermediate 80g: 2-(2-(((2R,3R)-3-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butan-2-yl)oxy)ethoxy)acetic Acid

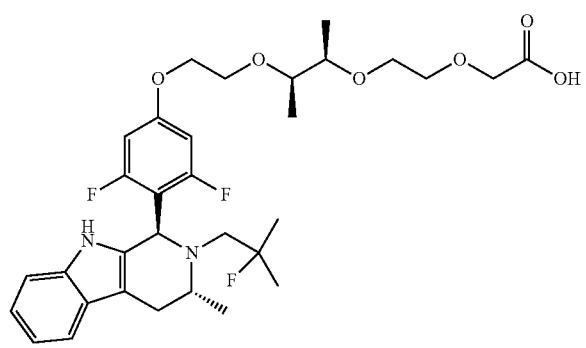 [SMILES: C[C@@H]1Cc2c([nH]c3ccccc23)[C@@H](c2c(F)cc(OCCO[C@H](C)[C@@H](C)OCCOCC(=O)O)cc2F)N1CC(C)(C)F]

Lithium hydroxide hydrate (23 mg, 0.55 mmol) was added in one portion to ethyl 2-(2-(((2R,3R)-3-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butan-2-yl)oxy)ethoxy)acetate (174 mg, 0.27 mmol) in THF (1 mL) and water (0.3 mL) at 20° C. The resulting solution was stirred at 20° C. for 30 minutes. The reaction mixture was diluted with water (10 mL) then was acidified with 2M HCl and extracted into EtOAc (50 mL). The organic layer was washed with brine (15 mL) and evaporated to afford the title compound (170 mg) as a yellow gum which was used in the next step without purification; m/z: ES+ [M+H]$^+$ 607.3.

Example 80: (2S,4R)-1-((2S,10R,11R)-2-(tert-butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-10,11-dimethyl-4-oxo-6,9,12-trioxa-3-azatetradecanoyl)-4-hydroxy-N-(4-(4-methylthiazol-5-yl)benzyl)pyrrolidine-2-carboxamide

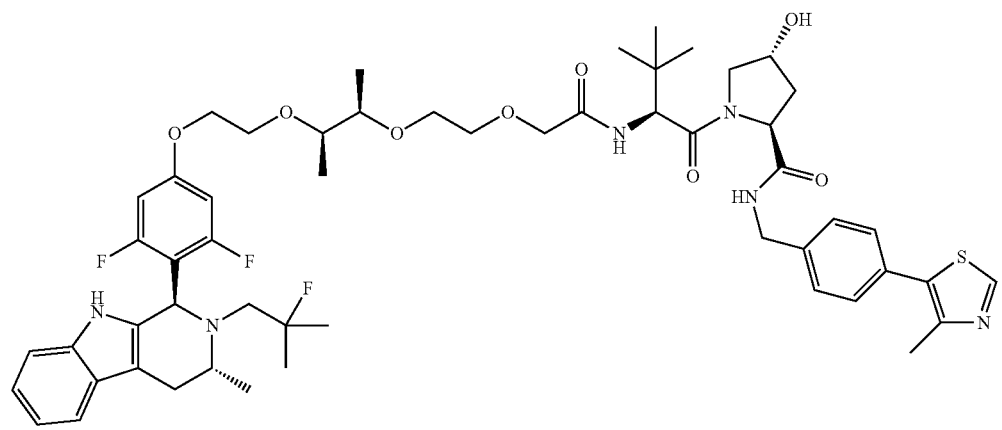 [SMILES: Cc1ncsc1-c1ccc(CNC(=O)[C@@H]2C[C@@H](O)CN2C(=O)[C@@H](NC(=O)COCCO[C@H](C)[C@@H](C)OCCOc2cc(F)c([C@@H]3c4[nH]c5ccccc5c4C[C@@H](C)N3CC(C)(C)F)c(F)c2)C(C)(C)C)cc1]

HATU (156 mg, 0.41 mmol) was added in one portion to 2-(2-(((2R,3R)-3-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butan-2-yl)oxy)ethoxy)acetic acid (166 mg, 0.27 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (128 mg, 0.27 mmol) and triethylamine (0.153 mL, 1.09 mmol) in DMF (5 mL) at 20° C. under nitrogen. The resulting mixture was stirred for 30 minutes. The reaction mixture was diluted with EtOAc (50 mL), and washed sequentially with water (50 mL) and saturated brine (25 mL). The organic layer was dried with MgSO$_4$, filtered and evaporated to afford crude product. The crude product was purified by preparative HPLC (Waters CSH C18 OBD column, 30×100 mm id, 5 micron particle size), using decreasingly polar mixtures of water (containing 1% by volume of NH$_4$OH (28%-30% in H$_2$O)) and MeCN as eluents to afford the title compound (75 mg, 27%) as a cream solid; $^1$H NMR (400 MHz, CDCl$_3$, 30° C.) 0.94 (9H, s), 1.04-1.13 (9H, m), 1.20 (6H, dd), 2.02-2.11 (1H, m), 2.40 (1H, dd), 2.49 (3H, s), 2.52-2.68 (3H, m), 2.84 (1H, dd), 3.07 (1H, dd), 3.40 (1H, p), 3.48 (1H, p), 3.55-3.71 (6H, m), 3.72-4.12 (7H, m), 4.33 (1H, dd), 4.45-4.62 (3H, m), 4.72 (1H, t), 5.19 (1H, s), 6.38 (2H, d), 7.03-7.12 (1H, m), 7.18-7.24 (2H, m), 7.29 (1H, d), 7.35 (4H, q), 7.50 (1H, dd), 8.38 (1H, s), 8.65 (1H, s); m/z: ES+ [M+H]$^+$ 1019.4.

Intermediate 82a: (2S,3S)-3-(2-(Benzyloxy)ethoxy)butan-2-ol

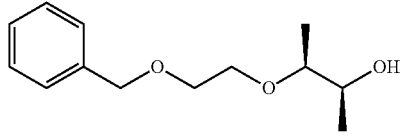 [SMILES: C[C@H](O)[C@H](C)OCCOCc1ccccc1]

Tetrabutylammonium hydrogen sulfate (0.565 g, 1.66 mmol) was added in one portion to ((2-bromoethoxy)methyl)benzene (2.10 mL, 13.3 mmol) and (2S,3S)-butane-2,3-diol (1.0 g, 11 mmol) in 50% sodium hydroxide solution (9 mL) at 20° C. under air. The resulting mixture was stirred at 70° C. for 3 days. The cooled reaction mixture was diluted with EtOAc (50 mL) separated and the organics were washed with water (20 mL), saturated brine solution (20 mL), dried (MgSO$_4$), filtered and evaporated to afford crude product as a yellow oil. The crude product was purified by flash silica chromatography, elution gradient 0 to 50% EtOAc in heptane to afford the title compound (0.800 g, 32%) as a yellow oil; $^1$H NMR (400 MHz, CDCl$_3$, 30° C.) 1.13 (6H, t), 3.16-3.24 (2H, m), 3.54-3.66 (4H, m), 3.8-3.88 (1H, m), 4.57 (2H, s), 7.27-7.4 (5H, m); m/z: ES+ [M+H]$^+$ 225.2.

Intermediate 82b: 2-(2-(((2S,3S)-3-(2-(Benzyloxy)ethoxy)butan-2-yl)oxy)ethoxy)tetrahydro-2H-pyran

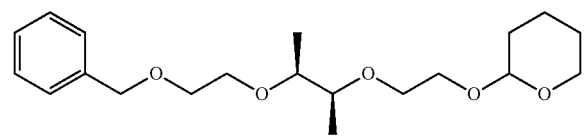 [SMILES: C[C@H](OCCOCc1ccccc1)[C@H](C)OCCOC1CCCCO1]

Tetrabutylammonium hydrogen sulfate (182 mg, 0.53 mmol) was added in one portion to 2-(2-bromoethoxy)tetrahydro-2H-pyran (1078 µl, 7.13 mmol) and (2S,3S)-3-(2-(benzyloxy)ethoxy)butan-2-ol (800 mg, 3.57 mmol) in 50% sodium hydroxide solution (2.5 mL) at 20° C. under air. The resulting mixture was stirred at 70° C. for 1 day. The reaction was incomplete and further 2-(2-bromoethoxy)tetrahydro-2H-pyran (1.08 mL, 7.13 mmol) was added and the mixture was stirred at 70° C. for a further 2 days. The cooled reaction mixture was diluted with EtOAc (50 mL) and water (10 mL). The organics were separated washed with water (20 mL), saturated brine solution (20 mL), dried (MgSO$_4$), filtered and evaporated to afford crude product as a yellow oil. The crude product was purified by flash silica chromatography, elution gradient 0 to 50% EtOAc in heptane to afford the title compound (593 mg, 47%) as a colourless oil; $^1$H NMR (400 MHz, CDCl$_3$, 30° C.) 1.11 (6H, d), 1.46-1.64 (4H, m), 1.72 (1H, ddt), 1.78-1.9 (1H, m), 3.45-3.76 (10H, m), 3.87 (2H, ddd), 4.57 (2H, s), 4.64 (1H, dt), 7.26-7.39 (5H, m).

Intermediate 82c: 2-(((2S,3S)-3-(2-(Benzyloxy)ethoxy)butan-2-yl)oxy)ethan-1-ol

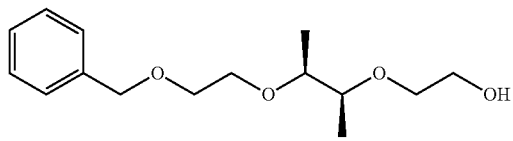 [SMILES: C[C@H](OCCO)[C@H](C)OCCOCc1ccccc1]

2-(2-(((2S,3S)-3-(2-(Benzyloxy)ethoxy)butan-2-yl)oxy)ethoxy)tetrahydro-2H-pyran (590 mg, 1.67 mmol) was dissolved in MeOH (5 mL) and 1M aq. HCl (2 mL) was added. The resulting mixture was stirred at 20° C. for 1 hour. The reaction mixture was diluted with water (10 mL) and saturated brine solution (10 mL), and extracted with EtOAc (3×50 mL). The combined organics were dried with MgSO$_4$, filtered and evaporated to afford the title compound (350 mg, 78%) which was used directly in the next step without purification; $^1$H NMR (400 MHz, CDCl$_3$, 30° C.) 1.10 (6H, d), 2.9-2.96 (1H, m), 3.4-3.48 (2H, m), 3.51-3.58 (1H, m), 3.59-3.78 (7H, m), 4.57 (2H, d), 7.27-7.38 (5H, m); m/z: ES+ [M+H]$^+$ 269.3.

Intermediate 82d: Ethyl (6S,7S)-6,7-dimethyl-1-phenyl-2,5,8,11-tetraoxatridecan-13-oate

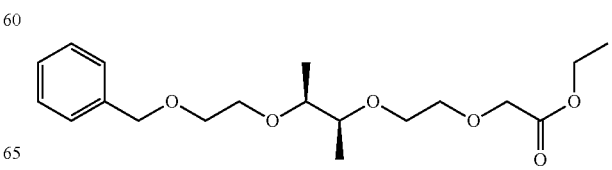

Ethyl 2-diazoacetate (0.40 mL, 3.25 mmol) in DCM (1 mL) was added slowly to 2-(((2S,3S)-3-(2-(benzyloxy)ethoxy)butan-2-yl)oxy)ethan-1-ol (349 mg, 1.30 mmol) and diacetoxyrhodium (29 mg, 0.07 mmol) in DCM (3.5 mL) at 20° C. over a period of 1 hour under nitrogen. The resulting solution was stirred for 18 hours. The mixture was diluted with DCM (50 mL) and washed with water (50 mL). The organic layer was collected and dried using phase separating cartridge then evaporated to dryness. The crude product was purified by flash silica chromatography, elution gradient 0 to 40% EtOAc in heptane to afford the title compound (190 mg, 41%) a colourless liquid; $^1$H NMR (400 MHz, CDCl$_3$, 30° C.) 1.11 (6H, dt), 1.28 (3H, t), 3.49 (2H, dt), 3.59-3.75 (8H, m), 4.13 (2H, s), 4.17-4.23 (2H, m), 4.56 (2H, s), 7.26-7.36 (5H, m).

Intermediate 82e: Ethyl 2-(2-(((2S,3S)-3-(2-hydroxyethoxy)butan-2-yl)oxy)ethoxy)acetate

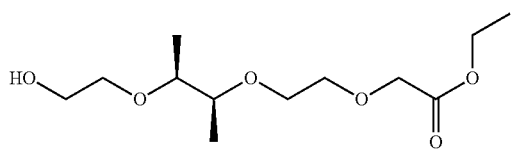 [SMILES: CCOC(=O)COCCO[C@@H](C)[C@H](C)OCCO]

Ethyl (6S,7S)-6,7-dimethyl-1-phenyl-2,5,8,11-tetraoxatridecan-13-oate (190 mg, 0.54 mmol) and 10% palladium on carbon (6 mg, 0.05 mmol) in ethanol (1 mL) stirred under an atmosphere of hydrogen (1.5 bar) at RT for 18 hours. The reaction mixture was filtered, washing with more EtOH then the solvent was evaporated to afford the title compound (141 mg, 100%) as a colourless oil which was used in the next step without further purification; $^1$H NMR (400 MHz, CDCl$_3$, 30° C.) 1.11 (6H, dd), 1.28 (3H, t), 2.83 (1H, s), 3.4-3.47 (2H, m), 3.5-3.59 (1H, m), 3.66-3.8 (7H, m), 4.14 (2H, d), 4.18-4.26 (2H, m); m/z: ES+ [M+H]$^+$ 265.2.

Intermediate 82f: Ethyl 2-(2-(((2S,3S)-3-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butan-2-yl)oxy)ethoxy)acetate

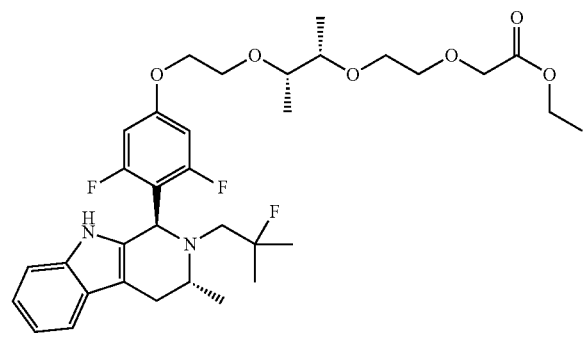 [SMILES: CCOC(=O)COCCO[C@@H](C)[C@H](C)OCCOc1cc(F)c([C@@H]2c3[nH]c4ccccc4c3C[C@@H](C)N2CC(C)(C)F)c(F)c1]

DIAD (0.104 mL, 0.53 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (103 mg, 0.26 mmol), ethyl 2-(2-(((2S,3S)-3-(2-hydroxyethoxy)butan-2-yl)oxy)ethoxy)acetate (140 mg, 0.53 mmol) and triphenylphosphine (139 mg, 0.53 mmol) in DCM (5 mL) at 20° C. The resulting mixture was stirred for 18 hours. DCM (15 mL) and water (25 mL) were added and the layers were separated and the DCM layer was concentrated to give the crude product. The crude product was purified by flash silica chromatography, elution gradient 0 to 50% EtOAc in heptane to afford the title compound (210 mg) as a cream solid, which was used without further purification; $^1$H NMR (400 MHz, CDCl$_3$, 30° C.) 1.08-1.24 (18H, m), 2.38 (1H, dd), 2.60 (1H, dd), 2.86 (1H, dd), 3.05-3.13 (1H, m), 3.43-3.52 (2H, m), 3.63-3.77 (5H, m), 3.8-3.9 (2H, m), 4.06 (2H, t), 4.12 (2H, s), 4.19 (2H, q), 5.18 (1H, s), 6.42 (2H, d), 7.06-7.14 (2H, m), 7.22 (1H, dd), 7.49-7.53 (2H, m); m/z: ES+ [M+H]$^+$ 635.3.

Intermediate 82g: 2-(2-(((2S,3S)-3-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butan-2-yl)oxy)ethoxy)acetic Acid

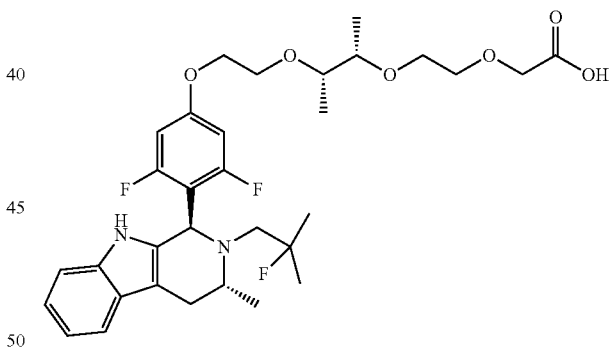

Lithium hydroxide hydrate (22 mg, 0.53 mmol) was added in one portion to ethyl 2-(2-(((2S,3S)-3-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butan-2-yl)oxy)ethoxy)acetate (168 mg, 0.26 mmol) in THF (1 mL) and water (0.3 mL) at 20° C. The resulting solution was stirred for 30 minutes. The reaction mixture was diluted with water (10 mL) then was acidified with 2M HCl and extracted into EtOAc (50 mL). The organic layer was washed with brine (15 mL) and evaporated to afford the title compound (160 mg, 100%) as a yellow gum, which was used in the next step without further purification; m/z: ES+ [M+H]$^+$ 607.3.

Example 82: (2S,4R)-1-((2S,10S,11S)-2-(tert-butyl)-14-(3,5-difluoro-4-((1R,3R)-2-(2-fluoro-2-methyl-propyl)-3-methyl-2,3,4,9-tetrahydro-1H-pyrido[3,4-b]indol-1-yl)phenoxy)-10,11-dimethyl-4-oxo-6,9,12-trioxa-3-azatetradecanoyl)-4-hydroxy-N-(4-(4-methylthiazol-5-yl)benzyl)pyrrolidine-2-carboxamide

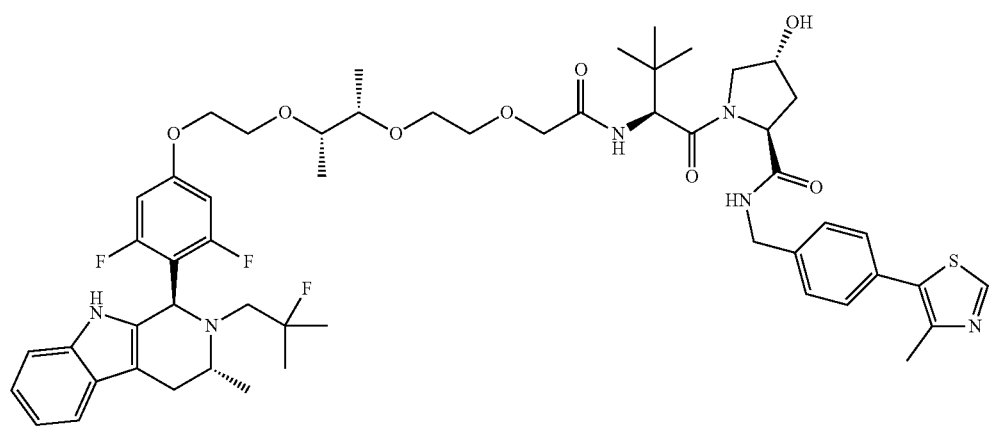 [SMILES: Cc1ncsc1-c1ccc(CNC(=O)[C@@H]2C[C@@H](O)CN2C(=O)[C@@H](NC(=O)COCCO[C@@H](C)[C@H](C)OCCOc2cc(F)c([C@@H]3c4[nH]c5ccccc5c4C[C@@H](C)N3CC(C)(C)F)c(F)c2)C(C)(C)C)cc1]

HATU (150 mg, 0.40 mmol) was added in one portion to 2-(2-(((2S,3S)-3-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butan-2-yl)oxy)ethoxy)acetic acid (160 mg, 0.26 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (123 mg, 0.26 mmol) and triethylamine (0.147 mL, 1.05 mmol) in DMF (5 mL) at 20° C. under nitrogen. The resulting mixture was stirred for 30 minutes. The reaction mixture was diluted with EtOAc (50 mL), and washed sequentially with water (50 mL) and saturated brine (25 mL). The organic layer was dried with MgSO₄, filtered and evaporated to afford crude product. The crude product was purified by preparative HPLC (Waters CSH C18 OBD column, 30×100 mm id, 5 micron particle size), using decreasingly polar mixtures of water (containing 1% by volume of NH₄OH (28%-30% in H₂O)) and MeCN as eluents to afford the title compound (95 mg, 35%) as a white solid; ¹H NMR (400 MHz, CDCl₃, 30° C.) 0.93 (9H, s), 1.05-1.13 (9H, m), 1.20 (6H, dd), 1.99-2.12 (1H, m), 2.40 (1H, dd), 2.50 (3H, s), 2.53-2.65 (3H, m), 2.83 (1H, dd), 3.01-3.14 (1H, m), 3.45 (2H, dp), 3.55-3.99 (10H, m), 3.99-4.11 (3H, m), 4.31 (1H, dd), 4.45-4.61 (3H, m), 4.72 (1H, t), 5.19 (1H, s), 6.39 (2H, d), 7.04-7.13 (2H, m), 7.15-7.24 (2H, m), 7.27-7.3 (1H, m), 7.35 (4H, q), 7.48-7.55 (1H, m), 8.21 (1H, s), 8.65 (1H, s); m/z: ES+ [M+H]⁺1019.3.

Intermediate 83a: Methyl 3,5-difluoro-4-((1R,3R)-2-(2-fluoro-2-methylpropyl)-3-methyl-2,3,4,9-tetrahydro-1H-pyrido[3,4-b]indol-1-yl)benzoate

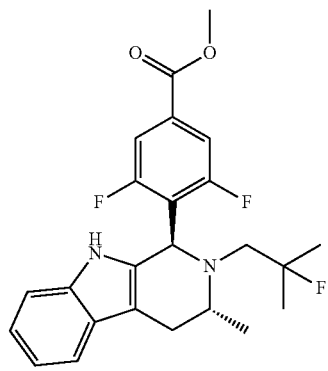 [SMILES: COC(=O)c1cc(F)c([C@@H]2c3[nH]c4ccccc4c3C[C@@H](C)N2CC(C)(C)F)c(F)c1]

A solution of (R)—N-(1-(1H-indol-3-yl)propan-2-yl)-2-fluoro-2-methylpropan-1-amine 33% in toluene (3.58 g, 4.76 mmol) was added to a stirred solution of methyl 3,5-difluoro-4-formylbenzoate (1 g, 5.00 mmol) in toluene (20 mL) and AcOH (2.5 mL) at 20° C. The resulting solution was stirred at 85° C. for 4 hours. The reaction was cooled to rt. The crude product was purified by ion exchange chromatography, using an SCX column, washing with MeOH. The desired product was eluted from the column using 1M NH₃/MeOH to afford crude product as a brown gum. The crude product was purified by flash silica chromatography, elution gradient 0 to 50% EtOAc in heptane to afford the title compound (1.78 g, 87%) as a cream solid; ¹H NMR (400 MHz, CDCl₃, 30° C.) 1.11 (3H, d), 1.21 (6H, dd), 2.39 (1H, dd), 2.63 (1H, dd), 2.89 (1H, dd), 3.09 (1H, dd), 3.65 (1H, p), 3.92 (3H, s), 5.34 (1H, s), 7.07-7.16 (2H, m), 7.23 (1H, dd), 7.40 (1H, s), 7.52 (3H, t); m/z: ES+ [M+H]⁺ 431.3.

Intermediate 83b: 3,5-Difluoro-4-((1R,3R)-2-(2-fluoro-2-methylpropyl)-3-methyl-2,3,4,9-tetrahydro-1H-pyrido[3,4-b]indol-1-yl)benzoic Acid

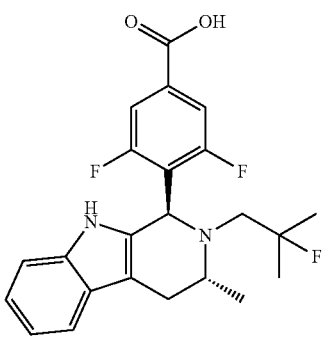 [SMILES: C[C@@H]1Cc2c([nH]c3ccccc23)[C@@H](c2c(F)cc(C(=O)O)cc2F)N1CC(C)(C)F]

A solution of aq. 2M NaOH (8.27 mL, 16.5 mmol) was added to a solution of methyl 3,5-difluoro-4-((1R,3R)-2-(2-fluoro-2-methylpropyl)-3-methyl-2,3,4,9-tetrahydro-1H-pyrido[3,4-b]indol-1-yl)benzoate (1.78 g, 4.14 mmol) in THF (8 mL)/MeOH (4 mL) and the reaction was stirred at room temperature for 3 hours. The reaction was diluted with water (50 mL), then was acidified with 2M HCl (aq.) solution. The mixture was extracted with EtOAc (100 mL) and the organics were washed with saturated brine solution (20 mL), dried with MgSO₄ and evaporated to afford the title compound (1.67 g, 97%) as a pale yellow solid; ¹H NMR (400 MHz, CDCl₃, 30° C.) 1.12 (3H, d), 1.15-1.31 (6H, m), 2.42 (1H, dd), 2.64 (1H, dd), 2.89 (1H, dd), 3.09 (1H, dd), 3.66 (1H, d), 5.38 (1H, s), 7.07-7.18 (2H, m), 7.23 (1H, dd), 7.42 (1H, s), 7.51-7.6 (3H, m); m/z: ES+ [M+H]⁺ 417.2.

Intermediate 83c: tert-Butyl (4-(2-(2-hydroxyethoxy)ethoxy)butyl)carbamate

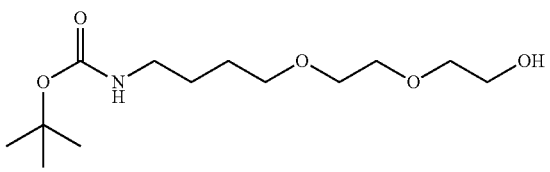 [SMILES: CC(C)(C)OC(=O)NCCCCOCCOCCO]

tert-Butyl (4-bromobutyl)carbamate (1.50 g, 5.95 mmol) was added in one portion to 2,2'-oxybis(ethan-1-ol) (2.82 mL, 29.7 mmol) and potassium 2-methylpropan-2-olate (1.335 g, 11.90 mmol) in THF (15 mL) at 20° C. under nitrogen. The resulting mixture was stirred at reflux for 18 hours. The reaction mixture was diluted with EtOAc (50 mL), and washed sequentially with saturated NH₄Cl (20 mL), water (2×20 mL) and saturated brine (20 mL). The organic layer was dried with MgSO₄, filtered and evaporated to afford crude product. The crude product was purified by flash silica chromatography, elution gradient 0 to 5% MeOH in DCM to afford the title compound (0.268 g, 16%) as a yellow oil; ¹H NMR (400 MHz, CDCl₃, 30° C.) 1.44 (9H, s), 1.61 (4H, dq), 2.08 (1H, s), 3.13 (2H, s), 3.49 (2H, q), 3.56-3.76 (8H, m), 4.2-4.26 (1H, m).

Intermediate 83d: Ethyl 2,2-dimethyl-4-oxo-3,10,13,16-tetraoxa-5-azaoctadecan-18-oate

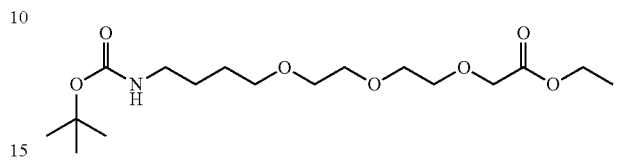

The title compound was prepared in a similar manner to Intermediate 72c using the appropriate alcohol to afford the desired product (132 mg, 39%) as a yellow liquid. ¹H NMR (400 MHz, CDCl₃, 30° C.) 1.28 (3H, t), 1.44 (9H, s), 1.59 (4H, dq), 3.13 (2H, d), 3.47 (2H, t), 3.58 (3H, dd), 3.61-3.67 (2H, m), 3.72 (4H, ddd), 4.15 (2H, s), 4.22 (2H, q).

Intermediate 83e: Ethyl 1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1-oxo-7,10,13-trioxa-2-azapentadecan-15-oate

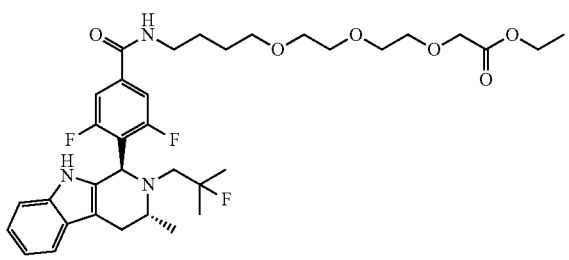 [SMILES: CCOC(=O)COCCOCCOCCCCNC(=O)c1cc(F)c([C@@H]2c3[nH]c4ccccc4c3C[C@@H](C)N2CC(C)(C)F)c(F)c1]

A solution of 4M HCl in dioxane (0.91 mL, 3.63 mmol) was added in one portion to ethyl 2,2-dimethyl-4-oxo-3,10,13,16-tetraoxa-5-azaoctadecan-18-oate (132 mg, 0.36 mmol) at 20° C. The resulting solution was stirred at 20° C. for 2 hours. The reaction mixture was evaporated to dryness to afford impure ethyl 2-(2-(2-(4-aminobutoxy)ethoxy)ethoxy)acetate hydrochloride salt. The crude material was dissolved in DMF (3 mL) and 3,5-difluoro-4-((1R,3R)-2-(2-fluoro-2-methylpropyl)-3-methyl-2,3,4,9-tetrahydro-1H-pyrido[3,4-b]indol-1-yl)benzoic acid (152 mg, 0.36 mmol), triethylamine (203 µl, 1.46 mmol) and HATU (208 mg, 0.55 mmol) were added. The resulting mixture was stirred at 20° C. for 3 days. The reaction mixture was diluted with EtOAc (50 mL), and washed sequentially with water (50 mL) and saturated brine (25 mL). The organic layer was dried with MgSO₄, filtered and evaporated to afford crude product. The crude product was purified by flash silica chromatography, elution gradient 0 to 100% EtOAc in heptane to afford the title compound (70 mg, 29%) as a yellow gum; m/z: ES+ [M+H]⁺ 662.3.

Intermediate 83f: 1-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)-1-oxo-7,10,13-trioxa-2-azapentadecan-15-oic Acid

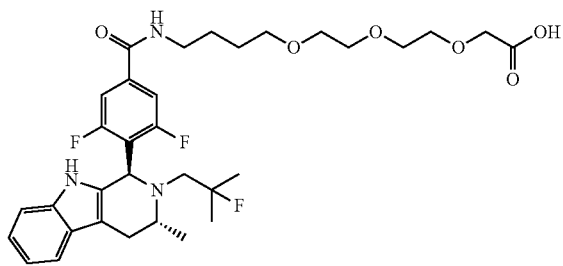 [SMILES: C[C@@H]1Cc2c([nH]c3ccccc23)[C@@H](c2c(F)cc(C(=O)NCCCCOCCOCCOCC(=O)O)cc2F)N1CC(C)(C)F]

The title compound was prepared in a similar manner to Intermediate 72f using the appropriate ester to afford the desired product (69 mg) as a yellow gum, which was used in the next step without further purification; m/z: ES+ [M+H]+ 634.3.

Example 83: (2S,4R)-1-((S)-17-(tert-Butyl)-1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1,15-dioxo-7,10,13-trioxa-2,16-diazaoctadecan-18-oyl)-4-hydroxy-N-(4-(4-methylthiazol-5-yl)benzyl)pyrrolidine-2-carboxamide The title compound was prepared in a similar manner to Example 68 using the appropriate carboxylic acid and amine to afford the desired product (55 mg, 50%) as a cream solid; $^1$H NMR (400 MHz, CDCl$_3$, 30° C.) 0.92 (9H, s), 1.10 (3H, d), 1.20 (6H, t), 1.72 (4H, dd), 2.02-2.14 (1H, m), 2.3-2.55 (5H, m), 2.63 (1H, dd), 2.88 (1H, dd), 3.08 (1H, dd), 3.14 (1H, d), 3.56 (14H, dtdd), 3.72-3.98 (3H, m), 4.36 (2H, dd), 4.49 (2H, dd), 4.69 (1H, t), 5.31 (1H, s), 7.03-7.14 (3H, m), 7.16-7.25 (2H, m), 7.28-7.44 (7H, m), 7.48-7.57 (1H, m), 8.55 (1H, s), 8.66 (1H, s); m/z: ES+ [M+H]+ 1046.3.

Intermediate 84a: tert-Butyl (3-(2-(2-hydroxyethoxy)ethoxy)propyl)carbamate

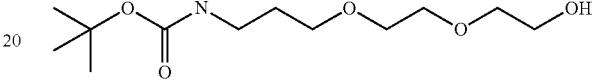

tert-Butyl (3-bromopropyl)carbamate (2.50 g, 10.5 mmol) was added in one portion to 2,2'-oxybis(ethan-1-ol) (4.98 mL, 52.5 mmol) and potassium 2-methylpropan-2-olate (2.36 g, 21.0 mmol) in THF (25 mL) at 20° C. under nitrogen. The resulting mixture was stirred at reflux for 18 hours. The reaction mixture was diluted with EtOAc (50 mL), and washed sequentially with saturated NH$_4$Cl (20 mL), water (2×20 mL) and saturated brine (20 mL). The organic layer was dried with MgSO$_4$, filtered and evaporated to afford crude product. The crude product was purified by flash silica chromatography, elution gradient 0 to 5% MeOH in DCM to afford the title compound (0.350 g, 13%) as a yellow oil; $^1$H NMR (400 MHz, CDCl$_3$, 30° C.) 1.44 (9H, s), 1.71-1.83 (2H, m), 2.40 (1H, s), 3.24 (2H, q), 3.52-3.7 (8H, m), 3.7-3.78 (2H, m), 4.96 (1H, s).

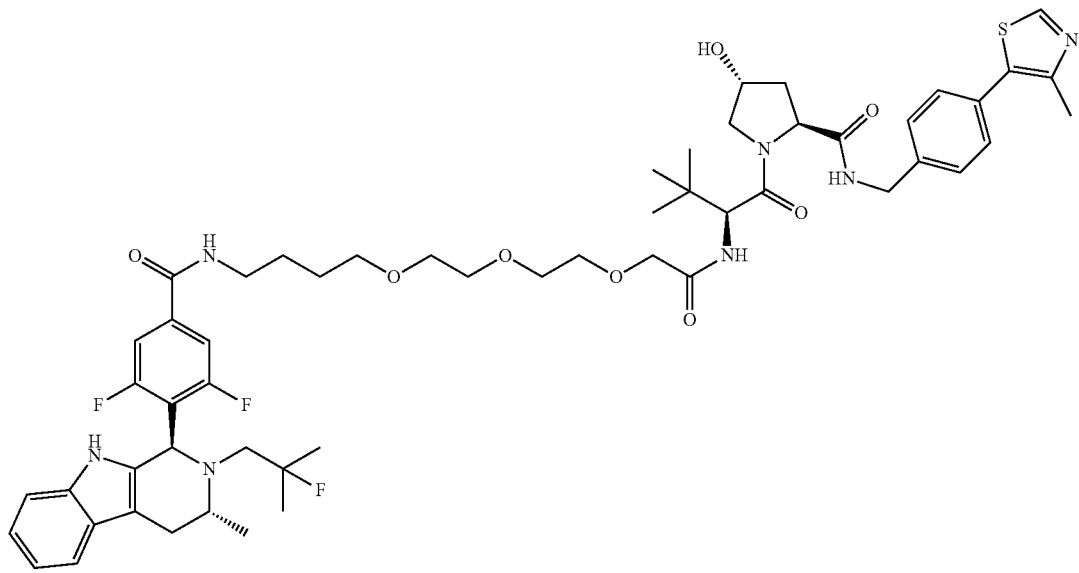 [SMILES: Cc1ncsc1-c1ccc(CNC(=O)[C@@H]2C[C@@H](O)CN2C(=O)[C@@H](NC(=O)COCCOCCOCCCCNC(=O)c2cc(F)c([C@@H]3c4[nH]c5ccccc5c4C[C@@H](C)N3CC(C)(C)F)c(F)c2)C(C)(C)C)cc1]

Intermediate 84b: Ethyl 2,2-dimethyl-4-oxo-3,9,12,
15-tetraoxa-5-azaheptadecan-17-oate

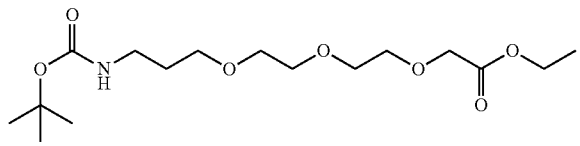 [SMILES: CCOC(=O)COCCOCCOCCCNC(=O)OC(C)(C)C]

The title compound was prepared in a similar manner to Intermediate 72c using the appropriate alcohol to afford the desired product (305 mg, 66%) a yellow liquid that was used without further purification; $^1$H NMR (400 MHz, CDCl$_3$, 30° C.) 1.28 (3H, t), 1.43 (9H, d), 1.76 (2H, p), 3.23 (2H, d), 3.54 (2H, t), 3.56-3.61 (2H, m), 3.61-3.67 (2H, m), 3.67-3.77 (4H, m), 4.15 (2H, s), 4.22 (2H, q), 4.96 (1H, s).

Intermediate 84c: Ethyl
2-(2-(2-(3-aminopropoxy)ethoxy)ethoxy)acetate

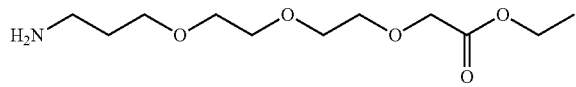 [SMILES: CCOC(=O)COCCOCCOCCCN]

A solution of 4M HCl in dioxane (2.18 mL, 8.73 mmol) was added in one portion to ethyl 2,2-dimethyl-4-oxo-3,9,12,15-tetraoxa-5-azaheptadecan-17-oate (305 mg, 0.87 mmol) at 20° C. The resulting solution was stirred for 2 hours. The reaction mixture was evaporated to dryness to afford the title compound (240 mg) as a yellow gum, which was used in the next step without further purification; $^1$H NMR (400 MHz, CDCl$_3$, 30° C.) 1.27-1.31 (3H, m), 2.11 (2H, dt), 3.22-3.28 (2H, m), 3.65 (8H, ddd), 3.78 (2H, t), 4.19 (4H, d), 8.15 (2H, s).

Intermediate 84d: Ethyl 1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1-oxo-6,9,12-trioxa-2-azatetradecan-14-oate

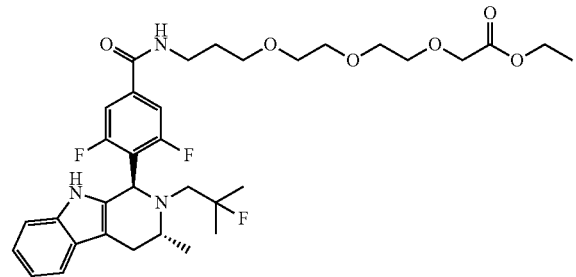 [SMILES: CCOC(=O)COCCOCCOCCCNC(=O)c1cc(F)c([C@@H]2c3[nH]c4ccccc4c3C[C@@H](C)N2CC(C)(C)F)c(F)c1]

HATU (229 mg, 0.60 mmol) was added in one portion to 3,5-difluoro-4-((1R,3R)-2-(2-fluoro-2-methylpropyl)-3-methyl-2,3,4,9-tetrahydro-1H-pyrido[3,4-b]indol-1-yl)benzoic acid (167 mg, 0.40 mmol), ethyl 2-(2-(2-(3-aminopropoxy)ethoxy)ethoxy)acetate (100 mg, 0.40 mmol) and triethylamine (0.22 mL, 1.60 mmol) in DMF (4 mL) at 20° C. under nitrogen. The reaction mixture was stirred for 2 days then diluted with EtOAc (50 mL), and washed sequentially with water (50 mL) and saturated brine (25 mL). The organic layer was dried with MgSO$_4$, filtered and evaporated to afford crude product. The crude product was purified by flash silica chromatography, elution gradient 0 to 100% EtOAc in heptane to afford the title compound (63 mg, 24%) as a yellow gum; m/z: ES+ [M+H]$^+$ 648.3.

Intermediate 84e: 1-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)-1-oxo-6,9,12-trioxa-2-azatetradecan-14-oic Acid

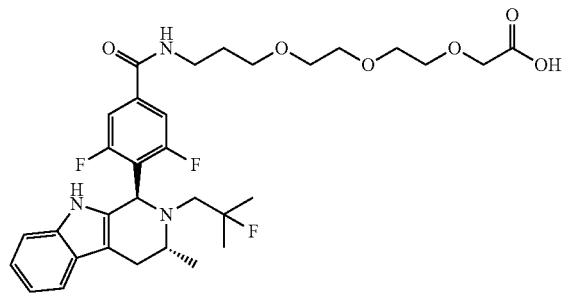 [SMILES: C[C@@H]1Cc2c([nH]c3ccccc23)[C@@H](c2c(F)cc(C(=O)NCCCOCCOCCOCC(=O)O)cc2F)N1CC(C)(C)F]

The title compound was prepared in a similar manner to Intermediate 72f using the appropriate ester to afford the desired product (63 mg, 100%) as a yellow gum, which was used in the next step without further purification; m/z: ES+ [M+H]$^+$ 620.3.

Example 84: (2S,4R)-1-((S)-16-(tert-Butyl)-1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1,14-dioxo-6,9,12-trioxa-2,15-diazaheptadecan-17-oyl)-4-hydroxy-N-(4-(4-methylthiazol-5-yl)benzyl)pyrrolidine-2-carboxamide

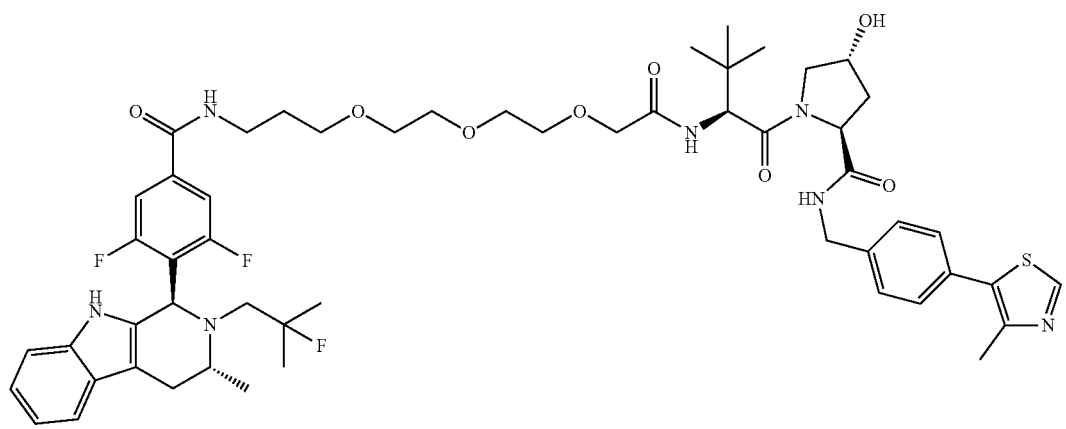 [SMILES: Cc1ncsc1-c1ccc(CNC(=O)[C@@H]2C[C@@H](O)CN2C(=O)[C@@H](NC(=O)COCCOCCOCCCNC(=O)c2cc(F)c([C@@H]3c4[nH]c5ccccc5c4C[C@@H](C)N3CC(C)(C)F)c(F)c2)C(C)(C)C)cc1]

The title compound was prepared in a similar manner to Example 68 using the appropriate carboxylic acid and amine to afford the desired product (65 mg, 62%) as a cream solid; $^1$H NMR (400 MHz, CDCl$_3$, 30° C.) 0.92 (9H, s), 1.09 (3H, d), 1.19 (6H, t), 1.82 (2H, d), 2.13 (1H, dd), 2.3-2.56 (5H, m), 2.63 (1H, dd), 2.88 (1H, dd), 3.10 (1H, dd), 3.38-3.48 (3H, m), 3.48-3.75 (13H, m), 3.81 (1H, d), 3.93 (1H, d), 4.39 (3H, ddd), 4.51 (1H, d), 4.69 (1H, t), 5.31 (1H, s), 7.00 (1H, t), 7.04-7.15 (3H, m), 7.18 (1H, dd), 7.28-7.41 (6H, m), 7.52 (2H, dt), 8.66 (1H, s), 8.84 (1H, s); m/z: ES+ [M+H]$^+$ 1032.3.

Intermediate 85a: Methyl 6-(((tert-butyldimethylsilyl)oxy)methyl)nicotinate

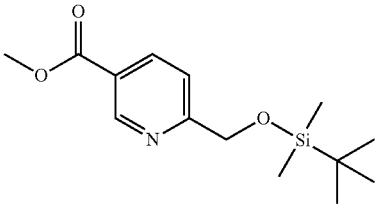 [SMILES: COC(=O)c1ccc(CO[Si](C)(C)C(C)(C)C)nc1]

tert-Butylchlorodimethylsilane (3.97 g, 26.3 mmol) was added in one portion to methyl 6-(hydroxymethyl)nicotinate (4.00 g, 23.9 mmol) and 1H-imidazole (1.79 g, 26.3 mmol) in DCM (40 mL) at 20° C. under nitrogen. The resulting cream suspension was stirred for 2 hours. The reaction mixture was diluted with DCM (100 mL), and washed with water (50 mL) and saturated brine (100 mL). The organic layer was dried with MgSO$_4$, filtered and evaporated to afford crude product. The crude product was purified by flash silica chromatography, elution gradient 0 to 50% EtOAc in heptane to afford the title compound (4.47 g, 66%) as a colourless oil; $^1$H NMR (400 MHz, CDCl$_3$, 30° C.) 0.13 (6H, s), 0.97 (9H, s), 3.95 (3H, s), 4.88 (2H, s), 7.61 (1H, d), 8.31 (1H, dd), 9.10 (1H, d); m/z: ES+ [M+H]$^+$ 282.5.

Intermediate 85b: (6-(((tert-Butyldimethylsilyl)oxy)methyl)pyridin-3-yl)methanol

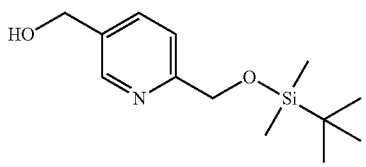 [SMILES: CC(C)(C)[Si](C)(C)OCc1ccc(CO)cn1]

A solution of 1M lithium aluminium hydride in THF (20.65 mL, 20.65 mmol) was added dropwise to a solution of methyl 6-(((tert-butyldimethylsilyl)oxy)methyl)nicotinate (4.47 g, 15.9 mmol) in THF (60 mL) at 0° C. over a period of 15 minutes under nitrogen. The resulting mixture was stirred at 0° C. for 1 hour. The reaction mixture was quenched with careful dropwise addition of water (0.7 mL), 2M NaOH solution (1.4 mL) and water (2.1 mL). The mixture was stirred for 5 minutes. The solids were removed by filtration and the filtrate was evaporated to dryness. The crude product was purified by flash silica chromatography, elution gradient 0 to 75% EtOAc in heptane to afford the title compound (1.53 g, 38%) as a white solid; $^1$H NMR (400 MHz, CDCl$_3$, 30° C.) 0.12 (6H, s), 0.96 (9H, s), 1.77 (1H, s), 4.72 (2H, d), 4.84 (2H, s), 7.51 (1H, d), 7.73 (1H, d), 8.49 (1H, s); m/z: ES+ [M+H]$^+$ 254.2.

Intermediate 85c: Ethyl 2-((6-(((tert-butyldimethylsilyl)oxy)methyl)pyridin-3-yl)methoxy)acetate

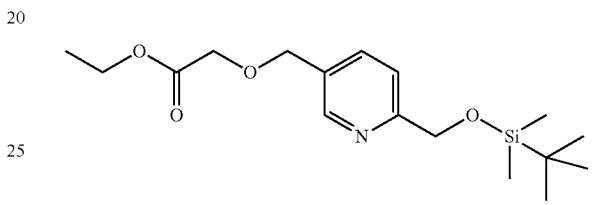

The title compound was prepared in a similar manner to Intermediate 72c using the appropriate alcohol to afford the desired product (164 mg, 31%) a red gum; $^1$H NMR (400 MHz, CDCl$_3$, 30° C.) 0.12 (6H, s), 0.96 (9H, s), 1.30 (3H, t), 4.11 (2H, s), 4.24 (2H, q), 4.65 (2H, s), 4.85 (2H, s), 7.53 (1H, d), 7.76 (1H, d), 8.49 (1H, s); m/z: ES+ [M+H]$^+$ 340.2.

Intermediate 85d: ethyl 2-((6-(hydroxymethyl)pyridin-3-yl)methoxy)acetate

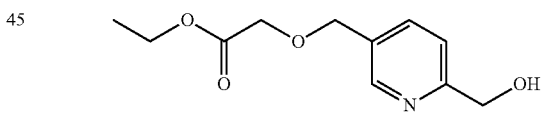

A solution of 1M TBAF in THF (0.73 mL, 0.73 mmol) was added in one portion to ethyl 2-((6-(((tert-butyldimethylsilyl)oxy)methyl)pyridin-3-yl)methoxy)acetate (164 mg, 0.48 mmol) in THF (4 mL) at 20° C. The resulting solution was stirred for 2 hours. The reaction mixture was diluted with EtOAc (50 mL), and washed sequentially with saturated NH$_4$Cl (20 mL), water (20 mL), and saturated brine (20 mL). The organic layer was dried with MgSO$_4$, filtered and evaporated to afford crude product. The crude product was purified by flash silica chromatography, elution gradient 0 to 100% EtOAc in heptane to afford the title compound (55 mg, 51%) as a red oil; $^1$H NMR (400 MHz, CDCl$_3$, 30° C.) 1.30 (3H, t), 3.59 (1H, s), 4.13 (2H, s), 4.24 (2H, q), 4.66 (2H, s), 4.78 (2H, s), 7.26 (1H, s), 7.77 (1H, d), 8.56 (1H, s); m/z: ES+ [M+H]$^+$ 226.1.

Intermediate 85e: Ethyl 2-((6-((3,5-difluoro-4-((1R, 3R)-2-(2-fluoro-2-methylpropyl)-3-methyl-2,3,4,9-tetrahydro-1H-pyrido[3,4-b]indol-1-yl)phenoxy)methyl)pyridin-3-yl)methoxy)acetate Intermediate 85f: 2-((6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methoxy)acetic Acid

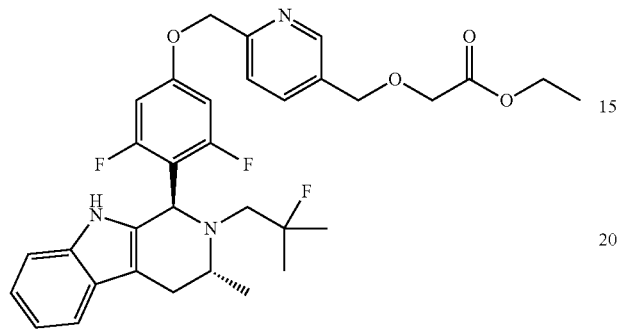

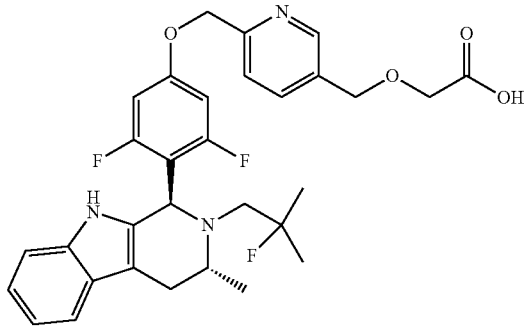 [SMILES: C[C@@H]1Cc2c([nH]c3ccccc23)[C@@H](c2c(F)cc(OCc3ccc(COCC(=O)O)cn3)cc2F)N1CC(C)(C)F]

The title compound was prepared in a similar manner to Intermediate 72e using the appropriate phenol and alcohol to afford the desired product (106 mg, 95%) as a yellow gum; ¹H NMR (400 MHz, CDCl₃, 30° C.) 1.10 (3H, d), 1.20 (6H, dd), 1.30 (3H, t), 2.38 (1H, dd), 2.60 (1H, dd), 2.86 (1H, dd), 3.08 (1H, dd), 3.67 (1H, d), 4.15 (2H, s), 4.24 (2H, q), 4.66 (2H, s), 5.15 (2H, s), 5.19 (1H, s), 6.50 (2H, d), 7.05-7.14 (2H, m), 7.22 (1H, dd), 7.40 (1H, s), 7.45-7.54 (2H, m), 7.80 (1H, d), 8.58 (1H, s); m/z: ES+ [M+H]⁺ 596.1.

The title compound was prepared in a similar manner to Intermediate 72f using the appropriate ester to afford the desired product (90 mg, 90%) as a yellow gum which was used in the next step without further purification; m/z: ES− [M−H]⁻ 566.2.

Example 85: (2S,4R)-1-((S)-2-(2-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methoxy)acetamido)-3,3-dimethylbutanoyl)-4-hydroxy-N-(4-(4-methylthiazol-5-yl)benzyl)pyrrolidine-2-carboxamide

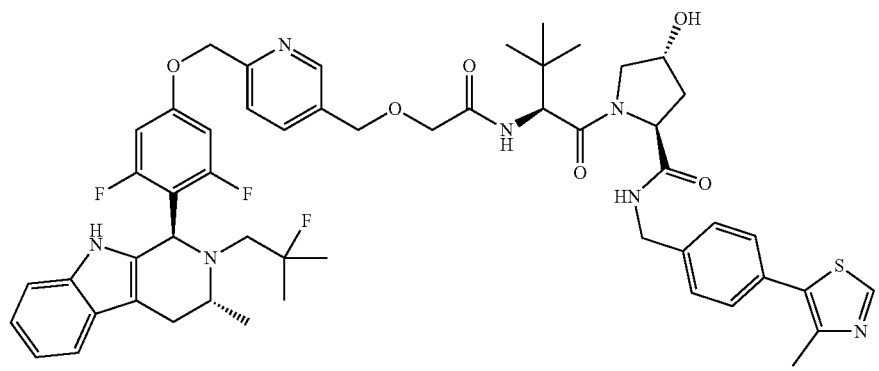 [SMILES: Cc1ncsc1-c1ccc(CNC(=O)[C@@H]2C[C@@H](O)CN2C(=O)[C@@H](NC(=O)COCc2ccc(COc3cc(F)c([C@@H]4c5[nH]c6ccccc6c5C[C@@H](C)N4CC(C)(C)F)c(F)c3)nc2)C(C)(C)C)cc1]

The title compound was prepared in a similar manner to Example 68 using the appropriate carboxylic acid and amine to afford the desired product (95 mg, 61%) as a white solid; ¹H NMR (400 MHz, CDCl₃, 30° C.) 0.93 (9H, s), 1.10 (3H, d), 1.20 (6H, dd), 2.12 (1H, s), 2.39 (1H, dd), 2.48 (3H, s), 2.54-2.65 (3H, m), 2.86 (1H, dd), 3.08 (1H, dd), 3.59-3.72 (2H, m), 3.91-4.11 (3H, m), 4.34 (1H, dd), 4.50 (1H, d), 4.53-4.6 (2H, m), 4.61 (2H, s), 4.73 (1H, t), 5.12 (2H, s), 5.20 (1H, s), 6.48 (2H, d), 7.05-7.19 (3H, m), 7.19-7.25 (2H, m), 7.3-7.42 (4H, m), 7.45-7.56 (2H, m), 7.73 (1H, dd), 7.81 (1H, s), 8.58 (1H, d), 8.64 (1H, s); m/z: ES+ [M+H]⁺ 980.5.

Intermediate 86a: (1R,3R)-1-(4-((6-(((tert-Butyldimethylsilyl)oxy)methyl)pyridin-3-yl)methoxy)-2,6-difluorophenyl)-2-(2-fluoro-2-methylpropyl)-3-methyl-2,3,4,9-tetrahydro-1H-pyrido[3,4-b]indole

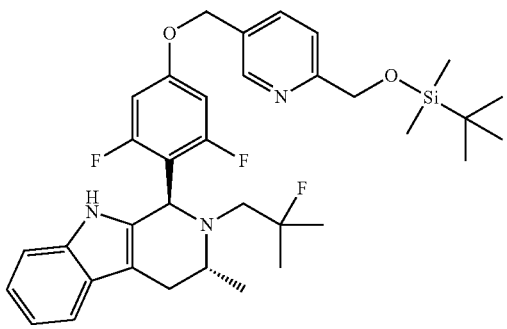 [SMILES: C[C@@H]1Cc2c([nH]c3ccccc23)[C@@H](c2c(F)cc(OCc3ccc(CO[Si](C)(C)C(C)(C)C)nc3)cc2F)N1CC(C)(C)F]

DIAD (0.203 mL, 1.03 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (200 mg, 0.51 mmol), (6-(((tert-butyldimethylsilyl)oxy)methyl)pyridin-3-yl)methanol (196 mg, 0.77 mmol) and triphenylphosphine (270 mg, 1.03 mmol) in DCM (5 mL) at 20° C. The resulting mixture was stirred for 18 hours. DCM (15 mL) and water (25 mL) were added and the layers were separated and concentrated to give the crude product. The crude product was purified by flash silica chromatography, elution gradient 0 to 50% EtOAc in heptane to afford impure title compound (321 mg) as a yellow gum, which was used without further purification; ¹H NMR (400 MHz, CDCl₃, 30° C.) 0.13 (6H, d), 0.96 (9H, d), 1.10 (3H, d), 1.19-1.33 (6H, m), 2.40 (1H, dd), 2.61 (1H, dd), 2.86 (1H, dd), 3.09 (1H, dd), 3.67 (1H, d), 4.85 (2H, s), 5.01 (2H, d), 5.21 (1H, s), 6.48 (2H, d), 7.05-7.16 (2H, m), 7.23 (1H, dd), 7.40 (1H, s), 7.46-7.63 (2H, m), 7.75 (1H, dd), 8.54 (1H, d); m/z: ES+ [M+H]⁺ 624.3.

Intermediate 86b: (5-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)methanol

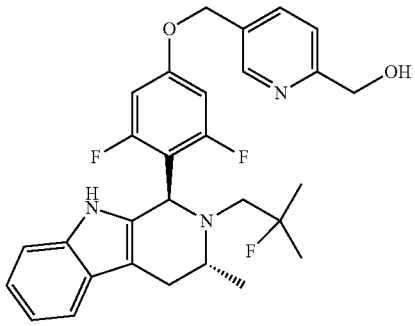 [SMILES: C[C@@H]1Cc2c([nH]c3ccccc23)[C@@H](c2c(F)cc(OCc3ccc(CO)nc3)cc2F)N1CC(C)(C)F]

A solution of 1M TBAF in THF (0.77 mL, 0.77 mmol) was added in one portion to (1R,3R)-1-(4-((6-(((tert-butyldimethylsilyl)oxy)methyl)pyridin-3-yl)methoxy)-2,6-difluorophenyl)-2-(2-fluoro-2-methylpropyl)-3-methyl-2,3,4,9-tetrahydro-1H-pyrido[3,4-b]indole (321 mg, 0.51 mmol) in THF (4 mL) at 20° C. The resulting solution was stirred for 2 hours. The reaction mixture was diluted with EtOAc (50 mL), and washed sequentially with saturated NH₄Cl (20 mL), water (20 mL), and saturated brine (20 mL). The organic layer was dried with MgSO₄, filtered and evaporated to afford crude product. The crude product was purified by flash silica chromatography, elution gradient 0 to 50% EtOAc in heptane to afford the title compound (192 mg, 73%) as a yellow gum; ¹H NMR (400 MHz, CDCl₃, 30° C.) 1.10 (3H, d), 1.21 (6H, dd), 2.40 (1H, dd), 2.61 (1H, dd), 2.86 (1H, dd), 3.08 (1H, dd), 3.50 (1H, t), 3.62-3.72 (1H, m), 4.79 (2H, d), 5.03 (2H, s), 5.21 (1H, s), 6.36-6.55 (2H, m), 7.03-7.18 (2H, m), 7.19-7.24 (1H, m), 7.30 (1H, d), 7.40 (1H, s), 7.51 (1H, dd), 7.74 (1H, dd), 8.60 (1H, s); m/z: ES+ [M+H]⁺ 510.3.

Intermediate 86c: Ethyl 2-((5-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)methoxy)acetate

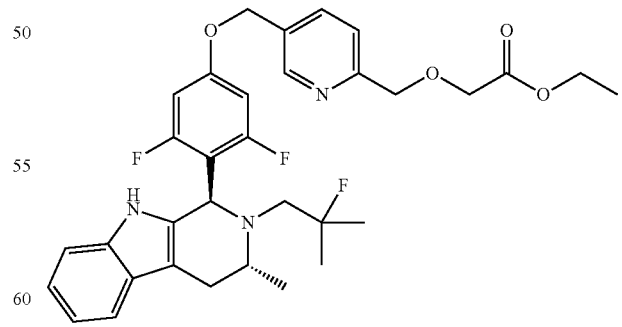

The title compound was prepared in a similar manner to Intermediate 72c using the appropriate alcohol to afford the desired product (56 mg, 25%) a red gum; ¹H NMR (400 MHz, CDCl₃, 30° C.) 1.10 (3H, d), 1.15-1.32 (9H, m), 2.40 (1H, dd), 2.60 (1H, dd), 2.86 (1H, dd), 3.08 (1H, dd), 3.67

(1H, d), 4.2-4.3 (4H, m), 4.91 (2H, s), 5.06 (2H, s), 5.21 (1H, s), 6.49 (2H, d), 7.05-7.16 (2H, m), 7.22 (1H, dd), 7.41 (1H, s), 7.46-7.57 (1H, m), 7.67 (1H, s), 7.83 (1H, s), 8.68 (1H, s); m/z: ES+ [M+H]+ 596.3.

Intermediate 86d: 2-((5-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)methoxy)acetic Acid

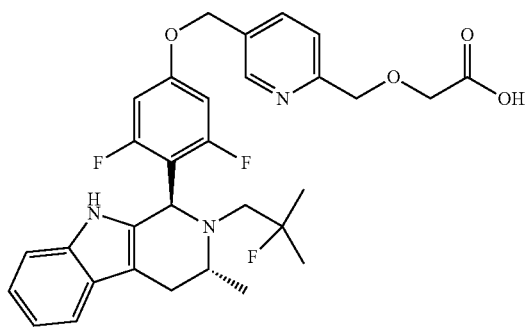 [SMILES: C[C@@H]1Cc2c([nH]c3ccccc23)[C@@H](c2c(F)cc(OCc3ccc(COCC(=O)O)nc3)cc2F)N1CC(C)(C)F]

The title compound was prepared in a similar manner to Intermediate 72f using the appropriate ester to afford the desired product; m/z: ES+ [M+H]+ 568.3.

Example 86: (2S,4R)-1-((S)-2-(2-((5-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)methoxy)acetamido)-3,3-dimethylbutanoyl)-4-hydroxy-N-(4-(4-methylthiazol-5-yl)benzyl)pyrrolidine-2-carboxamide

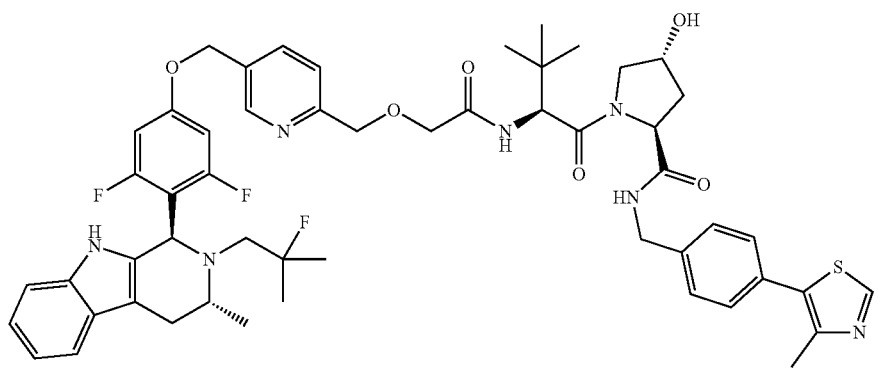 [SMILES: Cc1ncsc1-c1ccc(CNC(=O)[C@@H]2C[C@@H](O)CN2C(=O)[C@@H](NC(=O)COCc2ccc(COc3cc(F)c([C@@H]4c5[nH]c6ccccc6c5C[C@@H](C)N4CC(C)(C)F)c(F)c3)cn2)C(C)(C)C)cc1]

The title compound was prepared in a similar manner to Example 68 using the appropriate carboxylic acid and amine to afford the desired product (35 mg, 41%) as a white solid; $^1$H NMR (400 MHz, CDCl$_3$, 30° C.) 0.98 (9H, s), 1.11 (3H, d), 1.21 (6H, dd), 2.11 (1H, dd), 2.32-2.5 (4H, m), 2.52-2.74 (3H, m), 2.86 (1H, dd), 3.09 (1H, dd), 3.58-3.72 (2H, m), 4.01-4.2 (3H, m), 4.32 (1H, dd), 4.47-4.63 (3H, m), 4.67-4.79 (3H, m), 4.98 (2H, s), 5.22 (1H, s), 6.44 (2H, d), 7.04-7.15 (2H, m), 7.19-7.24 (1H, m), 7.27-7.45 (6H, m), 7.47-7.57 (1H, m), 7.7-7.79 (2H, m), 7.95 (1H, s), 8.55-8.67 (2H, m); m/z: ES− [M−H]− 979.2.

Intermediate 88a:
((Hepta-1,6-dien-4-yloxy)methyl)benzene

Hepta-1,6-dien-4-ol (7.99 mL, 61.5 mmol) was added dropwise to 60% sodium hydride in mineral oil (3.44 g, 86.1 mmol) in DMF (70 mL) at 0° C. The resulting solution was stirred at 0° C. for 15 minutes. (Bromomethyl)benzene (8.05 mL, 67.7 mmol) was added portionwise over 5 minutes. The reaction was allowed to warm slowly to RT and was stirred for 18 hours. The reaction mixture was quenched with water (50 mL), extracted with EtOAc (3×75 mL), the organic layer was washed with water (100 mL), saturated brine solution (50 mL), dried over MgSO$_4$, filtered and evaporated to afford crude product as a yellow oil. The crude product was purified by flash silica chromatography, elution gradient 0 to 10% EtOAc in heptane to afford the title compound (11.28 g, 91%) as a pale yellow liquid; $^1$H NMR (400 MHz, CDCl$_3$, 30° C.) 2.28-2.41 (4H, m), 3.51 (1H, p), 4.55 (2H, s), 5.02-5.17 (4H, m), 5.85 (2H, ddt), 7.26-7.38 (5H, m).

Intermediate 88b: 4-(Benzyloxy)heptane-1,7-diol

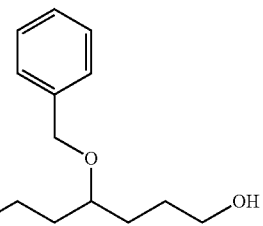

A solution of 0.5 M 9-borabicyclo(3.3.1)nonane in THF (119 mL, 59.3 mmol) was added dropwise to ((hepta-1,6-dien-4-yloxy)methyl)benzene (6.00 g, 29.7 mmol) over 15 minutes at 0° C. under nitrogen. The colourless solution was stirred at 20° C. for 18 hours. The reaction was cooled to 0° C. and EtOH (48 mL) was added followed by dropwise addition of 5 M aq. sodium hydroxide (14 mL, 70 mmol) and dropwise addition of 30% aq. hydrogen peroxide (21 mL, 208 mmol) over 30 minutes. The ice bath was removed and the reaction mixture was warmed to 50° C. and was stirred at this temperature for 6 hours. The reaction mixture was diluted with EtOAc (50 mL), and washed with saturated brine (25 mL). The organic layer was dried with MgSO$_4$, filtered and evaporated to afford crude product. The crude product was purified by flash silica chromatography, elution gradient 0 to 100% EtOAc in heptane to afford impure title compound (13.11 g) as a colourless oil, which was used without further purification; $^1$H NMR (400 MHz, CDCl$_3$, 30° C.) 1.59-1.69 (8H, m), 3.50 (1H, s), 3.81 (4H, t), 4.53 (2H, s), 7.26-7.37 (5H, m); m/z: ES+ [M+H]$^+$ 239.3.

Intermediate 88c: Ethyl 2-((4-(benzyloxy)-7-hydroxyheptyl)oxy)acetate

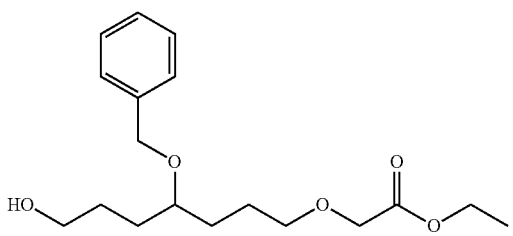 [SMILES: CCOC(=O)COCCCC(CCCO)OCc1ccccc1]

The title compound was prepared in a similar manner to Intermediate 72c using the appropriate alcohol to afford the desired product (2.73 g, 57%) as a colourless oil; m/z: ES+ [M+H]$^+$ 325.2

Intermediate 88d: Ethyl 2-((4,7-dihydroxyheptyl)oxy)acetate

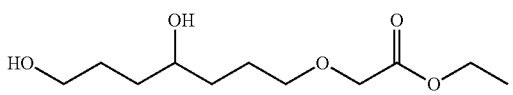 [SMILES: CCOC(=O)COCCCC(O)CCCO]

The title compound was prepared in a similar manner to Intermediate 72d using the appropriate benzyl ether to afford the desired product (0.938 g, 51%) as a colourless oil; $^1$H NMR (400 MHz, CDCl$_3$, 30° C.) 1.29 (3H, t), 1.46-1.81 (8H, m), 2.36 (1H, s), 2.83 (1H, s), 3.59 (2H, t), 3.63-3.75 (3H, m), 4.07 (2H, s), 4.22 (2H, q); m/z: ES+ [M+H]$^+$ 235.2

Intermediate 88e: Ethyl 2-[7-[3,5-difluoro-4-[(1R,3R)-2-(2-fluoro-2-methyl-propyl)-3-methyl-1,3,4,9-tetrahydropyrido[3,4-b]indol-1-yl]phenoxy]-4-hydroxy-heptoxy]acetate

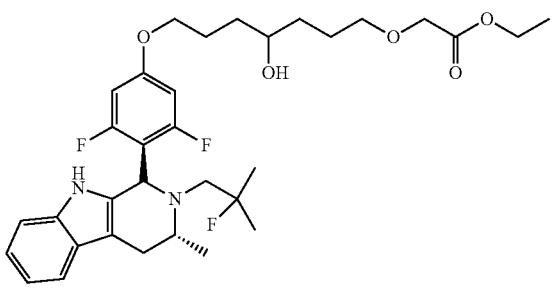

RockPhos Pd G3 (52.7 mg, 0.06 mmol) was added in one portion to a degassed mixture of (1R,3R)-1-(4-bromo-2,6-difluorophenyl)-2-(2-fluoro-2-methylpropyl)-3-methyl-2,3,4,9-tetrahydro-1H-pyrido[3,4-b]indole (566 mg, 1.25 mmol), ethyl 2-((4,7-dihydroxyheptyl)oxy)acetate (588 mg, 2.51 mmol) and cesium carbonate (1.00 g, 3.14 mmol) in toluene (50 mL) at 20° C. under nitrogen. The resulting mixture was stirred at 90° C. for 6 hours. The reaction was allowed to cool to RT and was filtered, the filtercup was washed with DCM (10 mL) then the mixture evaporated to afford crude product as a orange gum. The crude product was purified by flash silica chromatography, elution gradient 0 to 60% EtOAc in heptane to afford the title compound (300 mg, 40%) as a yellow gum; $^1$H NMR (400 MHz, CDCl$_3$, 8° C.) 1.10 (3H, d), 1.14-1.31 (9H, m), 1.48-2.03 (8H, m), 2.37 (1H, dd), 2.49 (1H, d), 2.60 (1H, dd), 2.77-2.95 (1H, m), 3.10 (1H, d), 3.60 (2H, t), 3.72 (2H, dq), 3.95 (2H, q), 4.09 (2H, s), 4.22 (2H, q), 5.18 (1H, s), 6.40 (2H, d), 7.05-7.16 (2H, m), 7.23 (1H, dt), 7.47 (1H, s), 7.52 (1H, dd); m/z: ES+ [M+H]$^+$ 605.4

Intermediate 88f: 2-[7-[3,5-Difluoro-4-[(1R,3R)-2-(2-fluoro-2-methyl-propyl)-3-methyl-1,3,4,9-tetrahydropyrido[3,4-b]indol-1-yl]phenoxy]-4-hydroxy-heptoxy]acetic Acid

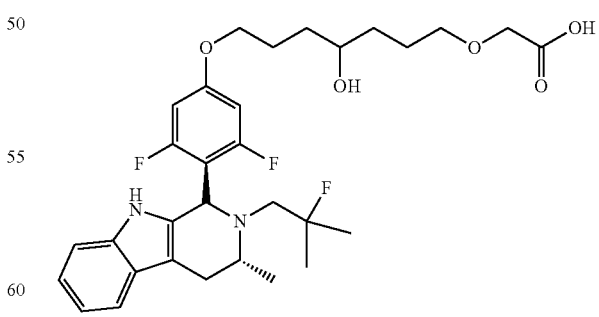

The title compound was prepared in a similar manner to Intermediate 72f using the appropriate ester to afford the desired product (60 mg, 100%) as a yellow gum which was used in the next step without purification; m/z: ES+ [M+H]$^+$ 577.4

Intermediate 88g: (2S,4R)-1-[(2S)-2-[[2-[7-[3,5-difluoro-4-[(1R,3R)-2-(2-fluoro-2-methyl-propyl)-3-methyl-1,3,4,9-tetrahydropyrido[3,4-b]indol-1-yl]phenoxy]-4-hydroxy-heptoxy]acetyl]amino]-3,3-dimethyl-butanoyl]-4-hydroxy-N-[[4-(4-methylthiazol-5-yl)phenyl]methyl]pyrrolidine-2-carboxamide

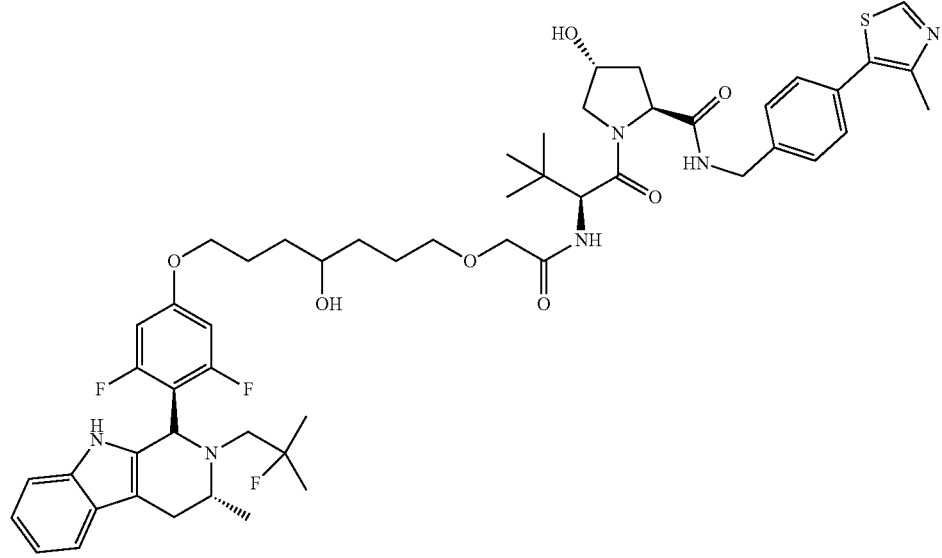

The title compound was prepared in a similar manner to Example 68 using the appropriate carboxylic acid and amine to afford the desired product (63 mg, 61%) as a white solid; $^1$H NMR (400 MHz, CDCl$_3$, 30° C.) 0.97 (9H, d), 1.07-1.13 (3H, m), 1.20 (6H, dd), 1.57 (4H, s), 1.67-1.94 (4H, m), 2.10 (1H, s), 2.32-2.42 (1H, m), 2.44 (3H, d), 2.46-2.67 (3H, m), 2.85 (1H, dd), 3.05-3.14 (1H, m), 3.37-3.76 (6H, m), 3.82 (3H, dd), 3.97-4.15 (2H, m), 4.26-4.38 (1H, m), 4.47-4.73 (4H, m), 5.19 (1H, s), 6.29 (2H, dd), 7.04-7.13 (2H, m), 7.15-7.25 (3H, m), 7.3-7.4 (4H, m), 7.51 (1H, dd), 8.37 (0.5H, s), 8.62 (1H, d), 8.66 (0.5H, s); m/z: ES− [M−H]⁻ 987.5

Intermediate 88h: Ethyl 2-[4-(2-tert-butoxy-2-oxo-ethoxy)-7-[3,5-difluoro-4-[(1R,3R)-2-(2-fluoro-2-methyl-propyl)-3-methyl-1,3,4,9-tetrahydropyrido[3,4-b]indol-1-yl]phenoxy]heptoxy]acetate

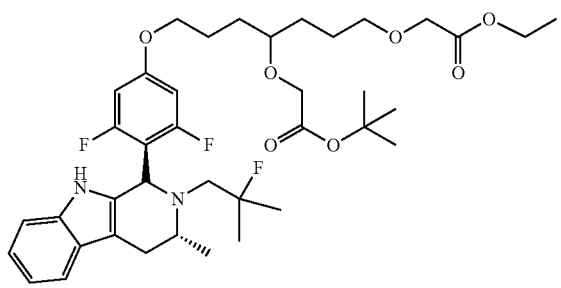

tert-Butyl 2-diazoacetate (0.172 mL, 1.24 mmol) was added slowly to ethyl 2-[7-[3,5-difluoro-4-[(1R,3R)-2-(2-fluoro-2-methyl-propyl)-3-methyl-1,3,4,9-tetrahydropyrido[3,4-b]indol-1-yl]phenoxy]-4-hydroxy-heptoxy]acetate (300 mg, 0.50 mmol) and diacetoxyrhodium (6.58 mg, 0.01 mmol) in DCM (10 mL) at 20° C. over a period of 1 hour under nitrogen. The resulting solution was stirred at 20° C. for 3 hours. The mixture was diluted with DCM (50 mL) and washed with water (2×50 mL). The organic layer was collected and dried using phase separating cartridge then evaporated to dryness. The crude product was purified by flash silica chromatography, elution gradient 0 to 60% EtOAc in heptane to afford the title compound (154 mg, 43%) as a yellow gum; m/z: ES+ [M+H]⁺ 719.5

Intermediate 88i: 2-[4-(2-tert-Butoxy-2-oxo-ethoxy)-7-[3,5-difluoro-4-[(1R,3R)-2-(2-fluoro-2-methyl-propyl)-3-methyl-1,3,4,9-tetrahydropyrido[3,4-b]indol-1-yl]phenoxy]heptoxy]acetic Acid

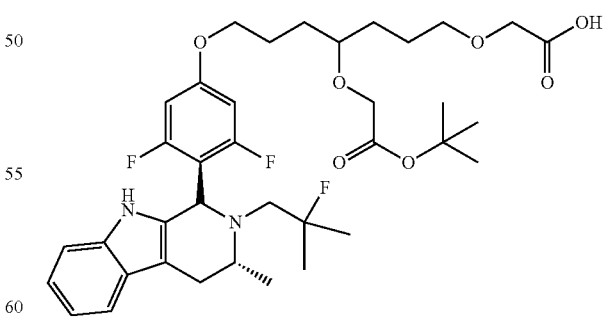

The title compound was prepared in a similar manner to Intermediate 72f using the appropriate ester to afford the desired product (148 mg, 100%) as a yellow gum which was used in the next step without purification; m/z: ES+ [M+H]⁺ 691.5

Example 88: tert-Butyl 2-[1-[3-[3,5-difluoro-4-[(1R,3R)-2-(2-fluoro-2-methyl-propyl)-3-methyl-1,3,4,9-tetrahydropyrido[3,4-b]indol-1-yl]phenoxy]propyl]-4-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]butoxy]acetate nyl)-2-(2-fluoro-2-methylpropyl)-3-methyl-2,3,4,9-tetrahydro-1H-pyrido[3,4-b]indole, HCl (500 mg, 1.03 mmol), pentane-1,5-diol (0.65 mL, 6.15 mmol) and cesium carbonate (1.17 g, 3.59 mmol) in toluene (7.5 mL) and heated to 90° C. for 2 h. The reaction mixture was cooled to RT, diluted with DCM (50 mL) and water (25 mL) and filtered through a phase separating cartridge. The solvents were removed under reduced pressure. The crude product was

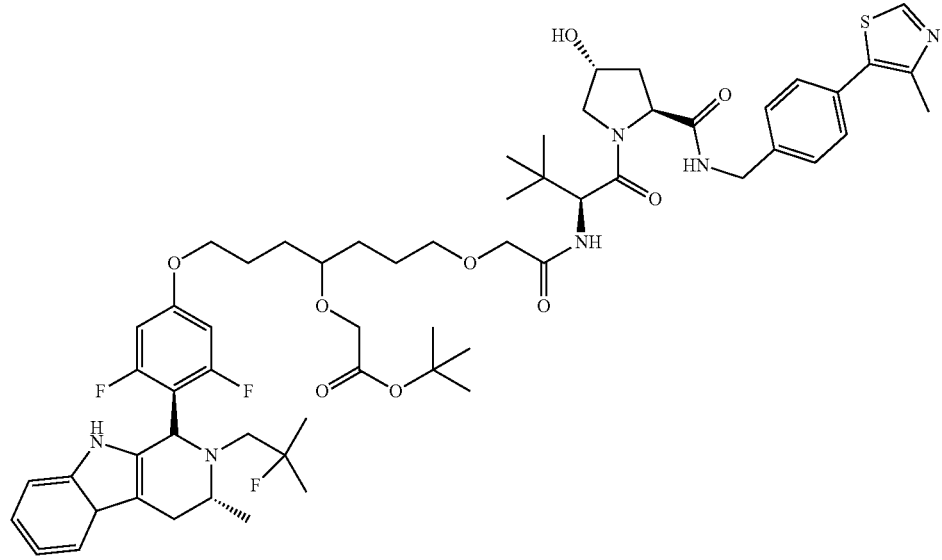

The title compound was prepared in a similar manner to Example 68 using the appropriate carboxylic acid and amine to afford the desired product (44 mg, 19%) as a cream solid; $^1$H NMR (400 MHz, CDCl$_3$, 30° C.) 0.94 (9H, d), 1.10 (3H, d), 1.20 (6H, dd), 1.46 (9H, d), 1.66 (6H, ddt), 1.86 (2H, s), 2.04-2.14 (1H, m), 2.31-2.53 (5H, m), 2.59 (2H, td), 2.85 (1H, dd), 3.09 (1H, d), 3.4-3.72 (5H, m), 3.79-3.99 (6H, m), 4.09 (1H, d), 4.30 (1H, dt), 4.48 (1H, dd), 4.52-4.63 (2H, m), 4.72 (1H, td), 5.19 (1H, s), 6.33 (2H, dd), 7.03-7.18 (3H, m), 7.19-7.25 (1H, m), 7.3-7.41 (5H, m), 7.51 (1H, dd), 8.22 (1H, s), 8.62 (1H, d); m/z: ES− [M−H]$^-$ 1101.4

Intermediate 89a: 5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentan-1-ol purified by flash silica chromatography, elution gradient 0 to 100% EtOAc in heptane. Pure fractions were evaporated to dryness to afford the title compound (335 mg, 69%) as a white foam; $^1$H NMR (400 MHz, CDCl$_3$, 30° C.) 1.10 (3H, d), 1.18 (3H, d), 1.21-1.25 (3H, m), 1.26 (1H, s), 1.54 (2H, s), 1.65 (2H, dd), 1.81 (2H, dt), 2.39 (1H, dd), 2.60 (1H, dd), 2.86 (1H, dd), 3.09 (1H, dd), 3.68 (3H, q), 3.92 (2H, t), 5.18 (1H, s), 6.35-6.42 (2H, m), 7.04-7.14 (2H, m), 7.18-7.24 (1H, m), 7.39 (1H, s), 7.51 (1H, dd); m/z: ES+ [M+H]$^+$ 473.3.

Intermediate 89b: 5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentanal

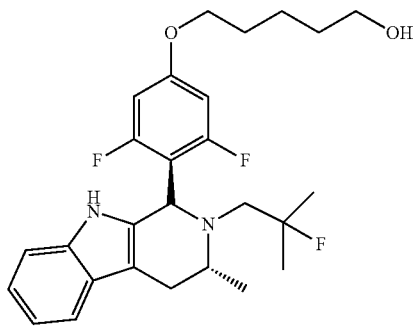

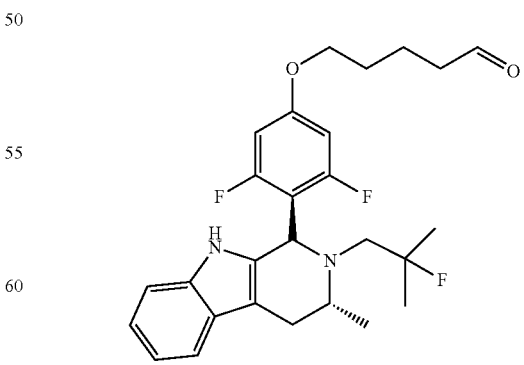

RockPhos Pd G3 (43 mg, 0.05 mmol) was added to a degassed solution of (1R,3R)-1-(4-bromo-2,6-difluorophe- SO$_3$—Pyridine complex (253 mg, 1.59 mmol) was added to a solution of 5-(3,5-difluoro-4-((1R,3R)-2-(2-fluoro-2-methylpropyl)-3-methyl-2,3,4,9-tetrahydro-1H-pyrido[3,4- b]indol-1-yl)phenoxy)pentan-1-ol (335 mg, 0.71 mmol) and triethylamine (0.25 mL, 1.76 mmol) in DCM (1.6 mL) and DMSO (1.6 mL) at 0° C. The reaction was allowed to warm to room temperature for 1 hour. The reaction was diluted with DCM (10 mL) and water (10 mL), then the layers were separated. The organic layer was washed with brine, passed through a phase separating cartridge and evaporated. The residue was purified by flash silica chromatography, elution gradient 0 to 60% EtOAc in heptane. Pure fractions were evaporated to afford the title compound (309 mg, 93%) as a colourless oil; $^1$H NMR (400 MHz, CDCl$_3$, 30° C.) 1.10 (3H, d), 1.18 (3H, d), 1.23 (3H, d), 1.78-1.84 (4H, m), 2.39 (1H, dd), 2.5-2.55 (2H, m), 2.60 (1H, dd), 2.86 (1H, dd), 3.09 (1H, dd), 3.63-3.73 (1H, m), 3.93 (2H, t), 5.19 (1H, s), 6.34-6.41 (2H, m), 7.05-7.14 (2H, m), 7.22 (1H, dd), 7.39 (1H, s), 7.51 (1H, dd), 9.80 (1H, t); m/z: ES+ [M+H]$^+$ 471.3.

Intermediate 89c: tert-Butyl (2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)carbamate

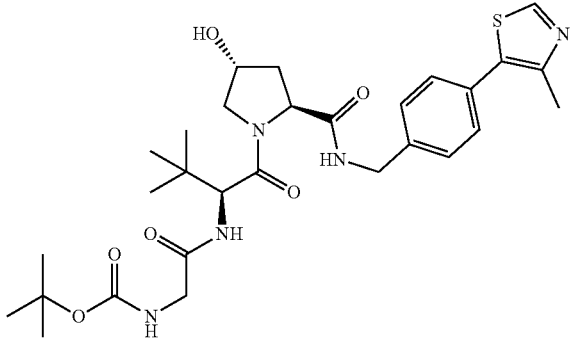 [SMILES: Cc1ncsc1-c1ccc(CNC(=O)[C@@H]2C[C@@H](O)CN2C(=O)[C@@H](NC(=O)CNC(=O)OC(C)(C)C)C(C)(C)C)cc1]

HATU (1.02 g, 2.68 mmol) was added to (tert-butoxycarbonyl)glycine (0.225 g, 1.28 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (0.50 g, 1.07 mmol) and triethylamine (0.60 mL, 4.28 mmol) in DMF (2 mL) at 20° C. under air. The resulting suspension was stirred at 20° C. for 30 minutes. The reaction mixture was diluted with EtOAc (5 mL), and washed sequentially with water (2×5 mL), saturated NaHCO$_3$ (2×2 mL), and saturated brine (2 mL). The organic layer was dried with MgSO$_4$, filtered and evaporated. The residue was purified by flash silica chromatography, elution gradient 0 to 10% MeOH in DCM. Pure fractions were evaporated to dryness to afford the title compound (0.32 g, 51%) as a yellow oil; $^1$H NMR (400 MHz, CDCl$_3$, 30° C.) 0.93 (9H, s), 1.45 (9H, s), 2.1-2.19 (1H, m), 2.52 (3H, s), 2.56 (1H, s), 3.49 (2H, d), 3.61 (1H, dd), 3.71 (1H, dd), 3.78 (1H, s), 4.07 (1H, d), 4.34 (1H, dd), 4.46 (1H, d), 4.57 (2H, dd), 4.75 (1H, t), 5.13 (1H, s), 6.80 (1H, s), 7.32-7.39 (4H, m), 8.67 (1H, s); m/z: ES− [M−H]$^-$ 586.3.

Intermediate 89d: (2S,4R)-1-((S)-2-(2-Aminoacetamido)-3,3-dimethylbutanoyl)-4-hydroxy-N-(4-(4-methylthiazol-5-yl)benzyl)pyrrolidine-2-carboxamide

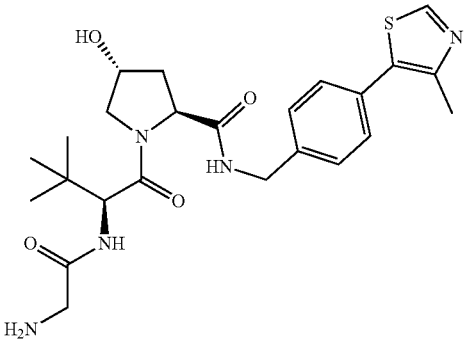 [SMILES: Cc1ncsc1-c1ccc(CNC(=O)[C@@H]2C[C@@H](O)CN2C(=O)[C@@H](NC(=O)CN)C(C)(C)C)cc1]

A solution of 4M HCl in dioxane (1.36 mL, 5.44 mmol) was added in one portion to tert-butyl (2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)carbamate (320 mg, 0.54 mmol) in MeOH (5 mL) at 20° C. under air and the resulting yellow solution was stirred at 20° C. for 18 hours. The reaction mixture was evaporated to dryness to afford the title compound (399 mg) as a white foamy solid that was in the next step without further purification; m/z: ES+ [M+H]$^+$ 488.0.

Example 89: (2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)amino)acetamido)-3,3-dimethylbutanoyl)-4-hydroxy-N-(4-(4-methylthiazol-5-yl)benzyl)pyrrolidine-2-carboxamide

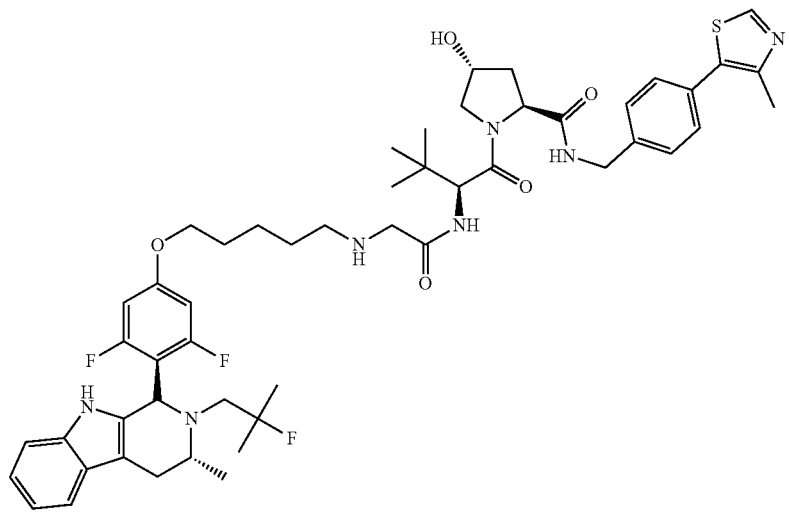

(2S,4R)-1-((S)-2-(2-aminoacetamido)-3,3-dimethylbutanoyl)-4-hydroxy-N-(4-(4-methythiazole-5-yl)benzyl)pyrrolidine-2-carboxamide, HCl (177 mg, 0.34 mmol) and 5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentanal (150 mg, 0.32 mmol) were stirred in DCM (5 mL) for 30 mins before sodium triacetoxyborohydride (341 mg, 1.61 mmol) was added and the reaction stirred for 1 hour. The reaction mixture was quenched with saturated NH₄Cl (10 mL), the organics separated and the aqueous extracted with DCM (2×25 mL), the organic layer was dried over MgSO₄, filtered and evaporated to afford crude product. The sample was purified by SFC to afford the title compound (41 mg, 14%) as a yellow solid; ¹H NMR (400 MHz, CDCl₃, 30° C.) 0.93 (9H, s), 1.10 (3H, d), 1.17 (3H, d), 1.23 (3H, d), 1.52 (4H, d), 1.73-1.82 (2H, m), 2.02-2.1 (1H, m), 2.40 (1H, dd), 2.47 (3H, s), 2.54-2.66 (5H, m), 2.85 (2H, dd), 3.08 (1H, dd), 3.18-3.3 (2H, m), 3.57 (1H, dd), 3.66 (1H, d), 3.88 (2H, t), 4.16 (1H, d), 4.30 (1H, dd), 4.42 (1H, d), 4.51 (1H, s), 4.58 (1H, dd), 4.71 (1H, t), 5.19 (1H, s), 6.34 (2H, d), 7.05-7.13 (2H, m), 7.23 (1H, dd), 7.31-7.41 (5H, m), 7.51 (1H, dd), 7.93 (1H, d), 8.11 (1H, s), 8.63 (1H, s); m/z: ES+ [M+H]⁺ 942.6.

Intermediate 90a: tert-Butyl (2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)(methyl)carbamate HATU (1.02 g, 2.68 mmol) was added to N-(tert-butoxycarbonyl)-N-methylglycine (243 mg, 1.28 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (500 mg, 1.07 mmol) and triethylamine (0.60 mL, 4.28 mmol) in DMF (2 mL) at 20° C. under air. The resulting suspension was stirred at 20° C. for 30 minutes. The reaction mixture was diluted with EtOAc (50 mL), and washed sequentially with water (2×50 mL), saturated NaHCO₃ (2×20 mL), and saturated brine (20 mL). The organic layer was dried with MgSO₄, filtered and evaporated. The residue was purified by flash silica chromatography, elution gradient 0 to 10% MeOH in DCM. Pure fractions were evaporated to dryness to afford the title compound (502 mg, 78%) as a yellow oil; ¹H NMR (400 MHz, CDCl₃, 30° C.) 0.92 (9H, s), 1.46 (10H, s), 2.11 (1H, dd), 2.52 (3H, s), 2.60 (1H, ddd), 2.80 (2H, s), 2.93 (3H, s), 3.59 (1H, d), 3.75-3.96 (2H, m), 4.07 (1H, d), 4.34 (1H, dd), 4.45 (1H, s), 4.56 (2H, dd), 4.74 (1H, t), 7.35 (4H, q), 8.68 (1H, s); m/z: ES− [M−H]⁻ 600.4.

Intermediate 90b: (2S,4R)-1-((S)-3,3-Dimethyl-2-(2-(methylamino)acetamido)butanoyl)-4-hydroxy-N-(4-(4-methylthiazol-5-yl)benzyl)pyrrolidine-2-carboxamide

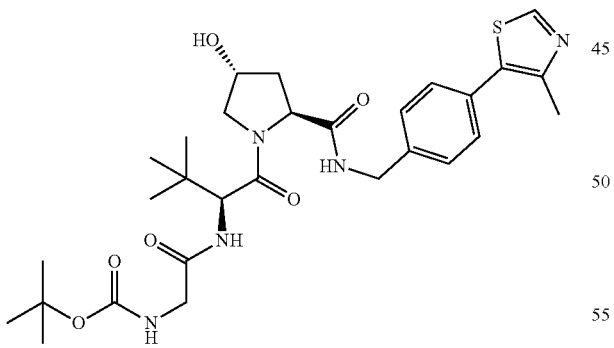

A solution of 4M HCl in dioxane (2.1 mL, 8.40 mmol) was added in one portion to tert-butyl (2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)(methyl)carbamate (502 mg, 0.83 mmol) in MeOH (2 mL) at 20° C. under air and the resulting yellow solution was stirred at 20° C. for 18 hours. The solvents were removed under reduced pressure to the title compound (521 mg, 116%) as a white solid that was used directly without further purification; ¹H NMR (400 MHz, DMSO, 30° C.) 0.98 (9H, s), 1.93 (1H, ddd), 2.02-2.1 (1H, m), 2.45 (3H, s), 2.56 (3H, t), 3.61 (1H, d), 3.69-3.75 (1H, m), 3.76-3.82 (2H, m), 4.23 (1H, dd), 4.38 (1H, s), 4.45 (2H, q), 4.59 (1H, d), 7.41 (4H, q), 8.59 (1H, t), 8.64 (1H, d), 8.77 (2H, s), 9.01 (1H, s); m/z: ES+ [M+H]⁺ 502.1.

Example 90: (2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido-[3,4-b]indol-1-yl)phenoxy)pentyl)(methyl)amino)acetamido)-3,3-dimethylbutanol)-4-hydroxy-N-(4-(4-methylthiazol-5-yl)benzyl)pyrrolidine-2-carboxamide

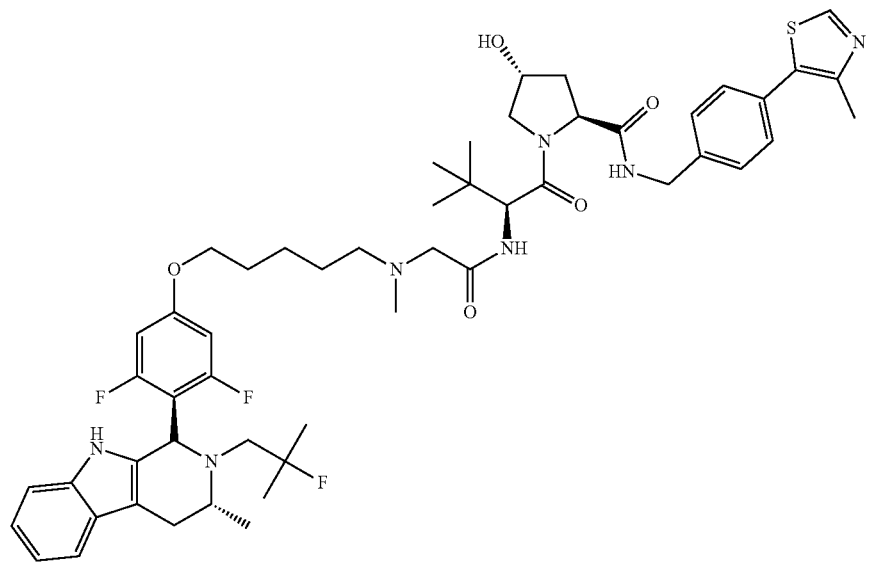

(2S,4R)-1-((S)-3,3-Dimethyl-2-(2-(methylamino)acetamido)butanoyl)-4-hydroxy-N-(4-(4-methylthiazol-5-yl)benzyl)pyrrolidine-2-carboxamide, HCl (182 mg, 0.34 mmol) and 5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentanal (152 mg, 0.32 mmol) were stirred in DCM (5 mL) for 5 mins, sodium triacetoxyborohydride (341 mg, 1.61 mmol) was added and the reaction stirred for 1 hour. The reaction mixture was quenched with saturated NH₄Cl (10 mL), the organics separated and the aqueous extracted with DCM (2×25 mL), the combined organic layers were dried over MgSO₄, filtered and evaporated. The residue was purified preparative HPLC and then ion exchange chromatography, using an SCX column. The desired product was eluted from the column using 1M NH₃/MeOH and pure fractions were evaporated to dryness to afford the title compound (78 mg, 25%) as a yellow solid; ¹H NMR (400 MHz, CDCl₃, 30° C.) 0.92 (9H, s), 1.10 (3H, d), 1.17 (3H, d), 1.23 (3H, d), 1.50 (5H, d), 1.67-1.82 (4H, m), 1.95-2.04 (1H, m), 2.29 (3H, s), 2.47 (3H, s), 2.55 (1H, dd), 2.62 (1H, d), 2.77-2.94 (2H, m), 2.97 (2H, d), 3-3.15 (1H, m), 3.56 (1H, dd), 3.61-3.71 (1H, m), 3.88 (2H, td), 4.14 (1H, d), 4.29 (1H, dd), 4.42 (1H, d), 4.50 (1H, s), 4.59 (1H, dd), 4.67 (1H, t), 5.19 (1H, s), 6.34 (2H, d), 7.04-7.13 (2H, m), 7.24 (1H, dd), 7.3-7.38 (4H, m), 7.38-7.44 (1H, m), 7.51 (1H, dd), 7.86 (1H, d), 8.28 (1H, s), 8.64 (1H, s); m/z: ES– [M–H]⁻ 956.6.

Intermediate 91a: tert-Butyl (2-(2-(2-hydroxyethoxy)ethoxy)ethyl)carbamate

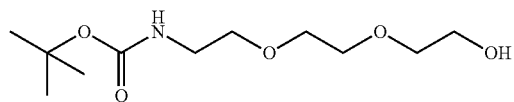 [SMILES: CC(C)(C)OC(=O)NCCOCCOCCO]

Di-tert-butyl dicarbonate (3.22 g, 14.75 mmol) in dioxane (10 mL) was added dropwise to 2-(2-(2-aminoethoxy)ethoxy)ethan-1-ol (2.00 g, 13.41 mmol) and potassium hydroxide (0.83 g, 14.75 mmol) in water (20 mL) at 20° C. over a period of 30 minutes. The resulting mixture was stirred at RT for 18 hours. The reaction mixture was diluted with water (10 mL), and extracted with DCM (2×50 mL). The combined organics were washed with saturated brine (20 mL). The organic layer was dried over MgSO₄, filtered and evaporated to afford the title compound (2.83 g, 85%) as a colourless oil; ¹H NMR (400 MHz, CDCl₃, 30° C.) 1.45 (9H, s), 2.65 (1H, s), 3.24-3.42 (2H, m), 3.56 (2H, t), 3.59-3.7 (6H, m), 3.72-3.78 (2H, m), 5.16 (1H, s); m/z: ES+ [M+H]⁺250.2.

Intermediate 91b: Ethyl 2,2-dimethyl-4-oxo-3,8,11,14-tetraoxa-5-azahexadecan-16-oate

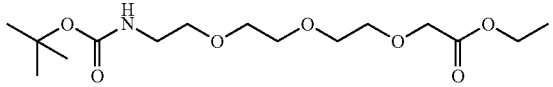 [SMILES: CCOC(=O)COCCOCCOCCNC(=O)OC(C)(C)C]

A solution of ethyl 2-diazoacetate (1.30 mL, 12.4 mmol) in DCM (10 mL) was added dropwise over a period of 60 minutes to a stirred suspension of tert-butyl (2-(2-(2-hydroxyethoxy)ethoxy)ethyl)carbamate (2.80 g, 11.2 mmol) and diacetoxyrhodium (50 mg, 0.11 mmol) in DCM (50 mL) cooled to 0° C. under air. The resulting suspension was stirred at 20° C. for 1 hour. The reaction was incomplete, the mixture was cooled to 0° C. and further ethyl 2-diazoacetate (1.3 mL, 12.35 mmol) dissolved in DCM (10 mL) was added dropwise over 20 min and the solution was stirred at 20° C. for a further 1 hour. The reaction mixture was diluted with DCM (50 mL) washed with water and brine. The organic later was passed through a phase separating cartridge and concentrated under reduced pressure and purified by flash silica chromatography, elution gradient 0 to 100% EtOAc in heptane. Pure fractions were evaporated to dryness to afford the title compound (1.40 g, 37%) as a colourless oil; $^1$H NMR (400 MHz, CDCl$_3$, 30° C.) 1.29 (3H, t), 1.44 (9H, s), 3.31 (2H, q), 3.54 (2H, t), 3.59-3.68 (4H, m), 3.68-3.72 (2H, m), 3.72-3.77 (2H, m), 4.15 (2H, s), 4.19-4.26 (2H, m), 5.04 (1H, s); m/z: ES+ [M+H]$^+$336.2.

Intermediate 91c: Ethyl 2-(2-(2-(2-aminoethoxy)ethoxy)ethoxy)acetate.HCl

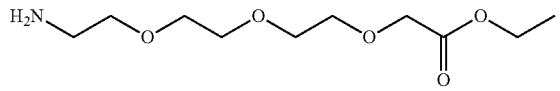 [SMILES: CCOC(=O)COCCOCCOCCN]

A solution of 4M HCl in dioxane (1.25 mL, 5.00 mmol) was added to a solution of ethyl 2,2-dimethyl-4-oxo-3,8,11,14-tetraoxa-5-azahexadecan-16-oate (500 mg, 1.49 mmol) in DCM (10 mL) and the reaction stirred at RT for 3 hours. The solvent was removed under reduced pressure to afford the title compound (453 mg) as a colourless oil that was used without further purification; $^1$H NMR (400 MHz, CDCl$_3$, 30° C.) 1.29 (3H, td), 3.23 (2H, q), 3.71 (4H, d), 3.74 (4H, d), 3.92 (2H, s), 4.20 (2H, s), 4.23 (2H, dd), 8.26 (3H, s); m/z: ES+ [M+H]$^+$236.2.

Intermediate 91d: Ethyl 1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1-oxo-5,8,11-trioxa-2-azatridecane-13-oate

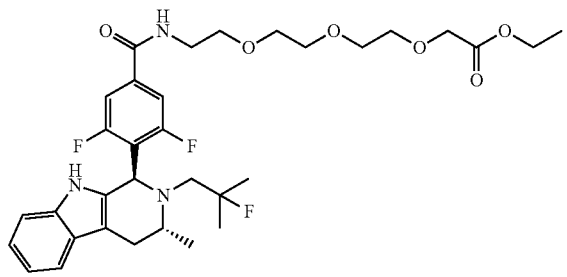 [SMILES: CCOC(=O)COCCOCCOCCNC(=O)c1cc(F)c([C@@H]2c3[nH]c4ccccc4c3C[C@@H](C)N2CC(C)(C)F)c(F)c1]

HATU (210 mg, 0.55 mmol) was added in one portion to 3,5-difluoro-4-((1R,3R)-2-(2-fluoro-2-methylpropyl)-3-methyl-2,3,4,9-tetrahydro-1H-pyrido[3,4-b]indol-1-yl)benzoic acid (153 mg, 0.37 mmol), ethyl 2-(2-(2-(2-aminoethoxy)ethoxy)ethoxy)acetate, HCl (100 mg, 0.37 mmol) and triethylamine (0.20 mL, 1.47 mmol) in DMF (3.5 mL) at 20° C. under nitrogen. The resulting mixture was stirred at 20° C. for 18 hours. The reaction mixture was diluted with EtOAc (50 mL) and washed sequentially with water (50 mL) and saturated brine (25 mL). The organic layer was dried over MgSO$_4$, filtered and evaporated. The residue was purified by flash silica chromatography, elution gradient 0 to 60% EtOAc in heptane. Pure fractions were evaporated to dryness to afford the title compound (135 mg, 58%) as a yellow gum; $^1$H NMR (400 MHz, CDCl$_3$, 30° C.) 1.08-1.15 (5H, m), 1.18-1.21 (4H, m), 1.24-1.28 (4H, m), 2.33-2.46 (1H, m), 2.63 (1H, dd), 2.89 (1H, dd), 3.10 (1H, dd), 3.66 (12H, d), 4.02 (2H, s), 4.11-4.17 (2H, m), 5.31 (1H, s), 7.10 (3H, tt), 7.22 (1H, dd), 7.32 (2H, d), 7.52 (1H, dd), 7.76 (1H, s); m/z: ES+ [M+H]$^+$ 634.3.

Intermediate 91e: 1-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)-1-oxo-5,8,11-trioxa-2-azatridecane-13-oic Acid

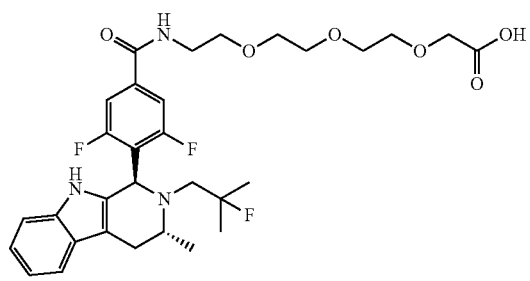 [SMILES: C[C@@H]1Cc2c([nH]c3ccccc23)[C@@H](c2c(F)cc(C(=O)NCCOCCOCCOCC(=O)O)cc2F)N1CC(C)(C)F]

The title compound was prepared in a similar manner to Intermediate 72f using the appropriate ester to afford the desired product (40 mg, 31%) as a yellow gum which was used directly without further purification; m/z: ES+ [M+H]$^+$ 606.3.

Example 91: (2S,4R)-1-((S)-15-(tert-Butyl)-1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1,13-dioxo-5,8,11-trioxa-2,14-diazahexadecan-16-oyl)-4-hydroxy-N-(4-(4-methylthiazol-5-yl)benzyl)pyrrolidine-2-carboxamide

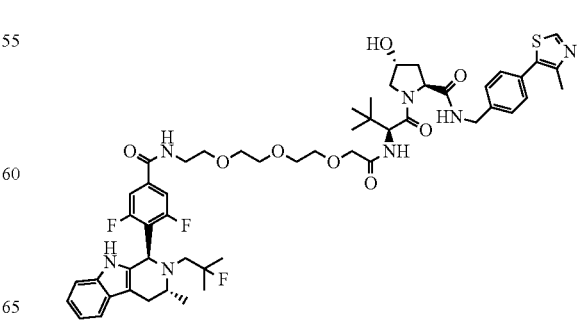

The title compound was prepared in a similar manner to Example 68 using the appropriate carboxylic acid and amine to afford the desired product (0.031 g, 46%) as a white solid; ¹H NMR (400 MHz, CDCl₃, 30° C.) 0.94 (9H, s), 1.09 (3H, d), 1.16 (3H, d), 1.22 (3H, d), 2.16 (1H, dd), 2.35 (1H, dd), 2.51 (4H, s), 2.61-2.68 (1H, m), 2.88 (1H, dd), 3.10 (2H, dd), 3.44-3.5 (2H, m), 3.53 (2H, dt), 3.62 (11H, dh), 3.78 (1H, d), 3.94 (1H, d), 4.37 (1H, dd), 4.48-4.59 (3H, m), 4.71 (1H, t), 5.30 (1H, s), 7.05-7.1 (3H, m), 7.17-7.25 (2H, m), 7.31 (2H, d), 7.33-7.41 (5H, m), 7.5-7.54 (1H, m), 8.67 (1H, s), 9.02 (1H, s); m/z: ES+ [M+H]⁺ 1018.3.

Intermediate 92a: tert-Butyl 3-(but-3-en-1-yloxy)propanoate

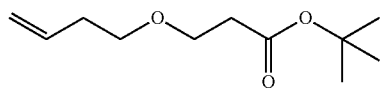

A solution of 40% N,N,N-trimethyl-1-phenylmethanaminium hydroxide in methanol (0.50 mL, 1.20 mmol) was evaporated to dryness and but-3-en-1-ol (2.4 mL, 27.50 mmol) added at 20° C. under nitrogen. The resulting solution was stirred for 25 min and tert-butyl acrylate (3.40 mL, 23.4 mmol) added. The resulting solution was stirred at 50° C. for 24 h. The crude reaction mixture was purified by flash silica chromatography, elution gradient 25 to 75% DCM in heptane. Pure fractions were evaporated to dryness to afford the title compound (3.40 g, 73%) as a colourless liquid; ¹H NMR (400 MHz, CDCl₃, 30° C.) 1.45 (9H, d), 2.24-2.35 (2H, m), 2.48 (2H, td), 3.43-3.52 (2H, m), 3.67 (2H, td), 4.97-5.14 (2H, m), 5.71-5.89 (1H, m).

Intermediate 92b: 3-(4-Bromobutoxy)propanoic Acid

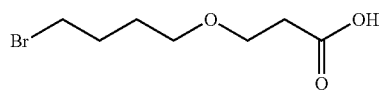 [SMILES: O=C(O)CCOCCCCBr]

A solution of 33% HBr in acetic acid (0.87 mL, 5.00 mmol) was added dropwise, over a period of 1 minute, to tert-butyl 3-(but-3-en-1-yloxy)propanoate (0.50 g, 2.50 mmol) in heptane (10 mL) cooled to 0° C. under nitrogen. The resulting solution was stirred vigorously at 20° C. for 20 hours. The reaction mixture was evaporated to dryness to afford the title compound as a light brown oil (assumed quantitative); ¹H NMR (400 MHz, CDCl₃, 30° C.) 1.65-1.76 (2H, m), 1.94 (2H, dt), 2.61 (2H, t), 3.43 (2H, t), 3.49 (2H, t), 3.70 (2H, t), 10.14 (1H, s).

Intermediate 92c: (2S,4R)-1-((S)-2-(3-(4-bromobutoxy)propanamido)-3,3-dimethylbutanoyl)-4-hydroxy-N-(4-(4-methylthiazol-5-yl)benzyl)pyrrolidine-2-carboxamide

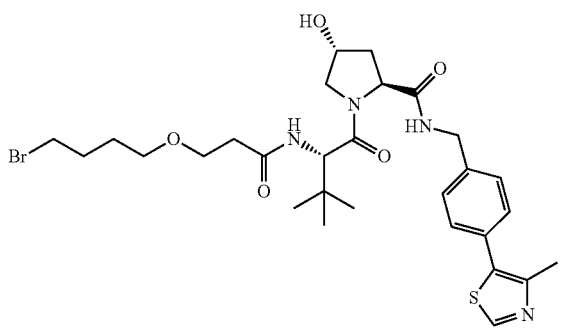 [SMILES: Cc1ncsc1-c1ccc(CNC(=O)[C@@H]2C[C@@H](O)CN2C(=O)[C@@H](NC(=O)CCOCCCCBr)C(C)(C)C)cc1]

HATU (1.20 g, 3.13 mmol) was added to 3-(4-bromobutoxy)propanoic acid (281 mg, 1.25 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (584 mg, 1.25 mmol) and triethylamine (0.70 mL, 5.00 mmol) in DCM (3 mL) and DMF (2 mL) at 20° C. under air. The resulting suspension was stirred at 20° C. for 30 minutes. The reaction mixture was diluted with EtOAc (5 mL), and washed sequentially with water (2×5 mL), saturated NaHCO₃ (2×2 mL), and saturated brine (2 mL). The organic layer was dried with MgSO₄, filtered and evaporated. The residue was purified by flash silica chromatography, elution gradient 0 to 10% MeOH in DCM. Pure fractions were evaporated to dryness to afford the title compound (352 mg, 44%) as a yellow oil; ¹H NMR (400 MHz, CDCl₃, 30° C.) 0.93 (9H, s), 1.7-1.77 (2H, m), 1.91-1.98 (2H, m), 2.07-2.15 (1H, m), 2.43-2.49 (2H, m), 2.52 (3H, s), 2.59-2.65 (1H, m), 2.85-3.02 (1H, m), 3.11 (OH, t), 3.41 (2H, t), 3.50 (2H, ddt), 3.54-3.59 (1H, m), 3.65 (2H, td), 4.15 (1H, d), 4.33 (1H, dd), 4.43 (1H, d), 4.49-4.62 (2H, m), 4.76 (1H, t), 6.99 (1H, d), 7.36 (5H, q), 8.68 (1H, s); m/z: ES+ [M+H]⁺ 637.2.

Example 92: (2S,4R)-1-((S)-2-(3-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)propanamido)-3,3-dimethylbutanoyl)-4-hydroxy-N-(4-(4-methylthiazol-5-yl)benzyl)pyrrolidine-2-carboxamide

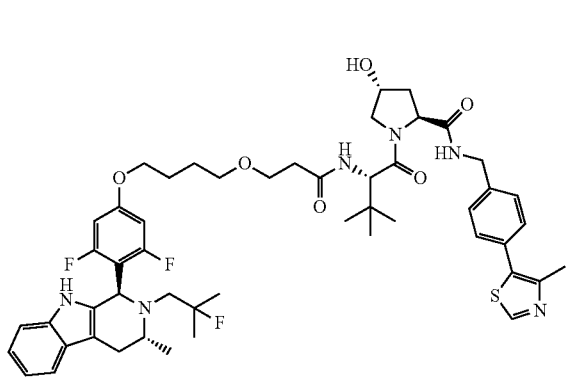 [SMILES: Cc1ncsc1-c1ccc(CNC(=O)[C@@H]2C[C@@H](O)CN2C(=O)[C@@H](NC(=O)CCOCCCCOc2cc(F)c([C@@H]3c4[nH]c5ccccc5c4C[C@@H](C)N3CC(C)(C)F)c(F)c2)C(C)(C)C)cc1]

Potassium carbonate (71 mg, 0.51 mmol) was added to (2S,4R)-1-((S)-2-(3-(4-bromobutoxy)propanamido)-3,3-dimethylbutanoyl)-4-hydroxy-N-(4-(4-methylthiazol-5-yl) benzyl)pyrrolidine-2-carboxamide (350 mg, 0.55 mmol) and 3,5-difluoro-4-((1R,3R)-2-(2-fluoro-2-methylpropyl)-3-methyl-2,3,4,9-tetrahydro-1H-pyrido[3,4-b]indol-1-yl)phenol (100 mg, 0.26 mmol) in acetonitrile (2 mL) at 20° C. under air. The resulting suspension was stirred at 80° C. for 7 hours. The reaction mixture was cooled to RT, filtered and concentrated under reduced pressure. The residue was purified by preparative HPLC to afford the title compound (75 mg, 31%); $^1$H NMR (400 MHz, CDCl$_3$, 30° C.) 0.92 (9H, s), 1.10 (3H, d), 1.17 (3H, d), 1.23 (3H, d), 1.75 (2H, q), 1.83 (2H, q), 2.06 (1H, dd), 2.34-2.44 (2H, m), 2.45 (4H, s), 2.52-2.63 (2H, m), 2.73 (1H, d), 2.85 (1H, dd), 3.09 (1H, dd), 3.52 (2H, t), 3.56 (1H, dd), 3.64 (3H, dq), 3.89 (2H, t), 4.12 (1H, d), 4.27 (1H, dd), 4.44 (1H, d), 4.50 (1H, s), 4.60 (1H, dd), 4.70 (1H, t), 5.20 (1H, s), 6.32 (2H, d), 7-7.06 (1H, m), 7.06-7.13 (2H, m), 7.2-7.24 (1H, m), 7.32-7.37 (5H, m), 7.48-7.55 (1H, m), 8.39 (1H, s), 8.62 (1H, s); m/z: ES− [M−H]$^-$ 943.8.

Intermediate 93a: 2-(4-(3-(Benzyloxy)propoxy)butoxy)tetrahydro-2H-pyran

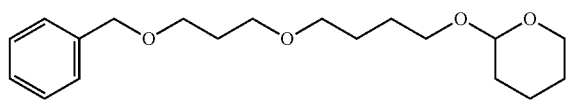 [SMILES: c1ccc(COCCCOCCCCOC2CCCCO2)cc1]

Tetrabutylammonium hydrogen sulfate (0.895 g, 2.64 mmol) was added in one portion to 3-(benzyloxy)propan-1-ol (2.80 mL, 17.6 mmol) and 2-(4-bromobutoxy)tetrahydro-2H-pyran (5.00 g, 21.10 mmol) in 50% sodium hydroxide solution (11.3 mL) at 20° C. under air. The resulting mixture was stirred at 70° C. for 18 hours. The cooled reaction mixture was diluted with water (20 mL) and extracted with EtOAc (3×25 mL). The combined organic extracts were washed with water (20 mL), saturated brine solution (20 mL), dried over MgSO$_4$, filtered and evaporated to afford. The residue was purified by flash silica chromatography, elution gradient 0 to 10% EtOAc in heptane. Pure fractions were evaporated to dryness to afford the title compound (4.35 g, 77%) as a colourless oil; $^1$H NMR (400 MHz, CDCl$_3$, 30° C.) 1.45-1.61 (4H, m), 1.61-1.67 (4H, m), 1.67-1.75 (1H, m), 1.78-1.85 (1H, m), 1.89 (2H, q), 3.38-3.46 (3H, m), 3.46-3.5 (1H, m), 3.51 (2H, t), 3.56 (2H, t), 3.71-3.8 (1H, m), 3.86 (1H, ddd), 4.50 (2H, s), 4.54-4.62 (1H, m), 7.22-7.3 (1H, m), 7.33 (4H, d).

Intermediate 93b: 4-(3-(Benzyloxy)propoxy)butan-1-ol

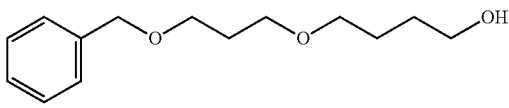 [SMILES: OCCCCOCCCOCc1ccccc1]

2-(4-(3-(Benzyloxy)propoxy)butoxy)tetrahydro-2H-pyran (4.35 g, 13.5 mmol) was dissolved in MeOH (36 mL) and 1M aq. HCl (18 mL) was added. The resulting mixture was stirred at 20° C. for 1 hour. The reaction mixture was diluted with water (100 mL), and extracted with EtOAc (3×100 mL). The combined organics were washed with saturated brine (50 mL). The organic layer was dried over MgSO$_4$, filtered and evaporated to afford crude product (3.40 g, 106%) which was used directly in the next step without purification; $^1$H NMR (400 MHz, CDCl$_3$, 30° C.) 1.62-1.69 (4H, m), 1.89 (2H, p), 2.47 (1H, s), 3.43-3.48 (2H, m), 3.55 (4H, q), 3.62 (2H, t), 4.50 (2H, s), 7.24-7.31 (1H, m), 7.33 (4H, d); m/z: ES+ [M+H]$^+$ 239.2.

Intermediate 93c: Ethyl 2-(4-(3-hydroxypropoxy)butoxy)acetate

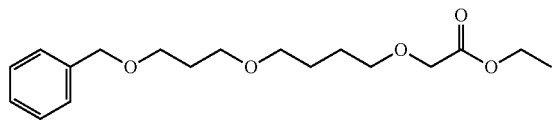 [SMILES: CCOC(=O)COCCCCOCCCOCc1ccccc1]

Ethyl 2-diazoacetate (4.40 mL, 35.7 mmol) in DCM (15 mL) was added slowly to 4-(3-(benzyloxy)propoxy)butan-1-ol (3.40 g, 14.3 mmol) and diacetoxyrhodium (315 mg, 0.71 mmol) in DCM (38 mL) at 20° C. over a period of 1 hour under nitrogen. The resulting solution was stirred at 20° C. for 18 hours. The mixture was diluted with DCM (50 mL) and washed with water (3×50 mL). The organic layer was collected and dried using phase separating cartridge then evaporated to dryness. The residue was purified by flash silica chromatography, elution gradient 0 to 10% EtOAc in heptane. Pure fractions were evaporated to dryness to afford the title compound (3.03 g, 66%) a colourless liquid; m/z: ES+ [M+H]$^+$ 325.2.

Intermediate 93d: Ethyl 2-(4-(3-hydroxypropoxy)butoxy)acetate

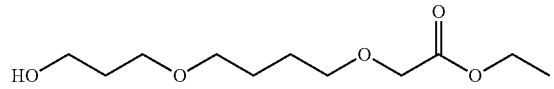 [SMILES: CCOC(=O)COCCCCOCCCO]

Ethyl 2-(4-(3-(benzyloxy)propoxy)butoxy)acetate (4.00 g, 12.33 mmol) was dissolved in EtOH (25 mL), 10% palladium on carbon (1.31 g, 1.23 mmol) was added and the reaction was stirred under an atmosphere of hydrogen (1 bar) for 4 hours. Acetic acid (0.5 mL) was added to the reaction mixture and stirred under an atmosphere of hydrogen (1 bar) for 18 hours. The reaction mixture was filtered through celite, eluted with MeOH. The solvent was removed under reduced pressure and the crude product was purified by flash silica chromatography, elution gradient 0 to 100% EtOAc in heptane. Pure fractions were evaporated to dryness to afford the title compound (1.40 g, 49%) as a colourless oil; $^1$H NMR (400 MHz, CDCl$_3$, 30° C.) 1.29 (3H, td), 1.64-1.71 (4H, m), 1.82 (2H, qd), 2.38-2.47 (1H, m), 3.43-3.5 (2H, m), 3.5-3.58 (2H, m), 3.61 (2H, td), 3.76 (2H, q), 4.06 (2H, d), 4.22 (2H, qd); m/z: ES+ [M+H]$^+$ 235.2.

Intermediate 93e: Ethyl 2-(4-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)butoxy)acetate

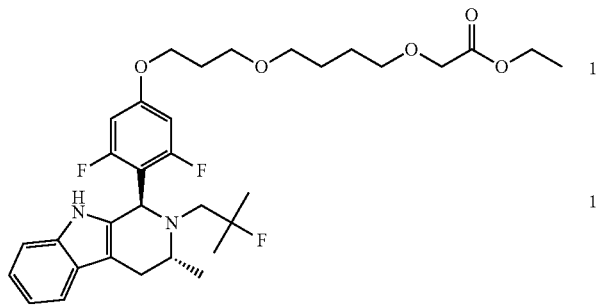

DIAD (0.15 mL, 0.77 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (150 mg, 0.39 mmol), ethyl 2-(4-(3-hydroxypropoxy)butoxy)acetate (180 mg, 0.77 mmol) and triphenylphosphine (203 mg, 0.77 mmol) in DCM (3 mL) at 5° C. The resulting mixture was stirred at 5° C. for 30 minutes and then at RT for 18 hours. DCM (10 mL) and water (25 mL) were added and the layers were separated through a phase separating cartridge. The organic layer was loaded on to a silica column and was purified by flash silica chromatography, elution gradient 10 to 100% EtOAc in heptane. Pure fractions were evaporated to dryness to afford the title compound (164 mg, 70%); H NMR (400 MHz, CDCl$_3$, 30° C.) 1.10 (3H, d), 1.18 (3H, d), 1.23 (3H, d), 1.28 (3H, d), 1.66 (4H, dt), 2.01 (2H, dt), 2.39 (1H, dd), 2.60 (1H, dd), 2.86 (1H, dd), 3.09 (1H, dd), 3.45 (2H, t), 3.48-3.61 (4H, m), 3.63-3.72 (1H, m), 3.98-4.05 (4H, m), 4.20 (2H, q), 5.18 (1H, s), 6.37-6.44 (2H, m), 7.05-7.13 (2H, m), 7.22 (1H, dd), 7.45-7.57 (2H, m); m/z: ES– [M–H]⁻ 603.6.

Intermediate 93f: 2-(4-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)butoxy)acetic Acid

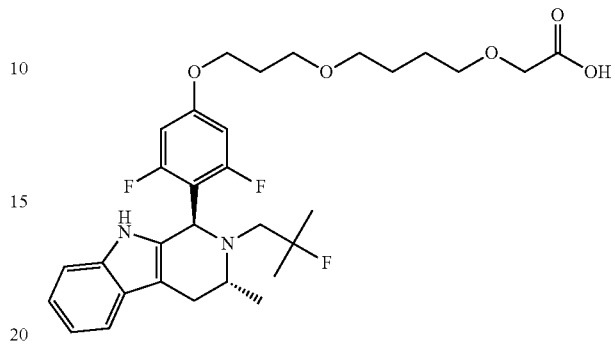

Lithium hydroxide hydrate (23 mg, 0.54 mmol) was added in one portion to ethyl 2-(4-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)butoxy)acetate (0.164 g, 0.27 mmol) in THF (6 mL) and water (2 mL) at 20° C. The resulting solution was stirred at RT for 30 mins. The organic solvent was removed under reduced pressure. The resulting mixture was acidified with 2M HCl and extracted into EtOAc (2×10 mL). The organic extracts were washed with brine (5 mL) and evaporated to afford crude product (0.142 g, 91%) as a yellow gum which was used in the next step without purification; m/z: ES+ [M+H]⁺ 577.4.

Example 93: ((2S,4R)-1-((S)-2-(2-(4-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)butoxy)acetamido)-3,3-dimethylbutanoyl)-4-hydroxy-N-(4-(4-methylthiazol-5-yl)benzyl)pyrrolidine-2-carboxamide

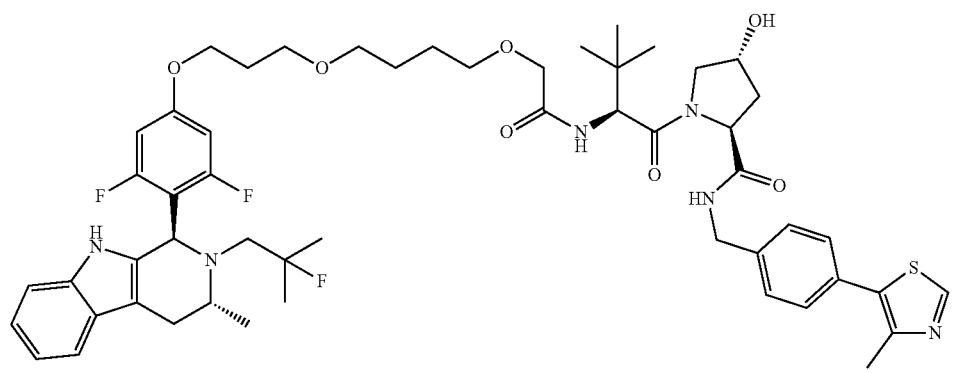

HATU (0.140 g, 0.37 mmol) was added portionwise to 2-(4-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)butoxy)acetic acid (140 mg, 0.25 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (110 mg, 0.23 mmol) and triethylamine (0.14 mL, 0.98 mmol) in DMF (5 mL) at 20° C. under nitrogen. The resulting mixture was stirred at 20° C. for 18 hours. The reaction mixture was diluted with EtOAc (25 mL), and washed sequentially with saturated NaHCO$_3$ (25 mL), water (25 mL), and saturated brine (25 mL). The organic layer was dried with MgSO$_4$, filtered and evaporated. The residue was purified by preparative HPLC to afford the title compound (0.131 g, 54%) as a white solid; $^1$H NMR (400 MHz, CDCl$_3$, 30° C.) 0.94 (9H, s), 1.10 (3H, d), 1.18 (3H, d), 1.24 (3H, d), 1.62-1.71 (4H, m), 1.99 (2H, p), 2.03-2.12 (1H, m), 2.41 (1H, dd), 2.50 (3H, s), 2.53-2.63 (2H, m), 2.65 (1H, d), 2.83 (1H, dd), 3.06 (1H, dd), 3.46 (4H, dt), 3.55 (2H, t), 3.63 (2H, ddd), 3.73 (1H, d), 3.86 (1H, d), 3.98 (2H, t), 4.06 (1H, d), 4.33 (1H, dd), 4.48-4.59 (3H, m), 4.73 (1H, t), 5.20 (1H, s), 6.34-6.4 (2H, m), 7.04-7.11 (2H, m), 7.15 (1H, d), 7.19-7.23 (1H, m), 7.28 (1H, s), 7.35 (4H, q), 7.51 (1H, dd), 8.22 (1H, s), 8.64 (1H, s); m/z: ES– [M–H]$^-$ 987.9.

Intermediate 94a: 3,5-Difluoro-4-((1R,3R)-3-methyl-2-(2,2,2-trifluoroethyl)-2,3,4,9-tetrahydro-1H-pyrido[3,4-b]indol-1-yl)phenol

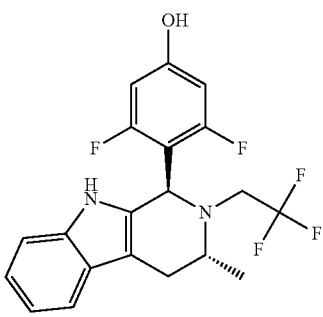 [SMILES: C[C@@H]1Cc2c([nH]c3ccccc23)[C@@H](c2c(F)cc(O)cc2F)N1CC(F)(F)F]

A solution of (R)-1-(1H-indol-3-yl)-N-(2,2,2-trifluoroethyl)propan-2-amine (4.15 g, 16.2 mmol) in toluene (12 mL) was added to a stirred solution of 2,6-difluoro-4-hydroxybenzaldehyde (2.79 g, 17.7 mmol) in toluene (60 mL) and AcOH (6.7 mL) at 20° C. under air. The resulting solution was stirred at 100° C. for 18 hours. Then the reaction was cooled to RT and was purified by ion exchange chromatography, using an SCX column. The desired product was eluted from the column using 1M NH$_3$/MeOH and pure fractions were evaporated to dryness to afford crude (1R,3R)-1-(4-bromo-2,6-difluorophenyl)-2-(2-fluoro-2-methylpropyl)-3-methyl-2,3,4,9-tetrahydro-1H-pyrido[3,4-b]indole as a brown gum. The residue was purified by flash silica chromatography, elution gradient 0 to 10% EtOAc in heptane. Pure fractions were evaporated to dryness to afford the title compound (4.04 g, 63%) as a pale yellow foam; $^1$H NMR (400 MHz, CDCl$_3$, 30° C.) 1.17 (3H, d), 2.63 (1H, ddd), 2.92-3.01 (1H, m), 3.10 (1H, ddd), 3.18-3.28 (1H, m), 3.60 (1H, dt), 5.26 (2H, s), 6.37 (2H, d), 7.12 (1H, pd), 7.22-7.25 (1H, m), 7.47 (1H, d), 7.51 (1H, d); m/z: ES– [M–H]$^-$ 395.4.

Intermediate 94b: Ethyl 2-(3-(2-(3,5-difluoro-4-((1R,3R)-3-methyl-2-(2,2,2-trifluoroethyl)-2,3,4,9-tetrahydro-1H-pyrido[3,4-b]indol-1-yl)phenoxy)ethoxy)propoxy)acetate

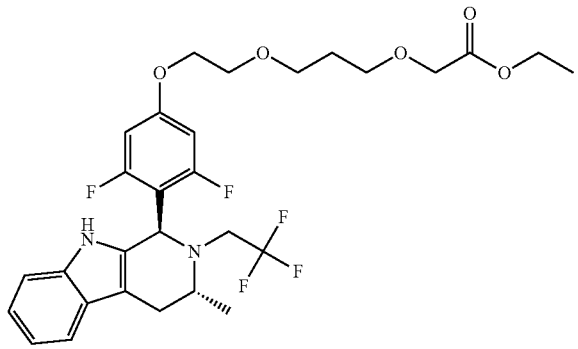 [SMILES: CCOC(=O)COCCCOCCOc1cc(F)c([C@@H]2c3[nH]c4ccccc4c3C[C@@H](C)N2CC(F)(F)F)c(F)c1]

DIAD (0.15 mL, 0.76 mmol) was added dropwise to a stirred solution of 3,5-difluoro-4-((1R,3R)-3-methyl-2-(2,2,2-trifluoroethyl)-2,3,4,9-tetrahydro-1H-pyrido[3,4-b]indol-1-yl)phenol (150 mg, 0.38 mmol), ethyl 2-(3-(2-hydroxyethoxy)propoxy)acetate (156 mg, 0.76 mmol) and triphenylphosphine (199 mg, 0.76 mmol) in DCM (15 mL) at 5° C. The resulting mixture was stirred at 5° C. for 30 minutes and then at 21° C. for 1 hour. DCM (15 mL) and water (25 mL) were added and the layers were separated through a phase separating cartridge. The solvent was removed under reduced pressure. The residue was purified by flash silica chromatography, elution gradient 10 to 40% EtOAc in heptane. Fractions containing product were evaporated to dryness. The crude material was further purified by flash silica chromatography, elution gradient 0 to 10% MeOH in DCM. Pure fractions were evaporated to dryness to afford the title compound (125 mg, 57%) as a yellow oil; $^1$H NMR (400 MHz, CDCl$_3$, 30° C.) 1.17 (3H, d), 1.31 (3H, d), 1.39-1.45 (1H, m), 1.90 (2H, p), 2.63 (1H, dd), 2.9-3.02 (1H, m), 3.11 (1H, dd), 3.23 (1H, dd), 3.75-3.8 (2H, m), 4.03 (2H, s), 4.08 (2H, dd), 4.20 (2H, q), 5.27 (1H, s), 6.29 (4H, s), 6.43-6.5 (2H, m), 7.07-7.15 (2H, m), 7.24 (1H, dd), 7.51 (1H, d), 7.59 (1H, s); m/z: ES+ [M+H]$^+$ 585.3.

Intermediate 94c: 2-(3-(2-(3,5-Difluoro-4-((1R,3R)-3-methyl-(2,2,2-trifluoroethyl)-2,3,4,9-tetrahydro-1H-pyrido[3,4-b]indol-1-yl)phenoxy)ethoxy)propoxy)acetic Acid

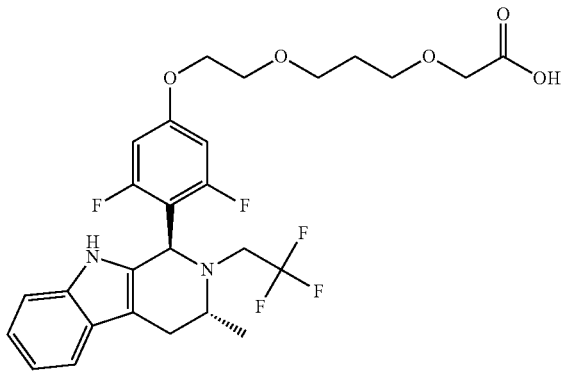

Lithium hydroxide hydrate (18 mg, 0.43 mmol) was added in one portion to ethyl 2-(3-(2-(3,5-difluoro-4-((1R,3R)-3-methyl-2-(2,2,2-trifluoroethyl)-2,3,4,9-tetrahydro-1H-pyrido[3,4-b]indol-1-yl)phenoxy)ethoxy)propoxy)acetate (125 mg, 0.21 mmol) in THF (6 mL) and water (2 mL) at 20° C. The resulting solution was stirred at RT for 30 mins. The organic solvent was removed under reduced pressure. The resulting mixture was acidified with 2M HCl and extracted into EtOAc (2×10 mL). The organic extracts were washed with brine (5 mL) and evaporated to afford crude product as a yellow gum which was used in the next step without further purification; m/z: ES+ [M+H]+ 557.2.

Example 94: (2S,4R)-1-((S)-2-(2-(3-(2-(3,5-Difluoro-4-((1R,3R)-3-methyl-2-(2,2,2-trifluoroethyl)-2,3,4,9-tetrahydro-1H-pyrido[3,4-b]indol-1-yl)phenoxy)ethoxy)propoxy)acetamido)-3,3-dimethylbutanoyl)-4-hydroxy-N-(4-(4-methylthiazol-5-yl)benzyl)pyrrolidine-2-carboxamide Intermediate 95a: Ethyl 2-(2-(2-(2-(3,5-difluoro-4-((1R,3R)-3-methyl-2-(2,2,2-trifluoroethyl)-2,3,4,9-tetrahydro-1H-pyrido[3,4-b]indol-1-yl)phenoxy)ethoxy)ethoxy)ethoxy)acetate

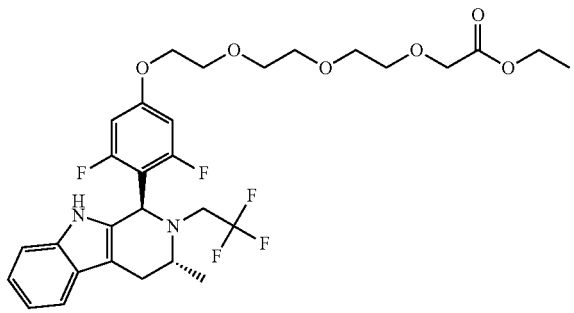

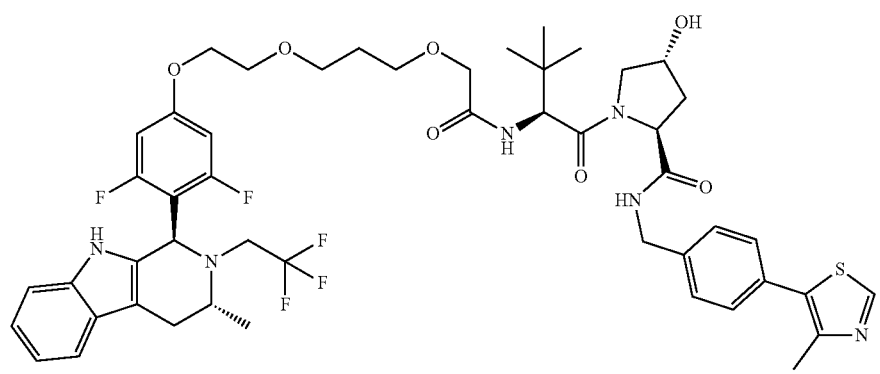 [SMILES: Cc1ncsc1-c1ccc(CNC(=O)[C@@H]2C[C@@H](O)CN2C(=O)[C@@H](NC(=O)COCCCOCCOc2cc(F)c([C@@H]3c4[nH]c5ccccc5c4C[C@@H](C)N3CC(F)(F)F)c(F)c2)C(C)(C)C)cc1]

HATU (123 mg, 0.32 mmol) was added portionwise to 2-(3-(2-(3,5-difluoro-4-((1R,3R)-3-methyl-2-(2,2,2-trifluoroethyl)-2,3,4,9-tetrahydro-1H-pyrido[3,4-b]indol-1-yl)phenoxy)ethoxy)propoxy)acetic acid (120 mg, 0.22 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (96 mg, 0.20 mmol) and triethylamine (0.12 mL, 0.86 mmol) in DMF (5 mL) at 20° C. under nitrogen. The resulting mixture was stirred at 20° C. for 18 hours. The reaction mixture was diluted with EtOAc (25 mL), and washed sequentially with saturated NaHCO$_3$ (25 mL), water (25 mL), and saturated brine (25 mL). The organic layer was dried with MgSO$_4$, filtered and evaporated. The residue was purified by preparative HPLC to afford the title compound (32 mg, 15%); $^1$H NMR (400 MHz, CDCl$_3$, 30° C.) 0.94 (9H, s), 1.16 (3H, d), 1.87 (2H, p), 2.08 (1H, dd), 2.47 (1H, s), 2.48 (3H, s), 2.54-2.69 (2H, m), 2.88-3.02 (1H, m), 3.10 (1H, dd), 3.18-3.31 (1H, m), 3.56 (3H, t), 3.62 (3H, t), 3.67 (1H, d), 3.71-3.84 (2H, m), 3.87 (1H, d), 3.97-4.11 (3H, m), 4.33 (1H, dd), 4.49-4.63 (3H, m), 4.73 (1H, t), 5.26 (1H, s), 6.41 (2H, d), 7.10 (2H, dtd), 7.17 (1H, d), 7.21-7.25 (2H, m), 7.32-7.39 (4H, m), 7.48-7.53 (1H, m), 8.55 (1H, s), 8.65 (1H, s); m/z: ES− [M−H]− 967.8.

DIAD (0.15 mL, 0.76 mmol) was added dropwise to a stirred solution of 3,5-difluoro-4-((1R,3R)-3-methyl-2-(2,2,2-trifluoroethyl)-2,3,4,9-tetrahydro-1H-pyrido[3,4-b]indol-1-yl)phenol (150 mg, 0.38 mmol), ethyl 2-(2-(2-(2-hydroxyethoxy)ethoxy)ethoxy)acetate (180 mg, 0.76 mmol) and triphenylphosphine (199 mg, 0.76 mmol) in DCM (3 mL) at 5° C. The resulting mixture was stirred at 5° C. for 30 minutes and then at RT for 18 hours. DCM (10 mL) and water (25 mL) were added and the layers were separated through a phase separating cartridge. The organic layer was loaded directly on to a silica column and was purified by flash silica chromatography, elution gradient 0 to 100% EtOAc in heptane. Pure fractions were evaporated to dryness to afford the title compound (121 mg, 52%); $^1$H NMR (400 MHz, CDCl$_3$, 30° C.) 1.17 (3H, d), 1.27 (3H, t), 2.63 (1H, dd), 2.92-2.99 (1H, m), 3.11 (1H, dd), 3.17-3.28 (1H, m), 3.59 (1H, q), 3.66-3.73 (8H, m), 3.81-3.86 (2H, m), 4.07-4.11 (2H, m), 4.11-4.14 (2H, m), 4.20 (2H, q), 5.27 (1H, s), 6.43-6.49 (2H, m), 7.07-7.15 (2H, m), 7.24 (1H, dd), 7.51 (1H, d), 7.60 (1H, s); m/z: ES− [M−H]− 613.5.

Intermediate 95b: 2-(2-(2-(2-(3,5-Difluoro-4-((1R,3R)-3-methyl-2-(2,2,2-trifluoroethyl)-2,3,4,9-tetrahydro-1H-pyrido[3,4-b]indol-1-yl)phenoxy)ethoxy)ethoxy)ethoxy)acetic Acid

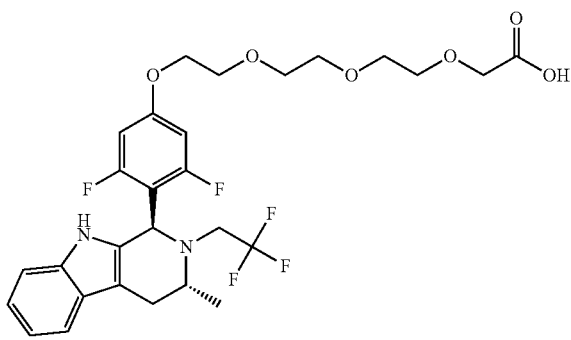 [SMILES: C[C@@H]1Cc2c([nH]c3ccccc23)[C@@H](c2c(F)cc(OCCOCCOCCOCC(=O)O)cc2F)N1CC(F)(F)F]

Lithium hydroxide hydrate (17 mg, 0.39 mmol) was added in one portion to ethyl 2-(2-(2-(2-(3,5-difluoro-4-((1R,3R)-3-methyl-2-(2,2,2-trifluoroethyl)-2,3,4,9-tetrahydro-1H-pyrido[3,4-b]indol-1-yl)phenoxy)ethoxy)ethoxy)ethoxy)acetate (120 mg, 0.20 mmol) in THF (6 mL) and water (2 mL) at 20° C. The resulting solution was stirred at RT for 30 mins. The organic solvent was removed under reduced pressure. The resulting mixture was acidified with 2M HCl and extracted into EtOAc (2×10 mL). The organic extracts were washed with brine (5 mL) and evaporated to afford crude product as a yellow gum which was used in the next step without purification (assumed quantitative); $^1$H NMR (400 MHz, DMSO, 30° C.) 1.13 (3H, d), 2.62 (1H, dd), 2.85 (1H, dd), 2.93-3.04 (1H, m), 3.38-3.51 (2H, m), 3.52-3.65 (9H, m), 3.69-3.76 (2H, m), 4.01 (2H, s), 4.1-4.18 (2H, m), 5.22 (1H, s), 6.70 (2H, d), 6.99 (2H, dt), 7.21 (1H, d), 7.41 (1H, d), 10.61 (1H, s); m/z: ES− [M−H]− 585.5.

Example 95: (2S,4R)-1-((S)-2-(tert-Butyl)-14-(3,5-difluoro-4-((1R,3R)-3-methyl-2-(2,2,2-trifluoroethyl)-2,3,4,9-tetrahydro-1H-pyrido[3,4-b]indol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide HATU (114 mg, 0.30 mmol) was added portionwise to 2-(2-(2-(2-(3,5-difluoro-4-((1R,3R)-3-methyl-2-(2,2,2-trifluoroethyl)-2,3,4,9-tetrahydro-1H-pyrido[3,4-b]indol-1-yl)phenoxy)ethoxy)ethoxy)ethoxy)acetic acid (117 mg, 0.20 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (89 mg, 0.19 mmol) and triethylamine (0.11 mL, 0.80 mmol) in DMF (5 mL) at 20° C. under nitrogen. The resulting mixture was stirred at 20° C. for 18 hours. The reaction mixture was diluted with EtOAc (25 mL), and washed sequentially with saturated NaHCO$_3$ (25 mL), water (25 mL), and saturated brine (25 mL). The organic layer was dried over MgSO$_4$, filtered and evaporated. The residue was purified by preparative HPLC to afford the title compound (65 mg, 33%) as a white solid; $^1$H NMR (400 MHz, CDCl$_3$, 30° C.) 0.94 (9H, s), 1.17 (3H, d), 2.06 (1H, dd), 2.48 (3H, s), 2.52-2.67 (3H, m), 2.87-3.04 (1H, m), 3.10 (1H, dd), 3.22 (1H, dt), 3.58 (2H, dt), 3.62-3.73 (8H, m), 3.79 (2H, t), 3.87-4.01 (2H, m), 4.01-4.11 (3H, m), 4.31 (1H, dd), 4.48 (2H, d), 4.57 (1H, dd), 4.71 (1H, t), 5.26 (1H, s), 6.40 (2H, d), 7.05-7.15 (2H, m), 7.22-7.25 (1H, m), 7.29 (2H, d), 7.35 (4H, q), 7.48-7.53 (1H, m), 8.37 (1H, s), 8.63 (1H, s); m/z: ES+ [M+H]+999.4.

Intermediate 96a: Ethyl 2-((5-(3,5-difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy)acetate

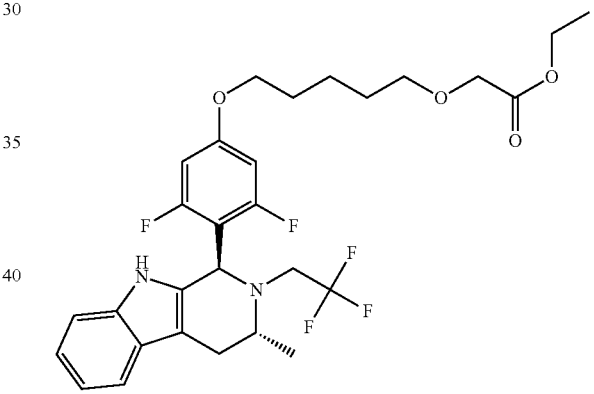

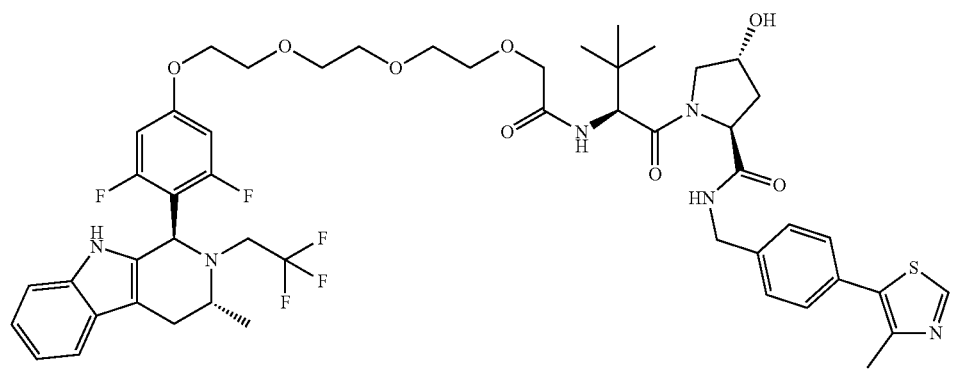 [SMILES: Cc1ncsc1-c1ccc(CNC(=O)[C@@H]2C[C@@H](O)CN2C(=O)[C@@H](NC(=O)COCCOCCOCCOc2cc(F)c([C@@H]3c4[nH]c5ccccc5c4C[C@@H](C)N3CC(F)(F)F)c(F)c2)C(C)(C)C)cc1]

The title compound was prepared in a similar manner to Intermediate 72e using the appropriate phenol and alcohol to afford the desired product (171 mg, 79%); $^1$H NMR (400 MHz, CDCl$_3$, 30° C.) 1.17 (3H, d), 1.26-1.31 (4H, m), 1.56 (2H, dd), 1.69 (2H, dt), 1.81 (2H, dt), 2.63 (1H, dd), 2.91-3.02 (1H, m), 3.11 (1H, dd), 3.23 (1H, dd), 3.55 (2H, t), 3.92 (2H, t), 4.05 (2H, s), 4.21 (2H, q), 5.26 (1H, s), 6.37-6.44 (2H, m), 7.11 (2H, pd), 7.24 (1H, dd), 7.47 (1H, s), 7.49-7.53 (1H, m); m/z: ES− [M−H]⁻ 567.5.

Intermediate 96b: 2-((5-(3,5-Difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy) acetic Acid

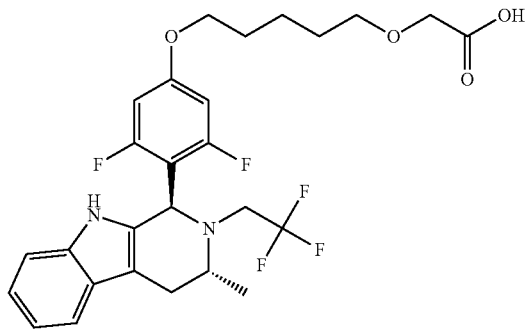 [SMILES: C[C@@H]1Cc2c([nH]c3ccccc23)[C@@H](c2c(F)cc(OCCCCCOCC(=O)O)cc2F)N1CC(F)(F)F]

The title compound was prepared in a similar manner to Intermediate 72f using the appropriate ester to afford the desired product as a yellow gum which was used in the next step without purification (assumed quantitative); $^1$H NMR (400 MHz, DMSO, 30° C.) 1.12 (3H, d), 1.21-1.36 (1H, m), 1.45 (2H, d), 1.52-1.59 (2H, m), 1.67-1.76 (2H, m), 2.61 (1H, dd), 2.79-2.9 (1H, m), 2.96 (1H, dd), 3.38-3.49 (4H, m), 3.97 (2H, s), 3.99 (2H, d), 5.21 (1H, s), 6.66 (2H, d), 6.98 (2H, dt), 7.20 (1H, d), 7.40 (1H, d), 10.59 (1H, s); m/z: ES− [M−H]⁻ 539.4.

Example 96: ((2S,4R)-1-((S)-2-(2-((5-(3,5-Difluoro-4-((1R,3R)-3-methyl-2-(2,2,2-trifluoroethyl)-2,3,4,9-tetrahydro-1H-pyrido[3,4-b]indol-1-yl)phenoxy) pentyl)oxy)acetamido)-3,3-dimethylbutanoyl)-4-hydroxy-N-(4-(4-methylthiazol-5-yl)benzyl) pyrrolidine-2-carboxamide

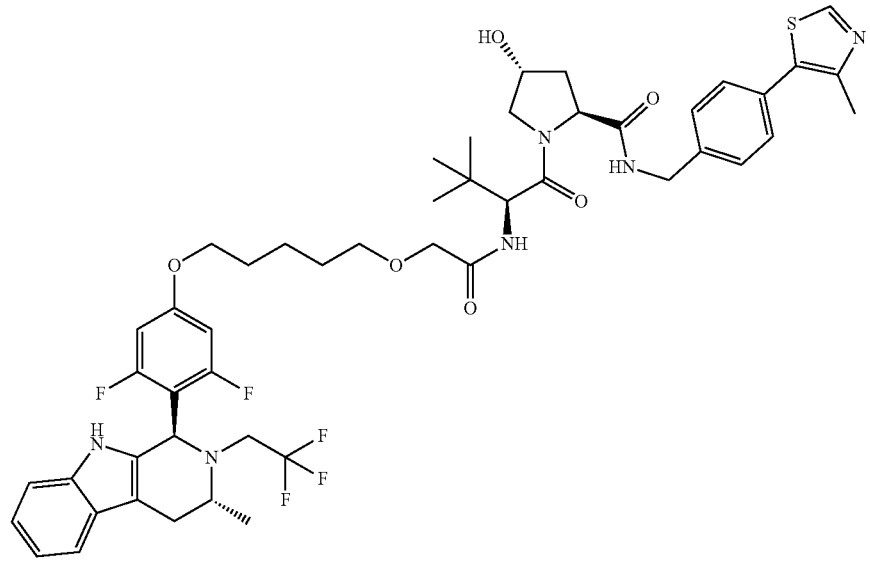 [SMILES: Cc1ncsc1-c1ccc(CNC(=O)[C@@H]2C[C@@H](O)CN2C(=O)[C@@H](NC(=O)COCCCCCOc2cc(F)c([C@@H]3c4[nH]c5ccccc5c4C[C@@H](C)N3CC(F)(F)F)c(F)c2)C(C)(C)C)cc1]

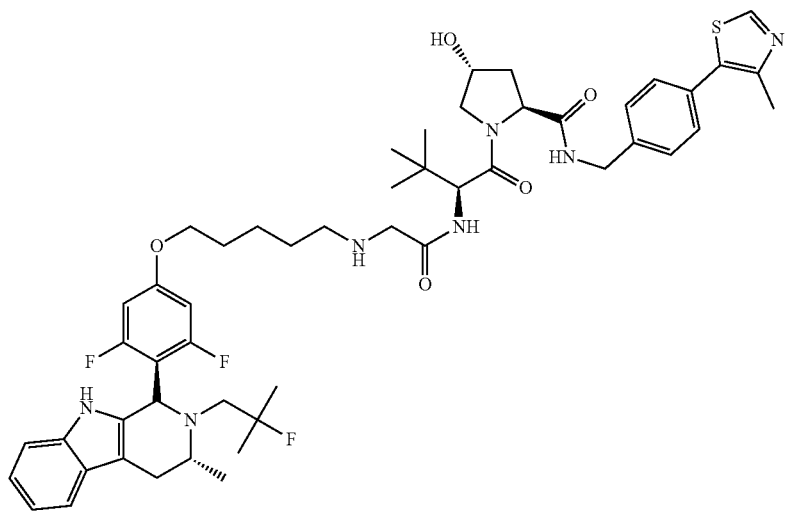

The title compound was prepared in a similar manner to Example 68 using the appropriate carboxylic acid and amine to afford the desired product (43 mg, 15%) as a white solid; $^1$H NMR (400 MHz, CDCl$_3$, 30° C.) 0.93 (9H, s), 1.17 (3H, d), 1.52 (2H, s), 1.68 (2H, p), 1.80 (2H, dt), 2.06 (1H, dd), 2.46 (3H, s), 2.53-2.66 (3H, m), 2.86-3.02 (1H, m), 3.10 (1H, dd), 3.16-3.29 (1H, m), 3.55 (4H, dtd), 3.83-3.99 (4H, m), 4.09 (1H, d), 4.28 (1H, dd), 4.48 (1H, d), 4.52-4.63 (2H, m), 4.69 (1H, t), 5.26 (1H, s), 5.30 (OH, s), 6.36 (2H, d), 7.06-7.18 (3H, m), 7.22-7.25 (1H, m), 7.29 (1H, d), 7.31-7.38 (4H, m), 7.48-7.54 (1H, m), 8.26 (1H, s), 8.63 (1H, s); m/z: ES− [M−H]− 951.8.

Intermediate 97a: 2-(2-((5-(Benzyloxy)pentyl)oxy)ethoxy)tetrahydro-2H-pyran

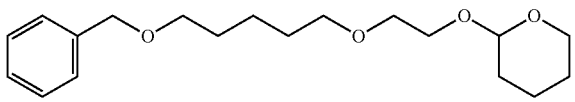 [SMILES: c1ccc(COCCCCCOCCOC2CCCCO2)cc1]

Tetrabutylammonium hydrogen sulfate (1.02 g, 3.00 mmol) was added in one portion to 5-(benzyloxy)pentan-1-ol (3.84 mL, 19.93 mmol) and 2-(2-bromoethoxy)tetrahydro-2H-pyran (3.60 mL, 23.90 mmol) in 50% sodium hydroxide solution (8.5 mL) at 20° C. under air. The resulting mixture was stirred at 70° C. for 18 hours. The cooled reaction mixture was diluted with water (20 mL) and extracted with EtOAc (3×25 mL). The combined organic extracts were washed with water (20 mL), saturated brine solution (20 mL), dried over MgSO$_4$, filtered and evaporated. The residue was purified by flash silica chromatography, elution gradient 0 to 10% EtOAc in heptane. Pure fractions were evaporated to dryness to afford the title compound (3.36 g, 52%) as a colourless oil; $^1$H NMR (400 MHz, CDCl$_3$, 30° C.) 1.38-1.47 (2H, m), 1.52 (2H, dddd), 1.57-1.69 (6H, m), 1.72 (1H, ddt), 1.83 (1H, ddt), 3.47 (5H, td), 3.55-3.63 (3H, m), 3.78-3.9 (2H, m), 4.49 (2H, s), 4.61-4.65 (1H, m), 7.33 (5H, d).

Intermediate 97b: 2-((5-(Benzyloxy)pentyl)oxy)ethan-1-ol

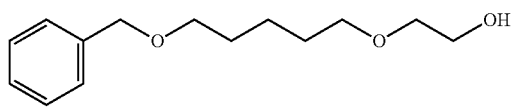 [SMILES: OCCOCCCCCOCc1ccccc1]

2-(2-((5-(Benzyloxy)pentyl)oxy)ethoxy)tetrahydro-2H-pyran (3.36 g, 10.42 mmol) was dissolved in MeOH (30 mL) and 1M aq. HCl (14 mL) was added. The resulting mixture was stirred at 20° C. for 1 hour. The reaction mixture was diluted with water (100 mL), and extracted with EtOAc (3×100 mL). The combined organics were washed with saturated brine (50 mL). The organic layer was dried over MgSO$_4$, filtered and evaporated to afford crude product that was used without further purification; $^1$H NMR (400 MHz, CDCl$_3$, 30° C.) 1.39-1.49 (2H, m), 1.56-1.69 (4H, m), 2.23 (1H, s), 3.47 (4H, t), 3.5-3.54 (2H, m), 3.69-3.75 (2H, m), 4.50 (2H, s), 7.33 (5H, d); m/z: ES+ [M+H]+ 239.2.

Intermediate 97c: Ethyl 2-(2-((5-(benzyloxy)pentyl)oxy)ethoxy)acetate

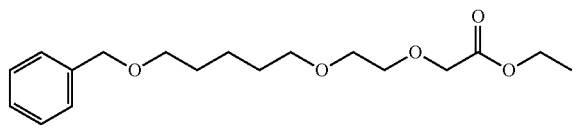 [SMILES: CCOC(=O)COCCOCCCCCOCc1ccccc1]

Ethyl 2-diazoacetate (3.19 mL, 26.00 mmol) in DCM (10 mL) was added slowly to 2-((5-(benzyloxy)pentyl)oxy)ethan-1-ol (2.48 g, 10.40 mmol) and diacetoxyrhodium (230 mg, 0.52 mmol) in DCM (30 mL) at 20° C. over a period of 1 hour under nitrogen. The resulting solution was stirred at 20° C. for 18 hours. The mixture was diluted with DCM (50 mL) and washed with water (3×50 mL). The organic layer was collected and dried using phase separating cartridge then evaporated to dryness. The residue was purified by flash silica chromatography, elution gradient 0 to 10% EtOAc in heptane. Pure fractions were evaporated to dryness to afford the title compound (2.70 g, 80%) a colourless liquid; $^1$H NMR (400 MHz, CDCl$_3$, 30° C.) 1.25-1.3 (3H, m), 1.4-1.47 (2H, m), 1.61 (4H, ddd), 3.46 (4H, td), 3.58-3.64 (2H, m), 3.68-3.73 (2H, m), 4.14 (2H, s), 4.18-4.22 (2H, m), 4.49 (2H, s), 7.21-7.38 (5H, m); m/z: ES+ [M+H]$^+$ 325.2.

Intermediate 97d: Ethyl 2-(2-((5-hydroxypentyl)oxy)ethoxy)acetate

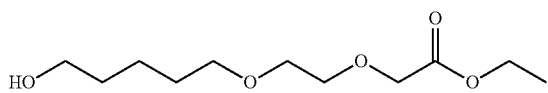 [SMILES: CCOC(=O)COCCOCCCCCO]

Ethyl 2-(2-((5-(benzyloxy)pentyl)oxy)ethoxy)acetate (2.70 g, 8.32 mmol) was dissolved in EtOH (25 mL), 10% palladium on carbon (0.89 g, 0.83 mmol) was added and the reaction mixture stirred at room temperature under an atmosphere of hydrogen (1 bar) for 4 hours. Acetic acid (0.5 mL) was added to the reaction mixture and stirred at room temperature under an atmosphere of hydrogen (1 bar) for 18 hours. The reaction mixture was filtered through celite, eluted with MeOH. The solvent was removed under reduced pressure to afford the title compound (1.90 g, 97%) as a colourless oil; $^1$H NMR (400 MHz, CDCl$_3$, 30° C.) 1.29 (3H, td), 1.44 (2H, td), 1.55-1.65 (4H, m), 3.48 (2H, t), 3.6-3.69 (4H, m), 3.72 (2H, dd), 4.15 (2H, s), 4.22 (3H, q); m/z: ES+ [M+H]$^+$ 235.2.

Intermediate 97e: Ethyl 2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)ethoxy)acetate

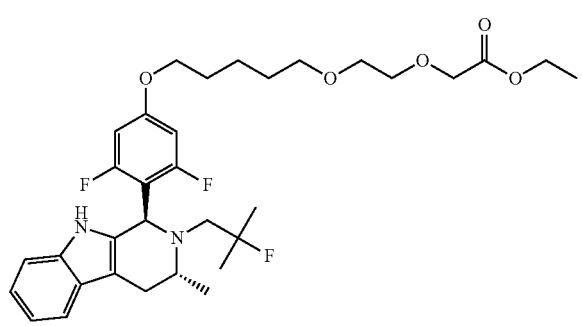 [SMILES: CCOC(=O)COCCOCCCCCOc1cc(F)c([C@@H]2c3[nH]c4ccccc4c3C[C@@H](C)N2CC(C)(C)F)c(F)c1]

DIAD (0.15 mL, 0.77 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (150 mg, 0.39 mmol), ethyl 2-(2-((5-hydroxypentyl)oxy)ethoxy)acetate (181 mg, 0.77 mmol) and triphenylphosphine (203 mg, 0.77 mmol) in DCM (3 mL) at 5° C. The resulting mixture was stirred at 5° C. for 30 minutes and then at 21° C. for 18 hours. DCM (10 mL) and water (25 mL) were added and the layers were separated through a phase separating cartridge. The organic layer was loaded on to a silica column and was purified by flash silica chromatography, elution gradient 10 to 100% EtOAc in heptane. Pure fractions were evaporated to afford the title compound (210 mg, 90%); m/z: ES– [M–H]$^-$ 603.6.

Intermediate 97f: 2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)ethoxy)acetic Acid

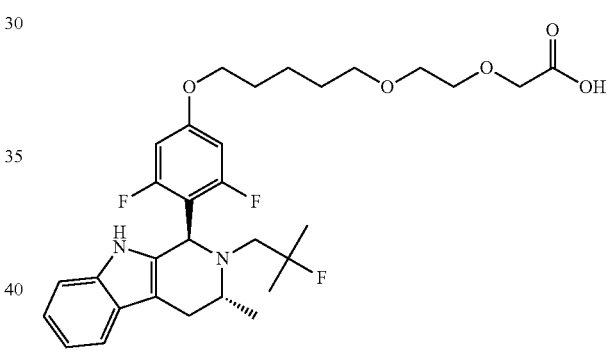

Lithium hydroxide hydrate (29 mg, 0.69 mmol) was added in one portion to ethyl 2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy) ethoxy)acetate (0.21 g, 0.35 mmol) in THF (6 mL) and water (2 mL) at 20° C. The resulting solution was stirred at RT for 30 mins. The organic solvent was removed under reduced pressure. The resulting mixture was acidified with 2M HCl and extracted into EtOAc (2×10 mL). The organic extracts were washed with brine (5 mL) and evaporated to afford crude product as a yellow gum which was used in the next step without purification (assumed quantitative); $^1$H NMR (400 MHz, DMSO, 30° C.) 1.04 (3H, d), 1.18 (3H, s), 1.19-1.22 (3H, m), 1.39-1.46 (2H, m), 1.51-1.57 (2H, m), 1.70 (2H, q), 2.37 (1H, d), 2.53-2.59 (1H, m), 2.77-2.95 (2H, m), 3.40 (2H, t), 3.49 (2H, dd), 3.57 (2H, dd), 3.94-4 (2H, m), 4.01 (2H, d), 4.02-4.06 (1H, m), 4.77 (1H, p), 5.12 (1H, s), 6.64 (2H, d), 6.96 (2H, dt), 7.18 (1H, d), 7.39 (1H, d), 10.49 (1H, s); m/z: ES+ [M+H]$^+$ 577.4.

Example 97: (2S,4R)-1-((S)-2-(2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)ethoxy)acetamido)-3,3-dimethylbutanoyl)-4-hydroxy-N-(4-(4-methylthiazol-5-yl)benzyl)pyrrolidine-2-carboxamide

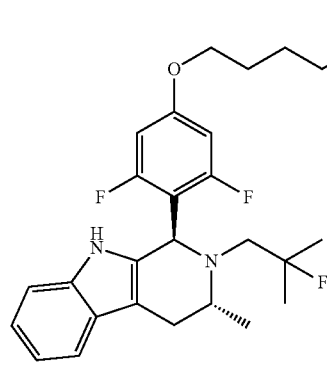
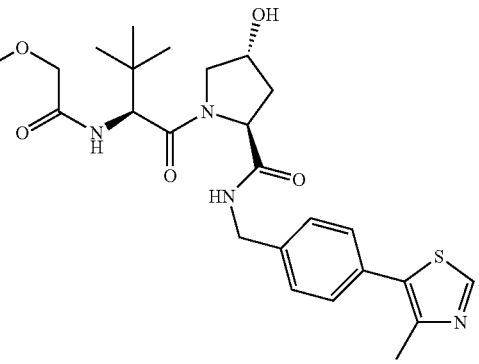

HATU (200 mg, 0.53 mmol) was added portionwise to 2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)ethoxy)acetic acid (202 mg, 0.35 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (155 mg, 0.33 mmol) and triethylamine (0.20 mL, 1.40 mmol) in DMF (5 mL) at RT under nitrogen. The resulting mixture was stirred at RT for 18 hours. The reaction mixture was diluted with EtOAc (25 mL), and washed sequentially with saturated NaHCO₃ (25 mL), water (25 mL), and saturated brine (25 mL). The organic layer was dried over MgSO₄, filtered and evaporated. The crude product was purified by preparative HPLC to afford the title compound (135 mg, 39%) as a white solid; $^1$H NMR (400 MHz, CDCl₃, 30° C.) 0.94 (9H, s), 1.10 (3H, d), 1.17 (3H, d), 1.23 (3H, d), 1.45-1.54 (2H, m), 1.65 (2H, dd), 1.76 (2H, dt), 2-2.1 (1H, m), 2.39 (1H, dd), 2.48 (3H, s), 2.53-2.64 (2H, m), 2.73 (1H, d), 2.85 (1H, dd), 3.09 (1H, dd), 3.49 (2H, t), 3.59 (3H, dq), 3.66 (3H, dd), 3.86 (2H, t), 3.91-4.03 (2H, m), 4.09 (1H, d), 4.30 (1H, dd), 4.42-4.64 (3H, m), 4.72 (1H, t), 5.19 (1H, s), 6.3-6.36 (2H, m), 7.05-7.12 (2H, m), 7.2-7.24 (1H, m), 7.29 (1H, s), 7.31-7.38 (5H, m), 7.51 (1H, dd), 8.15 (1H, s), 8.62 (1H, s); m/z: ES− [M−H]⁻ 987.8.

Intermediate 98a: 4-(Benzyloxy)butanal

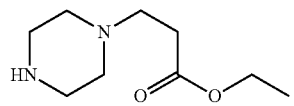

1,1,1-Triacetoxy-1,1-dihydro-1,2-benziodoxol-3(1H)-one (5.88 g, 13.90 mmol) was added to a stirred solution of 4-(benzyloxy)butan-1-ol (2.44 mL, 13.90 mmol) in DCM (50 mL) at RT under N₂ for 4 hours. The mixture was partitioned between 1M NaOH solution and DCM, the organics separated washed with water, dried over MgSO₄ and evaporated under reduced pressure. The residue was purified by flash silica chromatography, elution gradient 0 to 30% heptane in EtOAc. Pure fractions were evaporated to dryness to afford the title compound (1.74 g, 70%) as a colourless oil; $^1$H NMR (400 MHz, CDCl₃, 30° C.) 1.89-2 (2H, m), 2.54 (2H, td), 3.50 (2H, t), 4.48 (2H, s), 7.26-7.37 (5H, m), 9.77 (1H, t).

Intermediate 98b: tert-Butyl 4-(3-ethoxy-3-oxopropyl)piperazine-1-carboxylate

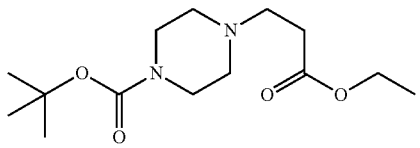 [SMILES: CCOC(=O)CCN1CCN(C(=O)OC(C)(C)C)CC1]

Ethyl 3-bromopropanoate (2.46 mL, 19.3 mmol) was added at RT to a solution of tert-butyl piperazine-1-carboxylate (3.00 g, 16.11 mmol) and potassium carbonate (6.68 g, 48.3 mmol) in acetonitrile (25 mL), and the reaction stirred at 25° C. for 18 hours. The reaction mixture was cooled to RT, diluted with EtOAc (50 mL) and filtered. The filtrate was concentrated under reduced pressure and purified by flash silica chromatography, elution gradient 0 to 10% 1M NH₃/MeOH in DCM. Pure fractions were evaporated to dryness to afford the title compound (3.03 g, 66%) as a colourless oil; $^1$H NMR (400 MHz, CDCl₃, 30° C.) 1.26 (3H, t), 1.46 (9H, s), 2.34-2.44 (4H, m), 2.48 (2H, t), 2.70 (2H, t), 3.36-3.45 (4H, m), 4.14 (2H, q); m/z: ES+ [M+H]⁺ 287.3.

Intermediate 98c: Ethyl 3-(piperazin-1-yl)propanoate.HCl

A solution of 4M HCl in dioxane (13.2 mL, 52.9 mmol) was added at RT to a solution of tert-butyl 4-(3-ethoxy-3-oxopropyl)piperazine-1-carboxylate (3.03 g, 10.58 mmol) in dioxane (10 mL) and the reaction stirred for 18 hours. Diethyl ether (100 mL) was added and the resulting solid was filtered under vacuum and washed with diethyl ether to afford the title compound (2.00 g) as a white solid that was used without further purification; ¹H NMR (400 MHz, MeOD, 30° C.) 1.28 (3H, t), 2.94 (2H, t), 3.53 (2H, t), 3.61 (8H, s), 4.21 (2H, q); m/z: ES+ [M+H]⁺ 187.2.

Intermediate 98d: Ethyl 3-(4-(4-(benzyloxy)butyl)piperazin-1-yl)propanoate

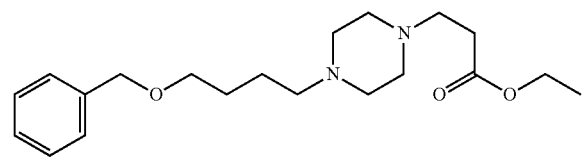 [SMILES: CCOC(=O)CCN1CCN(CCCCOCc2ccccc2)CC1]

Sodium triacetoxyborohydride (3.57 g, 16.8 mmol) was added to 4-(benzyloxy)butanal (1.00 g, 5.61 mmol), ethyl 3-(piperazin-1-yl)propanoate, HCl (1.50 g, 6.73 mmol) and acetic acid (0.16 mL, 2.81 mmol) in DCM (100 mL) at 20° C. The resulting solution was stirred at RT for 4 hours. The reaction mixture was washed with saturated NaHCO₃, dried over anhydrous Na₂SO₄ and the solvent was removed in vacuo. The crude product was purified by flash silica chromatography, elution gradient 0 to 10% MeOH in DCM. Pure fractions were evaporated to dryness to afford the title compound (1.60 g, 82%) as a colourless oil; ¹H NMR (400 MHz, CDCl₃, 30° C.) 1.25 (3H, t), 1.53-1.75 (5H, m), 2.26-2.37 (2H, m), 2.48 (9H, dd), 2.69 (2H, t), 3.48 (2H, t), 4.13 (2H, q), 4.49 (2H, s), 7.31-7.36 (5H, m); m/z: ES+ [M+H]⁺ 349.3.

Intermediate 98e: Ethyl 3-(4-(4-hydroxybutyl)piperazin-1-yl)propanoate

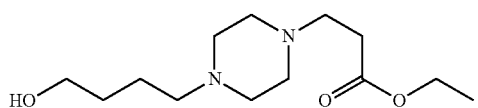 [SMILES: CCOC(=O)CCN1CCN(CCCCO)CC1]

Ethyl 3-(4-(4-(benzyloxy)butyl)piperazin-1-yl)propanoate (1.60 g, 4.59 mmol) was dissolved in EtOH (25 mL), 10% palladium on carbon (490 mg, 0.46 mmol) was added and the reaction was stirred at RT under an atmosphere of hydrogen for 4 hours. Acetic acid (0.5 mL) was added to the reaction and the suspension stirred under hydrogen for 18 hours. The reaction mixture was filtered through celite, eluted with MeOH. The solvent was removed under reduced pressure to afford the title compound (1.10 g, 93%) as a colourless oil; ¹H NMR (400 MHz, CDCl₃, 30° C.) 1.25 (3H, t), 1.61-1.73 (4H, m), 2.36-2.42 (2H, m), 2.49 (9H, dt), 2.70 (2H, t), 3.48 (1H, s), 3.54-3.6 (2H, m), 3.65-4.08 (1H, m), 4.11-4.18 (2H, m); m/z: ES+ [M+H]⁺ 259.3.

Intermediate 98f: Ethyl 3-(4-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butyl)piperazin-1-yl)propanoate

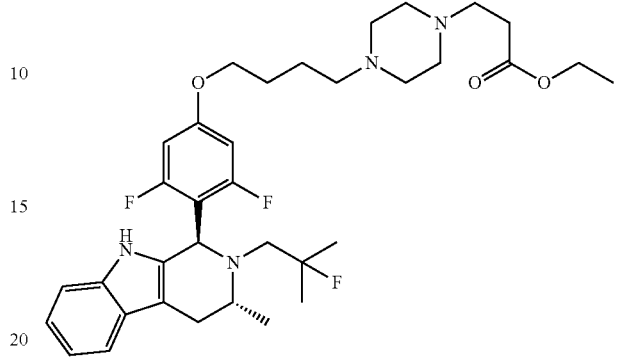

(1R,3R)-1-(4-Bromo-2,6-difluorophenyl)-2-(2-fluoro-2-methylpropyl)-3-methyl-2,3,4,9-tetrahydro-1H-pyrido[3,4-b]indole (150 mg, 0.33 mmol), ethyl 3-(4-(4-hydroxybutyl)piperazin-1-yl)propanoate (172 mg, 0.66 mmol), cesium carbonate (325 mg, 1.00 mmol) and RockPhos Pd G3 (14 mg, 0.02 mmol) were dissolved in toluene (5 mL) and degassed with N₂. The mixture was heated to 95° C. for 18 hours. The reaction mixture was cooled to RT, diluted with DCM (20 mL) and washed with water (20 mL). The organics were dried over anhydrous MgSO₄, filtered and concentrated. The residue was purified by flash silica chromatography, elution gradient 0 to 10% MeOH in DCM. Pure fractions were evaporated to dryness to afford the title compound (114 mg, 55%) as a brown gum; m/z: ES– [M–H]⁻ 627.7.

Intermediate 98g: 2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)ethoxy)acetic Acid

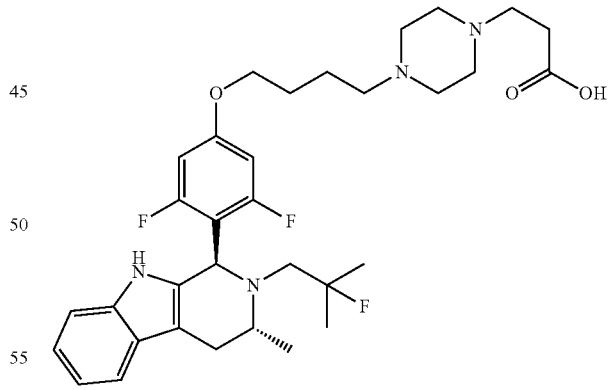

A solution of 2M sodium hydroxide (0.09 mL, 0.18 mmol) was added to a stirred solution of ethyl 3-(4-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butyl)piperazin-1-yl)propanoate (114 mg, 0.18 mmol) in EtOH (2 mL) at RT. The resulting mixture was stirred for 18 hours at RT. The reaction mixture was quenched with 2M HCl (0.09 mL) and evaporated to afford crude product which was used without further purification; m/z: ES+ [M+H]⁺ 601.5.

Example 98: (2S,4R)-1-((S)-2-(3-(4-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butyl)piperazin-1-yl)propanamido)-3,3-dimethylbutanoyl)-4-hydroxy-N-(4-(4-methylthiazol-5-yl)benzyl)pyrrolidine-2-carboxamide

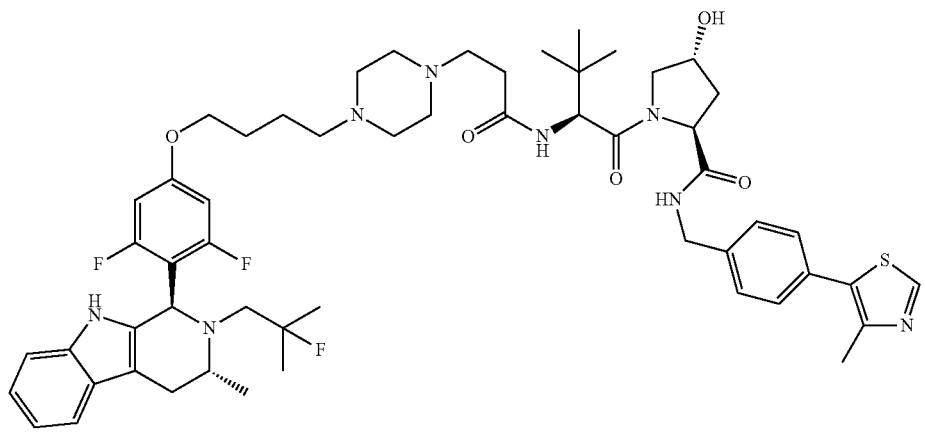 [SMILES: Cc1ncsc1-c1ccc(CNC(=O)[C@@H]2C[C@@H](O)CN2C(=O)[C@@H](NC(=O)CCN2CCN(CCCCOc3cc(F)c([C@@H]4c5[nH]c6ccccc6c5C[C@@H](C)N4CC(C)(C)F)c(F)c3)CC2)C(C)(C)C)cc1]

The title compound was prepared in a similar manner to Example 68 using the appropriate carboxylic acid and amine to afford the desired product (63 mg, 35%) as a white solid; $^1$H NMR (400 MHz, CDCl$_3$, 30° C.) 0.96 (9H, s), 1.10 (3H, d), 1.18 (3H, d), 1.23 (3H, d), 1.61-1.67 (2H, m), 1.77 (2H, p), 2.12 (1H, dd), 2.38 (7H, q), 2.50 (3H, s), 2.51-2.65 (10H, m), 2.86 (1H, dd), 3.09 (1H, dd), 3.25 (1H, s), 3.52 (1H, dd), 3.64-3.72 (1H, m), 3.90 (2H, t), 4.25 (1H, d), 4.28-4.38 (2H, m), 4.48 (1H, s), 4.57 (1H, dd), 4.78 (1H, t), 5.19 (1H, s), 6.36 (2H, d), 7.06-7.12 (2H, m), 7.21 (1H, dd), 7.31-7.38 (4H, m), 7.45 (1H, t), 7.51 (1H, dd), 7.72 (1H, s), 8.63 (1H, s), 9.20 (1H, d); m/z: ES– [M–H]⁻ 1011.9.

Intermediate 99a: (3R,5S)-1-((S)-2-(2-(2-(2-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetamido)-3,3-dimethylbutanoyl)-5-((4-(4-methylthiazol-5-yl)benzyl)carbamoyl)pyrrolidin-3-yl (tert-butoxycarbonyl)-L-isoleucinate

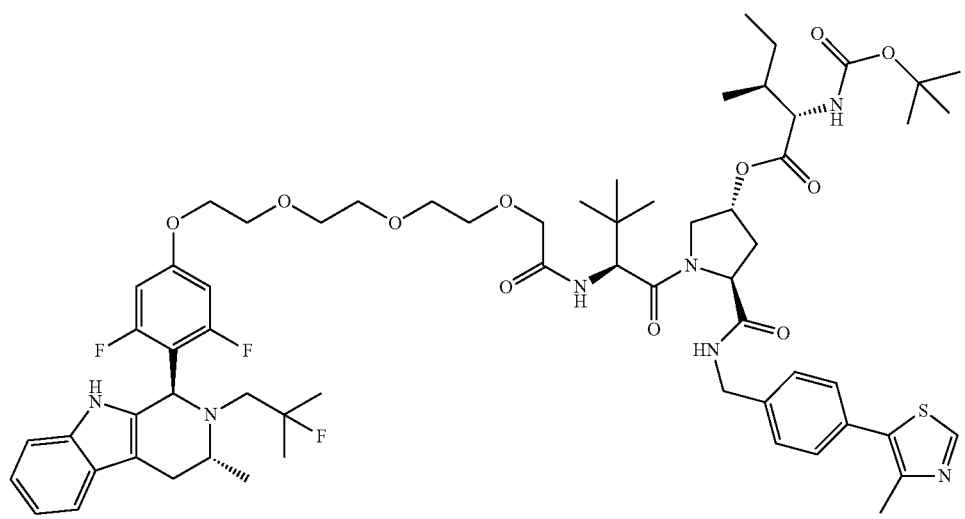 [SMILES: CC[C@H](C)[C@H](NC(=O)OC(C)(C)C)C(=O)O[C@@H]1C[C@@H](C(=O)NCc2ccc(-c3scnc3C)cc2)N(C(=O)[C@@H](NC(=O)COCCOCCOCCOc2cc(F)c([C@@H]3c4[nH]c5ccccc5c4C[C@@H](C)N3CC(C)(C)F)c(F)c2)C(C)(C)C)C1]

To a solution of (2S,4R)-1-((S)-2-(tert-butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide (150 mg, 0.15 mmol) and (tert-butoxycarbonyl)-L-isoleucine (70 mg, 0.30 mmol) in DCM (4 mL) was added N,N-dimethylpyridin-4-amine (4 mg, 0.03 mmol) and 3-(((ethylimino)methylene)amino)-N,N-dimethylpropan-1-amine hydrochloride (58 mg, 0.30 mmol). The solution was stirred at RT for 2 hours. The mixture was diluted with DCM and washed with water, 1M HCl and saturated NaHCO₃. The organics were concentrated and the residue was purified by flash silica chromatography, elution gradient 0 to 10% MeOH in DCM. Fractions containing product were evaporated to dryness to afford the title compound (163 mg, 89%) as a white solid; $^1$H NMR (400 MHz, CDCl₃, 27° C.) 0.89 (3H, d), 0.91 (11H, s), 1.10 (3H, d), 1.17 (3H, d), 1.22 (3H, d), 1.34-1.4 (1H, m), 1.43 (9H, s), 1.44 (1H, s), 1.84 (1H, s), 2.15 (1H, td), 2.38 (1H, dd), 2.47 (3H, s), 2.61 (1H, dd), 2.74-2.92 (2H, m), 3.09 (1H, dd), 3.65-3.74 (10H, m), 3.77-3.84 (3H, m), 3.96-4.04 (4H, m), 4.05-4.15 (1H, m), 4.23 (1H, dd), 4.30 (1H, dd), 4.48-4.63 (2H, m), 4.69 (1H, dd), 5.19 (1H, s), 5.34 (1H, d), 5.41 (1H, s), 6.36 (2H, d), 7.05-7.14 (2H, m), 7.22 (3H, dt), 7.35 (4H, q), 7.51 (1H, dd), 8.15 (1H, s), 8.63 (1H, s); m/z: ES− [M−H]⁻ 1203.0.

Example 99: (3R,5S)-1-((S)-2-(2-(2-(2-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetamido)-3,3-dimethylbutanoyl)-5-((4-(4-methylthiazol-5-yl)benzyl)carbamoyl)pyrrolidin-3-yl L-isoleucinate Formate

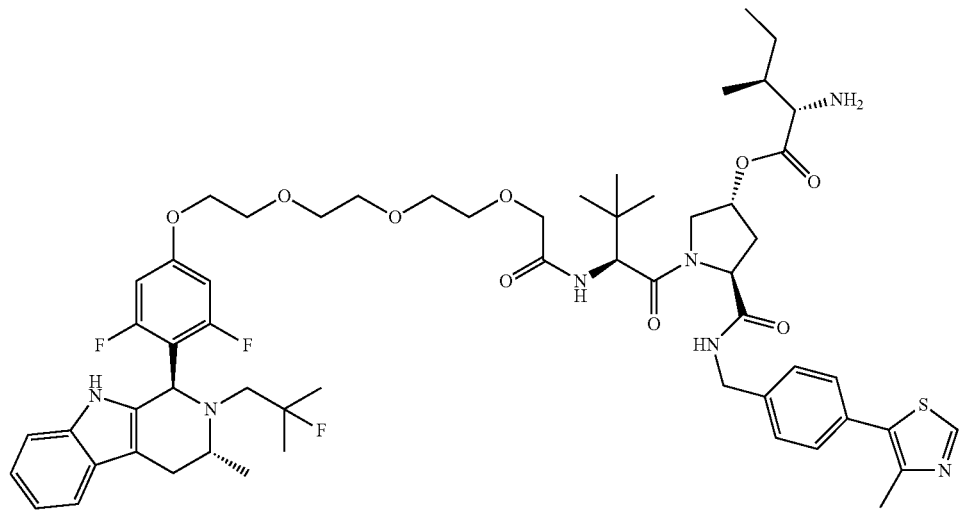 [SMILES: CC[C@H](C)[C@H](N)C(=O)O[C@@H]1C[C@@H](C(=O)NCc2ccc(-c3scnc3C)cc2)N(C(=O)[C@@H](NC(=O)COCCOCCOCCOc2cc(F)c([C@@H]3c4[nH]c5ccccc5c4C[C@@H](C)N3CC(C)(C)F)c(F)c2)C(C)(C)C)C1]

A solution of 4M HCl in dioxane (0.34 mL, 1.35 mmol) was added at RT to (3R,5S)-1-((S)-2-(2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetamido)-3,3-dimethylbutanoyl)-5-((4-(4-methylthiazol-5-yl)benzyl)carbamoyl)pyrrolidin-3-yl (tert-butoxycarbonyl)-L-isoleucinate (163 mg, 0.14 mmol) and the reaction stirred at room temperature for 30 mins. The solvent was remove under reduced pressure. The residue was purified by preparative HPLC to afford the title compound (70 mg, 45%); $^1$H NMR (400 MHz, DMSO, 100° C.) 0.86 (6H, dt), 0.98 (9H, s), 1.08 (3H, d), 1.17 (3H, d), 1.22 (3H, d), 1.39-1.52 (1H, m), 1.54-1.66 (1H, m), 2.26 (2H, d), 2.36-2.44 (1H, m), 2.46 (4H, s), 2.55-2.57 (1H, m), 2.60 (1H, d), 2.81-2.87 (1H, m), 2.9-2.94 (2H, m), 3.17 (1H, d), 3.62 (10H, dt), 3.76 (2H, d), 3.85-4.02 (4H, m), 4.1-4.18 (2H, m), 4.26-4.47 (2H, m), 4.47-4.62 (2H, m), 5.18 (1H, s), 5.33 (1H, s), 6.60 (2H, d), 6.91-7.02 (2H, m), 7.19-7.27 (2H, m), 7.40 (5H, d), 8.22 (1H, s), 8.90 (1H, s), 10.20 (1H, s); m/z: ES+ [M+H]$^+$ 1104.4.

Intermediate 100a: (3R,5S)-1-((S)-2-(2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetamido)-3,3-dimethylbutanoyl)-5-((4-(4-methylthiazol-5-yl)benzyl)carbamoyl)pyrrolidin-3-yl (tert-butoxycarbonyl)-L-valyl-L-alaninate To a solution of (2S,4R)-1-((S)-2-(tert-butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide (150 mg, 0.15 mmol) and (tert-butoxycarbonyl)-L-valyl-L-alanine (87 mg, 0.30 mmol) in DCM (4 mL) was added 3-(((ethylimino)methylene)amino)-N,N-dimethylpropan-1-amine hydrochloride (58 mg, 0.30 mmol) and N,N-dimethylpyridin-4-amine (4 mg, 0.03 mmol). The solution was stirred at RT for 2 hours. The mixture was diluted with DCM and washed with water, 1M HCl and saturated NaHCO$_3$. The residue was purified by flash silica chromatography, elution gradient 0 to 10% MeOH in DCM. Fractions containing product were evaporated to dryness to afford the title compound (141 mg, 74%) as a white solid; $^1$H NMR (400 MHz, CDCl$_3$, 27° C.) 0.85-0.96 (16H, m), 1.10 (3H, d), 1.17 (3H, d), 1.22 (3H, d), 1.30 (1H, d), 1.37 (2H, d), 1.43 (9H, d), 1.86-1.95 (1H, m), 2.11-2.24 (1H, m), 2.38 (1H, dd), 2.48 (3H, d), 2.61 (1H, dd), 2.85 (2H, dd), 3.02-3.13 (1H, m), 3.64-3.73 (10H, m), 3.75-3.81 (2H, m), 3.92 (1H, d), 4.02 (3H, dt), 4.17 (1H, d), 4.23 (1H, d), 4.31 (1H, d), 4.57 (2H, td), 4.72 (2H, q), 5.21 (2H, d), 5.36 (1H, s), 6.37 (2H, dd), 7.03-7.15 (2H, m), 7.18-7.24 (2H, m), 7.36 (4H, td), 7.44 (1H, s), 7.48-7.57 (1H, m), 8.14 (1H, d), 8.63 (1H, d).

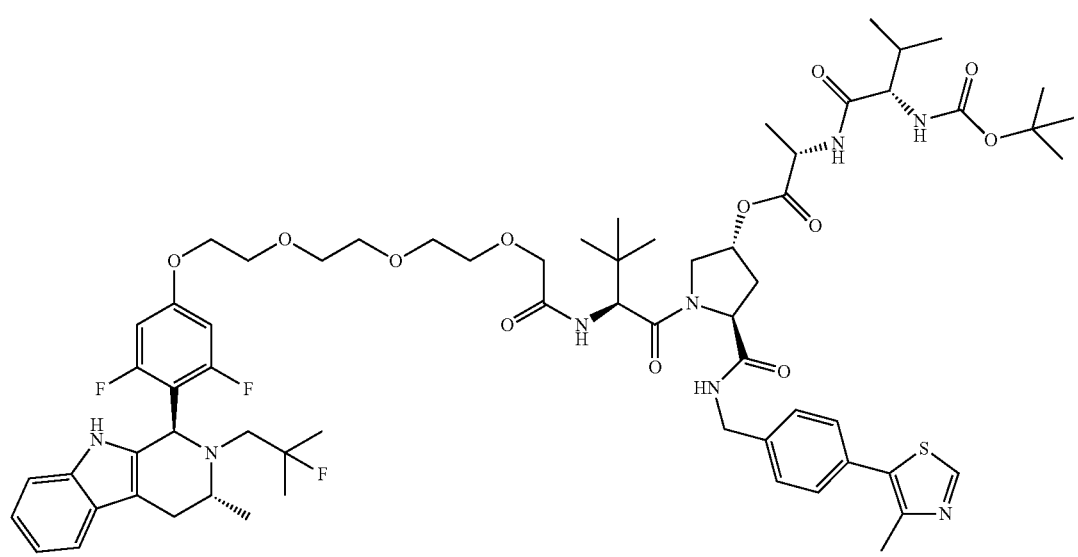 [SMILES: Cc1ncsc1-c1ccc(CNC(=O)[C@@H]2C[C@@H](OC(=O)[C@H](C)NC(=O)[C@@H](NC(=O)OC(C)(C)C)C(C)C)CN2C(=O)[C@@H](NC(=O)COCCOCCOCCOc2cc(F)c([C@@H]3c4[nH]c5ccccc5c4C[C@@H](C)N3CC(C)(C)F)c(F)c2)C(C)(C)C)cc1]

Example 100: (3R,5S)-1-((S)-2-(2-(2-(2-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetamido)-3,3-dimethylbutanoyl)-5-((4-(4-methylthiazol-5-yl)benzyl)carbamoyl)pyrrolidin-3-yl L-valyl-L-alaninate Formate

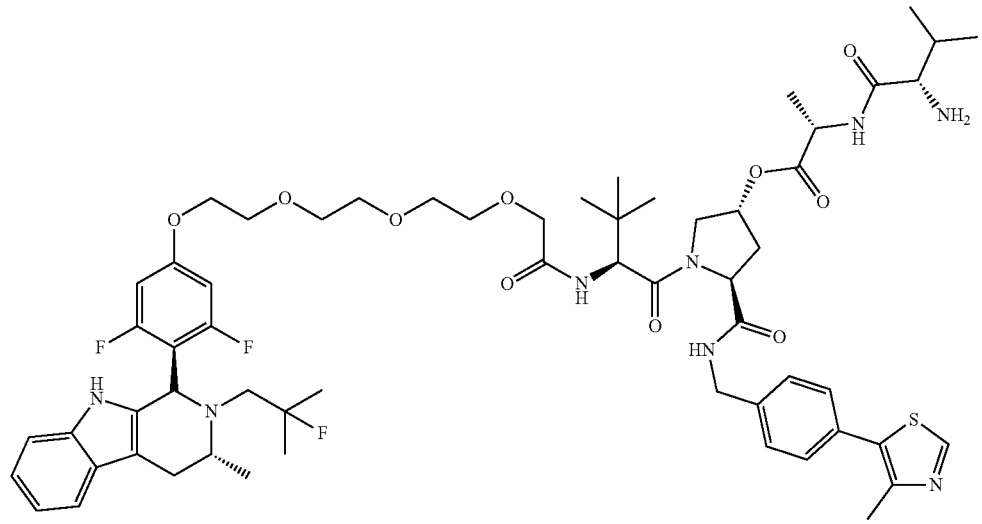

A solution of 4M HCl in dioxane (0.28 mL, 1.12 mmol) was added at RT to (3R,5S)-1-((S)-2-(2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetamido)-3,3-dimethylbutanoyl)-5-((4-(4-methylthiazol-5-yl)benzyl)carbamoyl)pyrrolidin-3-yl (tert-butoxycarbonyl)-L-valyl-L-alaninate (141 mg, 0.11 mmol) at RT, and the reaction stirred for 30 minutes. The solvent was removed under reduced pressure. The residue was purified by preparative HPLC to afford the title compound (80 mg, 59%); $^1$H NMR (400 MHz, DMSO, 30° C.) 0.80 (3H, dd), 0.87 (3H, d), 0.95 (9H, d), 1.04 (3H, d), 1.16 (6H, t), 1.26 (3H, dd), 1.87 (1H, dt), 2.15 (1H, s), 2.21 (1H, d), 2.37 (1H, d), 2.45 (3H, s), 2.46 (1H, s), 2.54-2.59 (1H, m), 2.79-2.93 (2H, m), 3.01 (1H, d), 3.52 (2H, d), 3.55-3.63 (9H, m), 3.69-3.73 (2H, m), 3.87 (2H, dd), 3.92-3.98 (2H, m), 4.05-4.14 (2H, m), 4.19-4.33 (2H, m), 4.38 (1H, t), 4.43-4.52 (2H, m), 5.13 (1H, s), 5.31 (1H, s), 6.65 (2H, d), 6.96 (2H, dt), 7.18 (1H, d), 7.37-7.41 (5H, m), 7.44 (1H, d), 8.22 (1H, s), 8.62 (1H, dt), 8.98 (1H, d), 10.50 (1H, s); m/z: ES− [M−H]− 1159.8.

Example 101: (2S,4R)-1-((S)-2-(tert-butyl)-14-(3,5-difluoro-4-((1R,3R)-2-((S)-3-hydroxy-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide

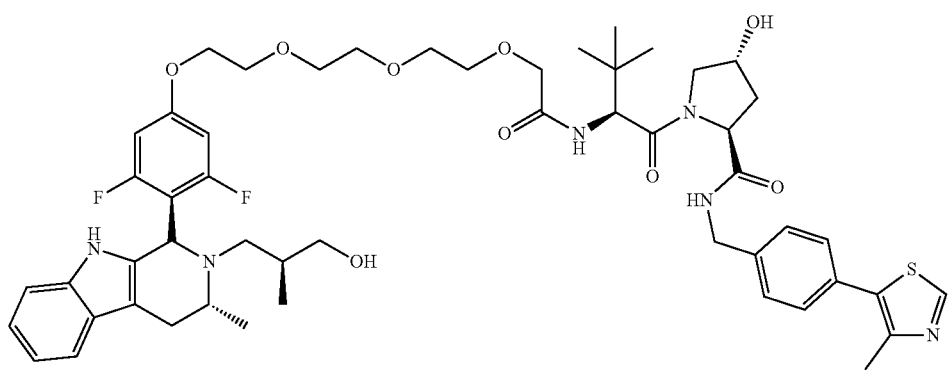

The title compound was prepared in a similar manner to Example 68 using the appropriate carboxylic acid and amine to afford the desired product (27 mg, 25%); ¹H NMR (400 MHz, CDCl₃, 30° C.) 0.64 (3H, d), 0.95 (9H, s), 1.25 (3H, d), 1.83 (1H, s), 2-2.09 (1H, m), 2.49 (3H, s), 2.54 (1H, ddd), 2.61 (1H, s), 2.62-2.73 (3H, m), 2.83 (1H, s), 2.97 (1H, d), 3.50 (2H, t), 3.59 (2H, dd), 3.64-3.72 (9H, m), 3.80 (2H, t), 3.86-4.01 (2H, m), 4.06 (3H, q), 4.31 (1H, dd), 4.50 (2H, d), 4.56 (1H, dd), 4.69 (1H, t), 5.24 (1H, s), 5.64 (1H, s), 6.44 (2H, d), 7.06-7.14 (2H, m), 7.31-7.39 (5H, m), 7.51 (1H, d), 8.34 (1H, s), 8.64 (1H, s); m/z: ES+ [M+H]⁺ 989.5.

Intermediate 102a: tert-Butyl 4-(5-ethoxy-5-oxopentyl)piperazine-1-carboxylate

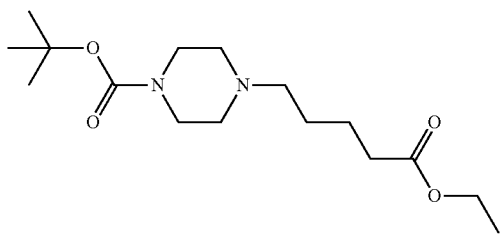 [SMILES: CCOC(=O)CCCCN1CCN(C(=O)OC(C)(C)C)CC1]

Ethyl 5-bromopentanoate (2.04 mL, 12.9 mmol) was added at RT to a solution of tert-butyl piperazine-1-carboxylate (2.00 g, 10.7 mmol) and potassium carbonate (4.45 g, 32.2 mmol) in acetonitrile (25 mL) and the reaction stirred at 85° C. for 18 hours. The reaction mixture was cooled to RT, diluted with EtOAc (50 mL) and filtered. The filtrate was concentrated under reduced pressure and purified by flash silica chromatography, elution gradient 0 to 100% EtOAc in heptane. Pure fractions were evaporated to dryness to afford the title compound (2.67 g, 79%) as a colourless oil; ¹H NMR (400 MHz, CDCl₃, 30° C.) 1.25 (3H, t), 1.46 (9H, s), 1.52 (2H, td), 1.65 (2H, dt), 2.28-2.41 (8H, m), 3.38-3.47 (4H, m), 4.12 (2H, q); m/z: ES+ [M+H]⁺ 315.3.

Intermediate 102b: Ethyl 5-(piperazin-1-yl)pentanoate.HCl

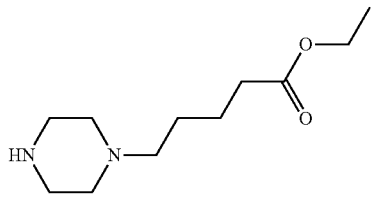

A solution of 4M HCl in dioxane (10.3 mL, 41.3 mmol) was added at RT to a solution of tert-butyl 4-(5-ethoxy-5-oxopentyl)piperazine-1-carboxylate (2.60 g, 8.27 mmol) in dioxane (25 mL) and the reaction stirred at RT for 2 hours. Diethyl ether (100 mL) was added and the resulting solid was filtered under vacuum and washed with diethyl ether to afford the title compound (2.11 g) as a white solid that was used without further purification; ¹H NMR (400 MHz, CDCl₃, 30° C.) 1.25 (3H, t), 1.74 (2H, q), 1.93 (1H, s), 2.40 (2H, t), 3.35 (2H, s), 3.43 (4H, s), 3.75 (2H, s), 3.92 (2H, d), 4.01 (2H, d), 4.11 (2H, q), 9.50 (1H, s).

Intermediate 102c: Ethyl 5-(4-(2-hydroxyethyl)piperazin-1-yl)pentanoate

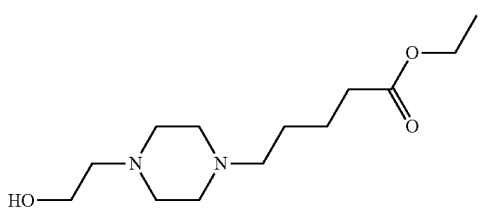 [SMILES: CCOC(=O)CCCCN1CCN(CCO)CC1]

2-Bromoethan-1-ol (0.70 mL, 9.9 mmol) was added to ethyl 5-(piperazin-1-yl)pentanoate, HCl (2.07 g, 8.27 mmol) and potassium carbonate (3.43 g, 24.8 mmol) in acetonitrile (20 mL) at 20° C. The resulting suspension was stirred at 85° C. for 4 hours. The reaction mixture was cooled to RT, diluted with EtOAc (20 mL) and filtered. The filtrate was concentrated under reduced pressure. The residue was purified by flash silica chromatography, elution gradient 0 to 10% MeOH in DCM. Pure fractions were evaporated to dryness to afford the title compound (400 mg, 19%) as a colourless oil; ¹H NMR (400 MHz, CDCl₃, 30° C.) 1.25 (3H, t), 1.46-1.58 (2H, m), 1.63 (2H, qd), 2.33 (4H, dt), 2.48 (4H, s), 2.56 (7H, dt), 3.58-3.64 (2H, m), 4.12 (2H, q); m/z: ES+ [M+H]⁺ 259.1.

Intermediate 102d: Ethyl 5-(4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)pentanoate

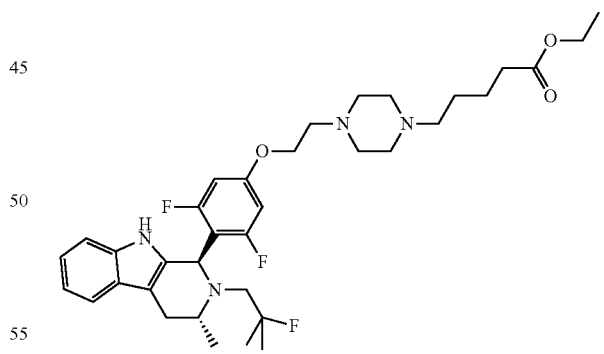

The title compound was prepared in a similar manner to Intermediate 72e using the appropriate phenol and alcohol to afford the desired product (134 mg, 55%) as a pale yellow oil; ¹H NMR (400 MHz, CDCl₃, 30° C.) 1.10 (3H, d), 1.17 (3H, d), 1.22 (7H, d), 1.52 (2H, s), 1.65 (2H, dt), 2.33 (5H, dt), 2.48 (4H, s), 2.56-2.63 (4H, m), 2.79 (2H, t), 2.82-2.91 (1H, m), 3.09 (1H, dd), 3.59-3.72 (1H, m), 4.01-4.08 (2H, m), 4.12 (2H, q), 5.19 (1H, s), 6.37-6.44 (2H, m), 7.05-7.13 (2H, m), 7.21 (1H, dt), 7.39 (1H, s), 7.51 (1H, dd); m/z: ES+ [M+H]⁺ 629.5.

Intermediate 102e: (5-(4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)pentanoic Acid

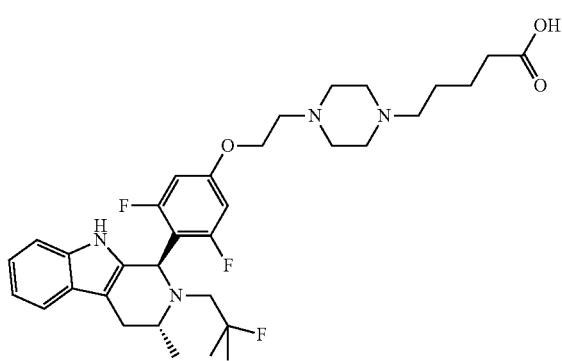 [SMILES: C[C@@H]1Cc2c([nH]c3ccccc23)[C@@H](c2c(F)cc(OCCN3CCN(CCCCC(=O)O)CC3)cc2F)N1CC(C)(C)F]

A solution of 2M sodium hydroxide (0.103 mL, 0.21 mmol) was added to a stirred solution of ethyl 5-(4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)pentanoate (130 mg, 0.21 mmol) in EtOH (1 mL) at RT. The resulting mixture was stirred for 30 minutes at RT and then quenched with 2M HCl (0.103 mL) and evaporated to afford crude product that was used directly without further purification; m/z: ES+ [M+H]+ 601.4.

Example 102: (2S,4R)-1-((S)-2-(5-(4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)pentanamido)-3,3-dimethylbutanoyl)-4-hydroxy-N-(4-(4-methylthiazol-5-yl)benzyl)pyrrolidine-2-carboxamide The title compound was prepared in a similar manner to Example 68 using the appropriate carboxylic acid and amine to afford the desired product (38 mg, 18%) as a cream solid; ¹H NMR (400 MHz, CDCl₃, 30° C.) 0.92 (9H, s), 1.10 (3H, d), 1.17 (3H, d), 1.23 (3H, d), 1.48 (2H, s), 1.62 (7H, dd), 2.03-2.11 (1H, m), 2.22 (2H, q), 2.33 (2H, s), 2.36-2.44 (2H, m), 2.47 (2H, s), 2.51 (3H, s), 2.56-2.63 (4H, m), 2.78 (2H, t), 2.81-2.9 (1H, m), 3.09 (1H, dd), 3.56 (1H, dd), 3.67 (1H, d), 4.02 (2H, t), 4.09 (1H, d), 4.33 (1H, dd), 4.49 (2H, d), 4.58 (1H, dd), 4.72 (1H, t), 5.19 (1H, s), 6.01 (1H, d), 6.39 (2H, d), 7.04-7.13 (2H, m), 7.21 (1H, dd), 7.35 (4H, q), 7.46-7.55 (1H, m), 7.68 (1H, s), 8.66 (1H, s); m/z: ES+ [M+H]+ 1013.5.

Intermediate 104a: tert-Butyl (1-(4-bromophenyl)-2-hydroxyethyl)carbamate

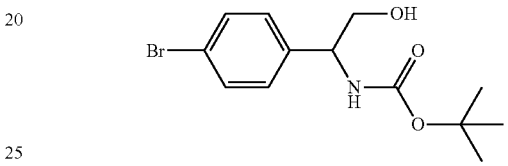

2-amino-2-(4-bromophenyl)acetic acid (4.95 g, 21.5 mmol) was added to 1 M lithium aluminium hydride in THF (44.0 mL, 44.0 mmol) cooled to 0° C. under nitrogen. The resulting suspension was stirred at 70° C. for 90 minutes. The reaction mixture was cooled to 40° C., water (3 mL) and 2 M aq. sodium hydroxide (1.5 mL) added. A solution of di-tert-butyl dicarbonate (5.0 g, 23 mmol) in THF (30 mL) was added to the resulting suspension at 20° C., over a period of 1 minute under air. The resulting suspension was stirred at 70° C. for 1 hour. The reaction mixture was filtered through celite washing with EtOAc (100 mL). The filtrate was evaporated to a brown oil which crystallised on standing. The crude product was purified by flash silica chromatography, elution gradient 5 to 40% EtOAc in heptane to afford the title compound (3.71 g, 55%) as a white solid. ¹H NMR (500 MHz, DMSO, 27° C.) 1.37 (9H, s), 3.41-3.54 (2H, m), 4.42-4.57 (1H, m), 4.74-4.84 (1H, m), 7.17-7.34 (4H, m), 7.50 (1H, d).

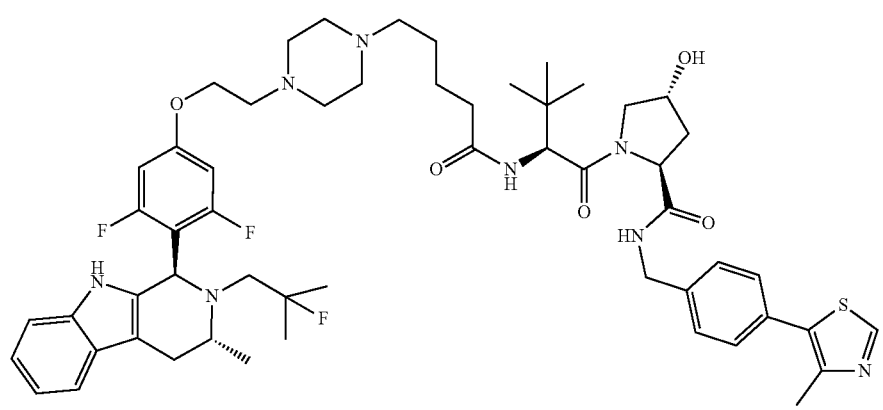 [SMILES: Cc1ncsc1-c1ccc(CNC(=O)[C@@H]2C[C@@H](O)CN2C(=O)[C@@H](NC(=O)CCCCN2CCN(CCOc3cc(F)c([C@@H]4c5[nH]c6ccccc6c5C[C@@H](C)N4CC(C)(C)F)c(F)c3)CC2)C(C)(C)C)cc1]

Intermediate 104b: tert-Butyl (2-hydroxy-1-(4-(4-methylthiazol-5-yl)phenyl)ethyl)carbamate

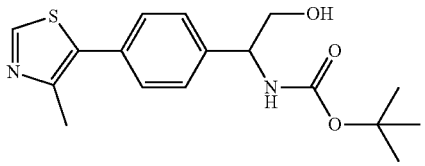 [SMILES: Cc1ncsc1-c1ccc(C(CO)NC(=O)OC(C)(C)C)cc1]

Palladium (II) acetate (0.071 g, 0.32 mmol) was added to tert-butyl (1-(4-bromophenyl)-2-hydroxyethyl)carbamate (1.00 g, 3.16 mmol), potassium carbonate (0.918 g, 6.64 mmol) and 4-methylthiazole (0.604 mL, 6.64 mmol) in NMP (9 mL) at 20° C. under nitrogen. The resulting mixture was vacuum degassed, back filling with nitrogen and stirred at 120° C. for 6 hours. The reaction mixture was diluted with EtOAc (200 mL), and washed sequentially with water (3×50 mL) and saturated brine (10 mL). The organic layer was dried with MgSO$_4$, filtered and evaporated to afford crude product. The crude product was purified by flash silica chromatography, elution gradient 20 to 80% EtOAc in heptane to afford the title compound (0.323 g, 31%) as a beige solid. $^1$H NMR (400 MHz, DMSO, 30° C.) 1.38 (9H, s), 2.46 (3H, s), 3.53 (2H, t), 4.57 (1H, d), 4.80 (1H, t), 7.25 (1H, d), 7.39 (2H, d), 7.44 (2H, d), 8.98 (1H, s); m/z: ES+ [M+H]$^+$ 335.3.

Intermediate 104c: tert-butyl (2-(1,3-dioxoisoindolin-2-yl)-1-(4-(4-methylthiazol-5-yl)phenyl)ethyl)carbamate

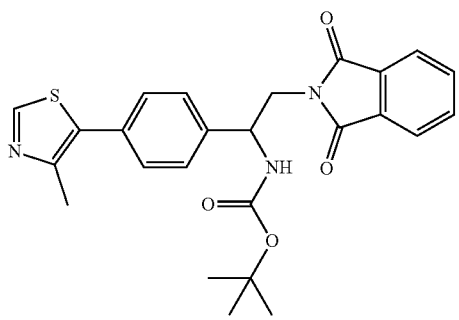 [SMILES: Cc1ncsc1-c1ccc(C(CN2C(=O)c3ccccc3C2=O)NC(=O)OC(C)(C)C)cc1]

Diisopropyl azodicarboxylate (0.32 mL, 1.6 mmol) was added to tert-butyl (2-hydroxy-1-(4-(4-methylthiazol-5-yl)phenyl)ethyl)carbamate (305 mg, 0.91 mmol), phthalimide (270 mg, 1.82 mmol) and triphenylphosphine (360 mg, 1.37 mmol) in THF (4 mL) cooled to 0° C. under nitrogen. The resulting solution was stirred at 20° C. for 20 hours. The reaction mixture was diluted with 2-MeTHF (20 mL), and washed sequentially with 2M NaOH (3×2 mL) and saturated brine (1 mL). The organic layer was dried with MgSO$_4$, filtered and evaporated to afford crude product. The crude product was purified by flash silica chromatography, elution gradient 20 to 60% EtOAc in heptane to afford the title compound (610 mg) as a yellow gum, which was used in the next step without further purification. $^1$H NMR (400 MHz, DMSO, 30° C.) 1.18 (9H, s), 2.43 (3H, s), 3.79-3.94 (2H, m), 5.04 (1H, d), 7.46 (4H, q), 7.58-7.64 (1H, m), 7.77-7.92 (4H, m), 8.99 (1H, s). m/z: ES+ [M+H]$^+$ 464.3.

Intermediate 104d: 2-(2-Amino-2-(4-(4-methylthiazol-5-yl)phenyl)ethyl)isoindoline-1,3-dione, Hydrochloride

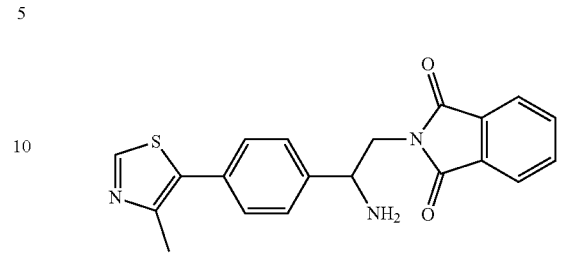

A solution of 6 N HCl in IPA (10 mL, 60 mmol) was added to tert-butyl (2-(1,3-dioxoisoindolin-2-yl)-1-(4-(4-methylthiazol-5-yl)phenyl)ethyl)carbamate (1.85 g, 2.39 mmol) at 20° C. under air. The resulting suspension was stirred at 60° C. for 1 hour. The reaction mixture was diluted with diethyl ether (25 mL), stirred at room temperature for 30 min and filtered. The filtercake was washed with diethyl ether (2×5 mL) to afford the title compound (0.970 g) as a pale yellow powder. $^1$H NMR (400 MHz, DMSO, 30° C.) 2.45 (3H, s), 4.03 (1H, dd), 4.15 (1H, dd), 4.56-4.75 (1H, m), 7.52-7.59 (2H, m), 7.67 (2H, d), 7.8-7.97 (4H, m), 8.83-9.03 (3H, m), 9.07 (1H, s); m/z: ES+ [M+H]$^+$ 364.0.

Intermediate 104e: (2S,4R)—N-[2-(1,3-dioxoisoindolin-2-yl)-[4-(4-methylthiazol-5-yl)phenyl]ethyl]-4-hydroxy-pyrrolidine-2-carboxamide

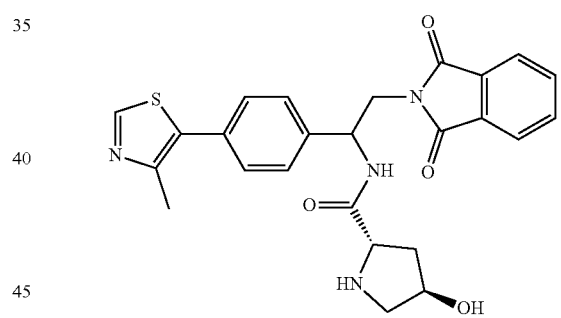

HATU (1.37 g, 3.60 mmol) was added to 2-(2-amino-2-(4-(4-methylthiazol-5-yl)phenyl)ethyl)isoindoline-1,3-dione (0.960 g, 2.40 mmol), Boc-Hyp-OH (0.720 g, 3.1 mmol) and triethylamine (0.90 mL, 6.5 mmol) in DMF (3 mL) at 20° C. under air. The resulting suspension was stirred at 20° C. for 18 hours. The reaction was incomplete and further HATU (1.37 g, 3.60 mmol) and triethylamine (0.90 mL, 6.5 mmol) were added and the suspension was stirred at 20° C. for a further 1 hour. The reaction mixture was diluted with EtOAc (100 mL), and washed sequentially with water (10 mL) 2 M aq. potassium carbonate (3×10 mL) and saturated brine (10 mL). The organic layer was dried with MgSO$_4$, filtered and evaporated to afford crude intermediate. The crude intermediate was purified by flash silica chromatography, elution gradient 1 to 9% MeOH in DCM to afford a pale yellow solid. A solution of 6 N HCl in IPA (6.0 mL, 36 mmol) was added to tert-butyl (2S,4R)-2-[[2-(1,3-dioxoisoindolin-2-yl)-1-[4-(4-methylthiazol-5-yl)phenyl]ethyl]carbamoyl]-4-hydroxy-pyrrolidine-1-carboxylate (0.68 g, 1.18 mmol) in IPA (5 mL) at 60° C. under air. The resulting suspension was stirred at 60° C. for 30 minutes. The reaction mixture was diluted with diethyl ether (25 mL) and stirred for 2 hours. The reaction mixture was filtered, the solid washed with diethyl ether (2×10 mL) and dried under reduced pressure to afford the title compound (1.20 g, 98%) as a pale yellow solid. m/z: ES+ [M+H]+ 477.0.

Intermediate 104f: tert-Butyl N-[(1S)-1-[(2S,4R)-2-[[2-(1,3-dioxoisoindolin-2-yl)-1-[4-(4-methylthiazol-5-yl)phenyl]ethyl]carbamoyl]-4-hydroxy-pyrrolidine-1-carbonyl]-2,2-dimethyl-propyl]carbamate

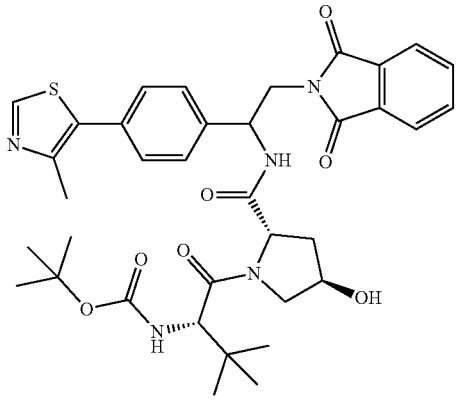 [SMILES: Cc1ncsc1-c1ccc(C(CN2C(=O)c3ccccc3C2=O)NC(=O)[C@@H]2C[C@@H](O)CN2C(=O)[C@@H](NC(=O)OC(C)(C)C)C(C)(C)C)cc1]

HATU (1.78 g, 4.68 mmol) was added to (2S,4R)—N-[2-(1,3-dioxoisoindolin-2-yl)-1-[4-(4-methylthiazol-5-yl)phenyl]ethyl]-4-hydroxy-pyrrolidine-2-carboxamide, HCl (1.2 g, 2.3 mmol), N-Boc-L-tert-leucine (0.65 g, 2.8 mmol) and triethylamine (1.14 mL, 8.19 mmol) in acetonitrile (20 mL) at 20° C. under air. The resulting suspension was stirred at 20° C. for 30 minutes. The reaction was incomplete and further triethylamine (0.57 mL, 4.1 mmol) was added and the solution was stirred at 20° C. for a further 17 hours. The reaction mixture was evaporated to dryness and redissolved in EtOAc (50 mL), and washed sequentially with 0.5 M aq. potassium carbonate (15 mL), 2 M aq. potassium carbonate (10 mL), and saturated brine (5 mL). The organic layer was dried with MgSO₄, filtered and evaporated to afford crude product. The crude product was purified by flash silica chromatography, elution gradient 0 to 5% MeOH in DCM to afford impure product as a pale yellow gum. The crude product was purified by flash silica chromatography, elution gradient 0 to 6% MeOH in DCM to afford the title compound (1.40 g, 87%) as a beige foam. m/z: ES+ [M+H]+ 690.2.

Intermediate 104g: tert-Butyl N-[(1S)-1-[(2S,4R)-2-[[(1R)-2-(1,3-dioxoisoindolin-2-yl)-1-[4-(4-methylthiazol-5-yl)phenyl]ethyl]carbamoyl]-4-hydroxy-pyrrolidine-1-carbonyl]-2,2-dimethyl-propyl]carbamate

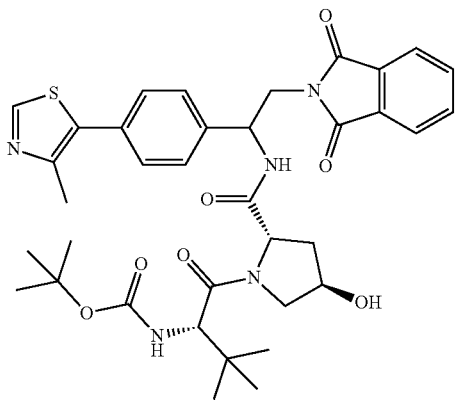 [SMILES: Cc1ncsc1-c1ccc(C(CN2C(=O)c3ccccc3C2=O)NC(=O)[C@@H]2C[C@@H](O)CN2C(=O)[C@@H](NC(=O)OC(C)(C)C)C(C)(C)C)cc1]

tert-Butyl N-[(1S)-1-[(2S,4R)-2-[[2-(1,3-dioxoisoindolin-2-yl)-1-[4-(4-methylthiazol-5-yl)phenyl]ethyl]carbamoyl]-4-hydroxy-pyrrolidine-1-carbonyl]-2,2-dimethyl-propyl]carbamate (1.4 g, 2.0 mmol) was purified using the normal phase conditions: Column: C2, 10×250 mm, 5 micron; Mobile phase: 50% ethanol/50% n-heptane+0.1% TEA; Flow rate: 40 mL/min; Instrumentation: Interchim 4250. Desired species were eluted isochratically using a mobile phase of 50:50 ethanol/n-heptane (+0.1% triethylamine) to afford the title compound (0.41 g, 29%), which eluted second as a pale yellow gum. ¹H NMR (400 MHz, DMSO, 30° C.) 0.83 (9H, s), 1.37 (9H, s), 1.45-1.58 (1H, m), 2.45 (3H, s), 3.49 (2H, s), 3.87-3.95 (2H, m), 4.06 (1H, d), 4.14 (1H, s), 4.40 (1H, t), 5.29-5.42 (1H, m), 6.30 (1H, d), 7.47 (2H, d), 7.56 (2H, d), 7.83-7.92 (4H, m), 8.60 (1H, d), 9.00 (1H, s); m/z: ES+ [M+H]+ 690.1.

Intermediate 104h: (2S,4R)-1-[(2S)-2-Amino-3,3-dimethyl-butanoyl]-N-[(1R)-2-(1,3-dioxoisoindolin-2-yl)-1-[4-(4-methylthiazol-5-yl)phenyl]ethyl]-4-hydroxy-pyrrolidine-2-carboxamide

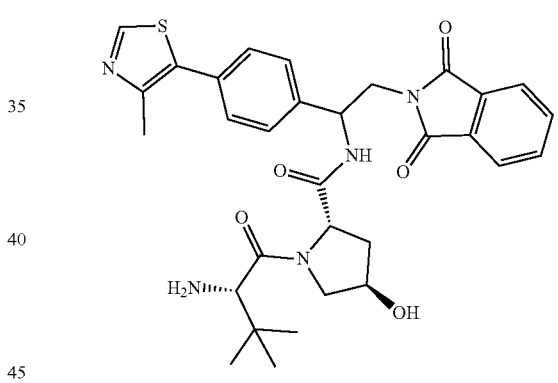

A solution of 6 N hydrogen chloride in IPA (3 mL, 18 mmol) was added to tert-butyl N-[(1S)-1-[(2S,4R)-2-[[(1R)-2-(1,3-dioxoisoindolin-2-yl)-1-[4-(4-methylthiazol-5-yl)phenyl]ethyl]carbamoyl]-4-hydroxy-pyrrolidine-1-carbonyl]-2,2-dimethyl-propyl]carbamate, ISOMER 2 (400 mg, 0.46 mmol) in IPA (1 mL) at 20° C. under air. The resulting suspension was stirred at 20° C. for 3 days. The reaction mixture was evaporated to dryness. The crude product was purified by flash silica chromatography, elution gradient 0 to 15% 1M NH₃/MeOH in DCM to afford the title compound (183 mg, 67%) as a white solid. ¹H NMR (400 MHz, DMSO, 30° C.) 0.80 (9H, s), 1.49-1.61 (1H, m), 1.87-2.08 (1H, m), 2.43-2.48 (3H, m), 3.12 (1H, s), 3.35-3.45 (1H, m), 3.48 (1H, d), 3.86-3.98 (2H, m), 3.97-4.17 (2H, m), 4.47 (1H, dt), 4.94 (1H, dd), 5.35 (1H, q), 7.44-7.5 (2H, m), 7.5-7.62 (2H, m), 7.87 (4H, tdd), 8.57 (1H, d), 8.93-9.01 (1H, m); m/z: ES+ [M+H]+ 590.1.

Intermediate 104i: (2S,4R)-1-[(2S)-2-[[2-[2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-N-[(1R)-2-(1,3-Dioxoisoindolin-2-yl)-1-[4-(4-methylthiazol-5-yl)phenyl]ethyl]-4-hydroxy-pyrrolidine-2-carboxamide

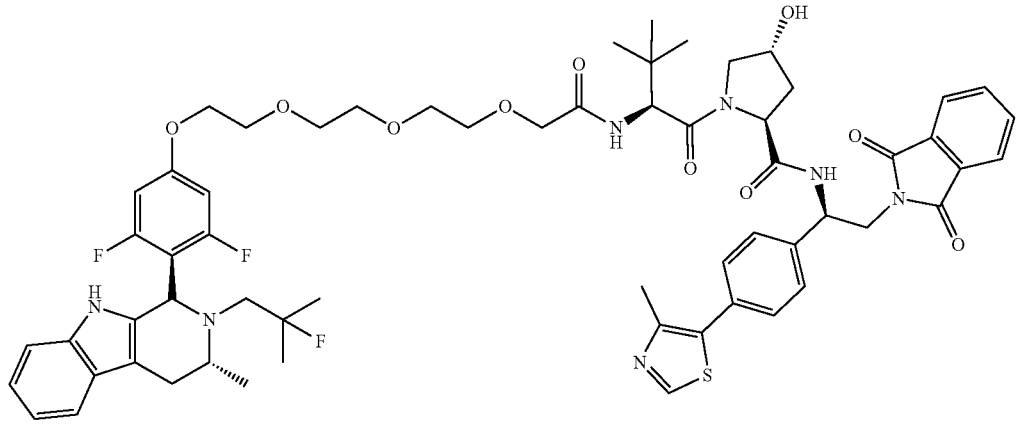

A solution of 2 M aq. sodium hydroxide (0.460 mL, 0.92 mmol) was added to ethyl 2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetate (280 mg, 0.46 mmol) in ethanol (2 mL) at 20° C. under air. The resulting solution was stirred at 20° C. for 20 minutes. 2 M aq. HCl (0.33 mL, 0.66 mmol) was added and the solution evaporated to dryness. The residue was suspended in N,N-dimethylformamide (2 mL) with DIPEA (0.23 mL, 1.3 mmol) and (2S,4R)-1-[(2S)-2-amino-3,3-dimethyl-butanoyl]-N-[(1R)-2-(1,3-dioxoisoindolin-2-yl)-1-[4-(4-methylthiazol-5-yl)phenyl]ethyl]-4-hydroxy-pyrrolidine-2-carboxamide (174 mg, 0.30 mmol). HATU (200 mg, 0.52 mmol) was added and the suspension stirred for 18 hours. The reaction mixture was diluted with EtOAc (25 mL), and washed sequentially with water (5 mL), water (2 mL), 2 M aq. potassium carbonate (2×2 mL), and saturated brine (2 mL). The organic layer was dried with $MgSO_4$, filtered and evaporated to afford crude product. The crude product was purified by flash silica chromatography, elution gradient 0 to 6% MeOH in DCM to afford the title compound (283 mg, 83%) as a pale yellow foam. $^1$H NMR (400 MHz, $CDCl_3$, 30° C.) 0.87 (9H, s), 1.09 (3H, d), 1.19 (6H, dd), 1.38-1.52 (2H, m), 1.88-2 (1H, m), 2.26 (1H, ddd), 2.32-2.52 (4H, m), 2.60 (1H, dd), 2.73-2.91 (2H, m), 3.08 (1H, dd), 3.49 (1H, dd), 3.65-3.74 (8H, m), 3.83 (2H, t), 3.87-3.98 (2H, m), 3.99-4.1 (4H, m), 4.35-4.49 (2H, m), 4.66 (1H, t), 5.19 (1H, s), 5.35 (1H, td), 6.33-6.44 (2H, m), 7.03-7.13 (2H, m), 7.17-7.24 (1H, m), 7.29 (1H, d), 7.36-7.43 (2H, m), 7.46-7.53 (3H, m), 7.65-7.75 (3H, m), 7.83 (2H, td), 8.36 (1H, s), 8.62 (1H, s); m/z: ES− [M−H]⁻ 1148.4.

Intermediate 104j: (2S,4R)—N-[(1R)-2-Amino-1-[4-(4-methylthiazol-5-yl)phenyl]ethyl]-1-[(2S)-2-[[2-[2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-4-hydroxy-pyrrolidine-2-carboxamide

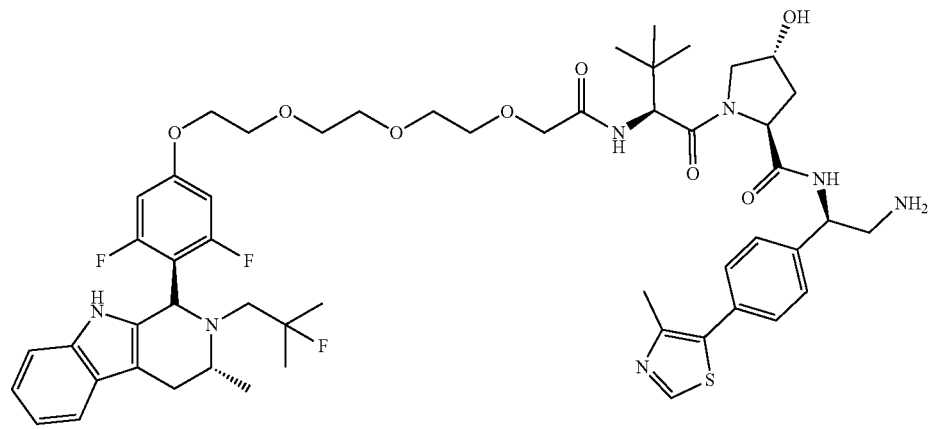

Ethylenediamine (0.037 mL, 0.56 mmol) was added to (2S,4R)-1-[(2S)-2-[[2-[2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-N-[(1R)-2-(1,3-dioxoisoindolin-2-yl)-1-[4-(4-methylthiazol-5-yl)phenyl]ethyl]-4-hydroxy-pyrrolidine-2-carboxamide (260 mg, 0.22 mmol) in ethanol (3 mL) at 20° C. under air. The resulting solution was stirred at 20° C. for 18 hours. The resulting mixture was evaporated to dryness and the residue purified by flash silica chromatography, elution gradient 0 to 15% 1M NH$_3$/MeOH in DCM. Pure fractions were evaporated to dryness to afford the title compound (186 mg, 82%) as a cream solid. $^1$H NMR (400 MHz, CDCl$_3$, 30° C.) 0.90 (9H, s), 1.09 (3H, d), 1.19 (6H, dd), 2.07 (2H, s), 2.33-2.45 (3H, m), 2.47 (3H, s), 2.59 (1H, dd), 2.84 (1H, dd), 2.95-3.29 (3H, m), 3.46-3.58 (1H, m), 3.68 (10H, d), 3.81 (2H, s), 3.9-4.16 (5H, m), 4.45 (2H, d), 4.70 (1H, s), 4.92 (1H, s), 5.18 (1H, s), 6.34 (2H, dd), 7.06 (2H, dq), 7.18 (1H, s), 7.36 (4H, s), 7.43-7.61 (2H, m), 7.70 (1H, s), 8.47 (1H, s), 8.60 (1H, d). m/z: ES– [M–H]⁻ 1018.5.

Example 104: (2S,4R)-1-[(2S)-2-[[2-[2-[2-[2-[3,5-Difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-N-[(1R)-2-(dimethylamino)-1-[4-(4-methylthiazol-5-yl)phenyl]ethyl]-4-hydroxy-pyrrolidine-2-carboxamide Sodium triacetoxyborohydride (104 mg, 0.49 mmol) was added to 37% formaldehyde in water (0.11 mL, 1.5 mmol), (2S,4R)—N-[(1R)-2-amino-1-[4-(4-methylthiazol-5-yl)phenyl]ethyl]-1-[(2S)-2-[[2-[2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-4-hydroxy-pyrrolidine-2-carboxamide, (100 mg, 0.10 mmol) and acetic acid (0.02 mL, 0.3 mmol) in chloroform (0.6 mL) and 1,2-dichloroethane (1.4 mL) at 20° C. under air. The resulting mixture was stirred at 20° C. for 20 hours. The reaction mixture was diluted with EtOAc (25 mL), and washed sequentially with 2 M aq. potassium carbonate (2×2 mL). The organic layer was dried with a phase separating cartridge, filtered and evaporated to afford crude product. The crude product was purified by preparative HPLC (Waters XSelect CSH C18 column, 5p silica, 30 mm diameter, 100 mm length), using decreasingly polar mixtures of water (containing by volume 1% NH$_4$OH (28-30% in H$_2$O)) and MeCN as eluents. Fractions containing the desired compound were evaporated to dryness to afford the title compound (41 mg, 40%) as a tan solid. $^1$H NMR (400 MHz, CDCl$_3$, 30° C.) 0.90 (9H, s), 1.08 (3H, d), 1.27 (6H, dd), 2.01-2.08 (1H, m), 2.24 (6H, s), 2.35 (1H, ddd), 2.45-2.55 (5H, m), 2.54-2.68 (3H, m), 2.75 (1H, dd), 2.92 (1H, dd), 3.54 (2H, td), 3.62-3.75 (8H, m), 3.81 (2H, dd), 3.94-4.05 (3H, m), 4.05-4.13 (2H, m), 4.39 (1H, s), 4.45 (1H, d), 4.67 (1H, t), 4.90 (1H, dt), 5.35 (1H, s), 6.45 (2H, d), 7.1-7.22 (2H, m), 7.24-7.31 (3H, m), 7.32-7.39 (5H, m), 7.48-7.55 (1H, m), 8.61 (1H, s). m/z: ES– [M–H]⁻ 1046.6.

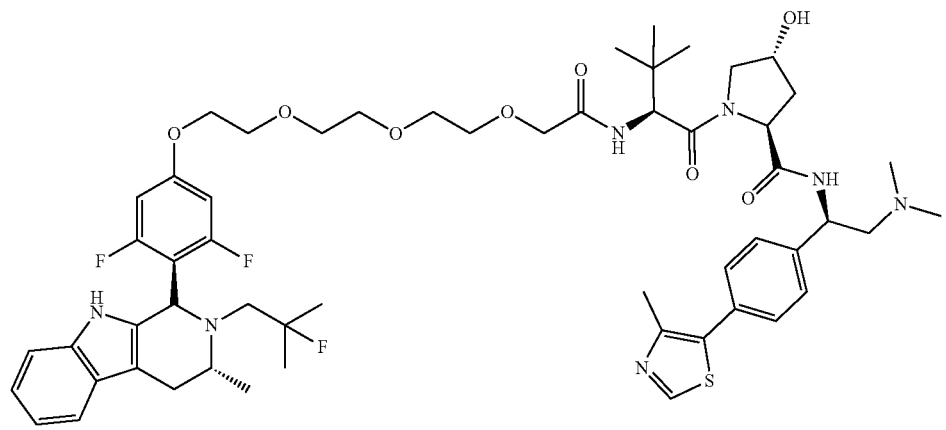

389

Intermediate 106a: tert-Butyl N-[(1S)-1-[(2S,4R)-2-[[(1S)-2-(1,3-dioxoisoindolin-2-yl)-1-[4-(4-methyl-thiazol-5-yl)phenyl]ethyl]carbamoyl]-4-hydroxy-pyrrolidine-1-carbonyl]-2,2-dimethyl-propyl] carbamate

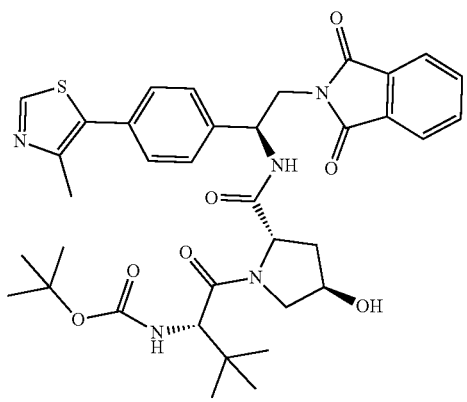 [SMILES: Cc1ncsc1-c1ccc([C@@H](CN2C(=O)c3ccccc3C2=O)NC(=O)[C@@H]2C[C@@H](O)CN2C(=O)[C@@H](NC(=O)OC(C)(C)C)C(C)(C)C)cc1]

tert-Butyl N-[(1S)-1-[(2S,4R)-2-[[2-(1,3-dioxoisoindolin-2-yl)-1-[4-(4-methylthiazol-5-yl)phenyl]ethyl]carbamoyl]-4-hydroxy-pyrrolidine-1-carbonyl]-2,2-dimethyl-propyl]carbamate (1.4 g, 2.03 mmol) was purified using the normal phase conditions: Column: C2, 10×250 mm, 5 micron; Mobile phase: 50% ethanol/50% n-heptane+0.1% TEA; Flow rate: 40 mL/min; Instrumentation: Interchim 4250. Desired species were eluted isochratically using a mobile phase of 50:50 ethanol/n-heptane (+0.1% triethylamine) to afford the title compound (0.550 g, 39%) as a yellow gum, which eluted first. $^1$H NMR (400 MHz, DMSO, 30° C.) 0.76 (9H, s), 1.40 (9H, s), 1.64-1.8 (1H, m), 1.95 (1H, d), 2.42 (3H, s), 3.48 (1H, d), 3.58 (1H, dd), 3.83-4.09 (3H, m), 4.27 (1H, s), 4.32 (1H, t), 5.29 (1H, q), 5.76 (1H, d), 7.36-7.51 (5H, m), 7.82 (4H, s), 8.44 (1H, d), 8.98 (1H, s); m/z: ES+ [M+H]$^+$ 690.1.

390

Intermediate 106b (2S,4R)-1-[(2S)-2-Amino-3,3-dimethyl-butanoyl]-N-[(1S)-2-(1,3-dioxoisoindolin-2-yl)-1-[4-(4-methylthiazol-5-yl)phenyl]ethyl]-4-hydroxy-pyrrolidine-2-carboxamide

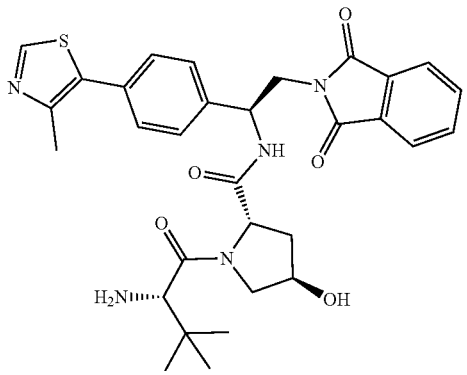 [SMILES: Cc1ncsc1-c1ccc([C@@H](CN2C(=O)c3ccccc3C2=O)NC(=O)[C@@H]2C[C@@H](O)CN2C(=O)[C@@H](N)C(C)(C)C)cc1]

A solution of 6 N hydrogen chloride in IPA (3 mL, 18 mmol) was added to tert-butyl N-[(1S)-1-[(2S,4R)-2-[[(1S)-2-(1,3-dioxoisoindolin-2-yl)-1-[4-(4-methylthiazol-5-yl)phenyl]ethyl]carbamoyl]-4-hydroxy-pyrrolidine-1-carbonyl]-2,2-dimethyl-propyl]carbamate (550 mg, 0.56 mmol) in IPA (1 mL) at 20° C. under air. The resulting mixture was stirred at 20° C. for 2 hours. The resulting suspension was filtered, and the filtercake washed sequentially with IPA (2×1 mL), IPA:diethyl ether (1:1, 2 mL) and diethyl ether (1 mL) to afford the title compound (182 mg, 52%) as a white solid. $^1$H NMR (400 MHz, DMSO, 30° C.) 0.93 (9H, s), 1.75 (1H, ddd), 2.01-2.11 (1H, m), 2.39 (3H, s), 3.51 (1H, dd), 3.68 (1H, d), 3.74-3.83 (1H, m), 3.86 (1H, d), 3.95 (3H, ddd), 4.31 (1H, s), 4.49 (1H, t), 5.25 (1H, q), 7.40 (4H, s), 7.83 (4H, dd), 7.97 (2H, s), 8.69 (1H, d), 8.99 (1H, s); m/z: ES+ [M+H]$^+$ 590.0.

Intermediate 106c: (2S,4R)-1-[(2S)-2-[[2-[2-[2-[2-[3,5-Difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-N-[(1S)-2-(1,3-dioxoisoindolin-2-yl)-1-[4-(4-methylthiazol-5-yl)phenyl]ethyl]-4-hydroxy-pyrrolidine-2-carboxamide

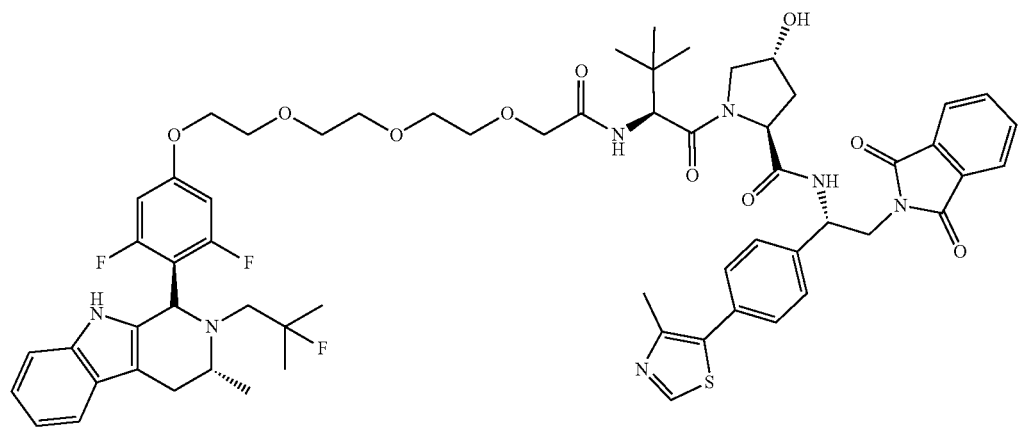

A solution of 2 M aq. sodium hydroxide (0.33 mL, 0.66 mmol) was added to ethyl 2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetate (200 mg, 0.33 mmol) in ethanol (2 mL) at 20° C. under air. The resulting solution was stirred at 20° C. for 20 minutes. 2 M aq. HCl (0.33 mL, 0.66 mmol) was added and the solution evaporated to dryness. The residue was suspended in N,N-dimethylformamide (2 mL) with DIPEA (0.230 mL, 1.32 mmol) and (2S,4R)-1-[(2S)-2-amino-3,3-dimethyl-butanoyl]-N-[(1S)-2-(1,3-dioxoisoindolin-2-yl)-1-[4-(4-methylthiazol-5-yl)phenyl]ethyl]-4-hydroxy-pyrrolidine-2-carboxamide (182 mg, 0.29 mmol). HATU (196 mg, 0.52 mmol) was added and the suspension stirred for 3 hours. The reaction mixture was diluted with EtOAc (25 mL), and washed sequentially with water (5 mL) and saturated NaHCO₃ (5 mL). The organic layer was dried with a phase separating cartridge, filtered and evaporated to afford crude product. The crude product was purified by flash silica chromatography, elution gradient 0 to 6% MeOH in DCM to afford the title compound (227 mg, 68%) as a yellow solid. $^1$H NMR (400 MHz, CDCl₃, 30° C.) 0.97 (9H, s), 1.09 (3H, d), 1.19 (6H, dd), 2.03-2.14 (2H, m), 2.38 (1H, dd), 2.47 (3H, s), 2.60 (1H, dd), 2.75 (1H, s), 2.84 (1H, dd), 3.07 (1H, dd), 3.56-3.75 (10H, m), 3.81 (2H, t), 3.85-4.07 (7H, m), 4.38 (1H, s), 4.57 (2H, t), 5.18 (1H, s), 5.32-5.43 (1H, m), 6.35 (2H, d), 7.03-7.11 (2H, m), 7.13-7.21 (2H, m), 7.33 (1H, d), 7.37-7.46 (4H, m), 7.50 (1H, dd), 7.70 (2H, dd), 7.81 (2H, dd), 8.35 (1H, s), 8.64 (1H, s); m/z: ES− [M−H]⁻ 1148.3.

Example 106: (2S,4R)—N-[(1S)-2-amino-1-[4-(4-methylthiazol-5-yl)phenyl]ethyl]-1-[(2S)-2-[[2-[2-[2-[2-[3,5-difluoro-4-[(1R,3R)-2-(2-fluoro-2-methylpropyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-4-hydroxy-pyrrolidine-2-carboxamide

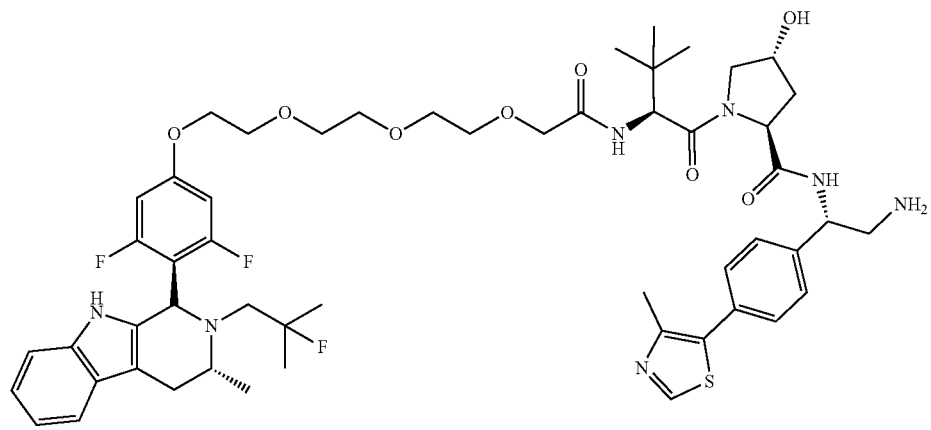

Ethylenediamine (0.030 mL, 0.47 mmol) was added to (2S,4R)-1-[(2S)-2-[[2-[2-[2-[2-[3,5-difluoro-4-[(1R,3R)-2-(2-fluoro-2-methyl-propyl)-3-methyl-1,3,4,9-tetrahydro-pyrido[3,4-b]indol-1-yl]phenoxy]ethoxy]ethoxy]ethoxy]acetyl]amino]-3,3-dimethyl-butanoyl]-N-[(1S)-2-(1,3-dioxoisoindolin-2-yl)-1-[4-(4-methylthiazol-5-yl)phenyl]ethyl]-4-hydroxy-pyrrolidine-2-carboxamide (215 mg, 0.19 mmol) in ethanol (3 mL) at 20° C. under air. The resulting solution was stirred at 20° C. for 18 hours. The reaction mixture was evaporated to dryness and redissolved in DCM (5 mL). The solution was purified by flash silica chromatography, elution gradient 0 to 15% 1M NH₃/MeOH in DCM to afford the title compound (143 mg, 75%) as a pale yellow solid. $^1$H NMR (400 MHz, CDCl₃, 30° C.) 1.03-1.12 (12H, m), 1.20 (6H, dd), 2.00 (1H, s), 2.04-2.14 (1H, m), 2.29-2.46 (2H, m), 2.50 (3H, s), 2.60 (1H, dd), 2.78-2.93 (1H, m), 2.96-3.03 (2H, m), 3.07 (1H, dd), 3.59-3.75 (10H, m), 3.81 (2H, t), 3.88-4.03 (2H, m), 4.03-4.13 (3H, m), 4.48 (1H, s), 4.56 (1H, d), 4.68 (1H, t), 4.92-5.05 (1H, m), 5.18 (1H, s), 6.34-6.44 (2H, m), 7.03-7.12 (2H, m), 7.18-7.25 (1H, m), 7.33 (3H, d), 7.38-7.44 (2H, m), 7.47-7.58 (2H, m), 8.25 (1H, s), 8.65 (1H, s); m/z: ES− [M−H]⁻ 1018.5.

Example 107: (2S,4R)-1-[(2S)-2-[[2-[2-[2-[2-[3,5-Difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-N-[(1S)-2-(dimethylamino)-1-[4-(4-methylthiazol-5-yl)phenyl]ethyl]-4-hydroxy-pyrrolidine-2-carboxamide

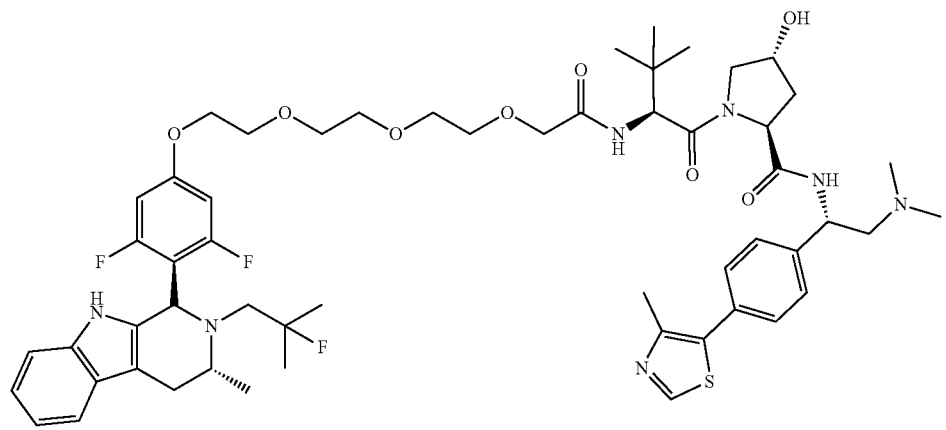

Sodium triacetoxyborohydride (75 mg, 0.35 mmol) was added to 37% formaldehyde in water (0.08 mL, 1.1 mmol), (2S,4R)—N-[(1S)-2-amino-1-[4-(4-methylthiazol-5-yl)phenyl]ethyl]-1-[(2S)-2-[[2-[2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-4-hydroxy-pyrrolidine-2-carboxamide, (72 mg, 0.07 mmol) and acetic acid (0.012 mL, 0.21 mmol) in 1,2-dichloroethane (2 mL) at 20° C. under air. The resulting mixture was stirred at 20° C. for 4 hours. The reaction was incomplete and further 37% formaldehyde in water (0.08 mL, 1.1 mmol) and sodium triacetoxyborohydride (75 mg, 0.35 mmol) were added and the mixture was stirred at 20° C. for a further 18 hours. The resulting mixture was evaporated to dryness and the residue purified by preparative HPLC (Waters XSelect CSH C18 column, 5μ silica, 30 mm diameter, 100 mm length), using decreasingly polar mixtures of water (containing by volume 1% NH$_4$OH (28-30% in H$_2$O)) and MeCN as eluents to afford the title compound (41 mg, 55.4%) as a tan solid. $^1$H NMR (400 MHz, CDCl$_3$, 30° C.) 0.98-1.15 (12H, m), 1.27 (6H, dd), 2.08 (1H, dd), 2.22 (6H, s), 2.34 (1H, ddd), 2.38-2.47 (1H, m), 2.48-2.53 (4H, m), 2.53-2.65 (2H, m), 2.76 (1H, dd), 2.92 (1H, dd), 3.56 (2H, dd), 3.62-3.75 (8H, m), 3.78-3.85 (2H, m), 3.92-4.05 (2H, m), 4.04-4.12 (3H, m), 4.40 (1H, s), 4.52 (1H, d), 4.72 (1H, t), 4.88 (1H, dt), 5.25 (2H, q), 5.34 (1H, s), 6.44 (2H, d), 7.16 (2H, dtd), 7.27-7.35 (3H, m), 7.35-7.43 (3H, m), 7.47-7.53 (1H, m), 7.56 (1H, d), 8.63 (1H, s); m/z: ES− [M−H]⁻ 1046.5.

Intermediate 108a: N1-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-N1,N2-dimethylethane-1,2-diamine

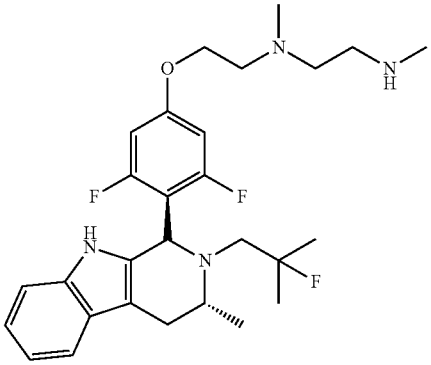

N,N-Dimethylethylenediamine (0.41 mL, 3.8 mmol) was added to potassium carbonate (210 mg, 1.53 mmol) and (1R,3R)-1-(4-(2-bromoethoxy)-2,6-difluorophenyl)-2-(2-fluoro-2-methylpropyl)-3-methyl-2,3,4,9-tetrahydro-1H-pyrido[3,4-b]indole (190 mg, 0.38 mmol) in acetonitrile (4 mL) at 20° C. under nitrogen. The resulting suspension was stirred at 80° C. for 1 hour. The reaction mixture was diluted with EtOAc (25 mL), and washed sequentially with water (5 mL), 2 M potassium carbonate (2×5 mL), and saturated brine (2 mL). The organic layer was dried with MgSO$_4$, filtered and evaporated to afford crude product. The crude product was purified by flash silica chromatography, elution gradient 0 to 20% 1M NH$_3$/MeOH in DCM to afford the title compound (160 mg, 83%) as a white solid. $^1$H NMR (400 MHz, DMSO, 30° C.) 1.05 (3H, d), 1.17 (6H, t), 2.24 (3H, s), 2.26 (3H, s), 2.29-2.42 (1H, m), 2.43-2.49 (2H, m), 2.53-2.6 (2H, m), 2.70 (2H, t), 2.88 (2H, td), 3.52 (1H, q), 3.97-4.15 (3H, m), 5.13 (1H, s), 6.66 (2H, d), 6.9-7.03 (2H, m), 7.19 (1H, d), 7.40 (1H, d), 10.51 (1H, s); m/z: ES− [M−H]⁻ 501.4.

Intermediate 108b: Ethyl 5-((2-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)ethyl)(methyl)amino)pentanoate

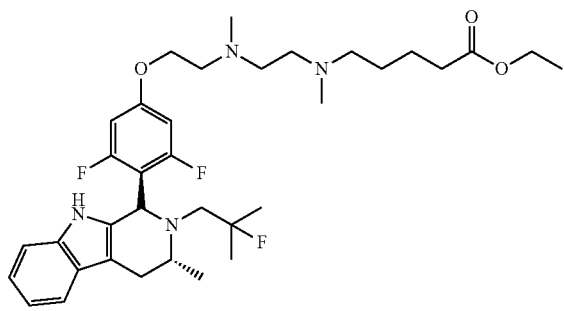

Ethyl 5-bromovalerate (0.058 mL, 0.37 mmol) was added to N1-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-N1,N2-dimethylethane-1,2-diamine (154 mg, 0.31 mmol) and potassium carbonate (170 mg, 1.2 mmol) in acetonitrile (5 mL) at 20° C. under nitrogen. The resulting suspension was stirred at 80° C. for 4 hours. The reaction mixture was adsorbed on to silica and evaporated to dryness. The residue was dry loaded and purified by flash silica chromatography, elution gradient 0 to 10% 1M $NH_3$/MeOH in DCM to the title compound (170 mg, 88%) as a colourless gum. $^1$H NMR (400 MHz, DMSO, 30° C.) 1.05 (3H, d), 1.1-1.23 (9H, m), 1.39 (2H, p), 1.52 (2H, p), 2.12 (3H, s), 2.24 (3H, s), 2.28 (4H, t), 2.35-2.41 (2H, m), 2.48 (2H, s), 2.54-2.61 (4H, m), 2.71 (2H, t), 2.78-2.95 (2H, m), 3.52 (1H, d), 4.05-4.09 (2H, m), 5.13 (1H, s), 6.65 (2H, d), 6.97 (2H, dt), 7.19 (1H, d), 7.40 (1H, d), 10.50 (1H, s); m/z: ES+ [M+H]$^+$ 631.5.

Example 108: (2S,4R)-1-((S)-2-(5-((2-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)ethyl)(methyl)amino)pentanamido)-3,3-dimethylbutanoyl)-4-hydroxy-N-(4-(4-methylthiazol-5-yl)benzyl)pyrrolidine-2-carboxamide

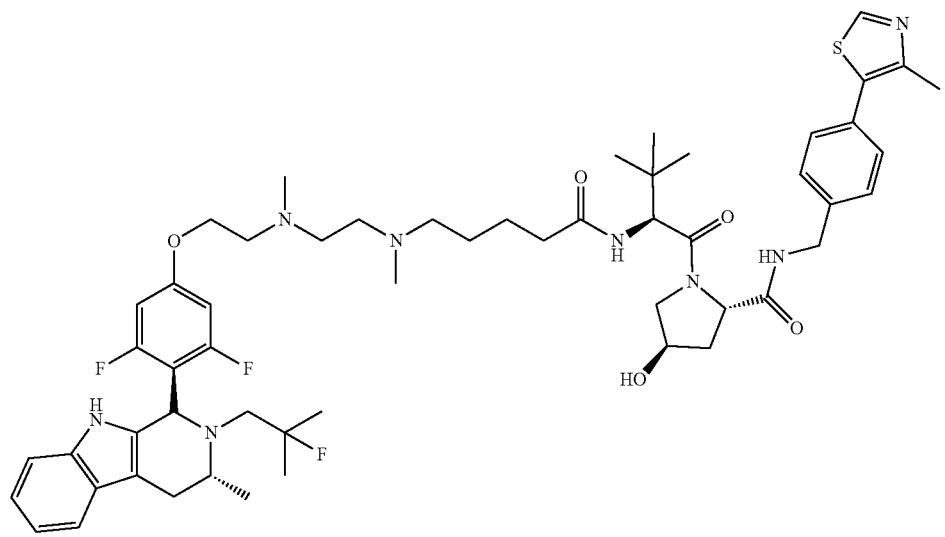

A solution of 2 M aq. sodium hydroxide (0.262 mL, 0.52 mmol) was added to ethyl 5-((2-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)ethyl)(methyl)amino)pentanoate (165 mg, 0.26 mmol) in MeOH at 20° C. under air. The resulting solution was stirred at 20° C. for 1 hour. The reaction was incomplete so the temperature was increased to 50° C. and the reaction mixture was stirred for a further 3 hours. The reaction mixture was evaporated to dryness, suspended in MeCN (5 mL) and 2 M aq. HCl (0.26 mL, 0.52 mmol) added. The mixture was evaporated to dryness. The residue was suspended in N,N-dimethylformamide (2 mL) at 20° C. under air with HATU (200 mg, 0.52 mmol) and triethylamine (0.13 mL, 0.92 mmol). HATU (200 mg, 0.52 mmol) was added and the suspension stirred for 1 hour. The reaction mixture was diluted with EtOAc (25 mL), and washed sequentially with 2 M aq. potassium carbonate (3×5 mL) and saturated brine (2 mL). The organic layer was dried with MgSO$_4$, filtered and evaporated to afford crude product. The crude product was purified by preparative HPLC (Waters CSH C18 OBD column, 30×100 mm id, 5 micron particle size), using decreasingly polar mixtures of water (containing 1% by volume of NH$_4$OH (28-30% in H$_2$O)) and MeCN as eluents to afford the title compound (72 mg, 27%) as a brown solid. $^1$H NMR (400 MHz, CDCl$_3$, 30° C.) 0.91 (9H, s), 1.09 (3H, d), 1.20 (6H, dd), 1.37-1.49 (2H, m), 1.58 (2H, dq), 2.02 (1H, dd), 2.18 (5H, d), 2.32 (5H, s), 2.37-2.66 (10H, m), 2.71-2.93 (3H, m), 3.07 (1H, dd), 3.50 (2H, dd), 3.66 (1H, d), 3.93-4.07 (3H, m), 4.31 (1H, dd), 4.42 (1H, s), 4.53 (2H, dd), 4.65 (1H, t), 5.19 (1H, s), 6.11 (1H, d), 6.40 (2H, d), 7.02-7.13 (2H, m), 7.22 (2H, dd), 7.27-7.4 (4H, m), 7.45-7.54 (1H, m), 8.11 (1H, s), 8.66 (1H, s); m/z: ES+ [M+H]$^+$ 1015.8.

Intermediate 109a: 6-hydroxyhexyl 4-bromobutanoate

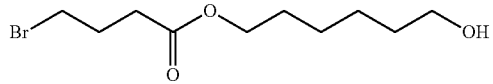 [SMILES: O=C(CCCBr)OCCCCCCO]

1,6-hexanediol (5.15 g, 43.6 mmol) was added to 4-bromobutyric acid (1.67 g, 10 mmol), 4-(dimethylamino)pyridine (0.12 g, 1.00 mmol) and N-(3-Dimethylaminopropyl)-N'-ethylcarbodiimide hydrochloride (2.30 g, 12.0 mmol) in DCM (50 mL) at 20° C. under air. The resulting solution was stirred at 20° C. for 2 days. The reaction mixture was diluted with EtOAc (200 mL), and washed sequentially with water (2×25 mL), 2M aq. HCl (2×25 mL) and saturated brine (2×10 mL). The organic layer was dried with MgSO$_4$, filtered and evaporated to afford crude product. The crude product was purified by flash silica chromatography, elution gradient 5 to 55% EtOAc in heptane to afford the title compound (1.47 g, 55%) as a colourless liquid. $^1$H NMR (400 MHz, DMSO, 30° C.) 1.24-1.37 (4H, m), 1.37-1.48 (2H, m), 1.48-1.64 (2H, m), 2.01-2.14 (2H, m), 2.45 (2H, t), 3.38 (2H, t), 3.55 (2H, t), 4.02 (2H, t), 4.19-4.44 (1H, m); m/z: ES+ [M+H]$^+$ 267.1.

Intermediate 109b: 6-(4-bromobutoxy)hexan-1-ol

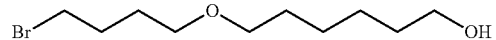 [SMILES: OCCCCCCOCCCCBr]

Indium(III) bromide (0.10 g, 0.27 mmol) was added to 6-hydroxyhexyl 4-bromobutanoate (1.46 g, 5.46 mmol) and triethylsilane (4.36 mL, 27.3 mmol) in CHCl3 (5.5 mL) at 20° C. under nitrogen. The resulting suspension was stirred at 60° C. for 18 hours. The reaction mixture was cooled to 20° C. and a solution of formic acid (1 mL, 27 mmol) in MeOH (9 mL) added. The resulting solution was stirred for 1 hour. The reaction mixture was diluted with 2-methyltetrahydrofuran (150 mL), and washed sequentially with 2M NaOH (2×20 mL), water (2×20 mL), and saturated brine (2×10 mL). The organic layer was dried with MgSO$_4$, filtered and evaporated to afford crude product. The crude product was purified by flash silica chromatography, elution gradient 5 to 50% EtOAc in heptane to afford the title compound (0.45 g, 33%) as a colourless oil. $^1$H NMR (400 MHz, DMSO, 30° C.) 1.24-1.35 (4H, m), 1.37-1.56 (4H, m), 1.56-1.65 (2H, m), 1.81-1.9 (2H, m), 3.31-3.4 (6H, m), 3.55 (2H, t), 4.21 (1H, s); m/z: ES+ [M+H]$^+$ 253.2.

Intermediate 109c: 6-(4-bromobutoxy)hexanoic Acid

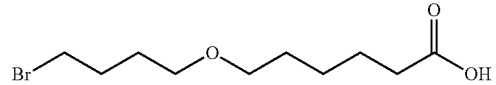 [SMILES: O=C(O)CCCCCOCCCCBr]

A solution of 2M aq. Jones' Reagent (1.74 mL, 3.48 mmol) was added to 6-(4-bromobutoxy)hexan-1-ol (0.44 g, 1.74 mmol) in acetone (1.2 mL) at 0° C. under air. The resulting mixture was stirred at 20° C. for 1 hour. 2-Propanol (2 mL) was added and the suspension stirred for 30 minutes. The reaction mixture was filtered through a sintered glass funnel and the solid washed with EtOAc (40 mL). The filtrate was washed sequentially with water (2 mL), 2M HCl (2×2 mL), and saturated brine (2 mL). The organic layer was dried with MgSO$_4$, filtered and evaporated to afford the title compound (0.42 g, 91%) as a pale green oil. $^1$H NMR (400 MHz, DMSO, 30° C.) 1.22-1.35 (2H, m), 1.41-1.55 (4H, m), 1.55-1.66 (2H, m), 1.78-1.91 (2H, m), 2.20 (2H, t), 3.36 (4H, m), 3.55 (2H, t), 11.96 (1H, s); m/z: ES+ [M+H]$^+$ 267.1.

Intermediate 109d: (2S,4R)-1-((S)-2-(6-(4-bromobutoxy)hexanamido)-3,3-dimethylbutanoyl)-4-hydroxy-N-(4-(4-methylthiazol-5-yl)benzyl)pyrrolidine-2-carboxamide

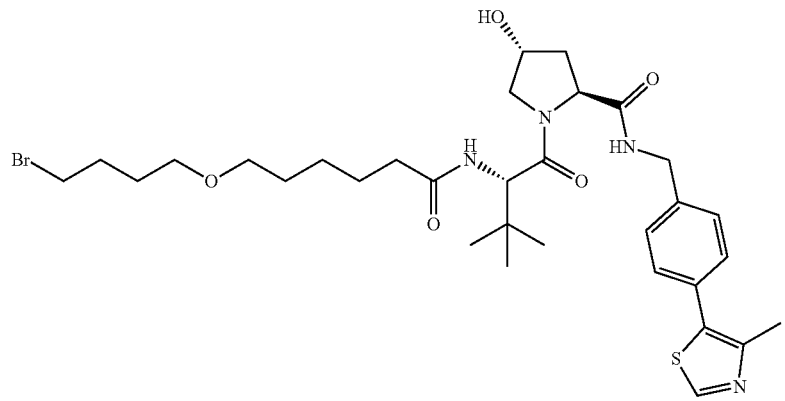

(2S,4R)-1-((S)-2-amino-3,3-dimethylbutanoyl)-4-hydroxy-N-(4-(4-methylthiazol-5-yl)benzyl)pyrrolidine-2-carboxamide, HCl (212 mg, 0.45 mmol) was added to 6-(4-bromobutoxy)hexanoic acid (110 mg, 0.41 mmol), HATU (235 mg, 0.62 mmol) and triethylamine (0.14 mL, 1.0 mmol) in DCM (5 mL) at 20° C. under air. The resulting suspension was stirred at 20° C. for 1 day. The reaction mixture was diluted with EtOAc (50 mL), and washed sequentially with 2 M aq. K2CO3 (3×3 mL), water (5 mL) and saturated brine (2 mL). The organic layer was dried with MgSO₄, filtered and evaporated to afford crude product. The crude product was purified by flash silica chromatography, elution gradient 0 to 10% MeOH in DCM to afford the title compound (207 mg, 74%) as a colourless gum; m/z: ES+ [M+H]⁺ 679.3.

Example 109: (2S,4R)-1-((S)-2-(6-(4-(3,5-difluoro-4-((1R,3R)-2-(2-fluoro-2-methylpropyl)-3-methyl-2,3,49-tetrahydro-1H-pyrido[3,4-b]indol-1-yl)phenoxy)butoxy)hexanamido)-3,3-dimethylbutanoyl)-4-hydroxy-N-(4-(4-methylthiazol-5-yl)benzyl)pyrrolidine-2-carboxamide

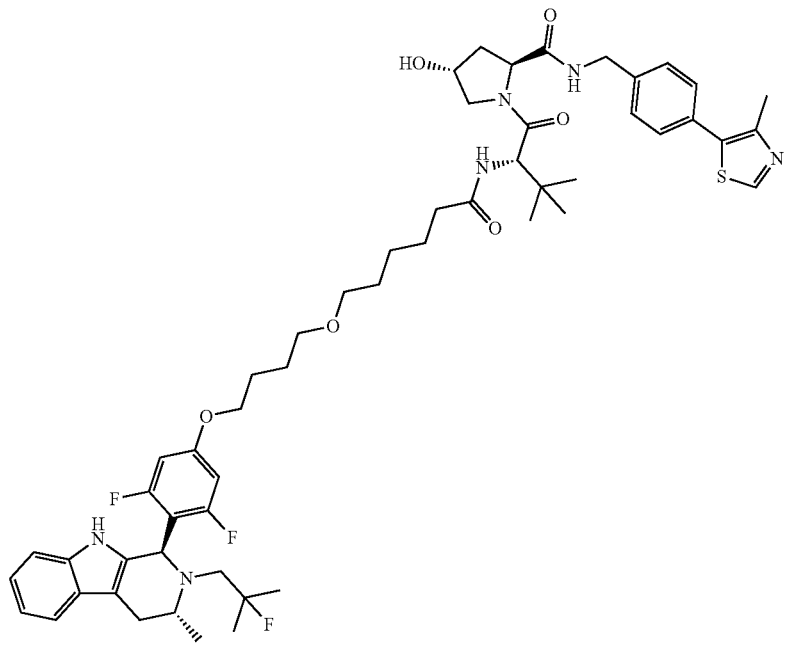 [SMILES: Cc1ncsc1-c1ccc(CNC(=O)[C@@H]2C[C@@H](O)CN2C(=O)[C@@H](NC(=O)CCCCCOCCCCOc2cc(F)c([C@@H]3c4[nH]c5ccccc5c4C[C@@H](C)N3CC(C)(C)F)c(F)c2)C(C)(C)C)cc1]

Potassium carbonate (57 mg, 0.41 mmol) was added to potassium iodide (20 mg, 0.12 mmol), (2S,4R)-1-((S)-2-(6-(4-bromobutoxy)hexanamido)-3,3-dimethylbutanoyl)-4-hydroxy-N-(4-(4-methylthiazol-5-yl)benzyl)pyrrolidine-2-carboxamide (200 mg, 0.30 mmol) and −3,5-difluoro-4-((1R, 3R)-2-(2-fluoro-2-methylpropyl)-3-methyl-2,3,4,9-tetrahydro-1H-pyrido[3,4-b]indol-1-yl)phenol (80 mg, 0.21 mmol) in acetonitrile (2 mL) at 20° C. under air. The resulting suspension was stirred at 75° C. for 20 hours. The reaction mixture was diluted with water (2 mL). The crude product was purified by ion exchange chromatography, using an SCX column. The product was eluted from the column using 1M NH$_3$/MeOH and product containing fractions were evaporated to dryness. The crude product was purified by preparative HPLC (Waters CSH C18 OBD column, 30×100 mm id, 5 micron particle size), using decreasingly polar mixtures of water (containing 1% by volume of NH$_4$OH (28-30% in H$_2$O)) and MeCN as eluents to afford the title compound (75 mg, 37%) as a white solid. $^1$H NMR (400 MHz, CDCl$_3$, 30° C.) 0.91 (9H, s), 1.10 (3H, d), 1.20 (6H, dd), 1.3-1.41 (2H, m), 1.5-1.75 (5H, m), 1.77-1.89 (2H, m), 2.06 (1H, dd), 2.18 (2H, t), 2.40 (1H, dd), 2.47-2.64 (5H, m), 2.79-2.94 (2H, m), 3.08 (1H, dd), 3.34-3.51 (5H, m), 3.56 (1H, dd), 3.62-3.73 (1H, m), 3.92 (2H, t), 4.05 (1H, d), 4.31 (1H, dd), 4.43-4.58 (3H, m), 4.67 (1H, t), 5.19 (1H, s), 6.05 (1H, d), 6.37 (2H, d), 7.03-7.14 (2H, m), 7.21 (2H, dd), 7.28-7.42 (4H, m), 7.51 (1H, dd), 7.88 (1H, s), 8.66 (1H, s); m/z: ES− [M−H]$^-$ 985.9.

Intermediate 110a: 7-Hydroxyheptyl 3-bromopropanoate

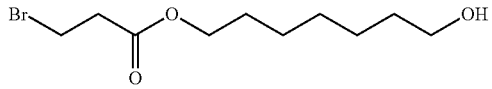 [SMILES: O=C(CCBr)OCCCCCCCO]

The title compound was prepared in a similar manner to Intermediate 109a using the appropriate carboxylic acid and alcohol to afford the desired product (0.92 g, 35%) as a colourless oil that was used without further purification. $^1$H NMR (400 MHz, DMSO, 30° C.) 1.23-1.37 (6H, m), 1.35-1.47 (2H, m), 1.51-1.67 (2H, m), 2.95 (2H, t), 3.38 (2H, q), 3.64 (2H, t), 4.07 (2H, t), 4.30 (1H, t); m/z: ES+ [M+H]$^+$ 267.1.

Intermediate 110b: 7-(3-Bromopropoxy)heptan-1-ol

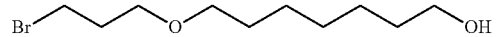 [SMILES: OCCCCCCCOCCCBr]

The title compound was prepared in a similar manner to Intermediate 109b using the appropriate ester to afford the desired product (569 mg, 77%) as a colourless oil. $^1$H NMR (400 MHz, DMSO, 30° C.) 1.27 (6H, s), 1.35-1.55 (4H, m), 1.97-2.06 (2H, m), 3.34-3.41 (4H, m), 3.45 (2H, t), 3.55 (2H, t), 4.29 (1H, t); m/z: ES+ [M+H]$^+$ 253.1.

Intermediate 110c: 7-(3-bromopropoxy)heptanoic Acid

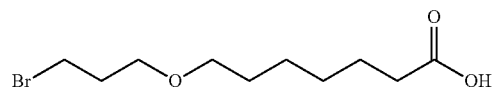 [SMILES: O=C(O)CCCCCCOCCCBr]

The title compound was prepared in a similar manner to Intermediate 109c using the appropriate alcohol to afford the desired product (537 mg, 91%) as a colourless oil. $^1$H NMR (400 MHz, DMSO, 30° C.) 1.2-1.36 (4H, m), 1.43-1.57 (4H, m), 1.97-2.06 (2H, m), 2.19 (2H, t), 3.36 (2H, t), 3.45 (2H, t), 3.55 (2H, t), 11.82 (1H, s); m/z: ES+ [M+H]$^+$ 267.3.

Intermediate 110d: (2S,4R)-1-((S)-2-(7-(3-Bromopropoxy)heptanamido)-3,3-dimethylbutanoyl)-4-hydroxy-N-(4-(4-methylthiazol-5-yl)benzyl)pyrrolidine-2-carboxamide

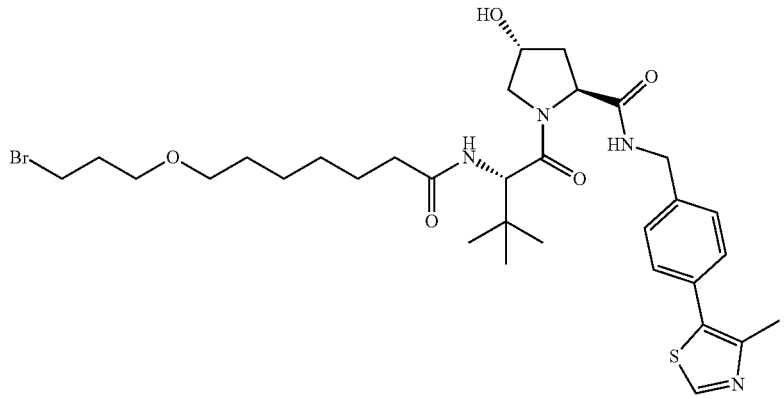

The title compound was prepared in a similar manner to Intermediate 109d using the appropriate carboxylic acid to afford the desired product (276 mg, 77%) as a white solid. $^1$H NMR (400 MHz, CDCl$_3$, 30° C.) 0.92 (9H, s), 1.27-1.4 (4H, m), 1.5-1.59 (3H, m), 2.05-2.16 (3H, m), 2.16-2.23 (2H, m), 2.52 (3H, s), 2.59 (1H, ddd), 2.78-2.91 (1H, m), 3.40 (2H, t), 3.47-3.54 (3H, m), 3.58 (1H, dd), 4.13 (1H, d), 4.33 (1H, dd), 4.48 (1H, d), 4.51-4.63 (2H, m), 4.73 (1H, t), 6.03 (1H, d), 7.29 (1H, s), 7.31-7.41 (4H, m), 8.68 (1H, s); m/z: ES+ [M+H]+ 679.3.

Example 110: (2S,4R)-1-((S)-2-(7-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)heptanamido)-3,3-dimethylbutanoyl)-4-hydroxy-N-(4-(4-methylthiazol-5-yl)benzyl)pyrrolidine-2-carboxamide

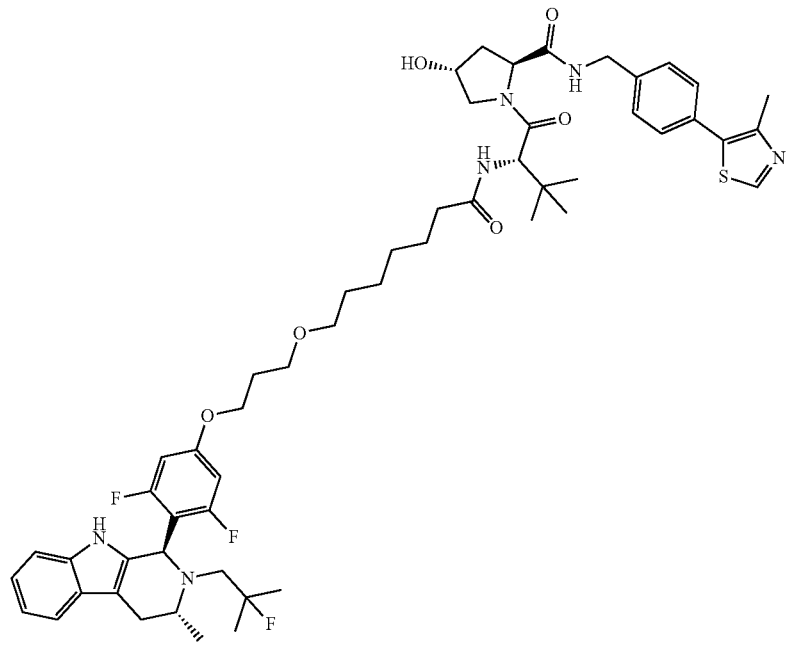 [SMILES: Cc1ncsc1-c1ccc(CNC(=O)[C@@H]2C[C@@H](O)CN2C(=O)[C@@H](NC(=O)CCCCCCOCCCOc2cc(F)c([C@@H]3c4[nH]c5ccccc5c4C[C@@H](C)N3CC(C)(C)F)c(F)c2)C(C)(C)C)cc1]

The title compound was prepared in a similar manner to Example 109 using the appropriate alkyl bromide to afford the desired product (94 mg, 41%) as a white solid. ¹H NMR (400 MHz, CDCl₃, 30° C.) 0.91 (9H, s), 1.10 (3H, d), 1.21 (6H, dd), 1.27-1.35 (4H, m), 1.48-1.58 (4H, m), 1.94-2.11 (3H, m), 2.15 (2H, t), 2.41 (1H, dd), 2.47-2.64 (5H, m), 2.66 (1H, d), 2.84 (1H, dd), 3.07 (1H, dd), 3.40 (2H, t), 3.49-3.59 (3H, m), 3.61-3.72 (1H, m), 3.96-4.07 (3H, m), 4.32 (1H, dd), 4.43-4.62 (3H, m), 4.69 (1H, t), 5.20 (1H, s), 6.03 (1H, d), 6.39 (2H, d), 7.03-7.12 (2H, m), 7.18-7.24 (2H, m), 7.29-7.41 (4H, m), 7.47-7.56 (1H, m), 8.00 (1H, s), 8.66 (1H, s); m/z: ES– [M–H]– 985.9.

Intermediate 111a: 8-Hydroxyoctyl 2-bromoacetate

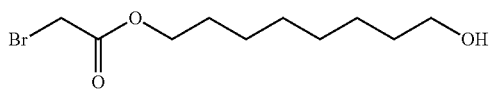 [SMILES: O=C(CBr)OCCCCCCCCO]

1,8-Octanediol (5.85 g, 40.00 mmol) was added to bromoacetic acid (1.39 g, 10 mmol), 4-(dimethylamino)pyridine (0.12 g, 1.00 mmol) and N-(3-Dimethylaminopropyl)-N′-ethylcarbodiimide hydrochloride (2.30 g, 12.0 mmol) in DCM (50 md) and acetonitrile (10 mL) at 20° C. under air. The resulting solution was stirred at 20° C. for 2 days. The reaction mixture was diluted with EtOAc (200 md), and washed sequentially with water (50 mL)-3.72 (H, 2M aq. HCl (20 mL), water (2×20 mL) and saturated brine (2×10 mL). The organic layer was dried with MgSO₄, filtered and evaporated to afford crude product. The resulting solid was slurried with DCM (10 mL) and filtered. The solid was washed with DCM (4×10 mL) and the combined filtrate evaporated to a colourless oil. The oil was purified by flash silica chromatography, elution gradient 10 to 60% EtOAc in heptane. Pure fractions were evaporated to dryness to afford the title compound (1.37 g, 51%) as a pale yellow liquid. ¹H NMR (400 MHz, DMSO, 30° C.) 1.27 (8H, s), 1.36-1.48 (2H, m), 1.60 (2H, p), 3.33-3.45 (2H, m), 4.07-4.18 (2H, m), 4.29 (1H, t), 4.37 (2H, s); m/z: ES+ [M+H]+ 267.2.

Intermediate 11b: 8-(2-bromoethoxy)octan-1-ol

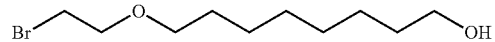 [SMILES: OCCCCCCCCOCCBr]

Indium(III) bromide (0.090 g, 0.25 mmol) was added to 8-hydroxyoctyl 2-bromoacetate (1.35 g, 5.05 mmol) and triethylsilane (4.04 mL, 25.27 mmol) in CHCl3 (5 mL) at 20° C. under nitrogen. The resulting suspension was stirred at 60° C. for 20 hours. The suspension was cooled to 20° C. and a solution of formic acid (1 mL, 26.5 mmol) in methanol (9 mL) added. The resulting solution was stirred at 20° C. for 20 minutes. The reaction mixture was evaporated to dryness and redissolved in 2-methyltetrahydrofuran (50 mL), and washed sequentially with 2M NaOH (2×5 mL) and saturated brine (5 mL). The organic layer was dried with MgSO₄, filtered and evaporated to afford crude product. The crude product was purified by flash silica chromatography, elution gradient 0 to 50% EtOAc in heptane to afford the title compound (1.01 g, 79%) as a colourless oil. ¹H NMR (400 MHz, DMSO, 30° C.) 1.22-1.35 (8H, m), 1.35-1.45 (2H, m), 1.45-1.55 (2H, m), 3.34-3.45 (4H, m), 3.56-3.64 (2H, m), 3.66-3.74 (2H, m), 4.29 (1H, t).

Intermediate 11c: 8-(2-chloroethoxy)octanoic Acid

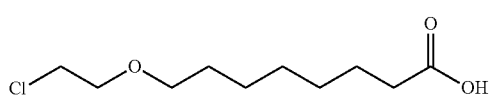 [SMILES: O=C(O)CCCCCCCOCCCl]

A solution of 2M aq. Jones' Reagent (3.95 mL, 7.90 mmol) was added to 8-(2-bromoethoxy)octan-1-ol (1.0 g, 4.0 mmol) in acetone (1.2 mL) at 20° C. under air. The resulting mixture was stirred at 20° C. for 1 hour. 2-Propanol (2 mL) was added and the suspension stirred for 30 minutes. The supernatant was decanted from the precipitate, the precipitate washed with EtOAc (3×50 mL) and the organic portions combined. The combined portions were washed sequentially with 2M HCl (3×15 mL) and saturated brine (10 mL). The organic layer was dried with $MgSO_4$, filtered and evaporated to afford crude product. The crude product was purified by flash silica chromatography, elution gradient 5 to 35% 9:1 EtOAc:acetic acid in heptane to afford the title compound (0.812 g, 92%) as a colourless oil. $^1$H NMR (400 MHz, DMSO, 30° C.) 1.22-1.35 (6H, m), 1.43-1.55 (4H, m), 2.19 (2H, t), 3.42 (2H, t), 3.6-3.64 (2H, m), 3.69-3.73 (2H, m), 11.93 (1H, s); m/z: ES− [M−H]$^-$ 221.0.

Intermediate 11d: (2S,4R)-1-((S)-2-(8-(2-Chloroethoxy)octanamido)-3,3-dimethylbutanoyl)-4-hydroxy-N-(4-(4-methylthiazol-5-yl)benzyl)pyrrolidine-2-carboxamide

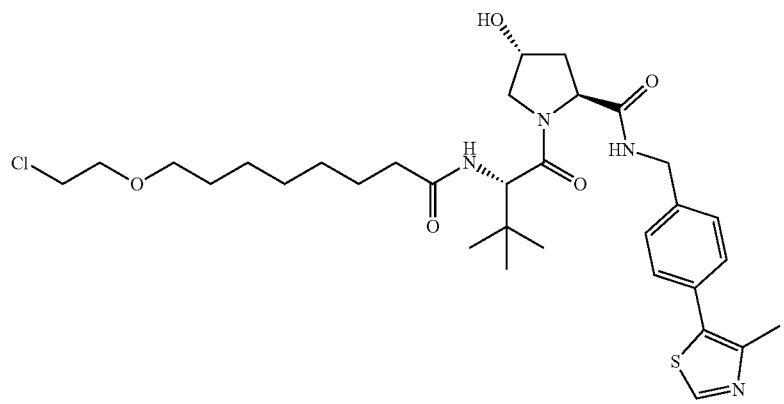 [SMILES: Cc1ncsc1-c1ccc(CNC(=O)[C@@H]2C[C@@H](O)CN2C(=O)[C@@H](NC(=O)CCCCCCCOCCCl)C(C)(C)C)cc1]

(2S,4R)-1-((S)-2-Amino-3,3-dimethylbutanoyl)-4-hydroxy-N-(4-(4-methylthiazol-5-yl)benzyl)pyrrolidine-2-carboxamide, HCl (0.27 g, 0.57 mmol) was added to 8-(2-chloroethoxy)octanoic acid (0.115 g, 0.52 mmol), HATU (0.295 g, 0.77 mmol) and triethylamine (0.18 mL, 1.3 mmol) in DCM (5 mL) at 20° C. under air. The resulting suspension was stirred at 20° C. for 1 day. The reaction mixture was diluted with EtOAc (50 mL), and washed sequentially with 2 M aq. potassium carbonate (20 mL), 2 M aq. potassium carbonate (2×10 mL), and saturated brine (5 mL). The organic layer was dried with $MgSO_4$, filtered and evaporated to afford crude product. The crude product was purified by flash silica chromatography, elution gradient 0 to 7% MeOH in DCM to afford the title compound (0.277 g, 84%) as a pale yellow solid. $^1$H NMR (400 MHz, CDCl$_3$, 30° C.) 0.93 (9H, s), 1.33 (4H, d), 1.40 (1H, t), 1.51-1.65 (4H, m), 2.06-2.16 (1H, m), 2.16-2.21 (2H, m), 2.49-2.59 (4H, m), 3.17 (1H, s), 3.23 (1H, q), 3.46 (2H, t), 3.57-3.63 (3H, m), 3.64-3.69 (2H, m), 4.10 (1H, d), 4.3-4.37 (1H, m), 4.47-4.6 (3H, m), 4.72 (1H, t), 6.08 (1H, d), 7.28-7.39 (5H, m), 8.68 (1H, s); m/z: ES+ [M+H]$^+$ 635.4.

Example 111: (2S,4R)-1-((S)-2-(8-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)octanamido)-3,3-dimethylbutanoyl)-4-hydroxy-N-(4-(4-methylthiazol-5-yl)benzyl)pyrrolidine-2-carboxamide

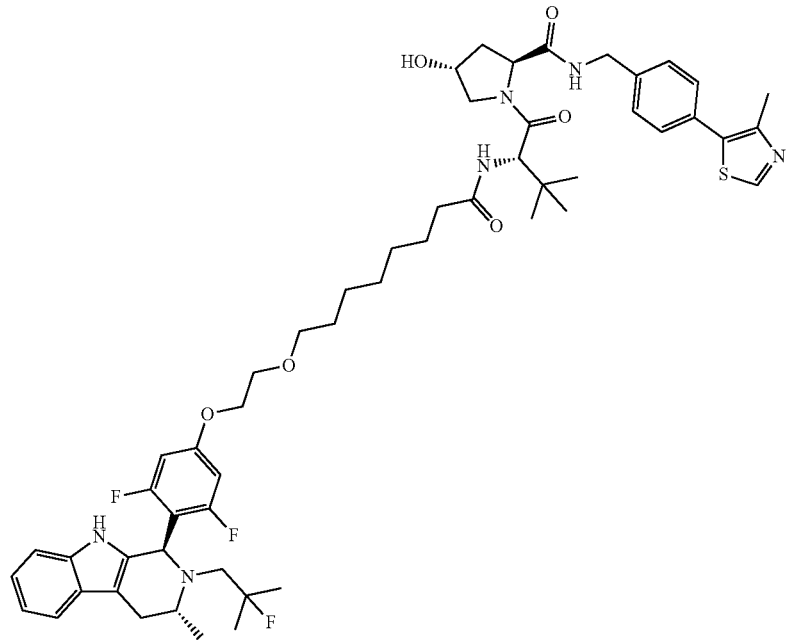 [SMILES: Cc1ncsc1-c1ccc(CNC(=O)[C@@H]2C[C@@H](O)CN2C(=O)[C@@H](NC(=O)CCCCCCCOCCOc2cc(F)c([C@@H]3c4[nH]c5ccccc5c4C[C@@H](C)N3CC(C)(C)F)c(F)c2)C(C)(C)C)cc1]

Potassium carbonate (43 mg, 0.31 mmol) was added to (2S,4R)-1-((S)-2-(8-(2-chloroethoxy)octanamido)-3,3-dimethylbutanoyl)-4-hydroxy-N-(4-(4-methylthiazol-5-yl)benzyl)pyrrolidine-2-carboxamide (120 mg, 0.19 mmol) and 3,5-difluoro-4-((1R,3R)-2-(2-fluoro-2-methylpropyl)-3-methyl-2,3,4,9-tetrahydro-1H-pyrido[3,4-b]indol-1-yl)phenol (60 mg, 0.15 mmol) in acetonitrile (2 mL) at 20° C. under air. The resulting suspension was stirred at 80° C. for 4 hours. The reaction was incomplete and potassium iodide (12 mg, 0.07 mmol) was added and the suspension was stirred at 80° C. for a further 2 days under nitrogen. The reaction mixture was dissolved in water (2 mL) and MeOH (2 mL). The mixture was purified by ion exchange chromatography, using an SCX column. The desired product was eluted from the column using 1M NH$_3$/MeOH and product containing fractions were evaporated to dryness. The crude product was purified by preparative HPLC (Waters XBridge Prep C18 OBD column, 5μ silica, 30 mm diameter, 100 mm length), using decreasingly polar mixtures of water (containing by volume 1% NH$_4$OH (28-30% in H$_2$O)) and MeCN as eluents to afford to afford (42 mg, 28%) as a pale yellow solid. $^1$H NMR (400 MHz, CDCl$_3$, 30° C.) 0.92 (9H, s), 1.10 (3H, d), 1.20 (6H, dd), 1.29 (6H, d), 1.52-1.59 (4H, m), 2.06 (1H, dd), 2.17 (2H, t), 2.39 (1H, dd), 2.51 (4H, s), 2.60 (1H, dd), 2.76 (1H, d), 2.85 (1H, dd), 3.08 (1H, dd), 3.43-3.58 (3H, m), 3.61-3.7 (1H, m), 3.71-3.78 (2H, m), 3.97-4.1 (3H, m), 4.32 (1H, dd), 4.41-4.52 (2H, m), 4.56 (1H, dd), 4.70 (1H, t), 5.19 (1H, s), 6.03 (1H, d), 6.42 (2H, d), 7.04-7.12 (2H, m), 7.18-7.23 (1H, m), 7.35 (4H, q), 7.48-7.56 (1H, m), 7.82 (1H, s), 8.66 (1H, s); m/z: ES- [M-H]$^-$ 985.8.

Intermediate 112a: 4-(Benzyloxy)butyl 6-bromohexanoate

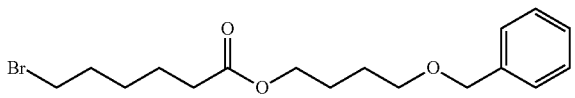 [SMILES: O=C(CCCCCBr)OCCCCOCc1ccccc1]

The title compound was prepared in a similar manner to Intermediate 109a using the appropriate carboxylic acid and alcohol to afford the desired product (1.674 g, 91%) as a colourless oil. $^1$H NMR (400 MHz, DMSO, 30° C.) 1.32-1.45 (2H, m), 1.48-1.69 (6H, m), 1.75-1.85 (2H, m), 2.30 (2H, t), 3.45 (2H, t), 3.51 (2H, t), 4.03 (2H, t), 4.46 (2H, s), 7.23-7.4 (5H, m).

Intermediate 112b: 4-((6-bromohexyl)oxy)butan-1-ol

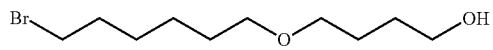 [SMILES: OCCCCOCCCCCCBr]

The title compound was prepared by 3 methods as detailed below.
Method 1
Indium(III) bromide (0.071 g, 0.20 mmol) was added to 4-(benzyloxy)butyl 6-bromohexanoate (1.44 g, 4.03 mmol) and triethylsilane (2.57 mL, 16.1 mmol) in CHCl3 (0.6 mL)

at 20° C. under nitrogen. The resulting suspension was stirred at 60° C. for 18 hours. The resulting mixture was evaporated to dryness and the residue purified by flash silica chromatography, elution gradient 0 to 70% EtOAc in heptane to afford the title compound (0.103 g, 10%) as a colourless oil. ¹H NMR (400 MHz, DMSO, 30° C.) 1.29-1.54 (10H, m), 1.80 (2H, p), 3.31-3.36 (4H, m), 3.36-3.42 (2H, m), 3.52 (2H, t), 4.33 (1H, t); m/z: ES+ [M+H]⁺ 253.2.

Method 2

((4-((6-Bromohexyl)oxy)butoxy)methyl)benzene (197 mg, 0.57 mmol) and 10% palladium on carbon (60 mg, 0.06 mmol) in ethanol (2 mL) were stirred under an atmosphere of hydrogen at 1 atm and 20° C. for 2 days. The reaction mixture was filtered through celite and the filtrate evaporated to dryness. The crude product was purified by flash silica chromatography, elution gradient 0 to 60% EtOAc in heptane to afford the title compound (91 mg, 63%) as a colourless oil. ¹H NMR (400 MHz, DMSO, 30° C.) 1.27-1.56 (10H, m), 1.76-1.85 (2H, m), 3.31-3.36 (4H, m), 3.36-3.43 (2H, m), 3.52 (2H, t), 4.33 (1H, t); m/z: ES+ [M+H]⁺ 253.2.

Method 3

Formic acid (0.35 mL, 9.3 mmol) was added to (4-((6-bromohexyl)oxy)butoxy)triethylsilane (670 mg, 1.82 mmol) in methanol (7 mL) at 20° C. under air. The resulting solution was stirred at 20° C. for 16 hours. The resulting mixture was evaporated to dryness and the residue purified by flash silica chromatography, elution gradient 20 to 60% EtOAc in heptane to afford the title compound (118 mg, 26%) as a colourless oil. ¹H NMR (400 MHz, DMSO, 30° C.) 1.27-1.56 (10H, m), 1.75-1.85 (2H, m), 3.31-3.37 (4H, m), 3.37-3.43 (2H, m), 3.52 (2H, t), 4.33 (1H, t); m/z: ES+ [M+H]⁺ 253.2.

Intermediate 112c: ((4-((6-Bromohexyl)oxy)butoxy)methyl)benzene

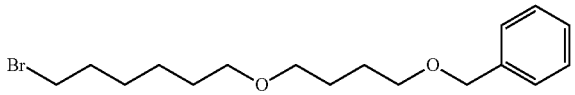 [SMILES: BrCCCCCCOCCCCOCc1ccccc1]

The title compound was obtained using the same method as intermediate 112b Method 1 to afford the title compound (0.217 g, 16%) as a colourless oil. ¹H NMR (400 MHz, DMSO, 30° C.) 1.27-1.43 (4H, m), 1.44-1.6 (6H, m), 1.79 (2H, p), 3.32-3.37 (4H, m), 3.44 (2H, t), 3.52 (2H, t), 4.45 (2H, s), 7.23-7.42 (5H, m); m/z: ES+ [M+H]⁺ 343.2.

Intermediate 112d: (4-((6-bromohexyl)oxy)butoxy)triethylsilane

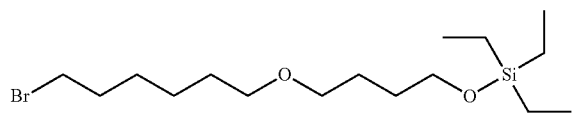 [SMILES: CC[Si](CC)(CC)OCCCCOCCCCCCBr]

The title compound was obtained using the same method as intermediate 112b Method 1 to afford the title compound (0.675 g, 46%) as a colourless oil, which was used without further purification. m/z: ES+ [M+H]⁺ 367.3.

Intermediate 112e: 4-((6-bromohexyl)oxy)butanoic Acid

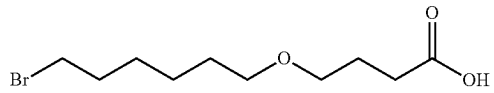 [SMILES: O=C(O)CCCOCCCCCCBr]

The title compound was prepared in a similar manner to Intermediate 109c using the appropriate alcohol to afford the desired product (231 mg, 80%) as a pale yellow oil. ¹H NMR (400 MHz, DMSO, 30° C.) 1.27-1.44 (4H, m), 1.49 (2H, p), 1.71 (2H, p), 1.80 (2H, p), 2.25 (2H, t), 3.34 (4H, td), 3.52 (2H, t), 12.02 (1H, s); m/z: ES+ [M+H]⁺267.1.

Intermediate 112f: (2S,4R)-1-((S)-2-(4-((6-Bromohexyl)oxy)butanamido)-3,3-dimethylbutanoyl)-4-hydroxy-N-(4-(4-methylthiazol-5-yl)benzyl)pyrrolidine-2-carboxamide

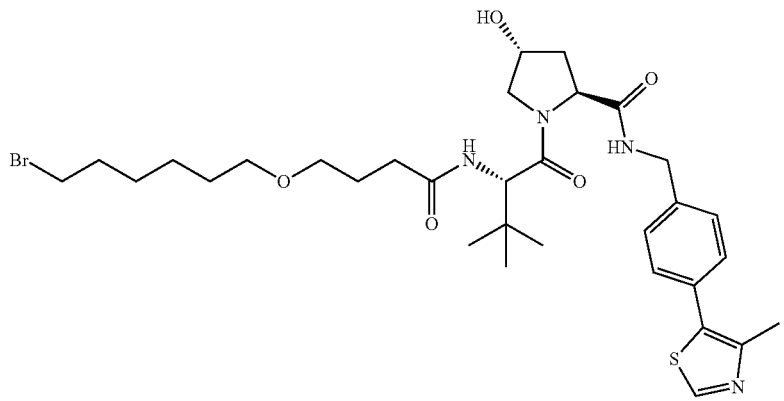

The title compound was prepared in a similar manner to Intermediate 109d using the appropriate carboxylic acid to afford the desired product (0.437 g, 75%) as a pale yellow gum, which was used without further purification; m/z: ES+ [M+H]+ 679.3.

Example 112: (2S,4R)-1-((S)-2-(4-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)butanamido)-3,3-dimethylbutanoyl)-4-hydroxy-N-(4-(4-methylthiazol-5-yl)benzyl)pyrrolidine-2-carboxamide

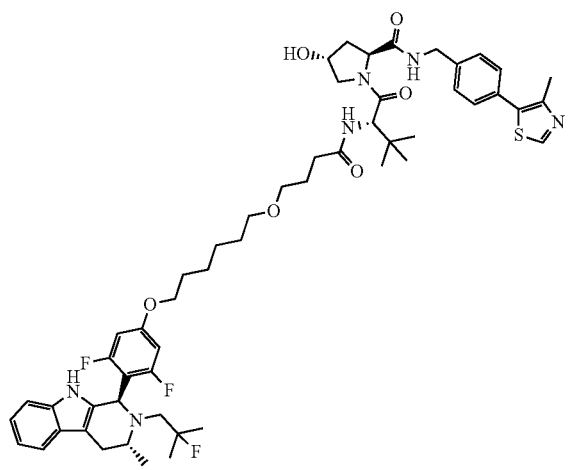 [SMILES: Cc1ncsc1-c1ccc(CNC(=O)[C@@H]2C[C@@H](O)CN2C(=O)[C@@H](NC(=O)CCCOCCCCCCOc2cc(F)c([C@@H]3c4[nH]c5ccccc5c4C[C@@H](C)N3CC(C)(C)F)c(F)c2)C(C)(C)C)cc1]

The title compound was prepared in a similar manner to Example 109 using the appropriate alkyl bromide to afford the desired product (0.066 g, 24%) as a brown solid. $^1$H NMR (400 MHz, CDCl$_3$, 30° C.) 0.92 (9H, s), 1.10 (3H, d), 1.20 (6H, dd), 1.33-1.51 (4H, m), 1.59 (2H, p), 1.75 (2H, q), 1.85 (2H, p), 2.04-2.14 (1H, m), 2.28 (2H, td), 2.40 (1H, dd), 2.49 (3H, s), 2.51-2.65 (2H, m), 2.85 (1H, dd), 2.95 (1H, d), 3.08 (1H, dd), 3.41 (4H, td), 3.56 (1H, dd), 3.62-3.74 (1H, m), 3.87 (2H, t), 4.10 (1H, d), 4.31 (1H, dd), 4.44-4.54 (2H, m), 4.56 (1H, dd), 4.71 (1H, t), 5.19 (1H, s), 6.35 (3H, dd), 7.01-7.14 (2H, m), 7.18-7.24 (1H, m), 7.27-7.4 (5H, m), 7.48-7.54 (1H, m), 7.95 (1H, s), 8.64 (1H, s); m/z: ES+ [M+H]+ 987.6.

Intermediate 113a: 5-Hydroxypentyl 5-bromopentanoate

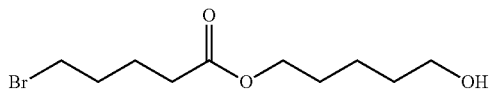 [SMILES: O=C(CCCCBr)OCCCCCO]

Pentane-1,5-diol (2.32 mL, 22.1 mmol) was added to 5-bromovaleric acid (1.00 g, 5.52 mmol), 4-(dimethylamino)pyridine (0.067 g, 0.55 mmol) and N-(3-Dimethylaminopropyl)-N'-ethylcarbodiimide hydrochloride (1.27 g, 6.63 mmol) in DCM (25 mL) at 20° C. under air. The resulting solution was stirred at 20° C. for 3 days. The reaction mixture was diluted with EtOAc (100 mL), and washed sequentially with water (3×10 mL), saturated NaHCO$_3$ (2×10 mL), and saturated brine (5 mL). The organic layer was dried with MgSO$_4$, filtered and evaporated to afford crude product. The crude product was purified by flash silica chromatography, elution gradient 5 to 50% EtOAc in heptane to afford the title compound (1.024 g, 69.4%) as a colourless oil. $^1$H NMR (400 MHz, DMSO, 30° C.) 1.28-1.38 (2H, m), 1.43 (2H, dt), 1.51-1.7 (4H, m), 1.77-1.88 (2H, m), 2.34 (2H, t), 3.34-3.44 (2H, m), 3.54 (2H, t), 4.01 (2H, t), 4.33 (1H, t); m/z: ES+ [M+H]+ 267.2.

Intermediate 113b: 5-((5-bromopentyl)oxy)pentan-1-ol

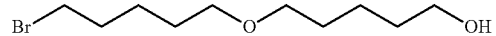 [SMILES: OCCCCCOCCCCCBr]

Indium(III) bromide (57.7 mg, 0.16 mmol) was added to 5-hydroxypentyl 5-bromopentanoate (870 mg, 3.26 mmol) and triethylsilane (2.60 mL, 16.28 mmol) in chloroform (2.5 mL) at 20° C. under nitrogen. The resulting suspension was stirred at 60° C. for 30 minutes. The reaction mixture was evaporated to afford crude product. The crude product was purified by flash silica chromatography, elution gradient 0 to 60% EtOAc in heptane to afford the title compound (357 mg, 43%) as a colourless liquid. $^1$H NMR (400 MHz, DMSO, 30° C.) 1.27-1.37 (2H, m), 1.37-1.58 (8H, m), 1.81 (2H, p), 3.31-3.43 (6H, m), 3.53 (2H, t), 4.30 (1H, t); m/z: ES+ [M+H]+ 253.2.

Intermediate 113c: 5-((5-Bromopentyl)oxy)pentanoic Acid

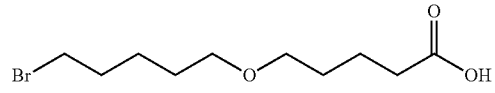 [SMILES: O=C(O)CCCCOCCCCCBr]

A solution of 2M aq. Jones' Reagent (1.38 mL, 2.76 mmol) was added to 5-((5-bromopentyl)oxy)pentan-1-ol (350 mg, 1.38 mmol) in acetone (1.2 mL) at 20° C. under air. The resulting mixture was stirred at 20° C. for 30 minutes. The reaction mixture was quenched with isopropyl alcohol (1 mL) and stirred for 5 min. The supernatant was decanted and diluted with EtOAc (40 mL), and washed sequentially with water (20 mL), 2M HCl (1 mL), and saturated brine (2 mL). The organic layer was dried with MgSO$_4$, filtered and evaporated to afford the title compound (356 mg, 96%) as a colourless oil. $^1$H NMR (400 MHz, DMSO, 30° C.) 1.37-1.59 (8H, m), 1.81 (2H, p), 2.22 (2H, t), 3.34 (4H, t), 3.53 (2H, t), 11.95 (1H, s); m/z: ES+ [M+H]+ 267.1.

Intermediate 113d: (2S,4R)-1-((S)-2-(5-((5-Bromopentyl)oxy)pentanamido)-3,3-dimethylbutanoyl)-4-hydroxy-N-(4-(4-methylthiazol-5-yl)benzyl)pyrrolidine-2-carboxamide

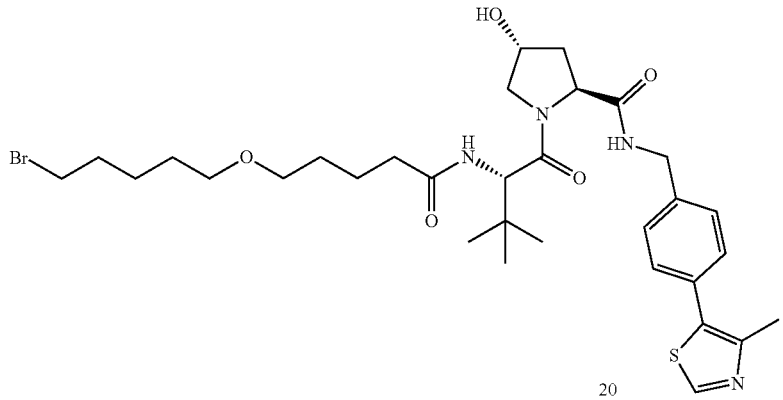

HATU (374 mg, 0.98 mmol) was added to 5-((5-bromopentyl)oxy)pentanoic acid (105 mg, 0.39 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (200 mg, 0.43 mmol) and triethylamine (0.082 mL, 0.59 mmol) in DCM (3 mL) at 20° C. under air. The resulting suspension was stirred at 20° C. for 30 minutes. The reaction was incomplete and DMF (0.5 mL) was added and the suspension was stirred at 20° C. for a further 1 hour. The reaction was incomplete and further triethylamine (0.082 mL, 0.59 mmol) was added and the suspension was stirred at 20° C. for a further 30 minutes. The reaction mixture was diluted with EtOAc (5 mL), and washed sequentially with water (2×5 mL), saturated NaHCO$_3$ (2×2 mL), and saturated brine (2 mL). The organic layer was dried with MgSO$_4$, filtered and evaporated to afford crude product. The crude product was purified by flash silica chromatography, elution gradient 0 to 10% MeOH in DCM to afford the title compound (230 mg, 86%) as a white solid. $^1$H NMR (400 MHz, CDCl$_3$, 30° C.) 0.93 (9H, s), 1.45-1.54 (2H, m), 1.53-1.63 (4H, m), 1.63-1.71 (2H, m), 1.87 (2H, dt), 2.06-2.18 (1H, m), 2.24 (2H, t), 2.52 (3H, s), 2.57 (1H, ddd), 3.21 (1H, qd), 3.40 (6H, td), 3.59 (1H, dd), 4.12 (1H, d), 4.28-4.4 (1H, m), 4.48 (1H, d), 4.5-4.62 (2H, m), 4.73 (1H, t), 6.18 (1H, d), 7.27-7.41 (5H, m), 8.68 (1H, s); m/z: ES+ [M+H]$^+$ 679.5.

Example 113: (2S,4R)-1-((S)-2-(5-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)pentanamido)-3,3-dimethylbutanoyl)-4-hydroxy-N-(4-(4-methylthiazol-5-yl)benzyl)pyrrolidine-2-carboxamide

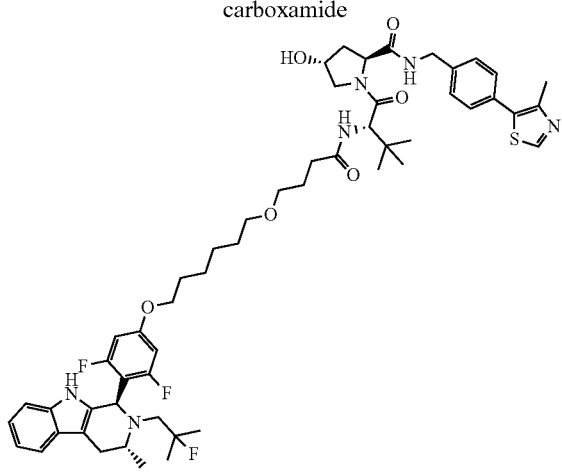

Potassium carbonate (0.071 g, 0.51 mmol) was added to (2S,4R)-1-((S)-2-(5-((5-bromopentyl)oxy)pentanamido)-3,3-dimethylbutanoyl)-4-hydroxy-N-(4-(4-methylthiazol-5-yl)benzyl)pyrrolidine-2-carboxamide (0.23 g, 0.34 mmol) and 3,5-difluoro-4-((1R,3R)-2-(2-fluoro-2-methylpropyl)-3-methyl-2,3,4,9-tetrahydro-1H-pyrido[3,4-b]indol-1-yl)phenol (0.10 g, 0.26 mmol) in acetonitrile (2 mL) at 20° C. under air. The resulting suspension was stirred at 80° C. for 7 hours. The reaction mixture was diluted with EtOAc (20 mL), and washed sequentially with water (2 mL), 2M aq. potassium carbonate (2×1 mL), and saturated brine (2 mL). The organic layer was dried with MgSO$_4$, filtered and evaporated to afford crude product. The crude product was purified by flash silica chromatography, elution gradient 0 to 8% MeOH in DCM. Product containing fractions were evaporated to dryness to afford crude product as a pale yellow solid. The crude product was purified by preparative HPLC (Waters XSelect CSH C18 column, 5μ silica, 30 mm diameter, 100 mm length), using decreasingly polar mixtures of water (containing by volume 1% NH$_4$OH (28-30% in H$_2$O)) and MeCN as eluents to afford the title compound (0.070 g, 28%) as a pale yellow solid. $^1$H NMR (400 MHz, CDCl$_3$, 30° C.) 0.92 (9H, s), 1.10 (3H, d), 1.20 (6H, dd), 1.44-1.68 (9H, m), 1.73-1.83 (2H, m), 2.03-2.12 (1H, m), 2.22 (2H, td), 2.39 (1H, dd), 2.50 (4H, s), 2.60 (1H, dd), 2.85 (1H, dd), 2.97 (1H, s), 3.08 (1H, dd), 3.35-3.44 (4H, m), 3.55 (1H, dd), 3.62-3.71 (1H, m), 3.89 (2H, t), 4.08 (1H, d), 4.31 (1H, dd), 4.45-4.51 (2H, m), 4.56 (1H, dd), 4.69 (1H, t), 5.19 (1H, s), 6.19 (1H, d), 6.31-6.47 (2H, m), 7-7.13 (2H, m), 7.19-7.24 (1H, m), 7.34 (4H, q), 7.51 (1H, dd), 7.90 (1H, s), 8.65 (1H, s). m/z: ES− [M−H]$^-$ 985.7

Intermediate 114a: tert-Butyl 3-(hept-6-en-1-yloxy)propanoate

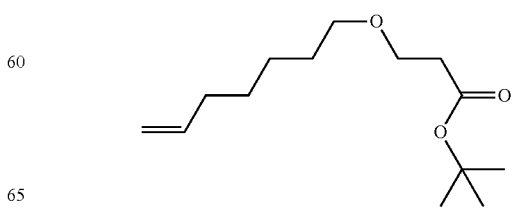

40% N,N,N-Trimethyl-1-phenylmethanaminium hydroxide in methanol (0.489 mL, 1.17 mmol) was evaporated to dryness and 6-heptene-1-ol (3.68 mL, 27.39 mmol) added at 20° C. under nitrogen. The resulting solution was stirred for 25 min and tert-butyl acrylate (3.43 mL, 23.41 mmol) added. The resulting solution was stirred at 50° C. for 3 days. The crude reaction mixture was purified by flash silica chromatography, elution gradient 25 to 75% DCM in heptane to afford tert-butyl 3-(hept-6-en-1-yloxy)propanoate (4.54 g, 80%) as a colourless liquid; $^1$H NMR (400 MHz, DMSO, 30° C.) 1.24-1.38 (4H, m), 1.40 (9H, s), 1.47 (2H, p), 1.96-2.08 (2H, m), 2.40 (2H, t), 3.35 (2H, t), 3.54 (2H, t), 4.94 (1H, ddt), 4.96-5.05 (1H, m), 5.72-5.86 (1H, m).

Intermediate 114b:
3-((7-bromoheptyl)oxy)propanoic Acid

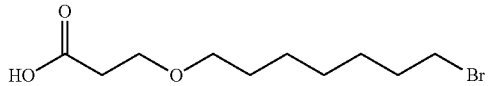

A solution of 33% hydrogen bromide in acetic acid (0.72 mL, 4.1 mmol) was added dropwise to tert-butyl 3-(hept-6-en-1-yloxy)propanoate (0.5 g, 2.1 mmol) in heptane (10 mL) cooled to 0° C. over a period of 1 minute under nitrogen. The resulting solution was stirred vigorously at 20° C. for 20 hours. The reaction mixture was evaporated to dryness to afford the title compound (0.582 g) as a light brown oil, which was used without further purification. $^1$H NMR (400 MHz, DMSO, 30° C.) 1.23-1.32 (4H, m), 1.33-1.42 (2H, m), 1.43-1.52 (2H, m), 1.74-1.86 (2H, m), 2.43 (2H, t), 3.36 (2H, t), 3.47-3.6 (4H, m), 12.05 (1H, s); m/z: ES− [M−H]$^-$ 267.1.

Intermediate 114c: 3-((7-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)propanoic Acid

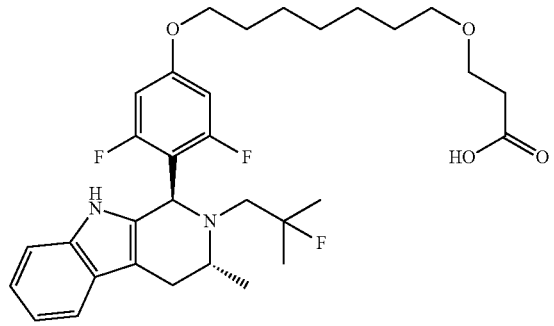 [SMILES: C[C@@H]1Cc2c([nH]c3ccccc23)[C@@H](c2c(F)cc(OCCCCCCCOCCC(=O)O)cc2F)N1CC(C)(C)F]

A solution of 3-((7-bromoheptyl)oxy)propanoic acid (76 mg, 0.28 mmol) in acetonitrile (0.5 mL) was added to a stirred suspension of 3,5-difluoro-4-((1R,3R)-2-(2-fluoro-2-methylpropyl)-3-methyl-2,3,4,9-tetrahydro-1H-pyrido[3,4-b]indol-1-yl)phenol (100 mg, 0.26 mmol) and 3-((7-bromoheptyl)oxy)propanoic acid (76 mg, 0.28 mmol) in acetonitrile (1.5 mL) at 20° C. under air. The resulting suspension was stirred at 80° C. for 1 day. 2 M aq. sodium hydroxide (1 mL, 2.00 mmol) was added and the resulting solution stirred for 3 hours. The reaction mixture was diluted with EtOAc (25 mL), and washed sequentially with 5% v/v aq. AcOH (2×5 mL) and saturated brine (2 mL). The organic layer was dried with MgSO$_4$, filtered and evaporated to afford crude product. The crude product was purified by ion exchange chromatography, using an SCX column. The desired product was eluted from the column using 1M NH$_3$/MeOH and pure fractions were evaporated to dryness to afford crude product. The crude product was purified by flash silica chromatography, elution gradient 0 to 5% MeOH:AcOH (9:1) in DCM to afford impure 3-((7-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)propanoic acid (91 mg, 61.5%) as a brown gum, which was used without further purification. m/z: ES+ [M+H]$^+$ 575.5.

Example 114: (2S,4R)-1-((S)-2-(3-((7-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)propanamido)-3,3-dimethylbutanoyl)-4-hydroxy-N—((S)-1-(4-(4-methylthiazol-5-yl)phenyl)ethyl)pyrrolidine-2-carboxamide

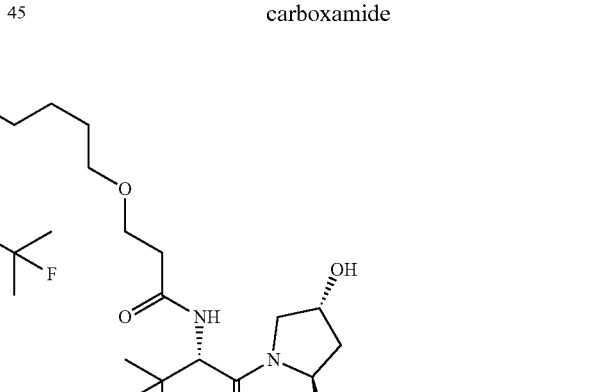

The title compound was prepared in a similar manner to Example 68 using the appropriate carboxylic acid and amine to afford the desired product (36 mg, 57%) as a white solid. ¹H NMR (400 MHz, CDCl₃, 52° C.) 1.05 (9H, s), 1.10 (3H, d), 1.20 (6H, dd), 1.33-1.48 (9H, m), 1.58-1.67 (2H, m), 1.73 (2H, p), 1.94-2.06 (1H, m), 2.33-2.43 (1H, m), 2.48 (5H, d), 2.52-2.66 (2H, m), 2.68 (1H, s), 2.85 (1H, dd), 3.09 (1H, dd), 3.47 (2H, t), 3.55 (1H, dd), 3.59-3.74 (3H, m), 3.85 (2H, t), 4.14 (1H, d), 4.49 (2H, d), 4.73 (1H, t), 5.07 (1H, p), 5.19 (1H, s), 6.33 (2H, d), 7-7.13 (3H, m), 7.16-7.23 (1H, m), 7.3-7.44 (4H, m), 7.45-7.55 (2H, m), 7.85 (1H, s), 8.62 (1H, s); m/z: ES+ [M+H]⁺ 1001.5.

Intermediate 115a: (2S,4R)-1-((S)-2-amino-3,3-dimethylbutanoyl)-4-((tert-butyldimethylsilyl)oxy)-N-(4-(4-methylthiazol-5-yl)benzyl)pyrrolidine-2-carboxamide

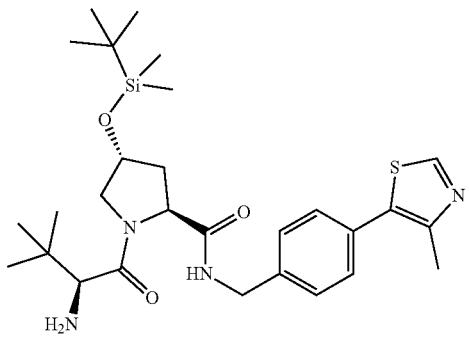 [SMILES: Cc1ncsc1-c1ccc(CNC(=O)[C@@H]2C[C@@H](O[Si](C)(C)C(C)(C)C)CN2C(=O)[C@@H](N)C(C)(C)C)cc1]

Tert-Butyldimethylsilyl chloride (138 mg, 0.92 mmol) was added to 1H-imidazole (104 mg, 1.53 mmol) and (2S,4R)-1-((S)-2-amino-3,3-dimethylbutanoyl)-4-hydroxy-N-(4-(4-methylthiazol-5-yl)benzyl)pyrrolidine-2-carboxamide (329 mg, 0.76 mmol) in DCM (5 mL) at 20° C. under air. The resulting solution was stirred at 20° C. for 13 days. The reaction mixture was diluted with EtOAc (25 mL), and washed sequentially with saturated NaHCO₃ (5 mL), saturated NaHCO₃ (2 mL), and saturated brine (2 mL). The organic layer was dried with MgSO₄, filtered and evaporated to afford crude product. The crude product was purified by flash silica chromatography, elution gradient 0 to 5% 1M NH₃/MeOH in DCM to afford the title compound (316 mg, 76%) as a pale yellow gum which crystallised on standing. ¹H NMR (400 MHz, CDCl₃, 30° C.) 0.09 (6H, d), 0.84 (1H, s), 0.88 (9H, s), 0.89 (9H, s), 0.95 (1H, s), 1.90 (1H, ddd), 2.52 (3H, d), 2.59 (1H, dt), 3.25 (1H, s), 3.46 (1H, dd), 3.63 (1H, dd), 4.35 (1H, dd), 4.51 (1H, dd), 4.61 (1H, p), 4.75 (1H, dd), 7.28-7.42 (4H, m), 7.48 (1H, t), 8.67 (1H, s); m/z: ES+ [M+H]⁺ 545.5.

Intermediate 115b: tert-butyl 3-((7-hydroxyheptyl)oxy)propanoate

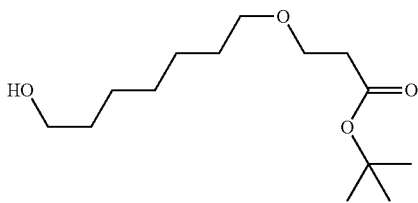 [SMILES: CC(C)(C)OC(=O)CCOCCCCCCCO]

A solution of 0.5 M 9-borabicyclo[3.3.1]nonane in THF (4.81 mL, 2.41 mmol) was added to tert-butyl 3-(hept-6-en-1-yloxy)propanoate (0.53 g, 2.19 mmol) in THF (10 mL) at 20° C. under nitrogen. The resulting solution was stirred at 20° C. for 6 hours. The reaction was incomplete so the temperature was increased to 50° C. and the reaction mixture was stirred for a further 30 minutes. The reaction was incomplete and further 0.5 M 9-borabicyclo[3.3.1]nonane in THF (2.2 mL, 1.1 mmol) was added and the solution was stirred at 20° C. for a further 17 hours. The reaction was incomplete so the temperature was increased to 50° C. and the reaction mixture was stirred for a further 45 minutes. The mixture was cooled to 0° C. and 2 M aq. sodium hydroxide (4.37 mL, 8.75 mmol) added. The emulsion was stirred vigorously for 5 min and 30% aq. hydrogen peroxide (0.670 mL, 6.56 mmol) added. The resulting emulsion was stirred under air for 1 hour at 20° C. The suspension was acidified with 2 M aq. HCl (5 mL, 10 mmol). The reaction mixture was diluted with EtOAc (25 mL), the aqueous layer removed and washed sequentially with 2M HCl (2×2 mL) and saturated brine (2 mL). The organic layer was dried with MgSO₄, filtered and evaporated to afford crude product. The crude product was purified by flash silica chromatography, elution gradient 10 to 50% EtOAc in heptane to afford the title compound (0.278 g, 49%) as a colourless oil. ¹H NMR (400 MHz, DMSO, 30° C.) 1.21-1.33 (6H, m), 1.34-1.52 (13H, m), 2.40 (2H, t), 3.31-3.41 (4H, m), 3.54 (2H, t), 4.29 (1H, t).

Intermediate 115c: 3-((7-(2,2,2-trifluoroacetoxy)heptyl)oxy)propanoic Acid

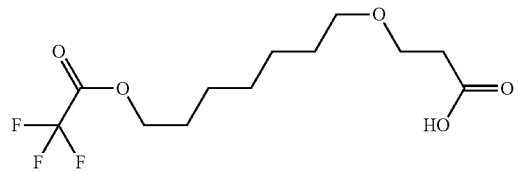 [SMILES: O=C(O)CCOCCCCCCCOC(=O)C(F)(F)F]

TFA (1 mL, 13 mmol) was added to tert-butyl 3-((7-hydroxyheptyl)oxy)propanoate (271 mg, 1.04 mmol) in DCM (1 mL) at 20° C. under air. The resulting solution was stirred at 20° C. for 2 hours. The reaction was incomplete so the temperature was increased to 40° C. and the reaction mixture was stirred for a further 2 hours. The reaction mixture was cooled to −20° C. for 2 days and evaporated to dryness to afford 3-((7-(2,2,2-trifluoroacetoxy)heptyl)oxy)propanoic acid (340 mg) as a dark brown oil, which was used without further purification. ¹H NMR (400 MHz, DMSO, 30° C.) 1.21-1.37 (6H, m), 1.41-1.54 (2H, m), 1.68 (2H, q), 2.43 (2H, t), 3.35 (2H, t), 3.56 (2H, t), 4.38 (2H, t); m/z: ES+ [M+H]⁺ 301.2.

419

Intermediate 115d: (2S,4R)-4-((tert-butyldimethylsilyl)oxy)-1-((S)-2-(3-((7-hydroxyheptyl)oxy)propanamido)-3,3-dimethylbutanoyl)-N-(4-(4-methylthiazol-5-yl)benzyl)pyrrolidine-2-carboxamide

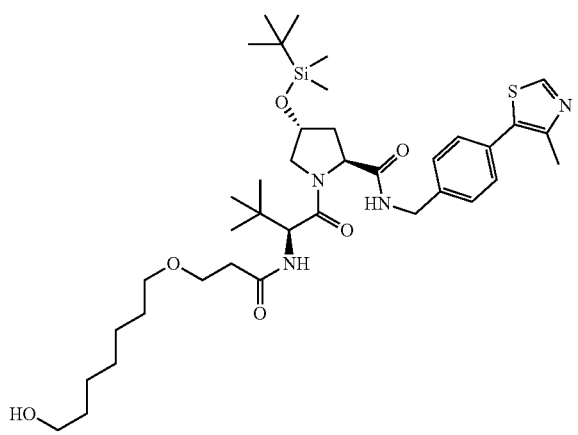 [SMILES: Cc1ncsc1-c1ccc(CNC(=O)[C@@H]2C[C@@H](O[Si](C)(C)C(C)(C)C)CN2C(=O)[C@@H](NC(=O)CCOCCCCCCCO)C(C)(C)C)cc1]

HATU (84 mg, 0.22 mmol) was added to (2S,4R)-1-((S)-2-amino-3,3-dimethylbutanoyl)-4-((tert-butyldimethylsilyl)oxy)-N-(4-(4-methylthiazol-5-yl)benzyl)pyrrolidine-2-carboxamide (100 mg, 0.18 mmol), 3-((7-(2,2,2-trifluoroacetoxy)heptyl)oxy)propanoic acid (66 mg, 0.22 mmol) and triethylamine (0.064 mL, 0.46 mmol) in DCM (2 mL) at 20° C. under air. The resulting suspension was stirred at 20° C. for 2 hours. The reaction mixture was diluted with EtOAc (20 mL), and washed sequentially with 2 M aq. potassium carbonate (3×2 mL) and saturated brine (1 mL). The organic layer was dried with MgSO$_4$, filtered and evaporated to afford crude product. The crude product was purified by flash silica chromatography, elution gradient 50 to 100% EtOAc in heptane followed by 0 to 5% MeOH in DCM to afford the title compound (97 mg, 72%) as a white solid. $^1$H NMR (400 MHz, DMSO, 30° C.) 0.01 (6H, d), 0.77 (9H, s), 0.88 (9H, s), 1.05-1.15 (2H, m), 1.19 (6H, s), 1.27-1.47 (4H, m), 1.83-2.03 (2H, m), 2.19-2.27 (1H, m), 2.39 (3H, s), 3.26-3.35 (3H, m), 3.4-3.57 (2H, m), 3.57-3.71 (2H, m), 4.12-4.27 (2H, m), 4.31-4.43 (2H, m), 4.42-4.53 (2H, m), 7.28-7.39 (4H, m), 7.80 (1H, d), 8.48 (1H, t), 8.92 (1H, s); m/z: ES+ [M+H]$^+$ 731.6.

Intermediate 115e: (2S,4R)-4-((tert-butyldimethylsilyl)oxy)-1-((S)-2-(3-((7-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)propanamido)-3,3-dimethylbutanoyl)-N-(4-(4-methylthiazol-5-yl)benzyl)pyrrolidine-2-carboxamide

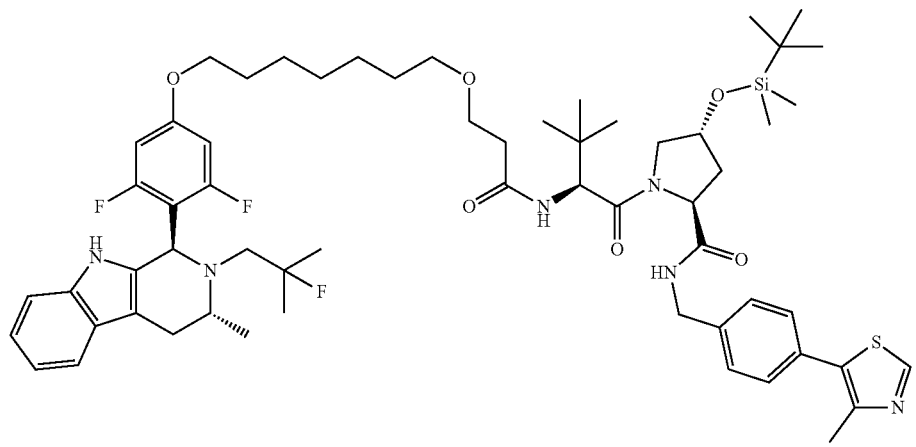 [SMILES: Cc1ncsc1-c1ccc(CNC(=O)[C@@H]2C[C@@H](O[Si](C)(C)C(C)(C)C)CN2C(=O)[C@@H](NC(=O)CCOCCCCCCCOc2cc(F)c([C@@H]3c4[nH]c5ccccc5c4C[C@@H](C)N3CC(C)(C)F)c(F)c2)C(C)(C)C)cc1]

DIAD (0.051 mL, 0.26 mmol) was added to triphenylphosphine (68 mg, 0.26 mmol), (2S,4R)-4-((tert-butyldimethylsilyl)oxy)-1-((S)-2-(3-((7-hydroxyheptyl)oxy)propanamido)-3,3-dimethylbutanoyl)-N-(4-(4-methylthiazol-5-yl)benzyl)pyrrolidine-2-carboxamide (95 mg, 0.13 mmol) and 3,5-difluoro-4-((1R,3R)-2-(2-fluoro-2-methylpropyl)-3-methyl-2,3,4,9-tetrahydro-1H-pyrido[3,4-b]indol-1-yl)phenol (65 mg, 0.17 mmol) in DCM (1 mL) at 20° C. under air. The resulting solution was stirred at 20° C. for 30 minutes. The reaction was incomplete and further triphenylphosphine (68.2 mg, 0.26 mmol) and DIAD (0.051 mL, 0.26 mmol) were added and the solution was stirred at 20° C. for a further 1 hour. The reaction mixture was diluted with MeOH (4 mL), purified by ion exchange chromatography, using an SCX column. The desired product was eluted from the column using 1M $NH_3$/MeOH and pure fractions were evaporated to dryness to afford crude product. The crude product was purified by flash silica chromatography, elution gradient 25 to 100% EtOAc in heptane and then flushed with 5% MeOH in DCM to afford the title compound (59 mg, 41%) as a colourless gum. $^1$H NMR (400 MHz, DMSO, 30° C.) 0.01 (6H, dd), 0.73-0.8 (9H, m), 0.84-0.92 (9H, m), 0.99 (3H, d), 1.05 (8H, s), 1.17-1.26 (5H, m), 1.27-1.34 (2H, m), 1.36-1.47 (2H, m), 1.54-1.67 (2H, m), 1.82-2.06 (2H, m), 2.19-2.26 (1H, m), 2.39 (3H, s), 2.48-2.52 (1H, m), 2.7-2.9 (1H, m), 3.27-3.35 (2H, m), 3.4-3.56 (3H, m), 3.56-3.7 (2H, m), 3.90 (2H, t), 4.18 (1H, dd), 4.31-4.42 (2H, m), 4.42-4.54 (2H, m), 5.07 (1H, s), 6.57 (2H, d), 6.81-6.98 (1H, m), 7.12 (1H, d), 7.27-7.42 (5H, m), 7.44-7.63 (1H, m), 7.80 (1H, d), 8.48 (1H, t), 8.92 (1H, d), 10.43 (1H, s). Assigned Hs: 83; m/z: ES+ [M+H]$^+$ 1101.9.

Example 115: (2S,4R)-1-((S)-2-(3-((7-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)propanamido)-3,3-dimethylbutanoyl)-4-hydroxy-N-(4-(4-methylthiazol-5-yl)benzyl)pyrrolidine-2-carboxamide

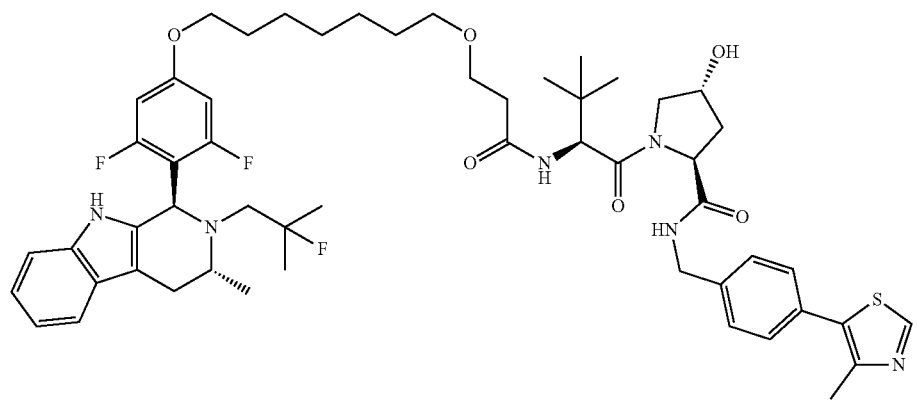 [SMILES: Cc1ncsc1-c1ccc(CNC(=O)[C@@H]2C[C@@H](O)CN2C(=O)[C@@H](NC(=O)CCOCCCCCCCOc2cc(F)c([C@@H]3c4[nH]c5ccccc5c4C[C@@H](C)N3CC(C)(C)F)c(F)c2)C(C)(C)C)cc1]

A solution of 1 M tetrabutylammonium fluoride in THF (0.107 mL, 0.11 mmol) was added to (2S,4R)-4-((tert-butyldimethylsilyl)oxy)-1-((S)-2-(3-((7-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)propanamido)-3,3-dimethylbutanoyl)-N-(4-(4-methylthiazol-5-yl)benzyl)pyrrolidine-2-carboxamide (59 mg, 0.05 mmol) in DMSO (0.6 mL) at 20° C. under air. The resulting solution was stirred at 20° C. for 30 minutes. The reaction mixture was combined with the title compound isolated in the preparation of intermediate 115e (12 mg) and evaporated under reduced pressure to remove the THF. The crude product was purified by preparative HPLC (Waters XSelect CSH C18 column, 5 silica, 30 mm diameter, 100 mm length), using decreasingly polar mixtures of water (containing by volume 1% $NH_4OH$ (28-30% in $H_2O$)) and MeCN as eluents to afford the title compound (30 mg, 57%) as a tan solid. $^1$H NMR (400 MHz, CDCl$_3$, 30° C.) 0.92 (9H, s), 1.10 (3H, d), 1.20 (6H, dd), 1.31-1.5 (6H, m), 1.55-1.65 (2H, m), 1.69-1.79 (2H, m), 2.08 (1H, dd), 2.32-2.42 (1H, m), 2.42-2.49 (5H, m), 2.52-2.65 (2H, m), 2.85 (1H, dd), 3.09 (1H, dd), 3.46 (2H, td), 3.55 (1H, dd), 3.65 (3H, dt), 3.85 (2H, t), 4.13 (1H, d), 4.27-4.36 (1H, m), 4.39-4.45 (1H, m), 4.49 (1H, s), 4.53-4.62 (1H, m), 4.74 (1H, t), 5.19 (1H, s), 6.3-6.39 (2H, m), 7.05-7.12 (2H, m), 7.14 (1H, d), 7.18-7.23 (1H, m), 7.29-7.38 (4H, m), 7.41 (1H, t), 7.48-7.55 (1H, m), 8.05 (1H, s), 8.62 (1H, s); m/z: ES+ [M+H]$^+$ 987.6.

Intermediate 116a:
2,2-Difluoro-2-(hex-5-en-1-yloxy)acetic Acid

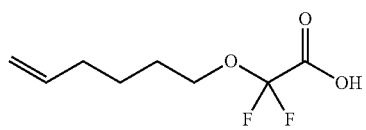

A solid suspension of 60% sodium hydride in mineral oil (0.40 g, 10.00 mmol) was added portionwise to sodium chlorodifluoroacetate (1.00 g, 6.56 mmol) and 5-hexen-1-ol (0.99 mL, 8.2 mmol) in THF at 20° C. over a period of 2 minutes under nitrogen. The resulting suspension was stirred at 65° C. for 18 hours. The reaction mixture was diluted with 2 M HCl (10 mL) and DCM (30 mL), the layers were separated, and the aqueous layer was extracted with (DCM) (2×20 mL). The combined organic layers were dried with MgSO$_4$, filtered and evaporated to afford crude product. The crude product was purified by flash silica chromatography, elution gradient 0 to 20% EtOAc:AcOH (19:1) in heptane to afford the title compound (0.139 g, 11%) as a pale yellow oil; $^1$H NMR (400 MHz, DMSO, 30° C.) 1.35-1.49 (2H, m), 1.58-1.71 (2H, m), 2.01-2.1 (2H, m), 3.97 (1H, t), 4.30 (1H, t), 4.93-4.99 (1H, m), 4.99-5.06 (1H, m), 5.71-5.86 (1H, m).

Intermediate 116b: 2-((6-Bromohexyl)oxy)-2,2-difluoroacetic Acid

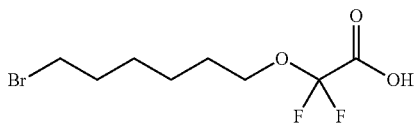 [SMILES: O=C(O)C(F)(F)OCCCCCCBr]

A solution of 33% w/v hydrobromic acid in acetic acid (0.24 mL, 1.3 mmol) was added to 2,2-difluoro-2-(hex-5-en-1-yloxy)acetic acid (130 mg, 0.67 mmol) in heptane (2 mL) at 20° C. under air. The resulting biphasic mixture was stirred vigorously at 20° C. for 1 hour. The reaction mixture was evaporated to afford the title compound (191 mg) as a brown oil that was used without further purification; $^1$H NMR (400 MHz, DMSO, 30° C.) 1.3-1.52 (4H, m), 1.57-1.72 (2H, m), 1.76-1.89 (2H, m), 3.53 (2H, td), 3.96 (1H, t), 4.29 (1H, t).

Intermediate 116c: 2-((6-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)-2,2-difluoroacetic Acid

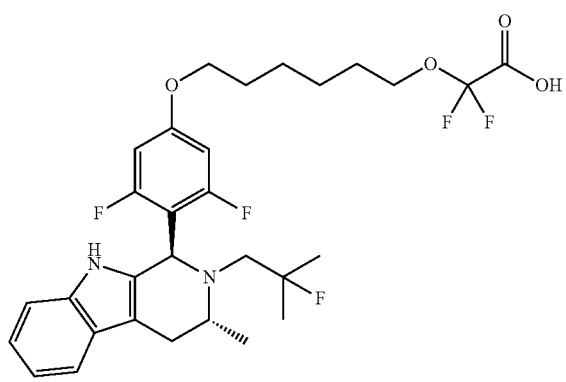

Potassium carbonate (362 mg, 2.62 mmol) was added to 2-((6-bromohexyl)oxy)-2,2-difluoroacetic acid (180 mg, 0.65 mmol) and 3,5-difluoro-4-((1R,3R)-2-(2-fluoro-2-methylpropyl)-3-methyl-2,3,4,9-tetrahydro-1H-pyrido[3,4-b]indol-1-yl)phenol (254 mg, 0.65 mmol) in acetonitrile (2 mL) at 20° C. under nitrogen. The resulting suspension was stirred at 80° C. for 20 hours. The reaction mixture was diluted with EtOAc (5 mL) and acidified to pH 6 with AcOH (1 mL) and water (1 mL). The biphasic mixture was further diluted with EtOAc (15 mL) and the aqueous portion removed. The organic layer was washed sequentially with 5% v/v aq. AcOH (2×2 mL) and saturated brine (2 mL). The organic layer was dried with MgSO$_4$, filtered and evaporated to afford crude product. The crude product was purified by flash silica chromatography, elution gradient 10 to 100% EtOAc:AcOH (19:1) in heptane to afford the title compound (163 mg, 43%) as a tan solid. $^1$H NMR (400 MHz, DMSO, 30° C.) 1.05 (3H, d), 1.18 (6H, t), 1.36-1.46 (4H, m), 1.59-1.65 (2H, m), 1.66-1.75 (2H, m), 2.58 (1H, d), 2.87 (2H, dd), 3.53 (2H, d), 3.89 (2H, t), 3.98 (2H, t), 5.13 (1H, s), 6.64 (2H, d), 6.89-7.04 (2H, m), 7.11-7.21 (1H, m), 7.39 (1H, d), 10.50 (1H, s), 11.91 (1H, s); m/z: ES− [M−H]⁻ 581.3.

Example 116: (2S,4R)-1-((S)-2-(2-((6-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)-2,2-difluoroacetamido)-3,3-dimethylbutanoyl)-4-hydroxy-N-(4-(4-methylthiazol-5-yl)benzyl)pyrrolidine-2-carboxamide

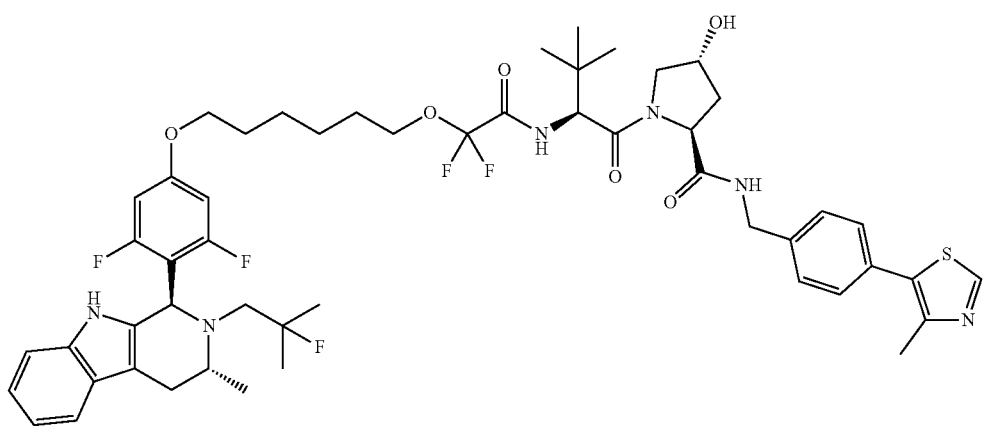

The title compound was prepared in a similar manner to Example 68 using the appropriate carboxylic acid and amine to afford the desired product (128 mg, 47.7%) as a cream solid; $^1$H NMR (400 MHz, CDCl3, 30° C.) 0.95 (9H, s), 1.06-1.28 (8H, m), 1.41-1.52 (4H, m), 1.74 (5H, dt), 2.04-2.15 (1H, m), 2.3-2.56 (6H, m), 2.58-2.68 (1H, m), 2.74-2.95 (1H, m), 3.03-3.15 (1H, m), 3.67 (2H, dd), 3.84-3.93 (3H, m), 3.98 (2H, t), 4.33 (1H, dd), 4.51-4.6 (3H, m), 4.66 (1H, t), 5.19 (1H, s), 6.36 (2H, d), 7.06 (4H, ddd), 7.23 (1H, d), 7.3-7.39 (4H, m), 7.51 (1H, dd), 7.89 (1H, s), 8.64 (1H, s); m/z: ES− [M−H]− 993.5.

Intermediate 117a: Hex-5-en-1-yl 4-methylbenzenesulfonate

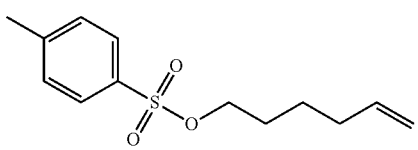 [SMILES: C=CCCCCOS(=O)(=O)c1ccc(C)cc1]

p-Toluenesulfonyl chloride (1.6 g, 8.4 mmol) was added to powdered potassium hydroxide (1.6 g, 24 mmol) and 5-hexen-1-ol (1.0 mL, 8.3 mmol) in DCM at 20° C. over a period of nitrogen. The resulting suspension was stirred at 20° C. for 1 day. The reaction mixture was filtered through celite, rinsing with DCM (100 mL). The filtrate was evaporated to dryness to afford a colourless oil. The crude product was purified by flash silica chromatography, elution gradient 0 to 20% EtOAc in heptane to afford the title compound (1.16 g, 55%) as a colourless oil. $^1$H NMR (400 MHz, CDCl3, 30° C.) 1.44 (2H, p), 1.64-1.73 (2H, m), 2.03 (2H, q), 2.47 (3H, s), 4.06 (2H, t), 4.92-5.05 (2H, m), 5.74 (1H, ddt), 7.37 (2H, d), 7.81 (2H, d).

Intermediate 117b: Ethyl 2-(hex-5-en-1-yloxy)-2-methylpropanoate

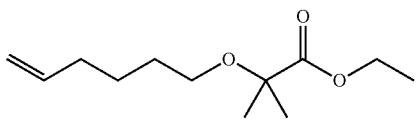

A solid suspension of 60% sodium hydride in mineral oil (84 mg, 2.09 mmol) was added to ethyl 2-hydroxyisobutyrate (0.25 mL, 1.8 mmol) in DMF (10 mL) at 20° C. under nitrogen. The resulting mixture was stirred at 20° C. for 1 hour. A solution of hex-5-en-1-yl 4-methylbenzenesulfonate (462 mg, 1.82 mmol) in DMF (2 mL) was added and the solution stirred at 80° C. for 4 hours. The reaction mixture was diluted with EtOAc (100 mL), and washed sequentially with water (3×10 mL), and saturated brine (5 mL). The organic layer was dried with MgSO4, filtered and evaporated to afford crude product. The crude product was purified by flash silica chromatography, elution gradient 0 to 40% EtOAc in heptane to afford the title compound (74 mg, 19%) as a colourless liquid; $^1$H NMR (400 MHz, CDCl3, 30° C.) 1.28 (2H, t), 1.41 (5H, s), 1.43-1.5 (2H, m), 1.56-1.62 (2H, m), 2.03-2.11 (2H, m), 3.36 (2H, t), 4.03-4.26 (2H, m), 4.91-5.07 (2H, m), 5.81 (1H, ddt); m/z: ES+ [M+H]+ 215.3

Intermediate 117c: Ethyl 2-((6-bromohexyl)oxy)-2-methylpropanoate

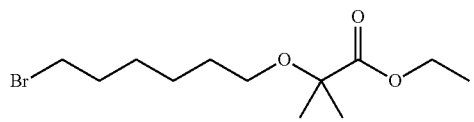 [SMILES: CCOC(=O)C(C)(C)OCCCCCCBr]

A solution of 33% w/v hydrobromic acid in acetic acid (0.12 mL, 0.69 mmol) was added to ethyl 2-(hex-5-en-1-yloxy)-2-methylpropanoate (74 mg, 0.35 mmol) in heptane (1.5 mL) at 20° C. under air. The resulting biphasic mixture was stirred vigorously at 20° C. for 1 hour. The reaction mixture was evaporated to afford the title compound (105 mg) as a brown oil that was used without further purification; $^1$H NMR (400 MHz, CDCl3, 30° C.) 1.21 (3H, t), 1.34 (6H, d), 1.45-1.57 (6H, m), 1.80 (2H, p), 3.25-3.36 (4H, m), 4.12 (2H, q).

Intermediate 117d: Ethyl 2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)-2-methylpropanoate

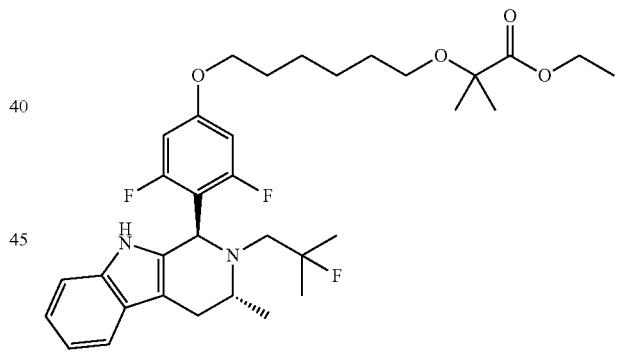

Potassium carbonate (190 mg, 1.37 mmol) was added to ethyl 2-((6-bromohexyl)oxy)-2-methylpropanoate (100 mg, 0.34 mmol) and 3,5-difluoro-4-((1R,3R)-2-(2-fluoro-2-methylpropyl)-3-methyl-2,3,4,9-tetrahydro-1H-pyrido[3,4-b]indol-1-yl)phenol (132 mg, 0.34 mmol) in acetonitrile (2 mL) at 20° C. under nitrogen. The resulting suspension was stirred at 80° C. for 20 hours. The reaction mixture was diluted with EtOAc (15 mL), and washed sequentially with 10% v/v aq. AcOH (6 mL), 10% v/v aq. AcOH (2×2 mL), and saturated brine (2 mL). The organic layer was dried with MgSO4, filtered and evaporated to afford crude product. The crude product was purified by flash silica chromatography, elution gradient 0 to 20% EtOAc:AcOH (19:1) in heptane to afford the title compound (63 mg, 31%) as a brown gum; m/z: ES− [M−H]− 601.3

Intermediate 117e: 2-((6-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)-2-methylpropanoic Acid

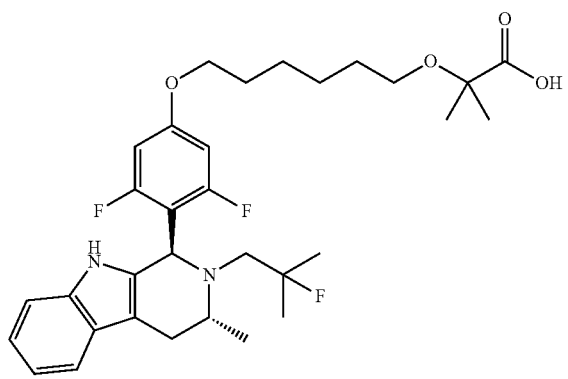 [SMILES: C[C@@H]1Cc2c([nH]c3ccccc23)[C@@H](c2c(F)cc(OCCCCCCOC(C)(C)C(=O)O)cc2F)N1CC(C)(C)F]

A solution of 2 M sodium hydroxide (0.10 mL, 0.20 mmol) was added to ethyl 2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)-2-methylpropanoate (60 mg, 0.10 mmol) in ethanol (1 mL) at 20° C. under air. The resulting solution was stirred at 20° C. for 30 minutes. The reaction was incomplete and further 2 M sodium hydroxide (0.100 mL, 0.20 mmol) was added and the mixture was stirred at 20° C. for a further 2 hours. The reaction mixture was diluted with EtOAc (15 mL), and washed sequentially with 10% v/v aq. AcOH (3×2 mL) and saturated brine (2 mL). The organic layer was dried with MgSO$_4$, filtered and evaporated to dryness and the residue was azeotroped with toluene to afford the title compound (62 mg) that was used without further purification; $^1$H NMR (400 MHz, DMSO, 30° C.) 1.05 (3H, d), 1.17 (6H, t), 1.29 (6H, s), 1.33-1.42 (4H, m), 1.45-1.53 (2H, m), 1.62-1.74 (2H, m), 2.38 (1H, d), 2.53-2.59 (1H, m), 2.78-2.94 (2H, m), 3.52 (1H, q), 3.97 (2H, t), 5.12 (1H, s), 6.64 (2H, d), 6.97 (2H, dtd), 7.12-7.21 (3H, m), 7.21-7.3 (1H, m), 7.39 (1H, d), 10.49 (1H, s); m/z: ES− [M−H]$^-$ 573.3

Example 117: (2S,4R)-1-((S)-2-(2-((6-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)-2-methylpropanamido)-3,3-dimethylbutanoyl)-4-hydroxy-N-(4-(4-methylthiazol-5-yl)benzyl)pyrrolidine-2-carboxamide

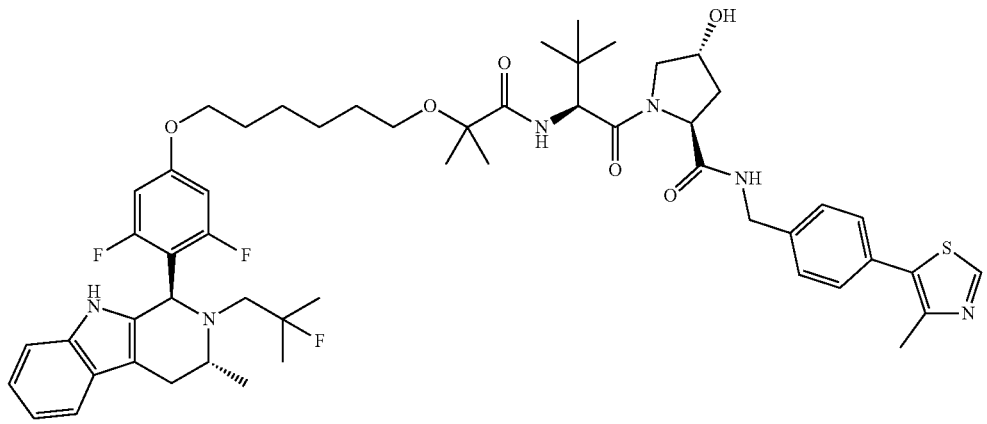 [SMILES: Cc1ncsc1-c1ccc(CNC(=O)[C@@H]2C[C@@H](O)CN2C(=O)[C@@H](NC(=O)C(C)(C)OCCCCCCOc2cc(F)c([C@@H]3c4[nH]c5ccccc5c4C[C@@H](C)N3CC(C)(C)F)c(F)c2)C(C)(C)C)cc1]

The title compound was prepared in a similar manner to Example 68 using the appropriate carboxylic acid and amine to afford the desired product (46 mg, 47%) as a pale yellow solid; ¹H NMR (400 MHz, CDCl3, 30° C.) 0.86 (9H, s), 0.98-1.32 (16H, m), 1.33-1.47 (5H, m), 1.64-1.8 (2H, m), 1.94-2.03 (1H, m), 2.39 (3H, s), 2.4-2.6 (2H, m), 2.79 (2H, s), 2.97-3.13 (1H, m), 3.18-3.29 (1H, m), 3.29-3.4 (1H, m), 3.50 (1H, dd), 3.61 (1H, s), 3.78 (2H, t), 4.08 (1H, d), 4.23 (1H, dd), 4.32 (1H, d), 4.44 (1H, s), 4.50 (1H, dd), 4.64 (1H, t), 5.13 (1H, s), 6.25 (2H, d), 6.94-7.11 (2H, m), 7.16 (1H, s), 7.21-7.39 (7H, m), 7.4-7.49 (1H, m), 8.23 (1H, s), 8.55 (1H, s); m/z: ES− [M−H]⁻ 985.9.

Intermediate 118a: Ethyl 1-(hex-5-en-1-yloxy)cyclopropane-1-carboxylate

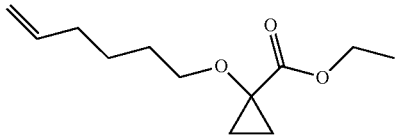

Ethyl 1-hydroxycyclopropane-1-carboxylate (0.31 mL, 2.6 mmol) was added to 60% sodium hydride in mineral oil (102 mg, 2.56 mmol) in DMF (10 mL) at 0° C. under nitrogen. The resulting mixture was stirred at 20° C. for 5 minutes. A solution of hex-5-en-1-yl 4-methylbenzenesulfonate (650 mg, 2.56 mmol) in DMF (2 mL) was added and the mixture was stirred at 20° C. for 3 days. The reaction mixture was quenched with saturated NH4Cl (3 mL), diluted with EtOAc (75 mL), and washed sequentially with 2M HCl (3×2 mL) and saturated brine (2 mL). The organic layer was dried with MgSO4, filtered and evaporated to afford crude product. The crude product was purified by flash silica chromatography, elution gradient 0 to 20% EtOAc in heptane to afford the title compound (73 mg, 13%) as a pale yellow oil; ¹H NMR (400 MHz, CDCl3, 30° C.) 0.99-1.1 (2H, m), 1.21 (3H, t), 1.29-1.43 (2H, m), 1.44-1.56 (3H, m), 1.53-1.67 (1H, m), 1.93-2.05 (2H, m), 3.51 (2H, t), 4.12 (2H, q), 4.83-5.02 (2H, m), 5.73 (1H, ddt); m/z: ES+ [M+H]⁺ 213.3

Intermediate 118b: Ethyl 1-((6-bromohexyl)oxy)cyclopropane-1-carboxylate

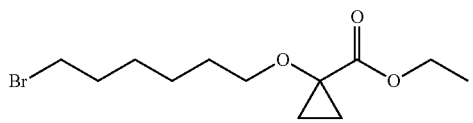 [SMILES: CCOC(=O)C1(OCCCCCCBr)CC1]

A solution of 33% w/v hydrobromic acid in acetic acid (0.11 mL, 0.65 mmol) was added to ethyl 1-(hex-5-en-1-yloxy)cyclopropane-1-carboxylate (70 mg, 0.33 mmol) in heptane (1 mL) at 20° C. under air. The resulting biphasic mixture was stirred vigorously at 20° C. for 1 hour. The reaction mixture was evaporated to afford the title compound (95 mg, 98%) as a brown oil; ¹H NMR (400 MHz, CDCl3, 30° C.) 1.01-1.1 (2H, m), 1.18-1.24 (3H, m), 1.28-1.43 (4H, m), 1.46-1.57 (4H, m), 1.77-1.86 (2H, m), 3.34 (2H, t), 3.51 (2H, t), 4.12 (2H, q).

Intermediate 118c: Ethyl 1-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)cyclopropane-1-carboxylate

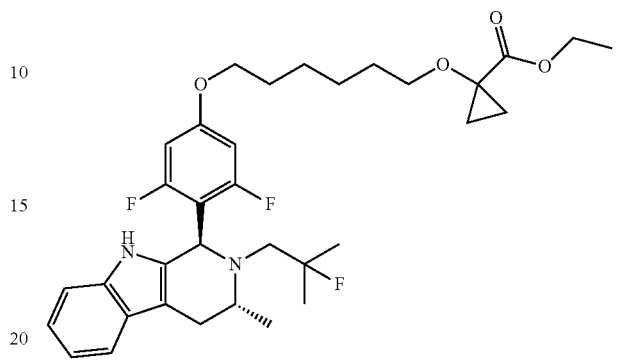

Potassium carbonate (190 mg, 1.37 mmol) was added to ethyl 1-((6-bromohexyl)oxy)cyclopropane-1-carboxylate (95 mg, 0.32 mmol) and 3,5-difluoro-4-((1R,3R)-2-(2-fluoro-2-methylpropyl)-3-methyl-2,3,4,9-tetrahydro-1H-pyrido[3,4-b]indol-1-yl)phenol (133 mg, 0.34 mmol) in at 20° C. under nitrogen. The resulting suspension was stirred at 80° C. for 20 hours. The reaction mixture was diluted with EtOAc (25 mL), and washed sequentially with water (2 mL) and saturated brine (2×2 mL). The organic layer was dried with MgSO4, filtered and evaporated to afford crude product. The crude product was purified by flash silica chromatography, elution gradient 0 to 20% EtOAc in heptane to afford the title compound (85 mg, 43.7%) as a pink gum; ¹H NMR (400 MHz, CDCl3, 30° C.) 1.04 (3H, dt), 1.08-1.29 (13H, m), 1.3-1.44 (4H, m), 1.51 (2H, d), 1.65-1.76 (2H, m), 2.25-2.41 (1H, m), 2.53 (1H, d), 2.73-2.86 (1H, m), 2.96-3.1 (1H, m), 3.51 (2H, t), 3.61 (1H, s), 3.83 (2H, t), 4.11 (2H, q), 5.11 (1H, s), 6.31 (2H, d), 6.97-7.1 (2H, m), 7.15 (1H, dd), 7.35 (1H, s), 7.44 (1H, dd); m/z: ES− [M−H]⁻ 599.3.

Intermediate 118d: 1-((6-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)cyclopropane-1-carboxylic Acid

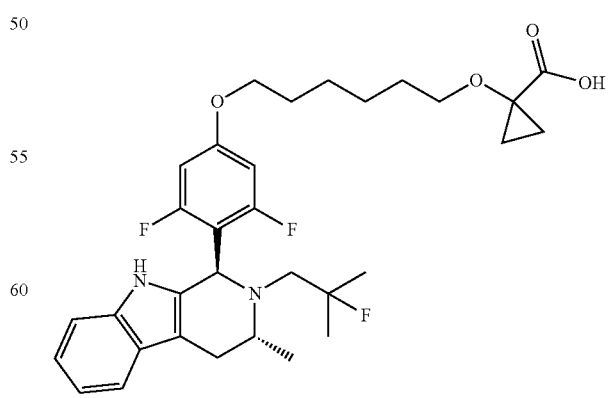

A solution of 2 M sodium hydroxide (0.27 mL, 0.53 mmol) was added to ethyl 1-((6-(3,5-difluoro-4-((1R,3R)-

2-(2-fluoro-2-methylpropyl)-3-methyl-2,3,4,9-tetrahydro-1H-pyrido[3,4-b]indol-1-yl)phenoxy)hexyl)oxy)cyclopropane-1-carboxylate (80 mg, 0.13 mmol) in ethanol (2 mL) at 20° C. under air. The resulting solution was stirred at 20° C. for 5 days. The reaction was incomplete and further 2 M sodium hydroxide (0.266 mL, 0.53 mmol) was added and the solution was stirred at 20° C. for a further 1 day. The reaction mixture was diluted with EtOAc (5 mL), and washed sequentially with 10% v/v aq. AcOH (2×1 mL), water (1 mL), and saturated brine (1 mL). The organic layer was dried with MgSO$_4$, filtered, evaporated to dryness and the residue was azeotroped with toluene to afford the title compound (73 mg, 96%) as a brown oil; $^1$H NMR (400 MHz, CDCl3, 30° C.) 1.10 (3H, d), 1.15-1.28 (8H, m), 1.31-1.4 (2H, m), 1.4-1.52 (4H, m), 1.54-1.66 (2H, m), 1.7-1.85 (2H, m), 2.42 (1H, m), 2.60 (1H, d), 2.78-2.96 (1H, m), 3.01-3.15 (1H, m), 3.60 (2H, t), 3.67 (1H, t), 3.90 (2H, t), 5.19 (1H, s), 6.39 (2H, d), 7.07-7.14 (2H, m), 7.28 (1H, s), 7.43 (1H, s), 7.51 (1H, dd); m/z: ES+ [M+H]$^+$ 573.1

Example 118: (2S,4R)-1-((S)-2-(1-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)cyclopropane-1-carboxamido)-3,3-dimethylbutanoyl)-4-hydroxy-N-(4-(4-methylthiazol-5-yl)benzyl)pyrrolidine-2-carboxamide Intermediate 119a: Ethyl 2-(3-(3-(benzyloxy)propoxy)propoxy)-2,2-difluoroacetate

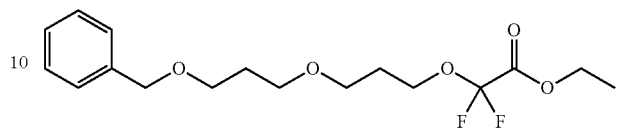

Sodium chlorodifluoroacetate (0.61 g, 4.0 mmol) was added to tetrabutylammonium iodide (0.15 g, 0.40 mmol), 3-(3-(benzyloxy)propoxy)propan-1-ol (0.9 g, 4.0 mmol) and 60% sodium hydride in mineral oil (0.21 g, 5.2 mmol) in tetrahydrofuran (14 mL) cooled to 0° C. under nitrogen. The resulting suspension was stirred at 65° C. for 1 day. The reaction mixture was diluted with 2 M HCl (10 mL), diluted with EtOAc (50 mL), the aqueous layer removed and the organic layer washed sequentially with 2M HCl (2 mL) and saturated brine (5 mL). The organic layer was dried with MgSO$_4$, filtered and evaporated to afford an oil that was dissolved in dry ethanol and cooled to 0° C. Chlorotrimethylsilane (1.0 mL, 7.9 mmol) was added slowly over 1 minute

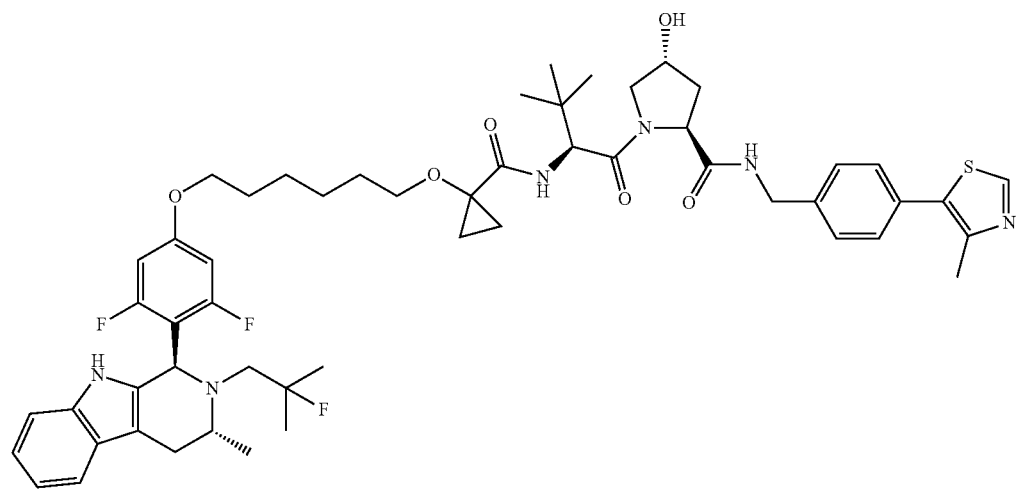 [SMILES: Cc1ncsc1-c1ccc(CNC(=O)[C@@H]2C[C@@H](O)CN2C(=O)[C@@H](NC(=O)C2(OCCCCCCOc3cc(F)c([C@@H]4c5[nH]c6ccccc6c5C[C@@H](C)N4CC(C)(C)F)c(F)c3)CC2)C(C)(C)C)cc1]

The title compound was prepared in a similar manner to Example 68 using the appropriate carboxylic acid and amine to afford the desired product (50 mg, 42%) as a white solid; $^1$H NMR (400 MHz, CDCl3, 30° C.) 0.89 (9H, s), 0.94-1.22 (13H, m), 1.39 (4H, s), 1.68 (2H, s), 1.94-2.02 (1H, m), 2.39 (4H, s), 2.42-2.59 (2H, m), 2.67-2.88 (2H, m), 3.04 (1H, d), 3.40 (2H, t), 3.51 (1H, dd), 3.62 (1H, s), 3.77 (2H, t), 4.03 (1H, d), 4.24 (1H, dd), 4.37-4.47 (2H, m), 4.51 (1H, dd), 4.65 (1H, t), 5.13 (1H, s), 6.25 (2H, d), 6.97-7.09 (2H, m), 7.19 (4H, s), 7.24-7.34 (5H, m), 7.41-7.49 (1H, m), 8.16 (1H, s), 8.55 (1H, s); m/z: ES− [M−H]$^-$ 983.9 to the solution and the resulting solution was stirred at 20° C. for 1 day. The reaction was incomplete and further chlorotrimethylsilane (1.0 mL, 7.88 mmol) was added slowly and the solution was stirred at 20° C. for a further 1 day. The reaction mixture was evaporated to dryness and redissolved in DCM. The solution was purified by flash silica chromatography, elution gradient 0 to 30% EtOAc in heptane to afford the title compound (535 mg, 39%) as a colourless oil. $^1$H NMR (400 MHz, CDCl3, 30° C.) 1.36 (3H, t), 1.83-1.96 (4H, m), 3.47-3.51 (2H, m), 3.54 (4H, dt), 4.05 (2H, t), 4.34 (2H, q), 4.50 (2H, s), 7.26-7.31 (1H, m), 7.31-7.37 (4H, m); m/z: ES+ [M+H]$^+$ 347.0.

Intermediate 119b: Ethyl 2,2-difluoro-2-(3-(3-hydroxypropoxy)propoxy)acetate

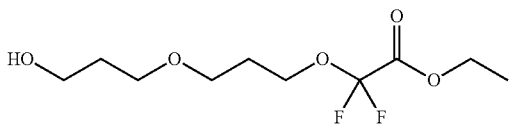 [SMILES: CCOC(=O)C(F)(F)OCCCOCCCO]

Ethyl 2-(3-(3-(benzyloxy)propoxy)propoxy)-2,2-difluoroacetate (0.53 g, 1.53 mmol) and 10% palladium on carbon (0.163 g, 0.15 mmol) in ethanol (10 mL) were stirred under an atmosphere of hydrogen at 1 atmosphere and 20° C. for 3 days. The reaction mixture was filtered through celite and the solids washed with EtOH (50 mL). The filtrate was evaporated to afford ethyl 2,2-difluoro-2-(3-(3-hydroxypropoxy)propoxy)acetate (0.397 g) as a pale yellow oil that was used without further purification; $^1$H NMR (400 MHz, DMSO, 30° C.) 1.28 (3H, t), 1.64 (2H, p), 1.85 (2H, p), 3.39-3.48 (6H, m), 4.01 (2H, t), 4.3-4.38 (3H, m); m/z: ES– [M-CH$_2$CH$_3$]– 227.1.

Intermediate 119c: Ethyl 2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)-2,2-difluoroacetate

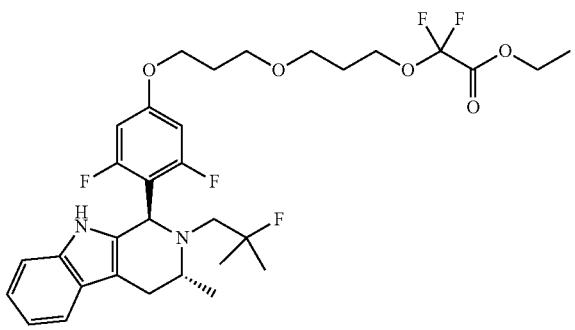 [SMILES: CCOC(=O)C(F)(F)OCCCOCCCOc1cc(F)c([C@@H]2c3[nH]c4ccccc4c3C[C@@H](C)N2CC(C)(C)F)c(F)c1]

The title compound was prepared in a similar manner to Intermediate 72e using the appropriate phenol and alcohol to afford the desired product (0.571 g, 60%) as a pale yellow solid; $^1$H NMR (400 MHz, CDCl3, 30° C.) 1.10 (3H, d), 1.20 (6H, dd), 1.34 (3H, t), 1.93 (2H, p), 1.98-2.05 (2H, m), 2.39 (1H, dd), 2.60 (1H, dd), 2.86 (1H, dd), 3.09 (1H, dd), 3.52 (2H, t), 3.57 (2H, t), 3.63-3.73 (1H, m), 4.03 (4H, dt), 4.32 (2H, q), 5.18 (1H, s), 6.37-6.43 (2H, m), 7.05-7.13 (2H, m), 7.2-7.23 (1H, m), 7.47 (1H, s), 7.49-7.54 (1H, m); m/z: ES+ [M+H]$^+$ 627.2.

Intermediate 119d: 2-(3-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)-2,2-difluoroacetic Acid

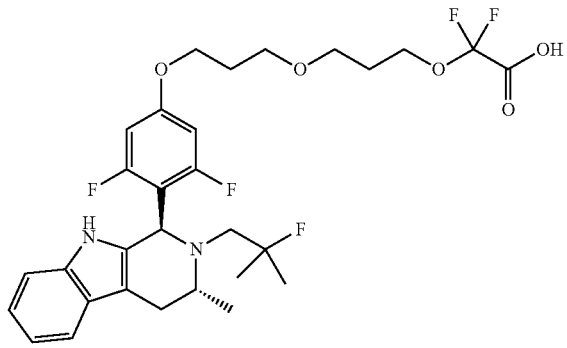 [SMILES: C[C@@H]1Cc2c([nH]c3ccccc23)[C@@H](c2c(F)cc(OCCCOCCCOC(F)(F)C(=O)O)cc2F)N1CC(C)(C)F]

A solution of 2 M aq. sodium hydroxide (0.89 mL, 1.8 mmol) was added to ethyl 2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)-2,2-difluoroacetate (0.56 g, 0.89 mmol) in ethanol (6 mL) at 20° C. under air. The resulting solution was stirred at 20° C. for 30 minutes. The reaction mixture was acidified with 2M HCl (3 mL) diluted with EtOAc (50 mL), and washed sequentially with water (5 mL) and saturated brine (5 mL). The organic layer was dried with MgSO$_4$, filtered and evaporated to afford the title compound (0.550 g, 97%) as a pale pink solid that was used without further purification; m/z: ES+ [M+H]$^+$ 599.4.

Example 119: (2S,4R)-1-((S)-2-(2-(3-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)-2,2-difluoroacetamido)-3,3-dimethylbutanoyl)-4-hydroxy-N-(4-(4-methylthiazol-5-yl)benzyl)pyrrolidine-2-carboxamide

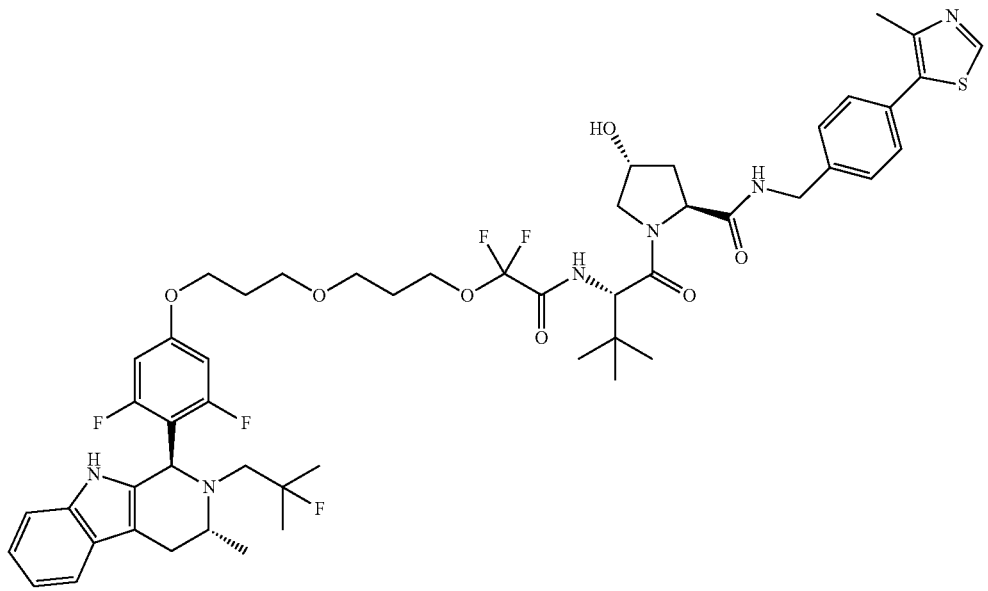 [SMILES: Cc1ncsc1-c1ccc(CNC(=O)[C@@H]2C[C@@H](O)CN2C(=O)[C@@H](NC(=O)C(F)(F)OCCCOCCCOc2cc(F)c([C@@H]3c4[nH]c5ccccc5c4C[C@@H](C)N3CC(C)(C)F)c(F)c2)C(C)(C)C)cc1]

The title compound was prepared in a similar manner to Example 68 using the appropriate carboxylic acid and amine to afford the desired product (106 mg, 63%) as a white solid; ¹H NMR (400 MHz, CDCl3, 30° C.) 0.94 (9H, s), 1.09 (3H, d), 1.20 (6H, dd), 1.92 (2H, q), 2.00 (2H, q), 2.03-2.14 (1H, m), 2.32-2.55 (6H, m), 2.60 (1H, dd), 2.84 (1H, dd), 3.07 (1H, dd), 3.51 (2H, t), 3.56 (2H, t), 3.61-3.72 (2H, m), 3.86 (1H, d), 3.97 (2H, t), 4.05 (2H, t), 4.33 (1H, dd), 4.47-4.6 (3H, m), 4.66 (1H, t), 5.19 (1H, s), 6.31-6.43 (2H, m), 7.01 (2H, t), 7.04-7.12 (2H, m), 7.18-7.25 (1H, m), 7.28-7.39 (4H, m), 7.50 (1H, dd), 8.03 (1H, s), 8.65 (1H, s); m/z: ES− [M−H]⁻ 1009.5

Example 120: (2S,4R)-1-((S)-2-(2-(3-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)-2,2-difluoroacetamido)-3,3-dimethylbutanoyl)-4-hydroxy-N—((S)-1-(4-(4-methylthiazol-5-yl)phenyl)ethyl)pyrrolidine-2-carboxamide

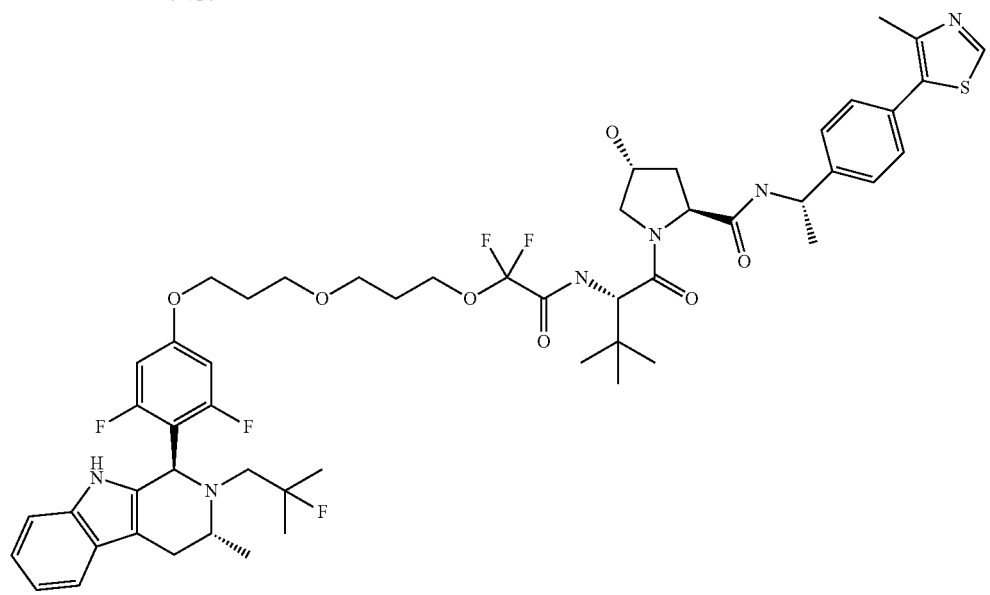 [SMILES: Cc1ncsc1-c1ccc([C@H](C)NC(=O)[C@@H]2C[C@@H](O)CN2C(=O)[C@@H](NC(=O)C(F)(F)OCCCOCCCOc2cc(F)c([C@@H]3c4[nH]c5ccccc5c4C[C@@H](C)N3CC(C)(C)F)c(F)c2)C(C)(C)C)cc1]

The title compound was prepared in a similar manner to Example 68 using the appropriate carboxylic acid and amine to afford the desired product (112 mg, 65%) as a white solid; ¹H NMR (400 MHz, CDCl3, 30° C.) 1.04 (9H, s), 1.09 (3H, d), 1.20 (6H, dd), 1.47 (3H, d), 1.89-2.07 (5H, m), 2.27-2.54 (6H, m), 2.60 (1H, dd), 2.84 (1H, dd), 3.07 (1H, dd), 3.52 (2H, t), 3.57 (2H, t), 3.65 (2H, dd), 3.86 (1H, d), 3.99 (2H, t), 4.06 (2H, t), 4.54 (1H, s), 4.59 (1H, d), 4.67 (1H, t), 5.07 (1H, p), 5.19 (1H, s), 6.32-6.41 (2H, m), 6.97-7.05 (1H, m), 7.05-7.13 (3H, m), 7.17-7.25 (1H, m), 7.3-7.36 (2H, m), 7.40 (2H, d), 7.50 (1H, dd), 7.94 (1H, s), 8.66 (1H, s); m/z: ES− [M−H]⁻ 1023.6

Intermediate 121a: Ethyl 2-(2-(4-(benzyloxy)butoxy)ethoxy)-2,2-difluoroacetate

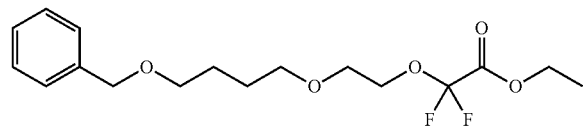 [SMILES: CCOC(=O)C(F)(F)OCCOCCCCOCc1ccccc1]

The title compound was prepared in a similar manner to Intermediate 119a using the appropriate alcohol to afford the desired product (0.880 g, 53%) as a tan oil; ¹H NMR (400 MHz, CDCl3, 30° C.) 1.35 (3H, t), 1.62-1.73 (4H, m), 3.42-3.57 (4H, m), 3.65 (2H, dd), 4-4.12 (2H, m), 4.33 (2H, q), 4.50 (2H, s), 7.26-7.38 (5H, m); m/z: ES+ [M+H]⁺ 347.0.

Intermediate 121b: Ethyl 2,2-difluoro-2-(2-(4-hydroxybutoxy)ethoxy)acetate

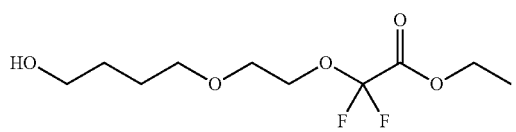 [SMILES: CCOC(=O)C(F)(F)OCCOCCCCO]

Ethyl 2-(2-(4-(benzyloxy)butoxy)ethoxy)-2,2-difluoroacetate (0.88 g, 2.54 mmol) and 10% palladium on carbon (0.270 g, 0.25 mmol) in ethanol (15 mL) was stirred under an atmosphere of hydrogen at 1 atm and 20° C. for 1 day. The reaction mixture was filtered through celite and the solids washed with EtOH (50 mL). The filtrate was evaporated to afford ethyl 2,2-difluoro-2-(2-(4-hydroxybutoxy)ethoxy)acetate (0.648 g, 100%) as a pale yellow oil; ¹H NMR (400 MHz, CDCl3, 30° C.) 1.37 (3H, t), 1.58-1.76 (5H, m), 3.54 (2H, t), 3.6-3.72 (4H, m), 4.10 (2H, dd), 4.35 (2H, q).

Intermediate 121c: Ethyl 2-(2-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)-2,2-difluoroacetate

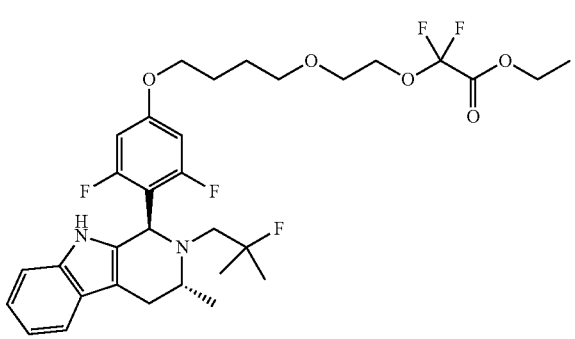 [SMILES: CCOC(=O)C(F)(F)OCCOCCCCOc1cc(F)c([C@@H]2c3[nH]c4ccccc4c3C[C@@H](C)N2CC(C)(C)F)c(F)c1]

The title compound was prepared in a similar manner to Intermediate 72e using the appropriate phenol and alcohol to afford the desired product (0.540 g, 69%) as a pale yellow gum; ¹H NMR (400 MHz, CDCl3, 30° C.) 1.10 (3H, d), 1.20 (6H, dd), 1.34 (3H, t), 1.68-1.8 (2H, m), 1.79-1.92 (2H, m), 2.39 (1H, dd), 2.60 (1H, ddd), 2.86 (1H, dd), 3.01-3.13 (1H, m), 3.55 (2H, t), 3.68 (3H, dd), 3.94 (2H, t), 4.07-4.1 (2H, m), 4.32 (2H, q), 5.18 (1H, s), 6.39 (2H, d), 7.04-7.14 (2H, m), 7.17-7.23 (1H, m), 7.44 (1H, s), 7.51 (1H, dd); m/z: ES– [M–H]⁻ 625.4

Intermediate 121d: 2-(2-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)-2,2-difluoroacetic Acid

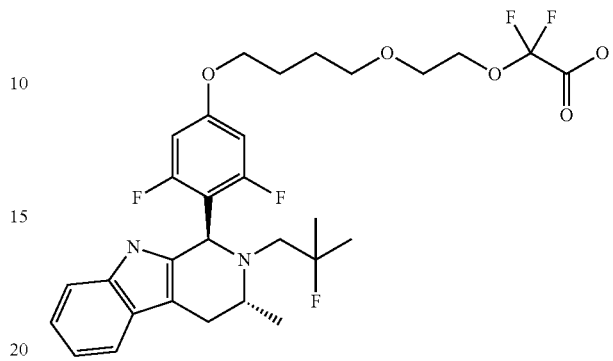

A solution of 2 M aq. sodium hydroxide (1 mL, 2.00 mmol) was added to ethyl 2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)-2,2-difluoroacetate (0.53 g, 0.85 mmol) in ethanol (6 mL) at 20° C. under air. The resulting solution was stirred at 20° C. for 30 minutes. The reaction mixture was acidified with 2M HCl (2 mL) diluted with EtOAc (30 mL), and washed sequentially with 2M HCl (2 mL) and saturated brine (2 mL). The organic layer was dried with MgSO4, filtered and evaporated to afford 2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)-2,2-difluoroacetic acid (0.508 g, 95%) as a purple solid that was used without further purification; m/z: ES– [M–H]⁻ 597.3

Example 121: (2S,4R)-1-((S)-2-(2-(2-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)-2,2-difluoroacetamido)-3,3-dimethylbutanoyl)-4-hydroxy-N-(4-(4-methylthiazol-5-yl)benzyl)pyrrolidine-2-carboxamide

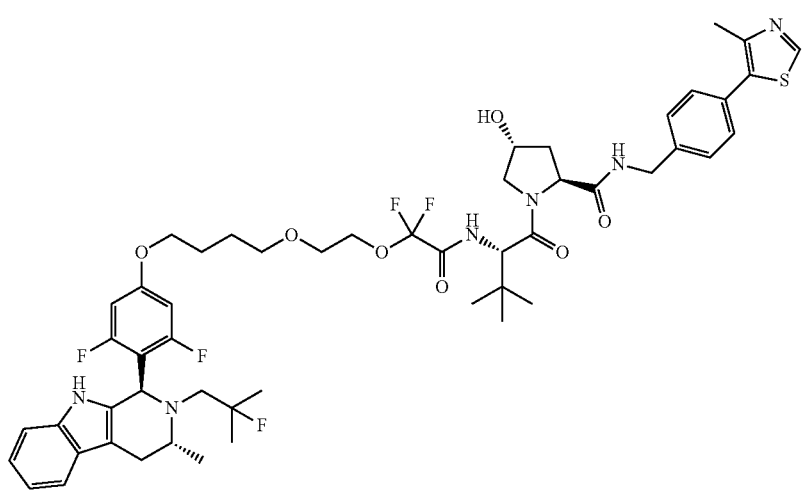 [SMILES: Cc1ncsc1-c1ccc(CNC(=O)[C@@H]2C[C@@H](O)CN2C(=O)[C@@H](NC(=O)C(F)(F)OCCOCCCCOc2cc(F)c([C@@H]3c4[nH]c5ccccc5c4C[C@@H](C)N3CC(C)(C)F)c(F)c2)C(C)(C)C)cc1]

The title compound was prepared in a similar manner to Example 68 using the appropriate carboxylic acid and amine to afford the desired product (53 mg, 31%) as a white solid; ¹H NMR (400 MHz, CDCl3, 30° C.) 0.94 (9H, s), 1.10 (3H, d), 1.20 (6H, dd), 1.69-1.78 (2H, m), 1.78-1.89 (2H, m), 2.01-2.12 (1H, m), 2.31-2.55 (6H, m), 2.60 (1H, dd), 2.85 (1H, dd), 3.08 (1H, dd), 3.54 (2H, t), 3.6-3.72 (4H, m), 3.79-3.93 (3H, m), 4.09 (2H, dd), 4.30 (1H, dd), 4.56 (3H, dd), 4.64 (1H, t), 5.19 (1H, s), 6.34 (2H, d), 7.07 (4H, ddd), 7.17-7.24 (1H, m), 7.34 (4H, q), 7.51 (1H, dd), 8.15 (1H, s), 8.63 (1H, s); m/z: ES− [M−H]⁻ 1009.6.

Example 122: (2S,4R)-1-((S)-2-(2-(2-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)-2,2-difluoroacetamido)-3,3-dimethylbutanoyl)-4-hydroxy-N—((S)-1-(4-(4-methylthiazol-5-yl)phenyl)ethyl)pyrrolidine-2-carboxamide Intermediate 123a: rac-((1R,2S)-2-((2-((Tetrahydro-2H-pyran-2-yl)oxy)ethoxy)methyl)cyclopropyl)methanol

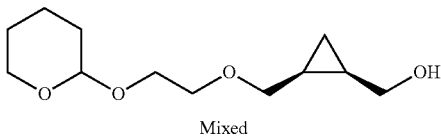

Mixed

A solid suspension of 60% sodium hydride in mineral oil (0.244 g, 6.11 mmol) was added to ((1R,2S)-cyclopropane-1,2-diyl)dimethanol (0.52 g, 5.09 mmol) in THF (10 mL) cooled to 0° C. under nitrogen. The resulting suspension was stirred at 0° C. for 45 minutes. 2-(2-bromoethoxy)tetrahydro-2H-pyran (0.77 mL, 5.10 mmol) was added and the mixture stirred at 20° C. for 3 days. The reaction was incomplete so the temperature was increased to 65° C. and

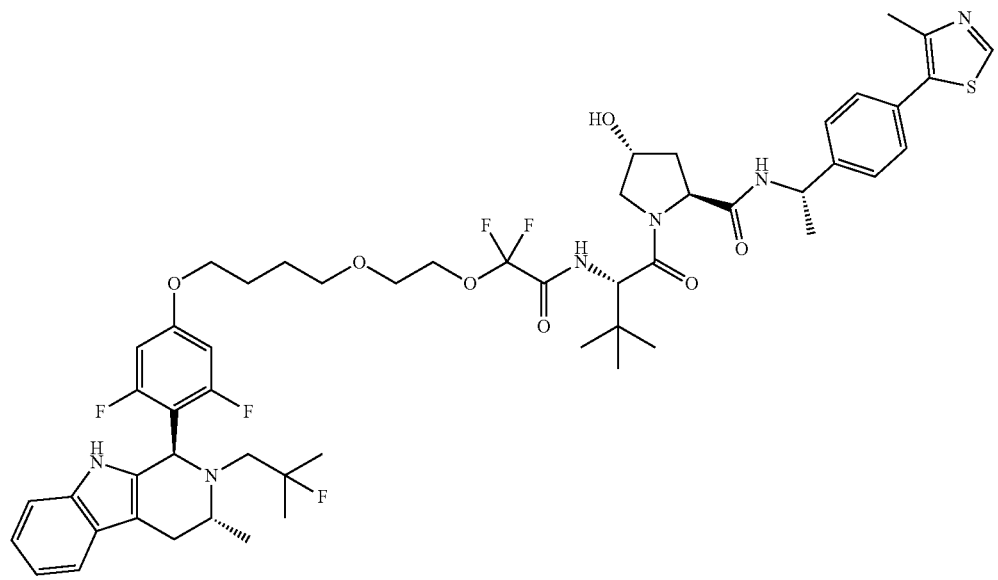 [SMILES: Cc1ncsc1-c1ccc([C@H](C)NC(=O)[C@@H]2C[C@@H](O)CN2C(=O)[C@@H](NC(=O)C(F)(F)OCCOCCCCOc2cc(F)c([C@@H]3c4[nH]c5ccccc5c4C[C@@H](C)N3CC(C)(C)F)c(F)c2)C(C)(C)C)cc1]

The title compound was prepared in a similar manner to Example 68 using the appropriate carboxylic acid and amine to afford the desired product (50 mg, 29%) as a white solid; ¹H NMR (400 MHz, CDCl3, 30° C.) 1.05 (9H, s), 1.09 (3H, d), 1.20 (6H, dd), 1.46 (3H, d), 1.7-1.79 (2H, m), 1.79-1.9 (2H, m), 1.93-2.04 (1H, m), 2.29-2.53 (6H, m), 2.60 (1H, dd), 2.85 (1H, dd), 3.08 (1H, dd), 3.55 (2H, t), 3.6-3.72 (4H, m), 3.82-3.94 (3H, m), 4.10 (2H, dd), 4.52 (1H, s), 4.59 (1H, d), 4.64 (1H, t), 5.06 (1H, p), 5.18 (1H, s), 6.35 (2H, d), 7.04-7.13 (3H, m), 7.16 (1H, d), 7.19-7.24 (1H, m), 7.34 (2H, d), 7.41 (2H, d), 7.48-7.55 (1H, m), 7.93 (1H, s), 8.65 (1H, s); m/z: ES− [M−H]⁻ 1023.5 the reaction mixture was stirred for a further 2 days. The reaction mixture was quenched with saturated NH4Cl (5 mL) and extracted with EtOAc (15 mL). The organic layer was washed sequentially with water (2×5 mL), saturated brine (2 mL) and dried over MgSO4, filtered and evaporated to afford a pale yellow oil. The crude product was purified by flash silica chromatography, elution gradient 20 to 80% EtOAc in heptane to the title compound (0.580 g, 49.5%) as a colourless oil; ¹H NMR (400 MHz, CDCl3, 30° C.) 0.20 (1H, qd), 0.80 (1H, tdd), 1.3-1.44 (2H, m), 1.46-1.68 (3H, m), 1.71 (1H, ddd), 1.85 (1H, tt), 3.1-3.34 (3H, m), 3.43-3.67 (4H, m), 3.67-3.79 (1H, m), 3.8-4.02 (4H, m), 4.63 (1H, q).

Intermediate 123b: rac-Ethyl 2-(((1R,2S)-2-((2-((tetrahydro-2H-pyran-2-yl)oxy)ethoxy)methyl)cyclopropyl)methoxy)acetate

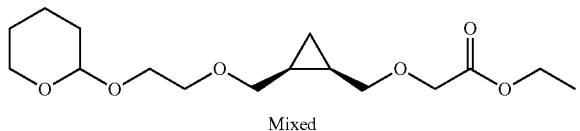 [SMILES: CCOC(=O)COC[C@@H]1C[C@@H]1COCCOC1CCCCO1]

Mixed

The title compound was prepared in a similar manner to Intermediate 72c using the appropriate alcohol to afford the desired product (0.455 g, 57%) as a pale yellow oil; $^1$H NMR (400 MHz, CDCl3, 30° C.) 0.25-0.42 (1H, m), 0.87 (1H, td), 1.27 (7H, dt), 1.45-1.59 (3H, m), 1.72 (1H, ddt), 1.83 (1H, dq), 3.42-3.73 (7H, m), 3.86 (2H, ddd), 4.10 (2H, s), 4.22 (2H, q), 4.51-4.75 (1H, m); m/z: ES+[M+Na]$^+$339.0.

Intermediate 123c: rac-Ethyl 2-(((1R,2S)-2-((2-hydroxyethoxy)methyl)cyclopropyl)methoxy)acetate

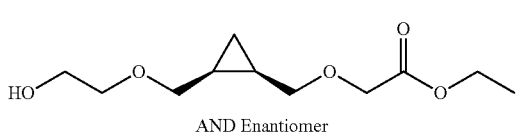 [SMILES: CCOC(=O)COC[C@@H]1C[C@@H]1COCCO]

AND Enantiomer

The title compound was prepared in a similar manner to Intermediate 72b using the appropriate tetrahydropyran protected alcohol to afford the desired product (0.187 g, 56.6%) as a colourless oil; $^1$H NMR (400 MHz, CDCl3, 30° C.) 0.24 (1H, q), 0.85 (1H, td), 1.21-1.37 (5H, m), 2.48 (1H, s), 3.49-3.56 (2H, m), 3.58-3.7 (4H, m), 3.7-3.75 (2H, m), 4.08-4.13 (2H, m), 4.22 (2H, q); m/z: ES+ [M+H]$^+$ 233.0

Intermediate 123d: Ethyl 2-[[(1RS,2SR)-2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxymethyl]cyclopropyl]methoxy]acetate

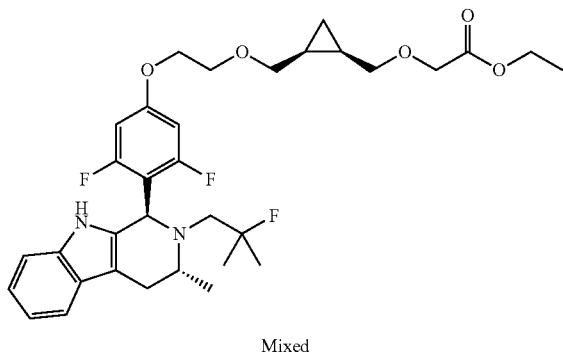 [SMILES: CCOC(=O)COC[C@@H]1C[C@@H]1COCCOc1cc(F)c([C@@H]2c3[nH]c4ccccc4c3C[C@@H](C)N2CC(C)(C)F)c(F)c1]

Mixed

The title compound was prepared in a similar manner to Intermediate 72e using the appropriate phenol and alcohol to afford the desired product (222 mg, 48%) as a colourless oil; $^1$H NMR (400 MHz, CDCl3, 30° C.) 0.30 (1H, dt), 0.82-0.93 (1H, m), 1.10 (3H, d), 1.13-1.33 (12H, m), 2.35 (1H, s), 2.60 (1H, dd), 2.87 (1H, dd), 3.09 (1H, dd), 3.45-3.6 (3H, m), 3.66 (2H, ddt), 3.72-3.9 (2H, m), 4.05-4.11 (4H, m), 4.20 (2H, qd), 5.18 (1H, s), 6.43 (2H, d), 7.04-7.13 (2H, m), 7.15-7.17 (2H, m), 7.27 (1H, d), 7.49-7.53 (1H, m), 7.59 (1H, d); m/z: ES− [M−H]$^−$ 601.3.

Intermediate 123e: 2-[[(1RS,2SR)-2-[2-[3,5-Difluoro-4-[(1R,3R)-2-(2-fluoro-2-methyl-propyl)-3-methyl-1,3,4,9-tetrahydropyrido[3,4-b]indol-1-yl]phenoxy]ethoxymethyl]cyclopropyl]methoxy]acetic Acid

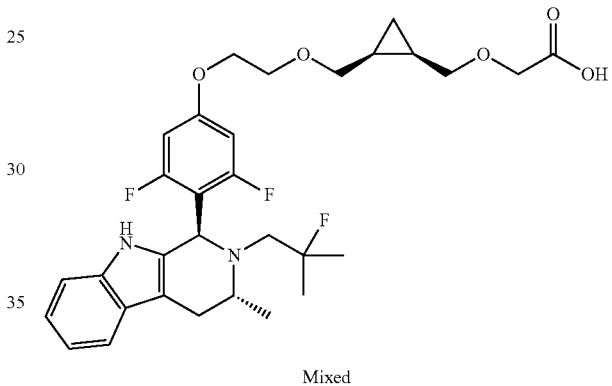

Mixed

A solution of 2M aq. sodium hydroxide (0.365 mL, 0.73 mmol) was added to ethyl 2-[[(1RS,2SR)-2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxymethyl]cyclopropyl]methoxy]acetate (0.22 g, 0.37 mmol) in ethanol (3 mL) at 20° C. under air. The resulting solution was stirred at 20° C. for 1 hour. The reaction mixture was acidified with 2M HCl (1 mL), diluted with EtOAc (15 mL), and washed sequentially with water (2×2 mL) and saturated brine (2 mL). The organic layer was dried with MgSO$_4$, filtered and evaporated to afford 2-[[(1RS,2SR)-2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxymethyl]cyclopropyl]methoxy]acetic acid (0.158 g, 75%) as a yellow solid that was used without further purification; $^1$H NMR (400 MHz, CDCl3, 30° C.) 0.25 (1H, p), 0.83-0.96 (1H, m), 1.04-1.23 (7H, m), 1.3-1.43 (3H, m), 2.35 (1H, s), 2.61 (1H, d), 2.87 (1H, s), 3.08 (1H, s), 3.26-3.46 (2H, m), 3.63-3.75 (1H, m), 3.81 (2H, s), 3.86-3.96 (2H, m), 3.97-4.23 (5H, m), 5.19 (1H, s), 6.41 (2H, d), 7.09 (2H, s), 7.24 (1H, s), 7.43-7.58 (1H, m), 7.71 (1H, s). Assigned Hs: 36. Missing 1 proton; m/z: ES+ [M+H]$^+$ 575.0

Intermediate 123f: (2S,4R)-1-[(2S)-2-[[2-[[(1RS,2SR)-2-[2-[3,5-Difluoro-4-[(1R,3R)-2-(2-fluoro-2-methyl-propyl)-3-methyl-1,3,4,9-tetrahydropyrido[3,4-b]indol-1-yl]phenoxy]ethoxymethyl]cyclopropyl]methoxy]acetyl]amino]-3,3-dimethyl-butanoyl]-4-hydroxy-N-[[4-(4-methylthiazol-5-yl)phenyl]methyl]pyrrolidine-2-carboxamide (2S,4R)-1-[(2S)-2-[[2-[[(1RS,2SR)-2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxymethyl]cyclopropyl]methoxy]acetyl]amino]-3,3-dimethyl-butanoyl]-4-hydroxy-N-[[4-(4-methylthiazol-5-yl)phenyl]methyl]pyrrolidine-2-carboxamide (200 mg, 0.2 mmol) was dissolved in MeOH. The resulting solution was purified using the SFC conditions detailed below: Column: YMC

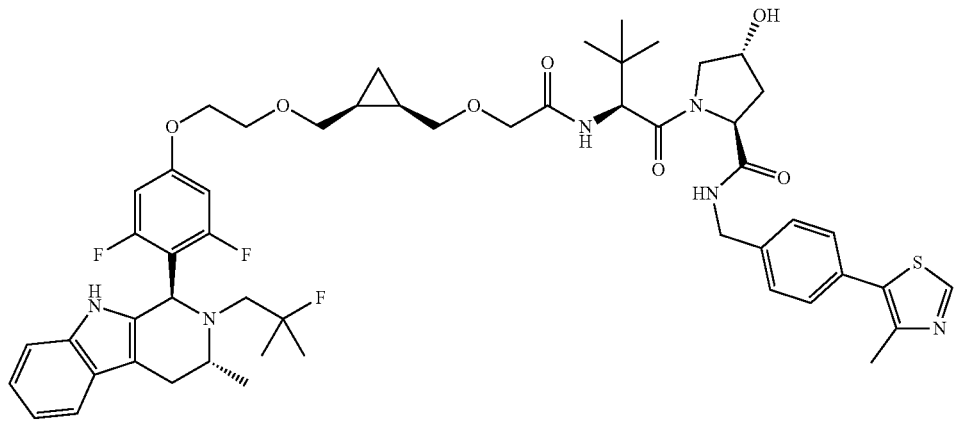

Mixed

The title compound was prepared in a similar manner to Example 68 using the appropriate carboxylic acid and amine to afford the desired product (0.201 g, 75%) as a yellow solid; m/z: ES– [M–H]⁻ 985.5

Example 123: (2S,4R)-1-[(2S)-2-[[2-[[(1R*2S*)-2-[2-[3,5-Difluoro-4-[(R,3R)-2-(2-fluoro-2-methyl-propyl)-3-methyl-1,3,4,9-tetrahydropyrido[3,4-b]indol-1-yl]phenoxy]ethoxymethyl]cyclopropyl]methoxy]acetyl]amino]-3,3-dimethyl-butanoyl]-4-hydroxy-N-[[4-(4-methylthiazol-5-yl)phenyl]methyl]pyrrolidine-2-carboxamide, Isomer 1

Amylose C, 20×250 mm, 5 micron; Mobile phase: 35% EtOH=0.1% NH3/65% scCO2; Flow rate: 60 ml/min; BPR: 120 bar; Column temperature: 40° C. to afford the title compound that eluted first from the column (14 mg, 5%) as a yellow solid; ¹H NMR (400 MHz, CDCl3, 30° C.) 0.24 (1H, q), 0.72 (1H, t), 0.86 (4H, dq), 0.95 (9H, s), 1.09 (3H, d), 1.20 (6H, dd), 2.07 (1H, dd), 2.40 (1H, dd), 2.49 (3H, s), 2.58 (2H, ddd), 2.85 (1H, dd), 3.07 (1H, dd), 3.38-3.55 (3H, m), 3.58-3.76 (5H, m), 3.77-3.91 (2H, m), 3.97-4.12 (3H, m), 4.33 (1H, dd), 4.5-4.61 (3H, m), 4.72 (1H, t), 5.19 (1H, s), 6.39 (2H, d), 7.02-7.14 (2H, m), 7.19-7.25 (2H, m), 7.31-7.4 (4H, m), 7.46-7.53 (1H, m), 8.61 (1H, s), 8.66 (1H, s); m/z: ES– [M–H]⁻ 985.5.

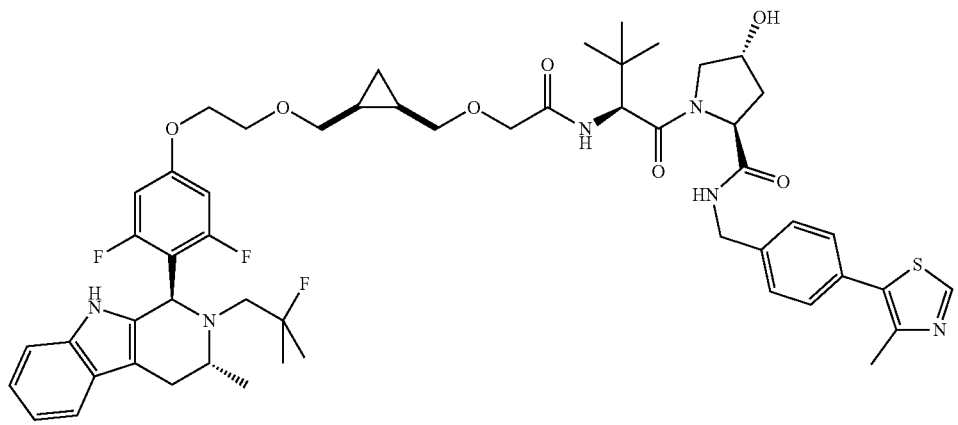

ISOMER 1

Example 124: (2S,4R)-1-[(2S)-2-[[2-[[(1R*2S*)-2-[2-[3,5-Difluoro-4-[(1R,3R)-2-(2-fluoro-2-methyl-propyl)-3-methyl-1,3,4,9-tetrahydropyrido[3,4-b]indol-1-yl]phenoxy]ethoxymethyl]cyclopropyl]methoxy]acetyl]amino]-3,3-dimethyl-butanoyl]-4-hydroxy-N-[[4-(4-methylthiazol-5-yl)phenyl]methyl]pyrrolidine-2-carboxamide, Isomer 2 filtered and evaporated to afford crude product which was purified by flash silica chromatography, elution gradient 0 to 30% EtOAc in heptane to afford the title compound (1.47 g, 33%) as a colourless oil. $^1$H NMR (400 MHz, CDCl$_3$, 30° C.) 1.94 (2H, p), 2.42 (3H, s), 3.50 (2H, t), 4.17 (2H, t), 4.40 (2H, s), 7.22-7.37 (7H, m), 7.75-7.81 (2H, m); m/z ES+[M+NH$_4$]$^+$ 338.0.

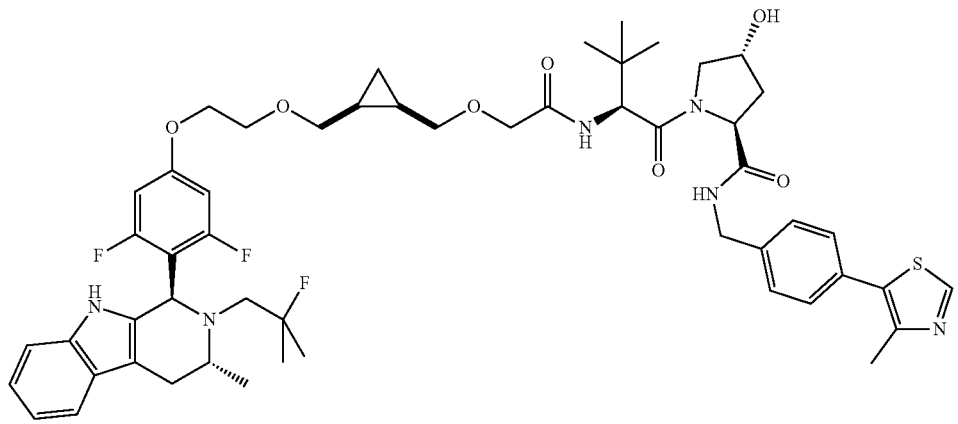

ISOMER 2

The title compound was isolated using the same method as Example 123 collecting the compound that eluted second from the column (37 mg, 14%) as a yellow solid; $^1$H NMR (400 MHz, CDCl3, 30° C.) 0.37 (1H, q), 0.82-0.91 (2H, m), 0.95 (9H, s), 1.09 (3H, d), 1.20 (7H, dd), 1.28-1.31 (1H, m), 2.03-2.14 (1H, m), 2.40 (1H, dd), 2.50 (3H, s), 2.52-2.64 (2H, m), 2.84 (1H, dd), 3.07 (1H, dd), 3.42 (2H, ddd), 3.54-3.76 (6H, m), 3.78-3.87 (1H, m), 3.92 (1H, d), 3.95-4.13 (3H, m), 4.33 (1H, dd), 4.47-4.63 (3H, m), 4.71 (1H, t), 5.20 (1H, s), 6.38 (2H, d), 7-7.13 (2H, m), 7.17-7.26 (3H, m), 7.3-7.42 (4H, m), 7.50 (1H, dd), 8.53 (1H, s), 8.66 (1H, s); m/z: ES- [M-H]$^-$ 985.6.

Intermediate 125a: 3-(Benzyloxy)propyl 4-methylbenzenesulfonate

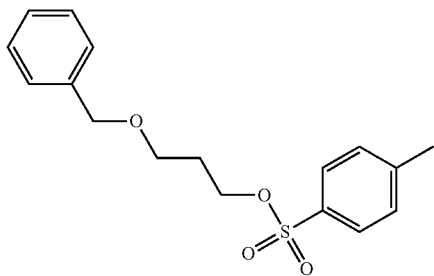 [SMILES: Cc1ccc(S(=O)(=O)OCCCOCc2ccccc2)cc1]

4-Methylbenzenesulfonyl chloride (3.17 g, 16.6 mmol) was added to a stirred solution of 3-(benzyloxy)propan-1-ol (2.3 g, 13.84 mmol) and pyridine (1.3 mL, 16.6 mmol) in DCM (80 mL) at RT, under nitrogen. The resulting solution was stirred at RT for 17 hours. The reaction mixture was diluted with DCM (25 mL), and washed sequentially with 2M HCl (100 mL), and saturated brine (150 mL). The organic layer was dried with a phase separating cartridge,

Intermediate 125b: ((3-(3-(Benzyloxy)propoxy)-2,2-difluoropropoxy)methanetriyl)tribenzene

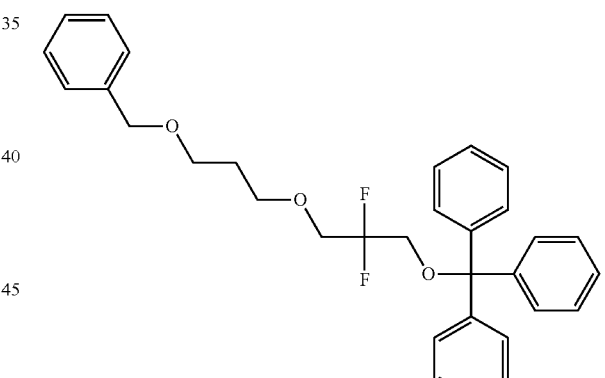

Sodium hydride (0.157 g, 3.93 mmol, 60% mineral oil dispersion) was added portionwise to a stirred solution of 2,2-difluoro-3-(trityloxy)propan-1-ol (preparation described in US2017/305909, 2017, A1) (1.16 g, 3.27 mmol) in THF (30 mL) at RT, under nitrogen. The resulting mixture was stirred at RT for 40 minutes. A solution of 3-(benzyloxy)propyl 4-methylbenzenesulfonate (1.1 g, 3.44 mmol) in THF (30 mL) was added, the resulting mixture was stirred at RT for 1 hour and warmed to 70° C. for 17 hours. The reaction mixture was allowed to cool to RT, quenched with water (50 mL), partitioned between EtOAc (125 mL), and saturated brine (50 mL). The aqueous layer was separated and further extracted with dried with EtOAc (75 mL), the organic extracts were combined, dried with a phase separating cartridge, filtered and evaporated to afford crude product which was purified by flash silica chromatography, elution gradient 0 to 30% EtOAc in heptane to afford the title compound (1.43 g, 87%) as a colourless gum. ¹H NMR (400 MHz, CDCl₃, 30° C.) 1.82 (2H, p), 3.35 (2H, t), 3.47 (2H, t), 3.61 (2H, t), 3.80 (2H, t), 4.44 (2H, s), 7.2-7.35 (14H, m), 7.39-7.46 (6H, m), m/z ES+[M+Na]⁺525.0.

Intermediate 125c: 3-(3-(Benzyloxy)propoxy)-2,2-difluoropropan-1-ol

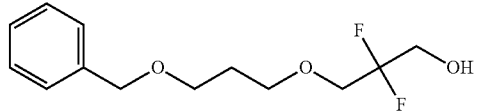 [SMILES: OCC(F)(F)COCCCOCc1ccccc1]

A solution of 1.25 M HCl in MeOH (5.7 mL, 7.1 mmol) was added to a stirred solution of ((3-(3-(benzyloxy)propoxy)-2,2-difluoropropoxy)methanetriyl)tribenzene (1.43 g, 2.85 mmol) in MeOH (6 mL) and the resulting solution was stirred at RT for 17 hours. The reaction mixture was evaporated to afford crude product which was purified by flash silica chromatography, elution gradient 0 to 30% EtOAc in heptane to afford the title compound (546 mg, 74%) as a colourless oil. ¹H NMR (400 MHz, CDCl₃, 30° C.) 1.89 (2H, p), 2.11-2.24 (1H, m), 3.56 (2H, t), 3.67 (2H, t), 3.75 (2H, d), 3.82 (2H, td), 4.50 (2H, s), 7.27-7.38 (5H, m), m/z ES+ [M+H]+ 261.0.

Intermediate 125d: Ethyl 2-(3-(3-Benzyloxy)propoxy)-2,2-difluoropropoxy)acetate

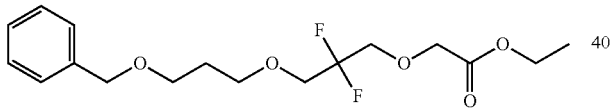

The title compound was prepared in a similar manner to Intermediate 72c using the appropriate alcohol to afford the desired product (410 mg, 56%) as a pale yellow oil. ¹H NMR (400 MHz, CDCl₃, 30° C.) 1.29 (3H, t), 1.90 (2H, p), 3.56 (2H, t), 3.64-3.77 (4H, m), 3.83 (2H, t), 4.16 (2H, s), 4.22 (2H, q), 4.50 (2H, s), 7.27-7.37 (5H, m), m/z ES+[M+NH₄] 364.0.

Intermediate 125e: Ethyl 2-(2,2-difluoro-3-(3-hydroxypropoxy)propoxy)acetate

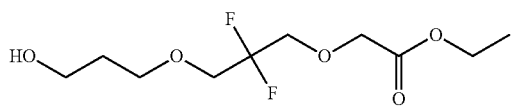 [SMILES: CCOC(=O)COCC(F)(F)COCCCO]

The title compound was prepared in a similar manner to Intermediate 72d using the appropriate benzyl ether to afford the desired product (298 mg, 86%) as a colourless oil. ¹H NMR (400 MHz, CDCl₃, 30° C.) 1.29 (3H, t), 1.85 (2H, p), 2.06 (1H, s), 3.71-3.93 (8H, m), 4.18 (2H, s), 4.23 (2H, q).

Intermediate 125f: Ethyl 2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)-2,2-difluoropropoxy)acetate

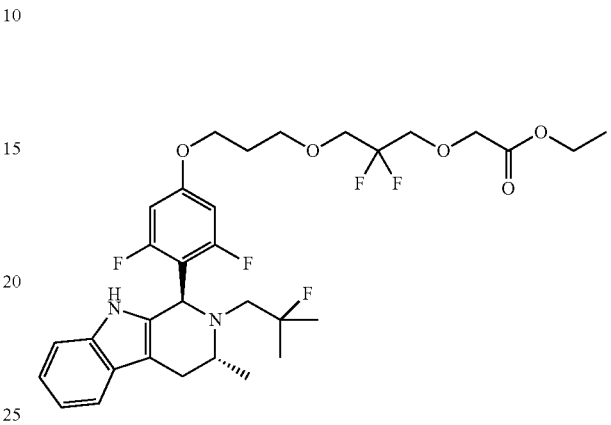

The title compound was prepared in a similar manner to Intermediate 72e using the appropriate phenol and alcohol to afford the desired product (512 mg, 77%) as a beige oil. ¹H NMR (400 MHz, CDCl₃, 30° C.) 1.10 (3H, d), 1.17 (3H, d), 1.23 (3H, d), 1.25 (3H, d), 1.98-2.1 (2H, m), 2.39 (1H, dd), 2.60 (1H, dd), 2.86 (1H, dd), 3.09 (1H, dd), 3.63-3.87 (7H, m), 4.03 (2H, t), 4.12 (2H, s), 4.20 (2H, q), 5.19 (1H, s), 6.37-6.45 (2H, m), 7.04-7.14 (2H, m), 7.19-7.24 (1H, m), 7.48-7.53 (1H, m), 7.55 (1H, s), m/z ES- [M+H]- 625.4.

Intermediate 125g: 2-(3-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)-2,2-difluoropropoxy)acetic Acid

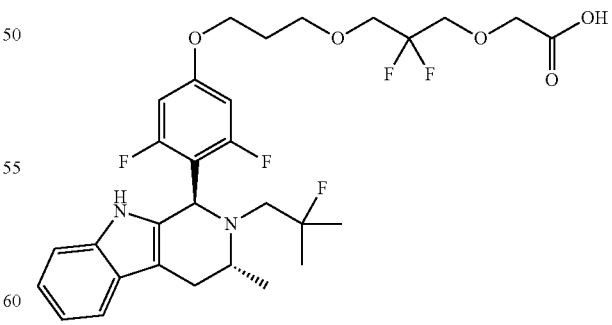

The title compound was prepared in a similar manner to Intermediate 72f using the appropriate ester to afford the desired product (476 mg, 97%) as a brown gum; m/z ES- [M-H]⁻ 597.3.

Example 125: (2S,4R)-1-((S)-2-(2-(3-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)-2,2-difluoropropoxy)acetamido)-3,3-dimethylbutanoyl)-4-hydroxy-N-(4-(4-methylthiazol-5-yl)benzyl)pyrrolidine-2-carboxamide

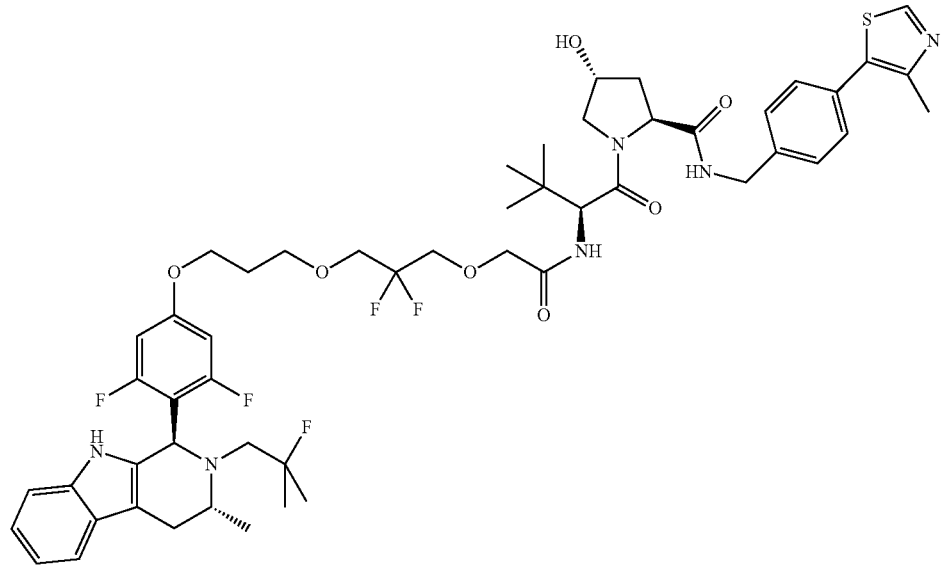 [SMILES: Cc1ncsc1-c1ccc(CNC(=O)[C@@H]2C[C@@H](O)CN2C(=O)[C@@H](NC(=O)COCC(F)(F)COCCCOc2cc(F)c([C@@H]3c4[nH]c5ccccc5c4C[C@@H](C)N3CC(C)(C)F)c(F)c2)C(C)(C)C)cc1]

The title compound was prepared in a similar manner to Example 68 using the appropriate carboxylic acid and amine to afford the desired product (92 mg, 51%) as a white solid; ¹H NMR (400 MHz, CDCl₃, 30° C.) 0.94 (9H, s), 1.09 (3H, d), 1.19 (3H, d), 1.24 (3H, d), 2-2.05 (2H, m), 2.06-2.15 (1H, m), 2.42 (1H, dd), 2.50 (3H, s), 2.53-2.64 (2H, m), 2.66 (3H, d), 2.83 (1H, dd), 3.06 (1H, dd), 3.58-3.81 (9H, m), 3.90 (1H, d), 3.93-4.07 (3H, m), 4.34 (1H, d), 4.54 (3H, d), 4.75 (1H, t), 5.20 (1H, s), 6.29-6.41 (2H, m), 7.03-7.13 (2H, m), 7.19-7.26 (2H, m), 7.32-7.41 (4H, m), 7.48-7.55 (1H, m), 8.65 (1H, s), m/z ES– [M–H]⁻ 1009.5.

Intermediate 126a: 5-(Benzyloxy)pentyl 4-methylbenzenesulfonate

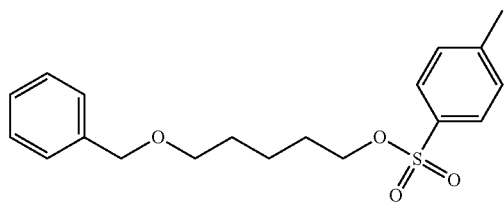 [SMILES: Cc1ccc(S(=O)(=O)OCCCCCOCc2ccccc2)cc1]

A solution of 4-methylbenzenesulfonyl chloride (2.0 g, 10.5 mmol) in pyridine (1 mL) was added dropwise to a stirred solution of 5-(benzyloxy)pentan-1-ol (1.7 g, 8.75 mmol) in pyridine (5 mL) at 0° C., under nitrogen. The resulting mixture was stirred at 0° C. for 2 hours, removed from the cooling bath and stirred at RT for 17 hours. The reaction mixture was diluted with ether (150 mL), and washed with 2M HCl (2×125 mL). The organic layer was dried with MgSO₄, filtered and evaporated to afford crude product. The crude product was purified by flash silica chromatography, elution gradient 0 to 30% EtOAc in heptane. Pure fractions were evaporated to dryness to afford the title compound (0.819 g, 27%); ¹H NMR (400 MHz, CDCl₃, 30° C.) 1.35-1.46 (2H, m), 1.52-1.61 (2H, m), 1.62-1.73 (2H, m), 2.44 (3H, s), 3.42 (2H, t), 4.02 (2H, t), 4.47 (2H, s), 7.27-7.38 (7H, m), 7.75-7.82 (2H, m); m/z ES+ [M+H]+ 249.2.

Intermediate 126b: ((3-((5-(Benzyloxy)pentyl)oxy)-2,2-difluoropropoxy)methanetriyl)tribenzene

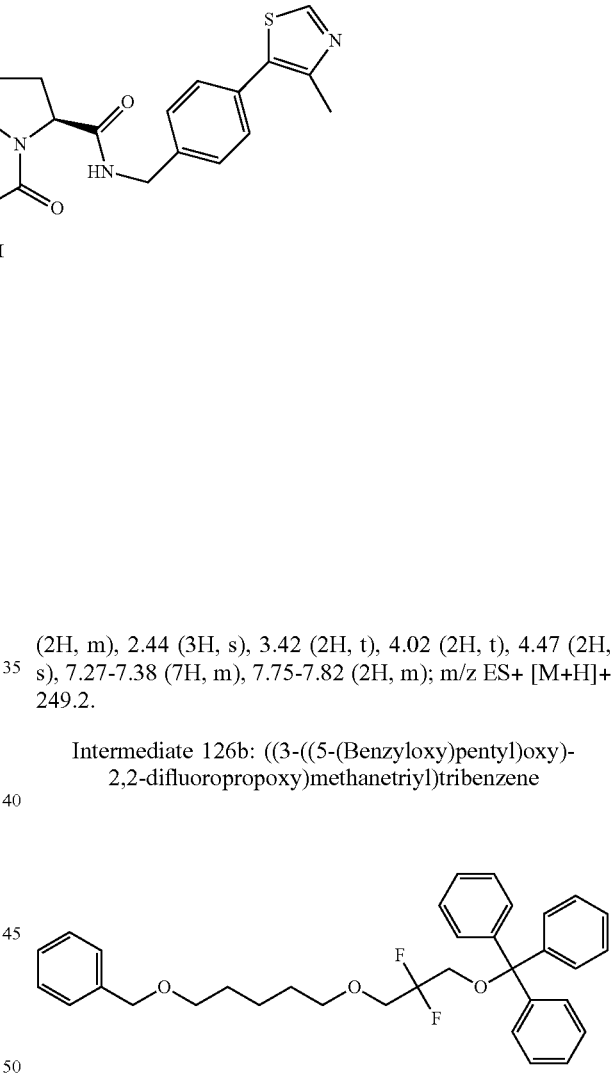

A solid suspension of 60% sodium hydride in mineral oil (111 mg, 2.77 mmol) was added portionwise to a stirred solution of 2,2-difluoro-3-(trityloxy)propan-1-ol (819 mg, 2.31 mmol) in THF (30 mL) at RT, under nitrogen. The resulting mixture was stirred at RT for 40 minutes. A solution of 5-(benzyloxy)pentyl 4-methylbenzenesulfonate (805 mg, 2.31 mmol) in THF (5 mL) was added and the resulting mixture was stirred at RT for 17 hours. The reaction mixture was allowed to cool to RT, quenched with water (50 mL), partitioned between EtOAc (125 mL), and saturated brine (50 mL). The aqueous layer was separated and further extracted with dried with EtOAc (75 mL), the organic extracts were combined, dried with a phase separating cartridge, filtered and evaporated to afford crude product. The crude product was purified by flash silica chromatography, elution gradient 0 to 30% EtOAc in heptane. Pure fractions were evaporated to dryness to afford the title compound (928 mg, 76%) as a colourless gum. $^1$H NMR (400 MHz, CDCl$_3$, 30° C.) 1.29-1.4 (2H, m), 1.48-1.66 (4H, m), 3.35 (2H, t), 3.43 (2H, t), 3.48 (2H, t), 3.80 (2H, t), 4.48 (2H, s), 7.21-7.35 (14H, m), 7.41-7.46 (6H, m).

Intermediate 126c: 3-((5-(Benzyloxy)pentyl)oxy)-2,2-difluoropropan-1-ol

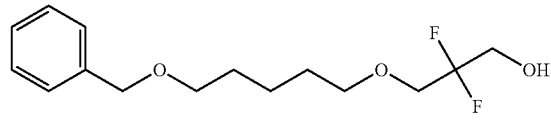 [SMILES: OCC(F)(F)COCCCCCOCc1ccccc1]

A solution of 1.25 M HCl in MeOH (3.5 mL, 4.37 mmol) was added to a stirred solution of ((3-((5-(benzyloxy)pentyl)oxy)-2,2-difluoropropoxy)methanetriyl)tribenzene (928 mg, 1.75 mmol) in MeOH (4 mL) and the resulting solution was stirred at RT for 17 hours. The reaction mixture was evaporated to afford crude product which was purified by flash silica chromatography, elution gradient 0 to 30% EtOAc in heptane to afford the title compound (378 mg, 75%) as a colourless oil. $^1$H NMR (400 MHz, CDCl$_3$, 30° C.) 1.39-1.51 (2H, m), 1.56-1.71 (4H, m), 2.13 (1H, t), 3.48 (2H, t), 3.55 (2H, t), 3.72 (2H, t), 3.84 (2H, td), 4.50 (2H, s), 7.27-7.39 (5H, m), m/z ES+ [M+H]+ 289.0.

Intermediate 126d: Ethyl 2-(3-((5-(benzyloxy)pentyl)oxy)-2,2-difluoropropoxy)acetate

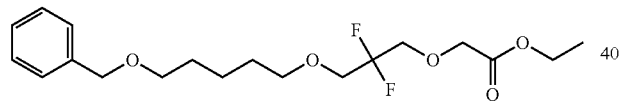

The title compound was prepared in a similar manner to Intermediate 72c using the appropriate alcohol to afford the desired product (207 mg, 42%) as a colourless oil. $^1$H NMR (400 MHz, CDCl$_3$, 30° C.) 1.28 (3H, t), 1.41-1.49 (2H, m), 1.61 (4H, ddd), 3.47 (2H, t), 3.54 (2H, t), 3.71 (2H, t), 3.84 (2H, t), 4.17 (2H, s), 4.22 (2H, q), 4.50 (2H, s), 7.26-7.36 (5H, m), m/z ES+[M+NH$_4$]+392.1.

Intermediate 126e: Ethyl 2-(2,2-difluoro-3-((5-hydroxypentyl)oxy)propoxy)acetate

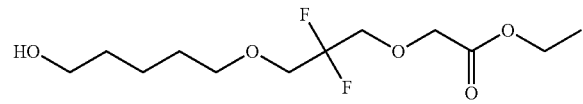 [SMILES: CCOC(=O)COCC(F)(F)COCCCCCO]

The title compound was prepared in a similar manner to Intermediate 72d using the appropriate benzyl ether to afford the desired product (140 mg, 89%) as a colourless oil. $^1$H NMR (400 MHz, CDCl$_3$, 30° C.) 1.29 (3H, t), 1.42-1.5 (2H, m), 1.55-1.67 (4H, m), 3.57 (2H, t), 3.65 (2H, t), 3.72 (2H, t), 3.85 (2H, t), 4.18 (2H, s), 4.23 (2H, q).

Intermediate 126f: Ethyl 2-(3-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)-2,2-difluoropropoxy)acetate

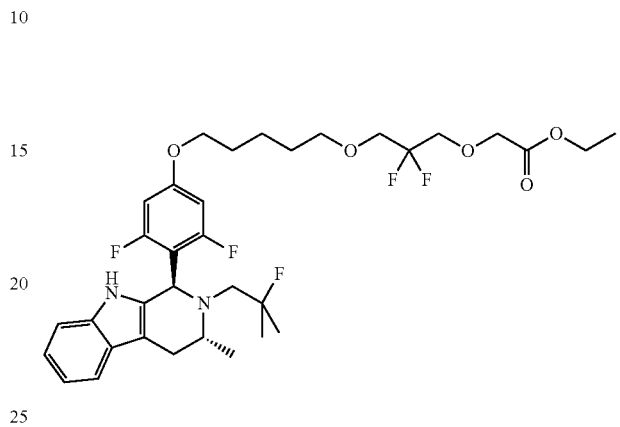

The title compound was prepared in a similar manner to Intermediate 72e using the appropriate phenol and alcohol to afford the desired product (223 mg, 78%) as a beige oil. $^1$H NMR (400 MHz, CDCl$_3$, 30° C.) 1.10 (3H, d), 1.18 (3H, d), 1.23 (3H, d), 1.25-1.3 (3H, m), 1.53 (2H, s), 1.61-1.7 (2H, m), 1.75-1.84 (2H, m), 2.39 (1H, dd), 2.60 (1H, dd), 2.86 (1H, dd), 3.09 (1H, dd), 3.58 (2H, t), 3.64-3.77 (3H, m), 3.84 (2H, t), 3.91 (2H, t), 4.17 (2H, s), 4.19-4.26 (2H, m), 5.18 (1H, s), 6.34-6.43 (2H, m), 7.04-7.14 (2H, m), 7.18-7.25 (1H, m), 7.43 (1H, s), 7.51 (1H, dd); m/z ES– [M–H]⁻ 653.4.

Intermediate 126g: 2-(3-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)-2,2-difluoropropoxy)acetic Acid

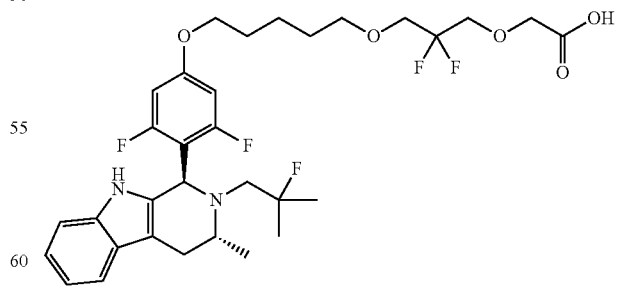

The title compound was prepared in a similar manner to Intermediate 72f using the appropriate ester to afford the desired product (202 mg, 95%) as a yellow gum, m/z ES– [M–H]⁻ 625.3.

Example 126: (2S,4R)-1-((S)-2-(2-(3-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)-2,2-difluoropropoxy)acetamido)-3,3-dimethylbutanoyl)-4-hydroxy-N-(4-(4-methylthiazol-5-yl)benzyl)pyrrolidine-2-carboxamide 2,2-Difluoro-3-(trityloxy)propan-1-ol

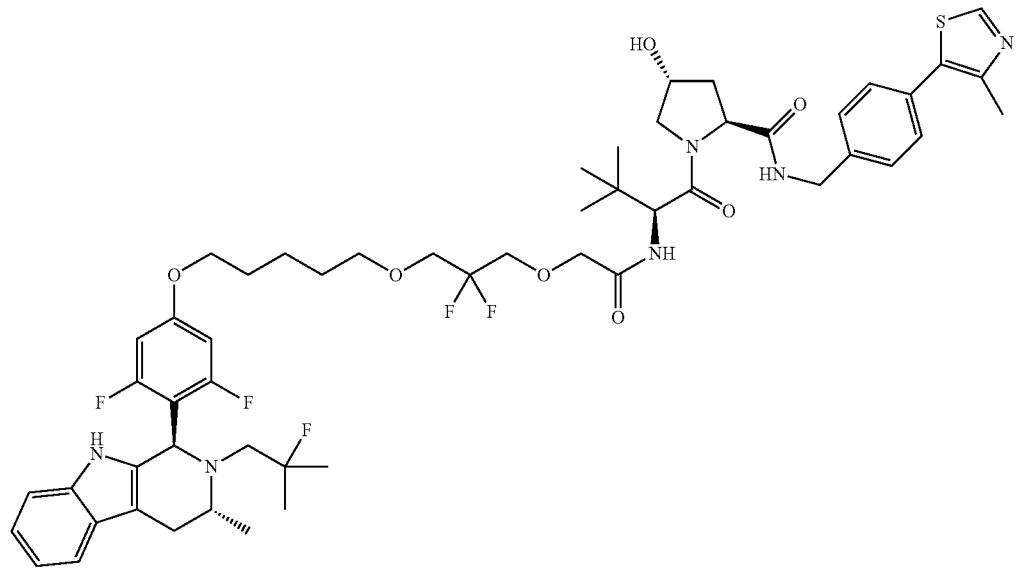 [SMILES: Cc1ncsc1-c1ccc(CNC(=O)[C@@H]2C[C@@H](O)CN2C(=O)[C@@H](NC(=O)COCC(F)(F)COCCCCCOc2cc(F)c([C@@H]3c4[nH]c5ccccc5c4C[C@@H](C)N3CC(C)(C)F)c(F)c2)C(C)(C)C)cc1]

The title compound was prepared in a similar manner to Example 68 using the appropriate carboxylic acid and amine to afford the desired product (37 mg, 24%) as a white solid; $^1$H NMR (400 MHz, CDCl$_3$, 30° C.) 0.94 (9H, s), 1.10 (3H, d), 1.17 (3H, d), 1.23 (3H, d), 1.45-1.69 (4H, m), 1.77 (2H, dt), 2.08 (1H, dd), 2.40 (1H, dd), 2.50 (3H, s), 2.53-2.65 (3H, m), 2.66 (1H, d), 2.85 (1H, dd), 3.08 (1H, dd), 3.54-3.63 (3H, m), 3.67 (2H, d), 3.71-3.84 (2H, m), 3.88 (2H, t), 4-4.11 (3H, m), 4.32 (1H, dd), 4.47 (1H, d), 4.5-4.62 (2H, m), 4.72 (1H, t), 5.19 (1H, s), 6.32-6.4 (2H, m), 7.06-7.14 (3H, m), 7.19-7.24 (1H, m), 7.24-7.29 (1H, m), 7.31-7.4 (4H, m), 7.46-7.55 (1H, m), 7.97 (1H, s), 8.64 (1H, s), m/z ES– [M–H]⁻ 1037.4.

Intermediate 127a: 3,3-Difluoropentane-1,5-diol

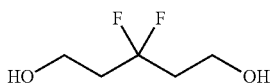

A solution of 1M aluminum lithium hydride in THF (29.0 mL, 29.0 mmol) was added dropwise to a solution of diethyl 3,3-difluoropentanedioate (5.0 g, 22 mmol) in THF anhydrous (20 mL) at 0° C. over a period of 15 minutes under nitrogen. The resulting grey suspension was stirred at 20° C. for 18 hours. The reaction mixture was cooled to 0° C. and quenched with careful dropwise addition of water (1.1 mL) and the mixture was stirred for 5 minutes, 2M NaOH solution (2.2 mL) was then added and the suspension stirred for 5 minutes. Water (3.3 mL) was added and the mixture was stirred for 5 minutes. The grey/white solids were removed by filtration and the filtrate was evaporated to dryness to afford the title compound (2.31 g, 74%) as a yellow liquid which was used in the next step without further purification. $^1$H NMR (400 MHz, CDCl$_3$, 30° C.) 1.81 (2H, t), 2.23 (4H, tt), 3.89 (4H, q).

Intermediate 127b: 5-(Benzyloxy)-3,3-difluoropentan-1-ol

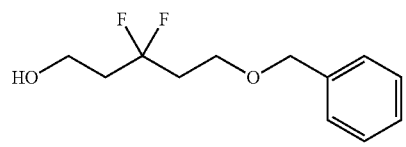 [SMILES: OCCC(F)(F)CCOCc1ccccc1]

A solution of 3,3-difluoropentane-1,5-diol (1.81 g, 12.92 mmol) in THF (20 mL) was added dropwise to 60% sodium hydride in mineral oil (1.03 g, 25.8 mmol) in THF (20 mL) at 0° C. over a period of 10 minutes under nitrogen. The resulting mixture was stirred at 0° C. for 45 minutes. (Bromomethyl)benzene (1.54 mL, 12.9 mmol) was added dropwise to the mixture over 10 minutes. Tetrabutylammonium iodide (0.477 g, 1.29 mmol) was added and the reaction was stirred at RT for 18 hours. The reaction mixture was quenched with saturated ammonium chloride solution (10 mL) then diluted with EtOAc (50 mL), and washed sequentially with water (25 mL) and saturated brine (25 mL). The organic layer was dried with MgSO$_4$, filtered and evaporated to afford crude product. The crude product was purified by flash silica chromatography, elution gradient 0 to 100% EtOAc in heptane. Pure fractions were evaporated to dryness to afford the title compound (1.34 g, 45%) as a colourless oil. $^1$H NMR (400 MHz, CDCl$_3$, 30° C.) 1.88 (1H, t), 2.24 (4H, dtt), 3.67 (2H, t), 3.85 (2H, q), 4.52 (2H, s), 7.27-7.4 (5H, m).

Intermediate 127c: 2-(2-((5-(Benzyloxy)-3,3-difluoropentyl)oxy)ethoxy)tetrahydro-2H-pyran

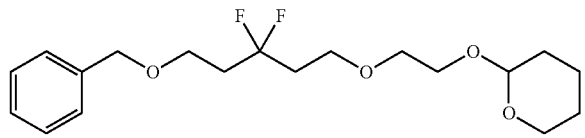 [SMILES: FC(F)(CCOCCOC1CCCCO1)CCOCc1ccccc1]

Tetrabutylammonium hydrogen sulfate (0.310 g, 0.91 mmol) was added in one portion to 2-(2-bromoethoxy)tetrahydro-2H-pyran (1.10 mL, 7.30 mmol) and 5-(benzyloxy)-3,3-difluoropentan-1-ol (1.4 g, 6.08 mmol) in sodium hydroxide solution 50% (3 mL) at 20° C. The resulting mixture was stirred at 70° C. for 18 hours. The cooled reaction mixture was diluted with water (20 mL) and extracted with EtOAc (3×25 mL). The combined organic extracts were washed with water (20 mL), saturated brine solution (20 mL), dried (MgSO$_4$), filtered and evaporated to afford crude product as a yellow oil. The crude product was purified by flash silica chromatography, elution gradient 0 to 30% EtOAc in heptane. Pure fractions were evaporated to dryness to afford the title compound (1.10 g, 51%) as a colourless oil. $^1$H NMR (400 MHz, CDCl$_3$, 30° C.) 1.46-1.52 (2H, m), 1.59 (2H, ddq), 1.67-1.76 (1H, m), 1.82 (1H, ddd), 2.23 (4H, tdt), 3.45-3.53 (1H, m), 3.54-3.62 (3H, m), 3.67 (4H, td), 3.81-3.9 (2H, m), 4.51 (2H, s), 4.6-4.64 (1H, m), 7.26-7.38 (5H, m).

Intermediate 127d: 2-((5-(Benzyloxy)-3,3-difluoropentyl)oxy)ethan-1-ol

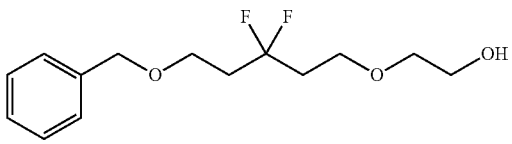 [SMILES: OCCOCCC(F)(F)CCOCc1ccccc1]

2-(2-((5-(Benzyloxy)-3,3-difluoropentyl)oxy)ethoxy)tetrahydro-2H-pyran (1.1 g, 3.07 mmol) was dissolved in MeOH (8 mL) and 1M aq. HCl (4 mL) was added. The resulting mixture was stirred at 20° C. for 1 hour. The reaction mixture was diluted with water (50 mL), and extracted with EtOAc (3×75 mL). The combined organics were washed with saturated brine (50 mL). The organic layer was dried with MgSO$_4$, filtered and evaporated to afford the title compound (0.940 g) that was used directly in the next step without purification. $^1$H NMR (400 MHz, CDCl$_3$, 30° C.) 2.23 (4H, tdt), 3.5-3.54 (2H, m), 3.67 (6H, td), 4.51 (2H, s), 7.26-7.39 (5H, m); m/z: ES+ [M+H]$^+$275.0.

Intermediate 127e: Ethyl 2-(2-((5-(benzyloxy)-3,3-difluoropentyl)oxy)ethoxy)acetate

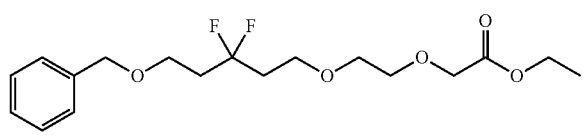 [SMILES: CCOC(=O)COCCOCCC(F)(F)CCOCc1ccccc1]

Ethyl 2-diazoacetate (0.63 mL, 5.1 mmol) in DCM (4 mL) was added slowly to 2-((5-(benzyloxy)-3,3-difluoropentyl)oxy)ethan-1-ol (0.94 g, 3.4 mmol) and diacetoxyrhodium (0.015 g, 0.03 mmol) in DCM (10 mL) at 20° C. over a period of 1 hour under nitrogen. The resulting solution was stirred at 20° C. for 18 hours. The mixture was diluted with DCM (50 mL) and washed with water (3×50 mL). The organic layer was collected and dried using phase separating cartridge then evaporated to dryness. The crude product was purified by flash silica chromatography, elution gradient 0 to 25% EtOAc in heptane. Pure fractions were evaporated to dryness to afford the title compound (0.850 g, 69%) a colourless liquid. $^1$H NMR (400 MHz, CDCl$_3$, 30° C.) 1.28 (3H, t), 2.22 (4H, tq), 3.59-3.74 (8H, m), 4.12 (2H, s), 4.22 (2H, q), 4.51 (2H, s), 7.26-7.39 (5H, m).

Intermediate 127f: Ethyl 2-(2-((3,3-Difluoro-5-hydroxypentyl)oxy)ethoxy)acetate

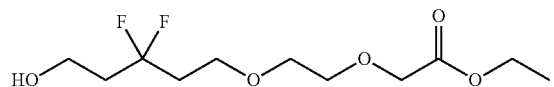 [SMILES: CCOC(=O)COCCOCCC(F)(F)CCO]

Ethyl 2-(2-((5-(benzyloxy)-3,3-difluoropentyl)oxy)ethoxy)acetate (850 mg, 2.36 mmol) and 10% palladium on carbon (25 mg, 0.24 mmol) in ethanol (5 mL) were stirred under an atmosphere of hydrogen at 2 bar and 20° C. for 2 hours. The reaction mixture was filtered, the solids washed with more EtOH, and the filtrate evaporated to afford the title compound (560 mg, 88%) as a colourless oil. $^1$H NMR (400 MHz, CDCl$_3$, 30° C.) 1.29 (3H, t), 2.15-2.33 (5H, m), 3.61-3.76 (6H, m), 3.84 (2H, q), 4.12 (2H, s), 4.23 (2H, q); m/z: ES+ [M+H]$^+$ 271.3.

Intermediate 127g: Ethyl 2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)oxy)ethoxy)acetate

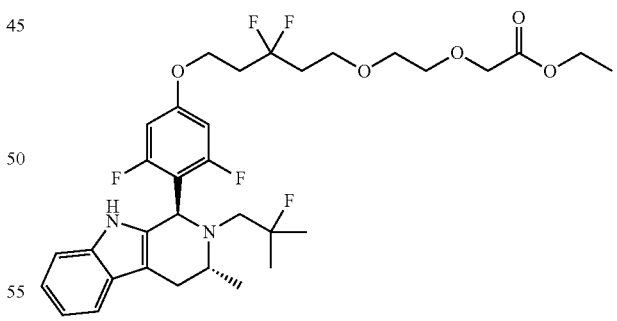

Diisopropyl (E)-diazene-1,2-dicarboxylate (0.304 mL, 1.54 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (300 mg, 0.77 mmol), ethyl 2-(2-((3,3-difluoro-5-hydroxypentyl)oxy)ethoxy)acetate (313 mg, 1.16 mmol) and triphenylphosphine (405 mg, 1.54 mmol) in DCM (10 mL) at 20° C. The resulting mixture was stirred for 1 hour. The reaction mixture was loaded directly onto a 24 g silica column and was purified by flash silica chromatography, elution gradient 0 to 40% EtOAc in heptane to afford the title compound (760 mg) as a yellow gum without further purification. m/z: ES+ [M+H]$^+$ 641.4.

Intermediate 127h: 2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)oxy)ethoxy)acetic Acid

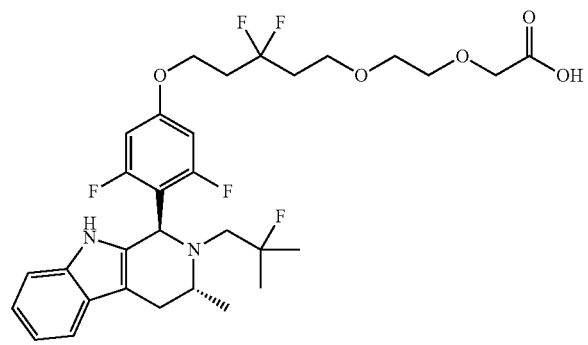 [SMILES: C[C@@H]1Cc2c([nH]c3ccccc23)[C@@H](c2c(F)cc(OCCC(F)(F)CCOCCOCC(=O)O)cc2F)N1CC(C)(C)F]

Lithium hydroxide hydrate (64 mg, 1.5 mmol) was added in one portion to ethyl 2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)oxy)ethoxy)acetate (490 mg, 0.76 mmol) in THF (3 mL) and water (1 mL) at 20° C. The resulting solution was stirred for 30 minutes. The reaction mixture was diluted with water (10 mL) then was acidified with 2M HCl and extracted into EtOAc (50 mL). The organic layer was washed with brine (15 mL) and evaporated to afford the title compound (430 mg, 92%) as a yellow gum which was used in the next step without further purification. m/z: ES+ [M+H]$^+$ 613.4.

Example 127: (2S,4R)-1-((S)-2-(2-(2-((5-(3,5-Difluoro-4-((R,3R)-2-(2-fluoro-2-methylpropyl)-3-methyl-2,3,4,9-tetrahydro-1H-pyrido[3,4-b]indol-1-yl)phenoxy)-3,3-difluoropentyl)oxy)ethoxy)acetamido)-3,3-dimethylbutanoyl)-4-hydroxy-N-(4-(4-methylthiazol-5-yl)benzyl)pyrrolidine-2-carboxamide HATU (214 mg, 0.56 mmol) was added portionwise to 2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)oxy)ethoxy)acetic acid (230 mg, 0.38 mmol), (2S,4R)-1-((S)-2-amino-3,3-dimethylbutanoyl)-4-hydroxy-N-(4-(4-methylthiazol-5-yl)benzyl)pyrrolidine-2-carboxamide, 2HCl (189 mg, 0.38 mmol) and triethylamine (0.209 ml, 1.50 mmol) in DMF (4 ml) at 20° C. under nitrogen. The resulting mixture was stirred at 20° C. for 30 minutes. The reaction mixture was diluted with EtOAc (50 mL), and washed sequentially with water (20 mL) and saturated brine (20 mL). The organic layer was dried with MgSO$_4$, filtered and evaporated to afford crude product. The crude product was purified by preparative HPLC (Waters CSH C18 OBD column, 30×100 mm id, 5 micron particle size), using decreasingly polar mixtures of water (containing 0.1% NH3) and MeCN as eluents to afford the title compound (106 mg, 28%) as a white solid; $^1$H NMR (400 MHz, CDCl3, 30° C.) 0.94 (9H, s), 1.09 (3H, d), 1.21 (6H, dd), 2.03-2.11 (1H, m), 2.12-2.24 (1H, m), 2.29-2.52 (8H, m), 2.52-2.66 (2H, m), 2.83 (1H, dd), 3.06 (1H, d), 3.5-3.73 (9H, m), 3.92 (1H, d), 4.08 (3H, ddd), 4.31 (1H, dd), 4.57 (3H, dd), 4.71 (1H, t), 5.19 (1H, s), 6.34 (2H, d), 7.03-7.12 (2H, m), 7.18-7.31 (3H, m), 7.32-7.41 (4H, m), 7.45-7.55 (1H, m), 8.65 (1H, s), 8.68 (1H, s); m/z: ES– [M–H]$^-$ 1023.5.

Intermediate 128a: 2-(2-(4-(Benzyloxy)butoxy)ethoxy)tetrahydro-2H-pyran

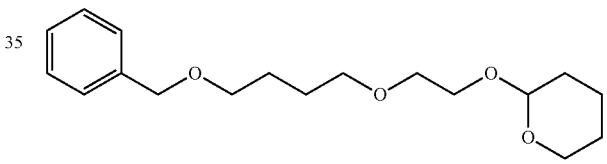

Tetrabutylammonium hydrogen sulfate (1.158 g, 3.41 mmol) was added in one portion to 2-(2-bromoethoxy)tetrahydro-2H-pyran (4.12 mL, 27.3 mmol) and 4-(benzyloxy)butan-1-ol (4.0 mL, 22.8 mmol) in sodium hydroxide solution 50% (7.0 mL) at 20° C. The resulting mixture was stirred at 70° C. for 18 hours. The cooled reaction mixture

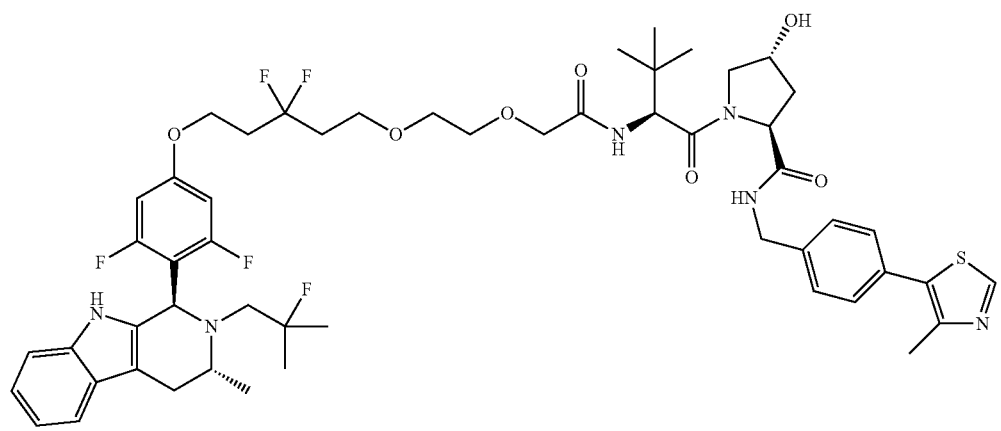 [SMILES: Cc1ncsc1-c1ccc(CNC(=O)[C@@H]2C[C@@H](O)CN2C(=O)[C@@H](NC(=O)COCCOCCC(F)(F)CCOc2cc(F)c([C@@H]3c4[nH]c5ccccc5c4C[C@@H](C)N3CC(C)(C)F)c(F)c2)C(C)(C)C)cc1]

was diluted with water (20 mL) and extracted with EtOAc (3×25 mL). The combined organic extracts were washed with water (20 mL), saturated brine solution (20 mL), dried (MgSO$_4$), filtered and evaporated to afford crude product as a yellow oil. The crude product was purified by flash silica chromatography, elution gradient 0 to 30% EtOAc in heptane. Pure fractions were evaporated to dryness to afford the title compound (4.00 g, 57.0%) as a yellow oil. $^1$H NMR (400 MHz, CDCl$_3$, 30° C.) 1.46-1.76 (9H, m), 1.83 (1H, ddt), 3.49 (5H, ddt), 3.56-3.65 (3H, m), 3.79-3.93 (2H, m), 4.50 (2H, s), 4.6-4.66 (1H, m), 7.28 (1H, dd), 7.3-7.37 (4H, m).

Intermediate 128b: 2-(4-(Benzyloxy)butoxy)ethan-1-ol

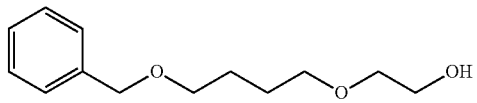 [SMILES: OCCOCCCCOCc1ccccc1]

2-(2-(4-(Benzyloxy)butoxy)ethoxy)tetrahydro-2H-pyran (4.0 g, 13 mmol) was dissolved in MeOH (35 mL) and 1M aq. HCl (15 mL) was added. The resulting mixture was stirred at 20° C. for 1 hour. The reaction mixture was diluted with water (50 mL), and extracted with EtOAc (3×75 mL). The combined organics were washed with saturated brine (50 mL). The organic layer was dried with MgSO$_4$, filtered and evaporated to afford the title compound (3.34 g) as a colourless oil that was used directly in the next step without purification. $^1$H NMR (400 MHz, CDCl$_3$, 30° C.) 1.67-1.72 (4H, m), 3.46-3.55 (6H, m), 3.68-3.74 (2H, m), 4.50 (2H, s), 7.26-7.31 (1H, m), 7.31-7.37 (4H, m); m/z: ES+ [M+H]$^+$ 225.3

Intermediate 128c: Ethyl 2-(2-(4-(benzyloxy)butoxy)ethoxy)acetate

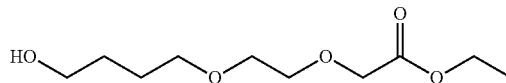

Ethyl 2-diazoacetate (1.9 mL, 15.6 mmol) in DCM (15 mL) was added slowly to 2-(4-(benzyloxy)butoxy)ethan-1-ol (2.91 g, 13.0 mmol) and diacetoxyrhodium (0.057 g, 0.13 mmol) in DCM (40 mL) at 20° C. over a period of 1 hour under nitrogen. The resulting solution was stirred at 20° C. for 3 hours. The mixture was diluted with DCM (50 mL) and washed with water (3×50 mL). The organic layer was collected and dried using a phase separating cartridge then evaporated to dryness. The crude product was purified by flash silica chromatography, elution gradient 0 to 25% EtOAc in heptane. Pure fractions were evaporated to dryness to afford the title compound (2.43 g, 60%) as a colourless liquid. $^1$H NMR (400 MHz, CDCl$_3$, 30° C.) 1.28 (3H, t), 1.64-1.72 (4H, m), 3.45-3.52 (4H, m), 3.59-3.64 (2H, m), 3.69-3.73 (2H, m), 4.14 (2H, s), 4.21 (2H, q), 4.50 (2H, s), 7.26-7.31 (1H, m), 7.31-7.36 (4H, m).

Intermediate 128d: Ethyl 2-(2-(4-hydroxybutoxy)ethoxy)acetate

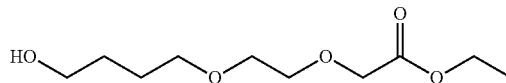

Ethyl 2-(2-(4-(benzyloxy)butoxy)ethoxy)acetate (2.4 g, 7.73 mmol) and 10% palladium on carbon (0.082 g, 0.77 mmol) in ethanol (15 mL) were placed in a glass pot inside a stainless steel hydrogenation vessel and connected to the H-generator (set to 1 bar). The vessel was purged with nitrogen then charged with hydrogen and evacuated four times. The vessel was then charged with hydrogen for a final time and stirred under an atmosphere of hydrogen at RT for 2 hours. The reaction mixture was filtered, washing with more EtOH then the solvent was evaporated to afford the title compound (1.75 g, 100%) as a colourless oil which was used in the next step without further purification. $^1$H NMR (400 MHz, CDCl$_3$, 30° C.) 1.29 (3H, t), 1.68 (4H, ddtd), 2.15 (1H, s), 3.53 (2H, t), 3.62-3.68 (4H, m), 3.71-3.74 (2H, m), 4.14 (2H, s), 4.22 (2H, q); m/z: ES+ [M+H]$^+$ 221.2

Intermediate 128e: Ethyl 2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)acetate

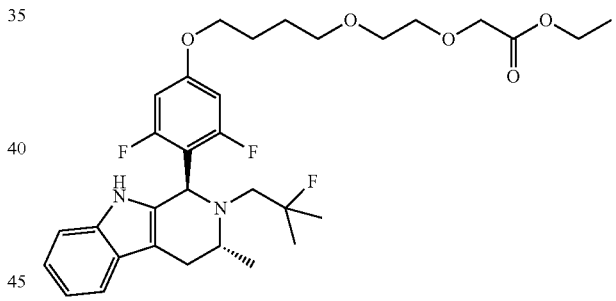

DIAD (0.30 mL, 1.54 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (300 mg, 0.77 mmol), ethyl 2-(2-(4-hydroxybutoxy)ethoxy)acetate (340 mg, 1.54 mmol) and triphenylphosphine (405 mg, 1.54 mmol) in DCM (10 mL) at 20° C. The resulting mixture was stirred for 1 hour. The reaction mixture was loaded directly onto a 24 g silica column and was purified by flash silica chromatography, elution gradient 0 to 50% EtOAc in heptane. Pure fractions were evaporated to dryness to afford the title compound (530 mg) as a yellow gum that was used without further purification. $^1$H NMR (400 MHz, CDCl$_3$, 30° C.) 1.10 (3H, d), 1.20 (6H, dd), 1.27 (3H, t), 1.7-1.79 (2H, m), 1.81-1.92 (2H, m), 2.39 (1H, dd), 2.60 (1H, dd), 2.86 (1H, dd), 3.09 (1H, dd), 3.53 (2H, t), 3.61-3.65 (2H, m), 3.66-3.7 (1H, m), 3.7-3.74 (2H, m), 3.95 (2H, t), 4.13 (2H, s), 4.20 (2H, q), 5.18 (1H, s), 6.35-6.43 (2H, m), 7.05-7.14 (2H, m), 7.19-7.24 (1H, m), 7.47 (1H, s), 7.49-7.53 (1H, m); m/z: ES+ [M+H]$^+$ 591.5

Intermediate 128f: 2-(2-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)acetic Acid

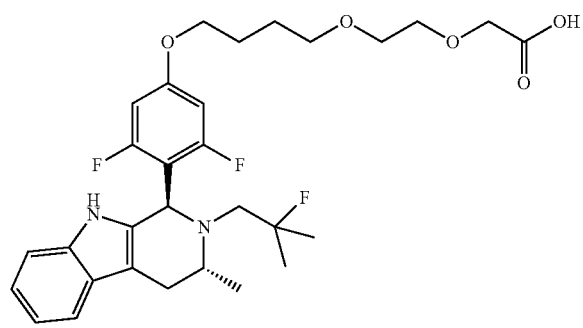 [SMILES: C[C@@H]1Cc2c([nH]c3ccccc23)[C@@H](c2c(F)cc(OCCCCOCCOCC(=O)O)cc2F)N1CC(C)(C)F]

Lithium hydroxide hydrate (64 mg, 1.5 mmol) was added in one portion to ethyl 2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)acetate (450 mg, 0.76 mmol) in THF (3 mL) and water (1 mL). The resulting solution was stirred at 20° C. for 30 minutes. The reaction mixture was diluted with water (10 mL), acidified with 2M HCl and extracted into EtOAc (50 mL). The organic layer was washed with brine (15 mL) and evaporated to afford the title compound (420 mg, 98%) as a yellow gum which was used in the next step without further purification; m/z: ES+ [M+H]+ 563.5.

Example 128: (2S,4R)-1-((S)-2-(2-(2-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)acetamido)-3,3-dimethylbutanoyl)-4-hydroxy-N-(4-(4-methylthiazol-5-yl)benzyl)pyrrolidine-2-carboxamide HATU (213 mg, 0.56 mmol) was added portionwise to 2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)acetic acid (210 mg, 0.37 mmol), (2S,4R)-1-((S)-2-amino-3,3-dimethylbutanoyl)-4-hydroxy-N-(4-(4-methylthiazol-5-yl)benzyl)pyrrolidine-2-carboxamide, 2HCl (188 mg, 0.37 mmol) and triethylamine (0.208 ml, 1.49 mmol) in DMF (4 ml) at 20'C under nitrogen. The resulting mixture was stirred at 20° C. for 30 minutes. The reaction mixture was diluted with EtOAc (50 mL), and washed sequentially with water (20 mL) and saturated brine (20 mL). The organic layer was dried with MgSO4, filtered and evaporated to afford crude product. The crude product was purified by preparative HPLC (Waters CSH C18 OBD column, 30×100 mm id, 5 micron particle size), using decreasingly polar mixtures of water (containing 0.1% NH3) and MeCN as eluents to afford the title compound (146 mg, 40%) as a white solid; $^1$H NMR (400 MHz, CDCl3, 30° C.) 0.94 (9H, s), 1.10 (3H, d), 1.20 (6H, dd), 1.73 (2H, dt), 1.78-1.89 (2H, m), 2-2.13 (1H, m), 2.40 (1H, dd), 2.46 (3H, s), 2.52-2.66 (2H, m), 2.73 (1H, d), 2.85 (1H, dd), 3.08 (1H, dd), 3.53 (2H, t), 3.56-3.72 (6H, m), 3.83-4.04 (4H, m), 4.08 (1H, d), 4.29 (1H, dd), 4.48 (1H, d), 4.51 (1H, s), 4.58 (1H, dd), 4.71 (1H, t), 5.19 (1H, s), 6.25-6.38 (2H, m), 7.01-7.14 (2H, m), 7.18-7.25 (1H, m), 7.28 (1H, s), 7.3-7.39 (5H, m), 7.48-7.54 (1H, m), 8.37 (1H, s), 8.61 (1H, s); m/z: ES− [M−H]− 973.5.

Intermediate 129a: 2-(3-(4-(Benzyloxy)butoxy)propoxy)tetrahydro-2H-pyran

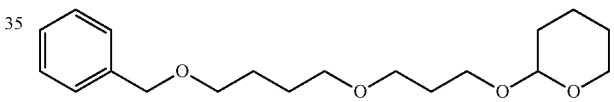

Tetrabutylammonium hydrogen sulfate (0.956 g, 2.81 mmol) was added in one portion to 2-(3-bromopropoxy)tetrahydro-2H-pyran (3.81 mL, 22.5 mmol) and 4-(benzy-

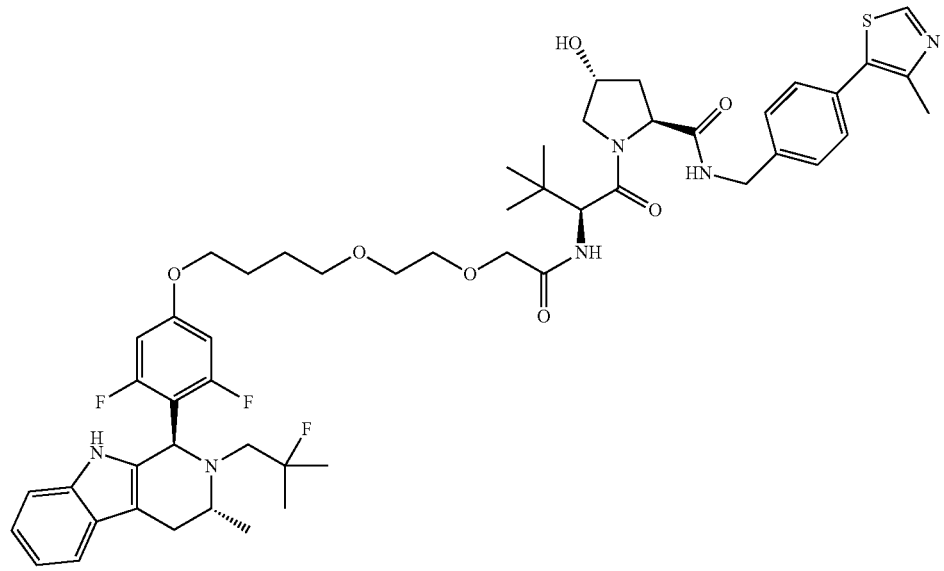 [SMILES: Cc1ncsc1-c1ccc(CNC(=O)[C@@H]2C[C@@H](O)CN2C(=O)[C@@H](NC(=O)COCCOCCCCOc2cc(F)c([C@@H]3c4[nH]c5ccccc5c4C[C@@H](C)N3CC(C)(C)F)c(F)c2)C(C)(C)C)cc1]

loxy)butan-1-ol (3.3 mL, 18.8 mmol) in sodium hydroxide solution 50% (5.40 mL) at 20° C. under air. The resulting mixture was stirred at 70° C. for 18 hours. The cooled reaction mixture was diluted with water (20 mL) and extracted with EtOAc (3×25 mL). The combined organic extracts were washed with water (20 mL), saturated brine solution (20 mL), dried (MgSO$_4$), filtered and evaporated to afford crude product as a yellow oil. The crude product was purified by flash silica chromatography, elution gradient 0 to 30% EtOAc in heptane to afford the title compound (3.88 g, 64%) as a colourless oil; $^1$H NMR (400 MHz, CDCl3, 30° C.) 1.46-1.61 (4H, m), 1.68 (5H, dqt), 1.77-1.9 (3H, m), 3.39-3.45 (2H, m), 3.45-3.56 (6H, m), 3.75-3.94 (2H, m), 4.50 (2H, s), 4.57 (1H, dd), 7.28 (1H, dd), 7.33 (4H, d).

Intermediate 129b:
3-(4-(Benzyloxy)butoxy)propan-1-ol

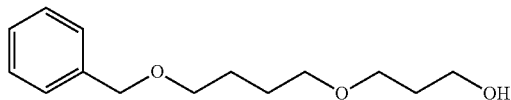 [SMILES: OCCCOCCCCOCc1ccccc1]

2-(3-(4-(Benzyloxy)butoxy)propoxy)tetrahydro-2H-pyran (3.88 g, 12.0 mmol) was dissolved in MeOH (30 ml) and 1M aq. HCl (15 ml) was added. The resulting mixture was stirred at 20° C. for 1 hour. The reaction mixture was diluted with water (100 mL), and extracted with EtOAc (3×100 mL). The combined organics were washed with saturated brine (50 mL). The organic layer was dried with MgSO$_4$, filtered and evaporated to afford the title compound (3.11 g) that was used directly in the next step without purification; $^1$H NMR (400 MHz, CDCl3, 30° C.) 1.65-1.7 (4H, m), 1.82 (2H, p), 2.37 (1H, s), 3.47 (4H, dddd), 3.58-3.62 (2H, m), 3.76 (2H, s), 4.50 (2H, s), 7.26-7.3 (1H, m), 7.31-7.35 (4H, m); m/z: ES+ [M+H]$^+$ 239.3.

Intermediate 129c: Ethyl
2-(3-(4-(benzyloxy)butoxy)propoxy)acetate

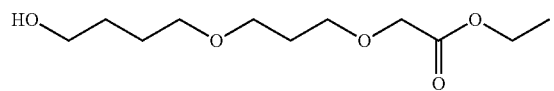 [SMILES: CCOC(=O)COCCCOCCCCO]

Ethyl 2-diazoacetate (2.16 ml, 17.6 mmol) in DCM (10 ml) was added slowly to 3-(4-(benzyloxy)butoxy)propan-1-ol (2.8 g, 11.75 mmol) and diacetoxyrhodium (0.052 g, 0.12 mmol) in DCM (32.4 ml) at 20° C. over a period of 1 hour under nitrogen. The resulting solution was stirred at 20° C. for 18 hours. The mixture was diluted with DCM (50 ml) and washed with water (3×50 ml). The organic layer was collected and dried using phase separating cartridge then evaporated to dryness. The crude product was purified by flash silica chromatography, elution gradient 0 to 30% EtOAc in heptane. Pure fractions were evaporated to dryness to afford the title compound (2.38 g, 62%) a colourless liquid; $^1$H NMR (400 MHz, CDCl3, 30° C.) 1.28 (3H, t), 1.61-1.72 (4H, m), 1.88 (2H, p), 3.41-3.45 (2H, m), 3.50 (4H, q), 3.61 (2H, t), 4.05 (2H, s), 4.22 (2H, q), 4.50 (2H, s), 7.28 (1H, dd), 7.33 (4H, d); m/z: ES+ [M+H]$^+$ 325.3

Intermediate 129d: Ethyl
2-(3-(4-hydroxybutoxy)propoxy)acetate

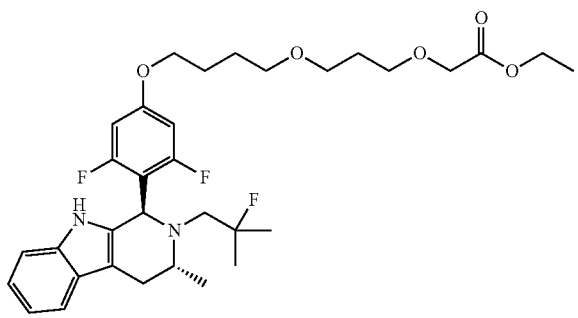 [SMILES: CCOC(=O)COCCCOCCCCOc1cc(F)c([C@@H]2c3[nH]c4ccccc4c3C[C@@H](C)N2CC(C)(C)F)c(F)c1]

Ethyl 2-(3-(4-(benzyloxy)butoxy)propoxy)acetate (2.38 g, 7.34 mmol) and 10% palladium on carbon (0.078 g, 0.73 mmol) in ethanol (25 ml) were placed in a glass pot inside a stainless steel hydrogenation vessel and connected to the H-generator. The vessel was purged with N2×4 then charged with H2 and evacuated ×4. The vessel was then charged to 1 bar and stirred under an atmosphere of hydrogen at RT for 4 hours. The reaction mixture was filtered, washing with more EtOH then the solvent was evaporated to afford the title compound (1.80 g) as a colourless oil that was used without further purification; $^1$H NMR (400 MHz, CDCl3, 30° C.) 1.29 (3H, t), 1.61-1.73 (4H, m), 1.90 (2H, p), 2.30 (1H, s), 3.44-3.5 (2H, m), 3.56 (2H, t), 3.59-3.68 (4H, m), 4.06 (2H, s), 4.18-4.27 (2H, m); m/z: ES+ [M+H]$^+$ 235.3

Intermediate 129e: Ethyl 2-(3-(4-(3,5-difluoro-4-
((1R,3R)-2-(2-fluoro-2-methylpropyl)-3-methyl-2,3,
4,9-tetrahydro-1H-pyrido[3,4-b]indol-1-yl)phenoxy)
butoxy)propoxy)acetate DIAD (0.30 ml, 1.5 mmol) was added dropwise to a stirred solution of 3,5-difluoro-4-((1R,3R)-2-(2-fluoro-2-methylpropyl)-3-methyl-2,3,4,9-tetrahydro-1H-pyrido[3,4-b]indol-1-yl)phenol (300 mg, 0.77 mmol), ethyl 2-(3-(4-hydroxybutoxy)propoxy)acetate (362 mg, 1.54 mmol) and triphenylphosphine (405 mg, 1.54 mmol) in DCM (10 ml) at 20° C. The resulting mixture was stirred at 20° C. for 1 hour. The reaction mixture was purified by flash silica chromatography, elution gradient 0 to 40% EtOAc in heptane to afford the title compound (397 mg, 85%) as a yellow gum; ¹H NMR (400 MHz, CDCl3, 30° C.) 1.10 (3H, d), 1.20 (6H, dd), 1.25-1.3 (3H, m), 1.67-1.77 (2H, m), 1.8-1.93 (4H, m), 2.39 (1H, dd), 2.60 (1H, dd), 2.86 (1H, dd), 3.09 (1H, dd), 3.47 (2H, t), 3.52 (2H, t), 3.61 (2H, t), 3.64-3.74 (1H, m), 3.94 (2H, t), 4.05 (2H, s), 4.21 (2H, q), 5.18 (1H, s), 6.33-6.45 (2H, m), 7.04-7.14 (2H, m), 7.19-7.24 (1H, m), 7.44-7.55 (2H, m); m/z: ES+ [M+H]⁺ 605.5

Intermediate 129f: 2-(3-(4-(3,5-Difluoro-4-((1R, 3R)-2-(2-fluoro-2-methylpropyl)-3-methyl-2,3,4,9-tetrahydro-1H-pyrido[3,4-b]indol-1-yl)phenoxy)butoxy)propoxy)acetic Acid Lithium hydroxide hydrate (55 mg, 1.31 mmol) was added in one portion to ethyl 2-(3-(4-(3,5-difluoro-4-((1R, 3R)-2-(2-fluoro-2-methylpropyl)-3-methyl-2,3,4,9-tetrahydro-1H-pyrido[3,4-b]indol-1-yl)phenoxy)butoxy)propoxy)acetate (397 mg, 0.66 mmol) in THF (3 ml) and water (1 ml) at 20° C. The resulting solution was stirred for 30 minutes. The reaction mixture was diluted with water (10 mL) then was acidified with 2M HCl and extracted into EtOAc (50 mL). The organic layer was washed with brine (15 mL) and evaporated to afford the title compound (378 mg, 100%) as a yellow gum that was used in the next step without purification; m/z: ES+ [M+H]⁺ 577.5.

Example 129: (2S,4R)-1-((S)-2-(2-(3-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy)propoxy)acetamido)-3,3-dimethylbutanoyl)-4-hydroxy-N-(4-(4-methylthiazol-5-yl)benzyl)pyrrolidine-2-carboxamide

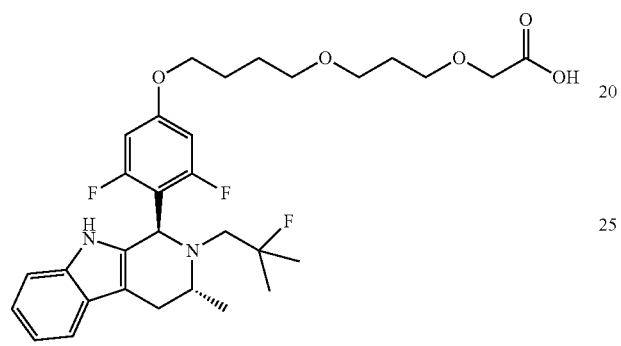

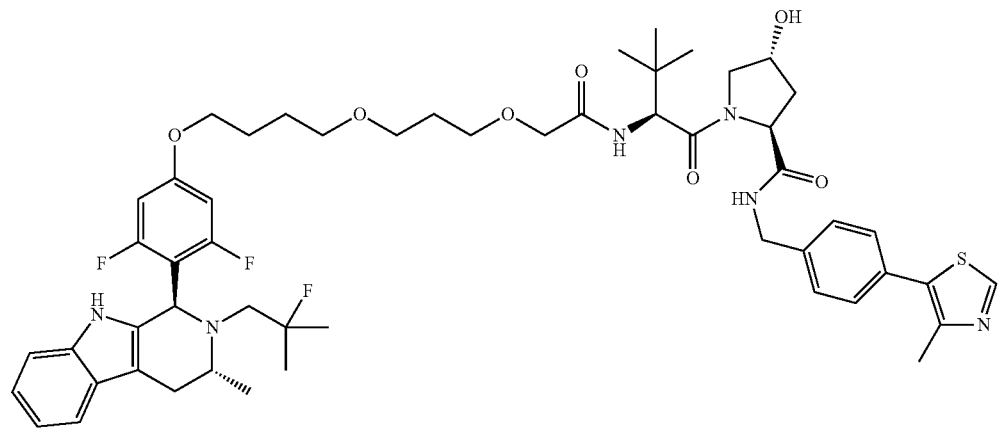 [SMILES: Cc1ncsc1-c1ccc(CNC(=O)[C@@H]2C[C@@H](O)CN2C(=O)[C@@H](NC(=O)COCCCOCCCCOc2cc(F)c([C@@H]3c4[nH]c5ccccc5c4C[C@@H](C)N3CC(C)(C)F)c(F)c2)C(C)(C)C)cc1]

HATU (187 mg, 0.49 mmol) was added portionwise to 2-(3-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)propoxy)acetic acid (189 mg, 0.33 mmol), (2S,4R)-1-((S)-2-amino-3,3-dimethylbutanoyl)-4-hydroxy-N-(4-(4-methylthiazol-5-yl)benzyl)pyrrolidine-2-carboxamide, 2HCl (165 mg, 0.33 mmol) and triethylamine (0.183 ml, 1.31 mmol) in DMF (4 ml) at 20° C. under nitrogen. The resulting mixture was stirred at 20° C. for 30 minutes. The reaction mixture was diluted with EtOAc (50 mL), and washed sequentially with water (20 mL) and saturated brine (20 mL). The organic layer was dried with MgSO$_4$, filtered and evaporated to afford crude product. The crude product was purified by preparative HPLC (Waters CSH C18 OBD column, 30×100 mm id, 5 micron particle size), using decreasingly polar mixtures of water (containing 0.1% NH3) and MeCN as eluents to afford the title compound (165 mg, 50.9%) as a white solid; $^1$H NMR (400 MHz, CDCl3, 30° C.) 0.94 (9H, s), 1.10 (3H, d), 1.20 (6H, dd), 1.66-1.72 (2H, m), 1.78-1.93 (4H, m), 2.02-2.12 (1H, m), 2.40 (1H, dd), 2.49 (3H, s), 2.5-2.64 (2H, m), 2.85 (1H, dd), 2.95 (1H, s), 3.08 (1H, dd), 3.46 (2H, t), 3.50 (2H, t), 3.54-3.71 (4H, m), 3.77-3.97 (4H, m), 4.05 (1H, d), 4.32 (1H, dd), 4.47-4.61 (3H, m), 4.71 (1H, t), 5.19 (1H, s), 6.24-6.41 (2H, m), 7.04-7.12 (2H, m), 7.15 (1H, d), 7.2-7.24 (1H, m), 7.27-7.4 (5H, m), 7.45-7.56 (1H, m), 8.09 (1H, s), 8.64 (1H, s); m/z: ES− [M−H]− 987.6.

Intermediate 130a: 5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentan-1-ol

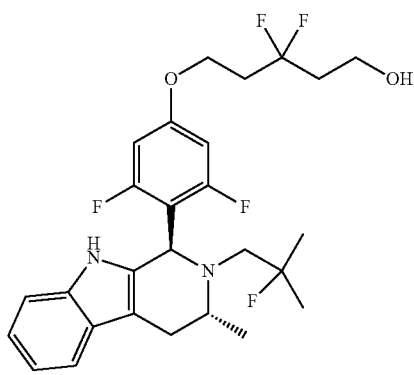 [SMILES: C[C@@H]1Cc2c([nH]c3ccccc23)[C@@H](c2c(F)cc(OCCC(F)(F)CCO)cc2F)N1CC(C)(C)F]

RockPhos Pd G3 (47 mg, 0.06 mmol) was added in one portion to a degassed mixture of (1R,3R)-1-(4-bromo-2,6-difluorophenyl)-2-(2-fluoro-2-methylpropyl)-3-methyl-2,3,4,9-tetrahydro-1H-pyrido[3,4-b]indole (500 mg, 1.11 mmol), 3,3-difluoropentane-1,5-diol (931 mg, 6.65 mmol) and cesium carbonate (902 mg, 2.77 mmol) in toluene (15 mL) at 20° C. under nitrogen. The resulting mixture was stirred at 90° C. for 5 hours. The reaction was allowed to cool to RT and was filtered, the solid was washed with DCM (10 mL) then the mixture evaporated to afford crude product as a orange gum. The crude product was purified by flash silica chromatography, elution gradient 0 to 50% EtOAc in heptane to afford the title compound (314 mg, 56%) as a yellow gum. $^1$H NMR (400 MHz, CDCl3, 30° C.) 1.10 (3H, d), 1.15-1.27 (6H, m), 2.22 (2H, tt), 2.32-2.51 (3H, m), 2.60 (1H, ddd), 2.86 (1H, dd), 3.03-3.15 (1H, m), 3.61-3.75 (1H, m), 3.91 (2H, q), 4.14 (2H, t), 5.20 (1H, s), 6.36-6.46 (2H, m), 7.04-7.15 (2H, m), 7.18-7.25 (1H, m), 7.39 (1H, s), 7.48-7.55 (1H, m); m/z: ES+ [M+H]+ 511.4

Intermediate 130b: Ethyl 2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)oxy)acetate

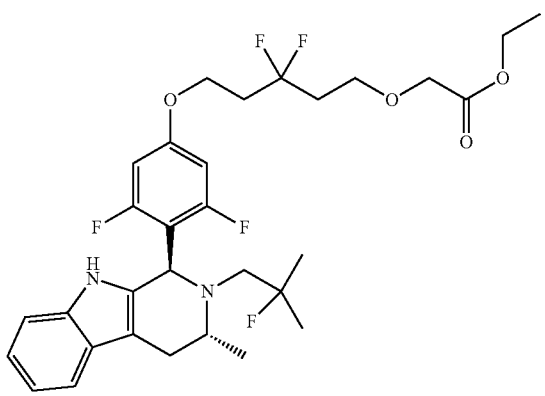 [SMILES: CCOC(=O)COCCC(F)(F)CCOc1cc(F)c([C@@H]2c3[nH]c4ccccc4c3C[C@@H](C)N2CC(C)(C)F)c(F)c1]

The title compound was prepared in a similar manner to Intermediate 72c using the appropriate alcohol to afford the desired product (55 mg, 31%) a yellow gum; m/z: ES+ [M+H]+ 597.4

Intermediate 130c: 2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)oxy)acetic Acid

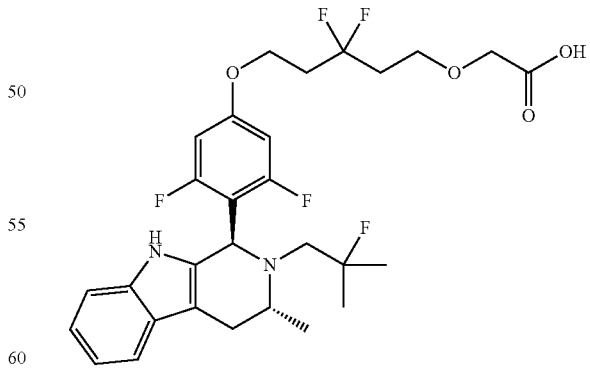

The title compound was prepared in a similar manner to Intermediate 72f using the appropriate ester to afford the desired product (52 mg, 99%) as a yellow gum that was used in the next step without purification; m/z: ES+ [M+H]+ 569.3.

Example 130: (2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)oxy)acetamido)-3,3-dimethylbutanoyl)-4-hydroxy-N-(4-(4-methylthiazol-5-yl)benzyl)pyrrolidine-2-carboxamide

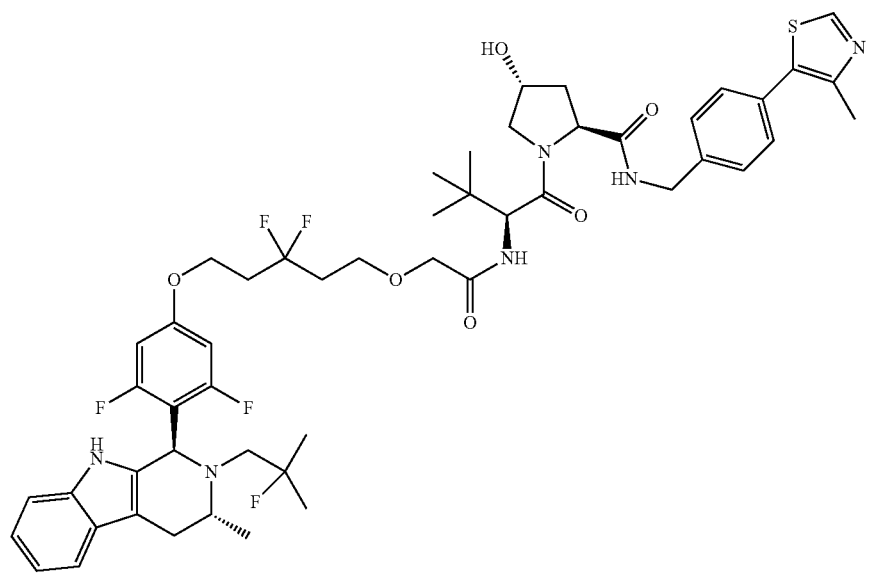 [SMILES: Cc1ncsc1-c1ccc(CNC(=O)[C@@H]2C[C@@H](O)CN2C(=O)[C@@H](NC(=O)COCCC(F)(F)CCOc2cc(F)c([C@@H]3c4[nH]c5ccccc5c4C[C@@H](C)N3CC(C)(C)F)c(F)c2)C(C)(C)C)cc1]

The title compound was prepared in a similar manner to Example 68 using the appropriate carboxylic acid and amine to afford the desired product (25 mg, 28%) as a yellow solid; $^1$H NMR (400 MHz, DMSO, 30° C.) 0.93 (9H, d), 1.04 (3H, d), 1.09-1.25 (6H, m), 1.92 (1H, d), 2.04 (1H, d), 2.23-2.37 (3H, m), 2.45 (5H, d), 2.57 (1H, s), 2.76-2.94 (2H, m), 3.49 (1H, d), 3.56-3.76 (4H, m), 3.98 (2H, s), 4.16 (2H, t), 4.26 (1H, dd), 4.32-4.49 (3H, m), 4.57 (1H, d), 5.13 (2H, d), 6.68 (2H, d), 6.86-7.06 (2H, m), 7.18 (1H, d), 7.40 (6H, s), 8.55 (1H, t), 8.97 (1H, s), 10.50 (1H, s); m/z: ES− [M−H]− 980.4.

Intermediate 131a: 5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl 4-methylbenzenesulfonate

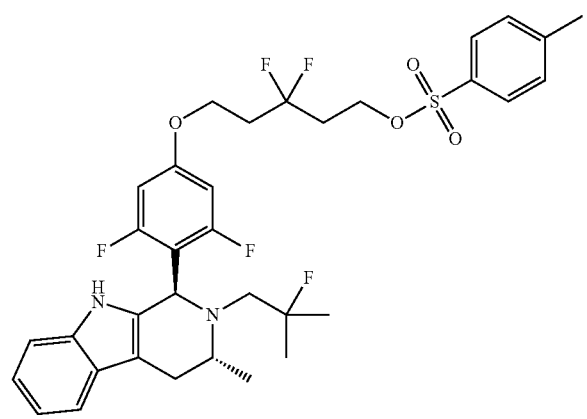 [SMILES: Cc1ccc(S(=O)(=O)OCCC(F)(F)CCOc2cc(F)c([C@@H]3c4[nH]c5ccccc5c4C[C@@H](C)N3CC(C)(C)F)c(F)c2)cc1]

4-Methylbenzenesulfonyl chloride (142 mg, 0.74 mmol) was added in one portion to 5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentan-1-ol (316 mg, 0.62 mmol) and triethylamine (0.13 mL, 0.93 mmol) in DCM (5 mL) at 20° C. The resulting solution was stirred at 20° C. for 18 hours. The reaction mixture was diluted with DCM (25 mL), and washed sequentially with saturated NH4Cl (10 mL), saturated NaHCO$_3$ (10 mL), water (20 mL) and saturated brine (10 mL). The organic layer was dried with a phase separating cartridge, filtered and evaporated to afford crude product that was purified by flash silica chromatography, elution gradient 0 to 60% EtOAc in heptane to afford the title compound (195 mg, 47%) as a yellow gum; $^1$H NMR (400 MHz, DMSO, 30° C.) 1.05 (3H, d), 1.09-1.24 (6H, m), 2.29-2.43 (9H, m), 2.77-2.92 (2H, m), 3.52 (1H, d), 4.11 (2H, t), 4.20 (2H, t), 5.14 (1H, s), 6.66 (2H, d), 6.88-7.06 (2H, m), 7.19 (1H, d), 7.40 (1H, d), 7.49 (2H, d), 7.74-7.87 (2H, m), 10.50 (1H, s); m/z: ES+ [M+H]+ 665.4.

Example 131: (2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)amino)acetamido)-3,3-dimethylbutanoyl)-4-hydroxy-N-(4-(4-methylthiazol-5-yl)benzyl)pyrrolidine-2-carboxamide

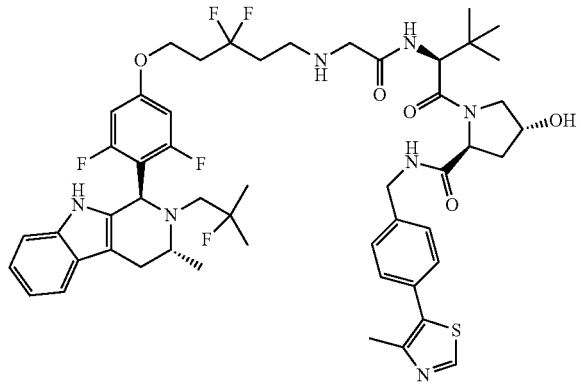 [SMILES: Cc1ncsc1-c1ccc(CNC(=O)[C@@H]2C[C@@H](O)CN2C(=O)[C@@H](NC(=O)CNCCC(F)(F)CCOc2cc(F)c([C@@H]3c4[nH]c5ccccc5c4C[C@@H](C)N3CC(C)(C)F)c(F)c2)C(C)(C)C)cc1]

DIPEA (0.052 mL, 0.30 mmol) was added in one portion to 5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl 4-methylbenzenesulfonate (100 mg, 0.15 mmol) and (2S,4R)-1-((S)-2-(2-aminoacetamido)-3,3-dimethylbutanoyl)-4-hydroxy-N-(4-(4-methylthiazol-5-yl)benzyl)pyrrolidine-2-carboxamide (147 mg, 0.30 mmol) in DMF (5 mL) at 20° C. The resulting suspension was stirred at 50° C. for 4 hours. The reaction was incomplete and the temperature increased to 70° C. and stirred for 18 hours. The reaction mixture was diluted with EtOAc (50 mL), and washed sequentially with water (25 mL) and saturated brine (25 mL). The organic layer was dried with MgSO$_4$, filtered and evaporated to afford crude product. The crude product was purified by preparative HPLC (Waters XSelect CSH C18 column, 30×100 mm id, 5 micron particle size), using decreasingly polar mixtures of water (containing 0.1% formic acid) and MeCN as eluents. Fractions containing the desired compound were evaporated to dryness, redissolved in MeOH (1 mL) and loaded onto a 1 g SCX column. The column was washed with MeOH and compound eluted with 1N NH3/MeOH and the solvent removed under reduced pressure to afford the title compound (12 mg, 9%) as a pale yellow solid; $^1$H NMR (400 MHz, CDCl3, 30° C.) 0.93 (9H, s), 1.10 (3H, d), 1.21 (6H, dd), 2.01-2.18 (3H, m), 2.3-2.42 (3H, m), 2.49 (4H, s), 2.54-2.64 (2H, m), 2.79-2.89 (3H, m), 3.07 (1H, d), 3.18-3.33 (2H, m), 3.57 (1H, dd), 3.64 (1H, s), 4.07-4.17 (3H, m), 4.29 (1H, dd), 4.43 (1H, d), 4.51 (1H, s), 4.58 (1H, dd), 4.69 (1H, t), 5.21 (1H, s), 6.37 (2H, d), 7.07-7.12 (2H, m), 7.23 (1H, dd), 7.34 (6H, q), 7.47-7.54 (1H, m), 7.79 (1H, d), 8.03 (1H, s), 8.65 (1H, s); m/z: ES− [M−H]− 978.

Intermediate 132a: (6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)methanol

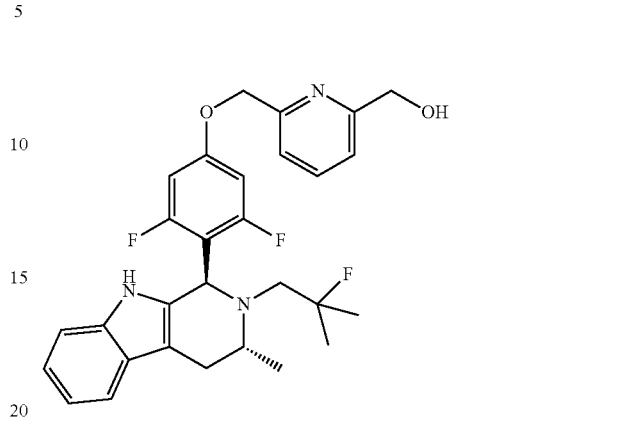

RockPhos Pd G3 (47 mg, 0.06 mmol) was added in one portion to a degassed mixture of (1R,3R)-1-(4-bromo-2,6-difluorophenyl)-2-(2-fluoro-2-methylpropyl)-3-methyl-2,3,4,9-tetrahydro-1H-pyrido[3,4-b]indole (500 mg, 1.11 mmol), pyridine-2,6-diyldimethanol (308 mg, 2.22 mmol) and cesium carbonate (902 mg, 2.77 mmol) in toluene (20 mL) at 20° C. under nitrogen. The resulting mixture was stirred at 90° C. for 4 hours. The reaction was allowed to cool to RT, filtered, the solids washed with DCM (10 mL) and the filtrate evaporated to afford crude product as a orange gum. The crude product was purified by flash silica chromatography, elution gradient 0 to 100% EtOAc in heptane. Pure fractions were evaporated to dryness to afford the title compound (307 mg, 54%) as a yellow gum; $^1$H NMR (400 MHz, CDCl3, 30° C.) 1.10 (3H, d), 1.13-1.25 (6H, m), 2.39 (1H, dd), 2.60 (1H, ddd), 2.86 (1H, dd), 3.09 (1H, dd), 3.53 (1H, t), 3.6-3.75 (1H, m), 4.77 (2H, d), 5.16 (2H, s), 5.20 (1H, s), 6.46-6.56 (2H, m), 7.02-7.16 (2H, m), 7.18-7.25 (2H, m), 7.37 (1H, d), 7.46 (1H, s), 7.49-7.54 (1H, m), 7.73 (1H, t); m/z: ES+ [M+H]+ 510.3.

Intermediate 132b: Ethyl 2-((6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)methoxy)acetate

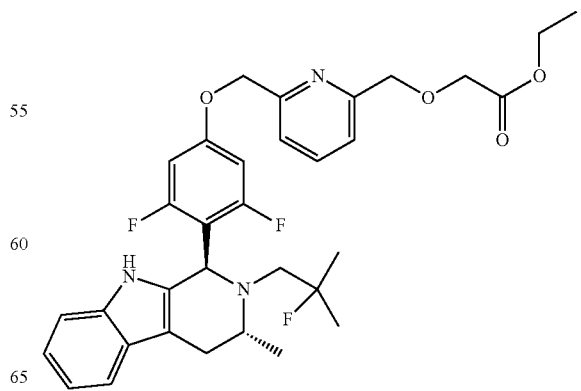

The title compound was prepared in a similar manner to Intermediate 72c using the appropriate alcohol to afford the desired product (95 mg, 27%) a yellow gum; m/z: ES+ [M+H]+ 596.4.

Intermediate 132c: 2-((6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)methoxy)acetic Acid

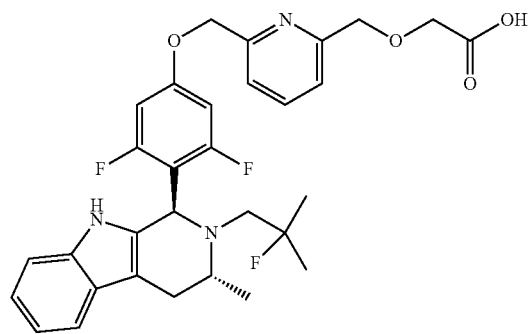 [SMILES: C[C@@H]1Cc2c([nH]c3ccccc23)[C@@H](c2c(F)cc(OCc3cccc(COCC(=O)O)n3)cc2F)N1CC(C)(C)F]

The title compound was prepared in a similar manner to Intermediate 72f using the appropriate ester to afford the desired product (84 mg, 93%) as a yellow gum which was used in the next step without purification; m/z: ES+ [M+H]+ 568.4.

Example 132: (2S,4R)-1-((S)-2-(2-((6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)methoxy)acetamido)-3,3-dimethylbutanoyl)-4-hydroxy-N-(4-(4-methylthiazol-5-yl)benzyl)pyrrolidine-2-carboxamide The title compound was prepared in a similar manner to Example 68 using the appropriate carboxylic acid and amine to afford the desired product (39 mg, 27%) as a cream solid; ¹H NMR (400 MHz, CDCl3, 30° C.) 0.95 (9H, s), 1.10 (3H, d), 1.20 (6H, dd), 2.07 (1H, dd), 2.40 (1H, dd), 2.48 (3H, s), 2.59 (3H, ddd), 2.84 (1H, dd), 3.06 (1H, dd), 3.55-3.73 (2H, m), 3.96-4.14 (3H, m), 4.28 (1H, dd), 4.47-4.64 (3H, m), 4.64-4.76 (3H, m), 5.07-5.19 (2H, m), 5.21 (1H, s), 6.41-6.53 (2H, m), 7.04-7.13 (2H, m), 7.18-7.24 (1H, m), 7.26-7.44 (8H, m), 7.47-7.55 (1H, m), 7.74 (1H, t), 8.15 (1H, s), 8.64 (1H, s); m/z: ES− [M−H]⁻ 978.5

Intermediate 133a: 2-(Isopropoxycarbonyl)nicotinic Acid

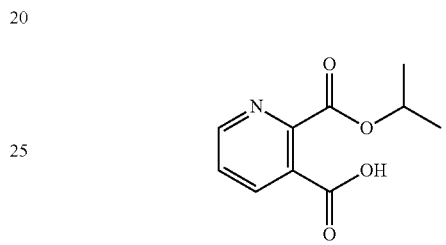

A suspension of furo[3,4-b]pyridine-5,7-dione (5.00 g, 33.5 mmol) in IPA (10 mL) was heated at 85° C. for 18 hours. The resulting pale yellow solution was evaporated to dryness and the resulting residue was slurried in refluxing EtOAc (10 mL) for 10 minutes. The white suspension was allowed to cool and was filtered to afford the title compound (4.22 g, 60%) as a white solid; ¹H NMR (400 MHz, CDCl3, 30° C.) 1.41 (6H, d), 5.36 (1H, hept), 7.52 (1H, dd), 8.33 (1H, dd), 8.84 (1H, dd).

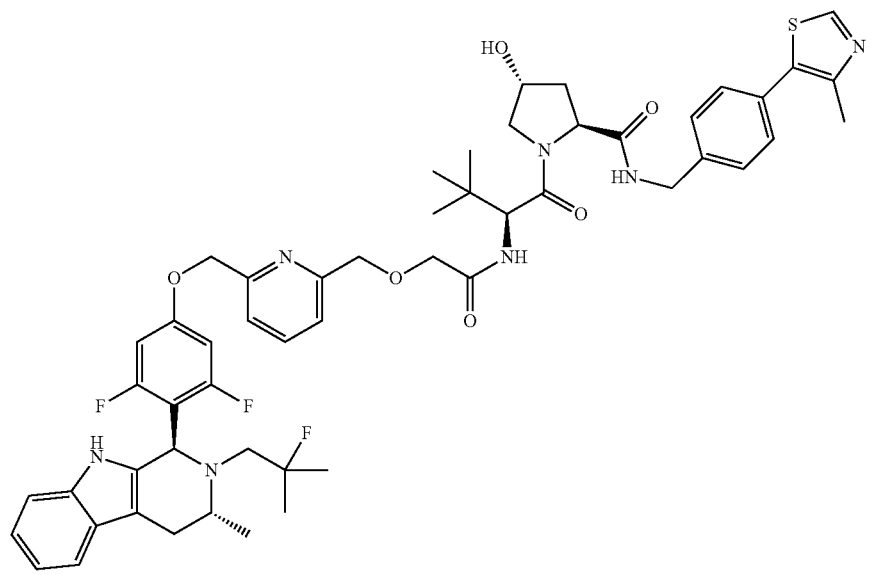 [SMILES: Cc1ncsc1-c1ccc(CNC(=O)[C@@H]2C[C@@H](O)CN2C(=O)[C@@H](NC(=O)COCc2cccc(COc3cc(F)c([C@@H]4c5[nH]c6ccccc6c5C[C@@H](C)N4CC(C)(C)F)c(F)c3)n2)C(C)(C)C)cc1]

Intermediate 133b: Isopropyl 3-(hydroxymethyl)picolinate

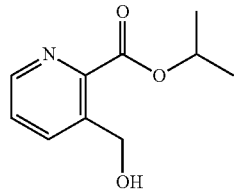

Sulfur dichloride (1.54 mL, 21.2 mmol) and DMF (0.200 mL) were added to a suspension of 2-(isopropoxycarbonyl)nicotinic acid (4.22 g, 20.2 mmol) in DCM (25 mL) at 20° C. under nitrogen. The resulting mixture was stirred at 40° C. for 4 hours until a pale yellow solution formed. The reaction mixture was evaporated to dryness, dissolved in THF (10 mL) and evaporated to dryness. The resulting orange oil was dissolved in THF (20 mL) and cooled to 0° C. Sodium borohydride (0.99 g, 26 mmol) was added in one portion and the reaction as stirred at 0° C. for 1 hour and warmed to RT for 2 hours. The reaction was poured carefully onto ice then extracted with DCM (2×50 mL). The combined organics were passed through a phase separating cartridge and evaporated to dryness to afford crude product as a yellow oil. The crude product was purified by flash silica chromatography, elution gradient 0 to 100% EtOAc in heptane to afford the title compound (2.54 g, 65%) as a colourless oil which solidified on standing; $^1$H NMR (400 MHz, CDCl3, 30° C.) 1.46 (6H, d), 3.52 (1H, t), 4.81 (2H, d), 5.36 (1H, p), 7.46 (1H, dd), 7.87 (1H, dd), 8.69 (1H, dd); m/z: ES+ [M+H]$^+$ 196.1.

Intermediate 133c: Isopropyl 3-(((tert-butyldimethylsilyl)oxy)methyl)picolinate

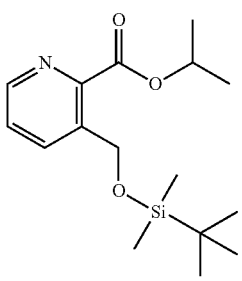 [SMILES: CC(C)OC(=O)c1ncccc1CO[Si](C)(C)C(C)(C)C]

tert-Butylchlorodimethylsilane (0.85 g, 5.6 mmol) was added in one portion to isopropyl 3-(hydroxymethyl)picolinate (1.0 g, 5.1 mmol) and 1H-imidazole (0.38 g, 5.6 mmol) in DCM (8.40 ml) at 20° C. under nitrogen. The resulting cream suspension was stirred for 2 hours. The reaction mixture was diluted with DCM (100 mL), and washed with water (50 mL) and saturated brine (100 mL). The organic layer was dried with MgSO$_4$, filtered and evaporated to afford crude product. The crude product was purified by flash silica chromatography, elution gradient 0 to 40% EtOAc in heptane to dryness to afford the title compound (1.520 g, 96%) as a colourless oil; $^1$H NMR (400 MHz, CDCl3, 30° C.) 0.00 (6H, s), 0.83 (9H, s), 1.30 (6H, d), 4.96 (2H, s), 5.18 (1H, hept), 7.33 (1H, dd), 8.04 (1H, ddt), 8.45-8.55 (1H, m); m/z: ES+ [M+H]$^+$ 310.3.

Intermediate 133d: (3-(((tert-Butyldimethylsilyl)oxy)methyl)pyridin-2-yl)methanol

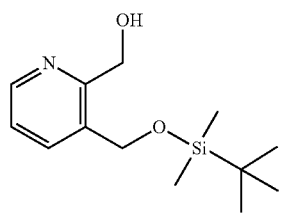 [SMILES: CC(C)(C)[Si](C)(C)OCc1cccnc1CO]

A solution of 1M lithium aluminum hydride in THF (6.30 ml, 6.30 mmol) was added dropwise to a solution of isopropyl 3-(((tert-butyldimethylsilyl)oxy)methyl)picolinate (1.5 g, 4.85 mmol) in anhydrous THF (17.9 ml) at 0° C. over a period of 15 minutes under nitrogen. The resulting mixture was stirred at 0° C. for 1 hour. The reaction mixture was quenched with careful dropwise addition of water (0.24 mL), 2M NaOH solution (0.48 mL) and water (0.72 mL). The mixture was stirred for 5 minutes. The solids were removed by filtration and the filtrate was evaporated to dryness. The crude product was purified by flash silica chromatography, elution gradient 0 to 50% EtOAc in heptane to afford the title compound (0.302 g, 25%) as a yellow oil; $^1$H NMR (400 MHz, CDCl3, 30° C.) −0.00 (6H, s), 0.82 (9H, s), 4.51-4.63 (5H, m), 7.1-7.14 (1H, m), 7.6-7.67 (1H, m), 8.35 (1H, dd); m/z: ES+ [M+H]$^+$ 254.3.

Intermediate 133e: (1R,3R)-1-(4-((3-(((tert-Butyldimethylsilyl)oxy)methyl)pyridin-2-yl)methoxy)-2,6-difluorophenyl)-2-(2-fluoro-2-methylpropyl)-3-methyl-2,3,4,9-tetrahydro-1H-pyrido[3,4-b]indole

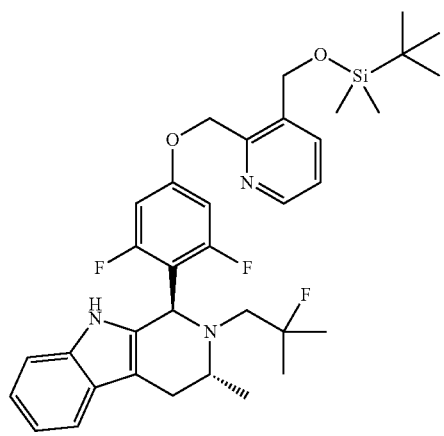 [SMILES: C[C@@H]1Cc2c([nH]c3ccccc23)[C@@H](c2c(F)cc(OCc3ncccc3CO[Si](C)(C)C(C)(C)C)cc2F)N1CC(C)(C)F]

The title compound was prepared in a similar manner to Intermediate 72e using the appropriate phenol and alcohol to afford the desired product (432 mg) as a yellow gum that was used without further purification; ¹H NMR (400 MHz, CDCl3, 30° C.) 0.10 (6H, s), 0.93 (9H, s), 1.10 (3H, d), 1.19 (6H, dd), 2.37 (1H, dd), 2.60 (1H, dd), 2.86 (1H, dd), 3.08 (1H, dd), 3.63-3.74 (1H, m), 4.84 (2H, s), 5.18 (1H, s), 5.20 (2H, s), 6.48-6.59 (2H, m), 7.05-7.15 (2H, m), 7.19-7.25 (1H, m), 7.31 (1H, dd), 7.40 (1H, s), 7.51 (1H, dd), 7.82-7.9 (1H, m), 8.50 (1H, dd); m/z: ES+ [M+H]⁺ 624.4.

Intermediate 133f: (2-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methanol

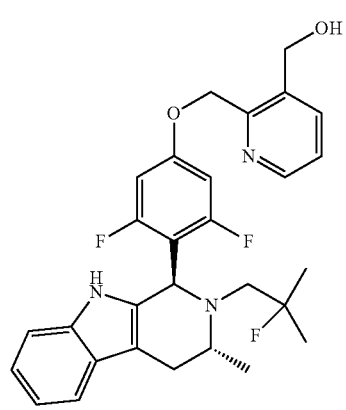 [SMILES: C[C@@H]1Cc2c([nH]c3ccccc23)[C@@H](c2c(F)cc(OCc3ncccc3CO)cc2F)N1CC(C)(C)F]

A solution of 1M TBAF in THF (0.96 mL, 0.96 mmol) was added in one portion to (1R,3R)-1-(4-((3-(((tert-butyldimethylsilyl)oxy)methyl)pyridin-2-yl)methoxy)-2,6-difluorophenyl)-2-(2-fluoro-2-methylpropyl)-3-methyl-2,3,4,9-tetrahydro-1H-pyrido[3,4-b]indole (400 mg, 0.64 mmol) in THF (5 mL) at 20° C. The resulting solution was stirred at 20° C. for 2 hours. The reaction mixture was diluted with EtOAc (50 mL), and washed sequentially with saturated NH4Cl (20 mL), water (20 mL), and saturated brine (20 mL). The organic layer was dried with MgSO₄, filtered and evaporated to afford crude product. The crude product was purified by flash silica chromatography, elution gradient 0 to 50% EtOAc in heptane to afford the title compound (255 mg, 78%) as a white foamy solid; ¹H NMR (400 MHz, CDCl3, 30° C.) 1.09 (3H, d), 1.14-1.25 (6H, m), 2.38 (1H, dd), 2.60 (1H, dd), 2.85 (1H, dd), 3.07 (1H, dd), 3.61-3.74 (1H, m), 4.83 (2H, d), 5.19 (1H, s), 5.25 (2H, s), 6.46-6.62 (2H, m), 7.05-7.16 (2H, m), 7.19-7.24 (1H, m), 7.33 (1H, dd), 7.43 (1H, s), 7.51 (1H, dd), 7.84 (1H, dd), 8.54 (1H, dd); m/z: ES+ [M+H]⁺ 510.4.

Intermediate 133g: Ethyl 2-((2-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methoxy)acetate

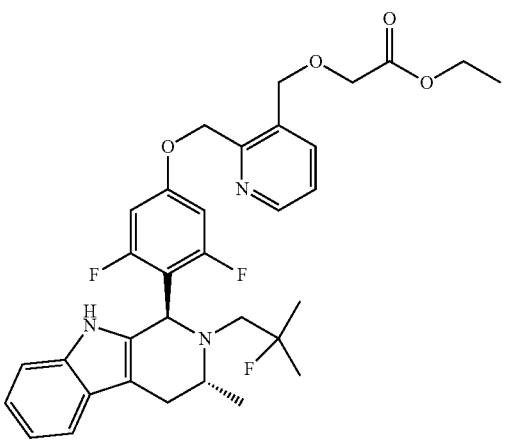 [SMILES: CCOC(=O)COCc1cccnc1COc1cc(F)c([C@@H]2c3[nH]c4ccccc4c3C[C@@H](C)N2CC(C)(C)F)c(F)c1]

The title compound was prepared in a similar manner to Intermediate 72c using the appropriate alcohol to afford the desired product (66 mg, 23%) a yellow gum; m/z: ES+ [M+H]⁺ 596.4.

Intermediate 133h: 2-((2-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methoxy)acetic Acid

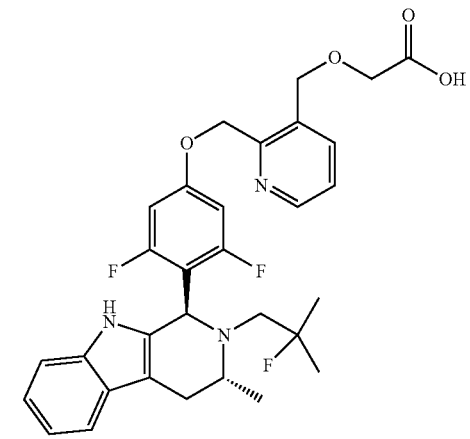 [SMILES: C[C@@H]1Cc2c([nH]c3ccccc23)[C@@H](c2c(F)cc(OCc3ncccc3COCC(=O)O)cc2F)N1CC(C)(C)F]

The title compound was prepared in a similar manner to Intermediate 72f using the appropriate ester to afford the desired product (63 mg, 100%) as a yellow gum that was used in the next step without purification; m/z: ES+ [M+H]⁺ 568.3.

Example 133: (2S,4R)-1-((S)-2-(2-((2-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methoxy)acetamido)-3,3-dimethylbutanoyl)-4-hydroxy-N-(4-(4-methylthiazol-5-yl)benzyl)pyrrolidine-2-carboxamide

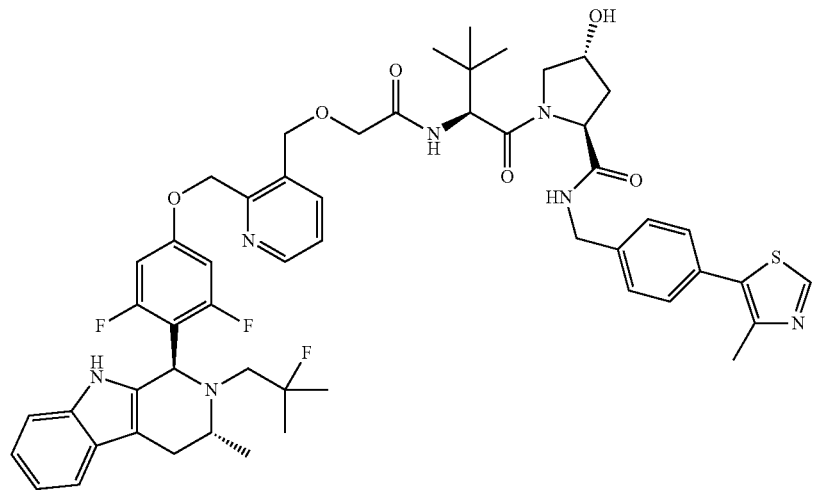 [SMILES: Cc1ncsc1-c1ccc(CNC(=O)[C@@H]2C[C@@H](O)CN2C(=O)[C@@H](NC(=O)COCc2cccnc2COc2cc(F)c([C@@H]3c4[nH]c5ccccc5c4C[C@@H](C)N3CC(C)(C)F)c(F)c2)C(C)(C)C)cc1]

The title compound was prepared in a similar manner to Example 68 using the appropriate carboxylic acid and amine to afford the desired product (44 mg, 38%) as a cream solid; ¹H NMR (400 MHz, CDCl3, 30° C.) 0.90 (9H, s), 1.09 (3H, d), 1.20 (6H, dd), 2.02-2.14 (1H, m), 2.41 (1H, dd), 2.49 (3H, s), 2.52-2.63 (3H, m), 2.82 (1H, dd), 3.04 (1H, dd), 3.59-3.68 (2H, m), 3.85 (2H, dd), 4.03 (1H, d), 4.32 (1H, dd), 4.48-4.59 (3H, m), 4.59-4.79 (3H, m), 5.14-5.39 (3H, m), 6.45-6.58 (2H, m), 7.02-7.12 (3H, m), 7.16 (1H, t), 7.2-7.25 (1H, m), 7.28-7.4 (5H, m), 7.46-7.55 (1H, m), 7.72 (1H, dd), 8.27 (1H, s), 8.56 (1H, dd), 8.66 (1H, s); m/z: ES− [M−H]⁻ 978.8.

Intermediate 134a: Methyl 4-(((tert-Butyldimethylsilyl)oxy)methyl)picolinate

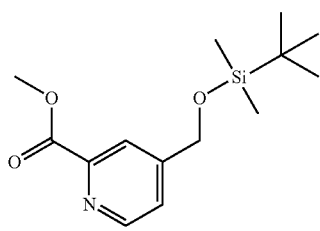 [SMILES: COC(=O)c1cc(CO[Si](C)(C)C(C)(C)C)ccn1]

tert-Butylchlorodimethylsilane (0.992 g, 6.58 mmol) was added in one portion to methyl 4-(hydroxymethyl)picolinate (1.0 g, 6.0 mmol) and 1H-imidazole (0.45 g, 6.6 mmol) in DCM (10 mL) at 20° C. under nitrogen. The resulting cream suspension was stirred for 2 hours. The reaction mixture was diluted with DCM (100 mL), and washed with water (50 mL) and saturated brine (100 mL). The organic layer was dried with MgSO₄, filtered and evaporated to afford crude product. The crude product was purified by flash silica chromatography, elution gradient 0 to 50% EtOAc in heptane to afford the title compound (1.330 g, 79%) as a colourless oil; ¹H NMR (400 MHz, CDCl3, 30° C.) 0.13 (6H, s), 0.96 (9H, s), 4.01 (3H, s), 4.81 (2H, s), 7.48 (1H, ddt), 8.07 (1H, dd), 8.69 (1H, dd); m/z: ES+ [M+H]⁺ 282.3.

Intermediate 134b: (4-(((tert-Butyldimethylsilyl)oxy)methyl)pyridin-2-yl)methanol

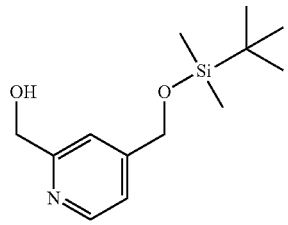 [SMILES: CC(C)(C)[Si](C)(C)OCc1ccnc(CO)c1]

A solution of 1M lithium aluminum hydride 1M in THF (3.70 ml, 3.70 mmol) was added dropwise to a solution of methyl 4-(((tert-butyldimethylsilyl)oxy)methyl)picolinate (0.8 g, 2.8 mmol) in anhydrous THF (10 ml) at 0° C. over a period of 15 minutes under nitrogen. The resulting mixture was stirred at 0° C. for 15 minutes. The reaction mixture was quenched with careful dropwise addition of water (0.24 mL), 2M NaOH solution (0.48 mL) and water (0.72 mL). The mixture was stirred for 5 minutes. The solids were removed by filtration and the filtrate was evaporated to dryness. The crude product was purified by flash silica chromatography, elution gradient 0 to 100% EtOAc in heptane to afford the title compound (0.300 g, 42%) as a yellow oil; ¹H NMR (400 MHz, CDCl3, 30° C.) 0.12 (6H, s), 0.96 (9H, s), 3.69 (1H, s), 4.75 (4H, s), 7.14-7.19 (1H, m), 7.18-7.22 (1H, m), 8.49 (1H, d); m/z: ES+ [M+H]⁺ 254.2.

Intermediate 134c: (1R,3R)-1-(4-((4-(((tert-Butyldimethylsilyl)oxy)methyl)pyridin-2-yl)methoxy)-2,6-difluorophenyl)-2-(2-fluoro-2-methylpropyl)-3-methyl-2,3,4,9-tetrahydro-1H-pyrido[3,4-b]indole

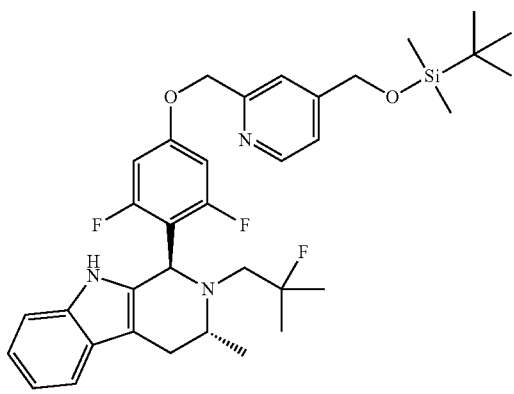 [SMILES: C[C@@H]1Cc2c([nH]c3ccccc23)[C@@H](c2c(F)cc(OCc3cc(CO[Si](C)(C)C(C)(C)C)ccn3)cc2F)N1CC(C)(C)F]

The title compound was prepared in a similar manner to Intermediate 72e using the appropriate phenol and alcohol to afford the desired product (420 mg) as a yellow gum that was used without further purification; $^1$H NMR (400 MHz, CDCl3, 30° C.) 0.11 (6H, s), 0.95 (9H, s), 1.10 (3H, d), 1.15-1.25 (6H, m), 2.39 (1H, dd), 2.60 (1H, dd), 2.86 (1H, dd), 3.08 (1H, dd), 3.67 (1H, d), 4.76 (2H, s), 5.14 (2H, s), 5.20 (1H, s), 6.47-6.54 (2H, m), 7.03-7.16 (2H, m), 7.16-7.25 (2H, m), 7.42 (2H, d), 7.45-7.54 (1H, m), 8.53 (1H, d); m/z: ES+ [M+H]$^+$ 624.5.

Intermediate 134d: (2-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-4-yl)methanol

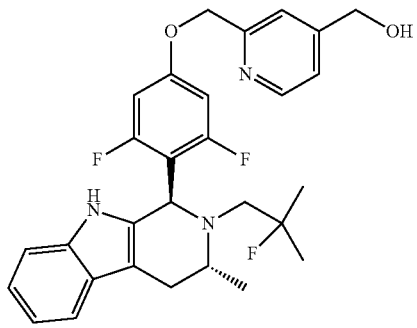 [SMILES: C[C@@H]1Cc2c([nH]c3ccccc23)[C@@H](c2c(F)cc(OCc3cc(CO)ccn3)cc2F)N1CC(C)(C)F]

A solution of 1M TBAF in THF (0.96 mL, 0.96 mmol) was added in one portion to (1R,3R)-1-(4-((4-(((tert-butyldimethylsilyl)oxy)methyl)pyridin-2-yl)methoxy)-2,6-difluorophenyl)-2-(2-fluoro-2-methylpropyl)-3-methyl-2,3,4,9-tetrahydro-1H-pyrido[3,4-b]indole (400 mg, 0.64 mmol) in THF (5 mL) at 20° C. The resulting solution was stirred at 20° C. for 2 hours. The reaction mixture was diluted with EtOAc (50 mL), and washed sequentially with saturated NH4Cl (20 mL), water (20 mL), and saturated brine (20 mL). The organic layer was dried with MgSO4, filtered and evaporated to afford crude product. The crude product was purified by flash silica chromatography, elution gradient 0 to 100% EtOAc in heptane to afford the title compound (203 mg, 62%) as a yellow gum; $^1$H NMR (400 MHz, CDCl3, 30° C.) 1.10 (3H, d), 1.14-1.25 (6H, m), 1.88 (1H, t), 2.39 (1H, dd), 2.60 (1H, dd), 2.86 (1H, dd), 3.08 (1H, dd), 3.66 (1H, d), 4.77 (2H, d), 5.15 (2H, s), 5.20 (1H, s), 6.45-6.56 (2H, m), 7.04-7.14 (2H, m), 7.2-7.25 (2H, m), 7.44 (1H, s), 7.46-7.49 (1H, m), 7.49-7.54 (1H, m), 8.56 (1H, d); m/z: ES+ [M+H]$^+$ 510.4.

Intermediate 134e: Ethyl 2-((2-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-4-yl)methoxy)acetate

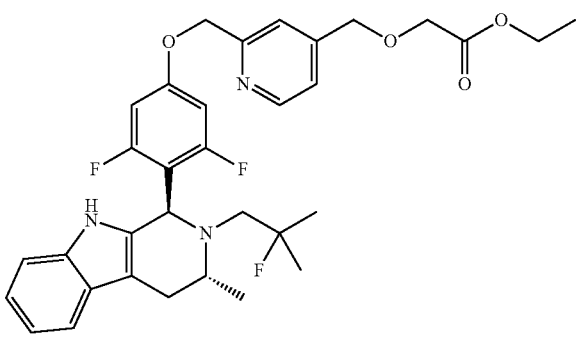 [SMILES: CCOC(=O)COCc1ccnc(COc2cc(F)c([C@@H]3c4[nH]c5ccccc5c4C[C@@H](C)N3CC(C)(C)F)c(F)c2)c1]

The title compound was prepared in a similar manner to Intermediate 72c using the appropriate alcohol to afford the desired product (95 mg, 41%) a red gum; m/z: ES+ [M+H]$^+$ 596.4

Intermediate 134f: 2-((2-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-4-yl)methoxy)acetic Acid

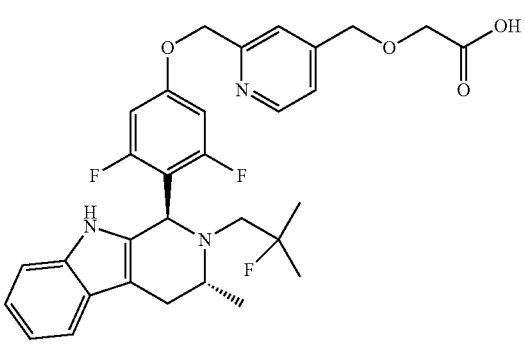 [SMILES: C[C@@H]1Cc2c([nH]c3ccccc23)[C@@H](c2c(F)cc(OCc3cc(COCC(=O)O)ccn3)cc2F)N1CC(C)(C)F]

The title compound was prepared in a similar manner to Intermediate 72f using the appropriate ester to afford the desired product (90 mg, 99%) as a yellow gum that was used in the next step without purification; m/z: ES+ [M+H]$^+$ 568.4.

Example 134: (2S,4R)-1-((S)-2-(2-((2-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-4-yl)methoxy)acetamido)-3,3-dimethylbutanoyl)-4-hydroxy-N-(4-(4-methylthiazol-5-yl)benzyl)pyrrolidine-2-carboxamide

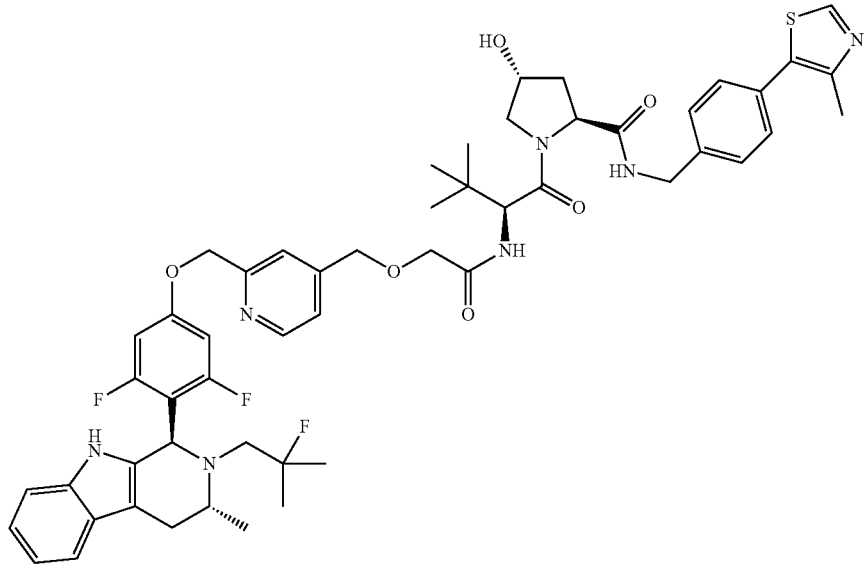

The title compound was prepared in a similar manner to Example 68 using the appropriate carboxylic acid and amine to afford the desired product (67.0 mg, 43%) as a cream solid; $^1$H NMR (400 MHz, DMSO, 30° C.) 0.94 (9H, d), 1.04 (3H, d), 1.16 (6H, dd), 1.91 (1H, ddd), 2.07 (1H, d), 2.26-2.41 (1H, m), 2.44 (3H, s), 2.75-2.95 (2H, m), 3.51 (1H, d), 3.58-3.73 (2H, m), 4.09 (2H, s), 4.26 (1H, dd), 4.32-4.5 (3H, m), 4.59 (1H, d), 4.67 (2H, s), 5.14 (2H, d), 5.19 (2H, s), 6.78 (2H, d), 6.97 (2H, dtd), 7.18 (1H, d), 7.34 (1H, d), 7.40 (5H, s), 7.51 (1H, s), 7.61 (1H, d), 8.56 (2H, t), 8.98 (1H, s), 10.52 (1H, s); m/z: ES+ [M+H]$^+$ 980.6.

Intermediate 135a: Ethyl 1-(3-(3-(benzyloxy)propoxy)propoxy)cyclopropane-1-carboxylate

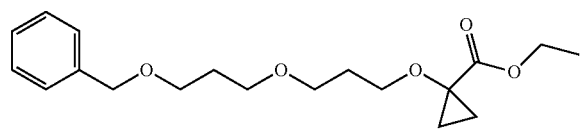 [SMILES: CCOC(=O)C1(OCCCOCCCOCc2ccccc2)CC1]

Trifluoromethanesulfonic anhydride (0.47 mL, 2.8 mmol) was added dropwise to a stirred solution of 3-(3-(benzyloxy)propoxy)propan-1-ol (575 mg, 2.56 mmol), and 2,6-dimethylpyridine (0.33 mL, 2.8 mmol) in DCM (6 mL) at −78° C., under nitrogen. The resulting solution was stirred at −78° C. for 1 hour. The reaction mixture was diluted with DCM (25 mL), and washed sequentially with saturated NH4Cl (20 mL) and water (25 mL). The organic layer was dried with a phase separating cartridge, filtered and evaporated to afford crude 3-(3-(benzyloxy)propoxy)propyl trifluoromethanesulfonate that was dissolved in THF (9.42 mL). Ethyl 1-hydroxycyclopropane-1-carboxylate (0.311 ml, 2.56 mmol) was added to the mixture and cooled to −78° C. under nitrogen. A solution of 1 N lithium bis(trimethylsilyl)amide THF (3.07 ml, 3.07 mmol) was added dropwise to the solution over 10 minutes. The resulting mixture was stirred at −78° C. for 40 minutes and warmed to 0° C. The reaction mixture was warmed to room temperature and stirred at 25° C. for 2 days. The reaction mixture was diluted with saturated NH4Cl (30 mL), ethyl acetate (50 mL) and 5 mL of 2N HCl. The layers were separated and the aqueous phase back extracted with ethyl acetate (3×30 mL). The combined organic phases were washed with brine (50 mL), dried over MgSO$_4$, filtered and concentrated to a crude oil. The crude product was purified by flash silica chromatography, elution gradient 0 to 20% EtOAc in heptane to afford ethyl 1-(3-(3-(benzyloxy)propoxy)propoxy)cyclopropane-1-carboxylate (213 mg, 25%) as a colourless oil; $^1$H NMR (400 MHz, CDCl3, 30° C.) 1.09-1.15 (2H, m), 1.24-1.32 (5H, m), 1.81 (2H, p), 1.88 (2H, q), 3.47 (2H, t), 3.51 (2H, t), 3.56 (2H, t), 3.66 (2H, t), 4.19 (2H, q), 4.50 (2H, s), 7.26-7.37 (5H, m).

Intermediate 135b: Ethyl 1-(3-(3-hydroxypropoxy)propoxy)cyclopropane-1-carboxylate

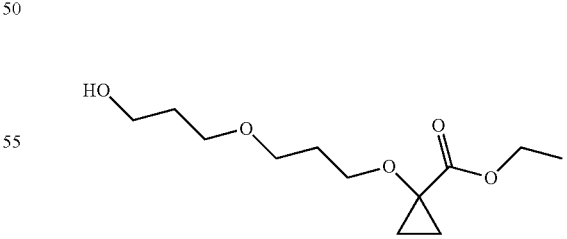

The title compound was prepared in a similar manner to Intermediate 72d using the appropriate benzyl ether to afford the desired product (162 mg) as a colourless oil that was used without further purification; $^1$H NMR (400 MHz, CDCl3, 30° C.) 1.06-1.17 (2H, m), 1.24-1.34 (5H, m), 1.74-1.92 (4H, m), 2.43 (1H, s), 3.53 (2H, t), 3.62 (2H, t), 3.67 (2H, t), 3.77 (2H, q), 4.19 (2H, q).

Intermediate 135c: Ethyl 1-[3-(3-{3,5-difluoro-4-[(1R,3R)-2-(2-fluoro-2-methylpropyl)-3-methyl-2,3,4,9-tetrahydro-1H-pyrido[3,4-b]indol-1-yl]phenoxy}propoxy)propoxy]cyclopropane-1-carboxylate

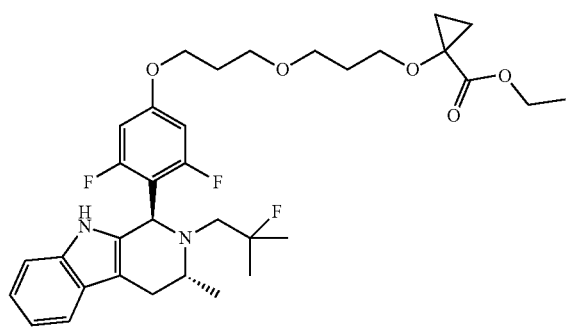 [SMILES: CCOC(=O)C1(OCCCOCCCOc2cc(F)c([C@@H]3c4[nH]c5ccccc5c4C[C@@H](C)N3CC(C)(C)F)c(F)c2)CC1]

The title compound was prepared in a similar manner to Intermediate 72e using the appropriate phenol and alcohol to afford the desired product (73 mg, 20%) as a colourless oil; $^1$H NMR (400 MHz, CDCl3, 30° C.) 1.02-1.14 (5H, m), 1.17 (3H, d), 1.2-1.3 (8H, m), 1.81 (2H, p), 2.01 (2H, p), 2.39 (1H, dd), 2.60 (1H, dd), 2.64-2.7 (1H, m), 2.86 (1H, dd), 3.09 (1H, dd), 3.50 (2H, t), 3.56 (2H, t), 3.65 (3H, dtt), 4.01 (2H, tq), 4.09-4.24 (2H, m), 5.19 (1H, s), 6.3-6.49 (2H, m), 7.02-7.14 (2H, m), 7.17-7.23 (1H, m), 7.43-7.58 (1H, m); m/z: ES+ [M+H]$^+$617.3.

Example 135: (2S,4R)-1-((S)-2-(1-(3-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)cyclopropane-1-carboxamido)-3,3-dimethylbutanoyl)-4-hydroxy-N-(4-(4-methylthiazol-5-yl)benzyl)pyrrolidine-2-carboxamide A solution of 1 M lithium hydroxide hydrate (0.24 ml, 0.24 mmol) was added to a stirred solution of ethyl 1-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)cyclopropane-1-carboxylate (0.073 g, 0.12 mmol) in EtOH (1 ml). The resulting solution was stirred at rt for 1 hour. A further aliquot of 1M lithium hydroxide hydrate solution (0.24 mL, 0.24 mmol) was added to the reaction mixture and left to stir for a further hour. The reaction mixture was partially evaporated, the aqueous residue was adjusted to pH 5 with 2M HCl, diluted with water (15 mL) and extracted with EtOAc (2×25 mL). The organic extracts were combined, washed with saturated brine (25 mL) and evaporated to afford a colourless gum. The gum was dissolved in DMF (2.5 mL), (2S,4R)-1-((S)-2-amino-3,3-dimethylbutanoyl)-4-hydroxy-N-(4-(4-methylthiazol-5-yl)benzyl)pyrrolidine-2-carboxamide, 2HCl (0.043 g, 0.09 mmol) and triethylamine (0.048 mL, 0.34 mmol) added. HATU (0.049 g, 0.13 mmol) was added under nitrogen. The resulting solution was stirred at RT for 17 hours. The reaction mixture was diluted with water (10 mL) and extracted with EtOAc (25 mL). The organic extract was washed with saturated brine (25 mL), dried with a phase separating cartridge, filtered and evaporated to afford crude product. The crude product was purified by preparative HPLC (Waters CSH C18 OBD column, 30×100 mm id, 5 micron particle size), using decreasingly polar mixtures of water (containing 0.1% NH3 aq) and MeCN as eluents to afford the impure compound. The sample (20 mg) was purified using the SFC conditions detailed: Column: Princeton Diol, 30×250 mm, 5 micron; Mobile phase: 25 to 45% MeOH+0.1% NH3/75-55% scCO2 over 8 minutes; Flow rate: 100 ml/min; BPR: 120 bar; Column temperature: 40° C. to afford the title compound (14 mg, 17%) as a white solid. $^1$H NMR (400 MHz, CDCl3, 30° C.) 0.93 (1H, d), 0.96 (9H, s), 1.02 (1H, dd), 1.06 (1H, dd), 1.10 (3H, d), 1.20 (7H, dd), 1.76-1.89 (2H, m), 1.98 (2H, p), 2.07 (1H, dd), 2.41 (1H, dd), 2.48 (3H, s), 2.52-2.65 (2H, m), 2.77-2.9 (2H, m), 3.07 (1H, dd), 3.42-3.61 (7H, m), 3.61-3.72 (1H, m), 3.95 (2H, tt), 4.08 (1H, d), 4.32 (1H, dd), 4.47 (1H, d), 4.51 (1H, s), 4.57 (1H, dd), 4.73 (1H, t), 5.20 (1H, s), 6.31-6.37 (2H, m), 7.04-7.11 (2H, m), 7.18-7.25 (2H, m), 7.3-7.39 (5H, m), 7.48-7.53 (1H, m), 8.34 (1H, s), 8.63 (1H, s); m/z: ES− [M−H]$^-$ 999.1.

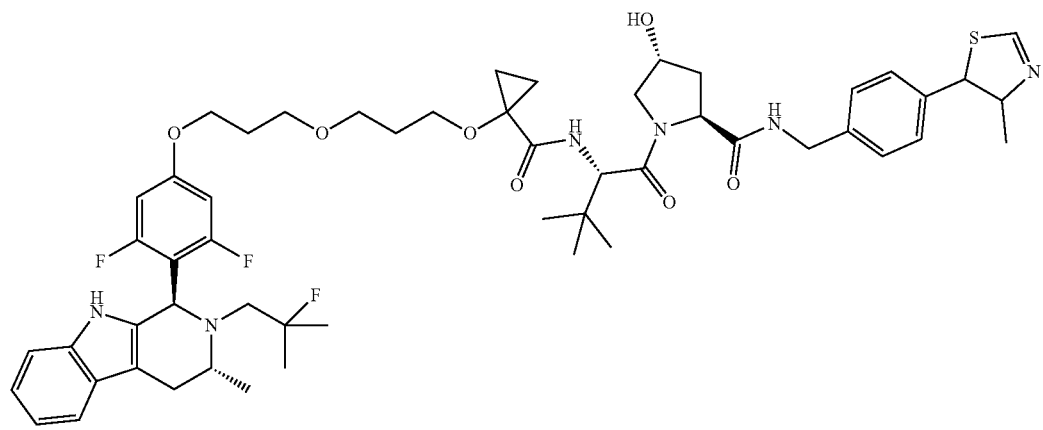 [SMILES: CC1N=CSC1c1ccc(CNC(=O)[C@@H]2C[C@@H](O)CN2C(=O)[C@@H](NC(=O)C2(OCCCOCCCOc3cc(F)c([C@@H]4c5[nH]c6ccccc6c5C[C@@H](C)N4CC(C)(C)F)c(F)c3)CC2)C(C)(C)C)cc1]

Intermediate 136a: 2-(3-((5-(Benzyloxy)pentyl)oxy)propoxy)tetrahydro-2H-pyran

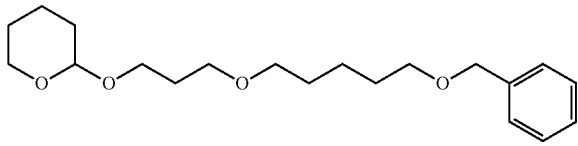 [SMILES: c1ccc(COCCCCCOCCCOC2CCCCO2)cc1]

Tetrabutylammonium hydrogen sulfate (0.957 g, 2.82 mmol) was added in one portion to 5-(benzyloxy)pentan-1-ol (3.62 mL, 18.79 mmol) and 2-(3-bromopropoxy)tetrahydro-2H-pyran (3.82 mL, 22.55 mmol) in 50% sodium hydroxide solution (5.08 mL) at 20° C. under air. The resulting mixture was stirred at 70° C. for 18 hours. The cooled reaction mixture was diluted with water (20 mL) and extracted with EtOAc (3×25 mL). The combined organic extracts were washed with water (20 mL), saturated brine solution (20 mL), dried over MgSO$_4$, filtered and evaporated to afford crude product as a yellow oil. The crude product was purified by flash silica chromatography, elution gradient 0 to 50% EtOAc in heptane to afford the title compound (4.06 g, 64%) as a colourless oil; $^1$H NMR (400 MHz, CDCl$_3$, 30° C.) 1.38-1.47 (2H, m), 1.48-1.56 (3H, m), 1.56-1.67 (5H, m), 1.68-1.74 (1H, m), 1.77-1.91 (3H, m), 3.41 (2H, t), 3.48 (6H, dtd), 3.77-3.89 (2H, m), 4.49 (2H, s), 4.57 (1H, dd), 7.23-7.29 (1H, m), 7.31-7.35 (4H, m).

Intermediate 136b: 5-(3-((Tetrahydro-2H-pyran-2-yl)oxy)propoxy)pentan-1-ol

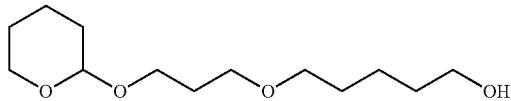 [SMILES: OCCCCCOCCCOC1CCCCO1]

2-(3-((5-(Benzyloxy)pentyl)oxy)propoxy)tetrahydro-2H-pyran (1.90 g, 5.65 mmol) and 10% palladium on carbon (0.601 g, 0.56 mmol) were stirred in EtOH (25 mL) under an atmosphere of hydrogen for 3 hours. The reaction mixture was filtered through celite and eluted with MeOH. The filtrate was evaporated under reduced pressure to afford the title compound (1.50 g) as a colourless oil that was used without further purification; $^1$H NMR (400 MHz, CDCl$_3$, 30° C.) 1.28 (3H, t), 1.39-1.47 (2H, m), 1.57 (2H, d), 1.61-1.68 (2H, m), 1.88 (2H, p), 3.41 (2H, t), 3.49 (4H, dt), 3.61 (2H, t), 4.05 (2H, s), 4.22 (2H, d), 4.50 (2H, s), 7.26 (1H, s), 7.31-7.35 (4H, m); m/z: ES+ [M+H]$^+$ 339.3.

Intermediate 136c: Ethyl 2-((5-(3-((tetrahydro-2H-pyran-2-yl)oxy)propoxy)pentyl)oxy)acetate

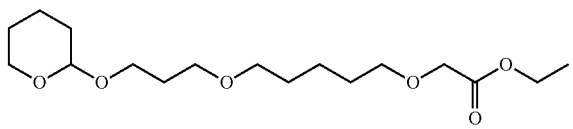 [SMILES: CCOC(=O)COCCCCCOCCCOC1CCCCO1]

Ethyl 2-diazoacetate (1.68 mL, 13.70 mmol) in DCM (5.6 mL) was added slowly to 5-(3-((tetrahydro-2H-pyran-2-yl)oxy)propoxy)pentan-1-ol (1.35 g, 5.48 mmol) and diacetoxyrhodium (0.12 g, 0.27 mmol) in DCM (15 mL) at 20° C. over a period of 1 hour under nitrogen. The resulting solution was stirred at 0° C. for 1 hour. The mixture was diluted with DCM (50 mL) and washed with water (3×50 mL). The organic layer was collected and dried using phase separating cartridge then evaporated to dryness. The crude product was purified by flash silica chromatography, elution gradient 0 to 50% EtOAc in heptane to afford the title compound (1.05 g, 58%) as a colourless liquid; $^1$H NMR (400 MHz, CDCl$_3$, 30° C.) 1.27-1.3 (3H, m), 1.39-1.47 (2H, m), 1.49-1.55 (2H, m), 1.55-1.61 (4H, m), 1.61-1.67 (2H, m), 1.68-1.74 (1H, m), 1.77-1.84 (1H, m), 1.87 (2H, q), 3.41 (2H, t), 3.45-3.56 (6H, m), 3.77-3.89 (2H, m), 4.05 (2H, s), 4.19-4.23 (2H, m), 4.58 (1H, dd); m/z: ES− [M−H]$^-$ 331.4.

Intermediate 136d: Ethyl 2-[5-(3-hydroxypropoxy)pentoxy]acetate

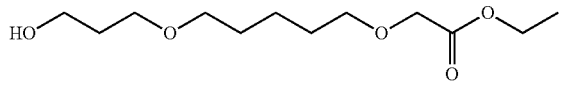 [SMILES: CCOC(=O)COCCCCCOCCCO]

Ethyl 2-((5-(3-((tetrahydro-2H-pyran-2-yl)oxy)propoxy)pentyl)oxy)acetate (1.12 g, 3.37 mmol) was dissolved in MeOH (9.0 mL) and 1M aq. HCl (4.5 mL) was added. The resulting mixture was stirred at 20° C. for 1 hour. The reaction mixture was diluted with water (100 mL), and extracted with EtOAc (3×100 mL). The combined organics were washed with saturated brine (50 mL). The organic layer was dried with MgSO$_4$, filtered and evaporated. The crude product was purified by flash silica chromatography, elution gradient 0 to 50% EtOAc in heptane to afford a the title compound (267 mg, 32%) as a colourless oil; m/z: ES+ [M+H]$^+$ 249.3.

Intermediate 136e: Ethyl 2-((5-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)pentyl)oxy)acetate

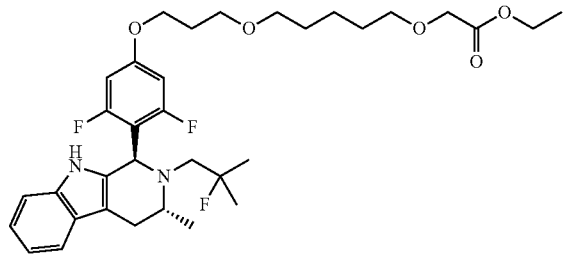 [SMILES: CCOC(=O)COCCCCCOCCCOc1cc(F)c([C@@H]2c3[nH]c4ccccc4c3C[C@@H](C)N2CC(C)(C)F)c(F)c1]

DIAD (0.212 mL, 1.08 mmol) was added dropwise to a stirred solution of ethyl 2-((5-(3-hydroxypropoxy)pentyl)oxy)acetate (0.267 g, 1.08 mmol), 3,5-difluoro-4-((1R,3R)-2-(2-fluoro-2-methylpropyl)-3-methyl-2,3,4,9-tetrahydro-1H-pyrido[3,4-b]indol-1-yl)phenol (0.209 g, 0.54 mmol) and triphenylphosphine (0.282 g, 1.08 mmol) in DCM (10 mL) at 0° C. under nitrogen. The resulting solution was stirred at room temperature for 18 hours. DCM (50 mL) and water (30 mL) were added and the organic layer was separated via a phase separating cartridge and concentrated.

The crude product was purified by flash silica chromatography, elution gradient 0 to 100% EtOAc in heptane to afford the title compound (165 mg, 50%) as a mixture of Methyl and Ethyl esters carried over from previous step; m/z: ES− [M−H]− 617.5.

Intermediate 136f: 2-((5-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)pentyl)oxy)acetic Acid

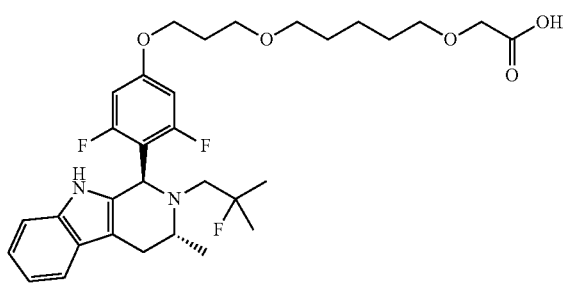 [SMILES: C[C@@H]1Cc2c([nH]c3ccccc23)[C@@H](c2c(F)cc(OCCCOCCCCCOCC(=O)O)cc2F)N1CC(C)(C)F]

Lithium hydroxide hydrate (22 mg, 0.53 mmol) was added in one portion to ethyl 2-((5-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)pentyl)oxy)acetate (165 mg, 0.27 mmol) in THF (3 mL) and water (1 mL) at 20° C. The resulting solution was stirred at room temperature for 30 mins. The organic solvent was removed under reduced pressure and the resulting mixture was acidified with 2M HCl and extracted into EtOAc (2×10 mL). The organic extracts were washed with brine (5 mL) and evaporated to afford crude product. The crude product was purified by preparative HPLC (Waters XSelect CSH C18 ODB column, 5μ silica, 30 mm diameter, 100 mm length), using decreasingly polar mixtures of water (containing 1% NH$_3$) and MeCN as eluents to afford the title compound (69 mg, 44%) as a pale yellow oil; $^1$H NMR (400 MHz, DMSO, 30° C.) 1.05 (3H, d), 1.11 (3H, s), 1.22 (3H, s), 1.29-1.37 (2H, m), 1.51 (4H, dt), 1.88-1.96 (2H, m), 2.38 (1H, d), 2.54-2.59 (1H, m), 2.78-2.93 (2H, m), 3.36 (2H, t), 3.42 (2H, t), 3.50 (3H, dt), 3.95 (2H, s), 4.04 (2H, t), 5.13 (1H, s), 6.65 (2H, d), 6.97 (2H, dtd), 7.18 (1H, d), 7.39 (1H, d), 10.49 (1H, s), 12.47 (1H, s); m/z: ES+ [M+H]+ 591.4.

Example 136: (2S,4R)-1-((S)-2-(2-((5-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)pentyl)oxy)acetamido)-3,3-dimethylbutanoyl)-4-hydroxy-N-(4-(4-methylthiazol-5-yl)benzyl)pyrrolidine-2-carboxamide

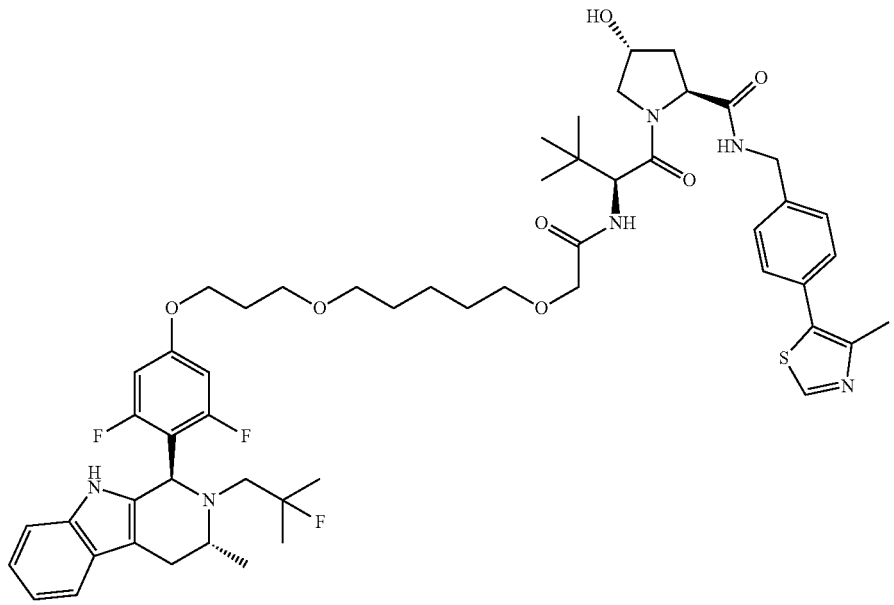

HATU (39 mg, 0.10 mmol) was added portionwise to 2-((5-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)pentyl)oxy)acetic acid (30 mg, 0.05 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (24 mg, 0.05 mmol) and N-ethyl-N-isopropylpropan-2-amine (36 μL, 0.20 mmol) in DMF (1 mL) at 20° C. under nitrogen. The resulting mixture was stirred at 20° C. for 30 mins. The crude product was purified by preparative HPLC (Waters CSH C18 OBD column, 30×100 mm id, 5 micron particle size), using decreasingly polar mixtures of water (containing 0.1% NH$_3$) and MeCN as eluents to afford the title compound (28 mg, 55%); $^1$H NMR (400 MHz, CDCl₃, 30° C.) 0.94 (9H, s), 1.10 (3H, d), 1.18 (3H, d), 1.23 (3H, d), 1.37-1.47 (2H, m), 1.61 (4H, dt), 1.96-2.03 (2H, m), 2.05-2.11 (1H, m), 2.33-2.46 (1H, m), 2.50 (3H, s), 2.54-2.64 (3H, m), 2.79-2.89 (1H, m), 3.07 (1H, dd), 3.42 (2H, t), 3.45-3.5 (2H, m), 3.54 (2H, t), 3.60 (1H, dd), 3.63-3.7 (1H, m), 3.76-3.93 (2H, m), 3.98 (2H, t), 4.09 (1H, d), 4.33 (1H, dd), 4.48 (1H, d), 4.56 (2H, dd), 4.73 (1H, t), 5.20 (1H, s), 6.34-6.4 (2H, m), 7.04-7.12 (2H, m), 7.14 (1H, d), 7.19-7.23 (1H, m), 7.29 (1H, s), 7.32-7.39 (4H, m), 7.47-7.54 (1H, m), 8.04 (1H, s), 8.64 (1H, s). m/z: ES+ [M+H]⁺ 1003.6.

Intermediate 137a:
3-((5-(Benzyloxy)pentyl)oxy)propan-1-ol

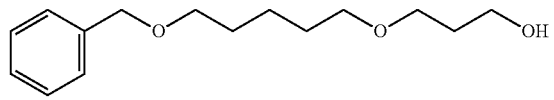 [SMILES: OCCCOCCCCCOCc1ccccc1]

2-(3-((5-(Benzyloxy)pentyl)oxy)propoxy)tetrahydro-2H-pyran (1.80 g, 5.35 mmol) was dissolved in MeOH (14 mL) and 1M aq HCl (7.1 mL) was added. The resulting mixture was stirred at 20° C. for 1 hour. The reaction mixture was diluted with water (100 mL), and extracted with EtOAc (3×100 mL). The combined organics were washed with saturated brine (50 mL). The organic layer was dried with MgSO₄, filtered and evaporated to afford crude product (1.50 g) that was used directly in the next step without purification; ¹H NMR (400 MHz, CDCl₃, 30° C.) 1.38-1.47 (2H, m), 1.57-1.61 (2H, m), 1.62-1.67 (2H, m), 1.82 (2H, dt), 2.44 (1H, s), 3.42 (2H, dd), 3.47 (2H, t), 3.57-3.62 (2H, m), 3.76 (2H, t), 4.50 (2H, s), 7.27-7.36 (5H, m); m/z: ES+ [M+H]⁺ 253.3.

Intermediate 137b: Ethyl 2-(3-((5-(benzyloxy)pentyl)oxy)propoxy)acetate

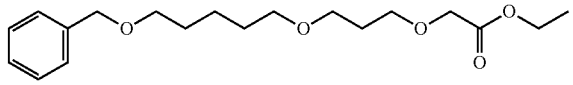 [SMILES: CCOC(=O)COCCCOCCCCCOCc1ccccc1]

Ethyl 2-diazoacetate (1.64 mL, 13.4 mmol) in DCM (5.5 mL) was added slowly to 3-((5-(benzyloxy)pentyl)oxy)propan-1-ol (1.35 g, 5.35 mmol) and diacetoxyrhodium (0.118 g, 0.27 mmol) in DCM (14.2 mL) at 0° C. over a period of 1 hour under nitrogen. The resulting solution was stirred at 0° C. for 1 hour. The mixture was diluted with DCM (50 mL) and washed with water (3×50 mL). The organic layer was collected and dried using phase separating cartridge then evaporated to dryness. The crude product was purified by flash silica chromatography, elution gradient 0 to 50% EtOAc in heptane to afford the title compound (1.12 g, 62%) as a colourless liquid; ¹H NMR (400 MHz, CDCl₃, 30° C.) 1.28 (3H, t), 1.39-1.47 (2H, m), 1.57 (2H, d), 1.61-1.68 (2H, m), 1.88 (2H, p), 3.41 (2H, t), 3.49 (4H, dt), 3.61 (2H, t), 4.05 (2H, s), 4.22 (2H, d), 4.50 (2H, s), 7.26 (1H, s), 7.31-7.35 (4H, m); m/z: ES+ [M+H]⁺ 339.3.

Intermediate 137c: Ethyl 2-(3-((5-hydroxypentyl)oxy)propoxy)acetate

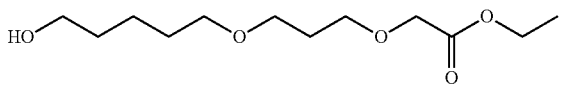 [SMILES: CCOC(=O)COCCCOCCCCCO]

Ethyl 2-(3-((5-(benzyloxy)pentyl)oxy)propoxy)acetate (1.05 g, 3.10 mmol) was dissolved in EtOH (25 mL) and 10% palladium on carbon (0.33 g, 0.31 mmol). The suspension was stirred under hydrogen for 3 hours. The reaction mixture was filtered through celite and washed with MeOH. The solvent was removed under reduced pressure. The crude product was purified by flash silica chromatography, elution gradient 0 to 50% EtOAc in heptane to afford the title compound (0.571 g, 74%) as a colourless oil; ¹H NMR (400 MHz, CDCl₃, 30° C.) 1.29 (3H, t), 1.34 (1H, t), 1.4-1.47 (2H, m), 1.55-1.65 (4H, m), 1.89 (2H, p), 3.43 (2H, t), 3.52 (2H, t), 3.58-3.69 (4H, m), 4.06 (2H, s), 4.22 (2H, q); m/z: ES+ [M+H]⁺ 249.3.

Intermediate 137d: Ethyl 2-(3-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)propoxy)acetate

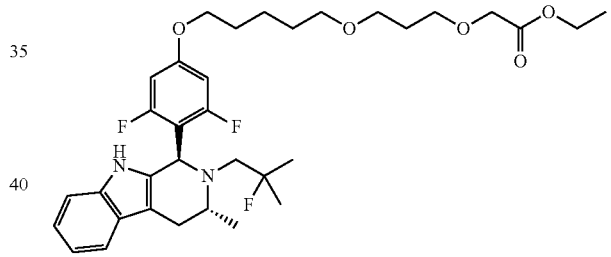

DIAD (0.46 mL, 2.32 mmol) was added dropwise to a stirred solution of ethyl 2-((9-hydroxynonyl)oxy)acetate (0.57 g, 2.32 mmol), 3,5-difluoro-4-((1R,3R)-2-(2-fluoro-2-methylpropyl)-3-methyl-2,3,4,9-tetrahydro-1H-pyrido[3,4-b]indol-1-yl)phenol (0.60 g, 1.54 mmol) and triphenylphosphine (0.61 g, 2.3 mmol) in DCM (10 mL) at 20° C. under nitrogen. The resulting solution was stirred at 0° C. for 18 hours. DCM (50 mL) and water (30 mL) were added and the layers were separated and concentrated to give the crude residue. The product was purified by flash silica chromatography, elution gradient 0 to 100% EtOAc in heptane to afford the title compound (0.275 g, 29%); ¹H NMR (400 MHz, CDCl₃, 30° C.) 1.10 (3H, d), 1.17 (3H, d), 1.23 (3H, d), 1.29 (3H, t), 1.49 (2H, dd), 1.63 (2H, dt), 1.75-1.84 (2H, m), 1.88 (2H, t), 2.39 (1H, dd), 2.60 (1H, dd), 2.86 (1H, dd), 3.09 (1H, dd), 3.36-3.48 (2H, m), 3.52 (2H, t), 3.61 (2H, t), 3.63-3.71 (1H, m), 3.91 (2H, t), 4.05 (2H, d), 4.17-4.23 (2H, m), 5.18 (1H, s), 6.35-6.43 (2H, m), 7.04-7.14 (2H, m), 7.18-7.24 (1H, m), 7.45 (1H, s), 7.51 (1H, dd); m/z: ES+ [M+H]⁺ 619.4.

Intermediate 137e: 2-(3-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)propoxy)acetic Acid

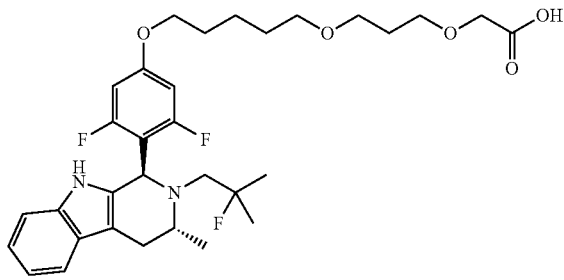 [SMILES: C[C@@H]1Cc2c([nH]c3ccccc23)[C@@H](c2c(F)cc(OCCCCCOCCCOCC(=O)O)cc2F)N1CC(C)(C)F]

Lithium hydroxide hydrate (37 mg, 0.89 mmol) was added in one portion to ethyl 2-(3-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)propoxy)acetate (275 mg, 0.44 mmol) in THF (3 mL) and water (1 mL) at 20° C. The resulting solution was stirred at room temperature for 30 mins. The organic solvent was removed under reduced pressure and the resulting mixture was acidified with 2M HCl and extracted into EtOAc (2×10 mL). The organic extracts were washed with brine (5 mL) and evaporated to afford the title compound (260 mg, 99%) as a colourless gum which was used in the next step without purification; m/z: ES+ [M+H]$^+$ 591.1

Example 137: (2S,4R)-1-((S)-2-(2-(3-((5-(3,5-Difluoro-4-((R,3R)-2-(2-fluoro-2-methylpropyl)-3-methyl-2,3,4,9-tetrahydro-1H-pyrido[3,4-b]indol-1-yl)phenoxy)pentyl)oxy)propoxy)acetamido)-3,3-dimethylbutanoyl)-4-hydroxy-N-((S)-1-(4-(4-methylthiazol-5-yl)phenyl)ethyl)pyrrolidine-2-carboxamide HATU (129 mg, 0.34 mmol) was added portionwise to 2-(3-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)propoxy)acetic acid (100 mg, 0.17 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide, HCl (82 mg, 0.17 mmol) and N-ethyl-N-isopropylpropan-2-amine (0.121 mL, 0.68 mmol) in DMF (5 mL) at 20° C. under nitrogen. The resulting mixture was stirred at 20° C. for 30 mins. The reaction was diluted with EtOAc (20 mL) and water. The organics were washed sequentially with saturated NaHCO$_3$ (20 mL) and saturated brine (20 mL). The organic layer was dried with Na$_2$SO$_4$, filtered and evaporated. The crude product was purified by preparative HPLC (Waters CSH C18 OBD column, 30×100 mm id, 5 micron particle size), using decreasingly polar mixtures of water (containing 0.1% NH$_3$) and MeCN as eluents to afford the title compound (71 mg, 41%); $^1$H NMR (400 MHz, CDCl3, 30° C.) 0.94 (9H, s), 1.06 (9H, s), 1.10 (3H, d), 1.17 (3H, d), 1.23 (3H, d), 1.47 (3H, d), 1.49-1.54 (2H, m), 1.61-1.67 (2H, m), 1.78 (2H, dt), 1.89 (2H, p), 1.98-2.07 (1H, m), 2.39 (1H, dd), 2.51 (3H, s), 2.54-2.63 (2H, m), 2.68 (1H, d), 2.85 (1H, dd), 3.08 (1H, dd), 3.44 (2H, t), 3.51 (2H, t), 3.56-3.63 (3H, m), 3.63-3.71 (1H, m), 3.84-3.99 (4H, m), 4.11 (1H, d), 4.53 (2H, d), 4.74 (1H, t), 5.08 (1H, p), 5.19 (1H, s), 6.29-6.42 (2H, m), 7.05-7.12 (2H, m), 7.16-7.24 (2H, m), 7.33-7.42 (4H, m), 7.44 (1H, s), 7.47-7.53 (1H, m), 7.89 (1H, s), 8.65 (1H, s); m/z: ES- [M-H]$^-$ 1015.5.

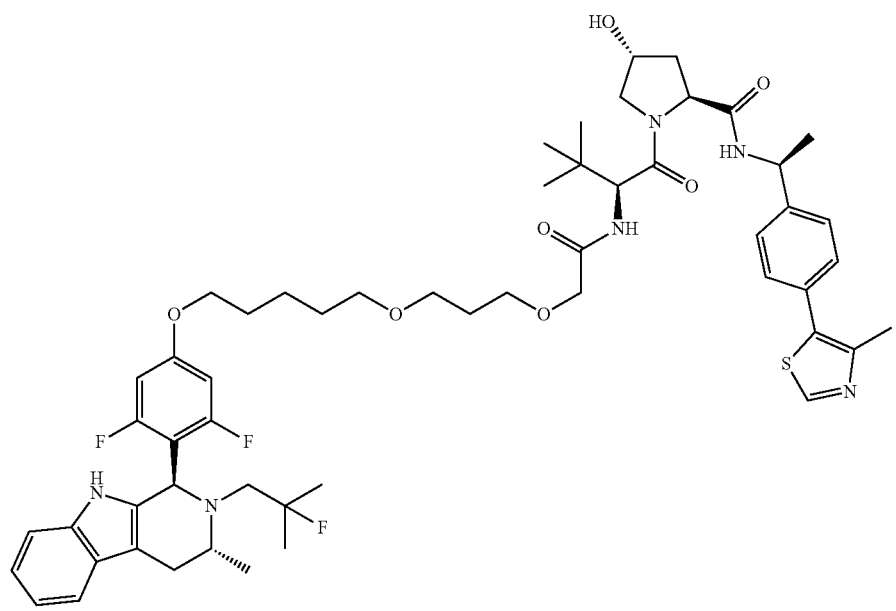 [SMILES: Cc1ncsc1-c1ccc([C@H](C)NC(=O)[C@@H]2C[C@@H](O)CN2C(=O)[C@@H](NC(=O)COCCCOCCCCCOc2cc(F)c([C@@H]3c4[nH]c5ccccc5c4C[C@@H](C)N3CC(C)(C)F)c(F)c2)C(C)(C)C)cc1]

Example 138: (2S,4R)-1-((S)-2-(2-(3-((5-(3,5-Difluoro-4-((R,3R)-2-(2-fluoro-2-methylpropyl)-3-methyl-2,3,4,9-tetrahydro-1H-pyrido[3,4-b]indol-1-yl)phenoxy)pentyl)oxy)propoxy)acetamido)-3,3-dimethylbutanoyl)-4-hydroxy-N-(4-(4-methylthiazol-5-yl)benzyl)pyrrolidine-2-carboxamide

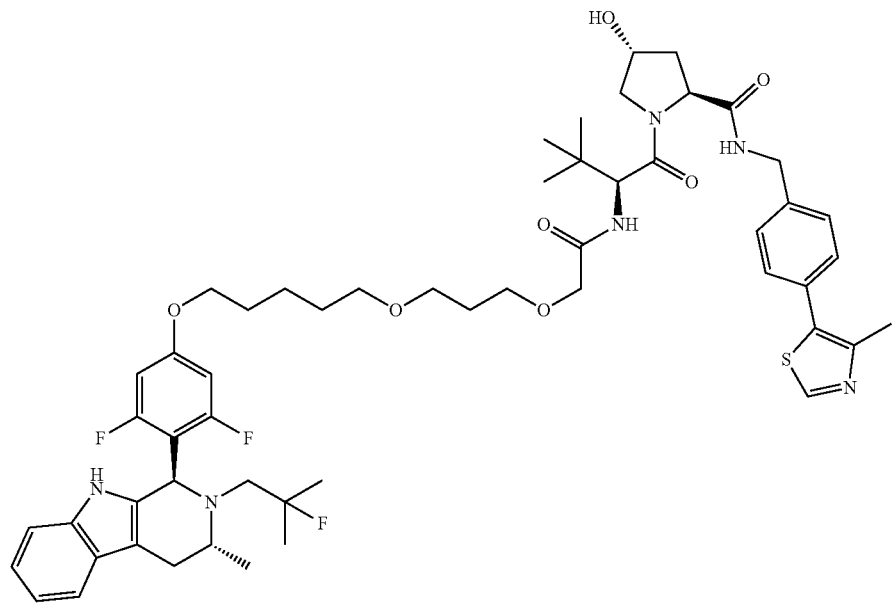 [SMILES: Cc1ncsc1-c1ccc(CNC(=O)[C@@H]2C[C@@H](O)CN2C(=O)[C@@H](NC(=O)COCCCOCCCCCOc2cc(F)c([C@@H]3c4[nH]c5ccccc5c4C[C@@H](C)N3CC(C)(C)F)c(F)c2)C(C)(C)C)cc1]

HATU (129 mg, 0.34 mmol) was added portionwise to 2-(3-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)propoxy)acetic acid (100 mg, 0.17 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (79 mg, 0.17 mmol) and N-ethyl-N-isopropylpropan-2-amine (0.121 mL, 0.68 mmol) in DMF (5 mL) at 20° C. under nitrogen. The resulting mixture was stirred at 20° C. for 30 mins. The reaction was diluted with EtOAc (20 mL) and water. The organics were washed sequentially with saturated NaHCO₃ (20 mL) and saturated brine (20 mL). The organic layer was dried over Na₂SO₄, filtered and evaporated. The crude product was purified by preparative HPLC (Waters CSH C18 OBD column, 30×100 mm id, 5 micron particle size), using decreasingly polar mixtures of water (containing 0.1% NH₃) and MeCN as eluents to afford the title compound (60 mg, 35%); ¹H NMR (400 MHz, CDCl3, 30° C.) 0.94 (9H, s), 1.10 (3H, d), 1.17 (3H, d), 1.23 (3H, d), 1.45-1.54 (2H, m), 1.58-1.66 (2H, m), 1.77 (2H, dt), 1.87 (2H, p), 2.08 (1H, dd), 2.40 (1H, dd), 2.50 (3H, s), 2.55-2.64 (2H, m), 2.66 (1H, d), 2.85 (1H, dd), 3.08 (1H, dd), 3.43 (2H, t), 3.50 (2H, t), 3.59 (3H, t), 3.63-3.71 (1H, m), 3.82-3.96 (4H, m), 4.10 (1H, d), 4.33 (1H, dd), 4.48 (1H, d), 4.56 (2H, dd), 4.73 (1H, t), 5.19 (1H, s), 6.31-6.41 (2H, m), 7.05-7.12 (2H, m), 7.14 (1H, d), 7.19-7.24 (1H, m), 7.27-7.32 (1H, m), 7.36 (4H, dd), 7.47-7.56 (1H, m), 7.91 (1H, s), 8.64 (1H, s); m/z: ES− [M−H]⁻ 1001.5.

Intermediate 139a: Ethyl 2-(3-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)propoxy)acetate

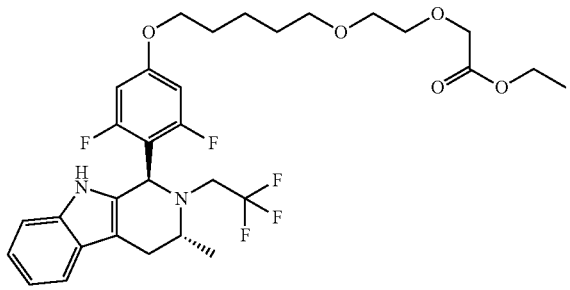 [SMILES: CCOC(=O)COCCOCCCCCOc1cc(F)c([C@@H]2c3[nH]c4ccccc4c3C[C@@H](C)N2CC(F)(F)F)c(F)c1]

DIAD (0.50 mL, 2.52 mmol) was added dropwise to a stirred solution of 3,5-difluoro-4-((1R,3R)-3-methyl-2-(2,2,2-trifluoroethyl)-2,3,4,9-tetrahydro-1H-pyrido[3,4-b]indol-1-yl)phenol (500 mg, 1.26 mmol), ethyl 2-(2-((5-hydroxypentyl)oxy)ethoxy)acetate (443 mg, 1.89 mmol) and triphenylphosphine (662 mg, 2.52 mmol) in DCM (10 mL) at 5° C. The resulting mixture was stirred at 5° C. for 30 minutes and then at room temperature for 30 mins. DCM (10 mL) and water (25 mL) were added and the layers were separated through a phase separating cartridge. The organic layer was loaded on to a silica column and purified by flash silica chromatography, elution gradient 10 to 100% EtOAc in heptane to afford the title compound (801 mg) that was used without further purification; ¹H NMR (400 MHz, CDCl₃, 30° C.) 1.17 (3H, d), 1.30 (3H, d), 1.51 (2H, ddt), 1.61-1.71 (2H, m), 1.79 (2H, dt), 2.62 (1H, ddd), 2.9-3.01 (1H, m), 3.11 (1H, ddd), 3.19-3.29 (1H, m), 3.49 (2H, td), 3.56-3.65 (3H, m), 3.71 (2H, dd), 3.92 (2H, t), 4.14 (2H, d), 4.21 (2H, q), 5.26 (1H, s), 6.38-6.44 (2H, m), 7.07-7.15 (2H, m), 7.23 (1H, dd), 7.51 (2H, dd); m/z: ES− [M−H]⁻ 611.3.

Intermediate 139b: 2-(2-((5-(3,5-Difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy)ethoxy)acetic Acid

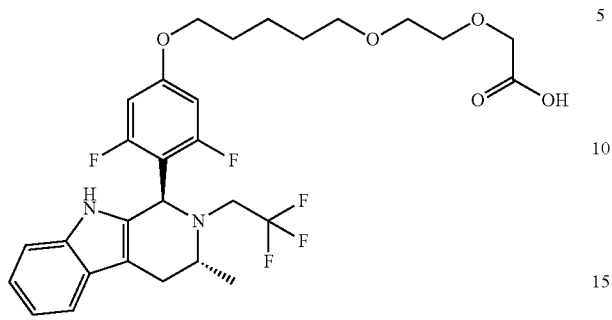

Lithium hydroxide hydrate (105 mg, 2.51 mmol) was added in one portion to ethyl 2-(2-((5-(3,5-difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy)ethoxy)acetate (0.77 g, 1.26 mmol) in THF (6 mL) and water (2 mL) at 20° C. The resulting solution was stirred at room temperature for 30 mins. The organic solvent was removed under reduced pressure and the resulting mixture was acidified with 2M HCl and extracted into EtOAc (2×10 mL). The organic extracts were washed with brine (5 mL) and evaporated to afford the title compound (0.723 g, 98%) as a yellow gum that was used in the next step without purification; $^1$H NMR (400 MHz, DMSO, 30° C.) 1.13 (3H, d), 1.4-1.49 (2H, m), 1.55 (2H, dt), 1.72 (2H, p), 2.62 (1H, dd), 2.86 (1H, dd), 2.96 (1H, dt), 3.30 (2H, s), 3.40 (2H, t), 3.51 (2H, dq), 3.58 (2H, dd), 3.99 (2H, t), 4.02 (2H, d), 5.22 (1H, s), 6.67 (2H, d), 6.93-6.99 (1H, m), 7.02 (1H, td), 7.21 (1H, d), 7.41 (1H, d), 10.60 (1H, s), 12.32 (1H, s); m/z: ES− [M−H]⁻ 583.3.

Example 139: (2S,4R)-1-((S)-2-(2-(2-((5-(3,5-Difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy)ethoxy)acetamido)-3,3-dimethylbutanoyl)-4-hydroxy-N-(4-(4-methylthiazol-5-yl)benzyl)pyrrolidine-2-carboxamide

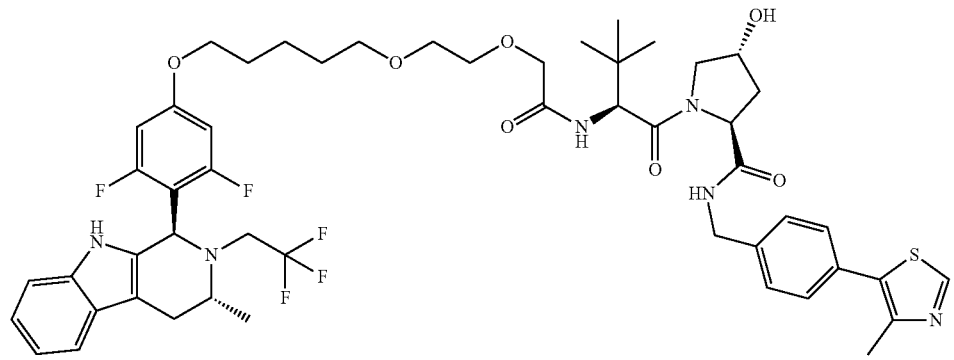 [SMILES: Cc1ncsc1-c1ccc(CNC(=O)[C@@H]2C[C@@H](O)CN2C(=O)[C@@H](NC(=O)COCCOCCCCCOc2cc(F)c([C@@H]3c4[nH]c5ccccc5c4C[C@@H](C)N3CC(F)(F)F)c(F)c2)C(C)(C)C)cc1]

HATU (0.146 g, 0.38 mmol) was added portionwise to 2-(2-((5-(3,5-difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy)ethoxy)acetic acid (0.150 g, 0.26 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (0.120 g, 0.26 mmol) and triethylamine (0.143 mL, 1.03 mmol) in DMF (5 mL) at 20° C. under nitrogen. The resulting mixture was stirred at 20° C. for 18 hours. The reaction mixture was diluted with EtOAc (25 mL), and washed sequentially with saturated NaHCO₃ (25 mL), water (25 mL) and saturated brine (25 mL). The organic layer was dried with MgSO₄, filtered and evaporated. The product was further purified by preparative HPLC (Waters XSelect CSH C18 ODB column, 5μ silica, 30 mm diameter, 100 mm length), using decreasingly polar mixtures of water (containing 1% NH₃) and MeCN as eluents. Fractions containing the desired compound were evaporated to dryness to afford the title compound (0.021 g, 8%) as a white solid; $^1$H NMR (400 MHz, CDCl₃, 30° C.) 0.94 (9H, s), 1.17 (3H, d), 1.49 (2H, ddt), 1.62 (1H, d), 1.67 (1H, d), 1.76 (2H, dt), 2-2.09 (1H, m), 2.47 (3H, s), 2.55 (1H, ddd), 2.59-2.69 (1H, m), 2.88 (1H, d), 2.92-3.01 (1H, m), 3.06-3.15 (1H, m), 3.15-3.27 (1H, m), 3.50 (2H, t), 3.59 (4H, dd), 3.66 (2H, dd), 3.87 (2H, t), 3.92-4.04 (2H, m), 4.09 (1H, d), 4.29 (1H, dd), 4.49 (2H, t), 4.56 (1H, dd), 4.71 (1H, t), 5.26 (1H, s), 6.31-6.39 (2H, m), 7.06-7.14 (2H, m), 7.22-7.26 (1H, m), 7.29 (1H, d), 7.31-7.38 (5H, m), 7.49-7.55 (1H, m), 8.32 (1H, s), 8.62 (1H, s); m/z: ES– [M–H]⁻ 995.4.

Example 140: (2S,4R)-1-((S)-2-(2-(2-((5-(3,5-Difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide Intermediate 141a: Ethyl 4-(6-(((tert-butyldimethylsilyl)oxy)methyl)pyridin-3-yl)butanoate

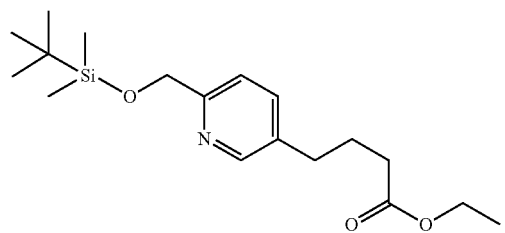

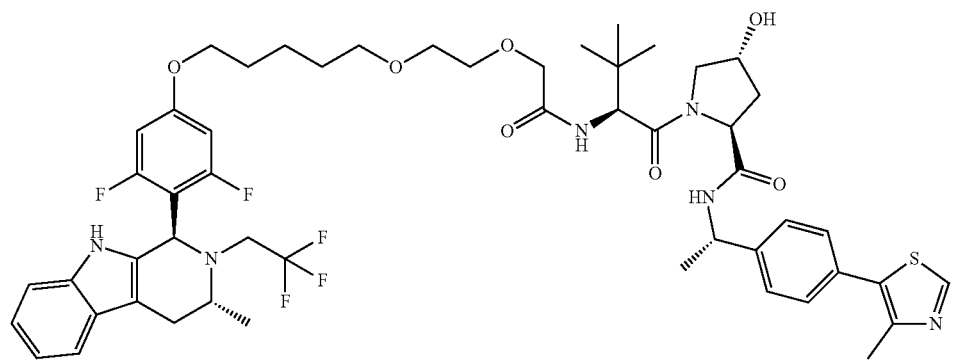 [SMILES: Cc1ncsc1-c1ccc([C@H](C)NC(=O)[C@@H]2C[C@@H](O)CN2C(=O)[C@@H](NC(=O)COCCOCCCCCOc2cc(F)c([C@@H]3c4[nH]c5ccccc5c4C[C@@H](C)N3CC(F)(F)F)c(F)c2)C(C)(C)C)cc1]

HATU (0.146 g, 0.38 mmol) was added portionwise to 2-(2-((5-(3,5-difluoro-4-((1R,3R)-3-methyl-2-(2,2,2-trifluoroethyl)-2,3,4,9-tetrahydro-1H-pyrido[3,4-b]indol-1-yl) phenoxy)pentyl)oxy)ethoxy)acetic acid (0.150 g, 0.26 mmol), (2S,4R)-1-((S)-2-amino-3,3-dimethylbutanoyl)-4-hydroxy-N—((S)-1-(4-(4-methylthiazol-5-yl)phenyl)ethyl) pyrrolidine-2-carboxamide, HCl (0.123 g, 0.26 mmol) and triethylamine (0.143 mL, 1.03 mmol) in DMF (5 mL) at 20° C. under nitrogen. The resulting mixture was stirred at 20° C. for 18 hours. The reaction mixture was diluted with EtOAc (25 mL), and washed sequentially with saturated NaHCO₃ (25 mL), water (25 mL), and saturated brine (25 mL). The organic layer was dried over MgSO₄, filtered and evaporated. The crude product was purified by preparative HPLC (Waters CSH C18 OBD column, 30×100 mm id, 5 micron particle size), using decreasingly polar mixtures of water (containing 0.1% formic acid) and MeCN as eluents to afford the title compound (0.054 g, 21%); ¹H NMR (400 MHz, CDCl₃, 30° C.) 1.07 (9H, s), 1.17 (3H, d), 1.45 (3H, d), 1.48-1.54 (2H, m), 1.67 (2H, dt), 1.77 (2H, dt), 1.94-2.05 (1H, m), 2.48 (3H, s), 2.52-2.7 (3H, m), 2.88-3.01 (1H, m), 3.07-3.15 (1H, m), 3.17-3.29 (1H, m), 3.52 (2H, t), 3.55-3.59 (1H, m), 3.59-3.64 (3H, m), 3.68 (2H, dd), 3.86 (2H, t), 3.95-4.06 (2H, m), 4.11 (1H, d), 4.50 (1H, s), 4.54 (1H, d), 4.73 (1H, t), 5.07 (1H, p), 5.26 (1H, s), 6.3-6.37 (2H, m), 7.06-7.15 (2H, m), 7.22-7.25 (1H, m), 7.33-7.43 (5H, m), 7.47-7.55 (2H, m), 8.20 (1H, s), 8.64 (1H, s); m/z: ES– [M–H]⁻ 1009.5.

(4,4'-Di-t-butyl-2-2'-bipyridine)bis[3,5-diflouro-2-[5-trifluoromethyl-2-pyridyl-kn)phenyl-kc]iridium(III) hexafluorophosphate (7.42 mg, 6.62 mol), 5-bromo-2-(((tert-butyldimethylsilyl)oxy)methyl)pyridine (200 mg, 0.66 mmol), ethyl 4-bromobutanoate (0.189 mL, 1.32 mmol), 1,1,1,3,3,3-hexamethyl-2-(trimethylsilyl)trisilane (0.204 mL, 0.66 mmol) and anhydrous sodium carbonate (140 mg, 1.32 mmol) were placed in a 5 mL microwave vial and sealed. The vial was placed under a N₂ atmosphere and DME (4 mL) was added. In a separate vial NiCl₂.diglyme (0.727 mg, 3.31 μmol) and 4,4'-di-tert-butyl-2,2'-bipyridine (1.06 mg, 3.97 μmol) were purged with N₂ and DME (0.1 mL) was added. The mixture was stirred for 5 mins then sonicated for 2 mins. The catalyst solution was transferred via syringe to the reaction mixture. The vial was placed in a Penn Photoreactor and stirred at 30° C. (fan speed 3500 rpm, stir 350 rpm, LED 100%) for 2 hours. The reaction mixture was diluted with DCM (20 mL) and washed with saturated NaHCO₃ (20 mL). The organic layer was dried over Na₂SO₄, filtered and evaporated to afford crude product. The crude product was purified by flash silica chromatography, elution gradient 0 to 60% EtOAc in heptane to afford the title compound (165 mg, 74%) as a colourless oil; ¹H NMR (400 MHz, CDCl₃, 30° C.) 0.00 (6H, s), 0.84 (9H, s), 1.14 (3H, d), 1.78-1.89 (2H, m), 2.21 (2H, t), 2.5-2.57 (2H, m), 4.01 (2H, q), 4.69 (2H, s), 7.27-7.35 (1H, m), 7.40 (1H, dd), 8.21 (1H, d); m/z: ES+ [M+H]⁺ 338.4.

Intermediate 141b: Ethyl 4-(6-(hydroxymethyl)pyridin-3-yl)butanoate

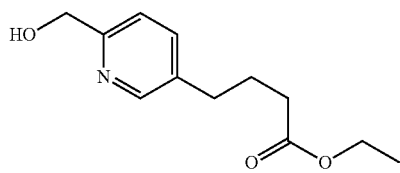 [SMILES: CCOC(=O)CCCc1ccc(CO)nc1]

Tetrabutylammonium fluoride 1M in THF (0.733 mL, 0.73 mmol) was added in one portion to ethyl 4-(6-(((tert-butyldimethylsilyl)oxy)methyl)pyridin-3-yl)butanoate (165 mg, 0.49 mmol) in THF (5 mL) at 20° C. The resulting solution was stirred at 20° C. for 1 hour. The reaction mixture was diluted with EtOAc (50 mL), and washed sequentially with saturated NH$_4$Cl (20 mL), water (20 mL), and saturated brine (20 mL). The organic layer was dried over MgSO$_4$, filtered and evaporated to afford crude product. The crude product was purified by flash silica chromatography, elution gradient 0 to 10% MeOH in DCM to afford the title compound (52 mg, 48%) as a colourless oil; $^1$H NMR (400 MHz, CDCl$_3$, 30° C.) 1.26 (3H, t), 1.89-2.03 (2H, m), 2.33 (2H, t), 2.61-2.73 (2H, m), 3.62-3.95 (1H, m), 4.13 (2H, q), 4.73 (2H, s), 7.18 (1H, d), 7.51 (1H, dd), 8.39 (1H, d); m/z: ES+ [M+H]$^+$224.3.

Intermediate 141c: Ethyl 4-(6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)butanoate

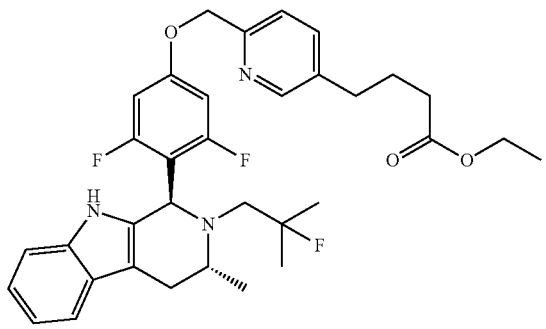 [SMILES: CCOC(=O)CCCc1ccc(COc2cc(F)c([C@@H]3c4[nH]c5ccccc5c4C[C@@H](C)N3CC(C)(C)F)c(F)c2)nc1]

The title compound was prepared in a similar manner to Intermediate 72e using the appropriate phenol and alcohol to afford the desired product (0.140 g) that was used without further purification; $^1$H NMR (400 MHz, CDCl$_3$, 30° C.) 1.10 (3H, d), 1.17 (3H, d), 1.22 (6H, d), 1.97 (2H, p), 2.34 (3H, t), 2.60 (1H, dd), 2.64-2.72 (2H, m), 2.86 (1H, dd), 3.08 (1H, dd), 3.63-3.71 (1H, m), 4.13 (2H, q), 5.11 (2H, s), 5.19 (1H, s), 6.47-6.55 (2H, m), 7.05-7.14 (2H, m), 7.19-7.23 (1H, m), 7.38 (1H, d), 7.47 (1H, d), 7.51 (1H, dd), 7.56 (1H, dd), 8.43 (1H, d); m/z: ES− [M−H]$^-$ 592.3.

Intermediate 141d: 4-(6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)butanoic Acid

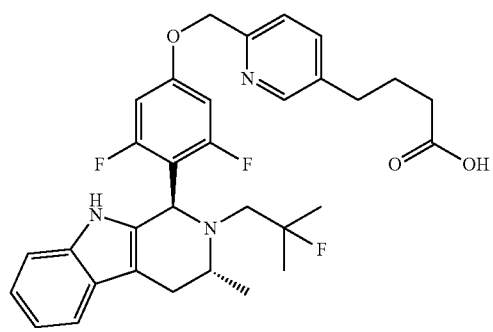 [SMILES: C[C@@H]1Cc2c([nH]c3ccccc23)[C@@H](c2c(F)cc(OCc3ccc(CCCC(=O)O)cn3)cc2F)N1CC(C)(C)F]

The title compound was prepared in a similar manner to Intermediate 72f using the appropriate ester to afford the desired product (25 mg, 19%); m/z: ES+ [M+H]$^+$ 566.5.

Example 141: (2S,4R)-1-((S)-2-(4-(6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)butanamido)-3,3-dimethylbutanoyl)-4-hydroxy-N-(4-(4-methylthiazol-5-yl)benzyl)pyrrolidine-2-carboxamide

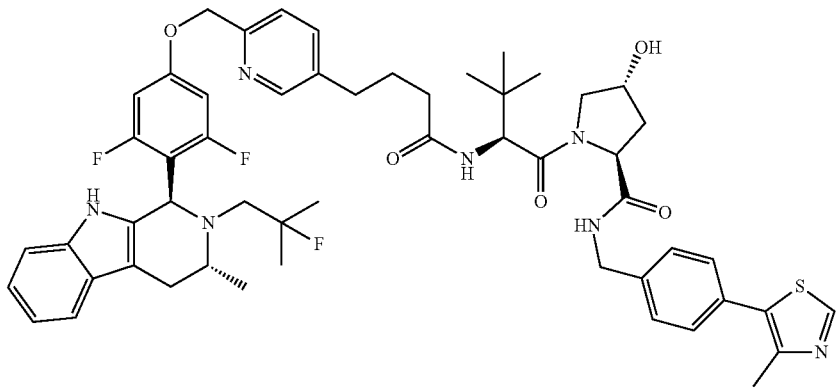 [SMILES: Cc1ncsc1-c1ccc(CNC(=O)[C@@H]2C[C@@H](O)CN2C(=O)[C@@H](NC(=O)CCCc2ccc(COc3cc(F)c([C@@H]4c5[nH]c6ccccc6c5C[C@@H](C)N4CC(C)(C)F)c(F)c3)nc2)C(C)(C)C)cc1]

The title compound was prepared in a similar manner to Example 68 using the appropriate carboxylic acid and amine to afford the desired product (2.6 mg, 7%); ¹H NMR (400 MHz, CDCl₃, 30° C.) 0.92 (9H, s), 1.09 (3H, d), 1.17 (3H, d), 1.22 (3H, d), 1.95 (2H, td), 2.08-2.16 (1H, m), 2.16-2.3 (2H, m), 2.39 (1H, dd), 2.50 (3H, s), 2.53-2.69 (4H, m), 2.85 (1H, dd), 3.03-3.12 (2H, m), 3.60 (1H, dd), 3.62-3.73 (1H, m), 4.10 (1H, d), 4.33 (1H, dd), 4.49 (1H, d), 4.58 (2H, dd), 4.72 (1H, t), 5.09 (2H, s), 5.19 (1H, s), 6.05 (1H, d), 6.44-6.52 (2H, m), 7.05-7.12 (2H, m), 7.18-7.24 (2H, m), 7.32-7.39 (5H, m), 7.53 (2H, ddd), 7.66 (1H, s), 8.38 (1H, d), 8.66 (1H, s); m/z: ES+ [M+H]⁺ 978.8.

Intermediate 142a: tert-Butyl (2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)carbamate

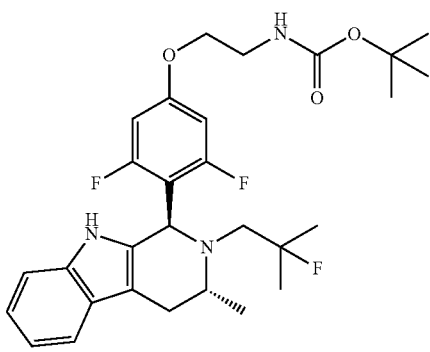 [SMILES: C[C@@H]1Cc2c([nH]c3ccccc23)[C@@H](c2c(F)cc(OCCNC(=O)OC(C)(C)C)cc2F)N1CC(C)(C)F]

The title compound was prepared in a similar manner to Intermediate 72e using the appropriate phenol and alcohol to afford the desired product (0.243 g, 71%); ¹H NMR (400 MHz, CDCl₃, 30° C.) 1.10 (3H, d), 1.16-1.2 (3H, m), 1.22 (3H, s), 1.45 (9H, s), 2.39 (1H, dd), 2.60 (1H, dd), 2.86 (1H, dd), 3.09 (1H, dd), 3.52 (2H, d), 3.66 (1H, s), 3.98 (2H, t), 4.79-5 (1H, m), 5.19 (1H, s), 6.37-6.43 (2H, m), 7.05-7.14 (2H, m), 7.22 (1H, dd), 7.39 (1H, s), 7.51 (1H, dd).

Intermediate 142b: 2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethan-1-amine

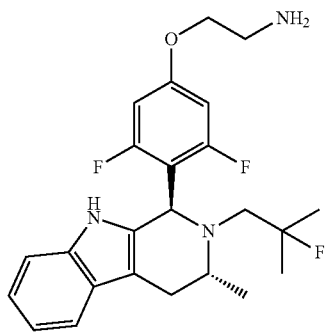

tert-Butyl (2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)carbamate (243 mg, 0.46 mmol) was stirred in formic acid (3 mL) at 40° C. for 1 hour. The volatiles were evaporated and the residue was dissolved in DCM (25 mL) and washed with saturated NaHCO₃ solution (25 mL). The aqueous layer was extracted with DCM (25 mL) and the combined organics were dried over Na₂SO₄ and evaporated to afford the title compound (192 mg, 97%) as a yellow gum; m/z: [M−H]⁻ 430.3.

Intermediate 142c: 5-(2-Ethoxy-2-oxoethoxy)pentanoic Acid

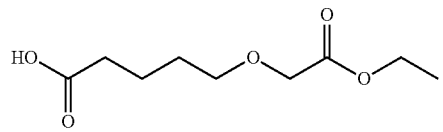

Sodium periodate (2.25 g, 10.51 mmol) was dissolved in water (2 mL) and 1:1 MeCN/dimethyl carbonate (10 mL) and ruthenium(III) chloride hydrate (0.024 g, 0.11 mmol) was added. The solution was cooled in an ice-bath and a solution of ethyl 2-((5-hydroxypentyl)oxy)acetate (1.00 g, 5.26 mmol) in 1:1 MeCN/dimethyl carbonate (10 mL) was added slowly over 15 minutes. On addition, the solution was brought to room temperature and stirred for 1 hour. The mixture was diluted with water (50 mL) and extracted with EtOAc (3×50 mL). The combined organics were washed with brine (50 mL), dried over MgSO₄, filtered through celite and concentrated under reduced pressure to give the title compound (1.05 g, 98%) as a dark oil; ¹H NMR (400 MHz, CDCl₃, 30° C.) 1.29 (3H, td), 1.64-1.81 (4H, m), 2.41 (2H, t), 3.56 (2H, t), 4.06 (2H, s), 4.22 (2H, q), 10.82 (1H, s); m/z: ES+ [M+H]⁺ 205.2.

Intermediate 142d: Ethyl 2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)-5-oxopentyl)oxy)acetate

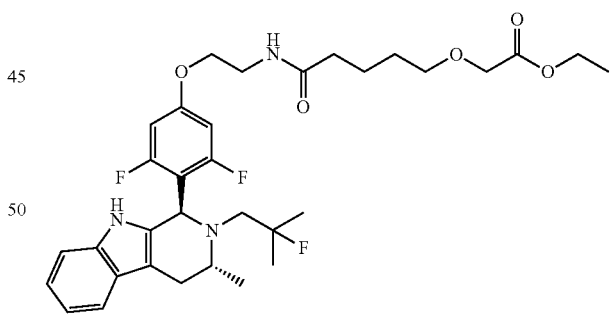

HATU (254 mg, 0.67 mmol) was added portionwise to 2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethan-1-amine (192 mg, 0.44 mmol), 5-(2-ethoxy-2-oxoethoxy)pentanoic acid (136 mg, 0.67 mmol) and N-ethyl-N-isopropylpropan-2-amine (0.317 mL, 1.78 mmol) in DMF (2 mL) at 20° C. under nitrogen. The resulting mixture was stirred at 20° C. for 30 mins. The reaction was diluted with EtOAc (20 mL) and water. The organics were washed sequentially with saturated NaHCO₃ (20 mL) and saturated brine (20 mL). The organic layer was dried with Na₂SO₄, filtered and evaporated. The crude product was purified by flash silica chromatography, elution gradient 0 to 100% EtOAc in heptane to afford the title compound (133 mg, 48%) as a colourless oil; $^1$H NMR (400 MHz, CDCl$_3$, 30° C.) 1-1.06 (3H, m), 1.10 (3H, d), 1.14-1.17 (3H, m), 1.19 (3H, d), 1.55 (2H, p), 1.63-1.7 (2H, m), 2.18 (2H, t), 2.25-2.41 (1H, m), 2.53 (1H, d), 2.72 (2H, s), 2.74 (OH, s), 3.01 (1H, d), 3.45 (2H, t), 3.5-3.56 (2H, m), 3.59 (1H, s), 3.91 (2H, t), 3.94 (2H, s), 4.11 (2H, q), 5.12 (1H, s), 6.32 (2H, d), 7.01 (2H, td), 7.14 (1H, dd), 7.43 (1H, dt), 7.63 (1H, s); m/z: ES+ [M+H]$^+$ 618.1.

Intermediate 142e: 2-((5-((2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)-5-oxopentyl)oxy)acetic Acid

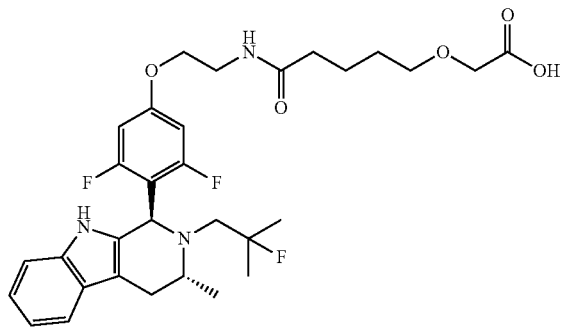 [SMILES: C[C@@H]1Cc2c([nH]c3ccccc23)[C@@H](c2c(F)cc(OCCNC(=O)CCCCOCC(=O)O)cc2F)N1CC(C)(C)F]

The title compound was prepared in a similar manner to Intermediate 72f using the appropriate ester to afford the desired product (125 mg, 98%) as a colourless gum; m/z: ES+ [M+H]$^+$ 590.1.

Example 142: (2S,4R)-1-((S)-2-(2-((5-((2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)-5-oxopentyl)oxy)acetamido)-3,3-dimethylbutanoyl)-4-hydroxy-N-(4-(4-methylthiazol-5-yl)benzyl)pyrrolidine-2-carboxamide HATU (175 mg, 0.46 mmol) was added portionwise to 2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)-5-oxopentyl)oxy)acetic acid (136 mg, 0.23 mmol), (2S,4R)-1-((S)-2-amino-3,3-dimethylbutanoyl)-4-hydroxy-N-(4-(4-methylthiazol-5-yl)benzyl)pyrrolidine-2-carboxamide, HCl (108 mg, 0.23 mmol) and —N-ethyl-N-isopropylpropan-2-amine (0.16 mL, 0.92 mmol) in DMF (5 mL) at 20° C. under nitrogen. The resulting mixture was stirred at 20° C. for 30 mins. The reaction was diluted with EtOAc (20 mL) and water. The organics were washed sequentially with saturated NaHCO$_3$ (20 mL) and saturated brine (20 mL). The organic layer was dried over Na$_2$SO$_4$, filtered and evaporated. The crude product was purified by preparative HPLC (Waters CSH C18 OBD column, 30×100 mm id, 5 micron particle size), using decreasingly polar mixtures of water (containing 0.1% NH$_3$) and MeCN as eluents to afford the title compound (79 mg, 34%); $^1$H NMR (400 MHz, CDCl$_3$, 30° C.) 0.95 (9H, s), 1.09 (3H, d), 1.18 (3H, d), 1.23 (3H, d), 1.6-1.69 (2H, m), 1.75 (2H, tt), 2.08 (1H, dd), 2.25 (2H, t), 2.41 (1H, dd), 2.48 (3H, s), 2.5-2.57 (1H, m), 2.60 (2H, dt), 2.83 (1H, dd), 3.07 (1H, dd), 3.43 (1H, dt), 3.48 (1H, s), 3.54 (2H, dt), 3.63 (2H, dd), 3.73 (1H, d), 3.88-3.96 (3H, m), 4.06 (1H, d), 4.33 (1H, dd), 4.51-4.58 (3H, m), 4.70 (1H, t), 5.20 (1H, s), 6.22 (1H, t), 6.31-6.37 (2H, m), 7.05-7.11 (2H, m), 7.12 (1H, d), 7.19-7.24 (2H, m), 7.31-7.39 (4H, m), 7.5-7.53 (1H, m), 8.28 (1H, s), 8.65 (1H, s); m/z: ES– [M–H]$^-$ 1000.5.

Intermediate 143a: tert-Butyl (2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)carbamate

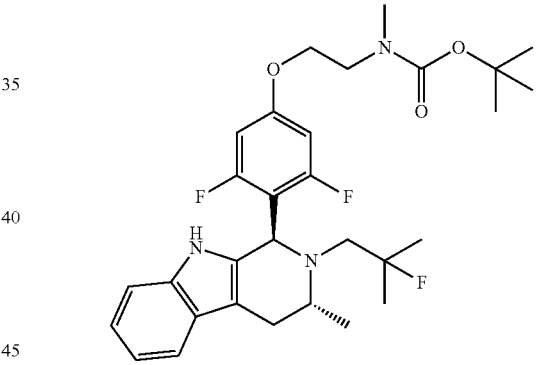

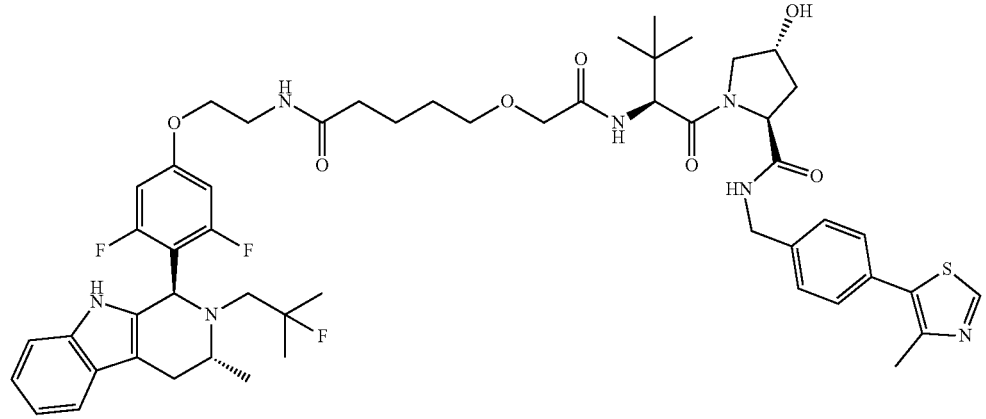 [SMILES: Cc1ncsc1-c1ccc(CNC(=O)[C@@H]2C[C@@H](O)CN2C(=O)[C@@H](NC(=O)COCCCCC(=O)NCCOc2cc(F)c([C@@H]3c4[nH]c5ccccc5c4C[C@@H](C)N3CC(C)(C)F)c(F)c2)C(C)(C)C)cc1]

The title compound was prepared in a similar manner to Intermediate 72e using the appropriate phenol and alcohol to afford the desired product (0.083 g, 24%); m/z: ES− [M−H]⁻ 544.4.

Intermediate 143b: 2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-N-methyl-ethan-1-amine

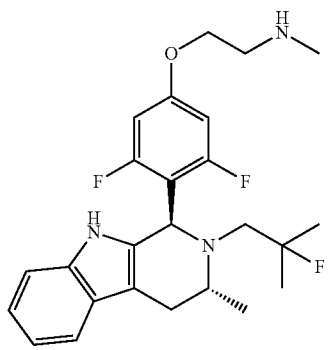 [SMILES: CNCCOc1cc(F)c([C@@H]2c3[nH]c4ccccc4c3C[C@@H](C)N2CC(C)(C)F)c(F)c1]

tert-Butyl (2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)carbamate (83 mg, 0.15 mmol) was stirred in formic acid (1 mL) at 40° C. for 1 hour. The crude product was purified by ion exchange chromatography, using an SCX column. The desired product was eluted from the column using 1M NH₃/MeOH and pure fractions were evaporated to dryness to afford the title compound (61 mg, 90%) as a yellow oil; m/z: ES+ [M+H]⁺ 446.5.

Intermediate 143c: Ethyl 2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)-5-oxopentyl)oxy)acetate

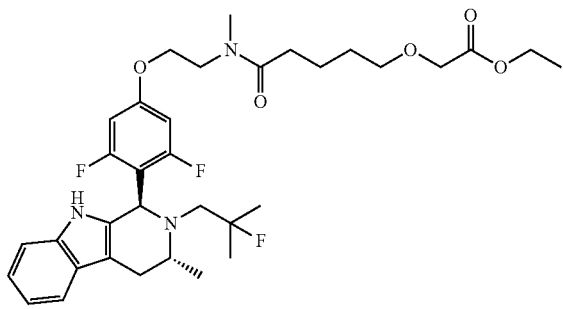 [SMILES: CCOC(=O)COCCCCC(=O)N(C)CCOc1cc(F)c([C@@H]2c3[nH]c4ccccc4c3C[C@@H](C)N2CC(C)(C)F)c(F)c1]

HATU (78 mg, 0.21 mmol) was added portionwise to 2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-N-methylethan-1-amine (61 mg, 0.14 mmol), 5-(2-ethoxy-2-oxoethoxy)pentanoic acid (42 mg, 0.21 mmol) and N-ethyl-N-isopropylpropan-2-amine (0.097 mL, 0.55 mmol) in DMF (5 mL) at 20° C. under nitrogen. The resulting mixture was stirred at 20° C. for 30 mins. The reaction was diluted with EtOAc (20 mL) and water. The organics were washed sequentially with saturated NaHCO₃ (20 mL) and saturated brine (20 mL). The crude product was purified by flash silica chromatography, elution gradient 0 to 100% EtOAc in heptane to afford the title compound (52 mg, 60%) as a yellow oil; m/z: ES− [M−H]⁻ 630.5.

Intermediate 143d: 2-((5-((2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)-5-oxopentyl)oxy)acetic Acid

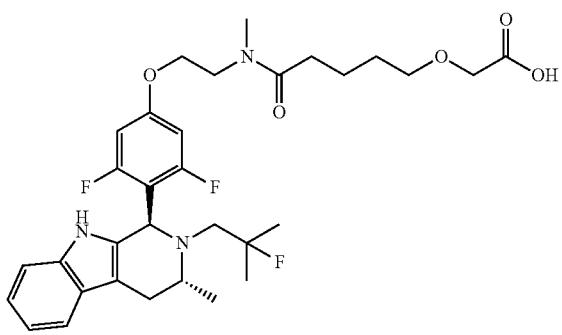 [SMILES: C[C@@H]1Cc2c([nH]c3ccccc23)[C@@H](c2c(F)cc(OCCN(C)C(=O)CCCCOCC(=O)O)cc2F)N1CC(C)(C)F]

The title compound was prepared in a similar manner to Intermediate 72f using the appropriate ester to afford the desired product (50 mg) as a colourless gum that was used in the next step without further purification; m/z: ES− [M−H]⁻ 602.4.

Example 143: (2S,4R)-1-((S)-2-(2-((5-((2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)-5-oxopentyl)oxy)acetamido)-3,3-dimethylbutanoyl)-4-hydroxy-N-(4-(4-methylthiazol-5-yl)benzyl)pyrrolidine-2-carboxamide

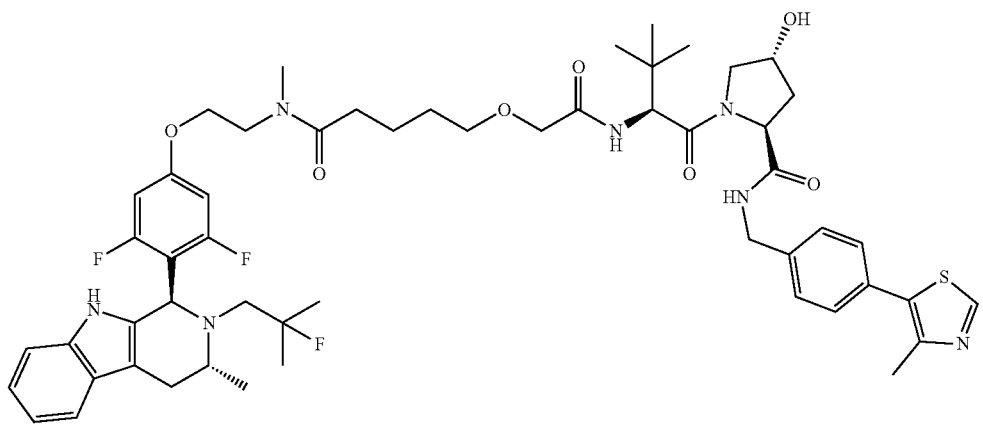 [SMILES: Cc1ncsc1-c1ccc(CNC(=O)[C@@H]2C[C@@H](O)CN2C(=O)[C@@H](NC(=O)COCCCCC(=O)N(C)CCOc2cc(F)c([C@@H]3c4[nH]c5ccccc5c4C[C@@H](C)N3CC(C)(C)F)c(F)c2)C(C)(C)C)cc1]

HATU (58 mg, 0.15 mmol) was added portionwise to 2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)-5-oxopentyl)oxy) acetic acid (46 mg, 0.08 mmol), (2S,4R)-1-((S)-2-amino-3,3-dimethylbutanoyl)-4-hydroxy-N-(4-(4-methylthiazol-5-yl)benzyl)pyrrolidine-2-carboxamide (33 mg, 0.08 mmol) and N-ethyl-N-isopropylpropan-2-amine (0.054 mL, 0.30 mmol) in DMF (2 mL) at 20° C. under nitrogen. The resulting mixture was stirred at 20° C. for 24 h. The reaction was diluted with EtOAc (20 mL) and water (20 mL). The organics were washed sequentially with saturated NaHCO₃ (20 mL) and saturated brine (20 mL). The organic layer was dried with Na₂SO₄, filtered and evaporated to afford crude product. The crude product was purified by preparative HPLC (Waters CSH C18 OBD column, 30×100 mm id, 5 micron particle size), using decreasingly polar mixtures of water (containing 0.1% NH₃) and MeCN as eluents to afford the title compound (16 mg, 21%); ¹H NMR (400 MHz, CDCl₃, 30° C.) 0.94 (9H, s), 1.09 (3H, d), 1.18 (3H, d), 1.23 (3H, d), 1.61-1.77 (4H, m), 2.03-2.15 (1H, m), 2.35 (2H, t), 2.38-2.46 (1H, m), 2.49 (3H, s), 2.60 (3H, dd), 2.84 (1H, dd), 2.96 (1H, s), 3.11 (3H, s), 3.49 (2H, td), 3.59 (1H, dd), 3.62-3.71 (3H, m), 3.80 (1H, dd), 3.92 (1H, dd), 3.99-4.13 (3H, m), 4.34 (1H, dd), 4.46-4.6 (3H, m), 4.75 (1H, t), 5.20 (1H, s), 6.35 (2H, dd), 7.08 (2H, td), 7.13 (1H, d), 7.21 (1H, dd), 7.3-7.4 (5H, m), 7.48-7.54 (1H, m), 8.03 (1H, d), 8.65 (1H, s); m/z: ES− [M]⁻ 1015.4.

Intermediate 144a: Methyl 6-((3,5-difluoro-4-((1R, 3R)-2-(2-fluoro-2-methylpropyl)-3-methyl-2,3,4,9-tetrahydro-1H-pyrido[3,4-b]indol-1-yl)phenyl)carbamoyl)nicotinate

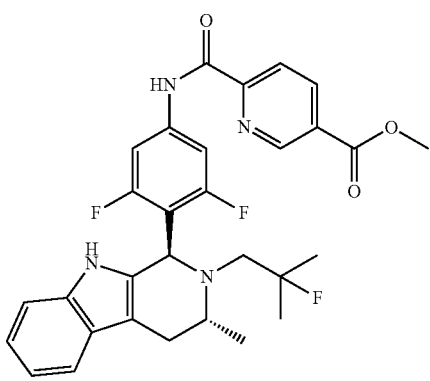 [SMILES: COC(=O)c1ccc(C(=O)Nc2cc(F)c([C@@H]3c4[nH]c5ccccc5c4C[C@@H](C)N3CC(C)(C)F)c(F)c2)nc1]

HATU (981 mg, 2.58 mmol) was added in one portion to 3,5-difluoro-4-((1R,3R)-2-(2-fluoro-2-methylpropyl)-3-methyl-2,3,4,9-tetrahydro-1H-pyrido[3,4-b]indol-1-yl)aniline (500 mg, 1.29 mmol), 5-(methoxycarbonyl)picolinic acid (468 mg, 2.58 mmol) and triethylamine (0.72 mL, 5.17 mmol) in DMF (5 mL) at 20° C. under nitrogen. The resulting mixture was stirred at 20° C. for 18 hours. The reaction mixture was diluted with EtOAc (50 mL), and washed sequentially with water (50 mL) and saturated brine (25 mL). The organic layer was dried over MgSO₄, filtered and evaporated. The crude product was purified by flash silica chromatography, elution gradient 0 to 50% EtOAc in heptane to afford the title compound (554 mg, 78%) as a pale yellow solid; ¹H NMR (400 MHz, CDCl₃, 30° C.) 1.13 (3H, s), 1.18 (3H, s), 1.27 (3H, d), 2.42 (1H, s), 2.63 (1H, d), 2.88 (1H, d), 3.11 (1H, d), 3.71 (1H, s), 4.01 (3H, s), 5.28 (1H, s), 7.07-7.15 (2H, m), 7.23 (1H, s), 7.38 (2H, d), 7.44 (1H, s), 7.53 (1H, d), 8.36 (1H, d), 8.52 (1H, dd), 9.16-9.22 (1H, m), 10.06 (1H, s); m/z: ES− [M−H]⁻ 549.3.

Intermediate 144b: N-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)-5-(hydroxymethyl)picolinamide

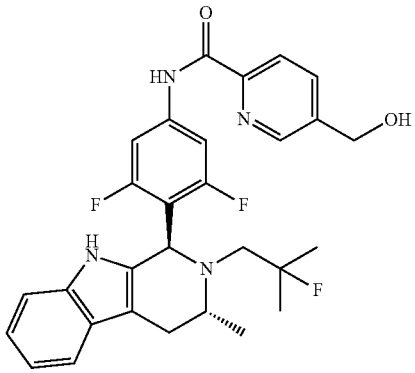 [SMILES: C[C@@H]1Cc2c([nH]c3ccccc23)[C@@H](c2c(F)cc(NC(=O)c3ccc(CO)cn3)cc2F)N1CC(C)(C)F]

A 1 M solution of lithium aluminum hydride in THF (0.40 mL, 0.40 mmol) was added dropwise to a solution of methyl 6-((3,5-difluoro-4-((1R,3R)-2-(2-fluoro-2-methylpropyl)-3-methyl-2,3,4,9-tetrahydro-1H-pyrido[3,4-b]indol-1-yl)phenyl)carbamoyl)nicotinate (220 mg, 0.40 mmol) in anhydrous THF (20 mL) at 0° C. over a period of 2 minutes under nitrogen. The resulting mixture was stirred at 0° C. for 10 minutes. The reaction was quenched with careful dropwise addition of water (0.02 mL), 2M NaOH solution (0.04 mL) and water (0.06 mL). The mixture was stirred for 5 minutes. The solids were removed by filtration and the filtrate was evaporated to dryness. The crude product was purified by flash silica chromatography, elution gradient 0 to 100% EtOAc in heptane to afford the title compound (202 mg, 97%) as a cream solid; ¹H NMR (400 MHz, CDCl₃, 30° C.) 1.11 (3H, d), 1.19 (3H, d), 1.23 (3H, d), 1.91 (1H, t), 2.42 (1H, dd), 2.62 (1H, dd), 2.89 (1H, dd), 3.11 (1H, dd), 3.62-3.76 (1H, m), 4.86 (2H, d), 5.26 (1H, s), 7.06-7.15 (2H, m), 7.24 (1H, dd), 7.36 (2H, d), 7.46 (1H, s), 7.52 (1H, dd), 7.93 (1H, dd), 8.26 (1H, d), 8.59 (1H, d), 10.06 (1H, s); m/z: ES− [M−H]⁻ 521.3.

Intermediate 144c: Ethyl 2-((6-((3,5-difluoro-4-((1R,3R)-2-(2-fluoro-2-methylpropyl)-3-methyl-2,3,4,9-tetrahydro-1H-pyrido[3,4-b]indol-1-yl)phenyl)carbamoyl)pyridin-3-yl)methoxy)acetate

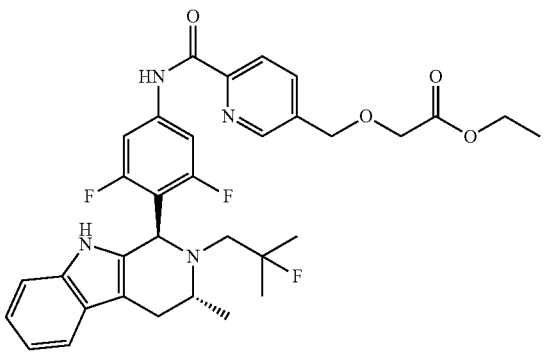 [SMILES: CCOC(=O)COCc1ccc(C(=O)Nc2cc(F)c([C@@H]3c4[nH]c5ccccc5c4C[C@@H](C)N3CC(C)(C)F)c(F)c2)nc1]

The title compound was prepared in a similar manner to Intermediate 72c using the appropriate alcohol to afford the desired product (62 mg, 27%) an orange gum; m/z: ES− [M−H]⁻ 607.4.

Intermediate 144d: 2-((6-((3,5-Difluoro-4-((1R,3R)-2-(2-fluoro-2-methylpropyl)-3-methyl-2,3,4,9-tetrahydro-1H-pyrido[3,4-b]indol-1-yl)phenyl)carbamoyl)pyridin-3-yl)methoxy)acetic Acid

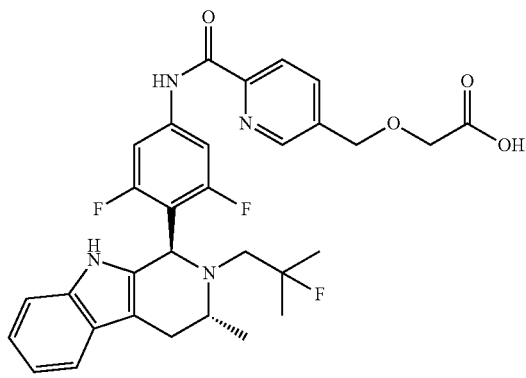 [SMILES: C[C@@H]1Cc2c([nH]c3ccccc23)[C@@H](c2c(F)cc(NC(=O)c3ccc(COCC(=O)O)cn3)cc2F)N1CC(C)(C)F]

The title compound was prepared in a similar manner to Intermediate 72f using the appropriate ester to afford the desired product (30 mg); m/z: ES− [M−H]⁻ 579.3.

Example 144: N-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)-5-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)methyl)picolinamide

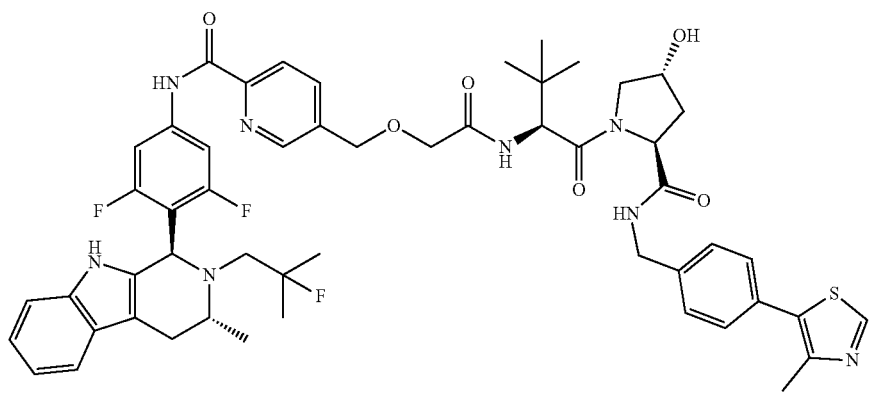 [SMILES: Cc1ncsc1-c1ccc(CNC(=O)[C@@H]2C[C@@H](O)CN2C(=O)[C@@H](NC(=O)COCc2ccc(C(=O)Nc3cc(F)c([C@@H]4c5[nH]c6ccccc6c5C[C@@H](C)N4CC(C)(C)F)c(F)c3)nc2)C(C)(C)C)cc1]

HATU (39 mg, 0.10 mmol) was added portionwise to 2-((6-((3,5-difluoro-4-((1R,3R)-2-(2-fluoro-2-methylpropyl)-3-methyl-2,3,4,9-tetrahydro-1H-pyrido[3,4-b]indol-1-yl)phenyl)carbamoyl)pyridin-3-yl)methoxy)acetic acid (30 mg, 0.05 mmol), (2S,4R)-1-((S)-2-amino-3,3-dimethylbutanoyl)-4-hydroxy-N-(4-(4-methylthiazol-5-yl)benzyl)pyrrolidine-2-carboxamide (22 mg, 0.05 mmol) and N-ethyl-N-isopropylpropan-2-amine (0.037 mL, 0.21 mmol) in DMF (5 mL) at 20° C. under nitrogen. The resulting mixture was stirred at 20° C. for 1 hour. The reaction was diluted with EtOAc (20 mL) and water (20 mL). The organics were washed sequentially with saturated NaHCO₃ (20 mL) and saturated brine (20 mL). The organic layer was dried over Na₂SO₄, filtered and evaporated. The product was purified by SFC to afford the title compound (11 mg, 21%) as a yellow solid; ¹H NMR (400 MHz, CDCl₃, 30° C.) 0.95 (9H, s), 1.12 (3H, d), 1.19 (3H, d), 1.24 (3H, d), 2.12 (1H, dd), 2.35-2.45 (1H, m), 2.48 (3H, s), 2.53-2.67 (3H, m), 2.89 (1H, dd), 3.12 (1H, d), 3.63 (1H, dd), 3.70 (1H, d), 3.97-4.16 (3H, m), 4.34 (1H, dd), 4.5-4.63 (3H, m), 4.71 (3H, d), 5.27 (1H, s), 7.06-7.16 (3H, m), 7.18 (1H, d), 7.21-7.25 (1H, m), 7.32 (2H, d), 7.34-7.39 (4H, m), 7.49-7.57 (1H, m), 7.86-7.93 (2H, m), 8.28 (1H, d), 8.60 (1H, d), 8.62 (1H, s), 10.01 (1H, s); m/z: ES− [M−H]⁻ 991.5.

Intermediate 145a: Methyl 6-((4-(benzyloxy)butyl)(tert-butoxycarbonyl)amino)hexanoate

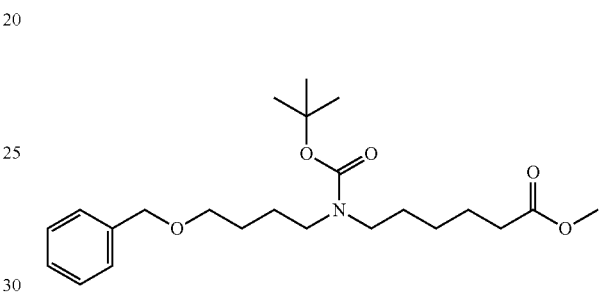

Methyl 6-aminohexanoate, HCl (1.51 g, 8.30 mmol) and 4-(benzyloxy)butanal (0.74 g, 4.15 mmol) were dissolved in 1,2-dichloroethane (10 mL) and stirred for 30 mins. Sodium triacetoxyhydroborate (1.76 g, 8.30 mmol) was added and the reaction stirred overnight. The reaction mixture was quenched with saturated NH₄Cl (20 mL), extracted with DCM (2×20 mL). The organic layer washed with brine (20 mL) and passed through a phase separating cartridge. To the resulting DCM solution, di-tert-butyl dicarbonate (1.812 g, 8.30 mmol), triethylamine (1.751 mL, 12.46 mmol) and DMAP (0.025 g, 0.21 mmol) were added and the reaction stirred for 30 mins. The reaction mixture was diluted with water (50 mL) and passed through a phase separating cartridge. The crude product was purified by flash silica chromatography, elution gradient 0 to 100% EtOAc in heptane to afford the title compound (0.613 g, 36%) as a colourless oil; ¹H NMR (400 MHz, CDCl₃, 30° C.) 1.28

(2H, tt), 1.44 (9H, s), 1.51 (2H, dq), 1.59 (2H, d), 1.6-1.62 (2H, m), 1.62-1.69 (2H, m), 2.30 (2H, ddt), 3.16 (3H, s), 3.45-3.52 (2H, m), 3.66 (3H, d), 4.46-4.51 (3H, m), 7.3-7.35 (5H, m); m/z: ES+ [M+H]+ 408.4.

Intermediate 145b: Methyl 6-((tert-butoxycarbonyl)(4-hydroxybutyl)amino)hexanoate

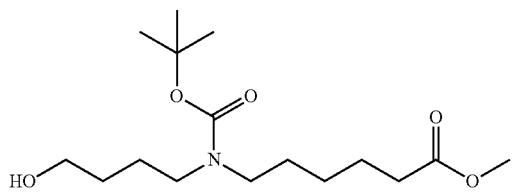 [SMILES: COC(=O)CCCCCN(CCCCO)C(=O)OC(C)(C)C]

The title compound was prepared in a similar manner to Intermediate 72d using the appropriate benzyl ether to afford the desired product (0.413 g, 87%) as a colourless oil; $^1$H NMR (400 MHz, CDCl$_3$, 30° C.) 1.24 (1H, t), 1.26-1.34 (3H, m), 1.45 (9H, s), 1.5-1.58 (4H, m), 1.6-1.71 (4H, m), 2.31 (2H, t), 3.17 (3H, dd), 3.64 (1H, d), 3.67 (3H, s), 3.68-3.76 (1H, m); m/z: ES+ [M+H]+ 318.3.

Intermediate 145c: Methyl 6-((tert-butoxycarbonyl)(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butyl)amino)hexanoate

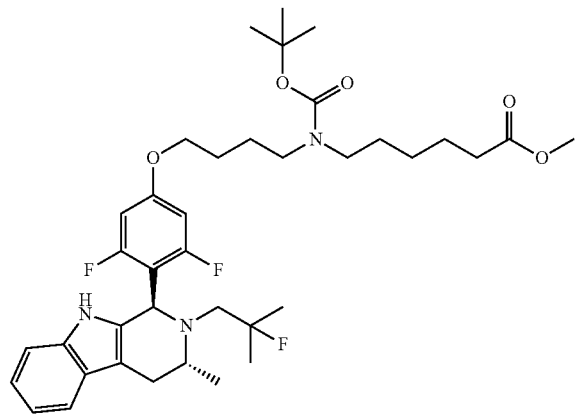 [SMILES: COC(=O)CCCCCN(CCCCOc1cc(F)c([C@@H]2c3[nH]c4ccccc4c3C[C@@H](C)N2CC(C)(C)F)c(F)c1)C(=O)OC(C)(C)C]

The title compound was prepared in a similar manner to Intermediate 72e using the appropriate phenol and alcohol to afford the desired product (262 mg, 45%); $^1$H NMR (400 MHz, CDCl$_3$, 30° C.) 1.10 (3H, d), 1.18 (3H, d), 1.23 (3H, d), 1.28-1.34 (2H, m), 1.45 (9H, s), 1.48-1.54 (2H, m), 1.55 (3H, s), 1.65 (4H, dq), 1.74 (2H, q), 2.31 (2H, td), 2.32-2.46 (1H, m), 2.60 (1H, dd), 2.86 (1H, dd), 3.09 (1H, dd), 3.13-3.19 (2H, m), 3.22 (1H, s), 3.66 (4H, d), 3.92 (2H, t), 5.01 (OH, s), 5.18 (1H, s), 6.35-6.42 (2H, m), 7.05-7.14 (2H, m), 7.18-7.24 (1H, m), 7.50 (2H, dt); m/z: ES– [M–H]– 686.6.

Intermediate 145d: 6-((tert-Butoxycarbonyl)(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butyl)amino)hexanoic Acid

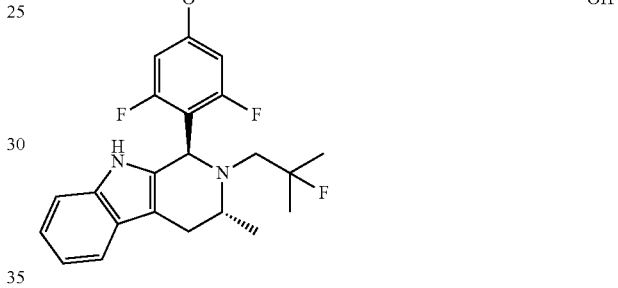

The title compound was prepared in a similar manner to Intermediate 72f using the appropriate ester to afford the desired product (186 mg, 73%); m/z: ES– [M–H]– 672.4.

Example 145: (2S,4R)-1-((S)-2-(6-((4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butyl)amino)hexanamido)-3,3-dimethylbutanoyl)-4-hydroxy-N-(4-(4-methylthiazol-5-yl)benzyl)pyrrolidine-2-carboxamide

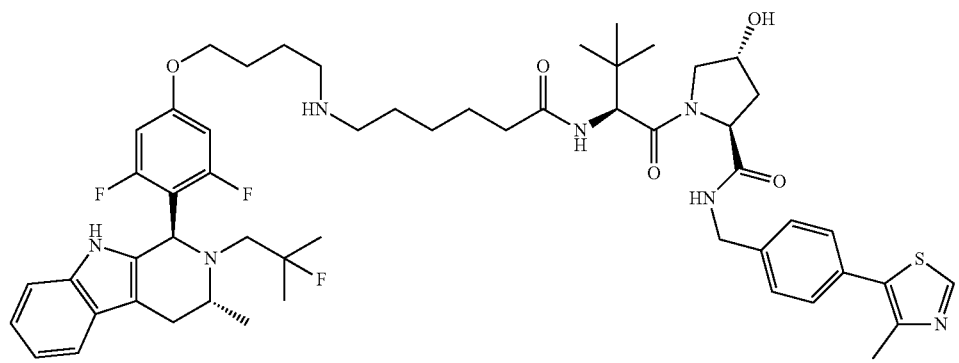 [SMILES: Cc1ncsc1-c1ccc(CNC(=O)[C@@H]2C[C@@H](O)CN2C(=O)[C@@H](NC(=O)CCCCCNCCCCOc2cc(F)c([C@@H]3c4[nH]c5ccccc5c4C[C@@H](C)N3CC(C)(C)F)c(F)c2)C(C)(C)C)cc1]

HATU (210 mg, 0.55 mmol) was added portionwise to 6-((tert-butoxycarbonyl)(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butyl)amino)hexanoic acid (186 mg, 0.28 mmol), (2S,4R)-1-((S)-2-amino-3,3-dimethylbutanoyl)-4-hydroxy-N-(4-(4-methylthiazol-5-yl)benzyl)pyrrolidine-2-carboxamide, 2HCl (139 mg, 0.28 mmol) and N-ethyl-N-isopropylpropan-2-amine (0.20 mL, 1.10 mmol) in DMF (5 mL) at 20° C. under nitrogen. The resulting mixture was stirred at 20° C. for 24 hours. The reaction was diluted with EtOAc (20 mL) and water (20 mL). The organics were washed sequentially with saturated NaHCO₃ (20 mL) and saturated brine (20 mL). The organic layer was dried over Na₂SO₄, filtered and evaporated. The residue was dissolved in formic acid (2 mL), warmed to 40° C. and stirred at this temperature for 2 hours. The crude product was purified by ion exchange chromatography, using an SCX column. The desired product was eluted from the column using 1M NH₃/MeOH. The product was purified by preparative HPLC (Waters XSelect CSH C18 ODB column, 5μ silica, 30 mm diameter, 100 mm length), using decreasingly polar mixtures of water (containing 0.1% formic acid) and MeCN as eluents. The product was further purified by ion exchange chromatography, using an SCX column. The desired product was eluted from the column using 1M NH₃/MeOH and pure fractions were evaporated to dryness to afford the title compound (95 mg, 35%) as a yellow gum. $^1$H NMR (400 MHz, CDCl3, 30° C.) 0.92 (9H, s), 1.09 (3H, d), 1.17 (3H, d), 1.23 (3H, d), 1.33 (2H, s), 1.48 (2H, s), 1.57 (1H, d), 1.66 (4H, s), 1.78 (4H, d), 2.05-2.13 (1H, m), 2.13-2.2 (1H, m), 2.26 (1H, dt), 2.40 (2H, dd), 2.50 (3H, s), 2.56-2.63 (3H, m), 2.66 (2H, t), 2.85 (1H, dd), 3.08 (1H, d), 3.54 (1H, dd), 3.67 (1H, d), 3.91 (2H, t), 4.04 (1H, d), 4.33 (1H, dd), 4.46 (1H, s), 4.5-4.62 (2H, m), 4.69 (1H, t), 5.19 (1H, s), 6.15 (1H, s), 6.36 (2H, d), 7.04-7.12 (2H, m), 7.17-7.23 (1H, m), 7.35 (4H, q), 7.51 (1H, dd), 7.93 (1H, s), 8.66 (1H, s); m/z: ES− [M−H]⁻ 984.7.

Intermediate 146a: Methyl 6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)nicotinate

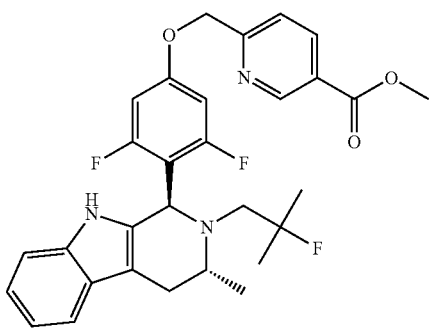 [SMILES: COC(=O)c1ccc(COc2cc(F)c([C@@H]3c4[nH]c5ccccc5c4C[C@@H](C)N3CC(C)(C)F)c(F)c2)nc1]

The title compound was prepared in a similar manner to Intermediate 72e using the appropriate phenol and alcohol to afford the desired product (0.511 g, 74%); $^1$H NMR (400 MHz, CDCl₃, 30° C.) 1.10 (3H, d), 1.17 (3H, d), 1.21-1.25 (3H, m), 2.39 (1H, dd), 2.60 (1H, dd), 2.85 (1H, dd), 3.08 (1H, dd), 3.66 (1H, d), 3.97 (3H, s), 5.20 (3H, s), 6.45-6.54 (2H, m), 7.05-7.15 (2H, m), 7.18-7.24 (1H, m), 7.40 (1H, s), 7.51 (1H, dd), 7.57 (1H, dd), 8.34 (1H, dd), 9.19 (1H, dd); m/z: ES+ [M+H]⁺ 538.3.

Intermediate 146b: (6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methanol

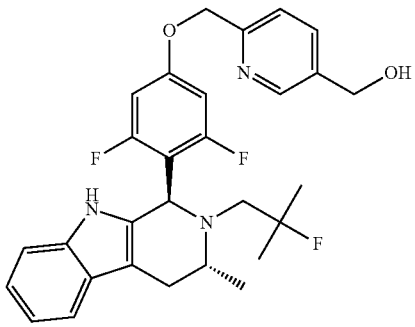 [SMILES: C[C@@H]1Cc2c([nH]c3ccccc23)[C@@H](c2c(F)cc(OCc3ccc(CO)cn3)cc2F)N1CC(C)(C)F]

A 1 M solution of lithium aluminum hydride in THF (1.24 mL, 1.24 mmol) was added dropwise to a solution of methyl 6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)nicotinate (511 mg, 0.95 mmol) in THF (20 mL) at 0° C. over a period of 2 minutes under nitrogen. The resulting mixture was stirred at 0° C. for 30 minutes. The reaction was quenched with careful dropwise addition of water (0.02 mL), 2M NaOH solution (0.04 mL) and water (0.06 mL). The mixture was stirred for 5 minutes. The solids were removed by filtration and the filtrate was evaporated. The product was purified by flash silica chromatography, elution gradient 0 to 70% EtOAc in heptane to afford the title compound (277 mg, 57%) as a colourless gum; $^1$H NMR (400 MHz, CDCl₃, 30° C.) 1.10 (3H, d), 1.17 (3H, d), 1.23 (3H, d), 1.77 (1H, s), 2.39 (1H, dd), 2.60 (1H, d), 2.78-2.92 (1H, m), 3.08 (1H, d), 3.68 (1H, d), 4.76 (2H, d), 5.15 (2H, s), 5.19 (1H, s), 6.45-6.57 (2H, m), 7.05-7.13 (2H, m), 7.22 (1H, dd), 7.41 (1H, s), 7.44-7.54 (2H, m), 7.77 (1H, dd), 8.59 (1H, d); m/z: ES− [M−H]⁻ 508.3.

Intermediate 146c: 6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)nicotinaldehyde

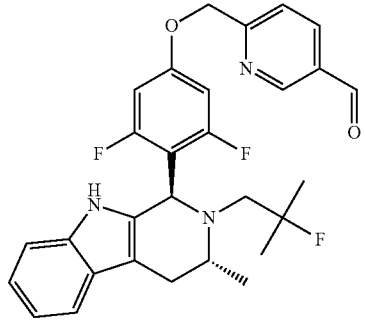 [SMILES: C[C@@H]1Cc2c([nH]c3ccccc23)[C@@H](c2c(F)cc(OCc3ccc(C=O)cn3)cc2F)N1CC(C)(C)F]

Manganese(IV) oxide (473 mg, 5.44 mmol) was added in one portion to (6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methanol (277 mg, 0.54 mmol) in DCM (10 mL) at 20° C. under air. The resulting suspension was stirred at 20° C. for 1 hour. The reaction mixture was filtered through celite, washed with DCM (10 mL) and the filtrate evaporated to afford the title compound (277 mg, 100%) as a colourless gum; ¹H NMR (400 MHz, CDCl₃, 30° C.) 1.10 (3H, d), 1.18 (3H, d), 1.23 (3H, d), 2.40 (1H, dd), 2.60 (1H, ddd), 2.85 (1H, dd), 3.03-3.12 (1H, m), 3.61-3.7 (1H, m), 5.22 (3H, d), 6.45-6.55 (2H, m), 7.05-7.15 (2H, m), 7.18-7.24 (1H, m), 7.42 (1H, s), 7.48-7.54 (1H, m), 7.67 (1H, d), 8.22 (1H, dd), 9.05 (1H, dd), 10.12 (1H, s); m/z: ES+ [M+H]⁺ 508.3.

Example 146: ((2S,4R)-1-((S)-2-(2-(((6-((3,5-Difluoro-4-((1R,3R)-2-(2-fluoro-2-methylpropyl)-3-methyl-2,3,4,9-tetrahydro-1H-pyrido[34-b]indol-1-yl)phenoxy)methyl)pyridin-3-yl)methyl)amino)acetamido)-3,3-dimethylbutanoyl)-4-hydroxy-N-(4-(4-methylthiazol-5-yl)benzyl)pyrrolidine-2-carboxamide

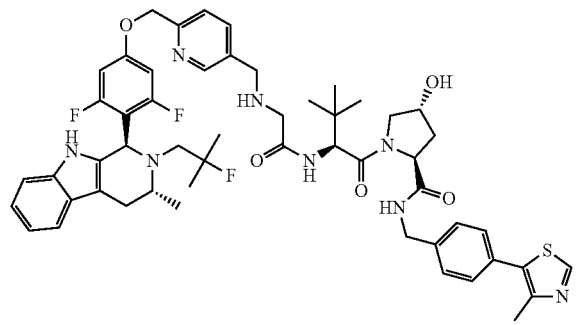 [SMILES: Cc1ncsc1-c1ccc(CNC(=O)[C@@H]2C[C@@H](O)CN2C(=O)[C@@H](NC(=O)CNCc2ccc(COc3cc(F)c([C@@H]4c5[nH]c6ccccc6c5C[C@@H](C)N4CC(C)(C)F)c(F)c3)nc2)C(C)(C)C)cc1]

(2S,4R)-1-((S)-2-(2-aminoacetamido)-3,3-dimethylbutanoyl)-4-hydroxy-N-(4-(4-methylthiazol-5-yl)benzyl)pyrrolidine-2-carboxamide (117 mg, 0.24 mmol) and 6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)nicotinaldehyde (83 mg, 0.16 mmol) were stirred in 1,2-dichloroethane (5 mL) for 30 mins before sodium triacetoxyborohydride (68 mg, 0.32 mmol) was added and the reaction stirred for 18 hours. The reaction mixture was quenched with saturated NH₄Cl (10 mL), the organics separated and the aqueous extracted with DCM (2×25 mL), the combined organics were dried over MgSO₄, filtered and evaporated to afford. The crude product was purified by preparative HPLC (Waters CSH C18 OBD column, 30×100 mm id, 5 micron particle size), using decreasingly polar mixtures of water (containing 0.1% formic acid) and MeCN as eluents. The product was then purified by ion exchange chromatography, using an SCX column. The desired product was eluted from the column using 1M NH₃/MeOH and pure fractions were evaporated to dryness to afford the title compound (43 mg, 27%) as a yellow solid; ¹H NMR (400 MHz, CDCl₃, 30° C.) 0.94 (10H, s), 1.10 (3H, d), 1.17 (3H, d), 1.23 (3H, d), 2.14 (1H, s), 2.39 (1H, dd), 2.48 (3H, s), 2.60 (2H, dd), 2.86 (1H, dd), 3.09 (1H, d), 3.33 (2H, s), 3.49 (1H, s), 3.56-3.71 (2H, m), 3.81 (2H, s), 4.12 (1H, d), 4.33 (1H, d), 4.45 (1H, d), 4.56 (2H, d), 4.74 (1H, t), 5.09 (2H, s), 5.20 (1H, s), 6.46 (2H, d), 7.04-7.14 (2H, m), 7.20 (1H, d), 7.36 (5H, q), 7.43 (1H, d), 7.48-7.55 (1H, m), 7.75 (2H, s), 7.92 (1H, s), 8.56 (1H, s), 8.65 (1H, d); m/z: ES– [M⁻] 978.5.

Intermediate 147a: 8-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)octan-1-ol

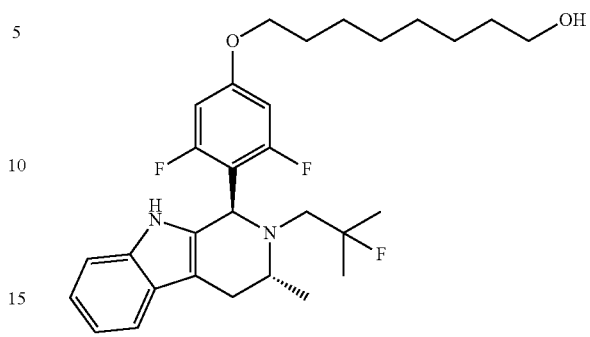

RockPhos Pd G3 (25.8 mg, 0.03 mmol) was added in one portion to a degassed mixture of octane-1,8-diol (540 mg, 3.69 mmol), (1R,3R)-1-(4-bromo-2,6-difluorophenyl)-2-(2-fluoro-2-methylpropyl)-3-methyl-2,3,4,9-tetrahydro-1H-pyrido[3,4-b]indole (300 mg, 0.62 mmol) and cesium carbonate (701 mg, 2.15 mmol) in toluene (7.5 mL) at 20° C. under nitrogen. The resulting mixture was stirred at 80° C. for 18 hours. The reaction was allowed to cool to RT and diluted with EtOAc (50 mL) and water (15 mL). The organic layer was collected and washed with saturated brine solution, dried over MgSO₄, filtered and evaporated to afford crude product as an orange gum. The crude product was purified by flash silica chromatography, elution gradient 0 to 100% EtOAc in heptane to afford the title compound (219 mg, 69%) as a yellow oil; ¹H NMR (400 MHz, CDCl₃, 30° C.) 1.10 (3H, d), 1.15-1.49 (15H, m), 1.52-1.62 (2H, m), 1.76 (2H, p), 2.39 (1H, dd), 2.60 (1H, ddd), 2.86 (1H, dd), 3.05-3.14 (1H, m), 3.58-3.73 (3H, m), 3.90 (2H, t), 5.18 (1H, s), 6.34-6.43 (2H, m), 7.04-7.13 (2H, m), 7.17-7.23 (1H, m), 7.43 (1H, s), 7.47-7.53 (1H, m); m/z: ES+ [M+H]⁺ 517.4.

Intermediate 147b: 8-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)octanal

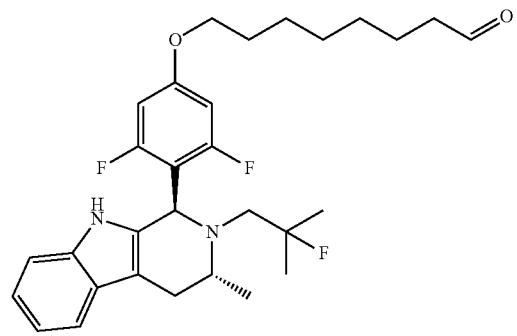 [SMILES: C[C@@H]1Cc2c([nH]c3ccccc23)[C@@H](c2c(F)cc(OCCCCCCCC=O)cc2F)N1CC(C)(C)F]

Sulfur trioxide pyridine complex (68 mg, 0.43 mmol) was added to 8-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)octan-1-ol (100 mg, 0.19 mmol) and triethylamine (0.07 mL, 0.48 mmol) in DCM (0.45 mL)/DMSO (0.45 mL) cooled to 0° C. under nitrogen. The resulting suspension was stirred at 20° C. for 2 hours. The reaction was incomplete and further pyridine compound with sulfur trioxide (190 mg, 1.19 mmol) and triethylamine (0.15 mL, 1.07 mmol) were added in one portion and the solution was stirred at 20° C. for a further 30 minutes. The reaction was diluted with DCM (50 mL) and water (20 mL), then the layers were separated. The organic was washed with brine (20 mL), then dried over a hydrophobic frit and evaporated. The crude product was purified by flash silica chromatography, elution gradient 0 to 50% EtOAc in heptane to afford the title compound (80 mg, 80%) as an orange dry film. ¹H NMR (400 MHz, CDCl₃, 30° C.) 1.10 (3H, d), 1.17 (3H, d), 1.23 (3H, d), 1.3-1.52 (5H, m), 1.64 (3H, p), 1.71-1.81 (2H, m), 2.31-2.46 (3H, m), 2.60 (1H, ddd), 2.86 (1H, dd), 3.03-3.17 (1H, m), 3.62-3.73 (1H, m), 3.90 (2H, t), 5.18 (1H, s), 6.31-6.45 (2H, m), 7.03-7.16 (2H, m), 7.17-7.25 (1H, m), 7.42 (1H, s), 7.48-7.58 (1H, m), 9.76 (1H, t); m/z: ES− [M−H]⁻ 514.0.

Example 147: (2S,4R)-1-((S)-2-(2-((8-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)octyl)amino)acetamido)-3,3-dimethylbutanoyl)-4-hydroxy-N-(4-(4-methylthiazol-5-yl)benzyl)pyrrolidine-2-carboxamide added in one portion and the resulting suspension was stirred at room temperature for 10 minutes. The reaction mixture was diluted with EtOAc (50 mL), and washed sequentially with saturated NaHCO₃ (25 mL) and saturated brine (25 mL). The organic layer was dried with Na₂SO₄, filtered and evaporated. The crude product was purified by preparative HPLC, using decreasingly polar mixtures of water (containing 1% by volume of NH₄OH (28-30% in H₂O)) and MeCN as eluents to afford the title compound (27 mg, 21%) as a white solid. ¹H NMR (400 MHz, CDCl₃, 30° C.) 0.94 (9H, s), 1.10 (3H, d), 1.17 (3H, d), 1.23 (3H, d), 1.29-1.51 (11H, m), 1.74 (2H, p), 2.03-2.16 (1H, m), 2.39 (1H, dd), 2.49 (3H, s), 2.52-2.68 (4H, m), 2.86 (1H, dd), 3.09 (1H, dd), 3.20 (1H, d), 3.27 (1H, d), 3.56 (1H, dd), 3.63-3.73 (1H, m), 3.87 (2H, t), 4.20 (1H, d), 4.32 (1H, dd), 4.40 (1H, d), 4.49-4.53 (1H, m), 4.57 (1H, dd), 4.75 (1H, t), 5.19 (1H, s), 6.3-6.43 (2H, m), 7.02-7.16 (2H, m), 7.19-7.23 (1H, m), 7.31-7.43 (5H,

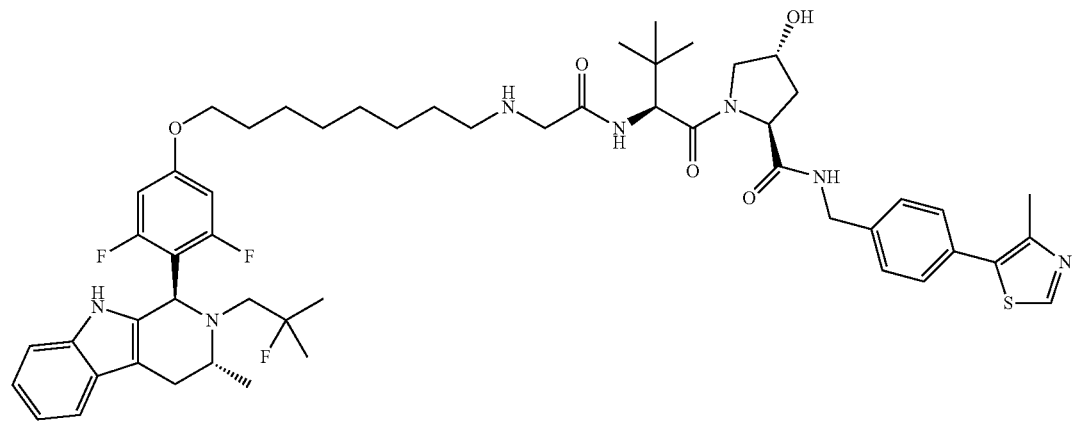 [SMILES: Cc1ncsc1-c1ccc(CNC(=O)[C@@H]2C[C@@H](O)CN2C(=O)[C@@H](NC(=O)CNCCCCCCCCOc2cc(F)c([C@@H]3c4[nH]c5ccccc5c4C[C@@H](C)N3CC(C)(C)F)c(F)c2)C(C)(C)C)cc1]

8-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)octanal (67 mg, 0.13 mmol) was added to a stirred suspension of (2S,4R)-1-((S)-2-(2-aminoacetamido)-3,3-dimethylbutanoyl)-4-hydroxy-N-(4-(4-methylthiazol-5-yl)benzyl)pyrrolidine-2-carboxamide (83 mg, 0.17 mmol) in DCM (1 mL) at room temperature under nitrogen. The resulting suspension was stirred at 20° C. for 30 minutes. Sodium triacetoxyhydroborate (83 mg, 0.39 mmol) was then m), 7.47-7.56 (1H, m), 7.80 (1H, s), 7.96 (1H, d), 8.64 (1H, s); m/z: ES− [M−H]⁻ 984.9.

Example 150: (2S,4R)-1-((S)-2-(6-((4-(3,5-Difluoro-4-((1R,3R)-2-(2-fluoro-2-methylpropyl)-3,9-dimethyl-2,3,4,9-tetrahydro-1H-pyrido[3,4-b]indol-1-yl)phenoxy)butyl)amino)hexanamido)-3,3-dimethylbutanoyl)-4-hydroxy-N-(4-(4-methylthiazol-5-yl)benzyl)pyrrolidine-2-carboxamide

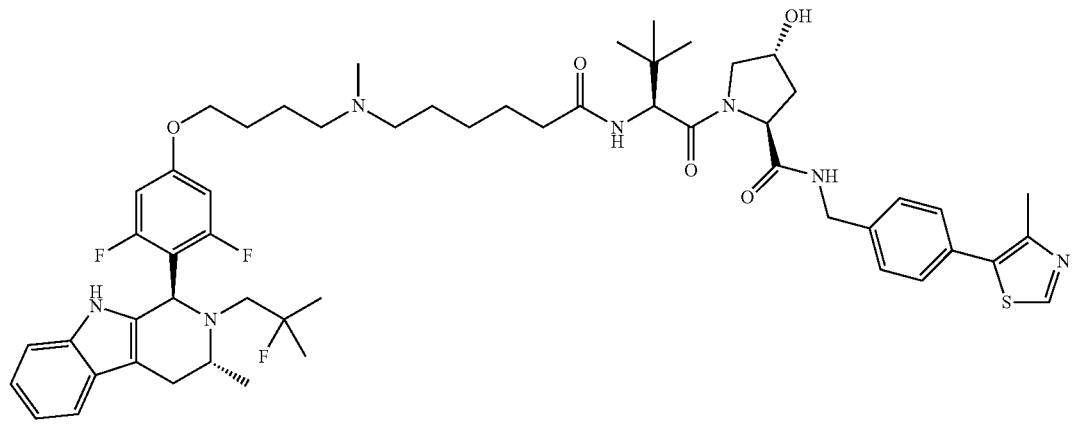 [SMILES: Cc1ncsc1-c1ccc(CNC(=O)[C@@H]2C[C@@H](O)CN2C(=O)[C@@H](NC(=O)CCCCCN(C)CCCCOc2cc(F)c([C@@H]3c4[nH]c5ccccc5c4C[C@@H](C)N3CC(C)(C)F)c(F)c2)C(C)(C)C)cc1]

Sodium triacetoxyborohydride (223 mg, 1.05 mmol) was added in one portion to a stirred solution of (2S,4R)-1-((S)-2-(6-((4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butyl)amino)hexanamido)-3,3-dimethylbutanoyl)-4-hydroxy-N-(4-(4-methylthiazol-5-yl)benzyl)pyrrolidine-2-carboxamide (207 mg, 0.21 mmol) and a solution of 37% formaldehyde in water (0.11 mL, 1.47 mmol) in chloroform (2.83 mL) at 20° C., under nitrogen. The resulting solution was stirred at 20° C. for 18 hours. The reaction mixture was quenched with saturated NaHCO₃ (30 mL), diluted with DCM (50 mL) and stirred at room temperature for 30 minutes. The layers were separated and the aqueous phase was extracted with DCM (3×50 mL). The combined organic phases was dried over a phase separator and concentrated. The crude product was purified twice by preparative HPLC, using decreasingly polar mixtures of water (containing 1% NH₃) and MeCN as eluents. Two sets of fractions containing the desired mass were evaporated to dryness and kept separate. The first fraction contained the isomer where methylation of the indole. The second set of fractions afforded the title compound (10 mg, 5%) as a yellow dry film. ¹H NMR (400 MHz, CDCl₃, 30° C.) 0.91 (9H, s), 1.10 (3H, d), 1.18 (3H, d), 1.23 (3H, d), 1.32 (2H, dd), 1.44 (2H, p), 1.53-1.68 (4H, m), 1.7-1.83 (2H, m), 2-2.11 (2H, m), 2.12-2.22 (5H, m), 2.24-2.41 (5H, m), 2.43-2.55 (4H, m), 2.56-2.65 (1H, m), 2.85 (1H, dd), 3.08 (1H, dd), 3.54 (1H, dd), 3.6-3.76 (1H, m), 3.91 (2H, t), 4.03 (1H, d), 4.32 (1H, dd), 4.41-4.48 (1H, m), 4.49-4.61 (2H, m), 4.68 (1H, t), 5.19 (1H, s), 6.08 (1H, d), 6.31-6.48 (2H, m), 7.01-7.14 (2H, m), 7.18-7.25 (2H, m), 7.31-7.41 (4H, m), 7.47-7.52 (1H, m), 7.90 (1H, s), 8.66 (1H, s); m/z: ES− [M−H]⁻ 999.0.

Intermediate 151a: tert-Butyl (4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)carbamate

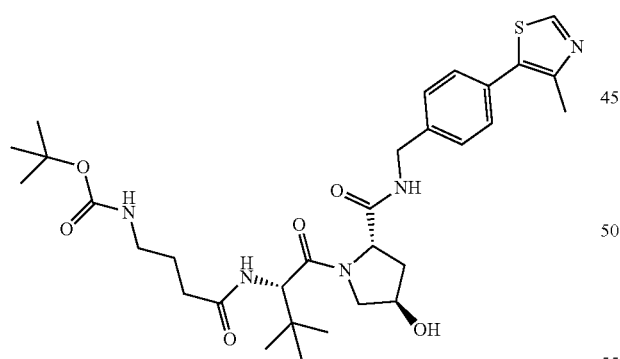

HATU (331 mg, 0.87 mmol) was added in one portion to 4-((tert-butoxycarbonyl)amino)butanoic acid (124 mg, 0.61 mmol), (2S,4R)-1-((S)-2-amino-3,3-dimethylbutanoyl)-4-hydroxy-N-(4-(4-methylthiazol-5-yl)benzyl)pyrrolidine-2-carboxamide (250 mg, 0.58 mmol), 4-((tert-butoxycarbonyl)amino)butanoic acid (124 mg, 0.61 mmol) and N-ethyl-N-isopropylpropan-2-amine (0.30 mL, 1.74 mmol) in DMF (1.6 mL) at 20° C. under nitrogen. The resulting suspension was stirred at 20° C. for 2 hours. The reaction was allowed to cool to RT and diluted with EtOAc (50 mL) and water (20 mL). The organic layer was collected and washed with saturated brine solution (20 mL), dried over MgSO₄, filtered and evaporated. The crude product was purified by flash silica chromatography, elution gradient 0 to 100% (4:1 ethyl acetate/methanol) in heptane to afford the title compound (269 mg, 75%) as a colorless dry film. m/z: ES+ [M+H]⁺ 616.6.

Intermediate 151b: (2S,4R)-1-((S)-2-(4-Aminobutanamido)-3,3-dimethylbutanoyl)-4-hydroxy-N-(4-(4-methylthiazol-5-yl)benzyl)pyrrolidine-2-carboxamide

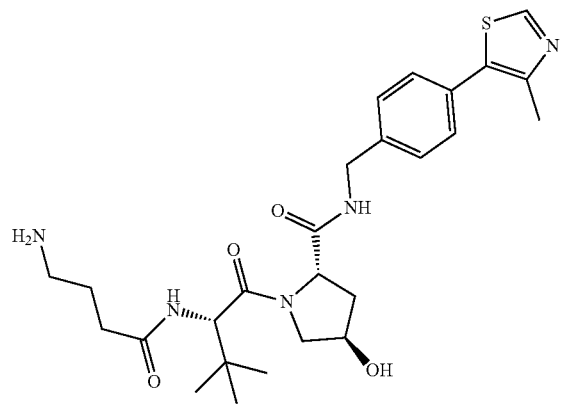 [SMILES: Cc1ncsc1-c1ccc(CNC(=O)[C@@H]2C[C@@H](O)CN2C(=O)[C@@H](NC(=O)CCCN)C(C)(C)C)cc1]

A solution of 4 N hydrogen chloride in dioxane (2.2 mL, 8.8 mmol) was added in one portion to tert-butyl (4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)carbamate (269 mg, 0.44 mmol) under nitrogen. The resulting suspension was stirred at 20° C. for 18 hours. The reaction mixture was evaporated and the crude product was purified by SCX filtration, eluting with 1M NH₃/MeOH to afford the title compound as a white dry film that was used in the next step without further purification. m/z: ES+ [M+H]⁺ 516.6.

Intermediate 151c: 6-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)hexan-1-ol

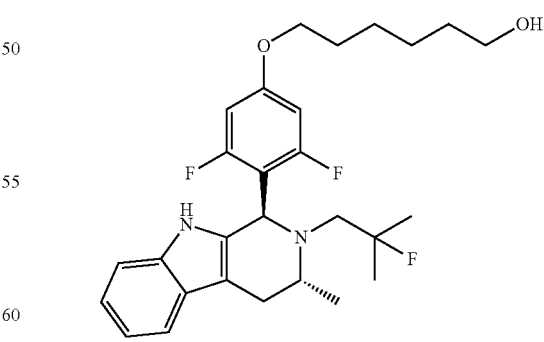

RockPhos Pd G3 (25.8 mg, 0.03 mmol) was added in one portion to a degassed mixture of hexane-1,6-diol (436 mg, 3.69 mmol), (1R,3R)-1-(4-bromo-2,6-difluorophenyl)-2-(2-fluoro-2-methylpropyl)-3-methyl-2,3,4,9-tetrahydro-1H-pyrido[3,4-b]indole (300 mg, 0.62 mmol) and cesium carbonate (701 mg, 2.15 mmol) in toluene (7.5 mL) at 20° C. under nitrogen. The resulting mixture was stirred at 80° C. for 18 hours. The reaction was allowed to cool to RT and diluted with EtOAc (50 mL) and water (15 mL). The organic layer was collected and washed with saturated brine solution (20 mL), dried over MgSO$_4$, filtered and evaporated to afford crude product as an orange gum. The crude product was purified by flash silica chromatography, elution gradient 0 to 80% EtOAc in heptane to afford the title compound (200 mg, 67%) as a yellow oil. $^1$H NMR (400 MHz, CDCl$_3$, 30° C.) 1.10 (3H, d), 1.14-1.37 (7H, m), 1.36-1.53 (4H, m), 1.54-1.67 (2H, m), 1.78 (2H, p), 2.39 (1H, dd), 2.60 (1H, ddd), 2.86 (1H, dd), 3.09 (1H, ddd), 3.6-3.75 (3H, m), 3.91 (2H, t), 5.18 (1H, s), 6.32-6.43 (2H, m), 7.03-7.15 (2H, m), 7.17-7.24 (1H, m), 7.42 (1H, s), 7.46-7.56 (1H, m); m/z: ES+ [M+H]$^+$ 489.4.

Intermediate 151d: 6-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)hexyl 4-methylbenzenesulfonate 4-Methylbenzenesulfonyl chloride (43.5 mg, 0.23 mmol) was added in one portion to 6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexan-1-ol (93 mg, 0.19 mmol) and triethylamine (0.04 mL, 0.29 mmol) in DCM (1 mL) at 20° C. The resulting solution was stirred at 20° C. for 18 hours. The reaction mixture was diluted with DCM (25 mL), and washed sequentially with saturated NH$_4$Cl (10 mL), saturated NaHCO$_3$ (10 mL), water (20 mL) and saturated brine (10 mL). The organic layer was dried with a phase separating cartridge, filtered and evaporated. The crude material was purified by flash silica chromatography, elution gradient 0 to 60% EtOAc in heptane to afford the title compound (67.0 mg, 55%) as a yellow gum. $^1$H NMR (400 MHz, CDCl$_3$, 30° C.) 1.10 (3H, d), 1.17 (3H, d), 1.23 (3H, d), 1.40 (4H, dd), 1.69 (4H, dq), 2.33-2.46 (4H, m), 2.60 (1H, dd), 2.86 (1H, dd), 3.09 (1H, dd), 3.62-3.74 (1H, m), 3.87 (2H, t), 4.04 (2H, t), 5.19 (1H, s), 6.27-6.48 (2H, m), 7.03-7.16 (2H, m), 7.18-7.23 (1H, m), 7.3-7.38 (2H, m), 7.41 (1H, s), 7.48-7.56 (1H, m), 7.71-7.87 (2H, m); m/z: ES+ [M+H]$^+$ 643.5.

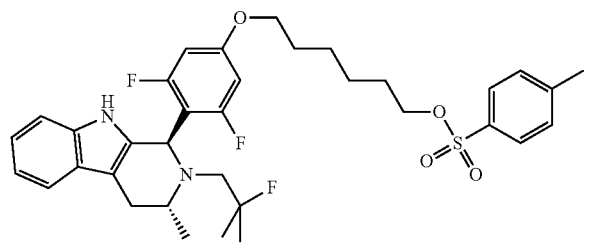 [SMILES: Cc1ccc(S(=O)(=O)OCCCCCCOc2cc(F)c([C@@H]3c4[nH]c5ccccc5c4C[C@@H](C)N3CC(C)(C)F)c(F)c2)cc1]

Example 151: (2S,4R)-1-((S)-2-(4-((6-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)hexyl)amino)butanamido)-3,3-dimethylbutanoyl)-4-hydroxy-N-(4-(4-methylthiazol-5-yl)benzyl)pyrrolidine-2-carboxamide

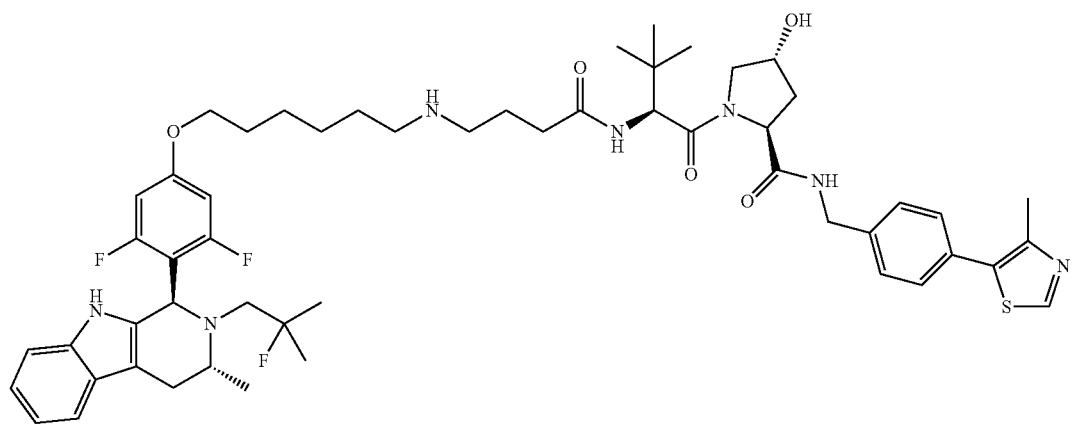 [SMILES: Cc1ncsc1-c1ccc(CNC(=O)[C@@H]2C[C@@H](O)CN2C(=O)[C@@H](NC(=O)CCCNCCCCCCOc2cc(F)c([C@@H]3c4[nH]c5ccccc5c4C[C@@H](C)N3CC(C)(C)F)c(F)c2)C(C)(C)C)cc1]

Potassium carbonate (45 mg, 0.32 mmol) was added to a stirred solution of 6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl 4-methylbenzenesulfonate (69 mg, 0.11 mmol) and ((2S,4R)-1-((S)-2-(4-aminobutanamido)-3,3-dimethylbutanoyl)-4-hydroxy-N-(4-(4-methylthiazol-5-yl)benzyl)pyrrolidine-2-carboxamide (66 mg, 0.13 mmol) in acetonitrile (2.2 mL) at 20° C., under nitrogen. The resulting solution was stirred at 80° C. for 18 hours. The reaction mixture was filtered, concentrated. The crude product was purified by preparative HPLC (Waters XSelect CSH C18 ODB column, 5μ silica, 30 mm diameter, 100 mm length), using decreasingly polar mixtures of water (containing 0.1% formic acid) and MeCN as eluents. Fractions containing the desired compound were evaporated to dryness to afford impure desired product (30 mg). The crude product was purified by preparative HPLC, using decreasingly polar mixtures of water (containing 0.1% formic acid) and MeCN as eluents to afford 14 mg of product. The material was dissolved in MeOH (1 mL) and passed through an SCX column eluting with 1M $NH_3$/MeOH to afford the title compound (14 mg, 13%) as a yellow dry film. $^1$H NMR (400 MHz, $CDCl_3$, 30° C.) 0.93 (9H, s), 1.10 (3H, d), 1.17 (3H, d), 1.23 (3H, d), 1.31-1.58 (7H, m), 1.71-1.84 (6H, m), 2.06-2.14 (1H, m), 2.30 (1H, q), 2.39 (1H, dd), 2.49 (3H, s), 2.56-2.71 (6H, m), 2.85 (1H, dd), 3.03-3.12 (1H, m), 3.52 (1H, dd), 3.62-3.72 (1H, m), 3.88 (2H, t), 4.12 (1H, d), 4.33 (1H, dd), 4.44-4.5 (2H, m), 4.55 (1H, dd), 4.72 (1H, t), 5.19 (1H, s), 6.27-6.41 (2H, m), 6.72-6.83 (1H, m), 7.05-7.13 (2H, m), 7.19-7.23 (1H, m), 7.28-7.39 (5H, m), 7.46-7.57 (1H, m), 7.90 (1H, s), 8.64 (1H, s).

Example 152: (2S,4R)-1-((S)-2-(2-(3-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)acetamido)-3,3-dimethylbutanoyl)-4-hydroxy-N—((S)-1-(4-(4-methylthiazol-5-yl)phenyl)ethyl)pyrrolidine-2-carboxamide

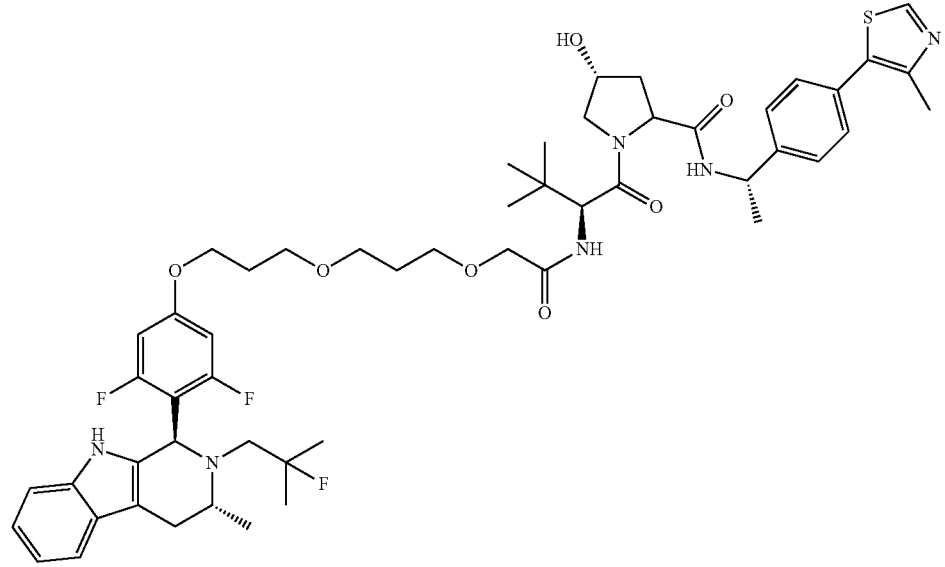 [SMILES: Cc1ncsc1-c1ccc([C@H](C)NC(=O)C2C[C@@H](O)CN2C(=O)[C@@H](NC(=O)COCCCOCCCOc2cc(F)c([C@@H]3c4[nH]c5ccccc5c4C[C@@H](C)N3CC(C)(C)F)c(F)c2)C(C)(C)C)cc1]

HATU (0.101 g, 0.27 mmol) was added portionwise to 2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)acetic acid (0.100 g, 0.18 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (0.079 g, 0.18 mmol) and triethylamine (0.124 ml, 0.89 mmol) in DMF (2.1 ml) at 20° C. under nitrogen. The resulting mixture was stirred at 20° C. for 2 hours. The reaction mixture was purified by preparative HPLC, using decreasingly polar mixtures of water (containing 1% $NH_3$) and MeCN as eluents to afford the title compound (61 mg, 35%) as a beige solid. $^1$H NMR (400 MHz, $CDCl_3$, 30° C.) 1.06 (9H, s), 1.09 (3H, d), 1.18 (3H, d), 1.24 (3H, d), 1.48 (3H, d), 1.81-1.93 (2H, m), 1.96-2.1 (3H, m), 2.42 (1H, dd), 2.51 (3H, s), 2.53-2.63 (3H, m), 2.76-2.88 (1H, m), 3.05 (1H, dd), 3.46-3.69 (9H, m), 3.83 (1H, d), 3.98 (2H, t), 4.05 (1H, d), 4.53 (1H, s), 4.59 (1H, d), 4.75 (1H, t), 5.08 (1H, p), 5.20 (1H, s), 6.29-6.43 (2H, m), 7.03-7.13 (2H, m), 7.16-7.25 (2H, m), 7.32-7.46 (5H, m), 7.48-7.57 (1H, m), 8.55 (1H, s), 8.66 (1H, s); m/z: ES+ [M+H]⁺989.7.

Example 153: (2S,4R)-1-((S)-2-(2-(2-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide

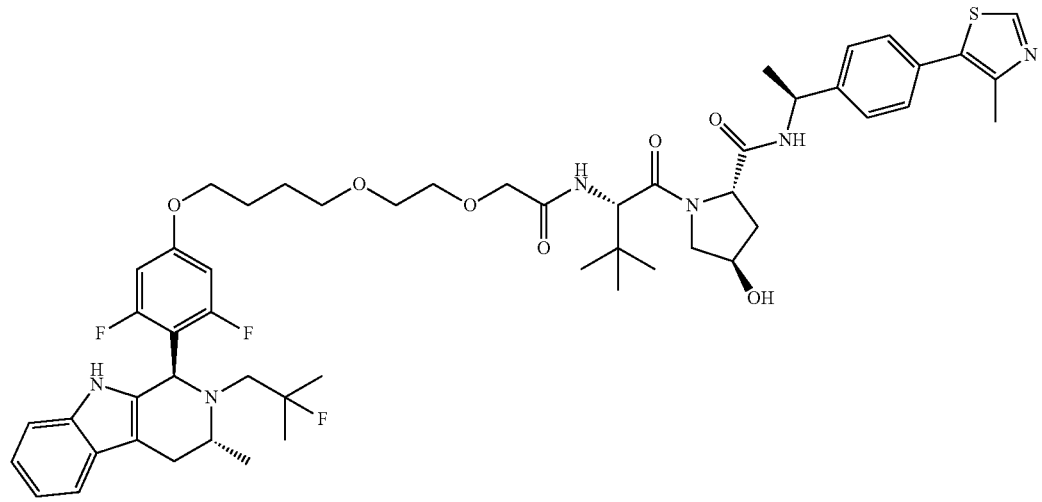 [SMILES: Cc1ncsc1-c1ccc([C@H](C)NC(=O)[C@@H]2C[C@@H](O)CN2C(=O)[C@@H](NC(=O)COCCOCCCCOc2cc(F)c([C@@H]3c4[nH]c5ccccc5c4C[C@@H](C)N3CC(C)(C)F)c(F)c2)C(C)(C)C)cc1]

HATU (165 mg, 0.44 mmol) was added portionwise to 2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)acetic acid (163 mg, 0.29 mmol) in DMF (1.5 mL), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (135 mg, 0.30 mmol) and triethylamine (0.20 mL, 1.45 mmol) in additional DMF (3.4 mL) at 20° C. under nitrogen. The resulting mixture was stirred at 20° C. for 2 hours. The reaction mixture was purified by preparative HPLC, using decreasingly polar mixtures of water (containing 1% NH₃) and MeCN as eluents to the title compound (86 mg, 30%) as a beige solid. ¹H NMR (400 MHz, CDCl₃, 30° C.) 1.07 (9H, s), 1.09 (3H, d), 1.17 (3H, d), 1.22 (3H, d), 1.46 (3H, d), 1.7-1.8 (2H, m), 1.81-1.91 (2H, m), 1.94-2.06 (1H, m), 2.39 (1H, dd), 2.49 (3H, s), 2.51 (1H, d), 2.54-2.64 (2H, m), 2.84 (1H, dd), 3.08 (1H, dd), 3.56 (2H, t), 3.58-3.71 (6H, m), 3.90 (2H, t), 3.94 (1H, d), 4.02 (1H, d), 4.10 (1H, d), 4.47-4.56 (2H, m), 4.73 (1H, t), 5.07 (1H, p), 5.18 (1H, s), 6.28-6.38 (2H, m), 7.05-7.13 (2H, m), 7.2-7.25 (1H, m), 7.29-7.42 (5H, m), 7.44-7.54 (2H, m), 8.11 (1H, s), 8.64 (1H, s); m/z: ES+ [M+H]⁺ 989.8.

Example 154: (2S,4R)-1-((S)-2-(2-(4-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propoxy)butoxy)acetamido)-3,3-dimethylbutanoyl)-4-hydroxy-N—((S)-1-(4-(4-methylthiazol-5-yl)phenyl)ethyl)pyrrolidine-2-carboxamide

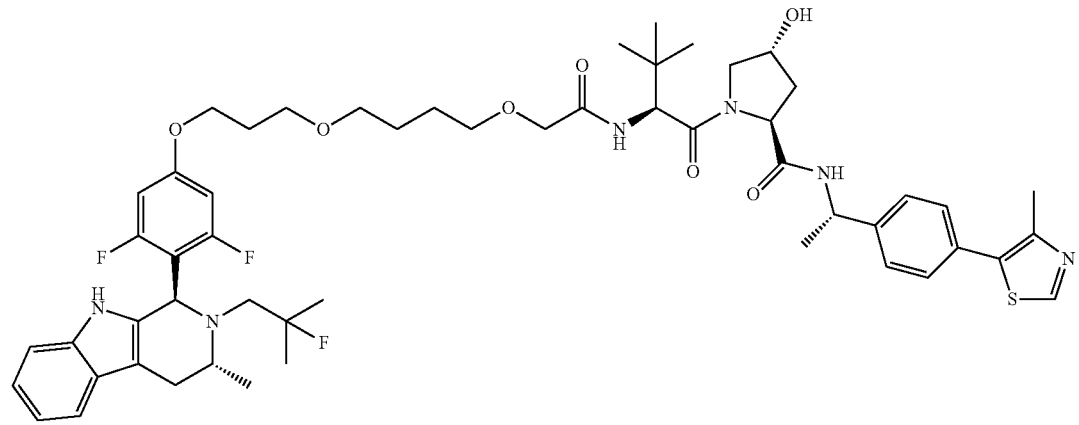 [SMILES: Cc1ncsc1-c1ccc([C@H](C)NC(=O)[C@@H]2C[C@@H](O)CN2C(=O)[C@@H](NC(=O)COCCCCOCCCOc2cc(F)c([C@@H]3c4[nH]c5ccccc5c4C[C@@H](C)N3CC(C)(C)F)c(F)c2)C(C)(C)C)cc1]

HATU (120 mg, 0.32 mmol) was added to a stirred solution of 2-(4-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)butoxy)acetic acid (121 mg, 0.21 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (103 mg, 0.23 mmol) and triethylamine (0.15 mL, 1.1 mmol) in DMF (1.954 mL) at 20° C. under air. The resulting solution was stirred at 20° C. for 3 hours. The crude product was purified by preparative HPLC, using decreasingly polar mixtures of water (containing 1% $NH_3$) and MeCN as eluents to afford the title compound (71 mg, 34%) as a beige solid. $^1$H NMR (400 MHz, $CDCl_3$, 30° C.) 1.06 (9H, s), 1.09 (3H, d), 1.14-1.27 (6H, m), 1.46 (3H, d), 1.6-1.75 (4H, m), 1.95-2.06 (3H, m), 2.34-2.49 (2H, m), 2.51 (3H, s), 2.53-2.64 (2H, m), 2.83 (1H, dd), 3.06 (1H, dd), 3.43-3.52 (4H, m), 3.56 (2H, t), 3.58-3.69 (2H, m), 3.72-3.78 (1H, m), 3.88 (1H, d), 3.98 (2H, t), 4.06-4.13 (1H, m), 4.48-4.6 (2H, m), 4.74 (1H, t), 5.06 (1H, q), 5.20 (1H, s), 7.15-7.23 (2H, m), 6.26-6.48 (2H, m), 7.04-7.12 (2H, m), 7.33-7.46 (5H, m), 7.49-7.57 (1H, m), 8.15 (1H, s), 8.65 (1H, s); m/z: ES+ [M+H]$^+$ 1003.7.

Example 155: (2S,4R)-1-((S)-2-(2-(3-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy)propoxy)acetamido)-3,3-dimethylbutanoyl)-4-hydroxy-N—((S)-1-(4-(4-methylthiazol-5-yl)phenyl)ethyl)pyrrolidine-2-carboxamide HATU (108 mg, 0.29 mmol) was added portionwise to 2-(3-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)propoxy)acetic acid (110 mg, 0.19 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (89 mg, 0.20 mmol) and triethylamine (0.13 mL, 0.95 mmol) in DMF (2.2 mL) at 20° C. under nitrogen. The resulting mixture was stirred at 20° C. for 2 hours. The reaction was incomplete and further HATU (108 mg, 0.29 mmol) and triethylamine (0.13 mL, 0.95 mmol) were added in one portion and the solution was stirred at 20° C. for a further 2 days. The reaction mixture was purified by preparative HPLC, using decreasingly polar mixtures of water (containing 1% $NH_3$) and MeCN as eluents to afford the title compound (26 mg, 14%) as a beige dry film. $^1$H NMR (400 MHz, $CDCl_3$, 30° C.) 1.06 (7H, s), 1.09 (3H, d), 1.17 (3H, d), 1.23 (3H, d), 1.47 (3H, d), 1.66-1.94 (9H, m), 1.97-2.07 (1H, m), 2.31-2.46 (1H, m), 2.47-2.65 (5H, m), 2.85 (1H, dd), 3.08 (1H, dd), 3.48 (2H, t), 3.52 (2H, t), 3.56-3.63 (3H, m), 3.65-3.72 (1H, m), 3.82-3.99 (4H, m), 4.08 (1H, dd), 4.50 (1H, s), 4.55 (1H, d), 4.72 (1H, t), 5.07 (1H, p), 5.19 (1H, s), 6.31-6.38 (2H, m), 7.03-7.13 (2H, m), 7.16-7.24 (2H, m), 7.33-7.46 (5H, m), 7.47-7.54 (1H, m), 8.05 (1H, s), 8.64 (1H, s); m/z: ES+ [M+H]$^+$ 1003.6.

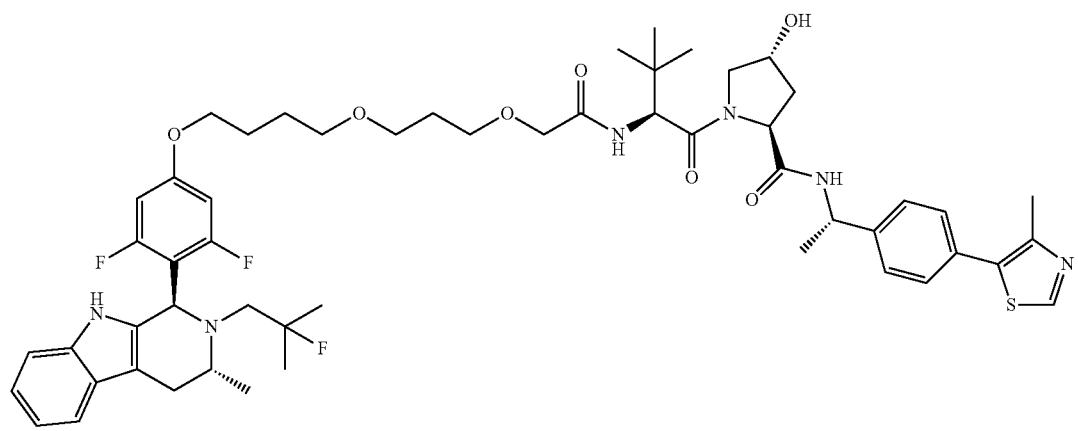 [SMILES: Cc1ncsc1-c1ccc([C@H](C)NC(=O)[C@@H]2C[C@@H](O)CN2C(=O)[C@@H](NC(=O)COCCCOCCCCOc2cc(F)c([C@@H]3c4[nH]c5ccccc5c4C[C@@H](C)N3CC(C)(C)F)c(F)c2)C(C)(C)C)cc1]

Example 156: (2S,4R)-1-((S)-2-(2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide

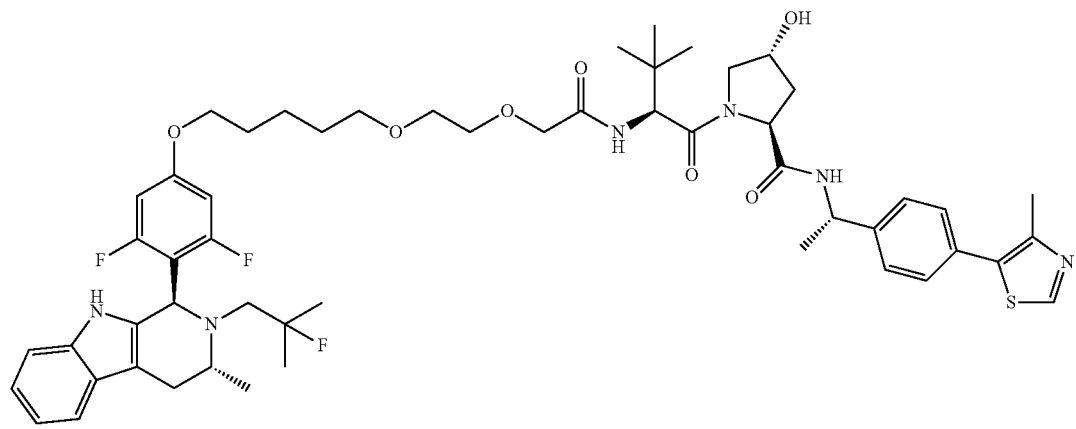 [SMILES: Cc1ncsc1-c1ccc([C@H](C)NC(=O)[C@@H]2C[C@@H](O)CN2C(=O)[C@@H](NC(=O)COCCOCCCCCOc2cc(F)c([C@@H]3c4[nH]c5ccccc5c4C[C@@H](C)N3CC(C)(C)F)c(F)c2)C(C)(C)C)cc1]

HATU (0.125 g, 0.33 mmol) was added portionwise to 2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)ethoxy)acetic acid (0.126 g, 0.22 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide, HCl (0.110 g, 0.23 mmol) and triethylamine (0.15 ml, 1.09 mmol) in DMF (2.033 ml) at 20° C. under nitrogen. The resulting mixture was stirred at 20° C. for 2 hours. The reaction mixture was purified by preparative HPLC, using decreasingly polar mixtures of water (containing 1% $NH_3$) and MeCN as eluents to afford impure title compound. The residue was dissolved in MeOH (2 mL) and repurified by SFC chromatography, eluting with 10-40% $CO_2$ in MeOH (0.1% $NH_3$-MeOH) to afford the title compound (87 mg, 40%) as a beige solid. $^1$H NMR (400 MHz, $CDCl_3$, 30° C.) 1.07 (9H, d), 1.10 (3H, s), 1.17 (3H, d), 1.22 (3H, d), 1.46 (3H, d), 1.48-1.55 (2H, m), 1.61-1.71 (2H, m), 1.73-1.84 (2H, m), 1.94-2.06 (1H, m), 2.39 (1H, dd), 2.49 (3H, s), 2.52-2.65 (3H, m), 2.85 (1H, dd), 3.08 (1H, dd), 3.52 (2H, t), 3.55-3.72 (6H, m), 3.86 (2H, t), 3.97 (1H, d), 4.03 (1H, d), 4.11 (1H, d), 4.47-4.57 (2H, m), 4.74 (1H, t), 5.07 (1H, p), 5.18 (1H, s), 6.29-6.37 (2H, m), 7.02-7.14 (2H, m), 7.18-7.24 (1H, m), 7.3-7.43 (5H, m), 7.47-7.56 (2H, m), 8.05 (1H, s), 8.64 (1H, s); m/z: ES– [M–H]⁻ 1002.0.

Example 157: (2S,4R)-1-((S)-2-((5-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)pentyl)oxy)acetamido)-3,3-dimethylbutanoyl)-4-hydroxy-N—((S)-1-(4-(4-methylthiazol-5-yl)phenyl)ethyl)pyrrolidine-2-carboxamide

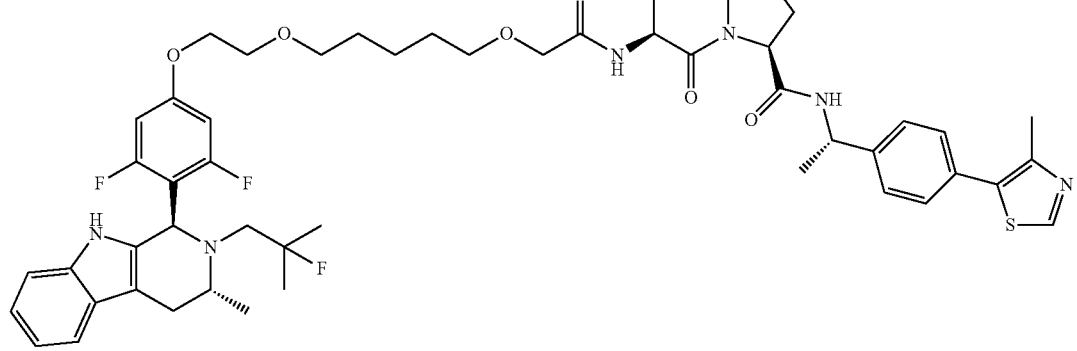

HATU (57.0 mg, 0.15 mmol) was added in one portion to a stirred solution of 2-((5-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)pentyl)oxy)acetic acid (57.7 mg, 0.10 mmol), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (53.4 mg, 0.12 mmol) and triethylamine (0.070 mL, 0.50 mmol) in DMF (0.93 mL) at 20° C. under air. The resulting solution was stirred at 20° C. for 2 hours. The crude product was purified by preparative HPLC, using decreasingly polar mixtures of water (containing 1% $NH_3$) and MeCN as eluents to afford the title compound (29 mg, 29%) as a beige solid. $^1$H NMR (400 MHz, $CDCl_3$, 30° C.) 1.06 (9H, s), 1.09 (3H, d), 1.17 (3H, d), 1.22 (3H, d), 1.4-1.5 (6H, m), 1.59-1.69 (4H, m), 1.98-2.07 (1H, m), 2.39 (1H, dd), 2.50 (3H, s), 2.52-2.56 (1H, m), 2.60 (1H, dd), 2.78-2.9 (1H, m), 3.08 (1H, dd), 3.46-3.56 (4H, m), 3.60 (1H, dd), 3.63-3.7 (1H, m), 3.71-3.76 (2H, m), 3.85 (1H, d), 3.93 (1H, d), 3.98-4.12 (3H, m), 4.50 (1H, s), 4.55 (1H, d), 4.73 (1H, t), 5.07 (1H, p), 5.19 (1H, s), 6.33-6.45 (2H, m), 7.04-7.14 (2H, m), 7.18-7.24 (2H, m), 7.33-7.46 (5H, m), 7.48-7.53 (1H, m), 7.94-8.04 (1H, m), 8.64 (1H, s); m/z: ES– [M–H]⁻ 1001.9.

Intermediate 158a: 5-(2-((tert-Butyldimethylsilyl)oxy)ethyl)-2-chloropyridine

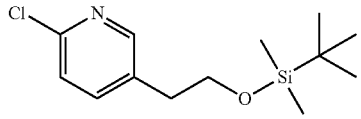 [SMILES: CC(C)(C)[Si](C)(C)OCCc1ccc(Cl)nc1]

Tert-butylchlorodimethylsilane (5.74 g, 38.1 mmol) was added in one portion to 2-(6-chloropyridin-3-yl)ethan-1-ol (5.0 g, 31.73 mmol) and 1H-imidazole (4.32 g, 63.45 mmol) in DMF (64 mL) at 20° C. under nitrogen. The resulting solution was stirred at 20° C. for 2 days. The reaction mixture was diluted with EtOAc (100 mL) and washed with water (3×50 mL) and brine (50 mL). The organic phase was dried over $MgSO_4$, filtered, concentrated. The crude product was purified by flash silica chromatography, elution gradient 0 to 10% EtOAc in heptane to afford the title compound (8.40 g, 97%) as a colourless oil. $^1$H NMR (400 MHz, $CDCl_3$, 30° C.) 0.00 (6H, s), 0.88 (9H, s), 2.81 (2H, t), 3.83 (2H, t), 7.26 (1H, d), 7.55 (1H, dd), 8.23-8.28 (1H, m); m/z: ES+ [M+H]⁺ 272.3.

Intermediate 158b: Methyl 5-(2-((tert-butyldimethylsilyl)oxy)ethyl)picolinate

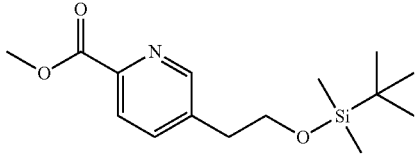 [SMILES: COC(=O)c1ccc(CCO[Si](C)(C)C(C)(C)C)cn1]

5-(2-((tert-butyldimethylsilyl)oxy)ethyl)-2-chloropyridine (4.75 g, 17.47 mmol), Pd(dppf)Cl₂ complex with dichloromethane (0.713 g, 0.87 mmol) and triethylamine (3.93 mL, 27.96 mmol) were stirred in MeOH (80 mL) in a steel pressure reaction vessel and the mixture was flushed with carbon monoxide and placed under 4 atm of carbon monoxide and heated to 100° C. for 18 hours. The mixture was cooled to RT, the orange solid was removed by filtration, the filtrate evaporated. The residue was dissolved in ethyl acetate (200 mL) then washed with water (200 mL). The organics were dried over $MgSO_4$, filtered, evaporated then purified by flash silica chromatography, elution gradient 0 to 60% EtOAc in heptane to afford the title compound (3.76 g, 73%) as a colorless oil. $^1$H NMR (400 MHz, $CDCl_3$, 30° C.) –0.03-0.08 (6H, m), 0.88 (9H, s), 2.92 (2H, t), 3.89 (2H, t), 4.05 (3H, s), 7.74 (1H, dd), 8.10 (1H, dd), 8.64 (1H, d); m/z: ES+ [M+H]⁺ 296.3.

Intermediate 158c: (5-(2-((tert-Butyldimethylsilyl)oxy)ethyl)pyridin-2-yl)methanol

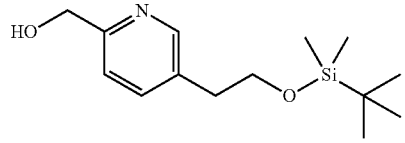 [SMILES: CC(C)(C)[Si](C)(C)OCCc1ccc(CO)nc1]

Methyl 5-(2-((tert-butyldimethylsilyl)oxy)ethyl)picolinate (3.09 g, 10.46 mmol) was added dropwise to a solution of 1 M aluminum(III) lithium hydride (13.6 mL, 13.6 mmol) in anhydrous THF (38.7 ml) at 0° C. over a period of 15 minutes under nitrogen. The resulting mixture was stirred at 20° C. for 2 hours. The reaction mixture was quenched with careful dropwise addition of water (0.52 mL), 15% NaOH solution (0.52 mL) and water (1.56 mL). The mixture was stirred for 5 minutes. The solids were removed by filtration on a bed of celite and the filtrate was evaporated to dryness. The crude product was purified by flash silica chromatography, elution gradient 0 to 50% EtOAc in heptane to afford the title compound (0.760 g, 27.2%) as a colourless liquid. $^1$H NMR (400 MHz, $CDCl_3$, 30° C.) –0.00 (6H, s), 0.89 (9H, s), 2.84 (2H, t), 3.65 (1H, s), 3.84 (2H, t), 4.72-4.8 (2H, m), 7.18 (1H, d), 7.57 (1H, dd), 8.44 (1H, d).

Intermediate 158d: 2-(6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)ethan-1-ol

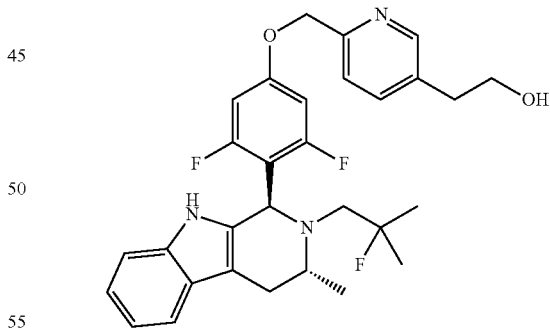

DIAD (0.71 mL, 3.60 mmol) was added dropwise to a stirred solution of (5-(2-((tert-butyldimethylsilyl)oxy)ethyl)pyridin-2-yl)methanol (771 mg, 2.88 mmol), 3,5-difluoro-4-((1R,3R)-2-(2-fluoro-2-methylpropyl)-3-methyl-2,3,4,9-tetrahydro-1H-pyrido[3,4-b]indol-1-yl)phenol (700 mg, 1.80 mmol) and triphenylphosphane (945 mg, 3.60 mmol) in DCM (5.0 mL) at 20° C. under air. The resulting solution was stirred at 20° C. for 30 minutes. The mixture was diluted with DCM (30 mL) and washed with water (3×50 mL). The organic layer was collected and dried using phase separating cartridge then evaporated to dryness. The crude product was purified by flash silica chromatography, elution gradient 0 to 100% EtOAc in heptane to afford the title compound (713 mg, 76%) as a pale yellow waxy solid. $^1$H NMR (400 MHz, CDCl$_3$, 30° C.) 1.10 (3H, d), 1.17 (3H, d), 1.22 (3H, d), 1.43 (1H, t), 2.39 (1H, dd), 2.60 (1H, dd), 2.79-2.93 (3H, m), 3.08 (1H, dd), 3.6-3.74 (1H, m), 3.86-3.96 (2H, m), 5.12 (2H, s), 5.19 (1H, s), 6.45-6.56 (2H, m), 7.06-7.15 (2H, m), 7.19-7.24 (1H, m), 7.36-7.46 (2H, m), 7.48-7.55 (1H, m), 7.59-7.67 (1H, m), 8.48 (1H, d); m/z: ES+ [M+H]$^+$ 524.4.

Intermediate 158e: 2-(2-(6-((3,5-Difluoro-4-((1R, 3R)-2-(2-fluoro-2-methylpropyl)-3-methyl-2,3,4,9-tetrahydro-1H-pyrido[3,4-b]indol-1-yl)phenoxy) methyl)pyridin-3-yl)ethoxy)acetic Acid A solid suspension of 60% sodium hydride in mineral oil (22.92 mg, 0.57 mmol) was added slowly to 2-(6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy) methyl)pyridin-3-yl)ethan-1-ol (50 mg, 0.10 mmol) and 2-bromo acetic acid (46.4 mg, 0.33 mmol) in THF (0.48 mL) at 0° C. over a period of 2 minutes under nitrogen. The resulting solution was stirred at 20° C. for 18 hours. The mixture was diluted with DCM (30 mL) and washed with water (3×50 mL). The organic layer was collected and dried using phase separating cartridge then evaporated to dryness. The crude product was purified by preparative HPLC, using decreasingly polar mixtures of water (containing 1% NH$_3$) and MeCN as eluents to afford the title compound (24 mg, 43%) as a colourless dry film. $^1$H NMR (400 MHz, MeOD, 30° C.) 1.09 (3H, d), 1.12 (3H, d), 1.18 (3H, d), 2.39 (1H, dd), 2.55-2.7 (1H, m), 2.85-3.08 (4H, m), 3.6-3.76 (3H, m), 3.86 (2H, s), 5.13 (2H, s), 5.19 (1H, s), 6.52-6.67 (2H, m), 6.91-7.11 (2H, m), 7.15-7.22 (1H, m), 7.37-7.43 (1H, m), 7.48 (1H, d), 7.83 (1H, dd), 8.45 (1H, d); m/z: ES− [M−H]$^-$ 580.4.

Example 158: (2S,4R)-1-((S)-2-(2-(2-(6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)ethoxy)acetamido)-3,3-dimethylbutanoyl)-4-hydroxy-N-(4-(4-methylthiazol-5-yl)benzyl)pyrrolidine-2-carboxamide

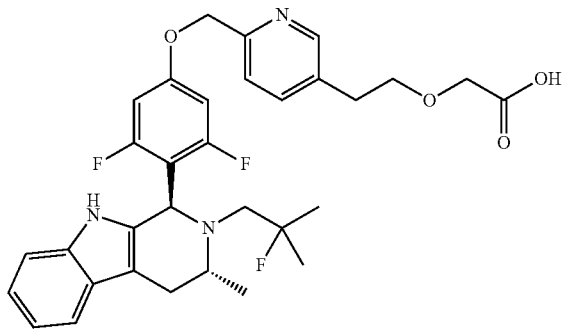 [SMILES: C[C@@H]1Cc2c([nH]c3ccccc23)[C@@H](c2c(F)cc(OCc3ccc(CCOCC(=O)O)cn3)cc2F)N1CC(C)(C)F]

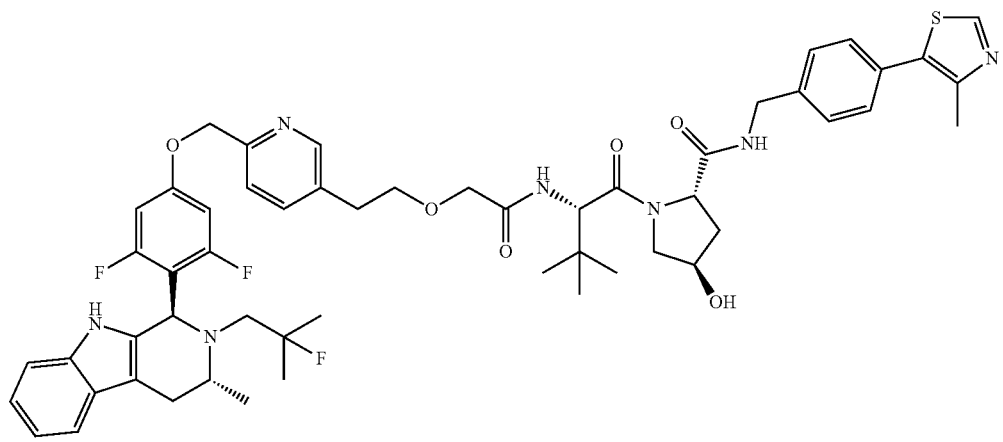 [SMILES: Cc1ncsc1-c1ccc(CNC(=O)[C@@H]2C[C@@H](O)CN2C(=O)[C@@H](NC(=O)COCCc2ccc(COc3cc(F)c([C@@H]4c5[nH]c6ccccc6c5C[C@@H](C)N4CC(C)(C)F)c(F)c3)nc2)C(C)(C)C)cc1]

The title compound was prepared in a similar manner to Example 68 using the appropriate carboxylic acid and amine to afford the desired product (19 mg, 43%) as a white solid. ¹H NMR (400 MHz, CDCl₃, 30° C.) 0.87 (9H, s), 1.10 (3H, d), 1.17 (3H, d), 1.22 (3H, d), 2.03-2.18 (1H, m), 2.39 (1H, dd), 2.45 (3H, s), 2.54-2.67 (2H, m), 2.77 (1H, d), 2.85 (1H, dd), 2.93 (2H, t), 3.08 (1H, dd), 3.60 (1H, dd), 3.64-3.7 (1H, m), 3.71-3.78 (2H, m), 3.84 (1H, d), 3.96 (1H, d), 4.07 (1H, d), 4.31 (1H, dd), 4.42 (1H, d), 4.5-4.56 (1H, m), 4.60 (1H, dd), 4.71 (1H, t), 4.98-5.12 (2H, m), 5.20 (1H, s), 6.43 (2H, d), 6.96 (1H, d), 7.04-7.13 (2H, m), 7.17-7.23 (1H, m), 7.26-7.32 (1H, m), 7.32-7.41 (5H, m), 7.48-7.55 (1H, m), 7.62 (1H, dd), 8.34 (1H, s), 8.47 (1H, d), 8.61 (1H, s); m/z: ES− [M−H]⁻ 992.5.

Example 159: (2S,4R)-1-((S)-2-(2-(2-(6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)ethoxy)acetamido)-3,3-dimethylbutanoyl)-4-hydroxy-N—((S)-1-(4-(4-methylthiazol-5-yl)phenyl)ethyl)pyrrolidine-2-carboxamide

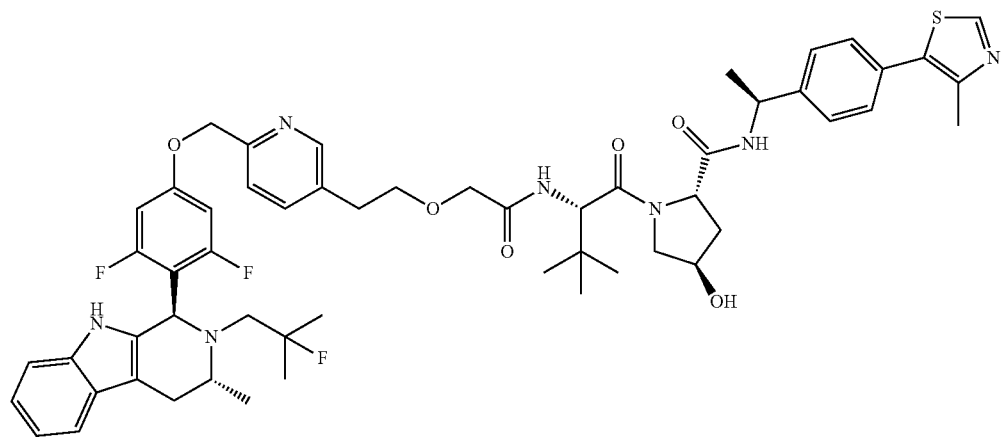 [SMILES: Cc1ncsc1-c1ccc([C@H](C)NC(=O)[C@@H]2C[C@@H](O)CN2C(=O)[C@@H](NC(=O)COCCc2ccc(COc3cc(F)c([C@@H]4c5[nH]c6ccccc6c5C[C@@H](C)N4CC(C)(C)F)c(F)c3)nc2)C(C)(C)C)cc1]

The title compound was prepared in a similar manner to Example 68 using the appropriate carboxylic acid and amine to afford the title compound (9 mg 20%) as a dry film; ¹H NMR (400 MHz, CDCl₃, 30° C.) 1.01 (9H, s), 1.09 (3H, d), 1.17 (3H, d), 1.22 (3H, d), 1.48 (3H, d), 2.04 (1H, dd), 2.39 (1H, dd), 2.47 (3H, s), 2.51-2.65 (2H, m), 2.84 (1H, dd), 2.9-3.01 (3H, m), 3.07 (1H, dd), 3.60 (1H, dd), 3.63-3.69 (1H, m), 3.7-3.79 (2H, m), 3.85 (1H, d), 3.99 (1H, d), 4.07 (1H, d), 4.46-4.57 (2H, m), 4.72 (1H, t), 5.08 (3H, dd), 5.19 (1H, s), 6.39-6.47 (2H, m), 7.02-7.14 (3H, m), 7.17-7.24 (1H, m), 7.32-7.46 (6H, m), 7.47-7.54 (1H, m), 7.63 (1H, dd), 8.09 (1H, s), 8.49 (1H, d), 8.64 (1H, s); m/z: ES− [M−H]⁻ 1006.5.

Intermediate 161a: (3R)-1-(4-((5-Bromopyridin-2-yl)methoxy)-2,6-difluorophenyl)-2-(2-fluoro-2-methylpropyl)-3-methyl-2,3,4,9-tetrahydro-1H-pyrido[3,4-b]indole

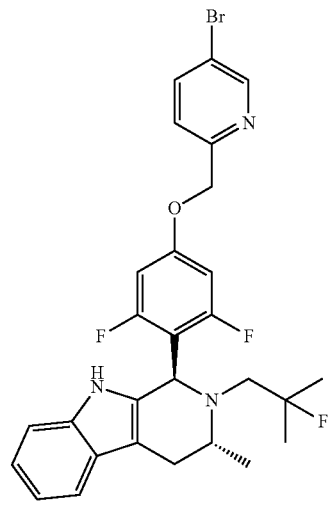 [SMILES: C[C@@H]1Cc2c([nH]c3ccccc23)[C@@H](c2c(F)cc(OCc3ccc(Br)cn3)cc2F)N1CC(C)(C)F]

The title compound was prepared in a similar manner to Intermediate 72e using the appropriate phenol and alcohol to afford the desired product (0.900 g, 89%) as a yellow gum. m/z: ES+ [M+H]⁺ 558.2.

Intermediate 161b: tert-Butyl 4-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)oxy)butanoate

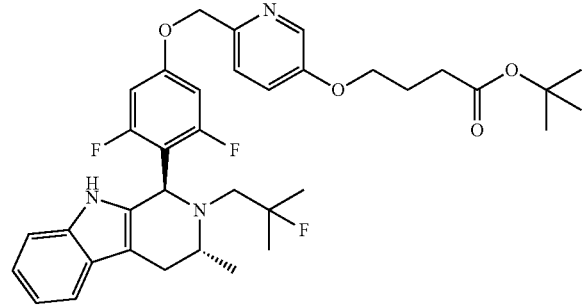 [SMILES: C[C@@H]1Cc2c([nH]c3ccccc23)[C@@H](c2c(F)cc(OCc3ccc(OCCCC(=O)OC(C)(C)C)cn3)cc2F)N1CC(C)(C)F]

RockPhos Pd (68 mg, 0.08 mmol) was added to (1R,3R)-1-(4-((5-bromopyridin-2-yl)methoxy)-2,6-difluorophenyl)-2-(2-fluoro-2-methylpropyl)-3-methyl-2,3,4,9-tetrahydro-1H-pyrido[3,4-b]indole (900 mg, 1.61 mmol), $Cs_2CO_3$ (1.58 g, 4.83 mmol) and tert-butyl 4-hydroxybutanoate (775 mg, 4.83 mmol) in toluene (2 mL) at 25° C. The resulting mixture was stirred at 80° C. for 4 hours. The reaction mixture was poured into water (50 mL), extracted with EtOAc (3×50 mL), the organic layer was dried over $Na_2SO_4$, filtered and evaporated. The crude product was purified by flash silica chromatography, elution gradient 0 to 10% EtOAc in petroleum ether to afford the title compound (600 mg, 58%) as a yellow gum; m/z: ES+ [M+H]$^+$=638.4.

Intermediate 161c: 4-((6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)oxy)butanoic Acid

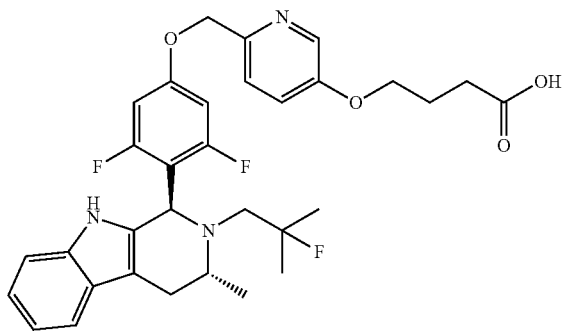 [SMILES: C[C@@H]1Cc2c([nH]c3ccccc23)[C@@H](c2c(F)cc(OCc3ccc(OCCCC(=O)O)cn3)cc2F)N1CC(C)(C)F]

tert-Butyl 4-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)oxy)butanoate (880 mg, 1.38 mmol) was added to formic acid (10 mL) at 25° C. The resulting mixture was stirred at 25° C. for 1 hour. The solvent was removed under reduced pressure. The crude product was purified by flash C18-flash chromatography, elution gradient 0 to 70% MeCN in water. Pure fractions were evaporated to dryness to afford the title compound (500 mg, 100%) as a yellow solid. $^1$H NMR (300 MHz, DMSO-d6, 22° C.) δ 1.00-1.27 (9H, m), 1.88-2.03 (2H, m), 2.24-2.45 (3H, m), 2.54-2.62 (1H, m), 2.71-2.97 (2H, m), 3.47-3.55 (1H, m), 4.02-4.13 (2H, m), 5.08-5.16 (3H, m), 6.71-6.83 (2H, m), 6.89-7.05 (2H, m), 7.14-7.23 (1H, m), 7.35-7.48 (2H, m), 7.43-7.52 (1H, m), 8.25-8.32 (1H, m), 10.55 (1H, s), 11.99 (1H, s); m/z: ES+ [M+H]$^+$=582.2.

Example 161: (2S,4R)-1-((S)-2-(4-((6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)oxy)butanamido)-3,3-dimethylbutanoyl)-4-hydroxy-N-(4-(4-methylthiazol-5-yl)benzyl)pyrrolidine-2-carboxamide

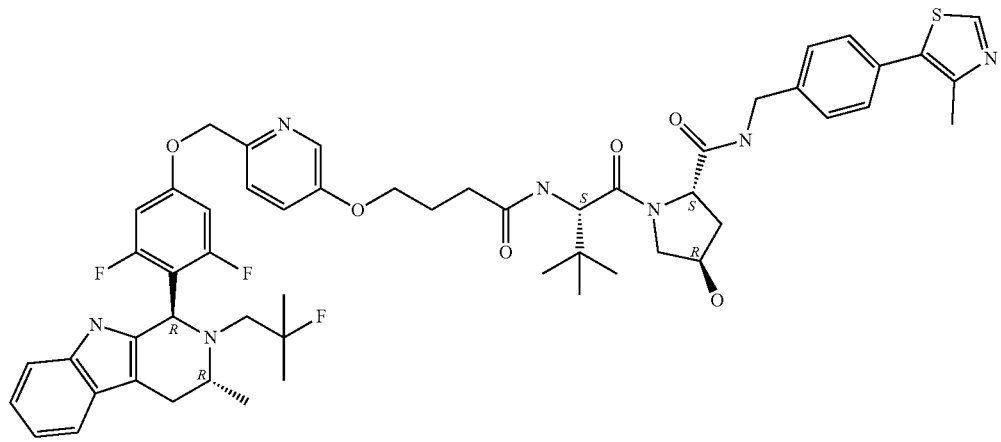

HATU (196 mg, 0.52 mmol) was added slowly to 4-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)oxy)butanoic acid (200 mg, 0.34 mmol), (2S,4R)-1-((S)-2-amino-3,3-dimethylbutanoyl)-4-hydroxy-N-(4-(4-methylthiazol-5-yl)benzyl)pyrrolidine-2-carboxamide (148 mg, 0.34 mmol) and DIPEA (0.120 mL, 0.69 mmol) in DMF (5 mL) at 25° C. The resulting mixture was stirred at 25° C. for 2 hours. The crude product was purified by flash C18-flash chromatography, elution gradient 0 to 70% MeCN in water to afford the title compound (150 mg, 44%) as a yellow solid. $^1$H NMR (300 MHz, CDCl$_3$, 22° C.) 0.94 (9H, s), 1.12 (3H, d), 1.18-1.26 (6H, dd), 2-2.19 (4H, m), 2.33-2.51 (7H, m), 2.62 (1H, dd), 2.87 (1H, dd), 3.09 (1H, dd), 3.52-3.78 (2H, m), 3.9-4.13 (3H, m), 4.34 (1H, dd), 4.47-4.71 (4H, m), 5.00 (2H, s), 5.22 (1H, s), 6.39 (2H, m), 6.42-6.52 (1H, m), 7-7.15 (2H, m), 7.19-7.26 (2H, m), 7.3-7.41 (6H, m), 7.5-7.58 (1H, m), 8.17-8.29 (2H, m), 8.66 (1H, s). LCMS: UPLC, ms detection: m/z (ES+), [M+H]+=994.4.

Intermediate 162a: (1S,3R)-1-(4-((6-Bromopyridin-2-yl)methoxy)-2,6-difluorophenyl)-2-(2-fluoro-2-methylpropyl)-3-methyl-2,3,4,9-tetrahydro-1H-pyrido[3,4-b]indole

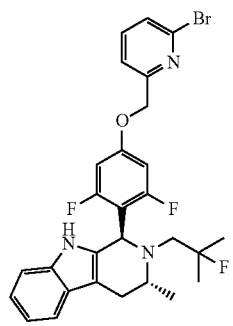 [SMILES: C[C@@H]1Cc2c([nH]c3ccccc23)[C@@H](c2c(F)cc(OCc3cccc(Br)n3)cc2F)N1CC(C)(C)F]

The title compound was prepared in a similar manner to Intermediate 72e using the appropriate phenol and alcohol to afford the desired product (1.26 g, 88%) as a pale yellow gum. $^1$H NMR (300 MHz, CDCl$_3$, 22° C.) 1.36-1.05 (9H, m), 2.52-2.22 (1H, m), 2.70-2.57 (1H, m), 2.97-2.80 (1H, m), 3.17-3.04 (1H, m), 3.75-3.63 (1H, m), 5.13 (2H, s), 5.23 (1H, s), 6.56-6.45 (2H, m), 7.19-7.06 (2H, m), 7.27-7.19 (1H, m), 7.52-7.43 (3H, m), 7.58-7.51 (1H, m), 7.70-7.59 (1H, m).

Intermediate 162b: tert-Butyl 4-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)oxy)butanoate

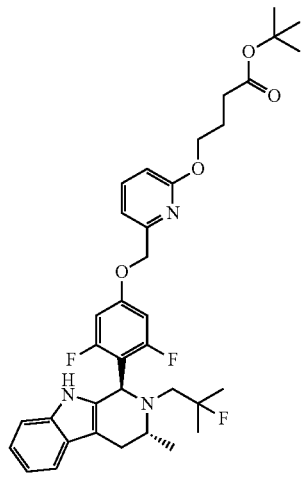 [SMILES: C[C@@H]1Cc2c([nH]c3ccccc23)[C@@H](c2c(F)cc(OCc3cccc(OCCCC(=O)OC(C)(C)C)n3)cc2F)N1CC(C)(C)F]

RockPhos Pd (38 mg, 0.04 mmol) was added to (1R,3R)-1-(4-((6-bromopyridin-2-yl)methoxy)-2,6-difluorophenyl)-2-(2-fluoro-2-methylpropyl)-3-methyl-2,3,4,9-tetrahydro-1H-pyrido[3,4-b]indole (500 mg, 0.90 mmol), Cs$_2$CO$_3$ (875 mg, 2.69 mmol) and tert-butyl 4-hydroxybutanoate (430 mg, 2.69 mmol) in toluene (5 mL) at 25° C. The resulting mixture was stirred at 80° C. for 4 hours. The reaction mixture was poured into water (50 mL), extracted with EtOAc (3×50 mL), the organic layer was dried over Na$_2$SO$_4$, filtered and evaporated. The crude product was purified by flash silica chromatography, elution gradient 0 to 20% EtOAc in petroleum ether to afford the title compound (430 mg, 75%) as a yellow solid. $^1$H NMR (300 MHz, CDCl$_3$, 22° C.) 1.12 (3H, d), 1.16-1.29 (6H, m), 1.47 (9H, s), 2.07 (2H, d), 2.3-2.5 (3H, m), 2.57-2.68 (1H, m), 2.8-2.99 (1H, m), 3.03-3.22 (1H, m), 3.70 (1H, s), 4.32 (2H, t), 5.04 (2H, s), 5.22 (1H, s), 6.49-6.61 (2H, m), 6.68 (1H, d), 7.01 (1H, d), 7.08-7.17 (2H, m), 7.21-7.31 (1H, m), 7.51-7.65 (3H, m).

Intermediate 162c: 4-((6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)oxy)butanoic Acid

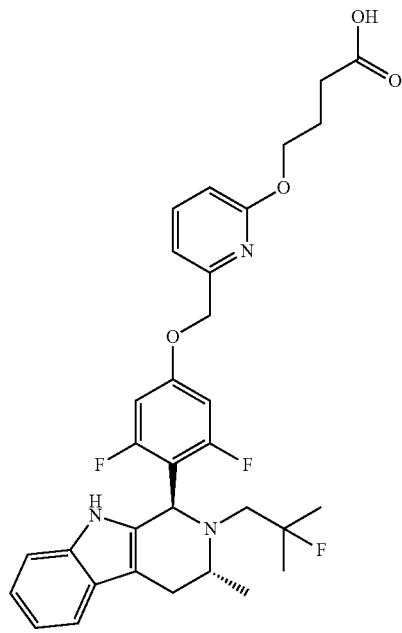 [SMILES: C[C@@H]1Cc2c([nH]c3ccccc23)[C@@H](c2c(F)cc(OCc3cccc(OCCCC(=O)O)n3)cc2F)N1CC(C)(C)F]

tert-Butyl 4-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)oxy)butanoate (430 mg, 0.67 mmol) was added to formic acid (8 mL) at 25° C. The resulting mixture was stirred at 25° C. for 4 hours. The solvent was removed under reduced pressure. The crude product was purified by flash C18-flash chromatography, elution gradient 0 to 70% MeCN in water to afford the title compound (300 mg, 76%) as a yellow solid. $^1$H NMR (300 MHz, DMSO-d6, 22° C.) 0.99-1.30 (m, 9H), 1.87-1.97 (m, 2H), 2.25-2.39 (m, 3H), 2.51-2.62 (m, 1H), 2.75-2.93 (m, 2H), 3.47-3.55 (m, 1H), 4.18-4.28 (m, 2H), 5.06-5.17 (m, 3H), 6.72-6.88 (m, 3H), 6.88-7.05 (m, 2H), 7.05-7.13 (m, 1H), 7.14-7.23 (m, 1H), 7.35-7.44 (m, 1H), 7.68-7.79 (m, 1H), 10.59 (s, 1H); m/z: ES+ [M+H]$^+$=582.2.

Example 162: (2S,4R)-1-((S)-2-(4-((6-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)oxy)butanamido)-3,3-dimethylbutanoyl)-4-hydroxy-N-(4-(4-methylthiazol-5-yl)benzyl)pyrrolidine-2-carboxamide

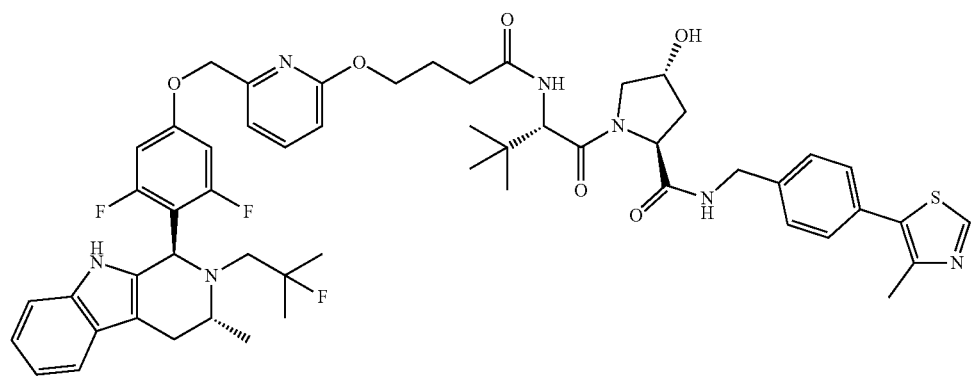 [SMILES: Cc1ncsc1-c1ccc(CNC(=O)[C@@H]2C[C@@H](O)CN2C(=O)[C@@H](NC(=O)CCCOc2cccc(COc3cc(F)c([C@@H]4c5[nH]c6ccccc6c5C[C@@H](C)N4CC(C)(C)F)c(F)c3)n2)C(C)(C)C)cc1]

The title compound was prepared in a similar manner to Example 161 using the appropriate carboxylic acid and amine to afford the desired product (140 mg, 41%) as a yellow solid. $^1$H NMR (300 MHz, CDCl$_3$, 22° C.) 0.92 (9H, s), 1.12 (3H, d), 1.16-1.34 (6H, m), 1.98-2.15 (3H, m), 2.3-2.55 (7H, m), 2.62 (1H, dd), 2.76-2.97 (1H, m), 3.02-3.18 (1H, m), 3.40 (1H, s), 3.52-3.74 (2H, m), 4.02 (1H, d), 4.22-4.39 (3H, m), 4.45-4.62 (3H, m), 4.67 (1H, t), 5.00 (2H, s), 5.23 (1H, s), 6.28 (1H, d), 6.47-6.59 (2H, m), 6.67 (1H, d), 7.00 (1H, d), 7.05-7.17 (2H, m), 7.2-7.28 (2H, m), 7.31-7.43 (4H, m), 7.48-7.65 (2H, m), 8.15 (1H, s), 8.67 (1H, s); m/z: ES+ [M+H]$^+$=994.5.

Intermediate 164a: (R)—N-(1-(1H-Indol-3-yl)propan-2-yl)-2,2-difluoropropanamide

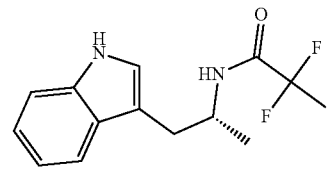 [SMILES: C[C@H](Cc1c[nH]c2ccccc12)NC(=O)C(C)(F)F]

HATU (5.24 g, 13.8 mmol) was added to (R)-1-(1H-indol-3-yl)propan-2-amine (2.00 g, 11.5 mmol), 2,2-difluoropropionic acid (1.263 g, 11.48 mmol) and DIPEA (4.01 mL, 22.96 mmol) in DMF (30 mL) at RT. The resulting mixture was stirred at 25° C. for 16 hours. The reaction mixture was poured into water (100 mL), extracted with EtOAc (3×75 mL), the organic layer was dried over Na$_2$SO$_4$, filtered and evaporated. The crude product was purified by flash silica chromatography, elution gradient 0 to 20% EtOAc in petroleum ether to afford the title compound (2.80 g, 92%) as a yellow oil. $^1$H NMR (300 MHz, CDCl$_3$, 22° C.) 1.21-1.27 (3H, m), 1.67-1.84 (3H, m), 2.91-3.12 (2H, m), 4.30-4.47 (1H, m), 6.30 (1H, s), 7.02-7.09 (1H, m), 7.11-7.29 (2H, m), 7.35-7.45 (1H, m), 7.62-7.72 (1H, m), 8.17 (1H, s); m/z: ES+ [M+H]$^+$=267.1.

Intermediate 164b: (R)—N-(1-(1H-Indol-3-yl)propan-2-yl)-2,2-difluoropropan-1-amine

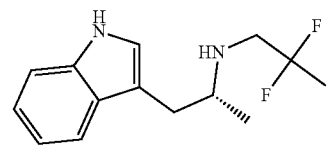 [SMILES: C[C@H](Cc1c[nH]c2ccccc12)NCC(C)(F)F]

A solution of 1 M borane:tetrahydrofuran complex in tetrahydrofuran (48.8 mL, 48.8 mmol) was added to (R)—N-(1-(1H-indol-3-yl)propan-2-yl)-2,2-difluoropropanamide (2.6 g, 9.76 mmol) in THF (50 mL) at 25° C. The resulting mixture was stirred at 25° C. for 16 hours. MeOH was added slowly after the reaction had been stirred for 4 hours. The solvent was removed under reduced pressure. The crude product was purified by flash silica chromatography, elution gradient 0 to 25% EtOAc in petroleum ether to afford the title compound (1.42 g, 58%) as a yellow gum. $^1$H NMR (300 MHz, CDCl$_3$, 22° C.) 1.11-1.19 (3H, m), 1.52-1.71 (3H, m), 2.83-2.94 (2H, m), 2.95-3.05 (1H, m), 3.05-3.18 (1H, m), 7.05-7.10 (1H, m), 7.10-7.20 (1H, m), 7.17-7.29 (1H, m), 7.35-7.45 (1H, m), 7.59-7.68 (1H, m), 8.05 (1H, s); m/z: ES+ [M+H]$^+$=253.2.

Intermediate 164c: (1S,3R)-1-(5-Bromo-3-fluoropyridin-2-yl)-2-(2,2-difluoropropyl)-3-methyl-2,3,4,9-tetrahydro-1H-pyrido[3,4-b]indole

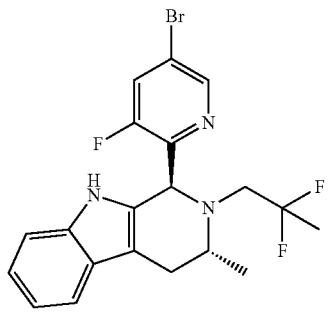 [SMILES: C[C@@H]1Cc2c([nH]c3ccccc23)[C@@H](c2ncc(Br)cc2F)N1CC(C)(F)F]

AcOH (0.32 mL, 5.6 mmol) was added in one portion to 5-bromo-3-fluoropicolinaldehyde (0.575 g, 2.82 mmol) and (R)—N-(1-(1H-indol-3-yl)propan-2-yl)-2,2-difluoropropan-1-amine (0.711 g, 2.82 mmol) in toluene (10 mL) at 25° C. The resulting solution was stirred at 80° C. for 16 hours. The reaction mixture was diluted with EtOAc (100 mL), and washed sequentially with saturated NaHCO$_3$ (50 mL), saturated brine (50 mL). The organic layer was dried over MgSO$_4$, filtered and evaporated. The crude product was purified by flash silica chromatography, elution gradient 0 to 20% EtOAc in petroleum ether to afford the title compound (0.90 g, 73%) as a pale yellow foam. $^1$H NMR (300 MHz, CDCl$_3$, 22° C.) 1.16-1.23 (3H, m), 1.61-1.78 (3H, m), 2.54-2.69 (1H, m), 2.74-2.91 (2H, m), 2.91-3.12 (1H, m), 3.59 (1H, s), 5.45 (1H, s), 7.07-7.24 (2H, m), 7.24-7.35 (1H, m), 7.51-7.60 (1H, m), 7.60-7.69 (1H, m), 7.74 (1H, s), 8.35-8.42 (1H, m); m/z: ES+ [M+H]$^+$=438.1.

Intermediate 164d: Ethyl 2-(2-((5-((6-((1S,3R)-2-(2,2-difluoropropyl)-3-methyl-2,3,4,9-tetrahydro-1H-pyrido[3,4-b]indol-1-yl)-5-fluoropyridin-3-yl)oxy)pentyl)oxy)ethoxy)acetate

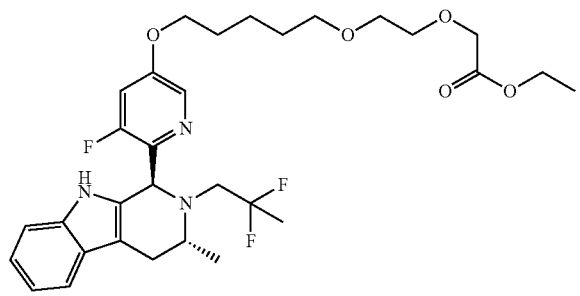

RockPhos Pd G3 (0.086 g, 0.10 mmol) was added to (1S,3R)-1-(5-bromo-3-fluoropyridin-2-yl)-2-(2,2-difluoropropyl)-3-methyl-2,3,4,9-tetrahydro-1H-pyrido[3,4-b]indole (0.9 g, 2.05 mmol), Cs$_2$CO$_3$ (2.01 g, 6.16 mmol) and ethyl 2-(2-((5-hydroxypentyl)oxy)ethoxy)acetate (1.20 g, 5.13 mmol) in toluene (10 mL) at 25° C. The resulting solution was stirred at 80° C. for 4 hours. The reaction mixture was poured into water (50 mL), extracted with EtOAc (3×50 mL), the organic layer was dried over Na$_2$SO$_4$, filtered and evaporated. The crude product was purified by flash silica chromatography, elution gradient 0 to 25% EtOAc in petroleum ether to afford the title compound (0.300 g, 25%) as a yellow gum. $^1$H NMR (300 MHz, CDCl$_3$, 22° C.) 1.18 (3H, d), 1.24-1.34 (6H, m), 1.42-1.75 (4H, m), 1.77-1.93 (2H, m), 2.60 (1H, dd), 2.72-3.12 (3H, m), 3.51 (2H, t), 3.59-3.68 (3H, m), 3.7-3.76 (2H, m), 4.00 (2H, t), 4.16 (2H, s), 4.23 (2H, q), 5.37 (1H, s), 6.97 (1H, dd), 7.07-7.21 (2H, m), 7.28 (1H, s), 7.49-7.6 (1H, m), 7.73 (1H, s), 8.04 (1H, d). m/z (ES+), [M+H]+=592.3.

Intermediate 164e: 2-(2-((5-((6-((1S,3R)-2-(2,2-Difluoropropyl)-3-methyl-2,3,4,9-tetrahydro-1H-pyrido[3,4-b]indol-1-yl)-5-fluoropyridin-3-yl)oxy)pentoxy)ethoxy)acetic Acid

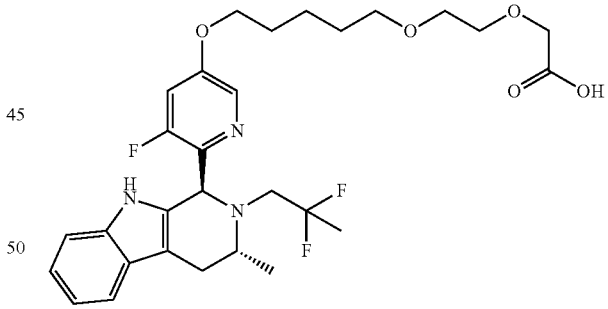

The title compound was prepared in a similar manner to Intermediate 72f using the appropriate ester to afford the desired product (260 mg, 91%) as a yellow solid. $^1$H NMR (300 MHz, CDCl$_3$, 22° C.) 1.15-1.23 (3H, m), 1.25-1.32 (3H, m), 1.51-1.77 (6H, m), 1.78-1.91 (2H, m), 2.54-2.68 (1H, m), 2.77-3.04 (2H, m), 3.55-3.60 (2H, m), 3.61-3.66 (2H, m), 3.71-3.81 (2H, m), 3.97-4.08 (2H, m), 4.11 (2H, s), 5.39 (1H, s), 6.94-7.04 (1H, m), 7.05-7.20 (2H, m), 7.49-7.58 (1H, m), 7.88 (1H, s), 8.00-8.07 (1H, m); m/z: ES− [M−H]$^-$=562.2.

Example 164: (2S,4R)-1-((S)-2-(2-(2-((5-(((1S,3R)-2-(2,2-Difluoropropyl)-3-methyl-2,3,4,9-tetrahydro-1H-pyrido[3,4-b]indol-1-yl)-5-fluoropyridin-3-yl)oxy)pentyl)oxy)ethoxy)acetamido)-3,3-dimethylbutanoyl)-4-hydroxy-N-(4-(4-methylthiazol-5-yl)benzyl)pyrrolidine-2-carboxamide

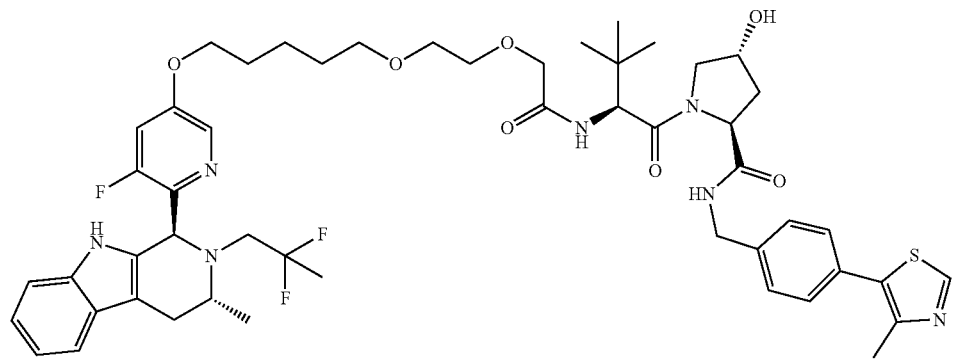 [SMILES: Cc1ncsc1-c1ccc(CNC(=O)[C@@H]2C[C@@H](O)CN2C(=O)[C@@H](NC(=O)COCCOCCCCCOc2cnc([C@@H]3c4[nH]c5ccccc5c4C[C@@H](C)N3CC(C)(F)F)c(F)c2)C(C)(C)C)cc1]

The title compound was prepared in a similar manner to Example 161 using the appropriate carboxylic acid and amine to afford the desired product (200 mg, 46%) as a white solid. $^1$H NMR (300 MHz, CDCl$_3$, 22° C.) 0.97 (9H, s), 1.14-1.22 (3H, m), 1.47-1.72 (7H, m), 1.72-1.87 (2H, m), 1.99-2.12 (2H, m), 2.50 (3H, s), 2.56-2.67 (1H, m), 2.71-3.11 (3H, m), 3.46-3.70 (8H, m), 3.87-4.11 (5H, m), 4.18-4.30 (1H, m), 4.44-4.57 (3H, m), 4.60-4.72 (1H, m), 5.38 (1H, s), 6.87-6.98 (1H, m), 7.04-7.20 (2H, m), 7.24-7.27 (1H, m), 7.28-7.45 (6H, m), 7.50-7.58 (1H, m), 7.97-8.04 (1H, m), 8.42 (1H, s), 8.66 (1H, s); m/z: ES+ [M+H]$^+$=976.5.

Intermediate 165a: (R)-1-(1H-Indol-3-yl)-N-(2,2,2-trifluoroethyl)propan-2-amine

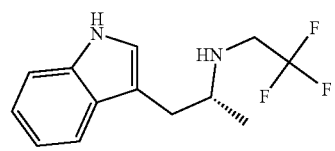 [SMILES: C[C@H](Cc1c[nH]c2ccccc12)NCC(F)(F)F]

(R)-1-(1H-indol-3-yl)propan-2-amine (2.25 g, 12.9 mmol) was added to 2,2,2-trifluoroethyl trifluoromethanesulfonate (2.00 g, 8.62 mmol) and DIPEA (1.94 mL, 11.1 mmol) in 1,4-dioxane (20 mL) at RT. The resulting mixture was stirred at 80° C. for 16 hours. The solvent was removed under reduced pressure. The crude product was purified by flash silica chromatography, elution gradient 0 to 25% EtOAc in petroleum ether to afford the title compound (2.20 g, 100%) as a yellow oil. $^1$H NMR (400 MHz, CDCl$_3$, 22° C.) 1.17 (3H, d), 2.83-2.91 (2H, m), 3.10-3.27 (3H, m), 7.07 (1H, d), 7.12-7.20 (1H, m), 7.20-7.28 (1H, m), 7.36-7.43 (1H, m), 7.60-7.67 (1H, m), 8.08 (1H, s); m/z: ES+ [M+H]$^+$=257.1.

Intermediate 165b: (1S,3R)-1-(5-Bromo-3-fluoropyridin-2-yl)-3-methyl-2-(2,2,2-trifluoroethyl)-2,3,4,9-tetrahydro-1H-pyrido[3,4-b]indole

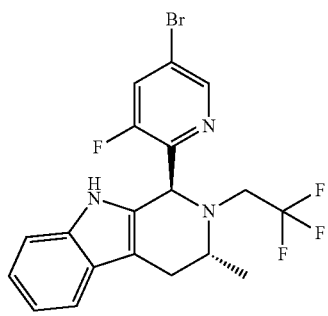 [SMILES: C[C@@H]1Cc2c([nH]c3ccccc23)[C@@H](c2ncc(Br)cc2F)N1CC(F)(F)F]

AcOH (0.447 mL, 7.80 mmol) was added in one portion to 5-bromo-3-fluoropicolinaldehyde (0.796 g, 3.90 mmol) and (R)-1-(1H-indol-3-yl)-N-(2,2,2-trifluoroethyl)propan-2-amine (1.0 g, 3.9 mmol) in toluene (10 mL) at 25° C. The resulting solution was stirred at 80° C. for 16 hours. The reaction mixture was diluted with EtOAc (100 mL), and washed sequentially with saturated NaHCO$_3$ (50 mL), saturated brine (50 mL). The organic layer was dried over MgSO$_4$, filtered and evaporated. The crude product was purified by flash silica chromatography, elution gradient 0 to 20% EtOAc in petroleum ether to afford the title compound (1.60 g, 93%) as a pale yellow foam. $^1$H NMR (300 MHz, CDCl$_3$, 22° C.) 1.21-1.26 (3H, m), 2.54-2.69 (1H, m), 2.84-2.97 (1H, m), 2.93-3.13 (1H, m), 3.23-3.44 (1H, m), 3.58-3.71 (1H, m), 5.41 (1H, s), 7.08-7.25 (2H, m), 7.26-7.35 (1H, m), 7.52-7.60 (1H, m), 7.61-7.72 (1H, m), 7.67-7.76 (1H, m), 8.36-8.43 (1H, m); m/z: ES+ [M+H]$^+$=442.0;

Intermediate 165c: Ethyl 2-(2-((5-((5-fluoro-6-((1S,3R)-3-methyl-2-(2,2,2-trifluoroethyl)-2,3,4,9-tetrahydro-1H-pyrido[3,4-b]indol-1-yl)pyridin-3-yl)oxy)pentyl)oxy)ethoxy)acetate

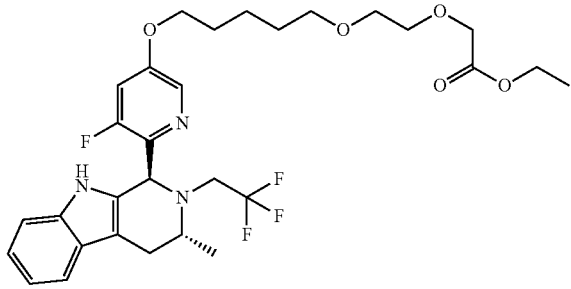

RockPhos Pd G3 (0.095 g, 0.11 mmol) was added to (1S,3R)-1-(5-bromo-3-fluoropyridin-2-yl)-3-methyl-2-(2,2,2-trifluoroethyl)-2,3,4,9-tetrahydro-1H-pyrido[3,4-b]indole (1.00 g, 2.26 mmol), ethyl 2-(2-((5-hydroxypentyl)oxy)ethoxy)acetate (1.32 g, 5.65 mmol) and $Cs_2CO_3$ (2.21 g, 6.78 mmol) in toluene (1 mL) at 25° C. The resulting solution was stirred at 80° C. for 5 hours. The reaction mixture was diluted with EtOAc (100 mL), and washed sequentially with saturated $NaHCO_3$ (50 mL), saturated brine (50 mL). The organic layer was dried over $Na_2SO_4$, filtered and evaporated. The crude product was purified by flash silica chromatography, elution gradient 0 to 20% EtOAc in petroleum ether to afford the title compound (0.330 g, 25%) as a pale yellow foam. $^1$H NMR (300 MHz, CDCl$_3$, 22° C.) 1.19-1.24 (3H, m), 1.25-1.29 (3H, m), 1.44-1.60 (2H, m), 1.61-1.67 (2H, m), 1.79-1.90 (2H, m), 2.53-2.67 (1H, m), 2.88-3.12 (2H, m), 3.19-3.40 (1H, m), 3.44-3.56 (2H, m), 3.56-3.78 (5H, m), 3.96-4.04 (2H, m), 4.07-4.19 (4H, m), 5.36 (1H, s), 6.93-7.04 (1H, m), 7.04-7.22 (2H, m), 7.23-7.32 (1H, m), 7.48-7.59 (1H, m), 7.80 (1H, s), 7.99-8.06 (1H, m); m/z: ES+ [M+H]$^+$=596.3.

Intermediate 165d: 2-(2-((5-((5-Fluoro-6-((1S,3R)-3-methyl-2-(2,2,2-trifluoroethyl)-2,3,4,9-tetrahydro-1H-pyrido[3,4-b]indol-1-yl)pyridin-3-yl)oxy)pentyl)oxy)ethoxy)acetic Acid

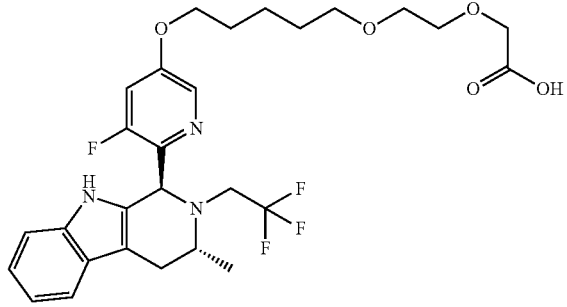 [SMILES: C[C@@H]1Cc2c([nH]c3ccccc23)[C@@H](c2ncc(OCCCCCOCCOCC(=O)O)cc2F)N1CC(F)(F)F]

The title compound was prepared in a similar manner to Intermediate 72f using the appropriate ester to afford the desired product (300 mg, 95%) as a yellow solid. $^1$H NMR (300 MHz, CDCl$_3$, 22° C.) 1.21 (3H, d), 1.53-1.63 (2H, m), 1.64-1.77 (2H, m), 1.79-1.92 (2H, m), 2.60 (1H, dd), 2.88-3.13 (2H, m), 3.21-3.39 (1H, m), 3.58 (2H, t), 3.62-3.72 (3H, m), 3.73-3.81 (2H, m), 4.03 (2H, t), 4.12 (2H, s), 5.37 (1H, s), 7.00 (1H, dd), 7.13 (2H, pd), 7.28 (1H, s), 7.54 (1H, d), 7.91 (1H, s), 8.03 (1H, d); m/z: ES– [M–H]$^-$=566.2.

Example 165: (2S,4R)-1-((S)-2-(2-(2-((5-((5-Fluoro-6-((1S,3R)-3-methyl-2-(2,2,2-trifluoroethyl)-2,3,4,9-tetrahydro-1H-pyrido[3,4-b]indol-1-yl)pyridin-3-yl)oxy)pentyl)oxy)ethoxy)acetamido)-3,3-dimethylbutanoyl)-4-hydroxy-N-(4-(4-methylthiazol-5-yl)benzyl)pyrrolidine-2-carboxamide

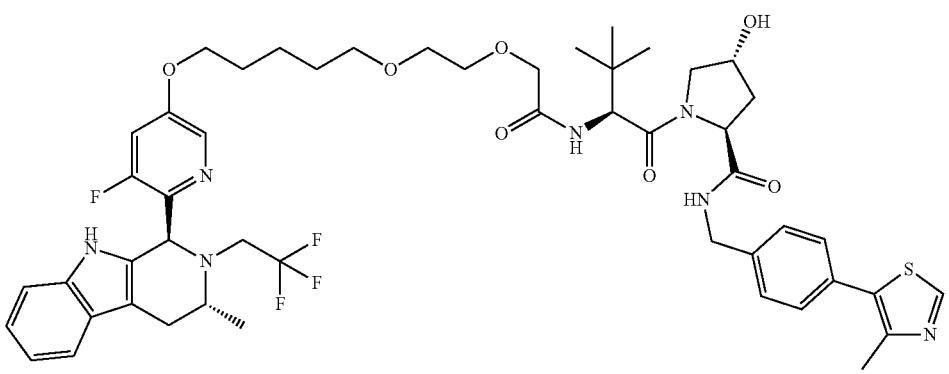 [SMILES: Cc1ncsc1-c1ccc(CNC(=O)[C@@H]2C[C@@H](O)CN2C(=O)[C@@H](NC(=O)COCCOCCCCCOc2cnc([C@@H]3c4[nH]c5ccccc5c4C[C@@H](C)N3CC(F)(F)F)c(F)c2)C(C)(C)C)cc1]

The title compound was prepared in a similar manner to Example 161 using the appropriate carboxylic acid and amine to afford the desired product (160 mg, 31%) as a white solid. $^1$H NMR (300 MHz, CDCl$_3$, 22° C.) 0.98 (9H, s), 1.16-1.24 (3H, m), 1.49-1.59 (2H, m), 1.59-1.71 (2H, m), 1.71-1.86 (2H, m), 1.99-2.12 (2H, m), 2.35-2.53 (4H, m), 2.56-2.67 (1H, m), 2.88-3.11 (2H, m), 3.19-3.36 (1H, m), 3.46-3.56 (2H, m), 3.56-3.71 (6H, m), 3.85-4.12 (5H, m), 4.19-4.31 (1H, m), 4.42-4.57 (3H, m), 4.58-4.70 (1H, m), 5.34 (1H, s), 6.88-6.98 (1H, m), 7.05-7.19 (2H, m), 7.24-7.27 (1H, m), 7.29-7.38 (5H, m), 7.42 (1H, s), 7.50-7.59 (1H, m), 7.95-8.02 (1H, m), 8.52 (1H, s), 8.65 (1H, s); m/z: ES+ [M+H]$^+$=980.5.

Intermediate 166a: (1R,3R)-1-(4-Bromo-2,6-difluorophenyl)-2-(2,2-difluoropropyl)-3-methyl-2,3,4,9-tetrahydro-1H-pyrido[3,4-b]indole

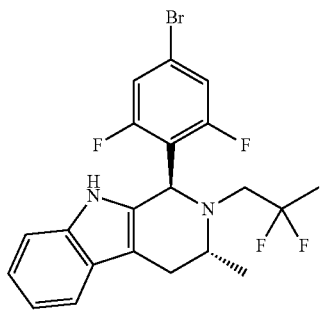 [SMILES: C[C@@H]1Cc2c([nH]c3ccccc23)[C@@H](c2c(F)cc(Br)cc2F)N1CC(C)(F)F]

AcOH (0.323 mL, 5.64 mmol) was added in one portion to 4-bromo-2,6-difluorobenzaldehyde (0.623 g, 2.82 mmol) and (R)—N-(1-(1H-indol-3-yl)propan-2-yl)-2,2-difluoropropan-1-amine (0.711 g, 2.82 mmol) in toluene (10 mL) at 25° C. The resulting solution was stirred at 80° C. for 16 hours. The reaction mixture was diluted with EtOAc (100 mL), and washed sequentially with saturated NaHCO₃ (50 mL), saturated brine (50 mL). The organic layer was dried over MgSO₄, filtered and evaporated. The crude product was purified by flash silica chromatography, elution gradient 0 to 20% EtOAc in petroleum ether to afford the title compound (1.00 g, 78%) as a pale yellow foam. ¹H NMR (300 MHz, CDCl₃, 22° C.) 1.13-1.22 (3H, m), 1.44-1.60 (3H, m), 2.58-2.67 (1H, m), 2.67-2.77 (1H, m), 2.98-3.16 (2H, m), 3.54-3.68 (1H, m), 5.31 (1H, s), 7.05-7.21 (4H, m), 7.17-7.34 (1H, m), 7.48 (1H, s), 7.52-7.59 (1H, m); m/z (ES+), [M+H]+=455.0.

Intermediate 166b: Ethyl 2-(2-((5-(4-((1R,3R)-2-(2,2-difluoropropyl)-3-methyl-2,3,4,9-tetrahydro-1H-pyrido[3,4-b]indol-1-yl)-3,5-difluorophenoxy)pentyl)oxy)ethoxy)acetate

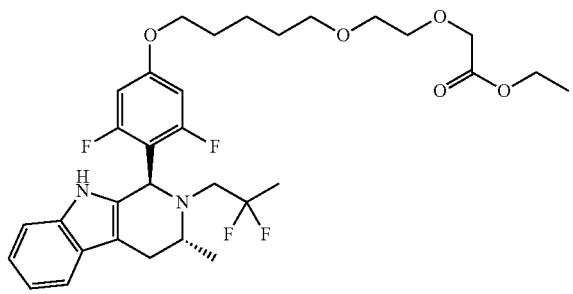 [SMILES: CCOC(=O)COCCOCCCCCOc1cc(F)c([C@@H]2c3[nH]c4ccccc4c3C[C@@H](C)N2CC(C)(F)F)c(F)c1]

RockPhos Pd G3 (0.092 g, 0.11 mmol) was added to (1R,3R)-1-(4-bromo-2,6-difluorophenyl)-2-(2,2-difluoropropyl)-3-methyl-2,3,4,9-tetrahydro-1H-pyrido[3,4-b]indole (1.00 g, 2.20 mmol), ethyl 2-(2-((5-hydroxypentyl)oxy)ethoxy)acetate (1.29 g, 5.49 mmol) and Cs₂CO₃ (2.15 g, 6.59 mmol) in toluene (10 mL) at 25° C. The resulting solution was stirred at 80° C. for 5 hours. The reaction mixture was diluted with EtOAc (100 mL), and washed sequentially with water (50 mL), saturated brine (50 mL). The organic layer was dried over MgSO₄, filtered and evaporated to afford crude product. The crude product was purified by flash silica chromatography, elution gradient 0 to 20% EtOAc in petroleum ether to afford the title compound (0.440 g, 33%) as a pale yellow foam. ¹H NMR (300 MHz, CDCl₃, 22° C.) 1.16 (3H, d), 1.24-1.36 (6H, m), 1.51-1.6 (2H, m), 1.6-1.74 (2H, m), 1.76-1.89 (2H, m), 2.53-2.78 (2H, m), 2.96-3.19 (2H, m), 3.52 (2H, t), 3.59-3.7 (3H, m), 3.74 (2H, dd), 3.94 (2H, t), 4.17 (2H, s), 4.23 (2H, q), 5.23 (1H, s), 6.31-6.5 (2H, m), 7.06-7.2 (2H, m), 7.21-7.32 (1H, m), 7.49-7.63 (2H, m); m/z: ES− [M−H]⁻=607.3.

Intermediate 166c: 2-(2-((5-(4-((1R,3R)-2-(2,2-Difluoropropyl)-3-methyl-2,3,4,9-tetrahydro-1H-pyrido[3,4-b]indol-1-yl)-3,5-difluorophenoxy)pentyl)oxy)ethoxy)acetic Acid

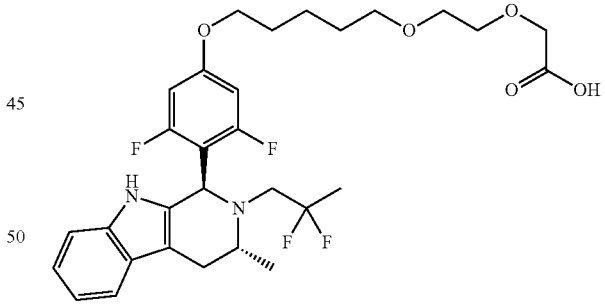

The title compound was prepared in a similar manner to Intermediate 72f using the appropriate ester to afford the desired product (350 mg, 83%) as a yellow solid. ¹H NMR (300 MHz, CDCl₃, 22° C.) 1.11-1.20 (3H, m), 1.24-1.33 (3H, m), 1.53-1.62 (2H, m), 1.65-1.76 (2H, m), 1.78-1.89 (2H, m), 2.58-2.78 (2H, m), 2.96-3.17 (2H, m), 3.54-3.69 (4H, m), 3.74-3.83 (2H, m), 3.90-4.00 (2H, m), 4.08-4.21 (3H, m), 5.23 (1H, s), 6.37-6.52 (2H, m), 7.05-7.20 (2H, m), 7.20-7.30 (1H, m), 7.48-7.58 (1H, m), 7.68 (1H, s), one exchangeable proton not observed; m/z (ES−), [M−H]⁻=579.2.

Example 166: (2S,4R)-1-((S)-2-(2-(2-(2-((5-(4-((1R, 3R)-2-(2,2-Difluoropropyl)-3-methyl-2,3,4,9-tetrahydro-1H-pyrido[3,4-b]indol-1-yl)-3,5-difluorophenoxy)pentyl)oxy)ethoxy)acetamido)-3,3-dimethylbutanoyl)-4-hydroxy-N-(4-(4-methylthiazol-5-yl)benzyl)pyrrolidine-2-carboxamide

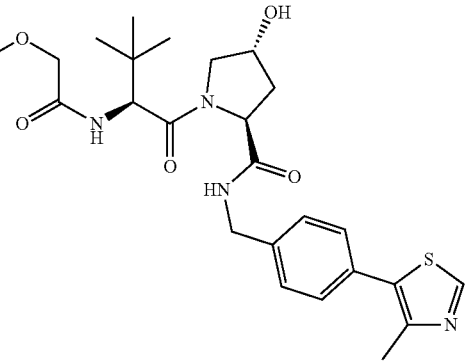

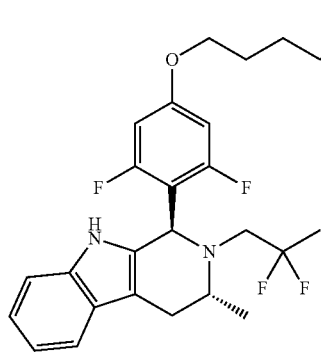

The title compound was prepared in a similar manner to Example 161 using the appropriate carboxylic acid and amine to afford the desired product (200 mg, 33%) as a yellow solid. $^1$H NMR (300 MHz, CDCl$_3$, 22° C.) 0.97 (9H, s), 1.11-1.19 (3H, m), 1.37-1.58 (5H, m), 1.62-1.71 (2H, m), 1.72-1.83 (2H, m), 1.89 (1H, s), 2.01-2.15 (1H, m), 2.46-2.76 (6H, m), 2.95-3.17 (2H, m), 3.48-3.72 (8H, m), 3.82-3.92 (2H, m), 3.93-4.13 (3H, m), 4.25-4.38 (1H, m), 4.48-4.64 (3H, m), 4.67-4.78 (1H, m), 5.23 (1H, s), 6.30-6.41 (2H, m), 7.04-7.19 (2H, m), 7.21-7.27 (1H, m), 7.30-7.46 (6H, m), 7.49-7.58 (1H, m), 8.43 (1H, s), 8.64 (1H, s); m/z: ES+ [M+H]$^+$=993.5.

Intermediate 167a: (1R,3R)-1-(4-Bromo-2,6-difluorophenyl)-2-(2,2-difluoroethyl)-3-methyl-2,3,4,9-tetrahydro-1H-pyrido[3,4-b]indole

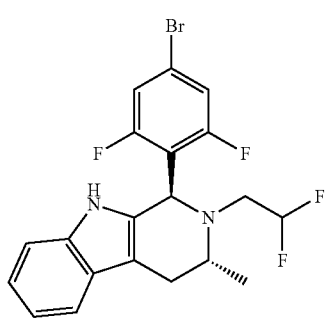 [SMILES: C[C@@H]1Cc2c([nH]c3ccccc23)[C@@H](c2c(F)cc(Br)cc2F)N1CC(F)F]

AcOH (0.480 mL, 8.39 mmol) was added in one portion to 4-bromo-2,6-difluorobenzaldehyde (0.927 g, 4.20 mmol) and (R)—N-(2,2-difluoroethyl)-1-(1H-indol-3-yl)propan-2-amine (preparation described in WO2018/19793, 2018, A1) (1.0 g, 4.2 mmol) in toluene (10 mL) at 25° C. The resulting solution was stirred at 80° C. for 16 hours. The reaction mixture was diluted with EtOAc (100 mL), and washed sequentially with saturated NaHCO$_3$ (50 mL) and saturated brine (50 mL). The organic layer was dried over MgSO$_4$, filtered and evaporated to afford crude product. The crude product was purified by flash silica chromatography, elution gradient 0 to 20% EtOAc in petroleum ether to afford the title compound (1.87 g) as a pale yellow foam that was used without further purification; m/z: ES+ [M+H]$^+$=441.0.

Intermediate 167b: Ethyl 2-(2-((5-(4-((1R,3R)-2-(2, 2-difluoroethyl)-3-methyl-2,3,4,9-tetrahydro-1H-pyrido[3,4-b]indol-1-yl)-3,5-difluorophenoxy)pentyl)oxy)ethoxy)acetate

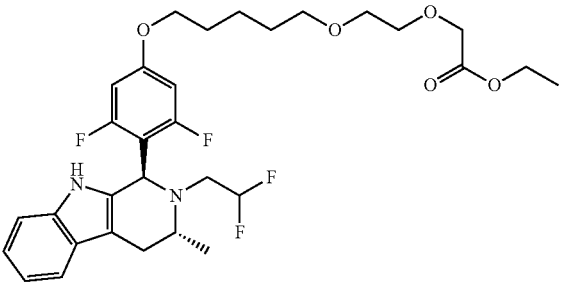 [SMILES: CCOC(=O)COCCOCCCCCOc1cc(F)c([C@@H]2c3[nH]c4ccccc4c3C[C@@H](C)N2CC(F)F)c(F)c1]

RockPhos Pd G3 (0.095 g, 0.11 mmol) was added to (1R,3R)-1-(4-bromo-2,6-difluorophenyl)-2-(2,2-difluoroethyl)-3-methyl-2,3,4,9-tetrahydro-1H-pyrido[3,4-b]indole (1 g, 2.27 mmol), Cs2CO3 (2.215 g, 6.80 mmol) and ethyl 2-(2-((5-hydroxypentyl)oxy)ethoxy)acetate (1.062 g, 4.53 mmol) in toluene (10 mL) at 25° C. The resulting solution was stirred at 80° C. for 16 hours. The reaction mixture was diluted with EtOAc (100 mL), and washed with saturated brine (50 mL). The organic layer was dried over MgSO$_4$, filtered and evaporated. The crude product was purified by flash silica chromatography, elution gradient 0 to 20% EtOAc in petroleum ether to afford the title compound (0.470 g, 35%) as a pale yellow foam. $^1$H NMR (300 MHz, CDCl$_3$, 22° C.) 1.13-1.23 (3H, m), 1.27-1.31 (3H, m), 1.38-1.46 (1H, m), 1.50-1.60 (2H, m), 1.61-1.74 (3H, m), 1.76-1.88 (2H, m), 2.58-2.91 (2H, m), 2.97-3.15 (2H, m), 3.46-3.57 (3H, m), 3.61-3.69 (2H, m), 3.70-3.78 (2H, m), 3.90-3.98 (2H, m), 4.15-4.18 (2H, m), 5.23 (1H, s), 5.40-5.72 (1H, m), 6.39-6.52 (2H, m), 7.07-7.20 (2H, m), 7.22-7.28 (1H, m), 7.47-7.56 (1H, m), 7.62 (1H, s); m/z: ES+ [M+H]$^+$=595.3.

Intermediate 167c: 2-(2-((5-(4-((1R,3R)-2-(2,2-Difluoroethyl)-3-methyl-2,3,4,9-tetrahydro-1H-pyrido[3,4-b]indol-1-yl)-3,5-difluorophenoxy)pentyl)oxy)ethoxy)acetic Acid

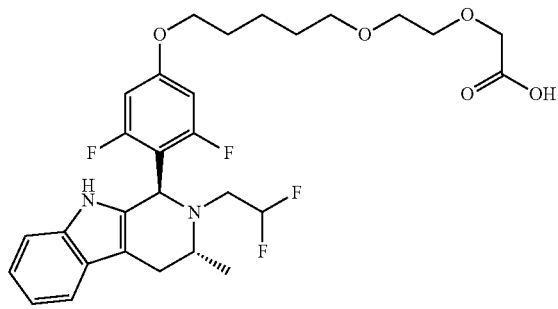 [SMILES: C[C@@H]1Cc2c([nH]c3ccccc23)[C@@H](c2c(F)cc(OCCCCCOCCOCC(=O)O)cc2F)N1CC(F)F]

The title compound was prepared in a similar manner to Intermediate 72f using the appropriate ester to afford the desired product (290 mg, 68%) as a yellow solid; $^1$H NMR (300 MHz, DMSO-d6, 22° C.) 1.06-1.14 (3H, m), 1.27-1.35 (1H, m), 1.44 (2H, s), 1.55 (2H, s), 1.71 (2H, s), 2.53-2.64 (1H, m), 2.74-2.90 (1H, m), 2.98-3.18 (1H, m), 3.40 (3H, s), 3.52 (6H, s), 3.94-4.04 (3H, m), 5.18 (1H, s), 5.59-6.19 (1H, m), 6.63-6.76 (2H, m), 6.89-7.06 (2H, m), 7.14-7.25 (1H, m), 7.34-7.45 (1H, m), 10.62 (1H, s); m/z (ES-), [M–H]–=565.2.

Example 167: (2S,4R)-1-((S)-2-(2-(2-((5-(4-((1R,3R)-2-(2,2-Difluoroethyl)-3-methyl-2,3,4,9-tetrahydro-1H-pyrido[3,4-b]indol-1-yl)-3,5-difluorophenoxy)pentyl)oxy)ethoxy)acetamido)-3,3-dimethylbutanoyl)-4-hydroxy-N-(4-(4-methylthiazol-5-yl)benzyl)pyrrolidine-2-carboxamide The title compound was prepared in a similar manner to Example 161 using the appropriate carboxylic acid and amine to afford the desired product (105 mg, 30%) as a yellow solid. $^1$H NMR (300 MHz, CDCl$_3$, 22° C.) 0.97 (9H, s), 1.20-1.28 (3H, m), 1.41-1.58 (2H, m), 1.61-1.85 (4H, m), 2.02-2.15 (1H, m), 2.48 (7H, s), 3.01-3.17 (2H, m), 3.46-3.72 (8H, m), 3.83-3.93 (2H, m), 3.95-4.12 (3H, m), 4.25-4.38 (1H, m), 4.46-4.62 (3H, m), 4.65-4.77 (1H, m), 5.32 (1H, s), 5.48-6.03 (1H, m), 6.33-6.42 (2H, m), 7.06-7.21 (2H, m), 7.23-7.30 (1H, m), 7.30-7.46 (6H, m), 7.49-7.58 (1H, m), 8.64 (2H, s); m/z: ES+ [M+H]$^+$=979.5.

Intermediate 168a: tert-butyl 4-(2-(2-ethoxy-2-oxoethoxy)ethyl)piperazine-1-carboxylate

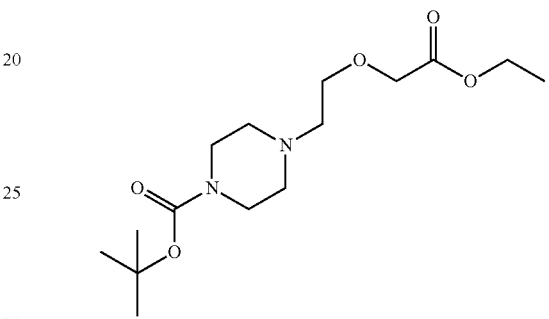

Diacetoxyrhodium (0.273 g, 0.62 mmol) was added to a stirred solution of tert-butyl 4-(2-hydroxyethyl)piperazine-1-carboxylate (1.42 g, 6.17 mmol) in DCM (30 mL) at 0° C. Ethyl 2-diazoacetate (0.938 g, 7.40 mmol) in DCM (5 mL) was added over a period of 5 minutes under nitrogen protection. The resulting suspension was stirred at room temperature for 4 hours. Water (20 mL) was added. The organic layer was separated, washed with brine (15 mL), and concentrated in vacuo. The resulting residue was purified by flash silica chromatography, elution gradient 0 to 10% flash MeOH in DCM. Product fractions were concentrated under reduced pressure to afford the title compound (0.650 g, 33.3%) as a brown oil. m/z: ES+ [M+H]$^+$=317.

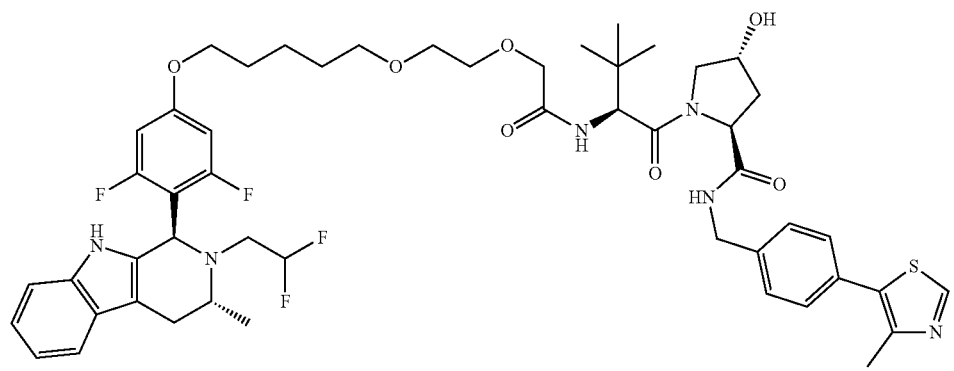 [SMILES: Cc1ncsc1-c1ccc(CNC(=O)[C@@H]2C[C@@H](O)CN2C(=O)[C@@H](NC(=O)COCCOCCCCCOc2cc(F)c([C@@H]3c4[nH]c5ccccc5c4C[C@@H](C)N3CC(F)F)c(F)c2)C(C)(C)C)cc1]

Intermediate 168b: ethyl 2-(2-(piperazin-1-yl)ethoxy)acetate hydrochloride

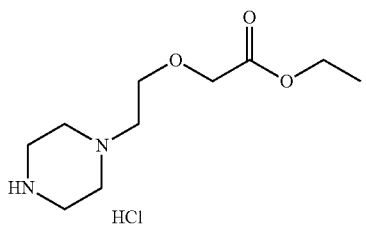

HCl 4M in Dioxane (1.15 mL, 33.2 mmol) was added to a stirred solution of tert-butyl 4-(2-(2-ethoxy-2-oxoethoxy)ethyl)piperazine-1-carboxylate (0.7 g, 2.21 mmol) in DCM (10 mL) at 0° C. The resulting solution was warmed to room temperature and stirred for 8 hours. Concentration under reduced pressure afforded the title compound (0.52 g, 93%). m/z: ES+ [M+H]$^+$=217.

Intermediate 168c: ethyl 2-(2-(4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)ethoxy)acetate

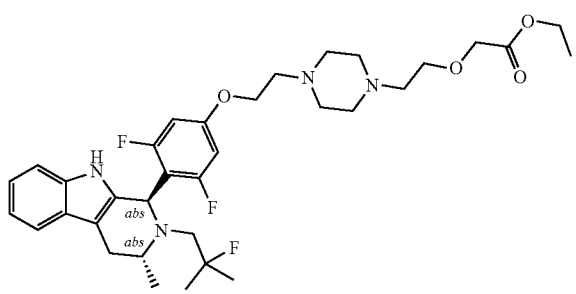 [SMILES: CCOC(=O)COCCN1CCN(CCOc2cc(F)c([C@@H]3c4[nH]c5ccccc5c4C[C@@H](C)N3CC(C)(C)F)c(F)c2)CC1]

(1R,3R)-1-[4-(2-bromoethoxy)-2,6-difluoro-phenyl]-2-(2-fluoro-2-methyl-propyl)-3-methyl-1,3,4,9-tetrahydro-pyrido[3,4-b]indole (0.24 g, 0.48 mmol) was dissolved in acetonitrile (30 mL). To the stirred solution was added ethyl 2-(2-(piperazin-1-yl)ethoxy)acetate hydrochloride (0.147 g, 0.58 mmol) and potassium carbonate (0.536 g, 3.88 mmol) at room temperature. The mixture was heated to 78° C. and stirred at that temperature overnight. The reaction mixture was cooled to room temperature and the solvent was removed under reduced pressure. To the residue was added DCM (30 mL) and water (30 mL). After partition, the organic layer was washed with brine (10 mL) and concentrated under reduced pressure. The resulting residue was purified by flash silica chromatography, elution gradient 0 to 10% MeOH in DCM. Product fractions were concentrated under reduced pressure to afford the title compound (0.280 g, 92%). m/z: ES+ [M+H]$^+$=631.

Intermediate 168d: 2-[2-[4-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethyl]piperazin-1-yl]ethoxy]acetic Acid

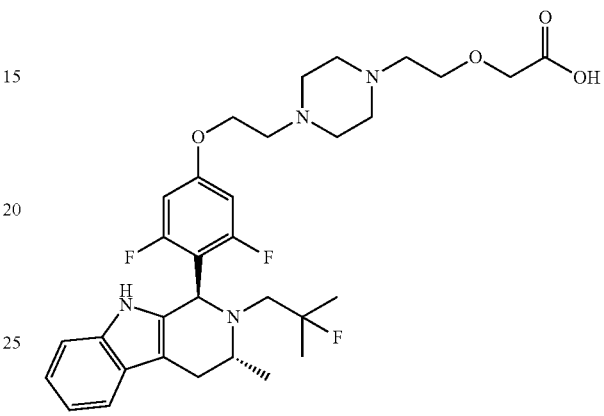

Lithium hydroxide (106 mg, 4.44 mmol) was added to ethyl 2-(2-(4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)ethoxy)acetate (280 mg, 0.44 mmol) in methanol (3 mL), THF (3.00 mL), and water (1.00 mL) at 20° C. under air. The resulting solution was stirred at 50° C. for 2 hours. The mixture was directly concentrated, and the crude product was taken to next step directly. m/z: ES+ [M+H]$^+$=603.

Example 168: (2S,4R)-1-((S)-2-(2-(2-(4-(2-(3,5-difluoro-4-((R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)ethoxy)acetamido)-3,3-dimethylbutanoyl)-4-hydroxy-N-(4-(4-methylthiazol-5-yl)benzyl)pyrrolidine-2-carboxamide

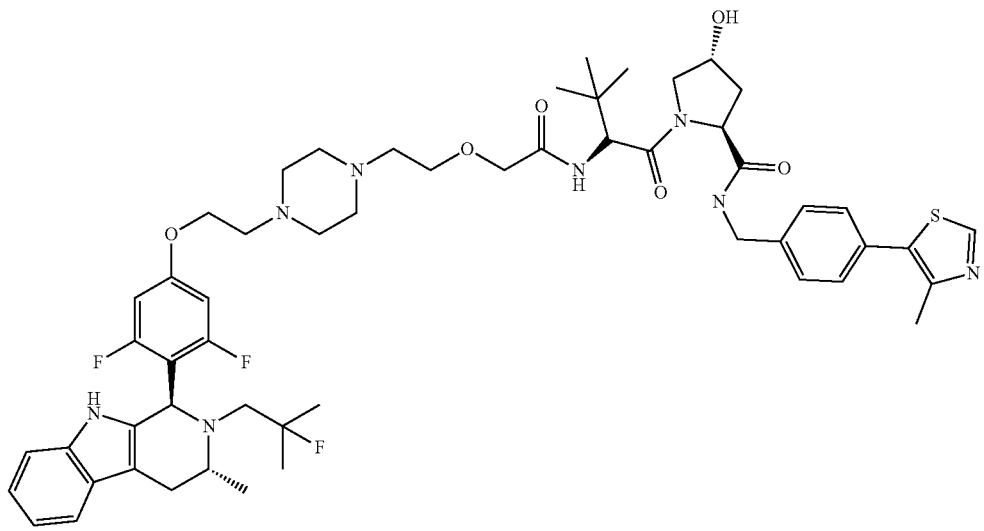

2-(2-(4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)ethoxy)acetic acid (80 mg, 0.13 mmol) was added to a stirred solution of (2S,4R)-1-((S)-2-amino-3,3-dimethylbutanoyl)-4-hydroxy-N-(4-(4-methylthiazol-5-yl)benzyl)pyrrolidine-2-carboxamide hydrochloride (68.2 mg, 0.15 mmol) and triethylamine (0.056 mL, 0.40 mmol) in DMF (2 mL) at 20° C. under nitrogen protection. HATU (70.7 mg, 0.19 mmol) was added. The resulting mixture was stirred at room temperature for 10 minutes. The solution was directly taken to preparative HPLC for purification. The resulting residue was purified by preparative HPLC (XBridge Prep C18 OBD column), using an elution gradient of 50 to 75% MeCN in water containing 0.2% $NH_4OH$. Fractions containing the product were concentrated under reduced pressure to afford the title compound (65.0 mg, 48.2%) as a white solid. $^1$H NMR (500 MHz, DMSO-d6) 0.95 (9H, s), 1.04 (3H, d), 1.11-1.23 (7H, m), 1.91 (1H, m), 2.06 (1H, m), 2.29-2.38 (2H, m), 2.45 (10H, s), 2.52-2.54 (1H, m), 2.55-2.59 (1H, m), 2.60-2.66 (2H, m), 2.78-2.92 (2H, m), 3.49-3.54 (1H, m), 3.59 (3H, m), 3.65-3.70 (1H, m), 3.95 (2H, d), 4.03 (1H, br t), 4.22-4.28 (1H, m), 4.33-4.38 (1H, m), 4.44 (2H, br d), 4.56 (1H, d), 5.10-5.14 (1H, m), 5.14-5.18 (1H, m), 6.65 (2H, br d), 6.95 (1H, d), 6.99 (1H, s), 7.16-7.21 (1H, m), 7.36-7.44 (6H, m), 8.55-8.63 (1H, m), 8.97 (1H, s), 10.51 (1H, s); m/z: ES+ [M+H]$^+$=1015.

The above description of illustrative embodiments is intended only to acquaint others skilled in the art with the Applicant's specification, its principles, and its practical application so that others skilled in the art may readily adapt and apply the specification in its numerous forms, as they may be best suited to the requirements of a particular use. This description and its specific examples, while indicating embodiments of this specification, are intended for purposes of illustration only. This specification, therefore, is not limited to the illustrative embodiments described in this specification, and may be variously modified. In addition, it is to be appreciated that various features of the specification that are, for clarity reasons, described in the context of separate embodiments, also may be combined to form a single embodiment. Conversely, various features of the specification that are, for brevity reasons, described in the context of a single embodiment, also may be combined to form sub-combinations thereof.

The invention claimed is:

1. A compound of Formula (I):

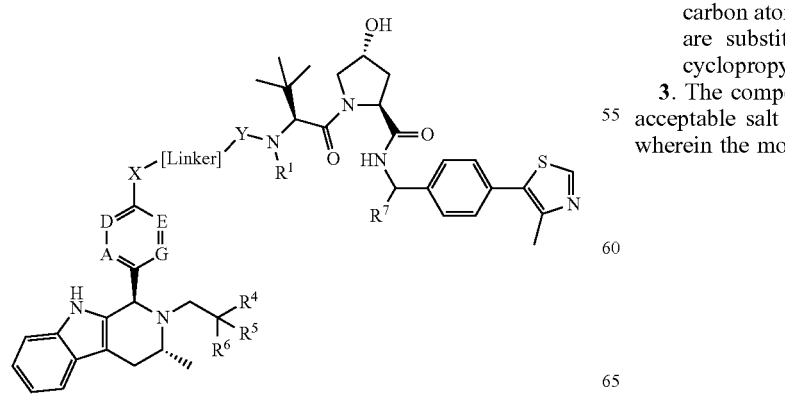

or a pharmaceutically acceptable salt or prodrug thereof, wherein:

$R^1$ represents H or methyl;

A and G are independently $CR^2$ or N;

$R^2$ is independently selected from H, F, Cl, CN, methyl or methoxy;

D and E are independently $CR^3$ or N;

$R^3$ is independently selected from H, F, Cl, or methyl;

$R^4$ represents H, methyl or F;

$R^5$ represents H, methyl or F;

or $R^4$ and $R^5$ taken together with the carbon atom to which they are attached form a cyclopropyl ring or an oxetanyl ring;

$R^6$ represents H, methyl, F, $CH_2F$, $CHF_2$, $CF_3$, CN, $CH_2CN$, $CH_2OMe$, $CH_2OH$, C(O)OH, C(O)OMe or $SO_2Me$;

$R^7$ represents H, methyl, —$CH_2NHMe$, —$CH_2NMe_2$ or $CH_2NH_2$;

X represents —O—, —CH=CH—C(O)NH—, —NHC(O)—, —C(O)NH— or -pyrrolidinyl-NMeC(O)—;

Y represents a bond or —C(O)—; and

Linker is an optionally substituted linking moiety comprising a branched or unbranched, cyclized or uncyclized, saturated or unsaturated chain of 4 to 20 carbon atoms in length, wherein 1 to 6 of the carbon atoms are optionally replaced with a heteroatom independently selected from O, N and S.

2. The compound of Formula (I), or a pharmaceutically acceptable salt or prodrug thereof, as claimed in claim 1, wherein the linker is selected from the group comprising:

a) a $C_{4-14}$ alkyl chain;
b) a $C_{3-14}$ alkoxy chain;
c) a $C_{3-14}$ alkenyloxy chain;
d) a $C_{3-14}$ alkynyloxy chain; and
e) $L^1$-Ar-$L^2$ or $L^1$-Het-$L^2$; wherein $L^1$ is a bond, $C_{1-6}$ alkyl, $C_{1-2}$ alkyl-C(O)— or $C_{1-4}$ alkoxy; Ar is a 6 membered optionally substituted aryl; Het is a 4 to 6 membered heterocycloalkyl or a 9 to 10 membered spirocyclic bicyclic heterocycloalkyl or a 3 to 6 membered optionally substituted heteroaryl; $L^2$ is a bond, $C_{1-4}$ alkyl, $C_{1-6}$ alkoxy or -Ph-, wherein a carbon atom in the $C_{1-4}$ alkyl is optionally replaced with an optionally substituted N;

optionally wherein a carbon atom in the chain of any one of groups a) to d) is replaced with an optionally substituted N; and optionally wherein a carbon atom in the chain of any one of groups a) to d) is substituted with one or more F groups, a cyclopropyl group or oxo, or two adjacent carbon atoms in the chain of any one of groups a) to d) are substituted so that taken together they form a cyclopropyl group.

3. The compound of Formula (I), or a pharmaceutically acceptable salt or prodrug thereof, as claimed in claim 1, wherein the moiety:

is selected from the group consisting of

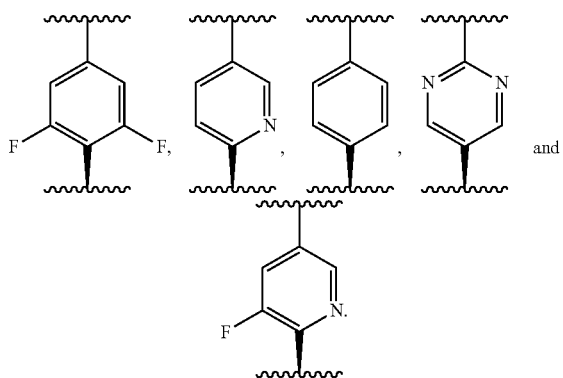

4. The compound of Formula (I), or a pharmaceutically acceptable salt thereof, as claimed in claim 1, wherein the group —CH$_2$—C(R$^4$)(R$^5$)(R$^6$) is selected from the group consisting of:

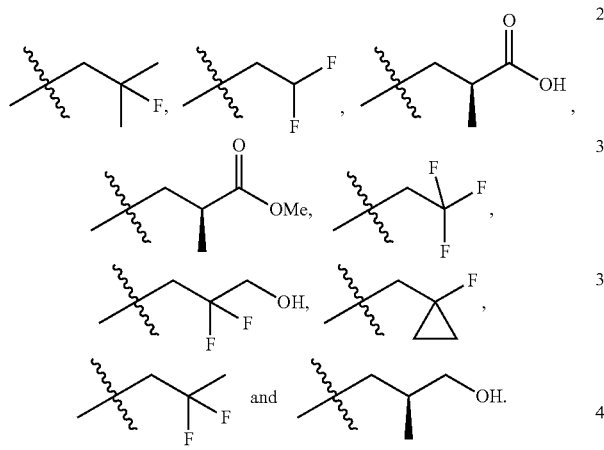

5. The compound of Formula (I), or a pharmaceutically acceptable salt or prodrug thereof, as claimed in claim 1, wherein R$^7$ represents H, methyl, CH$_2$NH$_2$ or CH$_2$NMe$_2$.

6. The compound of Formula (I), or a pharmaceutically acceptable salt or prodrug thereof, as claimed in claim 1, wherein X represents —O—, CHCH—C(O)NH—, —NHC(O)— or —C(O)NH—.

7. The compound of Formula (I), or a pharmaceutically acceptable salt or prodrug thereof, as claimed in claim 2, wherein the Linker represents:
a) —C$_{4-10}$alkyl-, wherein one or two —CH$_2$— units are optionally independently replaced with —NH—, —NMe- or —CF$_2$—, or wherein two adjacent —CH$_2$— units are optionally replaced with —N(H)C(O)— or —N(Me)C(O)—;
b) —C$_{2-5}$alkyl-O—C$_{2-5}$alkyl-O—CH$_2$, —(C$_2$H$_4$O)$_{2-4}$CH$_2$— or —C$_{1-3}$ alkyl(OC$_2$H$_4$)OCH$_2$—, wherein one or two —CH$_2$— units are optionally independently replaced with a unit selected from —CF$_2$—, —CHMe-, —CMe$_2$-, —C(cyclopropyl)-, —NH—, —NMe-, —N(C(O)OCH$_2$Ph), or wherein two adjacent —CH$_2$— units are optionally replaced with —N(H)C(O)—, —N(Me)C(O)— or a cyclopropyl;
c) —C$_2$H$_4$CH═CHC$_2$H$_4$OCH$_2$—;
d) —CH$_2$C≡C—C≡C—CH$_2$OCH$_2$—; or
e) L$^1$-Ar-L$^2$ or L$^1$-Het-L$^2$; wherein L$^1$ represents a bond, C$_{1-5}$ alkyl, —(C$_2$H$_4$O)$_{1-2}$ C$_2$H$_4$OC$_2$H$_4$— or —CH$_2$C(O)—; Ar represents phenyl; Het represents a group selected from:

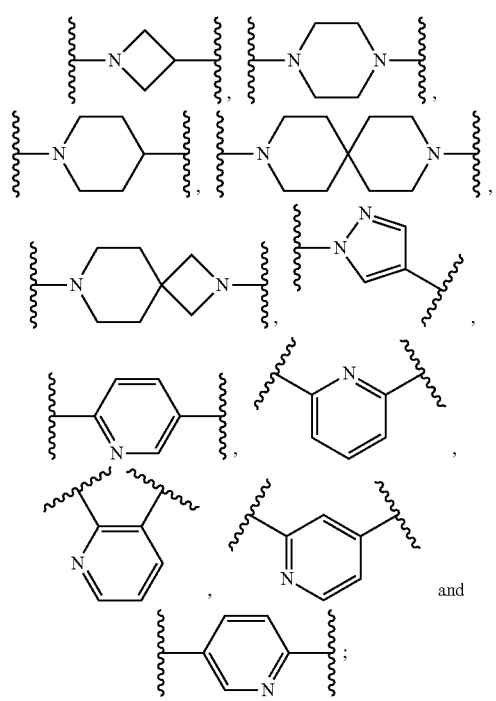

and L$^2$ represents a bond, —C$_{1-4}$ alkyl-, —C$_{1-5}$alkyl-O—CH$_2$—, —O—C$_{1-3}$alkyl-, —OC$_2$H$_4$OCH$_2$— or phenyl, wherein one —CH$_2$— unit in the —C$_{1-4}$ alkyl- is optionally replaced with NH.

8. The compound of Formula (I), or a pharmaceutically acceptable salt or prodrug thereof, as claimed in claim 1, wherein the group —X-[Linker]-Y— is selected from the group consisting of:

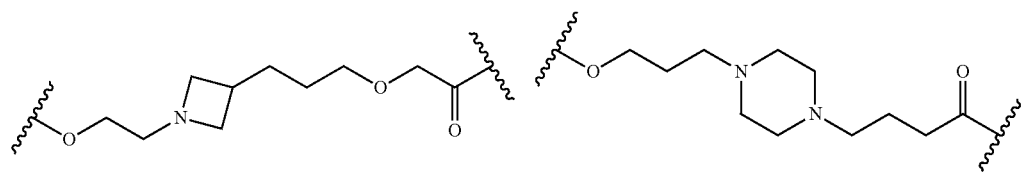

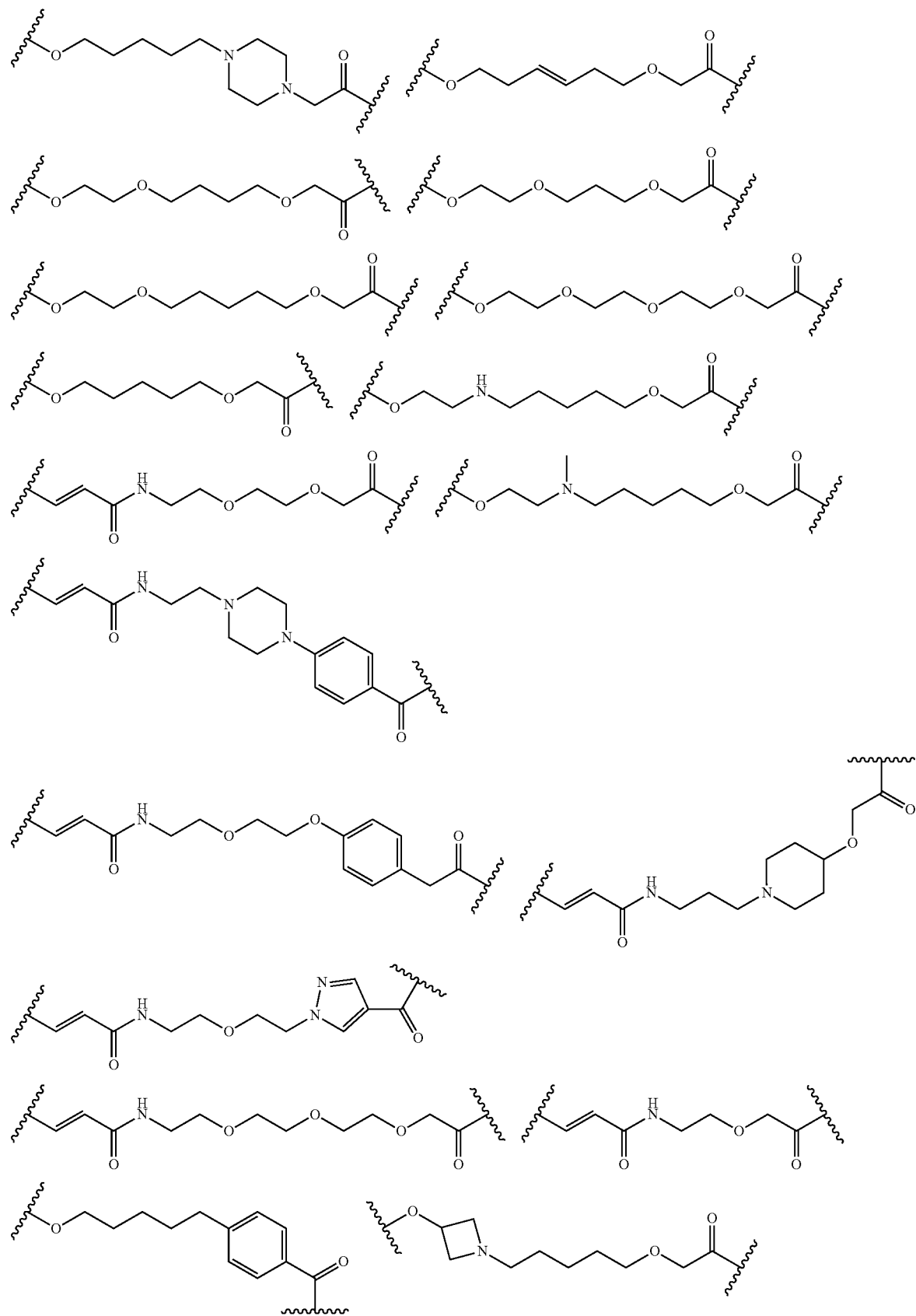

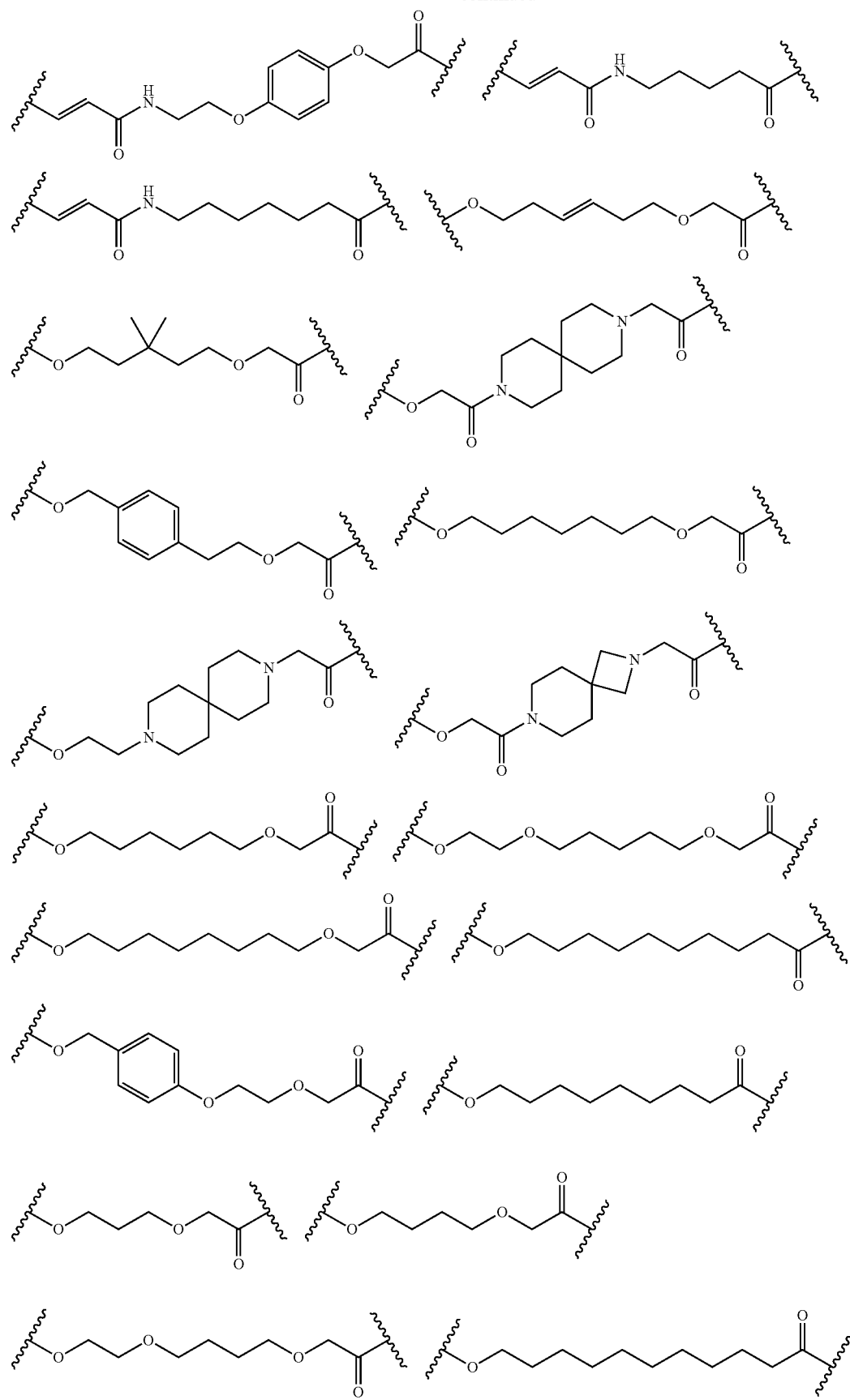

567
-continued
568
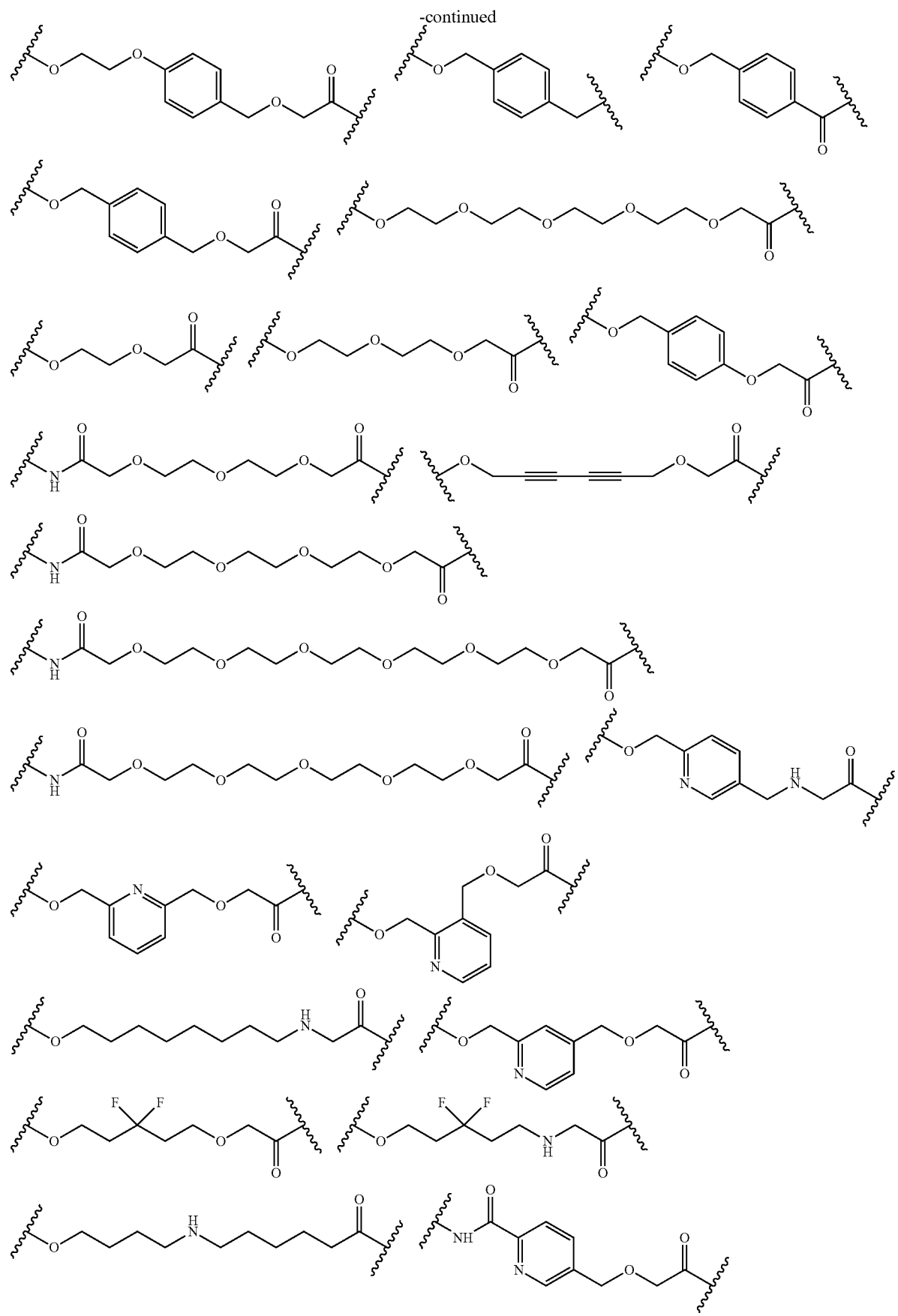

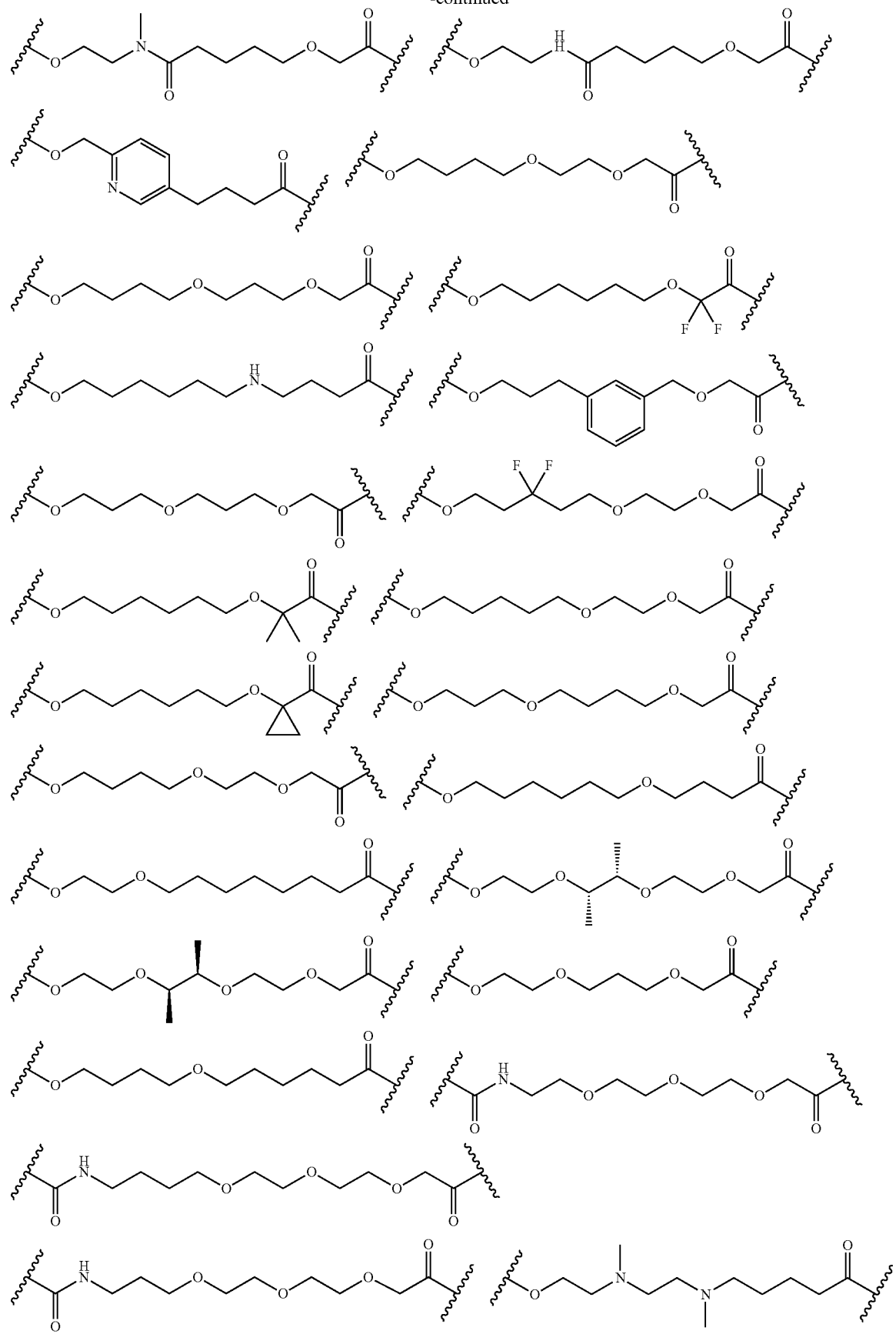

-continued

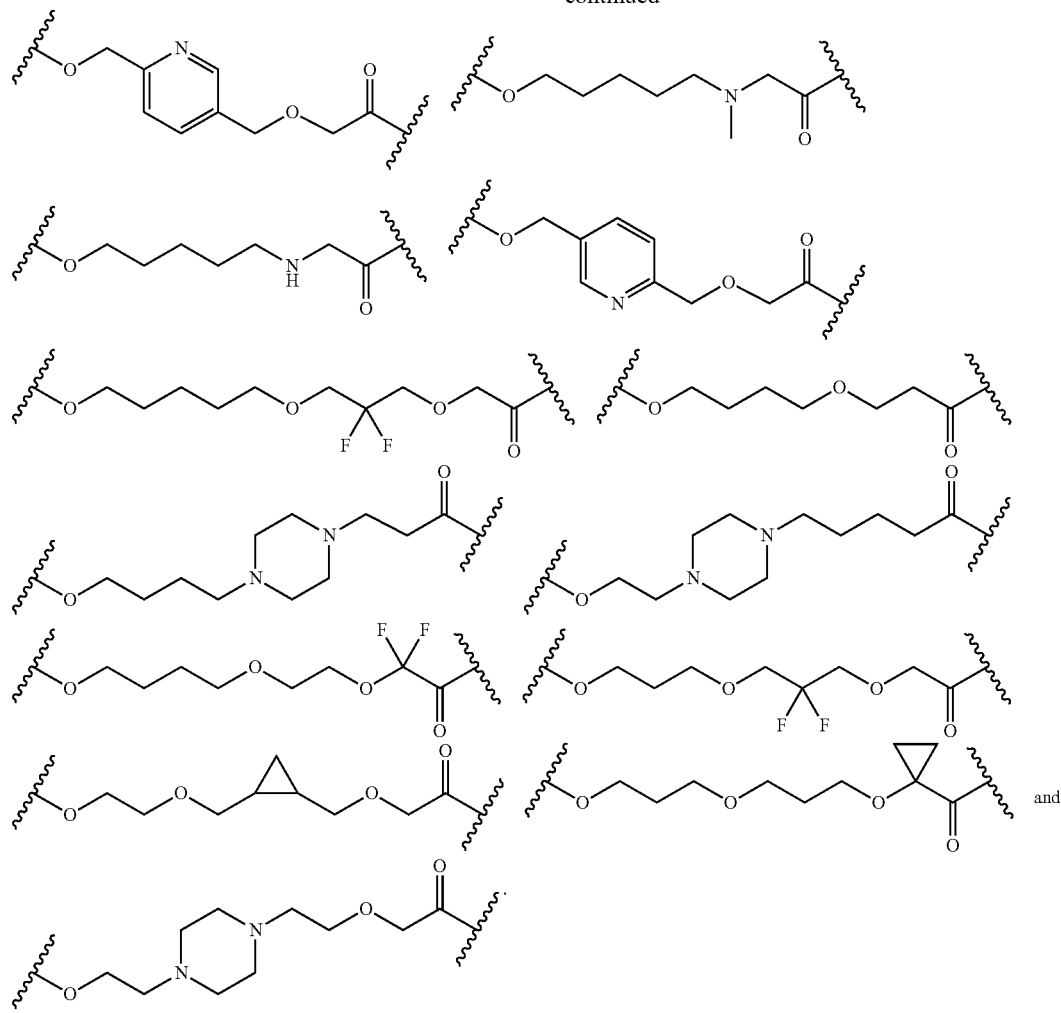

9. The compound of Formula (I), or a pharmaceutically acceptable salt thereof, as claimed in claim 1, wherein the compound is selected from the group consisting of:

(2S,4R)-1-((S)-2-(4-(4-(3-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)propyl)piperazin-1-yl)butanamido)-3,3-dimethylbutanoyl)-4-hydroxy-N-(4-(4-methylthiazol-5-yl)benz yl)pyrrolidine-2-carboxamide;

(2S,4R)-1-((S)-2-(2-(4-(5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)piperazin-1-yl)acetamido)-3,3-dimethylbutanoyl)-4-hydroxy-N-(4-(4-methylthiazol-5-yl)benz yl)pyrrolidine-2-carboxamide;

(2S,4R)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-4-hydroxy-N—((S)-1-(4-(4-methylthiazol-5-yl)phenyl)ethyl)pyrrolidine-2-carboxamide;

(2S,4R)-1-((S)-2-(2-((4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)benzyl)oxy)acetamido)-3,3-dimethylbutanoyl)-4-hydroxy-N-(4-(4-methylthiazol-5-yl)benz yl)pyrrolidine-2-carboxamide;

(2S,4R)-1-((S)-2-(2-(2-(4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)ethoxy)acetamido)-3,3-dimethylbutanoyl)-4-hydroxy-N-(4-(4-methylthiazol-5-yl)benz yl)pyrrolidine-2-carboxamide;

(2S,4R)-1-((S)-2-(2-((7-((6-((1S,3R)-2-(2,2-Difluoroethyl)-3-methyl-2,3,4,9-tetrahydro-1H-pyrido[3,4-b]indol-1-yl)pyridin-3-yl)oxy)heptyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((7-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)acetamido)-3,3-dimethylbutanoyl)-4-hydroxy-N-(4-(4-methylthiazol-5-yl)benz yl)pyrrolidine-2-carboxamide;

(2S,4R)-1-((S)-2-(2-((6-((6-((1S,3R)-2-(2,2-Difluoroethyl)-3-methyl-2,3,4,9-tetrahydro-1H-pyrido[3,4-b]indol-1-yl)pyridin-3-yl)oxy)hexyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(2-((6-((1S,3R)-2-(2,2-Difluoroethyl)-3-methyl-2,3,4,9-tetrahydro-1H-pyrido[3,4-b]indol-1-yl)pyridin-3-yl)oxy)ethoxy)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(10-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)decanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((8-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)octyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((8-((6-((1S,3R)-2-(2,2-Difluoroethyl)-3-methyl-2,3,4,9-tetrahydro-1H-pyrido[3,4-b]indol-1-yl)pyridin-3-yl)oxy)octyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)butoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(9-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)nonanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)butoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-((6-((1S,3R)-2-(2,2-Difluoroethyl)-3-methyl-2,3,4,9-tetrahydro-1H-pyrido[3,4-b]indol-1-yl)pyridin-3-yl)oxy)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(((E)-6-((6-((1S,3R)-2-(2,2-Difluoroethyl)-3-methyl-2,3,4,9-tetrahydro-1H-pyrido[3,4-b]indol-1-yl)pyridin-3-yl)oxy)hex-3-en-1-yl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(((E)-6-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)hex-3-en-1-yl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)-3,3-dimethylpentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(2-((6-((1S,3R)-2-(2,2-Difluoroethyl)-3-methyl-2,3,4,9-tetrahydro-1H-pyrido[3,4-b]indol-1-yl)pyridin-3-yl)oxy)ethoxy)butoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(2-((6-((1S,3R)-2-(2,2-Difluoroethyl)-3-methyl-2,3,4,9-tetrahydro-1H-pyrido[3,4-b]indol-1-yl)pyridin-3-yl)oxy)ethoxy)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(4-(5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)benzamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)acetamido)-3,3-dimethylbutanoyl)-4-hydroxy-N—((S)-1-(4-(4-methylthiazol-5-yl)phenyl)ethyl)pyrrolidine-2-carboxamide;

(Methyl (S)-3-((1R,3R)-1-(2,6-difluoro-4-(((S)-13-((2S,4R)-4-hydroxy-2-((4-(4-methylthiaiazol-5-yl)benzyl)carbamoyl)pyrrolidine-1-carbonyl)-14,14-dimethyl-11-oxo-3,6,9-trioxa-12-azapentadecyl)oxy)phenyl)-3-methyl-1,3,4,9-tetrahydro-2H-pyrido[3,4-b]indol-2-yl)-2-methylpropanoate;

(S)-3-((1R,3R)-1-(2,6-Difluoro-4-(((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)oxy)phenyl)-3-methyl-1,3,4,9-tetrahydro-2H-pyrido[3,4-b]indol-2-yl)-2-methylpropanoic acid;

(2S,4R)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3-methyl-4-oxo-6,9,12-trioxa-3-azatetradecanoyl)-4-hydroxy-N-(4-(4-methylthiazol-5-yl)benzyl)pyrrolidine-2-carboxamide;

(2S,4R)-1-((S)-2-(11-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)undecanamido)-3,3-dimethylbutanoyl)-4-hydroxy-N-(4-(4-methylthiazol-5-yl)benzyl)pyrrolidine-2-carboxamide;

(3R,5S)-1-((S)-2-(11-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)undecanamido)-3,3-dimethylbutanoyl)-5-((4-(4-methylthiazol-5-yl)benzyl)carbamoyl)pyrrolidin-3-yl L-prolinate;

(3R,5S)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-5-((4-(4-methylthiazol-5-yl)benzyl)carbamoyl)pyrrolidin-3-yl acetate;

(2S,4R)-1-((S)-2-((4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzyl)amino)-3,3-dimethylbutanoyl)-4-hydroxy-N-(4-(4-methylthiazol-5-yl)benzyl)pyrrolidine-2-carboxamide;

(2S,4R)-1-((S)-2-(4-((3,5-Difluoro-4-((1R,3R)-2-(2-fluoro-2-methylpropyl)-3-methyl-2,3,4,9-tetrahydro-1H-pyrido[3,4-b]indol-1-yl)phenoxy)methyl)benzamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-Butyl)-17-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12,15-tetraoxa-3-azaheptadecanoyl)-4-hydroxy-N-(4-(4-methylthiazol-5-yl)benzyl)pyrrolidine-2-carboxamide;

(2S,4R)-1-((S)-2-(tert-Butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide;

(2S,4R)-1-((S)-2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-(3,5-Difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(7-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-2,7-diazaspiro[3.5]nonan-2-yl)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)-3,9-diazaspiro[5.5]undecan-3-yl)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(9-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)acetyl)-3,9-diazaspiro[5.5]undecan-3-yl)acetamido)-3,3-dimethylbutanoyl)-4-hydroxy-N-(4-(4-methylthiazol-5-yl)benzyl)pyrrolidine-2-carboxamide;

Benzyl (2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(5-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)pentyl)carbamate;

(2S,4R)-1-((S)-2-(2-((5-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)azetidin-1-yl)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(1-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)azetidin-3-yl)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)amino)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexa-2,4-diyn-1-yl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)acetamido)-3,3-dimethylbutanoyl)-4-hydroxy-N-(4-(4-methylthiazol-5-yl)benzyl)pyrrolidine-2-carboxamide;

(3R,5S)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)acetamido)-3,3-dimethylbutanoyl)-5-((4-(4-methylthiazol-5-yl)benzyl)carbamoyl)pyrrolidin-3-yl acetate;

(2S,4R)-1-((S)-2-(2-(4-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenethoxy)acetamido)-3,3-dimethylbutanoyl)-4-hydroxy-N-(4-(4-methylthiazol-5-yl)benzyl)pyrrolidine-2-carboxamide;

$N^1$-(4-((1R,3R)-2-(2-fluoro-2-methylpropyl)-3-methyl-2,3,4,9-tetrahydro-1H-pyrido[3,4-b]indol-1-yl)phenyl)-$N^{18}$—(S)-1-((2S,4R)-4-hydroxy-2-(4-(4-methylthiazol-5-yl)benzylcarbamoyl)pyrrolidin-1-yl)-3,3-dimethyl-1-oxobutan-2-yl)-2,5,8,11,14,17-hexaoxaoctadecane-1,18-dicarboxamide;

$N^1$-(4-((1R,3R)-2-(2-fluoro-2-methylpropyl)-3-methyl-2,3,4,9-tetrahydro-1H-pyrido[3,4-b]indol-1-yl)phenyl)-$N^{14}$—(S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12-tetraoxatetradecanediamide;

$N^1$-(4-((1R,3R)-2-(2-fluoro-2-methylpropyl)-3-methyl-2,3,4,9-tetrahydro-1H-pyrido[3,4-b]indol-1-yl)phenyl)-$N^{17}$—(S)-1-((2S,4R)-4-hydroxy-2-((4-(4-methylthiazol-5-yl)benzyl)carbamoyl)pyrrolidin-1-yl)-3,3- dimethyl-1-oxobutan-2-yl)-3,6,9,12,15-pentaoxaheptadecanediamide;

(2S,4R)-1-((S)-2-(tert-butyl)-14-((4-((1R,3R)-2-(2-fluoro-2-methylpropyl)-3-methyl-2,3,4,9-tetrahydro-1H-pyrido[3,4-b]indol-1-yl)phenyl)amino)-4,14-dioxo-6,9,12-trioxa-3-azatetradecanoyl)-4-hydroxy-N-(4-(4-methylthiazol-5-yl)benzyl)pyrrolidine-2-carboxamide;

(2S,4R)-1-((S,E)-2-(tert-butyl)-15-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-4,13-dioxo-6,9-dioxa-3,12-diazapentadec-14-enoyl)-4-hydroxy-N-(4-(4-methylthiazol-5-yl)benzyl)pyrrolidine-2-carboxamide;

(2S,4R)-1-((S)-2-(7-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)heptanamido)-3,3-dimethylbutanoyl)-4-hydroxy-N-(4-(4-methylthiazol-5-yl)benzyl)pyrrolidine-2-carboxamide;

(2S,4R)-1-((S)-2-(5-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)pentanamido)-3,3-dimethylbutanoyl)-4-hydroxy-N-(4-(4-methylthiazol-5-yl)benzyl)pyrrolidine-2-carboxamide;

(2S,4R)-1-((S)-2-(4-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)phenoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S,E)-2-(tert-butyl)-18-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-4,16-dioxo-6,9,12-trioxa-3,15-diazaoctadec-17-enoyl)-4-hydroxy-N-(4-(4-methylthiazol-5-yl)benzyl)pyrrolidine-2-carboxamide;

1-(2-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)ethyl)-N—((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-1H-pyrazole-4-carboxamide;

(2S,4R)-1-((S)-2-(2-((1-(3-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)propyl)piperidin-4-yl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(4-(2-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethoxy)ethoxy)phenyl)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(4-(4-(2-((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylamido)ethyl)piperazin-1-yl)benzamido)-3,3-dimethylbutanoyl)-4-hydroxy-N-(4-(4-methylthiazol-5-yl)benzyl)pyrrolidine-2-carboxamide;

N1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-N14-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12-tetraoxatetradecanediamide;

(2S,4R)-1-((S)-2-(2-((5-(4-((1R,3R)-2-(2,2-difluoro-3-hydroxypropyl)-3-methyl-2,3,4,9-tetrahydro-1H-pyrido[3,4-b]indol-1-yl)-3,5-difluorophenoxy)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-14-(4-((1R,3R)-2-(2,2-difluoro-3-hydroxypropyl)-3-methyl-2,3,4,9-tetrahydro-1H-pyrido[3,4-b]indol-1-yl)-3,5-difluorophenoxy)-4-oxo-6,9,12-trioxa-3-azatetradecanoyl)-4-hydroxy-N-(4-(4-methylthiazol-5-yl)benzyl)pyrrolidine-2-carboxamide;

(2S,4R)-1-((S)-2-(2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(3-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)phenyl)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propyl)benzyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(tert-butyl)-14-(3,5-difluoro-4-((1R,3R)-2-((1-fluorocyclopropyl)methyl)-3-methyl-2,3,4,9-tetrahydro-1H-pyrido[3,4-b]indol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide;

(2S,4R)-1-((S)-2-(2-((7-(4-((1R,3R)-2-(2,2-difluoro-3-hydroxypropyl)-3-methyl-2,3,4,9-tetrahydro-1H-pyrido[3,4-b]indol-1-yl)-3,5-difluorophenoxy)heptyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-difluoro-4-((1R,3R)-2-((1-fluorocyclopropyl)methyl)-3-methyl-2,3,4,9-tetrahydro-1H-pyrido[3,4-b]indol-1-yl)phenoxy)pentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((2S,10R,11R)-2-(tert-butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-10,11-dimethyl-4-oxo-6,9,12-trioxa-3-azatetradecanoyl)-4-hydroxy-N-(4-(4-methylthiazol-5-yl)benzyl)pyrrolidine-2-carboxamide;

(2S,4R)-1-((2S,10S,11S)-2-(tert-butyl)-14-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-10,11-dimethyl-4-oxo-6,9,12-trioxa-3- azatetradecanoyl)-4-hydroxy-N-(4-(4-methylthiazol-5-yl)benzyl)pyrrolidine-2-carboxamide;
(2S,4R)-1-((S)-17-(tert-butyl)-1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1,15-dioxo-7,10,13-trioxa-2,16-diazaoctadecan-18-oyl)-4-hydroxy-N-(4-(4-methylthiazol-5-yl)benzyl)pyrrolidine-2-carboxamide;
(2S,4R)-1-((S)-16-(tert-butyl)-1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1,14-dioxo-6,9,12-trioxa-2,15-diazaheptadecan-17-oyl)-4-hydroxy-N-(4-(4-methylthiazol-5-yl)benzyl)pyrrolidine-2-carboxamide;
(2S,4R)-1-((S)-2-(2-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methoxy)acetamido)-3,3-dimethylbutanoyl)-4-hydroxy-N-(4-(4-methylthiazol-5-yl)benzyl)pyrrolidine-2-carboxamide;
(2S,4R)-1-((S)-2-(2-((5-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)methoxy)acetamido)-3,3-dimethylbutanoyl)-4-hydroxy-N-(4-(4-methylthiazol-5-yl)benzyl)pyrrolidine-2-carboxamide;
(2S,4R)-1-((S)-2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)amino)acetamido)-3,3-dimethylbutanoyl)-4-hydroxy-N-(4-(4-methylthiazol-5-yl)benzyl)pyrrolidine-2-carboxamide;
(2S,4R)-1-((S)-2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)(methyl)amino)acetamido)-3,3-dimethylbutanoyl)-4-hydroxy-N-(4-(4-methylthiazol-5-yl)benzyl)pyrrolidine-2-carboxamide;
(2S,4R)-1-((S)-15-(tert-butyl)-1-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-1,13-dioxo-5,8,11-trioxa-2,14-diazahexadecan-16-oyl)-4-hydroxy-N-(4-(4-methylthiazol-5-yl)benzyl)pyrrolidine-2-carboxamide;
(2S,4R)-1-((S)-2-(3-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)propanamido)-3,3-dimethylbutanoyl)-4-hydroxy-N-(4-(4-methylthiazol-5-yl)benzyl)pyrrolidine-2-carboxamide;
(2S,4R)-1-((S)-2-(2-(4-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)butoxy)acetamido)-3,3-dimethylbutanoyl)-4-hydroxy-N-(4-(4-methylthiazol-5-yl)benzyl)pyrrolidine-2-carboxamide;
(2S,4R)-1-((S)-2-(2-(3-(2-(3,5-difluoro-4-((1R,3R)-3-methyl-2-(2,2,2-trifluoroethyl)-2,3,4,9-tetrahydro-1H-pyrido[3,4-b]indol-1-yl)phenoxy)ethoxy)propoxy)acetamido)-3,3-dimethylbutanoyl)-4-hydroxy-N-(4-(4-methylthiazol-5-yl)benzyl)pyrrolidine-2-carboxamide;
(2S,4R)-1-((S)-2-(tert-butyl)-14-(3,5-difluoro-4-((1R,3R)-3-methyl-2-(2,2,2-trifluoroethyl)-2,3,4,9-tetrahydro-1H-pyrido[3,4-b]indol-1-yl)phenoxy)-4-oxo-6,9,12-trioxa-3-azatetradecanoyl)-4-hydroxy-N-(4-(4-methylthiazol-5-yl)benzyl)pyrrolidine-2-carboxamide;
(2S,4R)-1-((S)-2-((5-(3,5-difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy)acetamido)-3,3-dimethylbutanoyl)-4-hydroxy-N-(4-(4-methylthiazol-5-yl)benzyl)pyrrolidine-2-carboxamide;
(2S,4R)-1-((S)-2-(2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)ethoxy)acetamido)-3,3-dimethylbutanoyl)-4-hydroxy-N-(4-(4-methylthiazol-5-yl)benzyl)pyrrolidine-2-carboxamide;
(2S,4R)-1-((S)-2-(3-(4-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butyl)piperazin-1-yl)propanamido)-3,3-dimethylbutanoyl)-4-hydroxy-N-(4-(4-methylthiazol-5-yl)benzyl)pyrrolidine-2-carboxamide;
(3R,5S)-1-((S)-2-(2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetamido)-3,3-dimethylbutanoyl)-5-((4-(4-methylthiazol-5-yl)benzyl)carbamoyl)pyrrolidin-3-yl L-isoleucinate;
(3R,5S)-1-((S)-2-(2-(2-(2-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)ethoxy)ethoxy)acetamido)-3,3-dimethylbutanoyl)-5-((4-(4-methylthiazol-5-yl)benzyl)carbamoyl)pyrrolidin-3-yl L-valyl-L-alaninate;
(2S,4R)-1-((S)-2-(tert-butyl)-14-(3,5-difluoro-4-((1R,3R)-2-((S)-3-hydroxy-2-methylpropyl)-3-methyl-2,3,4,9-tetrahydro-1H-pyrido[3,4-b]indol-1-yl)phenoxy)-4-oxo-6,9,12-trioxa-3-azatridecanoyl)-4-hydroxy-N-(4-(4-methylthiazol-5-yl)benzyl)pyrrolidine-2-carboxamide;
(2S,4R)-1-((S)-2-(5-(4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)pentanamido)-3,3-dimethylbutanoyl)-4-hydroxy-N-(4-(4-methylthiazol-5-yl)benzyl)pyrrolidine-2-carboxamide;
(2S,4R)-1-[(2S)-2-[[2-[2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-N-[(1R*)-2-(dimethylamino)-1-[4-(4-methylthiazol-5-yl)phenyl]ethyl]-4-hydroxy-pyrrolidine-2-carboxamide;
(2S,4R)—N-[(1R*)-2-amino-1-[4-(4-methylthiazol-5-yl)phenyl]ethyl]-1-[(2S)-2-[[2-[2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-4-hydroxy-pyrrolidine-2-carboxamide;
(2S,4R)-1-[(2S)-2-[[2-[2-[2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxy]ethoxy]ethoxy]acetyl]amino]-3,3-dimethyl-butanoyl]-N-[(1R*)-2-(dimethylamino)-1-[4-(4-methylthiazol-5-yl)phenyl]ethyl]-4-hydroxy-pyrrolidine-2-carboxamide;
(2S,4R)-1-((S)-2-(5-((2-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)(methyl)amino)ethyl)(methyl)amino)pentanamido)-3,3-dimethylbutanoyl)-4-hydroxy-N-(4-(4-methylthiazol-5-yl)benzyl)pyrrolidine-2-carboxamide;
(2S,4R)-1-((S)-2-(6-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)hexanamido)-3,3-dimethylbutanoyl)-4-hydroxy-N-(4-(4-methylthiazol-5-yl)benzyl)pyrrolidine-2-carboxamide;

(2S,4R)-1-((S)-2-(7-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)heptanamido)-3,3-dimethylbutanoyl)-4-hydroxy-N-(4-(4-methylthiazol-5-yl)benzyl)pyrrolidine-2-carboxamide;

(2S,4R)-1-((S)-2-(8-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)octanamido)-3,3-dimethylbutanoyl)-4-hydroxy-N-(4-(4-methylthiazol-5-yl)benzyl)pyrrolidine-2-carboxamide;

(2S,4R)-1-((S)-2-(4-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(5-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)pentanamido)-3,3-dimethylbutanoyl)-4-hydroxy-N-(4-(4-methylthiazol-5-yl)benzyl)pyrrolidine-2-carboxamide;

(2S,4R)-1-((S)-2-(3-((7-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)propanamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(3-((7-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)heptyl)oxy)propanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)-2,2-difluoroacetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)-2-methylpropanamido)-3,3-dimethylbutanoyl)-4-hydroxy-N-(4-(4-methylthiazol-5-yl)benzyl)pyrrolidine-2-carboxamide;

(2S,4R)-1-((S)-2-(1-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)oxy)cyclopropane-1-carboxamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)-2,2-difluoroacetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)propoxy)-2,2-difluoroacetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)-2,2-difluoroacetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)-2,2-difluoroacetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-[(2S)-2-[[2-[[(1R*,2S*)-2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxymethyl]cyclopropyl]methoxy]acetyl]amino]-3,3-dimethyl-butanoyl]-4-hydroxy-N-[[4-(4-methylthiazol-5-yl)phenyl]methyl]pyrrolidine-2-carboxamide, isomer 1;

(2S,4R)-1-[(2S)-2-[[2-[[(1R*,2S*)-2-[2-[3,5-difluoro-4-[(1R,3R)-2-(2-fluoro-2-methyl-propyl)-3-methyl-1,3,4,9-tetrahydropyrido[3,4-b]indol-1-yl]phenoxy]ethoxymethyl]cyclopropyl]methoxy]acetyl]amino]-3,3-dimethyl-butanoyl]-4-hydroxy-N-[[4-(4-methylthiazol-5-yl)phenyl]methyl]pyrrolidine-2-carboxamide, isomer 2;

(2S,4R)-1-((S)-2-(2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)-2,2-difluoropropoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)oxy)-2,2-difluoropropoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)oxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)propoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)-3,3-difluoropentyl)amino)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)methoxy)acetamido)-3,3-dimethylbutanoyl)-4- hydroxy-N-(4-(4-methylthiazol-5-yl)benzyl)
pyrrolidine-2-carboxamide;

(2S,4R)-1-((S)-2-(2-((2-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methoxy)acetamido)-3,3-dimethylbutanoyl)-4-hydroxy-N-(4-(4-methylthiazol-5-yl)benzyl)
pyrrolidine-2-carboxamide;

(2S,4R)-1-((S)-2-(2-((2-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-4-yl)methoxy)acetamido)-3,3-dimethylbutanoyl)-4-hydroxy-N-(4-(4-methylthiazol-5-yl)benzyl)
pyrrolidine-2-carboxamide;

(2S,4R)-1-((S)-2-(1-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)
propoxy)cyclopropane-1-carboxamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)
pentyl)oxy)acetamido)-3,3-dimethylbutanoyl)-4-hydroxy-N-(4-(4-methylthiazol-5-yl)benzyl)
pyrrolidine-2-carboxamide;

(2S,4R)-1-[(2S)-2-[[2-[3-[5-[3,5-difluoro-4-[(1R,3R)-2-(2-fluoro-2-methyl-propyl)-3-methyl-1,3,4,9-tetrahydropyrido[3,4-b]indol-1-yl]phenoxy]pentoxy]
propoxy]acetyl]amino]-3,3-dimethyl-butanoyl]-4-hydroxy-N-[(1 S)-1-[4-(4-methylthiazol-5-yl)phenyl]
ethyl]pyrrolidine-2-carboxamide;

(2S,4R)-1-((S)-2-(2-(3-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)
oxy)propoxy)acetamido)-3,3-dimethylbutanoyl)-4-hydroxy-N-(4-(4-methylthiazol-5-yl)benzyl)
pyrrolidine-2-carboxamide;

(2S,4R)-1-((S)-2-(2-(2-((5-(3,5-difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy)ethoxy)
acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-(3,5-difluoro-4-((1R,3R)-3-methyl-2-(2,2,2-trifluoroethyl)-2,3,4,9-tetrahydro-1H-pyrido[3,4-b]indol-1-yl)phenoxy)pentyl)oxy)ethoxy)
acetamido)-3,3-dimethylbutanoyl)-4-hydroxy-N—((S)-1-(4-(4-methylthiazol-5-yl)phenyl)ethyl)
pyrrolidine-2-carboxamide;

(2S,4R)-1-((S)-2-(4-(6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)
amino)-5-oxopentyl)oxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-((5-((2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)
(methyl)amino)-5-oxopentyl)oxy)acetamido)-3,3-dimethylbutanoyl)-4-hydroxy-N-(4-(4-methylthiazol-5-yl)benzyl)pyrrolidine-2-carboxamide;

N-(3,5-difluoro-4-((1R,3R)-2-(2-fluoro-2-methylpropyl)-3-methyl-2,3,4,9-tetrahydro-1H-pyrido[3,4-b]indol-1-yl)phenyl)-5-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)
methyl)picolinamide;

(2S,4R)-1-((S)-2-(6-((4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butyl)amino)
hexanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)methyl)amino)acetamido)-3,3-dimethylbutanoyl)-4-hydroxy-N-(4-(4-methylthiazol-5-yl)benzyl)
pyrrolidine-2-carboxamide;

(2S,4R)-1-((S)-2-(2-((8-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)octyl)amino)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(4-((6-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)hexyl)amino)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(3-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)
propoxy)acetamido)-3,3-dimethylbutanoyl)-4-hydroxy-N—((S)-1-(4-(4-methylthiazol-5-yl)phenyl)
ethyl)pyrrolidine-2-carboxamide;

(2S,4R)-1-((S)-2-(2-(2-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)ethoxy)
acetamido)-3,3-dimethylbutanoyl)-4-hydroxy-N—
((S)-1-(4-(4-methylthiazol-5-yl)phenyl)ethyl)
pyrrolidine-2-carboxamide;

(2S,4R)-1-((S)-2-(2-(4-(3-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)propoxy)butoxy)
acetamido)-3,3-dimethylbutanoyl)-4-hydroxy-N—
((S)-1-(4-(4-methylthiazol-5-yl)phenyl)ethyl)
pyrrolidine-2-carboxamide;

(2S,4R)-1-((S)-2-(2-(3-(4-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)butoxy)propoxy)
acetamido)-3,3-dimethylbutanoyl)-4-hydroxy-N—
((S)-1-(4-(4-methylthiazol-5-yl)phenyl)ethyl)
pyrrolidine-2-carboxamide;

(2S,4R)-1-((S)-2-(2-2-((5-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)pentyl)
oxy)ethoxy)acetamido)-3,3-dimethylbutanoyl)-4-hydroxy-N—((S)-1-(4-(4-methylthiazol-5-yl)phenyl)
ethyl)pyrrolidine-2-carboxamide;

(2S,4R)-1-((S)-2-(2-((5-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethoxy)
pentyl)oxy)acetamido)-3,3-dimethylbutanoyl)-4-hydroxy-N—((S)-1-(4-(4-methylthiazol-5-yl)phenyl)
ethyl)pyrrolidine-2-carboxamide;

(2S,4R)-1-((S)-2-(2-(2-(6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)

pyridin-3-yl)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-(6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)ethoxy)acetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(4-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-3-yl)oxy)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(4-((6-((3,5-difluoro-4-((1R,3R)-2-(2-fluoro-2-methylpropyl)-3-methyl-2,3,4,9-tetrahydro-1H-pyrido[3,4-b]indol-1-yl)phenoxy)methyl)pyridin-2-yl)oxy)butanamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-((6-((1 S,3R)-2-(2,2-difluoropropyl)-3-methyl-2,3,4,9-tetrahydro-1H-pyrido[3,4-b]indol-1-yl)-5-fluoropyridin-3-yl)oxy)pentyl)oxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-((5-fluoro-6-((1 S,3R)-3-methyl-2-(2,2,2-trifluoroethyl)-2,3,4,9-tetrahydro-1H-pyrido[3,4-b]indol-1-yl)pyridin-3-yl)oxy)pentyl)oxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-(4-((1R,3R)-2-(2,2-difluoropropyl)-3-methyl-2,3,4,9-tetrahydro-1H-pyrido[3,4-b]indol-1-yl)-3,5-difluorophenoxy)pentyl)oxy)ethoxy)acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-((5-(4-((1R,3R)-2-(2,2-difluoroethyl)-3-methyl-2,3,4,9-tetrahydro-1H-pyrido[3,4-b]indol-1-yl)-3,5-difluorophenoxy)pentyl)oxy)ethoxy)acetamido)-3,3-dimethylbutanoyl)-4-hydroxy-N-(4-(4-methylthiazol-5-yl)benzyl)pyrrolidine-2-carboxamide; and (2S,4R)-1-((S)-2-(2-(2-(4-(2-(3,5-difluoro-4-((1R,3R)-2-(2-fluoro-2-methylpropyl)-3-methyl-2,3,4,9-tetrahydro-1H-pyrido[3,4-b]indol-1-yl)phenoxy)ethyl)piperazin-1-yl)ethoxy)acetamido)-3,3-dimethylbutanoyl)-4-hydroxy-N-(4-(4-methylthiazol-5-yl)benzyl)pyrrolidine-2-carboxamide.

10. A pharmaceutical composition comprising a compound of Formula (I), or a pharmaceutically acceptable salt thereof, as claimed in claim 1, and at least one pharmaceutically acceptable excipient.

11. A method for the treatment of cancer in a warm-blooded animal in need of such treatment, wherein the method comprises administering to said warm-blooded animal a therapeutically effective amount of a compound of Formula (I), or a pharmaceutically acceptable salt thereof, as claimed in claim 1.

12. The method of treatment as claimed in claim 11, wherein the cancer is breast cancer or a gynaecological cancer.

* * * * *